US012723053B2

(12) United States Patent
Abraham et al.

(10) Patent No.: US 12,723,053 B2
(45) Date of Patent: Sep. 1, 2026

(54) KRAS INHIBITORS

(71) Applicant: ELI LILLY AND COMPANY, Indianapolis, IN (US)

(72) Inventors: Adedoyin David Abraham, Thornton, CO (US); Alberto Valero De La Cruz, Madrid (ES); Alicia Marcos Llorente, Madrid (ES); Alvaro Enriquez Garcia, Madrid (ES); Andrew Dilger, Golden, CO (US); Deqi Guo, Carmel, IN (US); Desta Bume, Commerce City, CO (US); Frederic Laurent Cordier, Madrid (ES); Gaiying Zhao, Carmel, IN (US); Isabel Rojo Garcia, Madrid (ES); James Robert Henry, James City, FL (US); Jason Eric Lamar, Indianapolis, IN (US); Jolie Anne Bastian, Indianapolis, IN (US); Maria Lourdes Prieto Vallejo, Madrid (ES); Mario Barberis, Madrid (ES); Matthew Patrick Baumgartner, Aldan, PA (US); Miguel Garzón Sanz, Madrid (ES); Pablo Garcia Losada, Madrid (ES); Ramkumar Rajamani, Acton, MA (US); Richard Duane Johnston, Greenfield, IN (US); Robert Hazlitt, Broomfield, CO (US); Santiago Carballares Martin, Madrid (ES); Sean Aronow, Boulder, CO (US); Shane Michael Walls, Broomfield, CO (US); Sonia Maria Gutierrez Sanfeliciano, Carmel, IN (US); Steven Andrews, Erie, CO (US); Timothy Scott Kercher, Longmont, CO (US); Victoriano Molero Flórez, Madrid (ES); Wenceslao Lumeras Amador, Madrid (ES); William Rush Scaggs, Broomfield, CO (US); Juan Antonio Rincon Cabezudo, Madrid (ES); Julián Priego Soler, Madrid (ES); Xiaohong Chen, Broomfield, CO (US)

(73) Assignee: Eli Lilly and Company, Indianapolis, IN (US)

( * ) Notice: Subject to any disclaimer, the term of this patent is extended or adjusted under 35 U.S.C. 154(b) by 140 days.

(21) Appl. No.: 18/621,388

(22) Filed: Mar. 29, 2024

(65) Prior Publication Data

US 2024/0368193 A1 Nov. 7, 2024

(30) Foreign Application Priority Data

Mar. 31, 2023 (EP) .................................... 23382315
Jun. 2, 2023 (EP) .................................... 23382531
Aug. 18, 2023 (EP) .................................... 23382857
Sep. 27, 2023 (EP) .................................... 23382985
Mar. 12, 2024 (EP) .................................... 24382267

(51) Int. Cl.

*C07D 519/00* (2006.01)
*A61K 31/517* (2006.01)
*A61K 31/5377* (2006.01)
*A61K 31/5386* (2006.01)
*A61K 31/553* (2006.01)
*A61K 45/06* (2006.01)
*A61P 35/00* (2006.01)
*C07B 59/00* (2006.01)
*C07D 491/048* (2006.01)

(52) U.S. Cl.

CPC .......... *C07D 519/00* (2013.01); *A61K 31/517* (2013.01); *A61K 31/5377* (2013.01); *A61K 31/5386* (2013.01); *A61K 31/553* (2013.01); *A61K 45/06* (2013.01); *C07B 59/002* (2013.01); *C07D 491/048* (2013.01); *C07B 2200/05* (2013.01)

(58) Field of Classification Search

CPC .............. C07D 519/00; C07D 491/048; A61K 31/517; A61K 31/5377; A61K 31/5386; A61K 31/553; A61K 45/06; C07B 59/002; C07B 2200/05

See application file for complete search history.

(56) References Cited

FOREIGN PATENT DOCUMENTS

| | | | |
|---|---|---|---|
| CN | 120535536 | A | 8/2025 |
| WO | 2021/118877 | A1 | 6/2021 |
| WO | 2022-047260 | A1 | 3/2022 |
| WO | 2022/148422 | A1 | 7/2022 |

(Continued)

OTHER PUBLICATIONS

International Search Report and Written Opinion mailed Jul. 1, 2024, for PCT application PCT/US2024/022154 filed Mar. 29, 2024.

*Primary Examiner* — Rayna Rodriguez
(74) *Attorney, Agent, or Firm* — Stefan Ochiana

(57) ABSTRACT

The present invention provides compounds of the formula:

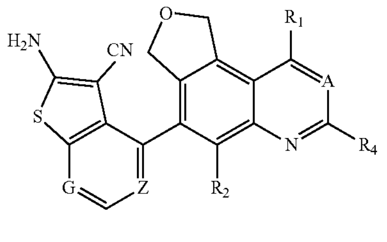

wherein A, Z, G, $R_1$, $R_2$, and $R_4$ are as described herein, pharmaceutically acceptable salts thereof, and methods of using these compounds and pharmaceutically acceptable salts thereof for treating patients for cancer.

28 Claims, No Drawings

(56) References Cited

FOREIGN PATENT DOCUMENTS

| | | | |
|---|---|---|---|
| WO | 2022/152233 | A1 | 7/2022 |
| WO | 2022/177917 | A2 | 8/2022 |
| WO | 2022/221739 | A1 | 10/2022 |
| WO | 2022/261154 | A1 | 12/2022 |
| WO | 2023/061294 | A1 | 4/2023 |
| WO | 2023-183585 | A1 | 9/2023 |
| WO | 2024/030633 | A1 | 2/2024 |
| WO | 2024/064335 | A1 | 3/2024 |
| WO | 2024/206747 | A1 | 10/2024 |
| WO | 2024/206766 | A1 | 10/2024 |
| WO | 2025/072457 | A1 | 4/2025 |
| WO | 2025/092798 | A1 | 5/2025 |

KRAS INHIBITORS

CROSS-REFERENCE TO RELATED PATENT APPLICATIONS

The present application claims the benefit of priority to European Patent Application Nos. EP 23382315.2, filed on Mar. 31, 2023, EP 23382531.4, filed on Jun. 2, 2023, EP 23382857.3, filed on Aug. 18, 2023, EP 23382985.2, filed on Sep. 27, 2023, and EP 24382267.3, filed on Mar. 12, 2024, the contents of which are incorporated herein by reference in their entireties.

BACKGROUND

The MAPK/ERK signaling pathway relays extracellular stimuli to the nucleus, thereby regulating diverse cellular responses including cell proliferation, differentiation, and apoptosis. KRas protein is an initiator of the MAPK/ERK signaling pathway and functions as a switch responsible for inducing cell division. In its inactive state, KRas binds guanosine diphosphate (GDP), effectively sending a negative signal to suppress cell division. In response to an extracellular signal, KRas is allosterically activated allowing for nucleotide exchange of GDP for guanosine triphosphate (GTP). In its GTP-bound active state, KRas recruits and activates proteins necessary for the propagation of growth factor induced signaling, as well as other cell signaling receptors. Examples of the proteins recruited by KRas-GTP are c-Raf and PI3-kinase. KRas, as a GTP-ase, converts the bound GTP back to GDP, thereby returning itself to an inactive state, and again propagating signals to suppress cell division. KRas gain of function mutations exhibit an increased degree of GTP binding and a decreased ability to convert GTP into GDP. The result is an increased MAPK/ERK signal which promotes cancerous cell growth. Missense mutations of KRas at codon 12 are the most common mutations and markedly diminish GTPase activity.

Oncogenic KRas mutations have been identified in approximately 30% of human cancers and have been demonstrated to activate multiple downstream signaling pathways. Despite the prevalence of KRas mutations, it has been a difficult therapeutic target. (Cox, A. D. *Drugging the Undruggable RAS: Mission Possible*? Nat. Rev. Drug Disc. 2014, 13, 828-851; Pylayeva-Gupta, y et al. *RAS Oncogenes: Weaving a Tumorigenic Web*. Nat. Rev. Cancer 2011, 11, 761-774).

Thus far, work has focused on KRas G12C mutant inhibitors (e.g., WO2019/099524, WO2020/081282, WO2020/101736, WO2020/146613, and WO2021/118877 disclose KRas G12C inhibitors), whereas WO2021/041671 discloses small molecules inhibitors of KRas G12D and WO2017/011920 discloses small molecule inhibitors of KRas G12C, G12D, and G12V.

There remains a need to provide alternative, small molecule KRas inhibitors. In particular, there is a need to provide more potent, orally deliverable KRas inhibitors that are useful for treating cancer. More particularly, there is a need to provide small molecule inhibitors that specifically inhibit KRas GTP activity. Further, there is a desire to provide KRas inhibitors that exhibit better pharmacokinetic/pharmacodynamic properties. Also, there is a need to provide more potent KRas inhibitors that exhibit increased efficacy with reduced or minimized untoward or undesired effects. Further, there is a need to provide more potent KRas inhibitors that exhibit selective inhibition preference for KRas G12D mutant over KRas wild-type. Further, there is also a need to provide more potent KRas inhibitors that exhibit selective inhibition preference for KRas G12C, G12D, and/or G12V mutants over HRAS or NRAS. Even further, there is also a need to provide more potent KRas inhibitors that exhibit selective inhibition preference for KRas G12C, G12D, and G12V mutants over HRAS or NRAS. These panKRas inhibitors could also be KRas wild-type inhibitors or they could be selective over KRas wild-type. The present invention addresses one or more of these needs by providing novel KRas inhibitors.

SUMMARY

Compounds of Formula I are provided herein:

Formula I

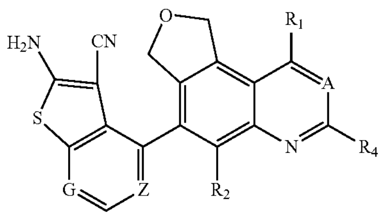

wherein

A is —C(H)— or —N—;

Z is —$C(R_{3c})$— or —N—;

G is —$C(R_{3b})$— or —N—;

$R_1$ is H, or a group of the formula

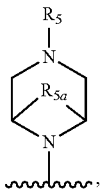, 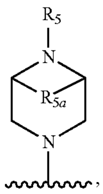, or 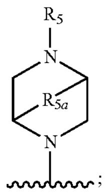;

$R_2$ is H, halogen, or methyl;

$R_{3b}$, and $R_{3c}$ are each independently H, halogen, or methyl;

$R_4$ is a N-linked cyclic amine or a group of the formula

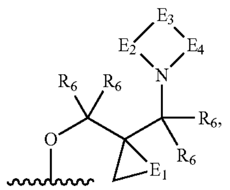

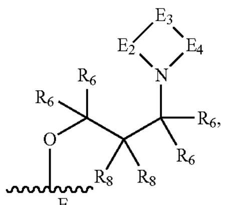, or

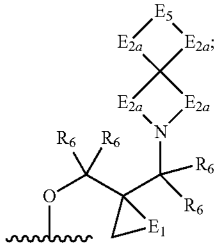

wherein the N-linked cyclic amine is a N-linked:

i. azetidine substituted with $R_{4a}$ and $R_{4b}$;

ii. pyrrolidine, piperidine, piperazine, morpholine, diazepane, imidazole or pyrazole; each of which is optionally bridged by a $C_{1-3}$ alkylene, and each of which is optionally substituted with one or more halogen; hydroxyl; —$NR_{6a}R_{6a}$; (1-methylpiperidin-4-yl)oxy; $C_{1-3}$ alkoxy optionally substituted with —$NR_{6a}R_{6a}$; $C_{1-3}$ alkyl optionally substituted with one or more halogen, —$NR_{6a}R_{6a}$ or hydroxyl; an imidazole optionally substituted with a methyl; a monocyclic ring selected from azetidine, piperidine, piperazine, morpholine, oxazepane, or diazepane; a bicycle selected from hexahydro-1H-furo[3,4-c]pyrrole, octahydropyrrolo[3,4-c]pyrrole, or octahydropyrrolo[1,2-a]pyrazine; or a spirocycle selected from 4,7-diazaspiro[2.5]octane, 2-oxa-7-azaspiro[3.5]nonane, 2,6-diazaspiro[3.4]octane, or 2-azaspiro[3.3]heptane; wherein the monocyclic ring is optionally bridged by a $C_{1-3}$ alkylene, and can optionally be substituted with one or more halogen, hydroxyl, —CN, $C_{1-3}$ alkoxy, —$NR_{10}R_{10}$, cyclopropyl, oxetane, —CO—$C_{1-3}$ alkyl, or a $C_{1-3}$ alkyl optionally substituted with hydroxyl, $C_{1-3}$ alkoxy, —$NR_{10}R_{10}$, halogen, or —$CF_3$; and wherein the bicyclo or spirocyclo is each optionally substituted with a methyl or a halogen; or iii. 2,6-diazabicyclo[3.2.0]heptane, 3,6-diazabicyclo[3.2.0]heptane, 3,6-diazabicyclo[3.2.1]octane, 2,6-diazabicyclo[3.2.1]octane, 3-azabicyclo[3.1.0]hexane, 3-azabicyclo[3.2.0]heptane, 2-azabicyclo[3.2.0]heptane, octahydro-1H-pyrrolo[3,4-b]pyridine, octahydro-1H-pyrrolo[3,2-b]pyridine, octahydro-6H-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, hexahydro-1H-furo[3,4-b]pyrrole, octahydro-1H-pyrrolo[3,2-b]pyridine, (3as,6as)-tetrahydro-1H,4H-3a,6a-(methanooxymethano)pyrrolo[3,4-c]pyrrole, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, 5-azaspiro[2.4]heptane, 2-oxa-6-azaspiro[3.4]octane, 2,7-diazaspiro[4.4]nonane, 2-oxa-6-azaspiro[3.4]octane or 1-oxa-7-azaspiro[4.4]nonane; each of which is optionally substituted with one or more halogen, —$NR_{6a}R_{6a}$ or a $C_{1-3}$ alkyl optionally substituted with —$NR_{6a}R_{6a}$ or hydroxyl;

$R_{4a}$ is $NR_{4c}R_{4d}$, cyclopropyl, azetidine, pyrrolidine, piperidine, piperazine, morpholine or imidazole, wherein the cyclopropyl, azetidine, pyrrolidine, piperidine, piperazine, or morpholine is optionally substituted with halogen, hydroxyl, $C_{1-3}$ alkoxy or —$NR_{6a}R_{6a}$;

$R_{4b}$ is H, hydroxyl, or $C_{1-3}$ alkyl;

$R_{4c}$ is independently cyclopropyl, or oxetane; $R_{4d}$ is independently $C_{1-3}$ alkyl;

$R_5$ is trideuteromethyl, oxetane, or a $C_{1-4}$ alkyl optionally substituted with one or more halogen, trifluoromethyl, hydroxyl, methoxy, trifluoromethoxy, difluoromethoxy, trideuteromethoxy, oxetane, cyclopropyl, imidazole, pyrazole, —CO—$NR_{6a}R_{6a}$, —O—$(CH_2)_2$—$OR_{6a}$, or —O—CO—$C_{1-3}$ alkyl, wherein the cyclopropyl is optionally substituted with a hydroxyl, or hydroxymethyl, and the imidazole, or pyrazole are each optionally substituted with a hydroxyl, or a $C_{1-3}$ alkyl substituted with one or more hydroxyl;

$R_{5a}$ is $C_{1-3}$ alkylene;

each $R_6$ is independently H or deuterium;

each $R_{6a}$ is independently H, trideuteromethyl, a $C_{3-5}$ cycloalkyl, a N-methyl pyrrolidine, tetrahydrofuran, tetrahydropyran, bicyclo[1.1.1]pentan-1-yl, bicyclo[1.1.1]pentan-1-ol, or a $C_{1-3}$ alkyl optionally substituted with one or more deuterium, hydroxyl, methyl, methoxy, halogen, cyclopropyl, oxetane, tetrahydrofuran, tetrahydropyran, —CO—NHMe, or —CO—$NH_2$, wherein the $C_{3-5}$ cycloalkyl is optionally substituted with one or more hydroxyl or methyl;

$E_1$ is —O—$C_{1-3}$ alkylene, or $C_{1-3}$ alkylene optionally substituted with one or more halogens;

$E_2$, and $E_4$ are each independently $C_{1-3}$ alkylene optionally substituted with one or more hydroxyl, $C_{1-3}$ alkoxy or halogen, and wherein $E_2$ and $E_4$ can optionally be bridged by a bond or a $C_{1-3}$ alkylene; and $E_3$ is —O—, —$CR_7R_7$—, —$NR_9$—, or —CO—$NR_{6a}$—; or the ring

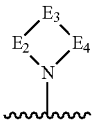

is hexahydro-1H-furo[3,4-c]pyrrole;

Each $E_{2a}$ is independently a $C_{1-3}$ alkylene optionally substituted with one or more hydroxyls;

$E_5$ is —O—, —$CR_7R_7$—, or —$NR_9$—;

Each $R_7$ is independently H, halogen, CN, hydroxyl, $C_{1-3}$ alkoxy, or $C_{1-3}$ alkyl optionally substituted with one or more halogens or hydroxyls;

each $R_8$ is independently a $C_{1-3}$ alkyl;

$R_9$ is each independently H, optionally substituted $C_{1-3}$ alkyl or —CO—$C_{1-3}$ alkyl; wherein the optionally substituted $C_{1-3}$ alkyl is optionally substituted with one or more halogens; and $R_{10}$ is H or $C_{1-3}$ alkyl optionally substituted with one or more deuterium; or a pharmaceutically acceptable salt thereof.

Also provided herein are methods of using the compounds of Formula I, pharmaceutically acceptable salts thereof, and pharmaceutical compositions thereof, to treat cancer, in particular for the treatment of lung cancer, pancreatic cancer, cervical cancer, esophageal cancer, endometrial cancer, ovarian cancer, cholangiocarcinoma, and colorectal cancer. The methods include administering a therapeutically effective amount of a compound of Formula I, or a pharmaceutically acceptable salt thereof, to a patient in need thereof.

Further provided herein, are compounds of Formula I, and pharmaceutically acceptable salts thereof, for use in therapy. Additionally provided herein, are the compounds of Formula I, and pharmaceutically acceptable salts thereof, for use in the treatment of cancer, in particular for the treatment of lung cancer, pancreatic cancer, cervical cancer, esophageal cancer, endometrial cancer, ovarian cancer, cholangiocarcinoma, and colorectal cancer. Also additionally provided herein is the use of compounds of Formula I, or pharmaceutically acceptable salts thereof, in the manufacture of a medicament for treating cancer, in particular for the treatment of lung cancer, pancreatic cancer, cervical cancer, esophageal cancer, endometrial cancer, ovarian cancer, cholangiocarcinoma, and colorectal cancer.

DETAILED DESCRIPTION

Novel inhibitors of the KRas gain of function mutation G12C, G12D, and/or G12V are described herein. These new compounds could address the needs noted above for inhibitors of KRas GTP activity in gain of function mutants in the treatment of cancers such as lung cancer, colorectal cancer, pancreatic cancer, bladder cancer, cervical cancer, endometrial cancer, ovarian cancer, cholangiocarcinoma or esophageal cancer. Some of these new KRas inhibitor compounds are selective to KRas G12D mutants over wild-type KRas (and likely other mutant types such as G12C or G12V). Additionally, some of these new KRas inhibitor compounds are non-selective and inhibit both wild-type KRas and KRas G12D mutants (and/or possibly other mutant types such as G12C or G12V). Also, some of these new KRas inhibitor compounds are non-selective and inhibit both wild-type KRas and Kras G12C, G12D, and/or G12V mutants.

The present invention provides a compound of Formula I:

Formula I

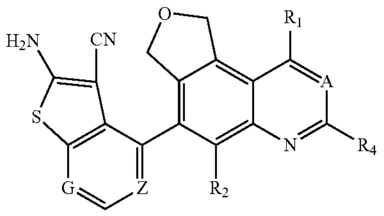

wherein A, Z, G, $R_1$, $R_2$, and $R_4$ are as defined above, or a pharmaceutically acceptable salt thereof.

As used herein, the term halogen means fluoro (F), chloro (Cl), bromo (Br), or iodo (I). As used herein, the term alkyl means saturated linear or branched-chain monovalent hydrocarbon radicals of one to a specified number of carbon atoms, e.g., "$C_{1-4}$ alkyl" or "$C_{1-3}$ alkyl." Examples of alkyls include, but are not limited to, methyl, ethyl, propyl, 1-propyl, isopropyl, butyl, and iso-butyl. As used herein, the term alkylene means saturated linear or branched-chain bivalent hydrocarbon radicals of one to a specified number of carbon atoms, e.g., "$C_{1-3}$ alkylene." Examples of alkylenes include, but are not limited to, methylene, ethylene, propylene, 1-propylene, and isopropylene. Examples of $C_{1-3}$ alkoxy groups include, but are not limited to, methoxy, ethoxy, propoxy, 1-propoxy, and isopropoxy.

In an embodiment of a compound of Formula I or a pharmaceutically acceptable salt thereof, $R_4$ is a N-linked cyclic amine or a group of the formula

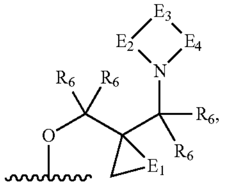

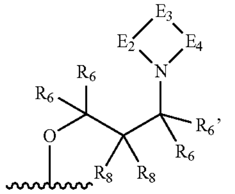

or

-continued

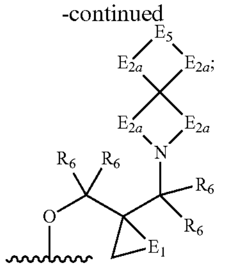

wherein the N-linked cyclic amine is a N-linked:

i. azetidine substituted with $R_{4a}$ and $R_{4b}$;

ii. pyrrolidine, piperidine, piperazine, morpholine, imidazole or pyrazole; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, piperazine, morpholine, a $C_{1-3}$ alkyl, or an imidazole optionally substituted with a methyl; wherein the azetidine is optionally substituted with hydroxyl or $C_{1-3}$ alkoxy; the piperazine is optionally substituted with a methyl, and the $C_{1-3}$ alkyl is optionally substituted with one or more halogen, —$NR_{6a}R_{6a}$ or hydroxyl; or iii. 2,6-diazabicyclo[3.2.0]heptane, 3,6-diazabicyclo[3.2.0]heptane, 3,6-diazabicyclo[3.2.1]octane, 2,6-diazabicyclo[3.2.1]octane, 3-azabicyclo[3.1.0]hexane, 3-azabicyclo[3.2.0]heptane, 2-azabicyclo[3.2.0]heptane, octahydro-1H-pyrrolo[3,4-b]pyridine, octahydro-1H-pyrrolo[3,2-b]pyridine, octahydro-6H-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, 5-azaspiro[2.4]heptane, or 2-oxa-6-azaspiro[3.4]octane; each of which is optionally substituted with one or more halogen, —$NR_{6a}R_{6a}$ or a $C_{1-3}$ alkyl optionally substituted with —$NR_{6a}R_{6a}$;

$R_{4a}$ is —$NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or —$NR_{6a}R_{6a}$; and each $R_{6a}$ is independently H, trideuteromethyl, a $C_{3-5}$ cycloalkyl, tetrahydrofuran, tetrahydropyran, bicyclo[1.1.1]pentan-1-yl, or a $C_{1-3}$ alkyl optionally substituted with one or more hydroxyl, methyl, methoxy, halogen, cyclopropyl, oxetane, tetrahydrofuran, tetrahydropyran, —CO—NHMe, or —CO—$NH_2$, wherein the $C_{3-5}$ cycloalkyl is optionally substituted with one or more hydroxyl or methyl.

In an embodiment of a compound of Formula I or a pharmaceutically acceptable salt thereof, $R_4$ is a N-linked cyclic amine or a group of the formula

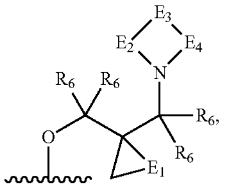, 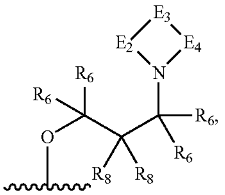 or

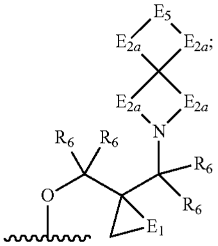

wherein the N-linked cyclic amine is a N-linked:

i. azetidine substituted with $R_{4a}$ and $R_{4b}$;

ii. pyrrolidine, piperidine, piperazine, morpholine, imidazole or pyrazole; each of which is optionally bridged by a $C_{1-3}$ alkylene, and each of which is optionally substituted with one or more halogen, hydroxyl, $C_{1-3}$ alkoxy, $—NR_{6a}R_{6a}$, azetidine, a $C_{1-3}$ alkyl, or an imidazole optionally substituted with a methyl; wherein the azetidine is optionally substituted with hydroxyl or $C_{1-3}$ alkoxy; and the $C_{1-3}$ alkyl is optionally substituted with halogen-$NR_{6a}R_{6a}$ or hydroxyl; or iii. 2,6-diazabicyclo[3.2.0]heptane, 3,6-diazabicyclo [3.2.0]heptane, 3-azabicyclo[3.1.0]hexane, 3-azabicyclo[3.2.0]heptane, octahydro-1H-pyrrolo[3,4-b]pyridine, octahydro-6-pyrrolo[3,4-b]pyrazine, octahydropyrrolo[1,2-a]pyrazine, octahydropyrrolo [3,2 -b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4] nonane, 1,6-diazaspiro[3.3]heptane, 1,6-diazaspiro [3.4]octane, 2,5-diazaspiro[3.4]octane, 2,5-diazaspiro [3.5]nonane, 2,6-diazaspiro[3.3]heptane, 2,6-diazaspiro[3.4]octane, 2-azaspiro[3.3]heptane, 4-azaspiro[2.4]heptane, or 5-azaspiro[2.4]heptane; each of which is optionally substituted with one or more halogen, $—NR_{6a}R_{6a}$ or a $C_{1-3}$ alkyl optionally substituted with $—NR_{6a}R_{6a}$;

$R_{4a}$ is $NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or $—NR_{6a}R_{6a}$;

and each $R_{6a}$ is independently H, trideuteromethyl, a $C_{3-5}$ cycloalkyl or a $C_{1-3}$ alkyl optionally substituted with hydroxyl.

In an embodiment of a compound of Formula I or a pharmaceutically acceptable salt thereof, $R_{3b}$, and $R_{3c}$ are each independently H or halogen, and $R_4$ is a N-linked cyclic amine or a group of the formula

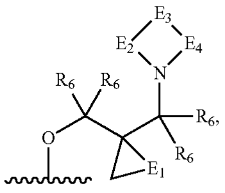, 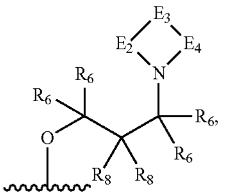 or

-continued

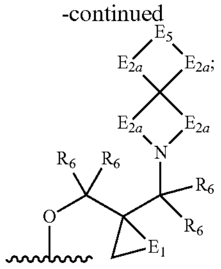

wherein the N-linked cyclic amine is a N-linked:

i. azetidine substituted with $R_{4a}$ and $R_{4b}$;

ii. pyrrolidine, piperidine, piperazine, or morpholine; each of which is optionally bridged by a $C_{1-3}$ alkylene, and each of which is optionally substituted with one or more halogen, hydroxyl, $—NR_{6a}R_{6a}$, imidazole or a $C_{1-3}$ alkyl; wherein the imidazole is optionally substituted with a methyl; and the $C_{1-3}$ alkyl is optionally substituted with $—NR_{6a}R_{6a}$ or hydroxyl; or iii. octahydropyrrolo[1,2-a]pyrazine, octahydropyrrolo[3,4-c]pyrrole, 1,6-diazaspiro[3.3]heptane, or 1,6-diazaspiro[3.4]octane; each of which is optionally substituted with one or more halogen, or a $C_{1-3}$ alkyl;

$R_{4a}$ is $NR_{4c}R_{4d}$, cyclopropyl, azetidine, pyrrolidine, morpholine, wherein the cyclopropyl, azetidine, pyrrolidine or morpholine is optionally substituted with halogen, or $—NR_{6a}R_{6a}$;

$R_{4b}$ is H, or $C_{1-3}$ alkyl;

$R_{4c}$ is independently cyclopropyl, or oxetane;

$R_{4d}$ is independently $C_{1-3}$ alkyl;

$R_5$ is trideuteromethyl, oxetane, or a $C_{1-4}$ alkyl optionally substituted with one or more halogen, trifluoromethyl, hydroxyl, methoxy, trifluoromethoxy, difluoromethoxy, trideuteromethoxy, oxetane, cyclopropyl, imidazole, pyrazole, $—CO—NR_{6a}R_{6a}$, $—O—(CH_2)_2—OR_{6a}$, or $—O—CO—C_{1-3}$ alkyl, wherein the cyclopropyl is optionally substituted with a hydroxyl, or hydroxymethyl, and the imidazole, or pyrazole are each optionally substituted with a hydroxyl, or a $C_{1-3}$ alkyl substituted with one or more hydroxyl;

$R_{5a}$ is $C_{1-3}$ alkylene;

each $R_6$ is independently H or deuterium;

each $R_{6a}$ is independently H or $C_{1-3}$ alkyl;

$E_1$ is $—O—C_{1-3}$ alkylene, or $C_{1-3}$ alkylene optionally substituted with one or more halogens;

$E_2$, and $E_4$ are each independently $C_{1-3}$ alkylene optionally substituted with one or more hydroxyl or halogen, and wherein $E_2$ and $E_4$ can optionally be bridged by a bond or a $C_{1-3}$ alkylene; each $E_{2a}$ is independently a $C_{1-3}$ alkylene optionally substituted with one or more hydroxyls;

$E_3$ is $—O—$, $—CR_7R_7—$, $—NR_9—$, or $—CO—NR_{6a}—$;

$E_5$ is $—O—$, $—CR_7R_7—$, or $—NR_9—$;

each $R_7$ is independently H, halogen, CN, hydroxyl, $C_{1-3}$ alkoxy, or $C_{1-3}$ alkyl optionally substituted with one or more halogens or hydroxyls;

each $R_8$ is independently a $C_{1-3}$ alkyl; and $R_9$ is each independently H, optionally substituted $C_{1-3}$ alkyl or $—CO—C_{1-3}$ alkyl; wherein the optionally substituted $C_{1-3}$ alkyl is optionally substituted with one or more halogens.

In an embodiment of a compound of Formula I or a pharmaceutically acceptable salt thereof, $R_{3b}$, and $R_{3c}$ are each independently H or halogen, and $R_4$ is a group of the formula

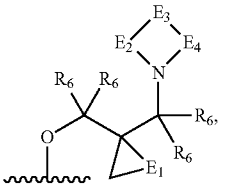

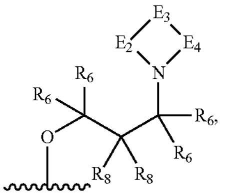 or

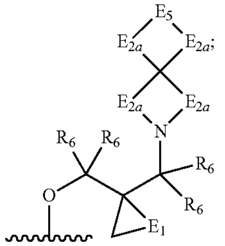

$E_1$ is $C_{1-3}$ alkylene optionally substituted with one or more halogens;

$E_2$, and $E_4$ are each independently $C_{1-3}$ alkylene optionally substituted with one or more hydroxyls, and wherein $E_2$ and $E_4$ can optionally be bridged by a bond or a $C_{1-3}$ alkylene;

$E_3$ is —O—, —$CR_7R_7$—, —$NR_9$—, or —CO—$NR_{6a}$—;

each $R_{6a}$ is independently H or $C_{1-3}$ alkyl;

each $R_7$ is independently H, halogen, hydroxyl, $C_{1-3}$ alkoxy, or $C_{1-3}$ alkyl optionally substituted with one or more halogens or hydroxyls; and $R_9$ is each independently H, $C_{1-3}$ alkyl or —CO—$C_{1-3}$ alkyl.

In an embodiment of a compound of Formula I or a pharmaceutically acceptable salt thereof, G is —N—.

In an embodiment of a compound of Formula I or a pharmaceutically acceptable salt thereof, G is —C(R3b)-.

In an embodiment of a compound of Formula I or a pharmaceutically acceptable salt thereof, G is —C(R3b)-, wherein R3b is H or halogen.

In an embodiment of a compound of Formula I or a pharmaceutically acceptable salt thereof, G is —C(F)—.

In an embodiment of a compound of Formula I or a pharmaceutically acceptable salt thereof, G is —C(Cl)—.

In an embodiment of a compound of Formula I or a pharmaceutically acceptable salt thereof, G is —C(H)—.

In an embodiment of a compound of Formula I or a pharmaceutically acceptable salt thereof, G is —C(CH3)-.

In an embodiment of a compound of Formula I or a pharmaceutically acceptable salt thereof, Z is —N—.

In an embodiment of a compound of Formula I or a pharmaceutically acceptable salt thereof, Z is —C(R3c)-.

In an embodiment of a compound of Formula I or a pharmaceutically acceptable salt thereof, Z is —C(R3c)-, wherein R3c is H or halogen.

In an embodiment of a compound of Formula I or a pharmaceutically acceptable salt thereof, Z is —C(H)—.

In an embodiment of a compound of Formula I or a pharmaceutically acceptable salt thereof, Z is —C(F)—.

In an embodiment of a compound of Formula I or a pharmaceutically acceptable salt thereof, G is —N—, and Z is —C(R3c)-.

In an embodiment of a compound of Formula I or a pharmaceutically acceptable salt thereof, G is —N—, and Z is —C(H)—.

In an embodiment of a compound of Formula I or a pharmaceutically acceptable salt thereof, G is —N—, and Z is —C(F)—.

In an embodiment of a compound of Formula I or a pharmaceutically acceptable salt thereof, G is —C(R3b)-, and Z is —N—.

In an embodiment of a compound of Formula I or a pharmaceutically acceptable salt thereof, G is —C(R3b)-, wherein R3b is H or halogen, and Z is —N—.

In an embodiment of a compound of Formula I or a pharmaceutically acceptable salt thereof, G is —C(F)—, and Z is —N—.

In an embodiment of a compound of Formula I or a pharmaceutically acceptable salt thereof, G is —C(Cl)—, and Z is —N—.

In an embodiment of a compound of Formula I or a pharmaceutically acceptable salt thereof, G is —C(H)—, and Z is —N—.

In an embodiment of a compound of Formula I or a pharmaceutically acceptable salt thereof, G is —C(CH3)-, and Z is —N—.

In an embodiment of a compound of Formula I or a pharmaceutically acceptable salt thereof, R3b, and R3c are each independently H or halogen.

In an embodiment of a compound of Formula I or a pharmaceutically acceptable salt thereof, A is —N—.

In an embodiment of a compound of Formula I or a pharmaceutically acceptable salt thereof, A is —C(H)—.

In an embodiment of a compound of Formula I or a pharmaceutically acceptable salt thereof, R2 is F or Cl.

In an embodiment of a compound of Formula I, or a pharmaceutically acceptable salt thereof, A is —C(H)—, Z is —C(F)—, G is —N—, and R2 is F.

In an embodiment of a compound of Formula I, or a pharmaceutically acceptable salt thereof, A is —N—, Z is —C(F)—, G is —N—, and R2 is F.

In an embodiment of a compound of Formula I, or a pharmaceutically acceptable salt thereof, A is —C(H)—, Z is —C(H)—, G is —N—, and R2 is F.

In an embodiment of a compound of Formula I, or a pharmaceutically acceptable salt thereof, A is —N—, Z is —C(H)—, G is —N—, and R2 is F.

In an embodiment of a compound of Formula I, or a pharmaceutically acceptable salt thereof, A is —C(H)—, Z is —N—, G is —N—, and R2 is F.

In an embodiment of a compound of Formula I, or a pharmaceutically acceptable salt thereof, A is —N—, Z is —N—, G is —N—, and R2 is F.

In an embodiment of a compound of Formula I, or a pharmaceutically acceptable salt thereof, A is —C(H)—, Z is —C(F)—, G is —C(H)—, and R2 is F.

In an embodiment of a compound of Formula I, or a pharmaceutically acceptable salt thereof, A is —N—, Z is —C(F)—, G is —C(H)—, and R2 is F.

In an embodiment of a compound of Formula I, or a pharmaceutically acceptable salt thereof, A is —C(H)—, Z is —C(H)—, G is —C(H)—, and R2 is F.

In an embodiment of a compound of Formula I, or a pharmaceutically acceptable salt thereof, A is —N—, Z is —C(H)—, G is —C(H)—, and R2 is F.

In an embodiment of a compound of Formula I, or a pharmaceutically acceptable salt thereof, A is —C(H)—, Z is —N—, G is —C(H)—, and R2 is F.

In an embodiment of a compound of Formula I, or a pharmaceutically acceptable salt thereof, A is —N—, Z is —N—, G is —C(H)—, and R2 is F.

In an embodiment of a compound of Formula I, or a pharmaceutically acceptable salt thereof, A is —C(H)—, Z is —C(F)—, G is —C(F)—, and R2 is F.

In an embodiment of a compound of Formula I, or a pharmaceutically acceptable salt thereof, A is —N—, Z is —C(F)—, G is —C(F)—, and R2 is F.

In an embodiment of a compound of Formula I, or a pharmaceutically acceptable salt thereof, A is —C(H)—, Z is —C(H)—, G is —C(F)—, and R2 is F.

In an embodiment of a compound of Formula I, or a pharmaceutically acceptable salt thereof, A is —N—, Z is —C(H)—, G is —C(F)—, and R2 is F.

In an embodiment of a compound of Formula I, or a pharmaceutically acceptable salt thereof, A is —C(H)—, Z is —N—, G is —C(F)—, and R2 is F.

In an embodiment of a compound of Formula I, or a pharmaceutically acceptable salt thereof, A is —N—, Z is —N—, G is —C(F)—, and R2 is F.

In an embodiment of a compound of Formula I, or a pharmaceutically acceptable salt thereof, A is —C(H)—, Z is —C(F)—, G is —N—, and R2 is Cl.

In an embodiment of a compound of Formula I, or a pharmaceutically acceptable salt thereof, A is —N—, Z is —C(F)—, G is —N—, and R2 is Cl.

In an embodiment of a compound of Formula I, or a pharmaceutically acceptable salt thereof, A is —C(H)—, Z is —C(H)—, G is —N—, and R2 is Cl.

In an embodiment of a compound of Formula I, or a pharmaceutically acceptable salt thereof, A is —N—, Z is —C(H)—, G is —N—, and R2 is Cl.

In an embodiment of a compound of Formula I, or a pharmaceutically acceptable salt thereof, A is —C(H)—, Z is —N—, G is —N—, and R2 is Cl.

In an embodiment of a compound of Formula I, or a pharmaceutically acceptable salt thereof, A is —N—, Z is —N—, G is —N—, and R2 is Cl.

In an embodiment of a compound of Formula I, or a pharmaceutically acceptable salt thereof, A is —C(H)—, Z is —C(F)—, G is —C(H)—, and R2 is Cl.

In an embodiment of a compound of Formula I, or a pharmaceutically acceptable salt thereof, A is —N—, Z is —C(F)—, G is —C(H)—, and R2 is Cl.

In an embodiment of a compound of Formula I, or a pharmaceutically acceptable salt thereof, A is —C(H)—, Z is —C(H)—, G is —C(H)—, and R2 is Cl.

In an embodiment of a compound of Formula I, or a pharmaceutically acceptable salt thereof, A is —N—, Z is —C(H)—, G is —C(H)—, and R2 is Cl.

In an embodiment of a compound of Formula I, or a pharmaceutically acceptable salt thereof, A is —C(H)—, Z is —N—, G is —C(H)—, and R2 is Cl.

In an embodiment of a compound of Formula I, or a pharmaceutically acceptable salt thereof, A is —N—, Z is —N—, G is —C(H)—, and R2 is Cl.

In an embodiment of a compound of Formula I, or a pharmaceutically acceptable salt thereof, A is —C(H)—, Z is —C(F)—, G is —C(F)—, and R2 is Cl.

In an embodiment of a compound of Formula I, or a pharmaceutically acceptable salt thereof, A is —N—, Z is —C(F)—, G is —C(F)—, and R2 is Cl.

In an embodiment of a compound of Formula I, or a pharmaceutically acceptable salt thereof, A is —C(H)—, Z is —C(H)—, G is —C(F)—, and R2 is Cl.

In an embodiment of a compound of Formula I, or a pharmaceutically acceptable salt thereof, A is —N—, Z is —C(H)—, G is —C(F)—, and R2 is Cl.

In an embodiment of a compound of Formula I, or a pharmaceutically acceptable salt thereof, A is —C(H)—, Z is —N—, G is —C(F)—, and R2 is Cl.

In an embodiment of a compound of Formula I, or a pharmaceutically acceptable salt thereof, A is —N—, Z is —N—, G is —C(F)—, and R2 is Cl.

In an embodiment of a compound of Formula I or a pharmaceutically acceptable salt thereof, R1 is H.

In an embodiment of a compound of Formula I or a pharmaceutically acceptable salt thereof, A is —C(H)—, Z is —C(F)—, G is —N—, R2 is F, R1 is H, and R4 is a N-linked cyclic amine.

In an embodiment of a compound of Formula I or a pharmaceutically acceptable salt thereof, A is —N—, Z is —C(F)—, G is —N—, R2 is F, R1 is H, and R4 is a N-linked cyclic amine.

In an embodiment of a compound of Formula I or a pharmaceutically acceptable salt thereof, A is —C(H)—, Z is —C(H)—, G is —N—, R2 is F, R1 is H, and R4 is a N-linked cyclic amine.

In an embodiment of a compound of Formula I or a pharmaceutically acceptable salt thereof, A is —N—, Z is —C(H)—, G is —N—, R2 is F, R1 is H, and R4 is a N-linked cyclic amine.

In an embodiment of a compound of Formula I or a pharmaceutically acceptable salt thereof, A is —C(H)—, Z is —N—, G is —N—, R2 is F, R1 is H, and R4 is a N-linked cyclic amine.

In an embodiment of a compound of Formula I or a pharmaceutically acceptable salt thereof, A is —N—, Z is —N—, G is —N—, R2 is F, R1 is H, and R4 is a N-linked cyclic amine.

In an embodiment of a compound of Formula I or a pharmaceutically acceptable salt thereof, A is —C(H)—, Z is —C(F)—, G is —C(H)—, R2 is F, R1 is H, and R4 is a N-linked cyclic amine.

In an embodiment of a compound of Formula I or a pharmaceutically acceptable salt thereof, A is —N—, Z is —C(F)—, G is —C(H)—, R2 is F, R1 is H, and R4 is a N-linked cyclic amine.

In an embodiment of a compound of Formula I or a pharmaceutically acceptable salt thereof, A is —C(H)—, Z is —C(H)—, G is —C(H)—, R2 is F, R1 is H, and R4 is a N-linked cyclic amine.

In an embodiment of a compound of Formula I or a pharmaceutically acceptable salt thereof, A is —N—, Z is —C(H)—, G is —C(H)—, R2 is F, R1 is H, and R4 is a N-linked cyclic amine.

In an embodiment of a compound of Formula I or a pharmaceutically acceptable salt thereof, A is —C(H)—, Z is —N—, G is —C(H)—, R2 is F, R1 is H, and R4 is a N-linked cyclic amine.

In an embodiment of a compound of Formula I or a pharmaceutically acceptable salt thereof, A is —N—, Z is —N—, G is —C(H)—, R2 is F, R1 is H, and R4 is a N-linked cyclic amine.

In an embodiment of a compound of Formula I or a pharmaceutically acceptable salt thereof, A is —C(H)—, Z is —C(F)—, G is —C(F)—, R2 is F, R1 is H, and R4 is a N-linked cyclic amine.

In an embodiment of a compound of Formula I or a pharmaceutically acceptable salt thereof, A is —N—, Z is —C(F)—, G is —C(F)—, R2 is F, R1 is H, and R4 is a N-linked cyclic amine.

In an embodiment of a compound of Formula I or a pharmaceutically acceptable salt thereof, A is —C(H)—, Z is —C(H)—, G is —C(F)—, R2 is F, R1 is H, and R4 is a N-linked cyclic amine.

In an embodiment of a compound of Formula I or a pharmaceutically acceptable salt thereof, A is —N—, Z is —C(H)—, G is —C(F)—, R2 is F, R1 is H, and R4 is a N-linked cyclic amine.

In an embodiment of a compound of Formula I or a pharmaceutically acceptable salt thereof, A is —C(H)—, Z is —N—, G is —C(F)—, R2 is F, R1 is H, and R4 is a N-linked cyclic amine.

In an embodiment of a compound of Formula I or a pharmaceutically acceptable salt thereof, A is —N—, Z is —N—, G is —C(F)—, R2 is F, R1 is H, and R4 is a N-linked cyclic amine.

In an embodiment of a compound of Formula I or a pharmaceutically acceptable salt thereof, A is —C(H)—, Z is —C(F)—, G is —N—, R2 is Cl, R1 is H, and R4 is a N-linked cyclic amine.

In an embodiment of a compound of Formula I or a pharmaceutically acceptable salt thereof, A is —N—, Z is —C(F)—, G is —N—, R2 is Cl, R1 is H, and R4 is a N-linked cyclic amine.

In an embodiment of a compound of Formula I or a pharmaceutically acceptable salt thereof, A is —C(H)—, Z is —C(H)—, G is —N—, R2 is Cl, R1 is H, and R4 is a N-linked cyclic amine.

In an embodiment of a compound of Formula I or a pharmaceutically acceptable salt thereof, A is —N—, Z is —C(H)—, G is —N—, R2 is Cl, R1 is H, and R4 is a N-linked cyclic amine.

In an embodiment of a compound of Formula I or a pharmaceutically acceptable salt thereof, A is —C(H)—, Z is —N—, G is —N—, R2 is Cl, R1 is H, and R4 is a N-linked cyclic amine.

In an embodiment of a compound of Formula I or a pharmaceutically acceptable salt thereof, A is —N—, Z is —N—, G is —N—, R2 is Cl, R1 is H, and R4 is a N-linked cyclic amine.

In an embodiment of a compound of Formula I or a pharmaceutically acceptable salt thereof, A is —C(H)—, Z is —C(F)—, G is —C(H)—, R2 is Cl, R1 is H, and R4 is a N-linked cyclic amine.

In an embodiment of a compound of Formula I or a pharmaceutically acceptable salt thereof, A is —N—, Z is —C(F)—, G is —C(H)—, R2 is Cl, R1 is H, and R4 is a N-linked cyclic amine.

In an embodiment of a compound of Formula I or a pharmaceutically acceptable salt thereof, A is —C(H)—, Z is —C(H)—, G is —C(H)—, R2 is Cl, R1 is H, and R4 is a N-linked cyclic amine.

In an embodiment of a compound of Formula I or a pharmaceutically acceptable salt thereof, A is —N—, Z is —C(H)—, G is —C(H)—, R2 is Cl, R1 is H, and R4 is a N-linked cyclic amine.

In an embodiment of a compound of Formula I or a pharmaceutically acceptable salt thereof, A is —C(H)—, Z is —N—, G is —C(H)—, R2 is Cl, R1 is H, and R4 is a N-linked cyclic amine.

In an embodiment of a compound of Formula I or a pharmaceutically acceptable salt thereof, A is —N—, Z is —N—, G is —C(H)—, R2 is Cl, R1 is H, and R4 is a N-linked cyclic amine.

In an embodiment of a compound of Formula I or a pharmaceutically acceptable salt thereof, A is —C(H)—, Z is —C(F)—, G is —C(F)—, R2 is Cl, R1 is H, and R4 is a N-linked cyclic amine.

In an embodiment of a compound of Formula I or a pharmaceutically acceptable salt thereof, A is —N—, Z is —C(F)—, G is —C(F)—, R2 is Cl, R1 is H, and R4 is a N-linked cyclic amine.

In an embodiment of a compound of Formula I or a pharmaceutically acceptable salt thereof, A is —C(H)—, Z is —C(H)—, G is —C(F)—, R2 is Cl, R1 is H, and R4 is a N-linked cyclic amine.

In an embodiment of a compound of Formula I or a pharmaceutically acceptable salt thereof, A is —N—, Z is —C(H)—, G is —C(F)—, R2 is Cl, R1 is H, and R4 is a N-linked cyclic amine.

In an embodiment of a compound of Formula I or a pharmaceutically acceptable salt thereof, A is —C(H)—, Z is —N—, G is —C(F)—, R2 is Cl, R1 is H, and R4 is a N-linked cyclic amine.

In an embodiment of a compound of Formula I or a pharmaceutically acceptable salt thereof, A is —N—, Z is —N—, G is —C(F)—, R2 is Cl, R1 is H, and R4 is a N-linked cyclic amine.

In an embodiment of a compound of Formula I or a pharmaceutically acceptable salt thereof, $R_1$ is a group of the formula

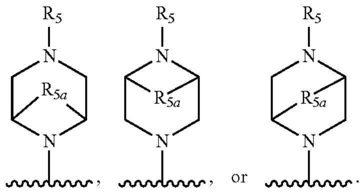

In an embodiment of a compound of Formula I or a pharmaceutically acceptable salt thereof, $R_1$ is a group of the formula

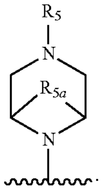

In an embodiment of a compound of Formula I or a pharmaceutically acceptable salt thereof, $R_5$ is a $C_{1-4}$ alkyl optionally substituted with one or more hydroxyl, methoxy or oxetane.

In an embodiment of a compound of Formula I or a pharmaceutically acceptable salt thereof, $R_5$ is a $C_{1-4}$ alkyl optionally substituted with one or more hydroxyl, or methoxy.

In an embodiment of a compound of Formula I or a pharmaceutically acceptable salt thereof, $R_1$ is a group of the formula

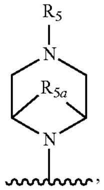

wherein $R_{5a}$ is ethylene.

In an embodiment of a compound of Formula I or a pharmaceutically acceptable salt thereof, $R_1$ is a group of the formula

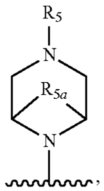

wherein $R_5$ is a $C_{1-4}$ alkyl optionally substituted with one or more hydroxyl, methoxy or oxetane and preferably $R_{5a}$ is ethylene.

In an embodiment of a compound of Formula I or a pharmaceutically acceptable salt thereof, $R_1$ is a group of the formula

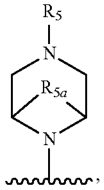

wherein $R_5$ is a $C_{1-4}$ alkyl optionally substituted with one or more hydroxyl, or methoxy and preferably $R_{5a}$ is ethylene.

In an embodiment of a compound of Formula I or a pharmaceutically acceptable salt thereof, $R_1$ is selected from

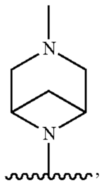 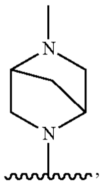 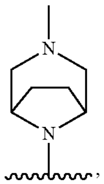 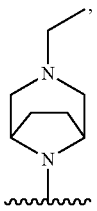 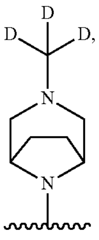

-continued

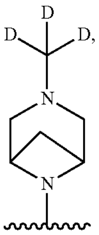 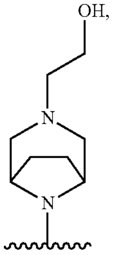 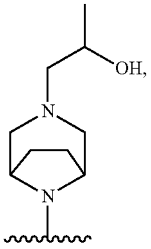 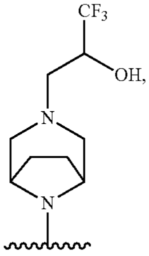

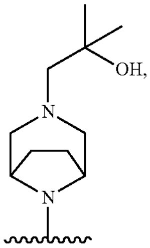 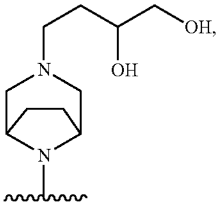 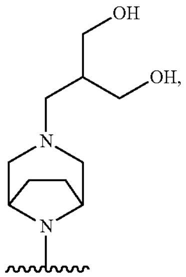

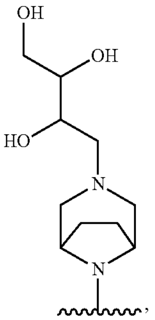 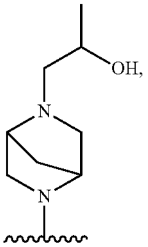 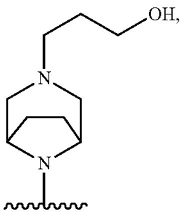

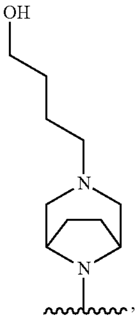

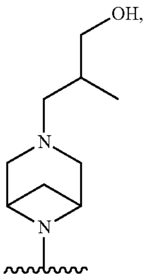 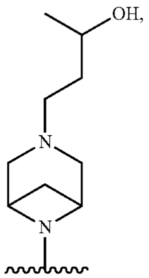

-continued
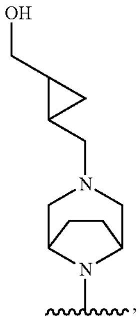
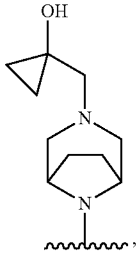
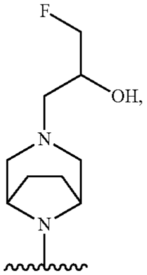
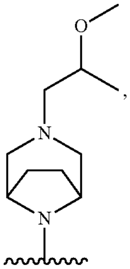
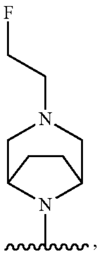
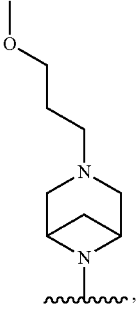
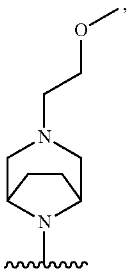
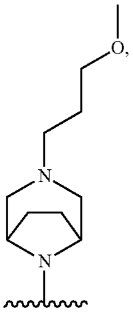
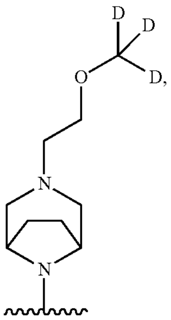
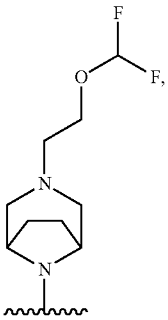
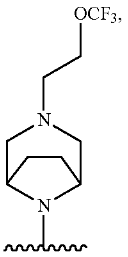
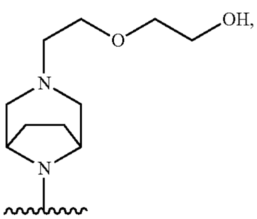
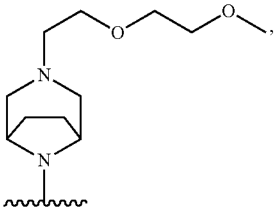
-continued
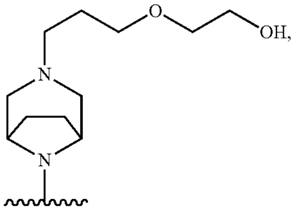
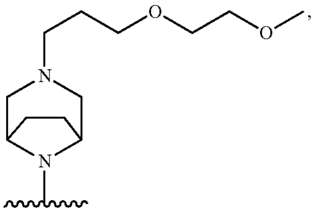
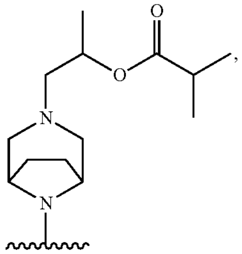
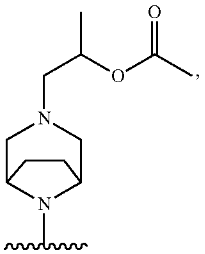
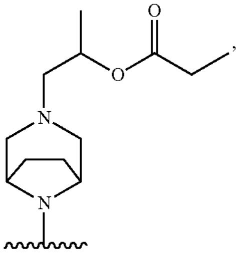
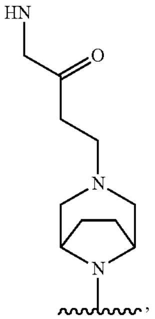
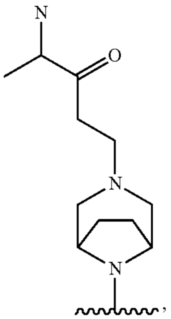
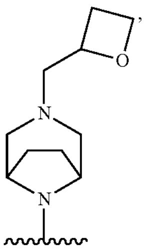

-continued

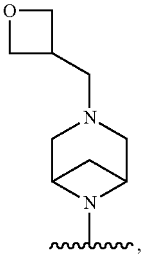
,
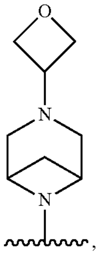
,
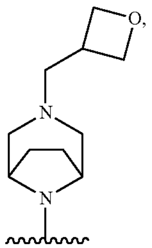

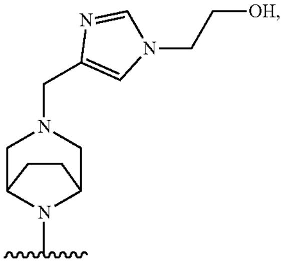
or
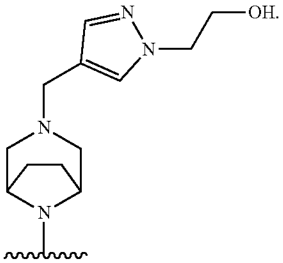

In an embodiment of a compound of Formula I or a pharmaceutically acceptable salt thereof, $R_1$ is selected from

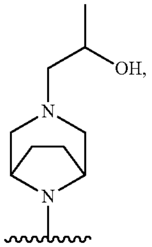

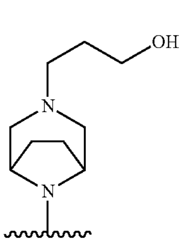
,
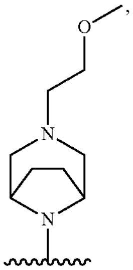

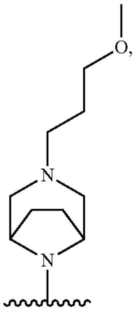
,
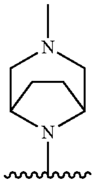

-continued

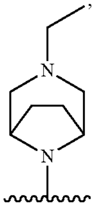
, or
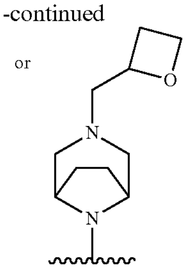
.

In an embodiment of a compound of Formula I or a pharmaceutically acceptable salt thereof, $R_1$ is selected from

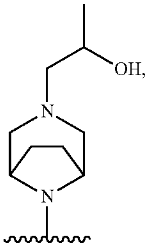

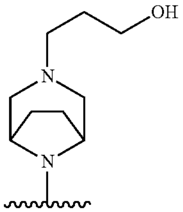
, or
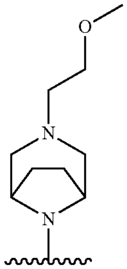
.

In an embodiment of a compound of Formula I or a pharmaceutically acceptable salt thereof, the ring

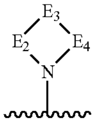

is hexahydro-1H-furo[3,4-c]pyrrole:

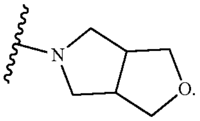 [SMILES: *N1CC2COCC2C1]

In an embodiment of a compound of Formula I or a pharmaceutically acceptable salt thereof, $R_4$ is a N-linked azetidine substituted with $R_{4a}$ and $R_{4b}$.

In an embodiment of a compound of Formula I or a pharmaceutically acceptable salt thereof, $R_4$ is a N-linked pyrrolidine, piperidine, piperazine, or morpholine; each of which is optionally bridged by a $C_{1-3}$ alkylene, and each of which is optionally substituted with one or more halogen, hydroxyl, —$NR_{6a}R_{6a}$, imidazole or a $C_{1-3}$ alkyl; wherein the imidazole is optionally substituted with a methyl; and the $C_{1-3}$ alkyl is optionally substituted with —$NR_{6a}R_{6a}$ or hydroxyl.

In an embodiment of a compound of Formula I or a pharmaceutically acceptable salt thereof, $R_4$ is a N-linked octahydropyrrolo[1,2-a]pyrazine, octahydropyrrolo[3,4-c]pyrrole, 1,6-diazaspiro[3.3]heptane, or 1,6-diazaspiro[3.4]octane; each of which is optionally substituted with one or more halogen, or a $C_{1-3}$ alkyl.

In an embodiment of a compound of Formula I or a pharmaceutically acceptable salt thereof, $R_4$ is a N-linked pyrrolidine, piperidine, piperazine, morpholine, imidazole or pyrazole; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, a $C_{1-3}$ alkyl, or an imidazole optionally substituted with a methyl; the azetidine is optionally substituted with hydroxyl or $C_{1-3}$ alkoxy; and the $C_{1-3}$ alkyl is optionally substituted with —$NR_{6a}R_{6a}$ or hydroxyl.

In an embodiment of a compound of Formula I or a pharmaceutically acceptable salt thereof, $R_4$ is a N-linked 2,6-diazabicyclo[3.2.0]heptane, 3,6-diazabicyclo[3.2.0]heptane, 3 -azabicyclo[3.1.0]hexane, 3-azabicyclo[3.2.0]heptane, octahydro-1H-pyrrolo[3,4-b]pyridine, octahydro-6-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4]nonane, 1,6-diazaspiro[3.3]heptane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, or 5-azaspiro[2.4]heptane; each of which is optionally substituted with one or more halogen, —$NR_{6a}R_{6a}$ or a $C_{1-3}$ alkyl optionally substituted with —$NR_{6a}R_{6a}$.

In an embodiment of a compound of Formula I or a pharmaceutically acceptable salt thereof, $R_4$ is selected from

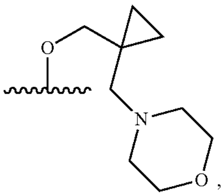,

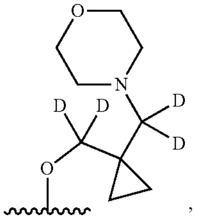,

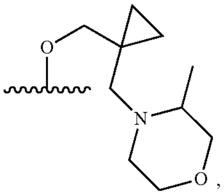,

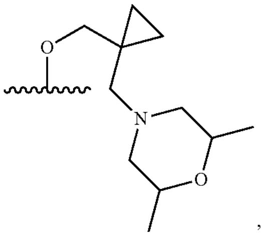,

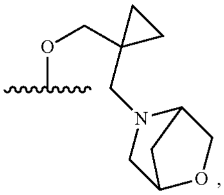,

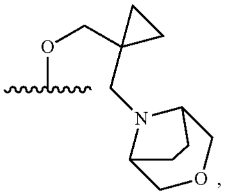,

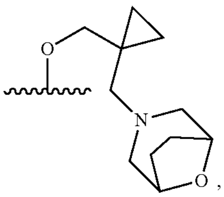,

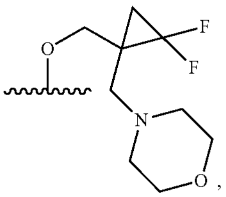,

-continued

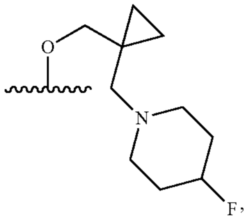,

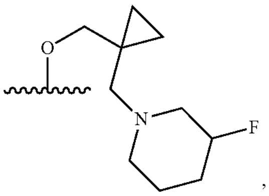,

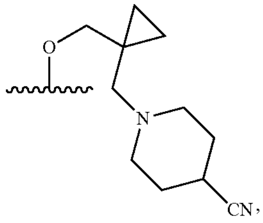,

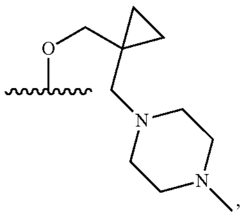,

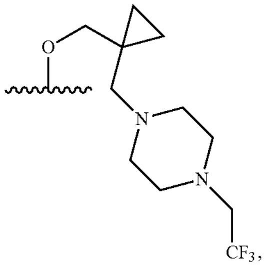,

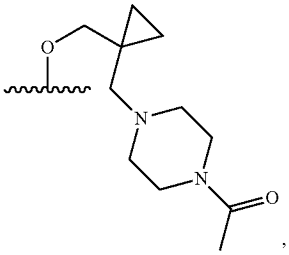,

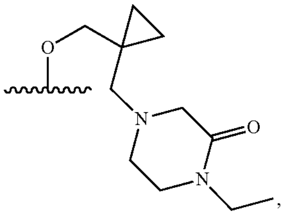,

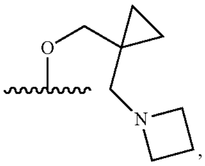,

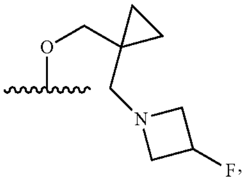,

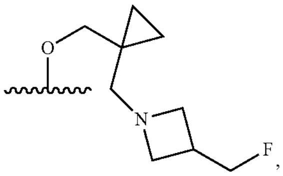,

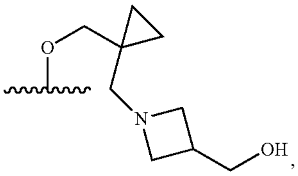,

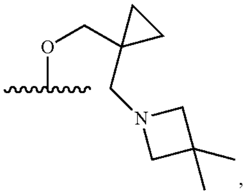,

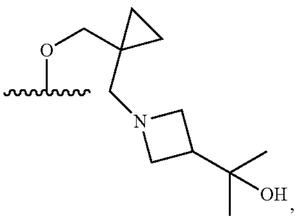,

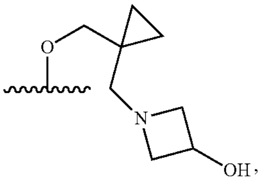,

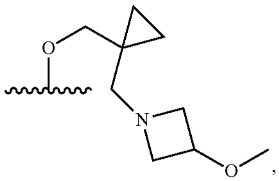,

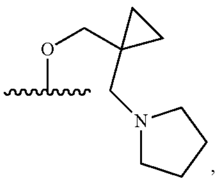,

-continued
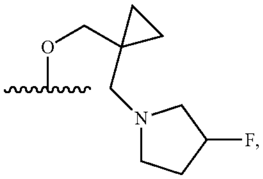
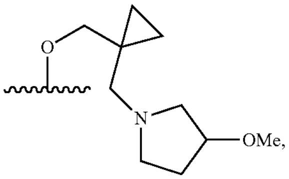
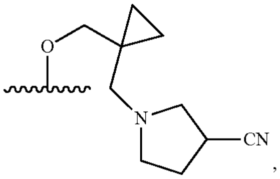
,
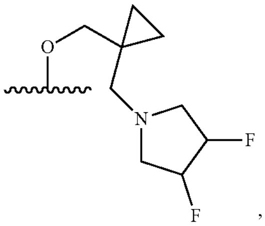
,
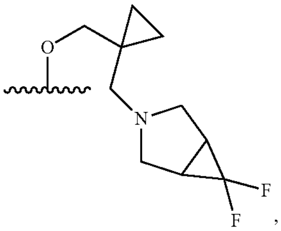
,
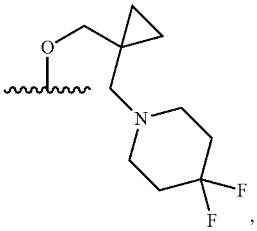
,
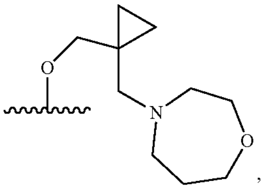
,
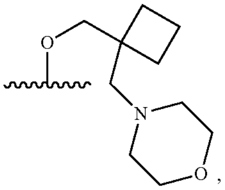
,
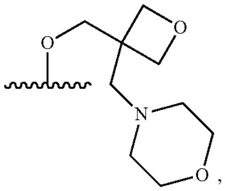
,
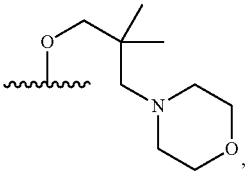
,
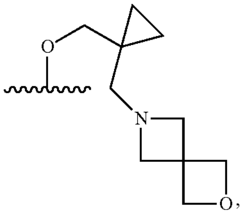
,
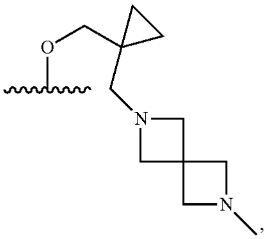
,
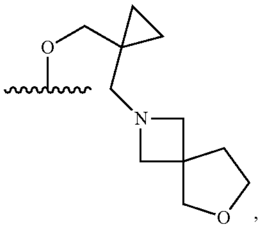
,
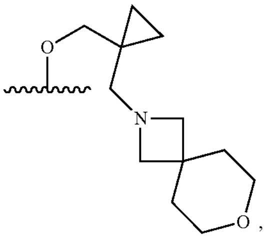
,
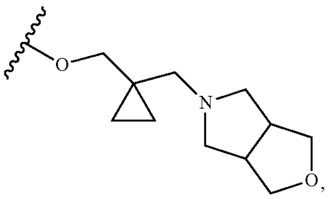
,
-continued
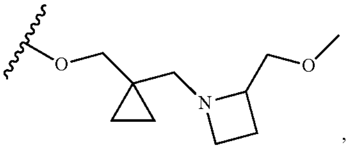
,
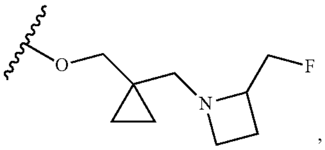
,
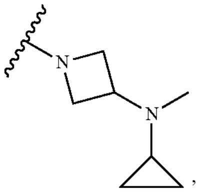
,
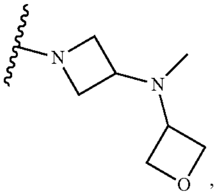
,
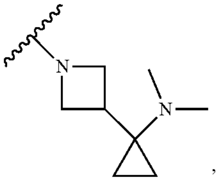
,
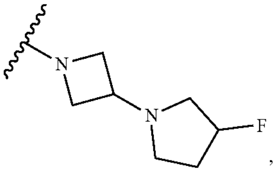
,
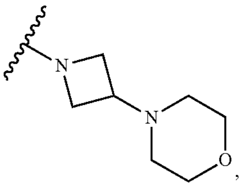
,
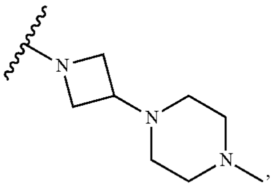
,
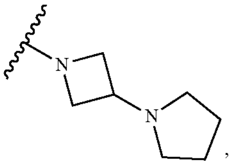
,
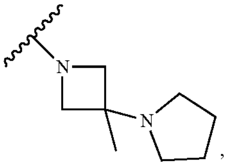
,
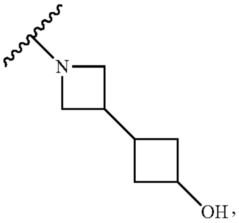
,
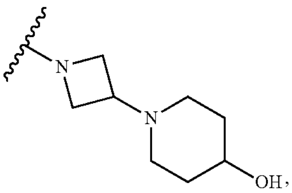
,
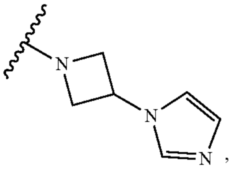
,
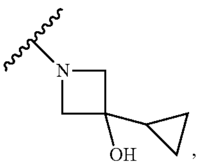
,
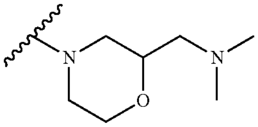
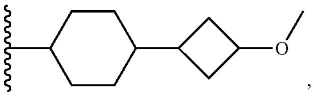
,
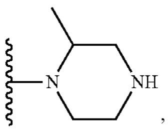
,
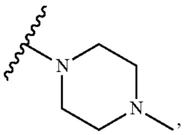
,
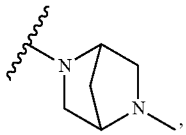
, -continued
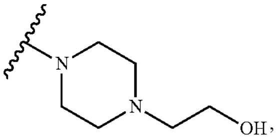,
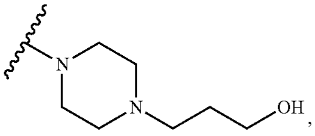, 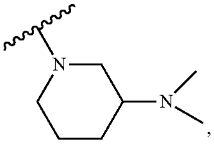,
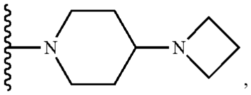, 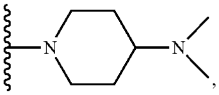,
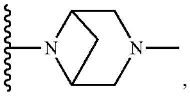, 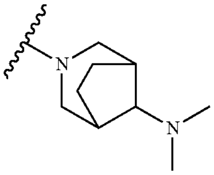
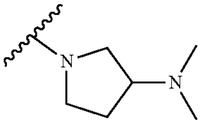 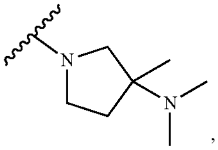,
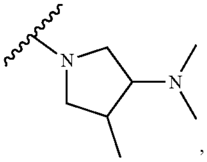, 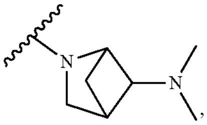,
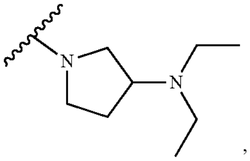, 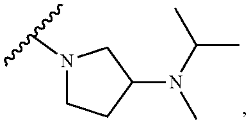,
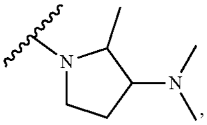, 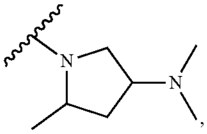,
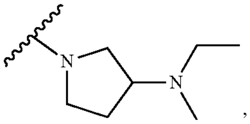, 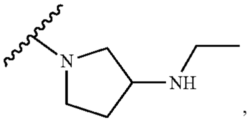,
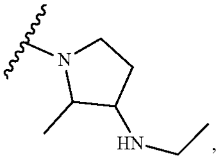, 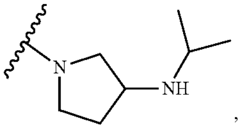,
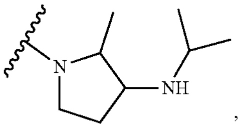, 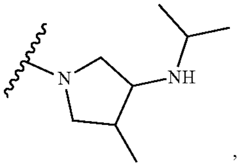,
-continued
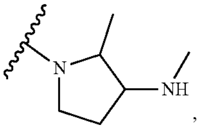, 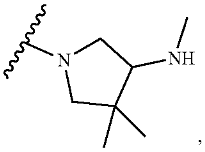,
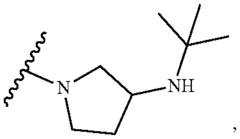, 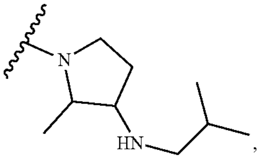,
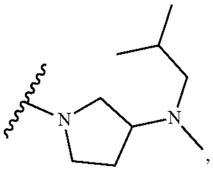, 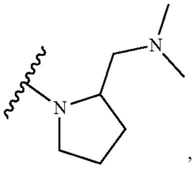,
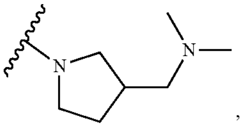, 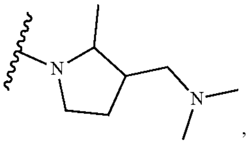,
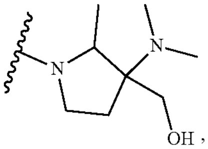, 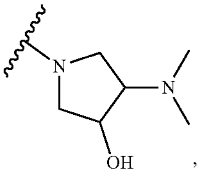,
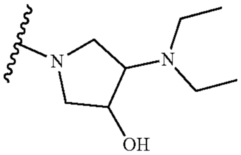, 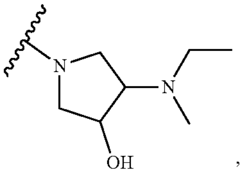,
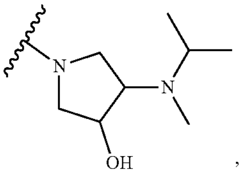, 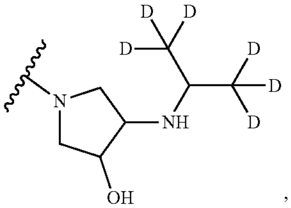,
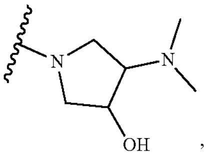, 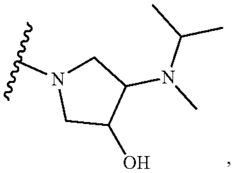,
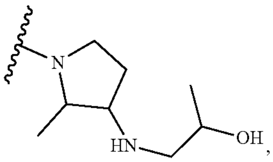, 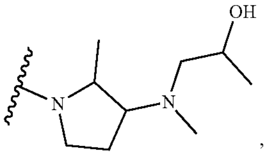,
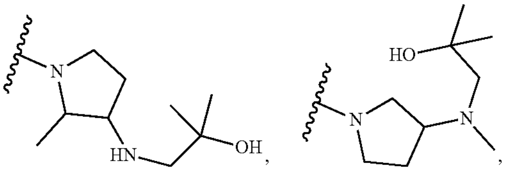, -continued
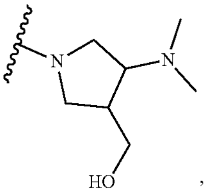,
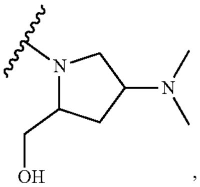,
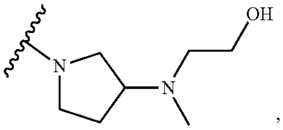,
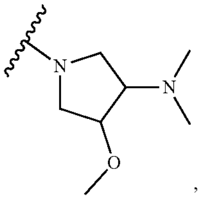,
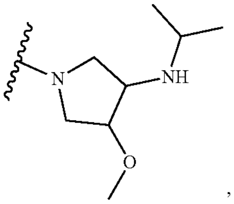,
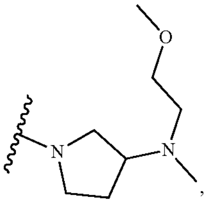,
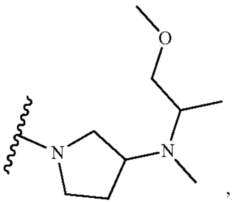,
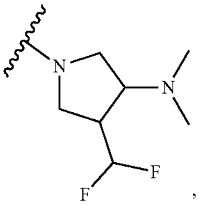,
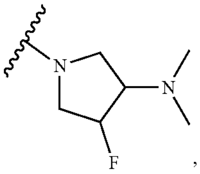,
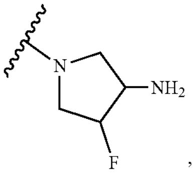,
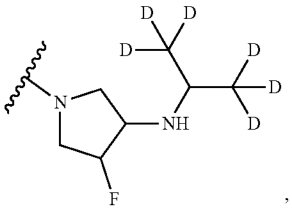,
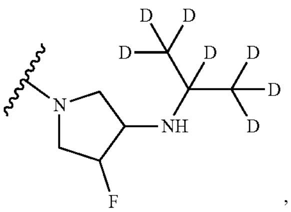,
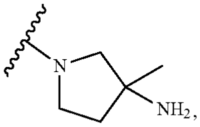,
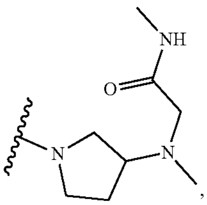,
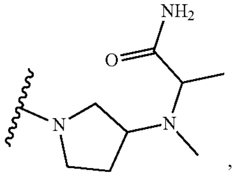,
-continued
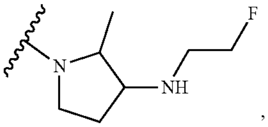,
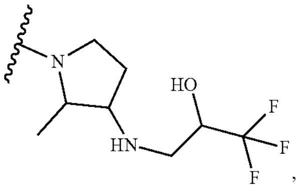,
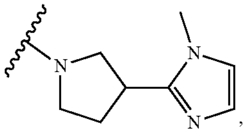,
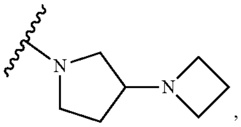,
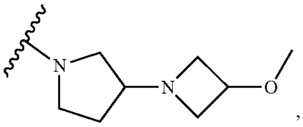,
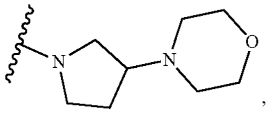,
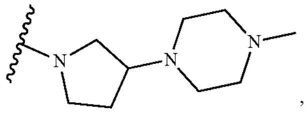,
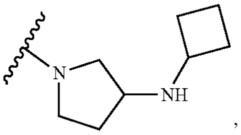,
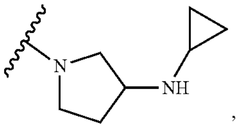,
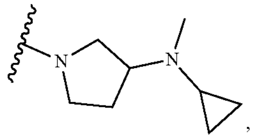,
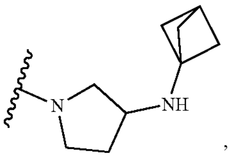,
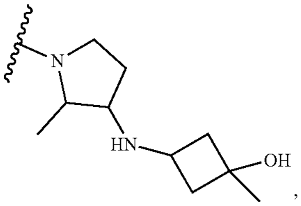,
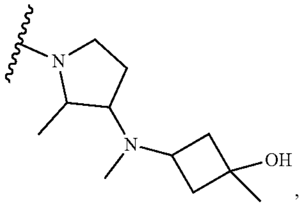,
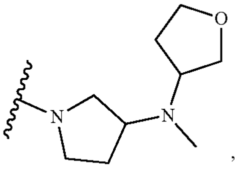,
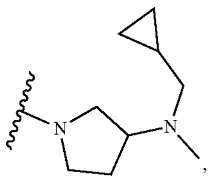,
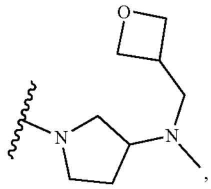,
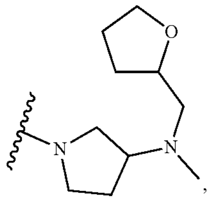,
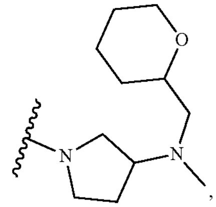,
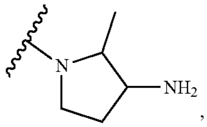,
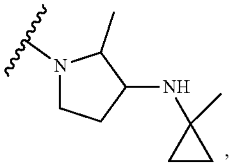, -continued
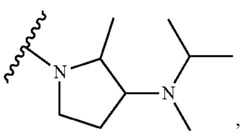,
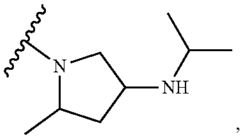,
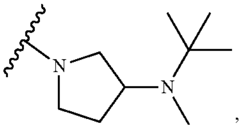,
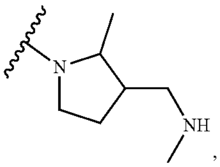,
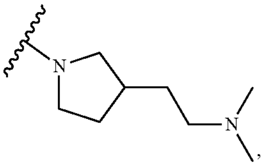,
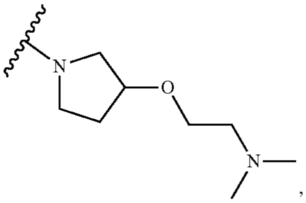,
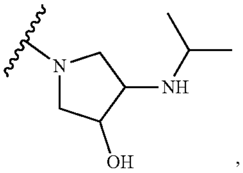,
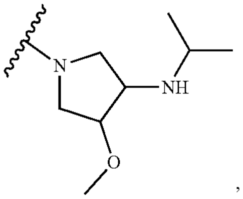,
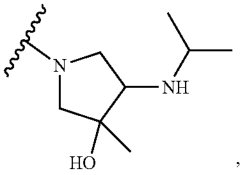,
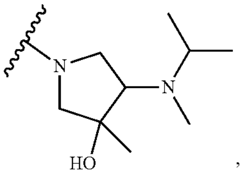,
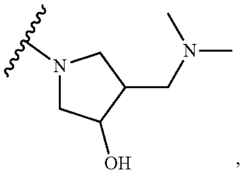,
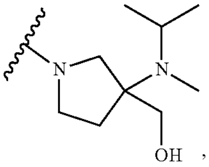,
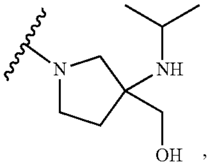,
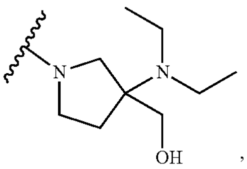,
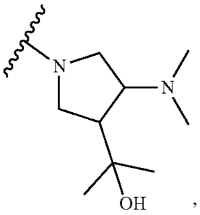,
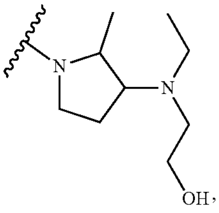,
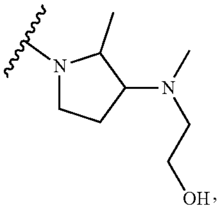,
-continued
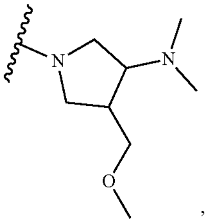,
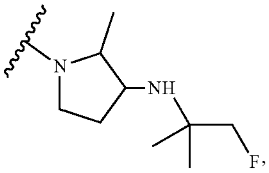,
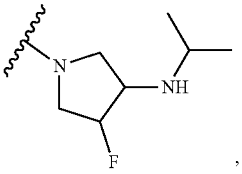,
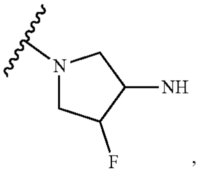,
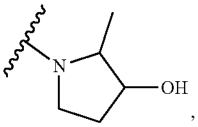,
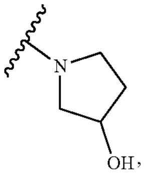,
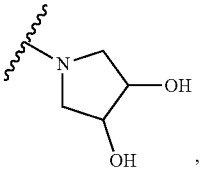,
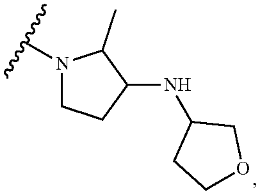,
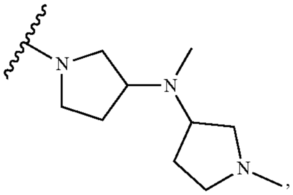,
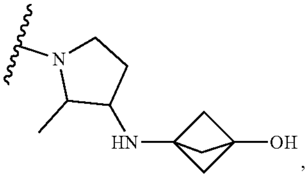,
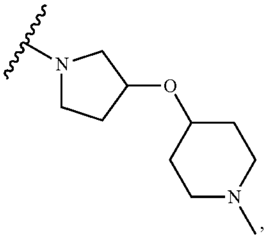,
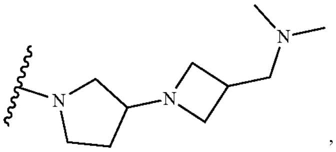, -continued
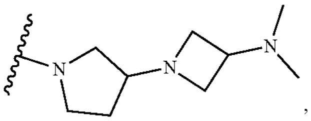,
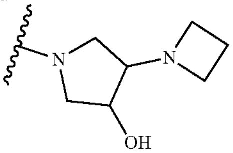,
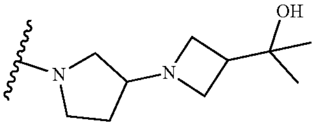,
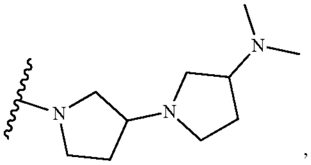,
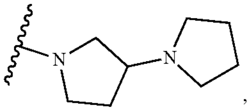,
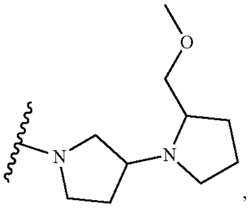,
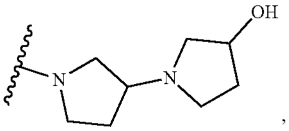,
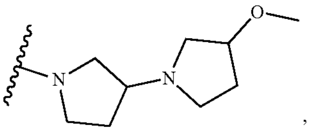,
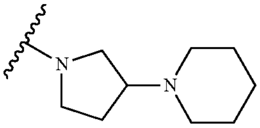,
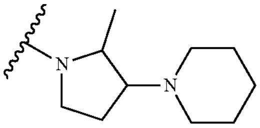,
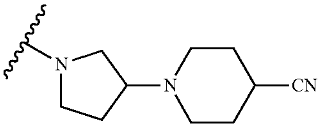,
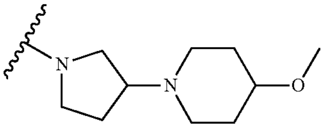,
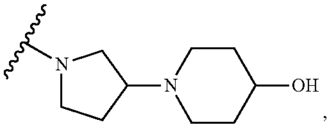,
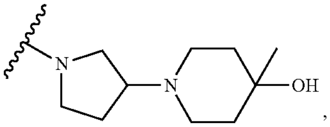,
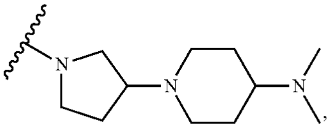,
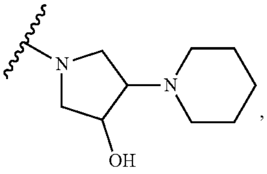,
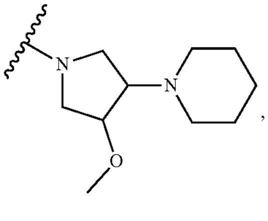,
-continued
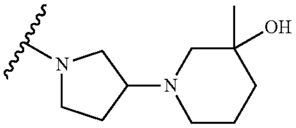,
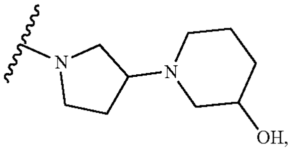,
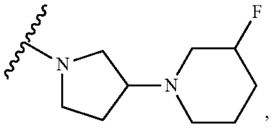,
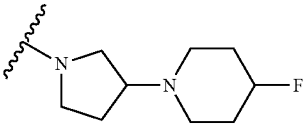,
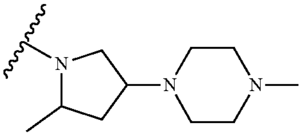,
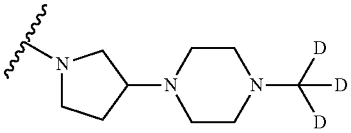,
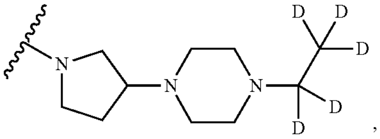,
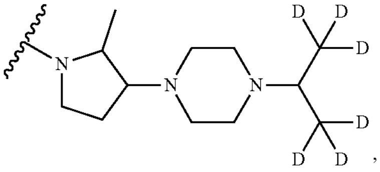,
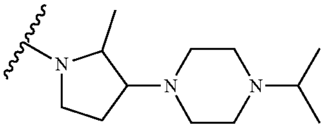,
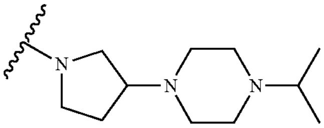,
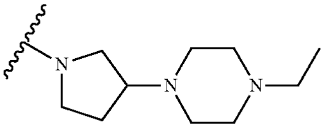,
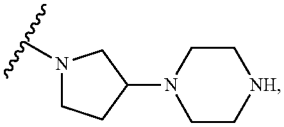

-continued
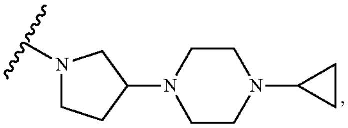
,
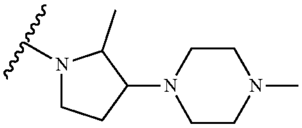
,
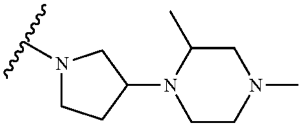
,
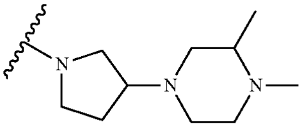
,
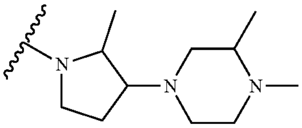
,
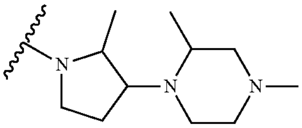
,
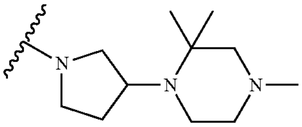
,
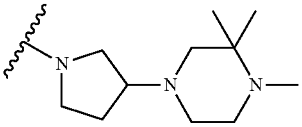
,
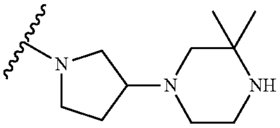
,
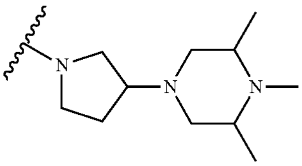
,
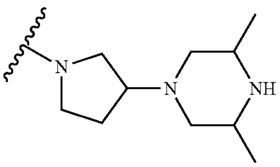
,
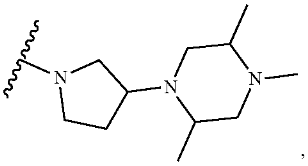
,
-continued
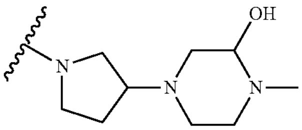
,
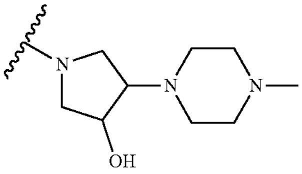
,
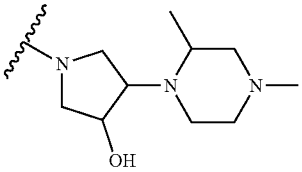
,
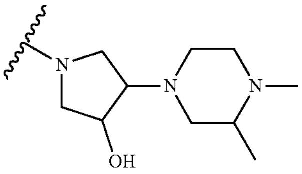
,
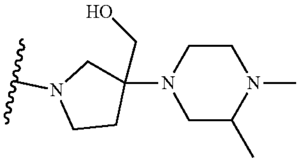
,
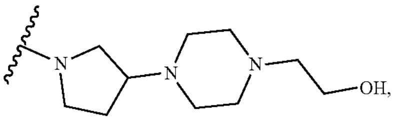
,
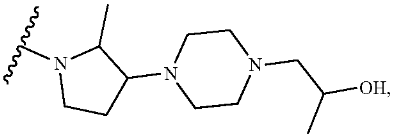
,
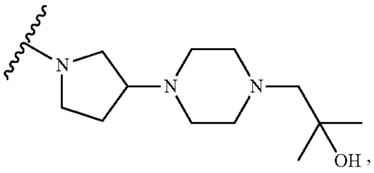
,
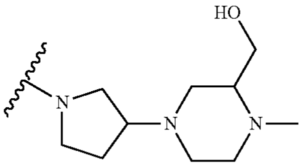
,
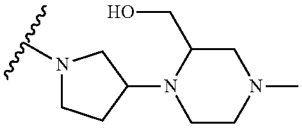
,
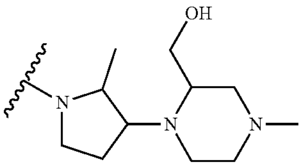
, -continued
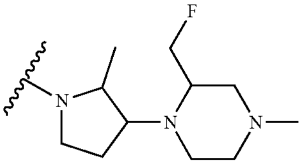
,
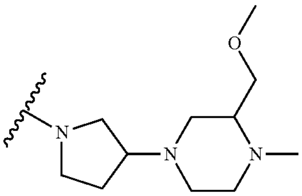
,
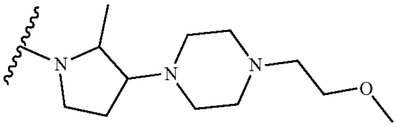
,
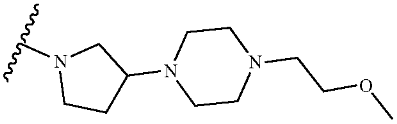
,
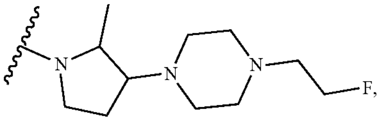
,
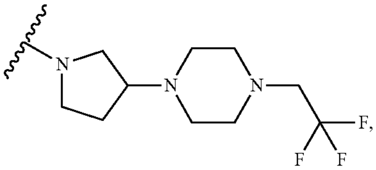
,
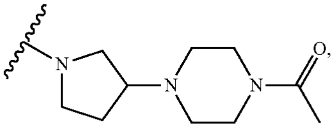
,
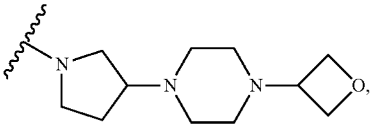
,
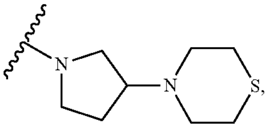
,
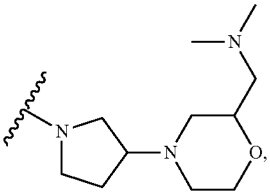
,
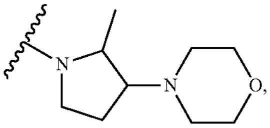
,
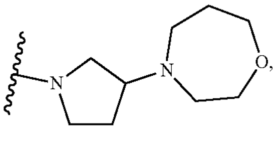
,
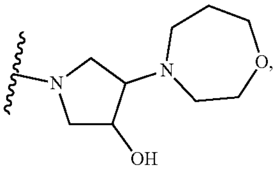
,
-continued
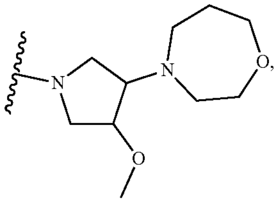
,
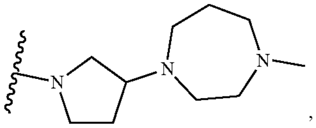
,
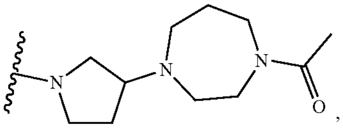
,
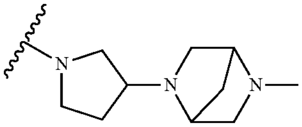
,
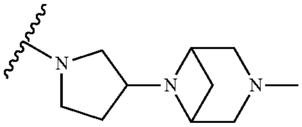
,
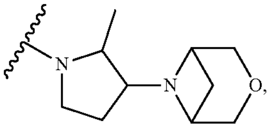
,
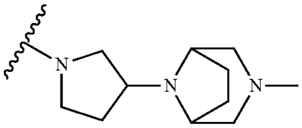
,
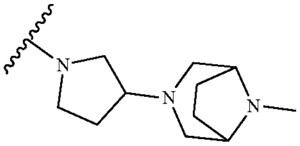
,
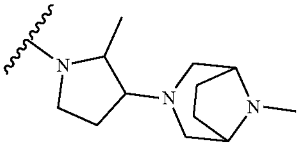
,
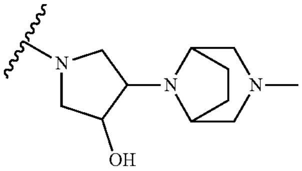
,
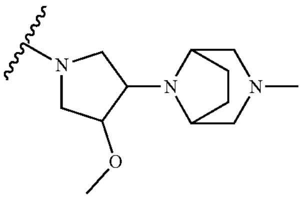
, -continued
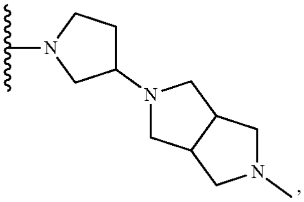
,
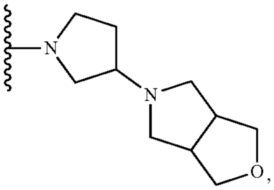
,
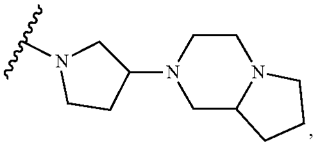
,
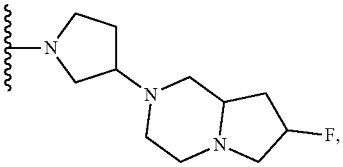
,
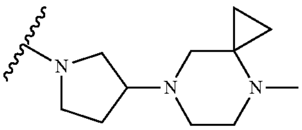
,
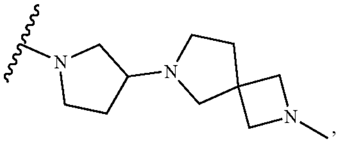
,
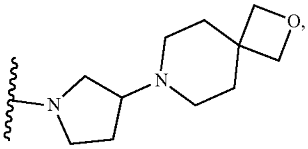
,
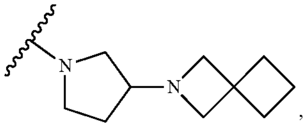
,
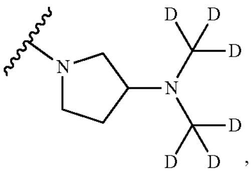
,
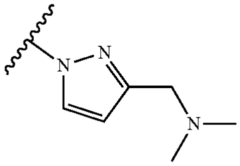
,
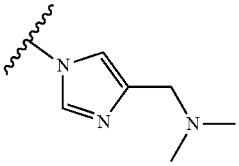
,
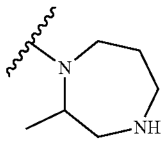
,
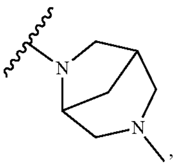
,
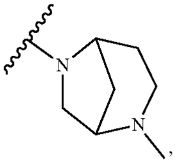
,
-continued
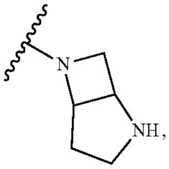
,
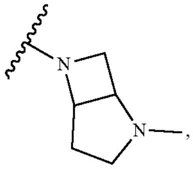
,
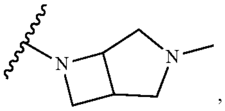
,
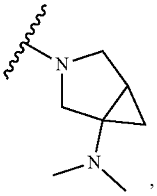
,
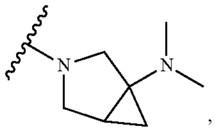
,
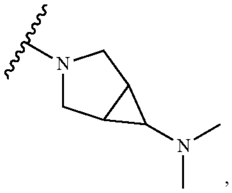
,
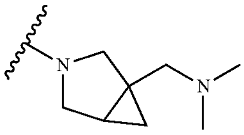
,
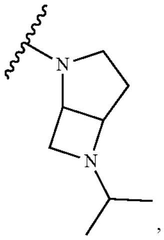
,
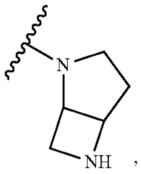
,
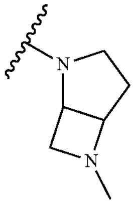
,
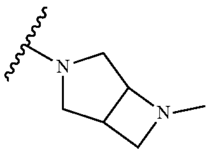
,
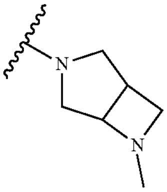
,
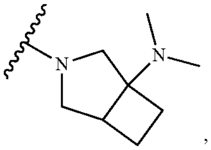
,
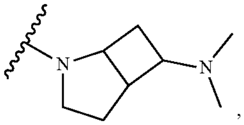
,
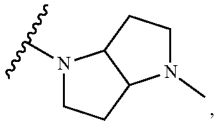
,
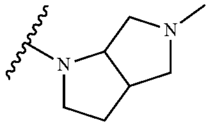
,
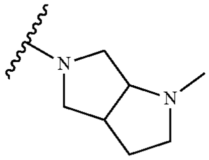
,
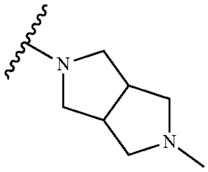
,
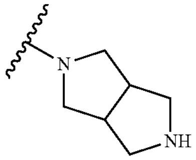
,
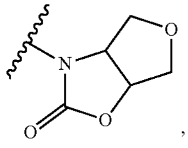
, -continued
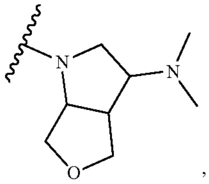,
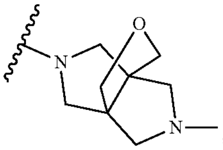,
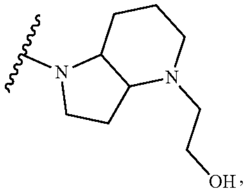,
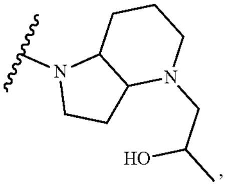,
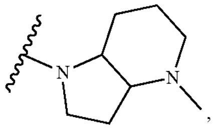,
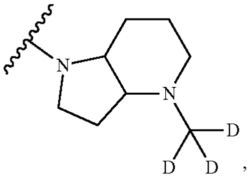,
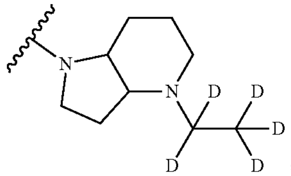,
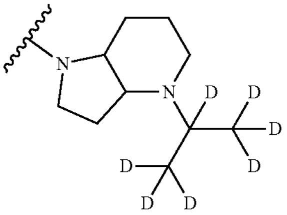,
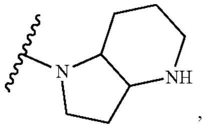,
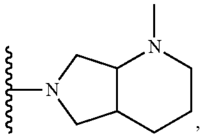,
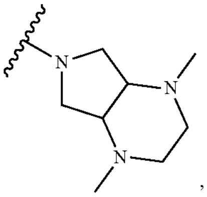,
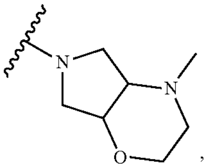,
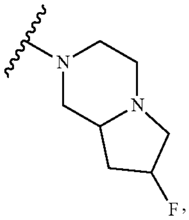,
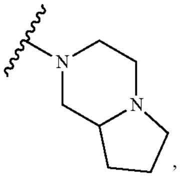,
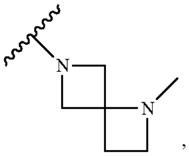,
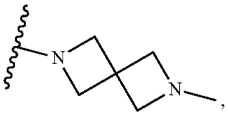,
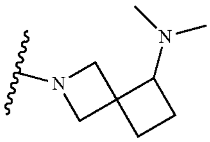,
-continued
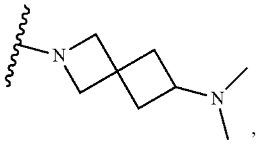,
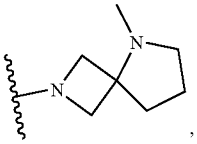,
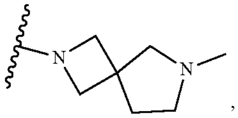,
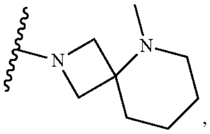,
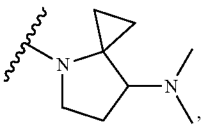,
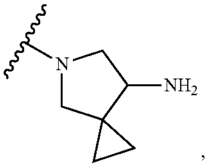,
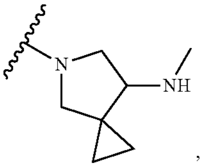,
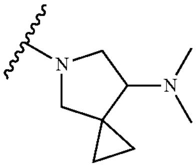,
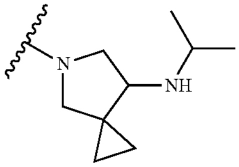,
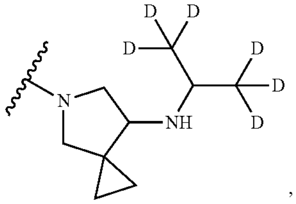,
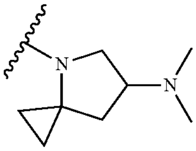,
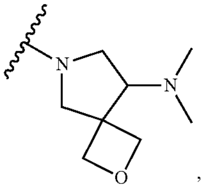,
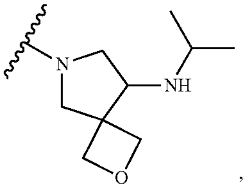,
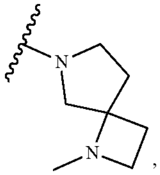,
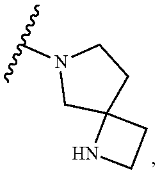,
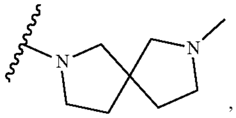,
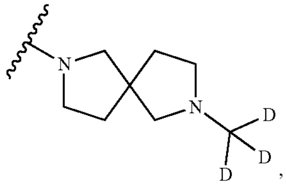,
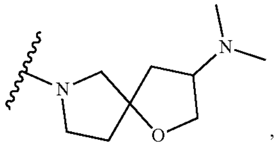,
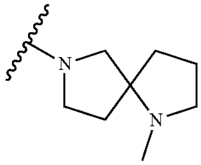,
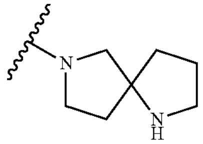,
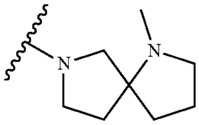, or -continued
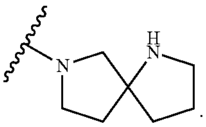.
In an embodiment of a compound of Formula I or a pharmaceutically acceptable salt thereof, $R_4$ is a N-linked cyclic amine selected from
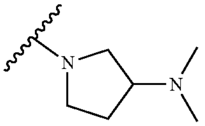
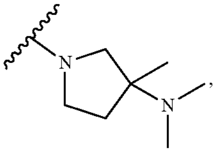,
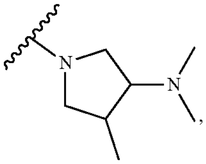,
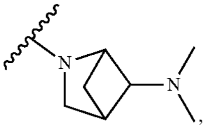,
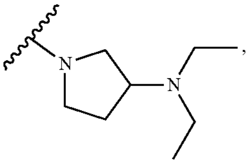,
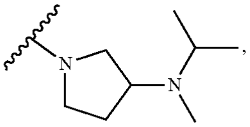,
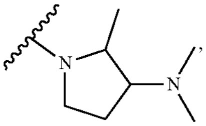,
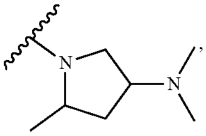,
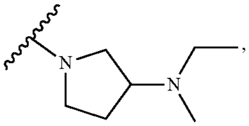,
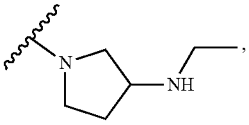,
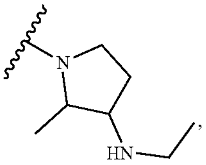,
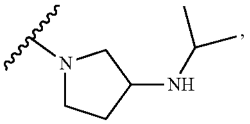,
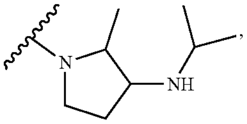,
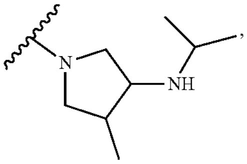,
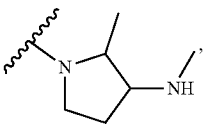,
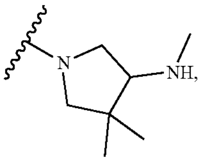,
-continued
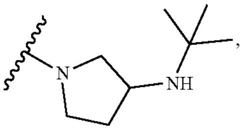,
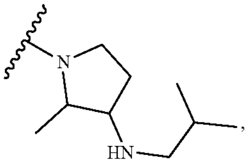,
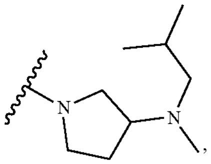,
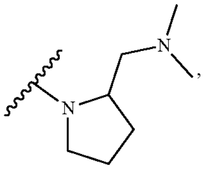,
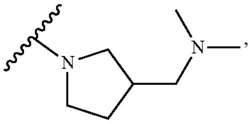,
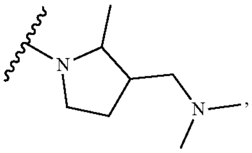,
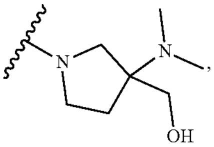,
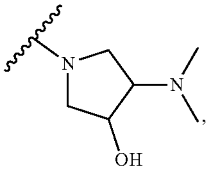,
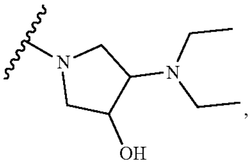,
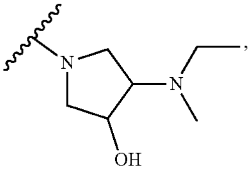,
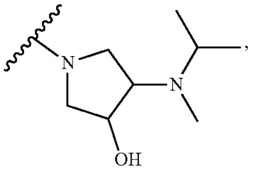,
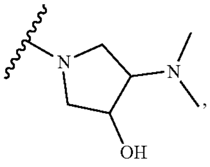,
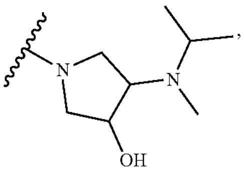,
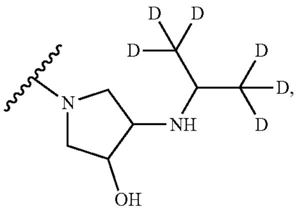, -continued
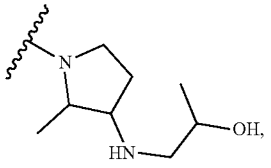
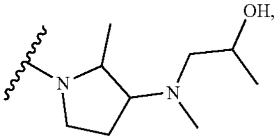
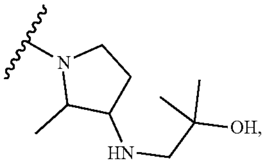
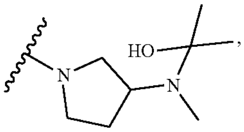
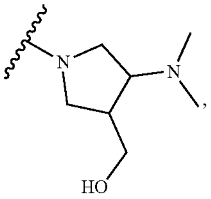
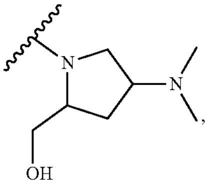
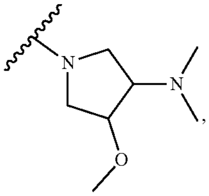
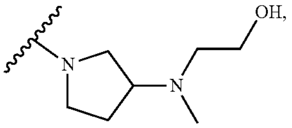
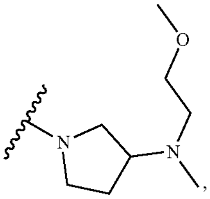
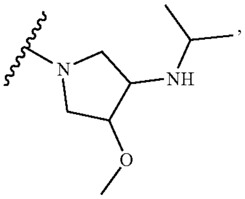
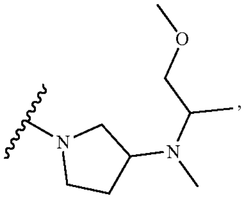
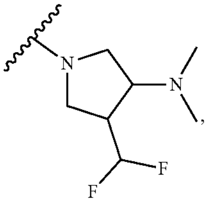
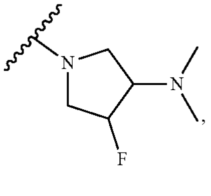
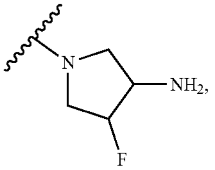
-continued
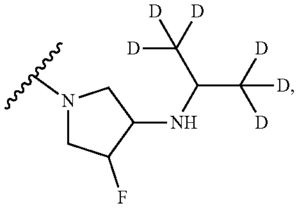
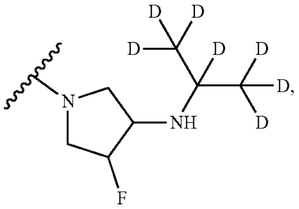
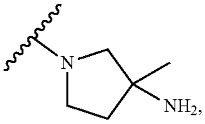
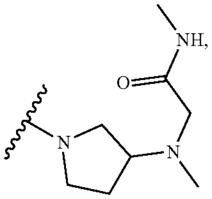
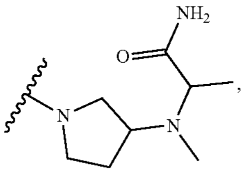
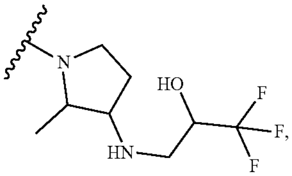
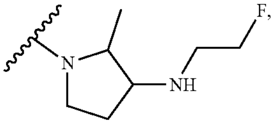
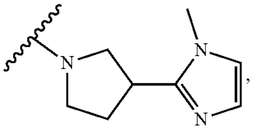
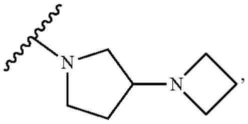
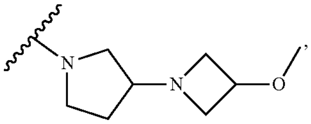
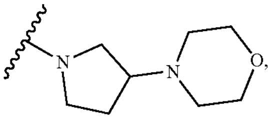
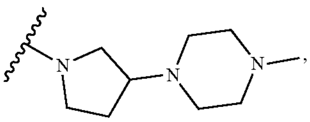
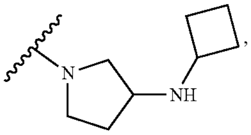
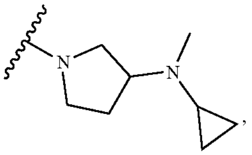
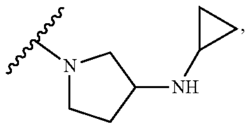

-continued
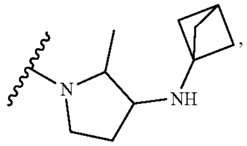
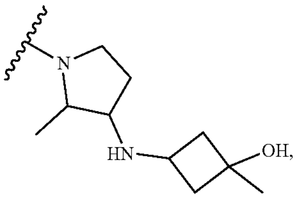
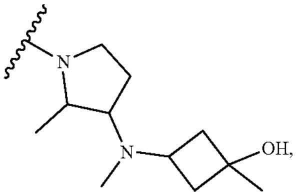
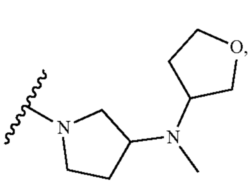
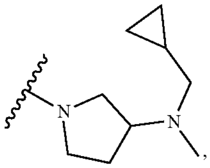
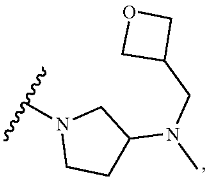
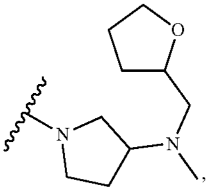
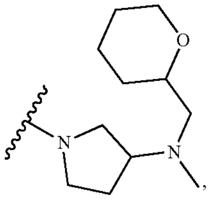
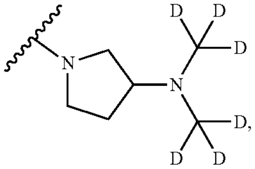
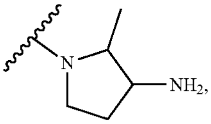
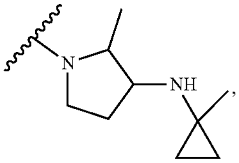
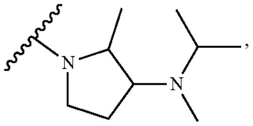
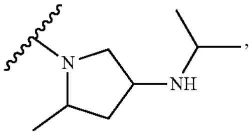
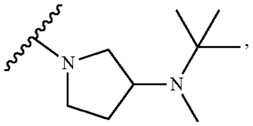
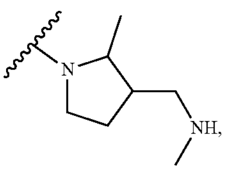
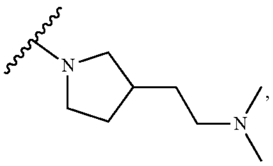
-continued
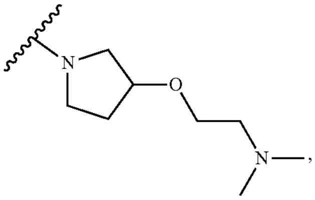
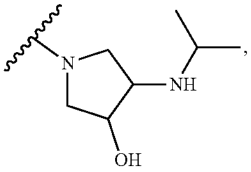
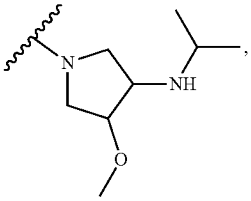
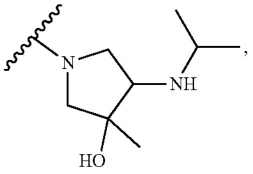
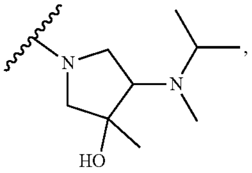
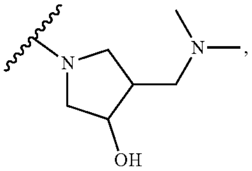
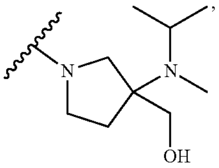
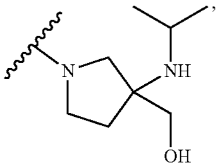
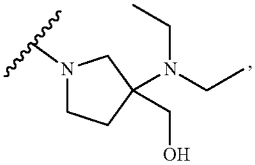
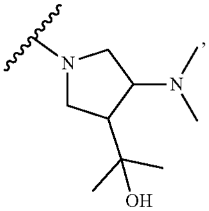
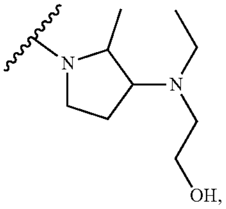
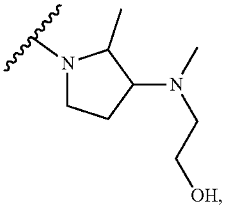
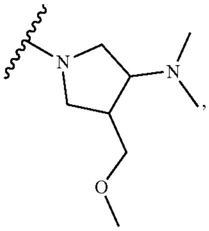
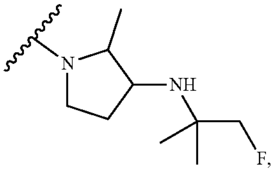

-continued
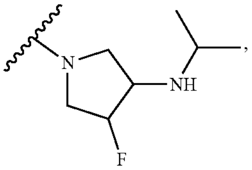
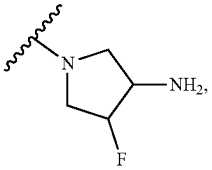
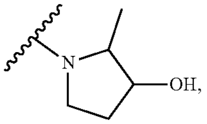
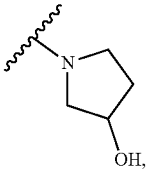
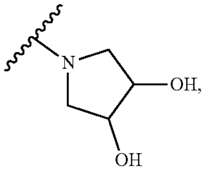
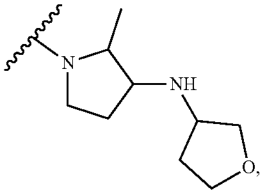
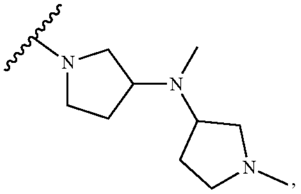
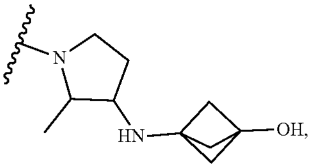
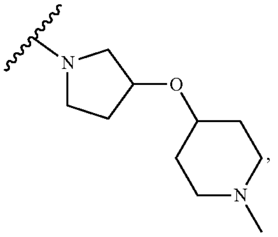
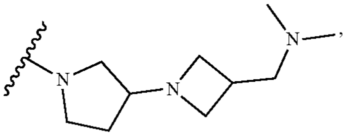
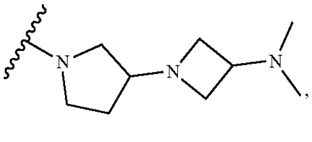
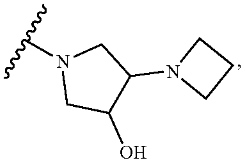
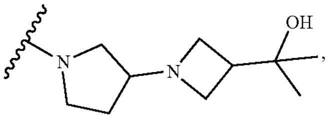
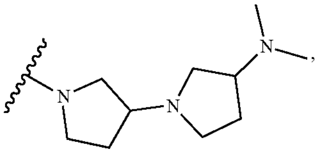
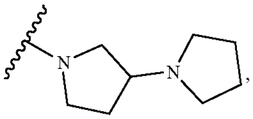
-continued
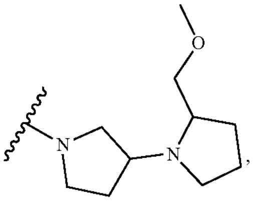
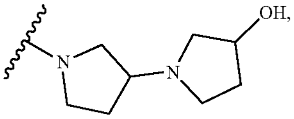
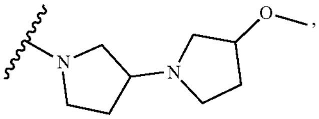
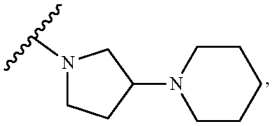
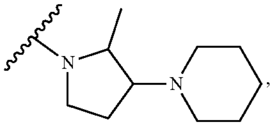
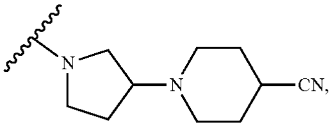
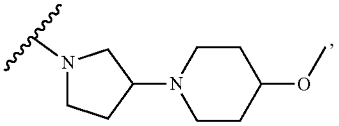
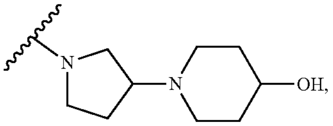
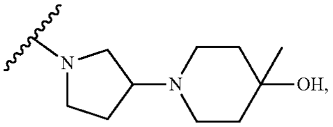
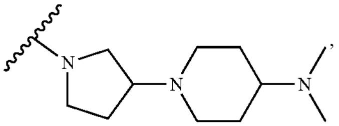
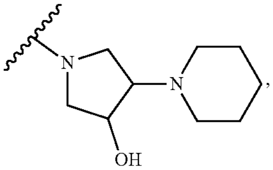
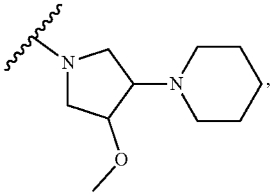
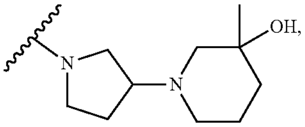
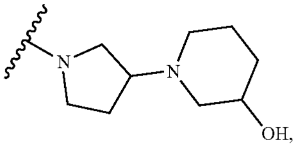
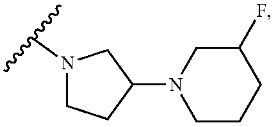

-continued
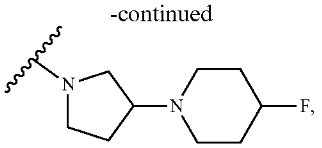
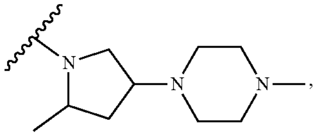
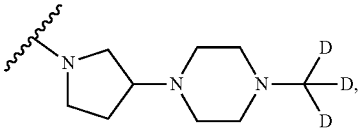
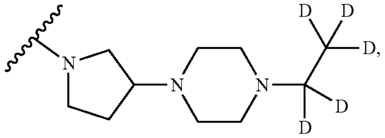
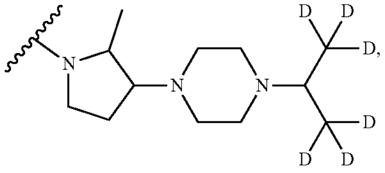
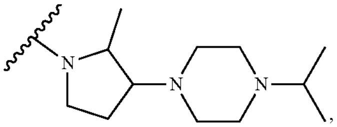
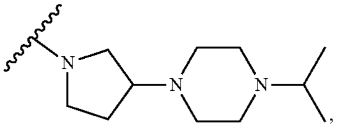
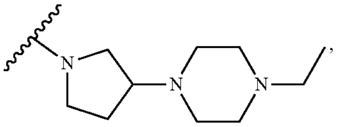
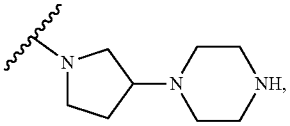
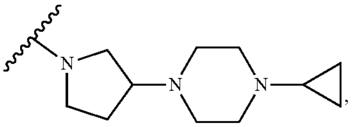
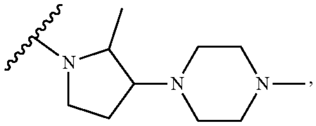
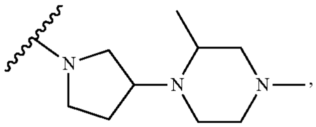
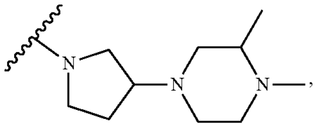
-continued
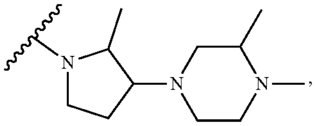
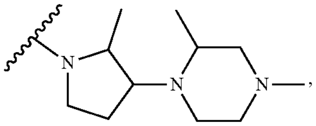
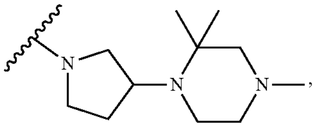
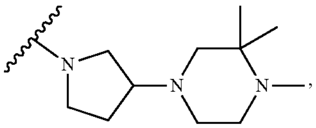
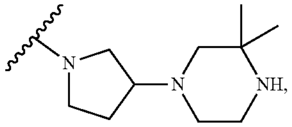
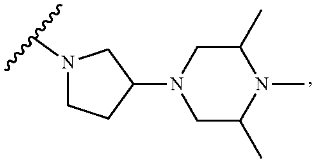
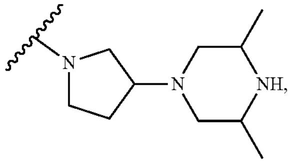
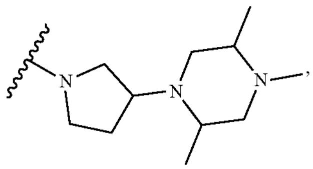
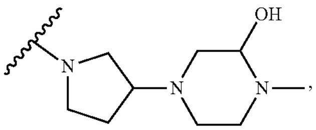
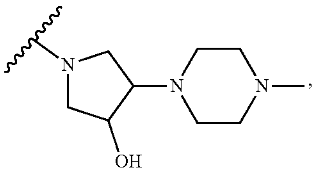
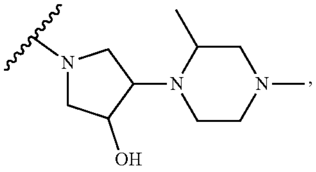

-continued
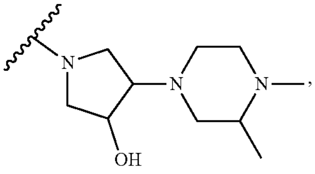
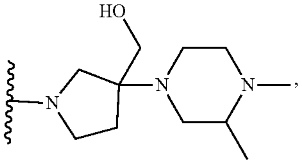
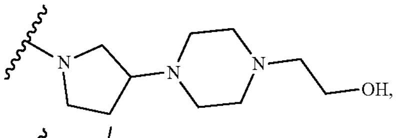
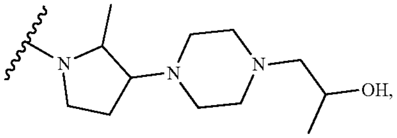
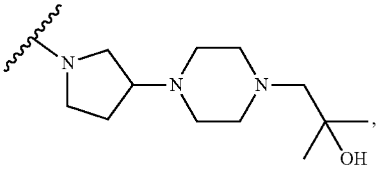
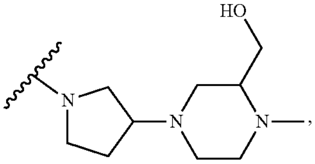
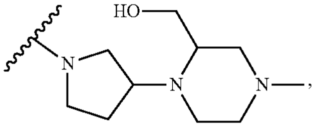
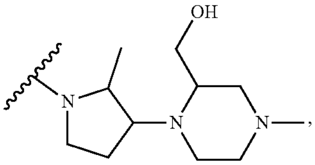
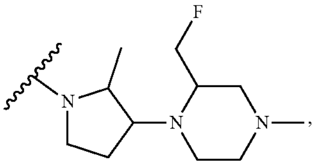
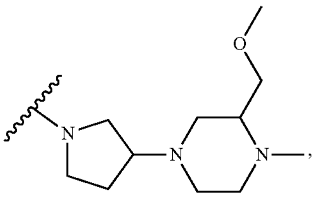
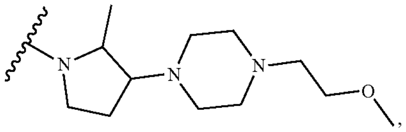
-continued
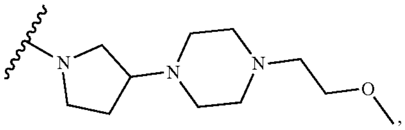
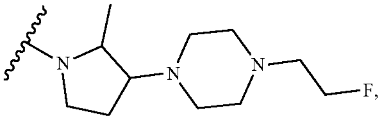
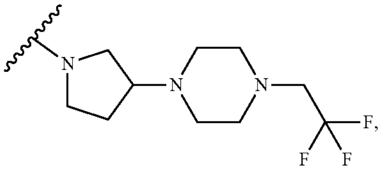
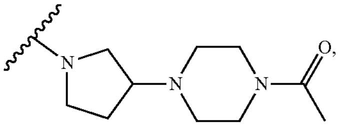
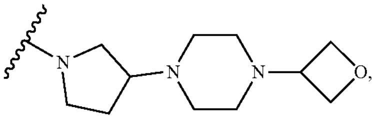
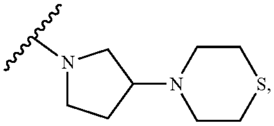
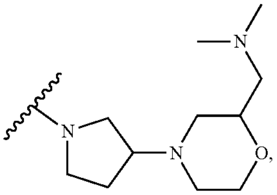
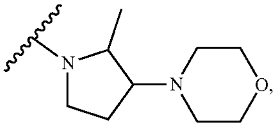
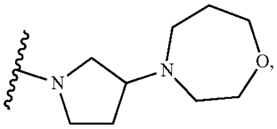
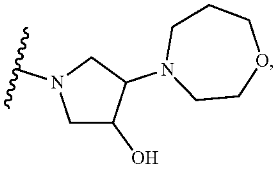
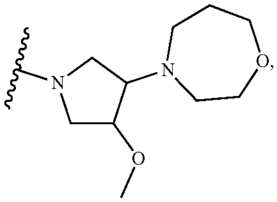
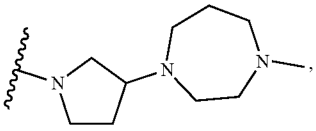
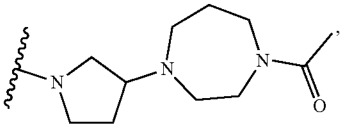
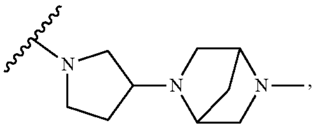
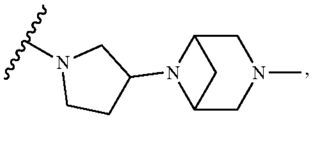

-continued
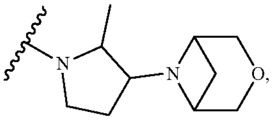
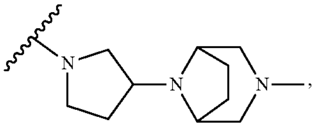
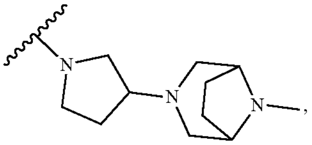
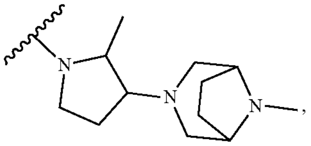
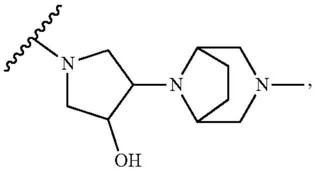
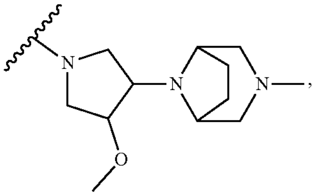
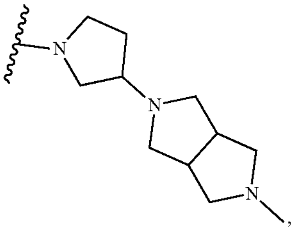
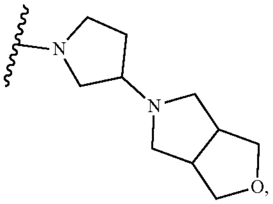
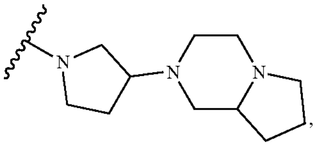
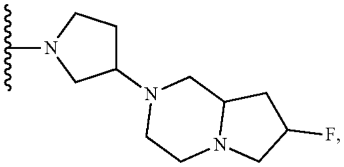
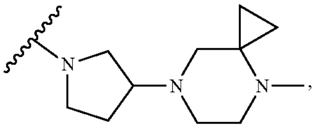
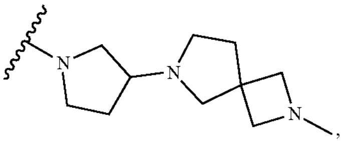
-continued
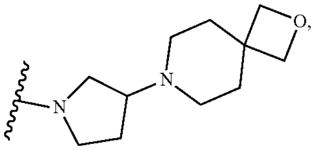
or
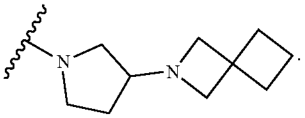
In an embodiment of a compound of Formula I or a pharmaceutically acceptable salt thereof, $R_4$ is a N-linked cyclic amine selected from
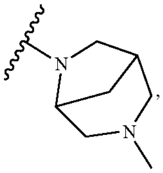
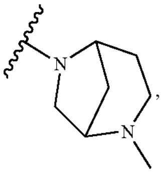
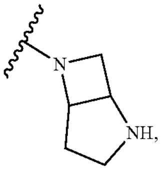
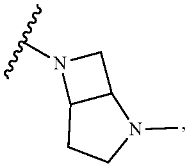
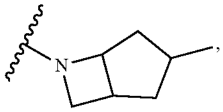
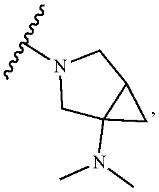
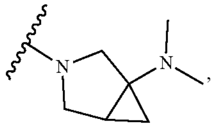
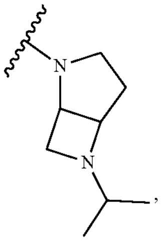
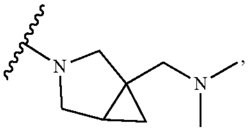
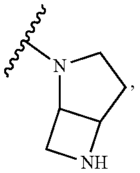
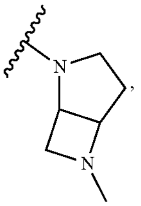
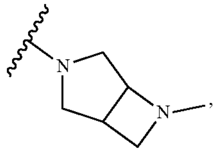
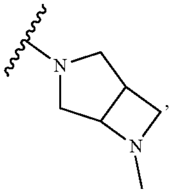
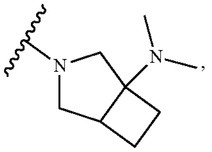
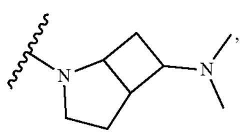

-continued
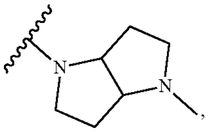
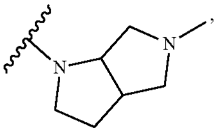
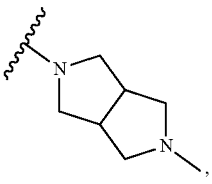
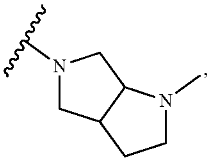
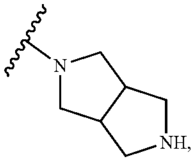
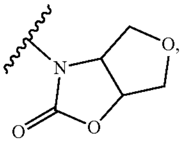
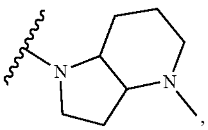
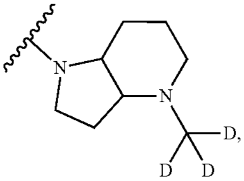
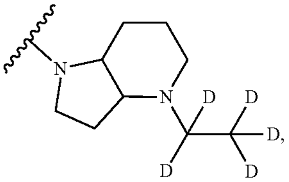
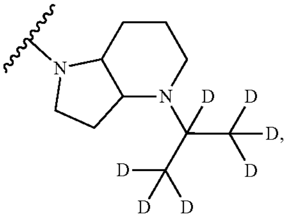
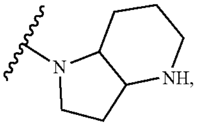
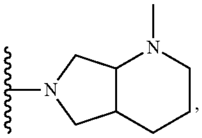
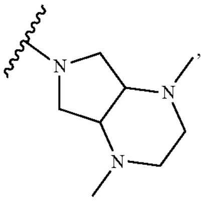
-continued
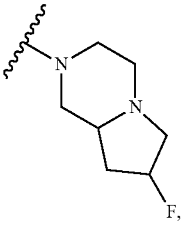
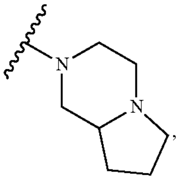
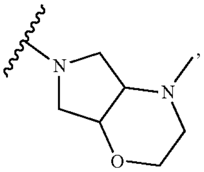
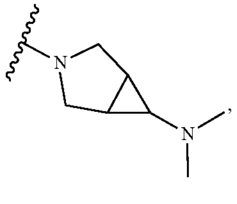
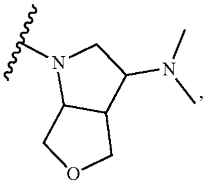
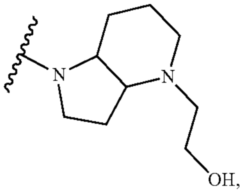
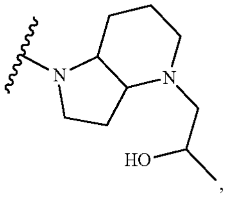
or
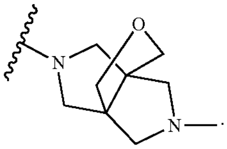
In an embodiment of a compound of Formula I or a pharmaceutically acceptable salt thereof, $R_4$ is a N-linked cyclic amine selected from
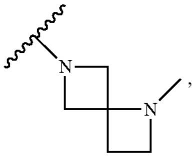
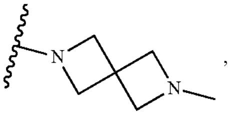
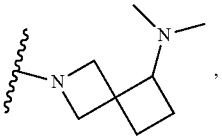
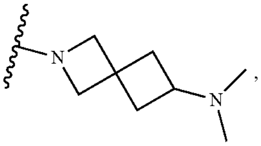
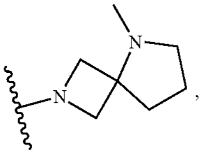
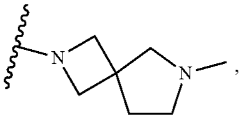
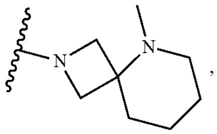
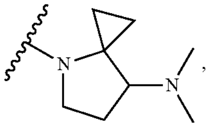

-continued
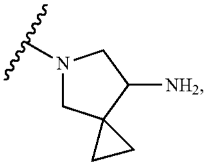
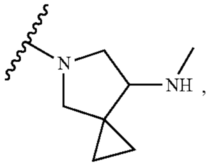
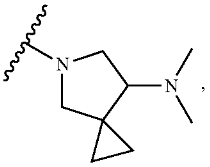
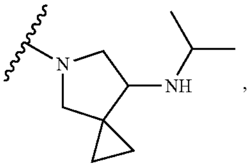
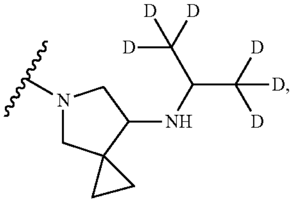
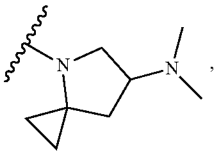
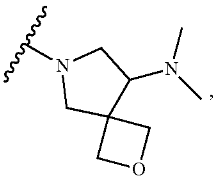
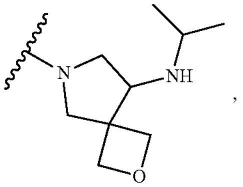
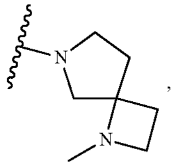
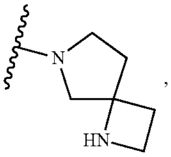
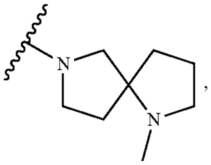
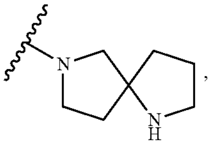
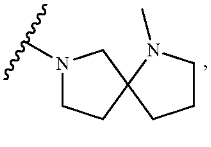
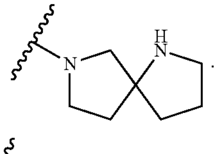
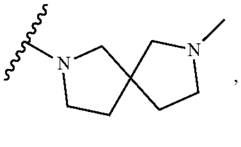
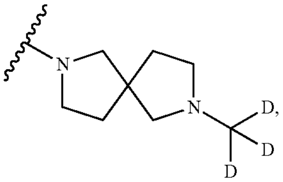
or
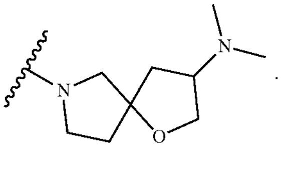
In an embodiment of a compound of Formula I or a pharmaceutically acceptable salt thereof, $R_4$ is selected from
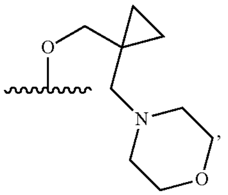
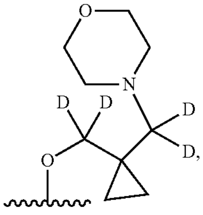
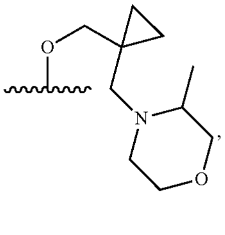
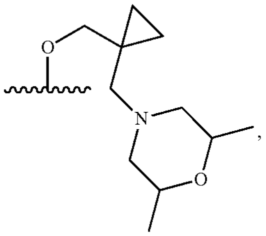
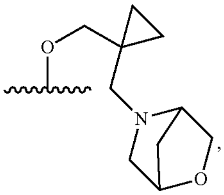
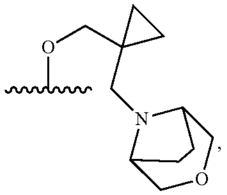
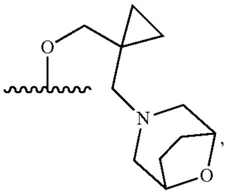
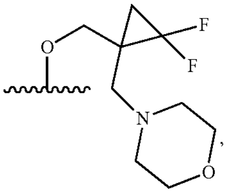
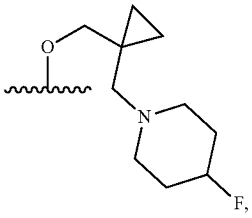
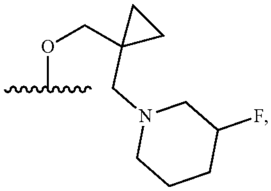
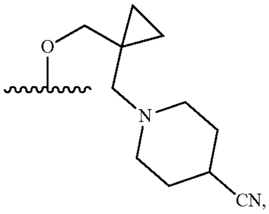
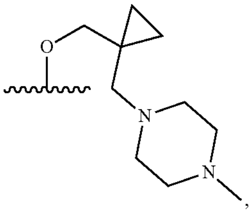
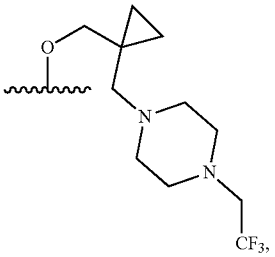
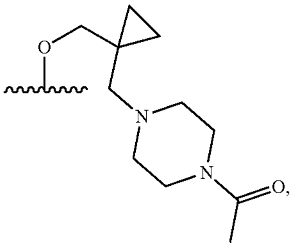

-continued
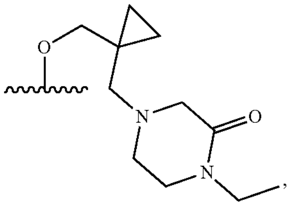
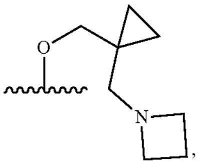
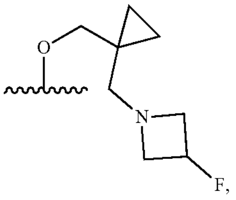
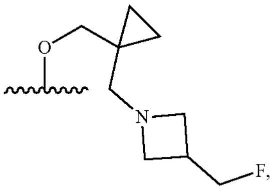
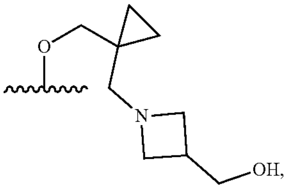
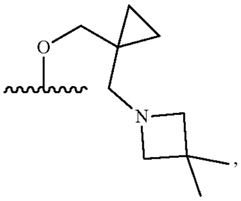
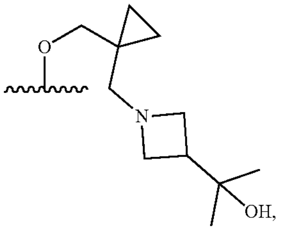
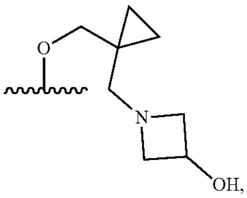
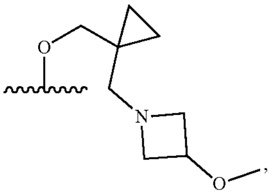
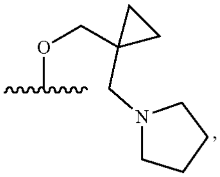
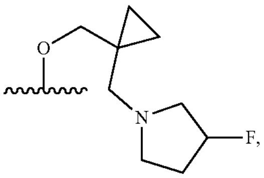
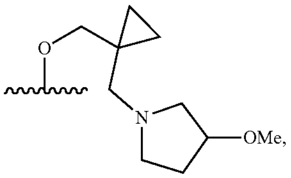
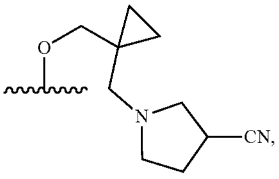
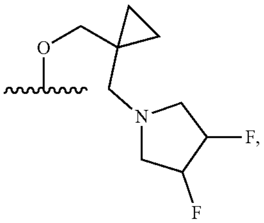
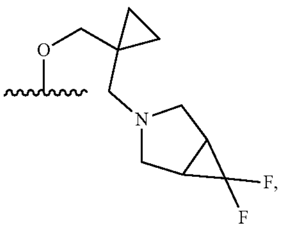
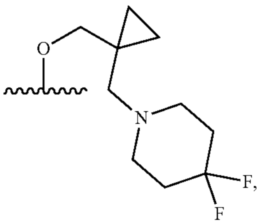
-continued
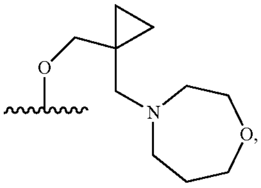
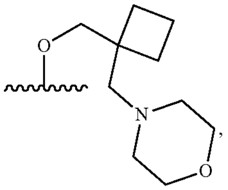
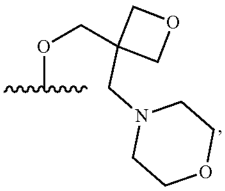
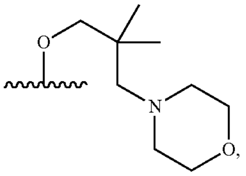
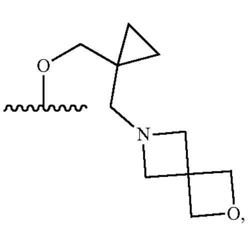
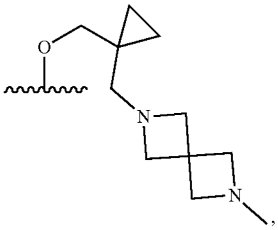
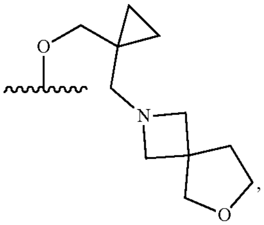
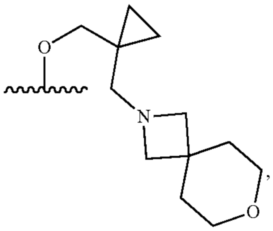
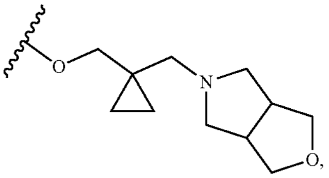
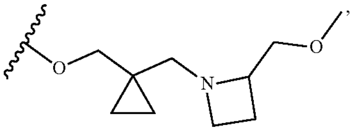
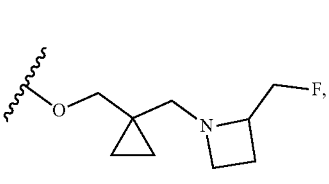
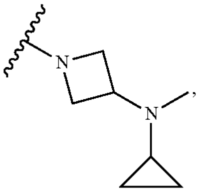
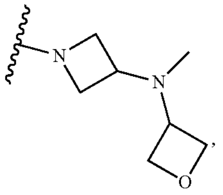
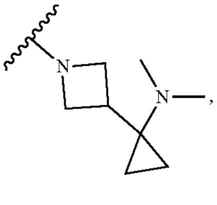

-continued
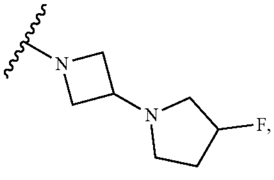
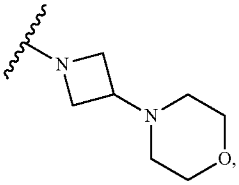
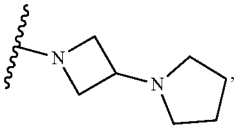
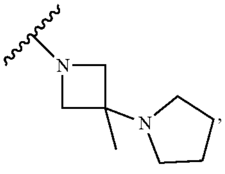
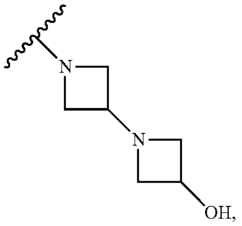
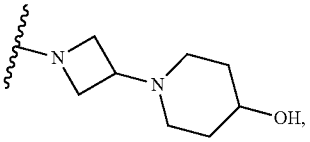
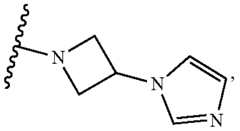
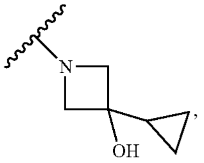
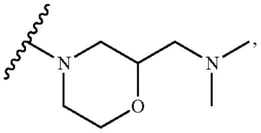
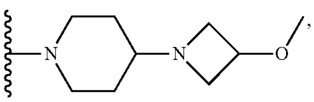
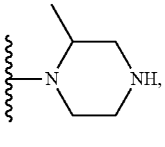
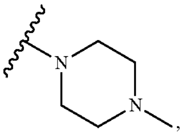
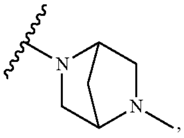
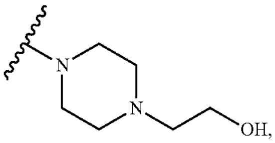
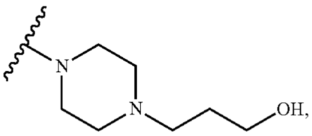
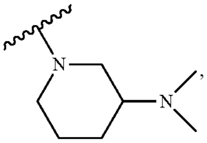
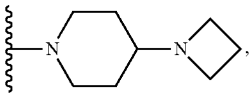
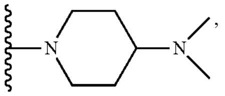
-continued
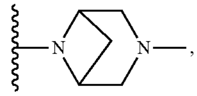
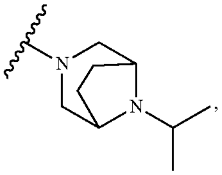
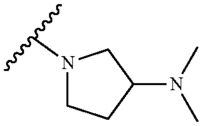
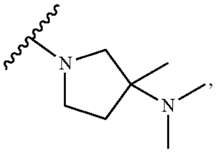
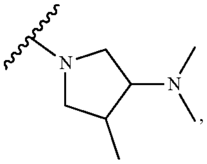
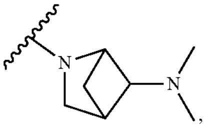
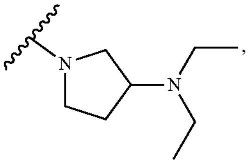
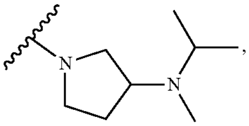
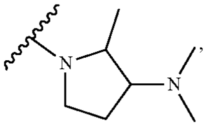
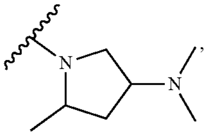
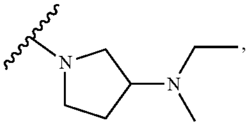
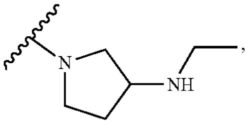
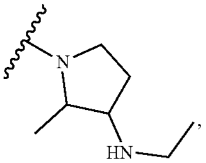
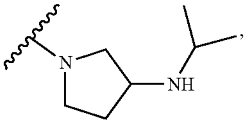
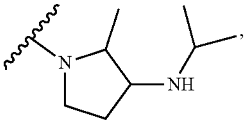
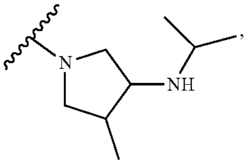
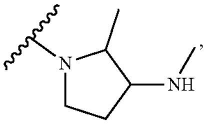
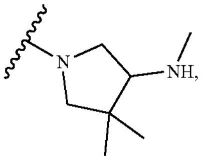
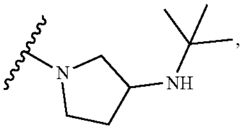
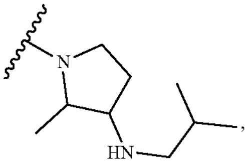

-continued
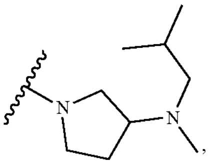
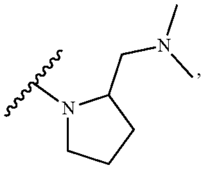
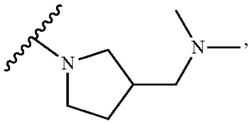
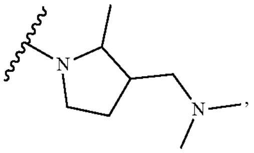
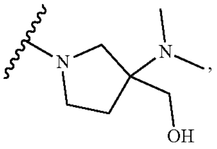
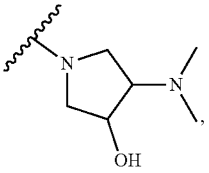
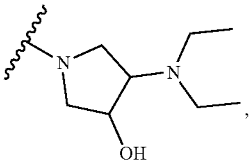
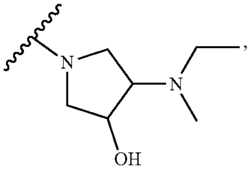
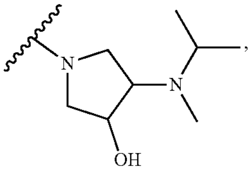
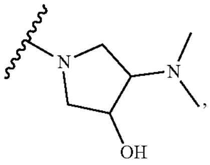
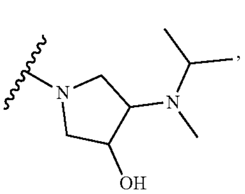
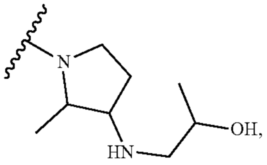
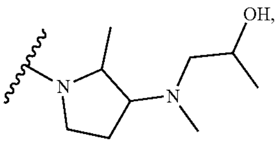
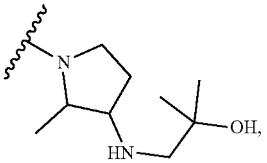
-continued
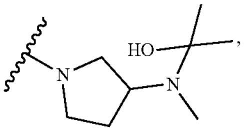
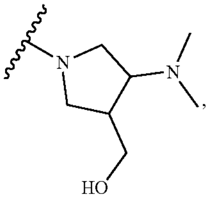
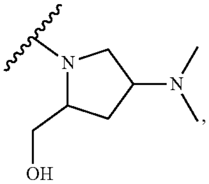
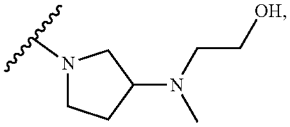
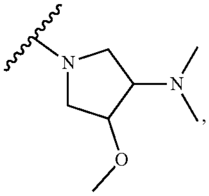
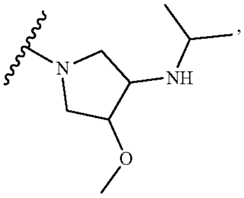
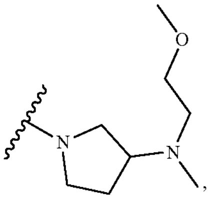
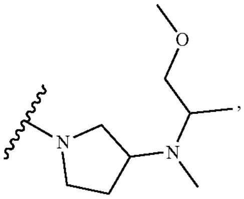
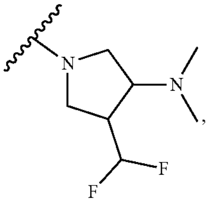
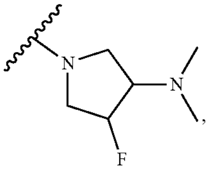
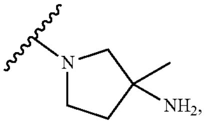
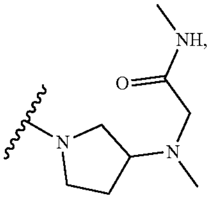
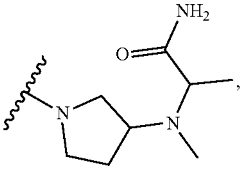
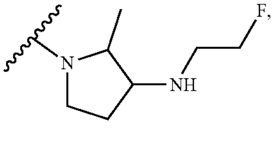

-continued
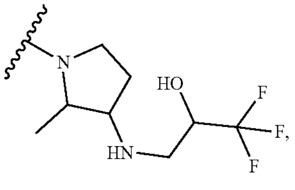
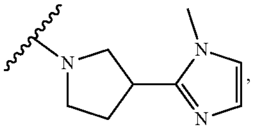
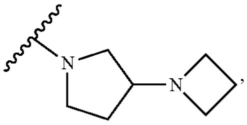
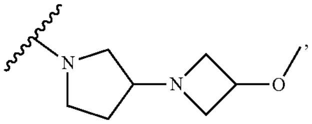
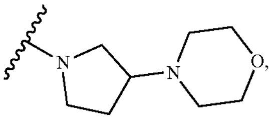
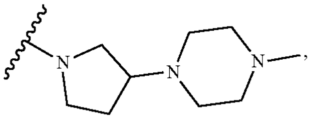
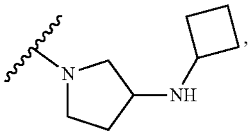
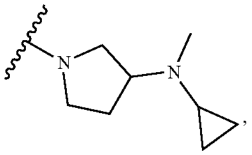
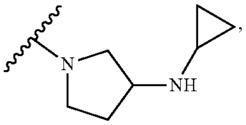
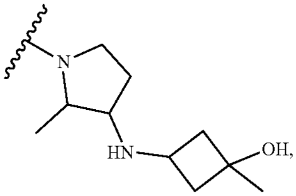
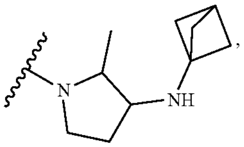
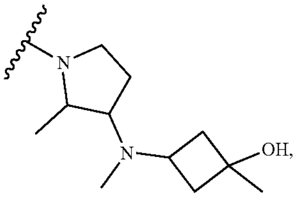
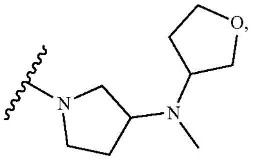
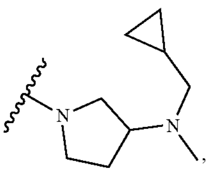
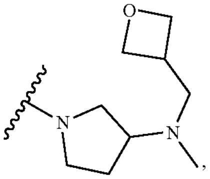
-continued
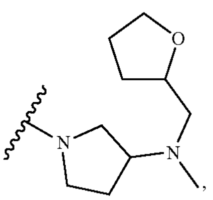
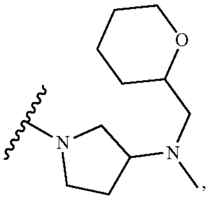
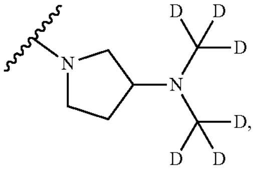
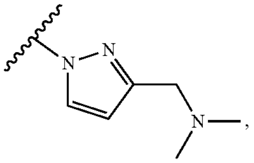
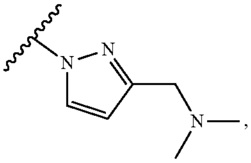
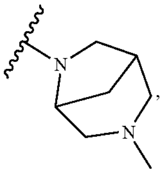
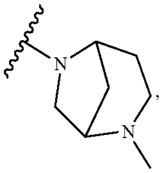
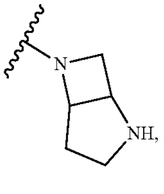
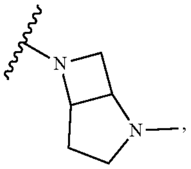
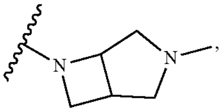
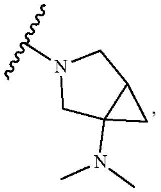
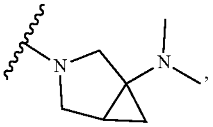
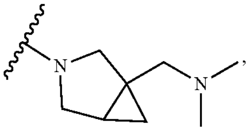
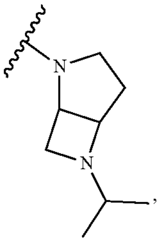
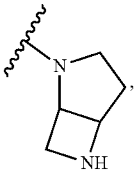
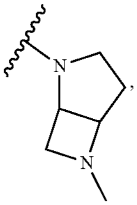
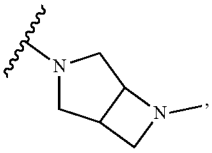
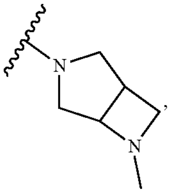

-continued
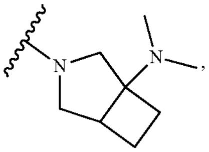
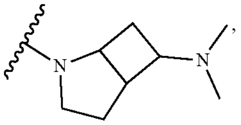
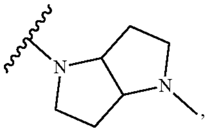
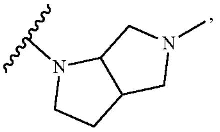
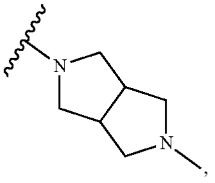
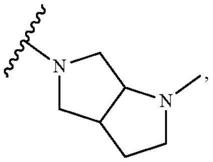
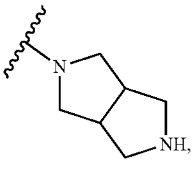
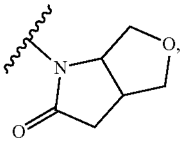
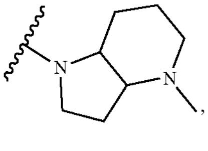
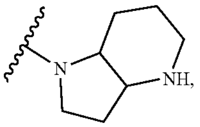
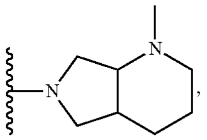
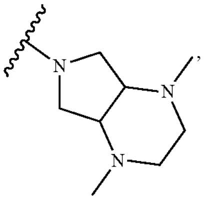
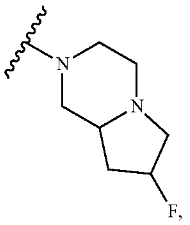
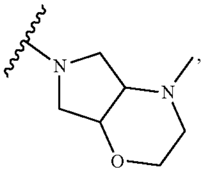
-continued
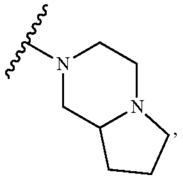
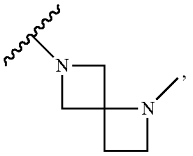
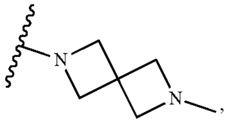
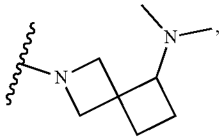
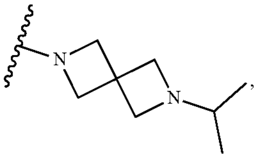
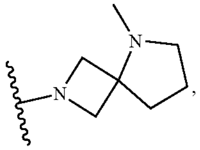
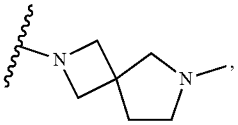
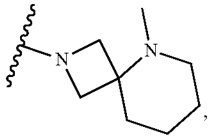
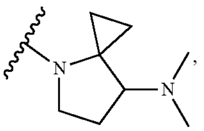
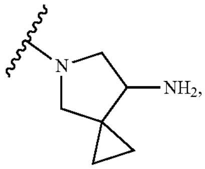
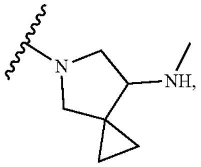
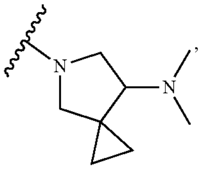
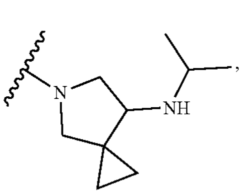
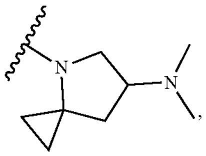
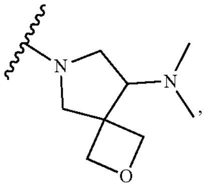
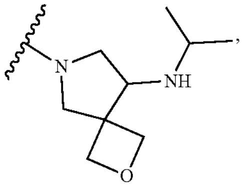

-continued
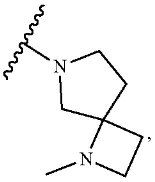
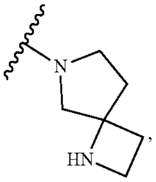
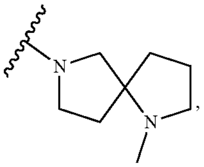
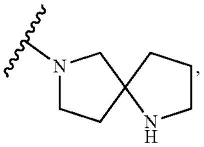
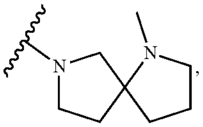
or
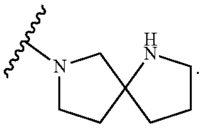
In an embodiment of a compound of Formula I or a pharmaceutically acceptable salt thereof, $R_4$ is a N-linked cyclic amine selected from
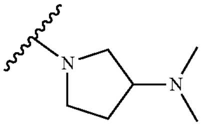
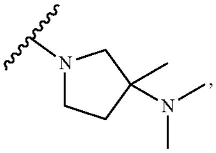
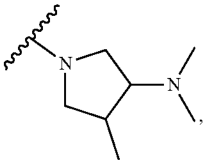
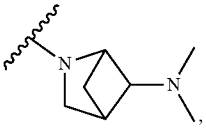
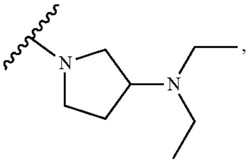
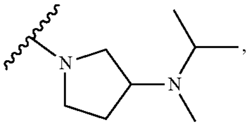
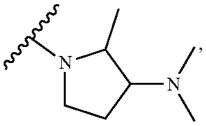
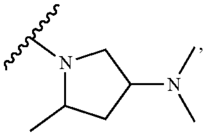
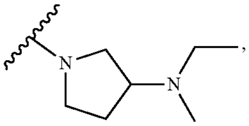
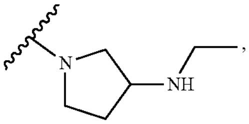
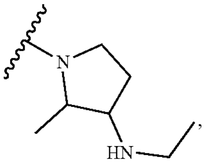
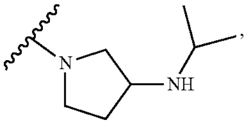
-continued
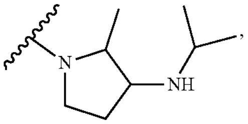
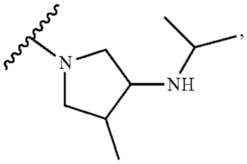
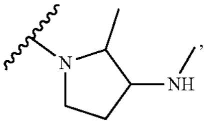
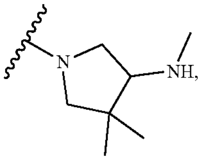
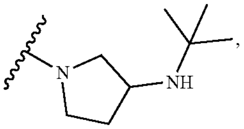
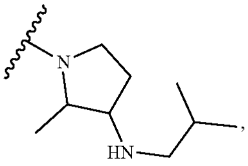
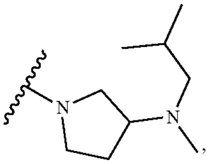
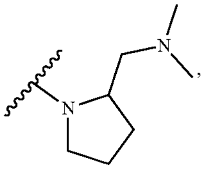
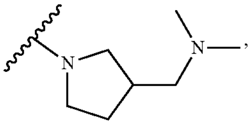
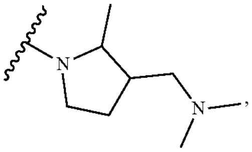
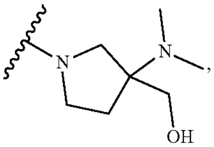
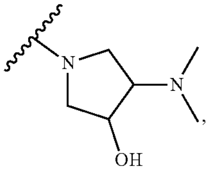
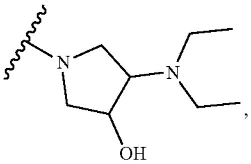
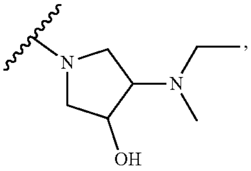
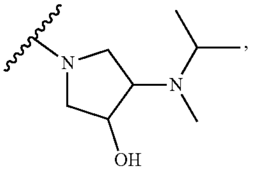
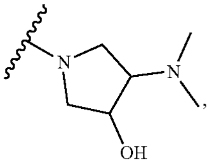

-continued
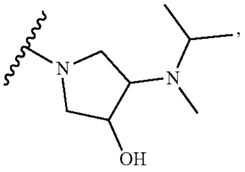
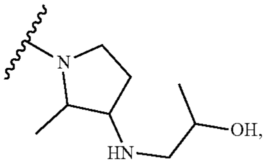
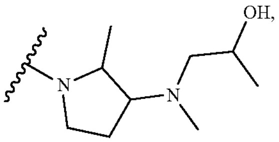
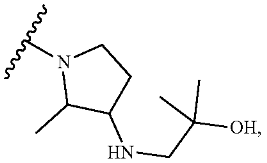
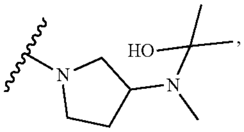
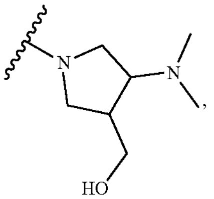
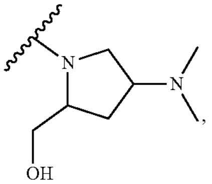
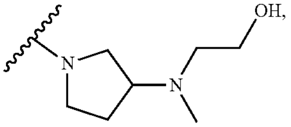
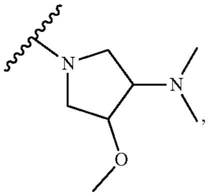
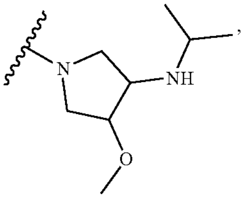
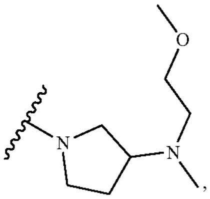
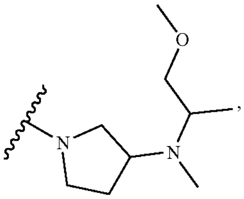
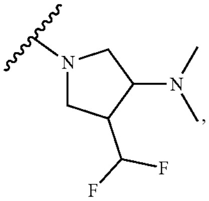
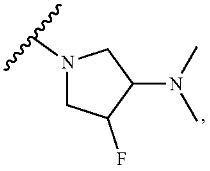
-continued
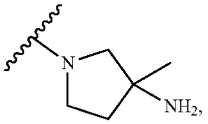
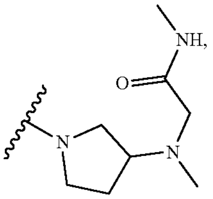
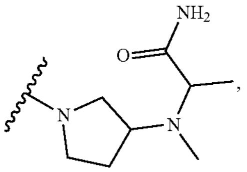
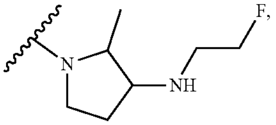
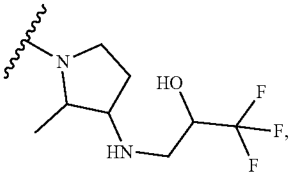
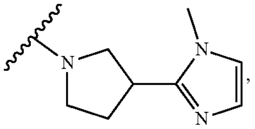
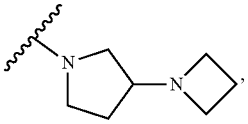
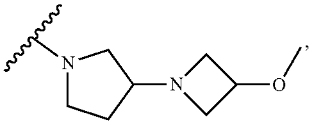
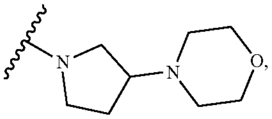
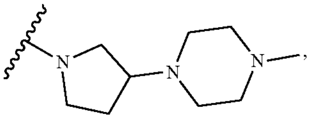
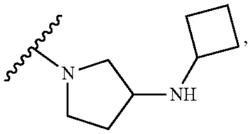
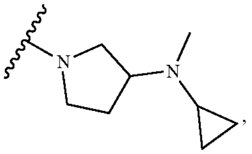
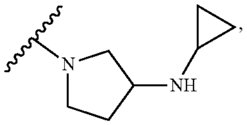
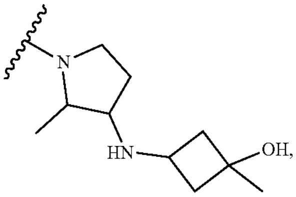
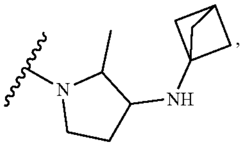

-continued
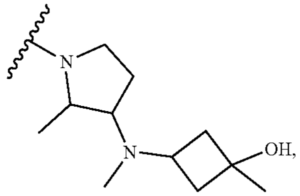
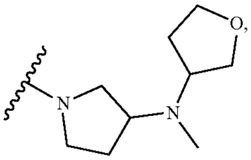
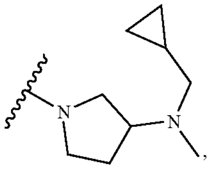
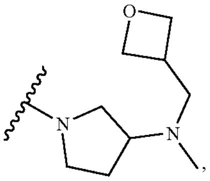
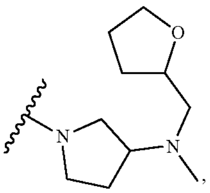
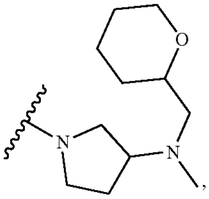
or
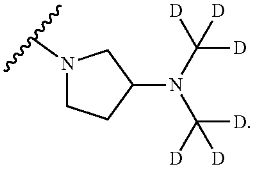
In an embodiment of a compound of Formula I or a pharmaceutically acceptable salt thereof, $R_4$ is a N-linked cyclic amine selected from
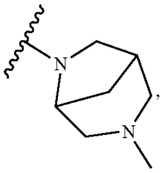
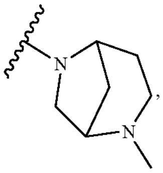
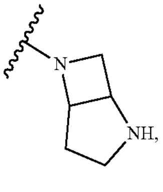
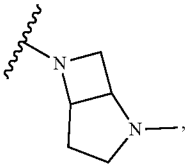
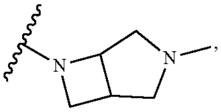
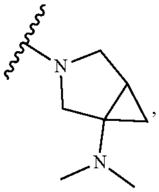
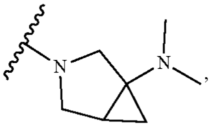
-continued
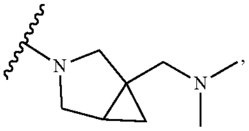
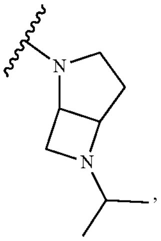
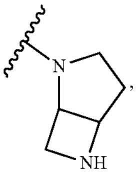
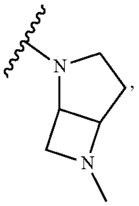
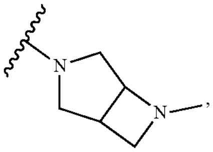
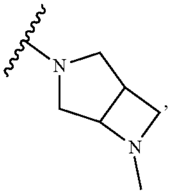
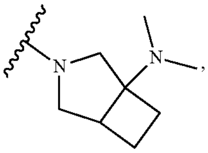
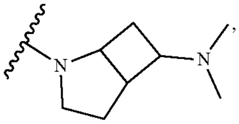
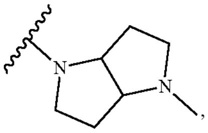
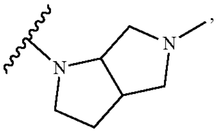
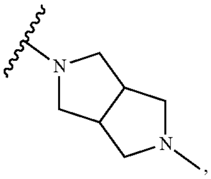
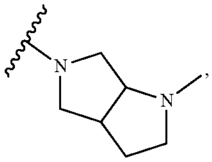
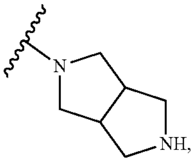
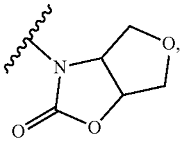
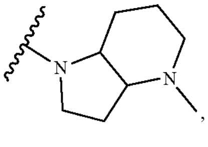
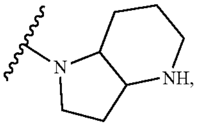

-continued
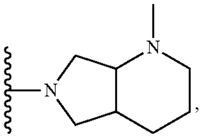,
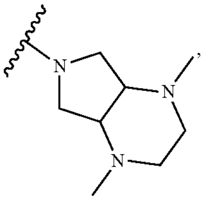,
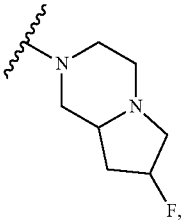
or
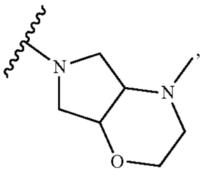,
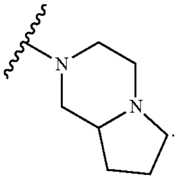.
In an embodiment of a compound of Formula I or a pharmaceutically acceptable salt thereof, $R_4$ is a N-linked cyclic amine selected from
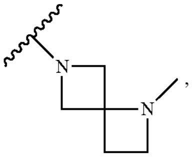,
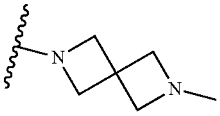,
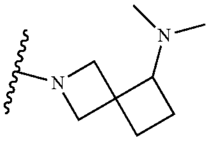,
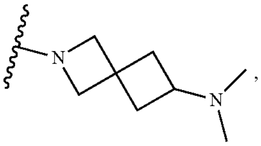,
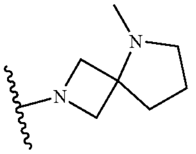,
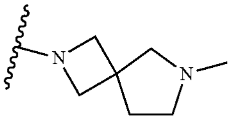,
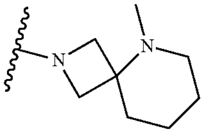,
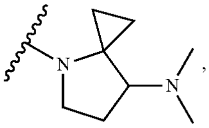,
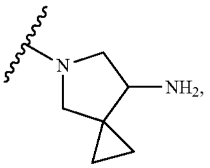
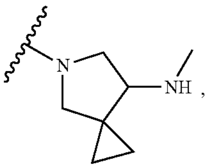,
-continued
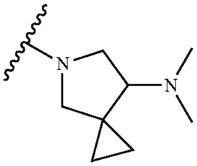,
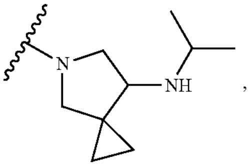,
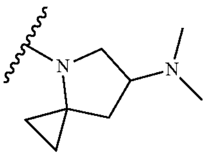,
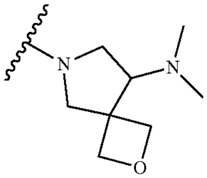,
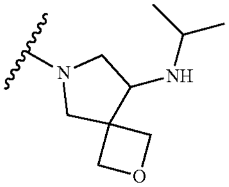,
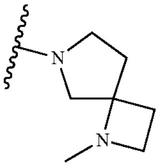,
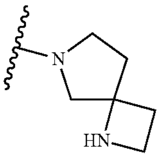,
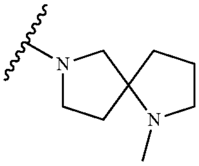,
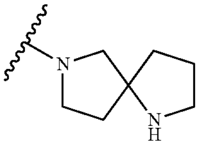,
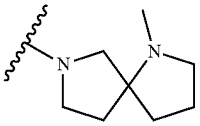,
or
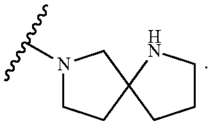.
In an embodiment of a compound of Formula I or a pharmaceutically acceptable salt thereof, $R_4$ is selected from
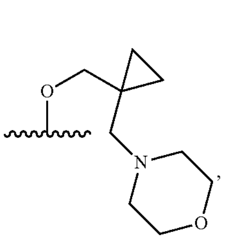,
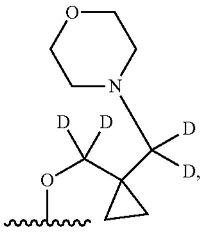
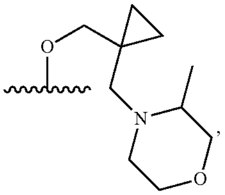,
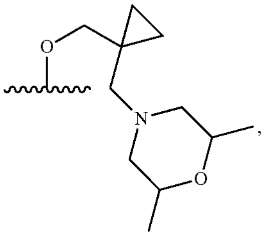, -continued
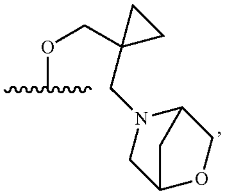
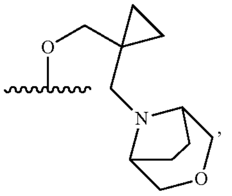
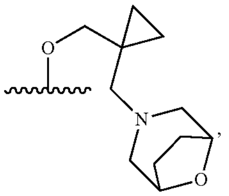
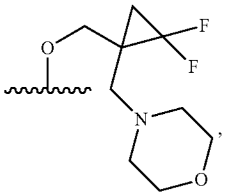
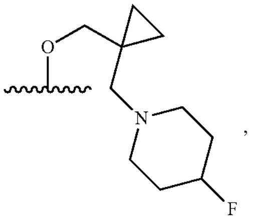
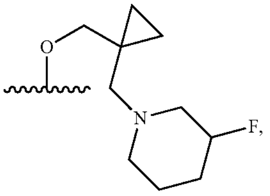
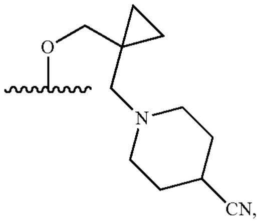
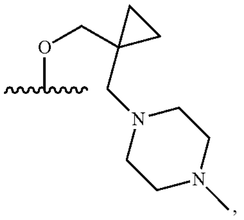
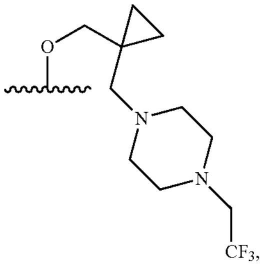
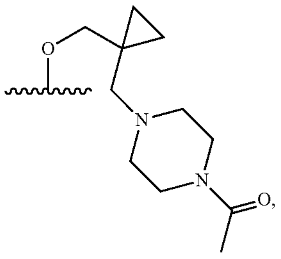
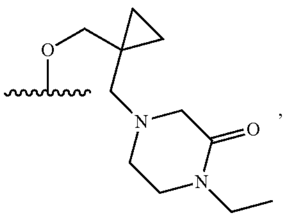
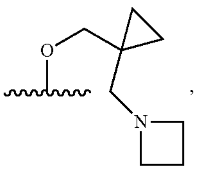
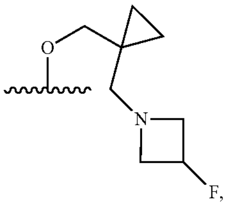
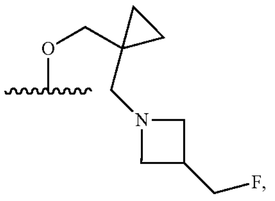
-continued
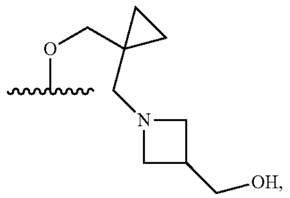
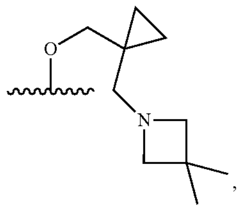
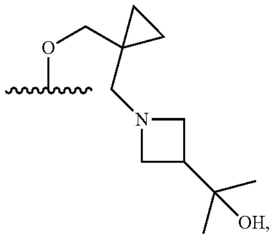
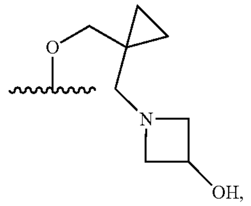
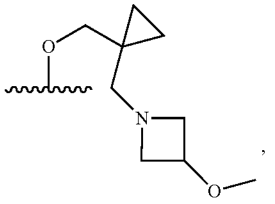
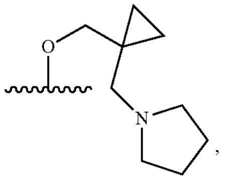
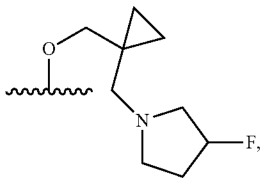
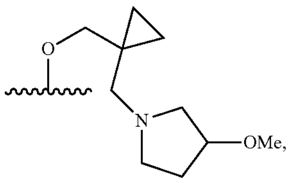
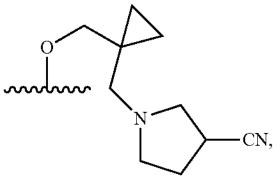
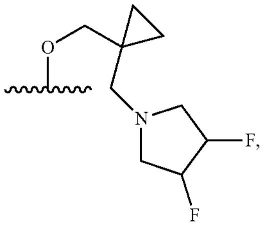
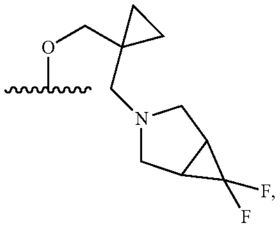
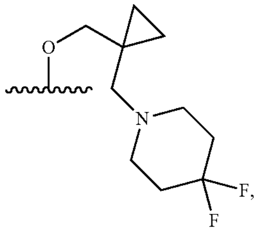
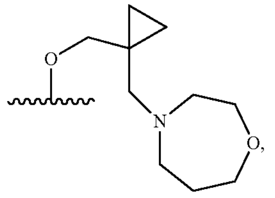
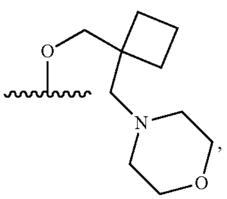
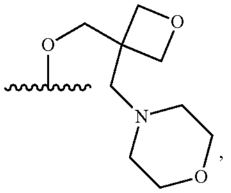
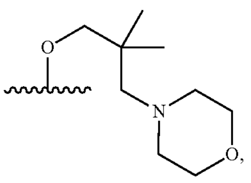

-continued
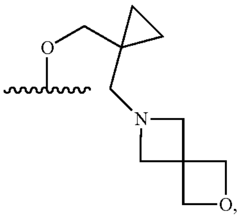
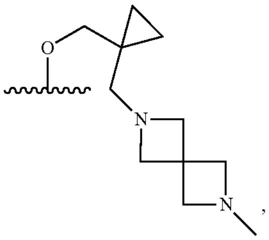
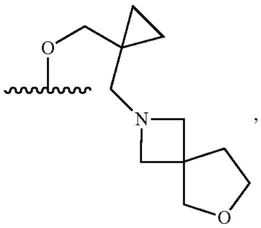
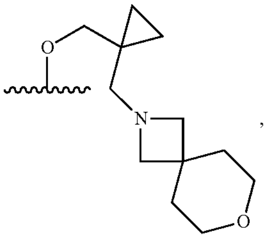
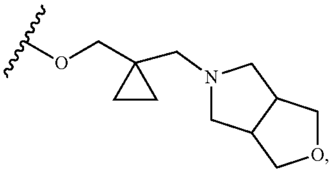
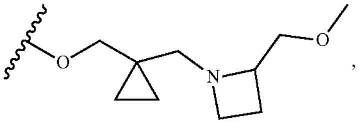
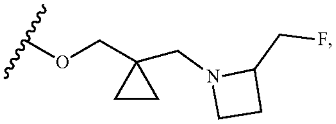
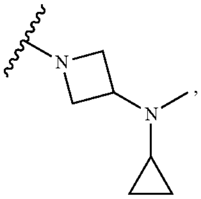
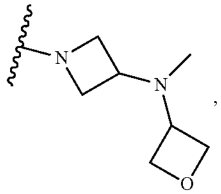
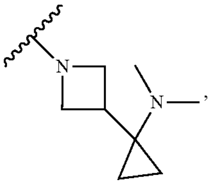
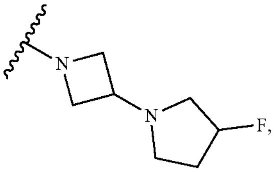
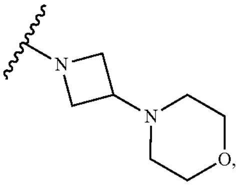
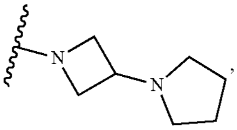
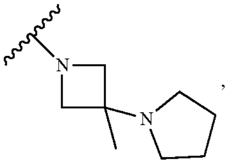
-continued
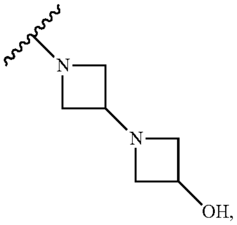
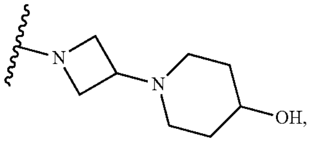
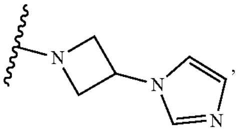
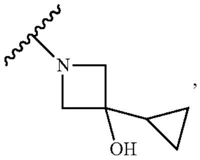
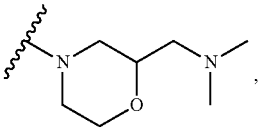
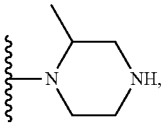
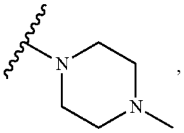
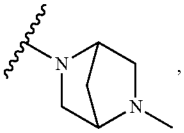
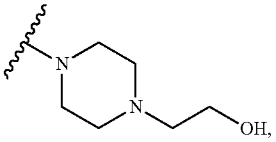
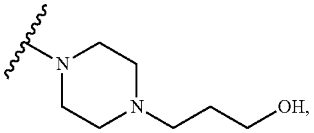
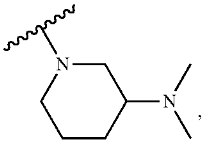
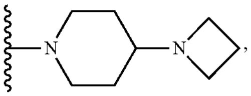
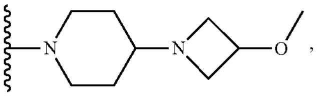
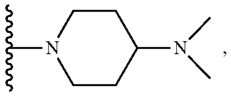
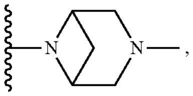
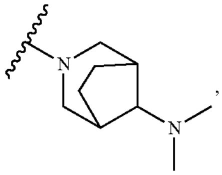
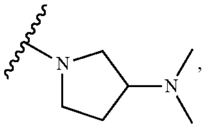
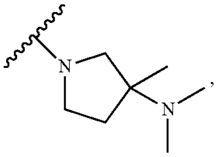
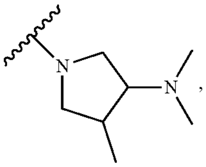
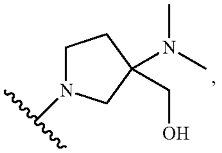
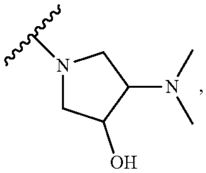

-continued
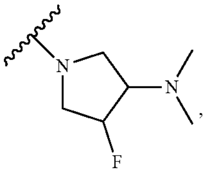,
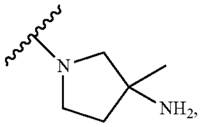,
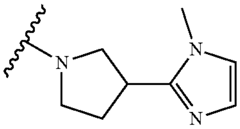,
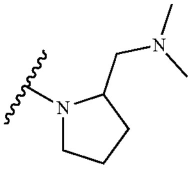,
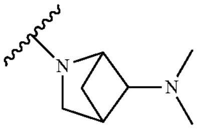,
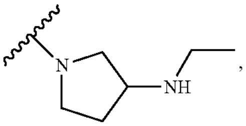,
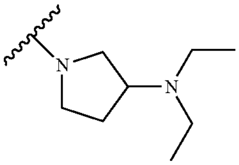,
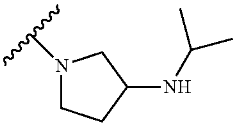,
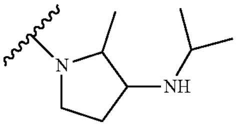,
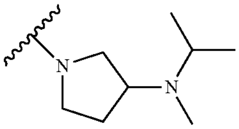,
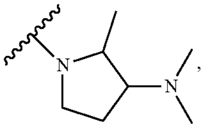,
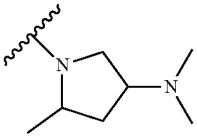,
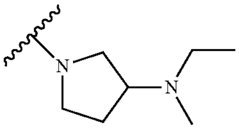,
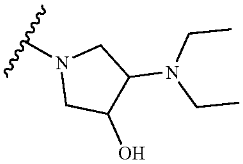,
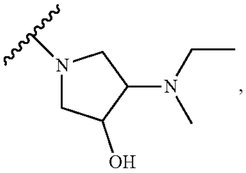,
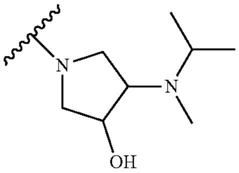,
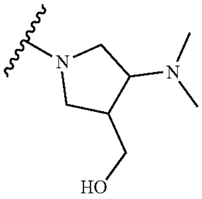,
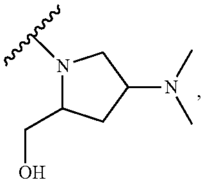,
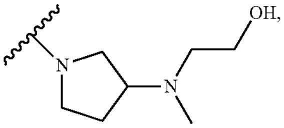,
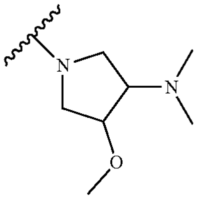,
-continued
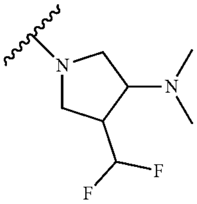,
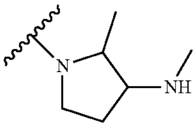,
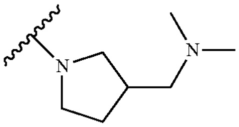,
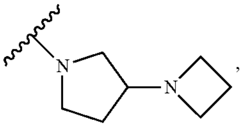,
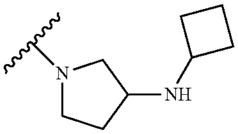,
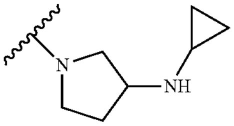,
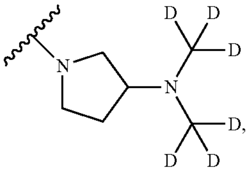,
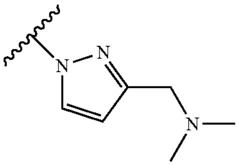,
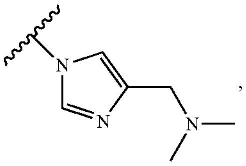,
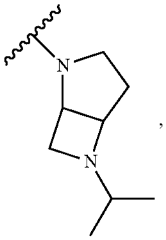,
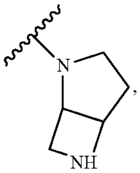,
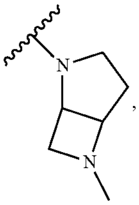,
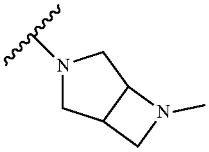,
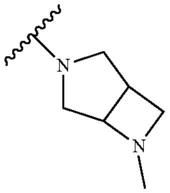,
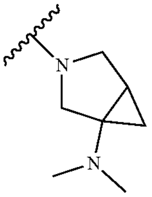,
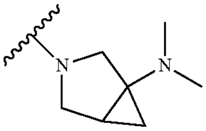,
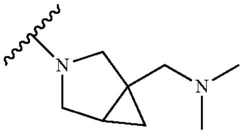,
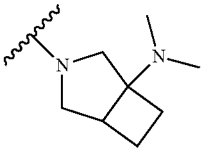,
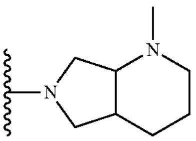, -continued
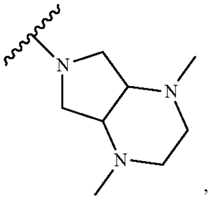
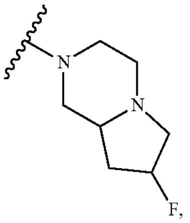
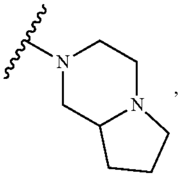
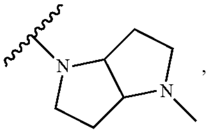
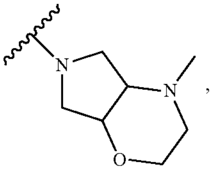
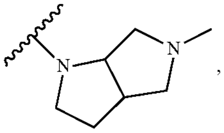
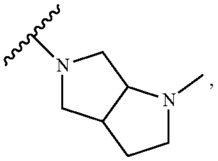
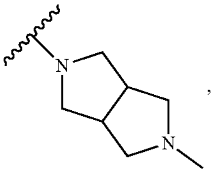
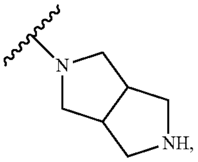
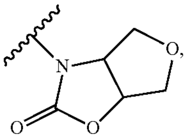
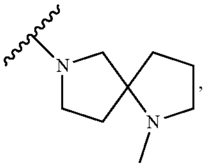
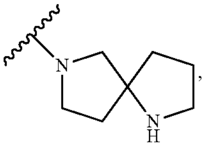
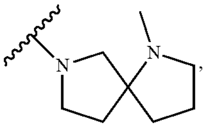
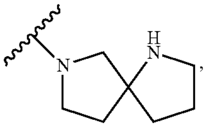
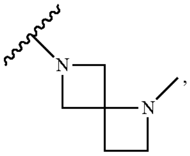
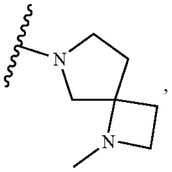
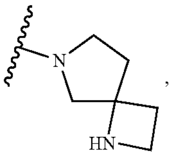
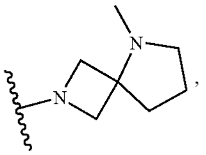
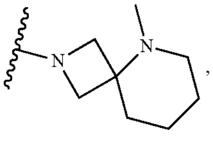
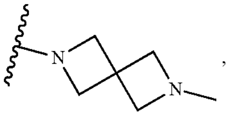
-continued
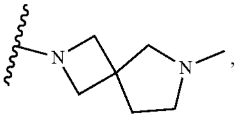
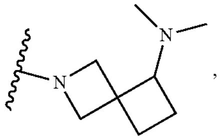
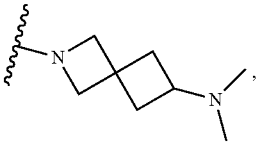
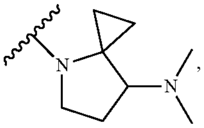
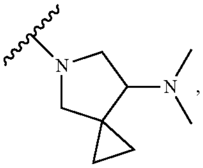
or
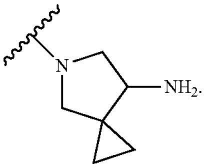
In an embodiment of a compound of Formula I or a pharmaceutically acceptable salt thereof, $R_4$ is selected from
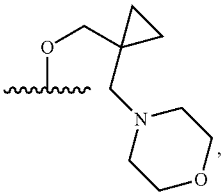
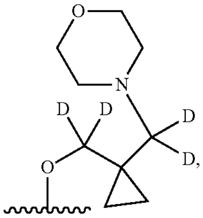
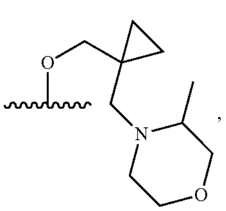
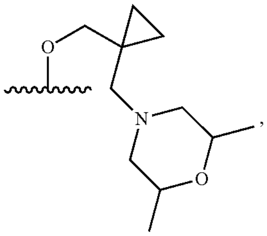
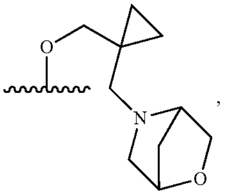
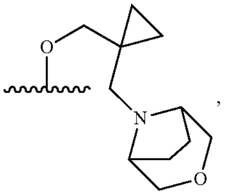
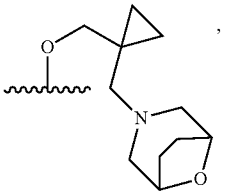
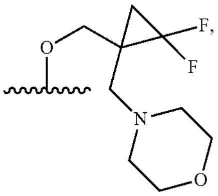
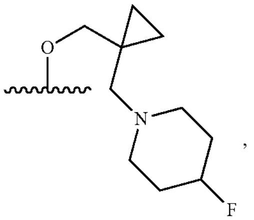
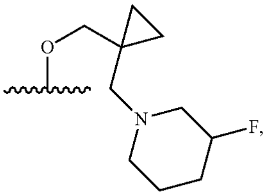

-continued
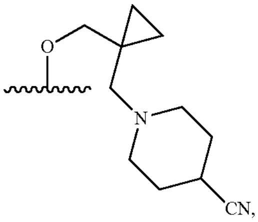
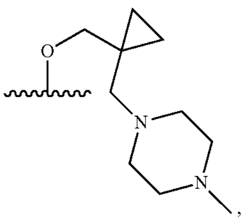
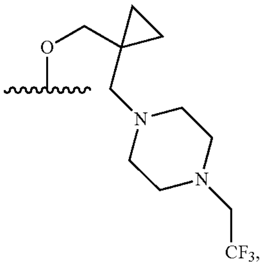
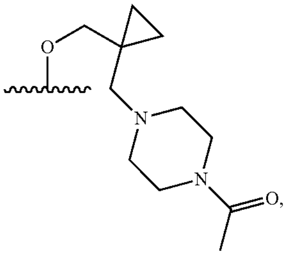
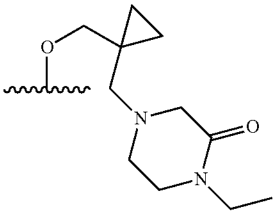
,
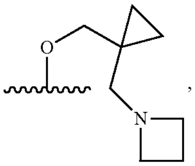
,
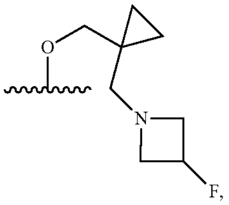
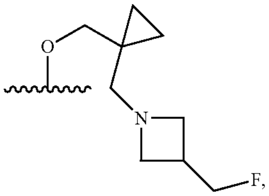
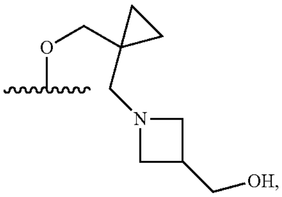
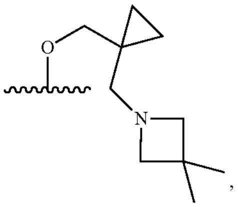
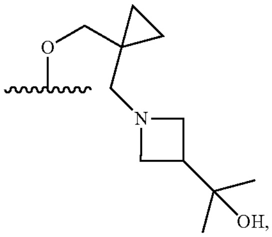
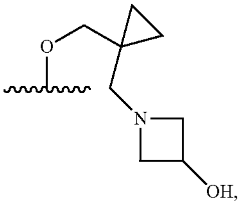
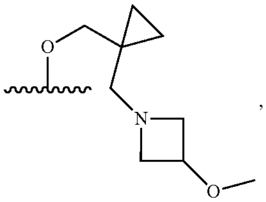
,
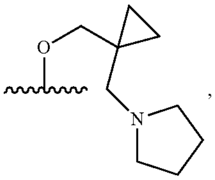
,
-continued
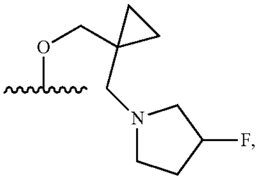
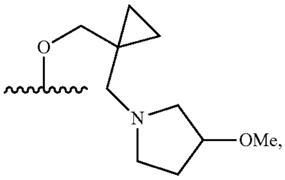
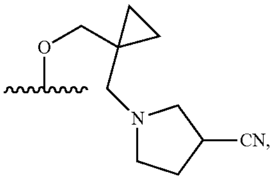
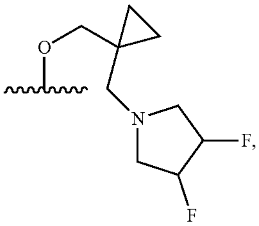
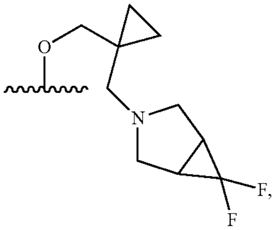
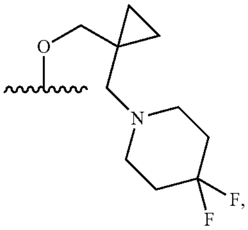
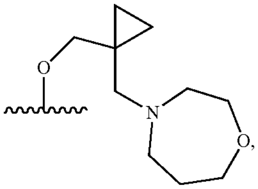
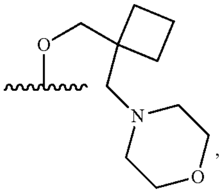
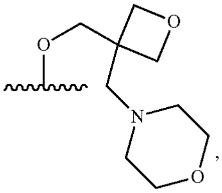
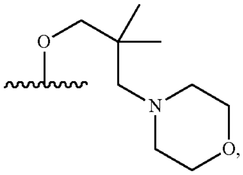
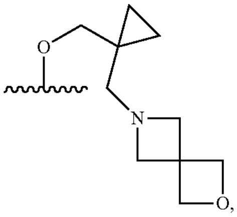
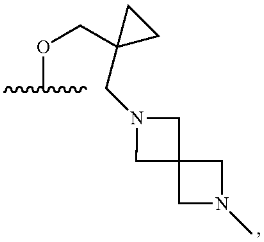
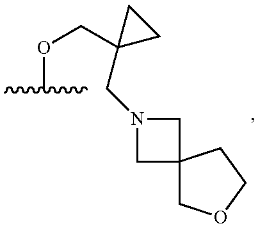
,
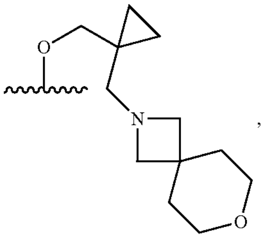
,
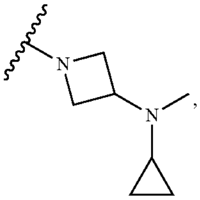
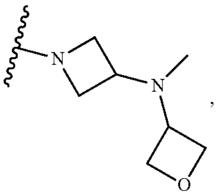

-continued
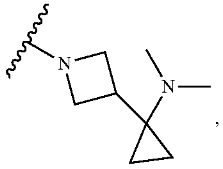
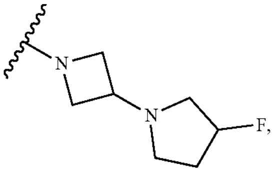
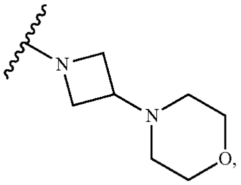
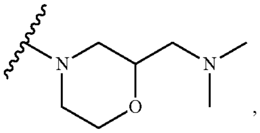
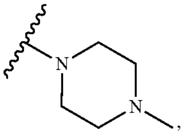
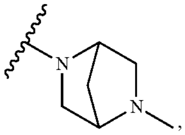
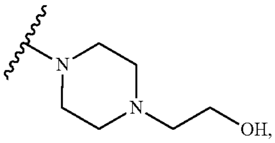
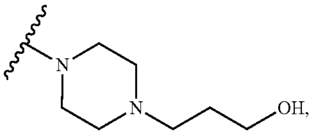
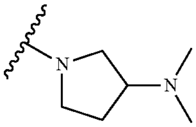
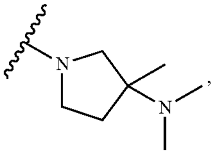
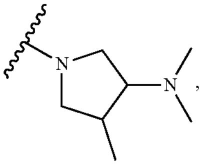
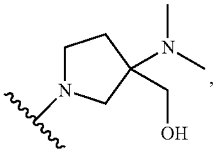
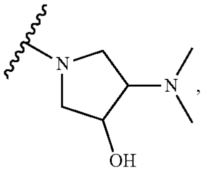
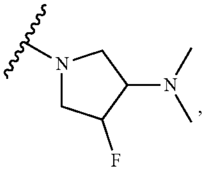
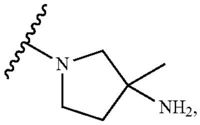
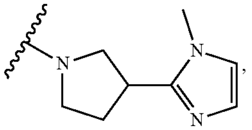
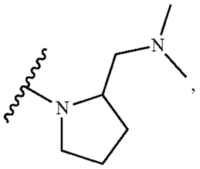
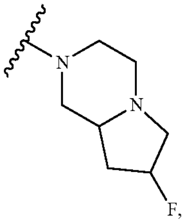
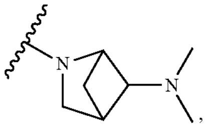
-continued
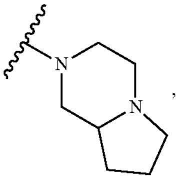
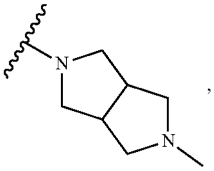
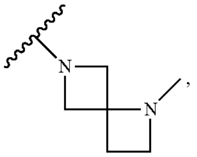
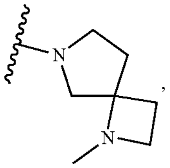
or
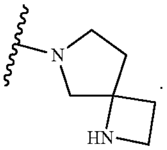
In an embodiment of a compound of Formula I or a pharmaceutically acceptable salt thereof, $R_4$ is a N-linked cyclic amine selected from
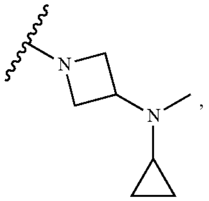
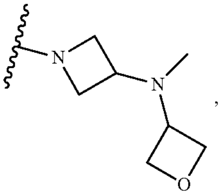
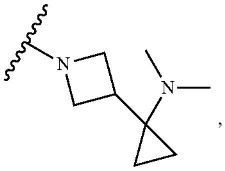
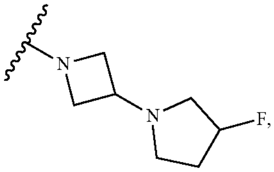
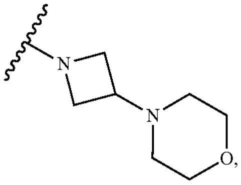
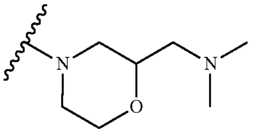
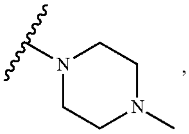
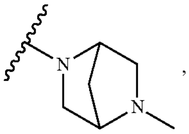
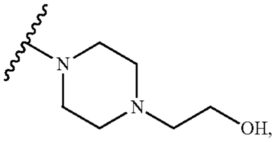
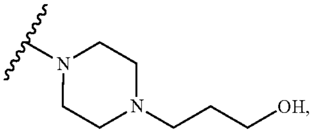
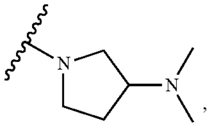

-continued

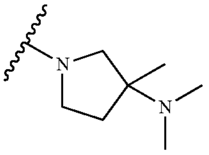,
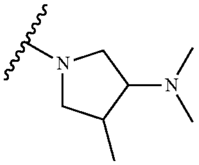,

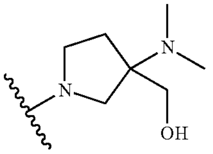,
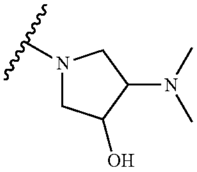,

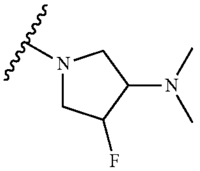,
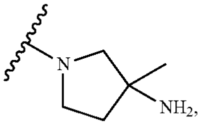

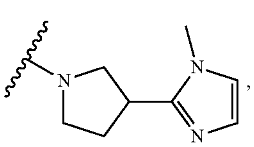,
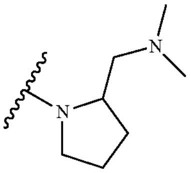,

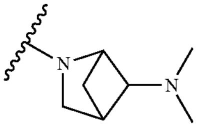,
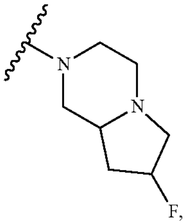

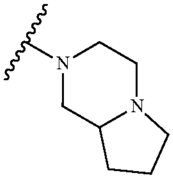,
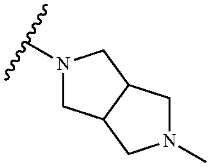,

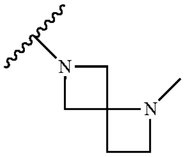,
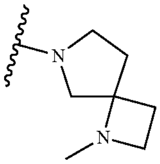, or

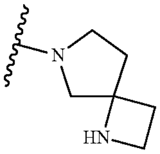.

In an embodiment of a compound of Formula I or a pharmaceutically acceptable salt thereof, $R_4$ is a N-linked cyclic amine selected from

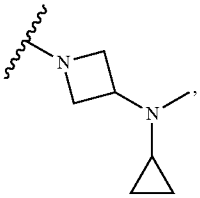
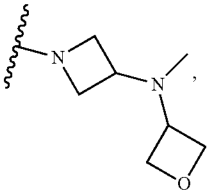

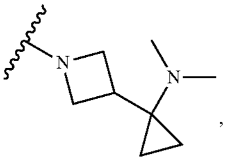,
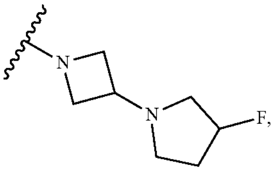 or

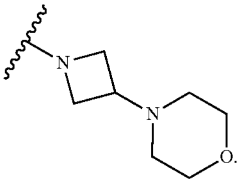

In an embodiment of a compound of Formula I or a pharmaceutically acceptable salt thereof, $R_4$ is a N-linked cyclic amine selected from

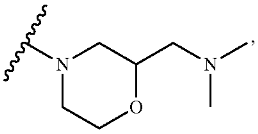
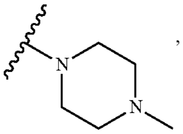,

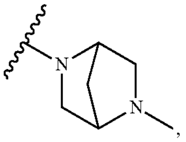
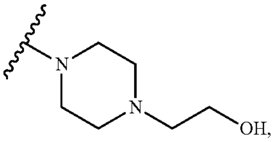 or

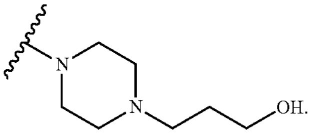

In an embodiment of a compound of Formula I or a pharmaceutically acceptable salt thereof, $R_4$ is a N-linked cyclic amine selected from

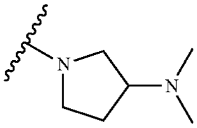
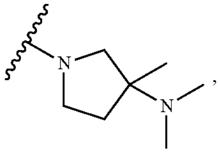

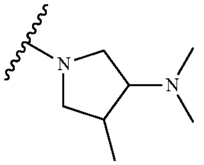,
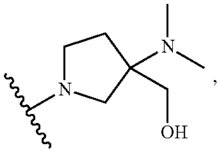,

-continued

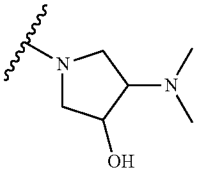, 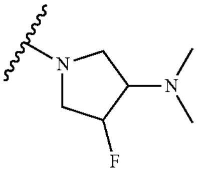,

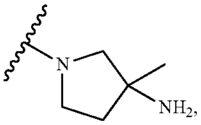 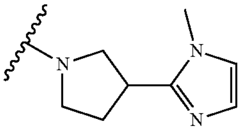,

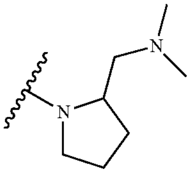, or 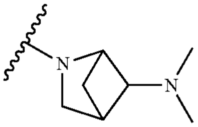.

In an embodiment of a compound of Formula I or a pharmaceutically acceptable salt thereof, $R_4$ is a N-linked cyclic amine selected from

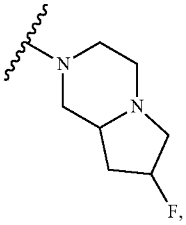 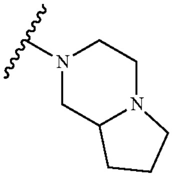,

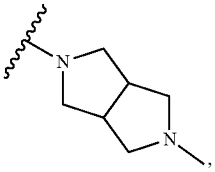 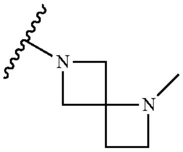,

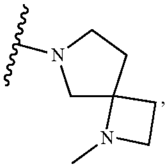, or 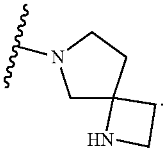.

In an embodiment of a compound of Formula I or a pharmaceutically acceptable salt thereof, $R_4$ is a N-linked cyclic amine selected from

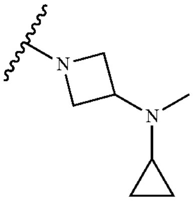, 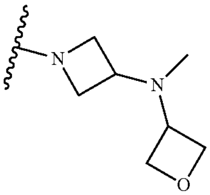,

-continued

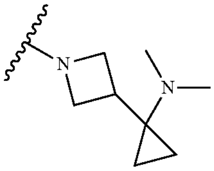, 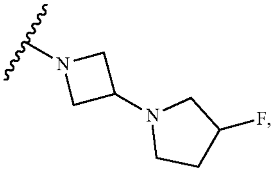

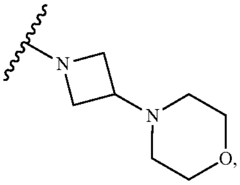 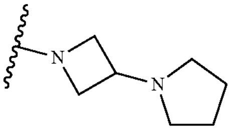,

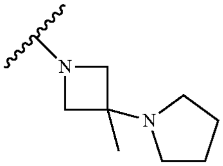, 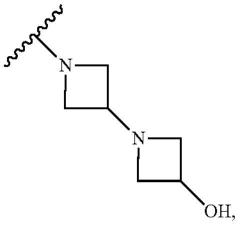

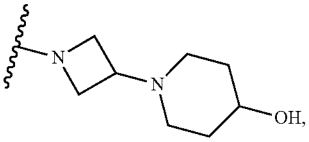

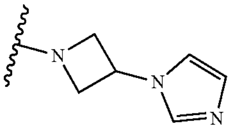, or 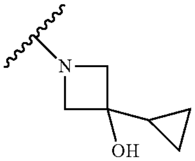.

In an embodiment of a compound of Formula I or a pharmaceutically acceptable salt thereof, $R_4$ is a N-linked cyclic amine selected from

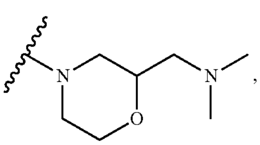, 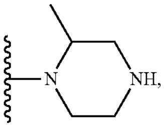

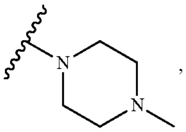, 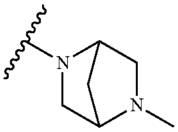,

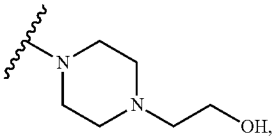

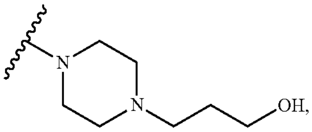 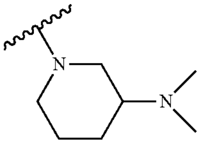,

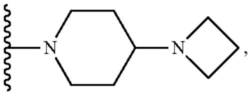

-continued

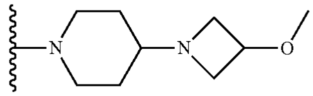, 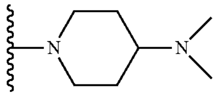,

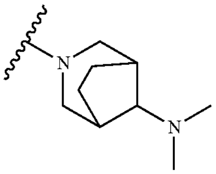, or 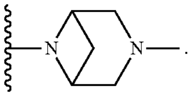.

In an embodiment of a compound of Formula I or a pharmaceutically acceptable salt thereof, $R_4$ is a N-linked cyclic amine selected from

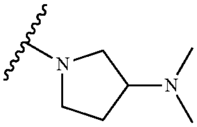, 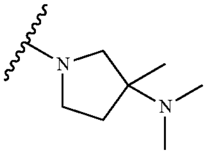,

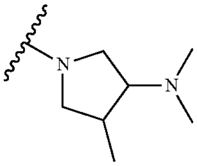, 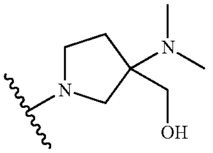,

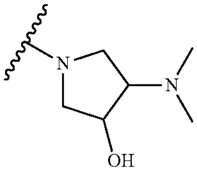, 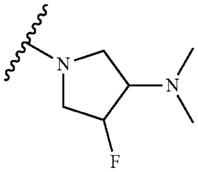,

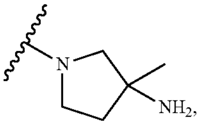 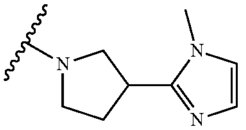,

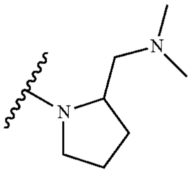, 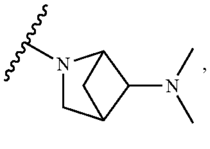,

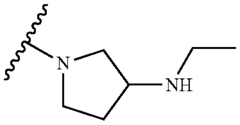, 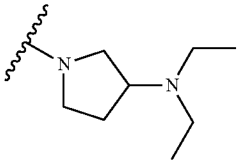,

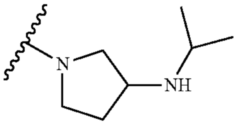, 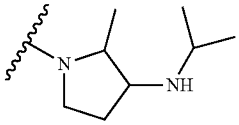,

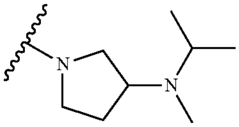, 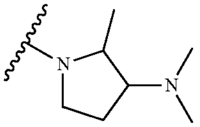,

-continued

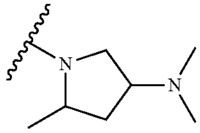, 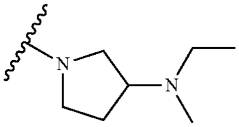,

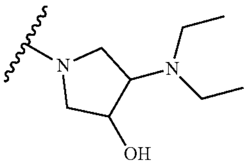, 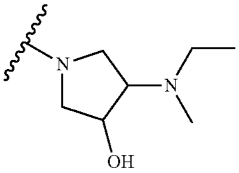,

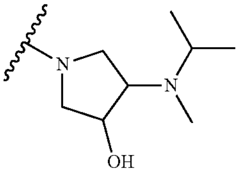, 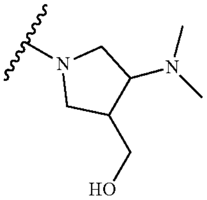,

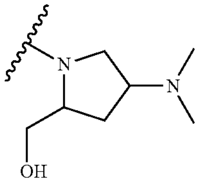, 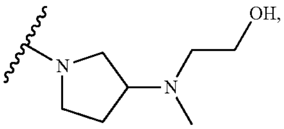

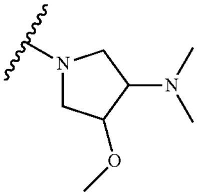, 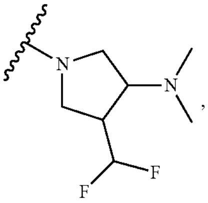,

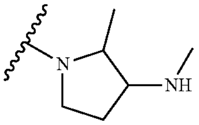, 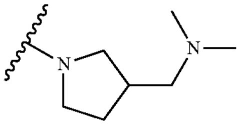,

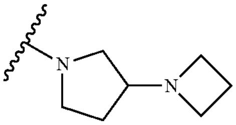, 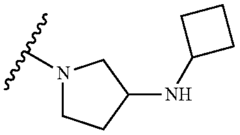,

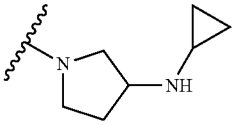, or 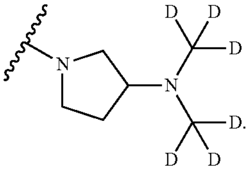.

In an embodiment of a compound of Formula I or a pharmaceutically acceptable salt thereof, $R_4$ is a N-linked cyclic amine selected from

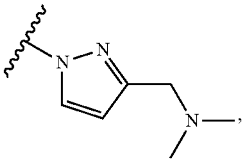, or 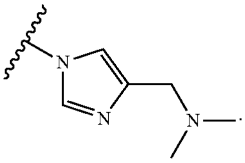.

In an embodiment of a compound of Formula I or a pharmaceutically acceptable salt thereof, $R_4$ is a N-linked cyclic amine selected from

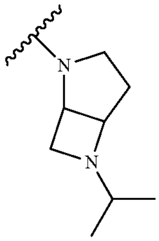,
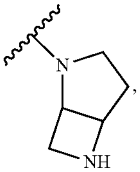,
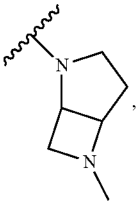,
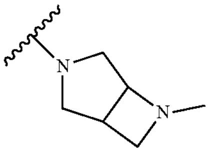,
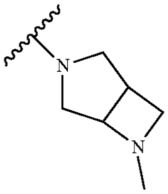,
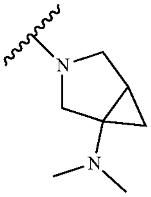,
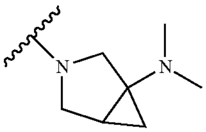,
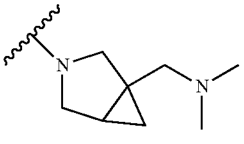,
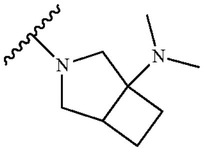,
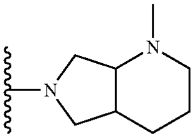,
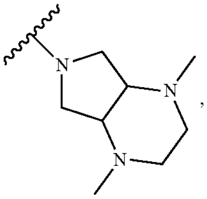,
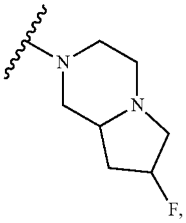
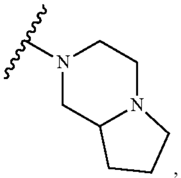,
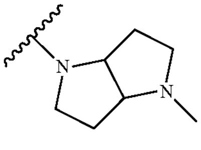,
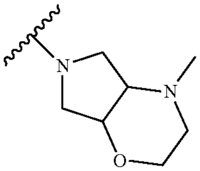,
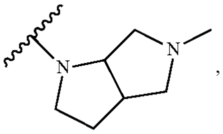,
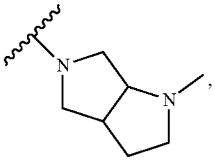,
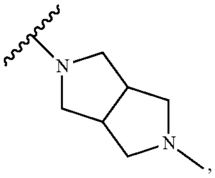
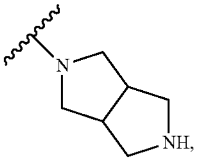
-continued
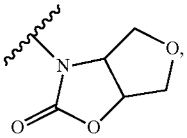
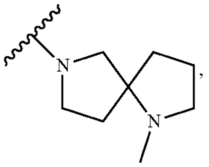,
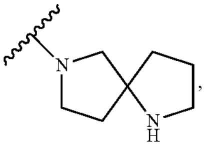,
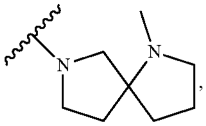,
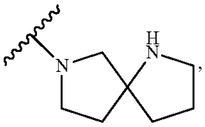,
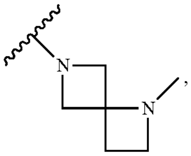
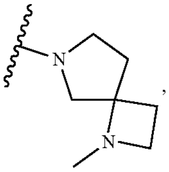,
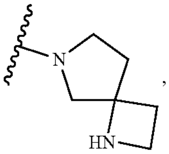,
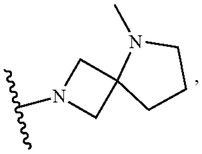,
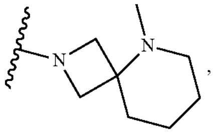,
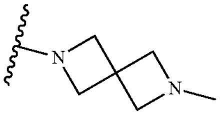,
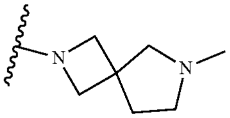,
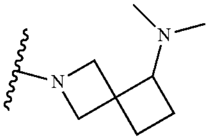,
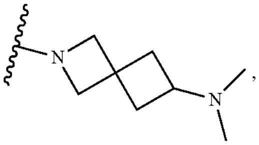,
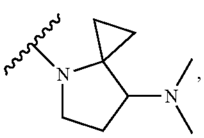
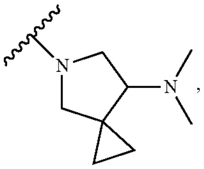, or
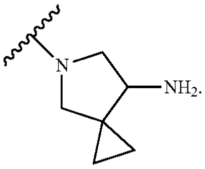
In an embodiment of a compound of Formula I, or a pharmaceutically acceptable salt thereof, wherein $R_4$ is a group of the formula

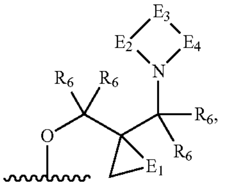

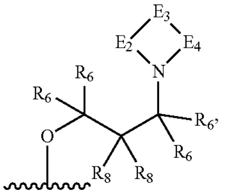

or

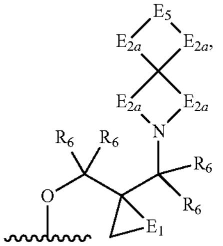

a) A is —C(H)—, Z is —C(F)—, G is —N—, and $R_2$ is F, and $R_1$ is H;

b) A is —N—, Z is —C(F)—, G is —N—, $R_2$ is F, and $R_1$ is H;

c) A is —C(H)—, Z is —C(H)—, G is —N—, $R_2$ is F, and $R_1$ is H;

d) A is —N—, Z is —C(H)—, G is —N—, $R_2$ is F, and $R_1$ is H;

e) A is —C(H)—, Z is —N—, G is —N—, $R_2$ is F, and $R_1$ is H;

f) A is —N—, Z is —N—, G is —N—, $R_2$ is F, and $R_1$ is H;

g) A is —C(H)—, Z is —C(F)—, G is —C(H)—, $R_2$ is F, and $R_1$ is H;

h) A is —N—, Z is —C(F)—, G is —C(H)—, $R_2$ is F, and $R_1$ is H;

i) A is —C(H)—, Z is —C(H)—, G is —C(H)—, $R_2$ is F, and $R_1$ is H;

j) A is —N—, Z is —C(H)—, G is —C(H)—, $R_2$ is F, and $R_1$ is H;

k) A is —C(H)—, Z is —N—, G is —C(H)—, $R_2$ is F, and $R_1$ is H;

l) A is —N—, Z is —N—, G is —C(H)—, $R_2$ is F, and $R_1$ is H;

m) A is —C(H)—, Z is —C(F)—, G is —C(F)—, $R_2$ is F, and $R_1$ is H;

n) A is —N—, Z is —C(F)—, G is —C(F)—, $R_2$ is F, and $R_1$ is H;

o) A is —C(H)—, Z is —C(H)—, G is —C(F)—, $R_2$ is F, and $R_1$ is H;

p) A is —N—, Z is —C(H)—, G is —C(F)—, $R_2$ is F, and $R_1$ is H;

q) A is —C(H)—, Z is —N—, G is —C(F)—, $R_2$ is F, and $R_1$ is H;

r) A is —N—, Z is —N—, G is —C(F)—, $R_2$ is F, and $R_1$ is H;

s) A is —C(H)—, Z is —C(F)—, G is —N—, $R_2$ is Cl, and $R_1$ is H;

t) A is —N—, Z is —C(F)—, G is —N—, $R_2$ is Cl, and $R_1$ is H;

u) A is —C(H)—, Z is —C(H)—, G is —N—, $R_2$ is Cl, and $R_1$ is H;

v) A is —N—, Z is —C(H)—, G is —N—, $R_2$ is Cl, and $R_1$ is H;

w) A is —C(H)—, Z is —N—, G is —N—, $R_2$ is Cl, and $R_1$ is H;

x) A is —N—, Z is —N—, G is —N—, $R_2$ is Cl, and $R_1$ is H;

y) A is —C(H)—, Z is —C(F)—, G is —C(H)—, $R_2$ is Cl, and $R_1$ is H;

z) A is —N—, Z is —C(H)—, G is —C(H)—, $R_2$ is Cl, and $R_1$ is H;

aa) A is —N—, Z is —C(H)—, G is —C(H)—, $R_2$ is Cl, and $R_1$ is H;

bb) A is —C(H)—, Z is —N—, G is —C(H)—, $R_2$ is Cl, and $R_1$ is H;

cc) A is —N—, Z is —N—, G is —C(H)—, $R_2$ is Cl, and $R_1$ is H;

dd) A is —C(H)—, Z is —C(F)—, G is —C(F)—, $R_2$ is Cl, and $R_1$ is H;

ee) A is —N—, Z is —C(F)—, G is —C(F)—, $R_2$ is Cl, and $R_1$ is H;

ff) A is —C(H)—, Z is —C(H)—, G is —C(F)—, $R_2$ is Cl, and $R_1$ is H;

gg) A is —N—, Z is —C(H)—, G is —C(F)—, $R_2$ is Cl, and $R_1$ is H;

hh) A is —C(H)—, Z is —N—, G is —C(F)—, $R_2$ is Cl, and $R_1$ is H; or ii) A is —N—, Z is —N—, G is —C(F)—, $R_2$ is Cl, and $R_1$ is H.

In an embodiment of a compound of Formula I or a pharmaceutically acceptable salt thereof, $R_4$ is selected from

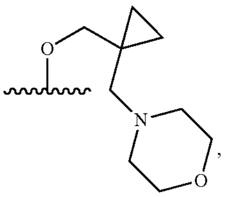

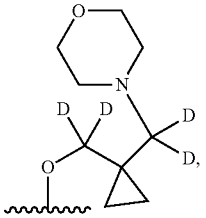

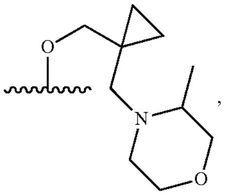

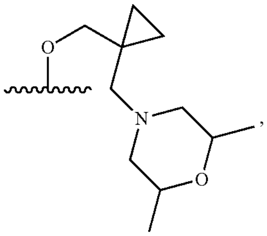

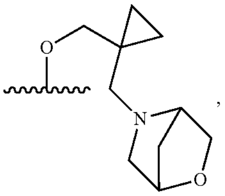

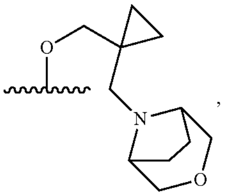

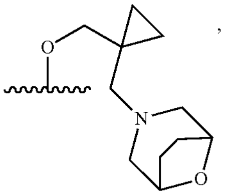

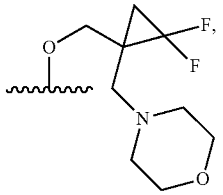

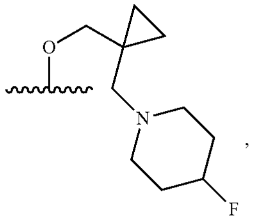

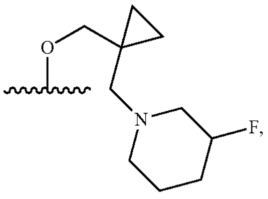

-continued
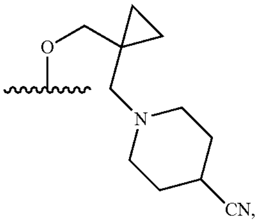
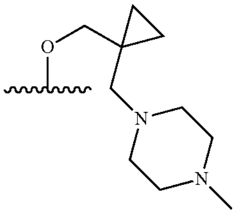
,
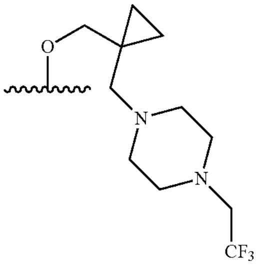
,
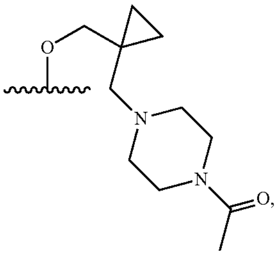
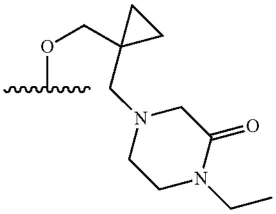
,
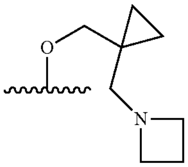
,
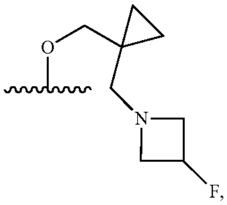
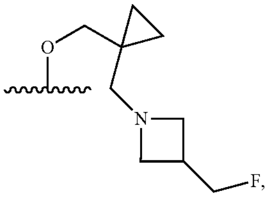
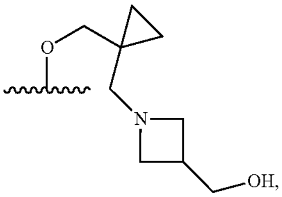
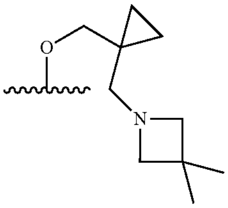
,
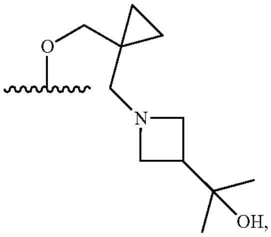
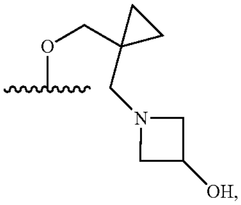
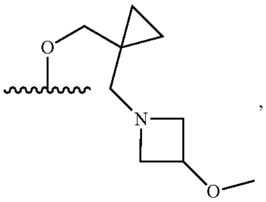
,
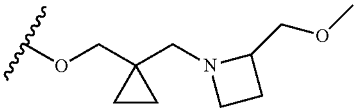
,
-continued
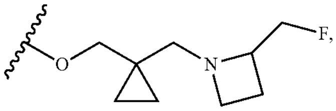
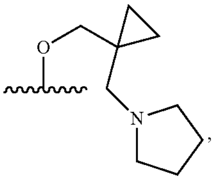
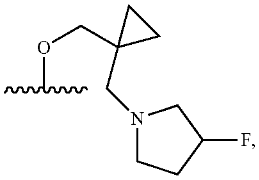
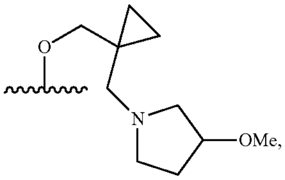
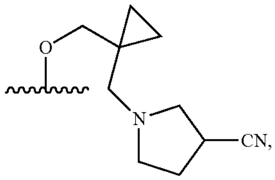
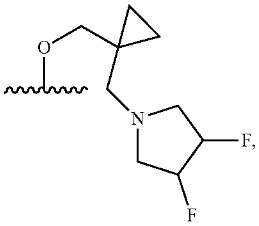
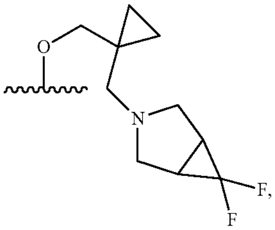
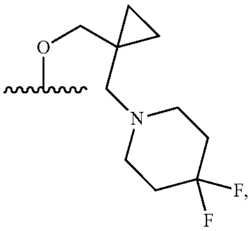
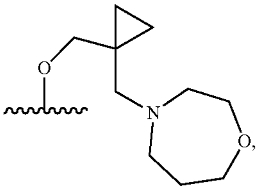
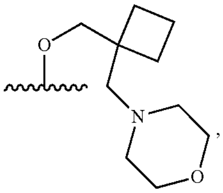
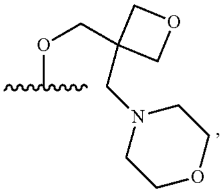
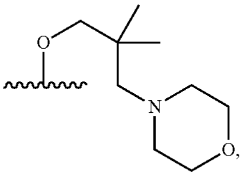
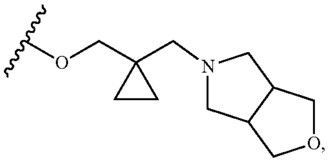

-continued
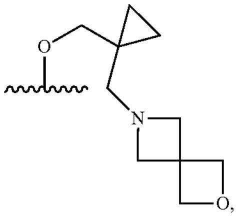
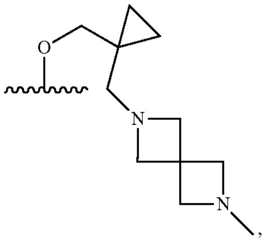
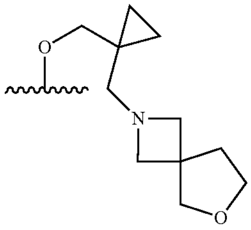
, or
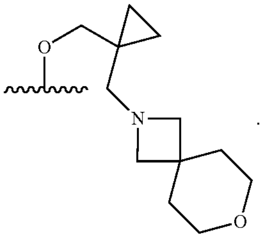
.
In an embodiment of a compound of Formula I or a pharmaceutically acceptable salt thereof, $R_4$ is selected from
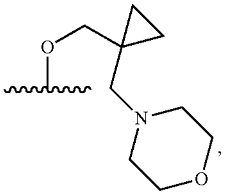
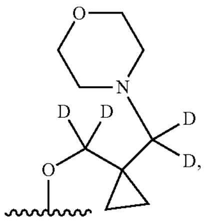
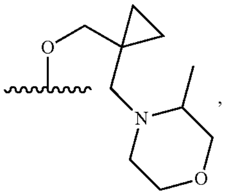
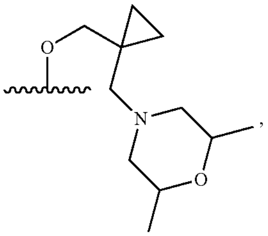
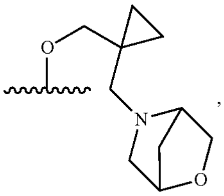
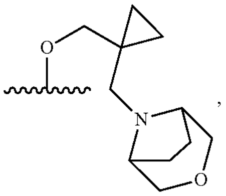
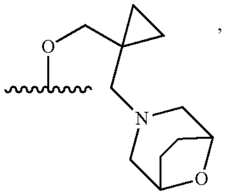
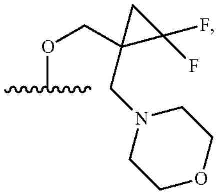
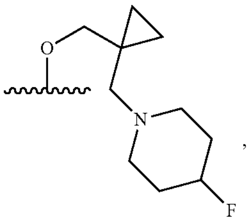
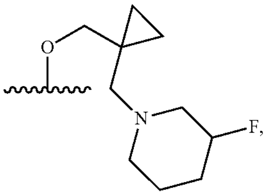
-continued
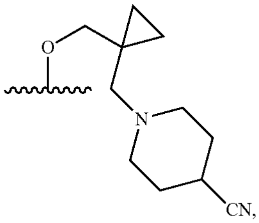
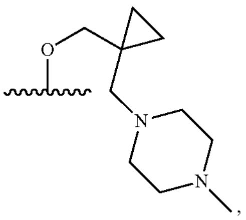
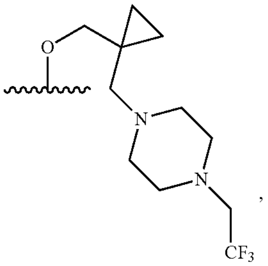
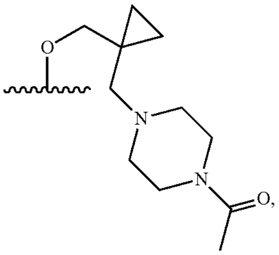
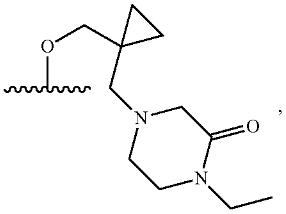
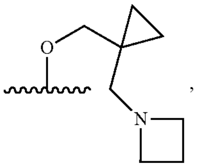
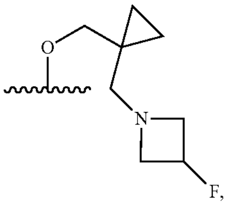
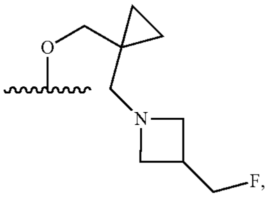
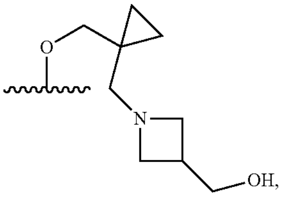
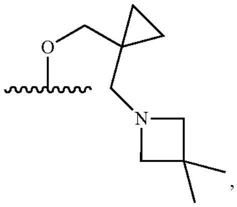
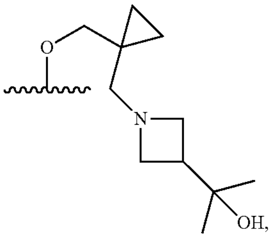
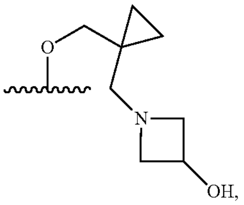
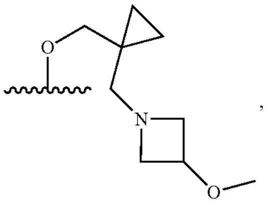
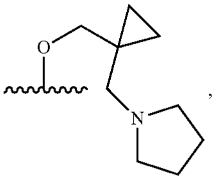

-continued
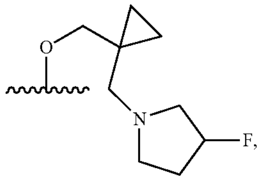
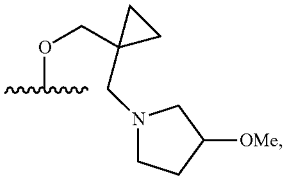
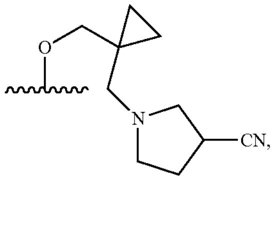
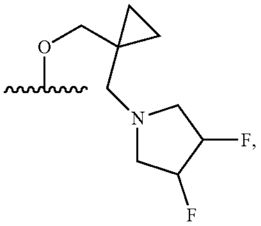
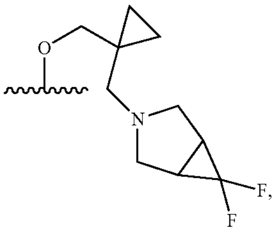
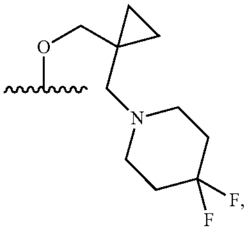
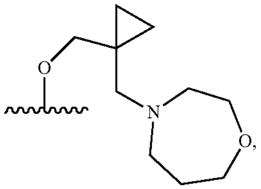
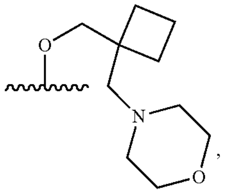
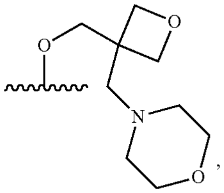
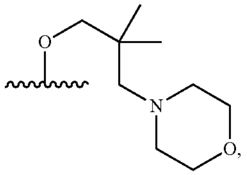
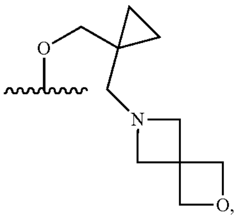
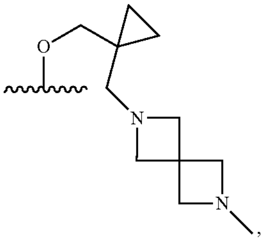
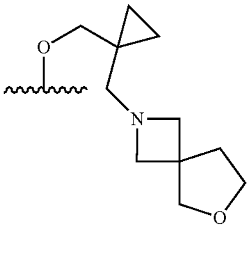
, or
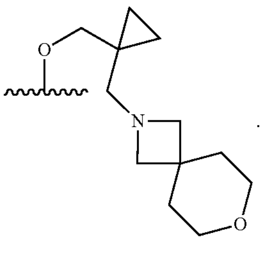
.
In an embodiment of a compound of Formula I or a pharmaceutically acceptable salt thereof, $R_4$ is selected from
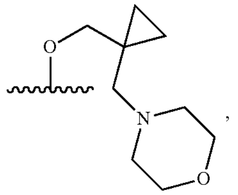
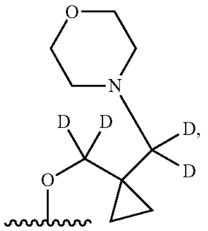
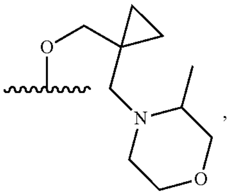
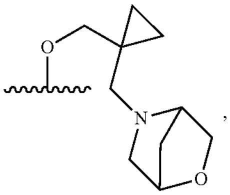
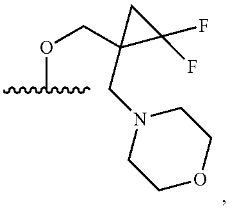
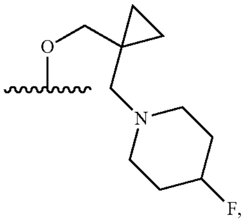
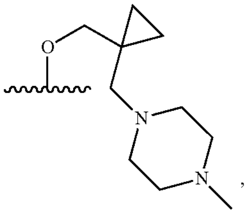
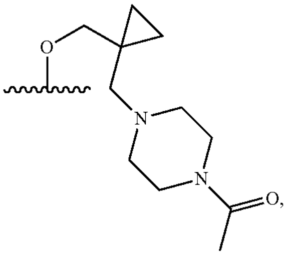
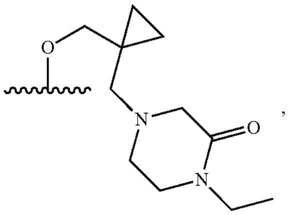
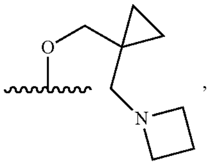
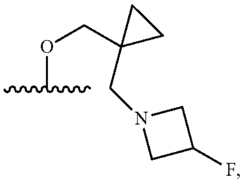
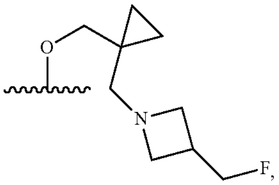
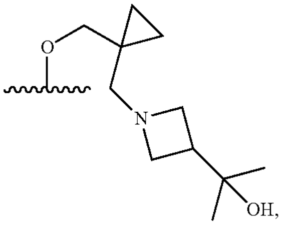
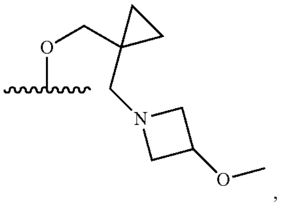

-continued
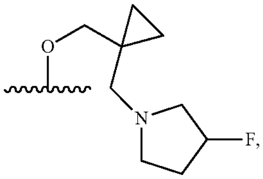
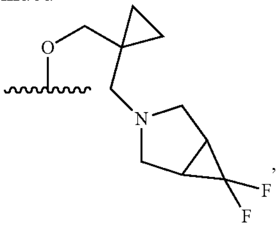
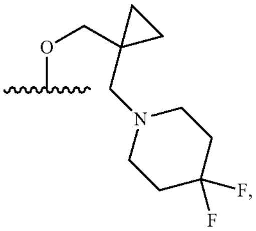
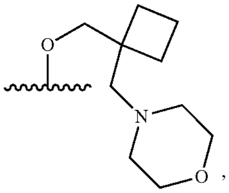
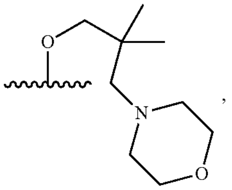
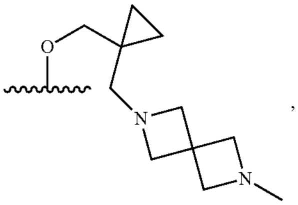
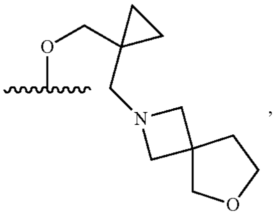
or
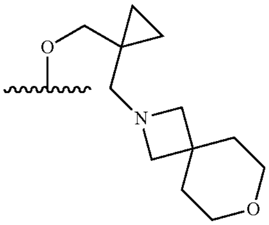
In an embodiment of a compound of Formula I or a pharmaceutically acceptable salt thereof, $R_4$ is
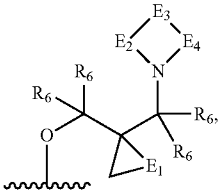
wherein preferably each $R_6$ is H.
In an embodiment of a compound of Formula I or a pharmaceutically acceptable salt thereof, $R_4$ is selected from
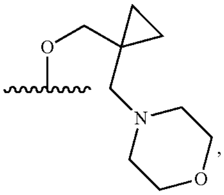
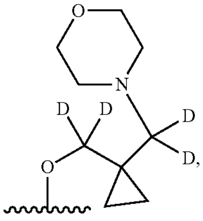
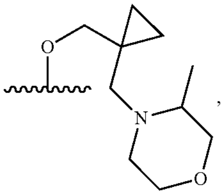
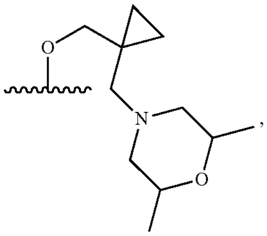
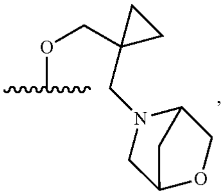
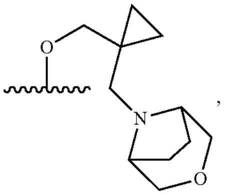
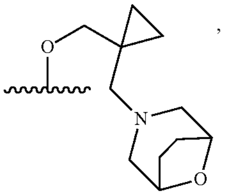
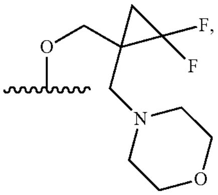
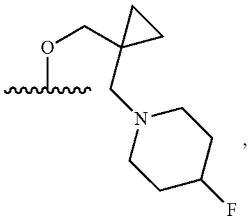
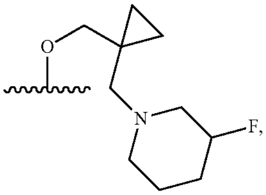
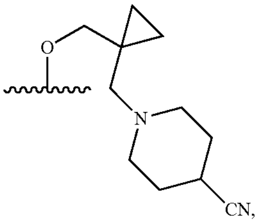
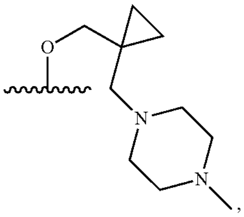
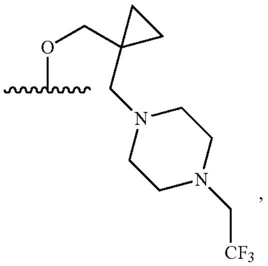
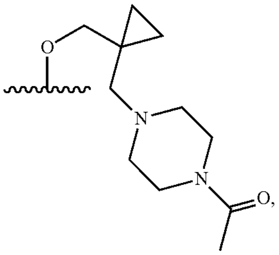

-continued
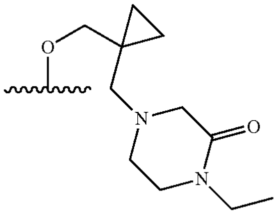,
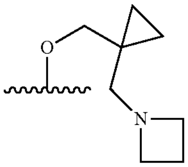,
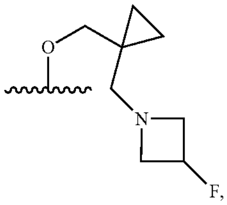
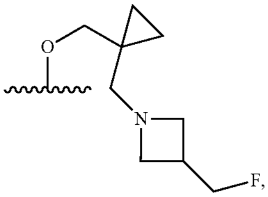
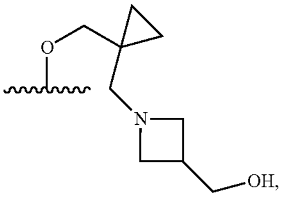
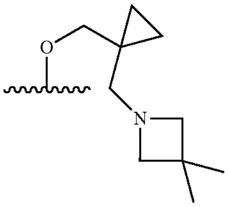,
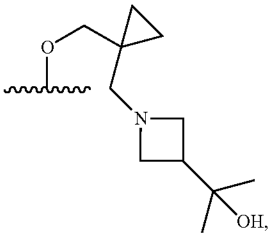
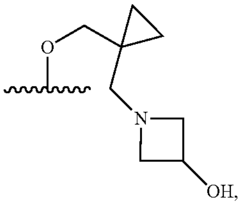
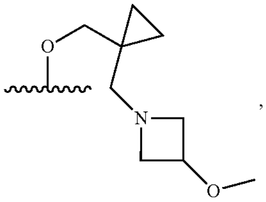,
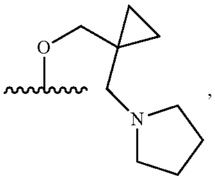,
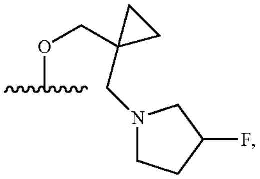
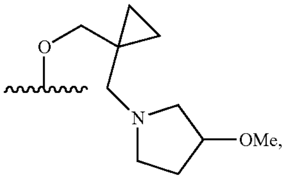
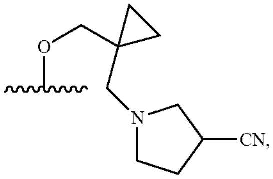
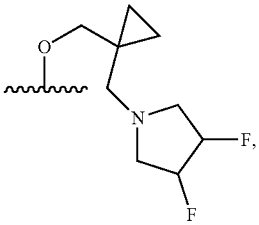
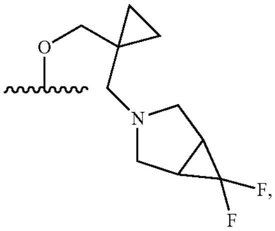
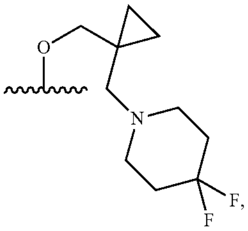
-continued
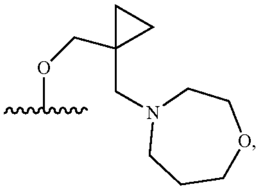
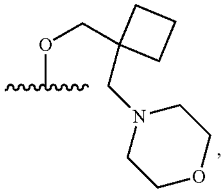 or
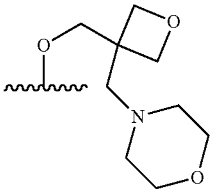.
In an embodiment of a compound of Formula I or a pharmaceutically acceptable salt thereof, $R_4$ is selected from
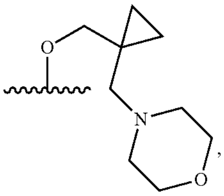
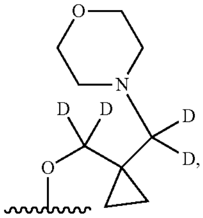
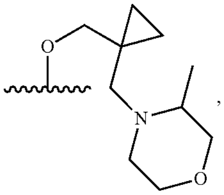,
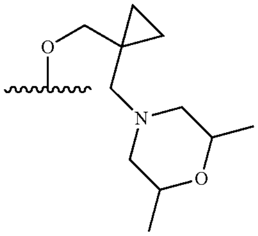,
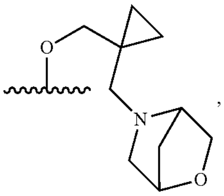,
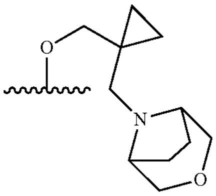,
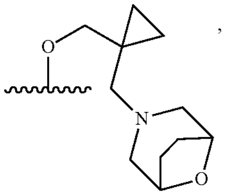,
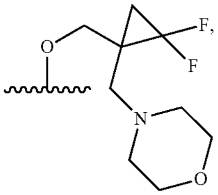
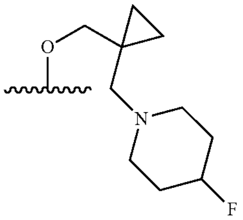,
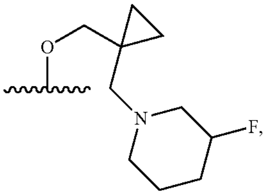

-continued
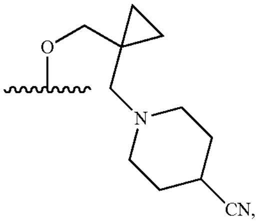
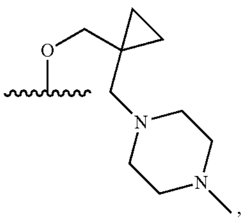
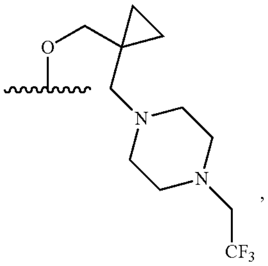
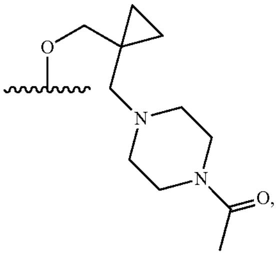
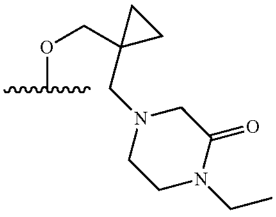
, or
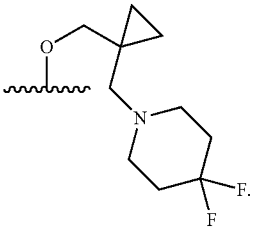
In an embodiment of a compound of Formula I or a pharmaceutically acceptable salt thereof, $R_4$ is selected from
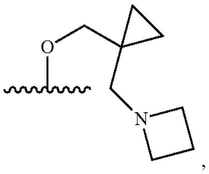
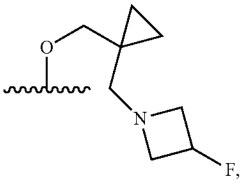
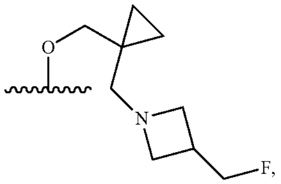
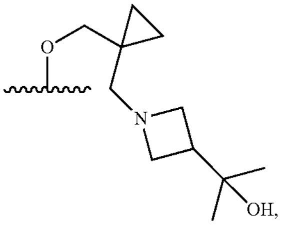
or
-continued
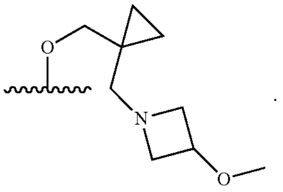
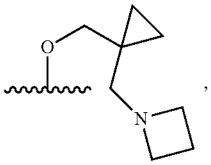
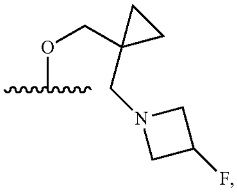
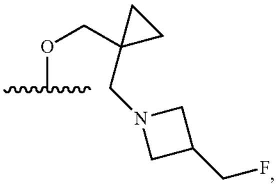
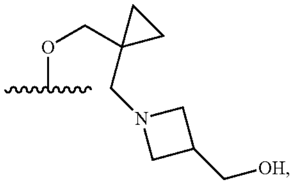
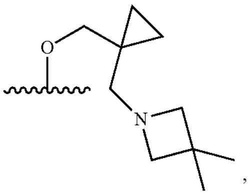
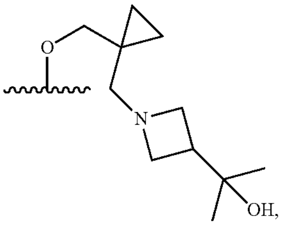
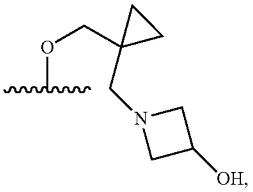
or
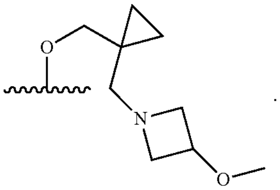
In an embodiment of a compound of Formula I or a pharmaceutically acceptable salt thereof, $R_4$ is selected from
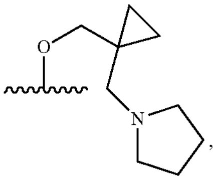
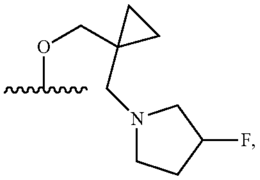
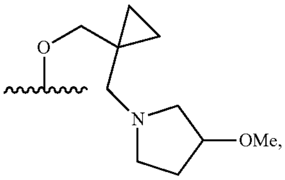
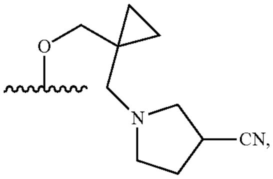

-continued
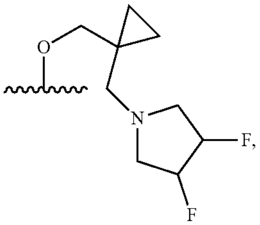
or
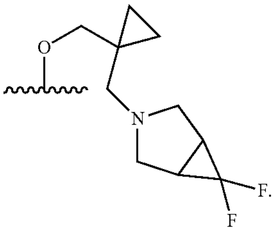
In an embodiment of a compound of Formula I or a pharmaceutically acceptable salt thereof, $R_4$ is
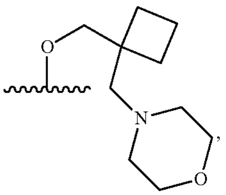
or
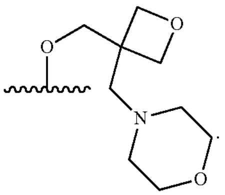
In an embodiment of a compound of Formula I or a pharmaceutically acceptable salt thereof, $R_4$ is selected from
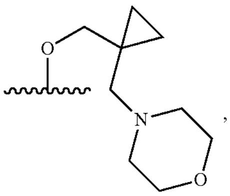
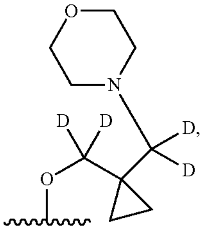
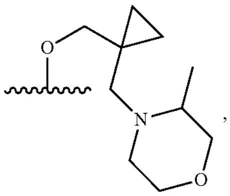
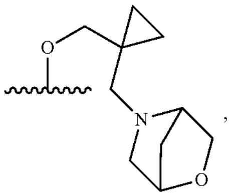
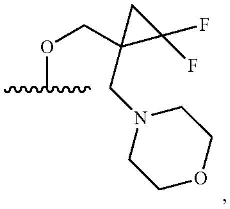
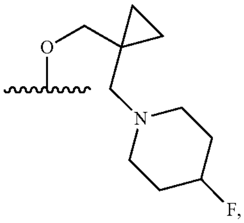
-continued
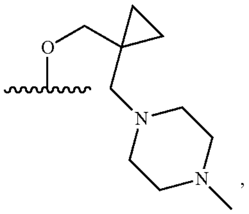
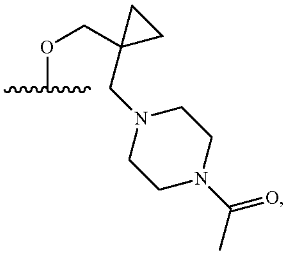
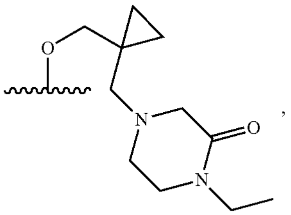
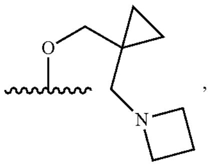
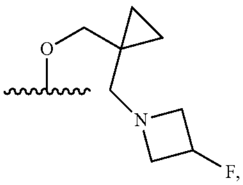
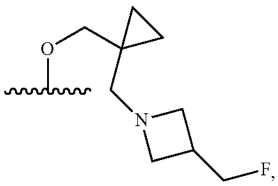
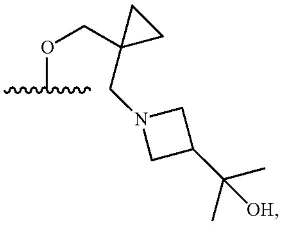
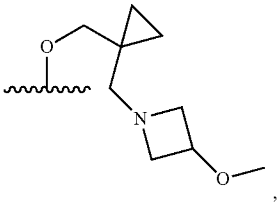
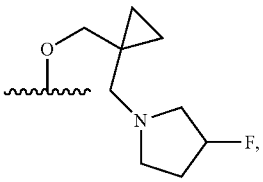
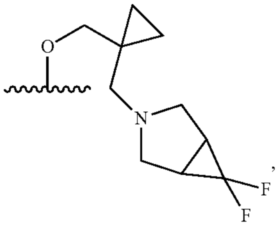
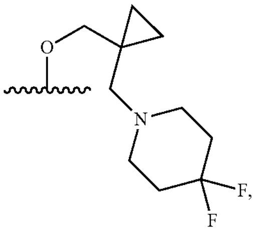
or
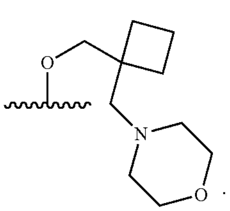
In an embodiment of a compound of Formula I or a pharmaceutically acceptable salt thereof, $R_4$ is selected from
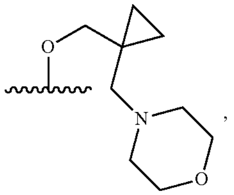
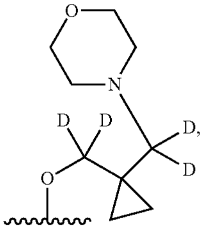

-continued

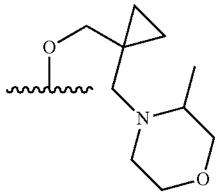
,
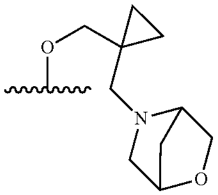
,
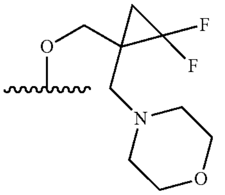
,
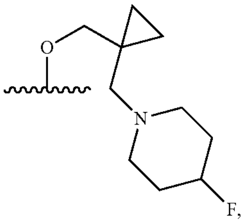

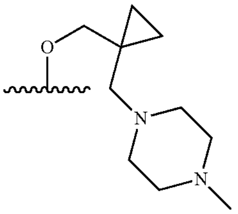
,
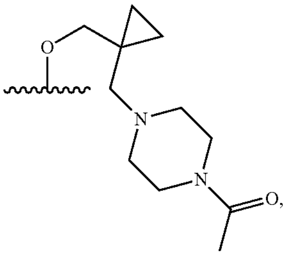

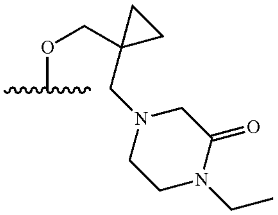
, or
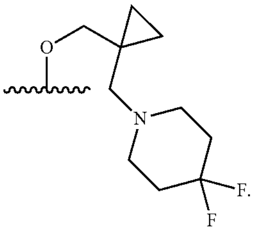

In an embodiment of a compound of Formula I or a pharmaceutically acceptable salt thereof, $R_4$ is selected from

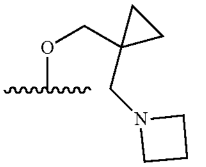
,
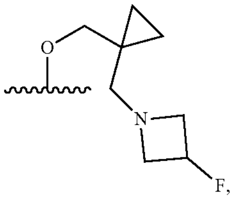

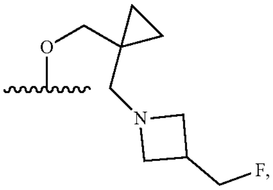

-continued

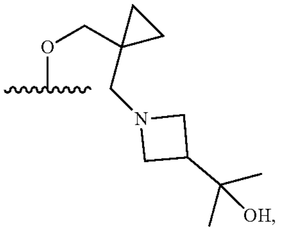
or
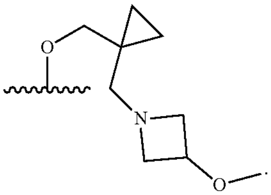

In an embodiment of a compound of Formula I or a pharmaceutically acceptable salt thereof, $R_4$ is selected from

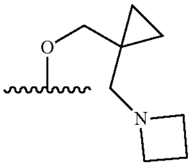
,
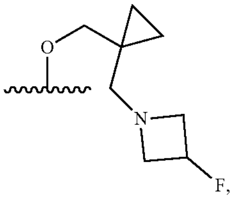

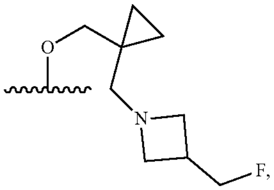

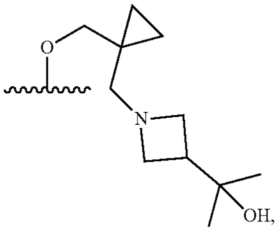

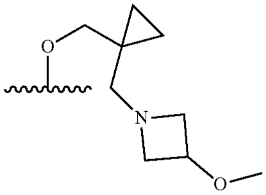

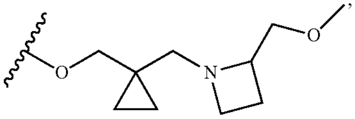
, or
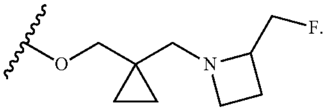

In an embodiment of a compound of Formula I or a pharmaceutically acceptable salt thereof, $R_4$ is selected from

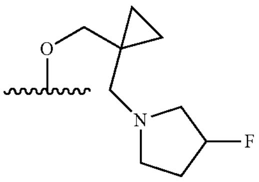

or

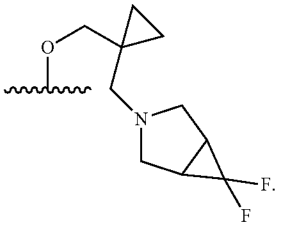

In an embodiment of a compound of Formula I or a pharmaceutically acceptable salt thereof, $R_4$ is

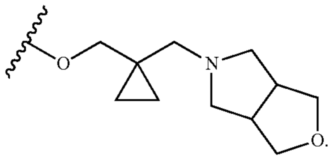 [SMILES: *OCC1(CN2CC3COCC3C2)CC1]

In an embodiment of a compound of Formula I or a pharmaceutically acceptable salt thereof, $R_4$ is

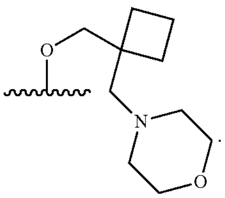 [SMILES: *OCC1(CN2CCOCC2)CCC1]

In an embodiment of a compound of Formula I or a pharmaceutically acceptable salt thereof, $R_4$ is

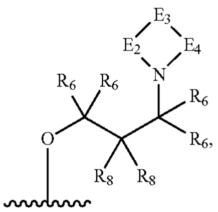

wherein preferably each $R_6$ is H.

In an embodiment of a compound of Formula I or a pharmaceutically acceptable salt thereof, $R_4$ is

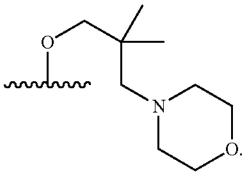 [SMILES: *OCC(C)(C)CN1CCOCC1]

In an embodiment of a compound of Formula I or a pharmaceutically acceptable salt thereof, $R_4$ is

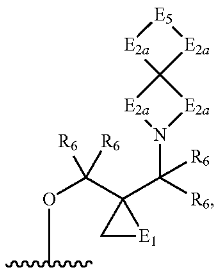

wherein preferably each $R_6$ is H.

In an embodiment of a compound of Formula I or a pharmaceutically acceptable salt thereof, $R_4$ is selected from

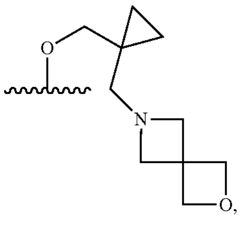

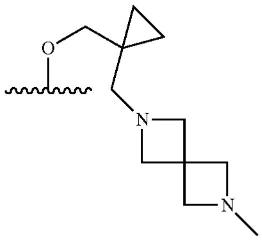

,

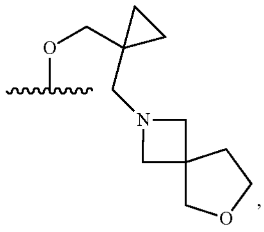

, or

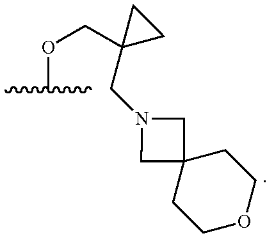

In an embodiment of a compound of Formula I or a pharmaceutically acceptable salt thereof, $R_4$ is selected from

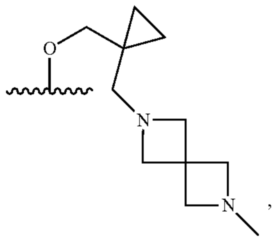

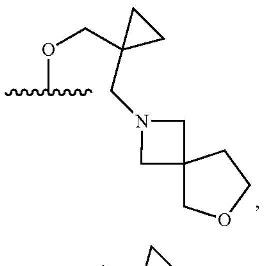

, or

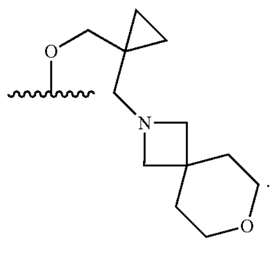

In the above embodiments of the compounds of Formula I, or a pharmaceutically acceptable salt thereof, $R_4$ is a group of the formula

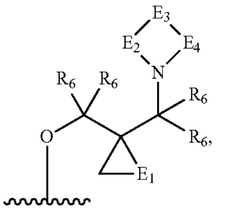

or

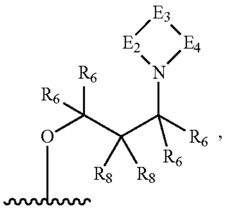

wherein $E_2$ and $E_4$ can optionally be bridged by a bond or a $C_{1-3}$ alkylene. Examples of these compounds of Formula I are shown below:

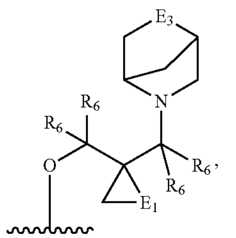

or

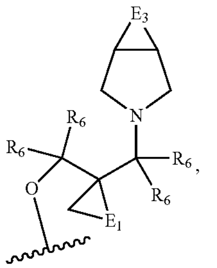

or a pharmaceutically acceptable salt thereof.

In the above embodiments of the compounds of Formula I, or a pharmaceutically acceptable salt thereof, $R_4$ is a group of the formula

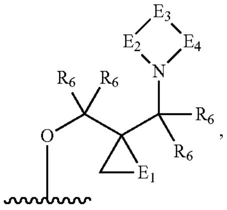

or

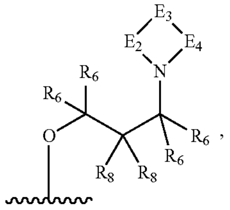

wherein $E_3$ can be —CO—$NR_{6a}$—.

Examples of these compounds of Formula I are shown below:

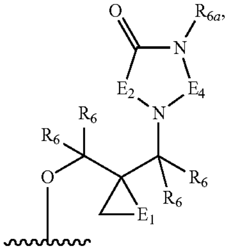

or a pharmaceutically acceptable salt thereof.

In the above embodiments of the compounds of Formula I, the chemical drawings are shown flat without chiral information. These compounds often have multiple chiral centers and are contemplated to exist is various forms with various combinations of chiral centers. Additionally, these compounds have various enantiomers, diastereomers, and atropisomers that can exist and are included herein.

In an embodiment of a compound of Formula I or a pharmaceutically acceptable salt thereof, the compound is an isotopic derivative of any one of the compounds described herein or a pharmaceutically acceptable salt thereof.

It is understood that the isotopic derivative can be prepared using any of a variety of art-recognized techniques. For example, the isotopic derivatives can generally be prepared by carrying out the procedures disclosed in the schemes and/or in the examples described herein or a pharmaceutically acceptable salt thereof, by substituting an isotopically labeled reagent for a non-isotopically labeled reagent.

In an embodiment of a compound of Formula I or a pharmaceutically acceptable salt thereof, the compound is a deuterium labeled compound of any one of the compounds described herein and pharmaceutically acceptable salts thereof.

In the compounds of this invention any atom not specifically designated as a particular isotope is meant to represent any stable isotope of that atom. Unless otherwise stated, when an atom is designated specifically as "H" or "hydrogen", the atom is understood to have hydrogen at its natural abundance isotopic composition. Also, unless otherwise stated, when an atom is designated specifically as "D" or "deuterium", the atom is understood to have deuterium at an abundance substantially greater than the natural abundance of deuterium, which is 0.015%.

A compound of Formula I or a pharmaceutically acceptable salt thereof, the compound is selected from -continued
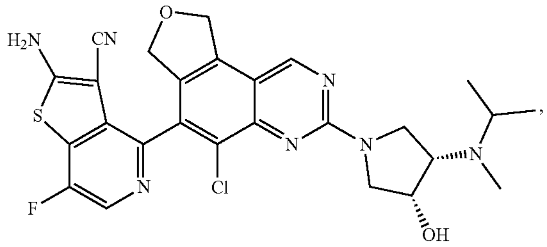,
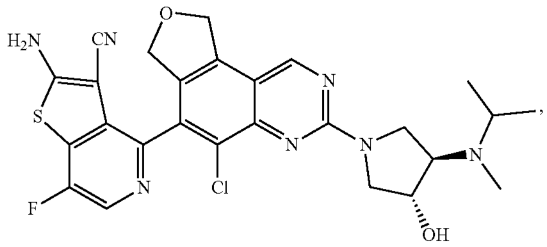,
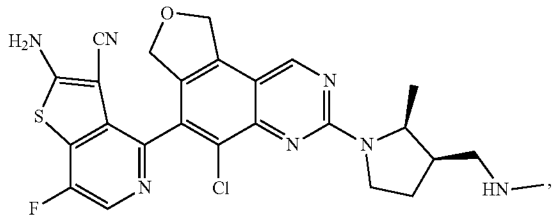,
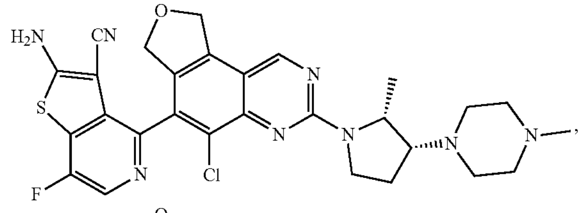,
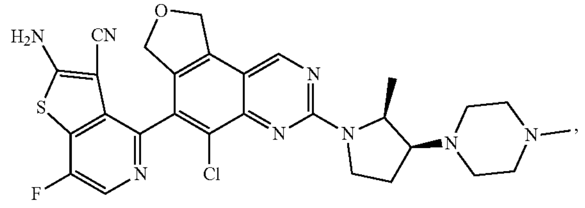,
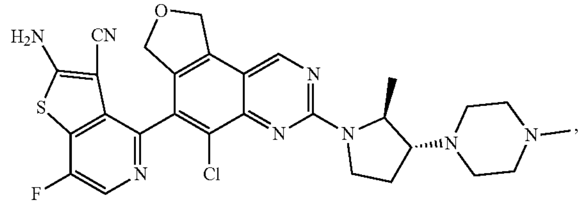,
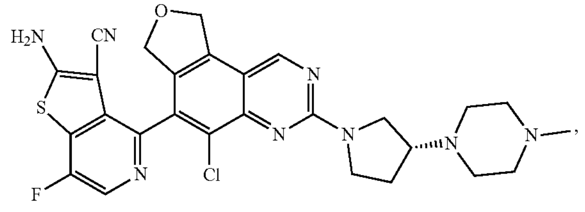,
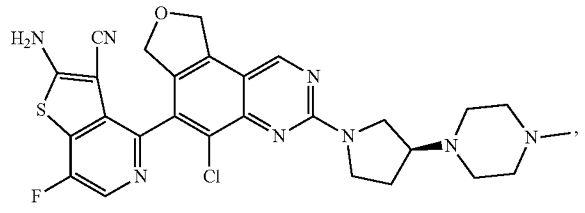,
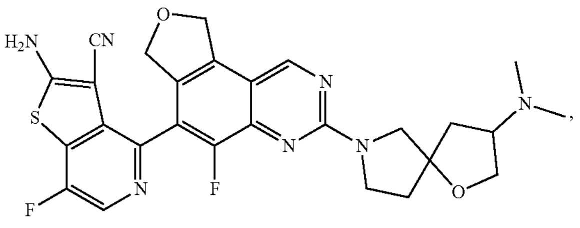,
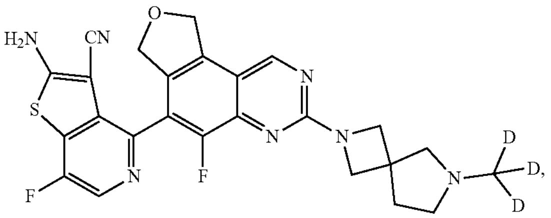,
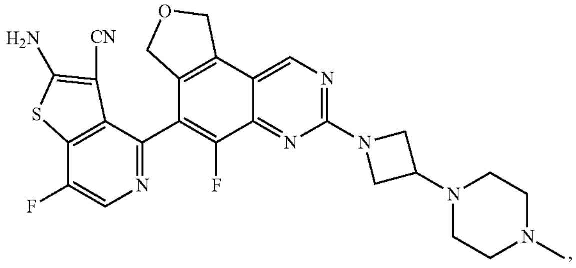,
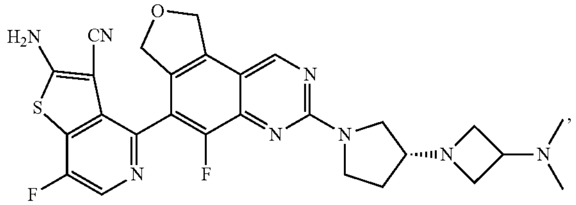,
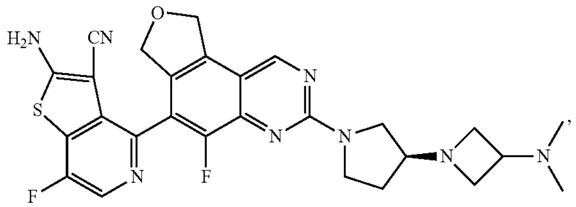,
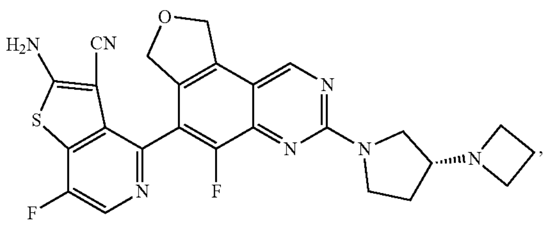,
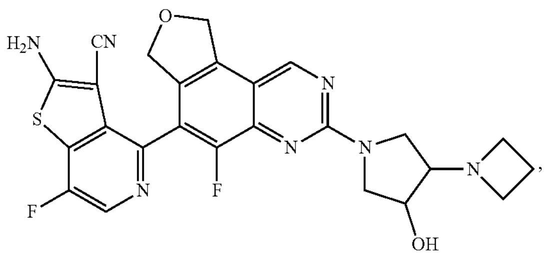, -continued
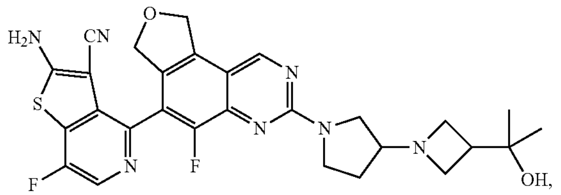
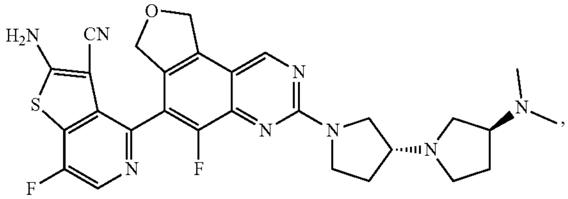
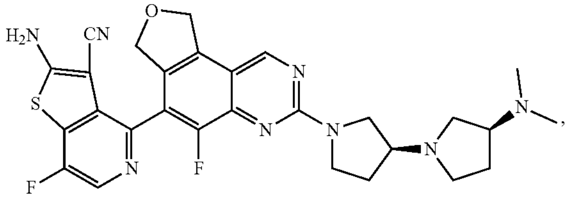
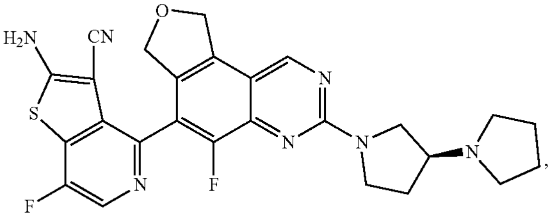
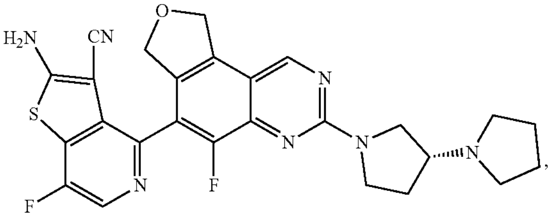
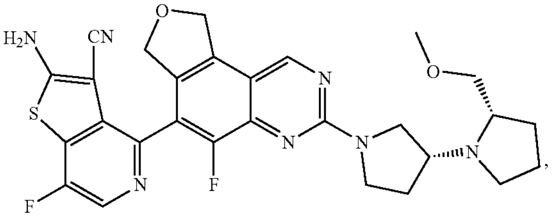
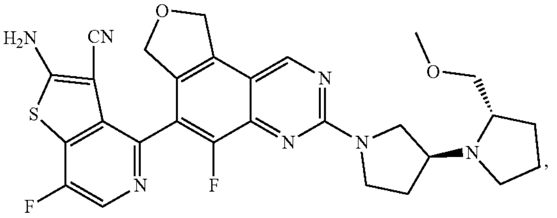
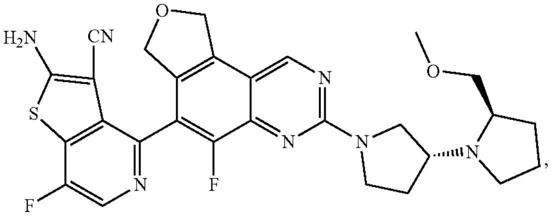
-continued
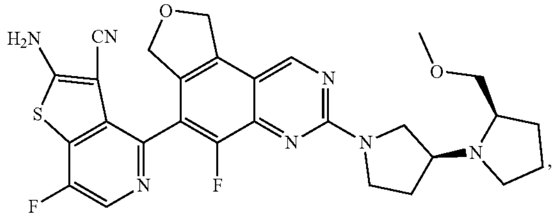
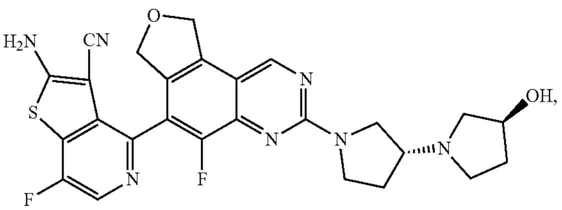
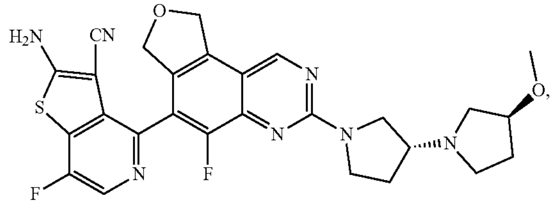
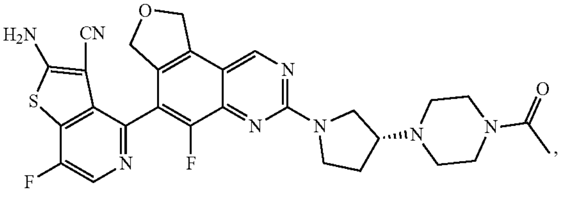
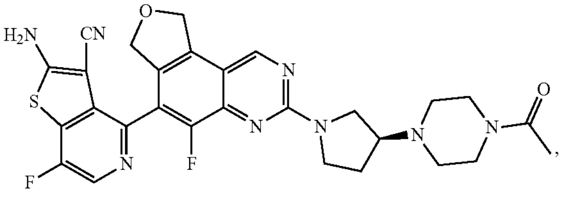
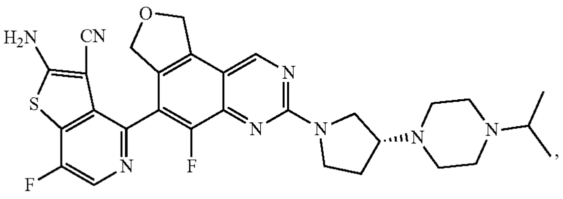
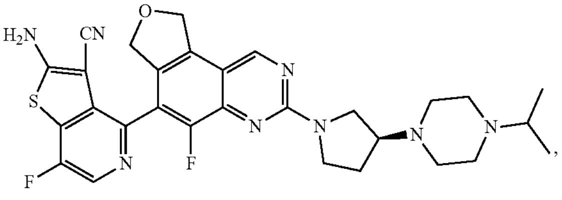
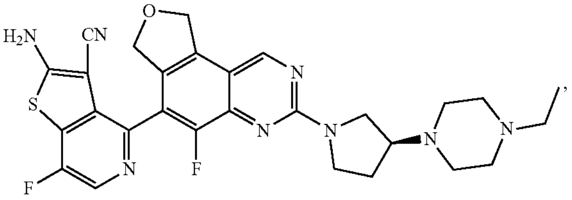

-continued
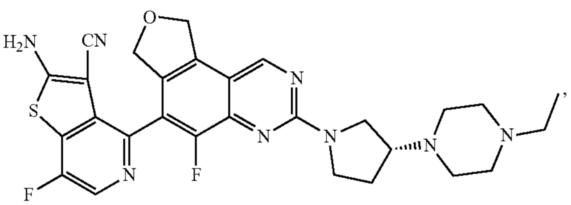
,
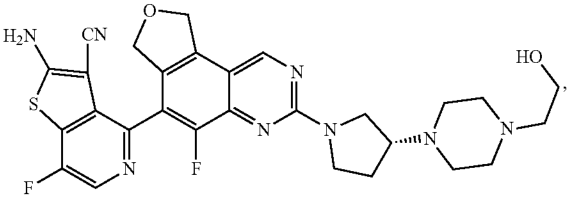
,
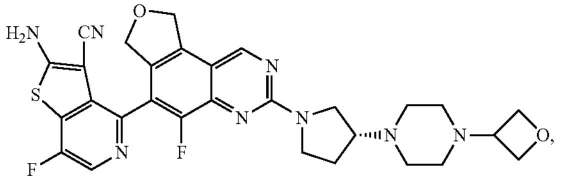
,
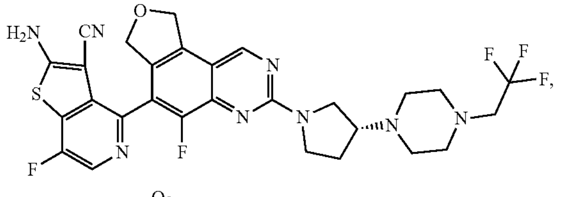
,
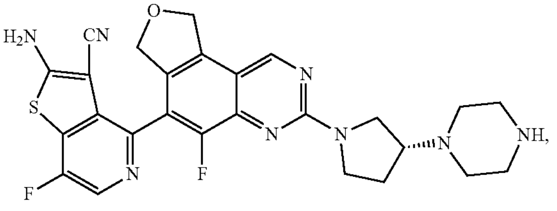
,
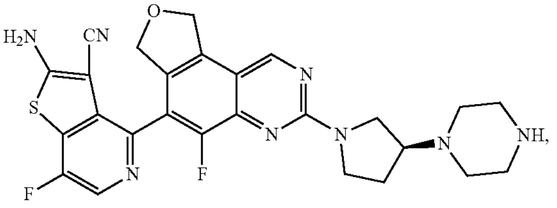
,
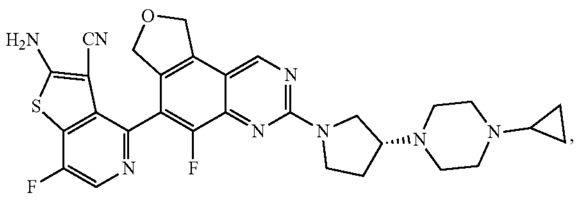
,
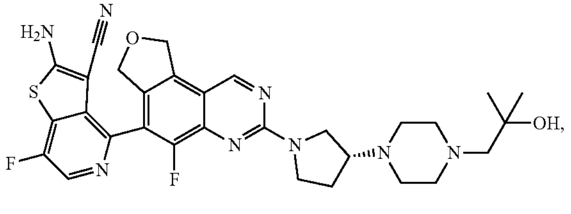
,
-continued
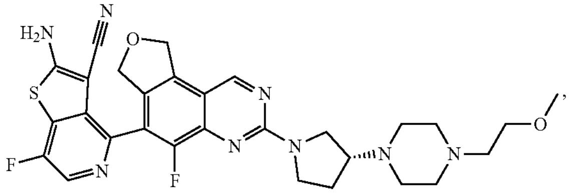
,
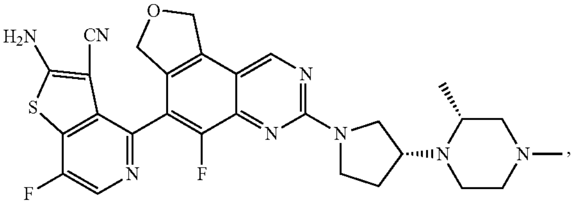
,
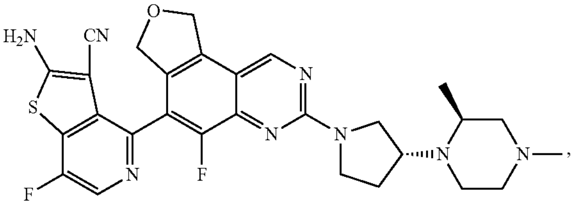
,
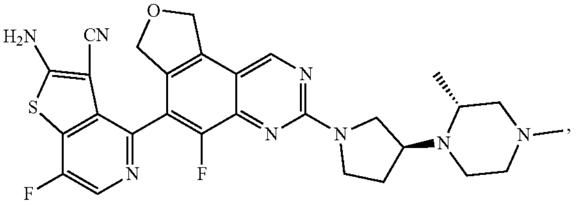
,
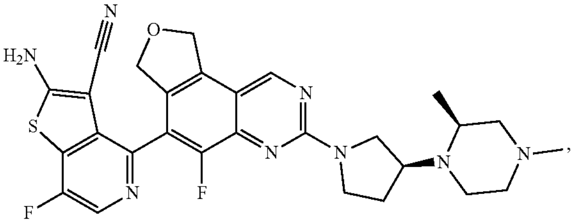
,
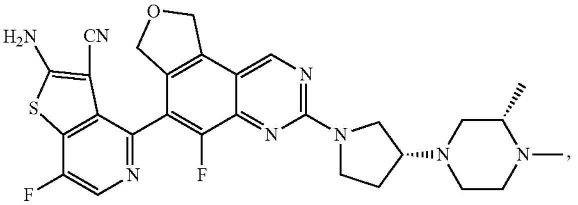
,
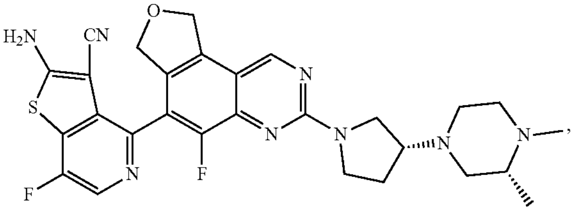
,
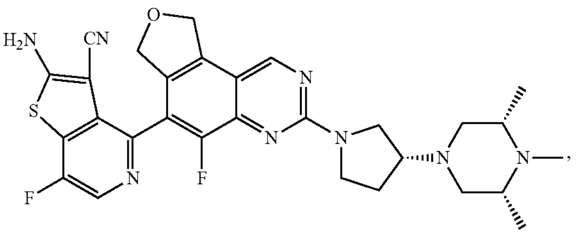
, -continued
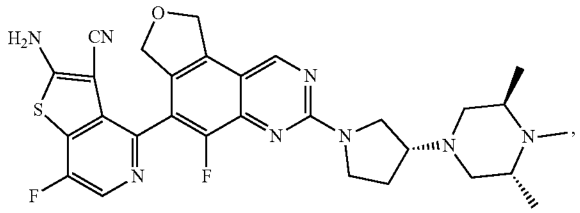
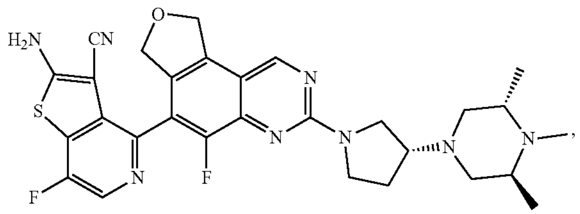
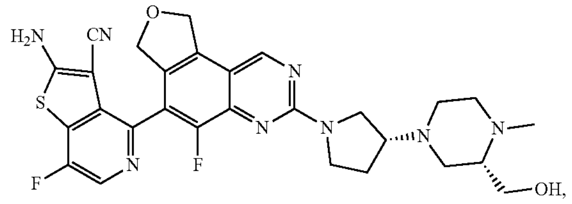
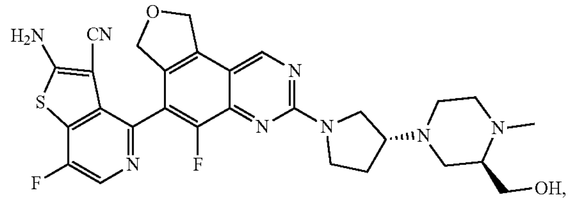
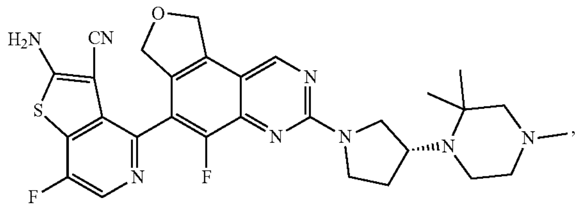
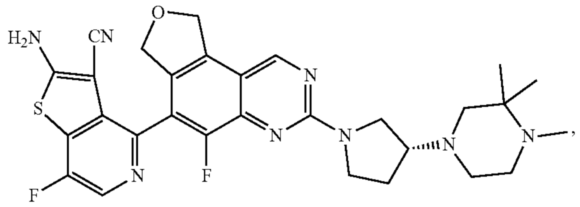
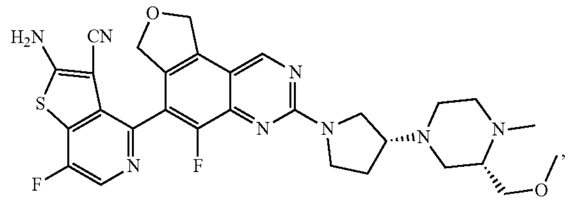
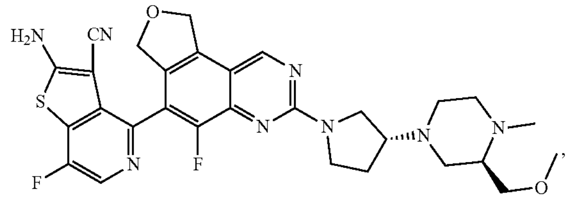
-continued
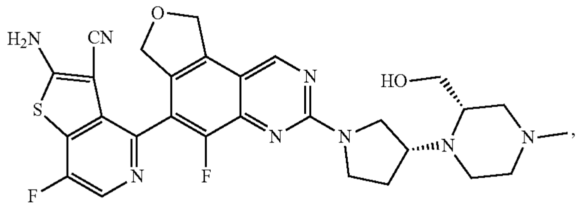
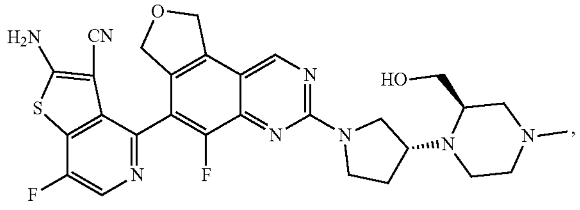
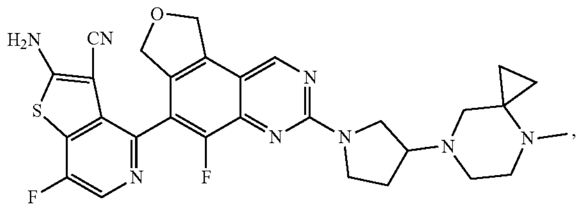
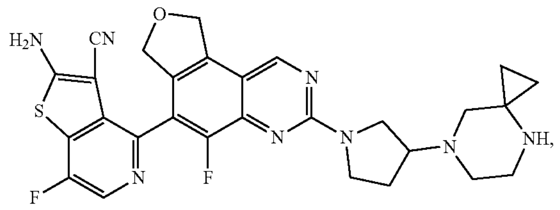
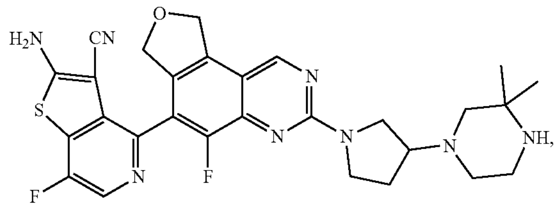
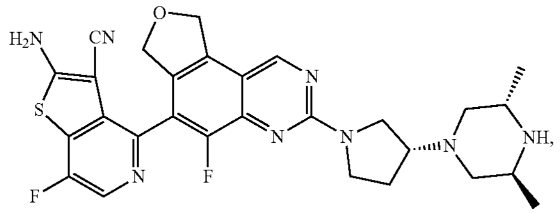
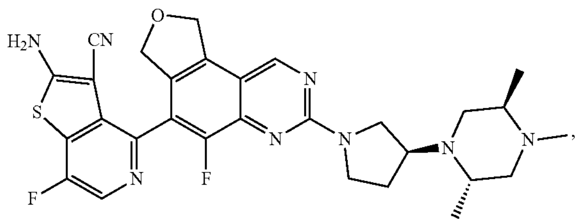
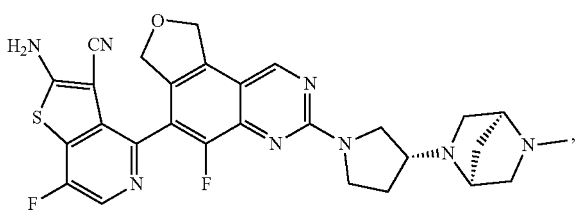

-continued
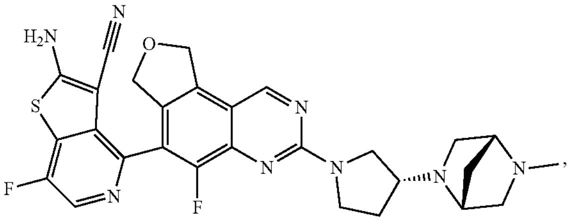
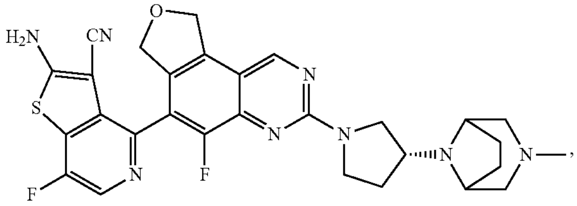
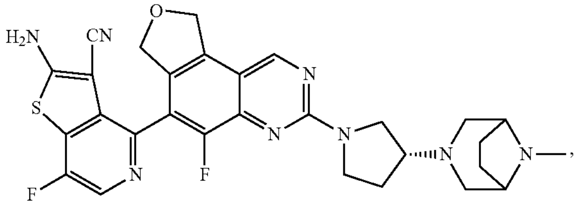
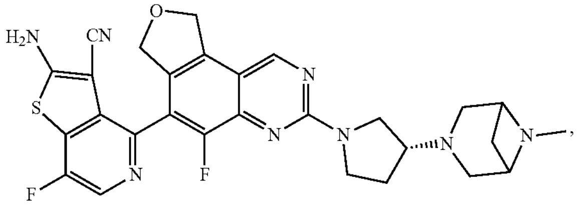
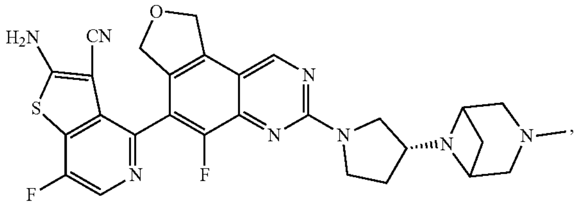
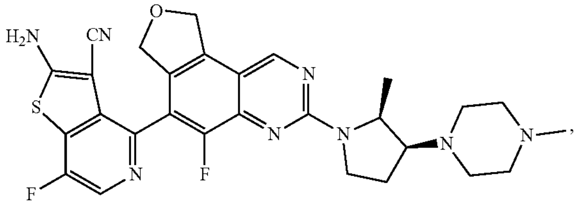
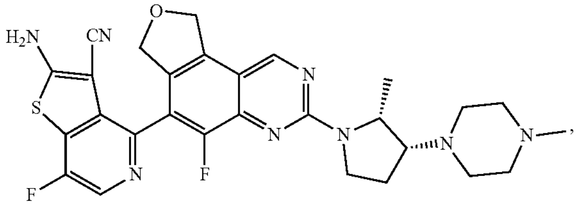
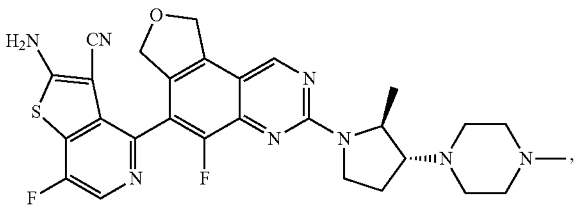
-continued
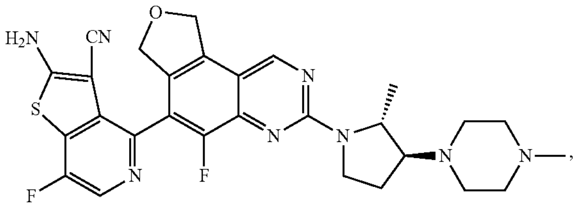
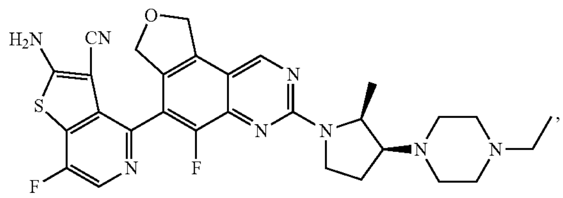
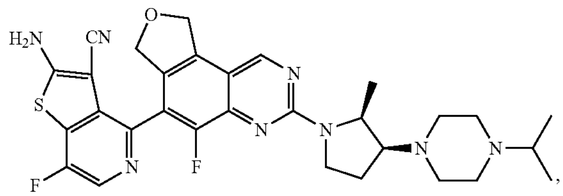
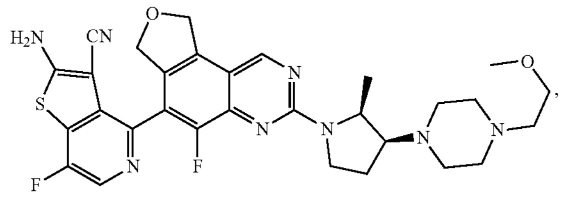
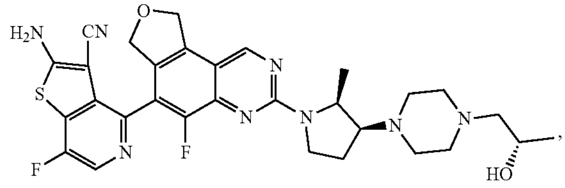
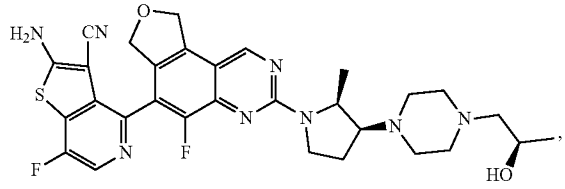
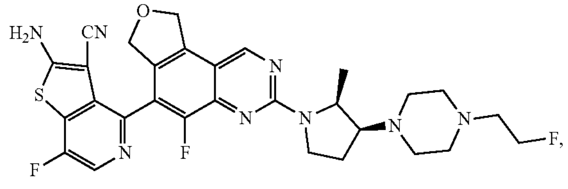
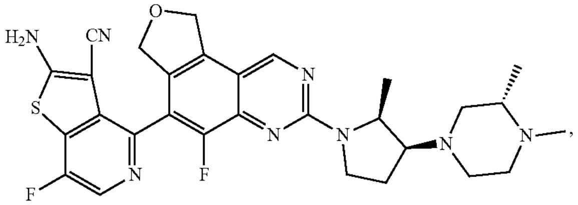

-continued
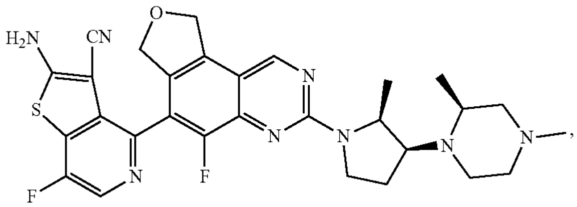,
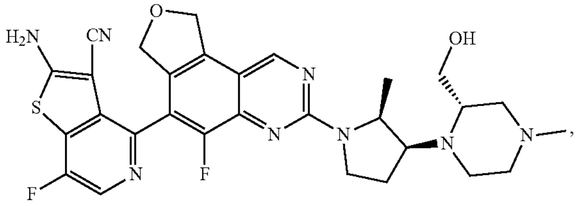,
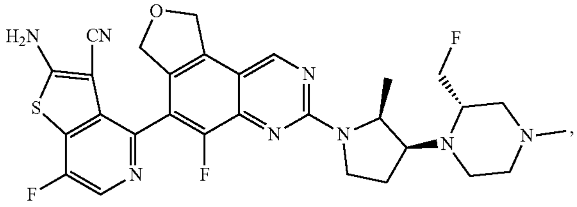,
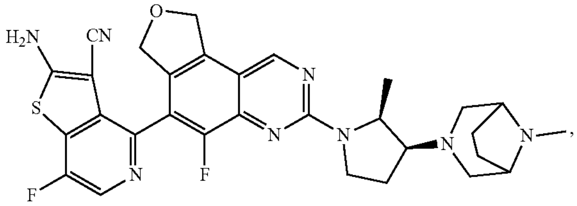,
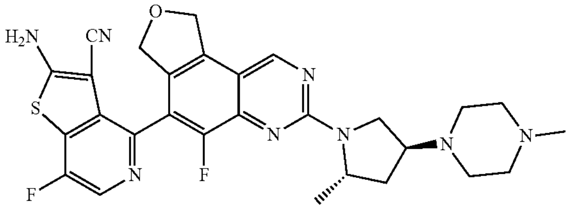,
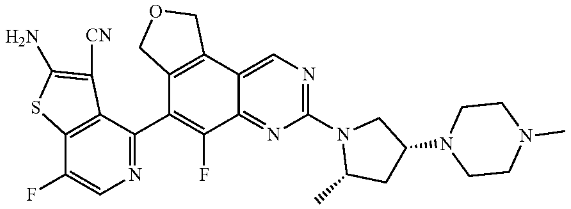,
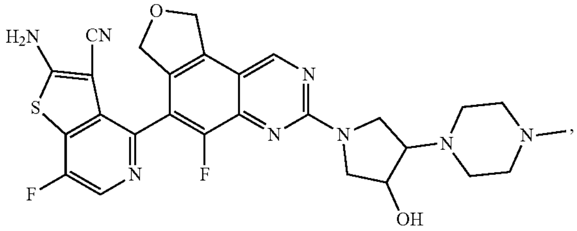,
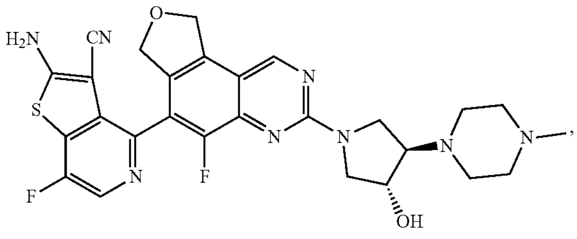,
-continued
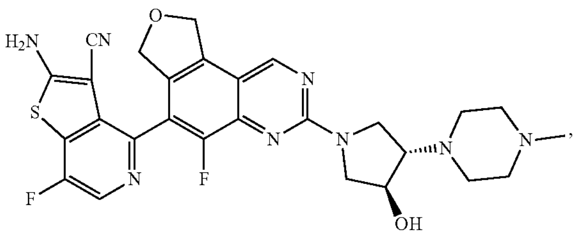,
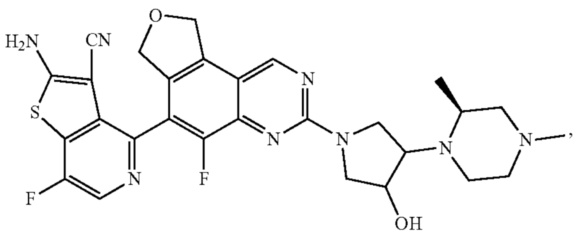,
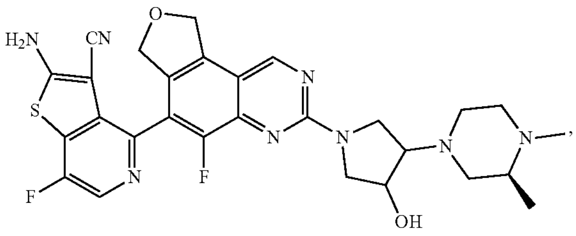,
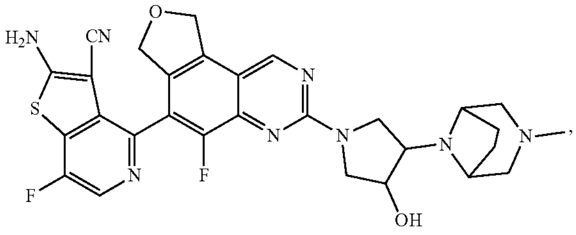,
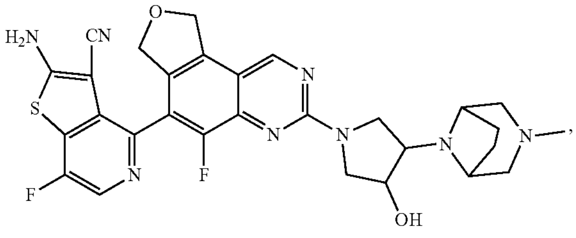,
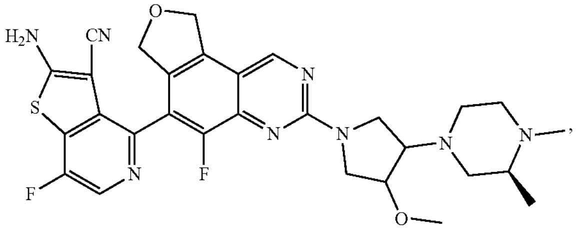,
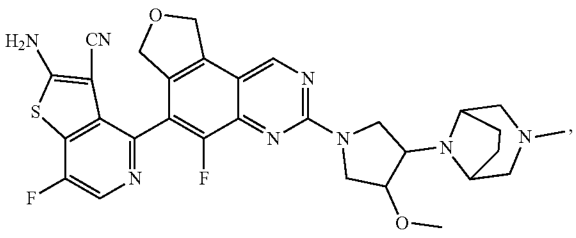, -continued
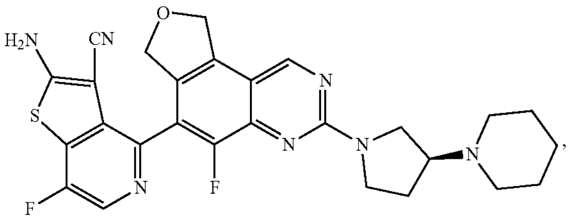
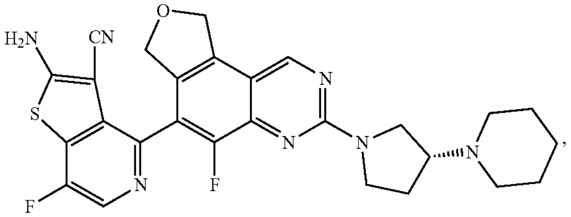
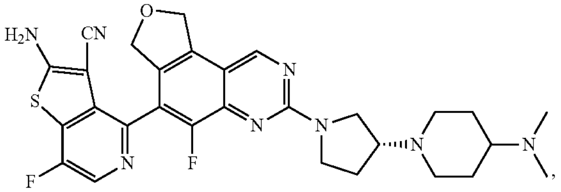
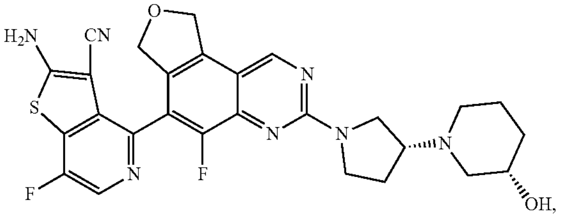
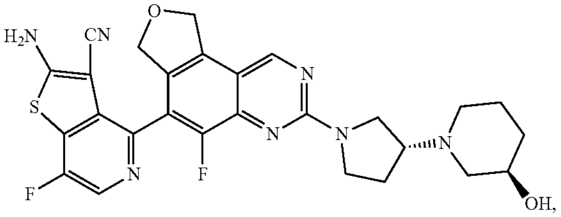
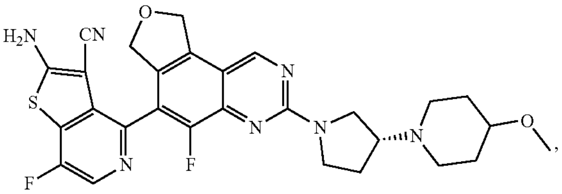
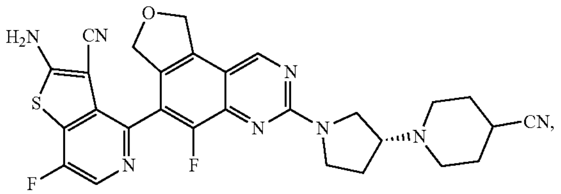
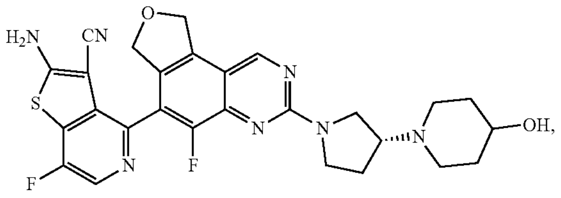
-continued
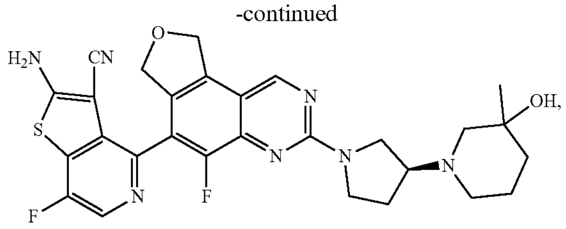
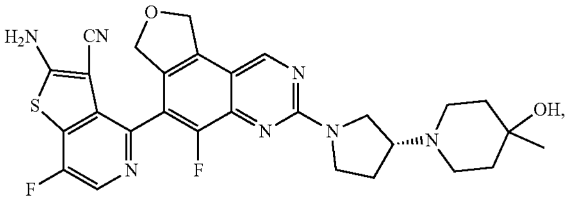
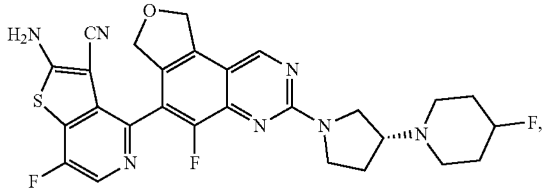
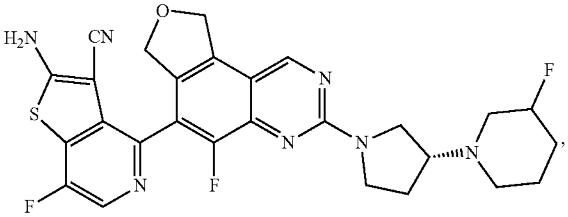
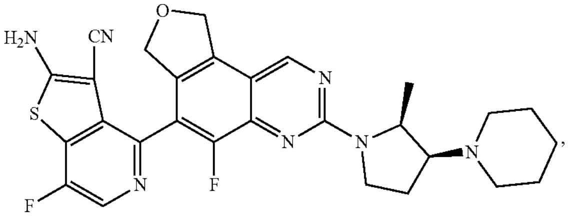
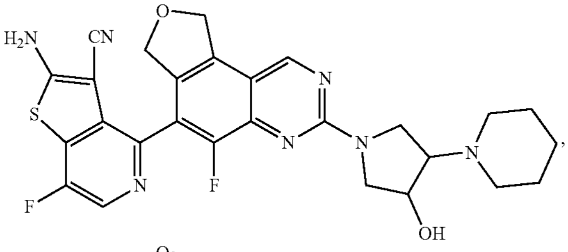
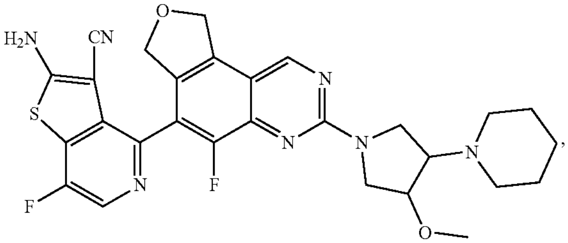
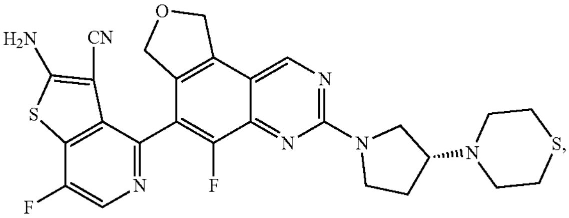

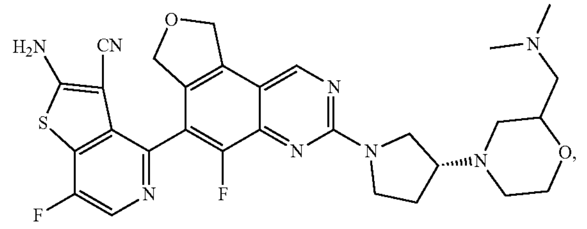
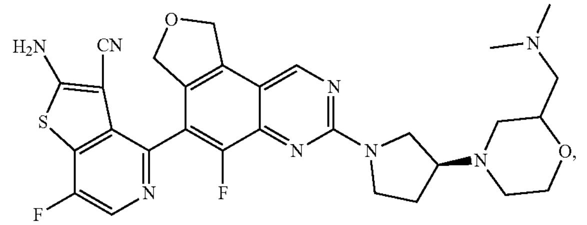
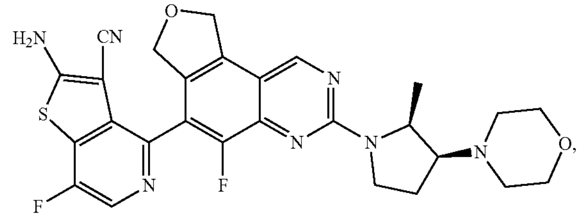
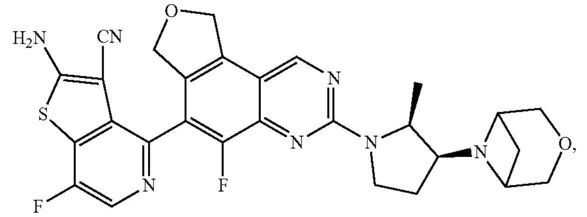
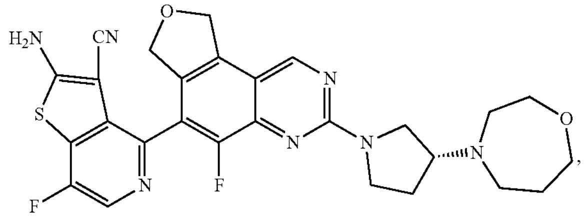
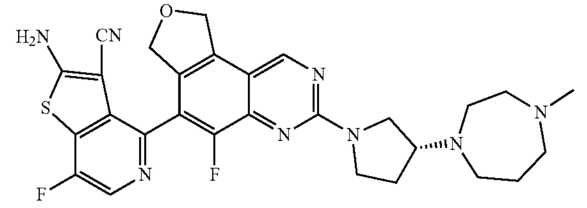
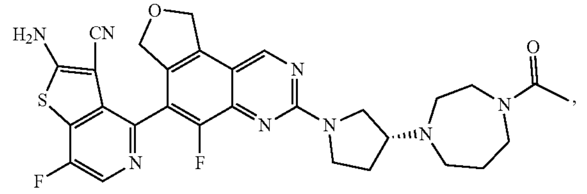
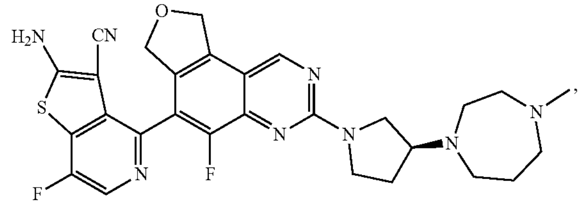
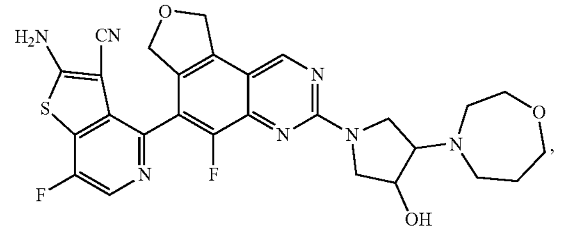
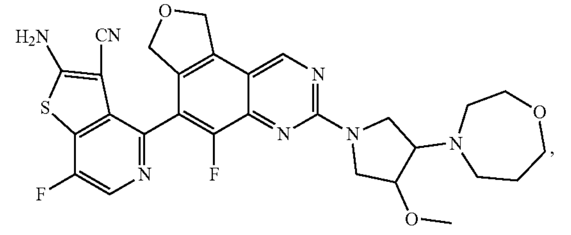
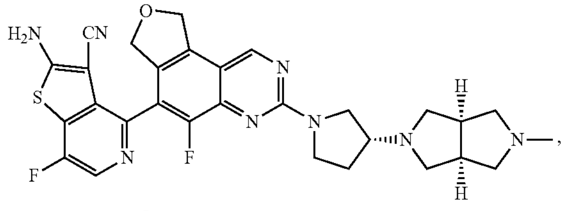
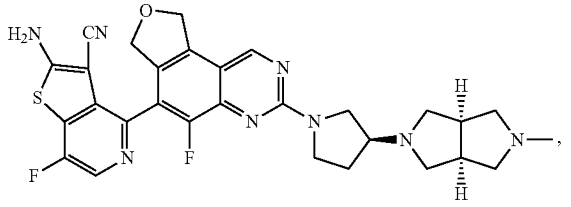
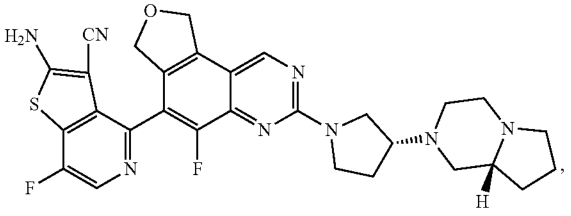
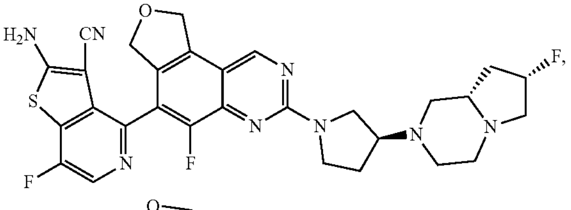
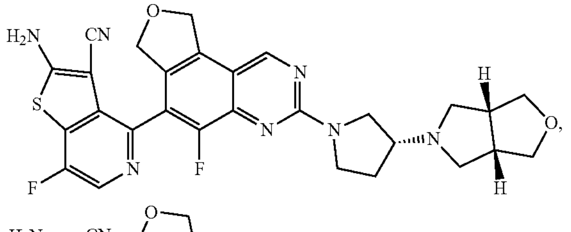
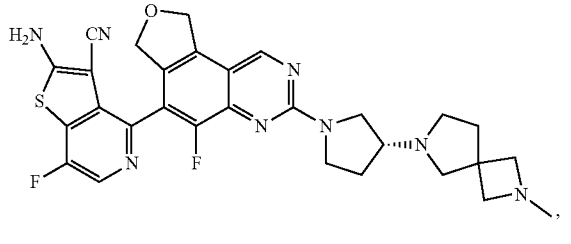

-continued
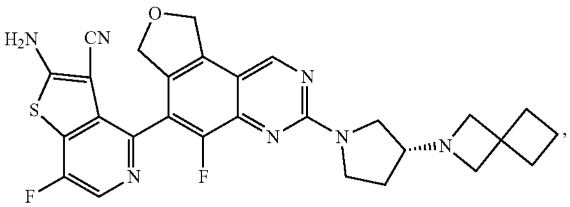
,
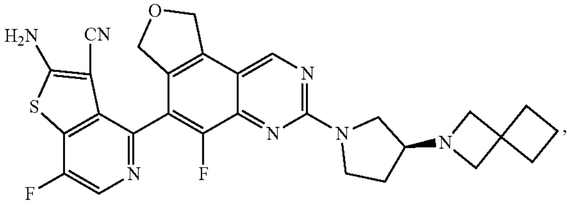
,
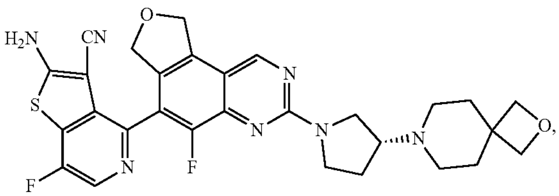
,
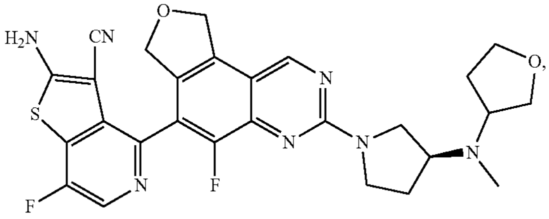
,
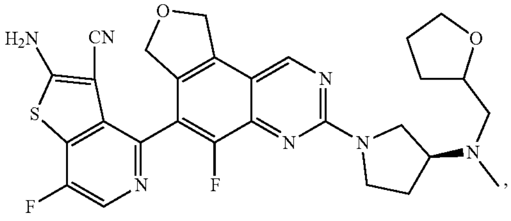
,
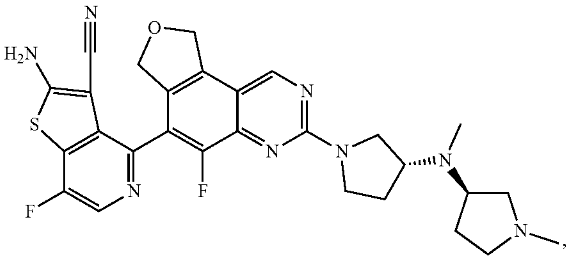
,
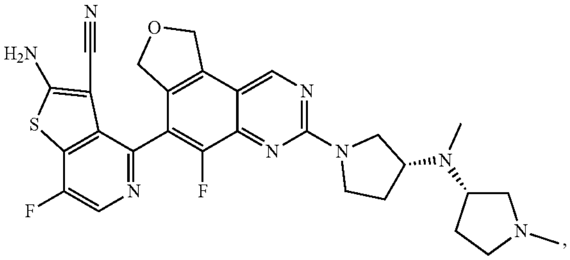
,
-continued
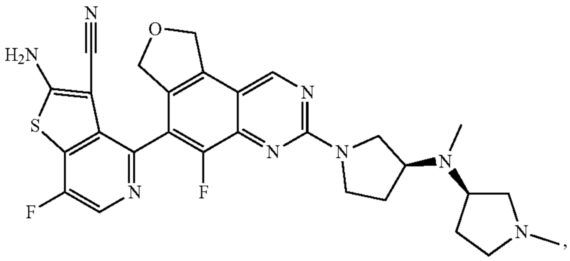
,
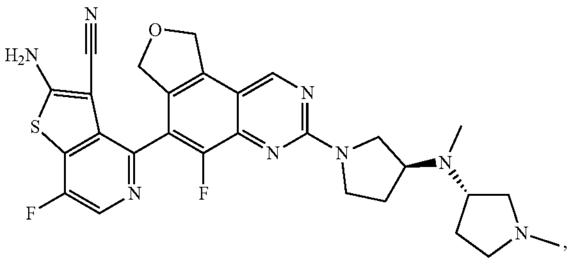
,
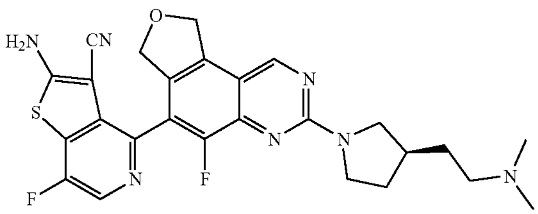
,
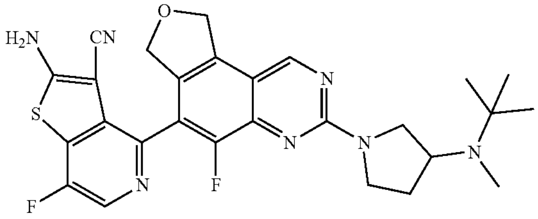
,
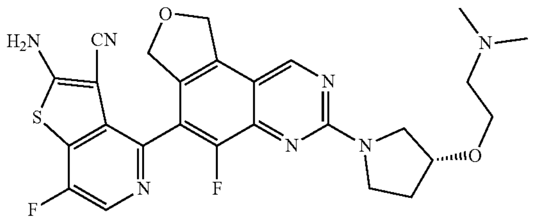
,
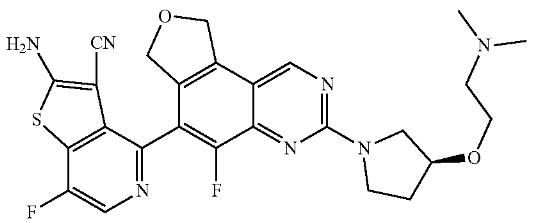
,
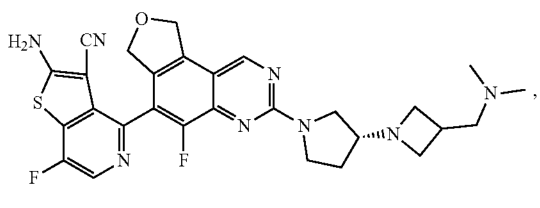
, -continued
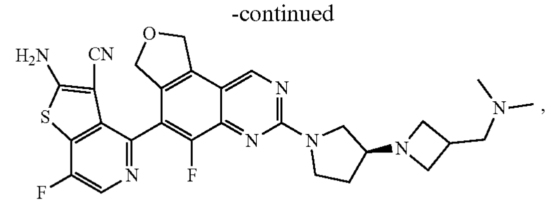
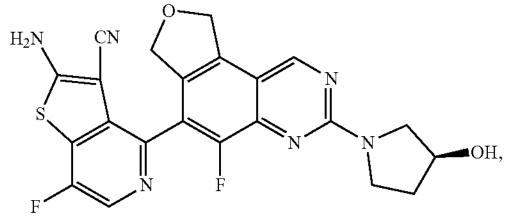
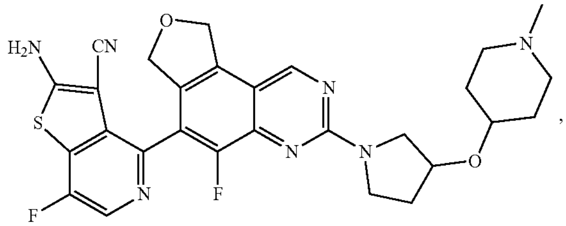
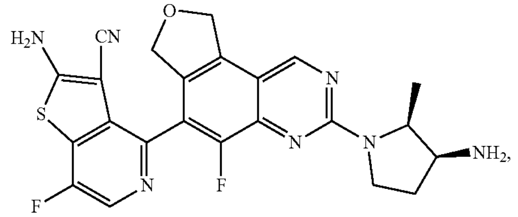
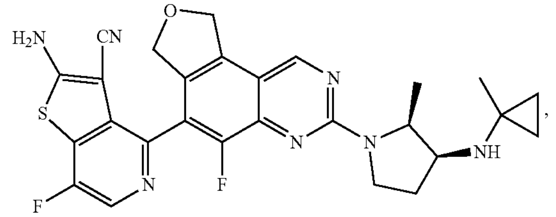
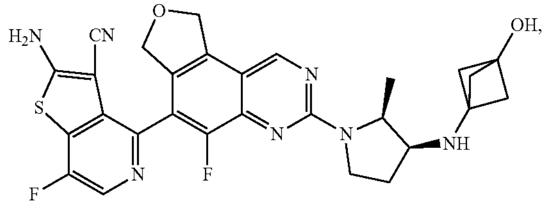
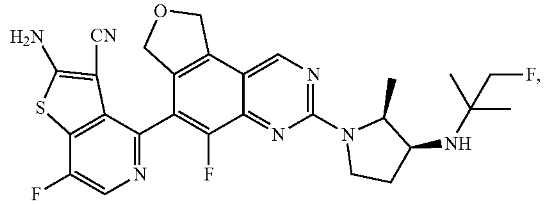
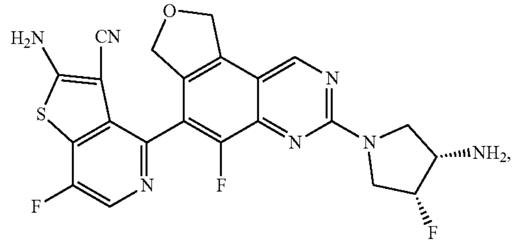
-continued
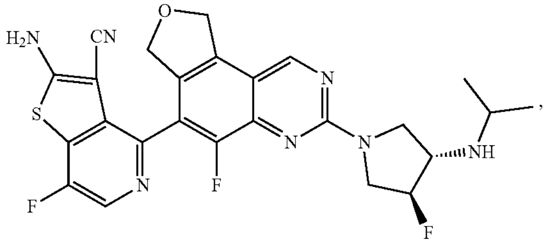
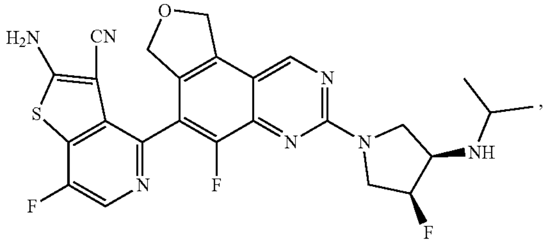
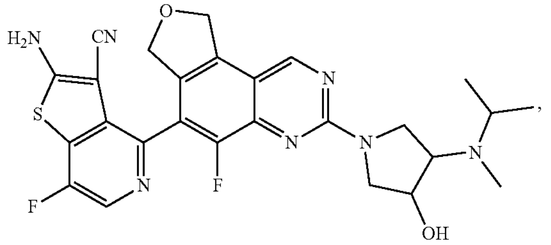
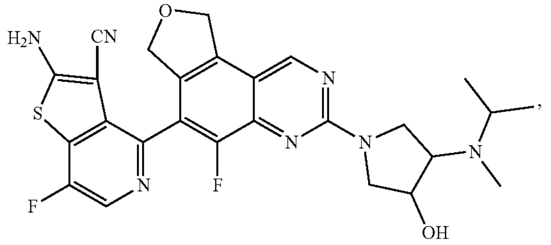
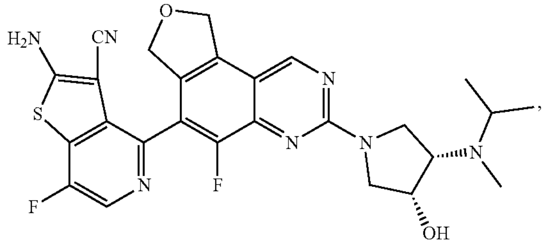
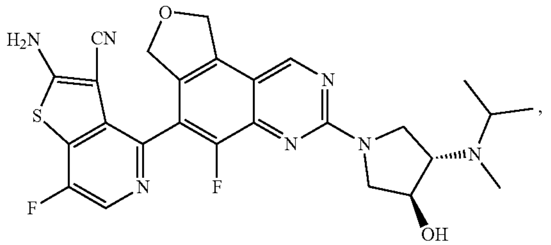
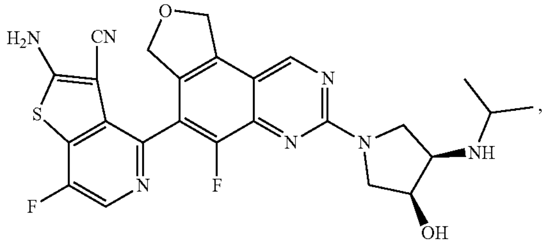

-continued
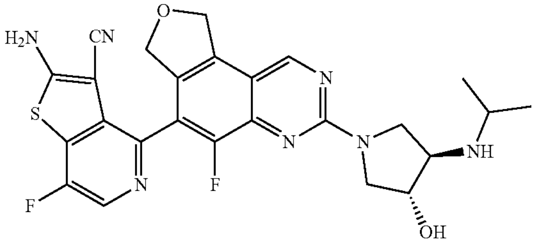
,
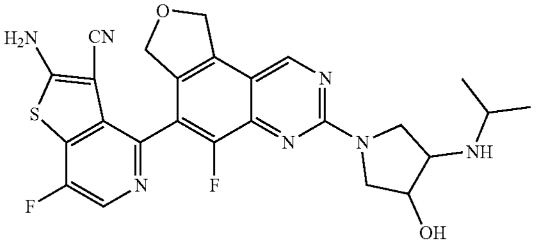
,
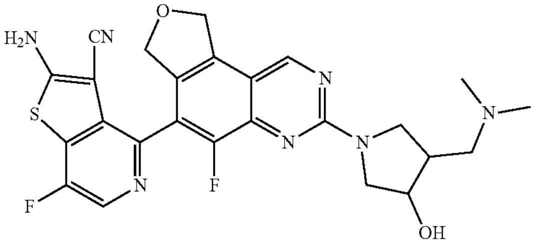
,
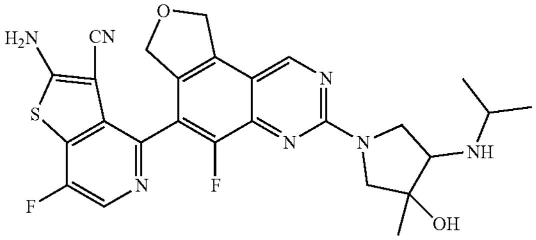
,
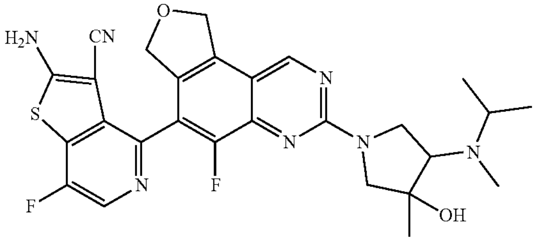
,
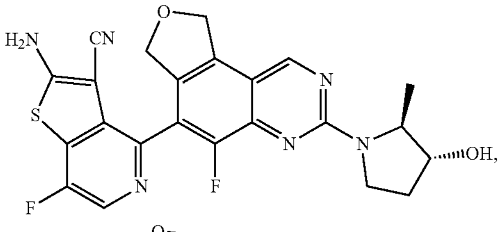
,
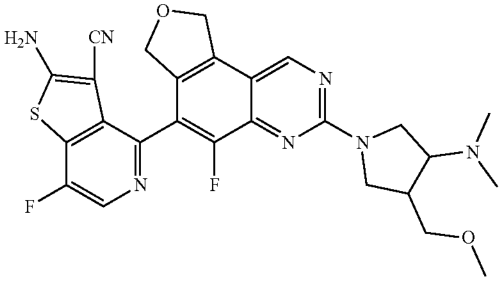
,
-continued
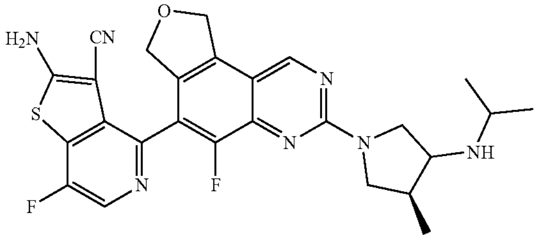
,
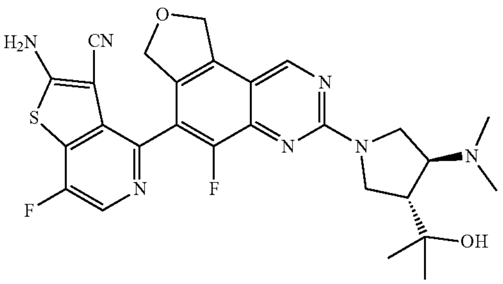
,
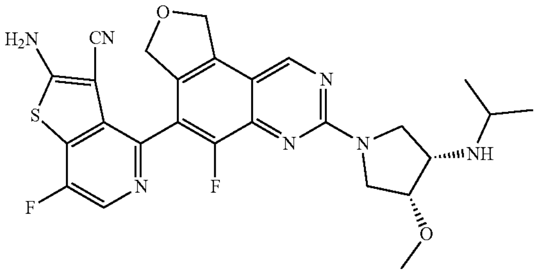
,
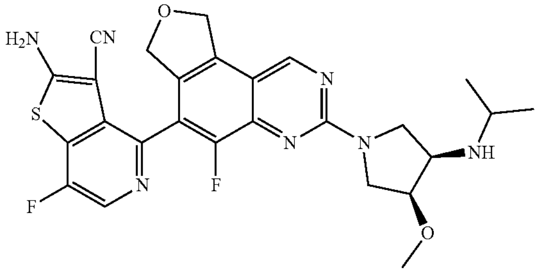
,
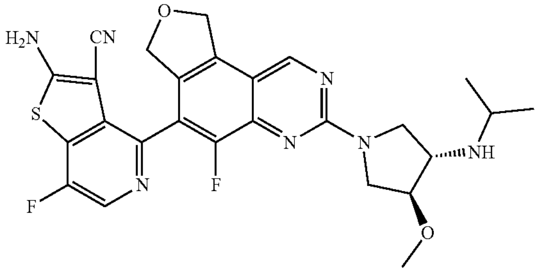
,
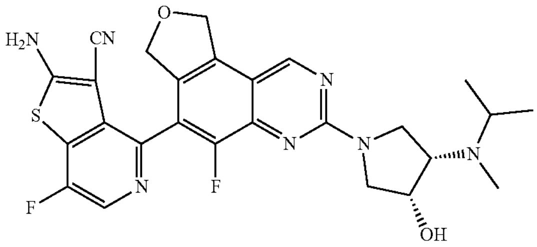
, -continued
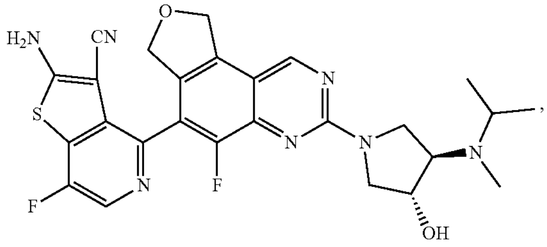
,
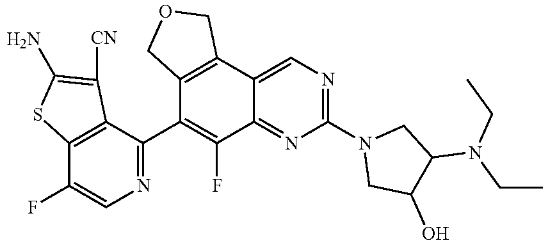
,
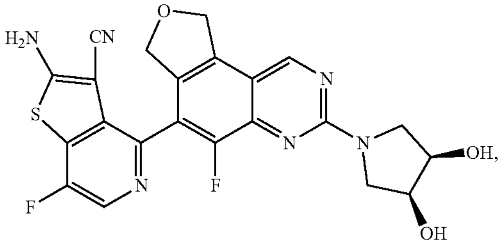
,
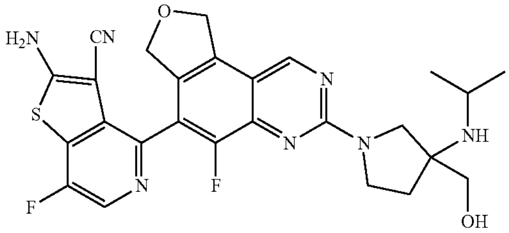
,
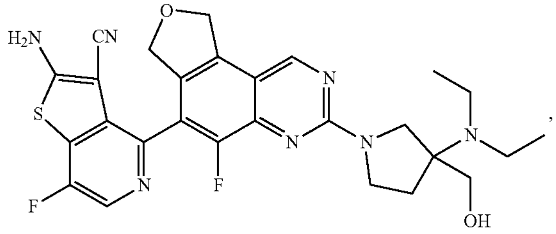
,
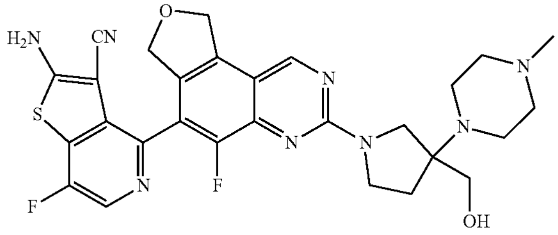
,
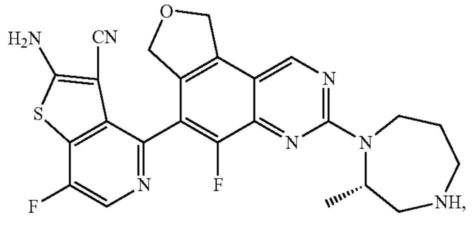
,
-continued
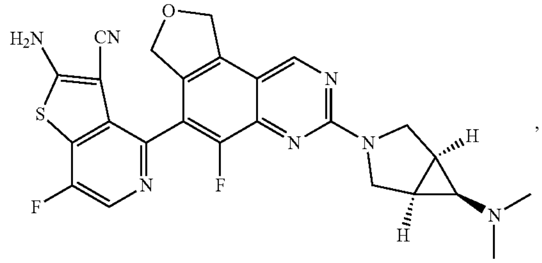
,
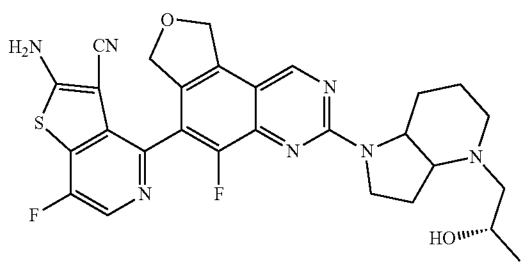
,
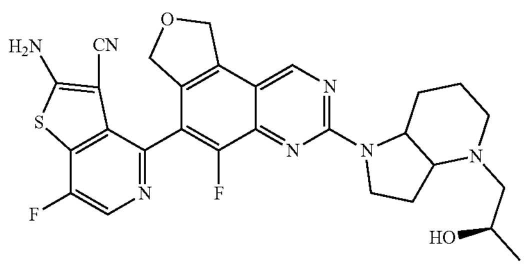
,
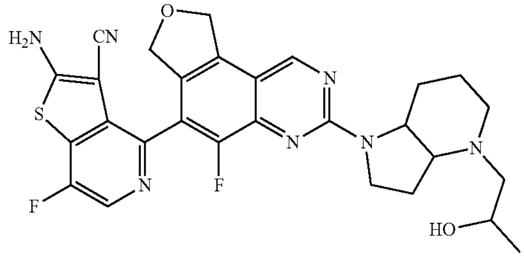
,
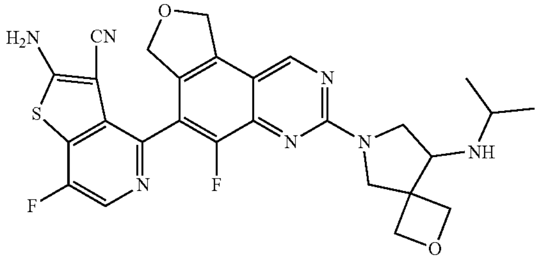
,
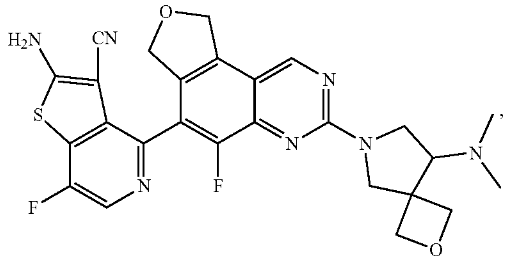
, -continued
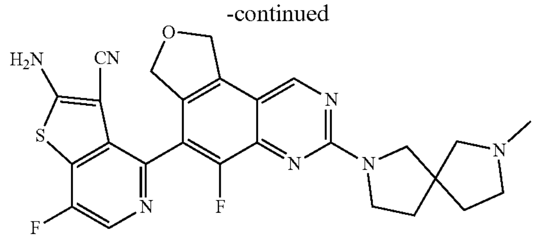
,
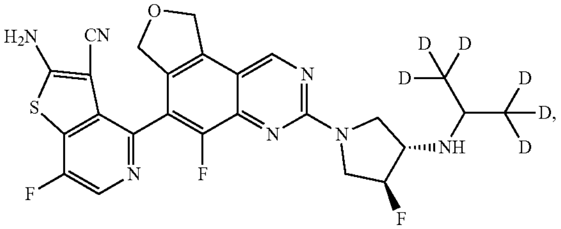
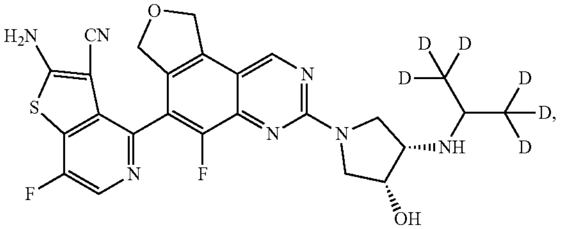
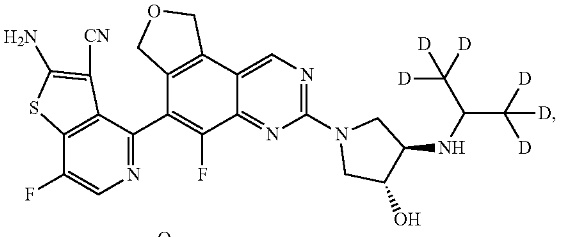
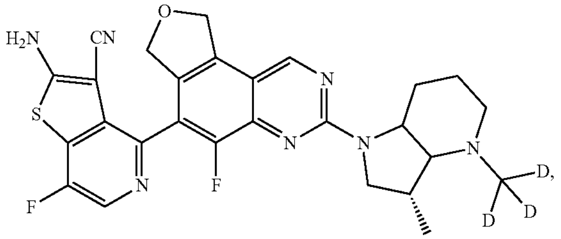
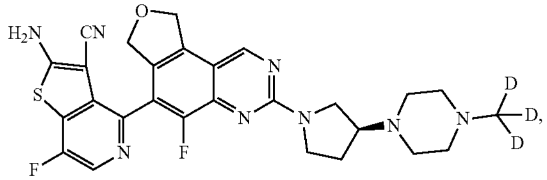
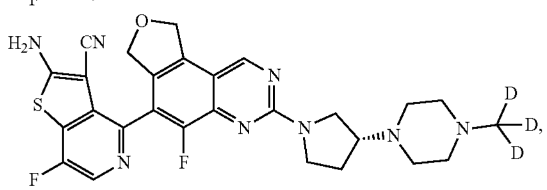
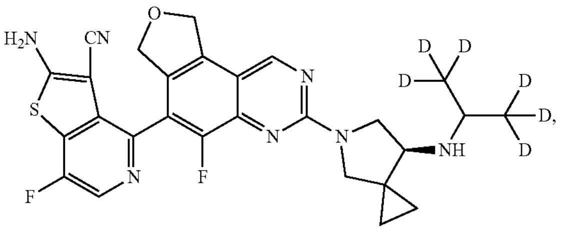
-continued
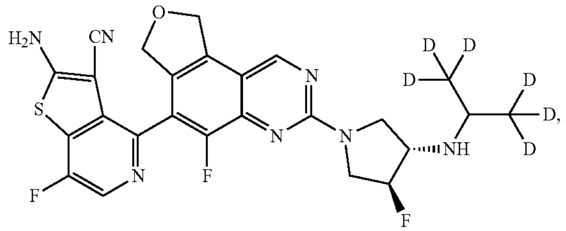
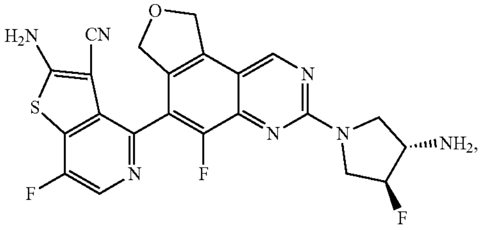
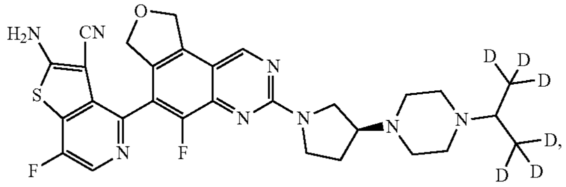
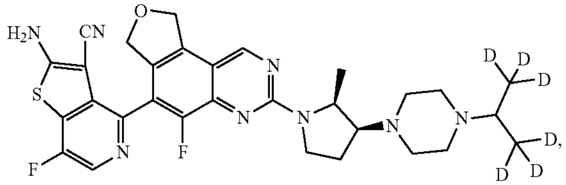
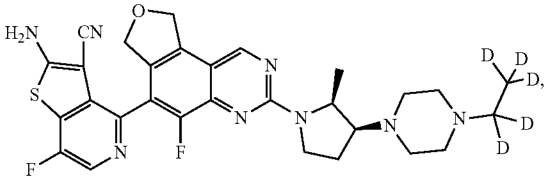
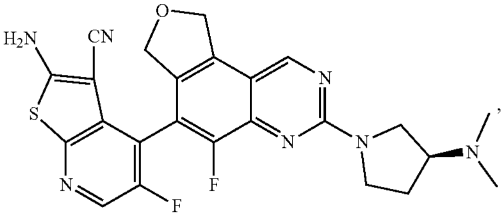
,
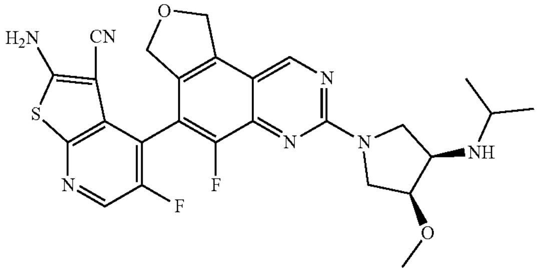
,
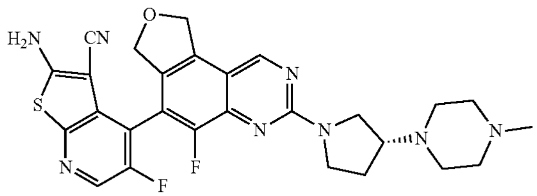
, -continued
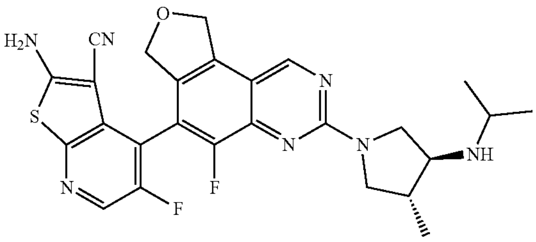
,
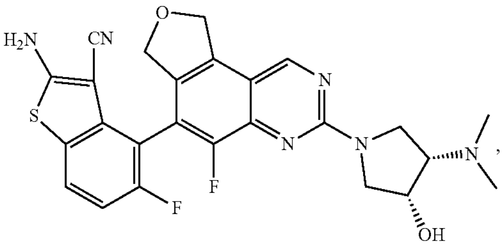
,
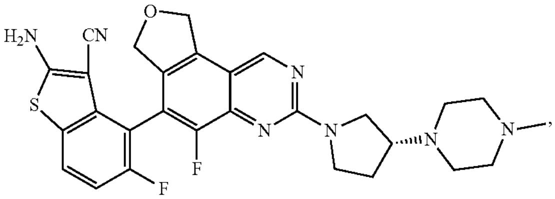
,
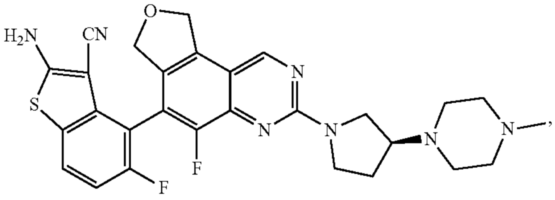
,
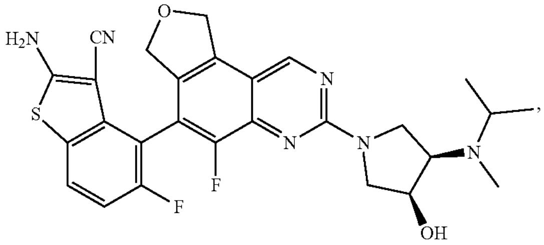
,
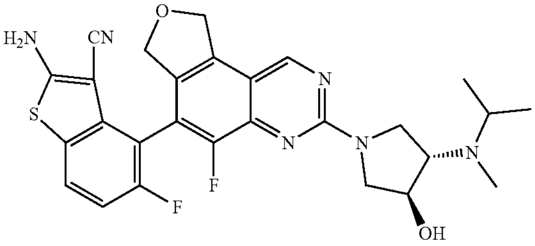
,
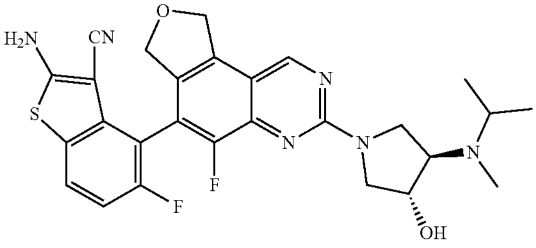
,
-continued
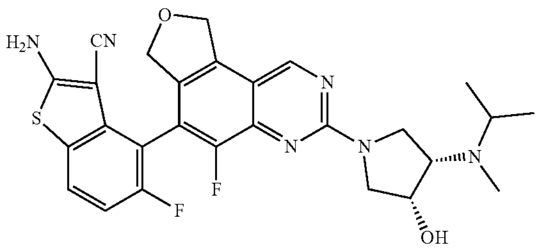
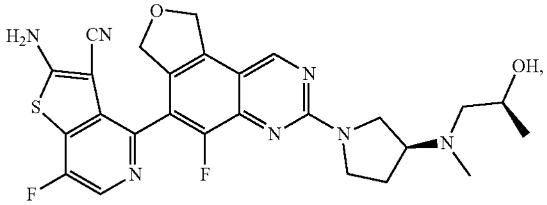
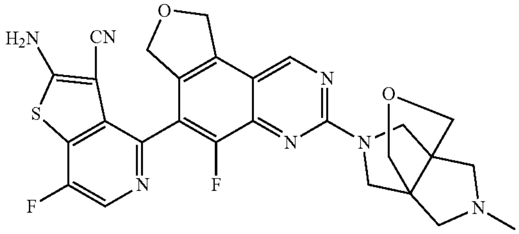
,
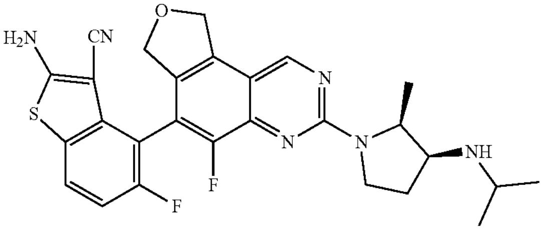
,
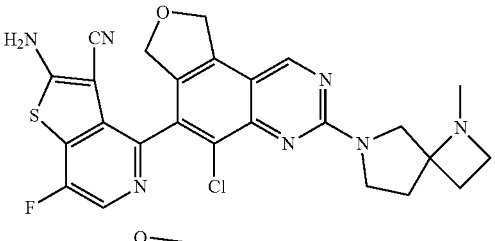
,
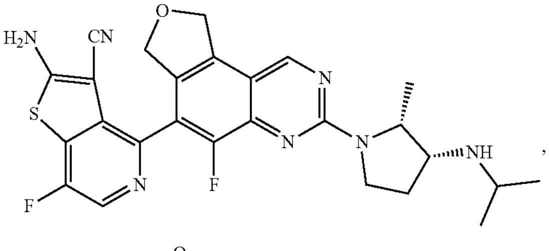
,
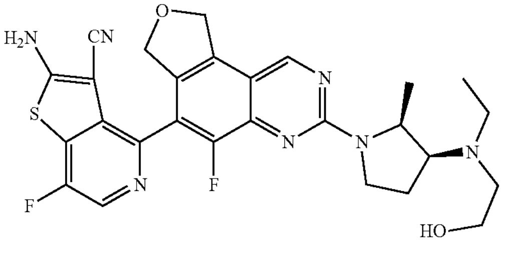
, -continued
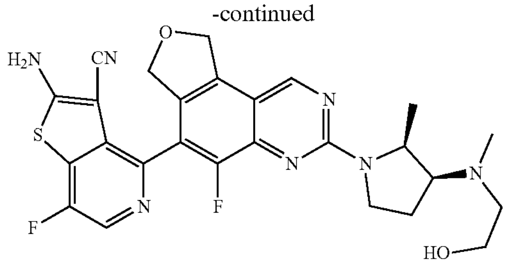
,
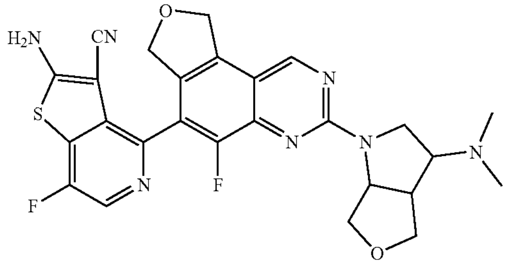
,
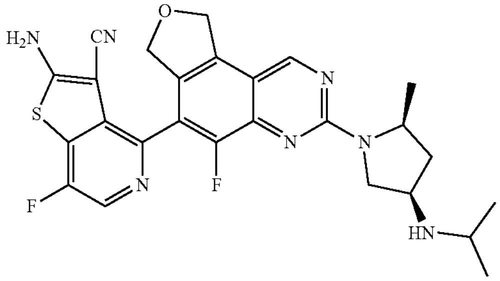
,
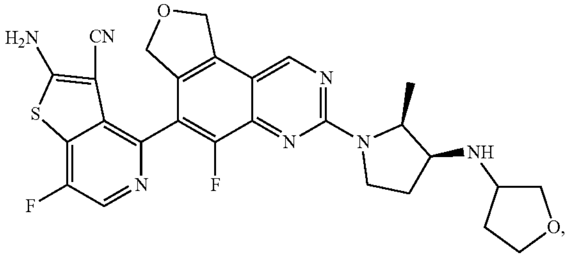
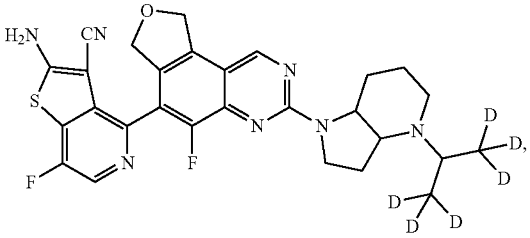
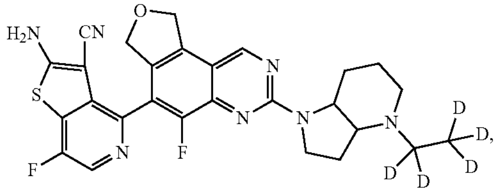
and
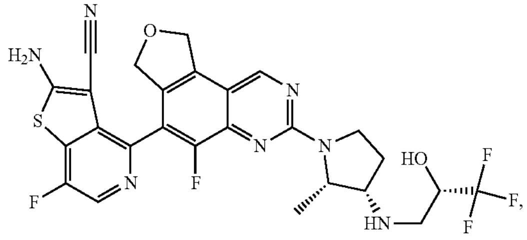
or a pharmaceutically acceptable salt thereof.
A compound of Formula I or a pharmaceutically acceptable salt thereof, the compound is selected from
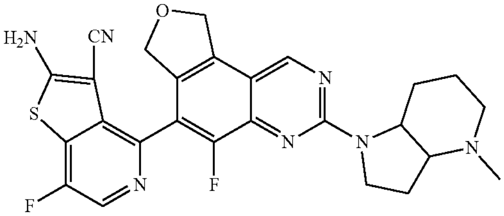
,
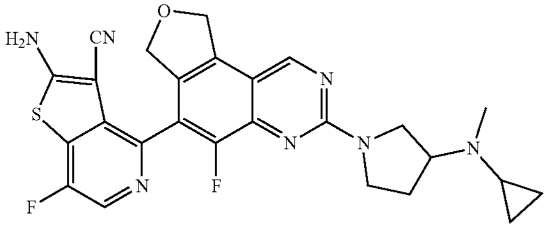
,
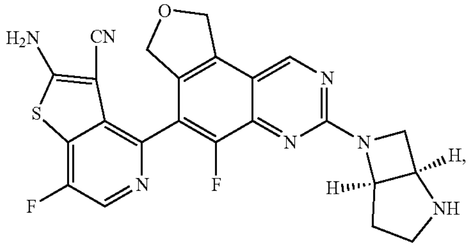
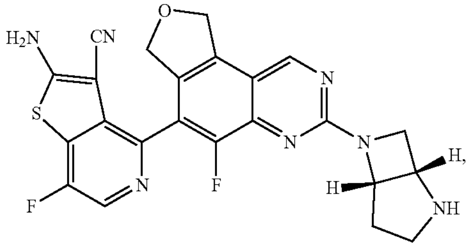
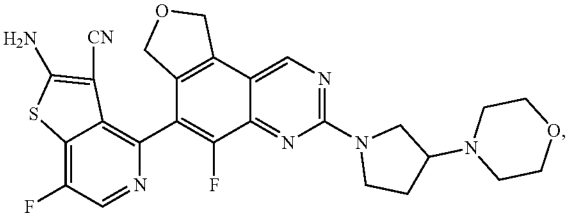
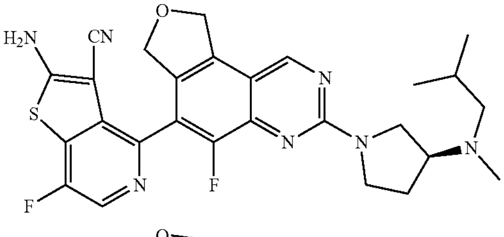
,
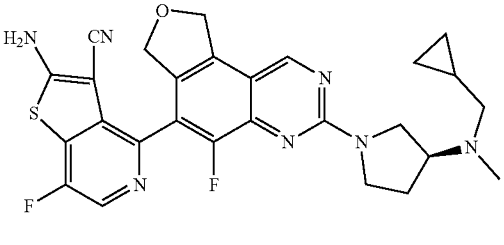
, -continued
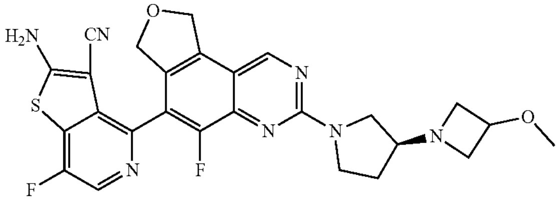
,
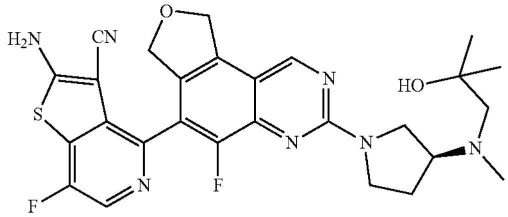
,
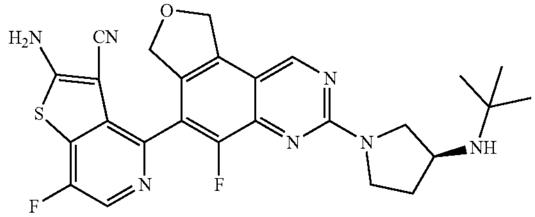
,
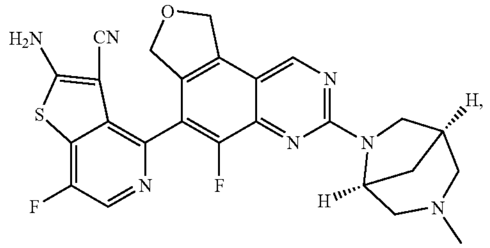
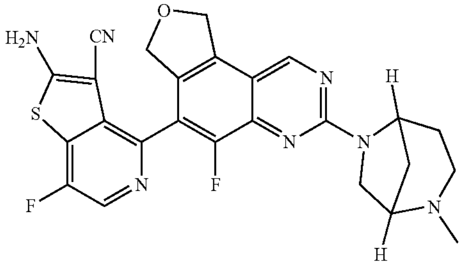
,
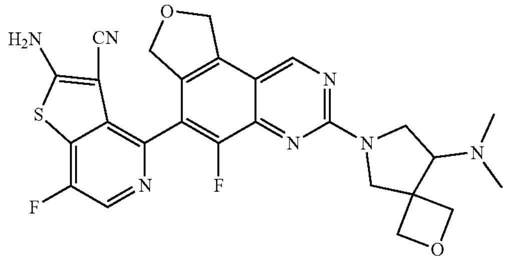
,
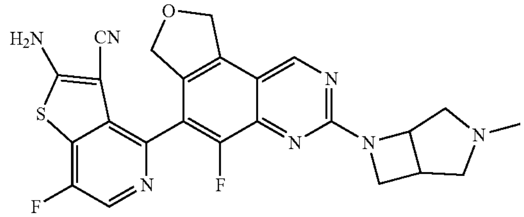
,
-continued
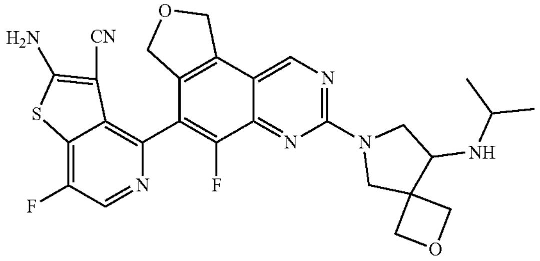
,
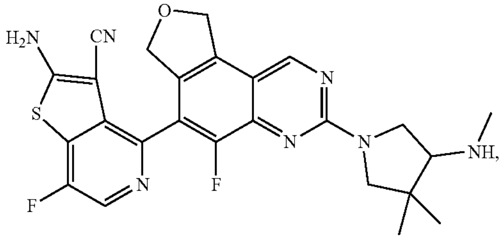
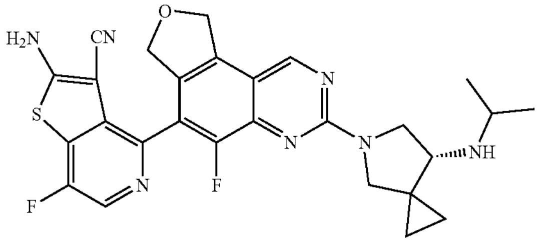
,
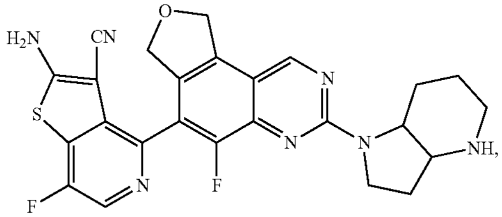
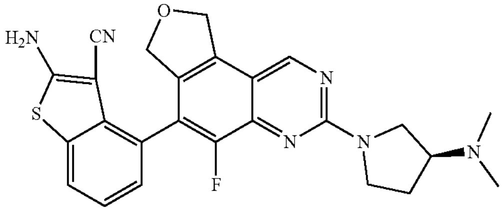
,
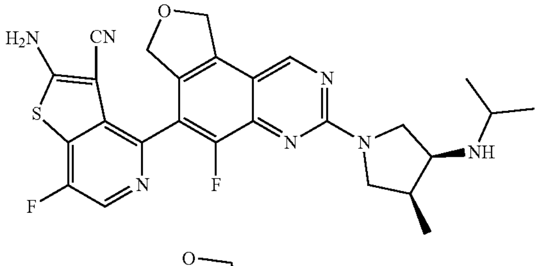
,
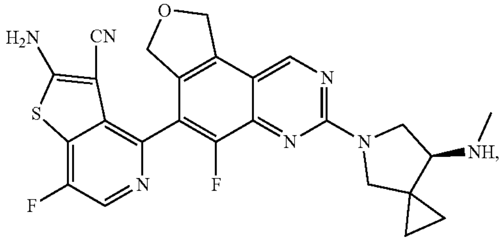

-continued
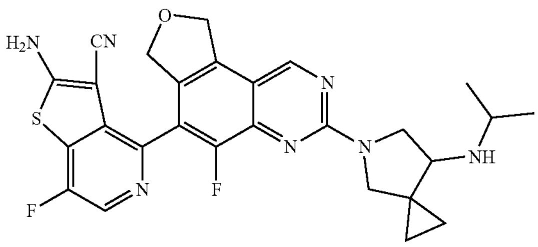
,
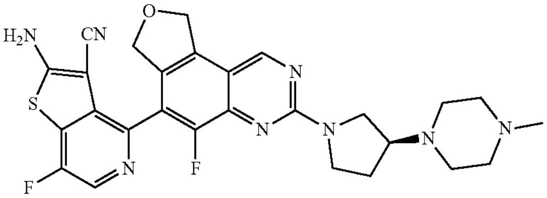
,
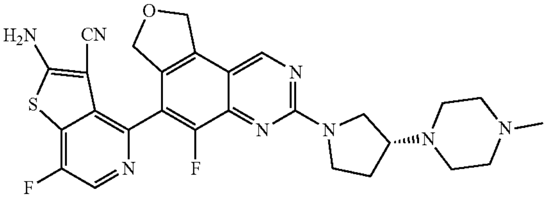
,
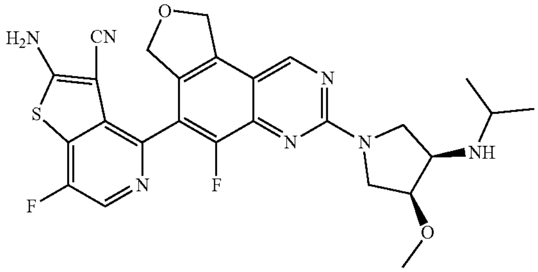
,
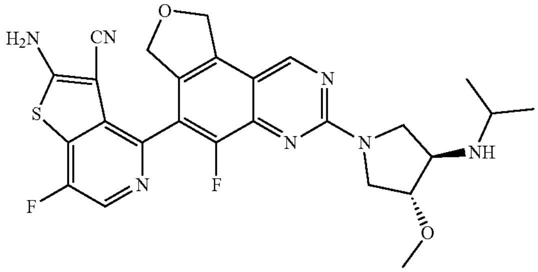
,
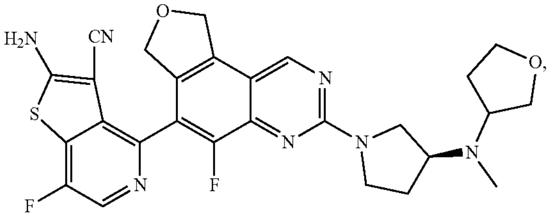
,
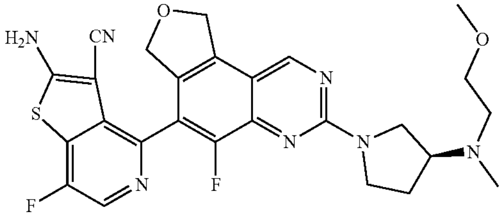
,
-continued
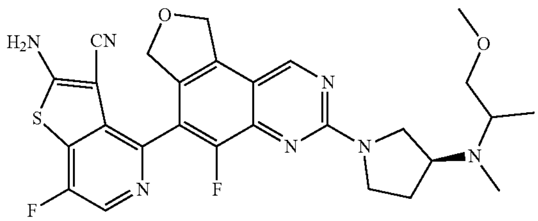
,
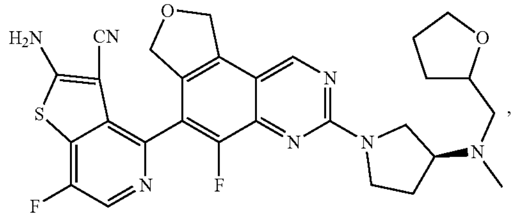
,
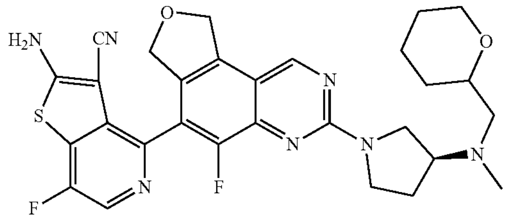
,
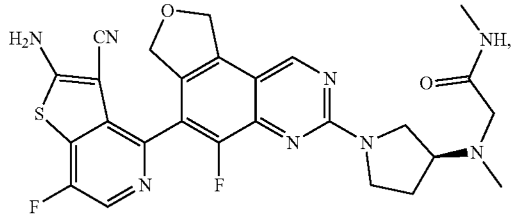
,
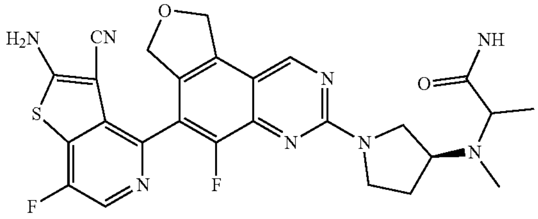
,
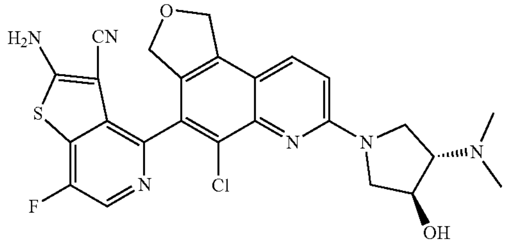
,
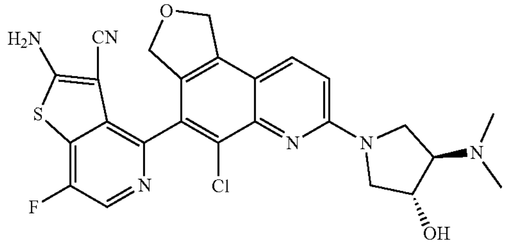
, -continued
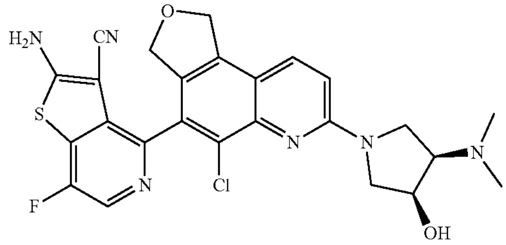
,
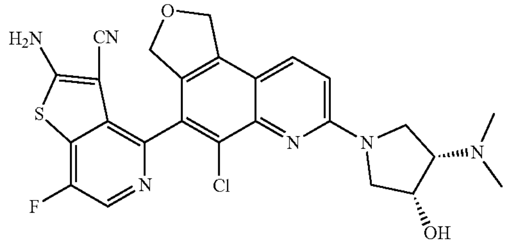
,
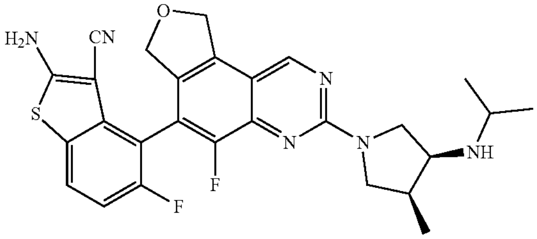
,
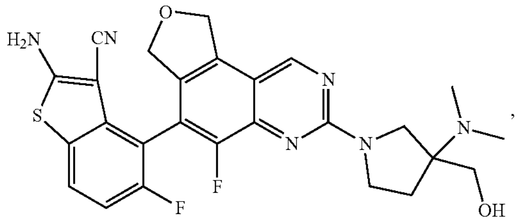
,
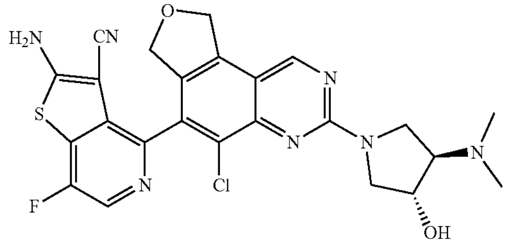
,
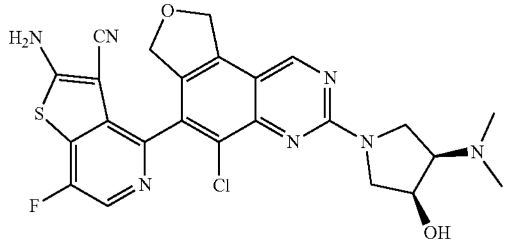
,
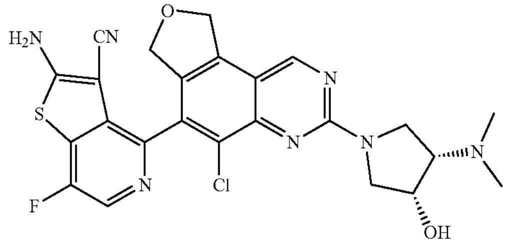
,
-continued
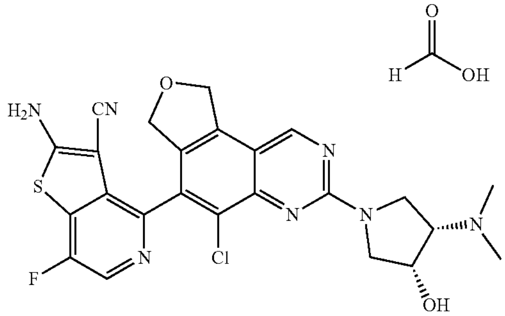
,
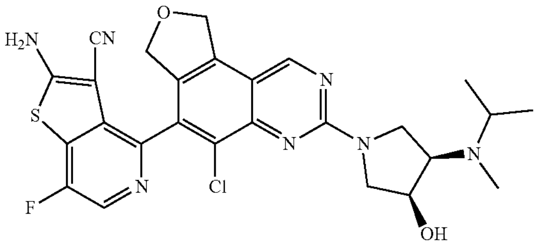
,
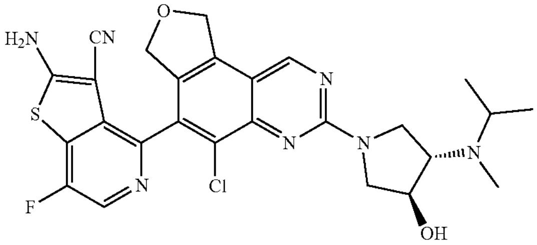
,
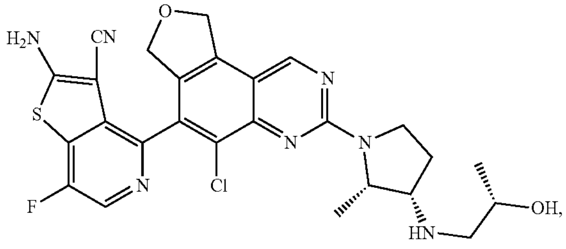
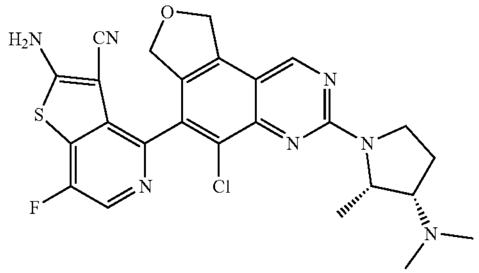
,
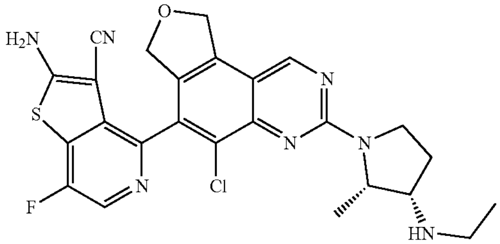
, -continued
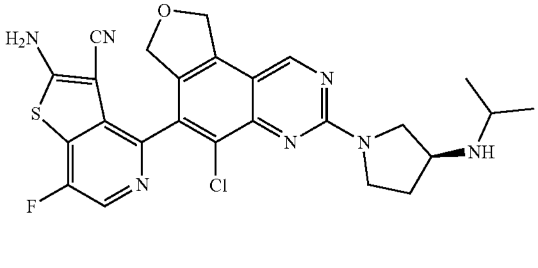
,
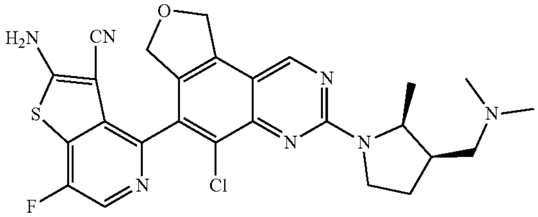
,
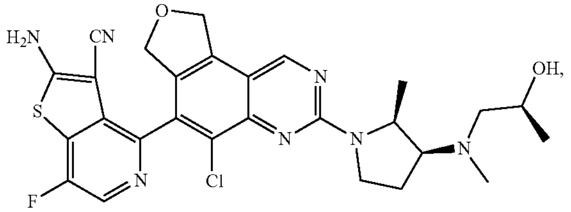
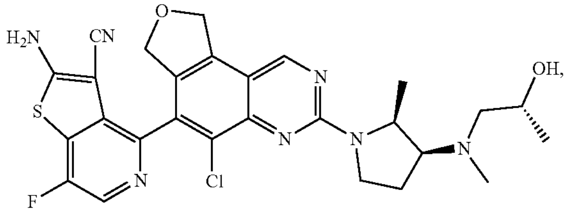
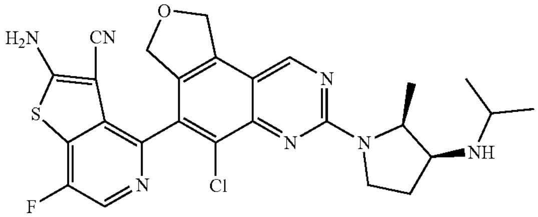
,
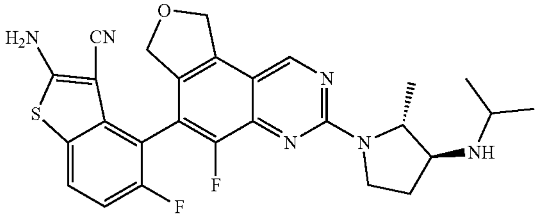
,
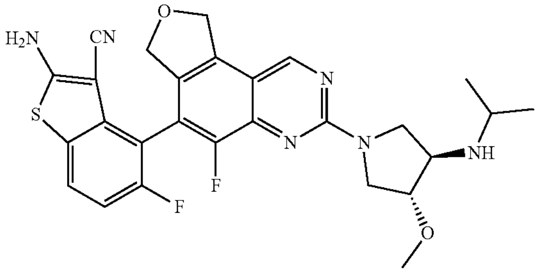
,
-continued
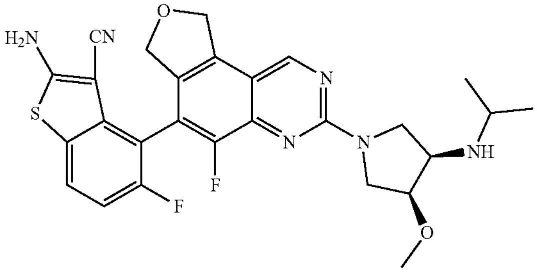
,
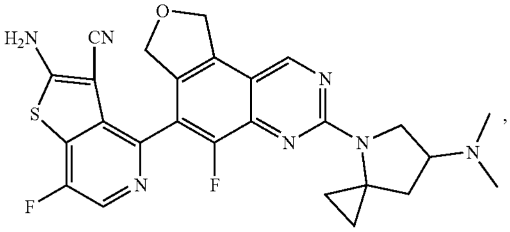
,
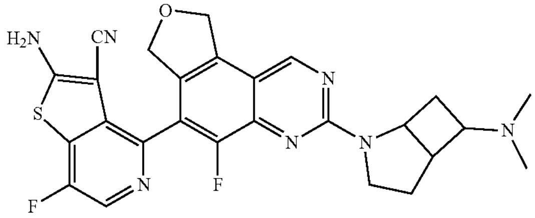
,
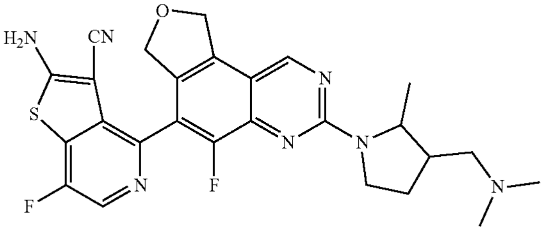
,
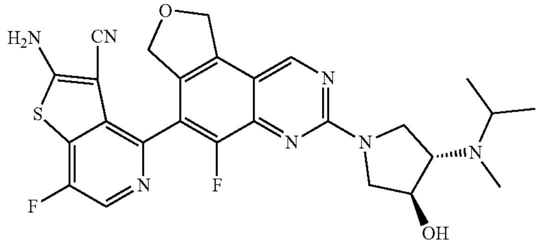
,
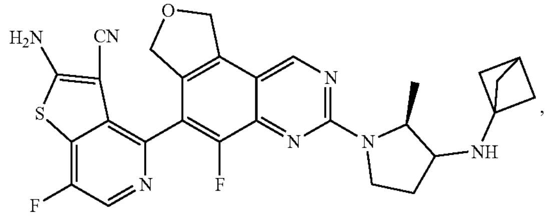
,
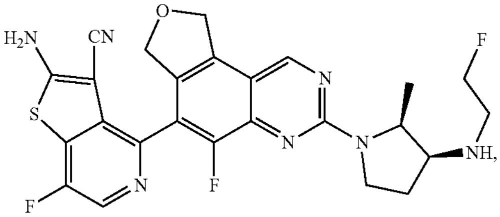

-continued
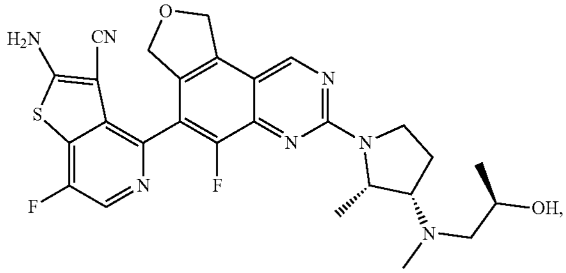
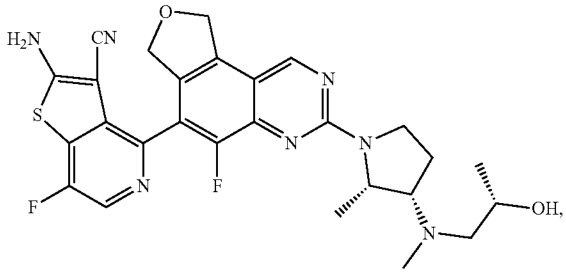
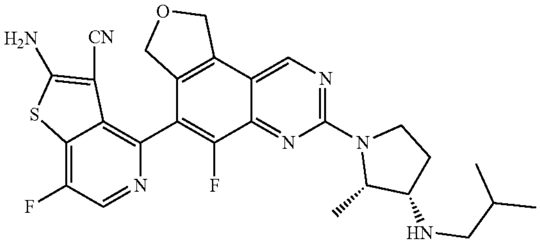
,
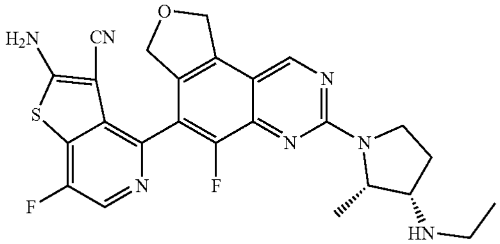
,
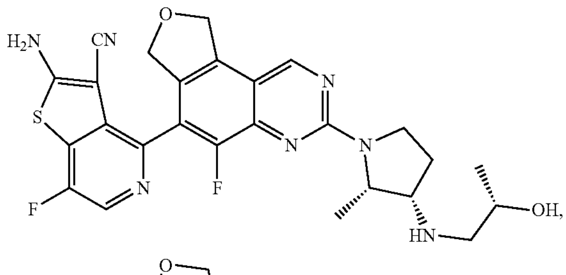
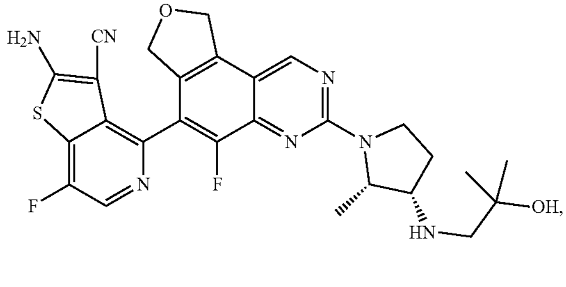
-continued
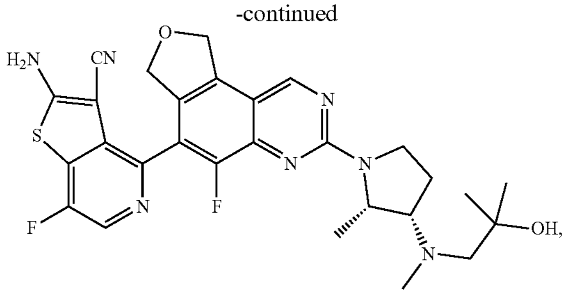
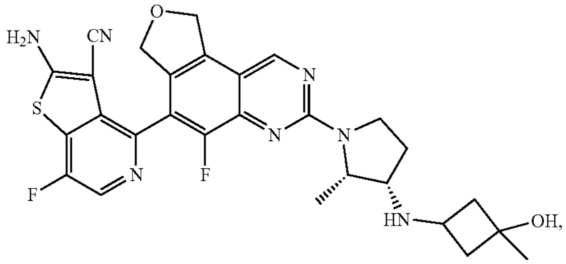
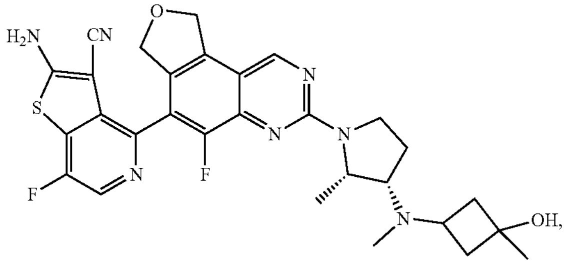
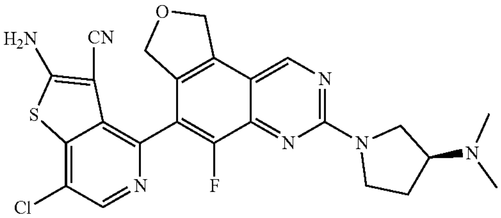
,
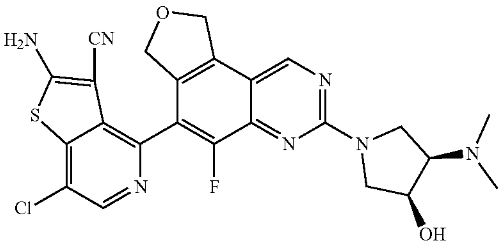
,
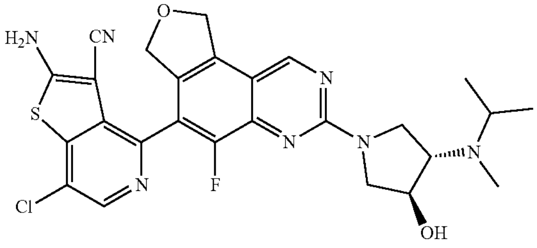
,
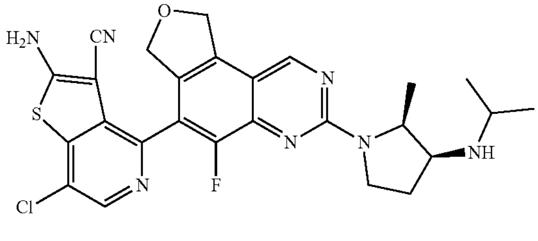
, -continued
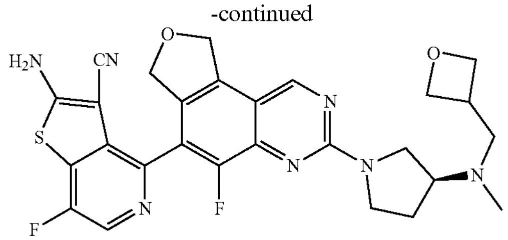
,
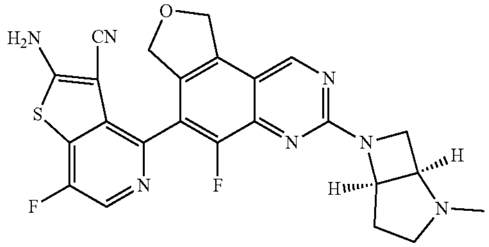
, and
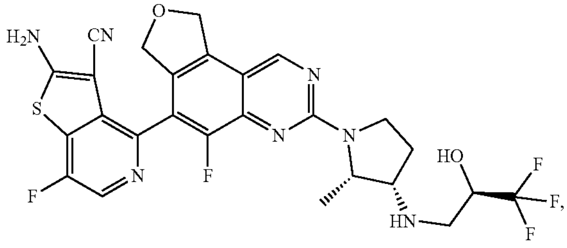
or a pharmaceutically acceptable salt thereof.
A compound of Formula I or a pharmaceutically acceptable salt thereof, the compound is selected from
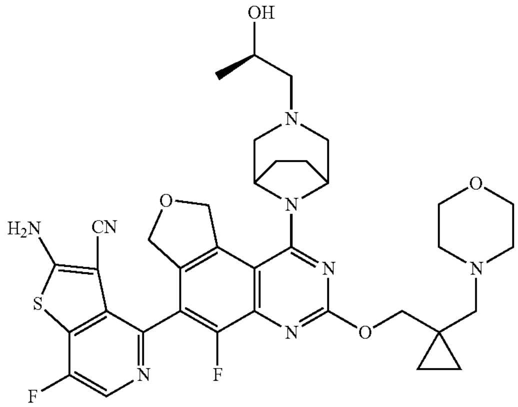
,
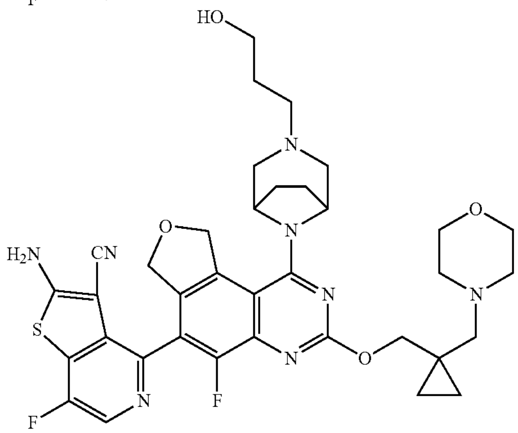
,
-continued
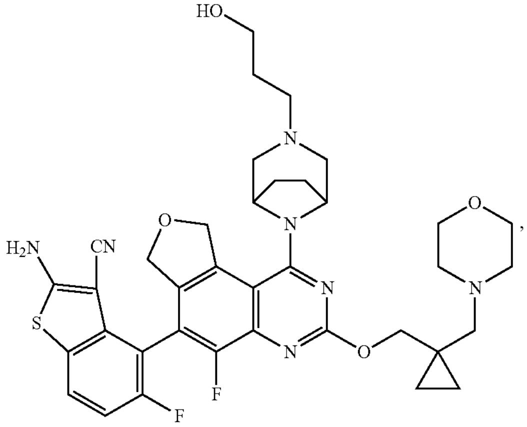
,
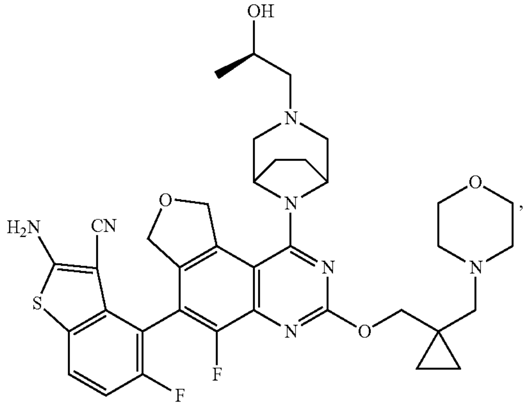
,
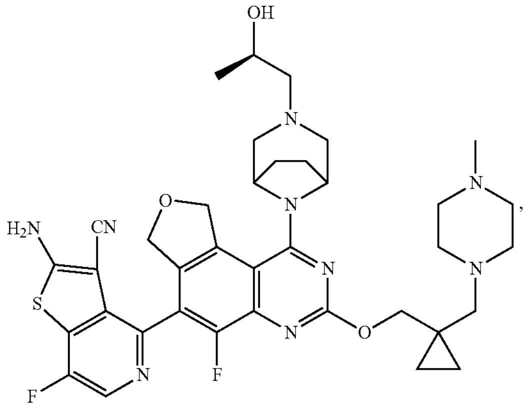
,
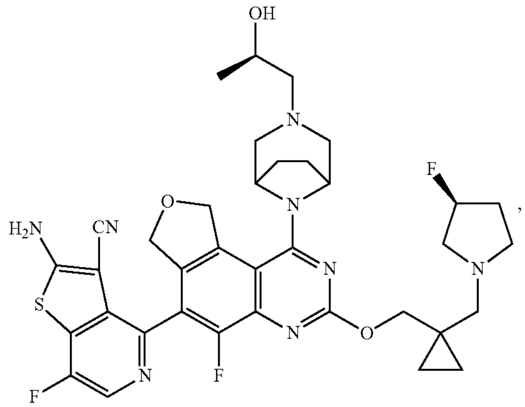
, -continued
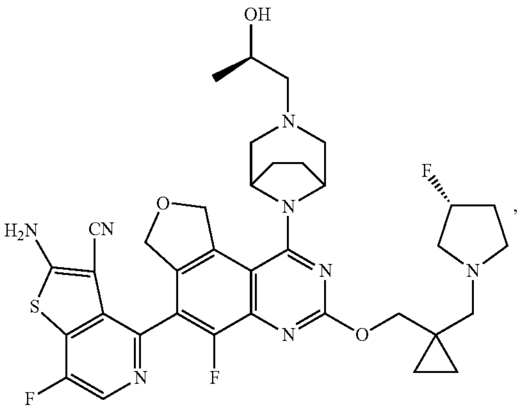
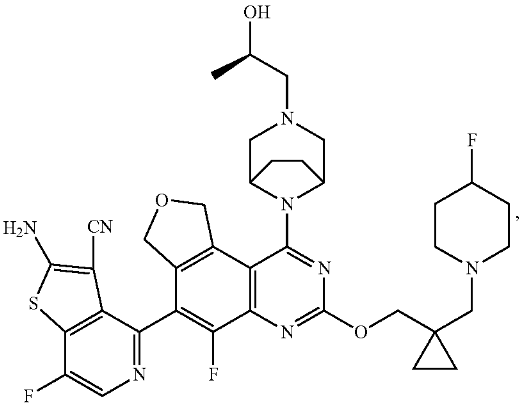
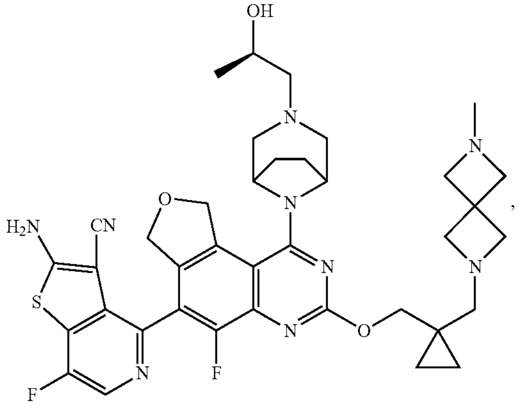
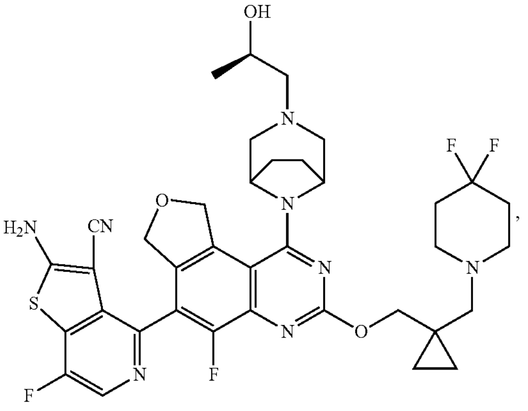
-continued
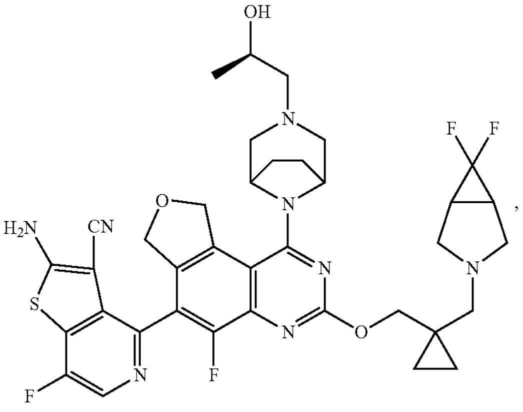
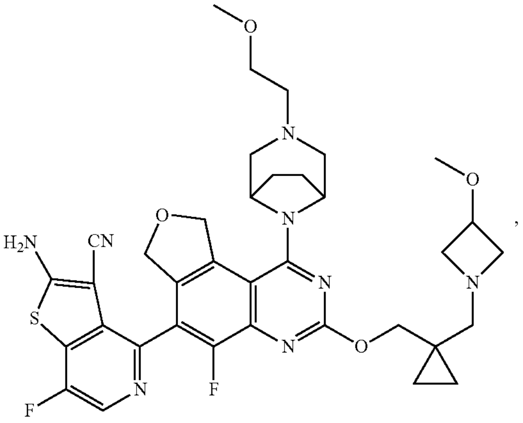
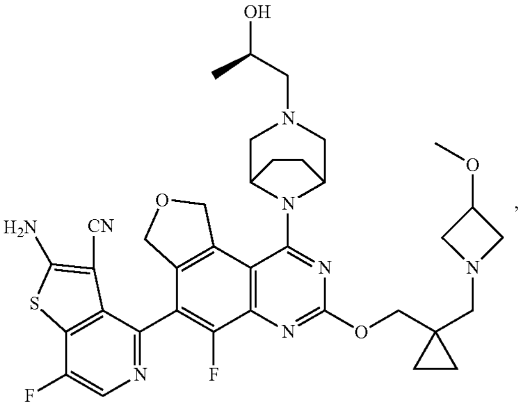
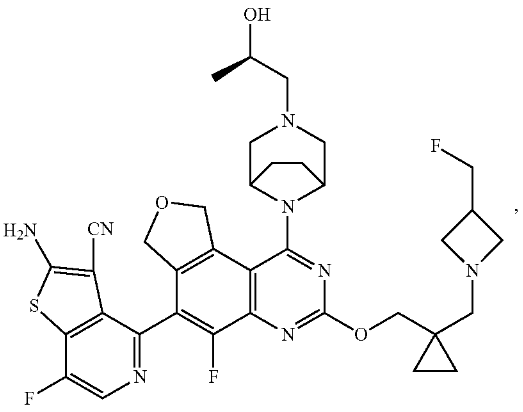

-continued
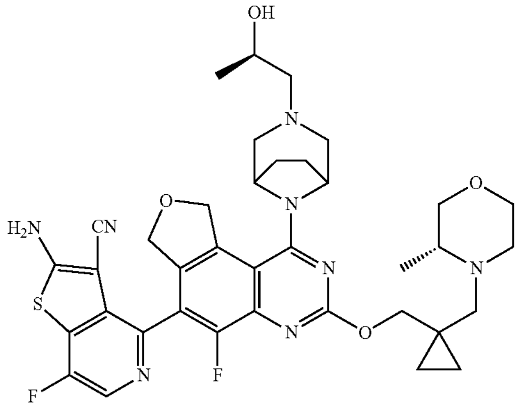,
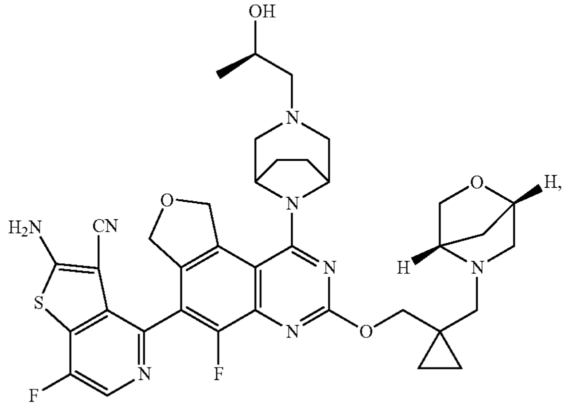,
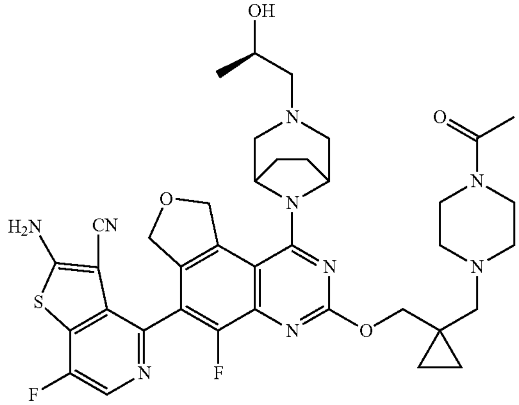,
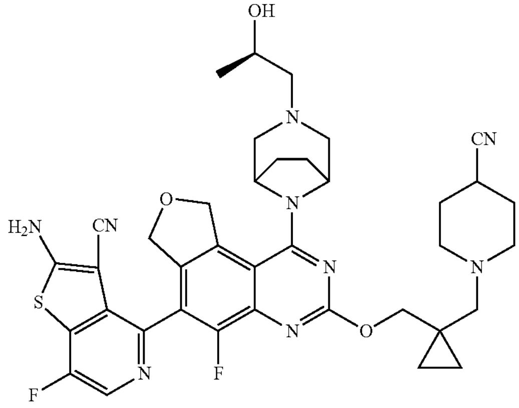,
-continued
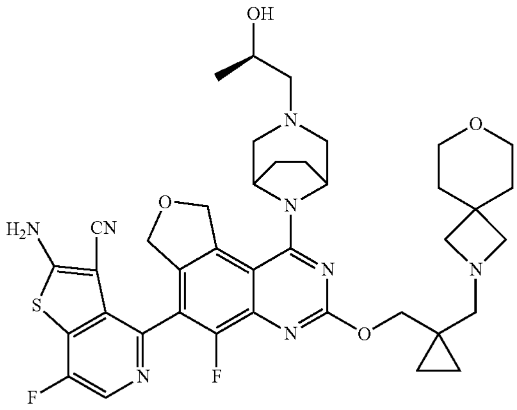,
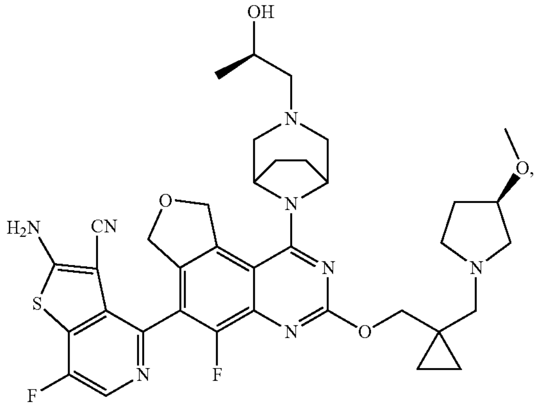,
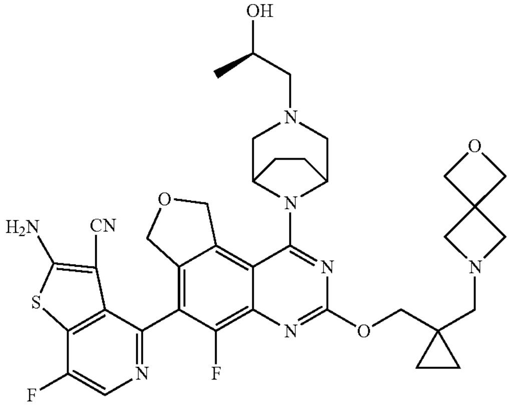,
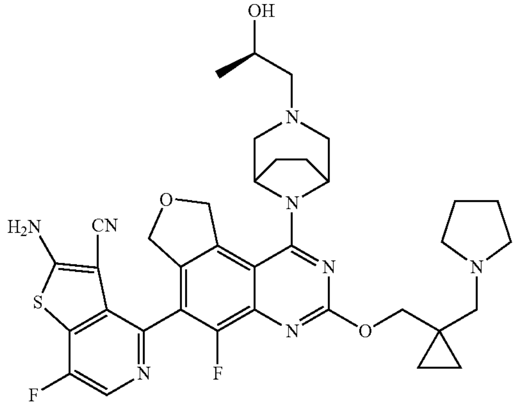, -continued
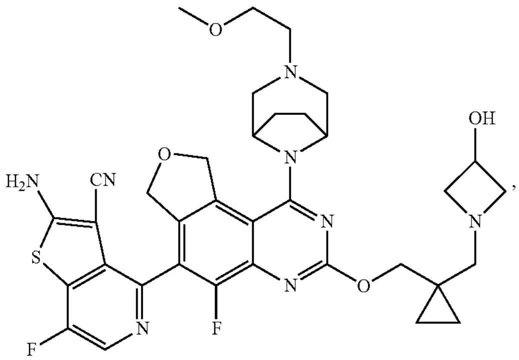
,
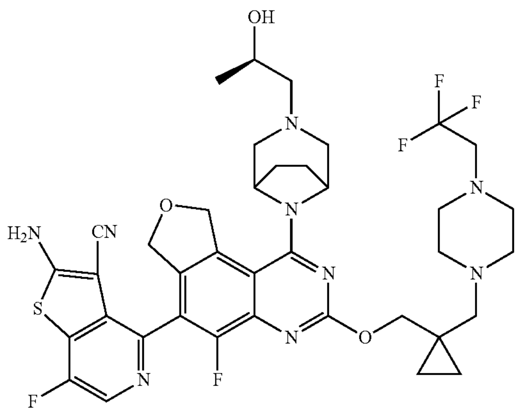
,
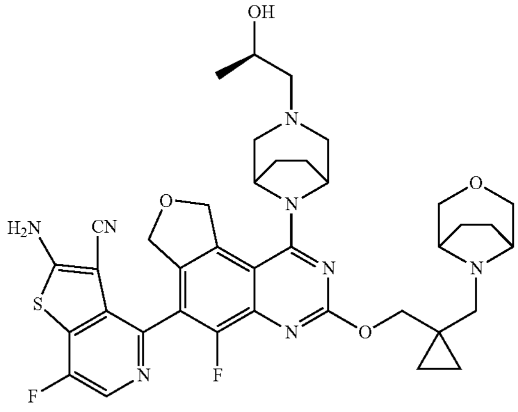
,
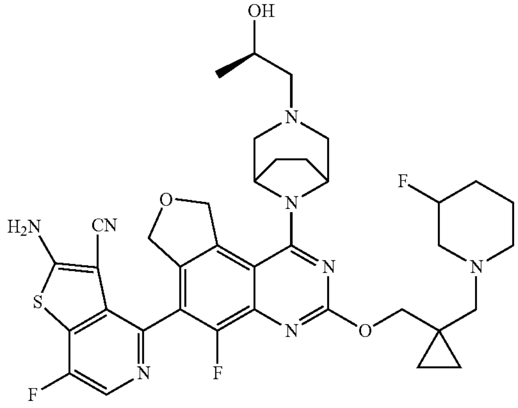
,
-continued
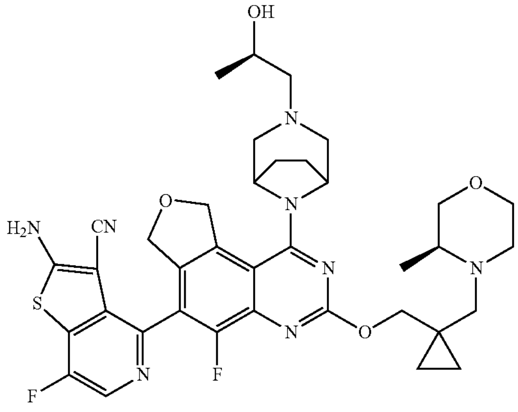
,
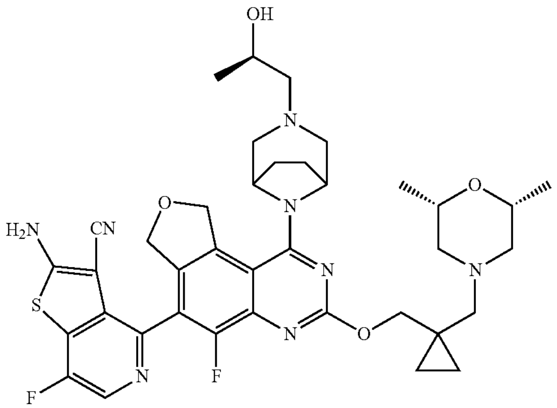
,
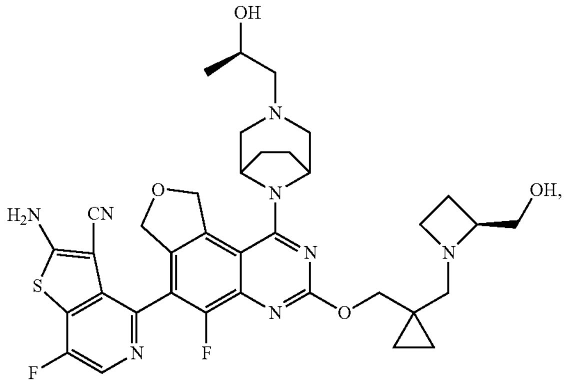
,
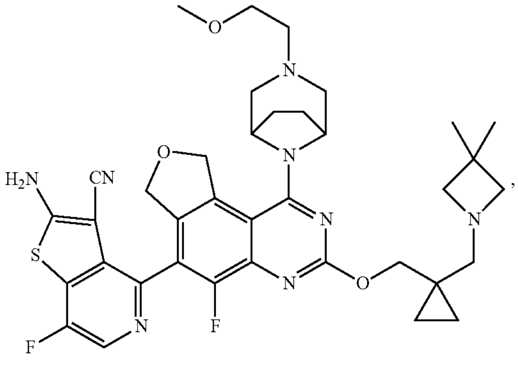
, -continued
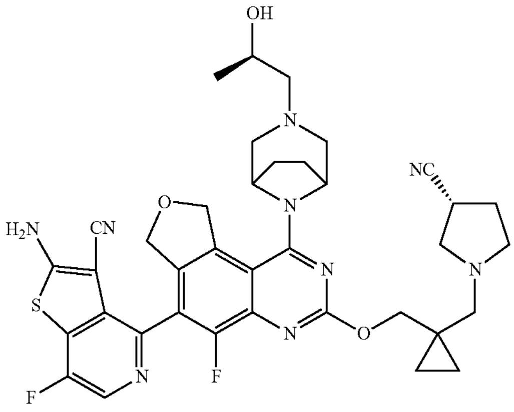
,
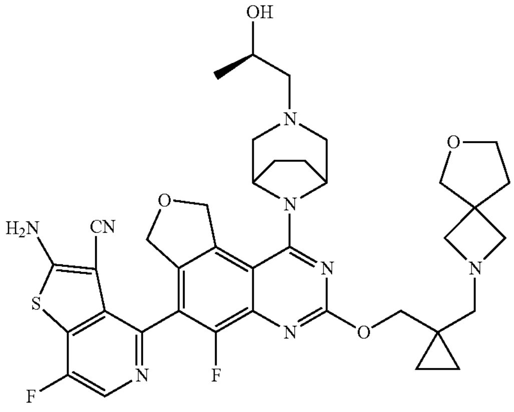
,
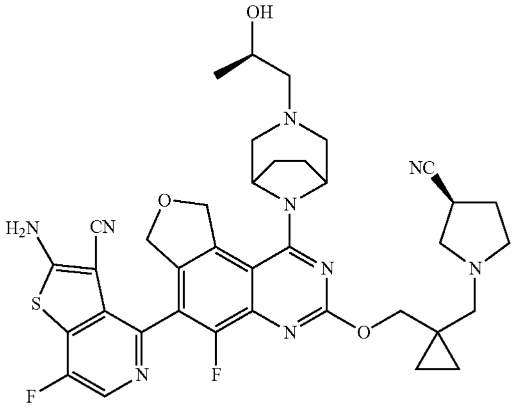
,
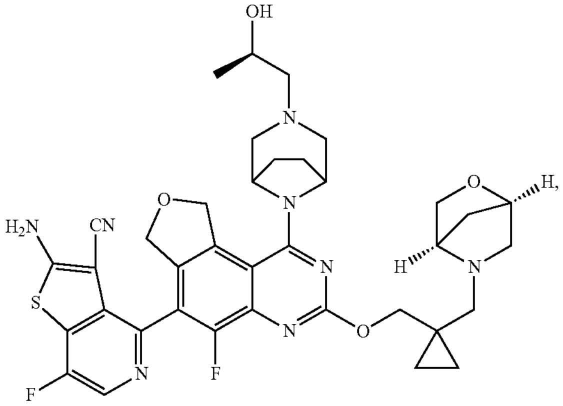
-continued
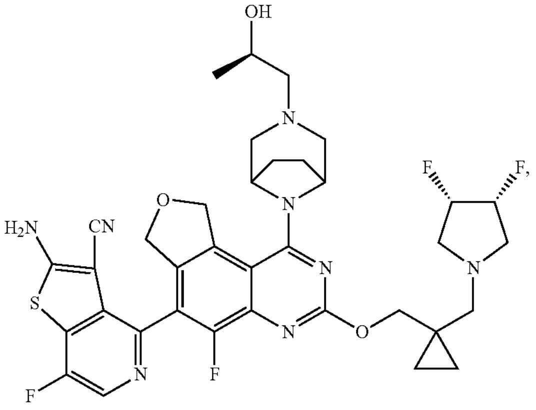
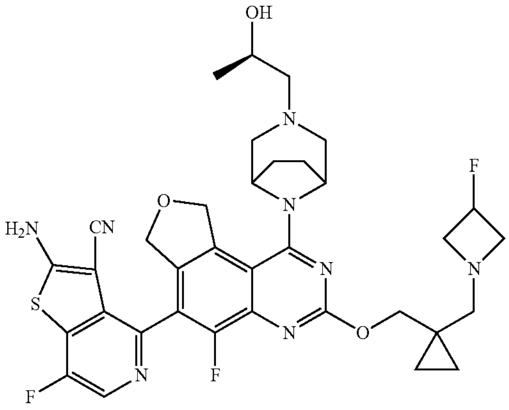
,
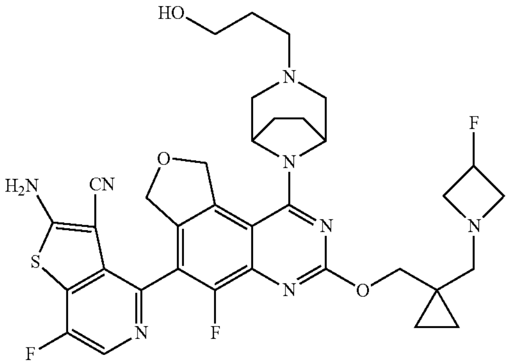
,
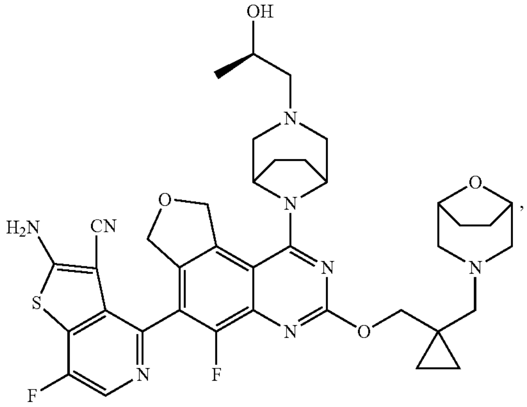
, -continued
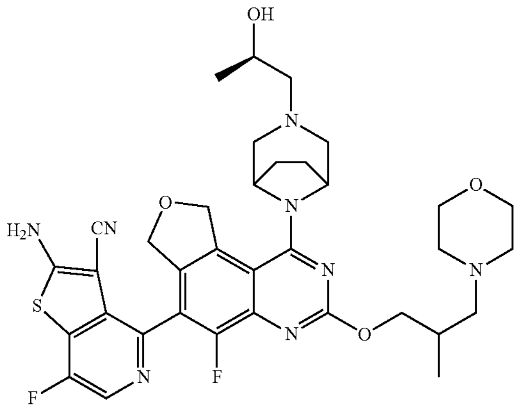
,
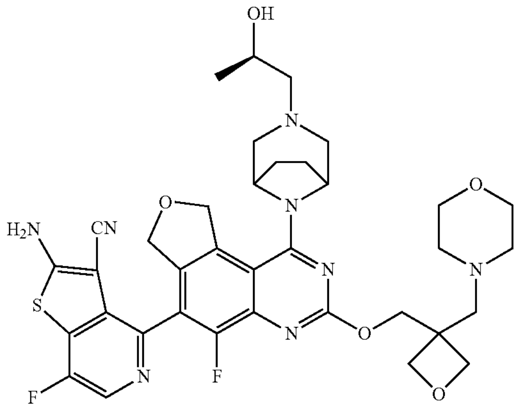
,
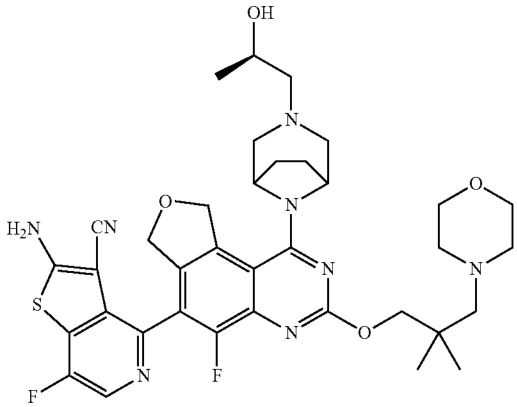
,
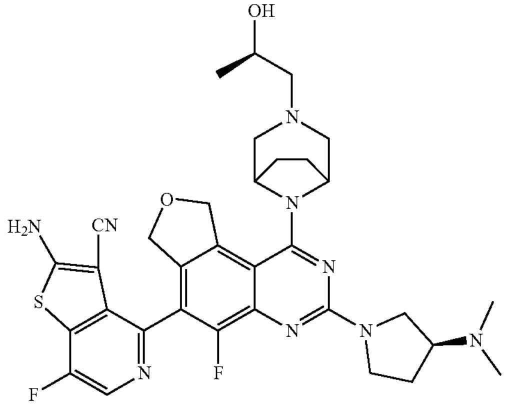
,
-continued
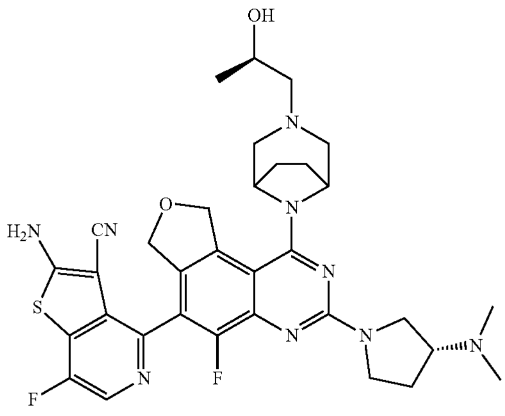
,
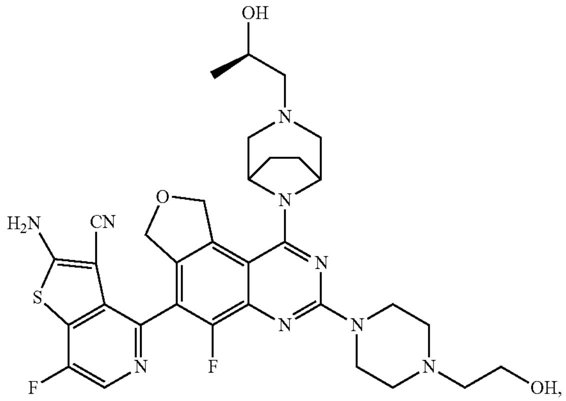
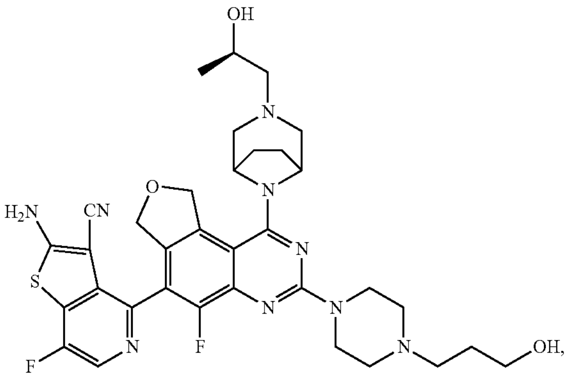
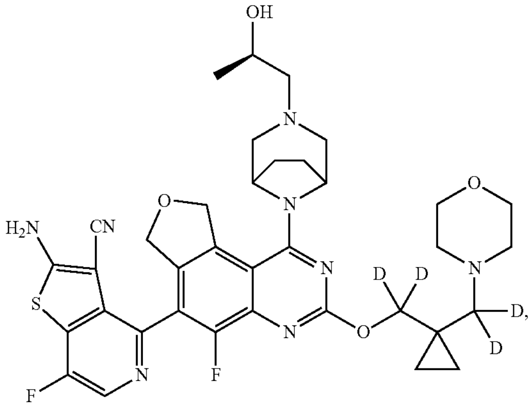

-continued
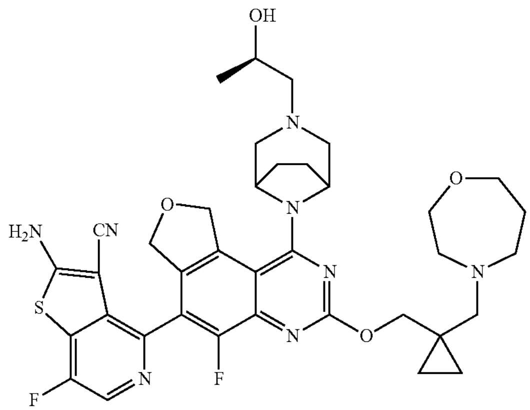
,
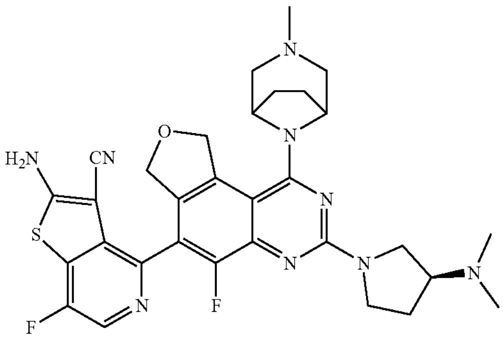
,
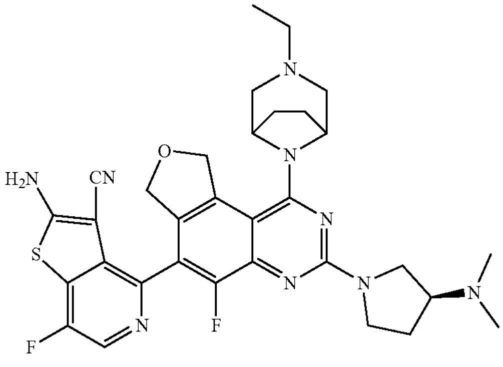
,
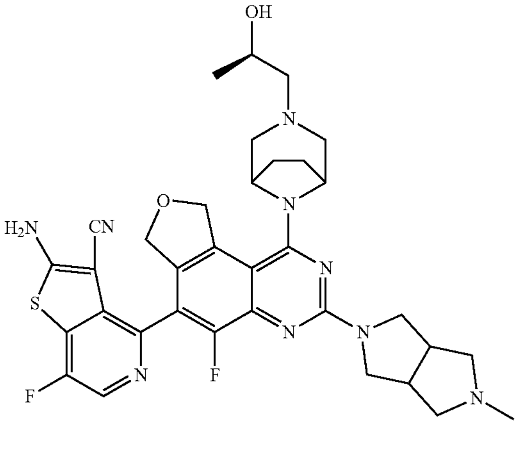
,
-continued
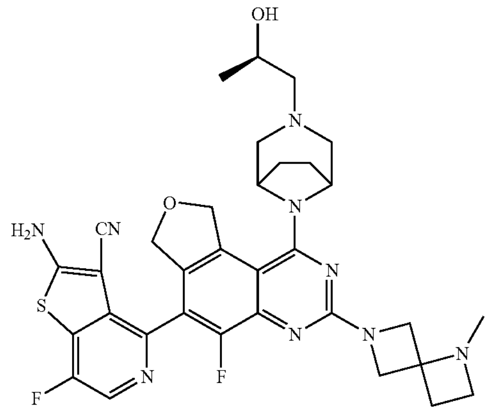
,
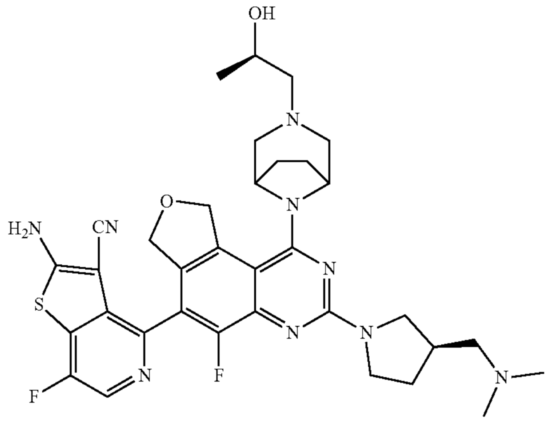
,
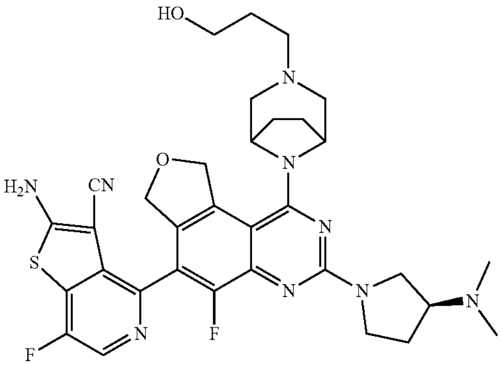
,
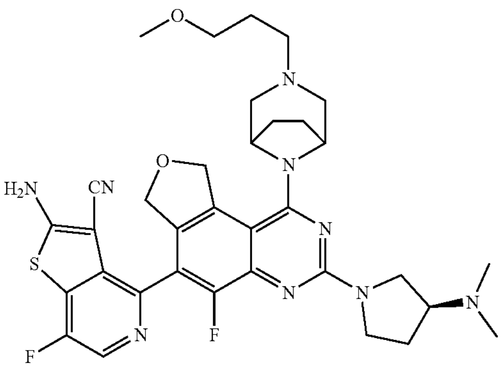
, -continued
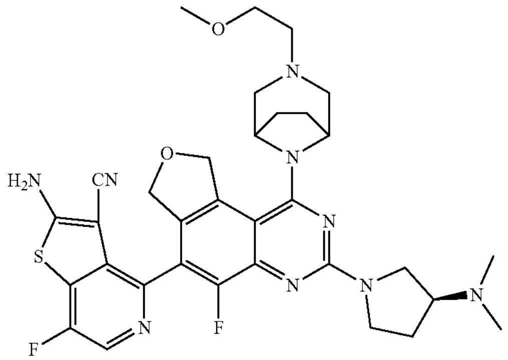
,
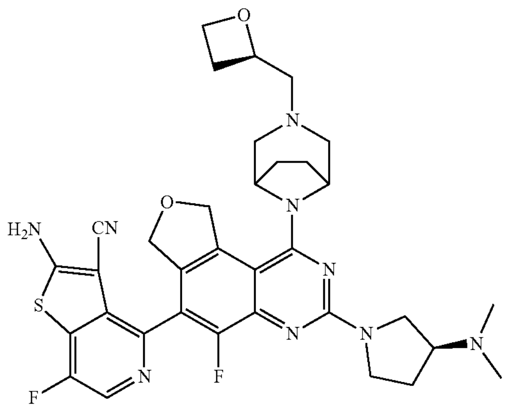
,
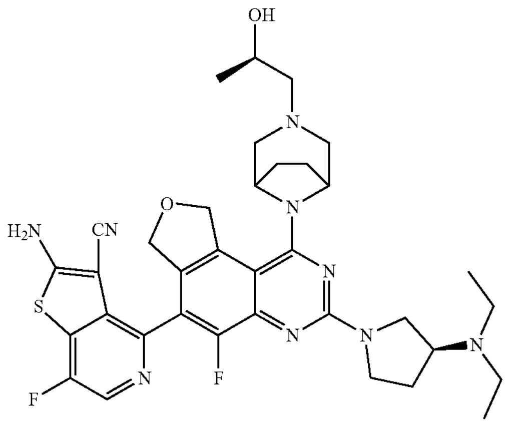
,
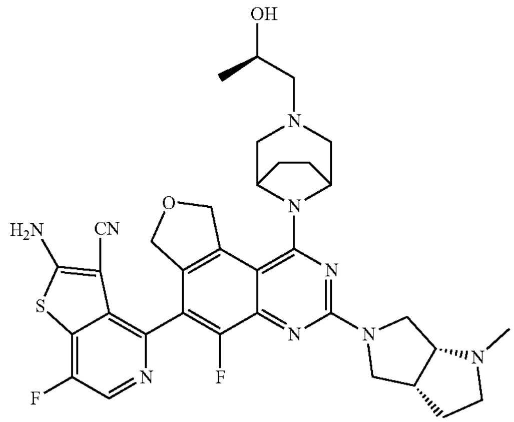
,
-continued
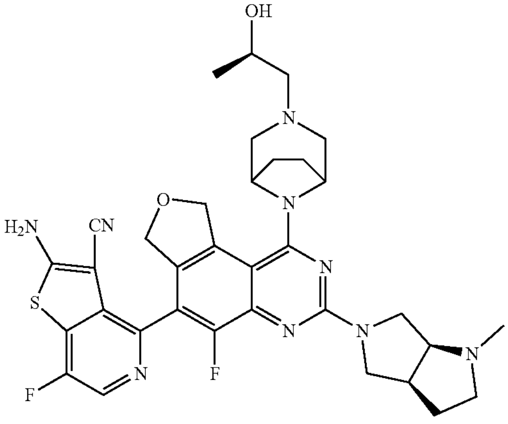
,
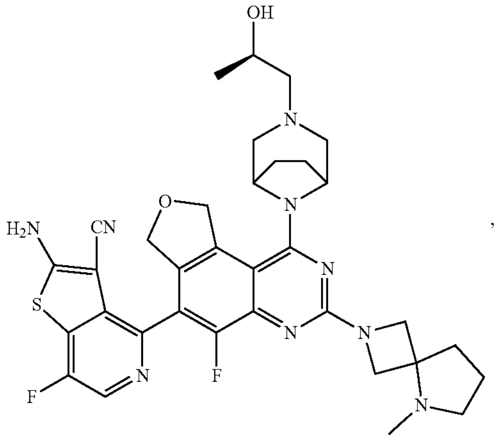
,
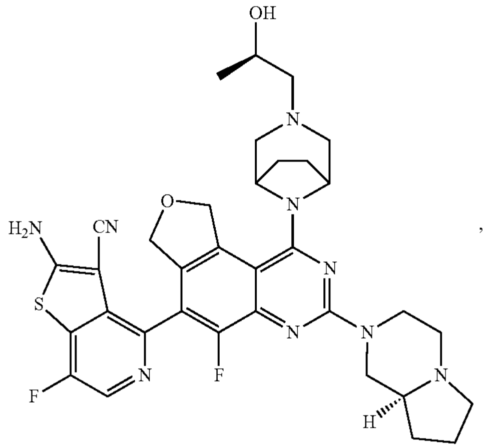
,
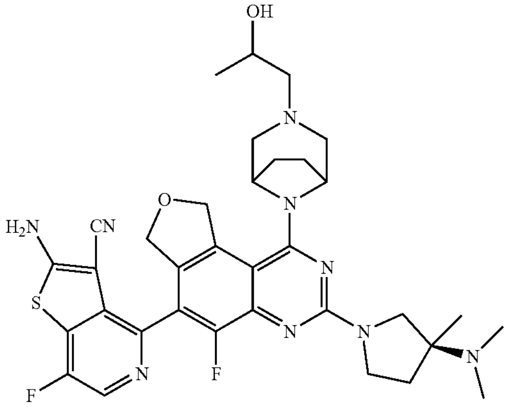
, -continued
-continued
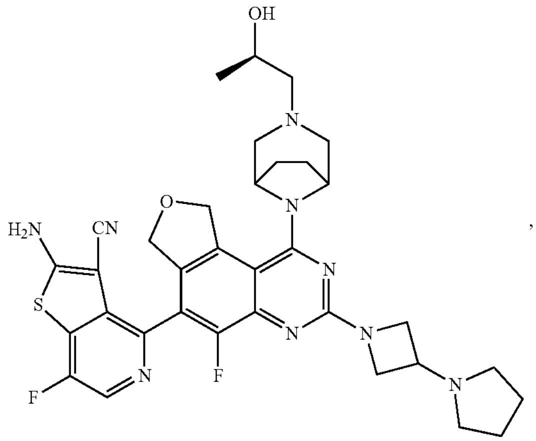,
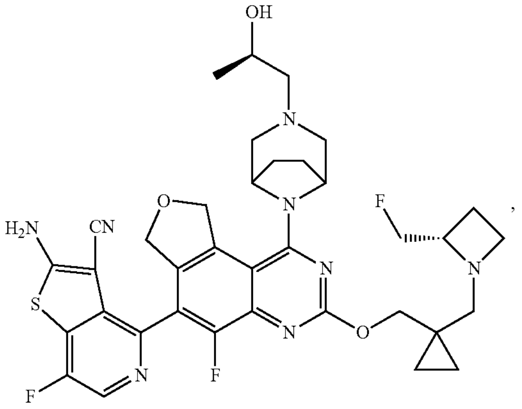,
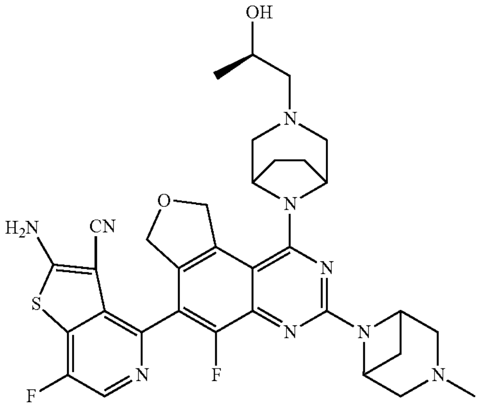,
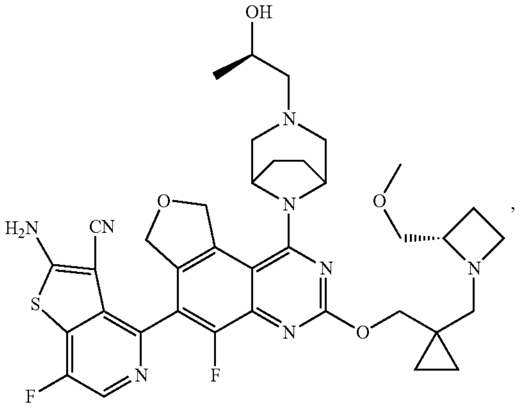,
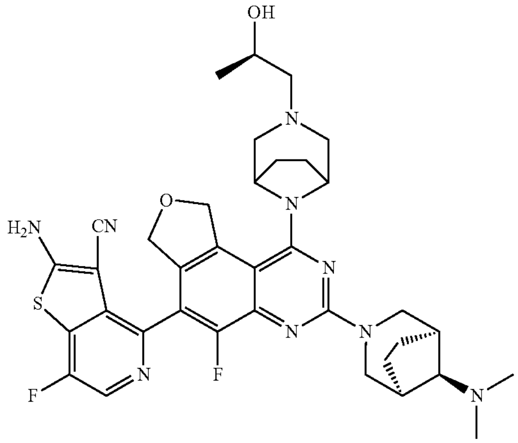,
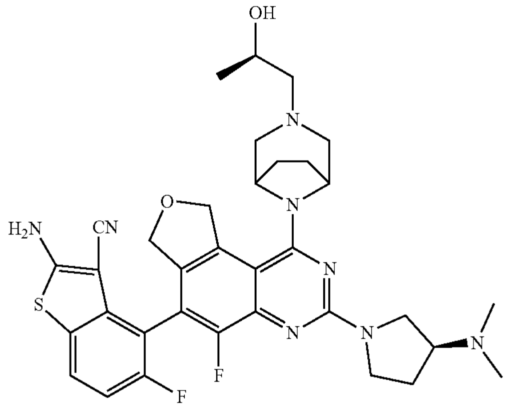,
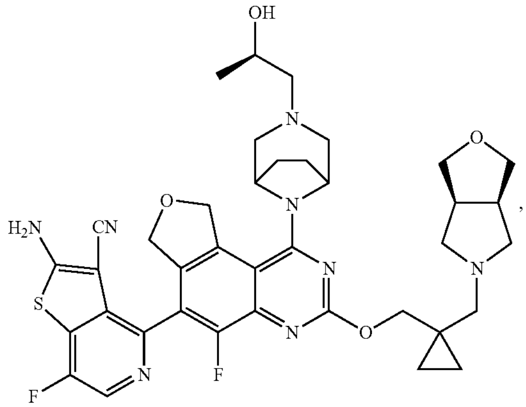,
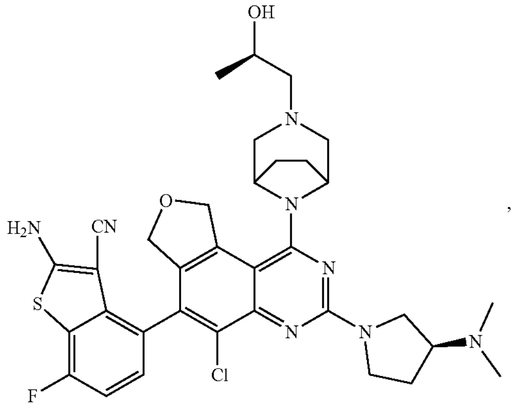, and -continued
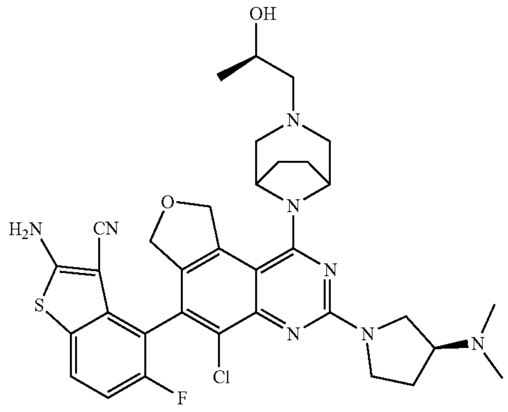
,
or a pharmaceutically acceptable salt thereof.
A compound of Formula I or a pharmaceutically acceptable salt thereof, the compound is selected from
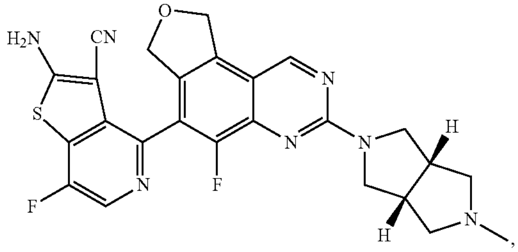
,
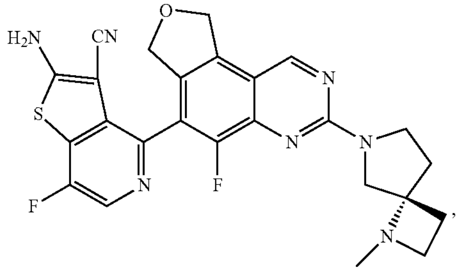
,
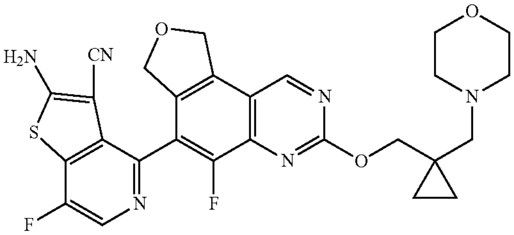
,
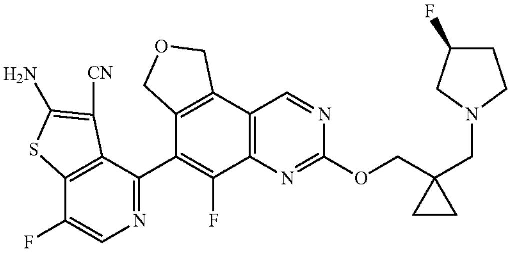
,
-continued
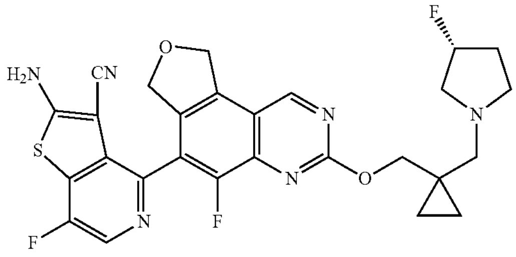
,
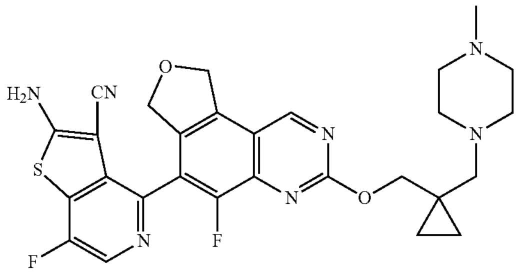
,
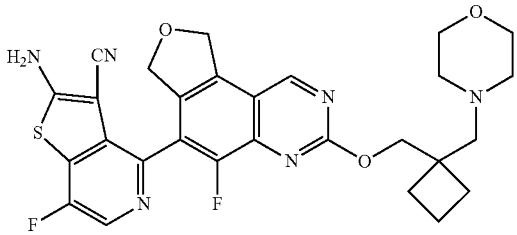
,
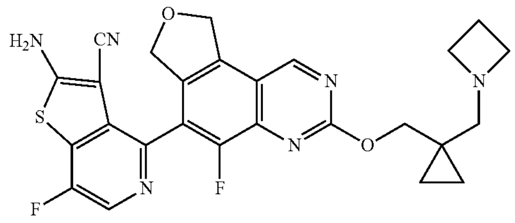
,
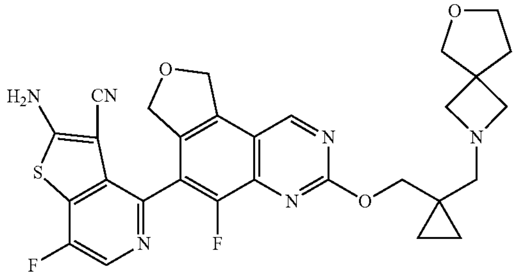
,
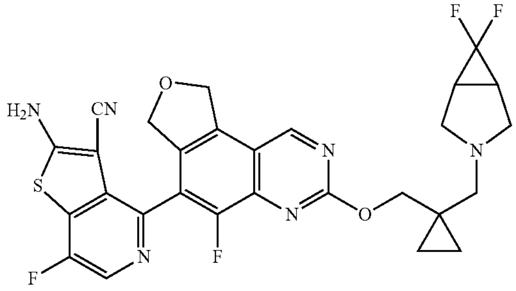
,

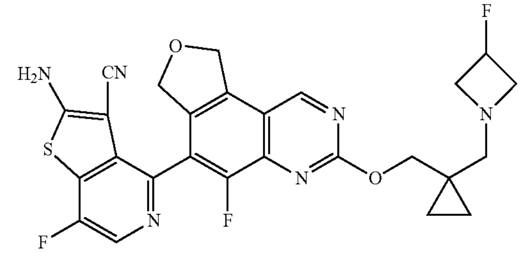
,
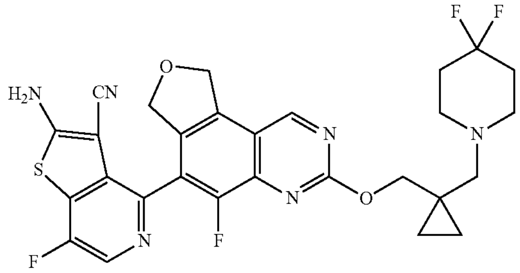
,
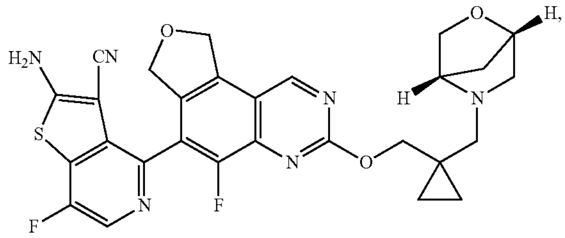
,
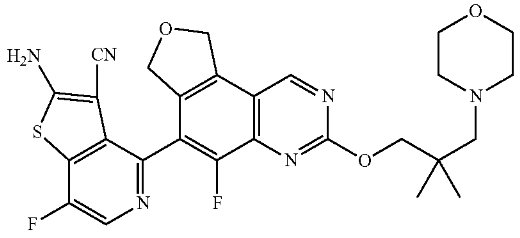
,
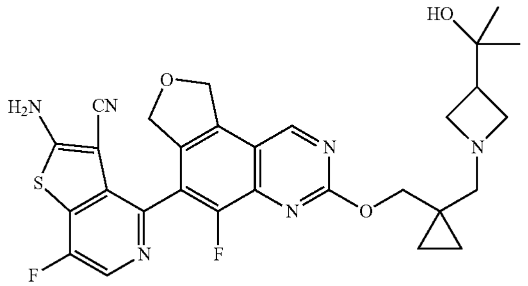
,
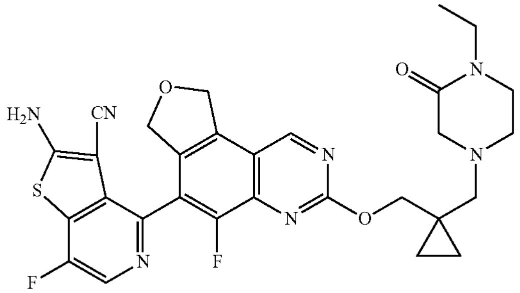
,
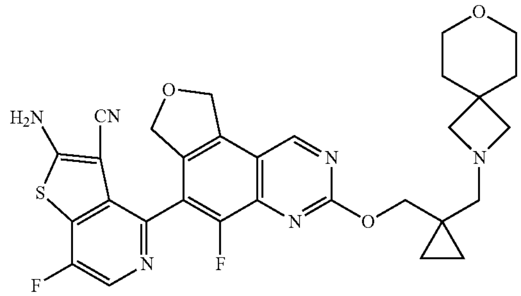
,
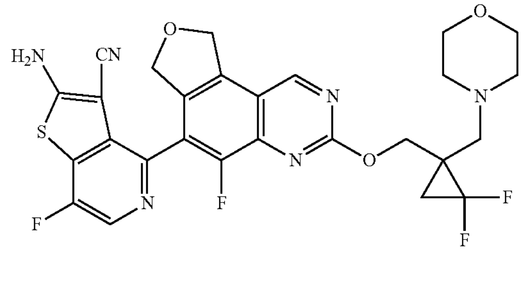
,
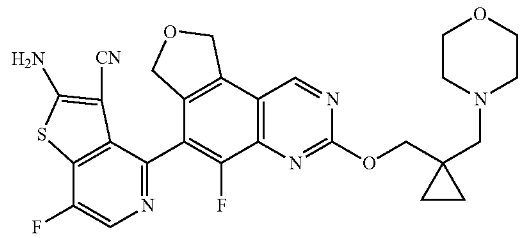
,
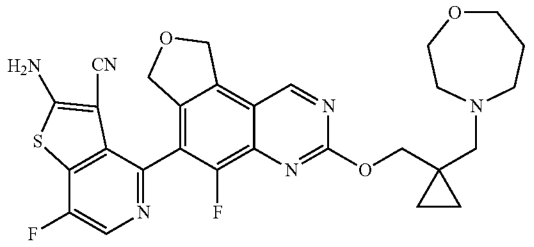
,
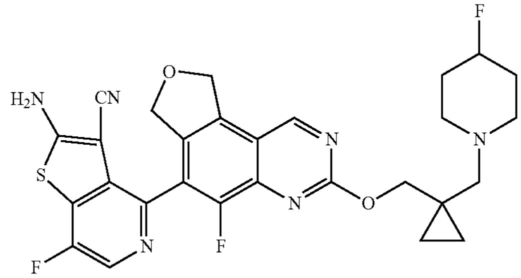
,
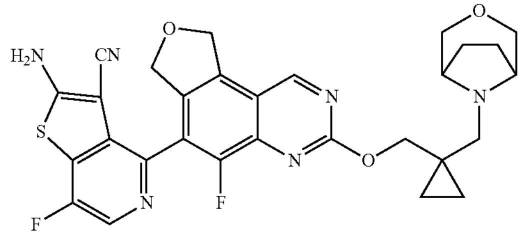
, -continued
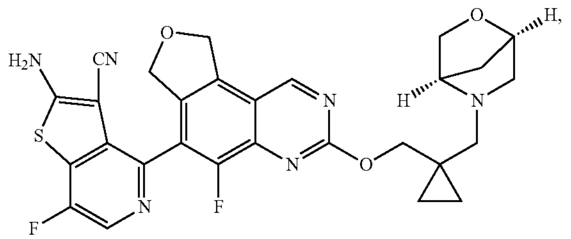
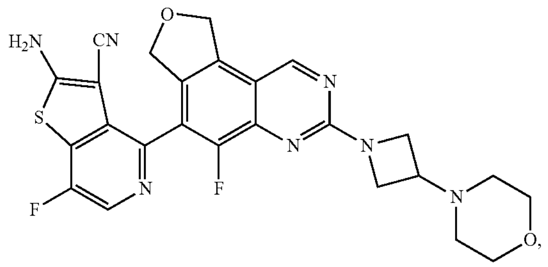
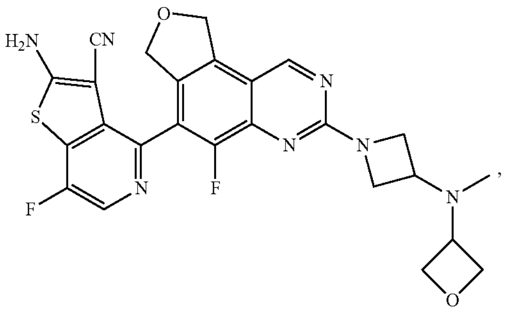
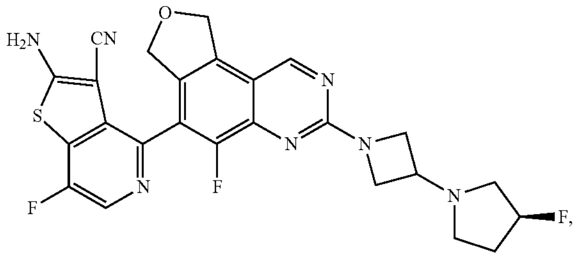
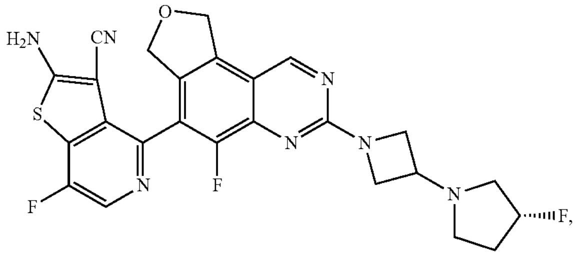
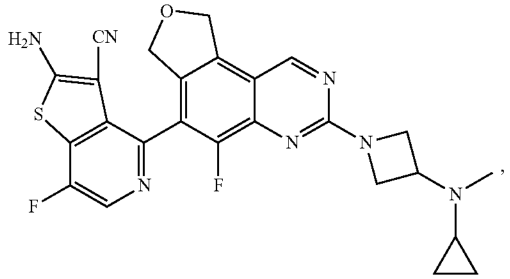
-continued
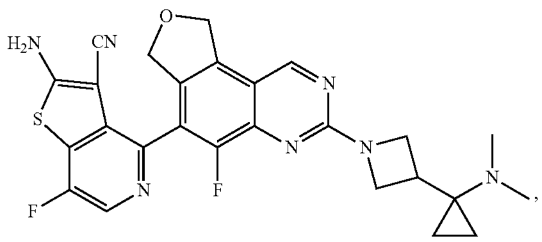
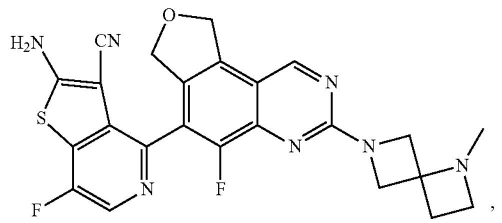
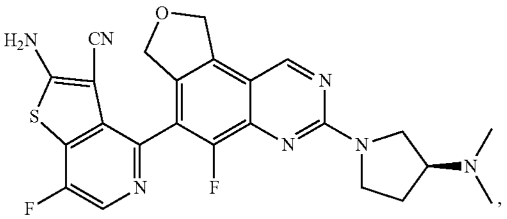
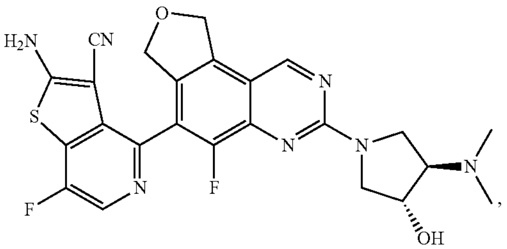
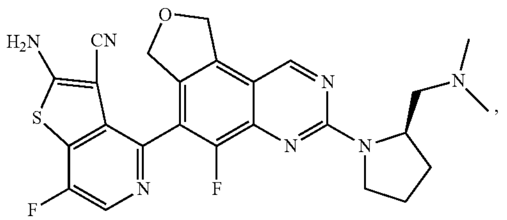
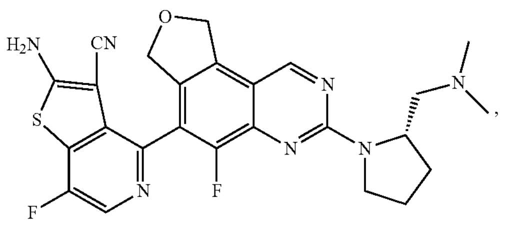
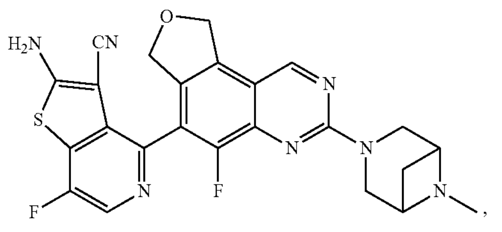

-continued
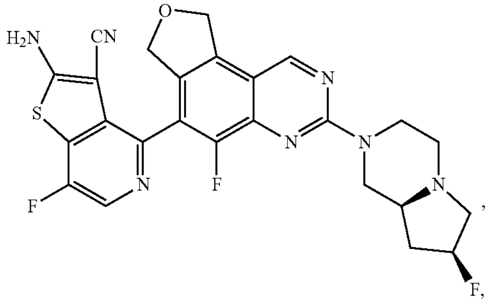
,
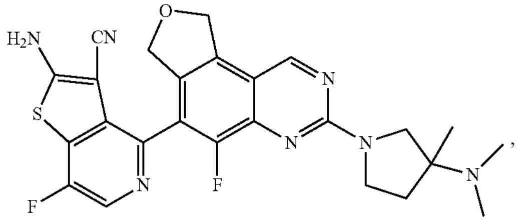
,
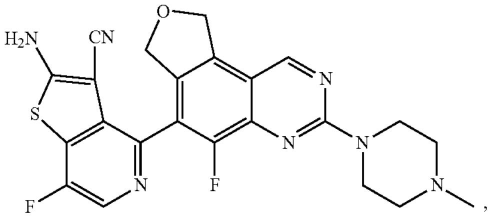
,
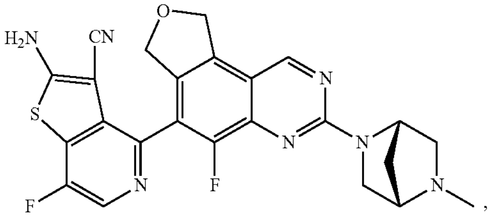
,
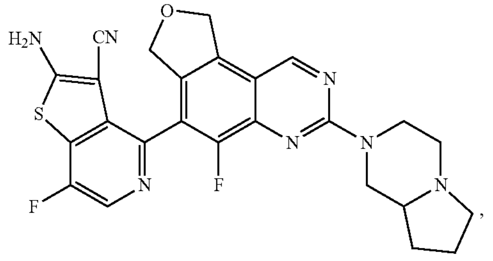
,
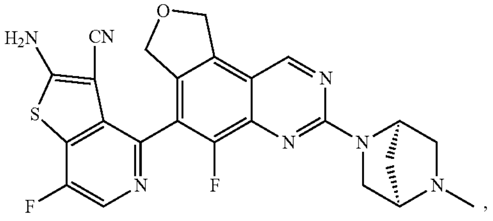
,
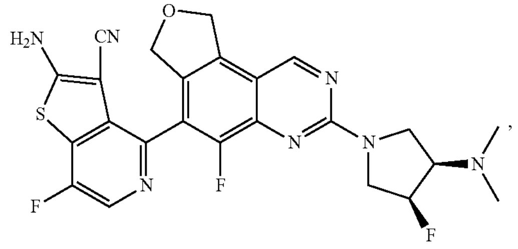
,
-continued
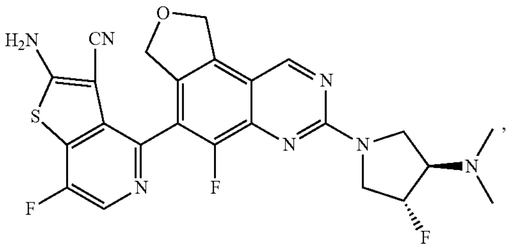
,
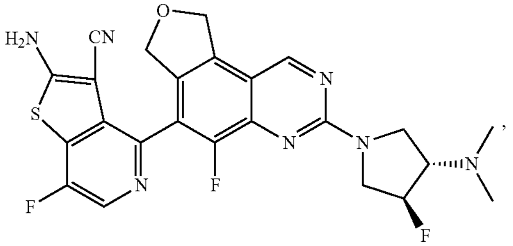
,
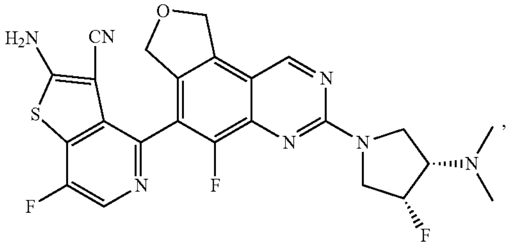
,
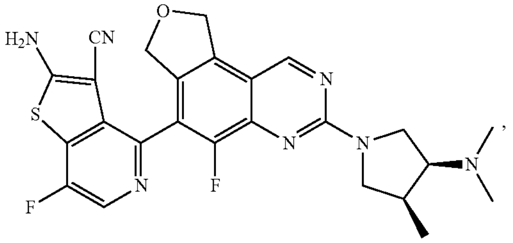
,
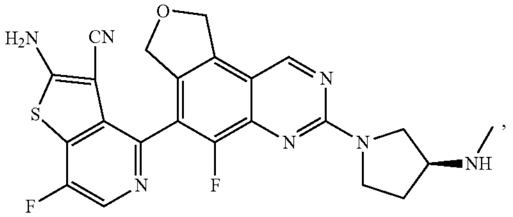
,
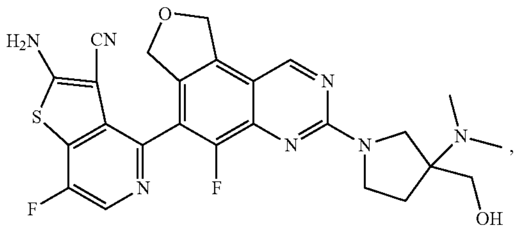
,
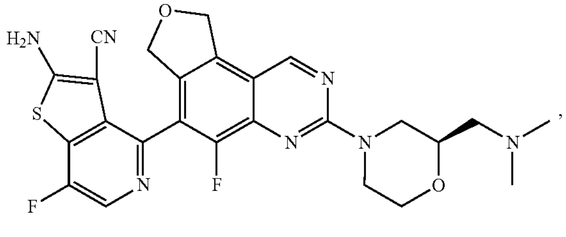
, -continued
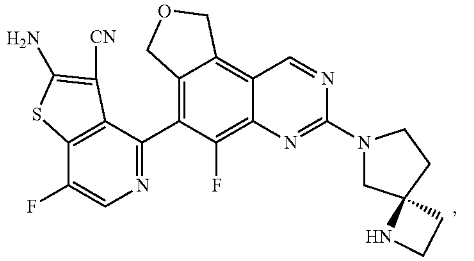
,
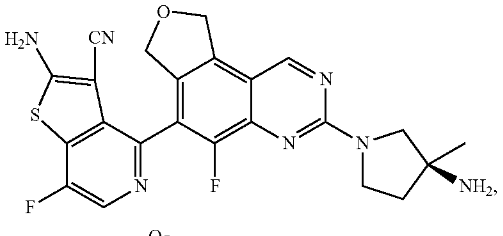
,
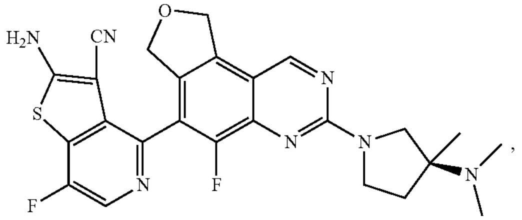
,
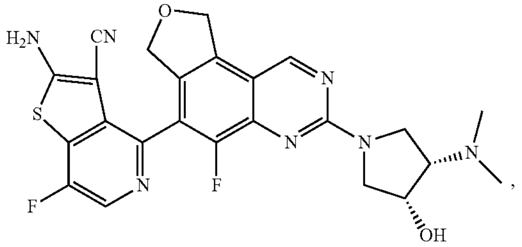
,
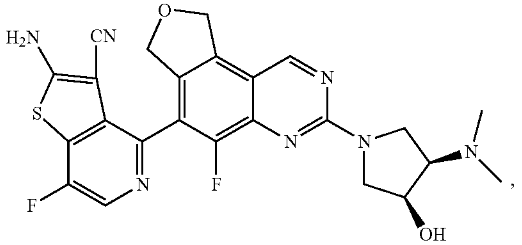
,
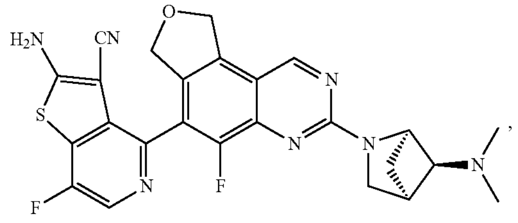
,
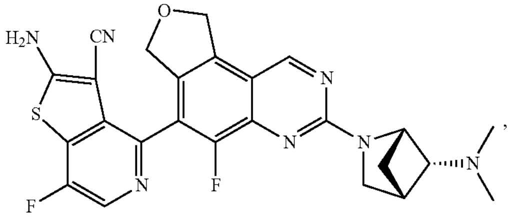
,
-continued
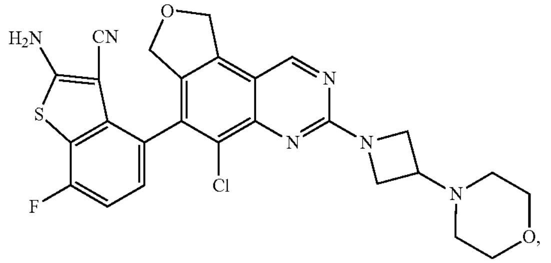
,
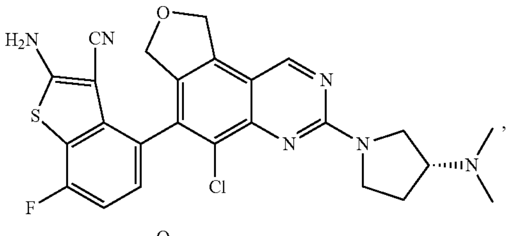
,
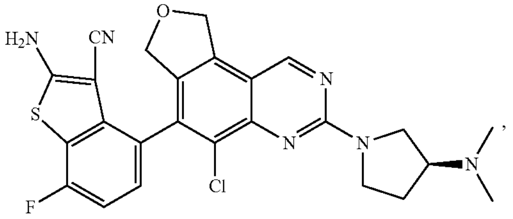
,
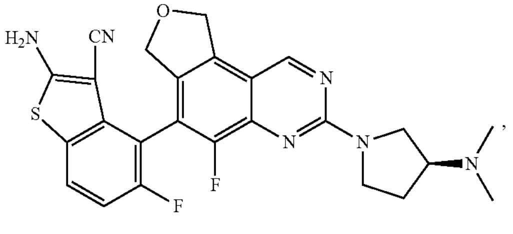
,
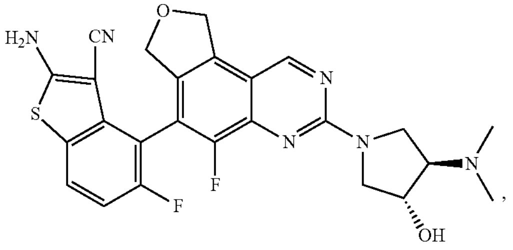
,
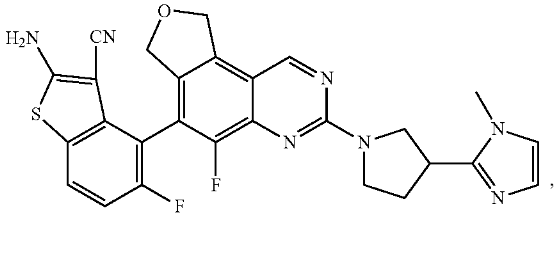
,
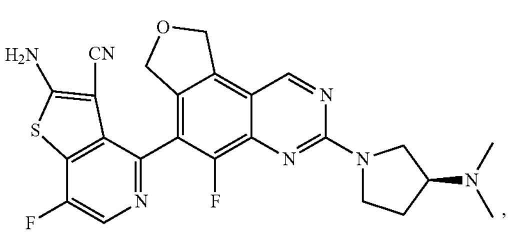
, -continued
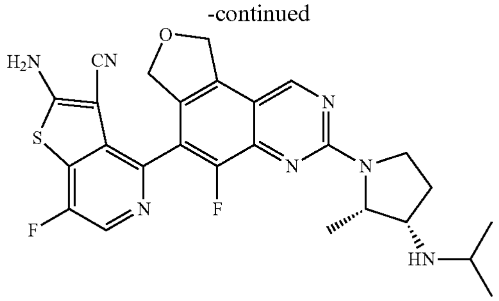
,
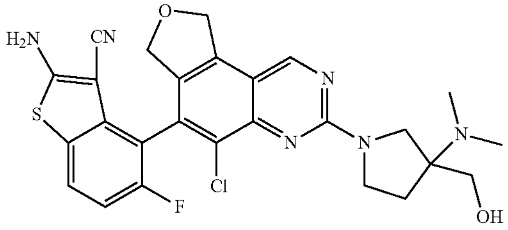
,
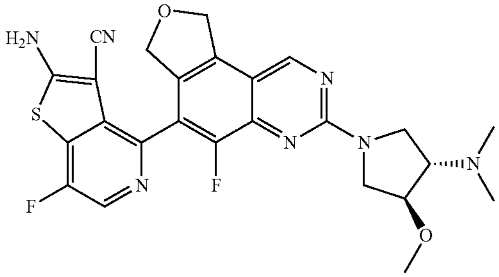
,
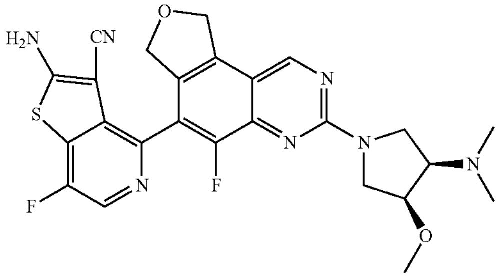
,
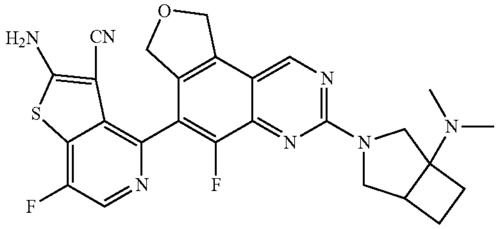
,
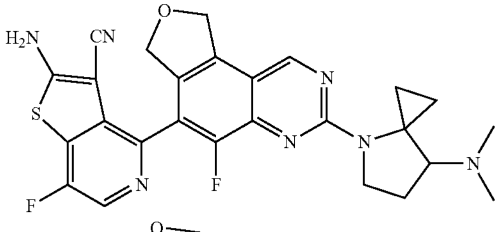
,
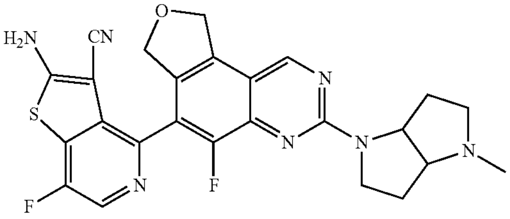
,
-continued
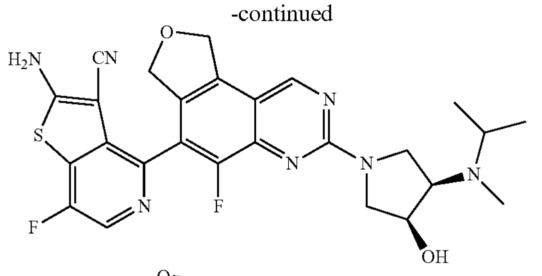
,
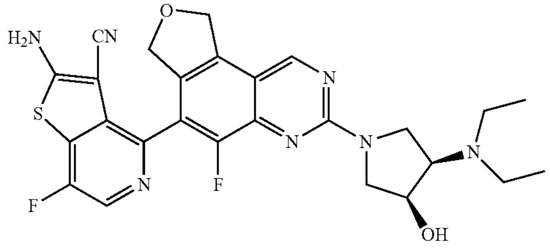
,
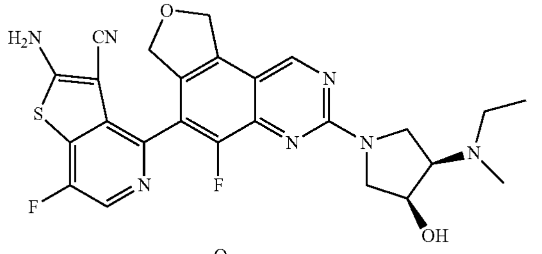
,
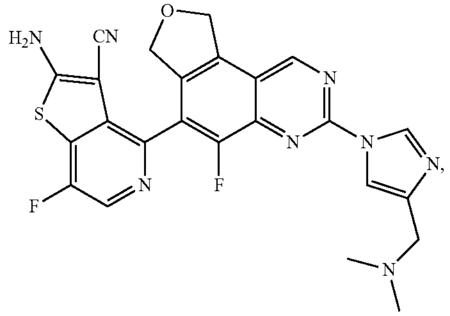
,
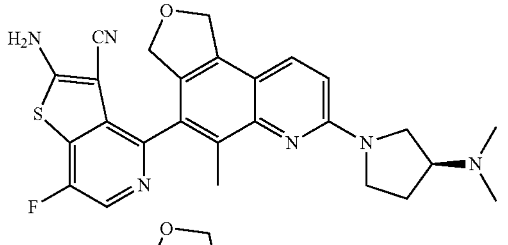
,
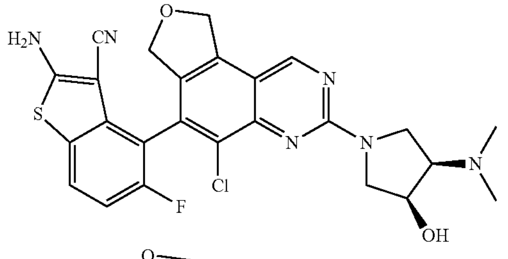
,
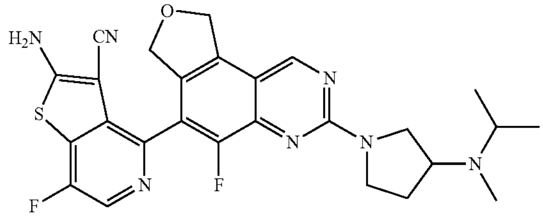
, -continued
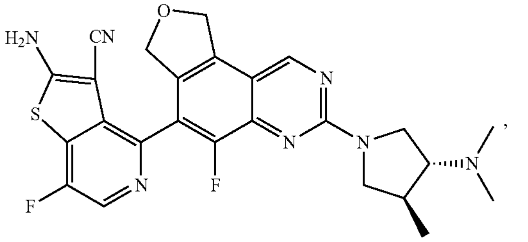
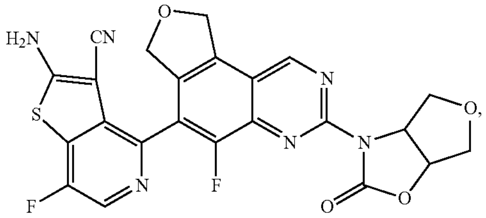
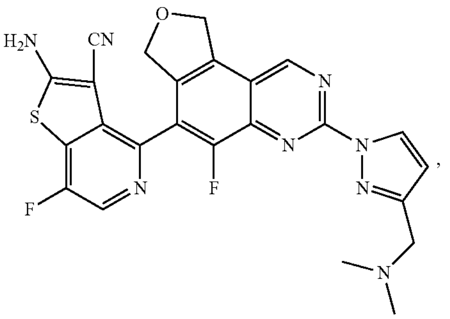
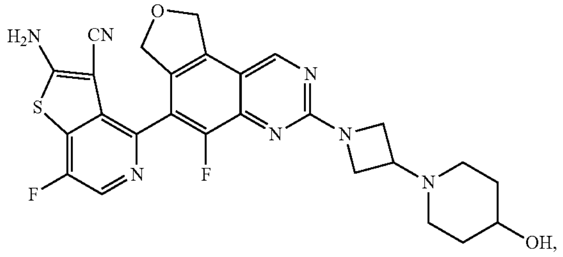
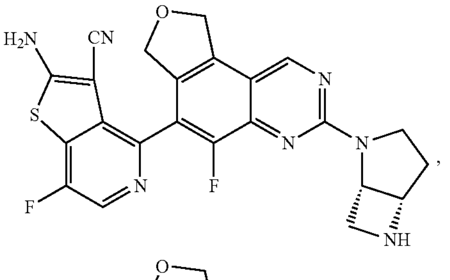
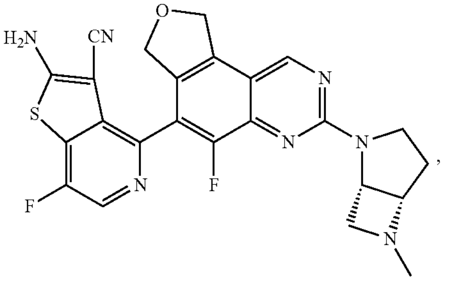
-continued
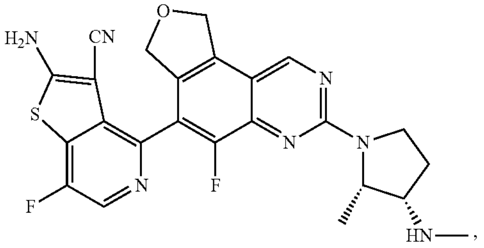
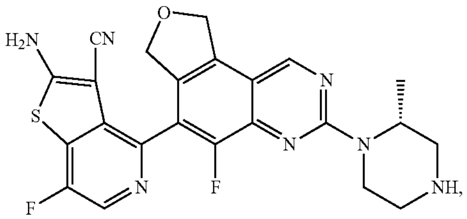
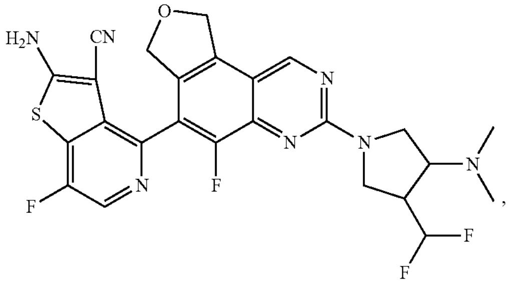
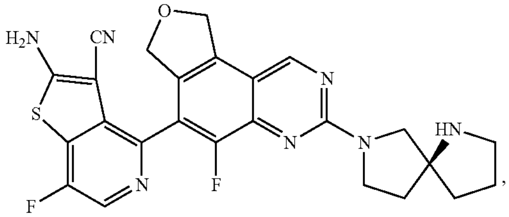
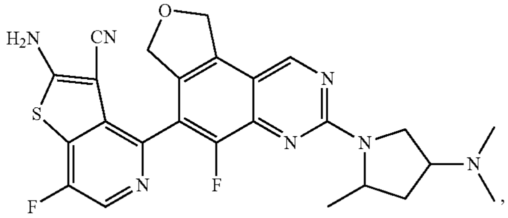
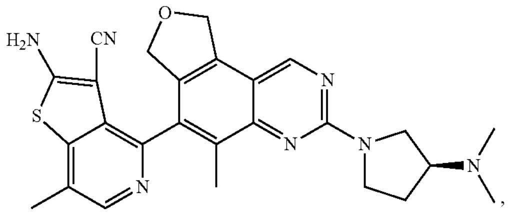
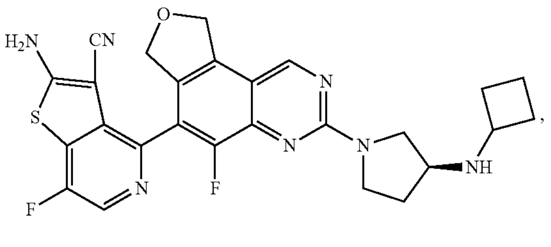

-continued
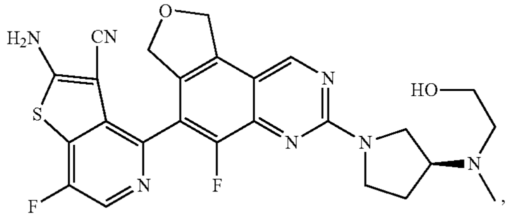
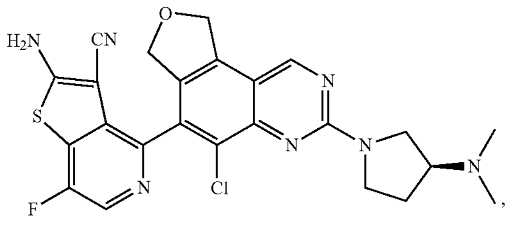
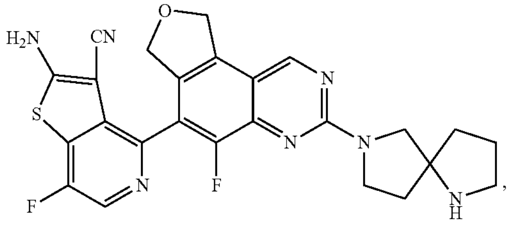
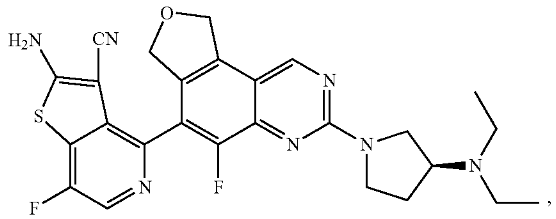
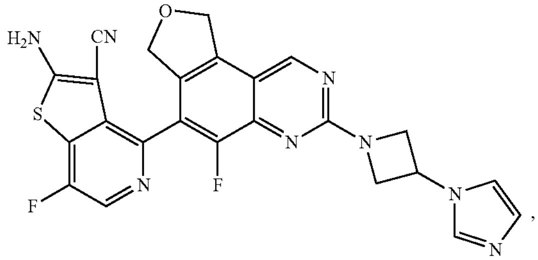
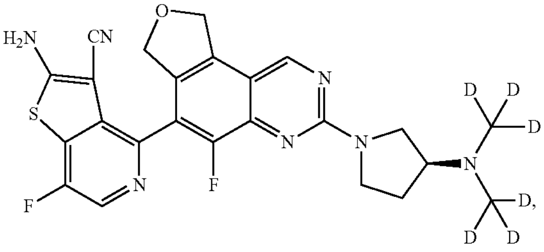
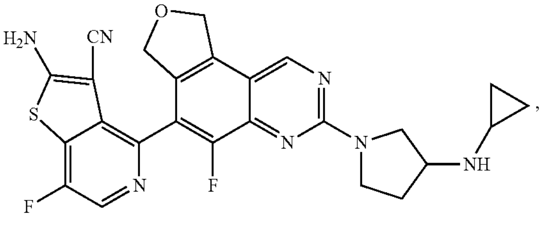
-continued
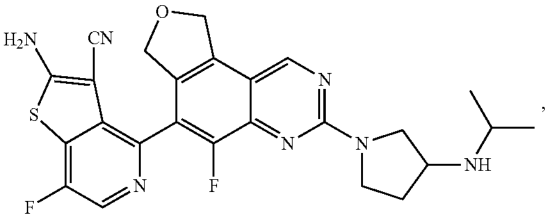
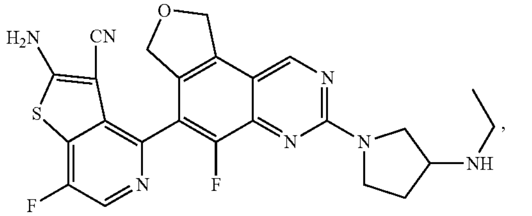
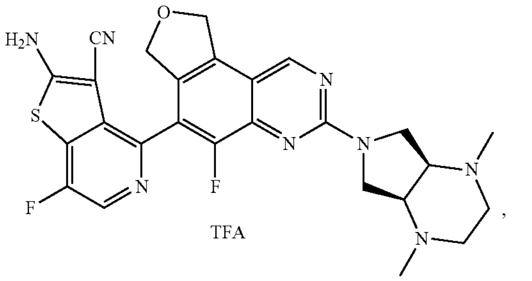
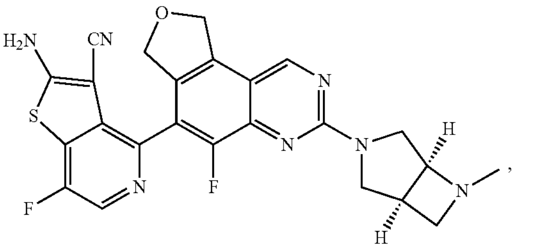
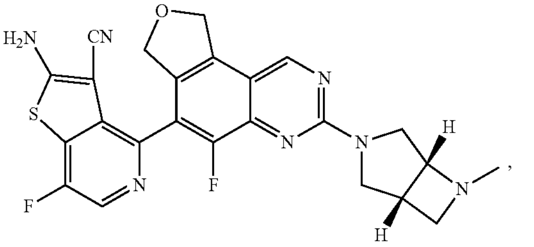
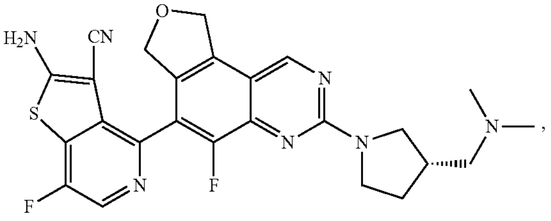
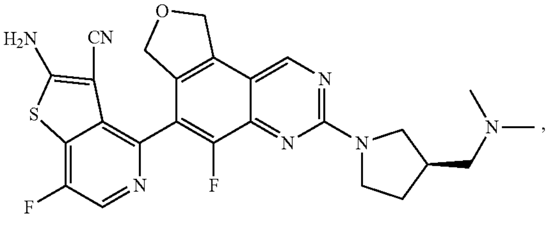

-continued
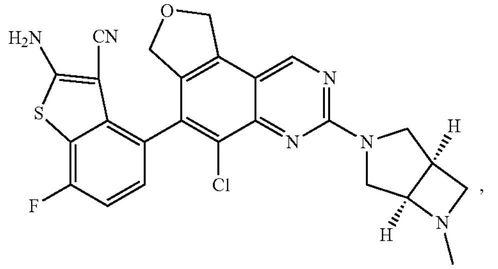
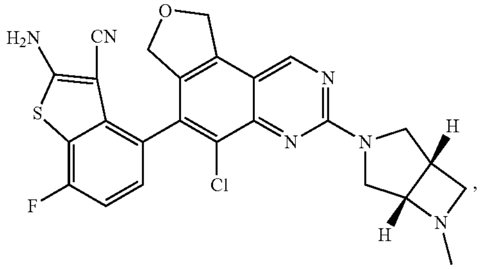
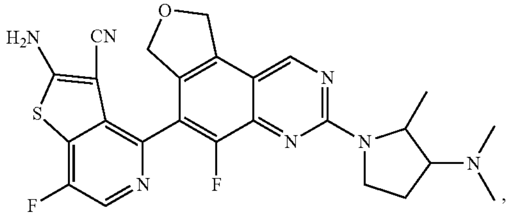
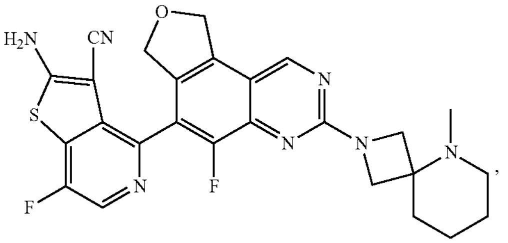
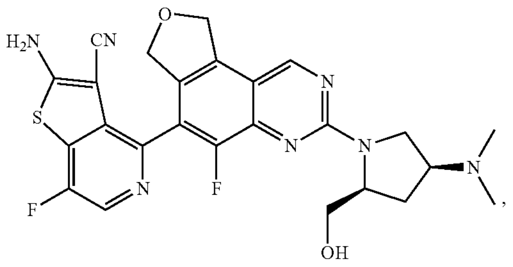
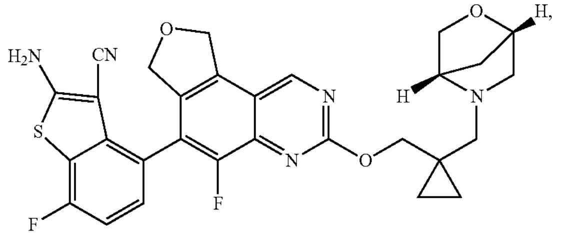
-continued
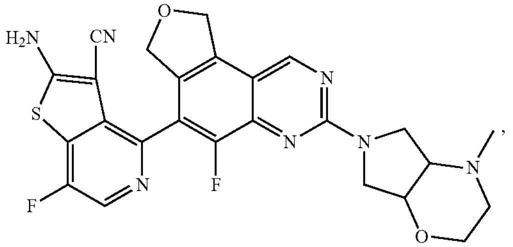
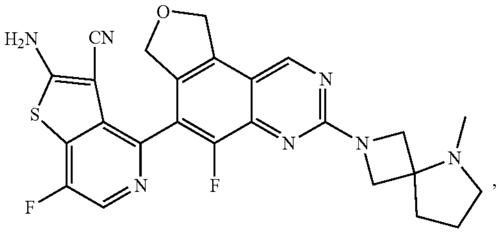
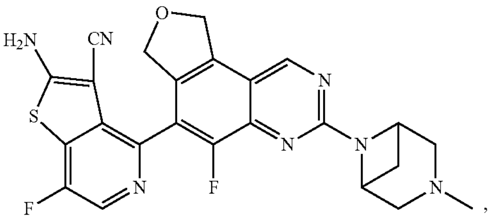
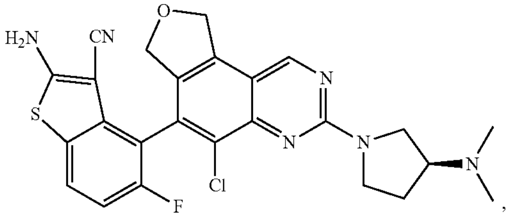
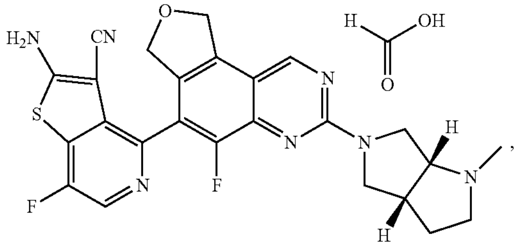
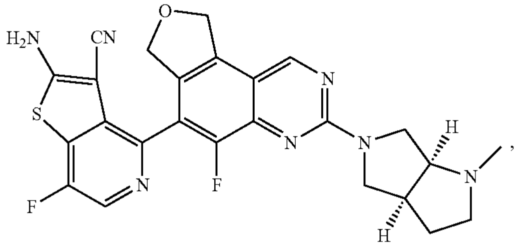
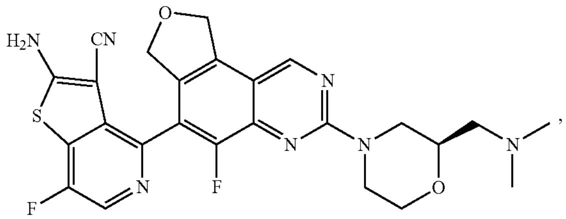

-continued
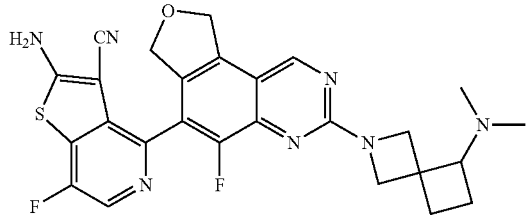
,
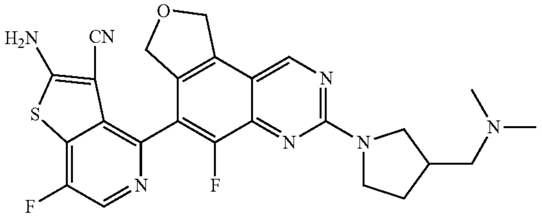
,
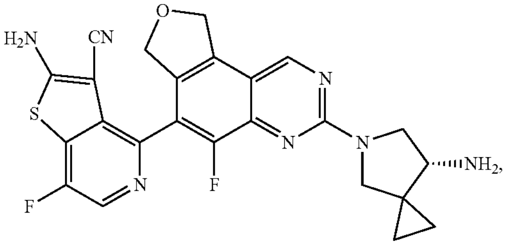
,
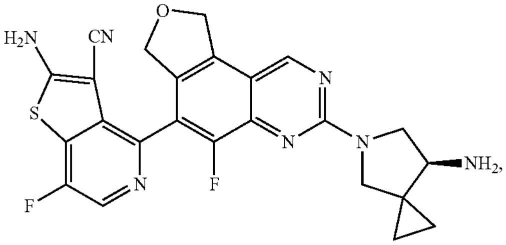
,
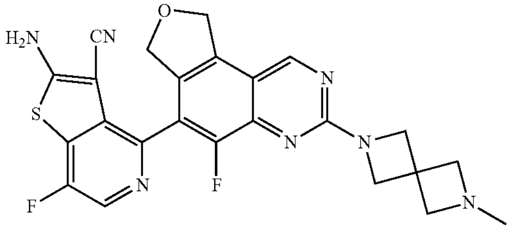
,
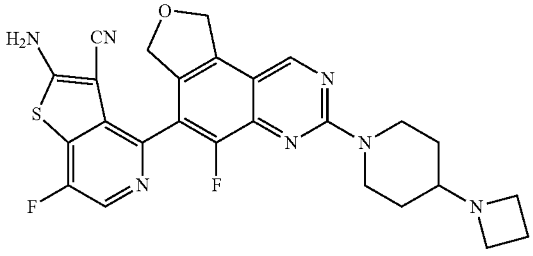
,
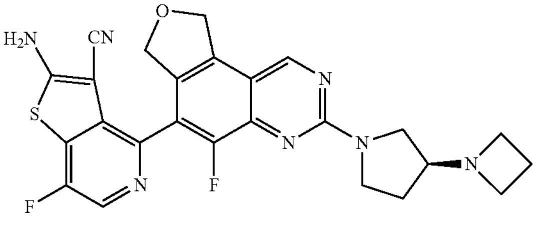
,
-continued
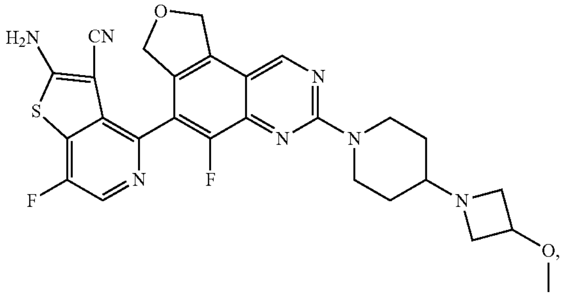
,
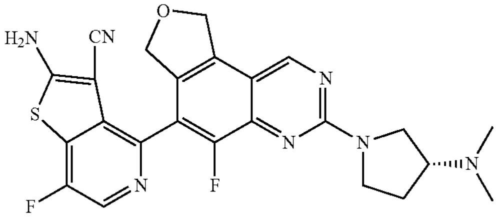
,
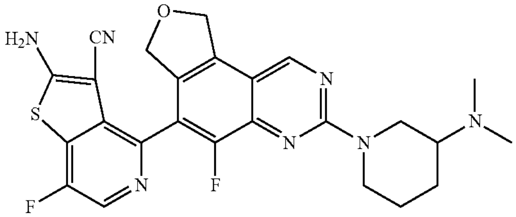
,
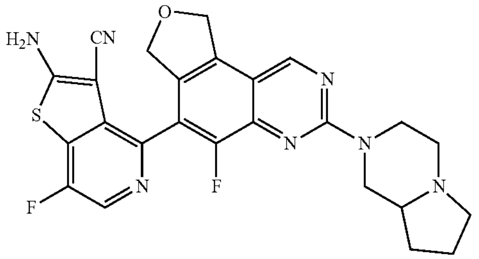
,
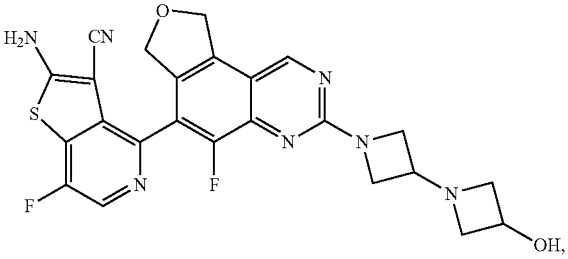
,
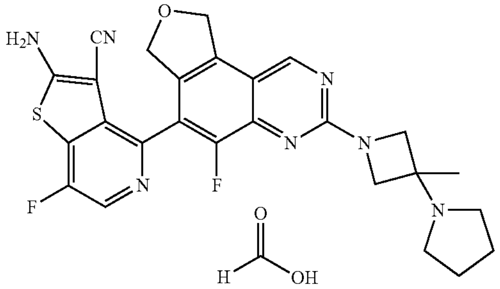
, -continued
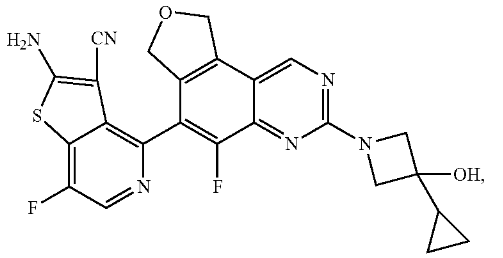
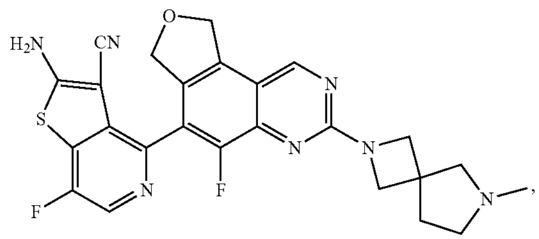
,
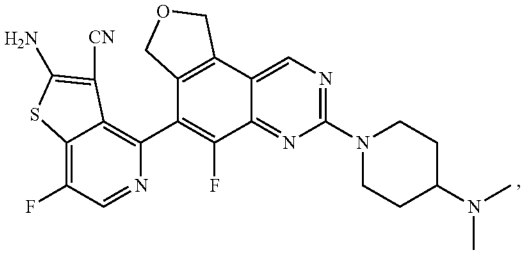
,
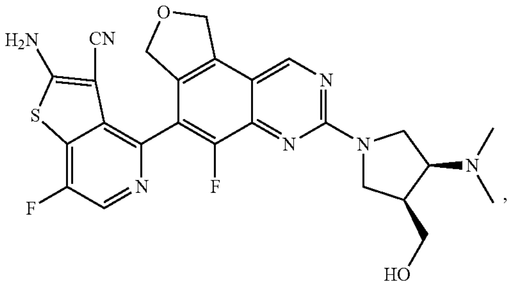
,
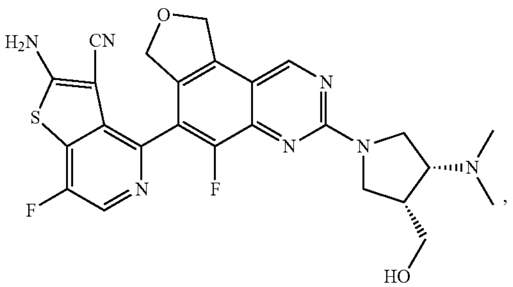
,
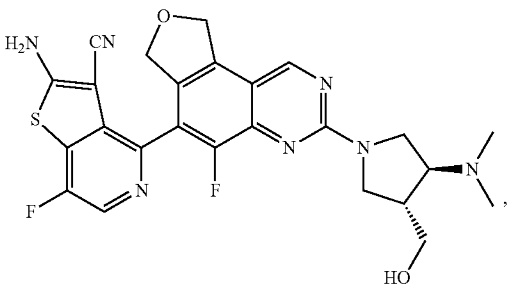
,
-continued
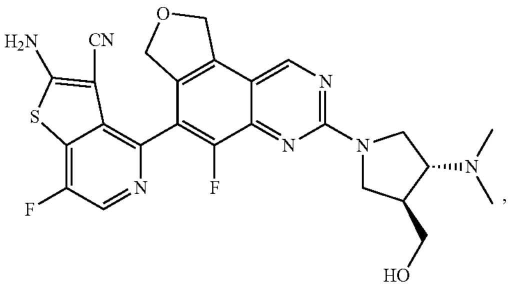
,
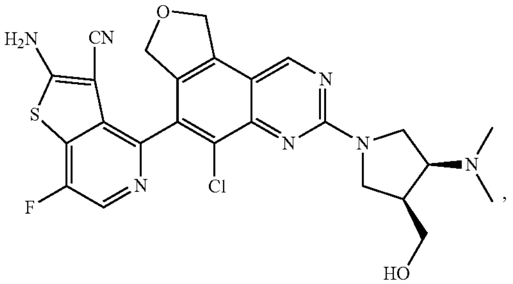
,
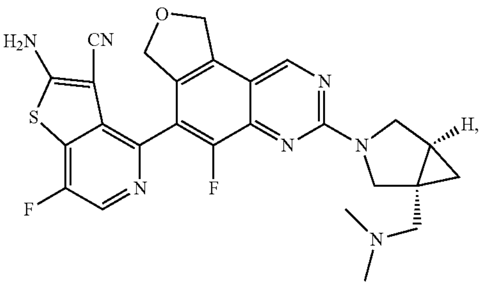
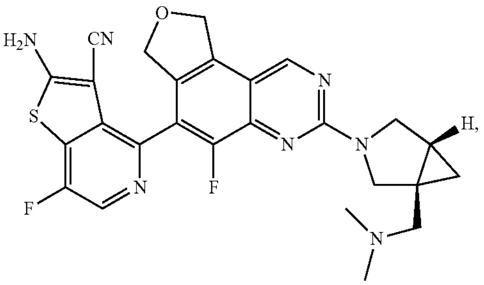
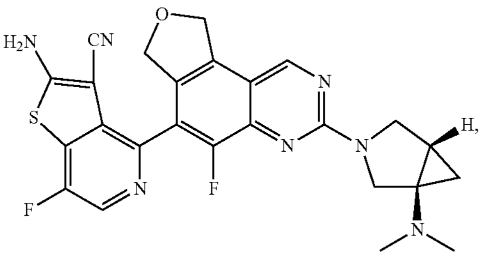
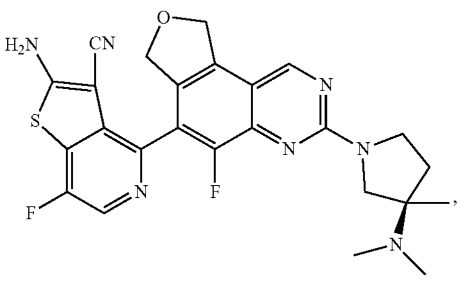
, -continued
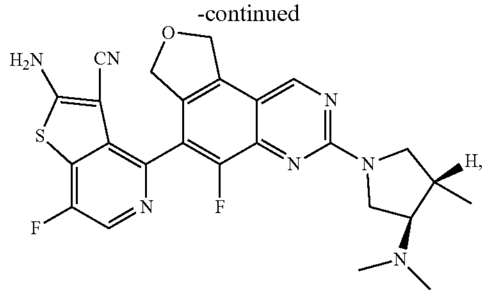
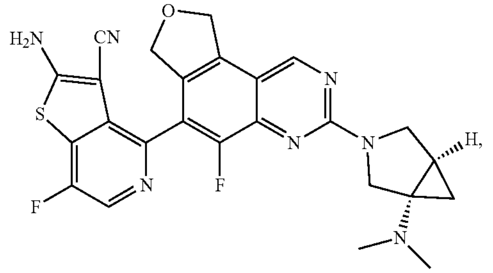
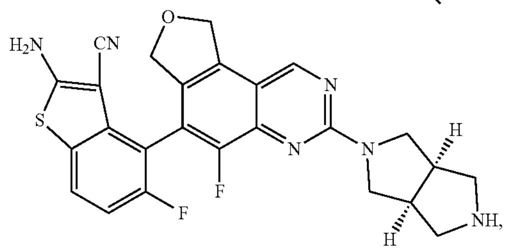
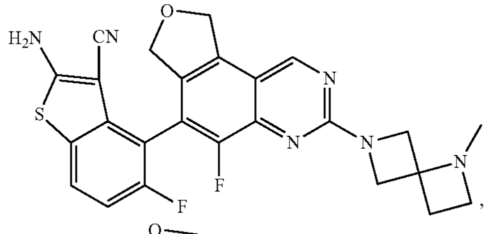
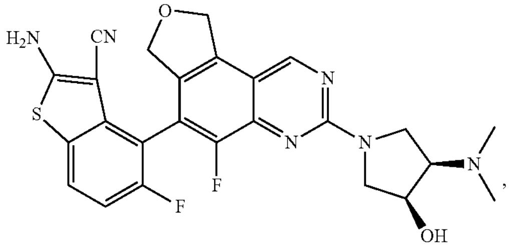
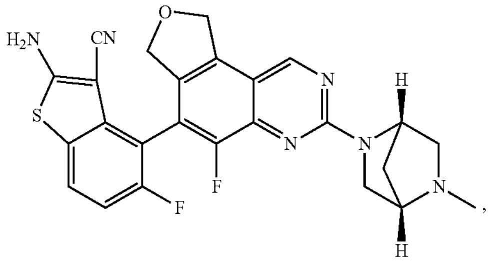
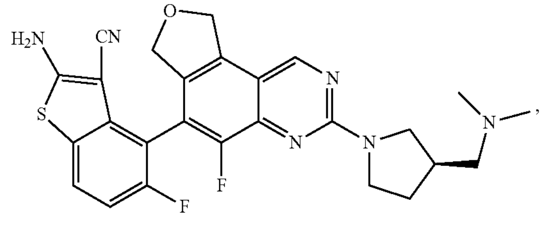
-continued
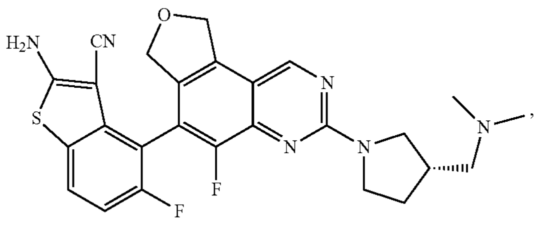
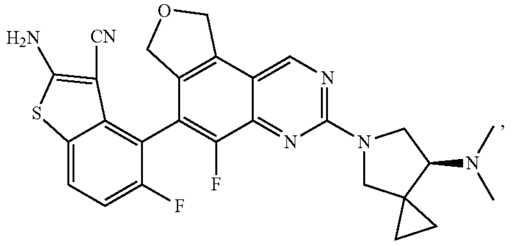
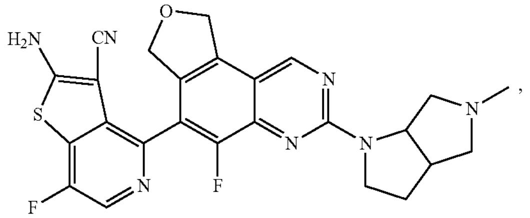
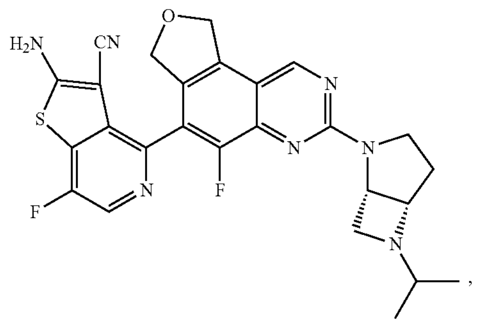
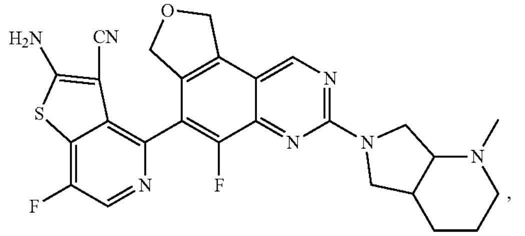
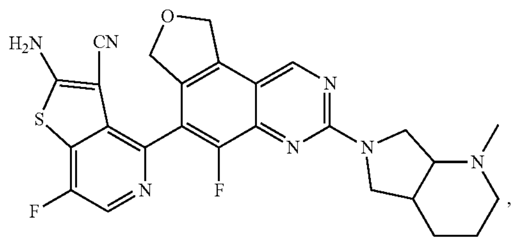
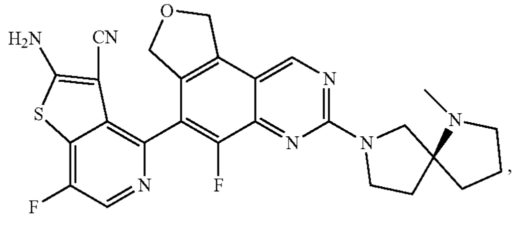

-continued
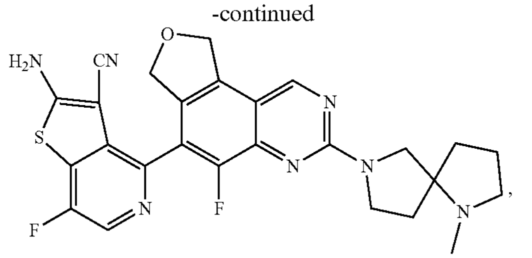
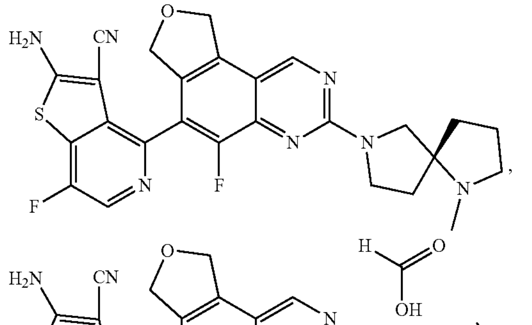
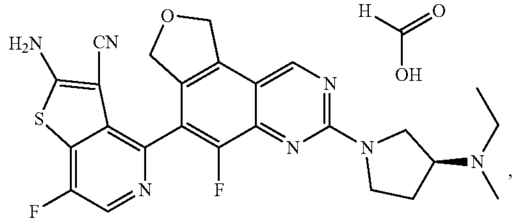
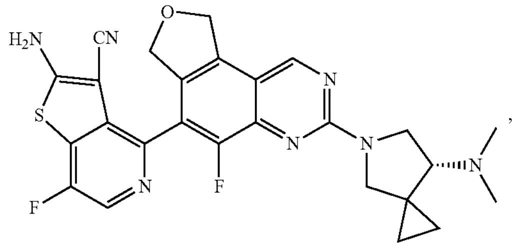
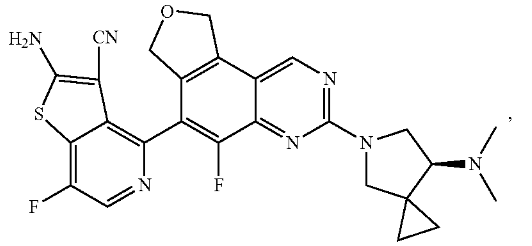
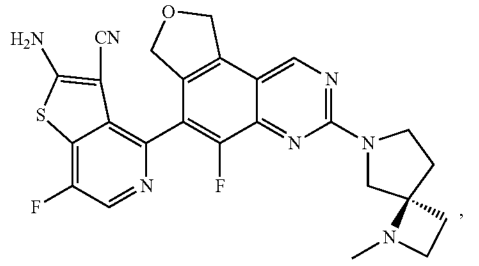
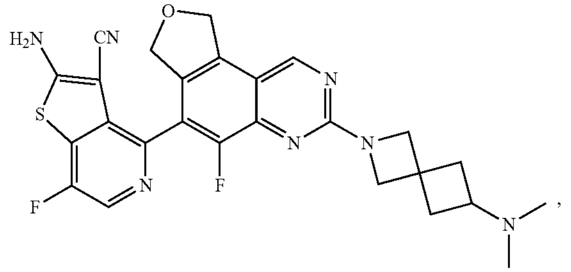
-continued
and
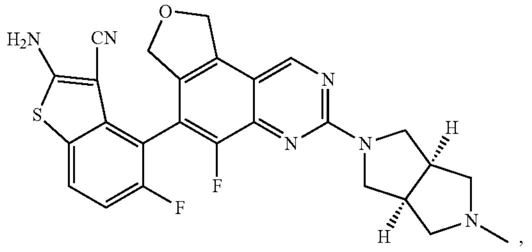
or a pharmaceutically acceptable salt thereof.
A compound of Formula I or a pharmaceutically acceptable salt thereof, the compound is selected from
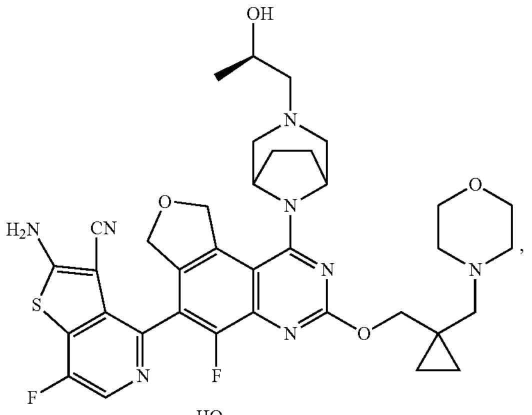
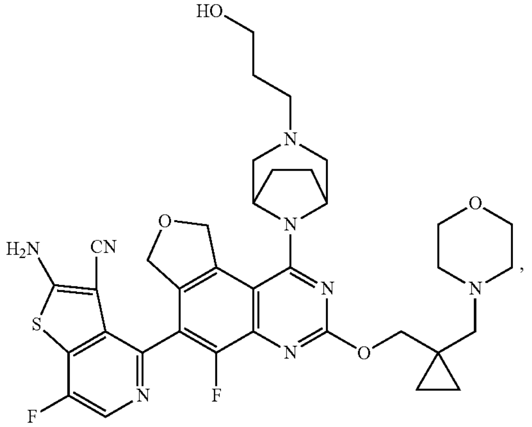
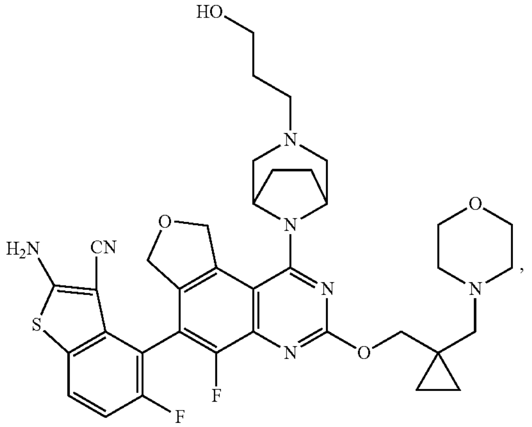

-continued
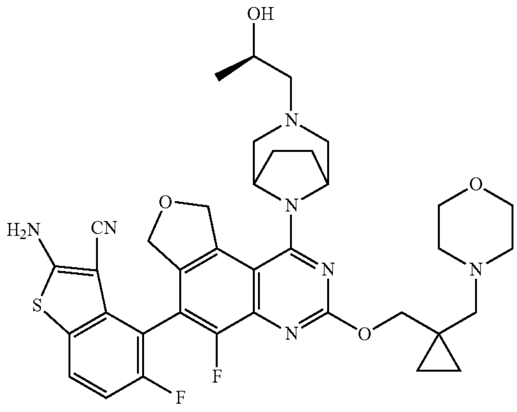
,
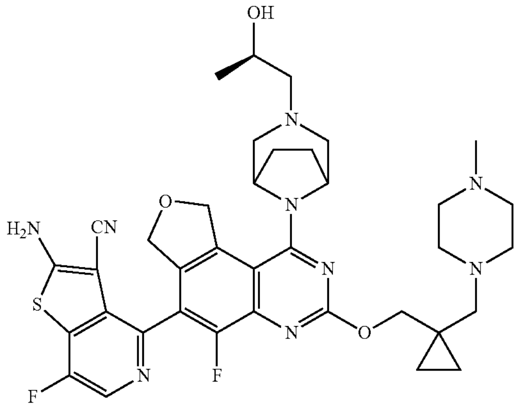
,
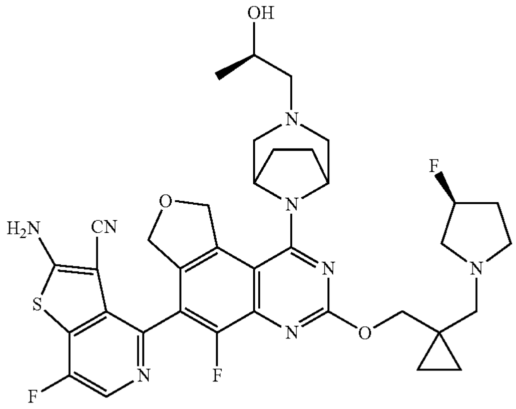
,
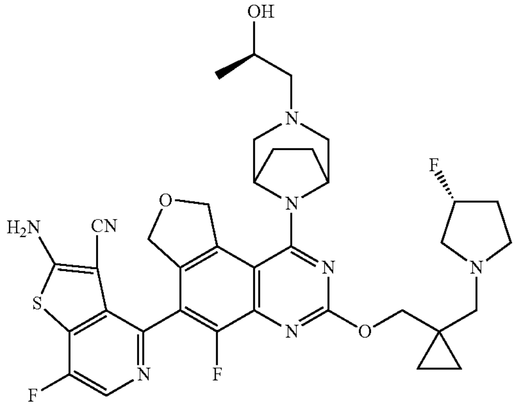
,
-continued
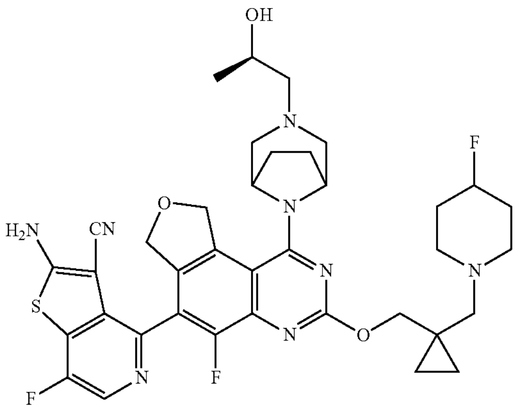
,
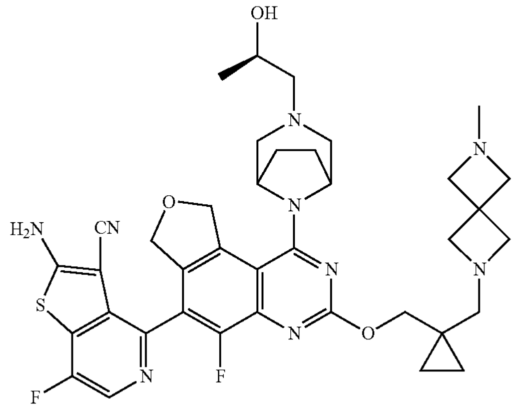
,
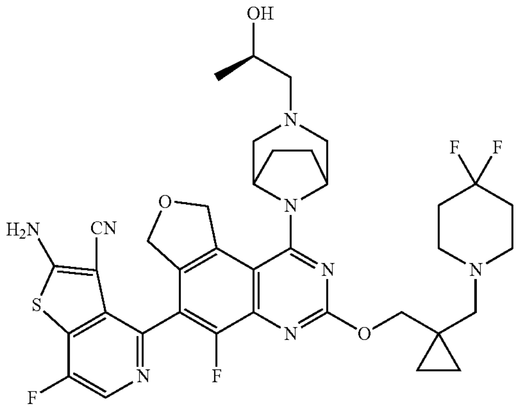
,
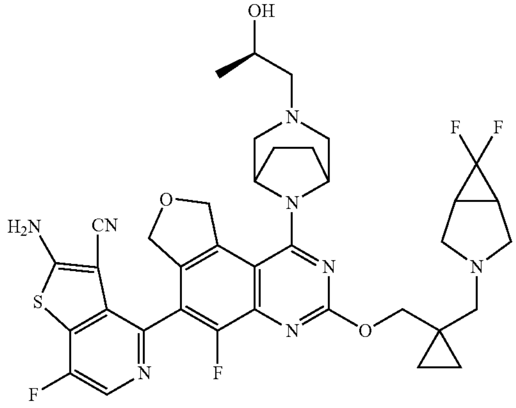
, -continued
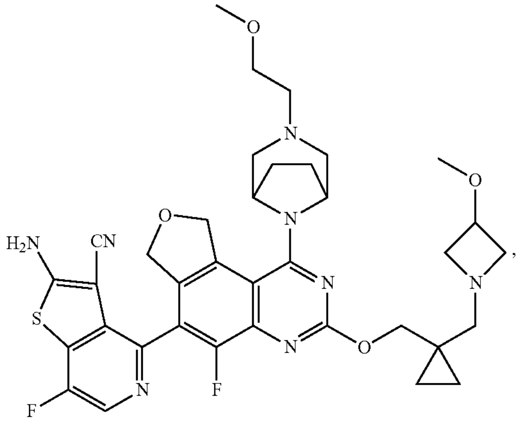
,
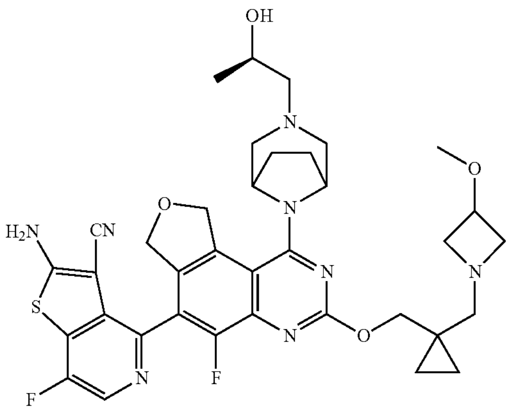
,
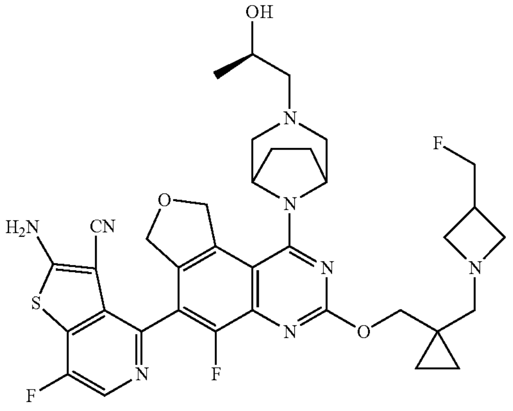
,
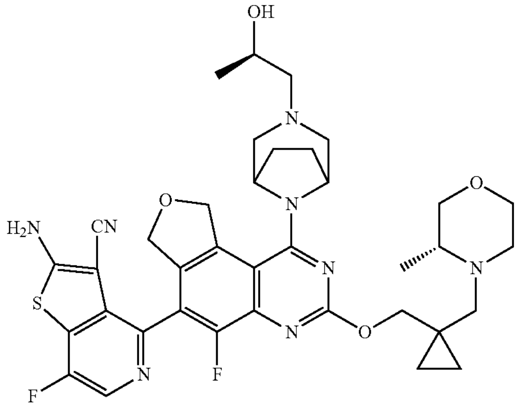
,
-continued
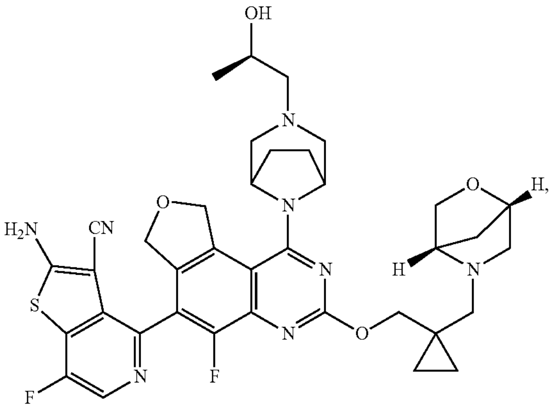
,
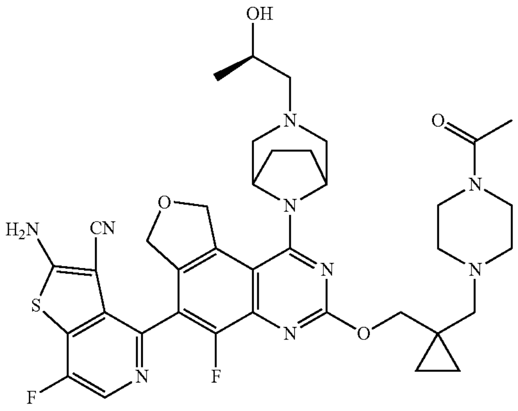
,
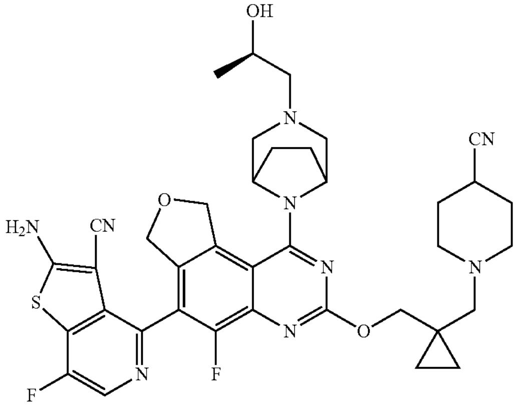
,
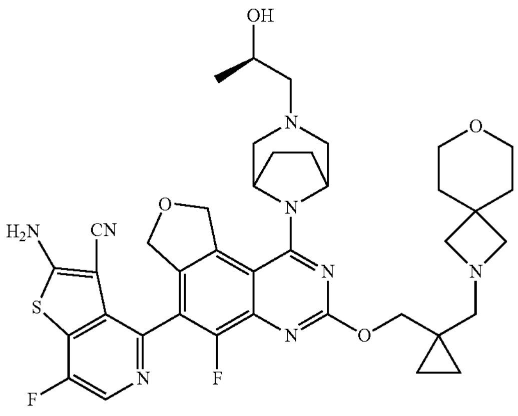
, -continued
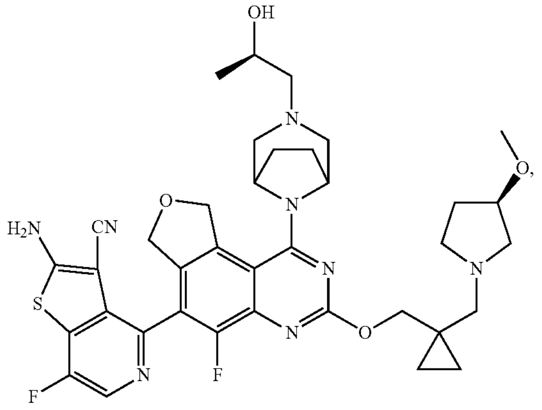
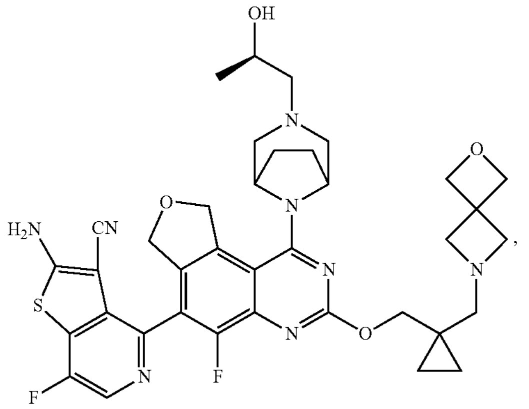
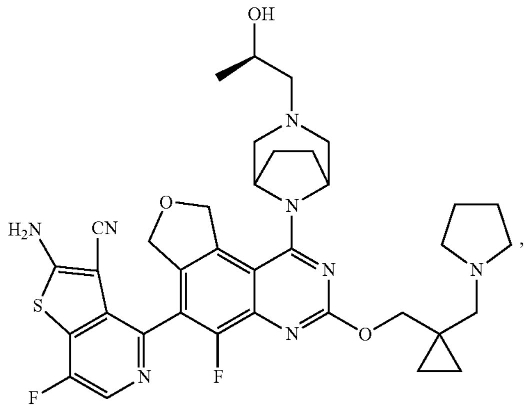
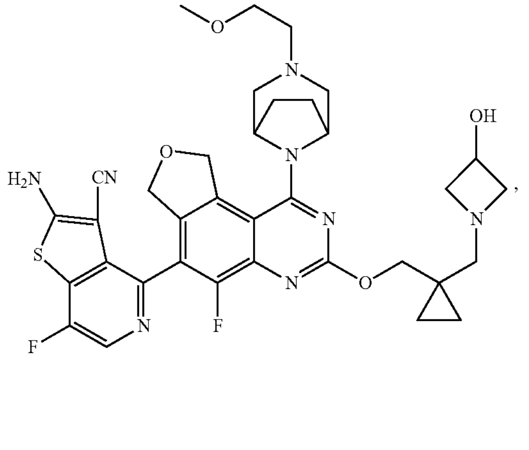
-continued
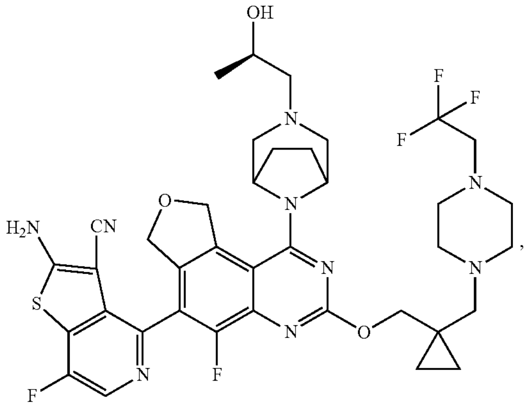
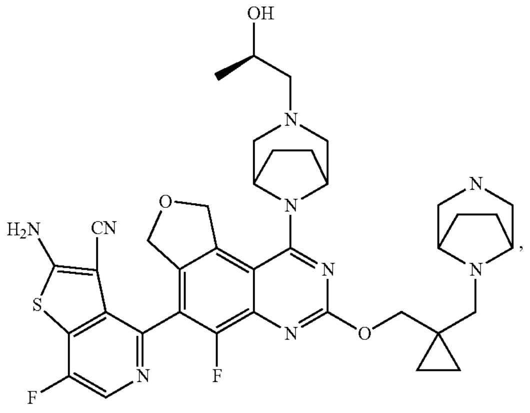
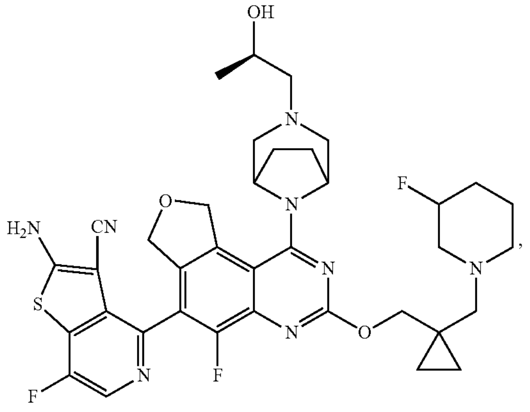
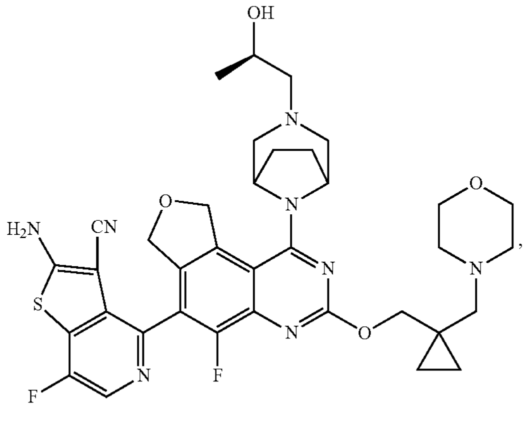

-continued
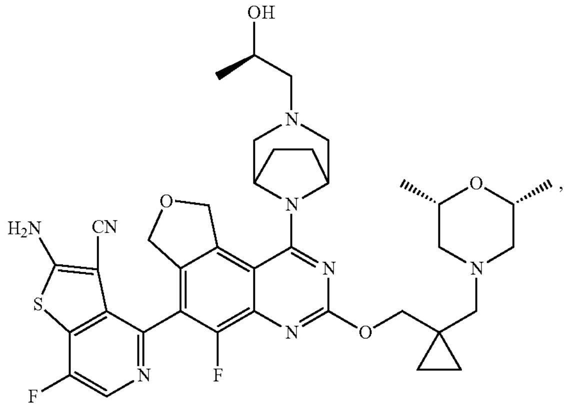
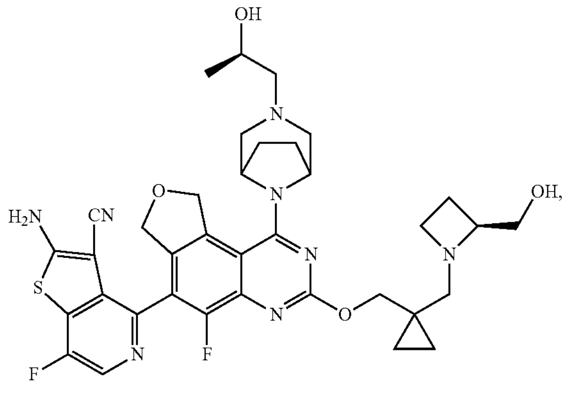
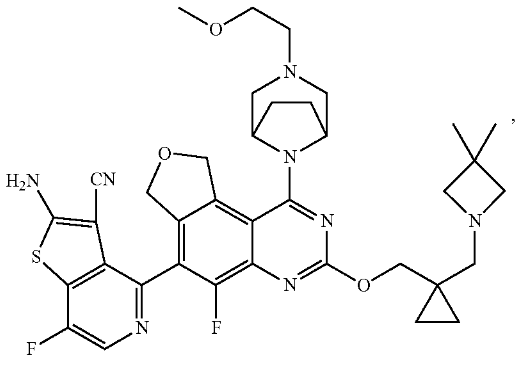
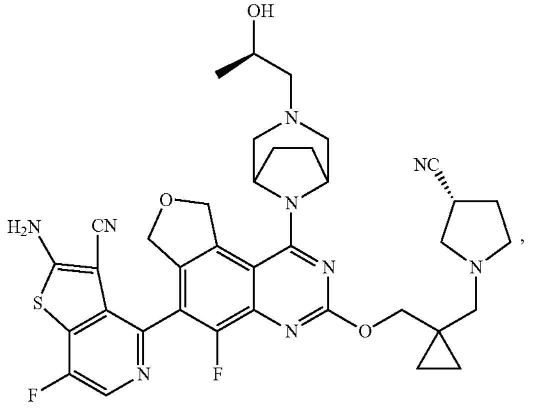
-continued
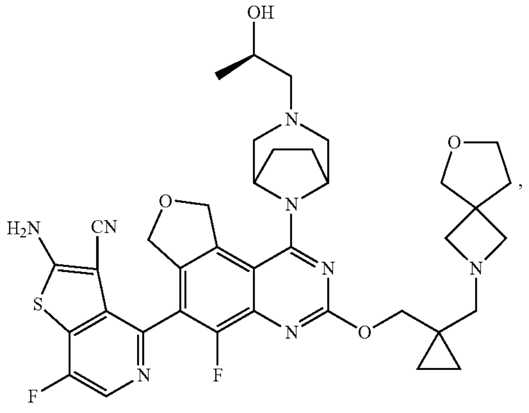
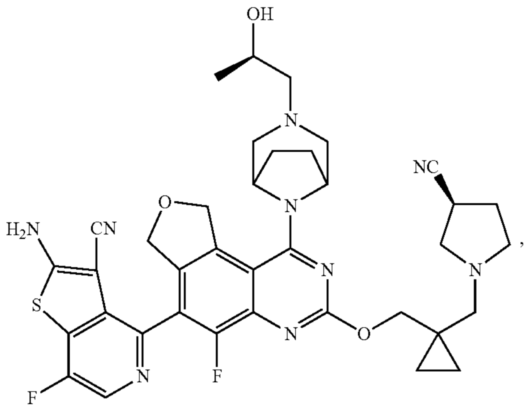
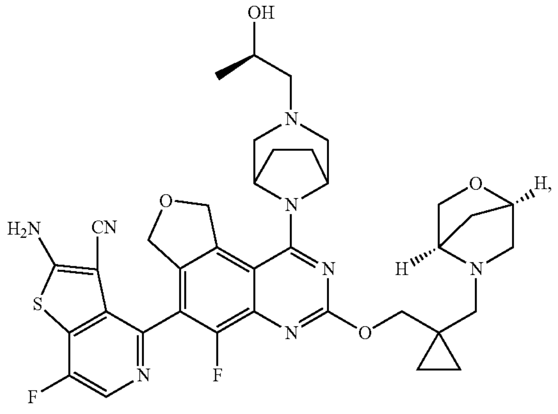
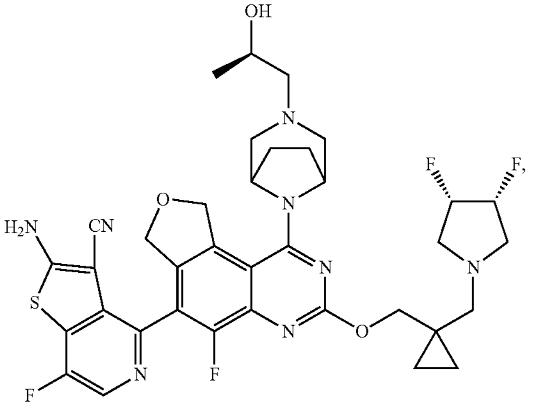

-continued
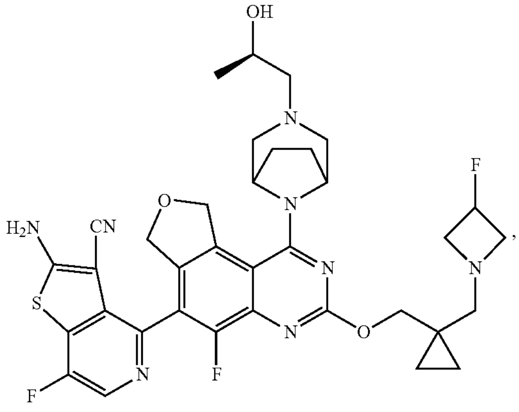
,
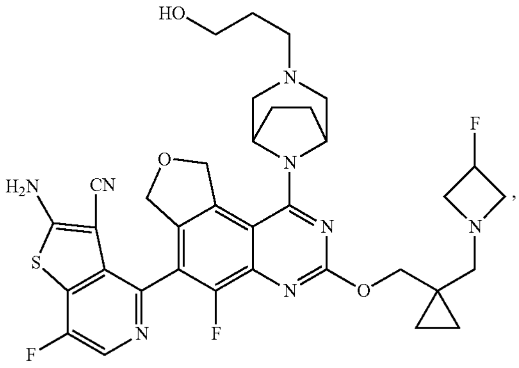
,
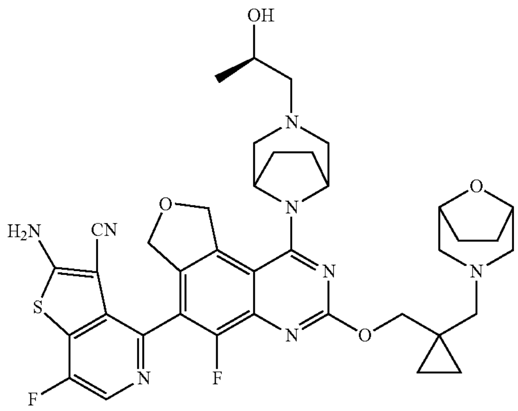
,
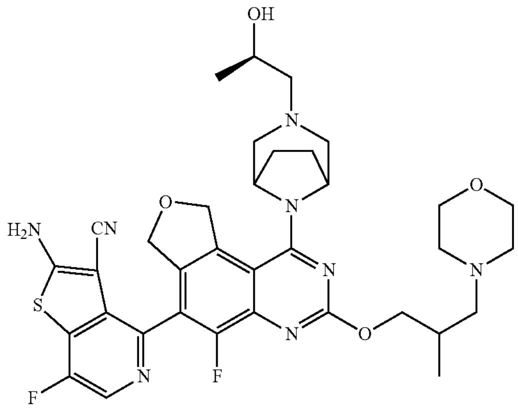
,
-continued
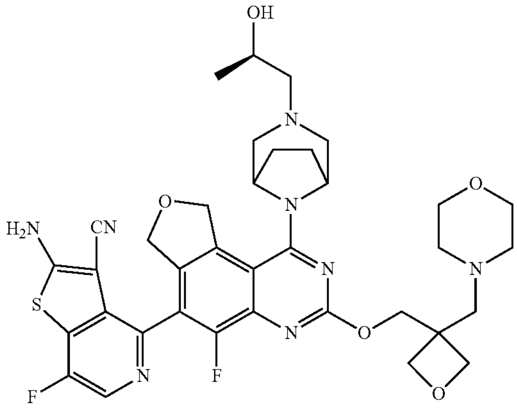
,
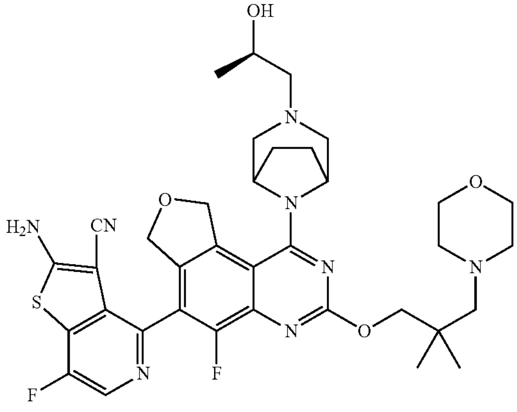
,
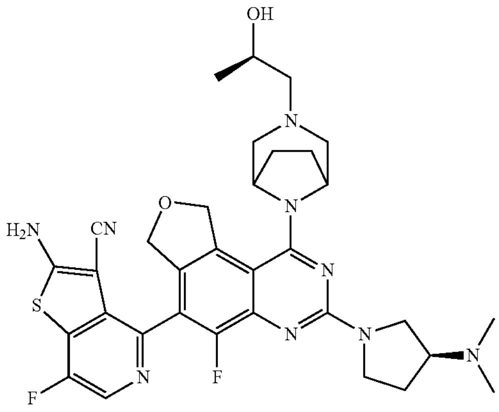
,
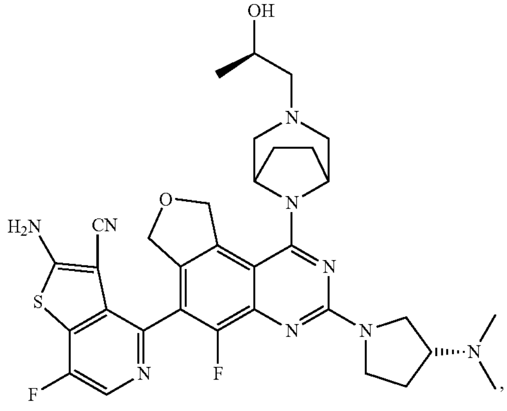
, -continued
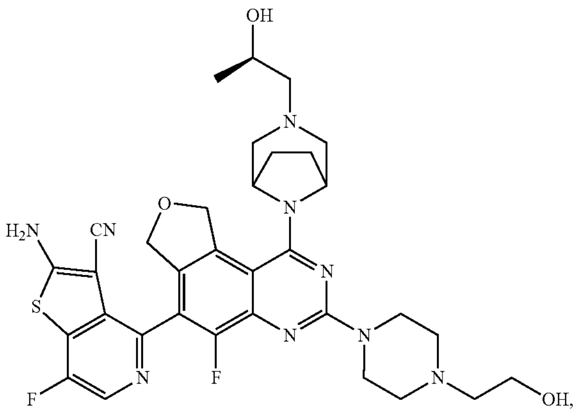
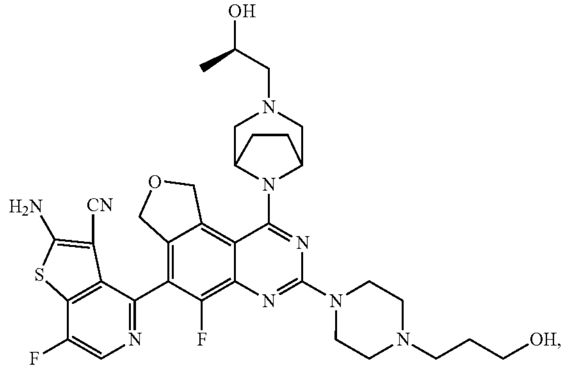
and
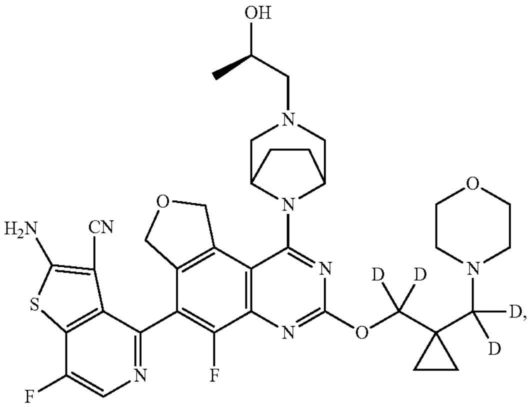
or a pharmaceutically acceptable salt thereof.
A compound of Formula I or a pharmaceutically acceptable salt thereof, the compound is selected from
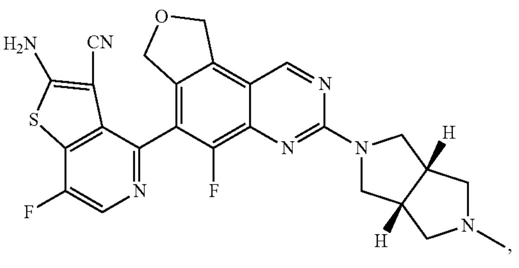
-continued
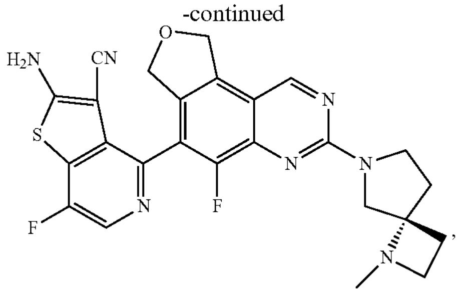
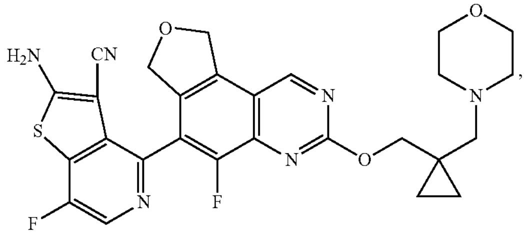 [SMILES: N#Cc1c(N)sc2c(F)cnc(-c3c4c(c5ccc(OCC6(CN7CCOCC7)CC6)nc5c3F)COC4)c12]
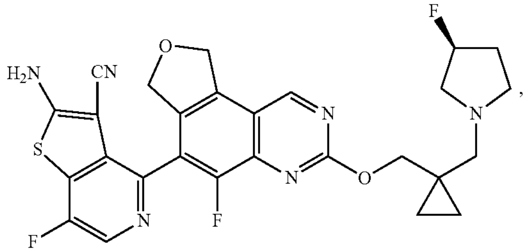
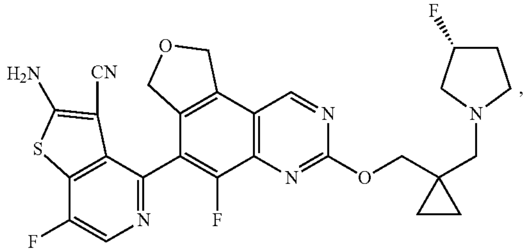
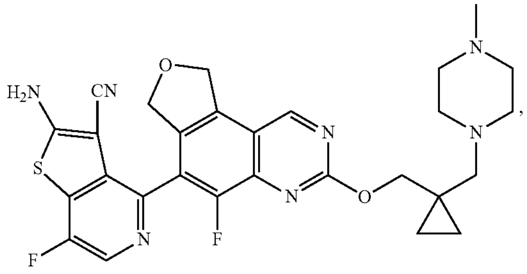
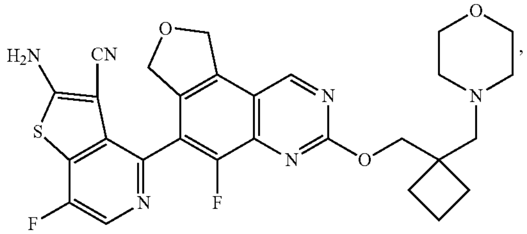
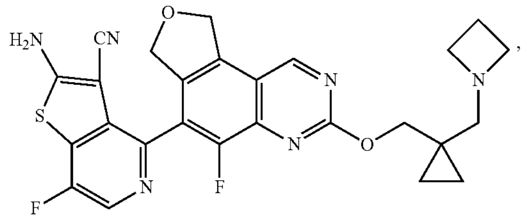

-continued
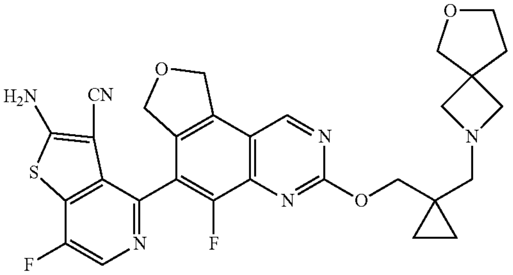
,
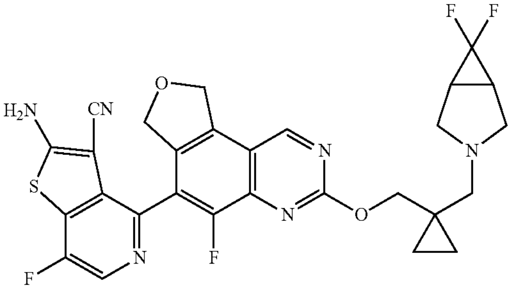
,
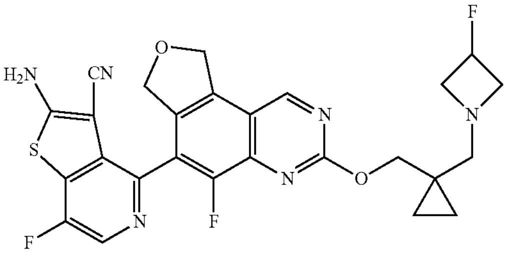
,
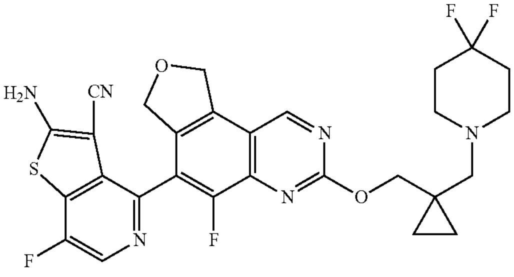
,
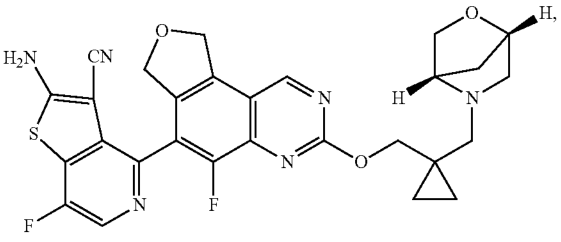
,
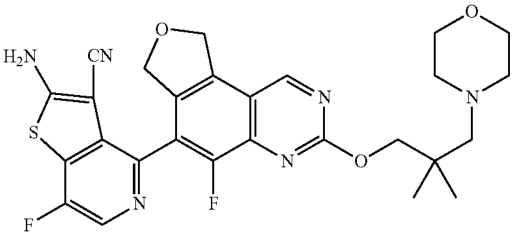
,
-continued
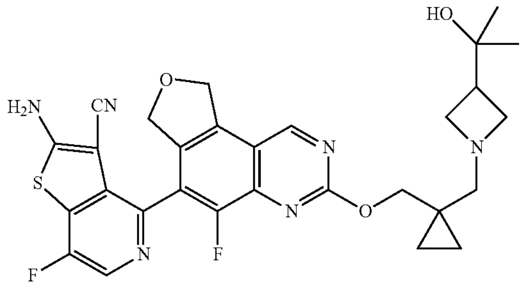
,
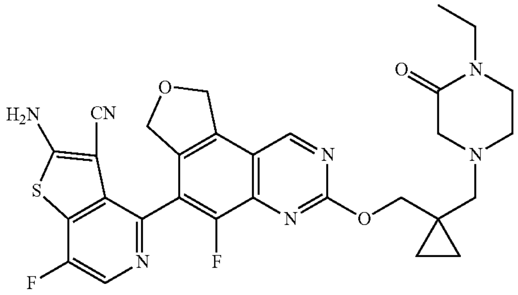
,
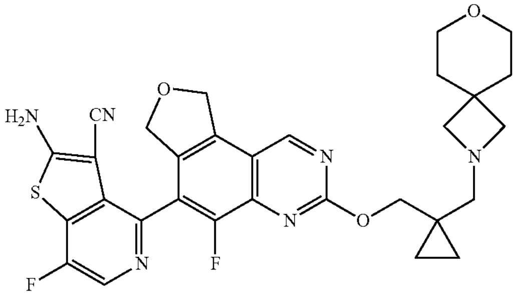
,
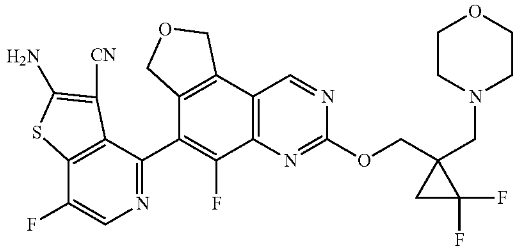
,
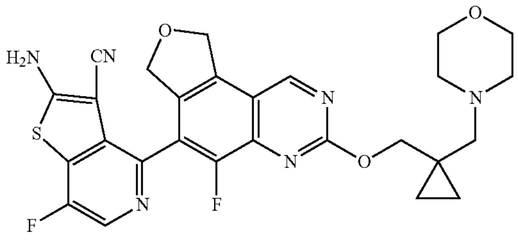
,
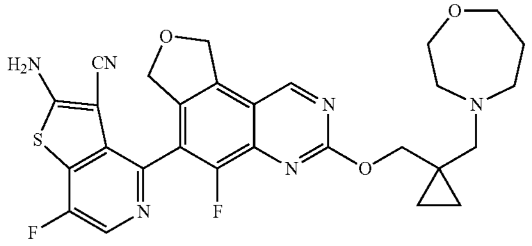
, -continued
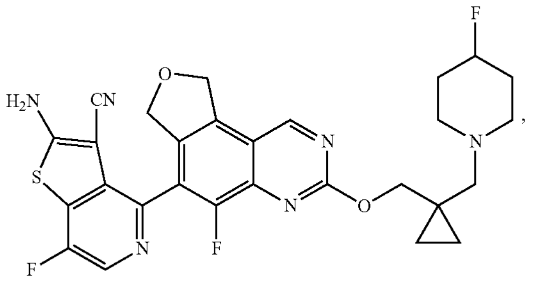
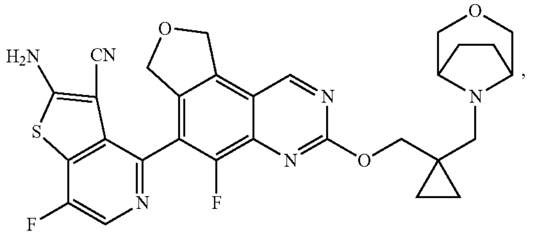
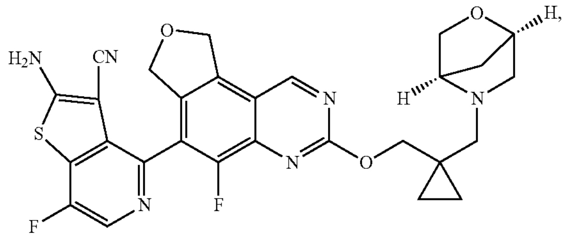
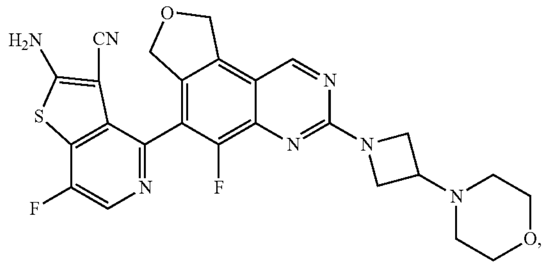
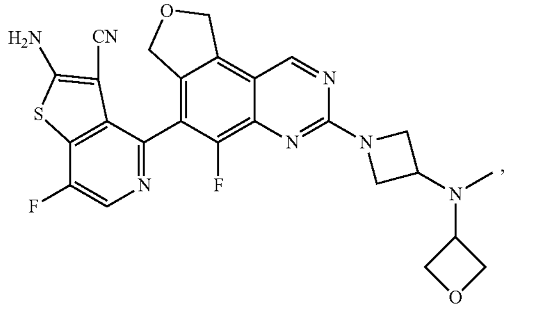
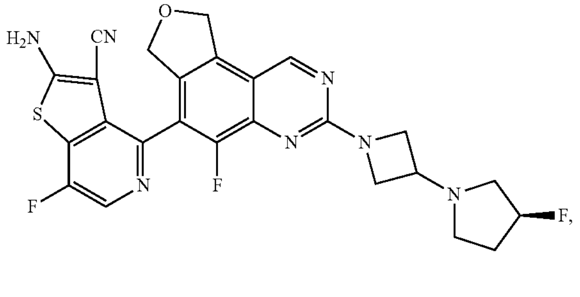
-continued
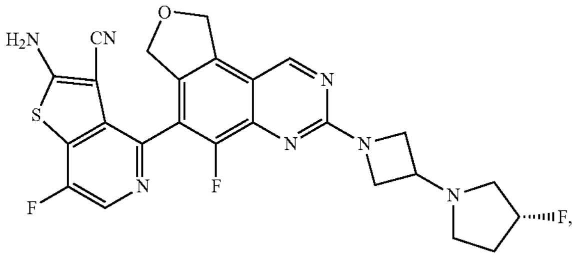
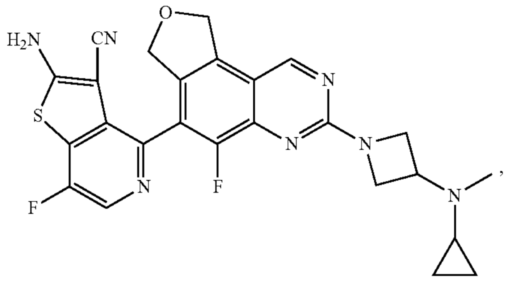
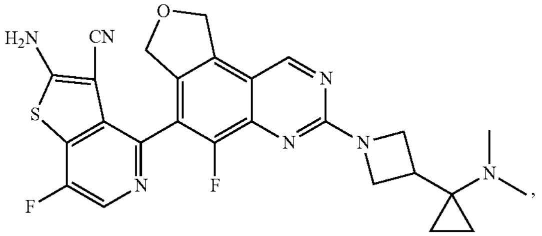
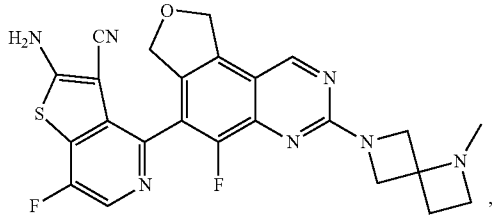
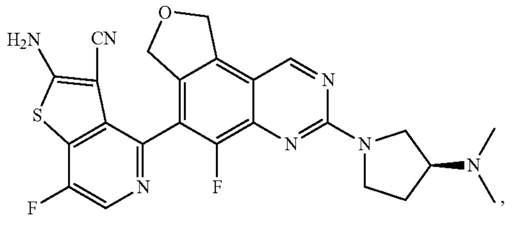
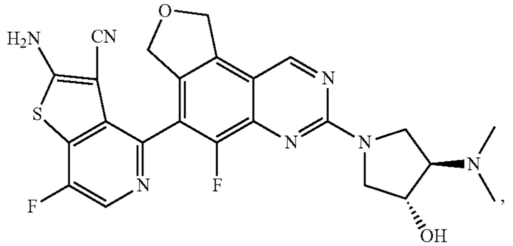
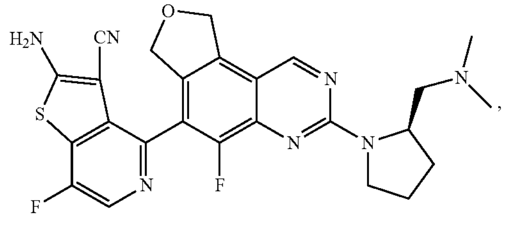

-continued
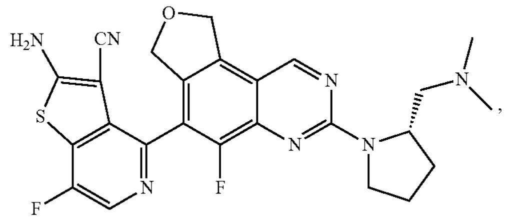
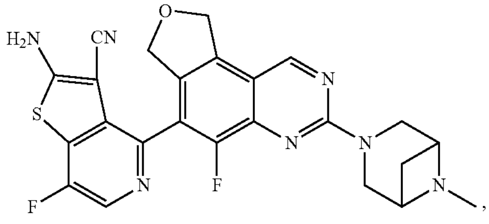
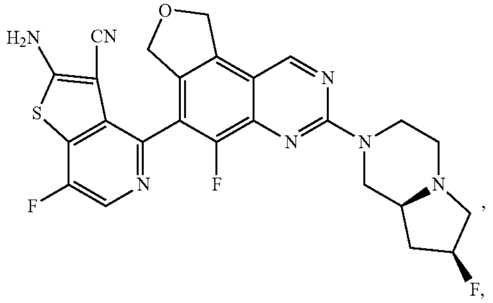
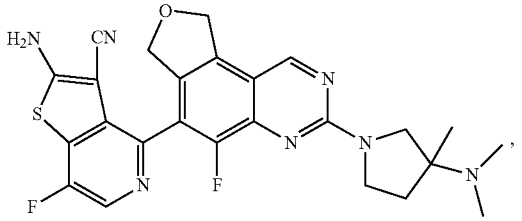
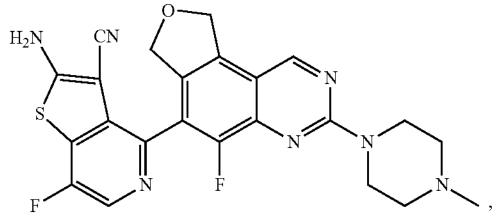
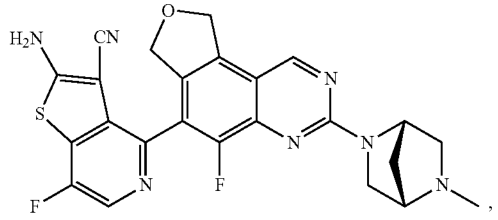
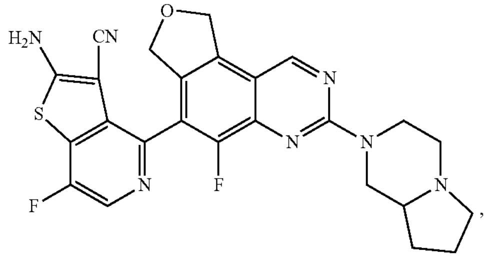
-continued
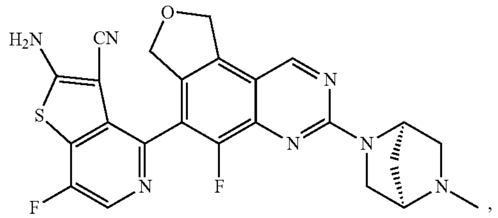
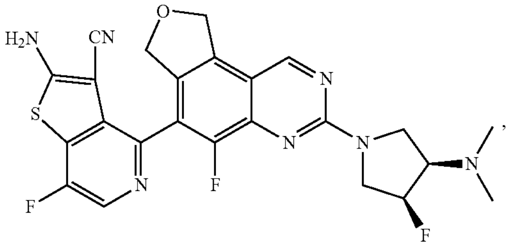
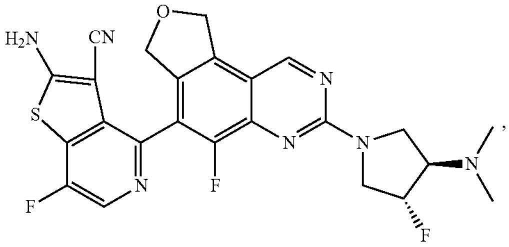
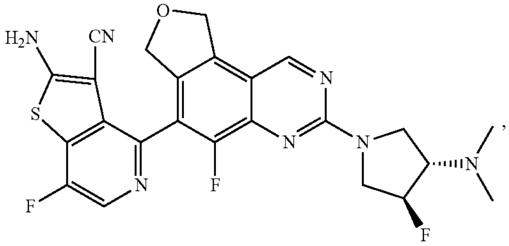
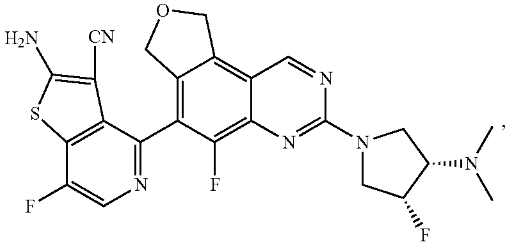
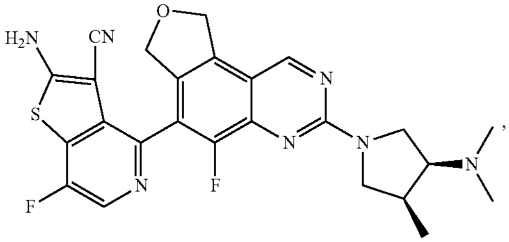
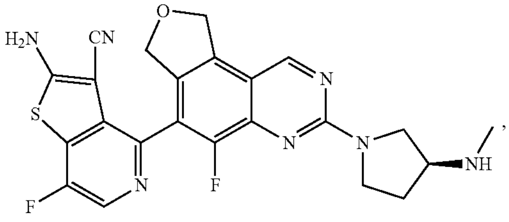

-continued
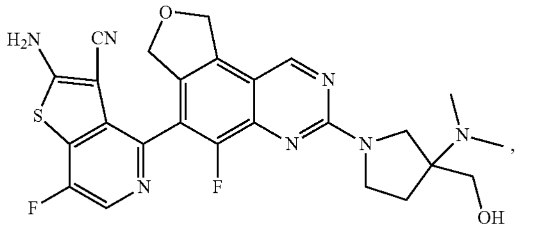
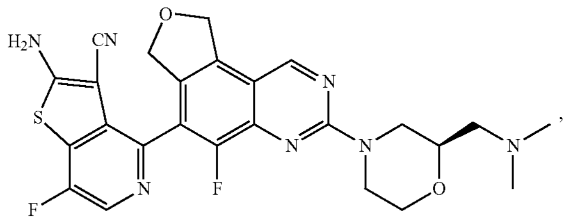
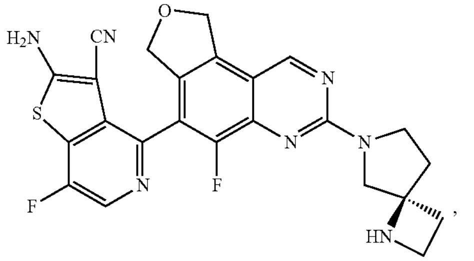
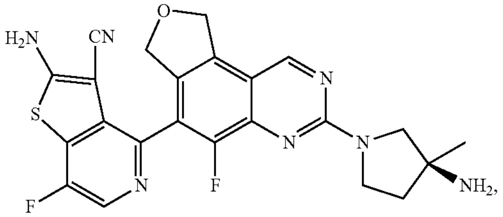
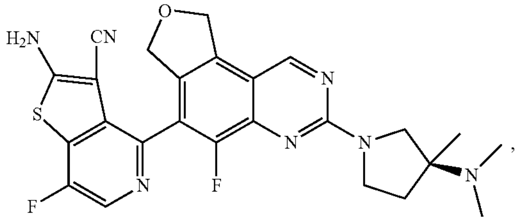
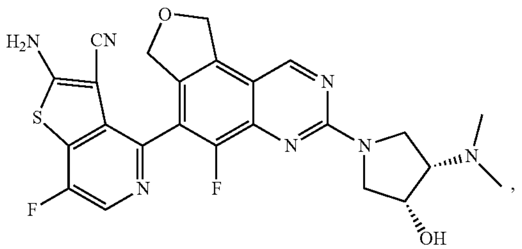
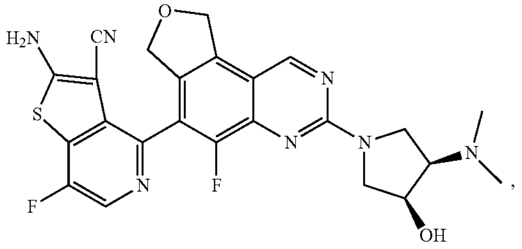
-continued
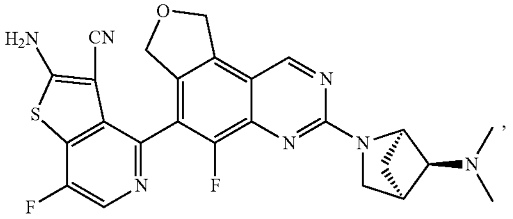
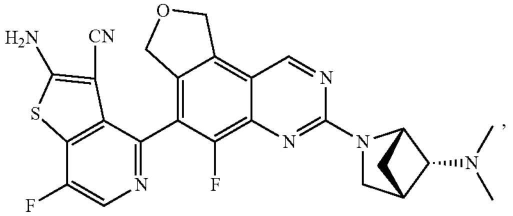
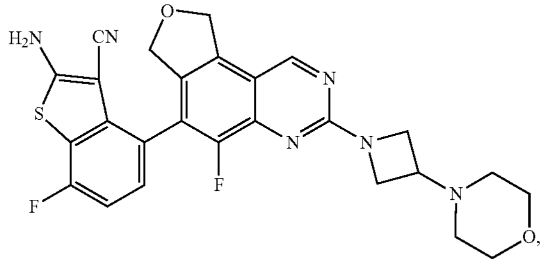
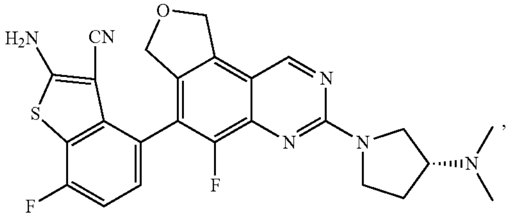
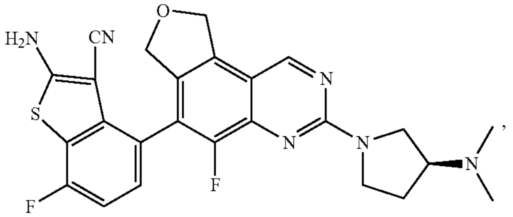
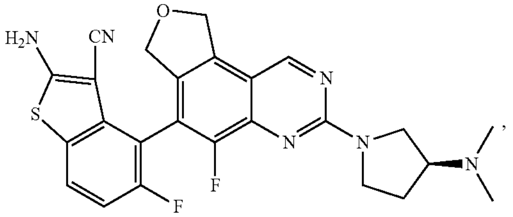
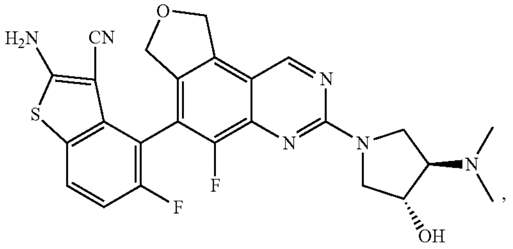

-continued
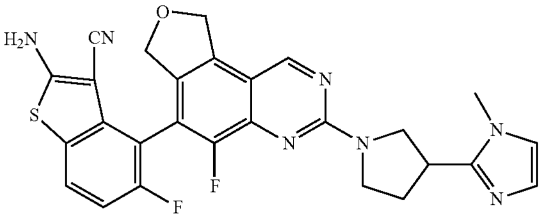
,
and
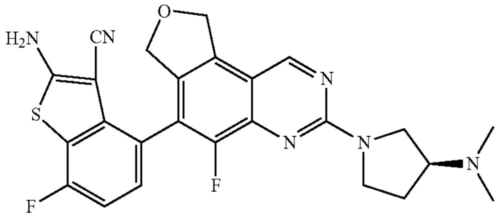
,
or a pharmaceutically acceptable salt thereof.
A compound of Formula I or a pharmaceutically acceptable salt thereof, the compound is selected from
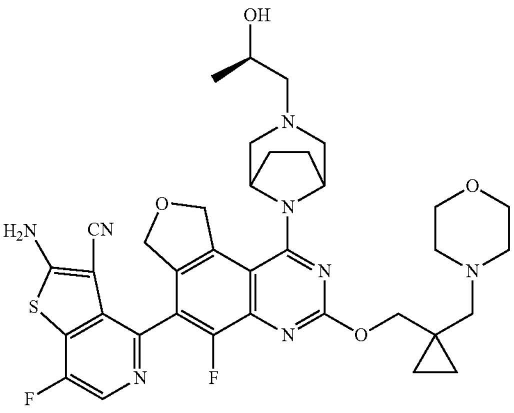
,
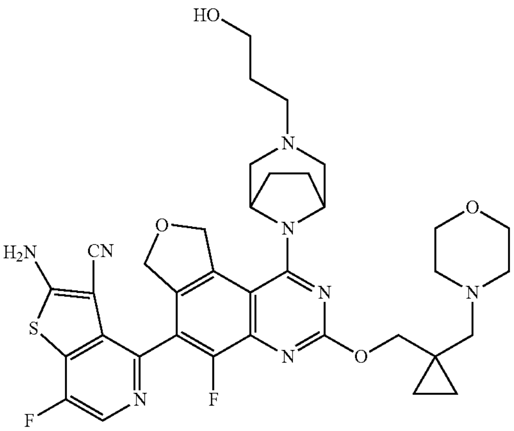
,
-continued
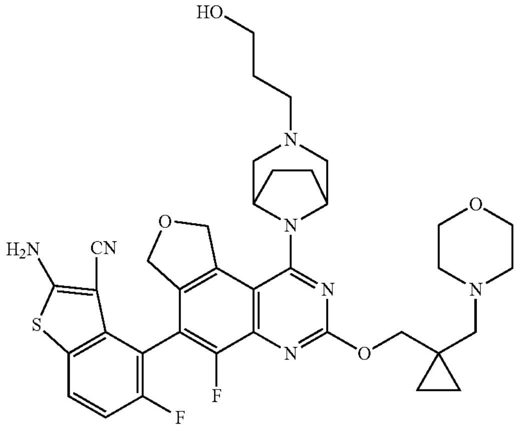
,
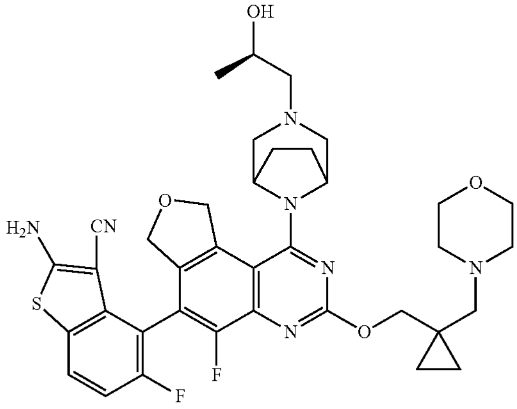
,
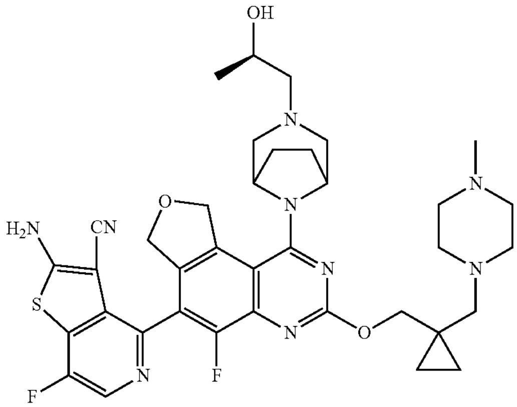
,
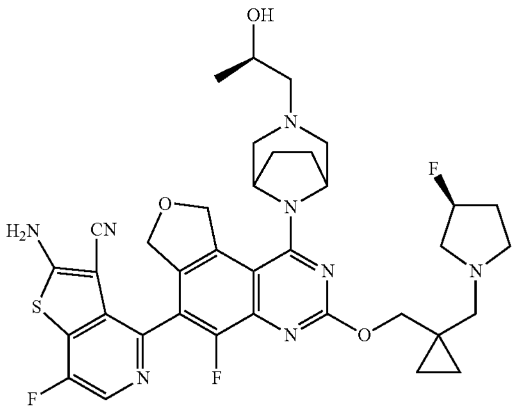
, -continued
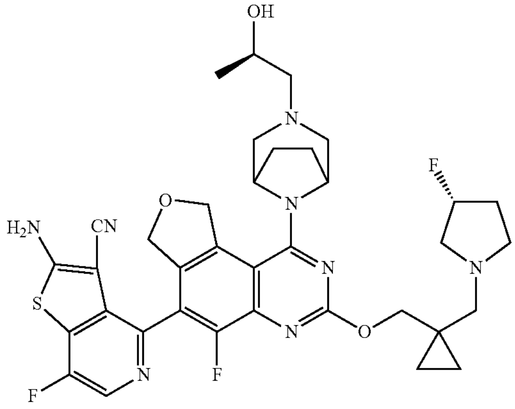
,
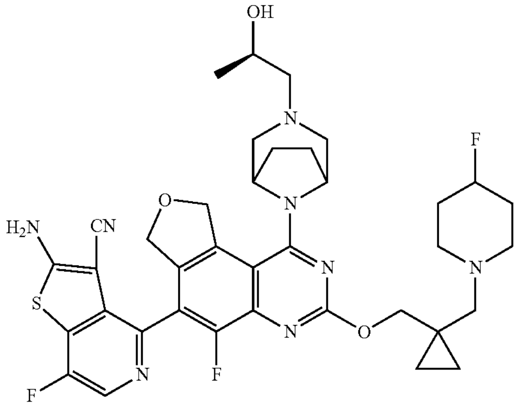
,
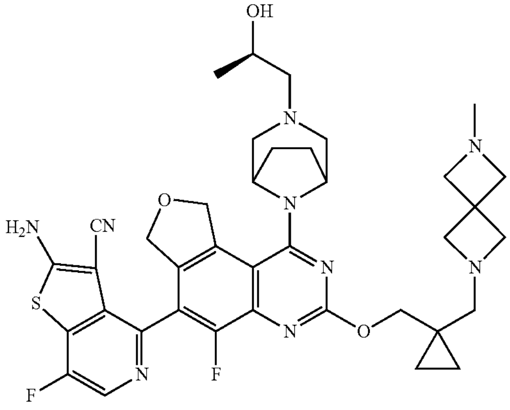
,
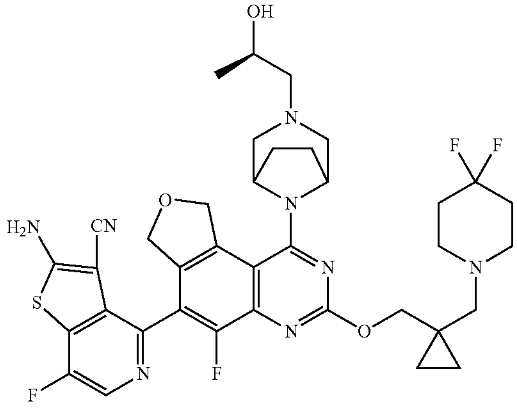
,
-continued
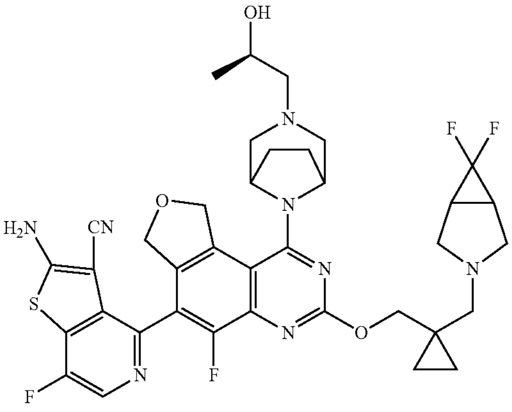
,
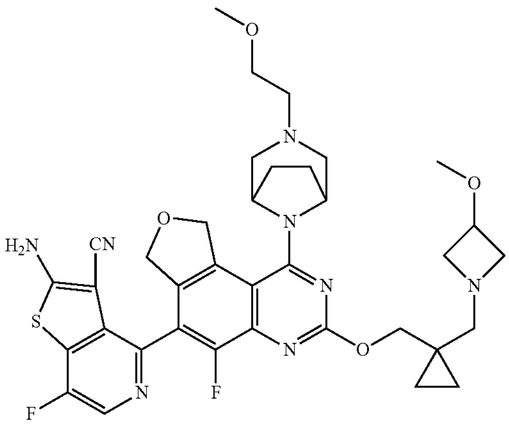
,
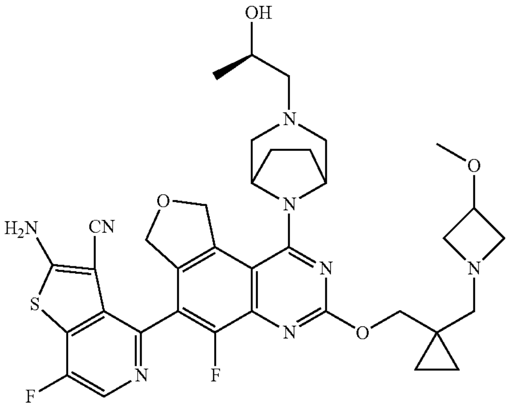
,
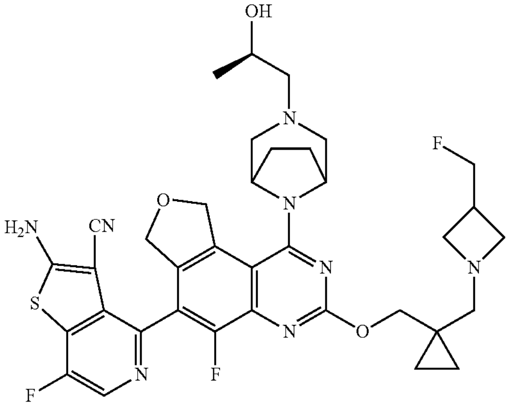
, -continued
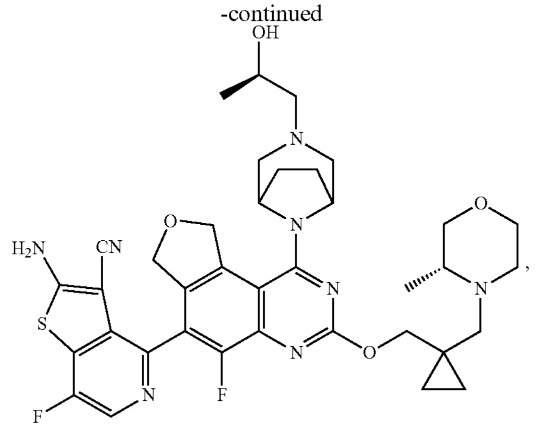
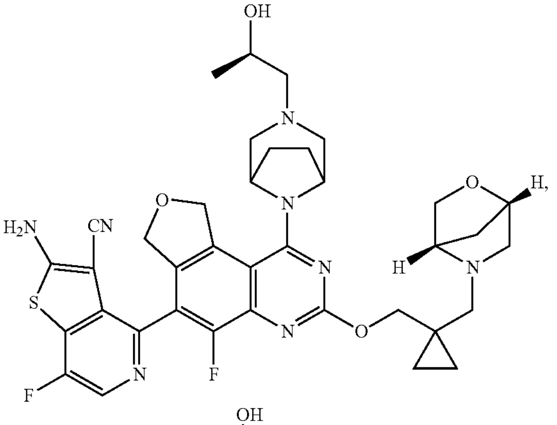
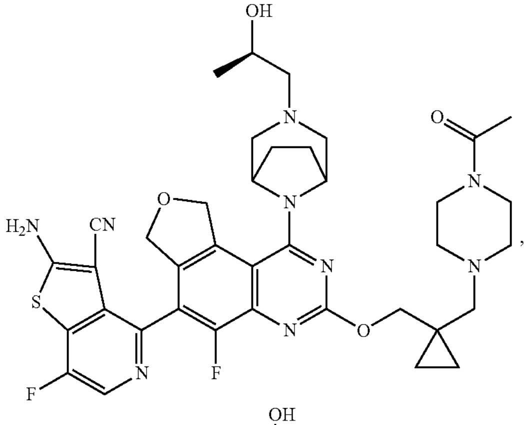
, and
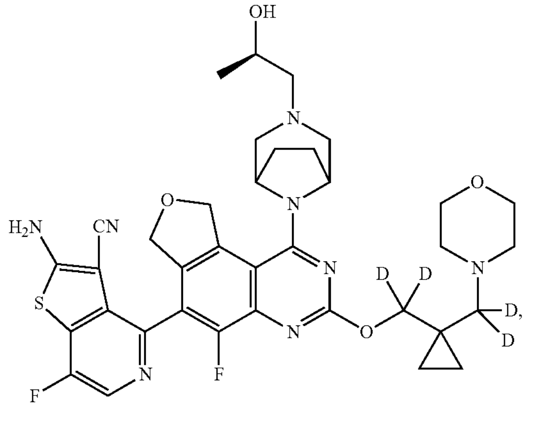
or a pharmaceutically acceptable salt thereof.
A compound of Formula I or a pharmaceutically acceptable salt thereof, the compound is selected from
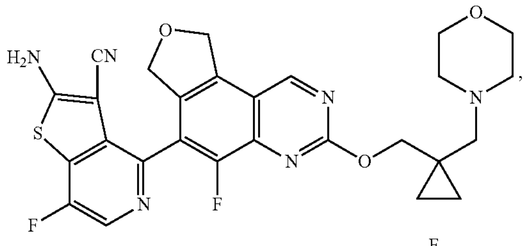
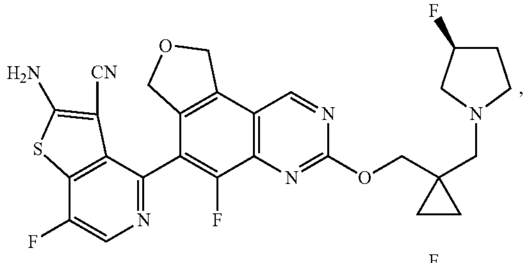
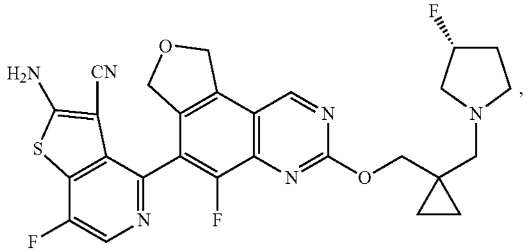
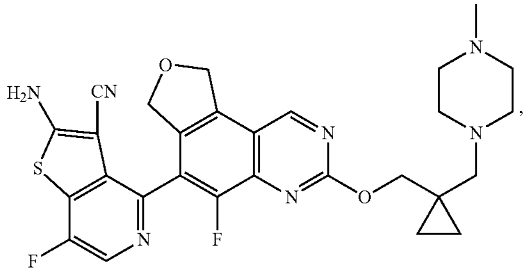
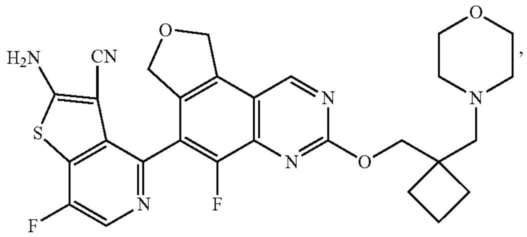
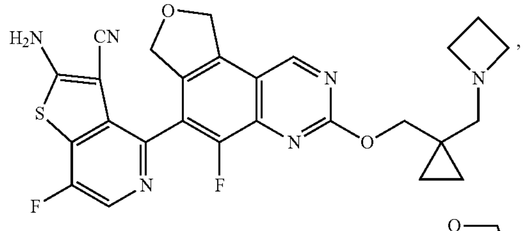
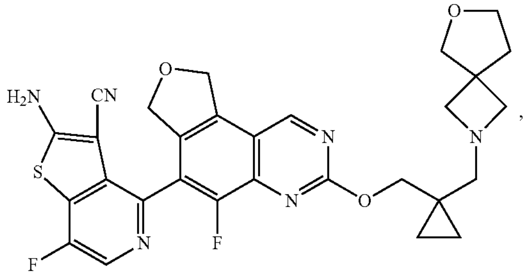

-continued

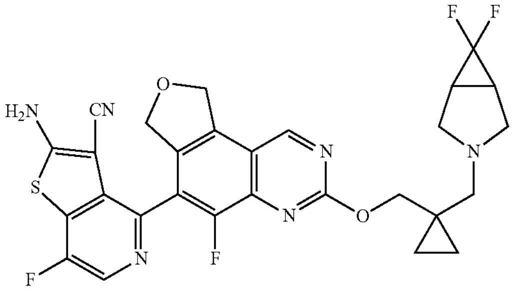

,

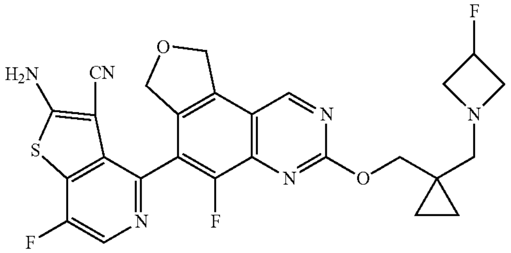

,

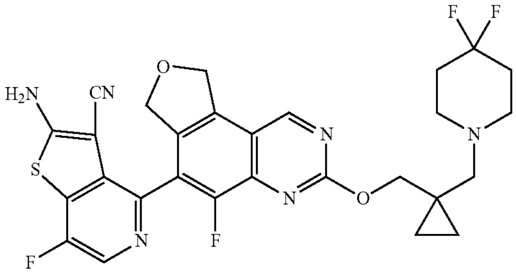

,

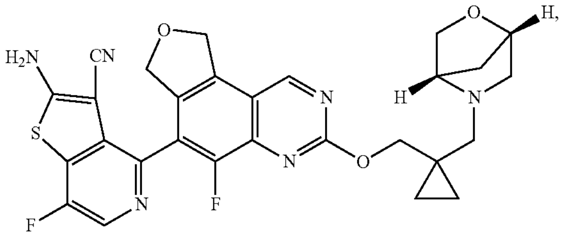

,

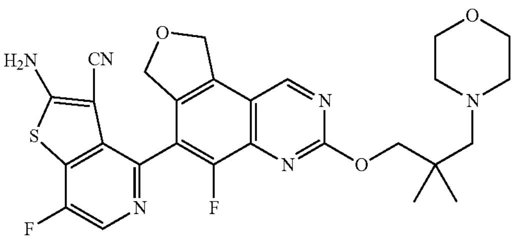

,

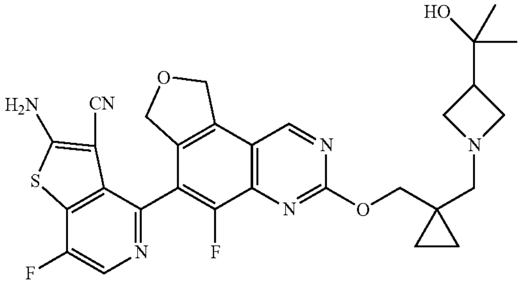

,

-continued

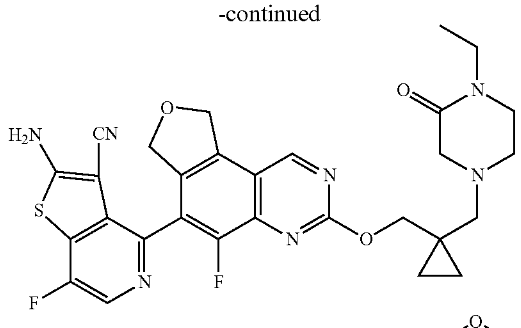

,

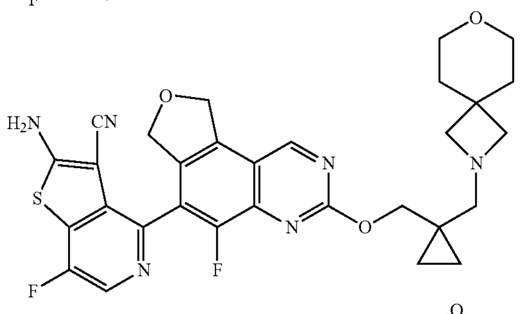

,

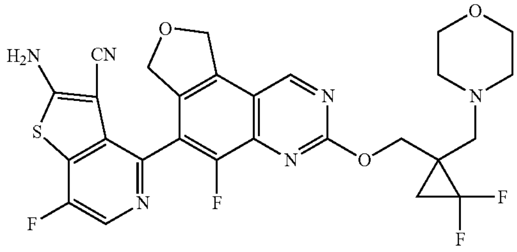

, and

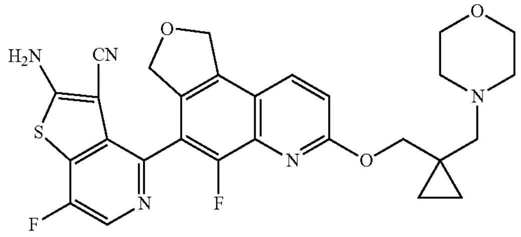

, or a pharmaceutically acceptable salt thereof.

The chemical drawings in the compounds above contain indications of chiral aspects of the specific compounds shown. However, the chemical drawings in the compounds above do not contain all the possible chiral features of these compounds and the chiral indications shown are not intended to exclude changes to the chiral aspects shown. Thus, alternate chiral versions of the compounds as well as different combinations of chiral attributes are contemplated and included herein.

Also provided herein are pharmaceutical compositions comprising a compound according to Formula I, or a pharmaceutically acceptable salt thereof, examples of which include, but are not limited to, the compounds disclosed herein, and a pharmaceutically acceptable carrier, diluent, or excipient.

Further provided herein are methods of treating cancer, comprising administering to a patient in need thereof, an effective amount of a compound according to Formula I, or a pharmaceutically acceptable salt thereof. In this method, the cancer can be lung cancer, colorectal cancer, pancreatic cancer, bladder cancer, cervical cancer, endometrial cancer, ovarian cancer, cholangiocarcinoma, gastric, or esophageal cancer. In this method, the cancer can more specifically be non-small cell lung cancer, pancreatic cancer, or colorectal cancer. In an embodiment the cancer can be non-small cell lung cancer. In an embodiment the cancer can be pancreatic cancer. In an embodiment the cancer can be colorectal cancer.

Also provided herein is a method of treating cancer, comprising administering to a patient in need thereof, an effective amount of a compound according to Formula I, or a pharmaceutically acceptable salt thereof, in which the cancer has one or more cells that express a mutant KRas G12D protein. In this method, the cancer can be non-small cell lung cancer, pancreatic cancer, or colorectal cancer, in which the cancer has one or more cells that express a KRas G12D mutant protein. In an embodiment, the cancer is non-small cell lung carcinoma in which the cancer has one or more cells that express a KRas G12D mutant protein. In an embodiment, the cancer is mutant pancreatic cancer in which the cancer has one or more cells that express a KRas G12D mutant protein. In an embodiment, the cancer is colorectal carcinoma in which the cancer has one or more cells that express a KRas G12D mutant protein. This method also includes treating KRas G12D mutant bearing cancers of other origins. Also provided herein is a method of treating cancer, comprising administering to a patient in need thereof, an effective amount of a compound according to Formula I, or a pharmaceutically acceptable salt thereof, in which the cancer has one or more cells that express a mutant KRas G12C, G12D, and/or G12V protein. In this method, the cancer can be non-small cell lung cancer, pancreatic cancer, or colorectal cancer, in which the cancer has one or more cells that express a KRas G12C, G12D, and/or G12V mutant protein. In an embodiment, the cancer is non-small cell lung carcinoma in which the cancer has one or more cells that express a KRas G12C, G12D, and/or G12V mutant protein. In an embodiment, the cancer is mutant pancreatic cancer in which the cancer has one or more cells that express a KRas G12C, G12D, and/or G12V mutant protein. In an embodiment, the cancer is colorectal carcinoma in which the cancer has one or more cells that express a KRas G12C, G12D, and/or G12V mutant protein. This method also includes treating KRas G12C, G12D, and/or G12V mutant bearing cancers of other origins.

Further provided herein is a method of treating a patient with a cancer that has a KRas G12D mutation comprising administering to a patient in need thereof an effective amount of a compound according to Formula I or a pharmaceutically acceptable salt thereof. In this method, the cancer that has a KRas G12D mutation can be KRas G12D mutant lung cancer, KRas G12D mutant pancreatic cancer, KRas G12D mutant cervical cancer, KRas G12D mutant esophageal cancer, KRas G12D mutant endometrial cancer, KRas G12D mutant ovarian cancer, KRas G12D mutant cholangiocarcinoma, and KRas G12D mutant colorectal cancer. In an embodiment the cancer that has a KRas G12D mutation can be KRas G12D mutant non-small cell lung cancer. In an embodiment the cancer that has a KRas G12D mutation can be KRas G12D mutant pancreatic cancer. In an embodiment the cancer that has a KRas G12D mutation can be KRas G12D mutant colorectal cancer.

Further provided herein is a method of treating a patient with a cancer that has a KRas G12C, G12D, and/or G12V mutation comprising administering to a patient in need thereof an effective amount of a compound according to Formula I or a pharmaceutically acceptable salt thereof. In this method, the cancer that has a KRas G12C, G12D, and/or G12V mutation can be KRas G12C, G12D, and/or G12V mutant lung cancer, KRas G12C, G12D, and/or G12V mutant pancreatic cancer, KRas G12C, G12D, and/or G12V mutant cervical cancer, KRas G12C, G12D, and/or G12V mutant esophageal cancer, KRas G12C, G12D, and/or G12V mutant endometrial cancer, KRas G12C, G12D, and/or G12V mutant ovarian cancer, KRas G12C, G12D, and/or G12V mutant cholangiocarcinoma, and KRas G12C, G12D, and/or G12V mutant colorectal cancer. In an embodiment the cancer that has a KRas G12C, G12D, and/or G12V mutation can be KRas G12C, G12D, and/or G12V mutant non-small cell lung cancer. In an embodiment the cancer that has a KRas G12C, G12D, and/or G12V mutation can be KRas G12C, G12D, and/or G12V mutant pancreatic cancer. In an embodiment the cancer that has a KRas G12C, G12D, and/or G12V mutation can be KRas G12C, G12D, and/or G12V mutant colorectal cancer.

Additionally provided herein is a method of modulating a mutant KRas G12D enzyme in a patient in need thereof, by administering a compound according to Formula I, or a pharmaceutically acceptable salt thereof. In one embodiment this method comprises inhibiting a human mutant KRas G12D enzyme. Additionally provided herein is a method of modulating a mutant KRas G12C, G12D, and/or G12V enzyme in a patient in need thereof, by administering a compound according to Formula I, or a pharmaceutically acceptable salt thereof. In one embodiment this method comprises inhibiting a human mutant KRas G12C, G12D, and/or G12V enzyme.

Also provided herein is a method of treating cancer in a patient in need thereof, wherein the patient has a cancer that was determined to express the KRas G12D mutant protein. The method comprises administering to a patient an effective amount of a compound according to Formula I, or a pharmaceutically acceptable salt thereof. Also provided herein is a method of treating cancer in a patient in need thereof, wherein the patient has a cancer that was determined to express the KRas G12C, G12D, and/or G12V mutant protein. The method comprises administering to a patient an effective amount of a compound according to Formula I, or a pharmaceutically acceptable salt thereof. The G12C, G12D, and/or G12V mutational status of one or more cancer cells can be determined by a number of assays known in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g., G12C, G12D, and/or G12V mutational status, in one or more cancer cells or in circulating cell-free DNA) include direct sequencing, next-generation sequencing, reverse transcription polymerase chain reaction (RT-PCR), multiplex PCR, and pyrosequencing and multi-analyte profiling.

Further provided herein is a compound or a pharmaceutically acceptable salt thereof according to Formula I for use in therapy. The compound or a pharmaceutically acceptable salt thereof, can be for use in treating cancer. For this use in treating cancer, the cancer can be lung cancer, colorectal cancer, pancreatic cancer, bladder cancer, cervical cancer, endometrial cancer, ovarian cancer, cholangiocarcinoma, or esophageal cancer. The cancer can more specifically be non-small cell lung cancer, pancreatic cancer, or colorectal cancer. In an embodiment, the cancer is non-small cell lung cancer. In an embodiment, the cancer is pancreatic cancer. In an embodiment, the cancer is colorectal cancer. The cancer can have one or more cancer cells that express the mutant KRas G12D protein such as KRas G12D mutant lung cancer, KRas G12D mutant pancreatic cancer, KRas G12D mutant cervical cancer, KRas G12D mutant esophageal cancer, KRas G12D mutant endometrial cancer, KRas G12D mutant ovarian cancer, KRas G12D mutant cholangiocarcinoma, and KRas G12D mutant colorectal cancer. In these uses, the cancer is selected from: KRas G12D mutant non-small cell lung cancer, KRas G12D mutant colorectal cancer, and KRas G12D mutant pancreatic cancer. Additionally, the cancer can be non-small cell lung cancer, and one or more cells express KRas G12D mutant protein. Further, the cancer can be colorectal cancer, and one or more cells express KRas G12D mutant protein. Additionally, the cancer can be pancreatic cancer, and one or more cells express KRas G12D mutant protein. The patient can have a cancer that was determined to have one or more cells expressing the KRas G12D mutant protein prior to administration of the compound or a pharmaceutically acceptable salt thereof. The cancer can have one or more cancer cells that express the mutant KRas G12C, G12D, and/or G12V protein such as KRas G12C, G12D, and/or G12V mutant lung cancer, KRas G12C, G12D, and/or G12V mutant pancreatic cancer, KRas G12C, G12D, and/or G12V mutant cervical cancer, KRas G12C, G12D, and/or G12V mutant esophageal cancer, KRas G12C, G12D, and/or G12V mutant endometrial cancer, KRas G12C, G12D, and/or G12V mutant ovarian cancer, KRas G12C, G12D, and/or G12V mutant cholangiocarcinoma, and KRas G12C, G12D, and/or G12V mutant colorectal cancer. In these uses, the cancer is selected from: KRas G12C, G12D, and/or G12V mutant non-small cell lung cancer, KRas G12C, G12D, and/or G12V mutant colorectal cancer, and KRas G12C, G12D, and/or G12V mutant pancreatic cancer. Additionally, the cancer can be non-small cell lung cancer, and one or more cells express KRas G12C, G12D, and/or G12V mutant protein. Further, the cancer can be colorectal cancer, and one or more cells express KRas G12C, G12D, and/or G12V mutant protein. Additionally, the cancer can be pancreatic cancer, and one or more cells express KRas G12C, G12D, and/or G12V mutant protein. The patient can have a cancer that was determined to have one or more cells expressing the KRas G12C, G12D, and/or G12V mutant protein prior to administration of the compound or a pharmaceutically acceptable salt thereof. The patient may have been treated with a different course of treatment prior to being treated as described herein.

The compounds provided herein according to Formula I, or a pharmaceutically acceptable salt thereof, may also be used in the manufacture of a medicament for treating cancer. When used in the manufacture of a medicament, the cancer can be lung cancer, colorectal cancer, pancreatic cancer, bladder cancer, cervical cancer, endometrial cancer, ovarian cancer, cholangiocarcinoma, or esophageal cancer. The cancer can more specifically be non-small cell lung cancer, pancreatic cancer, or colorectal cancer. In an embodiment, the cancer is non-small cell lung cancer. In an embodiment, the cancer is pancreatic cancer. In an embodiment, the cancer is colorectal cancer. The cancer can have one or more cancer cells that express the mutant KRas G12D protein. When the cancer cells express KRas G12D protein, the cancer can be selected from KRas G12D mutant non-small cell lung cancer, KRas G12D mutant colorectal cancer, and KRas G12D mutant pancreatic cancer. The cancer can have one or more cancer cells that express the mutant KRas G12C, G12D, and/or G12V protein. When the cancer cells express KRas G12C, G12D, and/or G12V protein, the cancer can be selected from KRas G12C, G12D, and/or G12V mutant non-small cell lung cancer, KRas G12C, G12D, and/or G12V mutant colorectal cancer, and KRas G12C, G12D, and/or G12V mutant pancreatic cancer.

Also provided herein is a method of treating cancer, comprising administering to a patient in need thereof, an effective amount of a compound according to Formula I, or a pharmaceutically acceptable salt thereof, and one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in which the cancer has one or more cells that express a mutant KRas G12D protein. Also provided herein is a method of treating cancer, comprising administering to a patient in need thereof, an effective amount of a compound according to Formula I, or a pharmaceutically acceptable salt thereof, and one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in which the cancer has one or more cells that express a mutant KRas G12C, G12D, and/or G12V protein. Further provided herein is a compound according to Formula I, or a pharmaceutically acceptable salt thereof, for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer. Additionally provided is a combination comprising a compound according to Formula I, or a pharmaceutically acceptable salt thereof, and one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, for simultaneous, separate, or sequential use in the treatment of cancer.

Also provided is a method of treating cancer, comprising administering to a patient in need thereof, an effective amount of a compound according to Formula I, or a pharmaceutically acceptable salt thereof, and a PD-1 or PD-L1 inhibitor, in which the cancer has one or more cells that express a mutant KRas G12D protein. Also provided is a method of treating cancer, comprising administering to a patient in need thereof, an effective amount of a compound according to Formula I, or a pharmaceutically acceptable salt thereof, and a PD-1 or PD-L1 inhibitor, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with a PD-1 or PD-L1 inhibitor, for use in the treatment of cancer. Additionally provided is a combination comprising a compound according to Formula I, or a pharmaceutically acceptable salt thereof, and a PD-1 or PD-L1 inhibitor, for simultaneous, separate, or sequential use in the treatment of cancer. As used herein, the PD-1 or PD-L1 inhibitor can be pembrolizumab; the PD-1 or PD-L1 inhibitor can be nivolumab; the PD-1 or PD-L 1 inhibitor can be cemiplimab; the PD-1 or PD-L1 inhibitor can be sintilimab; the PD-1 or PD-L1 inhibitor can be atezolizumab; the PD-1 or PD-L1 inhibitor can be avelumab; the PD-1 or PD-L1 inhibitor can be durvalumab; or the PD-1 or PD-L1 inhibitor can be lodapilimab. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; or the cancer can be mutant pancreatic cancer in which the cancer has one or more cells that express a KRas G12D mutant protein. This method also includes treating KRas G12D mutant bearing cancers of other origins. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and a CDK4/CDK6 inhibitor, or a pharmaceutically acceptable salt thereof, in which the cancer has one or more cells that express a mutant KRas G12D protein. Further provided is a compound according to Formula I, or a pharmaceutically acceptable salt thereof, for use in simultaneous, separate, or sequential combination with a CDK4/CDK6 inhibitor, or a pharmaceutically acceptable salt thereof, for use in the treatment of cancer, in which the cancer has one or more cells that express a mutant KRas G12D protein. Additionally provided is a combination comprising a compound according to Formula I, or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRas G12D protein. As used herein, the CDK4/CDK6 inhibitor can be abemaciclib; the CDK4/CDK6 inhibitor can be palbociclib; or the CDK4/CDK6 inhibitor can be ribociclib. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins. Also provided is a method of treating cancer, comprising administering to a patient in need thereof, an effective amount of a compound according to Formula I, or a pharmaceutically acceptable salt thereof, and a CDK4/CDK6 inhibitor, or a pharmaceutically acceptable salt thereof, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with a CDK4/CDK6 inhibitor, or a pharmaceutically acceptable salt thereof, for use in the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and a CDK4/CDK6 inhibitor, or a pharmaceutically acceptable salt thereof, for simultaneous, separate, or sequential use in the treatment of cancer, in which the cancer has one or more cells that express a mutant KRas G12C, G12D, and/or G12V protein. As used herein, the CDK4/CDK6 inhibitor can be abemaciclib; the CDK4/CDK6 inhibitor can be palbociclib; or the CDK4/CDK6 inhibitor can be ribociclib. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and an EGFR inhibitor, or a pharmaceutically acceptable salt thereof, in which the cancer has one or more cells that express a mutant KRas G12D protein. Further provided is a compound according to Formula I, or a pharmaceutically acceptable salt thereof, for use in simultaneous, separate, or sequential combination with an EGFR inhibitor, or a pharmaceutically acceptable salt thereof, for the treatment of cancer. Additional provided is a combination comprising a compound according to Formula I, or a pharmaceutically acceptable salt thereof, and an EGFR inhibitor, or a pharmaceutically acceptable salt thereof, for simultaneous, separate, or sequential use in the treatment of cancer. As used herein, the EGFR inhibitor can be erlotinib; the EGFR inhibitor can be afatinib; the EGFR inhibitor can be gefitinib; the EGFR inhibitor can be cetuximab. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; or the cancer can be mutant pancreatic cancer in which the cancer has one or more cells that express a KRas G12D mutant protein. This method also includes treating KRas G12D mutant bearing cancers of other origins.

Also provided is a method of treating cancer, comprising administering to a patient in need thereof, an effective amount of a compound according to Formula I, or a pharmaceutically acceptable salt thereof, and an EGFR inhibitor, or a pharmaceutically acceptable salt thereof, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with an EGFR inhibitor, or a pharmaceutically acceptable salt thereof, for the treatment of cancer. Additional provided is a combination comprising a compound according to Formula I, or a pharmaceutically acceptable salt thereof, and an EGFR inhibitor, or a pharmaceutically acceptable salt thereof, for simultaneous, separate, or sequential use in the treatment of cancer. As used herein, the EGFR inhibitor can be erlotinib; the EGFR inhibitor can be afatinib; the EGFR inhibitor can be gefitinib; the EGFR inhibitor can be cetuximab. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and an ERK inhibitor, or a pharmaceutically acceptable salt thereof, in which the cancer has one or more cells that express a mutant KRas G12D protein. Also provided is a method of treating cancer, comprising administering to a patient in need thereof, an effective amount of a compound according to Formula I, or a pharmaceutically acceptable salt thereof, and an ERK inhibitor, or a pharmaceutically acceptable salt thereof, in which the cancer has one or more cells that express a mutant KRas G12C, G12D, and/or G12V protein. Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRas G12D protein. Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRas G12C, G12D, and/or G12V. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRas G12D protein. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with an ERK inhibitor, or a pharmaceutically acceptable salt thereof, for the treatment of cancer, in which the cancer has one or more cells that express a mutant KRas G12D protein. Further provided is a compound according to Formula I, or a pharmaceutically acceptable salt thereof, for use in simultaneous, separate, or sequential combination with an ERK inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and an ERK inhibitor, or a pharmaceutically acceptable salt thereof, for simultaneous, separate, or sequential use in the treatment of cancer. As used herein, the ERK inhibitor can be LY3214996; the ERK inhibitor can be LTT462; or the ERK inhibitor can be KO-947. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRas G12D protein. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRas G12D protein. Additionally provided is a combination comprising a compound according to Formula I, or a pharmaceutically acceptable salt thereof, and an Aurora A inhibitor, for simultaneous, separate, or sequential use in the treatment of cancer. Also provided is a method of treating cancer, comprising administering to a patient in need thereof, an effective amount of a compound according to Formula I, or a pharmaceutically acceptable salt thereof, and an Aurora A inhibitor, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with an Aurora A inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and an Aurora A inhibitor, for simultaneous, separate, or sequential use in the treatment of cancer. As used herein, the Aurora A inhibitor can be alisertib, tozasertib, (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid, (2R,4R)-1-[(3-chloro-2-fluoro-phenyl)methyl] -4-[[3-fluoro-6-[(5-methyl-1H-pyrazol-3-yl)amino]-2-pyridyl]methyl]-2-methyl-piperidine-4-carboxylic acid:2-methylpropan-2-amine (1:1) salt, and (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid:amine (1:1) salt, or a pharmaceutically acceptable salt thereof. In one embodiment, the Aurora A inhibitor is (2R,4R)-1-[(3-chloro-2-fluoro-phenyl)methyl]-4-[[3-fluoro-6-[(5-methyl-1H-pyrazol-3-yl)amino]-2-pyridyl]methyl]-2-methyl-piperidine-4-carboxylic acid. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and a SHP2 inhibitor, in which the cancer has one or more cells that express a mutant KRas G12D protein. Further provided is a compound according to Formula I, or a pharmaceutically acceptable salt thereof, for use in simultaneous, separate, or sequential combination with a SHP2 inhibitor, or a pharmaceutically acceptable salt thereof, for the treatment of cancer, in which the cancer has one or more cells that express a mutant KRas G12D protein. Also provided is a method of treating cancer, comprising administering to a patient in need thereof, an effective amount of a compound according to Formula I, or a pharmaceutically acceptable salt thereof, and a SHP2 inhibitor, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with a SHP2 inhibitor, or a pharmaceutically acceptable salt thereof, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and a SHP2 inhibitor, for simultaneous, separate, or sequential use in the treatment of cancer. As used herein, the SHP2 inhibitor, or a pharmaceutically acceptable salt thereof, can be a Type I SHP2 Inhibitor or a Type II SHP2 Inhibitor. Examples of Type I SHP2 inhibitors include, but are not limited to, PHPS1, GS-493, NSC-87877, NSC-117199, and Cefsulodin, and pharmaceutically acceptable salts thereof. Examples of Type II SHP2 inhibitors include, but are not limited to, JAB-3068, JAB-3312, RMC-4550, RMC-4630, SHP099, SHP244, SHP389, SHP394, TNO155, RG-6433, and RLY-1971, and pharmaceutically acceptable salts thereof. Additional examples of SHP2 inhibitors include, but are not limited to, BBP-398, IACS-15509, IACS-13909, X37, ERAS-601, SH3809, HBI-2376, ETS-001, and PCC0208023, and pharmaceutically acceptable salts thereof. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and a platinum agent, in which the cancer has one or more cells that express a mutant KRas G12D protein. Also provided is a method of treating cancer, comprising administering to a patient in need thereof, an effective amount of a compound according to Formula I, or a pharmaceutically acceptable salt thereof, and a platinum agent, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with a platinum agent, or a pharmaceutically acceptable salt thereof, for the treatment of cancer, in which the cancer has one or more cells that express a mutant KRas G12D protein. Additionally provided is a combination comprising a compound according to Formula I, or a pharmaceutically acceptable salt thereof, and a platinum agent, for simultaneous, separate, or sequential use in the treatment of cancer. As used herein, the platinum agent can be cisplatin; the platinum agent can be carboplatin; or the platinum agent can be oxaliplatin. As described herein, the cancer can be non-small cell lung carcinoma, in which the cancer has one or more cells that express a KRas G12D mutant protein; the cancer can be colorectal carcinoma in which the cancer has one or more cells that express a KRas G12D mutant protein; the cancer can be mutant pancreatic cancer in which the cancer has one or more cells that express a KRas G12D mutant protein. This method also includes treating KRas G12D mutant bearing cancers of other origins. As used herein, the platinum agent can be cisplatin; the platinum agent can be carboplatin; or the platinum agent can be oxaliplatin. As described herein, the cancer can be non-small cell lung carcinoma, in which the cancer has one or more cells that express a KRas G12C, G12D, and/or G12V mutant protein; the cancer can be colorectal carcinoma in which the cancer has one or more cells that express a KRas G12C, G12D, and/or G12V mutant protein; the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

Also provided is a method of treating cancer, comprising administering to a patient in need thereof, an effective amount of a compound according to Formula I, or a pharmaceutically acceptable salt thereof, and pemetrexed, in which the cancer has one or more cells that express a mutant KRas G12D protein. Further provided is a compound according to Formula I, or a pharmaceutically acceptable salt thereof, for use in simultaneous, separate, or sequential combination with pemetrexed, for the treatment of cancer, in which the cancer has one or more cells that express a mutant KRas G12D protein. Additionally provided is a combination comprising a compound according to Formula I, or a pharmaceutically acceptable salt thereof, and pemetrexed, for simultaneous, separate, or sequential use in the treatment of cancer, in which the cancer has one or more cells that express a mutant KRas G12D protein. As described herein, the cancer has one or more cells that express a KRas G12D mutant protein. Further, a platinum agent can also be administered to the patient (and the platinum agent can be cisplatin, carboplatin, or oxaliplatin). As described herein, the cancer can be colorectal carcinoma in which the cancer has one or more cells that express a KRas G12D mutant protein or the cancer can be mutant pancreatic cancer in which the cancer has one or more cells that express a KRas G12D mutant protein. This method also includes treating KRas G12D mutant bearing cancers of other origins. Also provided is a method of treating cancer, comprising administering to a patient in need thereof, an effective amount of a compound according to Formula I, or a pharmaceutically acceptable salt thereof, and pemetrexed, in which the cancer has one or more cells that express a mutant KRas G12C, G12D, and/or G12V protein. Further provided is a compound according to Formula I, or a pharmaceutically acceptable salt thereof, for use in simultaneous, separate, or sequential combination with pemetrexed, for the treatment of cancer, in which the cancer has one or more cells that express a mutant KRas G12C, G12D, and/or G12V protein. Additionally provided is a combination comprising a compound according to Formula I, or a pharmaceutically acceptable salt thereof, and pemetrexed, for simultaneous, separate, or sequential use in the treatment of cancer, in which the cancer has one or more cells that express a mutant KRas G12C, G12D, and/or G12V protein. As described herein, the cancer has one or more cells that express a KRas G12C, G12D, and/or G12V mutant protein. Further, a platinum agent can also be administered to the patient (and the platinum agent can be cisplatin, carboplatin, or oxaliplatin). As described herein, the cancer can be colorectal carcinoma in which the cancer has one or more cells that express a KRas G12C, G12D, and/or G12V mutant protein or the cancer can be mutant pancreatic cancer in which the cancer has one or more cells that express a KRas G12C, G12D, and/or G12V mutant protein. This method also includes treating KRas G12C, G12D, and/or G12V mutant bearing cancers of other origins.

The term "pharmaceutically acceptable salt" as used herein refers to a salt of a compound considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences,* 1977, 66(1), 1-19. In an embodiment of a compound of Formula I, or a pharmaceutically acceptable salt thereof, the pharmaceutically acceptable salt is a mineral acid salt. Examples of mineral acids include, but are not limited to HCl, $H_2SO_4$, $H_3PO_4$ and $HNO_3$. In another embodiment, the pharmaceutically acceptable salt is a sulfonic acid salt. Examples of sulfonic acids include, but are not limited to para-toluenesulfonic acid, benzenesulfonic acid, methanesulfonic acid, ethanesulfonic acid, propane sulfonic acid and trifluoromethanesulfonic acid.

Pharmaceutical compositions containing the compounds of Formula I as described herein may be prepared using pharmaceutically acceptable additives. The term "pharmaceutically acceptable additive(s)" as used herein for the pharmaceutical compositions, refers to one or more carriers, diluents, and excipients that are compatible with the other additives of the composition or formulation and not deleterious to the patient. Examples of pharmaceutical compositions and processes for their preparation can be found in "Remington: The Science and Practice of Pharmacy", Loyd, V., et al. Eds., $22^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose, alginates, gelatin, and polyvinyl-pyrrolidone; kaolin and bentonite; and polyethyl glycols.

As used herein, the term "effective amount" refers to an amount that is a dosage, which is effective in achieve a desired therapeutic result such as treating a disorder or disease, like a cancerous lesion or progression of abnormal cell growth and/or cell division. Factors considered in the determination of an effective amount or dose of a compound include: whether the compound or its salt will be administered; the co-administration of other agents, if used; the species of patient to be treated; the patient's size, age, gender, and general health; the degree of involvement or stage and/or the severity of the disorder; the response of the individual patient; the mode of administration; the bioavailability characteristics of the preparation administered; the dose regimen selected; and the use of other concomitant medication.

A treating physician, veterinarian, or other medical person will be able to determine an effective amount of the compound for treatment of a patient in need. Pharmaceutical compositions can be formulated as a tablet or capsule for oral administration, a solution for oral administration, or an injectable solution. The tablet, capsule, or solution can include a compound of the present invention in an amount effective for treating a patient in need of treatment for cancer.

As used herein, the terms "treating", "to treat", or "treatment", includes slowing, controlling, delaying, reducing, stopping, reversing, preventing, or ameliorating the progression or severity of an existing symptom, disorder, condition, which can include specifically slowing the growth of a cancerous lesion or progression of abnormal cell growth and/or cell division. Treating does not necessarily indicate a total elimination of all disorder or disease symptoms.

As used herein, the term "patient" refers to a mammal in need of treatment. Specifically, the patient can be a human that is in need of treatment for cancer, for example, KRas G12C, G12D and/or G12V mutant bearing cancers.

Certain abbreviations are defined as follows: "ACN" refers to acetonitrile; "AcOH" or "HOAc" refer to acetic acid; AIBN" refers to azobisisobutyronitrile; "Alloc" refers to the allyloxycarbonyl group; "aq." refers to aqueous; "atm" refers to atmosphere or atmospheres; "Boc-Gly-OH" refers to N-(tert-butoxycarbonyl)glycine; "BrettPhos" refers to 2-dicyclohexylphosphino-3,6-dimethoxy-2',4',6'-triisopropyl-1,1'-biphenyl; "BroP" refers to bromo tris(dimethylamino) phosphonium hexafluorophosphate; "Cbz" refers to the benzyloxycarbonyl group; "Cbz-Cl" refers to benzyl chloroformate; "conc." refers to concentrated; "CSI" refers to chlorosulfonyl isocyanate; "CV" refers to column volumes; "DCM" refers to dichloromethane; "DIAD" refers to diisopropyl azodicarboxylate; "DIBAL-H" refers to diisobutylaluminum hydride; "DIEA" and "DIPEA" refer to N,N-diisopropyl ethylamine; "(dippf)Rh(cod)$BF_4$" refers to [1,4-bis(diphenylphosphino)butane](1,5-cyclooctadiene) rhodium(I) tetrafluoroborate; "DMAP" refers to 4-dimethylaminopyridine; "DMEA" refers to N,N-dimethylethylamine; "DMEM" refers to Dulbecco's modified Eagle's medium; "DMF" refers to N,N-dimethylformamide; "DMSO" refers to dimethylsulfoxide; "DNA" refers to deoxyribonucleic acid; "DPEPhosPd$Cl_2$" refers to dichlorobis(diphenylphosphinophenyl)ether palladium (II); "DTT" refers to dithiothreitol; "EDTA" refers to ethylenediaminetetraacetic acid; "EGTA" refers to ethylene glycol-bis(b-aminoethyl ether)-N,N,N',N'-tetraacetic acid; "ELISA" refers to enzyme-linked immunosorbent assay; "ERK" refers to extracellular signal-regulated kinases; "EtOAc" refers to ethyl acetate; "$Et_2O$" refers to diethyl ether; "EtOH" refers to ethanol; "FA" refers to formic acid; "FBS" refers to fetal bovine serum; "Fmoc" refers to the fluorenylmethyloxycarbonyl group; "GDP" refers to guanosine diphosphate; "GTP" refers to guanosine triphosphate; "h" refers to hour or hours; "HATU" refers to 1-[Bis(dimethylamino)methylene]-1H-1,2,3-triazolo[4,5-b]pyridinium 3-oxide hexafluorophosphate; "Hex" or "hex" refers to hexane or hexanes; "HPLC" refers to high-performance liquid chromatography; "HRP" refers to horseradish peroxidase; "IPA" refers to isopropyl alcohol; "IPAm" refers to isopropyl amine; "KOAc" refers to potassium acetate; "LC-ES/MS" refers to liquid chromatograph-electrospray mass spectrometry; "LC-MS" refers to liquid chromatography mass spectrometry; "LiHMDS" refers to lithium bis(trimethylsilyl)amide; "L-prolinol" refers to [(2S)-pyrrolidin-2yl] methanol; "MAPK" refers to mitogen-activated protein kinases; "mCPBA" refers to 3-chloro-peroxybenzoic acid; "Me" refers to a methyl group; "MeOH" refers to methanol; "min" refers to minute or minutes; "MTBE" refers to methyl tert-butyl ether; "NaBH(OAc)$_3$ refers to sodium triacetoxyborohydride; "NaOMe" refers to sodium methoxide; "NBS" refers to N-bromosuccinimide; "NCS" refers to N-chlorosuccinimide; "N-methyl-L-prolinol" refers to [(2S)-1-methylpyrrolidin-2-yl]methanol; "NMM" refers to N-methylmorpholine; "NMP" refers to 1-methylpyrrolidin-2-one; "NIS" refers to N-iodosuccinimide; "PCR" refers to polymerase chain reaction; "Pd-117" refers to dichloro[bis(2-(diphenylphosphino)phenyl)ether]palladium(II), CAS 205319-06-8; "Pd-118" refers to 1,1'-bis(di-tert-butylphosphino)ferrocene palladium dichloride, CAS 95408-45-0; "$Pd_2(dba)_3$" refers to tris(dibenzylideneacetone)dipalladium (0); "Pd(dppf)$Cl_2$" refers to [1,1'-bis(diphenylphosphino) ferrocene]dichloropalladium(II); "Pd(OAc)$_2$ refers to palladium (II) acetate; Pd(PPh3)$_4$ refers to tetrakis (triphenylphosphine)palladium(0); "PE" refers to petroleum ether or diethyl ether; "Ph" refers to phenyl; "RBF" refers to round bottom flask; "RPMI" refers to Roswell Park Memorial Institute; "RT" refers to room temperature; "RuPhos" refers to 2-dicyclohexylphosphino-2',6'-diisopropoxy-1,1'-biphenyl, CAS 787618-22-8; "sat." refers to saturated; "SCX" refers to strong cation exchange; "Selectfluor™" refers to 1-chloromethyl-4-fluoro-1,4-diazoniabicyclo [2.2.2]octane bis(tetrafluoroborate), "SPE" refers to solid phase extraction; "SPhos" refers to 2-dicyclohexylphosphino-2',6'-dimethoxy-1,1'-biphenyl; "TBAF" refers to tetrabutylammonium fluoride; "TBDMSCl" refers to tert-butyldimethylsilyl chloride; "TBDMS" refers to the tert-butyldimethylsilyl group; "ttBu" refers to the tert-butyl group; "t-BuOH" refers to tert-butanol or tert-butyl alcohol; A" refers to triethylamine; "TES" refers to triethylsilane; "$Tf_2O$" refers to trifluoromethanesulfonic anhydride; "TFA" refers to trifluoracetic acid; "THF" refers to tetrahydrofuran; "TMEDA" refers to tetramethylethylenediamine; "tR" refers to retention time; "XantPhos" refers to 4,5-bis(diphenylphosphino)-9,9-dimethylxanthene; "XPhos" refers to 2-(dicyclohexylphosphino)-2',4',6'-tri-isopropyl-1,1'-biphenyl; "XPhos Palladacycle G2" refers to chloro(2-dicyclohexylphosphino-2',4',6'-triisopropyl-1,1'-biphenyl)[2-(2'-amino-1,1'-biphenyl)]palladium(II), CAS 1310584-14-5; "XPhos Palladacycle Gen. 4" or "XPhos Pd G4" refer to methanesulfonato(2-dicyclohexylphosphino-2',4',6'-triisopropyl-1,1'-biphenyl)(2'-methylamino-1,1'-biphenyl-2-yl) palladium(II), CAS 1599466-81-5.

Individual isomers, enantiomers, diastereomers, and atropisomers may be separated or resolved at any convenient point in the synthesis of compounds listed below, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994). The molecules described herein include compounds that are atropisomers and which can exist in different conformations or as different rotomers. Atropisomers are compounds that exist in different conformations arising from restricted rotation about a single bond. Atropisomers can be isolated as separate chemical species if the energy barrier to rotation about the single bond is sufficiently high that the rate of interconversion is slow enough to allow the individual rotomers to be separated from each other. This description is intended to include all of the isomers, enantiomers, diastereomers, and atropisomers possible for the compounds disclosed herein or that could be made using the compounds disclosed herein. In the molecules described herein, only molecules in which the absolute conformation of a chiral center (or atropisomer conformation) is known have used naming conventions or chemical formula that are drawn to indicate the chirality or atropisomerism. Those of skill in the art will readily understand when other chiral centers are present in the molecules described herein and be able to identify the same.

Compounds of any one of Formula I that are chemically capable of forming salts are readily converted to and may be isolated as a pharmaceutically acceptable salt. Salt formation can occur upon the addition of a pharmaceutically acceptable acid to form the acid addition salt. Salts can also form simultaneously upon deprotection of a nitrogen or oxygen, i.e., removing the protecting group. Examples, reactions and conditions for salt formation can be found in Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and Berge, S. M., et al., "Pharmaceutical Salts," *Journal of Pharmaceutical Sciences,* 66: 1-19, (1977).

LIST OF EMBODIMENTS

The following is a list of embodiments which are illustrative and should not be interpreted to limit the scope of the claimed subject matter.

1. A compound of the formula:

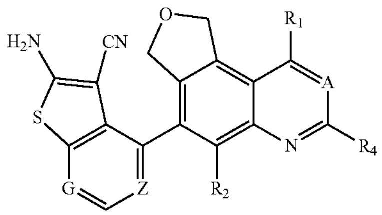

wherein:

A is —C(H)— or —N—;

Z is —C($R_{3c}$)— or —N—;

G is —C($R_{3b}$)— or —N—;

$R_1$ is H, or a group of the formula

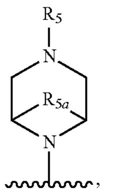,
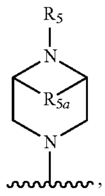,
or
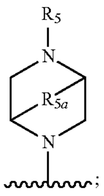;

$R_2$ is H, halogen, or methyl;

$R_{3b}$, and $R_{3c}$ are each independently H, halogen, or methyl;

$R_4$ is a N-linked cyclic amine or a group of the formula

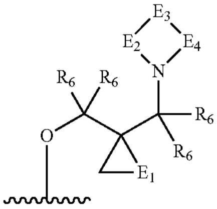
,
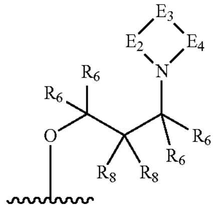
, or
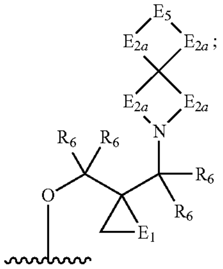
;

wherein the N-linked cyclic amine is a N-linked:

i. azetidine substituted with $R_{4a}$ and $R_{4b}$;

ii. pyrrolidine, piperidine, piperazine, morpholine, diazepane, imidazole or pyrazole; each of which is optionally bridged by a $C_{1-3}$ alkylene, and each of which is optionally substituted with one or more halogen; hydroxyl; —$NR_{6a}R_{6a}$; (1-methylpiperidin-4-yl)oxy; $C_{1-3}$ alkoxy optionally substituted with —$NR_{6a}R_{6a}$; $C_{1-3}$ alkyl optionally substituted with one or more halogen, —$NR_{6a}R_{6a}$ or hydroxyl; an imidazole optionally substituted with a methyl; a monocyclic ring selected from azetidine, piperidine, piperazine, morpholine, oxazepane, or diazepane; a bicycle selected from hexahydro-1H-furo[3,4-c]pyrrole, octahydropyrrolo[3,4-c]pyrrole, or octahydropyrrolo[1,2-a]pyrazine; or a spirocycle selected from 4,7-diazaspiro[2.5]octane, 2-oxa-7-azaspiro[3.5]nonane, 2,6-diazaspiro[3.4]octane, or 2-azaspiro[3.3]heptane; wherein the monocyclic ring is optionally bridged by a $C_{1-3}$ alkylene, and can optionally be substituted with one or more halogen, hydroxyl, —CN, $C_{1-3}$ alkoxy, —$NR_{10}R_{10}$, cyclopropyl, oxetane, —CO—$C_{1-3}$ alkyl, or a $C_{1-3}$ alkyl optionally substituted with hydroxyl, $C_{1-3}$ alkoxy, —$NR_{10}R_{10}$, halogen, or —$CF_3$; and wherein the bicyclo or spirocyclo is each optionally substituted with a methyl or a halogen; or iii. 2,6-diazabicyclo[3.2.0]heptane, 3,6-diazabicyclo[3.2.0]heptane, 3,6-diazabicyclo[3.2.1]octane, 2,6-diazabicyclo[3.2.1]octane, 3-azabicyclo[3.1.0]hexane, 3-azabicyclo[3.2.0]heptane, 2-azabicyclo[3.2.0]heptane, octahydro-1H-pyrrolo[3,4-b]pyridine, octahydro-1H-pyrrolo[3,2-b]pyridine, octahydro-6H-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, hexahydro-1H-furo[3,4-b]pyrrole, octahydro-1H-pyrrolo[3,2-b]pyridine, (3as,6as)-tetrahydro-1H,4H-3a,6a-(methanooxymethano)pyrrolo[3,4-c]pyrrole, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, 5-azaspiro[2.4]heptane, 2-oxa-6-azaspiro[3.4]octane, 2,7-diazaspiro[4.4]nonane, 2-oxa-6-azaspiro[3.4]octane or 1-oxa-7-azaspiro[4.4]nonane; each of which is optionally substituted with one or more halogen, —$NR_{6a}R_{6a}$ or a $C_{1-3}$ alkyl optionally substituted with —$NR_{6a}R_{6a}$ or hydroxyl;

$R_{4a}$ is $NR_{4c}R_{4d}$, cyclopropyl, azetidine, pyrrolidine, piperidine, piperazine, morpholine or imidazole, wherein the cyclopropyl, azetidine, pyrrolidine, piperidine, piperazine, or morpholine is optionally substituted with halogen, hydroxyl, $C_{1-3}$ alkoxy or —$NR_{6a}R_{6a}$;

$R_{4b}$ is H, hydroxyl, or $C_{1-3}$ alkyl;

$R_{4c}$ is independently cyclopropyl, or oxetane;

$R_{4d}$ is independently $C_{1-3}$ alkyl;

$R_5$ is trideuteromethyl, oxetane, or a $C_{1-4}$ alkyl optionally substituted with one or more halogen, trifluoromethyl, hydroxyl, methoxy, trifluoromethoxy, difluoromethoxy, trideuteromethoxy, oxetane, cyclopropyl, imidazole, pyrazole, —CO—$NR_{6a}R_{6a}$, —O—$(CH_2)_2$—$OR_{6a}$, or —O—CO—$C_{1-3}$ alkyl, wherein the cyclopropyl is optionally substituted with a hydroxyl, or hydroxymethyl, and the imidazole, or pyrazole are each optionally substituted with a hydroxyl, or a $C_{1-3}$ alkyl substituted with one or more hydroxyl;

$R_{5a}$ is $C_{1-3}$ alkylene;

each $R_6$ is independently H or deuterium;

each $R_{6a}$ is independently H, trideuteromethyl, a $C_{3-5}$ cycloalkyl, a N-methyl pyrrolidine, tetrahydrofuran, tetrahydropyran, bicyclo[1.1.1]pentan-1-yl, bicyclo[1.1.1]pentan-1-ol, or a $C_{1-3}$ alkyl optionally substituted with one or more deuterium, hydroxyl, methyl, methoxy, halogen, cyclopropyl, oxetane, tetrahydrofuran, tetrahydropyran, —CO—NHMe, or —CO—$NH_2$, wherein the $C_{3-5}$ cycloalkyl is optionally substituted with one or more hydroxyl or methyl;

$E_1$ is —O—$C_{1-3}$ alkylene, or $C_{1-3}$ alkylene optionally substituted with one or more halogens;

$E_2$, and $E_4$ are each independently $C_{1-3}$ alkylene optionally substituted with one or more hydroxyl, $C_{1-3}$ alkoxy or halogen, and wherein $E_2$ and $E_4$ can optionally be bridged by a bond or a $C_{1-3}$ alkylene; and $E_3$ is —O—, —$CR_7R_7$—, —$NR_9$—, or —CO—$NR_{6a}$—; or the ring

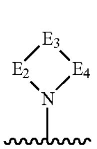

is hexahydro-1H-furo[3,4-c]pyrrole;

Each $E_{2a}$ is independently a $C_{1-3}$ alkylene optionally substituted with one or more hydroxyls;

$E_5$ is —O—, —$CR_7R_7$—, or —$NR_9$—;

Each $R_7$ is independently H, halogen, CN, hydroxyl, $C_{1-3}$ alkoxy, or $C_{1-3}$ alkyl optionally substituted with one or more halogens or hydroxyls;

each $R_8$ is independently a $C_{1-3}$ alkyl;

$R_9$ is each independently H, optionally substituted $C_{1-3}$ alkyl or —CO—$C_{1-3}$ alkyl; wherein the optionally substituted $C_{1-3}$ alkyl is optionally substituted with one or more halogens; and $R_{10}$ is H or $C_{1-3}$ alkyl optionally substituted with one or more deuterium; or a pharmaceutically acceptable salt thereof.

2. The compound according to embodiment 1, wherein $R_4$ is a N-linked cyclic amine or a group of the formula

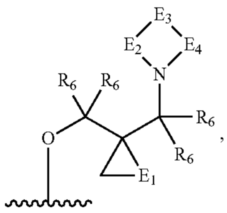
,
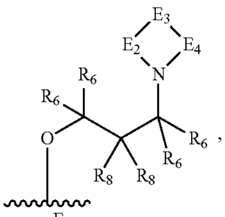
, or

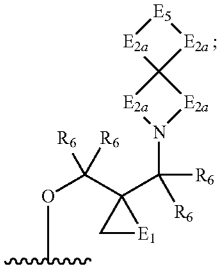

wherein the N-linked cyclic amine is a N-linked:

i. azetidine substituted with $R_{4a}$ and $R_{4b}$;

ii. pyrrolidine, piperidine, piperazine, morpholine, imidazole or pyrazole; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, piperazine, morpholine, a $C_{1-3}$ alkyl, or an imidazole optionally substituted with a methyl; wherein the azetidine is optionally substituted with hydroxyl or $C_{1-3}$ alkoxy; the piperazine is optionally substituted with a methyl, and the $C_{1-3}$ alkyl is optionally substituted with one or more halogen, —$NR_{6a}R_{6a}$ or hydroxyl; or iii. 2,6-diazabicyclo[3.2.0]heptane, 3,6-diazabicyclo[3.2.0]heptane, 3,6-diazabicyclo[3.2.1]octane, 2,6-diazabicyclo[3.2.1]octane, 3-azabicyclo[3.1.0]hexane, 3-azabicyclo[3.2.0]heptane, 2-azabicyclo[3.2.0]heptane, octahydro-1H-pyrrolo[3,4-b]pyridine, octahydro-1H-pyrrolo[3,2-b]pyridine, octahydro-6H-pyrrolo[3,4-b]pyrazine, octahydropyrrolo[1,2-a]pyrazine, octahydropyrrolo[3,2-b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, 5-azaspiro[2.4]heptane, or 2-oxa-6-azaspiro[3.4]octane; each of which is optionally substituted with one or more halogen, —$NR_{6a}R_{6a}$ or a $C_{1-3}$ alkyl optionally substituted with —$NR_{6a}R_{6a}$;

$R_{4a}$ is $NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or —$NR_{6a}R_{6a}$;

each $R_{6a}$ is independently H, trideuteromethyl, a $C_{3-5}$ cycloalkyl, tetrahydrofuran, tetrahydropyran, bicyclo[1.1.1]pentan-1-yl, or a $C_{1-3}$ alkyl optionally substituted with one or more hydroxyl, methyl, methoxy, halogen, cyclopropyl, oxetane, tetrahydrofuran, tetrahydropyran, —CO—NHMe, or —CO—$NH_2$, wherein the $C_{3-5}$ cycloalkyl is optionally substituted with one or more hydroxyl or methyl; or a pharmaceutically acceptable salt thereof.

3. The compound according to embodiment 1 or 2, wherein $R_4$ is a N-linked cyclic amine or a group of the formula

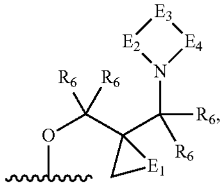
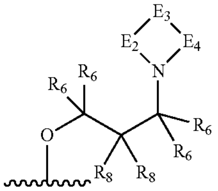
, or

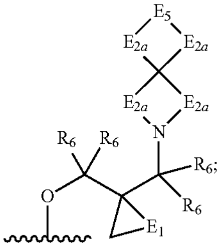

wherein the N-linked cyclic amine is a N-linked:

i. azetidine substituted with $R_{4a}$ and $R_{4b}$;

ii. pyrrolidine, piperidine, piperazine, morpholine, imidazole or pyrazole; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, a $C_{1-3}$ alkyl, or an imidazole optionally substituted with a methyl; wherein the azetidine is optionally substituted with hydroxyl or $C_{1-3}$ alkoxy; and the $C_{1-3}$ alkyl is optionally substituted with halogen-$NR_{6a}R_{6a}$ or hydroxyl; or iii. 2,6-diazabicyclo[3.2.0]heptane, 3,6-diazabicyclo[3.2.0]heptane, 3-azabicyclo[3.1.0]hexane, 3-azabicyclo[3.2.0]heptane, octahydro-1H-pyrrolo[3,4-b]pyridine, octahydro-6-pyrrolo[3,4-b]pyrazine, octahydropyrrolo[1,2-a]pyrazine, octahydropyrrolo[3,2 -b]pyrrole, octahydropyrrolo[3,4-b][1,4]oxazine, octahydropyrrolo[3,4-b]pyrrole, octahydropyrrolo[3,4-c]pyrrole, tetrahydrofuro[3,4-d]oxazol-2(3H)-one, (R)-1,7-diazaspiro[4.4]nonane, (S)-1,7-diazaspiro[4.4]nonane, 1,6-diazaspiro[3.3]heptane, 1,6-diazaspiro[3.4]octane, 2,5-diazaspiro[3.4]octane, 2,5-diazaspiro[3.5]nonane, 2,6-diazaspiro[3.3]heptane, 2,6-diazaspiro[3.4]octane, 2-azaspiro[3.3]heptane, 4-azaspiro[2.4]heptane, or 5-azaspiro[2.4]heptane; each of which is optionally substituted with one or more halogen, —$NR_{6a}R_{6a}$ or a $C_{1-3}$ alkyl optionally substituted with —$NR_{6a}R_{6a}$;

$R_{4a}$ is $NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or —$NR_{6a}R_{6a}$; and each $R_{6a}$ is independently H, trideuteromethyl, a $C_{3-5}$ cycloalkyl or a $C_{1-3}$ alkyl optionally substituted with hydroxyl; or a pharmaceutically acceptable salt thereof.

4. The compound according to any one of embodiments 1-3, wherein $R_{3b}$, and $R_{3c}$ are each independently H or halogen, and $R_4$ is a N-linked cyclic amine or a group of the formula

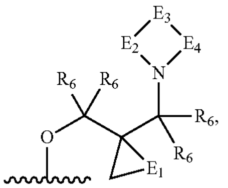
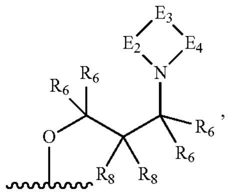
or
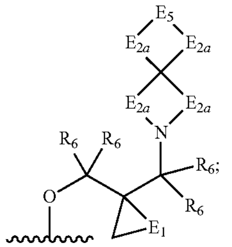

wherein the N-linked cyclic amine is a N-linked:

i. azetidine substituted with $R_{4a}$ and $R_{4b}$;

ii. pyrrolidine, piperidine, piperazine, or morpholine; each of which is optionally bridged by a $C_{1-3}$ alkylene, and each of which is optionally substituted with one or more halogen, hydroxyl, —$NR_{6a}R_{6a}$, imidazole or a $C_{1-3}$ alkyl; wherein the imidazole is optionally substituted with a methyl; and the $C_{1-3}$ alkyl is optionally substituted with —$NR_{6a}R_{6a}$ or hydroxyl; or iii. octahydropyrrolo[1,2-a]pyrazine, octahydropyrrolo[3,4-c]pyrrole, 1,6-diazaspiro[3.3]heptane, or 1,6-diazaspiro[3.4]octane; each of which is optionally substituted with one or more halogen, or a $C_{1-3}$ alkyl;

$R_{4a}$ is $NR_{4c}R_{4d}$, cyclopropyl, azetidine, pyrrolidine, morpholine, wherein the cyclopropyl, azetidine, pyrrolidine or morpholine is optionally substituted with halogen, or —$NR_{6a}R_{6a}$;

$R_{4b}$ is H, or $C_{1-3}$ alkyl;

each $R_{6a}$ is independently H or $C_{1-3}$ alkyl;

$E_2$, and $E_4$ are each independently $C_{1-3}$ alkylene optionally substituted with one or more hydroxyl or halogen, and wherein $E_2$ and $E_4$ can optionally be bridged by a bond or a $C_{1-3}$ alkylene; and $E_3$ is —O—, —$CR_7R_7$—, —$NR_9$—, or —CO—$NR_{6a}$—; or a pharmaceutically acceptable salt thereof.

5. The compound according to any one of embodiments 1-4, wherein $R_{3b}$, and $R_{3c}$ are each independently H or halogen, and $R_4$ is a group of the formula

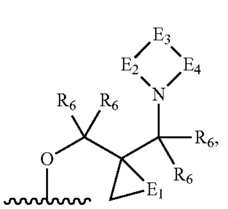
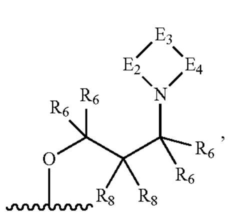
or
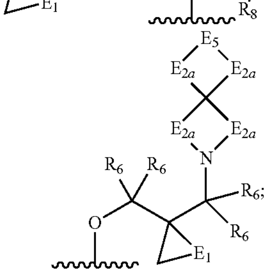

$E_1$ is $C_{1-3}$ alkylene optionally substituted with one or more halogens;

$E_2$, and $E_4$ are each independently $C_{1-3}$ alkylene optionally substituted with one or more hydroxyls, and wherein $E_2$ and $E_4$ can optionally be bridged by a bond or a $C_{1-3}$ alkylene;

$E_3$ is —O—, —$CR_7R_7$—, —$NR_9$—, or —CO—$NR_{6a}$—;

each $R_{6a}$ is independently H or $C_{1-3}$ alkyl;

each $R_7$ is independently H, halogen, hydroxyl, $C_{1-3}$ alkoxy, or $C_{1-3}$ alkyl optionally substituted with one or more halogens or hydroxyls; and $R_9$ is each independently H, $C_{1-3}$ alkyl or —CO—$C_{1-3}$ alkyl; or a pharmaceutically acceptable salt thereof.

6. The compound according to any one of embodiments 1-5, wherein G is —N—, or a pharmaceutically acceptable salt thereof.

7. The compound according to any one of embodiments 1-5, wherein G is —$C(R_{3b})$—, or a pharmaceutically acceptable salt thereof.

8. The compound according to embodiment 7, wherein $R_{3b}$ is F, or a pharmaceutically acceptable salt thereof.

9. The compound according to any one of embodiments 1-8, wherein Z is —N—, or a pharmaceutically acceptable salt thereof.

10. The compound according to any one of embodiments 1-8, wherein Z is —$C(R_{3c})$—, or a pharmaceutically acceptable salt thereof.

11. The compound according to embodiment 10, wherein $R_{3c}$ is H or F, or a pharmaceutically acceptable salt thereof.

12. The compound according to any one of embodiments 1-5, 7 or 10, wherein $R_{3b}$, and $R_{3c}$ are each independently H or halogen, or a pharmaceutically acceptable salt thereof.

13. The compound according to any one of embodiments 1-12, wherein A is —N—, or a pharmaceutically acceptable salt thereof.

14. The compound according to any one of embodiments 1-12, wherein A is —C(H)—, or a pharmaceutically acceptable salt thereof.

15. The compound according to any one of embodiments 1-14, wherein $R_2$ is F or Cl, or a pharmaceutically acceptable salt thereof.

16. The compound according to any one of embodiments 1-14, wherein $R_2$ is F, or a pharmaceutically acceptable salt thereof.

17. The compound according to any one of embodiments 1-14, wherein $R_2$ is Cl, or a pharmaceutically acceptable salt thereof.

18. The compound according to any one of embodiments 1-17, wherein $R_1$ is H, or a pharmaceutically acceptable salt thereof.

19. The compound according to any one of embodiments 1-17, wherein $R_1$ is a group of the formula

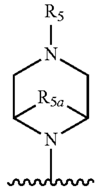
,
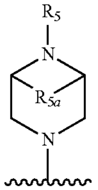
, or
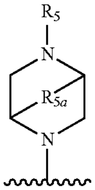
, or a pharmaceutically acceptable salt thereof.

20. The compound according to any one of embodiments 1-17, wherein $R_1$ is a group of the formula

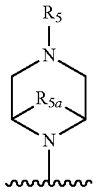, or a pharmaceutically acceptable salt thereof.

21. The compound according to embodiment 19 or 20, wherein $R_5$ is a $C_{1-4}$ alkyl optionally substituted with one or more hydroxyl, methoxy or oxetane, or a pharmaceutically acceptable salt thereof.

22. The compound according to any one of embodiments 19-21, wherein $R_{5a}$ is ethylene, or a pharmaceutically acceptable salt thereof.

23. The compound according to any one of embodiments 1-17, wherein $R_1$ is selected from

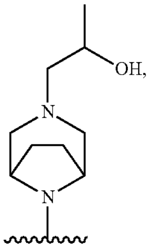 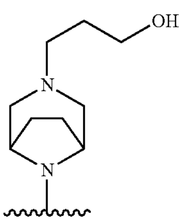, 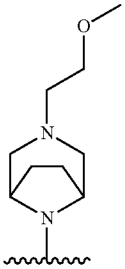,

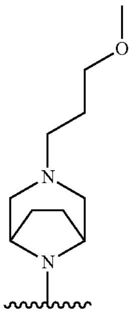, 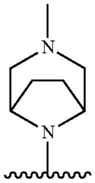, 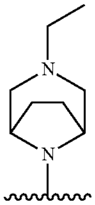, or

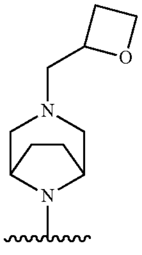, or a pharmaceutically acceptable salt thereof.

24. The compound according to any one of embodiments 1-17, wherein $R_1$ is selected from

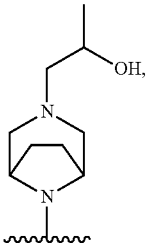 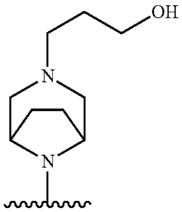, or 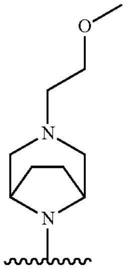, or a pharmaceutically acceptable salt thereof.

25. The compound according to any one of embodiments 1-24, wherein $R_4$ is

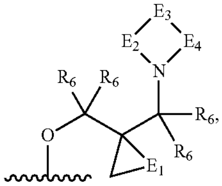

or a pharmaceutically acceptable salt thereof.

26. The compound according to any one of embodiments 1-24, wherein $R_4$ is

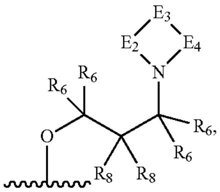

or a pharmaceutically acceptable salt thereof.

27. The compound according to any one of embodiments 1-24, wherein $R_4$ is

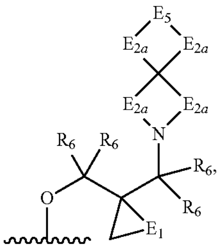

or a pharmaceutically acceptable salt thereof.

28. The compound according to any one of embodiments 1-27, wherein each $R_6$ is H, or a pharmaceutically acceptable salt thereof.

29. The compound according to any one of embodiments 1-4 and 6-24, wherein $R_4$ is a N-linked cyclic amine, or a pharmaceutically acceptable salt thereof.

30. The compound according to any one of embodiments 1 and 6-24, wherein $R_4$ is selected from -continued
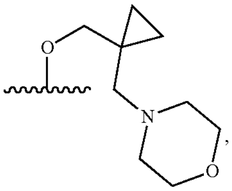,
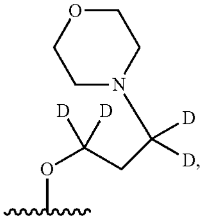,
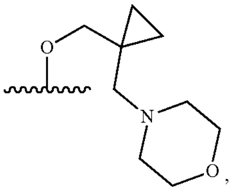,
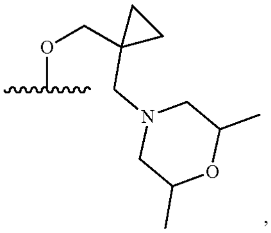,
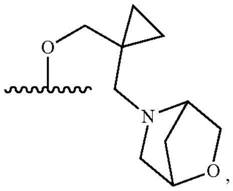,
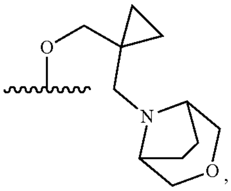,
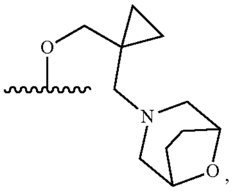,
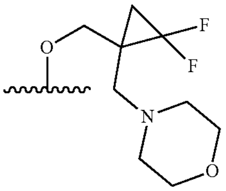,
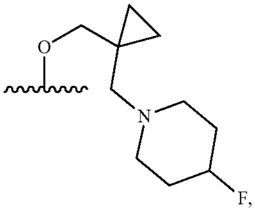,
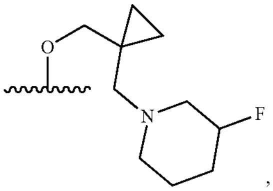,
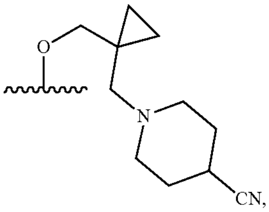,
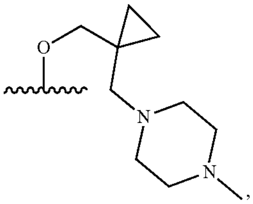,
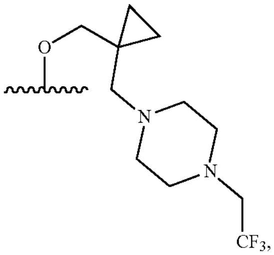,
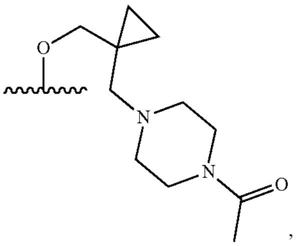,
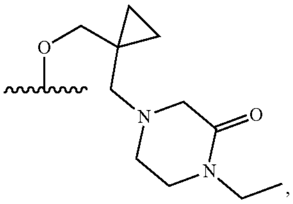,
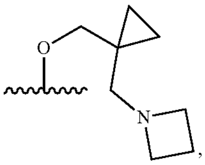,
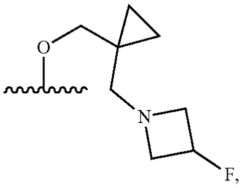,
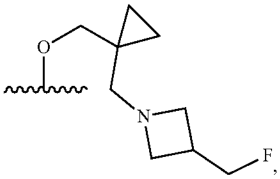,
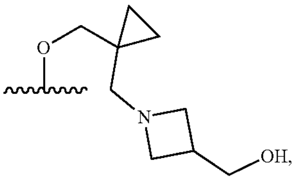,
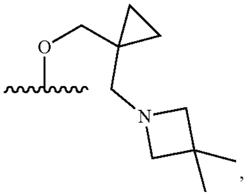,
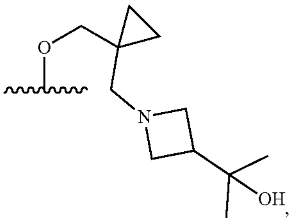,
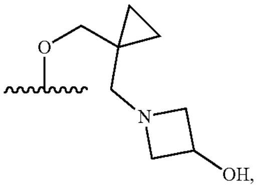,
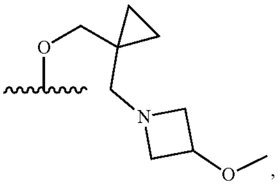,
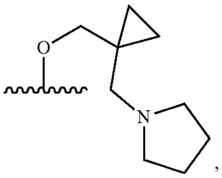,
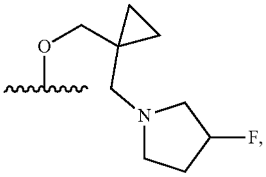,
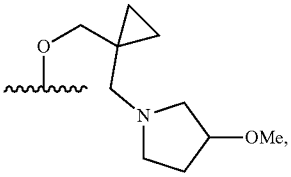,
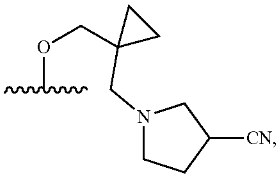,
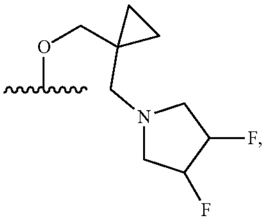,
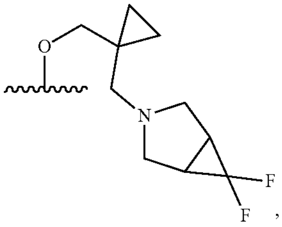,
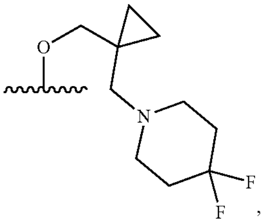,
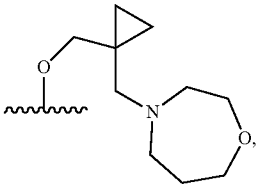,
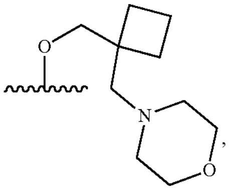, -continued
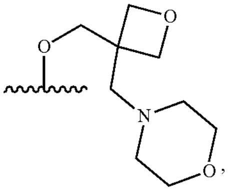
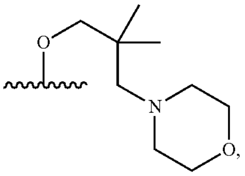
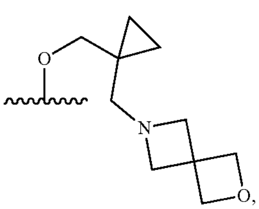
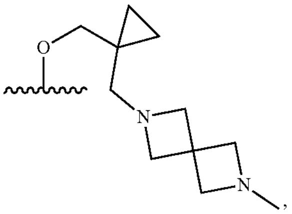
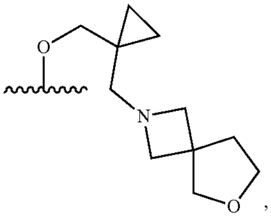
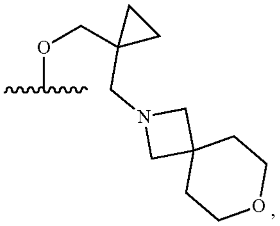
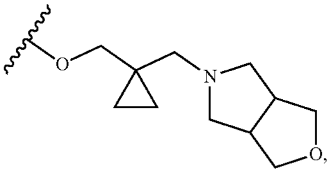
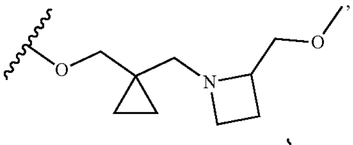
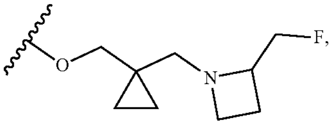
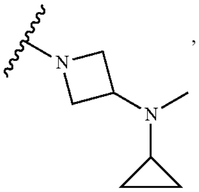
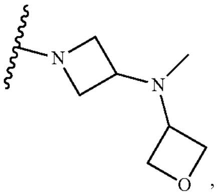
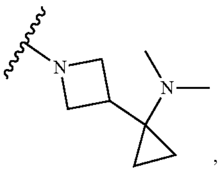
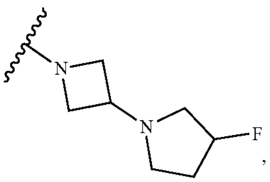
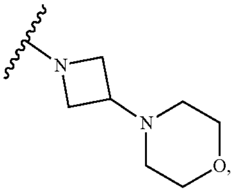
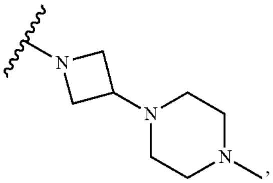
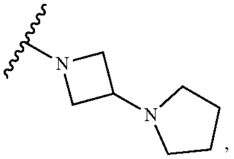
-continued
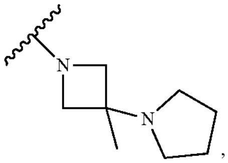
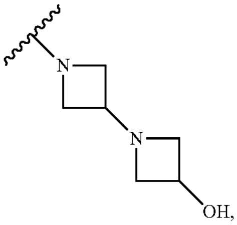
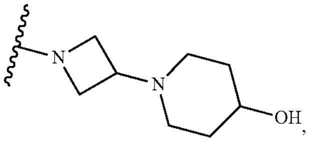
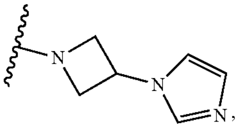
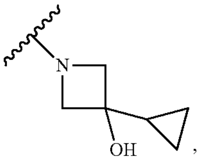
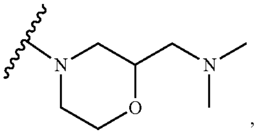
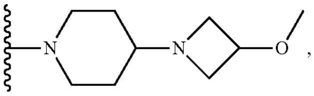
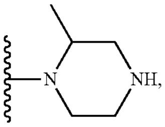
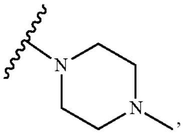
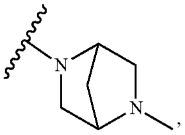
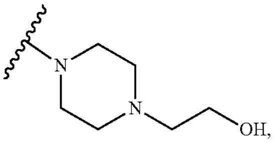
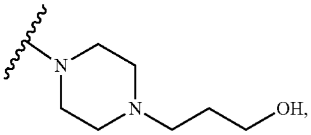
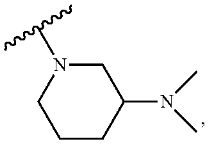
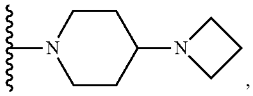
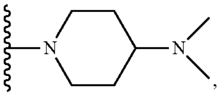
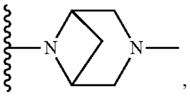
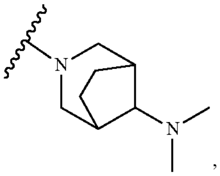
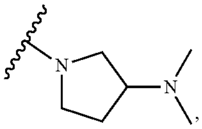
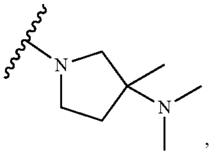
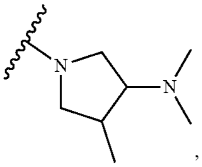
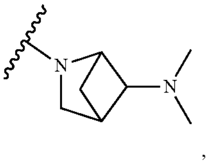

-continued
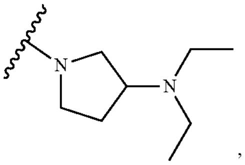, 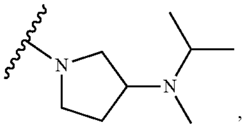,
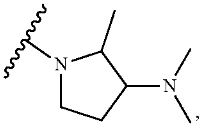, 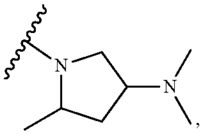,
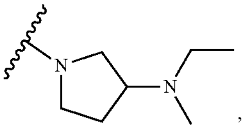, 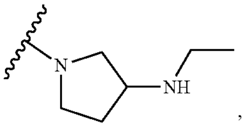,
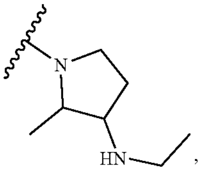, 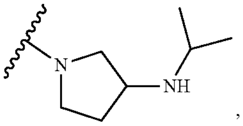,
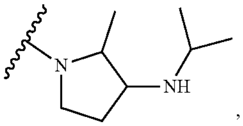, 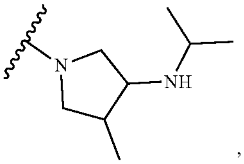,
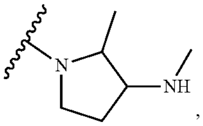, 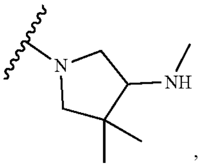,
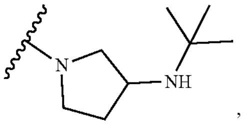, 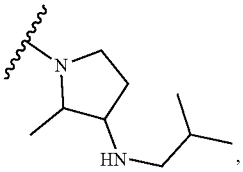,
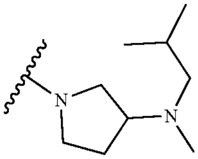, 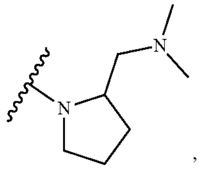,
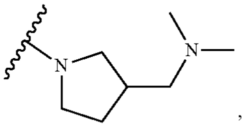, 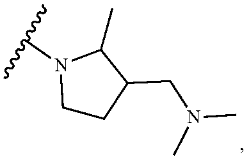,
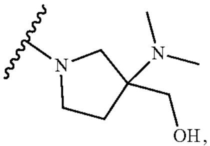, 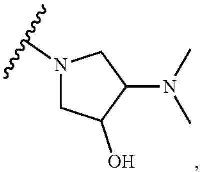,
-continued
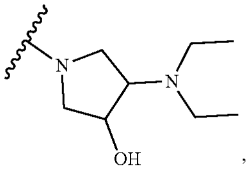, 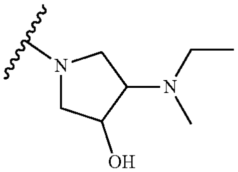,
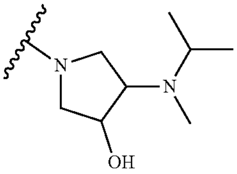, 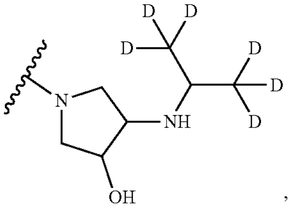,
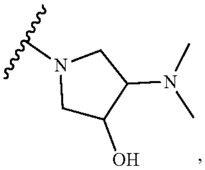, 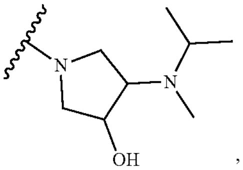,
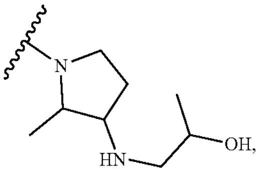 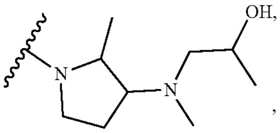,
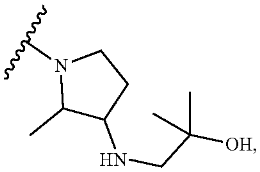 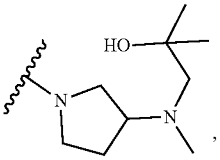,
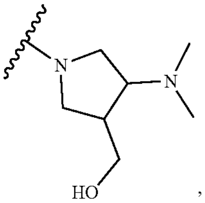, 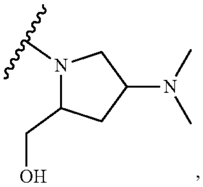,
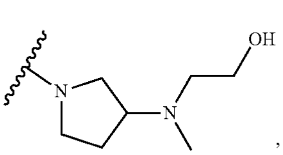, 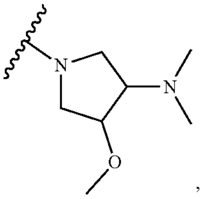,
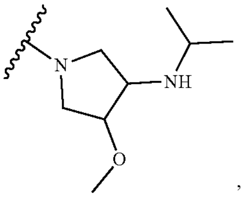, 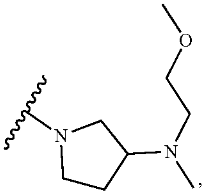
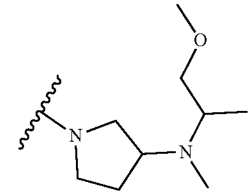, 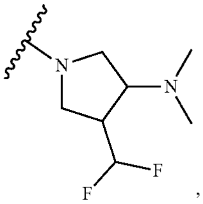, -continued
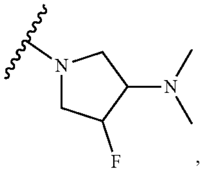 , 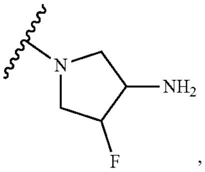 ,
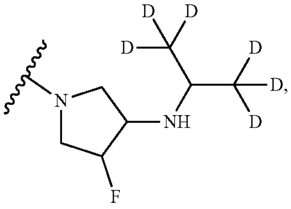
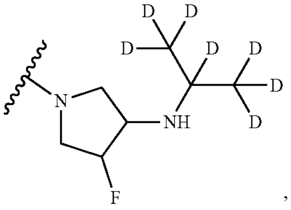 , 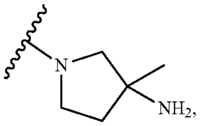
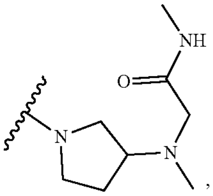 , 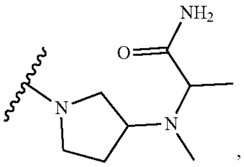 ,
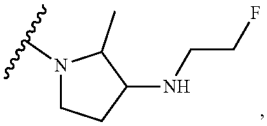 , 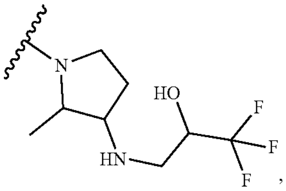 ,
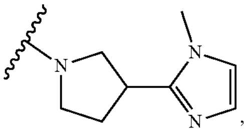 , 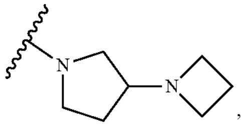 ,
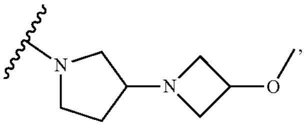
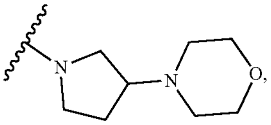
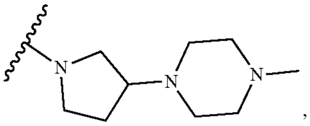 , 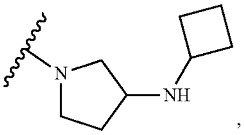 ,
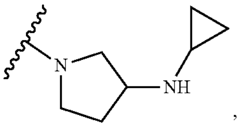 , 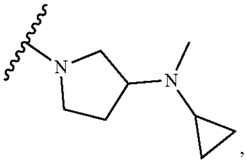 ,
-continued
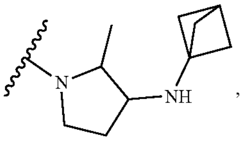 , 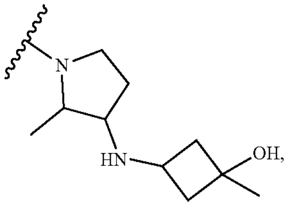
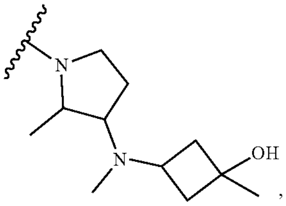 , 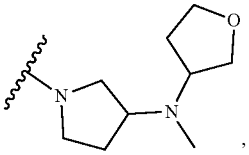 ,
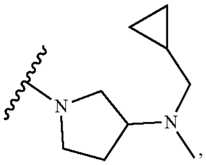 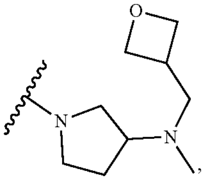
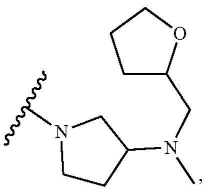 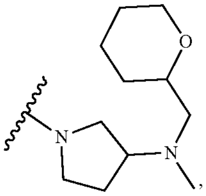
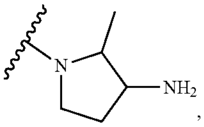 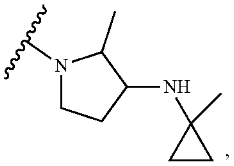
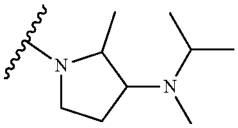 , 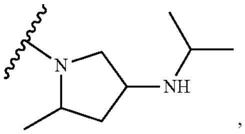 ,
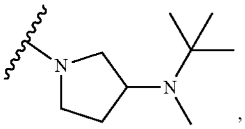 , 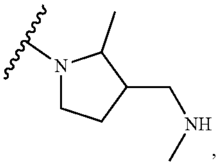
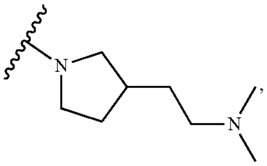
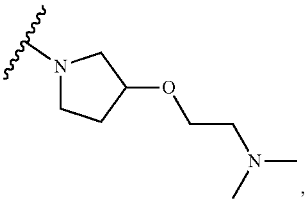 , 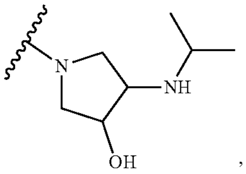 , -continued
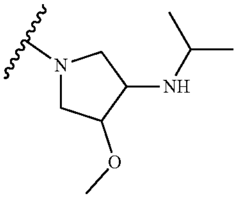
,
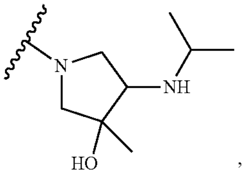
,
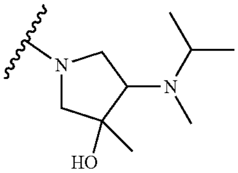
,
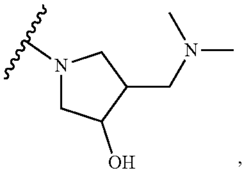
,
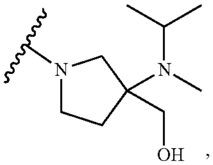
,
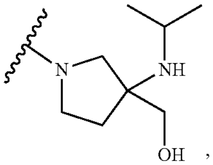
,
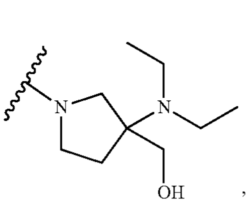
,
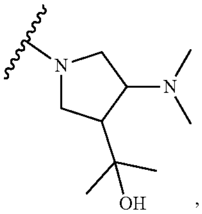
,
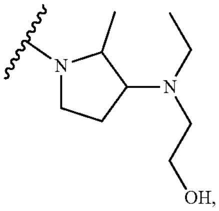
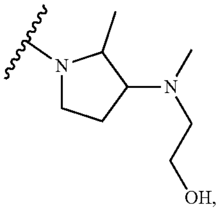
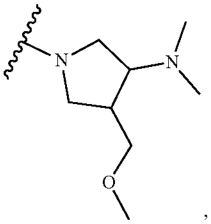
,
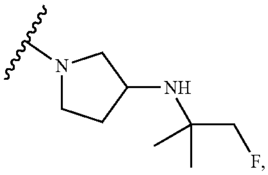
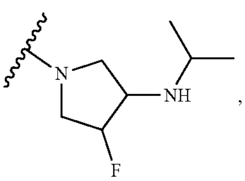
,
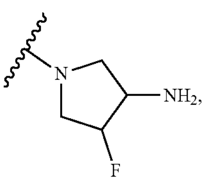
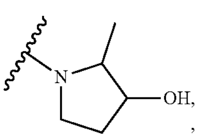
,
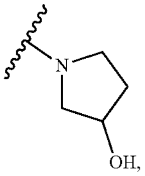
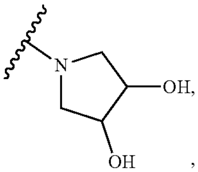
,
-continued
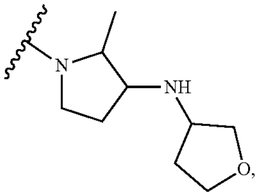
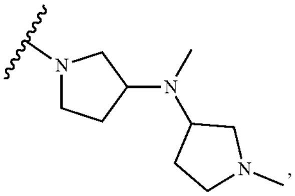
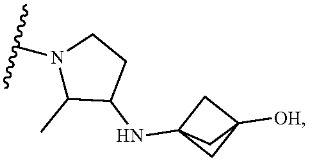
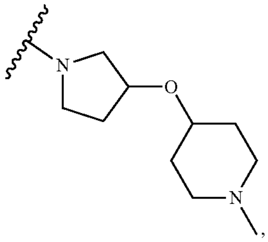
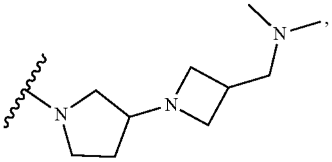
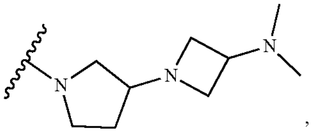
,
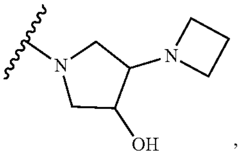
,
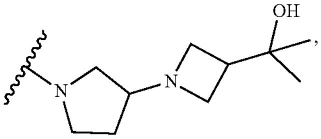
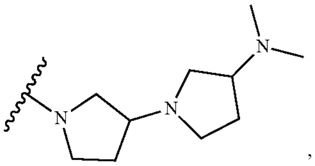
,
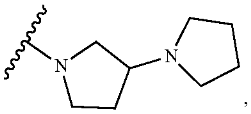
,
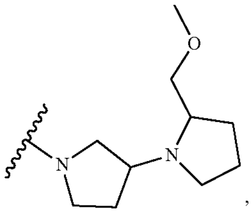
,
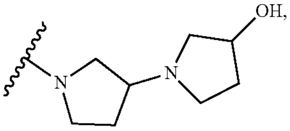
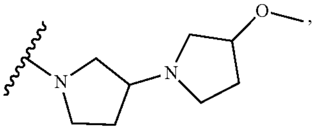
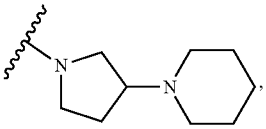
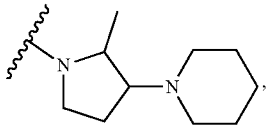

-continued
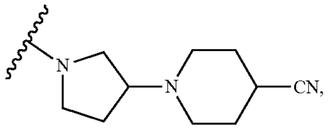
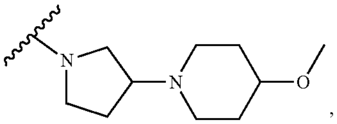
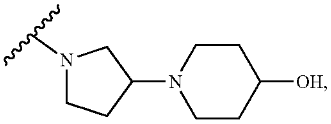
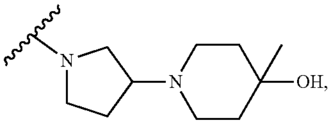
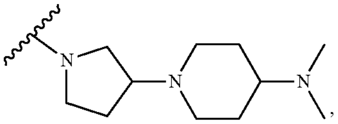
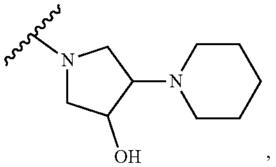
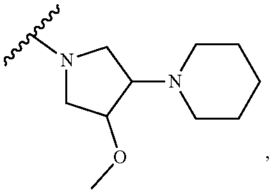
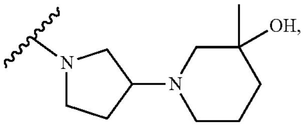
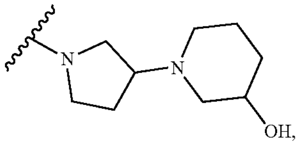
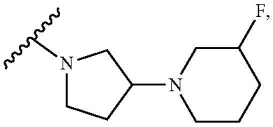
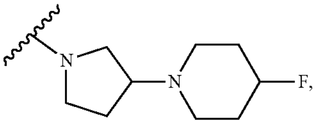
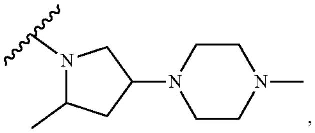
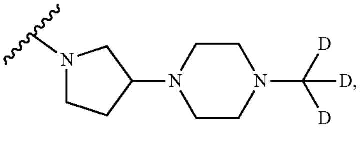
-continued
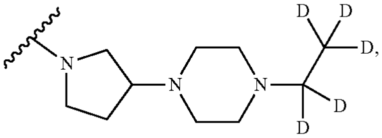
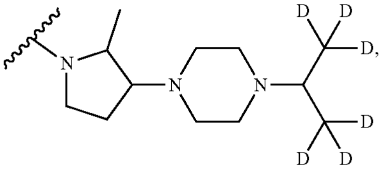
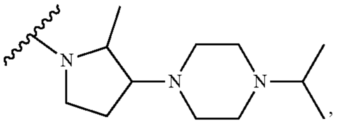
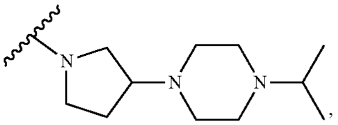
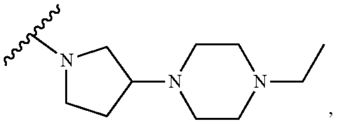
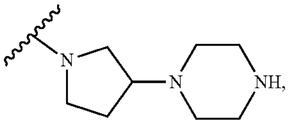
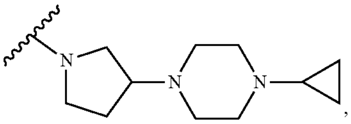
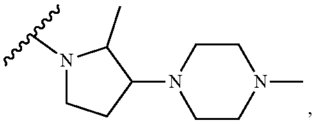
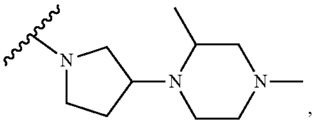
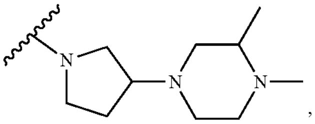
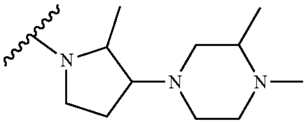
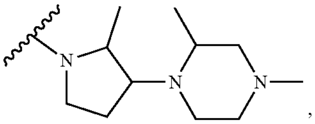
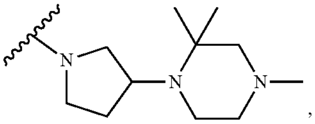

-continued
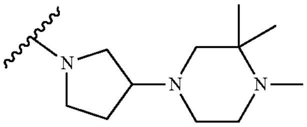
,
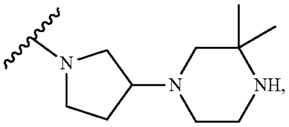
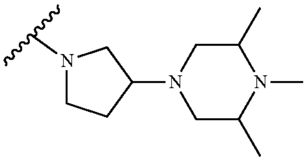
,
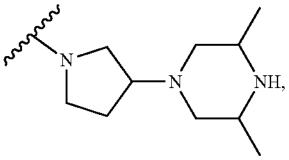
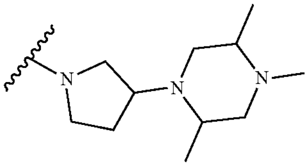
,
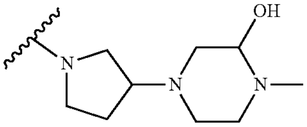
,
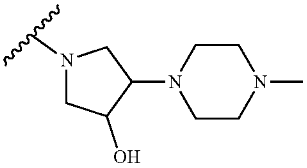
,
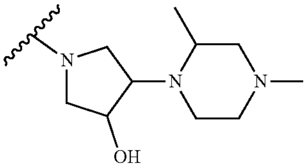
,
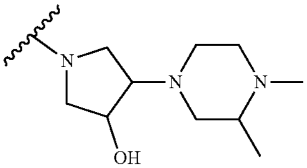
,
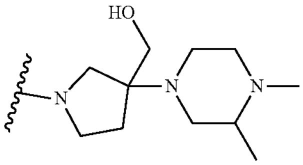
,
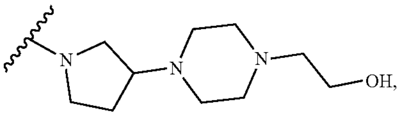
-continued
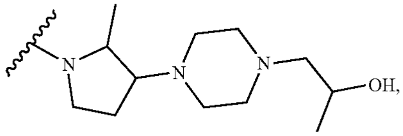
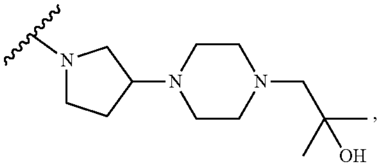
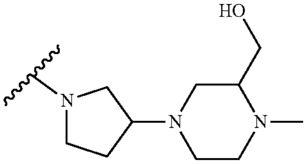
,
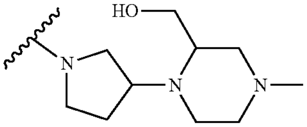
,
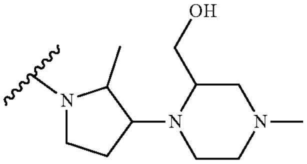
,
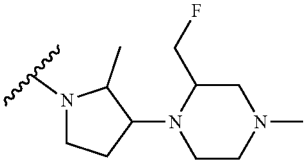
,
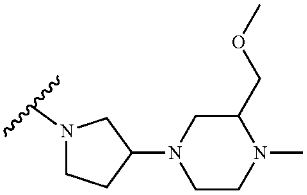
,
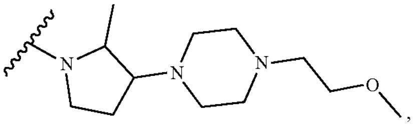
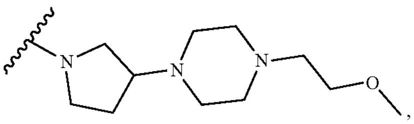
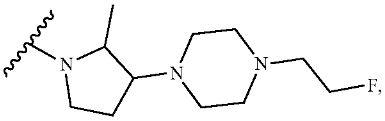
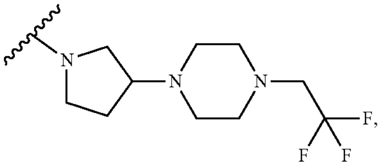

-continued
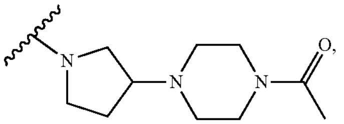
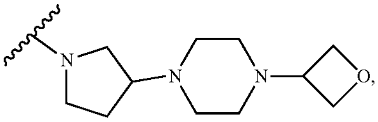
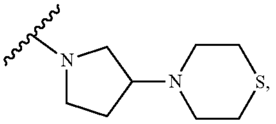
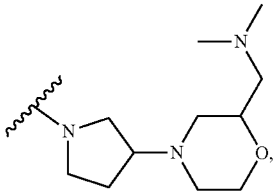
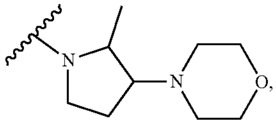
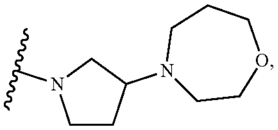
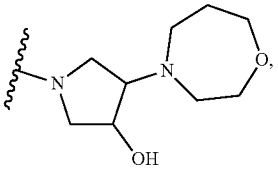
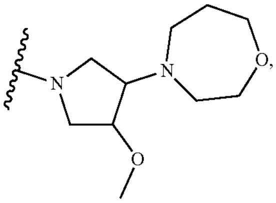
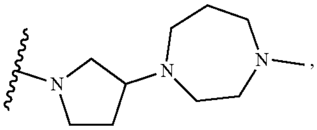
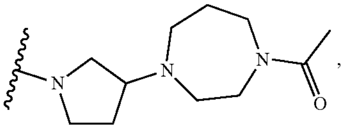
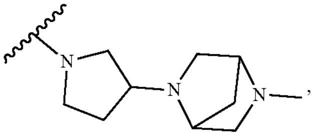
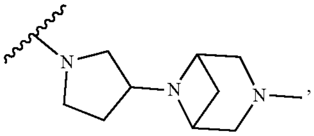
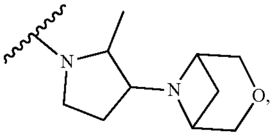
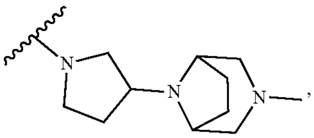
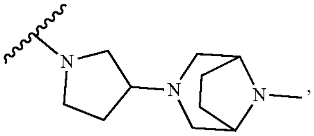
-continued
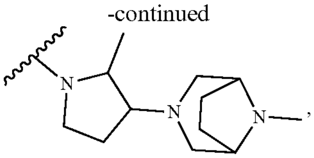
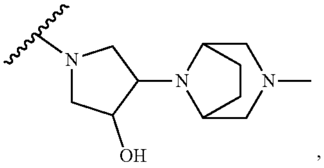
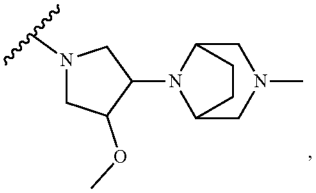
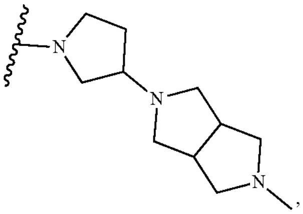
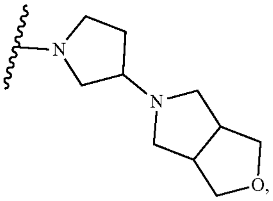
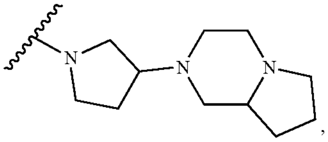
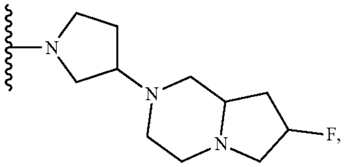
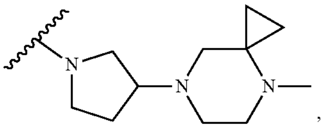
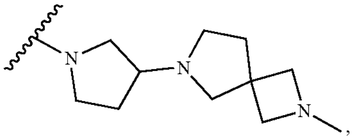
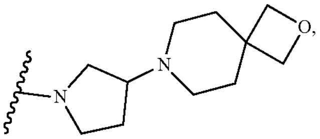
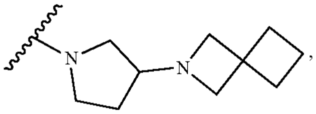

-continued
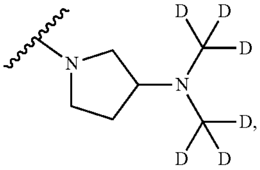
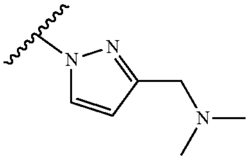,
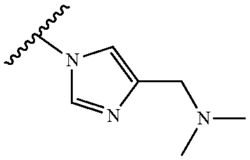,
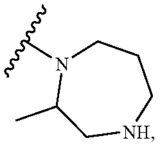
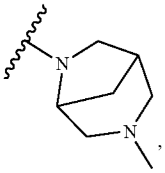,
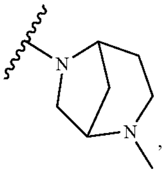,
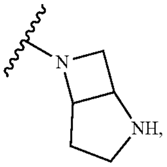
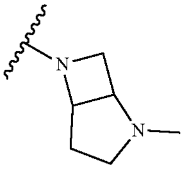,
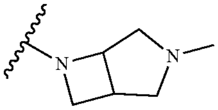,
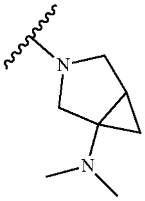,
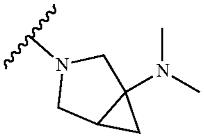,
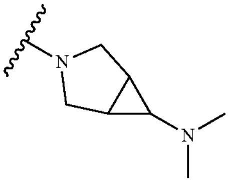,
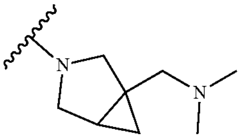,
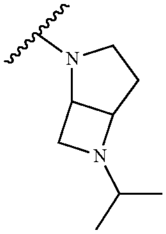,
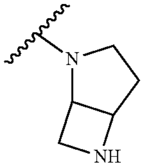,
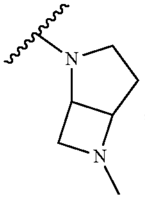,
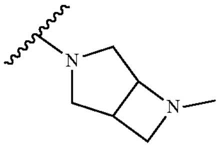,
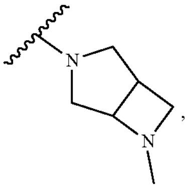,
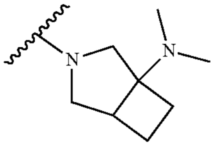,
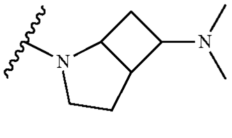,
-continued
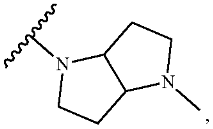,
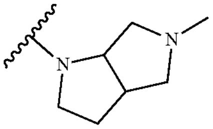,
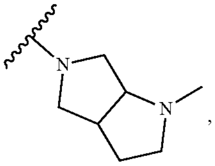,
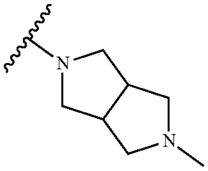,
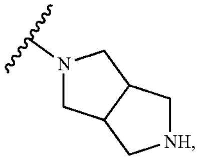
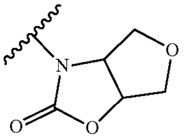,
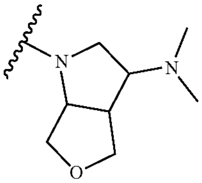,
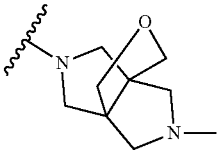
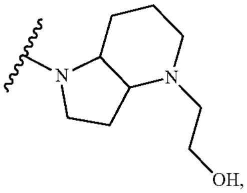
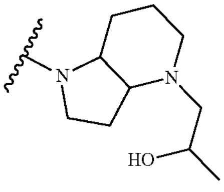,
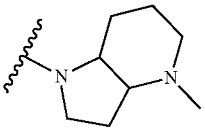,
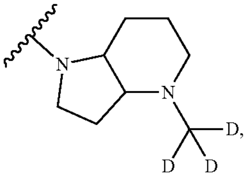
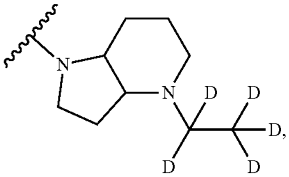
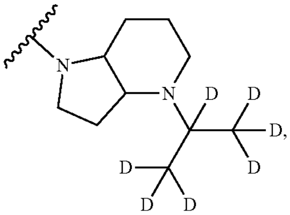
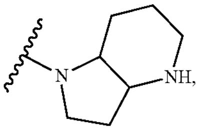
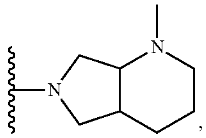,
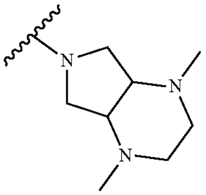,

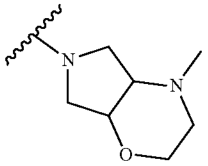,
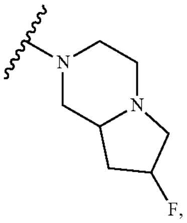
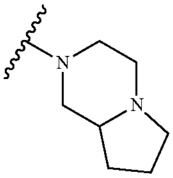,
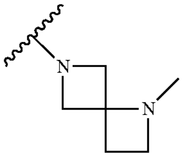,
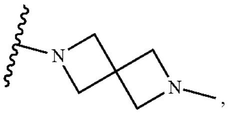,
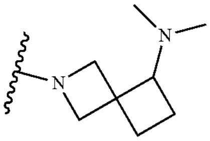,
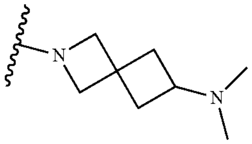,
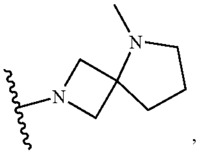,
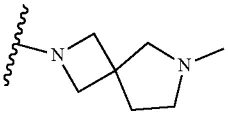,
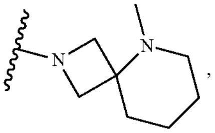,
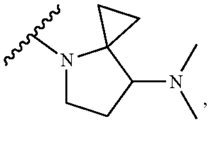,
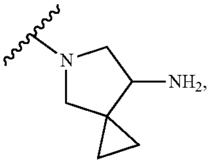
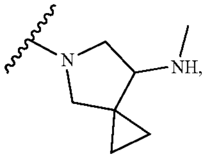
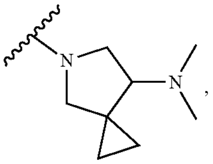,
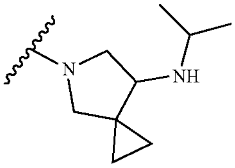,
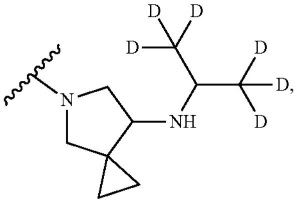
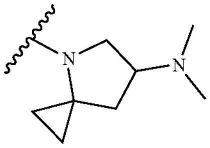,
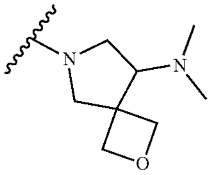,
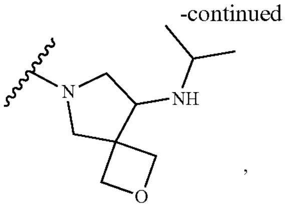,
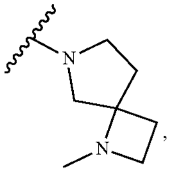,
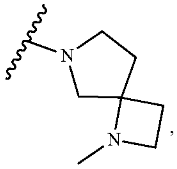,
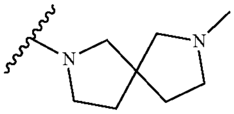,
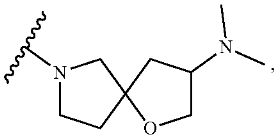,
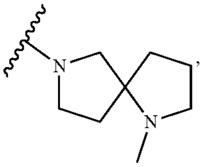,
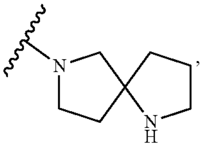,
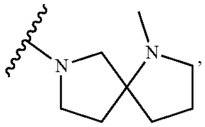, or
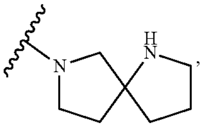,
or a pharmaceutically acceptable salt thereof.
31. The compound according to any one of embodiments 1 and 6-24, wherein $R_4$ is selected from
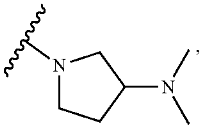,
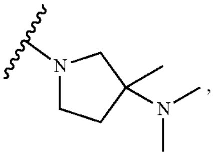,
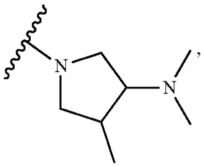,
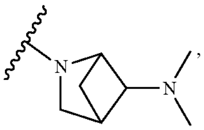,
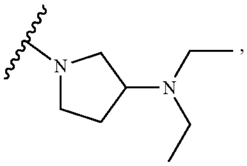, -continued
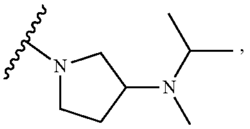
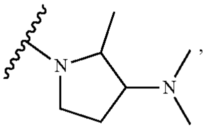
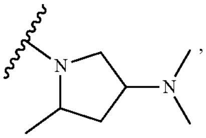
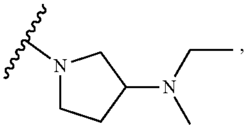
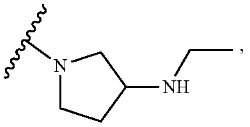
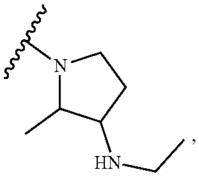
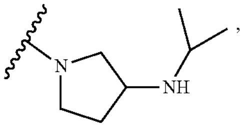
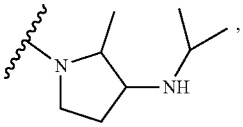
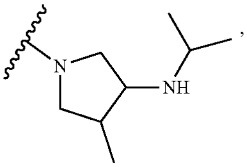
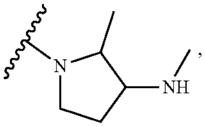
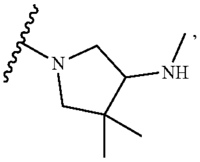
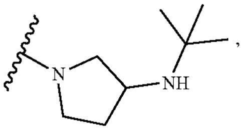
-continued
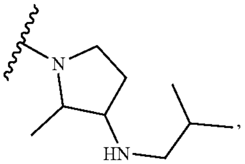
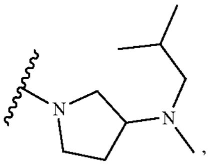
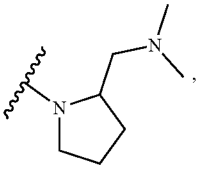
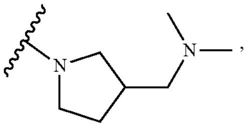
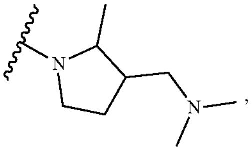
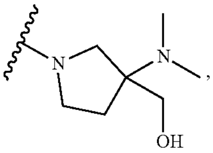
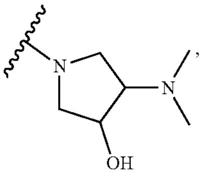
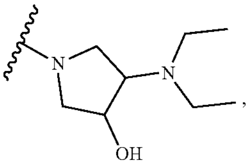
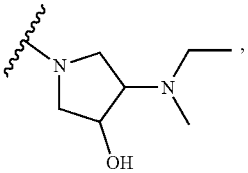
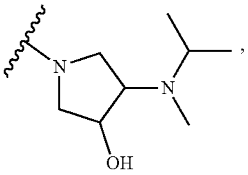

-continued
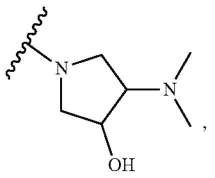
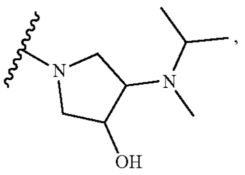
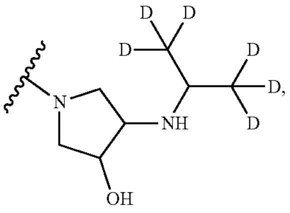
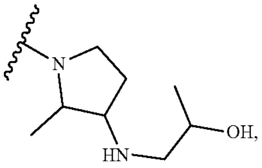
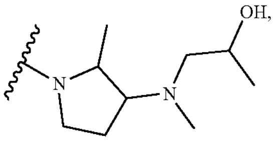
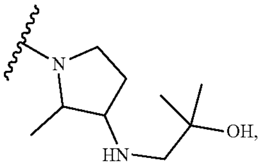
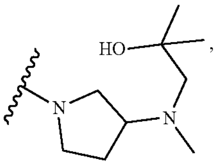
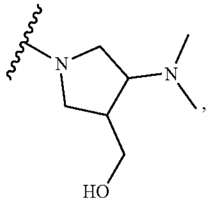
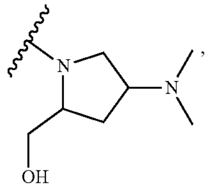
-continued
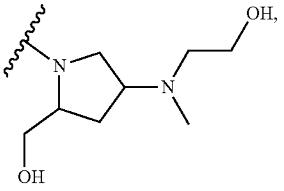
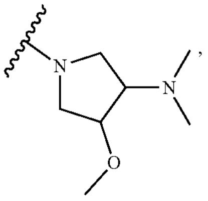
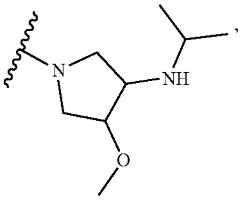
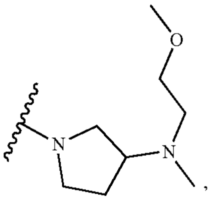
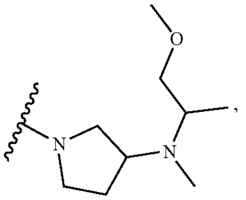
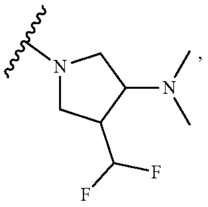
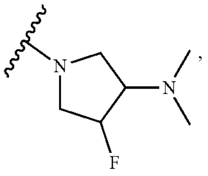
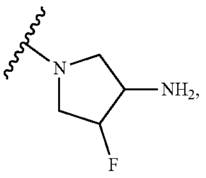

-continued
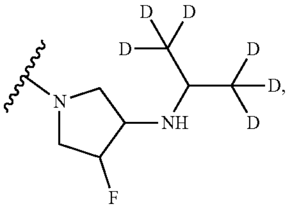
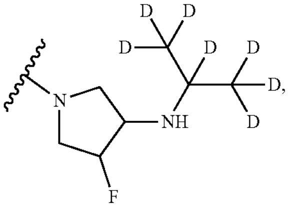
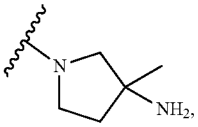
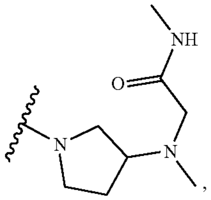
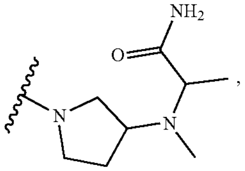
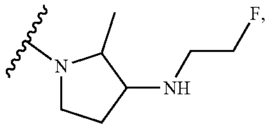
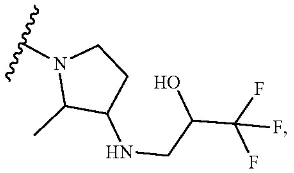
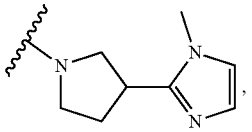
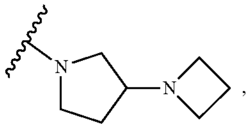
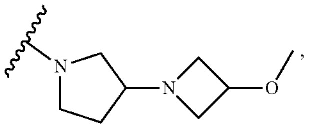
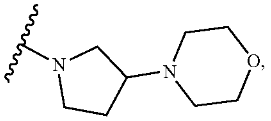
-continued
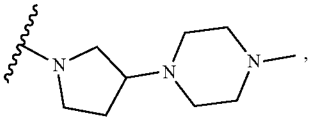
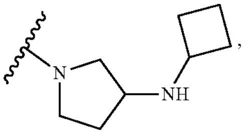
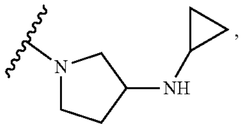
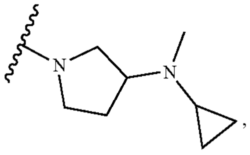
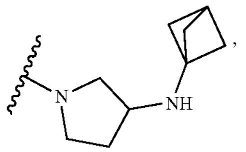
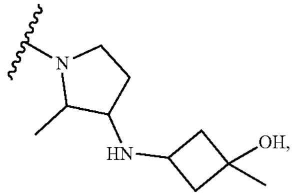
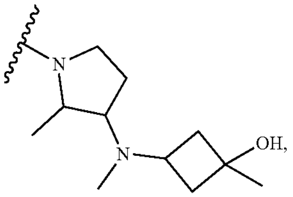
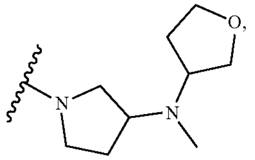
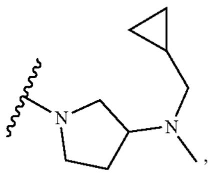
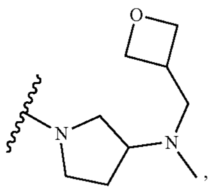

-continued
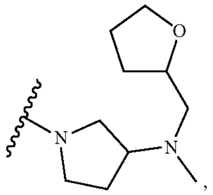
,
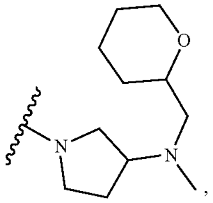
,
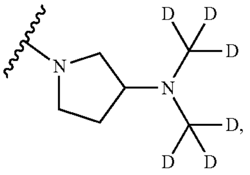
,
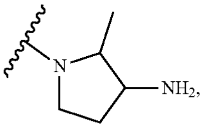
,
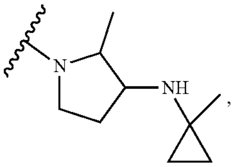
,
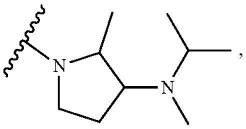
,
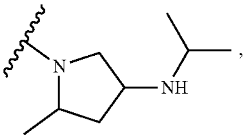
,
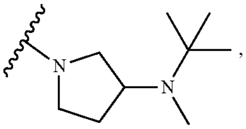
,
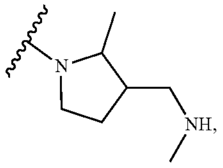
,
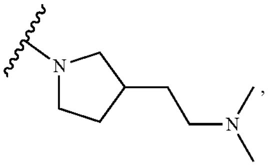
,
-continued
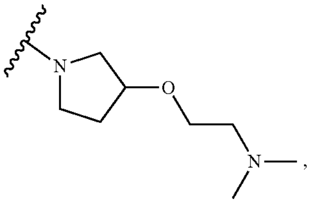
,
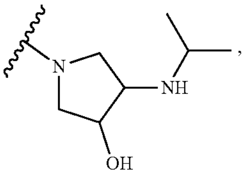
,
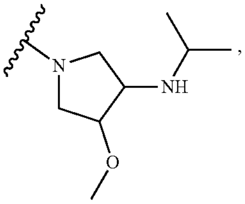
,
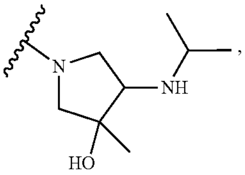
,
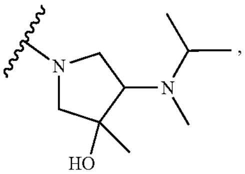
,
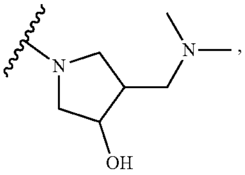
,
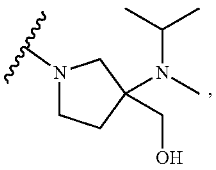
,
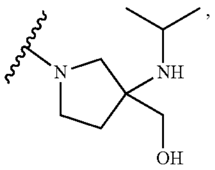
,
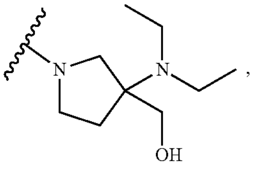
, -continued
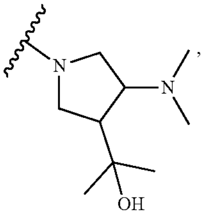
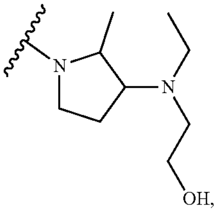
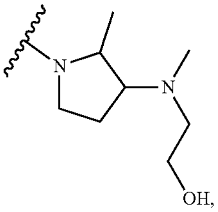
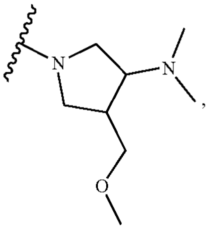
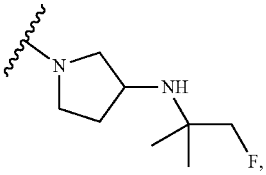
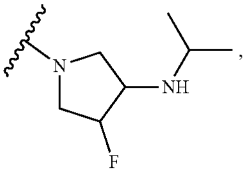
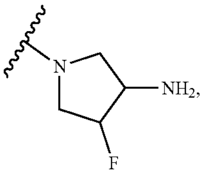
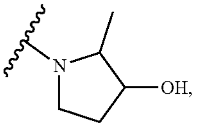
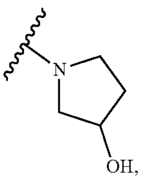
-continued
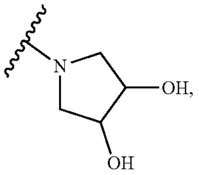
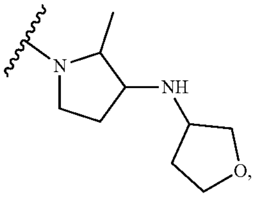
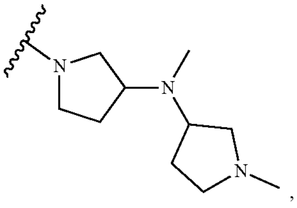
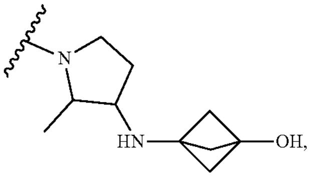
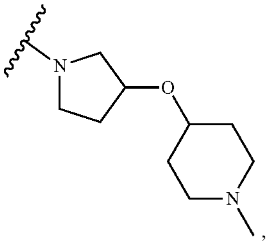
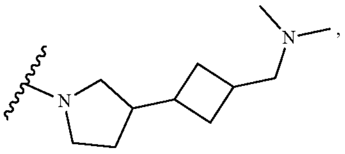
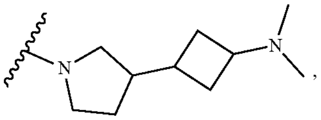
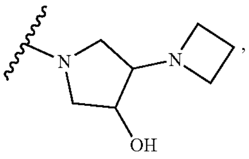
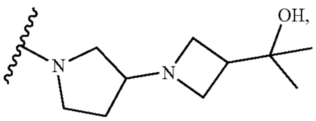
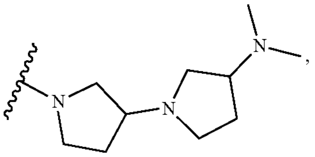

-continued
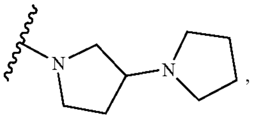
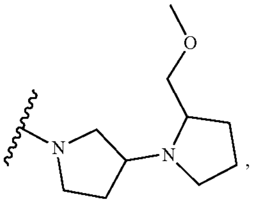
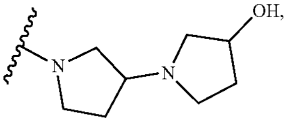
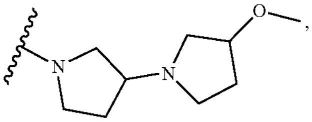
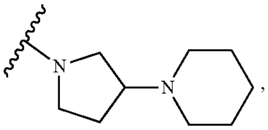
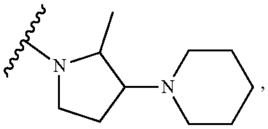
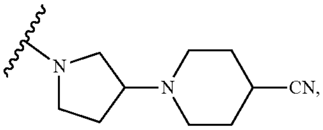
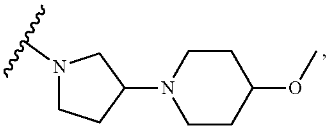
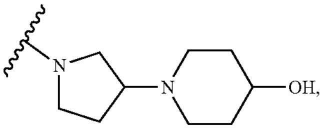
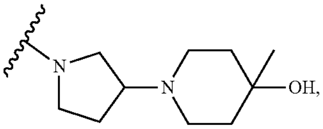
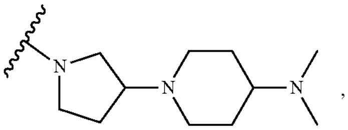
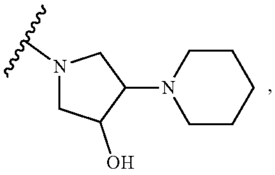
-continued
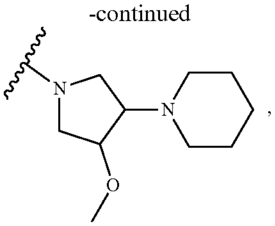
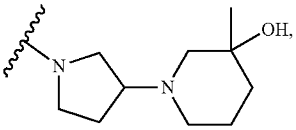
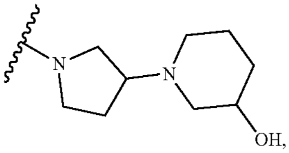
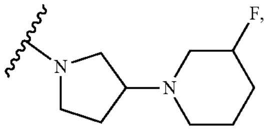
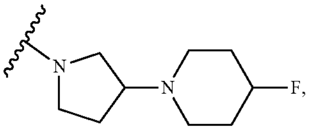
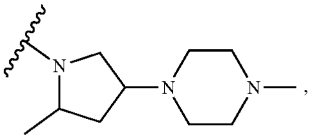
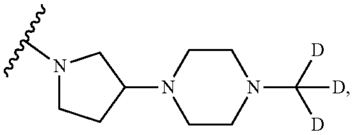
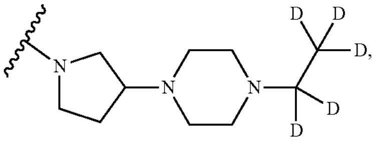
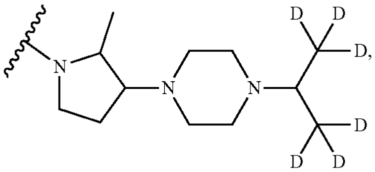
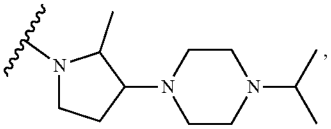
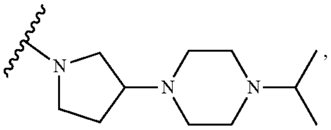
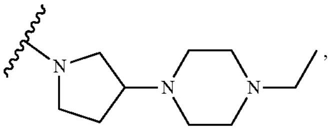

-continued
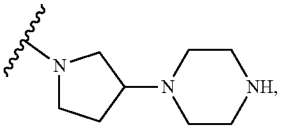
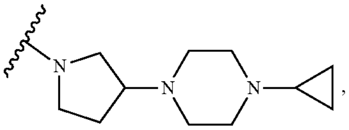
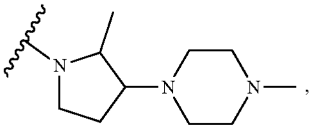
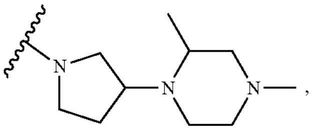
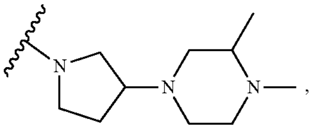
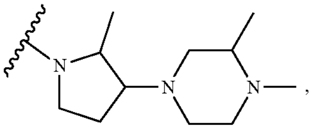
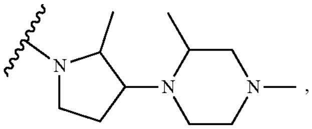
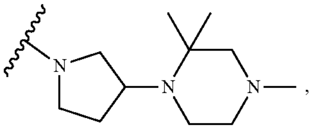
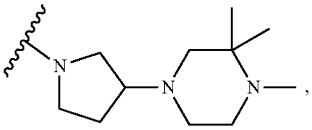
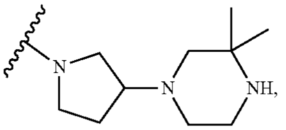
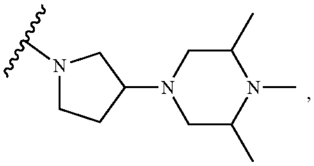
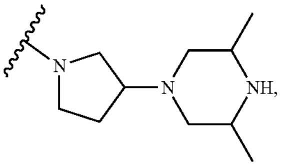
-continued
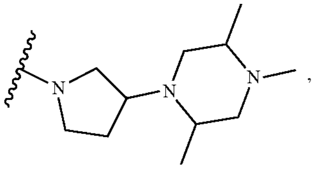
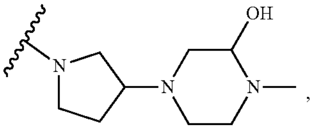
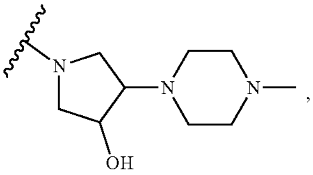
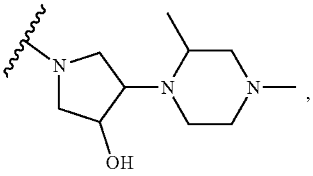
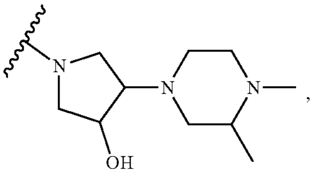
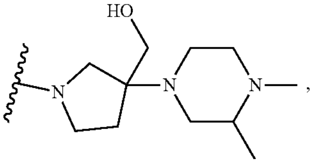
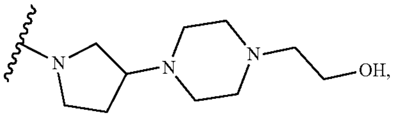
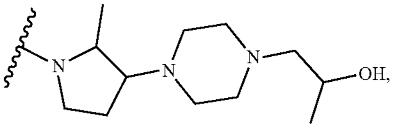
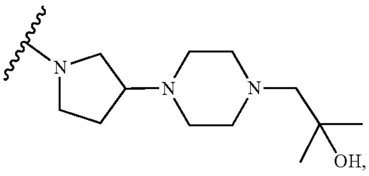
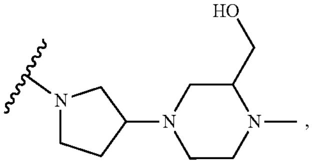
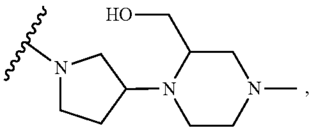

-continued
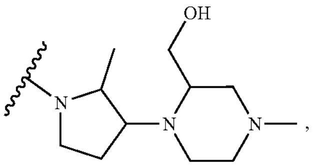
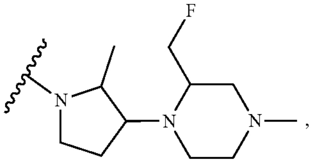
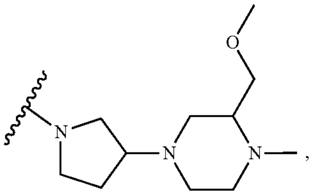
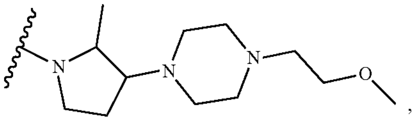
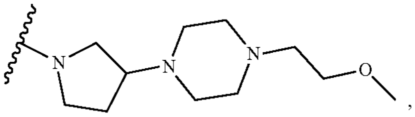
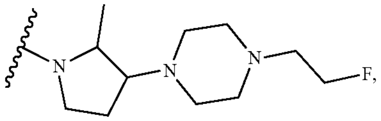
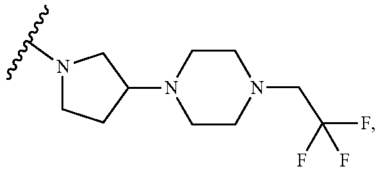
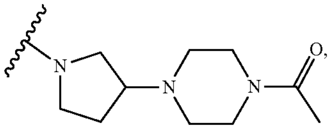
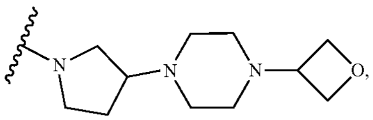
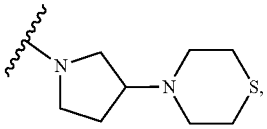
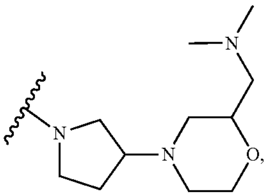
-continued
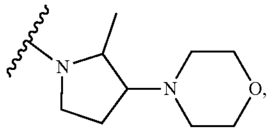
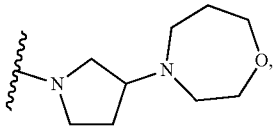
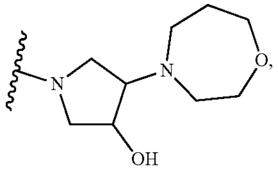
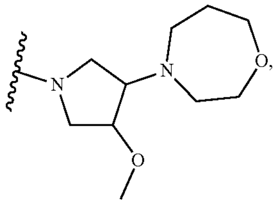
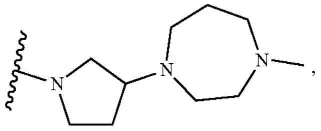
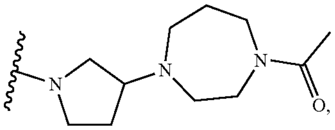
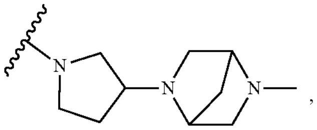
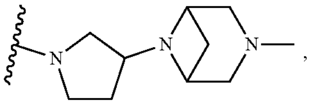
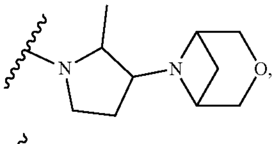
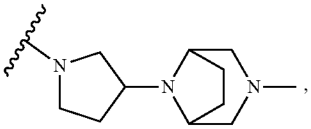
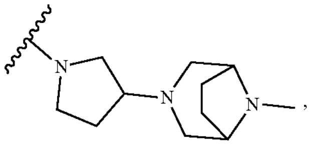
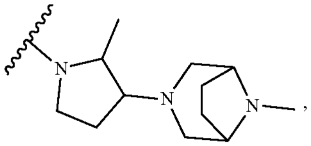

-continued
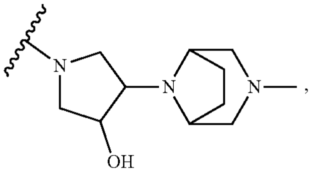
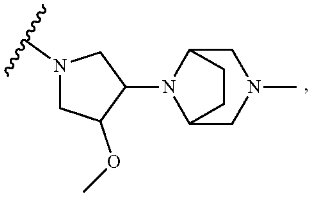
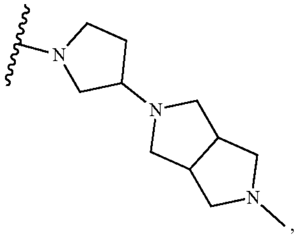
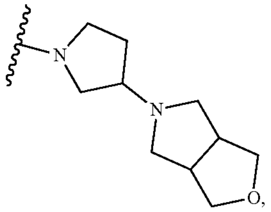
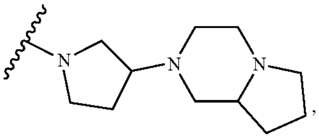
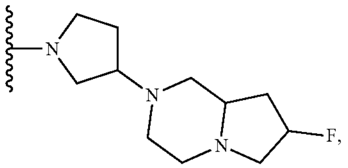
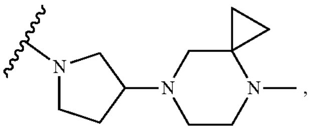
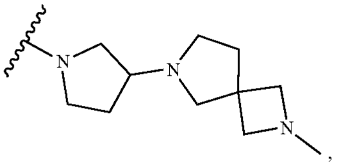
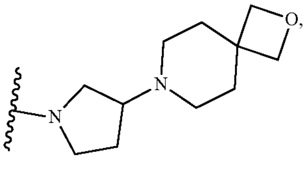
or
-continued
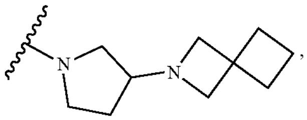
or a pharmaceutically acceptable salt thereof.
32. The compound according to any one of embodiments 1 and 6-24, wherein $R_4$ is selected from
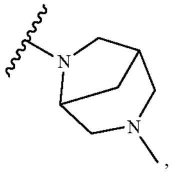
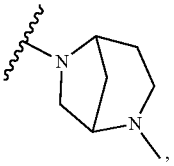
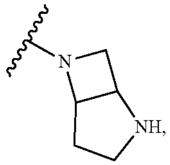
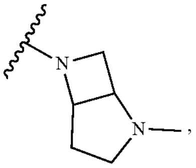
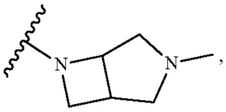
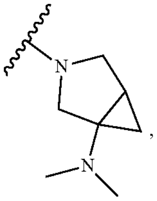
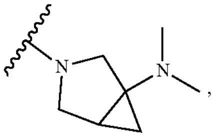
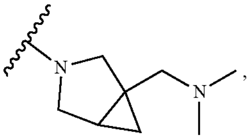

-continued
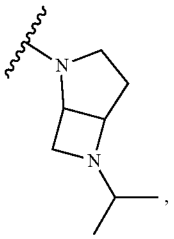
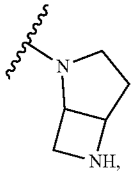
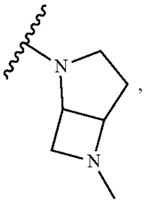
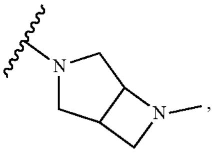
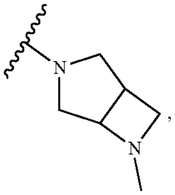
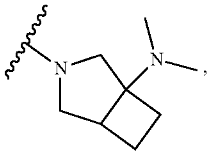
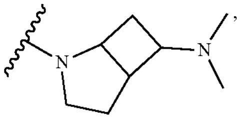
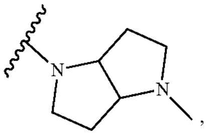
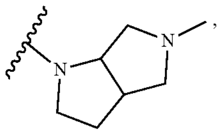
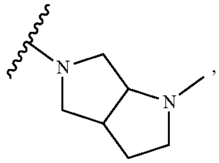
-continued
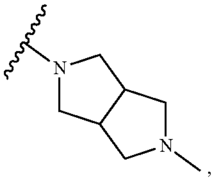
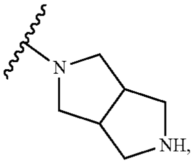
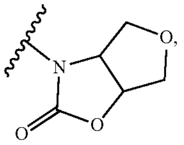
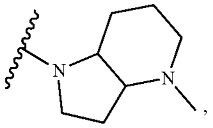
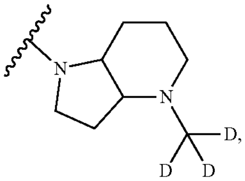
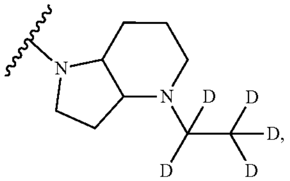
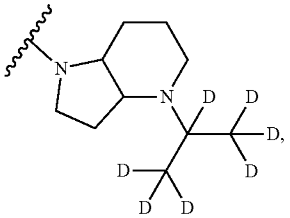
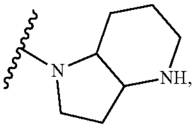
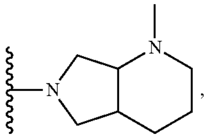
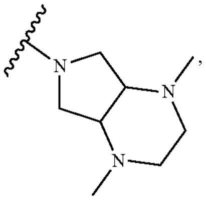

-continued
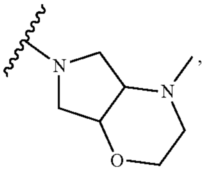
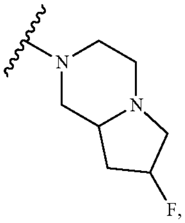
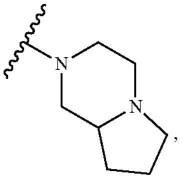
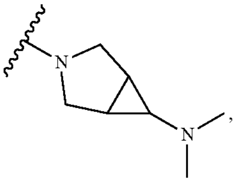
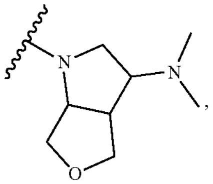
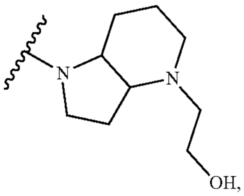
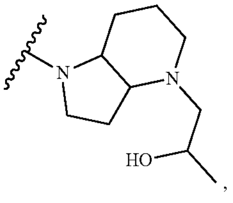
or
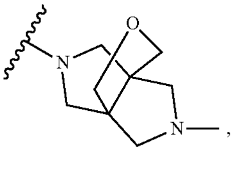
or a pharmaceutically acceptable salt thereof.
33. The compound according to any one of embodiments 1 and 6-24, wherein $R_4$ is selected from
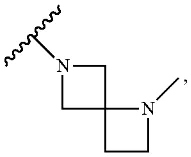
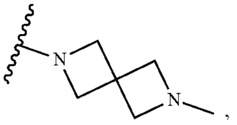
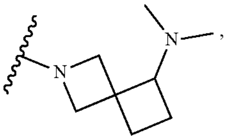
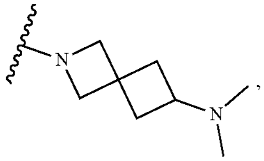
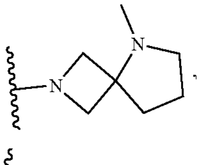
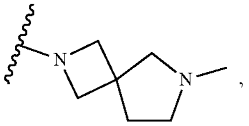
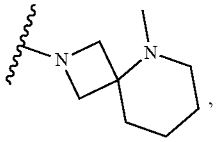
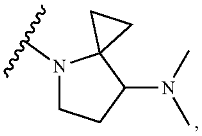
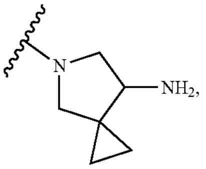
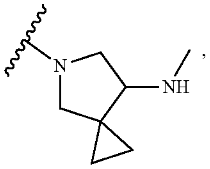
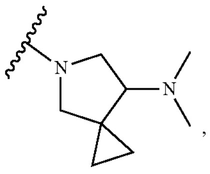

-continued

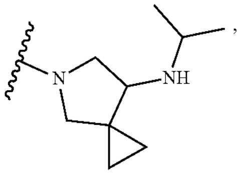

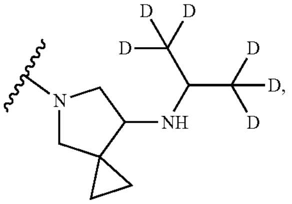

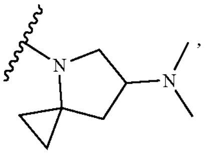

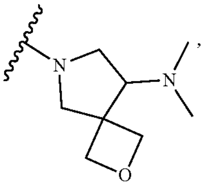

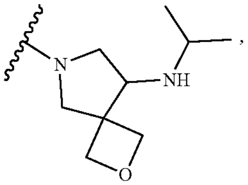

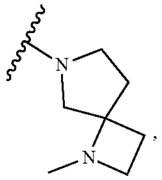

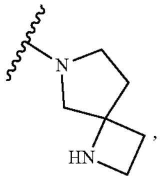

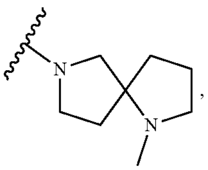

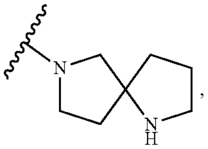

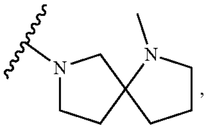

-continued

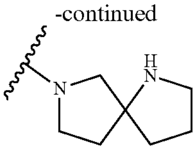

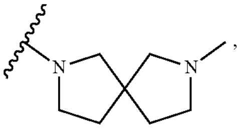

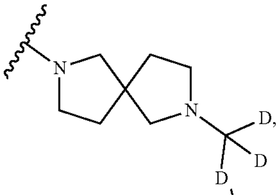

or

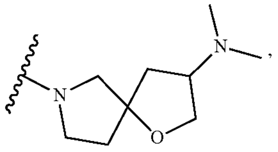

or a pharmaceutically acceptable salt thereof.

34. A pharmaceutical composition comprising a compound according to any one of embodiments 1-33, or a pharmaceutically acceptable salt thereof, and a pharmaceutically acceptable carrier, diluent or excipient.

35. A method of treating a patient for cancer, comprising administering to a patient in need thereof, an effective amount of a pharmaceutical composition according to embodiment 34, wherein the cancer is selected from lung cancer, pancreatic cancer, cervical cancer, esophageal cancer, endometrial cancer, ovarian cancer, cholangiocarcinoma, and colorectal cancer.

36. A method of treating a patient for cancer, comprising administering to a patient in need thereof, an effective amount of a compound according to any one of embodiments 1-33, or a pharmaceutically acceptable salt thereof, wherein the cancer is selected from lung cancer, pancreatic cancer, cervical cancer, esophageal cancer, endometrial cancer, ovarian cancer, cholangiocarcinoma, and colorectal cancer.

37. The method according to embodiments 35 or 36 wherein the patient has a cancer that was determined to have one or more cells expressing the KRas G12D mutant protein prior to administration of the compound or a pharmaceutically acceptable salt thereof.

38. The method according to embodiments 35 or 36 wherein the patient has a cancer that was determined to have one or more cells expressing the KRas G12C, G12D, and/or G12V mutant proteins prior to administration of the compound or a pharmaceutically acceptable salt thereof.

39. The method according to any one of embodiments 35-38, wherein the cancer is non-small cell lung cancer.

40. The method according to any one of embodiments 35-38, wherein the cancer is colorectal cancer.

41. The method according to any one of embodiments 35-38, wherein the cancer is pancreatic cancer.

42. The method according to any one of embodiments 35, 36, and 39-41, wherein one or more cells express KRas G12D mutant protein.

43. The method according to any one of embodiments 35, 36, and 39-41, wherein one or more cells express KRas G12C, G12D, and/or G12V mutant proteins.

44. A method of treating a patient with a cancer that has a KRas G12D mutation comprising administering to a patient in need thereof an effective amount of a compound according to any one of embodiments 1-33, or a pharmaceutically acceptable salt thereof.

45. A method of treating a patient with a cancer that has a KRas G12C, G12D, and/or G12V mutation comprising administering to a patient in need thereof an effective amount of a compound according to any one of embodiments 1-33, or a pharmaceutically acceptable salt thereof.

46. The method according to embodiment 44 or 45, wherein the cancer is selected from lung cancer, pancreatic cancer, cervical cancer, esophageal cancer, endometrial cancer, mutant ovarian cancer, cholangiocarcinoma, and colorectal cancer.

47. The method according to embodiment 46, wherein the cancer is non-small cell lung cancer.

48. The method according to embodiment 46, wherein the cancer is colorectal cancer.

49. The method according to embodiment 46, wherein the cancer is pancreatic cancer.

50. The method according to any one of embodiments 35-49, wherein the patient is also administered an effective amount of one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof.

51. The compound, or a pharmaceutically acceptable salt thereof, according to any one of embodiments 1-33, for use in therapy.

52. The compound, or a pharmaceutically acceptable salt thereof, according to any one of embodiments 1-33 for use in the treatment of cancer.

53. The compound, or a pharmaceutically acceptable salt thereof, for use according to embodiment 52 wherein the cancer has a KRas G12D mutation.

54. The compound, or a pharmaceutically acceptable salt thereof, for use according to embodiment 52 wherein the cancer has a KRas G12C, G12D, and/or G12V mutation.

55. The compound, or a pharmaceutically acceptable salt thereof, for use according to any one of embodiments 52-54 wherein the cancer is selected from lung cancer, pancreatic cancer, cervical cancer, esophageal cancer, endometrial cancer, ovarian cancer, cholangiocarcinoma, and colorectal cancer.

56. The compound, or a pharmaceutically acceptable salt thereof, according to any one of embodiments 1-33 for use in simultaneous, separate, or sequential combination with one or more of a PD-1 or PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof, in the treatment of cancer.

EXAMPLES

The compounds of the present invention, or salts thereof, may be prepared by a variety of procedures, some of which are illustrated in the Schemes, Preparations, and Examples below. The specific synthetic steps for each of the routes described may be combined in different ways, or in conjunction with steps from different routes, to prepare compounds or salts of the present invention. The products of each step in the Preparations below can be recovered by conventional methods, including extraction, evaporation, precipitation, chromatography, filtration, trituration, and crystallization.

Preparation 1

5-Fluoroisobenzofuran-1(3H)-one

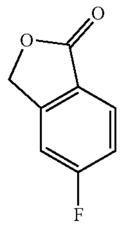 [SMILES: O=C1OCc2cc(F)ccc21]

To a stirred mixture of (2-bromo-5-fluorophenyl)methanol 500 g, 2.44 mol) and TEA (474.6 mL, 3.41 mol, 1.4 eq.) in ACN (2500 mL) was added $Pd(OAc)_2$ (10.95 g, 48.77 mmol, 0.02 eq.) and XantPhos (42.33 g, 73.16 mmol, 0.03 equiv.) at RT, then stirred for 3 days at 120° C. under 10 atm of carbon monoxide. The reaction was cooled to RT and concentrated. The residue was diluted with $H_2O$ (1,000 mL), then extracted with EtOAc (2×2000 mL). The combined organic layers were washed with brine (2×1,000 mL), dried over anhydrous $Na_2SO_4$, filtered and concentrated. The residue was triturated with 10:1 hexanes/EtOAc (1,100 mL) and then filtered. The filter cake was dried at 50° C. for ~18 h to obtain the title compound as a yellow solid (300 g, 81%). MS (ES) m/z=153 (M+1).

Preparation 2

4-Bromo-5-fluoro-6-nitroisobenzofuran-1(3H)-one

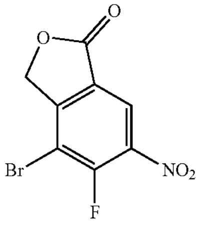 [SMILES: O=C1OCc2c1cc([N+](=O)[O-])c(F)c2Br]

To a stirred mixture of 5-fluoroisobenzofuran-1(3H)-one (300 g, 1.97 mol) in $H_2SO_4$ (1,500 mL) was added $HNO_3$ (273.38 g, 4.348 mol, 2.2 eq.) dropwise at 65° C. The reaction was stirred for 1 h then cooled to RT. 1,3-dibromo-5,5-dimethylimidazolidine-2,4-dione (2,255.43 g, 7.88 mol, 4 eq.) was added in portions over 20 min and was stirred at RT for ~18 h. The mixture was poured onto ice/water (pre-treated with 3 kg $Na_2SO_3$) and filtered. The filter cake was dissolved in EtOAc (3,000 mL), washed with sat. aq. $Na_2CO_3$ (2×1,000 mL), brine (2×1,000 mL), dried over anhydrous $Na_2SO_4$ and concentrated. The residue was triturated with 10:1 hexanes/EtOAc (660 mL) and was filtered and dried at 50° C. for ~18 h to obtain the title compound as a yellow solid (270 g, 49%) which was used in a subsequent step without further purification. $^1H$ NMR (400 MHz, DMSO-$d_6$) δ 8.58 (s, 1H), 5.51 (s, 2H).

Preparation 3

4-Bromo-5-fluoro-6-nitro-1,3-dihydroisobenzofuran

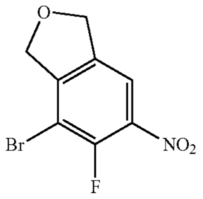 [SMILES: O=[N+]([O-])c1cc2c(c(Br)c1F)COC2]

To a stirred mixture of 4-bromo-5-fluoro-6-nitroisobenzofuran-1(3H)-one (270 g, 978 mmol) in DCM (2,500 mL) was added DIBAL-H (1M in THF, 1,467 mL, 1.467 mol, 1.5 eq.) dropwise at −78° C. under N2. The reaction was stirred for 5 h at −78° C., then was quenched with 5N NaOH (300 mL) at −78° C. The resulting mixture was allowed to warm to RT, then was concentrated. The residue was diluted with EtOAc (2,500 mL), washed with brine (2×1,000 mL) and dried over anhydrous $Na_2SO_4$ and concentrated. The residue was triturated with 10:1 hexanes/EtOAc (550 mL) and filtered. The solids were dried (190 g, 683.4 mmol) then dissolved in DCM (1,500 mL) and treated dropwise with $Et_3SiH$ (662 mL, 4.10 mol, 6 eq.) at 0° C. The reaction was stirred for 20 min at 0° C. TFA (152 mL, 2.05 mol, 3 eq.) was added dropwise at 0° C. The ice bath was removed, and the reaction was stirred at RT for ~18 h. The reaction was concentrated to an oil, which was diluted with EtOAc (2,000 mL), washed with sat. aq. $Na_2CO_3$ (2×500 mL) and brine (2×500 mL), dried over anhydrous $Na_2SO_4$, filtered and concentrated to obtain the title compound (110 g, 42%) which was used in a subsequent step without further purification. $^1H$ NMR (400 MHz, DMSO-$d_6$) δ 8.16 (d, J=6.2 Hz, 1H), 5.18-5.15 (m, 2H), 5.11-5.06 (m, 2H).

Preparation 4

7-Bromo-6-fluoro-1,3-dihydroisobenzofuran-5-amine

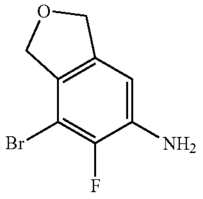 [SMILES: Nc1cc2c(c(Br)c1F)COC2]

To a stirred mixture of 4-bromo-5-fluoro-6-nitro-1,3-dihydroisobenzofuran (110 g, 420 mmol) and $NH_4Cl$ (112.3 g, 2.10 mol, 5 eq.) in EtOH (1,000 mL) and $H_2O$ (200 mL) was added Fe (117.22 g, 2.09 mol, 5 eq.) in portions at RT, then stirred for ~ 18 h at 80° C. The mixture was filtered and concentrated. The mixture was diluted with $H_2O$ (500 mL) and extracted with EtOAc (2×1,000 mL). The combined organic layers were washed with brine (2×500 mL), dried over anhydrous $Na_2SO_4$, filtered and concentrated. The residue was purified on silica (25% to 50% EtOAc/Hex) to afford the title compound (70 g, 72%) as a yellow solid. MS (ES) m/z=231 (M+1).

Preparation 5

(4-Chloro-1,2-phenylene)dimethanol

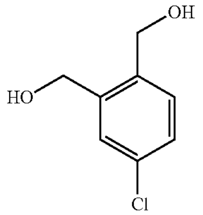

To a stirred mixture of $LiAlH_4$ (1.9 L, 2.74 mol, 2 eq., 2.5 M in THF) in THE (1 L) was added 4-chlorophthalic anhydride (250 g, 1.34 mol, 1.00 eq.) in THE (500 mL) dropwise at −20° C. under N2. The resulting mixture was stirred for 30 min at 45° C. under N2. The reaction was quenched by the addition of $H_2O$ (1.5 L) and 15% NaOH (500 mL) at RT. The mixture was filtered, and the filter cake was washed with MTBE (3×250 mL). The filtrate was extracted with MTBE (3×1.5 L). The combined organic layers were washed with brine (2×2 L) and dried over anhydrous $Na_2SO_4$. After filtration, the filtrate was concentrated under reduced pressure to obtain the title compound (219.5 g, 93%) as an off-white solid. $^1H$ NMR (300 MHz, DMSO-$d_6$) δ 7.45-7.36 (m, 2H), 7.28 (dd, J=8.2 Hz, 1H), 5.40-5.13 (m, 2H), 4.54 (s, 2H), 4.49 (s, 2H).

Preparation 6

5-Chloro-1,3-dihydroisobenzofuran

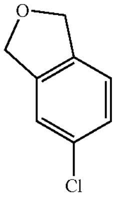

To a stirred mixture of (4-chloro-1,2-phenylene)dimethanol (219.5 g, 1.271 mol) and dimethyl carbonate (458.2 g, 5.082 mol, 4 eq.) in ACN (3 L) was added NaOMe (137.4 g, 2.544 mol, 2 eq.) in portions at RT. The resulting mixture was stirred for ~18 h at 80° C. under N2. The mixture was concentrated under reduced pressure, diluted with $H_2O$ (2 L) and extracted with EtOAc (3×2 L). The combined organic layers were washed with brine (2×2 L) and dried over anhydrous $Na_2SO_4$. After filtration, the filtrate was concentrated under reduced pressure. The residue was purified on silica (10:1 to 8:1 hex/EtOAc) to obtain the title compound (165 g, 82%) as a light-brown solid. $^1H$ NMR (300 MHz, DMSO-$d_6$) δ 7.42-7.37 (m, 1H), 7.33 (d, J=1.4 Hz, 2H), 4.99 (s, 4H).

Preparation 7

5-Chloro-6-nitro-1,3-dihydroisobenzofuran

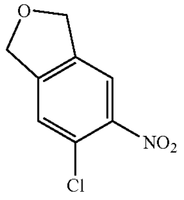 [SMILES: O=[N+]([O-])c1cc2c(cc1Cl)COC2]

A solution of 5-chloro-1,3-dihydroisobenzofuran (110 g, 712 mmol) in $H_2SO_4$ (700 mL) at −10° C. was charged with a solution of $KNO_3$ (64.74 g, 640 mmol, 0.9 eq.) in $H_2SO_4$ (200 mL) dropwise at −5° C.-0° C. The resulting mixture was stirred for additional 30 min at 0° C. and then was slowly added to stirred ice-cooled $H_2O$. The precipitated solids were collected by filtration and washed with $H_2O$ (3×1 L). The filter cake was dried in vacuo to afford the title compound (110 g, 77%) as a light-brown solid which was used in a subsequent step without further purification. $^1H$ NMR (400 MHz, DMSO-$d_6$) δ 8.05 (s, 1H), 7.75 (s, 1H), 5.07-5.02 (m, 4H).

Preparation 8

4-Bromo-5-chloro-6-nitro-1,3-dihydroisobenzofuran

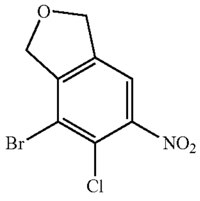 [SMILES: O=[N+]([O-])c1cc2c(c(Br)c1Cl)COC2]

To a stirred solution of 5-chloro-6-nitro-1,3-dihydroisobenzofuran (125 g, 626 mmol) in $H_2SO_4$ (700 mL) was added 1,3-dibromo-5,5-dimethylimidazolidine-2,4-dione (179.1 g, 626.3 mmol, 1 eq.) in portions at −10° C. The mixture was stirred for 1 h at −10° C. then slowly was added to stirred ice-cooled $H_2O$. The precipitated solids were collected by filtration and washed with $H_2O$ (3×0.5 L). The filter cake was dried in vacuo and purified on silica (10:1 to 5:1 Hex/EtOAc) to obtain the title compound (83.5 g, 47.9%) as a white solid. $^1H$ NMR (300 MHz, DMSO-$d_6$) δ 8.07 (d, J=1.1 Hz, 1H), 5.19 (dt, J=2.3, 1.1 Hz, 2H), 5.08 (t, 2H).

Preparation 9

7-Bromo-6-chloro-1,3-dihydroisobenzofuran-5-amine

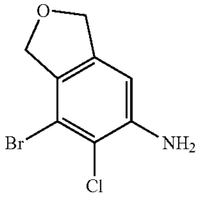 [SMILES: Nc1cc2c(c(Br)c1Cl)COC2]

To a stirred mixture of 4-bromo-5-chloro-6-nitro-1,3-dihydroisobenzofuran (37.0 g, 133 mmol) and $NH_4Cl$ (42.64 g, 797.2 mmol, 6 eq.) in EtOH (200 mL) and $H_2O$ (40 mL) was added Fe (44.52 g, 797.2 mmol, 6 equiv.) in portions at RT. The resulting mixture was stirred for ~18 h at 80° C. The resulting mixture was filtered hot and the filter cake was washed with EtOAc (3×500 mL). The filtrate was concentrated under reduced pressure and was purified on silica (15:1 to 10:1 Hex/EtOAc) to obtain the title compound (25 g, 76%) as a light-yellow solid. MS (ES) m/z=248 (M+1).

Preparation 10

N-(7-Bromo-6-chloro-1,3-dihydroisobenzofuran-5-yl)-3-ethoxyacrylamide

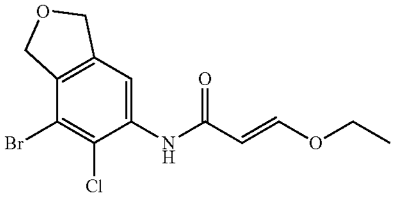

To a stirred solution of 7-bromo-6-chloro-1,3-dihydroisobenzofuran-5-amine (6.00 g, 24.1 mmol) and 3-ethoxyprop-2-enoyl chloride (4.06 g, 30.2 mmol) in THE (50 mL) was added pyridine (3.82 g, 48.3 mmol) dropwise at 0° C. The resulting mixture was stirred for 2 h at RT. The resulting mixture was concentrated under vacuum. The residue was purified by silica gel column chromatography, eluting with PE/EtOAc (5:1) to afford the product (6.00 g, 66.0%) as a yellow solid. MS (ES) m/z=346 (M+1).

Preparation 11

N-(7-Bromo-6-fluoro-1,3-dihydroisobenzofuran-5-yl)-3-ethoxyacrylamide

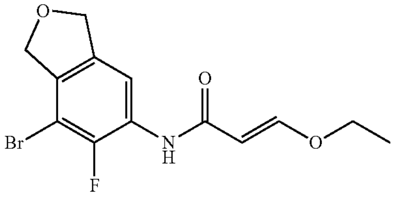 [SMILES: CCO/C=C/C(=O)Nc1cc2c(c(Br)c1Cl)COC2]

7-Bromo-6-fluoro-1,3-dihydroisobenzofuran-5-amine was used in a manner analogous to the method of Preparation 10 to afford the title compound (1.4 g, 89%) as a pale-yellow solid. MS (ES) m/z=332 (M+1).

Preparation 12

4-Bromo-5-chloro-3,6-dihydrofuro[3,4-f]quinolin-7(1H)-one

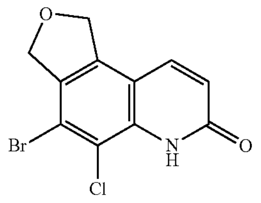 [SMILES: O=c1ccc2c3c(c(Br)c(Cl)c2[nH]1)COC3]

To a stirred solution of $H_2SO_4$ (20 mL) was added N-(7-bromo-6-chloro-1,3-dihydroisobenzofuran-5-yl)-3-ethoxyacrylamide (6.10 g, 17.6 mmol) in portions at 0° C. The resulting mixture was stirred for ~18 h at RT. The mixture was slowly added to stirred ice-cooled water (200 mL). The precipitated solids were collected by filtration and washed with $H_2O$ (3×100 mL). The filter cake was dried under vacuum to afford the product (5.00 g, 87.0%) as a yellow solid. MS (ES) m/z=300 (M+1).

Preparation 13

4-Bromo-5-fluoro-3,6-dihydrofuro[3,4-f]quinolin-7(1H)-one

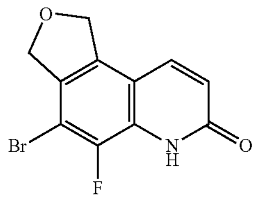 [SMILES: O=c1ccc2c3c(c(Br)c(F)c2[nH]1)COC3]

N-(7-Bromo-6-fluoro-1,3-dihydroisobenzofuran-5-yl)-3-ethoxyacrylamide was used in a manner analogous to that described for Preparation 12 to obtain the title compound (1.2 g, quantitative) as a tan solid. MS (ES) m/z=284 (M+1).

Preparation 14

4-Bromo-5,7-dichloro-1,3-dihydrofuro[3,4-f]quinoline

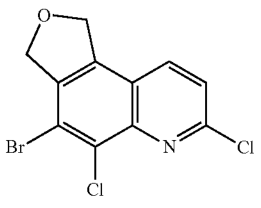 [SMILES: Clc1ccc2c3c(c(Br)c(Cl)c2n1)COC3]

To a stirred solution of 4-bromo-5-chloro-3,6-dihydrofuro[3,4-f]quinolin-7(1H)-one (5.00 g, 16.6 mmol) in DMF (20 mL) was added $POCl_3$ (9.30 mL, 99.8 mmol) dropwise at 0° C. The resulting mixture was stirred for 2 h at 90° C. The mixture was slowly added to stirred ice-cooled water (200 mL). The precipitated solids were collected by filtration and washed with $H_2O$ (3×100 mL). The filter cake was dried under vacuum to afford the product (3.50 g, 62.7%) as a yellow solid. MS (ES) m/z=318 (M+1).

Preparation 15

4-Bromo-7-chloro-5-fluoro-1,3-dihydrofuro[3,4-f]quinoline

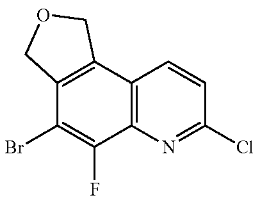 [SMILES: Fc1c(Br)c2c(c3ccc(Cl)nc13)COC2]

A suspension of 4-bromo-5-fluoro-3,6-dihydrofuro[3,4-f]quinolin-7(1H)-one (1.2 g, 4.2 mmol) stirred in DCM (40 mL) was charged with (chloromethylene)dimethyliminium chloride (2.2 g, 17 mmol, 4 eq.) and stirred at RT for ~18 h. The reaction was diluted with DCM and washed with $H_2O$ and brine. The organic layer was dried over $Na_2SO_4$, filtered and concentrated to a solid which was triturated with a small amount of DCM. The solids were filtered and washed with a small amount of DCM and air-dried to give Batch 1. The filtrate was concentrated and purified on silica gel, eluting with EtOAc/hexanes (0% to 80%) to give Batch 2. Both batches were combined to afford the title compound (1.0 g, 78%) as a tan solid. MS (ES) m/z=304 (M+1).

Preparation 16

(1-(((4-Bromo-5-fluoro-1,3-dihydrofuro[3,4-f]quinolin-7-yl)oxy)methyl)cyclopropyl)methanol

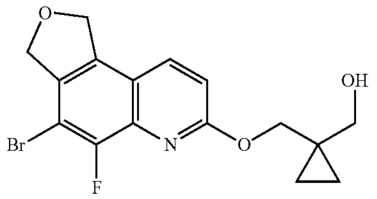 [SMILES: OCC1(COc2ccc3c4c(c(Br)c(F)c3n2)COC4)CC1]

To a solution of (1-(hydroxymethyl)cyclopropyl)methanol (1.52 g, 14.9 mmol) in DMF (30 mL) was added lithium bis(trimethylsilyl)amide (1 M in THF, 15 mL, 15.0 mmol) at 0° C. under nitrogen. After 15 min, a solution of 4-bromo-7-chloro-5-fluoro-1,3-dihydrofuro[3,4-f]quinoline (1.50 g, 4.96 mmol) in DMF (8 mL) was added dropwise. The reaction mixture was heated to 50° C. After 2 h, the reaction mixture was diluted with water (100 mL) and extracted with DCM (3×200 mL). The combined organics were washed with water (3×100 mL) and brine (3×100 mL). The organics were dried over anhydrous $Na_2SO_4$, filtered and concentrated under reduced pressure to afford the title compound (1.35 g, crude). MS (ES) m/z=368 (M+1).

Preparation 17

(1-(((4-Bromo-5-fluoro-1,3-dihydrofuro[3,4-f]quinolin-7-yl)oxy)methyl)cyclopropyl)methyl methanesulfonate

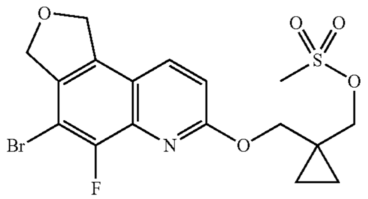 [SMILES: CS(=O)(=O)OCC1(COc2ccc3c4c(c(Br)c(F)c3n2)COC4)CC1]

A mixture of (1-(((4-bromo-5-fluoro-1,3-dihydrofuro[3,4-f]quinolin-7-yl)oxy)methyl)cyclopropyl)methanol (1.35 g, 3.66 mmol) and THE (10 mL) was cooled to 0° C. under nitrogen. Diisopropylethylamine (4.74 g, 36.7 mmol) was added. The mixture was stirred for 20 min, then warmed to RT. Methanesulfonic anhydride (3.19 g, 18.4 mmol) was added dropwise. After 2 h, the reaction mixture was concentrated under reduced pressure to give crude title compound. MS (ES) m/z=446 (M+1).

Preparation 18

4-Bromo-5-fluoro-7-((1-(morpholinomethyl)cyclopropyl)methoxy)-1,3-dihydrofuro[3,4-f]quinoline

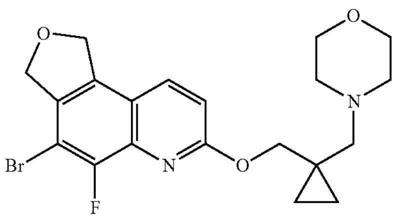 [SMILES: Fc1c(Br)c2c(c3ccc(OCC4(CN5CCOCC5)CC4)nc13)COC2]

To a mixture of (1-(((4-bromo-5-fluoro-1,3-dihydrofuro[3,4-f]quinolin-7-yl)oxy)methyl)cyclopropyl)methyl methanesulfonate (2.22 g, crude, 4.93 mmol) and DMF (50 mL) was added diisopropylethylamine (4.76 g, 24.6 mmol) at RT under nitrogen. The mixture was stirred for 10 min, morpholine (1.29 g, 10.1 mmol) was added dropwise, then heated at 90° C. After 3 h, the reaction mixture was diluted with EtOAc (200 mL) and washed with brine (3×50 mL). The organics were dried over anhydrous $Na_2SO_4$, filtered and concentrated under reduced pressure. The residue was purified on silica eluting with 25-50% EtOAc in PE to obtain the title compound (0.40 g, 18%) as a yellow solid. MS (ES) m/z=437 (M+1).

Preparation 19

Ethyl N-[(7-bromo-6-fluoro-1,3-dihydroisobenzofuran-5-yl)carbamothioyl]carbamate

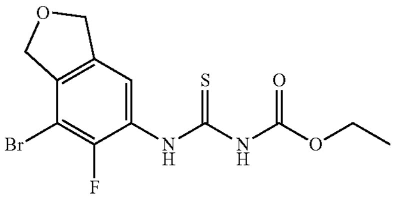

A solution of 7-bromo-6-fluoro-1,3-dihydroisobenzofuran-5-amine (20.4 g, 87.9 mmol) in DCM (550 mL) was charged with ethoxycarbonyl isothiocyanate (9.7 mL, 82 mmol, 0.93 eq.) slowly via addition funnel and subsequently stirred at RT for ~ 4 h. The solids were filtered. The filtrate was concentrated, suspended in DCM (100 mL) and hexanes (350 mL) and stirred at RT. The resultant filtered solids and previous filtered solids were dried under vacuum at 50° C. for 2 h. The batches were combined to obtain the title compound (32.6 g, quantitative) as a white solid. MS (ES) m/z=363 (M+1).

Preparation 1A

Ethyl N-[(7-bromo-6-chloro-1,3-dihydroisobenzofuran-5-yl)carbamothioyl]carbamate

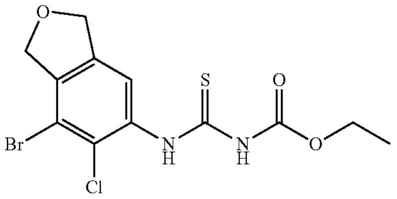 [SMILES: CCOC(=O)NC(=S)Nc1cc2c(c(Br)c1Cl)COC2]

7-Bromo-6-chloro-1,3-dihydroisobenzofuran-5-amine was used in a manner analogous to the method of Preparation 19 to afford the title compound (14 g, 92%) as a white solid. MS (ES) m/z=379 (M+1).

Preparation 20

Ethyl (((7-bromo-6-fluoro-1,3-dihydroisobenzofuran-5-yl)amino)(ethylthio)methylene)carbamate

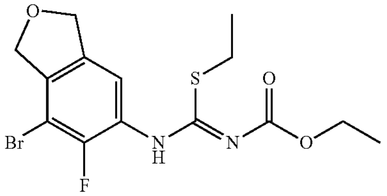 [SMILES: CCOC(=O)/N=C(/Nc1cc2c(c(Br)c1F)COC2)SCC]

A 2 L 3-necked RBF, equipped with an overhead stirrer, dropping funnel and thermocouple was charged with a suspension of ethyl N-[(7-bromo-6-fluoro-1,3-dihydroisobenzofuran-5-yl)carbamothioyl]carbamate (32.6 g, 89.8 mmol) and acetone (450 mL). To this was added solid $K_2CO_3$ (37.2 g, 269 mmol, 3.00 eq.) in several portions, followed by the dropwise addition of EtI (7.2 mL, 90 mmol, 1.0 eq.) over 20 min. The mixture was stirred at RT for ~18 h. The solids were filtered and the filtrate was concentrated and partitioned between DCM (500 mL) and $H_2O$ (500 mL). The organics were further washed with brine and dried over anhydrous $Na_2SO_4$, filtered and concentrated. The residue was purified on silica (0 to 30% EtOAc/Hex) to obtain the title compound (30.9 g, 85.6%) as a white solid. MS (ES) m/z=391 (M+1).

Preparation 2A

Ethyl (((7-bromo-6-chloro-1,3-dihydroisobenzofuran-5-yl)amino)(ethylthio)methylene)carbamate

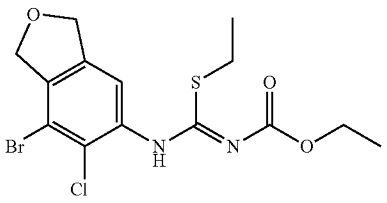 [SMILES: CCOC(=O)/N=C(/Nc1cc2c(c(Br)c1Cl)COC2)SCC]

Ethyl N-[(7-bromo-6-chloro-1,3-dihydroisobenzofuran-5-yl)carbamothioyl]carbamate was used in a manner analogous to the method of Preparation 20 to afford the title compound (15.4 g, crude) as a brown solid. MS (ES) m/z=407 (M+1).

Preparation 21

6-Bromo-3-(ethylthio)-5-fluoro-7,9-dihydrofuro[3,4-f]quinazolin-1-ol

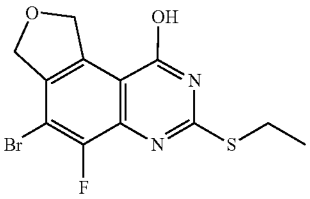 [SMILES: CCSc1nc(O)c2c3c(c(Br)c(F)c2n1)COC3]

A 2 L 4-necked RBF was equipped with an overhead stirrer, dropping funnel, N2 inlet and thermocouple and was purged with N2. NMP (anhydrous, 300 mL) was added. The mixture was heated to 175° C. In a second flask, ethyl (((7-bromo-6-fluoro-1,3-dihydroisobenzofuran-5-yl)amino)(ethylthio)methylene)carbamate (22.63 g, 57.83 mmol) and NMP (anhydrous, 100 mL) were combined and stirred under N2 until a homogeneous solution was obtained. When the first flask had reached 175° C., the contents of the second flask were poured into the dropping funnel and were added dropwise but rapidly to the hot NMP. After 30 min, the heat was turned off and the reaction cooled to 45° C. $H_2O$ (500 mL) was slowly added and the mixture was stirred at RT for 1 h. The solids were filtered, rinsed with $H_2O$ (300 mL) and dried under vacuum at 50° C. for ~18 h to afford the title compound (15.2 g, 73%) as an off-white solid. MS (ES) m/z=363 (M+1).

Preparation 3A

6-Bromo-5-chloro-3-(ethylthio)-7,9-dihydrofuro[3,4-f]quinazolin-1-ol

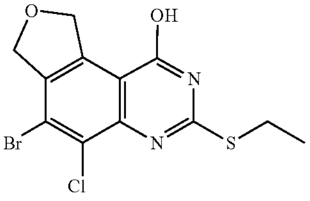 [SMILES: CCSc1nc(O)c2c3c(c(Br)c(Cl)c2n1)COC3]

Ethyl (((7-bromo-6-chloro-1,3-dihydroisobenzofuran-5-yl)amino)(ethylthio)methylene)carbamate was used in a manner analogous to the method of Preparation 21 to afford the title compound (11.4 g, 86%) as a white solid. MS (ES) m/z=361 (M+1).

Preparation 22

6-Bromo-1-chloro-3-(ethylthio)-5-fluoro-7,9-dihydrofuro[3,4-f]quinazoline

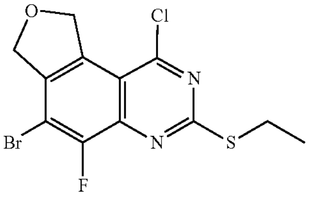 [SMILES: CCSc1nc(Cl)c2c3c(c(Br)c(F)c2n1)COC3]

A 5 L 3-necked RBF, equipped with a dropping funnel, thermocouple and an overhead stirrer was charged with a solution of DMF (50 mL, 646 mmol, 4 eq.) in DCM (1,000 mL) and was placed in an ice/water bath and cooled to −4° C. Oxalyl chloride (50.0 mL, 576 mmol, 4 eq.) was added dropwise via addition funnel over −40 min. When the addition was complete, the reaction was stirred at −4° C. for 15 min. Solid 6-bromo-3-(ethylthio)-5-fluoro-7,9-dihydrofuro[3,4-f]quinazolin-1-ol (50.4 g, 140 mmol) was added in several portions to the reaction mixture and the resulting suspension was stirred at −4° C. for 30 min. The ice bath was removed and the reaction was allowed to warm to RT and stir for 1 h. Then $H_2O$ (1 L) was added and the mixture was stirred for 15 min. The mixture was partitioned and the organic layer was washed with brine (1 L) and dried over anhydrous $Na_2SO_4$, filtered and concentrated. The residue was purified on silica, eluting with DCM/Hex (60% to 90%) to obtain the title compound (45.1 g, 89%) as a white solid. MS (ES) m/z=363 (M+1).

Preparation 1B

6-Bromo-1,5-dichloro-3-(ethylthio)-7,9-dihydrofuro[3,4-f]quinazoline

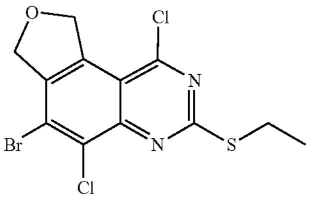 [SMILES: CCSc1nc(Cl)c2c3c(c(Br)c(Cl)c2n1)COC3]

6-Bromo-5-chloro-3-(ethylthio)-7,9-dihydrofuro[3,4-f]quinazolin-1-ol was used in a manner analogous to the method of Preparation 22 to afford the title compound (7.5 g, 63%) as a yellow solid. MS (ES) m/z=379 (M+1).

Preparation 23

6-Bromo-3-(ethylthio)-5-fluoro-7,9-dihydrofuro[3,4-f]quinazoline

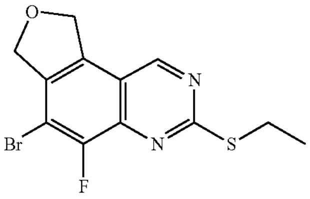 [SMILES: CCSc1ncc2c3c(c(Br)c(F)c2n1)COC3]

To a mixture of 6-bromo-1-chloro-3-(ethylthio)-5-fluoro-7,9-dihydrofuro[3,4-f]quinazoline (6.50 g, 17.9 mmol) and tetramethylethylenediamine (2.28 g, 19.7 mmol) in THF (100 mL) was added [1,1'-bis(diphenylphosphino)ferrocene] dichloropalladium(II) (0.73 g, 1.00 mmol) and sodium cyanoborohydride (in portions, 2.25 g, 35.8 mmol) at RT. The reaction mixture was stirred overnight under nitrogen, then diluted with water (500 mL) and extracted with EtOAc (3×500 mL). The combined organic layers were washed with brine (500 mL), dried over anhydrous $Na_2SO_4$, filtered and concentrated under reduced pressure. The residue was purified on silica, eluting with 16-20% EtOAc in PE to obtain the title compound (5.0 g, 75%) as a yellow solid. MS (ES) m/z=329 (M+1).

Preparation 2B

6-Bromo-5-chloro-3-(ethylthio)-7,9-dihydrofuro[3,4-f]quinazoline

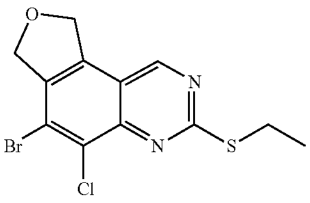 [SMILES: CCSc1ncc2c3c(c(Br)c(Cl)c2n1)COC3]

6-Bromo-1,5-dichloro-3-(ethylthio)-7,9-dihydrofuro[3,4-f]quinazoline was used in a manner analogous to the method of Preparation 23 to afford the title compound (1.2 g, 57%) as a yellow solid. MS (ES) m/z=345 (M+1).

Preparation 24 tert-Butyl 8-(6-bromo-3-(ethylthio)-5-fluoro-7,9-dihydrofuro[3,4-f]quinazolin-1-yl)-3,8-diazabicyclo[3.2.1]octane-3-carboxylate

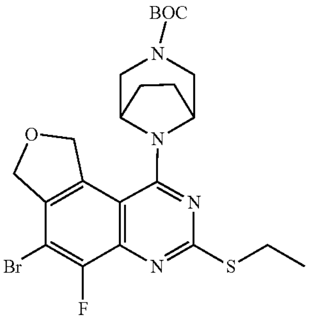 [SMILES: CCSc1nc(N2C3CCC2CN(C(=O)OC(C)(C)C)C3)c2c3c(c(Br)c(F)c2n1)COC3]

A suspension of 6-bromo-1-chloro-3-(ethylthio)-5-fluoro-7,9-dihydrofuro[3,4-f]quinazoline (21.0 g, 57.8 mmol) in ACN (580 mL) was charged with tert-butyl 3,8-diazabicyclo[3.2.1]octane-3-carboxylate (15.2 g, 69.5 mmol, 1.20 eq.) and DIPEA (40 mL, 229 mmol, 4 eq.) and was stirred at RT for 90 min. $H_2O$ (1 L) was added slowly via addition funnel and the mixture was stirred at RT for 1 h. The solids were filtered, rinsed with $H_2O$ (500 mL) and dried under vacuum at 50° C. to obtain the title compound (31 g, quantitative) as a white solid, MS (ES) m/z=539 (M+1).

Preparation 3B tert-Butyl 8-(6-bromo-5-chloro-3-(ethylthio)-7,9-dihydrofuro[3,4-f]quinazolin-1-yl)-3,8-diazabicyclo[3.2.1]octane-3-carboxylate

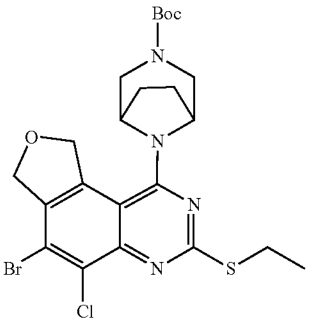 [SMILES: CCSc1nc(N2C3CCC2CN(C(=O)OC(C)(C)C)C3)c2c3c(c(Br)c(Cl)c2n1)COC3]

6-Bromo-1,5-dichloro-3-(ethylthio)-7,9-dihydrofuro[3,4-f]quinazoline was used in a manner analogous to the method of Preparation 24 to afford the title compound (6 g, 75%) as a yellow solid. MS (ES) m/z=555 (M+1).

Preparation 25

6-Bromo-1-(3-((R)-2-((tert-butyldimethylsilyl)oxy) propyl)-3,8-diazabicyclo[3.2.1]octan-8-yl)-3-(ethylthio)-5-fluoro-7,9-dihydrofuro[3,4-f]quinazoline

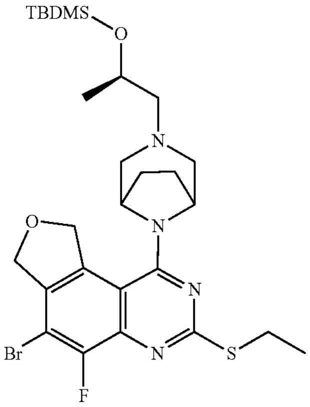

3-((R)-2-((tert-butyldimethylsilyl)oxy)propyl)-3,8-diazabicyclo[3.2.1]octane was used in a manner analogous to that described for Preparation 24 to obtain the title compound (4.7 g, 95%) as a tan solid.

Preparation 26

Methyl 4-bromo-5-fluorobenzo[b]thiophene-2-carboxylate

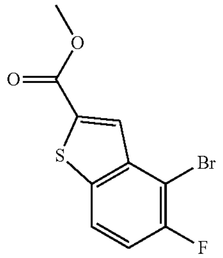

A solution of methyl thioglycolate (0.18 mL, 2.0 mmol, 1 eq.) in THE (5 mL) was flushed with N2 and charged with NaH (60 mass %) in mineral oil (0.101 g, 2.53 mmol, 1.24 eq.) at RT. Gas evolution was observed, and a precipitate formed in the flask. The reaction was stirred at RT for 20 min. A solution of 2-bromo-3,6-difluorobenzaldehyde (0.475 g, 2.04 mmol) in THF (5 mL) was added slowly via syringe over ~2 min. The reaction was stirred at RT for 9 h. Additional methyl thioglycolate (0.1 mL, 1 mmol, 0.5 eq.) and sodium hydride (60 mass %) in mineral oil (0.050 g, 1.3 mmol, 0.6 eq.) were added and stirring was continued at RT for ~18 h. The mixture was diluted with EtOAc and washed with sat. aq. $NH_4Cl$ and brine. The organics were dried over anhydrous $Na_2SO_4$, filtered and concentrated. The residue was purified on silica, eluting with 2% MTBE/Hex to obtain the title compound (0.346 g, 59%) as a white solid. $^1H$ NMR (400 MHz, DMSO-$d_6$) δ 8.23-8.19 (dd, J=4.49, 8.9 Hz, 1H), 8.05 (s, 1H), 7.62 (t, J=9.0 Hz, 1H), 3.93 (s, 3H).

Preparation 27

4-Bromo-5-fluorobenzo[b]thiophene-2-carboxylic acid

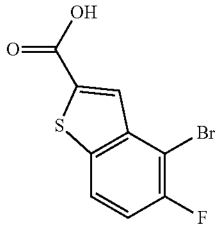 [SMILES: O=C(O)c1cc2c(Br)c(F)ccc2s1]

A solution of methyl 4-bromo-5-fluorobenzo[b]thiophene-2-carboxylate (19.2 g, 66.4 mmol, 1 eq.) in MeOH (130 mL) and THE (130 mL) was charged with 5N NaOH (66 mL, 330 mmol, 5 eq.) and stirred at RT for 40 min. The mixture was concentrated and $H_2O$ (500 mL) was added. The pH was adjusted to ~2 with 5N HCl. The mixture was extracted with EtOAc (2×500 mL) and the combined organic layers were dried over anhydrous $Na_2SO_4$, filtered and concentrated. The solids were dried under vacuum at 50° C. to afford the title compound (17.6 g, 96%) as a white solid. MS (ES) m/z=229 (M−1-$CO_2$).

Preparation 28 tert-Butyl (4-bromo-5-fluorobenzo[b]thiophen-2-yl) carbamate

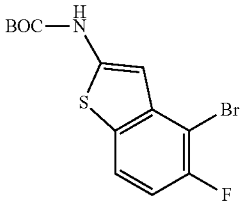 [SMILES: CC(C)(C)OC(=O)Nc1cc2c(Br)c(F)ccc2s1]

A solution of 4-bromo-5-fluorobenzo[b]thiophene-2-carboxylic acid (1.5 g, 5.5 mmol) in t-butanol (30 mL) was charged with TEA (1.5 mL, 11 mmol, 2.0 eq.) and diphenylphosphoryl azide (1.5 mL, 6.9 mmol, 1.3 eq.) and heated at 95° C. for 1 h. The mixture was cooled and concentrated. The residue was purified on silica, eluting with MTBE/Hex (4% to 20%) to obtain the title compound (0.987 g, 52%) as a white solid. MS (ES) m/z=290 (M+1).

Preparation 29 tert-Butyl (4-(5,5-dimethyl-1,3,2-dioxaborinan-2-yl)-5-fluorobenzo[b]thiophen-2-yl)carbamate

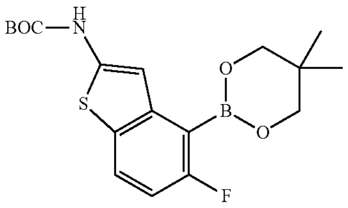 [SMILES: CC1(C)COB(c2c(F)ccc3sc(NC(=O)OC(C)(C)C)cc23)OC1]

A mixture of tert-butyl (4-bromo-5-fluorobenzo[b]thiophen-2-yl)carbamate (3.08 g, 8.90 mmol) and bis(neopentyl glycolato)diboron (4.02 g, 17.8 mmol, 2 eq.) and KOAc (2.62 g, 26.7 mmol, 3 eq.) in 1,4-dioxane (70 mL, 819.9 mmol) was sparged with N2 for 20 min. To the mixture was added Pd(ddpf)$Cl_2$ (0.69 g, 0.90 mmol, 0.1 eq.). The reaction was sonicated for 3 min, then put through a vacuum/N2 refill cycle (3×) and was heated at 100° C. for 3 h. The mixture was cooled to RT, filtered through diatomaceous earth and was rinsed with 1:4 EtOAc/Hex. The filtrate was concentrated and the residue was purified on silica (0-40% MTBE/Hex) to obtain the title compound (2.95 g, 87%) as a white solid. $^1$H NMR (400 MHz, DMSO-$d_6$) δ 10.81-10.79 (bs, 1H), 7.84-7.74 (dd, J=5.07, 8.59, 1H), 7.14 (s, 1H), 6.94-6.88 (m, 1H), 3.89 (bs, 4H), 1.49 (s, 10H), 1.03 (s, 6H).

Preparation 30 tert-Butyl (4-chloro-3-cyano-7-fluorothieno[3,2-c]pyridin-2-yl)carbamate

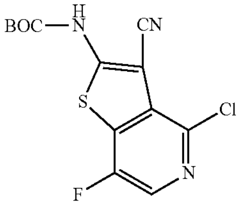 [SMILES: CC(C)(C)OC(=O)Nc1sc2c(F)cnc(Cl)c2c1C#N]

Ethyl (3-cyano-7-fluorothieno[3,2-c]pyridin-2-yl)carbamate. A solution of 2-(4-chloro-5-fluoropyridin-3-yl)acetonitrile (11.8 g, 56.1 mmol) in DMF (112 mL) was cooled to 0° C. Potassium tert-butoxide (7.00 g, 61.1 mmol) was added. After 15 min, ethoxycarbonyl isothiocyanate (7.45 mL, 61.8 mmol) was added dropwise. The reaction mixture was allowed to slowly warm to RT overnight. The reaction mixture was poured into a mixture of ice/water (1.5 L), stirred until all ice had melted, and filtered through diatomaceous earth. The solids were dried in a vacuum oven (60° C.) overnight and separated from the diatomaceous earth to give ethyl N-(3-cyano-7-fluoro-thieno[3,2-c]pyridin-2-yl)carbamate (11.9 g, 79%) as a solid. MS (ES) m/z=266 (M+1).

2-Amino-7-fluorothieno[3,2-c]pyridine-3-carbonitrile. A suspension of ethyl (3-cyano-7-fluorothieno[3,2-c]pyridin-2-yl)carbamate (11.9 g, 44.4 mmol) in DMSO (90 mL) was cooled to 0° C. NaOH (5 M in water, 90 mL) was added dropwise over 15 min. The reaction mixture was heated to 105° C. for 1 h, then cooled to RT. The reaction mixture was poured into a mixture of ice/water (1.8 L), stirred until all ice had melted, and filtered through diatomaceous earth. The solids were dried in a vacuum oven (50° C.) overnight and separated from the diatomaceous earth to give crude 2-amino-7-fluoro-thieno[3,2-c]pyridine-3-carbonitrile.

tert-Butyl (3-cyano-7-fluorothieno[3,2-c]pyridin-2-yl) carbamate. A mixture of crude 2-amino-7-fluorothieno[3,2-c]pyridine-3-carbonitrile (8.6 g, 44.4 mmol), DCM (90 mL), DMF (90 mL) and N,N-diisopropylethylamine (15.5 mL, 88.9 mmol) was cooled to 0° C. 4-dimethylaminopyridine (0.54 g, 4.42 mmol) and di-tert-butyl dicarbonate (14.6 g, 66.7 mmol) were added. The reaction mixture was stirred at RT for 2 h. The solvents were removed under reduced pressure and the remaining material was diluted with DCM (400 mL) and 5% aq. citric acid (250 mL). The aqueous phase was washed twice with DCM. The combined organic phases were washed with sat. aq. $NaHCO_3$, dried over $MgSO_4$, filtered, and concentrated to give tert-butyl N-(3-cyano-7-fluoro-thieno[3,2-c]pyridin-2-yl)carbamate (7.5 g, 58%) as a brown solid. MS (ES) m/z=294 (M+1).

2-((tert-Butoxycarbonyl)amino)-3-cyano-7-fluorothieno[3,2-c]pyridine 5-oxide. 3-Chloroperoxybenzoic acid (9.00 g, 40.2 mmol) was added to a solution of tert-butyl (3-cyano-7-fluorothieno[3,2-c]pyridin-2-yl)carbamate (7.85 g, 26.8 mmol) in DCM (180 mL). The reaction mixture was stirred at RT overnight, then cooled to 0° C. for −15 min. Solids were collected by filtration and dried in a vacuum oven (60° C.). The filtrate was diluted with MeOH and silica gel, concentrated, and the residue was purified on silica, eluting with 0-6% MeOH in DCM. Fractions containing desired material were combined with the solids from the filtration and concentrated to give tert-butyl N-(3-cyano-7-fluoro-5-oxido-thieno[3,2-c]pyridin-5-ium-2-yl)carbamate (7.26 g, 88%) as an off-white solid. MS (ES) m/z=310 (M+1).

tert-Butyl (4-chloro-3-cyano-7-fluorothieno[3,2-c]pyridin-2-yl)carbamate. A suspension of 2-((tert-butoxycarbonyl)amino)-3-cyano-7-fluorothieno[3,2-c]pyridine 5-oxide (5.27 g, 17.0 mmol) in 1,2-dichloroethane (34 mL) was cooled to 0° C. A solution of phosphoryl chloride (32 mL, 344 mmol) in 1,2-dichloroethane (34 mL) was added dropwise. The reaction mixture was stirred at RT for 30 min, at 45° C. for 90 min, and cooled to RT. The reaction mixture was diluted with 1,2-dichloroethane (100 mL) and added to a mixture of sat. aq. $NaHCO_3$ (500 mL), NaOH (5 M in water, 40 mL), and ice. Solid $NaHCO_3$ was added to the stirred mixture to maintain pH ~6-7. Once bubbling ceased, the phases were separated. The aqueous phase was extracted 3× with DCM. The combined organic phases were dried over $MgSO_4$ and filtered. The filtrate was diluted with MeOH and silica gel, concentrated, and the residue was purified on silica, eluting with 50-100% DCM in hexanes. Fractions containing desired material were concentrated to give the title compound (3.87 g, 69%) as a white solid. MS (ES) m/z=328 (M+1).

Preparation 1C tert-Butyl (4-bromo-7-chloro-3-cyanothieno[3,2-c] pyridin-2-yl)carbamate

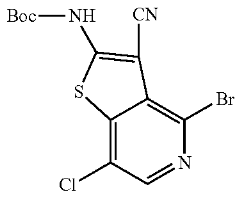 [SMILES: CC(C)(C)OC(=O)Nc1sc2c(Cl)cnc(Br)c2c1C#N]

3-Bromo-5-chloro-4-((4-methoxybenzyl)thio)pyridine. To a solution of 3-bromo-4,5-dichloropyridine (10.0 g, 44.1 mmol) in acetonitrile (90 mL) was added potassium carbonate (6.70 g, 48.5 mmol). The mixture was cooled to 0° C. and (4-methoxyphenyl)methanethiol (6.6 mL, 46.3 mmol) was added dropwise. The reaction mixture was allowed to slowly warm to RT and stirred overnight. The mixture was diluted with water (200 mL) and EtOAc (300 mL), then the layers were separated. The aqueous layer was extracted with EtOAc (2×300 mL). The combined organic layers were dried over sodium sulfate and concentrated under reduced pressure. The residue was purified on silica, eluting with 0-60% EtOAc in heptane. Fractions containing desired material were concentrated to give 3-bromo-5-chloro-4-((4-methoxybenzyl)thio)pyridine (8.6 g, 57%) as a white solid. MS (ES) m/z=344 (M+1).

2-(5-Chloro-4-((4-methoxybenzyl)thio)pyridin-3-yl)malononitrile. To a pressure vessel containing a solution of malonitrile (2.44 g, 37.0 mmol) in 1,4-dioxane (160 mL) was added a mixture of sodium tert-butoxide (7.11 g, 74.0 mmol) in THE (36 mL). The mixture was stirred for 15 min, then 3-bromo-5-chloro-4-((4-methoxybenzyl)thio)pyridine (8.50 g, 24.7 mmol) and tetrakis(triphenylphosphine)palladium(0) (2.85 g, 2.47 mmol) were added. The pressure vessel was sealed and the reaction mixture was heated at 85° C. overnight. The reaction mixture was filtered and the solids were washed with EtOAc. The combined filtrates were concentrated under reduced pressure, then diluted with DCM. The mixture was filtered, and the solids were washed with DCM to obtain 2-(5-chloro-4-((4-methoxybenzyl)thio) pyridin-3-yl)malononitrile (7.5 g, 92%) as a yellow solid. MS (ES) m/z=330 (M+1).

2-Amino-7-chlorothieno[3,2-c]pyridine-3-carbonitrile. Trifluoroacetic acid (5 mL) was added to a mixture of 2-(5-chloro-4-((4-methoxybenzyl)thio)pyridin-3-yl)malononitrile (0.740 g, 2.24 mmol) in DCM (25 mL). The reaction mixture was stirred at RT for 5 h, then concentrated under reduced pressure. The residue was diluted with DCM (5 mL) and trifluoroacetic acid (5 mL) was added. The reaction mixture was stirred at RT overnight, then concentrated under reduced pressure. The residue was diluted with 4:1 hexanes:EtOAc (30 mL) and stirred for 30 min. The mixture was filtered, and the solids were washed with minimal 4:1 hexanes:EtOAc to obtain 2-amino-7-chlorothieno[3,2-c]pyridine-3-carbonitrile (0.28 g, 60%) as a brown solid. MS (ES) m/z=210 (M+1).

tert-Butyl (7-chloro-3-cyanothieno[3,2-c]pyridin-2-yl) carbamate. 2-Amino-7-chlorothieno[3,2-c]pyridine-3-carbonitrile was used in an analogous manner to the method of Preparation 30 (Intermediate step tert-Butyl (3-cyano-7-fluorothieno[3,2-c]pyridin-2-yl)carbamate) to obtain tert-butyl (7-chloro-3-cyanothieno[3,2-c]pyridin-2-yl)carbamate (0.85 g, 52%) as a white solid. MS (ES) m/z=310 (M+1).

2-((tert-Butoxycarbonyl)amino)-7-chloro-3-cyanothieno [3,2-c]pyridine 5-oxide. 3-Chloroperoxybenzoic acid (75 wt %; 4.0 g, 17 mmol) was added to a solution of tert-butyl (7-chloro-3-cyanothieno[3,2-c]pyridin-2-yl)carbamate (4.1 g, 13 mmol) in DCM (60 mL). The reaction mixture was stirred at RT overnight, then concentrated under reduced pressure. The material was purified on silica, eluting with 0-10% MeOH in DCM. Fractions containing desired material were concentrated to give 2-((tert-butoxycarbonyl) amino)-7-chloro-3-cyanothieno[3,2-c]pyridine 5-oxide (4.3 g, 90%) as a white solid. MS (ES) m/z=326 (M+1).

tert-Butyl (4-bromo-7-chloro-3-cyanothieno[3,2-c]pyridin-2-yl)carbamate. Molecular sieves (4A, 4 g) were added to a mixture of 2-((tert-butoxycarbonyl)amino)-7-chloro-3-cyanothieno[3,2-c]pyridine 5-oxide (4.4 g, 12 mmol), tetrabutylammonium bromide (5.9 g, 18 mmol), and p-toluenesulfonic anhydride (6.0 g, 18 mmol) in THE (300 mL). The reaction mixture was stirred at RT overnight, then concentrated under reduced pressure. The material was purified on silica, eluting with 0-100% EtOAc in hexanes. Mixed fractions were purified on silica, eluting with MeOH in DCM. Fractions containing desired material from both silica purifications were combined and concentrated to give the title compound (3.0 g, 63%) as an off-white solid. MS (ES) m/z=388 (M+1).

Preparation 4B tert-Butyl (4-chloro-7-methylthieno[3,2-c]pyridin-2-yl)carbamate

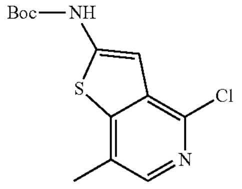 [SMILES: Cc1cnc(Cl)c2cc(NC(=O)OC(C)(C)C)sc12]

Methyl 4-chloro-7-methylthieno[3,2-c]pyridine-2-carboxylate. 2,4-Dichloro-5-methyl-pyridine-3-carbaldehyde (7.25 g, 38.2 mmol), potassium carbonate (10.5 g, 76.0 mmol), and DMF (127 mL) were combined, heated at 70° C. overnight, and cooled to RT. The reaction mixture was added to water (500 mL) and filtered. The solids were rinsed with water and dried to give methyl 4-chloro-7-methyl-thieno[3,2-c]pyridine-2-carboxylate (8.30 g, 90%) as a white solid. MS (ES) m/z=242 (M+1).

4-Chloro-7-methylthieno[3,2-c]pyridine-2-carboxylic acid. Methyl 4-chloro-7-methylthieno[3,2-c]pyridine-2-carboxylate was used in an analogous manner to the method of Preparation 27 to obtain 4-chloro-7-methyl-thieno[3,2-c] pyridine-2-carboxylic acid (6.5 g, 84%) as a white solid. MS (ES) m/z=228 (M+1).

tert-Butyl (4-chloro-7-methylthieno[3,2-c]pyridin-2-yl) carbamate. 4-Chloro-7-methylthieno[3,2-c]pyridine-2-carboxylic acid was used in an analogous manner to the method of Preparation 28 to obtain the title compound (0.83 g, 63%). MS (ES) m/z=299 (M+1).

Preparation 1D tert-Butyl (4-chloro-3-cyano-5-fluorothieno[2,3-b]pyridin-2-yl)carbamate

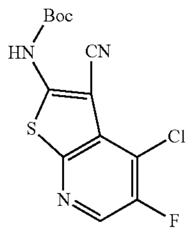 [SMILES: CC(C)(C)OC(=O)Nc1sc2ncc(F)c(Cl)c2c1C#N]

(2-Chloro-5-fluoropyridin-3-yl)methyl methanesulfonate. Methanesulfonicanhydride (11.0 g, 63.2 mmol) was added dropwise to a 0° C. solution of (2-chloro-5-fluoropyridin-3-yl)methanol (7.86 g, 48.7 mmol) and diisopropylethylamine (12.6 mL, 73.0 mmol) in THE (200 mL). The reaction mixture was allowed to warm to RT, then stirred overnight. The mixture was poured into water/ice and diluted with 1:1 MTBE:EtOAc. The layers were separated and the aqueous layer was extracted with 1:1 MTBE:EtOAc. The combined organic layers were washed with brine, dried over magnesium sulfate, filtered, and concentrated under reduced pressure to give crude (2-chloro-5-fluoropyridin-3-yl)methyl methanesulfonate (11.9 g). MS (ES) m/z=240 (M+1).

2-(2-Chloro-5-fluoropyridin-3-yl)acetonitrile. Trimethylsilylnitrile (7.80 mL, 59.6 mmol) was added dropwise to a 0° C. solution of (2-chloro-5-fluoropyridin-3-yl)methyl methanesulfonate (11.9 g, 49.7 mmol) in THE (125 mL) and acetonitrile (125 mL). Tetrabutylammonium fluoride (1M in THF; 59.6 mL, 59.6 mmol) was then added dropwise. The reaction mixture was allowed to warm to RT, stirred for 2 h, then concentrated under reduced pressure. The residue was dissolved in DCM (200 mL) and washed with a mixture of saturated aqueous sodium bicarbonate and brine. The aqueous layer was extracted with DCM (2×100 mL). The combined organic layers were dried over magnesium sulfate, filtered, and concentrated under reduced pressure. The residue was purified on silica, eluting with 0-50% EtOAc in Hexanes. Mixed fractions were combined and purified on silica, eluting with 0-5% (10% MeOH in DCM) in DCM to give 2-(2-chloro-5-fluoropyridin-3-yl)acetonitrile (5.60 g, 66%) as a yellow oil that solidifies in the freezer.

Ethyl (3-cyano-5-fluorothieno[2,3-b]pyridin-2-yl)carbamate. 2-(2-Chloro-5-fluoropyridin-3-yl)acetonitrile was used in a manner analogous to the method of Preparation 30 (substep ethyl (3-cyano-7-fluorothieno[3,2-c]pyridin-2-yl) carbamate) to afford ethyl (3-cyano-5-fluorothieno[2,3-b]pyridin-2-yl)carbamate (24.8 g, 80%) as a brown solid. MS (ES) m/z=266 (M+1).

2-Amino-5-fluorothieno[2,3-b]pyridine-3-carbonitrile. Ethyl (3-cyano-5-fluorothieno[2,3-b]pyridin-2-yl)carbamate was used in a manner analogous to the method of Preparation 30 (substep 2-amino-7-fluorothieno[3,2-c]pyridine-3-carbonitrile) to afford 2-amino-5-fluorothieno[2,3-b]pyridine-3-carbonitrile (17.4 g, 100%) as a brown solid.

tert-Butyl (3-cyano-5-fluorothieno[2,3-b]pyridin-2-yl) carbamate. 2-amino-5-fluorothieno[2,3-b]pyridine-3-carbonitrile was used in a manner analogous to the method of Preparation 30 (substep tert-butyl (3-cyano-7-fluorothieno [3,2-c]pyridin-2-yl)carbamate) to afford tert-butyl (3-cyano-5-fluorothieno[2,3-b]pyridin-2-yl)carbamate (19.6 g, 73%) as a brown solid. MS (ES) m/z=294 (M+1).

2-((tert-Butoxycarbonyl)amino)-3-cyano-5-fluorothieno [2,3-b]pyridine 7-oxide. tert-Butyl (3-cyano-5-fluorothieno [2,3-b]pyridin-2-yl)carbamate was used in a manner analogous to the method of Preparation 30 (substep 2-((tert-butoxycarbonyl)amino)-3-cyano-7-fluorothieno[3,2-c] pyridine 5-oxide) to afford 2-((tert-butoxycarbonyl)amino)-3-cyano-5-fluorothieno[2,3-b]pyridine 7-oxide (10.5 g, 94%) as a white solid. MS (ES) m/z=310 (M+1).

6-Bromo-2-((tert-butoxycarbonyl)amino)-3-cyano-5-fluorothieno[2,3-b]pyridine 7-oxide. To a 0° C. suspension of 2-((tert-butoxycarbonyl)amino)-3-cyano-5-fluorothieno [2,3-b]pyridine 7-oxide (10.5 g, 31.4 mmol) in DCM (150 mL) and EtOAc (150 mL) was added N-bromosuccinimide (6.21 g, 31.4 mmol), then THE (30 mL). The reaction mixture was allowed to warm to RT, stirred for 72 h, then diluted with THE (10 mL). The mixture was treated with silica (10 g) and the solvent was removed under reduced pressure. The remaining solids were purified on silica, eluting with 0-50% (10% EtOAc in DCM) in DCM to give 6-bromo-2-((tert-butoxycarbonyl)amino)-3-cyano-5-fluorothieno[2,3-b]pyridine 7-oxide (8.50 g, 70%). MS (ES) m/z=388 (M+1).

tert-Butyl (6-bromo-4-chloro-3-cyano-5-fluorothieno[2,3-b]pyridin-2-yl)carbamate. To a suspension of 6-bromo-2-((tert-butoxycarbonyl)amino)-3-cyano-5-fluorothieno[2,3-b]pyridine 7-oxide (8.35 g, 21.5 mmol) in THE (108 mL) was added bis(trimethylsilyl)amine (5.40 mL, 25.8 mmol) dropwise. The mixture was cooled to 0° C. and 2,2,2-trichloroacetyl chloride (24.0 mL, 215 mmol) was added dropwise. The reaction mixture was allowed to warm to RT, stirred for 30 min, then heated to 45° C. and stirred for 18 h. The mixture was diluted with aqueous NaOH (1N, 190 mL), DCM (500 mL), and saturated aqueous sodium bicarbonate. A precipitate formed that was removed by filtration. The solids were dissolved in THF/EtOAc. The solution was washed with brine, dried over magnesium sulfate, filtered, and concentrated under reduced pressure to give tert-butyl (6-bromo-4-chloro-3-cyano-5-fluorothieno[2,3-b]pyridin-2-yl)carbamate (5.60 g, 61%). MS (ES) m/z=406 (M+1).

tert-Butyl (4-chloro-3-cyano-5-fluorothieno[2,3-b]pyridin-2-yl)carbamate. A reaction vessel containing tert-butyl (6-bromo-4-chloro-3-cyano-5-fluorothieno[2,3-b]pyridin-2-yl)carbamate (4.00 g, 9.74 mmol) and sodium formate (0.662 g, 9.74 mmol) in DMF (49 mL) was flushed with nitrogen for 30 min, then tetrakis(triphenylphosphine)palladium(0) (2.25 g, 1.95 mmol) was added. The reaction vessel was sealed and stirred at 80° C. for 18 h. Additional tetrakis(triphenylphosphine)palladium(0) (1.1 g, 0.95 mmol) was added. The reaction vessel was sealed and stirred at 80° C. for 25 h, then poured into water/ice and diluted with 1:1 MTBE:EtOAc. The layers were separated and the aqueous layer was extracted with 1:1 MTBE:EtOAc twice more. The combined organic layers were washed with water and brine, dried over magnesium sulfate, filtered, and concentrated under reduced pressure. The residue was purified on silica, eluting with 0-30% EtOAc in Hexanes. Mixed fractions were combined and purified on silica, eluting with 0-10% (10% EtOAc in DCM) in DCM to give the title compound (0.80 g, 25%). MS (ES) m/z=328 (M+1).

Preparation 31 tert-Butyl 8-(6-(2-((tert-butoxycarbonyl)amino)-5-fluorobenzo[b]thiophen-4-yl)-3-(ethylthio)-5-fluoro-7,9-dihydrofuro[3,4-f]quinazolin-1-yl)-3,8-diazabicyclo[3.2.1]octane-3-carboxylate

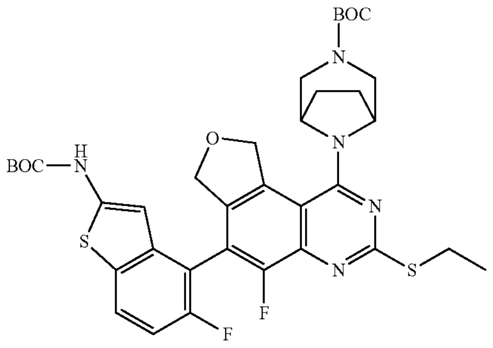 [SMILES: CCSc1nc(N2C3CCC2CN(C(=O)OC(C)(C)C)C3)c2c3c(c(-c4c(F)ccc5sc(NC(=O)OC(C)(C)C)cc45)c(F)c2n1)COC3]

A 250 mL 3-necked RBF, equipped with a thermocouple, condenser and N2 sparge line, was charged with a suspension of tert-butyl 8-(6-bromo-3-(ethylthio)-5-fluoro-7,9-dihydrofuro[3,4-f]quinazolin-1-yl)-3,8-diazabicyclo[3.2.1]octane-3-carboxylate (5.00 g, 9.27 mmol) and tert-butyl (4-(5,5-dimethyl-1,3,2-dioxaborinan-2-yl)-5-fluorobenzo[b]thiophen-2-yl)carbamate (5.53 g, 13.9 mmol, 1.5 eq.) in 1,4-dioxane (100 mL) and $H_2O$ (31 mL). The heat was set to 70° C. and started. At the same time, N2 sparge was started. When the internal temperature had reached −45° C., the sparge line was removed and $K_3PO_4$ (2.95 g, 13.9 mmol, 1.5 eq.) and Pd-118 (0.620 g, 0.932 mmol, 0.10 eq.) were added. The reaction temperature was allowed to reach 70° C. and was stirred for 90 min. The reaction was cooled to RT, then the mixture was diluted with EtOAc, washed with $H_2O$ and partitioned. The aqueous phase was extracted with EtOAc (100 mL), and the combined organics were washed with brine, dried over anhydrous $Na_2SO_4$, filtered and concentrated. MTBE (50 mL) was added and the mixture was sonicated for 20 min. Solids were filtered to obtain product as batch 1. The filtrate was concentrated and the residue was purified on silica, eluting with EtOAc/Hexanes (0-30%). Product-containing fractions were concentrated to a tan foam which was dissolved in DCM (20 mL) and treated dropwise with hexanes (60 mL) while stirring rapidly for 1 h. The resulting solids were filtered and rinsed with hexanes (50 mL) to obtain product as batch 2. The two batches were combined to give the title compound (6.4 g, 880%) as a white solid. MS (ES) m/z=726 (M+1).

The following compounds in Table 1 were prepared in similar manner as described in Preparation 31. Various methods were used to purify the compounds, which would be apparent to one skilled in the art.

TABLE 1

| Preparation | Chemical Name | Structure | MS (ES) m/z (M + 1) |
|---|---|---|---|
| 4A | tert-Butyl (4-(5-chloro-3-(ethylthio)-1-hydroxy-7,9-dihydrofuro[3,4-f]quinazolin-6-yl)-3-cyano-7-fluorobenzo[b]thiophen-2-yl)carbamate | 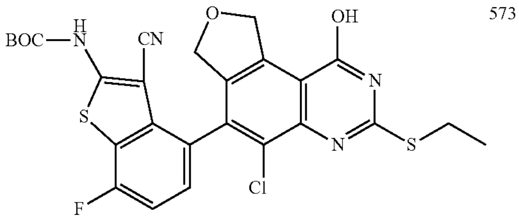 | 573 |
| 5A | tert-Butyl (4-(3-(ethylthio)-5-fluoro-1-hydroxy-7,9-dihydrofuro[3,4-f]quinazolin-6-yl)-5-fluorobenzo[b]thiophen-2-yl)carbamate | 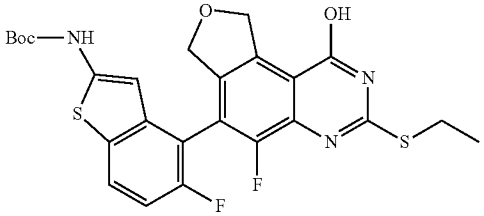 | 532 |
| 5B | tert-Butyl (4-(5-chloro-3-(ethylthio)-7,9-dihydrofuro[3,4-f]quinazolin-6-yl)-5-fluorobenzo[b]thiophen-2-yl)carbamate | 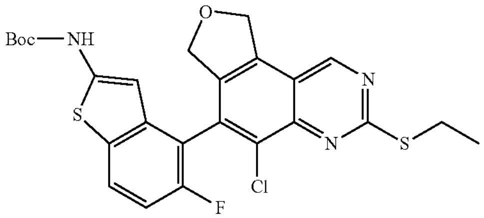 [SMILES: CCSc1ncc2c3c(c(-c4c(F)ccc5sc(NC(=O)OC(C)(C)C)cc45)c(Cl)c2n1)COC3] | 532 |

TABLE 1-continued

| Preparation | Chemical Name | Structure | MS (ES) m/z (M + 1) |
|---|---|---|---|
| 6B | tert-Butyl 8-(6-(2-((tert-butoxycarbonyl)amino)-5-fluorobenzo[b]thiophen-4-yl)-5-chloro-3-(ethylthio)-7,9-dihydrofuro[3,4-f]quinazolin-1-yl)-3,8-diazabicyclo[3.2.1]octane-3-carboxylate | 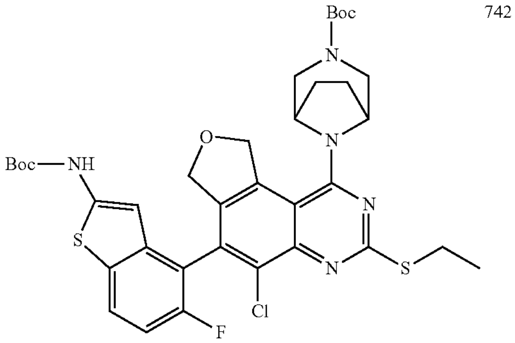 | 742 |
| 7B | tert-Butyl 8-(6-(2-((tert-butoxycarbonyl)amino)-3-cyano-7-fluorobenzo[b]thiophen-4-yl)-5-chloro-3-(ethylthio)-7,9-dihydrofuro[3,4-f]quinazolin-1-yl)-3,8-diazabicyclo[3.2.1]octane-3-carboxylate | 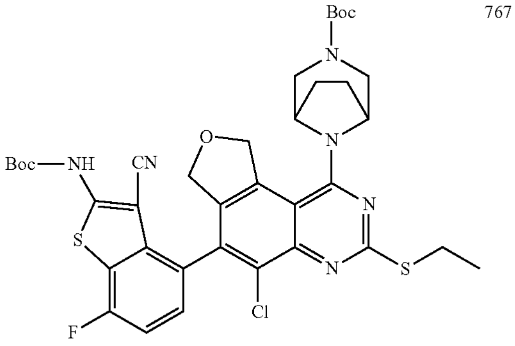 | 767 |
| 2C | tert-Butyl (3-cyano-4-(3-(ethylthio)-5-fluoro-7,9-dihydrofuro[3,4-f]quinazolin-6-yl)benzo[b]thiophen-2-yl)carbamate | 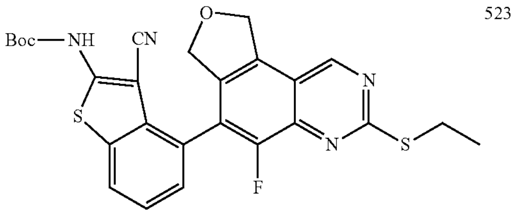 | 523 |

Preparation 32 tert-Butyl 8-(6-(2-((tert-butoxycarbonyl)amino)-3-cyano-5-fluorobenzo[b]thiophen-4-yl)-3-(ethylthio)-5-fluoro-7,9-dihydrofuro[3,4-f]quinazolin-1-yl)-3,8-diazabicyclo[3.2.1]octane-3 -carboxylate

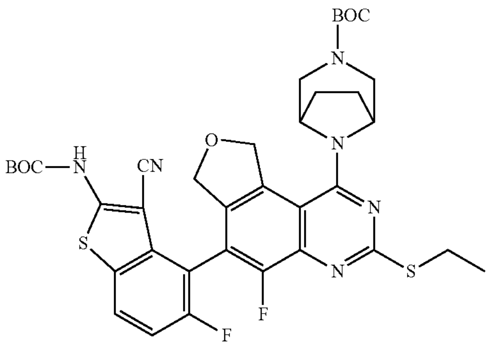 [SMILES: CCSc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3]

tert-Butyl 8-(6-(2-((tert-butoxycarbonyl)amino)-5-fluorobenzo[b]thiophen-4-yl)-3-(ethylthio)-5-fluoro-7,9-dihydrofuro[3,4-f]quinazolin-1-yl)-3,8-diazabicyclo[3.2.1]octane-3-carboxylate (9.00 g, 12.4 mmol) and THE (180 mL) were combined in a flask. The flask was placed in a −45° C. bath under nitrogen. ((Chlorosulfonyl)imino)methanone (7.90 g, 55.8 mmol) was added. After 4 h, the cold reaction mixture was poured into DMF (270 mL) and stirred at 0° C. for 1 h. The mixture was diluted with EtOAc (1 L), then washed with water (2×300 mL) and brine (2×200 mL). The organics were dried over anhydrous $Na_2SO_4$, filtered and concentrated under reduced pressure. The residue was purified on silica, eluting with 20-30% EtOAc in PE to obtain the title compound (6.5 g, 70%) as a white solid. MS (ES) m/z=751 (M+1).

Preparations 8B and 9B tert-Butyl 8-(6-(2-((tert-butoxycarbonyl)amino)-3-cyano-5-fluorobenzo[b]thiophen-4-yl)-3-(ethylthio)-5-fluoro-7,9-dihydrofuro[3,4-f]quinazolin-1-yl)-3,8-diazabicyclo[3.2.1]octane-3-carboxylate, Atropisomer 1 and Atropisomer 2

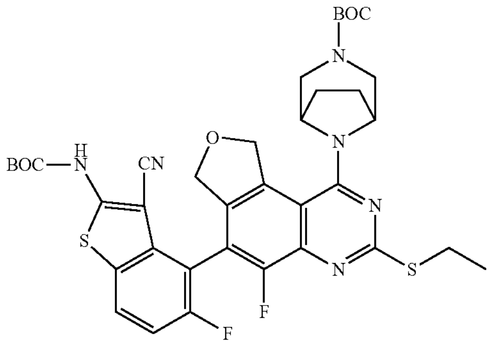 [SMILES: CCSc1nc(N2C3CCC2CN(C(=O)OC(C)(C)C)C3)c2c3c(c(-c4c(F)ccc5sc(NC(=O)OC(C)(C)C)c(C#N)c45)c(F)c2n1)COC3]

Chiral separation of tert-butyl 8-(6-(2-((tert-butoxycarbonyl)amino)-3-cyano-5-fluorobenzo[b]thiophen-4-yl)-3-(ethylthio)-5-fluoro-7,9-dihydrofuro[3,4-f]quinazolin-1-yl)-3,8-diazabicyclo[3.2.1]octane-3-carboxylate (supercritical fluid chromatography; CHIRALPAK AD-H, 50×250 mm, 30% EtOH. 70% $CO_2$, 180 mL/min) was performed, to afford the title compounds (Atropisomer 1 3.20 g; Atropisomer 2 3.25 g). MS (ES) m/z=751 (M+1), for both.

Preparation 10B tert-Butyl (4-(5-chloro-3-(ethylthio)-7,9-dihydrofuro[3,4-f]quinazolin-6-yl)-3-cyano-5-fluorobenzo[b]thiophen-2-yl)carbamate

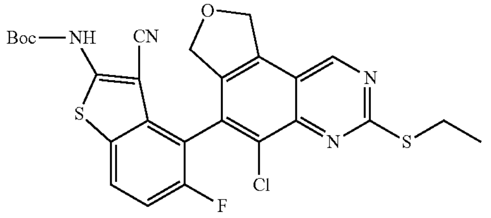 [SMILES: CCSc1ncc2c3c(c(-c4c(F)ccc5sc(NC(=O)OC(C)(C)C)c(C#N)c45)c(Cl)c2n1)COC3]

tert-Butyl (4-(5-chloro-3-(ethylthio)-7,9-dihydrofuro[3,4-f]quinazolin-6-yl)-5-fluorobenzo[b]thiophen-2-yl)carbamate was used in a manner analogous to the method of Preparation 32 to afford the title compound (0.69 g, 82%) as a yellow solid. MS (ES) m/z=557 (M+1).

Preparation 11B tert-Butyl 8-(6-(2-((tert-butoxycarbonyl)amino)-3-cyano-5-fluorobenzo[b]thiophen-4-yl)-5-chloro-3-(ethylthio)-7,9-dihydrofuro[3,4-f]quinazolin-1-yl)-3,8-diazabicyclo[3.2.1]octane-3-carboxylate

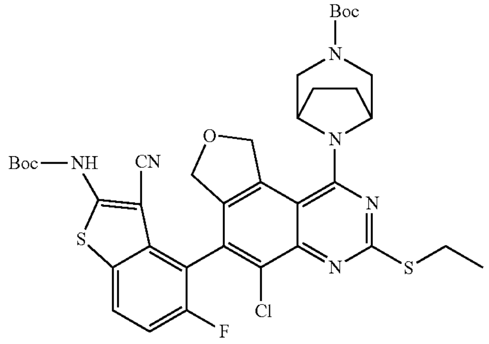 [SMILES: CCSc1nc(N2C3CCC2CN(C(=O)OC(C)(C)C)C3)c2c3c(c(-c4c(F)ccc5sc(NC(=O)OC(C)(C)C)c(C#N)c45)c(Cl)c2n1)COC3]

tert-Butyl 8-(6-(2-((tert-butoxycarbonyl)amino)-5-fluorobenzo[b]thiophen-4-yl)-5-chloro-3-(ethylthio)-7,9-dihydrofuro[3,4-f]quinazolin-1-yl)-3,8-diazabicyclo[3.2.1]octane-3-carboxylate was used in a manner analogous to the method of Preparation 32 to afford the title compound (0.72 g, 50%) as a yellow solid. MS (ES) m/z=767 (M+1).

Preparation 12B tert-Butyl (4-chloro-3-cyano-7-methylthieno[3,2-c]pyridin-2-yl)carbamate

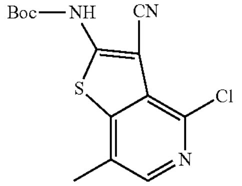 [SMILES: Cc1cnc(Cl)c2c(C#N)c(NC(=O)OC(C)(C)C)sc12]

tert-Butyl (4-chloro-7-methylthieno[3,2-c]pyridin-2-yl)carbamate was used in a manner analogous to the method of Preparation 32 to afford the title compound (0.54 g, 31%). MS (ES) m/z=324 (M+1).

Preparation 6A tert-Butyl (3-cyano-4-(3-(ethylthio)-5-fluoro-1-hydroxy-7,9-dihydrofuro[3,4-f]quinazolin-6-yl)-5-fluorobenzo[b]thiophen-2-yl)carbamate

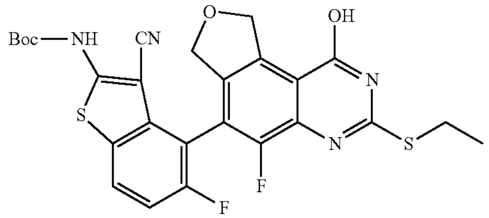 [SMILES: CCSc1nc(O)c2c3c(c(-c4c(F)ccc5sc(NC(=O)OC(C)(C)C)c(C#N)c45)c(F)c2n1)COC3]

A mixture of tert-butyl (4-(3-(ethylthio)-5-fluoro-1-hydroxy-7,9-dihydrofuro[3,4-f]quinazolin-6-yl)-5-fluorobenzo[b]thiophen-2-yl)carbamate (0.750 g, 1.41 mmol) and acetonitrile (10 mL) was stirred at −40° C. Sulfurisocyanatidic chloride (0.184 mL, 2.12 mmol) was slowly added and the mixture was allowed to warm to 0° C. After consumption of the starting material (monitored by LCMS), the mixture was cooled to 0° C. DMF (4 mL) was slowly added. Upon reaction completion (monitored by LCMS), the mixture was diluted with DCM (20 mL) and saturated aq. ammonium chloride (20 mL). The layers were separated and the aqueous layer was extracted with DCM (3×30 mL). The combined organics were passed through a hydrophobic frit and concentrated under reduced pressure to obtain the crude title compound. MS (ES) m/z=557 (M+1).

The following compounds in Table 2 were prepared in similar manner as described in Preparation 22. Various methods were used to purify the compounds, which would be apparent to one skilled in the art.

TABLE 2

| Preparation | Chemical Name | Structure | MS (ES) m/z (M + 1) |
|---|---|---|---|
| 7A | tert-Butyl (3-cyano-4-(1,5-dichloro-3-(ethylthio)-7,9-dihydrofuro[3,4-f]quinazolin-6-yl)-7-fluorobenzo[b]thiophen-2-yl)carbamate | 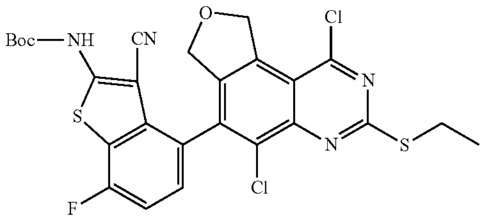 [SMILES: CCSc1nc(Cl)c2c3c(c(-c4ccc(F)c5sc(NC(=O)OC(C)(C)C)c(C#N)c45)c(Cl)c2n1)COC3] | 591 |
| 8A | tert-Butyl (4-(1-chloro-3-(ethylthio)-5-fluoro-7,9-dihydrofuro[3,4-f]quinazolin-6-yl)-3-cyano-5-fluorobenzo[b]thiophen-2-yl)carbamate | 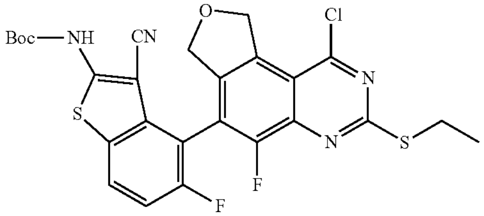 | 575 |

The following compounds in Table 3 were prepared in similar manner as described in Preparation 23. Various methods were used to purify the compounds, which would be apparent to one skilled in the art.

TABLE 3

| Preparation | Chemical Name | Structure | MS (ES) m/z (M + 1) |
|---|---|---|---|
| 9A | tert-Butyl (4-(5-chloro-3-(ethylthio)-7,9-dihydrofuro[3,4-f]quinazolin-6-yl)-3-cyano-7-fluorobenzo[b]thiophen-2-yl)carbamate | 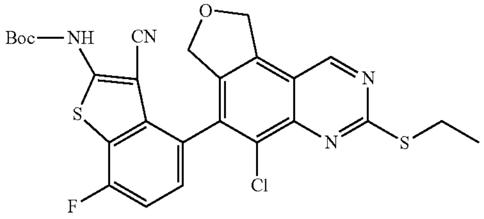 [SMILES: CCSc1ncc2c3c(c(-c4ccc(F)c5sc(NC(=O)OC(C)(C)C)c(C#N)c45)c(Cl)c2n1)COC3] | 557 |
| 10A | tert-Butyl (3-cyano-4-(3-(ethylthio)-5-fluoro-7,9-dihydrofuro[3,4-f]quinazolin-6-yl)-5-fluorobenzo[b]thiophen-2-yl)carbamate | 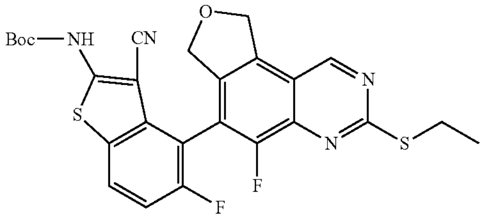 [SMILES: CCSc1ncc2c3c(c(-c4c(F)ccc5sc(NC(=O)OC(C)(C)C)c(C#N)c45)c(F)c2n1)COC3] | 541 |

Preparations 13B and 14B tert-Butyl (3-cyano-4-(3-(ethylthio)-5-fluoro-7,9-dihydrofuro[3,4-f]quinazolin-6-yl)-5-fluorobenzo[b]thiophen-2-yl)carbamate, Atropisomer 1 and Atropisomer 2

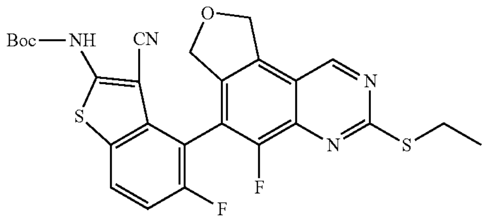 [SMILES: CCSc1ncc2c3c(c(-c4c(F)ccc5sc(NC(=O)OC(C)(C)C)c(C#N)c45)c(F)c2n1)COC3]

Chiral separation of tert-butyl (3-cyano-4-(3-(ethylthio)-5-fluoro-7,9-dihydrofuro[3,4-f]quinazolin-6-yl)-5-fluorobenzo[b]thiophen-2-yl)carbamate (supercritical fluid chromatography; CHIRALPAK IG, 20×250 mm, 35% Isopropanol (with 0.5% dimethylethylamine):65% $CO_2$, 80 mL/min) was performed, to afford the title compounds (Atropisomer 1 0.995 g; Atropisomer 2 0.990 g). MS (ES) m/z=541 (M+1), for both.

Preparation 33 tert-Butyl 8-(6-(2-((tert-butoxycarbonyl)amino)-3-cyano-7-fluorothieno[3,2-c]pyridin-4-yl)-3-(ethylthio)-5-fluoro-7,9-dihydrofuro[3,4-f]quinazolin-1-yl)-3,8-diazabicyclo[3.2.1]octane-3-carboxylate

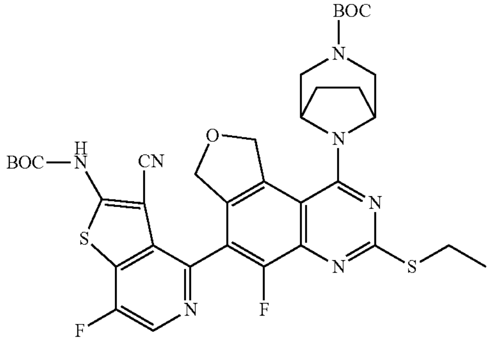 [SMILES: CCSc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3]

To a solution of tert-butyl 8-(6-bromo-3-(ethylthio)-5-fluoro-7,9-dihydrofuro[3,4-f]quinazolin-1-yl)-3,8-diazabicyclo[3.2.1]octane-3-carboxylate (25.0 g, 46.3 mmol) and 5,5,5',5'-tetramethyl-2,2'-bi(1,3,2-dioxaborinane) (20.9 g, 92.7 mmol) in 1,4-dioxane (300 mL) was added potassium acetate (13.6 g, 139 mmol) and dichloropalladium; {2-[2-(diphenylphosphanyl)phenoxy]phenyl}diphenylphosphane (4.98 g, 6.95 mmol) at RT under nitrogen. The mixture was stirred overnight at 85° C., then filtered. The filter cake was washed with 1,4-dioxane (2×100 mL). The filtrate was concentrated under reduced pressure and purified on silica, eluting with 0-20% EtOAc in PE to obtain tert-butyl 8-(6-(5,5-dimethyl-1,3,2-dioxaborinan-2-yl)-3-(ethylthio)-5-fluoro-7,9-dihydrofuro[3,4-f]quinazolin-1-yl)-3,8-diazabicyclo[3.2.1]octane-3-carboxylate (23 g, 87%) as a yellow solid.

To a stirred mixture of tert-butyl 8-(6-(5,5-dimethyl-1,3,2-dioxaborinan-2-yl)-3-(ethylthio)-5-fluoro-7,9-dihydrofuro[3,4-f]quinazolin-1-yl)-3,8-diazabicyclo[3.2.1]octane-3-carboxylate (6.99 g, 12.2 mmol) and tert-butyl (4-chloro-3-cyano-7-fluorothieno[3,2-c]pyridin-2-yl)carbamate (4.00 g, 12.2 mmol) in toluene (150 mL) was added potassium phosphate (7.77 g, 36.6 mmol), [2-dicyclohexylphosphino-2',4',6'-triisopropylbiphenyl] (1.75 g, 3.66 mmol), and XPhos Palladacycle Gen 4 (CAS 1599466-81-5; 0.026 g, 0.031 mmol) at RT under nitrogen. The mixture was stirred for 4 h at 80° C., then diluted with water (300 mL) and extracted with EtOAc (3×200 mL). The combined organic layers were washed with brine (2×300 mL), dried over anhydrous $Na_2SO_4$, filtered and concentrated under reduced pressure. The residue was purified on silica, eluting with 0-45% EtOAc in PE to obtain the title compound (6.0 g, 65%) as a yellow solid. MS (ES) m/z=752 (M+1).

The following compounds in Table 4 were prepared in similar manner as described in Preparation 33. Various methods were used to purify the compounds, which would be apparent to one skilled in the art.

TABLE 4

| Preparation | Chemical Name | Structure | MS (ES) m/z (M + 1) |
|---|---|---|---|
| 34 | tert-Butyl (3-cyano-4-(3-(ethylthio)-5-fluoro-7,9-dihydrofuro[3,4-f]quinazolin-6-yl)-7-fluorothieno[3,2-c]pyridin-2-yl)carbamate | 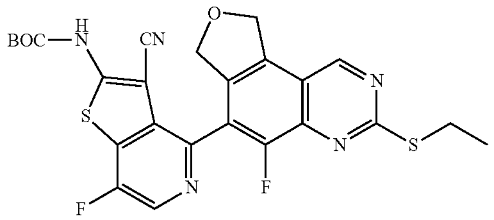 [SMILES: CCSc1ncc2c3c(c(-c4ncc(F)c5sc(NC(=O)OC(C)(C)C)c(C#N)c45)c(F)c2n1)COC3] | 542 |

TABLE 4-continued

| Preparation | Chemical Name | Structure | MS (ES) m/z (M + 1) |
|---|---|---|---|
| 35 | tert-Butyl (3-cyano-7-fluoro-4-(5-fluoro-7-((1-(morpholinomethyl)cyclo propyl)methoxy)-1,3-dihydrofuro[3,4-f]quinolin-4-yl)thieno[3,2-c]pyridin-2-yl)carbamate | 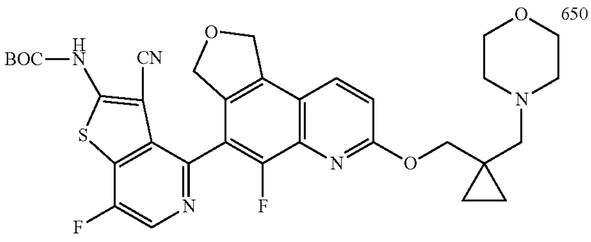 | 650 |
| 36 | tert-Butyl (4-(1-(3-((R)-2-((tert-butyldimethylsilyl)oxy) propyl)-3,8-diazabicyclo[3.2.1]octan-8-yl)-3-(ethylthio)-5-fluoro-7,9-dihydrofuro[3,4-f]quinazolin-6-yl)-3-cyano-7-fluorothieno[3,2-c]pyridin-2-yl)carbamate | 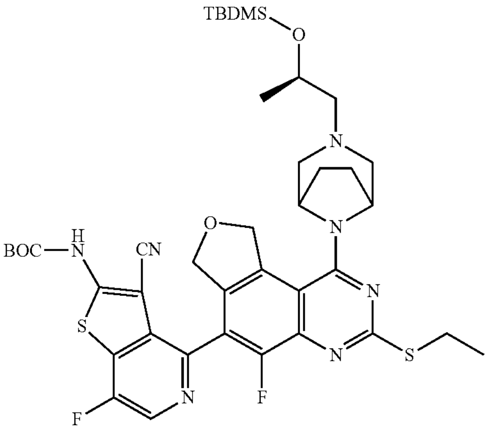 | 824 |
| 15B | tert-Butyl (3-cyano-4-(3-(ethylthio)-5-fluoro-7,9-dihydrofuro[3,4-f]quinazolin-6-yl)-7-methylthieno[3,2-c]pyridin-2-yl)carbamate | 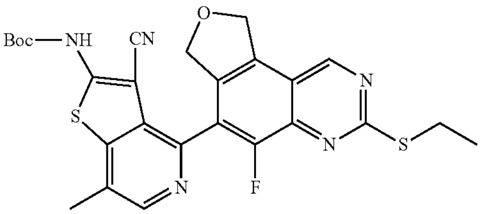 [SMILES: CCSc1ncc2c3c(c(-c4ncc(C)c5sc(NC(=O)OC(C)(C)C)c(C#N)c45)c(F)c2n1)COC3] | 538 |
| 16B | tert-Butyl (4-(5-chloro-3-(ethylthio)-7,9-dihydrofuro[3,4-f]quinazolin-6-yl)-3-cyano-7-fluorothieno[3,2-c]pyridin-2-yl)carbamate | 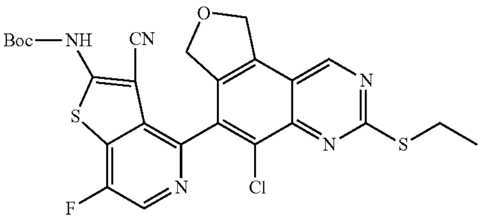 [SMILES: CCSc1ncc2c3c(c(-c4ncc(F)c5sc(NC(=O)OC(C)(C)C)c(C#N)c45)c(Cl)c2n1)COC3] | 558 |
| 17B [1] | tert-Butyl (4-(5-chloro-3-(ethylthio)-7,9-dihydrofuro[3,4-f]quinazolin-6-yl)-3-cyano-7-fluorothieno[3,2-c]pyridin-2-yl)carbamate, Atropisomer 1 | 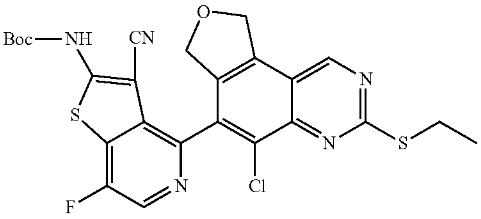 [SMILES: CCSc1ncc2c3c(c(-c4ncc(F)c5sc(NC(=O)OC(C)(C)C)c(C#N)c45)c(Cl)c2n1)COC3] | 558 |

TABLE 4-continued

| Preparation | Chemical Name | Structure | MS (ES) m/z (M + 1) |
|---|---|---|---|
| 18B [1] | tert-Butyl (4-(5-chloro-3-(ethylthio)-7,9-dihydrofuro[3,4-f]quinazolin-6-yl)-3-cyano-7-fluorothieno[3,2-c]pyridin-2-yl)carbamate, Atropisomer 2 | 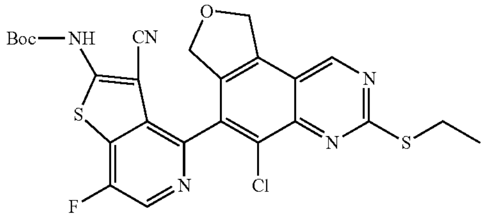 [SMILES: CCSc1ncc2c3c(c(-c4ncc(F)c5sc(NC(=O)OC(C)(C)C)c(C#N)c45)c(Cl)c2n1)COC3] | 558 |
| 3C | tert-Butyl (7-chloro-3-cyano-4-(3-(ethylthio)-5-fluoro-7,9-dihydrofuro[3,4-f]quinazolin-6-yl)thieno[3,2-c]pyridin-2-yl)carbamate | 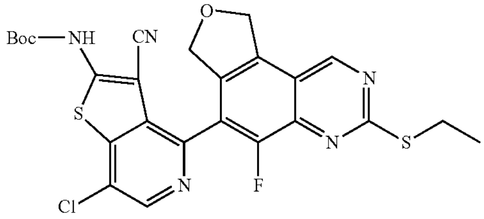 [SMILES: CCSc1ncc2c3c(c(-c4ncc(Cl)c5sc(NC(=O)OC(C)(C)C)c(C#N)c45)c(F)c2n1)COC3] | 558 |
| 2D | tert-Butyl (3-cyano-4-(3-(ethylthio)-5-fluoro-7,9-dihydrofuro[3,4-f]quinazolin-6-yl)-5-fluorothieno[2,3-b]pyridin-2-yl)carbamate | 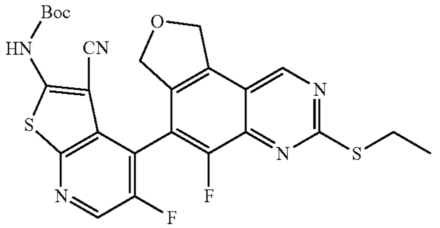 [SMILES: CCSc1ncc2c3c(c(-c4c(F)cnc5sc(NC(=O)OC(C)(C)C)c(C#N)c45)c(F)c2n1)COC3] | 542 |

[1] Prep-Chiral-HPLC; Phenomenex Lux i-Cellulose-5, 30 × 150 mm, 10-65% EtOH in Heptane, 42.5 mL/min

Preparation 37 tert-Butyl 8-(6-(2-((tert-butoxycarbonyl)amino)-3-cyano-7-fluorothieno[3,2-c]pyridin-4-yl)-3-(ethyl sulfonyl)-5-fluoro-7,9-dihydrofuro[3,4-f]quinazolin-1-yl)-3,8-diazabicyclo[3.2.1]octane-3-carboxylate

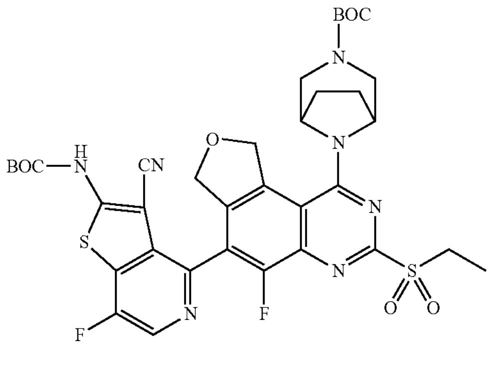 [SMILES: CCS(=O)(=O)c1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3]

To a solution of tert-butyl 8-(6-(2-((tert-butoxycarbonyl) amino)-3-cyano-7-fluorothieno[3,2-c]pyridin-4-yl)-3-(ethylthio)-5-fluoro-7,9-dihydrofuro[3,4-f]quinazolin-1-yl)-3,8-diazabicyclo[3.2.1]octane-3-carboxylate (8.4 g, 11.2 mmol) in DCM (100 mL) was added mCPBA (4.05 g, 23.5 mmol) in portions at 0° C. The reaction mixture was stirred for 3 h at 0° C. The mixture was diluted with DCM (800 mL) and washed with sat. aq. $NaHCO_3$ (3×400 mL) and brine (2×300 mL). The organics were dried over anhydrous $Na_2SO_4$, filtered and concentrated under reduced pressure. The residue was purified on silica, eluting with 0-10% MeOH in DCM to obtain the title compound (8.3 g, 95%) as an off-white solid. MS (ES) m/z=784 (M+1).

The following compounds in Table 5 were prepared in similar manner as described in Preparation 37. Various methods were used to purify the compounds, which would be apparent to one skilled in the art.

TABLE 5

| Preparation | Chemical Name | Structure | MS (ES) m/z (M + 1) |
|---|---|---|---|
| 38 | tert-Butyl 8-(6-(2-((tert-butoxycarbonyl)amino)-3-cyano-5-fluorobenzo[b]thiophen-4-yl)-3-(ethylsulfonyl)-5-fluoro-7,9-dihydrofuro[3,4-f]quinazolin-1-yl)-3,8-diazabicyclo[3.2.1] octane-3-carboxylate | 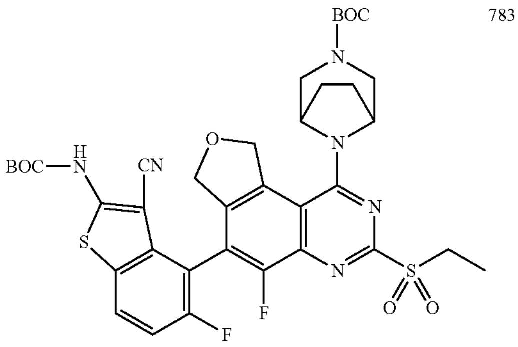 | 783 |
| 39 | tert-Butyl (3-cyano-4-(3-(ethylsulfonyl)-5-fluoro-7,9-dihydrofuro[3,4-f]quinazolin-6-yl)-7-fluorothieno[3,2-c]pyridin-2-yl)carbamate | 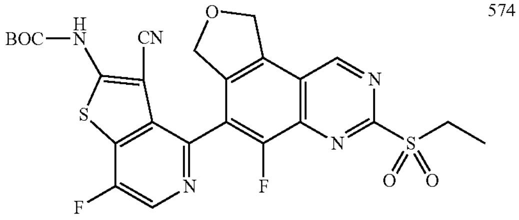 | 574 |
| 40 | 6-Bromo-3-(ethylsulfonyl)-5-fluoro-7,9-dihydrofuro[3,4-f]quinazoline | 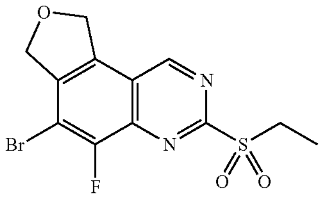 [SMILES: CCS(=O)(=O)c1ncc2c3c(c(Br)c(F)c2n1)COC3] | 360 |
| 11A | tert-Butyl (4-(5-chloro-3-(ethylsulfonyl)-7,9-dihydrofuro[3,4-f]quinazolin-6-yl)-3-cyano-7-fluorobenzo[b]thiophen-2-yl)carbamate | 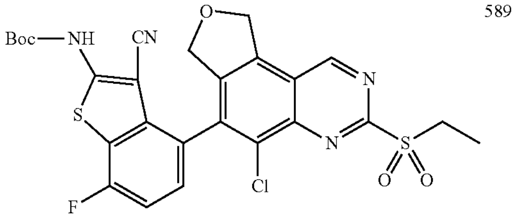 | 589 |
| 12A | tert-Butyl (3-cyano-4-(3-(ethylsulfonyl)-5-fluoro-7,9-dihydrofuro[3,4-f]quinazolin-6-yl)-5-fluorobenzo[b]thiophen-2-yl)carbamate | 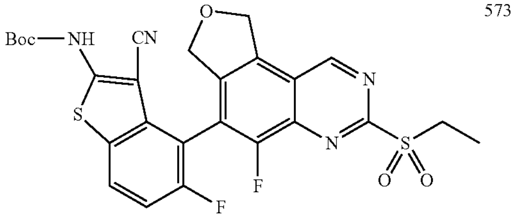 | 573 |
| 19B | tert-Butyl (4-(5-chloro-3-(ethylsulfonyl)-7,9-dihydrofuro[3,4-f]quinazolin-6-yl)-3-cyano-5-fluorobenzo[b]thiophen-2-yl)carbamate | 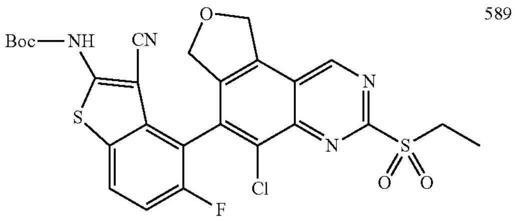 | 589 |

TABLE 5-continued

| Preparation | Chemical Name | Structure | MS (ES) m/z (M + 1) |
|---|---|---|---|
| 20B | tert-Butyl (3-cyano-4-(3-(ethylsulfonyl)-5-fluoro-7,9-dihydrofuro[3,4-f]quinazolin-6-yl)-7-methylthieno[3,2-c]pyridin-2-yl)carbamate | 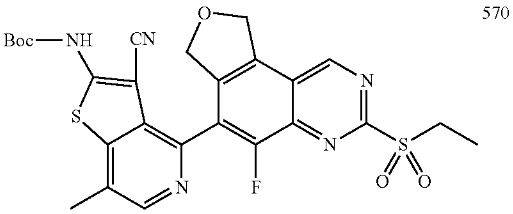 | 570 |
| 21B | tert-Butyl (4-(5-chloro-3-(ethylsulfonyl)-7,9-dihydrofuro[3,4-f]quinazolin-6-yl)-3-cyano-7-fluorothieno[3,2-c]pyridin-2-yl)carbamate | 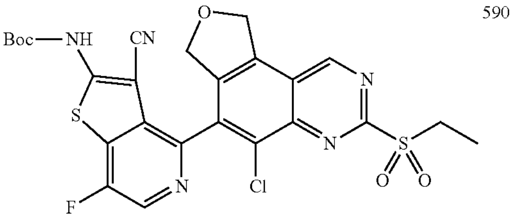 | 590 |
| 22B [1] | tert-Butyl (4-(5-chloro-3-(ethylsulfonyl)-7,9-dihydrofuro[3,4-f]quinazolin-6-yl)-3-cyano-7-fluorothieno[3,2-c]pyridin-2-yl)carbamate. Atropisomer 1 | 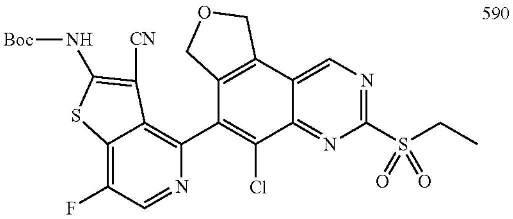 | 590 |
| 23B [2] | tert-Butyl (4-(5-chloro-3-(ethylsulfonyl)-7,9-dihydrofuro[3,4-f]quinazolin-6-yl)-3-cyano-7-fluorothieno[3,2-c]pyridin-2-yl)carbamate. Atropisomer 2 | 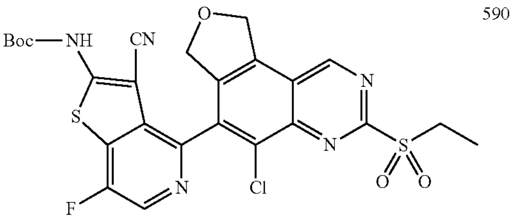 | 590 |
| 24B [3] | tert-Butyl (3-cyano-4-(3-(ethylsulfonyl)-5-fluoro-7,9-dihydrofuro[3,4-f]quinazolin-6-yl)-5-fluorobenzo[b]thiophen-2-yl)carbamate | 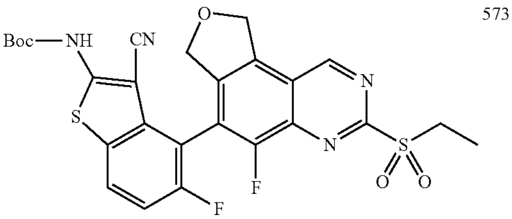 | 573 |
| 25B | tert-Butyl 8-(6-(2-((tert-butoxycarbonyl)amino)-3-cyano-5-fluorobenzo[b]thiophen-4-yl)-5-chloro-3-(ethylsulfonyl)-7,9-dihydrofuro[3,4-f]quinazolin-1-yl)-3,8-diazabicyclo[3.2.1]octane-3-carboxylate | 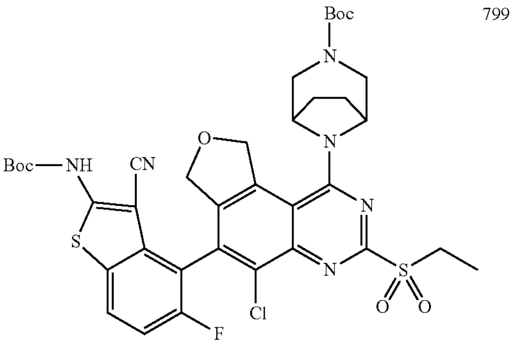 | 799 |

TABLE 5-continued

| Preparation | Chemical Name | Structure | MS (ES) m/z (M + 1) |
|---|---|---|---|
| 26B | tert-Butyl 8-(6-(2-((tert-butoxycarbonyl)amino)-3-cyano-7-fluorobenzo[b]thiophen-4-yl)-5-chloro-3-(ethylsulfonyl)-7,9-dihydrofuro[3,4-f]quinazolin-1-yl)-3,8-diazabicyclo[3.2.1] octane-3-carboxylate | 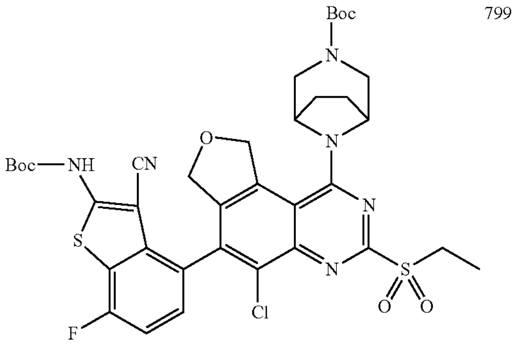 | 799 |
| 27B [4] | tert-Butyl 8-(6-(2-((tert-butoxycarbonyl)amino)-3-cyano-5-fluorobenzo[b]thiophen-4-yl)-3-(ethylsulfonyl)-5-fluoro-7,9-dihydrofuro[3,4-f]quinazolin-1-yl)-3,8-diazabicyclo[3.2.1] octane-3-carboxylate | 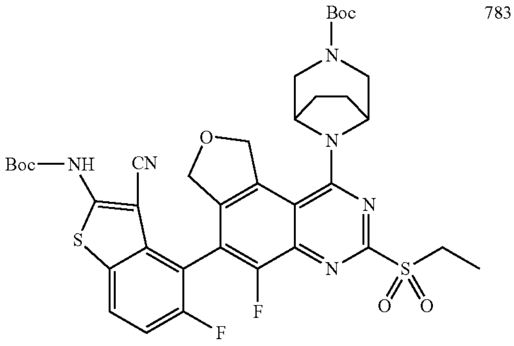 | 783 |
| 4C | tert-Butyl (3-cyano-4-(3-(ethylsulfonyl)-5-fluoro-7,9-dihydrofuro[3,4-f]quinazolin-6-yl)benzo[b]thiophen-2-yl)carbamate | 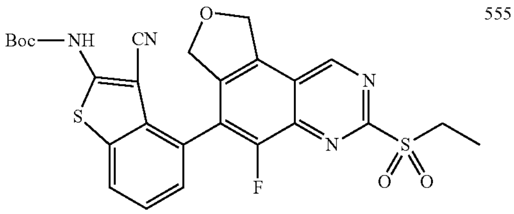 | 555 |
| 5C | tert-Butyl (7-chloro-3-cyano-4-(3-(ethylsulfonyl)-5-fluoro-7,9-dihydrofuro[3,4-f]quinazolin-6-yl)thieno[3,2-c]pyridin-2-yl)carbamate | 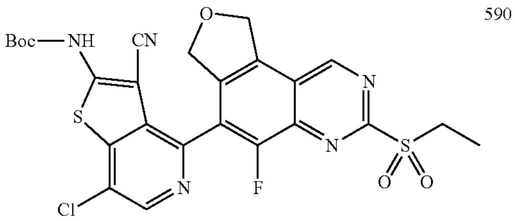 | 590 |
| 3D | tert-Butyl (3-cyano-4-(3-(ethylsulfonyl)-5-fluoro-7,9-dihydrofuro[3,4-f]quinazolin-6-yl)-5-fluorothieno[2,3-b]pyridin-2-yl)carbamate | 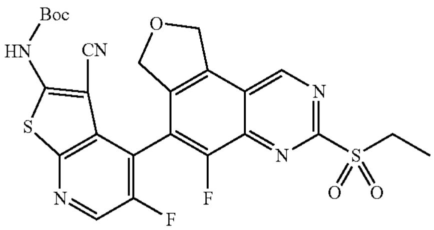 [SMILES: CCS(=O)(=O)c1ncc2c3c(c(-c4c(F)cnc5sc(NC(=O)OC(C)(C)C)c(C#N)c45)c(F)c2n1)COC3] | 574 |

[1] Single atropisomer (from precursor in Preparation 17B)

[2] Single atropisomer (from precursor in Preparation 18B)

[3] Single atropisomer (from precursor in Preparation 14B)

[4] Single atropisomer (from precursor in Preparation 9B)

Preparation 41 tert-Butyl (4-(1-(3-((R)-2-((tert-butyldimethylsilyl)oxy)propyl)-3,8-diazabicyclo[3.2.1]octan-8-yl)-3-(ethylsulfonyl)-5-fluoro-7,9-dihydrofuro[3,4-f]quinazolin-6-yl)-3-cyano-7-fluorothieno[3,2-c]pyridin-2-yl)carbamate

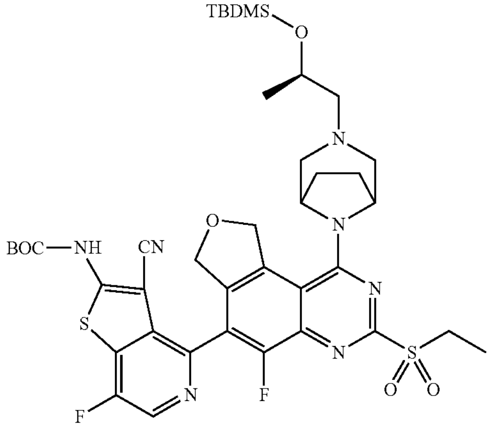

tert-Butyl (4-(1-(3-((R)-2-((tert-butyldimethylsilyl)oxy)propyl)-3,8-diazabicyclo[3.2.1]octan-8-yl)-3-(ethylthio)-5-fluoro-7,9-dihydrofuro[3,4-f]quinazolin-6-yl)-3-cyano-7-fluorothieno[3,2-c]pyridin-2-yl)carbamate (4 g, 5 mmol), hexaammonium heptamolybdate tetrahydrate (1 g, 1 mmol), and hydrogen peroxide (8 mL, 35 wt % in water, 100 mmol) were combined in DCM (30 mL) and EtOH (30 mL). The mixture was stirred at RT for 1 h, then concentrated under reduced pressure. Diluted with water (100 mL) and stirred 30 min. Filtered and dried the resulting solids in a vacuum oven (45° C.) to give the title compound (2 g, 50%) as a white solid. MS (ES) m/z=856 (M+1).

Preparation 28B (1-(((3aR,6aS)-Tetrahydro-1H-furo[3,4-c]pyrrol-5(3H)-yl)methyl)cyclopropyl)methanol

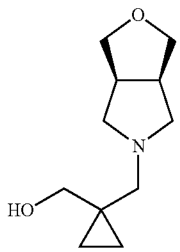 [SMILES: OCC1(CN2C[C@H]3COC[C@H]3C2)CC1]

To a stirred solution of ethyl 1-(bromomethyl)cyclopropane-1-carboxylate (1.5 g, 7.2 mmol) and (3aR,6aS)-hexahydro-1H-furo[3,4-c]pyrrole hydrochloride (0.82 g, 7.2 mmol) in acetonitrile (15 mL) was added potassium carbonate (2.00 g, 14.5 mmol) at RT under nitrogen. The mixture was stirred at RT for 3 h, then filtered. The filter cake was washed with acetonitrile (2×20 mL). The combined filtrates were concentrated under reduced pressure to give crude ethyl 1-(((3aR,6aS)-tetrahydro-1H-furo[3,4-c]pyrrol-5(3H)-yl)methyl)cyclopropane-1-carboxylate (1.2 g, 69%) as a colorless oil. MS (ES) m/z=240 (M+1).

The crude ethyl ester (1.2 g, 5.0 mmol) was mixed with THE (10 mL) and cooled to 0° C. under nitrogen. Lithium aluminum hydride (2.5M in THF, 10 mL, 25 mmol) was added dropwise and the mixture was allowed to stir at RT. After 1 h, the reaction mixture was cooled to 0° C. and quenched with water (0.95 g), aqueous NaOH (0.95 g), and water (3×0.95 g). The resulting mixture was filtered. The filter cake was washed with THF (3×100 mL). The combined filtrates were concentrated under reduced pressure to give crude (1-(((3aR,6aS)-tetrahydro-1H-furo[3,4-c]pyrrol-5(3H)-yl)methyl)cyclopropyl)methanol (0.75 g, 76%) as a colorless oil. MS (ES) m/z=198 (M+1).

Preparation 42

(1-((4-Fluoropiperidin-1-yl)methyl)cyclopropyl)methanol

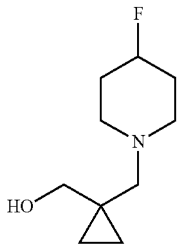 [SMILES: OCC1(CN2CCC(F)CC2)CC1]

1-(Methoxycarbonyl)cyclopropane-1-carboxylic acid (0.800 g, 5.55 mmol), oxalyl chloride (0.54 mL, 6.11 mmol), DCM (13.9 mL) and DMF (0.022 mL) were combined, stirred at RT for 1 h, and concentrated under reduced pressure to give crude methyl 1-(chlorocarbonyl)cyclopropane-1-carboxylate.

The crude acid chloride was combined with 4-fluoropiperidine (0.59 mL, 5.55 mmol) and triethylamine (3.87 mL, 27.8 mmol) in DCM (13.9 mL). The mixture was stirred at RT for 2 h, then concentrated under reduced pressure. The residue was dissolved in EtOAc (30 mL) and washed with aqueous $KHSO_4$ (1M, 30 mL) and saturated aqueous $NaHCO_3$ (30 mL). The organics were dried over magnesium sulfate and concentrated under reduced pressure to give crude methyl 1-(4-fluoropiperidine-1-carbonyl)cyclopropane-1-carboxylate (0.93 g, 73%).

The crude methyl ester was mixed with THE (20 mL) and cooled to 0° C. Lithium aluminum hydride (2M in THF, 4.05 mL, 8.10 mmol) was added dropwise and the mixture was allowed to stir at RT. After 1 h, the reaction mixture was diluted with EtOAc (20 mL). Water (0.31 mL), aqueous NaOH (2M, 0.31 mL), and water (0.62 mL) were added in succession. The mixture was stirred at RT. After 30 min, the mixture was filtered through diatomaceous earth. The filtrate was concentrated under reduced pressure to give the title compound (0.60 g, 790%) as a colorless oil, with no further purification. MS (ES) m/z=188 (M+1).

The following compounds in Table 6 were prepared in similar manner as described in Preparation 42. Various methods were used to purify the compounds, which would be apparent to one skilled in the art.

TABLE 6

| Preparation | Chemical Name | Structure | MS (ES) m/z (M + 1) |
| --- | --- | --- | --- |
| 43[1] | (1-((6-Methyl-2,6-diazaspiro[3.3 ]heptan-2-yl)methyl)cyclopropyl)methanol | 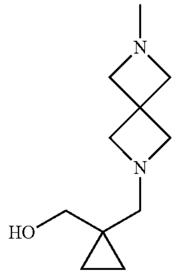 | |
| 44 | (1-((4,4-Difluoropiperidin-1-yl)methyl)cyclopropyl)methanol | 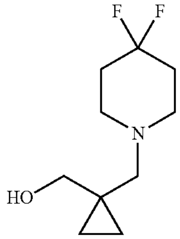 [SMILES: OCC1(CN2CCC(F)(F)CC2)CC1] | |
| 45 | (1-((6,6-Difluoro-3-azabicyclo[3.1.0]hexan-3-yl)methyl) cyclopropyl)methanol | 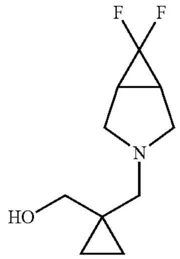 [SMILES: OCC1(CN2CC3C(C2)C3(F)F)CC1] | |
| 46 | (1-((3-Methoxyazetidin-1-yl)methyl) cyclopropyl)methanol | 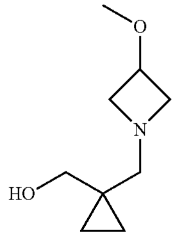 | 172 |
| 47 | (1-((3-(Fluoromethyl)azetidin-1-yl)methyl) cyclopropyl)methanol | 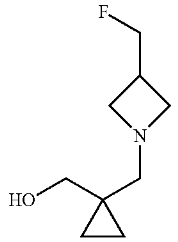 [SMILES: OCC1(CN2CC(CF)C2)CC1] | 174 |
| 48 | (R)-(1-((3-Methylmorpholino)methy1)cyclopropyl)methanol | 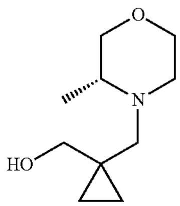 | |

TABLE 6-continued

| Preparation | Chemical Name | Structure | MS (ES) m/z (M + 1) |
|---|---|---|---|
| 49 | (1-(((1S,4S)-2-Oxa-5-azabicyclo[2.2.1]heptan-5-yl)methyl)cyclopropyl) methanol | 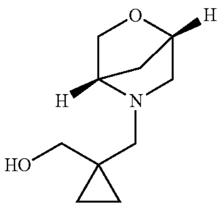 [SMILES: OCC1(CN2C[C@@H]3C[C@H]2CO3)CC1] | 184 |
| 50 | (1-(Morpholinomethyl) cyclobutyl)methanol | 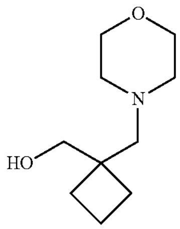 [SMILES: OCC1(CN2CCOCC2)CCC1] | 186 |
| 51 | (1-(Azetidin-1-ylmethyl)cyclopropyl) methanol | 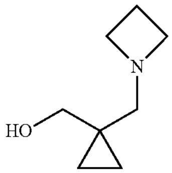 | |
| 52 | (1-((6-Oxa-2-azaspiro[3.4]octan-2-yl)methyl)cyclopropyl) methanol | 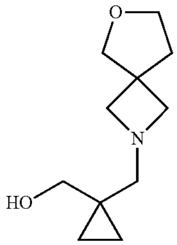 [SMILES: OCC1(CN2CC3(CCOC3)C2)CC1] | |
| 53 | (1-((3-Fluoroazetidin-1-yl)methyl)cyclopropyl) methanol | 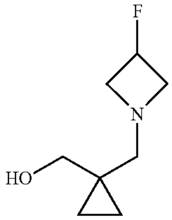 [SMILES: OCC1(CN2CC(F)C2)CC1] | 160 |
| 54 | 2-(1-((1-(Hydroxymethyl) cyclopropyl)methyl) azetidin-3-yl)propan-2-ol | 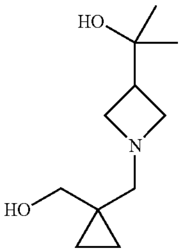 | 200 |

TABLE 6-continued

| Preparation | Chemical Name | Structure | MS (ES) m/z (M + 1) |
|---|---|---|---|
| 55 | (1-((7-Oxa-2-azaspiro[3.5]nonan-2-yl)methyl)cyclopropyl) methanol | 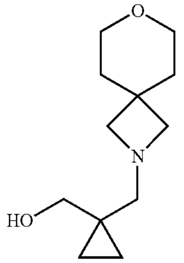 [SMILES: OCC1(CN2CC3(CCOCC3)C2)CC1] | |
| 56[2] | (1-(Morpholinomethyl-d2)cyclopropyl)methan-d2-ol | 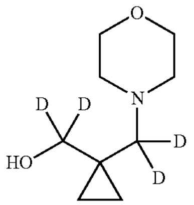 [SMILES: [2H]C([2H])(O)C1(C([2H])([2H])N2CCOCC2)CC1] | |
| 13A | (1-((1,4-Oxazepan-4-yl)methyl)cyclopropyl) methanol | 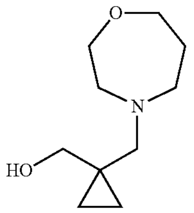 [SMILES: OCC1(CN2CCCOCC2)CC1] | 186 |
| 14A | (1-((-3-oxa-8-azabicyclo[3.2.1 ]octan-8-yl)methyl)cyclopropyl) methanol | 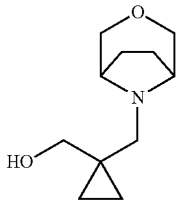 [SMILES: OCC1(CN2C3CCC2COC3)CC1] | 198 |
| 15A | (1-(((1R,4R)-2-Oxa-5-azabicyclo[2.2.1 ]heptan-5-yl)methyl) cyclopropyl)methanol | 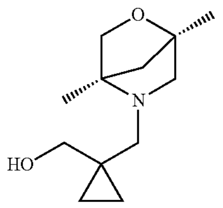 | 184 |
| 16A | (R)-(1-((3-Methoxypyrrolidin-1-yl)methyl)cyclopropyl) methanol | 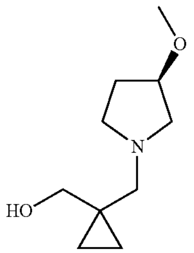 | 186 |

TABLE 6-continued

| Preparation | Chemical Name | Structure | MS (ES) m/z (M + 1) |
|---|---|---|---|
| 17A | 1-((1-(Hydroxymethyl) cyclopropyl)methyl) azetidin-3-ol | 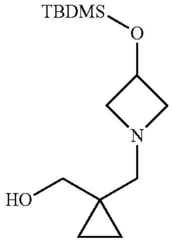 | 272 |
| 18A | (1-((3-Fluoropiperidin-1-yl)methyl)cyclopropyl) methanol | 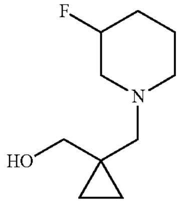 [SMILES: OCC1(CN2CCCC(F)C2)CC1] | 188 |
| 19A | (1-((3,3-Dimethylazetidin-1-yl)methyl)cyclopropyl) methanol | 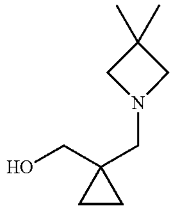 | |
| 20A | (1-(((3R,4S)-3,4-Difluoropyrrolidin-1-yl)methyl)cyclopropyl) methanol | 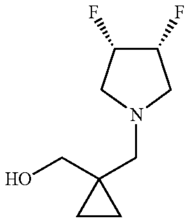 [SMILES: OCC1(CN2C[C@@H](F)[C@@H](F)C2)CC1] | |

[1]using tert-butyl 2-(2,6-diazaspiro[3.3]heptan-2-yl)acetate
[2]using deuterated lithium aluminum hydride

Preparation 29B tert-Butyl (3S,4R)-3-amino-4-(hydroxymethyl)pyrrolidine-1-carboxylate

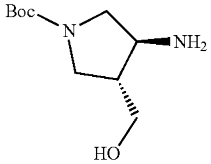 [SMILES: CC(C)(C)OC(=O)N1C[C@@H](CO)[C@H](N)C1]

To a solution of 1-(tert-butyl) 3-ethyl (3R,4S)-4-aminopyrrolidine-1,3-dicarboxylate (0.100 g, 0.387 mmol) in THE (3 mL) was added lithium aluminum hydride (1M in diethyl ether, 0.465 mL, 0.465 mmol). The reaction mixture was stirred for 3 h at 0° C., then diluted with MTBE (5 mL), water (5 drops, at which point fizzing ceased), and aqueous NaOH (1500, 5 drops). The mixture was stirred at RT. After 15 min, the mixture was dried with magnesium sulfate and filtered. The filtrate was concentrated under reduced pressure to give the crude title compound (0.084 g, 1000%) with no further purification.

Preparation 30B tert-Butyl (3R,4S)-3-amino-4-(hydroxymethyl)pyrrolidine-1-carboxylate

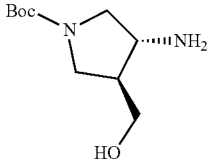 [SMILES: CC(C)(C)OC(=O)N1C[C@H](CO)[C@@H](N)C1]

1-(tert-Butyl) 3-ethyl (3S,4R)-4-aminopyrrolidine-1,3-dicarboxylate was used in a manner analogous to the method of Preparation 29B to afford the crude title compound (0.100 g, 100%).

Preparation 31B tert-Butyl (2S,3S)-3-((tert-butoxycarbonyl)amino)-2-methylpyrrolidine-1-carboxylate

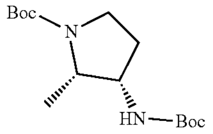 [SMILES: C[C@H]1[C@@H](NC(=O)OC(C)(C)C)CCN1C(=O)OC(C)(C)C]

tert-Butyl (2S,3S)-3-amino-2-methylpyrrolidine-1-carboxylate (0.450 g, 2.25 mmol), Boc-anhydride (0.687 g, 3.15 mmol) and diisopropylethylamine (1.96 mL, 11.2 mmol) were combined in chloroform (10 mL). The reaction mixture was stirred overnight at RT, then diluted with saturated aqueous ammonium chloride (20 mL). The mixture was extracted with DCM (3×20 mL). The combined organic layers were passed through a hydrophobic frit and the filtrate was concentrated under reduced pressure to give the crude title compound (0.60 g, 90%) with no further purification. MS (ES) m/z=323 (M+Na).

Preparation 4D tert-Butyl 3-(azetidin-1-yl)-4-hydroxypyrrolidine-1-carboxylate

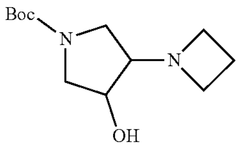 [SMILES: CC(C)(C)OC(=O)N1CC(O)C(N2CCC2)C1]

A mixture of tert-butyl 6-oxa-3-aza-bicyclo[3.1.0]hexane-3-carboxylate (3 g, 20 mmol) and azetidine (1 mL, 20 mmol) in water (20 mL) was heated at 80° C. for 4.5 h, then cooled to RT. The mixture was extracted with EtOAc. The organic layer was dried over magnesium sulfate, filtered, and concentrated under reduced pressure. The residue was purified by reversed phase purification, eluting with 2000 ACN in aq. $NH_4HCO_3$ with pH 9 buffer, to give the title compound (2.4 g, 60%) as a white solid. MS (ES) m/z=243 (M+1). The title compound is a mix of Trans Isomers.

The following compounds in Table 7 were prepared in similar manner as described in Preparation 4D. Various methods were used to purify the compounds, which would be apparent to one skilled in the art.

TABLE 7

| Preparation | Chemical Name | Structure | MS (ES) m/z (M + 1) |
|---|---|---|---|
| 5D [1] | tert-Butyl 3-((S)-2,4-dimethylpiperazin-1-yl)-4-hydroxypyrrolidine-1-carboxylate, Isomer 2 | 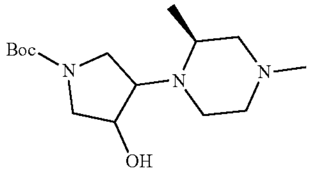 [SMILES: C[C@H]1CN(C)CCN1C1CN(C(=O)OC(C)(C)C)CC1O] | 300 |
| 6D [1] | tert-Butyl 3-((S)-2,4-dimethylpiperazin-1-yl)-4-hydroxypyrrolidine-1-carboxylate, Isomer 1 | 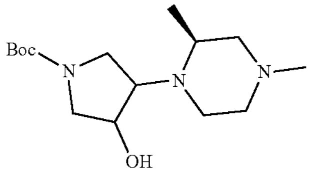 [SMILES: C[C@H]1CN(C)CCN1C1CN(C(=O)OC(C)(C)C)CC1O] | 300 |
| 7D [2] | tert-Butyl 3-((S)-3,4-dimethylpiperazin-1-yl)-4-hydroxypyrrolidine-1-carboxylate | 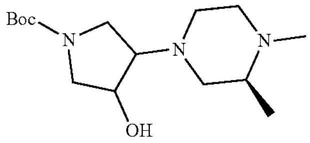 [SMILES: C[C@H]1CN(C2CN(C(=O)OC(C)(C)C)CC2O)CCN1C] | 300 |
| 8D [3] | tert-Butyl 3-hydroxy-4-(3-methyl-3,8-diazabicyclo[3.2.1]octan-8-yl)pyrrolidine-1-carboxylate | 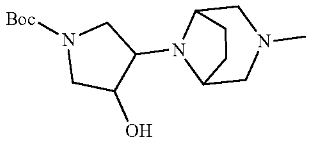 [SMILES: CN1CC2CCC(C1)N2C1CN(C(=O)OC(C)(C)C)CC1O] | 312 |
| 9D [4] | tert-Butyl 3-hydroxy-4-(piperidin-1-yl)pyrrolidine-1-carboxylate, Isomer 1 | 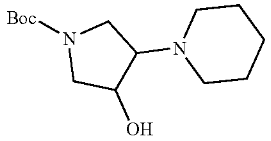 [SMILES: CC(C)(C)OC(=O)N1CC(O)C(N2CCCCC2)C1] | 271 |

TABLE 7-continued

| Preparation | Chemical Name | Structure | MS (ES) m/z (M + 1) |
|---|---|---|---|
| 10D [4] | tert-Butyl 3-hydroxy-4-(piperidin-1-yl)pyrrolidine-1-carboxylate, Isomer 2 | 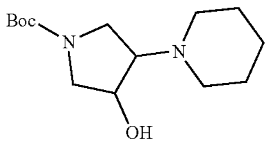 [SMILES: CC(C)(C)OC(=O)N1CC(O)C(N2CCCCC2)C1] | 271 |
| 11D [5] | tert-Butyl 3-hydroxy-4-(1,4-oxazepan-4-yl)pyrrolidine-1-carboxylate | 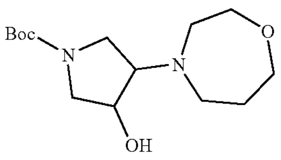 [SMILES: CC(C)(C)OC(=O)N1CC(O)C(N2CCCOCC2)C1] | 287 |
| 12D [6] | tert-Butyl 3-(diethylamino)-4-hydroxypyrrolidine-1-carboxylate, Isomer 1 | 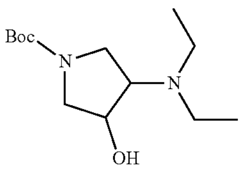 [SMILES: CCN(CC)C1CN(C(=O)OC(C)(C)C)CC1O] | 259 |
| 13D [6] | tert-Butyl 3-(diethylamino)-4-hydroxypyrrolidine-1-carboxylate, Isomer 2 | 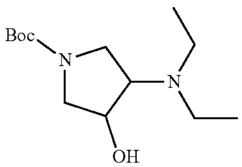 [SMILES: CCN(CC)C1CN(C(=O)OC(C)(C)C)CC1O] | 259 |

[1] Clean Trans Isomers, Analysis of Preparations 5D and 6D with Analytical-Chiral-SFC; Chiralpak-IC, 25-50% Isopropanol (w/ 0.2% isopropylamine) in $CO_2$ shows Preparation 6D to elute first and Preparation 5D to elute second

[2] Clean Trans Isomer, Prep-Chiral-SFC; Chiralpak-AD, 20 x 250 mm, 20% MeOH (w/ 0.5% dimethylethylamine) in $CO_2$, 65 g/min shows Preparation 7D to elute second

[3] Mix of Trans Isomers

[4] Clean Trans Isomers, Prep-Chiral-SFC; Chiralpak-AD, 20 x 250 mm, 25% MeOH (w/ 0.5% dimethylethylamine) in $CO_2$, 80 mL/min

[5] Mix of Trans Isomers

[6] Clean Trans Isomers, Prep-Chiral-SFC; Chiralpak-AD, 20 x 250 mm, 10% MeOH (w/ 0.5% dimethylethylamine) in $CO_2$, 80 mL/min

Preparation 32B tert-Butyl (2S,3S)-3-((tert-butoxycarbonyl)(methyl)amino)-2-methylpyrrolidine-1-carboxylate

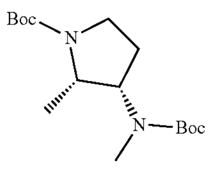 [SMILES: C[C@H]1[C@@H](N(C)C(=O)OC(C)(C)C)CCN1C(=O)OC(C)(C)C]

To a 0° C. solution of tert-butyl (2S,3S)-3-((tert-butoxycarbonyl)amino)-2-methylpyrrolidine-1-carboxylate (0.300 g, 1.00 mmol) in DMF (4.5 mL) was added sodium hydride (0.044 g, 1.10 mmol). The reaction mixture was stirred for 30 min at RT, then cooled to 0° C. Iodomethane (0.068 mL, 1.10 mmol) was added. The reaction mixture was stirred for 2 h at RT then diluted with saturated aqueous ammonium chloride (20 mL). The mixture was extracted with DCM (3×20 mL). The combined organic layers were passed through a hydrophobic frit and the filtrate was concentrated under reduced pressure to give the crude title compound with no further purification.

The following compounds in Table 8 were prepared in similar manner as described in Preparation 32B. Various methods were used to purify the compounds, which would be apparent to one skilled in the art.

TABLE 8

| Preparation | Chemical Name | Structure | MS (ES) m/z (M + 1) |
|---|---|---|---|
| 6C | tert-Butyl (S)-3-(isobutyl(methyl)amino) pyrrolidine-1-carboxylate | 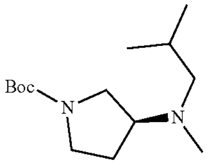 [SMILES: CC(C)CN(C)[C@H]1CCN(C(=O)OC(C)(C)C)C1] | 257 |
| 7C | tert-Butyl (3S)-3-(methyl(tetrahydrofuran-3-yl)amino)pyrrolidine-1-carboxylate | 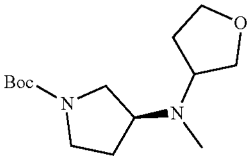 [SMILES: CN(C1CCOC1)[C@H]1CCN(C(=O)OC(C)(C)C)C1] | 271 |
| 8C | tert-Butyl (S)-3-((2-methoxyethyl)(methyl)amino)pyrrolidine-1-carboxylate | 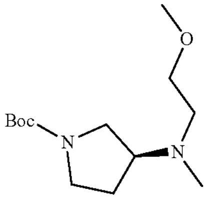 [SMILES: COCCN(C)[C@H]1CCN(C(=O)OC(C)(C)C)C1] | 259 |
| 9C | tert-Butyl (3S)-3-((1-methoxypropan-2-yl)(methyl)amino) pyrrolidine-1-carboxylate | 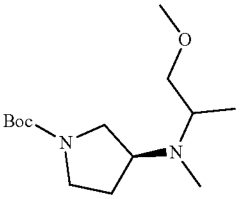 [SMILES: COCC(C)N(C)[C@H]1CCN(C(=O)OC(C)(C)C)C1] | 273 |
| 10C | tert-Butyl (3S)-3-(methyl((tetrahydrofuran-2-yl)methyl)amino) pyrrolidine-1-carboxylate | 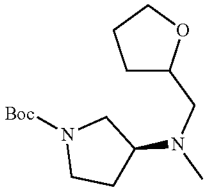 [SMILES: CN(CC1CCCO1)[C@H]1CCN(C(=O)OC(C)(C)C)C1] | 285 |
| 11C | tert-Butyl (3S)-3-(methyl((tetrahydro-2H-pyran-2-yl)methyl)amino) pyrrolidine-1-carboxylate | 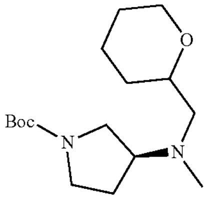 [SMILES: CN(CC1CCCCO1)[C@H]1CCN(C(=O)OC(C)(C)C)C1] | 299 |
| 12C | tert-Butyl (S)-3-(methyl(2-(methylamino)-2-oxoethyl)amino) pyrrolidine-1-carboxylate | 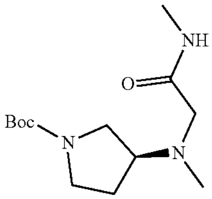 [SMILES: CNC(=O)CN(C)[C@H]1CCN(C(=O)OC(C)(C)C)C1] | 272 |
| 13C | tert-Butyl (3S)-3-((1-amino-1-oxopropan-2-yl)(methyl)amino) pyrrolidine-1-carboxylate | 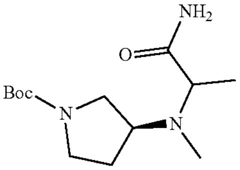 [SMILES: CC(C(N)=O)N(C)[C@H]1CCN(C(=O)OC(C)(C)C)C1] | 272 |

TABLE 8-continued

| Preparation | Chemical Name | Structure | MS (ES) m/z (M + 1) |
|---|---|---|---|
| 14C | tert-Butyl (2S,3S)-3-((tert-butoxycarbonyl)(2-fluoroethyl)amino)-2-methylpyrrolidine-1-carboxylate | 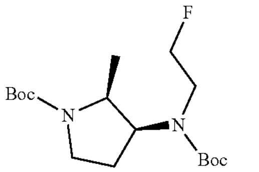 [SMILES: C[C@H]1[C@@H](N(CCF)C(=O)OC(C)(C)C)CCN1C(=O)OC(C)(C)C] | 347 |
| 14D | tert-Butyl 6-(methyl-d3)-2,6-diazaspiro[3.4]octane-2-carboxylate | 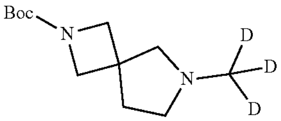 [SMILES: [2H]C([2H])([2H])N1CCC2(CN(C(=O)OC(C)(C)C)C2)C1] | 230 |
| 15D [1] | tert-Butyl 3-((S)-3,4-dimethylpiperazin-1-yl)-4-methoxypyrrolidine-1-carboxylate | 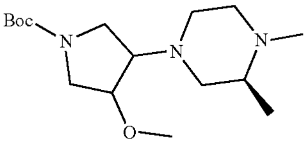 [SMILES: COC1CN(C(=O)OC(C)(C)C)CC1N1CCN(C)[C@@H](C)C1] | 314 |
| 16D [2] | tert-Butyl 3-methoxy-4-(3-methyl-3,8-diazabicyclo[3.2.1] octan-8-yl)pyrrolidine-1-carboxylate | 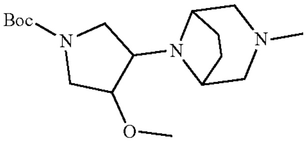 [SMILES: COC1CN(C(=O)OC(C)(C)C)CC1N1C2CCC1CN(C)C2] | 326 |
| 17D [3] | tert-Butyl 3-methoxy-4-(piperidin-1-yl)pyrrolidine-1-carboxylate, Isomer 1 | 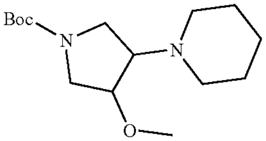 [SMILES: COC1CN(C(=O)OC(C)(C)C)CC1N1CCCCC1] | 285 |
| 18D [3] | tert-Butyl 3-methoxy-4-(piperidin-1-yl)pyrrolidine-1-carboxylate, Isomer 2 | 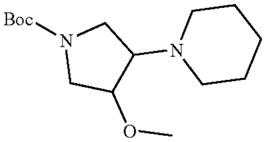 [SMILES: COC1CN(C(=O)OC(C)(C)C)CC1N1CCCCC1] | 285 |
| 19D [4] | tert-Butyl 3-methoxy-4-(1,4-oxazepan-4-yl)pyrrolidine-1-carboxylate | 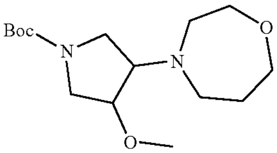 [SMILES: COC1CN(C(=O)OC(C)(C)C)CC1N1CCCOCC1] | 301 |
| 20D | tert-Butyl (R)-3-(2-(dimethylamino)ethoxy) pyrrolidine-1-carboxylate | 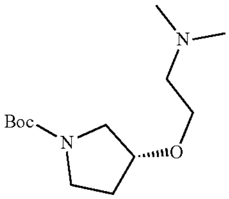 [SMILES: CN(C)CCO[C@@H]1CCN(C(=O)OC(C)(C)C)C1] | 259 |
| 21D | tert-Butyl (S)-3-(2-(dimethylamino)ethoxy) pyrrolidine-1-carboxylate | 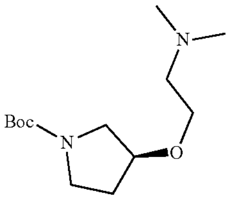 [SMILES: CN(C)CCO[C@H]1CCN(C(=O)OC(C)(C)C)C1] | 259 |

TABLE 8-continued

| Preparation | Chemical Name | Structure | MS (ES) m/z (M + 1) |
| --- | --- | --- | --- |
| 22D [5] | Benzyl 3-(methoxymethyl)-4-(methylamino) pyrrolidine-1-carboxylate | 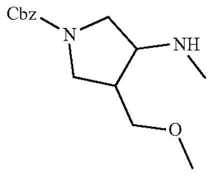 [SMILES: CNC1CN(C(=O)OCc2ccccc2)CC1COC] | 279 |
| 23D | tert-Butyl (2S,3S)-3-((tert-butoxycarbonyl) (2-((tert-butyldimethylsilyl)oxy) ethyl)amino)-2-methylpyrrolidine-1-carboxylate | 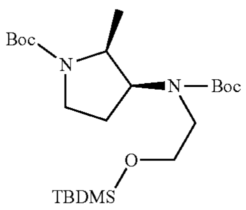 | 459 |

1 Clean Trans Isomer, Separated in Preparation 7D
[2] Mix of Trans Isomers
[3] Clean Trans Isomers, Separated in Preparations 9D and 10D
[4] Mix of Trans Isomers
[5] Mix of Cis Isomers

Preparation 24D tert-Butyl (2R,3S)-2-methyl-3-(4-methylpiperazin-1-yl)pyrrolidine-1-carboxylate

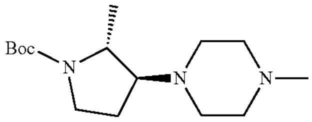 [SMILES: C[C@@H]1[C@@H](N2CCN(C)CC2)CCN1C(=O)OC(C)(C)C]

2-Chloro-N-(2-chloroethyl)-N-methylethan-1-amine hydrochloride (0.481 g, 2.50 mmol) was added to a mixture of tert-butyl (2R,3S)-3-amino-2-methylpyrrolidine-1-carboxylate (0.50 g, 2.50 mmol), potassium carbonate (1.73 g, 12.5 mmol), and potassium iodide (0.0104 g, 0.062 mmol) in acetonitrile (5 mL). The reaction mixture was stirred for 16 h at 82° C. overnight at RT, then cooled, diluted with DCM, and filtered to remove solids. The filtrate was concentrated under reduced pressure. The residue was purified by reversed phase purification, eluting with a gradient of ACN in water (with 0.1% formic acid), to give the title compound (0.319 g, 45%) as a yellow solid. MS (ES) m/z=284 (M+1).

Preparation 25D tert-Butyl (2S,3R)-2-methyl-3-(4-methylpiperazin-1-yl)pyrrolidine-1-carboxylate

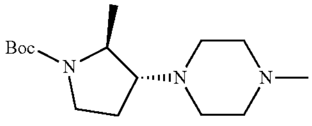 [SMILES: C[C@H]1[C@H](N2CCN(C)CC2)CCN1C(=O)OC(C)(C)C]

tert-Butyl (2S,3R)-3-amino-2-methylpyrrolidine-1-carboxylate was used in a manner analogous to the method of Preparation 24D to afford the title compound (0.298 g, 42%). MS (ES) m/z=284 (M+1).

Preparation 15C tert-Butyl (2S,3S)-3-(dimethylcarbamoyl)-2-methylpyrrolidine-1-carboxylate

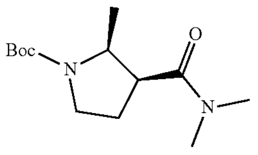 [SMILES: C[C@H]1[C@@H](C(=O)N(C)C)CCN1C(=O)OC(C)(C)C]

A mixture of (2S,3S)-1-(tert-butoxycarbonyl)-2-methylpyrrolidine-3-carboxylic acid (1.00 g, 4.36 mmol), hexafluorophosphate azabenzotriazole tetramethyl uranium (2.49 g, 6.54 mmol), and dimethylamine (2M in THf; 4.36 mL, 8.72 mmol) in DCM (30 mL) was treated with diisopropylethylamine (2.28 mL, 13.1 mmol). The reaction mixture was stirred overnight at RT, then concentrated under reduced pressure. The residue was purified on silica, eluting with 0-100% EtOAc in heptane to obtain the title compound (1.08 g, 97%). MS (ES) m/z=201 (M+1, -tBu).

The following compounds in Table 9 were prepared in similar manner as described in Preparation 15C. Various methods were used to purify the compounds, which would be apparent to one skilled in the art.

TABLE 9

| Preparation | Chemical Name | Structure | MS (ES) m/z (M + 1) |
|---|---|---|---|
| 26D | tert-Butyl (2S,3S)-2-methyl-3-(methylcarbamoyl) pyrrolidine-1-carboxylate | 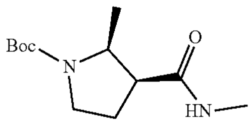 [SMILES: CNC(=O)[C@H]1CCN(C(=O)OC(C)(C)C)[C@H]1C] | 187-tBu |
| 27D | tert-Butyl (R)-3-(2-(dimethylamino)-2-oxoethyl)pyrrolidine-1-carboxylate | 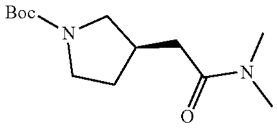 [SMILES: CN(C)C(=O)C[C@H]1CCN(C(=O)OC(C)(C)C)C1] | 201-tBu |

Preparation 16C tert-Butyl (S)-3-(3-methoxyazetidin-1-yl)pyrrolidine-1-carboxylate

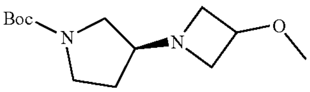 [SMILES: COC1CN([C@H]2CCN(C(=O)OC(C)(C)C)C2)C1]

3-methoxyazetidine (0.0985 g, 1.13 mmol) and diisopropylethylamine (0.433 mL, 2.49 mmol) were added to tert-butyl (R)-3-((methylsulfonyl)oxy)pyrrolidine-1-carboxylate (0.300 g, 1.13 mmol). The reaction mixture was stirred for 17 h at 80° C. The mixture was diluted with MeOH (1 mL). The material was purified on strong cation exchange media (25 g), eluting first with MeOH, then with 2M ammoniated MeOH. The basic fraction was concentrated under reduced pressure to obtain the crude title compound, which was used as-is.

Preparation 17C tert-Butyl (S)-3-((cyclopropylmethyl)(methyl)amino)pyrrolidine-1-carboxylate

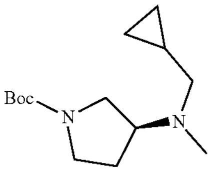 [SMILES: CN(CC1CC1)[C@H]1CCN(C(=O)OC(C)(C)C)C1]

1-Cyclopropyl-N-methylmethanamine was used in a manner analogous to the method of Preparation 16C to afford the crude title compound, which was used as-is.

The following compounds in Table 10 were prepared in similar manner as described in Preparation 16C. In some cases, tosylates were used in replacement of mesylates. Various methods were used to purify the compounds, which would be apparent to one skilled in the art.

TABLE 10

| Preparation | Chemical Name | Structure | MS (ES) m/z (M + 1) |
|---|---|---|---|
| 28D | tert-Butyl (R)-3-(3-(dimethylamino)azetidin-1-yl)pyrrolidine-1-carboxylate | 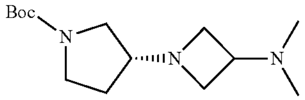 [SMILES: CN(C)C1CN([C@@H]2CCN(C(=O)OC(C)(C)C)C2)C1] | 270 |
| 29D | tert-Butyl (S)-3-(3-(dimethylamino)azetidin-1-yl)pyrrolidine-1-carboxylate | 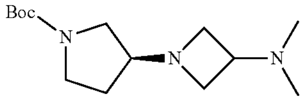 [SMILES: CN(C)C1CN([C@H]2CCN(C(=O)OC(C)(C)C)C2)C1] | 270 |
| 30D | tert-Butyl (R)-3-(azetidin-1-yl)pyrrolidine-1-carboxylate | 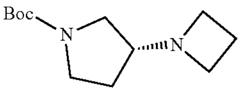 [SMILES: CC(C)(C)OC(=O)N1CC[C@@H](N2CCC2)C1] | 227 |
| 31D | tert-Butyl (R)-3-(3-(2-hydroxypropan-2-yl)azetidin-1-yl)pyrrolidine-1-carboxylate | 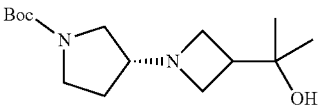 [SMILES: CC(C)(C)OC(=O)N1CC[C@@H](N2CC(C(C)(C)O)C2)C1] | 285 |

TABLE 10-continued

| Preparation | Chemical Name | Structure | MS (ES) m/z (M + 1) |
|---|---|---|---|
| 32D | tert-Butyl (3S,3'R)-3-(dimethylamino)-[1,3'-bipyrrolidine]-1'-carboxylate | 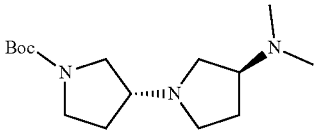 [SMILES: CN(C)[C@H]1CCN([C@@H]2CCN(C(=O)OC(C)(C)C)C2)C1] | 284 |
| 33D | tert-Butyl (3S,3'S)-3-(dimethylamino)-[1,3'-bipyrrolidine]-1'-carboxylate | 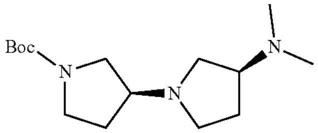 [SMILES: CN(C)[C@H]1CCN([C@H]2CCN(C(=O)OC(C)(C)C)C2)C1] | 284 |
| 34D | tert-Butyl (S)-[1,3'-bipyrrolidine]-1'-carboxylate | 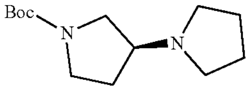 [SMILES: CC(C)(C)OC(=O)N1CC[C@H](N2CCCC2)C1] | 241 |
| 35D | tert-Butyl (R)-[1,3'-bipyrrolidine]-1'-carboxylate | 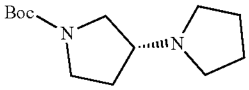 [SMILES: CC(C)(C)OC(=O)N1CC[C@@H](N2CCCC2)C1] | 241 |
| 36D | tert-Butyl (2S,3'R)-2-(methoxymethyl)-[1,3'-bipyrrolidine]-1'-carboxylate | 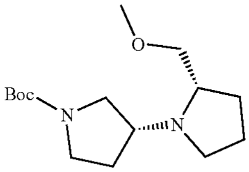 [SMILES: COC[C@@H]1CCCN1[C@@H]1CCN(C(=O)OC(C)(C)C)C1] | 285 |
| 37D | tert-Butyl (2S,3'S)-2-(methoxymethyl)-[1,3'-bipyrrolidine]-1'-carboxylate | 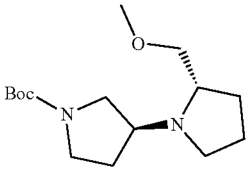 [SMILES: COC[C@@H]1CCCN1[C@H]1CCN(C(=O)OC(C)(C)C)C1] | 285 |
| 38D | tert-Butyl (2R,3'R)-2-(methoxymethyl)-[1,3'-bipyrrolidine]-1'-carboxylate | 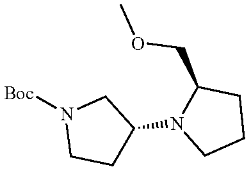 [SMILES: COC[C@H]1CCCN1[C@@H]1CCN(C(=O)OC(C)(C)C)C1] | 285 |
| 39D | tert-Butyl (2R,3'S)-2-(methoxymethyl)-[1,3'-bipyrrolidine]-1'-carboxylate | 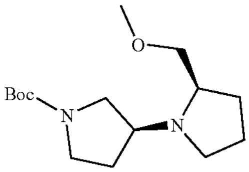 [SMILES: COC[C@H]1CCCN1[C@H]1CCN(C(=O)OC(C)(C)C)C1] | 285 |
| 40D | tert-Butyl (3S,3'R)-3-hydroxy-[1,3'-bipyrrolidine]-1'-carboxylate | 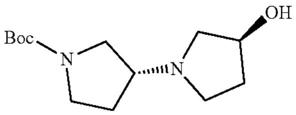 [SMILES: CC(C)(C)OC(=O)N1CC[C@@H](N2CC[C@H](O)C2)C1] | 257 |
| 41D | tert-Butyl (3S,3'R)-3-methoxy-[1,3'-bipyrrolidine]-1'-carboxylate | 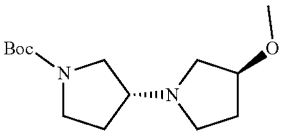 [SMILES: CO[C@H]1CCN([C@@H]2CCN(C(=O)OC(C)(C)C)C2)C1] | 271 |

TABLE 10-continued

| Preparation | Chemical Name | Structure | MS (ES) m/z (M + 1) |
|---|---|---|---|
| 42D | tert-Butyl (R)-3-(4-acetylpiperazin-1-yl)pyrrolidine-1-carboxylate | 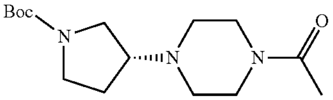 [SMILES: CC(=O)N1CCN([C@@H]2CCN(C(=O)OC(C)(C)C)C2)CC1] | 298 |
| 43D | tert-Butyl (S)-3-(4-acetylpiperazin-1-yl)pyrrolidine-1-carboxylate | 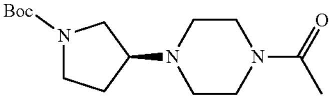 [SMILES: CC(=O)N1CCN([C@H]2CCN(C(=O)OC(C)(C)C)C2)CC1] | 298 |
| 44D | tert-Butyl (R)-3-(4-isopropylpiperazin-1-yl)pyrrolidine-1-carboxylate | 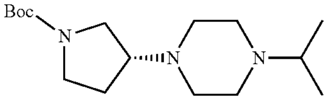 [SMILES: CC(C)N1CCN([C@@H]2CCN(C(=O)OC(C)(C)C)C2)CC1] | 298 |
| 45D | tert-Butyl (S)-3-(4-isopropylpiperazin-1-yl)pyrrolidine-1-carboxylate | 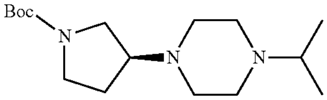 [SMILES: CC(C)N1CCN([C@H]2CCN(C(=O)OC(C)(C)C)C2)CC1] | 298 |
| 46D | tert-Butyl (S)-3-(4-ethylpiperazin-1-yl)pyrrolidine-1-carboxylate | 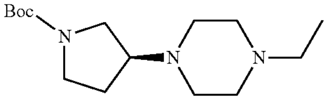 [SMILES: CCN1CCN([C@H]2CCN(C(=O)OC(C)(C)C)C2)CC1] | 284 |
| 47D | tert-Butyl (R)-3-(4-ethylpiperazin-1-yl)pyrrolidine-1-carboxylate | 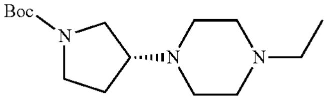 [SMILES: CCN1CCN([C@@H]2CCN(C(=O)OC(C)(C)C)C2)CC1] | 284 |
| 48D | tert-Butyl (R)-3-(4-(2-hydroxyethyl)piperazin-1-yl)pyrrolidine-1-carboxylate | 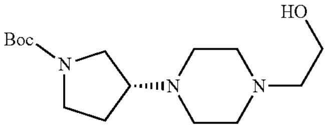 [SMILES: CC(C)(C)OC(=O)N1CC[C@@H](N2CCN(CCO)CC2)C1] | 300 |
| 49D | tert-Butyl (R)-3-(4-(oxetan-3-yl)piperazin-1-yl)pyrrolidine-1-carboxylate | 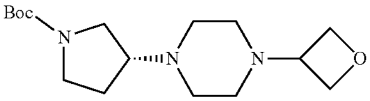 [SMILES: CC(C)(C)OC(=O)N1CC[C@@H](N2CCN(C3COC3)CC2)C1] | 312 |
| 50D | tert-Butyl (R)-3-(4-(2,2,2-trifluoroethyl)piperazin-1-yl)pyrrolidine-1-carboxylate | 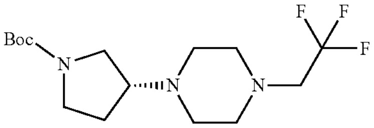 [SMILES: CC(C)(C)OC(=O)N1CC[C@@H](N2CCN(CC(F)(F)F)CC2)C1] | 338 |
| 51D | tert-Butyl (R)-4-(1-((benzyloxy)carbonyl) pyrrolidin-3-yl) piperazine-1-carboxylate | 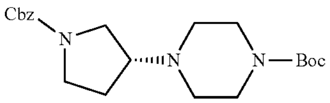 [SMILES: CC(C)(C)OC(=O)N1CCN([C@@H]2CCN(C(=O)OCc3ccccc3)C2)CC1] | 390 |
| 52D | tert-Butyl (S)-4-(1-((benzyloxy)carbonyl) pyrrolidin-3-yl) piperazine-1-carboxylate | 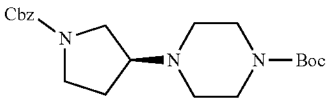 [SMILES: CC(C)(C)OC(=O)N1CCN([C@H]2CCN(C(=O)OCc3ccccc3)C2)CC1] | 390 |
| 53D | tert-Butyl (R)-3-(4-cyclopropylpiperazin-1-yl)pyrrolidine-1-carboxylate | 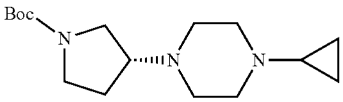 [SMILES: CC(C)(C)OC(=O)N1CC[C@@H](N2CCN(C3CC3)CC2)C1] | 296 |

TABLE 10-continued

| Preparation | Chemical Name | Structure | MS (ES) m/z (M + 1) |
| --- | --- | --- | --- |
| 54D | tert-Butyl (R)-3-(4-(2-hydroxy-2-methylpropyl)piperazin-1-yl)pyrrolidine-1-carboxylate | 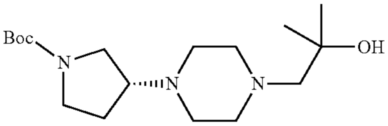 [SMILES: CC(C)(O)CN1CCN([C@@H]2CCN(C(=O)OC(C)(C)C)C2)CC1] | 328 |
| 55D | tert-Butyl (R)-3-(4-(2-methoxyethyl)piperazin-1-yl)pyrrolidine-1-carboxylate | 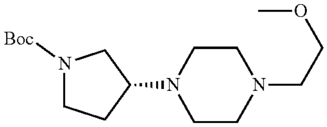 [SMILES: COCCN1CCN([C@@H]2CCN(C(=O)OC(C)(C)C)C2)CC1] | 314 |
| 56D | tert-Butyl (R)-3-((R)-2,4-dimethylpiperazin-1-yl)pyrrolidine-1-carboxylate | 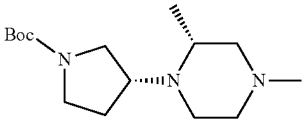 [SMILES: C[C@@H]1CN(C)CCN1[C@@H]1CCN(C(=O)OC(C)(C)C)C1] | 284 |
| 57D | tert-Butyl (R)-3-((S)-2,4-dimethylpiperazin-1-yl)pyrrolidine-1-carboxylate | 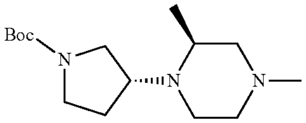 [SMILES: C[C@H]1CN(C)CCN1[C@@H]1CCN(C(=O)OC(C)(C)C)C1] | 284 |
| 58D | tert-Butyl (S)-3-((R)-2,4-dimethylpiperazin-1-yl)pyrrolidine-1-carboxylate | 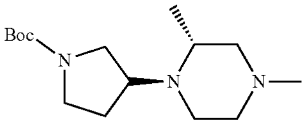 | 284 |
| 59D | tert-Butyl (S)-3-((S)-2,4-dimethylpiperazin-1-yl)pyrrolidine-1-carboxylate | 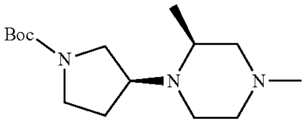 [SMILES: C[C@H]1CN(C)CCN1[C@H]1CCN(C(=O)OC(C)(C)C)C1] | 284 |
| 60D | tert-Butyl (R)-3-((S)-3,4-dimethylpiperazin-1-yl)pyrrolidine-1-carboxylate | 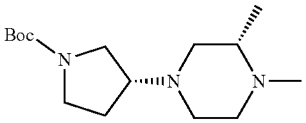 [SMILES: C[C@H]1CN([C@@H]2CCN(C(=O)OC(C)(C)C)C2)CCN1C] | 284 |
| 61D | tert-Butyl (R)-3-((R)-3,4-dimethylpiperazin-1-yl)pyrrolidine-1-carboxylate | 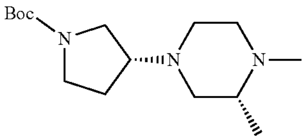 [SMILES: C[C@@H]1CN([C@@H]2CCN(C(=O)OC(C)(C)C)C2)CCN1C] | 284 |
| 62D | tert-Butyl (R)-3-((3R,5S)-3,5-dimethylpiperazin-1-yl)pyrrolidine-1-carboxylate | 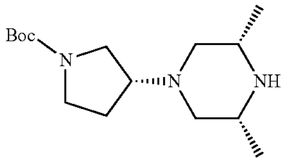 [SMILES: C[C@@H]1CN([C@@H]2CCN(C(=O)OC(C)(C)C)C2)C[C@H](C)N1] | 284 |
| 63D | tert-Butyl (R)-3-((3R,5R)-3,4,5-trimethylpiperazin-1-yl)pyrrolidine-1-carboxylate | 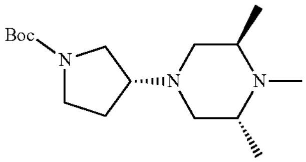 [SMILES: C[C@@H]1CN([C@@H]2CCN(C(=O)OC(C)(C)C)C2)C[C@@H](C)N1C] | 298 |

TABLE 10-continued

| Preparation | Chemical Name | Structure | MS (ES) m/z (M + 1) |
|---|---|---|---|
| 64D | tert-Butyl (R)-3-((3S,5S)-3,4,5-trimethylpiperazin-1-yl)pyrrolidine-1-carboxylate | 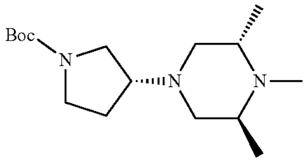 [SMILES: C[C@H]1CN([C@@H]2CCN(C(=O)OC(C)(C)C)C2)C[C@H](C)N1C] | 298 |
| 65D | tert-Butyl (R)-3-((S)-3-(hydroxymethyl)-4-methylpiperazin-1-yl)pyrrolidine-1-carboxylate | 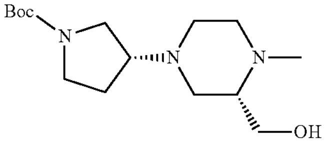 [SMILES: CN1CCN([C@@H]2CCN(C(=O)OC(C)(C)C)C2)C[C@H]1CO] | 300 |
| 66D | tert-Butyl (R)-3-((R)-3-(hydroxymethyl)-4-methylpiperazin-1-yl)pyrrolidine-1-carboxylate | 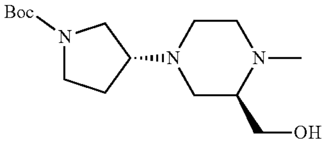 [SMILES: CN1CCN([C@@H]2CCN(C(=O)OC(C)(C)C)C2)C[C@@H]1CO] | 300 |
| 67D | tert-Butyl (R)-3-(2,2,4-trimethylpiperazin-1-yl)pyrrolidine-1-carboxylate | 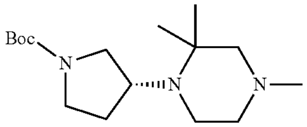 [SMILES: CN1CCN([C@@H]2CCN(C(=O)OC(C)(C)C)C2)C(C)(C)C1] | 298 |
| 68D | tert-Butyl (R)-3-(3,3,4-trimethylpiperazin-1-yl)pyrrolidine-1-carboxylate | 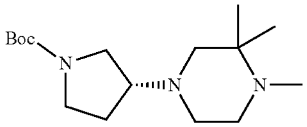 [SMILES: CN1CCN([C@@H]2CCN(C(=O)OC(C)(C)C)C2)CC1(C)C] | 298 |
| 69D | tert-Butyl (R)-3-((S)-2-(hydroxymethyl)-4-methylpiperazin-1-yl)pyrrolidine-1-carboxylate | 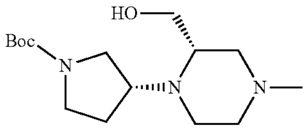 [SMILES: CN1CCN([C@@H]2CCN(C(=O)OC(C)(C)C)C2)[C@H](CO)C1] | 300 |
| 70D | tert-Butyl (R)-3-((R)-2-(hydroxymethyl)-4-methylpiperazin-1-yl)pyrrolidine-1-carboxylate | 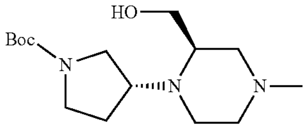 [SMILES: CN1CCN([C@@H]2CCN(C(=O)OC(C)(C)C)C2)[C@@H](CO)C1] | 300 |
| 71D | tert-Butyl (R)-3-((3S,5S)-3,5-dimethylpiperazin-1-yl)pyrrolidine-1-carboxylate | 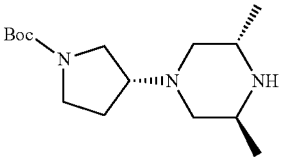 [SMILES: C[C@H]1CN([C@@H]2CCN(C(=O)OC(C)(C)C)C2)C[C@H](C)N1] | 284 |
| 72D | tert-Butyl (S)-3-((2S,5R)-2,4,5-trimethylpiperazin-1-yl)pyrrolidine-1-carboxylate | 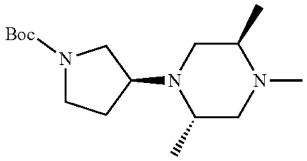 [SMILES: C[C@@H]1CN([C@H]2CCN(C(=O)OC(C)(C)C)C2)[C@@H](C)CN1C] | 298 |
| 73D | tert-Butyl (R)-3-((1S,4S)-5-methyl-2,5-diazabicyclo[2.2.1]heptan-2-yl)pyrrolidine-1-carboxylate | 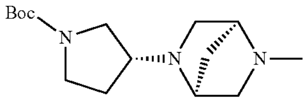 [SMILES: CN1C[C@@H]2C[C@H]1CN2[C@@H]1CCN(C(=O)OC(C)(C)C)C1] | 282 |

TABLE 10-continued

| Preparation | Chemical Name | Structure | MS (ES) m/z (M + 1) |
|---|---|---|---|
| 74D | tert-Butyl (R)-3-((1R,4R)-5-methyl-2,5-diazabicyclo[2.2.1] heptan-2-yl)pyrrolidine-1-carboxylate | 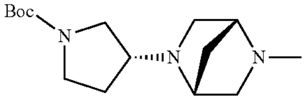 [SMILES: CN1C[C@H]2C[C@@H]1CN2[C@@H]1CCN(C(=O)OC(C)(C)C)C1] | 282 |
| 75D | tert-Butyl (3R)-3-(3-methyl-3,8-diazabicyclo[3.2.1]octan-8-yl)pyrrolidine-1-carboxylate | 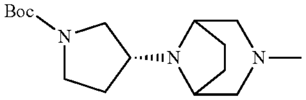 [SMILES: CN1CC2CCC(C1)N2[C@@H]1CCN(C(=O)OC(C)(C)C)C1] | 296 |
| 76D | Benzyl (3R)-3-(8-methyl-3,8-diazabicyclo [3.2.1]octan-3-yl)pyrrolidine-1-carboxylate | 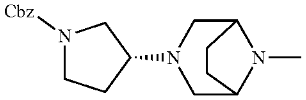 [SMILES: CN1C2CCC1CN([C@@H]1CCN(C(=O)OCc3ccccc3)C1)C2] | 330 |
| 77D | Benzyl (3R)-3-(6-methyl-3,6-diazabicyclo [3.1.1]heptan-3-yl) pyrrolidine-1-carboxylate | 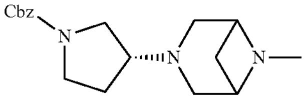 [SMILES: CN1C2CC1CN([C@@H]1CCN(C(=O)OCc3ccccc3)C1)C2] | 316 |
| 78D | tert-Butyl (3R)-3-(3-methyl-3,6-diazabicyclo [3.1.1]heptan-6-yl)pyrrolidine-1-carboxylate | 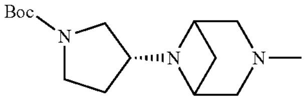 [SMILES: CN1CC2CC(C1)N2[C@@H]1CCN(C(=O)OC(C)(C)C)C1] | 282 |
| 79D | tert-Butyl (2S,4S)-2-methyl-4-(4-methylpiperazin-1-yl)pyrrolidine-1-carboxylate | 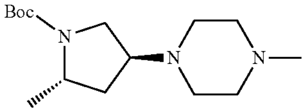 | 284 |
| 80D | tert-Butyl (2S,4R)-2-methyl-4-(4-methylpiperazin-1-yl)pyrrolidine-1-carboxylate | 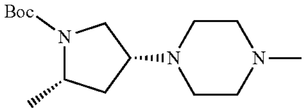 | 284 |
| 81D | tert-Butyl (S)-3-(piperidin-1-yl)pyrrolidine-1-carboxylate | 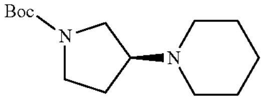 [SMILES: CC(C)(C)OC(=O)N1CC[C@H](N2CCCCC2)C1] | 255 |
| 82D | tert-Butyl (S)-3-(piperidin-1-yl)pyrrolidine-1-carboxylate | 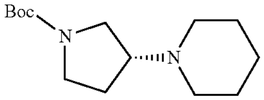 [SMILES: CC(C)(C)OC(=O)N1CC[C@@H](N2CCCCC2)C1] | 255 |
| 83D | tert-Butyl (R)-3-(4-(dimethylamino) piperidin-1-yl) pyrrolidine-1-carboxylate | 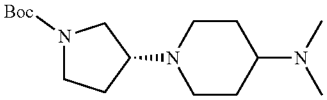 | 298 |
| 84D | tert-Butyl (R)-3-((S)-3-hydroxypiperidin-1-yl)pyrrolidine-1-carboxylate | 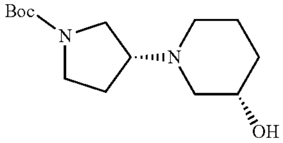 [SMILES: CC(C)(C)OC(=O)N1CC[C@@H](N2CCC[C@H](O)C2)C1] | 271 |
| 85D | tert-Butyl (R)-3-((R)-3-hydroxypiperidin-1-yl)pyrrolidine-1-carboxylate | 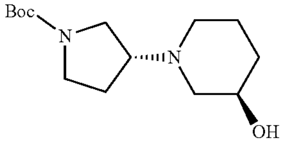 [SMILES: CC(C)(C)OC(=O)N1CC[C@@H](N2CCC[C@@H](O)C2)C1] | 271 |

TABLE 10-continued

| Preparation | Chemical Name | Structure | MS (ES) m/z (M + 1) |
|---|---|---|---|
| 86D | tert-Butyl (R)-3-(4-methoxypiperidin-1-yl)pyrrolidine-1-carboxylate | 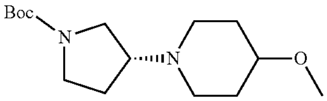 [SMILES: COC1CCN([C@@H]2CCN(C(=O)OC(C)(C)C)C2)CC1] | 285 |
| 87D | tert-Butyl (R)-3-(4-cyanopiperidin-1-yl)pyrrolidine-1-carboxylate | 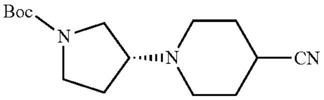 [SMILES: CC(C)(C)OC(=O)N1CC[C@@H](N2CCC(C#N)CC2)C1] | 280 |
| 88D | tert-Butyl (R)-3-(4-hydroxypiperidin-1-yl)pyrrolidine-1-carboxylate | 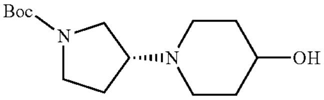 | 271 |
| 89D [1] | tert-Butyl (3S)-3-(3-hydroxy-3-methylpiperidin-1-yl)pyrrolidine-1-carboxylate, Isomer 1 | 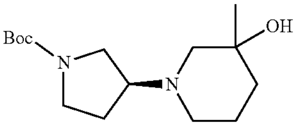 [SMILES: CC1(O)CCCN([C@H]2CCN(C(=O)OC(C)(C)C)C2)C1] | 285 |
| 90D [1] | tert-Butyl (3S)-3-(3-hydroxy-3-methylpiperidin-1-yl)pyrrolidine-1-carboxylate, Isomer 2 | 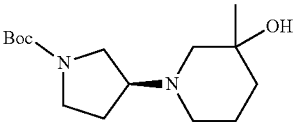 [SMILES: CC1(O)CCCN([C@H]2CCN(C(=O)OC(C)(C)C)C2)C1] | 285 |
| 91D | tert-Butyl (R)-3-(4-hydroxy-4-methylpiperidin-1-yl)pyrrolidine-1-carboxylate | 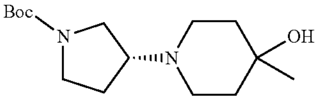 [SMILES: CC1(O)CCN([C@@H]2CCN(C(=O)OC(C)(C)C)C2)CC1] | 285 |
| 92D | tert-Butyl (R)-3-(4-fluoropiperidin-1-yl)pyrrolidine-1-carboxylate | 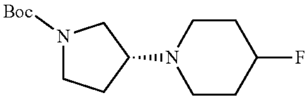 [SMILES: CC(C)(C)OC(=O)N1CC[C@@H](N2CCC(F)CC2)C1] | 273 |
| 93D | Benzyl (3R)-3-(3-fluoropiperidin-1-yl)pyrrolidine-1-carboxylate | 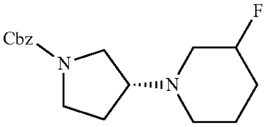 [SMILES: O=C(OCc1ccccc1)N1CC[C@@H](N2CCCC(F)C2)C1] | 307 |
| 94D | tert-Butyl (R)-3-thiomorpholino-pyrrolidine-1-carboxylate | 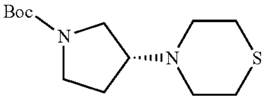 [SMILES: CC(C)(C)OC(=O)N1CC[C@@H](N2CCSCC2)C1] | 273 |
| 95D | tert-Butyl (3R)-3-(2-((dimethylamino)methyl) morpholino)pyrrolidine-1-carboxylate | 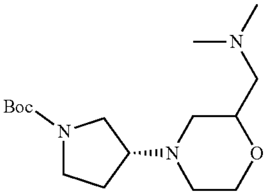 [SMILES: CN(C)CC1CN([C@@H]2CCN(C(=O)OC(C)(C)C)C2)CCO1] | 314 |
| 96D | tert-Butyl (3S)-3-(2-((dimethylamino)methyl) morpholino)pyrrolidine-1-carboxylate | 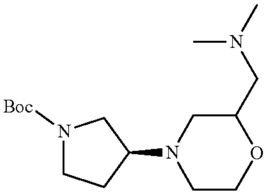 [SMILES: CN(C)CC1CN([C@H]2CCN(C(=O)OC(C)(C)C)C2)CCO1] | 314 |

TABLE 10-continued

| Preparation | Chemical Name | Structure | MS (ES) m/z (M + 1) |
|---|---|---|---|
| 97D | tert-Butyl (R)-3-(1,4-oxazepan-4-yl)pyrrolidine-1-carboxylate | 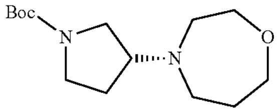 | 271 |
| 98D | tert-Butyl (R)-3-(4-methyl-1,4-diazepan-1-yl)pyrrolidine-1-carboxylate | 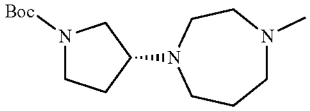 [SMILES: CN1CCCN([C@@H]2CCN(C(=O)OC(C)(C)C)C2)CC1] | 284 |
| 99D | tert-Butyl (R)-3-(4-acetyl-1,4-diazepan-1-yl)pyrrolidine-1-carboxylate | 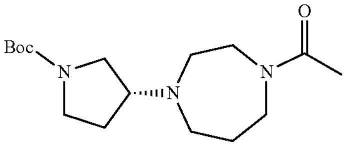 [SMILES: CC(=O)N1CCCN([C@@H]2CCN(C(=O)OC(C)(C)C)C2)CC1] | 312 |
| 100D | tert-Butyl (S)-3-(4-methyl-1,4-diazepan-1-yl)pyrrolidine-1-carboxylate | 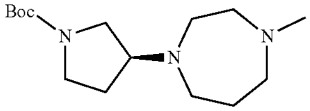 [SMILES: CN1CCCN([C@H]2CCN(C(=O)OC(C)(C)C)C2)CC1] | 284 |
| 101D | tert-Butyl (R)-3-((3aR,6aS)-5-methylhexahydro-pyrrolo[3,4-c]pyrrol-2(1H)-yl)pyrrolidine-1-carboxylate | 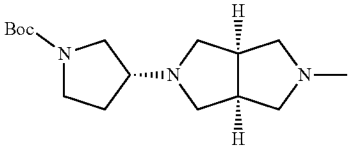 [SMILES: CN1C[C@@H]2CN([C@@H]3CCN(C(=O)OC(C)(C)C)C3)C[C@@H]2C1] | 296 |
| 102D | tert-Butyl (S)-3-((3aR,6aS)-5-methylhexahydro-pyrrolo[3,4-c]pyrrol-2(1H)-yl)pyrrolidine-1-carboxylate | 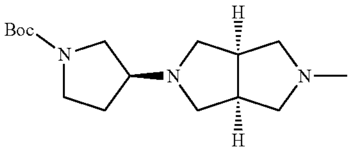 [SMILES: CN1C[C@@H]2CN([C@H]3CCN(C(=O)OC(C)(C)C)C3)C[C@@H]2C1] | 296 |
| 103D | tert-Butyl (R)-3-((R)-hexahydropyrrolo[1,2-a]pyrazin-2(1H)-yl)pyrrolidine-1-carboxylate | 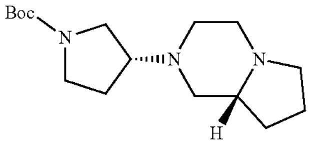 [SMILES: CC(C)(C)OC(=O)N1CC[C@@H](N2CCN3CCC[C@@H]3C2)C1] | 296 |
| 104D | tert-Butyl (S)-3-((7S,8aS)-7-fluorohexahydro-pyrrolo[1,2-a]pyrazin-2(1H)-yl)pyrrolidine-1-carboxylate | 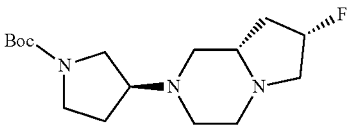 [SMILES: CC(C)(C)OC(=O)N1CC[C@H](N2CCN3C[C@@H](F)C[C@H]3C2)C1] | 314 |
| 105D | tert-Butyl (R)-3-((3aR,6aS)-tetrahydro-1H-furo[3,4-c]pyrrol-5(3H)-yl)pyrrolidine-1-carboxylate | 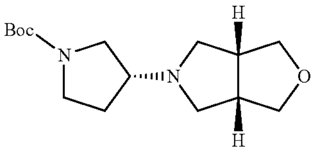 [SMILES: CC(C)(C)OC(=O)N1CC[C@@H](N2C[C@H]3COC[C@H]3C2)C1] | 283 |
| 106D | tert-Butyl (R)-3-(2-methyl-2,6-diazaspiro[3.4]octan-6-yl)pyrrolidine-1-carboxylate | 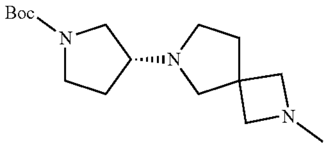 [SMILES: CN1CC2(CCN([C@@H]3CCN(C(=O)OC(C)(C)C)C3)C2)C1] | 296 |

TABLE 10-continued

| Preparation | Chemical Name | Structure | MS (ES) m/z (M + 1) |
|---|---|---|---|
| 107D | tert-Butyl (R)-3-(2-azaspiro[3.3 ]heptan-2-yl)pyrrolidine-1-carboxylate | 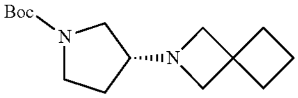 [SMILES: CC(C)(C)OC(=O)N1CC[C@@H](N2CC3(CCC3)C2)C1] | 267 |
| 108D | tert-Butyl (S)-3-(2-azaspiro[3.3]heptan-2-yl)pyrrolidine-1-carboxylate | 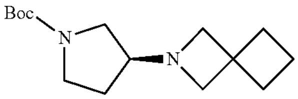 [SMILES: CC(C)(C)OC(=O)N1CC[C@H](N2CC3(CCC3)C2)C1] | 267 |
| 109D | tert-Butyl (R)-3-(((R)-1-methylpyrrolidin-3-yl)amino)pyrrolidine-1-carboxylate | 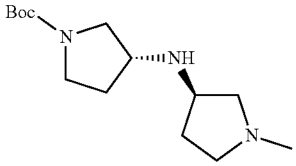 [SMILES: CN1CC[C@@H](N[C@@H]2CCN(C(=O)OC(C)(C)C)C2)C1] | 270 |
| 110D | tert-Butyl (R)-3-(((S)-1-methylpyrrolidin-3-yl)amino)pyrrolidine-1-carboxylate | 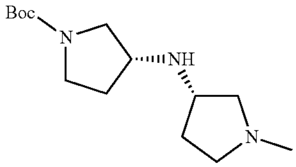 [SMILES: CN1CC[C@H](N[C@@H]2CCN(C(=O)OC(C)(C)C)C2)C1] | 270 |
| 111D | tert-Butyl (S)-3-(((R)-1-methylpyrrolidin-3-yl)amino)pyrrolidine-1-carboxylate | 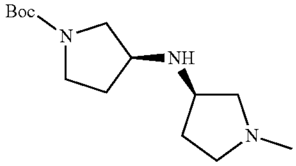 [SMILES: CN1CC[C@@H](N[C@H]2CCN(C(=O)OC(C)(C)C)C2)C1] | 270 |
| 112D | tert-Butyl (S)-3-(((S)-1-methylpyrrolidin-3-yl)amino)pyrrolidine-1-carboxylate | 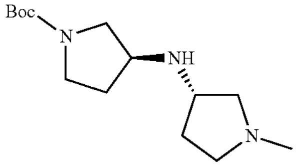 [SMILES: CN1CC[C@H](N[C@H]2CCN(C(=O)OC(C)(C)C)C2)C1] | 270 |
| 113D | tert-Butyl (R)-3-(3-((dimethylamino)methyl) azetidin-1-yl)pyrrolidine-1-carboxylate | 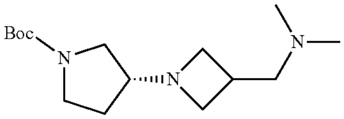 [SMILES: CN(C)CC1CN([C@@H]2CCN(C(=O)OC(C)(C)C)C2)C1] | 284 |
| 114D | tert-Butyl (S)-3-(3-((dimethylamino)methyl) azetidin-1-yl)pyrrolidine-1-carboxylate | 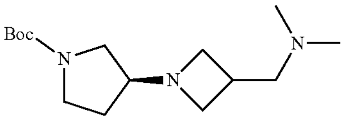 [SMILES: CN(C)CC1CN([C@H]2CCN(C(=O)OC(C)(C)C)C2)C1] | 284 |
| 115D | tert-Butyl (S)-4-(1-((benzyloxy)carbonyl)pyrrolidin-3-yl)piperazine-1-carboxylate | 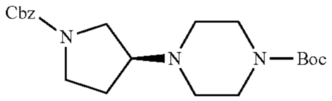 [SMILES: CC(C)(C)OC(=O)N1CCN([C@H]2CCN(C(=O)OCc3ccccc3)C2)CC1] | 390 |

[1] Prep-Chiral-SFC; Chiralpak-AD, 20 × 250 mm, 20% MeOH (w/ 0.5% dimethylethylamine) in $CO_2$, 80 mL/min The following compounds in Table 11 were prepared in similar manner as described in Preparation 32B. Various methods were used to purify the compounds, which would be apparent to one skilled in the art.

TABLE 11

| Preparation | Chemical Name | Structure | MS (ES) m/z (M + 1) |
|---|---|---|---|
| 116D | tert-Butyl (R)-3-((S)-3-(methoxymethyl)-4-methylpiperazin-1-yl)pyrrolidine-1-carboxylate | 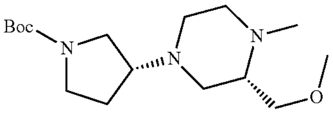 [SMILES: COC[C@@H]1CN([C@@H]2CCN(C(=O)OC(C)(C)C)C2)CCN1C] | 314 |
| 117D | tert-Butyl (R)-3-((R)-3-(methoxymethyl)-4-methylpiperazin-1-yl)pyrrolidine-1-carboxylate | 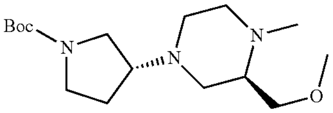 [SMILES: COC[C@H]1CN([C@@H]2CCN(C(=O)OC(C)(C)C)C2)CCN1C] | 314 |
| 118D | tert-Butyl (R)-3-(methyl((R)-1-methylpyrrolidin-3-yl)amino)pyrrolidine-1-carboxylate | 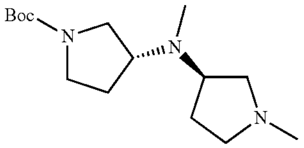 [SMILES: CN1CC[C@@H](N(C)[C@@H]2CCN(C(=O)OC(C)(C)C)C2)C1] | 284 |
| 119D | tert-Butyl (R)-3-(methyl((S)-1-methylpyrrolidin-3-yl)amino)pyrrolidine-1-carboxylate | 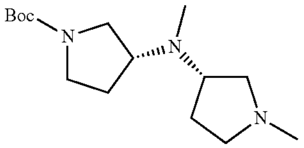 [SMILES: CN1CC[C@H](N(C)[C@@H]2CCN(C(=O)OC(C)(C)C)C2)C1] | 284 |
| 120D | tert-Butyl (S)-3-(methyl((R)-1-methylpyrrolidin-3-yl)amino)pyrrolidine-1-carboxylate | 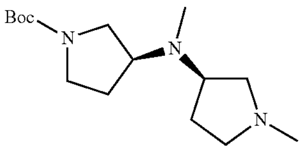 [SMILES: CN1CC[C@@H](N(C)[C@H]2CCN(C(=O)OC(C)(C)C)C2)C1] | 284 |
| 121D | tert-Butyl (S)-3-(methyl((S)-1-methylpyrrolidin-3-yl)amino)pyrrolidine-1-carboxylate | 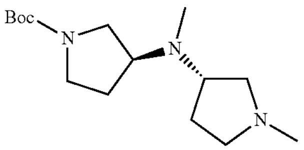 [SMILES: CN1CC[C@H](N(C)[C@H]2CCN(C(=O)OC(C)(C)C)C2)C1] | 284 |

Preparation 122D

Benzyl (S)-3-(piperazin-1-yl)pyrrolidine-1-carboxylate

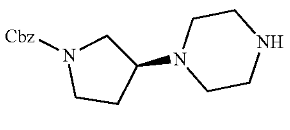 [SMILES: O=C(OCc1ccccc1)N1CC[C@H](N2CCNCC2)C1]

To a solution of tert-butyl (S)-4-(1-((benzyloxy)carbonyl)pyrrolidin-3-yl)piperazine-1-carboxylate (0.562 g, 1.30 mmol) in DCM (4 mL) was added TFA (3 mL). The reaction mixture was stirred for 4.5 h at RT. The mixture was concentrated. The residue was purified on strong cation exchange media (10 g), eluting first with MeOH, then with 2M ammoniated MeOH. The basic fraction was concentrated under reduced pressure to obtain the title compound (0.306 g, 79%) as a brown oil. MS (ES) m/z=290 (M+1).

Preparation 33B tert-Butyl (3S,4S)-3-(dimethylamino)-4-methoxypyrrolidine-1-carboxylate

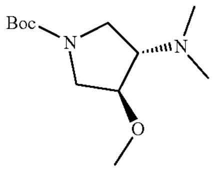 [SMILES: CO[C@H]1CN(C(=O)OC(C)(C)C)C[C@@H]1N(C)C]

tert-Butyl (3S,4S)-3-methoxy-4-(methylamino)pyrrolidine-1-carboxylate (0.500 g, 2.17 mmol), formaldehyde (37 wt % in water; 0.97 mL, 13.0 mmol) and sodium triacetoxyborohydride (2.76 g, 13.0 mmol) were dissolved in MeOH (6 mL). The reaction mixture was stirred for 18 h at 50° C. The mixture was concentrated under reduced pressure, poured into sat. aq. $NaHCO_3$ (20 mL), and extracted with EtOAc (3×50 mL). The combined organic layers were washed with brine (25 mL), dried over anhydrous $Na_2SO_4$, filtered, and concentrated under reduced pressure to obtain the crude title compound (0.53 g) as a waxy solid. MS (ES) m/z=245 (M+1).

The following compounds in Table 12 were prepared in similar manner as described in Preparation 33B. Various methods were used to purify the compounds, which would be apparent to one skilled in the art.

TABLE 12

| Preparation | Chemical Name | Structure | MS (ES) m/z (M + 1) |
|---|---|---|---|
| 34B | tert-Butyl (3R,4S)-3-(dimethylamino)-4-methoxypyrrolidine-1-carboxylate | 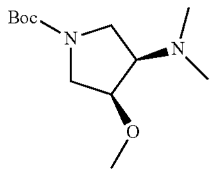 [SMILES: CO[C@H]1CN(C(=O)OC(C)(C)C)C[C@H]1N(C)C] | 245 |
| 35B | tert-Butyl 1-(dimethylamino)-3-azabicyclo[3.2.0]heptane-3-carboxylate | 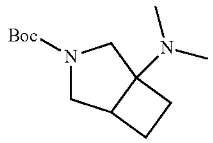 [SMILES: CN(C)C12CCC1CN(C(=O)OC(C)(C)C)C2] | |
| 36B | tert-Butyl 7-(dimethylamino)-4-azaspiro[2.4]heptane-4-carboxylate | 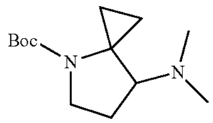 [SMILES: CN(C)C1CCN(C(=O)OC(C)(C)C)C12CC2] | 241 |
| 37B | tert-Butyl 4-methylhexahydropyrrolo[3,2-b]pyrrole-1(2H)-carboxylate | 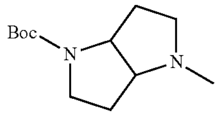 [SMILES: CN1CCC2C1CCN2C(=O)OC(C)(C)C] | 227 |
| 38B | tert-Butyl (3S,4R)-3-hydroxy-4-(isopropyl(methyl)amino)pyrrolidine-1-carboxylate | 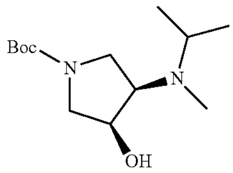 [SMILES: CC(C)N(C)[C@@H]1CN(C(=O)OC(C)(C)C)C[C@@H]1O] | 259 |
| 39B | tert-Butyl (3R,4S)-3-(dimethylamino)-4-hydroxypyrrolidine-1-carboxylate | 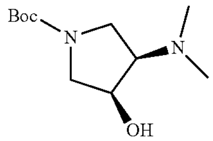 [SMILES: CN(C)[C@@H]1CN(C(=O)OC(C)(C)C)C[C@@H]1O] | 231 |
| 40B | tert-Butyl (1S,5S)-6-methyl-2,6-diazabicyclo[3.2.0]heptane-2-carboxylate | 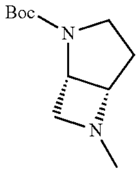 | 213 |
| 41B | tert-Butyl 3-(dimethylamino)-3-(hydroxymethyl)pyrrolidine-1-carboxylate | 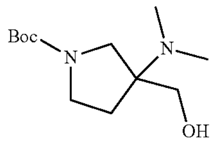 [SMILES: CN(C)C1(CO)CCN(C(=O)OC(C)(C)C)C1] | |

TABLE 12-continued

| Preparation | Chemical Name | Structure | MS (ES) m/z (M + 1) |
|---|---|---|---|
| 42B | tert-Butyl 3-(difluoromethyl)-4-(dimethylamino) pyrrolidine-1-carboxylate, Mix of Trans Isomers | 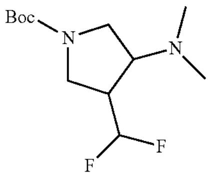 [SMILES: CN(C)C1CN(C(=O)OC(C)(C)C)CC1C(F)F] | 265 |
| 43B | tert-Butyl 4-(dimethylamino)-2-methylpyrrolidine-1-carboxylate | 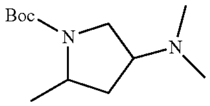 | 229 |
| 44B | tert-Butyl (S)-3-(cyclobutylamino) pyrrolidine-1-carboxylate | 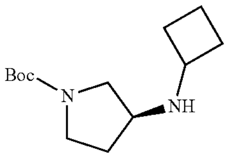 [SMILES: CC(C)(C)OC(=O)N1CC[C@H](NC2CCC2)C1] | 241 |
| 45B | tert-Butyl (4aR,7aS)-1,4-dimethyloctahydro-6H-pyrrolo[3,4-b]pyrazine-6-carboxylate | 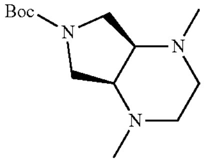 [SMILES: CN1CCN(C)[C@H]2CN(C(=O)OC(C)(C)C)C[C@H]21] | 256 |
| 46B | tert-Butyl 5-(dimethylamino)-2-azaspiro[3.3]heptane-2-carboxylate | 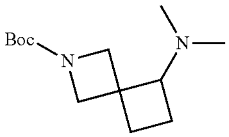 [SMILES: CN(C)C1CCC12CN(C(=O)OC(C)(C)C)C2] | |
| 47B | tert-Butyl (3S,4S)-3-(dimethylamino)-4-(hydroxymethyl) pyrrolidine-1-carboxylate | 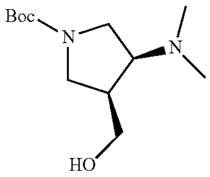 [SMILES: CN(C)[C@@H]1CN(C(=O)OC(C)(C)C)C[C@@H]1CO] | |
| 48B | tert-Butyl (3R,4R)-3-(dimethylamino)-4-(hydroxymethyl) pyrrolidine-1-carboxylate | 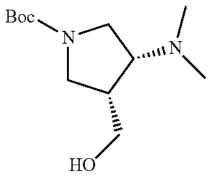 [SMILES: CN(C)[C@H]1CN(C(=O)OC(C)(C)C)C[C@H]1CO] | |
| 49B | tert-Butyl (3S,4R)-3-(dimethylamino)-4-(hydroxymethyl) pyrrolidine-1-carboxylate | 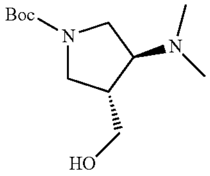 [SMILES: CN(C)[C@@H]1CN(C(=O)OC(C)(C)C)C[C@H]1CO] | |
| 50B | tert-butyl (3R,4S)-3-(dimethylamino)-4-(hydroxymethyl) pyrrolidine-1-carboxylate | 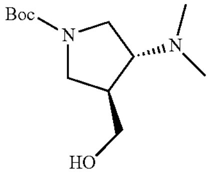 [SMILES: CN(C)[C@H]1CN(C(=O)OC(C)(C)C)C[C@@H]1CO] | |

TABLE 12-continued

| Preparation | Chemical Name | Structure | MS (ES) m/z (M + 1) |
|---|---|---|---|
| 51B | tert-Butyl 5-methyl-2,5-diazaspiro[3.4]octane-2-carboxylate | 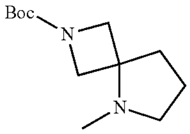 [SMILES: CN1CCCC12CN(C(=O)OC(C)(C)C)C2] | 227 |
| 52B | tert-Butyl (S)-3-(dimethylamino)-3-methylpyrrolidine-1-carboxylate | 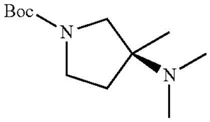 [SMILES: CN(C)[C@@]1(C)CCN(C(=O)OC(C)(C)C)C1] | 229 |
| 53B | tert-Butyl 5-methylhexahydropyrrolo[3,4-b]pyrrole-1(2H)-carboxylate, Mix of Cis Isomers | 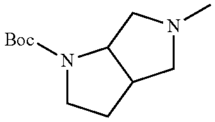 [SMILES: CN1CC2CCN(C(=O)OC(C)(C)C)C2C1] | |
| 18C | tert-Butyl (1R,5S)-3-methyl-3,6-diazabicyclo[3.2.1]octane-6-carboxylate | 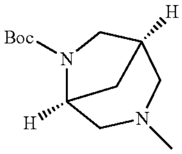 [SMILES: CN1C[C@H]2C[C@@H](C1)N(C(=O)OC(C)(C)C)C2] | 227 |
| 19C | tert-Butyl 8-(dimethylamino)-2-oxa-6-azaspiro[3.4]octane-6-carboxylate | 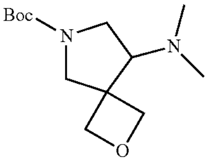 [SMILES: CN(C)C1CN(C(=O)OC(C)(C)C)CC12COC2] | 257 |
| 20C | tert-Butyl 8-(isopropylamino)-2-oxa-6-azaspiro[3.4]octane-6-carboxylate | 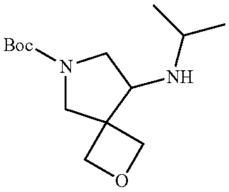 [SMILES: CC(C)NC1CN(C(=O)OC(C)(C)C)CC12COC2] | 271 |
| 21C | tert-Butyl 3,3-dimethyl-4-(methylamino)pyrrolidine-1-carboxylate | 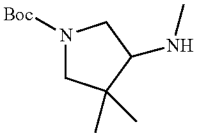 | 229 |
| 22C | tert-Butyl (R)-7-(isopropylamino)-5-azaspiro[2.4]heptane-5-carboxylate | 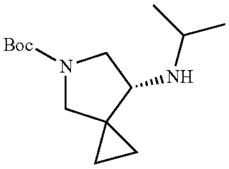 [SMILES: CC(C)N[C@H]1CN(C(=O)OC(C)(C)C)CC12CC2] | 255 |
| 23C | tert-Butyl 7-(isopropylamino)-5-azaspiro[2.4]heptane-5-carboxylate | 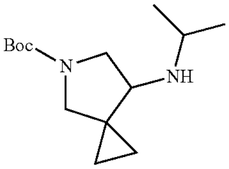 [SMILES: CC(C)NC1CN(C(=O)OC(C)(C)C)CC12CC2] | 255 |

TABLE 12-continued

| Preparation | Chemical Name | Structure | MS (ES) m/z (M + 1) |
|---|---|---|---|
| 24C | tert-Butyl (3S,4S)-3-(dimethylamino)-4-hydroxypyrrolidine-1-carboxylate | 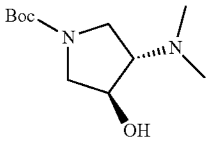 [SMILES: CN(C)[C@H]1CN(C(=O)OC(C)(C)C)C[C@@H]1O] | 231 |
| 25C | tert-Butyl (3R,4R)-3-(dimethylamino)-4-hydroxypyrrolidine-1-carboxylate | 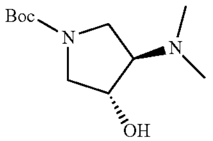 [SMILES: CN(C)[C@@H]1CN(C(=O)OC(C)(C)C)C[C@H]1O] | 231 |
| 26C | tert-Butyl (3S,4R)-3-(dimethylamino)-4-hydroxypyrrolidine-1-carboxylate | 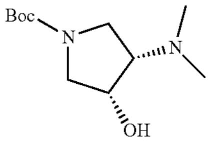 [SMILES: CN(C)[C@H]1CN(C(=O)OC(C)(C)C)C[C@H]1O] | 231 |
| 27C | tert-Butyl (3S,4S)-3-(isopropylamino)-4-methylpyrrolidine-1-carboxylate | 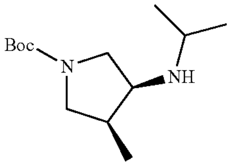 [SMILES: CC(C)N[C@@H]1CN(C(=O)OC(C)(C)C)C[C@@H]1C] | 243 |
| 28C | tert-Butyl (3S,4S)-3-hydroxy-4-(isopropyl(methyl)amino) pyrrolidine-1-carboxylate | 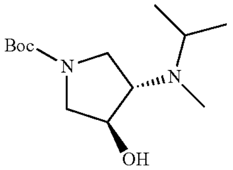 [SMILES: CC(C)N(C)[C@H]1CN(C(=O)OC(C)(C)C)C[C@@H]1O] | 259 |
| 29C | tert-Butyl (2S,3S)-3-(((S)-2-((tert-butyldimethylsilyl)oxy) propyl)amino)-2-methylpyrrolidine-1-carboxylate | 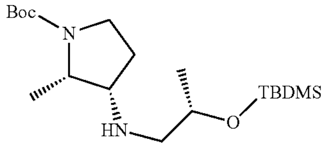 | 373 |
| 30C | tert-Butyl (2S,3S)-3-(((S)-2-((tert-butyldimethylsilyl)oxy) propyl)(methyl)amino)-2-methylpyrrolidine-1-carboxylate | 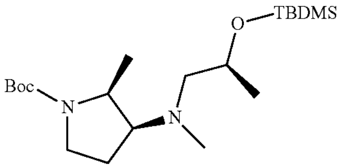 | 387 |
| 31C | tert-Butyl (2S,3S)-3-(((R)-2-((tert-butyldimethylsilyl)oxy) propyl)(methyl)amino)-2-methylpyrrolidine-1-carboxylate | 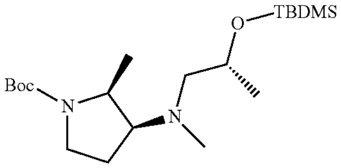 | 387 |
| 32C | tert-Butyl (2S,3S)-3-(isopropylamino)-2-methylpyrrolidine-1-carboxylate | 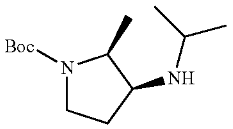 [SMILES: CC(C)N[C@H]1CCN(C(=O)OC(C)(C)C)[C@H]1C] | 243 |

TABLE 12-continued

| Preparation | Chemical Name | Structure | MS (ES) m/z (M + 1) |
|---|---|---|---|
| 33C | tert-Butyl (2R,3S)-3-(isopropylamino)-2-methylpyrrolidine-1-carboxylate | 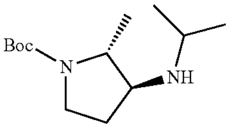 [SMILES: CC(C)N[C@H]1CCN(C(=O)OC(C)(C)C)[C@@H]1C] | |
| 34C | tert-Butyl (3R,4R)-3-(isopropylamino)-4-methoxypyrrolidine-1-carboxylate | 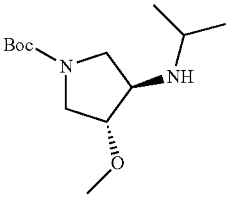 [SMILES: CO[C@@H]1CN(C(=O)OC(C)(C)C)C[C@H]1NC(C)C] | |
| 35C | tert-Butyl (3R,4S)-3-(isopropylamino)-4-methoxypyrrolidine-1-carboxylate | 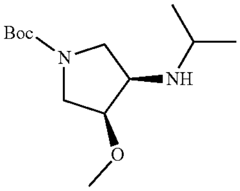 [SMILES: CO[C@H]1CN(C(=O)OC(C)(C)C)C[C@H]1NC(C)C] | |
| 36C | tert-Butyl 6-(dimethylamino)-2-azabicyclo[3.2.0]heptane-2-carboxylate | 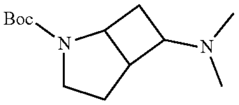 [SMILES: CN(C)C1CC2C1CCN2C(=O)OC(C)(C)C] | 241 |
| 37C | tert-Butyl 3-((dimethylamino) methyl)-2-methylpyrrolidine-1-carboxylate, Mix of Cis Isomers | 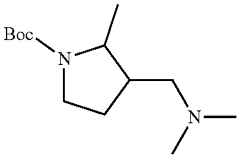 [SMILES: CC1C(CN(C)C)CCN1C(=O)OC(C)(C)C] | 243 |
| 38C | tert-Butyl (2S)-3-(bicyclo[1.1.1]pentan-1-ylamino)-2-methylpyrrolidine-1-carboxylate | 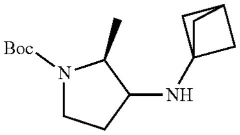 [SMILES: C[C@H]1C(NC23CC(C2)C3)CCN1C(=O)OC(C)(C)C] | 267 |
| 123D | tert-Butyl 3-(dimethylamino)-1-oxa-7-azaspiro[4.4]nonane-7-carboxylate | 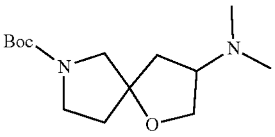 [SMILES: CN(C)C1COC2(CCN(C(=O)OC(C)(C)C)C2)C1] | 271 |
| 124D | tert-Butyl (R)-3-((3R,5S)-3,4,5-trimethylpiperazin-1-yl)pyrrolidine-1-carboxylate | 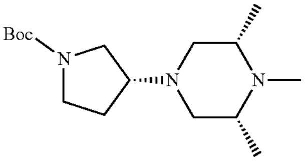 [SMILES: C[C@@H]1CN([C@@H]2CCN(C(=O)OC(C)(C)C)C2)C[C@H](C)N1C] | 298 |
| 125D | tert-Butyl (3S,4S)-3-fluoro-4-(isopropylamino) pyrrolidine-1-carboxylate | 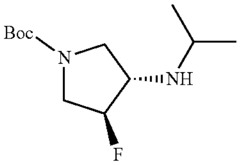 [SMILES: CC(C)N[C@H]1CN(C(=O)OC(C)(C)C)C[C@@H]1F] | 247 |

TABLE 12-continued

| Preparation | Chemical Name | Structure | MS (ES) m/z (M + 1) |
|---|---|---|---|
| 126D | tert-Butyl (3S,4R)-3-fluoro-4-(isopropylamino) pyrrolidine-1-carboxylate | 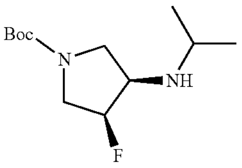 [SMILES: CC(C)N[C@@H]1CN(C(=O)OC(C)(C)C)C[C@@H]1F] | 247 |
| 127D | tert-Butyl (3R,4S)-3-hydroxy-4-(isopropylamino) pyrrolidine-1-carboxylate | 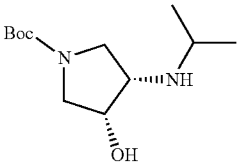 [SMILES: CC(C)N[C@H]1CN(C(=O)OC(C)(C)C)C[C@H]1O] | 245 |
| 128D | tert-Butyl (3S,4S)-3-hydroxy-4-(isopropylamino) pyrrolidine-1-carboxylate | 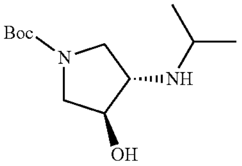 [SMILES: CC(C)N[C@H]1CN(C(=O)OC(C)(C)C)C[C@@H]1O] | 245 |
| 129D | tert-Butyl (3S,4R)-3-hydroxy-4-(isopropylamino) pyrrolidine-1-carboxylate | 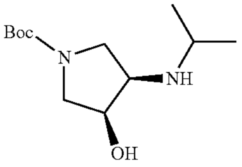 [SMILES: CC(C)N[C@@H]1CN(C(=O)OC(C)(C)C)C[C@@H]1O] | 245 |
| 130D | Benzyl (3R,4R)-3-hydroxy-4-(isopropylamino) pyrrolidine-1-carboxylate | 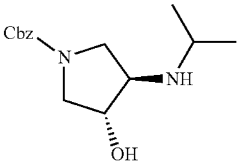 [SMILES: CC(C)N[C@@H]1CN(C(=O)OCc2ccccc2)C[C@H]1O] | 279 |
| 131D [1] | Benzyl 3-hydroxy-4-(isopropylamino) pyrrolidine-1-carboxylate | 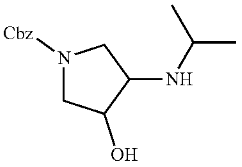 [SMILES: CC(C)NC1CN(C(=O)OCc2ccccc2)CC1O] | 279 |
| 132D [2] | tert-Butyl 3-((dimethylamino) methyl)-4-hydroxypyrrolidine-1-carboxylate | 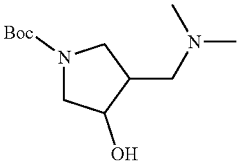 [SMILES: CN(C)CC1CN(C(=O)OC(C)(C)C)CC1O] | 245 |
| 133D [3] | tert-Butyl 3-((dimethylamino) methyl)-4-hydroxypyrrolidine-1-carboxylate | 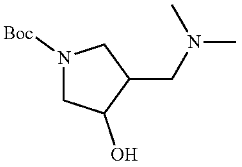 [SMILES: CN(C)CC1CN(C(=O)OC(C)(C)C)CC1O] | 245 |

TABLE 12-continued

| Preparation | Chemical Name | Structure | MS (ES) m/z (M + 1) |
|---|---|---|---|
| 134D [4] | Benzyl 3-(dimethylamino)-4-(methoxymethyl) pyrrolidine-1-carboxylate | 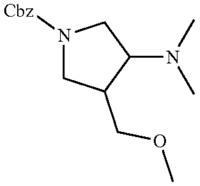 [SMILES: COCC1CN(C(=O)OCc2ccccc2)CC1N(C)C] | 293 |
| 135D | tert-Butyl (3R,4S)-3-(isopropylamino)-4-methylpyrrolidine-1-carboxylate | 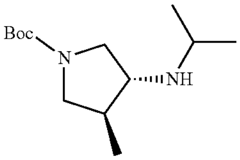 [SMILES: CC(C)N[C@H]1CN(C(=O)OC(C)(C)C)C[C@@H]1C] | 243 |
| 136D | tert-Butyl (3R,4S)-3-(isopropyl(methyl) amino)-4-methylpyrrolidine-1-carboxylate | 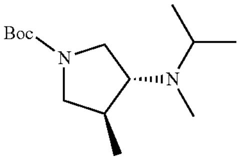 [SMILES: CC(C)N(C)[C@H]1CN(C(=O)OC(C)(C)C)C[C@@H]1C] | 257 |
| 137D | tert-Butyl (3S,4R)-3-(isopropylamino)-4-methoxypyrrolidine-1-carboxylate | 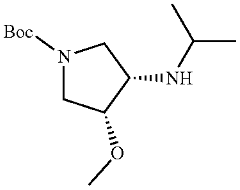 [SMILES: CO[C@@H]1CN(C(=O)OC(C)(C)C)C[C@@H]1NC(C)C] | 259 |
| 138D | tert-Butyl (3R,4S)-3-(isopropylamino)-4-methoxypyrrolidine-1-carboxylate | 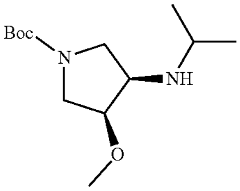 [SMILES: CO[C@H]1CN(C(=O)OC(C)(C)C)C[C@H]1NC(C)C] | 259 |
| 139D | tert-Butyl (3S,4S)-3-(isopropylamino)-4-methoxypyrrolidine-1-carboxylate | 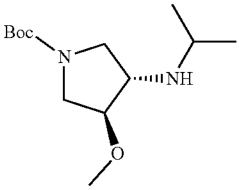 [SMILES: CO[C@H]1CN(C(=O)OC(C)(C)C)C[C@@H]1NC(C)C] | 259 |
| 140D | tert-Butyl (3R,4R)-3-(isopropylamino)-4-methoxypyrrolidine-1-carboxylate | 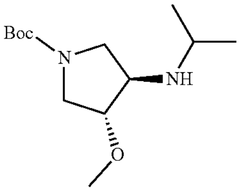 [SMILES: CO[C@@H]1CN(C(=O)OC(C)(C)C)C[C@H]1NC(C)C] | 259 |
| 141D | tert-Butyl 3-(hydroxymethyl)-3-(isopropylamino) pyrrolidine-1-carboxylate | 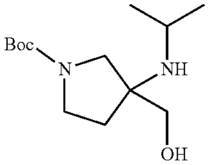 [SMILES: CC(C)NC1(CO)CCN(C(=O)OC(C)(C)C)C1] | 259 |

TABLE 12-continued

| Preparation | Chemical Name | Structure | MS (ES) m/z (M + 1) |
|---|---|---|---|
| 142D [5] | (1-Benzyl-3-(diethylamino)pyrrolidin-3-yl)methanol, Isomer 1 | 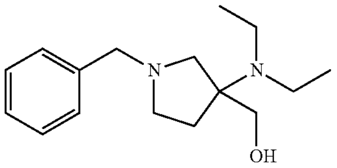 [SMILES: CCN(CC)C1(CO)CCN(Cc2ccccc2)C1] | 263 |
| 143D [5] | (1-Benzyl-3-(diethylamino)pyrrolidin-3-yl)methanol, Isomer 2 | 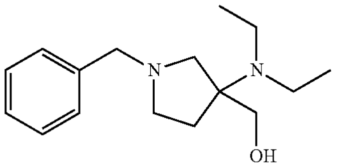 [SMILES: CCN(CC)C1(CO)CCN(Cc2ccccc2)C1] | 263 |
| 144D | tert-Butyl 4-((S)-2-((tert-butyldimethylsilyl)oxy) propyl)octahydro-1H-pyrrolo[3,2-b]pyridine-1-carboxylate | 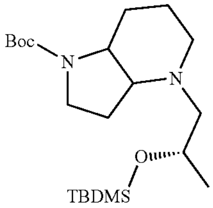 | 399 |
| 145D | tert-Butyl 4-((R)-2-((tert-butyldimethylsilyl)oxy) propyl)octahydro-1H-pyrrolo[3,2-b]pyridine-1-carboxylate | 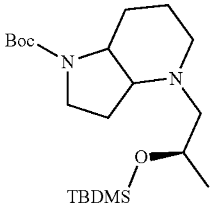 | 399 |
| 146D | tert-Butyl 4-(2-((tert-butyldimethylsilyl)oxy) ethyl)octahydro-1H-pyrrolo[3,2-b]pyridine-1-carboxylate | 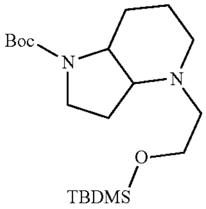 | 385 |
| 147D | tert-Butyl 8-(isopropylamino)-2-oxa-6-azaspiro[3.4]octane-6-carboxylate | 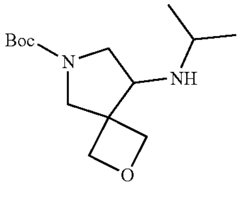 [SMILES: CC(C)NC1CN(C(=O)OC(C)(C)C)CC12COC2] | 271 |
| 148D | tert-Butyl 8-(dimethylamino)-2-oxa-6-azaspiro[3.4]octane-6-carboxylate | 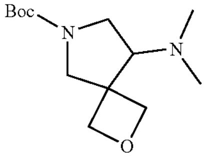 [SMILES: CN(C)C1CN(C(=O)OC(C)(C)C)CC12COC2] | 257 |
| 149D | tert-Butyl 7-methyl-2,7-diazaspiro[4.4]nonane-2-carboxylate | 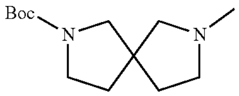 [SMILES: CN1CCC2(CCN(C(=O)OC(C)(C)C)C2)C1] | 241 |

TABLE 12-continued

| Preparation | Chemical Name | Structure | MS (ES) m/z (M + 1) |
|---|---|---|---|
| 150D | tert-Butyl (3S,4S)-3-fluoro-4-((propan-2-yl-1,1,1,3,3,3-d6)amino)pyrrolidine-1-carboxylate | 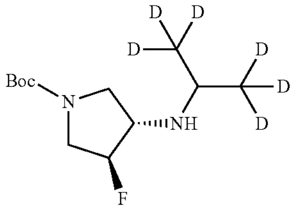 [SMILES: [2H]C([2H])([2H])C(N[C@H]1CN(C(=O)OC(C)(C)C)C[C@@H]1F)C([2H])([2H])[2H]] | 253 |
| 151D | tert-Butyl (3R,4S)-3-hydroxy-4-((propan-2-yl-1,1,1,3,3,3-d6)amino)pyrrolidine-1-carboxylate | 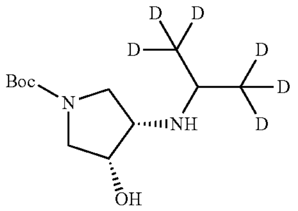 [SMILES: [2H]C([2H])([2H])C(N[C@H]1CN(C(=O)OC(C)(C)C)C[C@H]1O)C([2H])([2H])[2H]] | 251 |
| 152D | tert-Butyl (3R,4R)-3-hydroxy-4-((propan-2-yl-1,1,1,3,3,3-d6)amino)pyrrolidine-1-carboxylate | 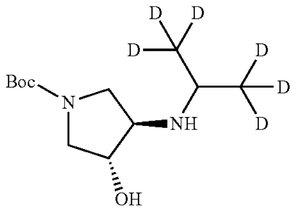 [SMILES: [2H]C([2H])([2H])C(N[C@@H]1CN(C(=O)OC(C)(C)C)C[C@H]1O)C([2H])([2H])[2H]] | 251 |
| 153D | tert-Butyl (S)-7-((propan-2-yl-1,1,1,3,3,3-d6)amino)-5-azaspiro[2.4]heptane-5-carboxylate | 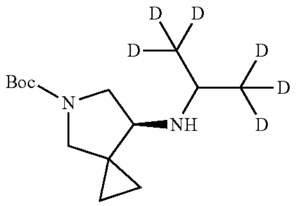 [SMILES: [2H]C([2H])([2H])C(N[C@@H]1CN(C(=O)OC(C)(C)C)CC12CC2)C([2H])([2H])[2H]] | 261 |
| 154D [6] | tert-Butyl (3S,4S)-3-fluoro-4-((propan-2-yl-d7)amino)pyrrolidine-1-carboxylate | 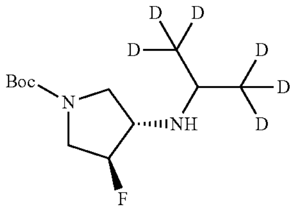 [SMILES: [2H]C([2H])([2H])C(N[C@H]1CN(C(=O)OC(C)(C)C)C[C@@H]1F)C([2H])([2H])[2H]] | 254 |
| 155D [7] | tert-Butyl (3S,4S)-3-amino-4-fluoropyrrolidine-1-carboxylate | 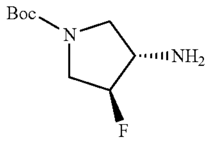 [SMILES: CC(C)(C)OC(=O)N1C[C@H](N)[C@@H](F)C1] | 205 |
| 156D | Benzyl (S)-3-(4-(propan-2-yl-1,1,1,3,3,3-d6)piperazin-1-yl)pyrrolidine-1-carboxylate | 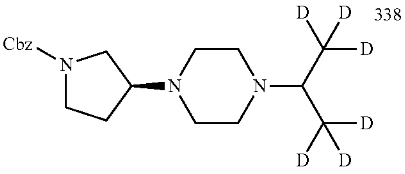 | 338 |

TABLE 12-continued

| Preparation | Chemical Name | Structure | MS (ES) m/z (M + 1) |
|---|---|---|---|
| 157D | tert-Butyl 4-(propan-2-yl-1,1,1,3,3,3-d6)piperazine-1-carboxylate | 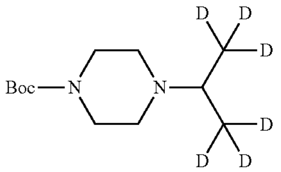 [SMILES: [2H]C([2H])([2H])C(N1CCN(C(=O)OC(C)(C)C)CC1)C([2H])([2H])[2H]] | 235 |
| 158D | tert-Butyl 4-(ethyl-d5)piperazine-1-carboxylate | 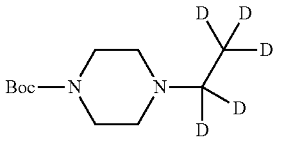 [SMILES: [2H]C([2H])([2H])C([2H])([2H])N1CCN(C(=O)OC(C)(C)C)CC1] | 220 |
| 159D | tert-Butyl (3S,4R)-3-(isopropylamino)-4-methylpyrrolidine-1-carboxylate | 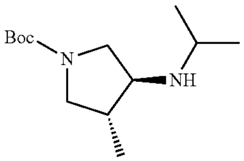 [SMILES: CC(C)N[C@@H]1CN(C(=O)OC(C)(C)C)C[C@H]1C] | 243 |

[1] Mix of Trans Isomers
[2] Mix of Cis Isomers
[3] Mix of Trans Isomers
[4] Mix of Cis Isomers
[5] Prep-Chiral-HPLC; Chiralpak-IF, 20 × 250 mm, 5% Hexanes (with 10 mM ammoniated methanol) : 95% EtOH, 20 mL/min
[6] Sodium borodeuteride was used
[7] Impurity contained in Preparation 154D The following compounds in Table 13 were prepared in similar manner as described in Preparation 122D. Various methods were used to purify the compounds, which would be apparent to one skilled in the art.

TABLE 13

| Preparation | Chemical Name | Structure | MS (ES) m/z (M + 1) |
|---|---|---|---|
| 160D | N,N-Dimethyl-2-oxa-6-azaspiro[3.4]octan-8-amine | 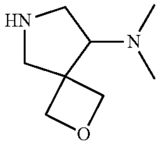 | 157 |
| 161D | 1 -(Propan-2-yl-1,1,1,3,3,3-d6)piperazine | 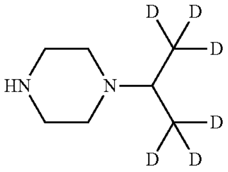 [SMILES: [2H]C([2H])([2H])C(N1CCNCC1)C([2H])([2H])[2H]] | 135 |
| 162D | 1-(Ethyl-d5)piperazine | 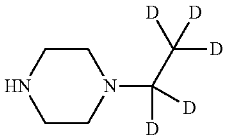 [SMILES: [2H]C([2H])([2H])C([2H])([2H])N1CCNCC1] | 120 |

Preparation 163D tert-Butyl (2S,3S)-2-methyl-3-(4-methylpiperazin-1-yl)pyrrolidine-1-carboxylate

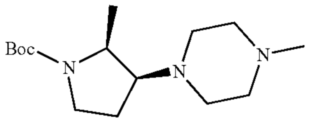 [SMILES: C[C@H]1[C@@H](N2CCN(C)CC2)CCN1C(=O)OC(C)(C)C]

To a solution of tert-butyl (S)-2-methyl-3-oxopyrrolidine-1-carboxylate (2.20 g, 11.0 mmol), 1-methylpiperazine (1.66 g, 16.6 mmol), and acetic acid (0.63 mL, 11.0 mmol) in DCM (15 mL) was added sodium triacetoxyborohydride (3.74 g, 17.7 mmol) in portions. The mixture was stirred at room temperature. After 28 h, the mixture was cooled to 0° C. and diluted with saturated aqueous sodium bicarbonate. The layers were separated and the aqueous layer was extracted with DCM. The combined organic layers were washed with brine (25 mL), dried over anhydrous $Na_2SO_4$, filtered, and concentrated under reduced pressure to give the crude title compound (3.18 g) as a yellow oil. MS (ES) m/z=284 (M+1).

The following compounds in Table 14 were prepared in similar manner as described in Preparation 163D. Various methods were used to purify the compounds, which would be apparent to one skilled in the art.

TABLE 14

| Preparation | Chemical Name | Structure | MS (ES) m/z (M + 1) |
|---|---|---|---|
| 164D | tert-Butyl 3-(4-methyl-4,7-diazaspiro[2.5]octan-7-yl)pyrrolidine-1-carboxylate | 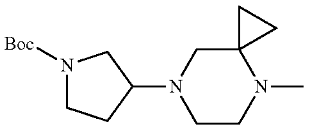 [SMILES: CN1CCN(C2CCN(C(=O)OC(C)(C)C)C2)CC12CC2] | 296 |
| 165D | tert-Butyl 3-(4,7-diazaspiro[2.5]octan-7-yl)pyrrolidine-1-carboxylate | 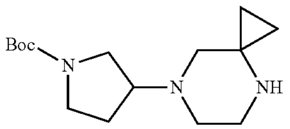 [SMILES: CC(C)(C)OC(=O)N1CCC(N2CCNC3(CC3)C2)C1] | 282 |
| 166D | tert-Butyl 3-(3,3-dimethylpiperazin-1-yl)pyrrolidine-1-carboxylate | 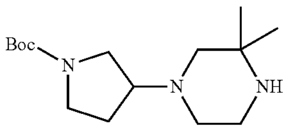 [SMILES: CC1(C)CN(C2CCN(C(=O)OC(C)(C)C)C2)CCN1] | 284 |
| 167D | tert-Butyl (2R,3R)-2-methyl-3-(4-methylpiperazin-1-yl)pyrrolidine-1-carboxylate | 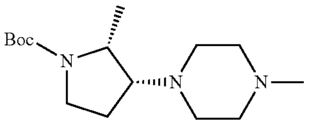 [SMILES: C[C@@H]1[C@H](N2CCN(C)CC2)CCN1C(=O)OC(C)(C)C] | 284 |
| 168D | tert-Butyl (2S,3S)-3-(4-ethylpiperazin-1-yl)-2-methylpyrrolidine-1-carboxylate | 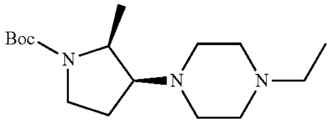 [SMILES: CCN1CCN([C@H]2CCN(C(=O)OC(C)(C)C)[C@H]2C)CC1] | 298 |
| 169D | tert-Butyl (2S,3S)-3-(4-isopropylpiperazin-1-yl)-2-methylpyrrolidine-1-carboxylate | 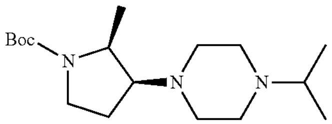 [SMILES: CC(C)N1CCN([C@H]2CCN(C(=O)OC(C)(C)C)[C@H]2C)CC1] | 312 |
| 170D | tert-Butyl (2S,3S)-3-(4-(2-methoxyethyl) piperazin-1-yl)-2-methylpyrrolidine-1-carboxylate | 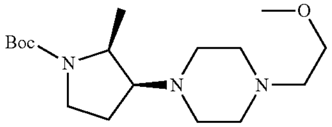 [SMILES: COCCN1CCN([C@H]2CCN(C(=O)OC(C)(C)C)[C@H]2C)CC1] | 328 |
| 171D | tert-Butyl (2S,3S)-3-(4-((S)-2-hydroxypropyl)piperazin-1-yl)-2-methylpyrrolidine-1-carboxylate | 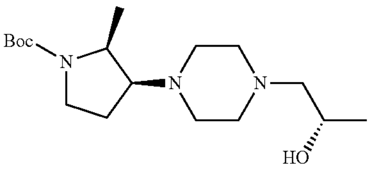 [SMILES: C[C@H](O)CN1CCN([C@H]2CCN(C(=O)OC(C)(C)C)[C@H]2C)CC1] | 328 |

TABLE 14-continued

| Preparation | Chemical Name | Structure | MS (ES) m/z (M + 1) |
|---|---|---|---|
| 172D | tert-Butyl (2S,3S)-3-(4-((R)-2-hydroxypropyl)piperazin-1-yl)-2-methylpyrrolidine-1-carboxylate | 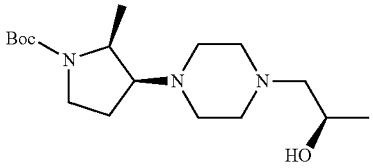 [SMILES: C[C@@H](O)CN1CCN([C@H]2CCN(C(=O)OC(C)(C)C)[C@H]2C)CC1] | 328 |
| 173D | tert-Butyl (2S,3S)-3-(4-(2-fluoroethyl)piperazin-1-yl)-2-methylpyrrolidine-1-carboxylate | 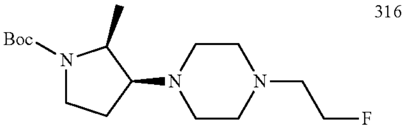 | 316 |
| 174D | tert-Butyl (2S,3S)-3-((S)-3,4-dimethylpiperazin-1-yl)-2-methylpyrrolidine-1-carboxylate | 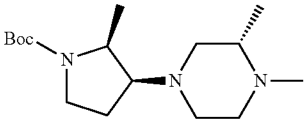 [SMILES: C[C@H]1CN([C@H]2CCN(C(=O)OC(C)(C)C)[C@H]2C)CCN1C] | 298 |
| 175D | tert-Butyl (2S,3S)-3-((S)-2,4-dimethylpiperazin-1-yl)-2-methylpyrrolidine-1-carboxylate | 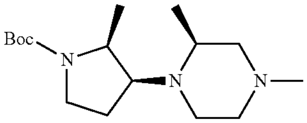 [SMILES: C[C@H]1[C@@H](N2CCN(C)C[C@@H]2C)CCN1C(=O)OC(C)(C)C] | 298 |
| 176D | tert-Butyl (2S,3S)-3-((S)-2-(hydroxymethyl)-4-methylpiperazin-1-yl)-2-methylpyrrolidine-1-carboxylate | 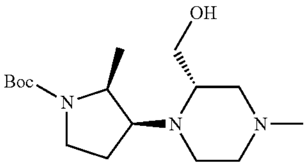 [SMILES: C[C@H]1[C@@H](N2CCN(C)C[C@H]2CO)CCN1C(=O)OC(C)(C)C] | 314 |
| 177D | tert-Butyl (2S,3S)-3-((S)-2-(fluoromethyl)-4-methylpiperazin-1-yl)-2-methylpyrrolidine-1-carboxylate | 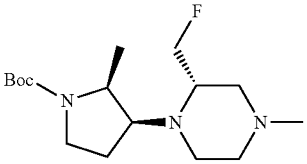 [SMILES: C[C@H]1[C@@H](N2CCN(C)C[C@H]2CF)CCN1C(=O)OC(C)(C)C] | 316 |
| 178D | tert-Butyl (2S,3S)-2-methyl-3-(8-methyl-3,8-diazabicyclo[3.2.1 ]octan-3-yl)pyrrolidine-1-carboxylate | 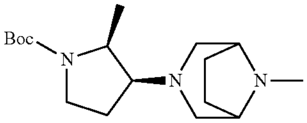 [SMILES: C[C@H]1[C@@H](N2CC3CCC(C2)N3C)CCN1C(=O)OC(C)(C)C] | 310 |
| 179D | tert-Butyl (2S,3S)-2-methyl-3-morpholinopyrrolidine-1-carboxylate | 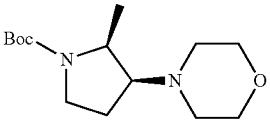 [SMILES: C[C@H]1[C@@H](N2CCOCC2)CCN1C(=O)OC(C)(C)C] | 271 |
| 180D | tert-Butyl (2S,3S)-3-(3-oxa-6-azabicyclo[3.1.1]heptan-6-yl)-2-methylpyrrolidine-1-carboxylate | 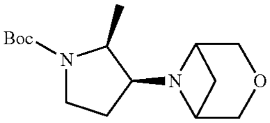 [SMILES: C[C@H]1[C@@H](N2C3COCC2C3)CCN1C(=O)OC(C)(C)C] | 283 |
| 181D | tert-Butyl (2S,3S)-2-methyl-3-((1-methylcyclopropyl) amino)pyrrolidine-1-carboxylate | 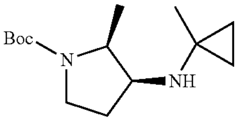 [SMILES: C[C@H]1[C@@H](NC2(C)CC2)CCN1C(=O)OC(C)(C)C] | 255 |

TABLE 14-continued

| Preparation | Chemical Name | Structure | MS (ES) m/z (M + 1) |
|---|---|---|---|
| 182D | tert-Butyl (2S)-3-((3-hydroxybicyclo[1.1.1] pentan-1-yl)amino)-2-methylpyrrolidine-1-carboxylate | 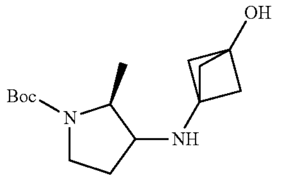 [SMILES: C[C@H]1C(NC23CC(O)(C2)C3)CCN1C(=O)OC(C)(C)C] | 283 |
| 183D | tert-Butyl (2S,3S)-3-((1-fluoro-2-methylpropan-2-yl)amino)-2-methylpyrrolidine-1-carboxylate | 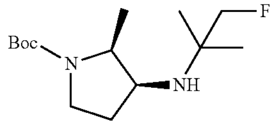 [SMILES: C[C@H]1[C@@H](NC(C)(C)CF)CCN1C(=O)OC(C)(C)C] | 275 |
| 184D | tert-Butyl (2S,3S)-2-methyl-3-(4-(propan-2-yl-1,1,1,3,3,3-d6)piperazin-1-yl)pyrrolidine-1-carboxylate | 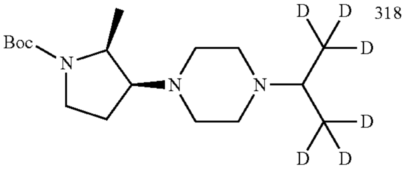 | 318 |
| 185D | tert-Butyl (2S,3S)-3-(4-(ethyl-d5)piperazin-1-yl)-2-methylpyrrolidine-1-carboxylate | 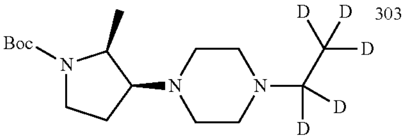 | 303 |

Preparation 186D tert-Butyl (3S,4R)-3-hydroxy-4-(isopropyl(methyl) amino)pyrrolidine-1-carboxylate

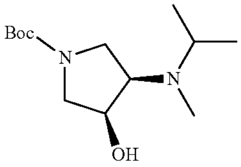 [SMILES: CC(C)N(C)[C@@H]1CN(C(=O)OC(C)(C)C)C[C@@H]1O]

To a solution of tert-butyl (3R,4S)-3-amino-4-hydroxy-pyrrolidine-1-carboxylate (1.00 g, 4.94 mmol) in acetone (20 mL) was added 20% palladium hydroxide on carbon (0.50 g). The mixture was hydrogenated for 2 h at RT under a hydrogen atmosphere (balloon), then filtered through diatomaceous earth. The filtrate was concentrated under reduced pressure to give crude (1.3 g) tert-butyl (3S,4R)-3-hydroxy-4-(isopropylamino)pyrrolidine-1-carboxylate as a gray solid. MS (ES) m/z=245 (M+1).

To a solution of tert-butyl (3S,4R)-3-hydroxy-4-(isopropylamino)pyrrolidine-1-carboxylate (1.30 g, 5.32 mmol) and $(HCHO)_n$ (0.32 g, 10.6 mmol) in methanol (20 mL) was added 20% palladium hydroxide on carbon (0.75 g). The mixture was hydrogenated for 2 h at RT under a hydrogen atmosphere (balloon), then filtered through diatomaceous earth. The filtrate was concentrated under reduced pressure and the residue was diluted with EtOAc (100 mL). The resulting mixture was washed with saturated aqueous sodium carbonate (50 mL), water (2×50 mL), and brine (50 mL). The organics were dried over anhydrous sodium sulfate, filtered, and concentrated under reduced pressure to give the title compound (1.1 g) as a yellow oil. MS (ES) m/z=259 (M+1).

The following compounds in Table 15 were prepared in similar manner as described in Preparation 186D. Various methods were used to purify the compounds, which would be apparent to one skilled in the art.

TABLE 15

| Preparation | Chemical Name | Structure | MS (ES) m/z (M + 1) |
|---|---|---|---|
| 187D | tert-Butyl (3S,4S)-3-hydroxy-4-(isopropyl(methyl)amino) pyrrolidine-1-carboxylate | 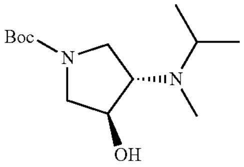 [SMILES: CC(C)N(C)[C@H]1CN(C(=O)OC(C)(C)C)C[C@@H]1O] | 259 |

TABLE 15-continued

| Preparation | Chemical Name | Structure | MS (ES) m/z (M + 1) |
|---|---|---|---|
| 188D | tert-Butyl (3R,4R)-3-hydroxy-4-(isopropyl(methyl)amino) pyrrolidine-1-carboxylate | 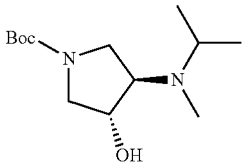 [SMILES: CC(C)N(C)[C@@H]1CN(C(=O)OC(C)(C)C)C[C@H]1O] | 259 |
| 189D | tert-Butyl (3R,4S)-3-hydroxy-4-(isopropyl(methyl)amino) pyrrolidine-1-carboxylate | 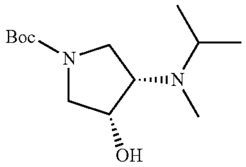 [SMILES: CC(C)N(C)[C@H]1CN(C(=O)OC(C)(C)C)C[C@H]1O] | 259 |

(3S,4S)-4-Methoxy-N,N-dimethylpyrrolidin-3-amine dihydrochloride

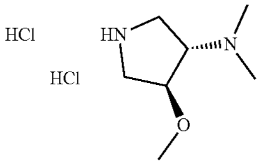

To a solution of tert-butyl (3S,4S)-3-(dimethylamino)-4-methoxypyrrolidine-1-carboxylate (0.53 g, 2.17 mmol) in DCM (6 mL) was added HCl (4M in 1,4-dioxane; 4 mL, 16.0 mmol). The reaction mixture was stirred for 18 h at RT, then concentrated under reduced pressure. The residue was diluted with DCM and concentrated under reduced pressure (3 cycles) to obtain the crude title compound (0.48 g, quant) as a yellow solid. MS (ES) m/z=145 (M+1).

The following compounds in Table 16 were prepared in similar manner as described in Preparation 54B. In some instances, TFA was substituted for HCl. Various methods were used to purify the compounds, which would be apparent to one skilled in the art.

TABLE 16

| Preparation | Chemical Name | Structure | MS (ES) m/z (M + 1) |
|---|---|---|---|
| 55B | (3R,4S)-4-Methoxy-N,N-dimethylpyrrolidin-3-amine dihydrochloride | 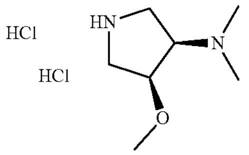 | 145 |
| 56B | N,N-Dimethyl-3-azabicyclo[3.2.0]heptan-1-amine hydrochloride | 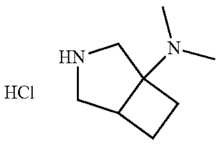 | |
| 57B | N,N-Dimethyl-4-azaspiro[2.4]heptan-7-amine hydrochloride | 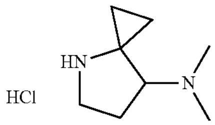 | 141 |
| 58B | 1-Methyloctahydropyrrolo [3,2-b]pyrrole hydrochloride | 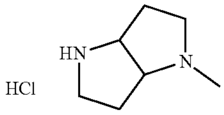 | 127 |

TABLE 16-continued

| Preparation | Chemical Name | Structure | MS (ES) m/z (M + 1) |
|---|---|---|---|
| 59B | (3S,4R)-4-(Isopropyl(methyl) amino)pyrrolidin-3-ol dihyrdrochloride | 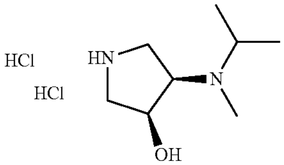 | |
| 60B | (3S,4R)-4-(Diethylamino) pyrrolidin-3-ol dihydrochloride | 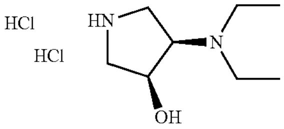 | 159 |
| 61B | (3S,4R)-4-(Ethyl(methyl)amino) pyrrolidin-3-ol dihydrochoride | 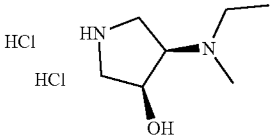 | 145 |
| 62B | (3S,4R)-4-(Dimethylamino)pyrrolidin-3-ol | 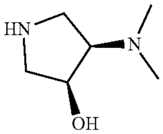 | 131 |
| 63B | (1S,5S)-2,6-Diazabicyclo[3.2.0] heptane dihydrochloride | 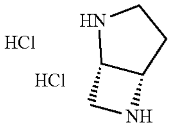 | |
| 64B | (1S,5S)-6-Methyl-2,6-diazabicyclo[3.2.0] heptane dihydrochloride | 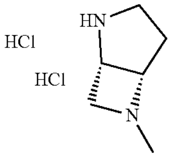 | 113 |
| 65B | (2S,3S)-2-Methylpyrrolidin-3-amine dihydrochloride | 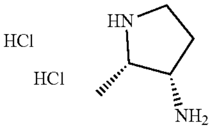 | 101 |
| 66B | (3-(Dimethylamino) pyrrolidin-3-yl)methanol | 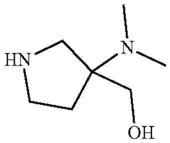 | |
| 67B | (2S,3S)-N,2-Dimethylpyrrolidin-3-amine dihydrochloride | 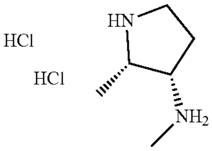 | 115 |
| 68B | 4-(Difluoromethyl)-N,N-dimethylpyrrolidin-3-amine hydrochloride, Mix of Trans Isomers | 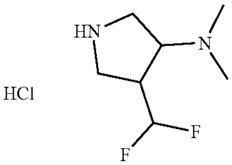 | 165 |

TABLE 16-continued

| Preparation | Chemical Name | Structure | MS (ES) m/z (M + 1) |
|---|---|---|---|
| 69B | N,N,5-trimethylpyrrolidin-3-amine trifluoroacetic acid | 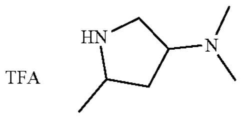 | 129 |
| 70B | (S)-N-Cyclobutylpyrrolidin-3-amine dihydrochloride | 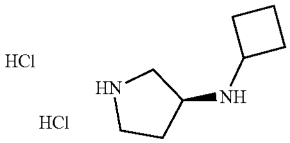 | 141 |
| 71B | N-Cyclopropylpyrrolidin-3-amine dihydrochloride | 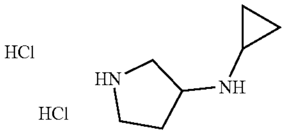 | 127 |
| 72B | (4aR,7aS)-1,4-Dimethyloctahydro-1H-pyrrolo[3,4-b]pyrazine dihydrochloride | 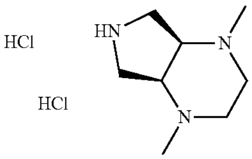 | 156 |
| 73B | N,N-Dimethyl-2-azaspiro[3.3 ]heptan-5-amine dihydrochloride | 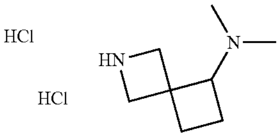 | 141 |
| 74B | ((3S,4S)-4-(Dimethylamino) pyrrolidin-3-yl)methanol hydrochloride | 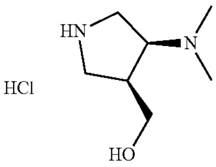 | |
| 75B | ((3R,4R)-4-(Dimethylamino)pyrrolidin-3-yl)methanol hydrochloride | 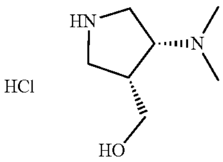 | |
| 76B | ((3R,4S)-4-(Dimethylamino) pyrrolidin-3-yl)methanol hydrochloride | 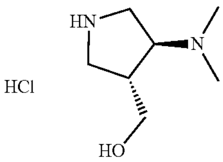 | |
| 77B | ((3S,4R)-4-(Dimethylamino)pyrrolidin-3-yl)methanol hydrochloride | 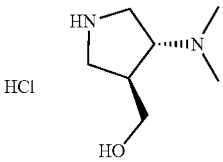 | |

TABLE 16-continued

| Preparation | Chemical Name | Structure | MS (ES) m/z (M + 1) |
|---|---|---|---|
| 78B | 5-Methyl-2,5-diazaspiro[3.4]octane dihydrochloride | 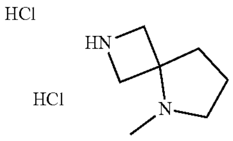 | 127 |
| 79B | (S)-N,N,3-Trimethylpyrrolidin-3-amine hydrochloride | 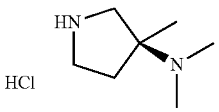 | 129 |
| 80B | 5-Methyloctahydropyrrolo[3,4-b]pyrrole hydrochloride, Mix of Cis Isomers | 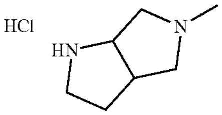 | |
| 39C | (S)-N-Isobutyl-N-methylpyrrolidin-3-amine hydrochloride | 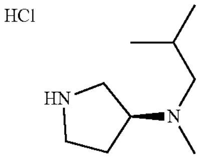 | 157 |
| 40C | (S)-N-(Cyclopropylmethyl)-N-methylpyrrolidin-3-amine trifluoroacetic acid | 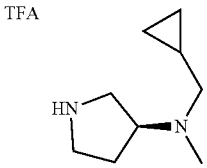 | 155 |
| 41C | (S)-3-(3-Methoxyazetidin-1-yl)pyrrolidine trifluoroacetic acid | 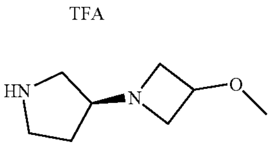 | 157 |
| 42C | (1S,5S)-3-Methyl-3,6-diazabicyclo[3.2.1]octane trifluoroacetic acid | 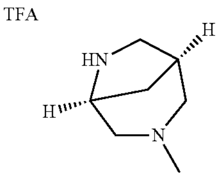 | 127 |
| 43C | N,N-Dimethyl-2-oxa-6-azaspiro[3.4]octan-8-amine trifluoroacetic acid | 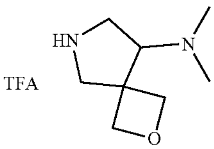 | 157 |
| 44C | N-Isopropyl-2-oxa-6-azaspiro[3.4]octan-8-amine | 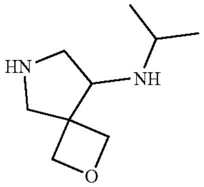 | 171 |

TABLE 16-continued

| Preparation | Chemical Name | Structure | MS (ES) m/z (M + 1) |
|---|---|---|---|
| 45C | N,4,4-Trimethylpyrrolidin-3-amine | 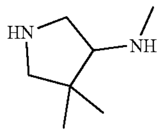 | 129 |
| 46C | (R)-N-Isopropyl-5-azaspiro[2.4]heptan-7-amine | 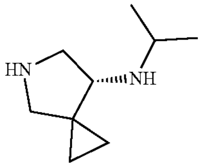 | 155 |
| 47C | N-Isopropyl-5-azaspiro[2.4]heptan-7-amine | 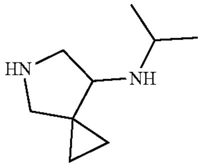 | 155 |
| 48C | (3S)-N-Methyl-N-(tetrahydrofuran-3-yl)pyrrolidin-3-amine | 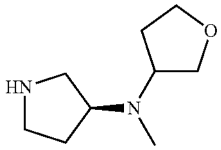 | 171 |
| 49C | (S)-N-(2-Methoxyethyl)-N-methylpyrrolidin-3-amine | 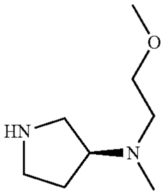 | 159 |
| 50C | (3S)-N-(1-Methoxypropan-2-yl)-N-methylpyrrolidin-3-amine | 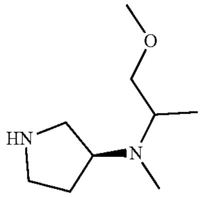 | 173 |
| 51C | (3S)-N-Methyl-N-((tetrahydrofuran-2-yl)methyl)pyrrolidin-3-amine | 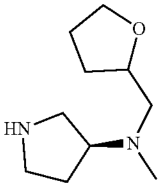 | 185 |
| 52C | (3S)-N-Methyl-N-((tetrahydro-2H-pyran-2-yl)methyl)pyrrolidin-3-amine | 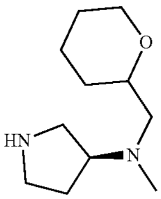 | 199 |

TABLE 16-continued

| Preparation | Chemical Name | Structure | MS (ES) m/z (M + 1) |
|---|---|---|---|
| 53C | (S)-N-Methyl-2-(methyl(pyrrolidin-3-yl)amino)acetamide | 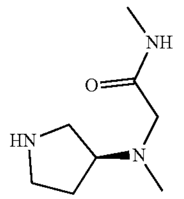 | 172 |
| 54C | 2-(Methyl((S)-pyrrolidin-3-yl)amino)propanamide | 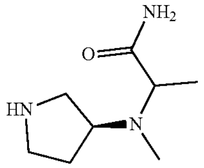 | 172 |
| 55C | (3S,4S)-4-(Dimethylamino) pyrrolidin-3-ol | 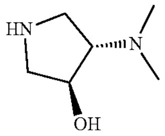 | 131 |
| 56C | (3R,4R)-4-(Dimethylamino) pyrrolidin-3-ol | 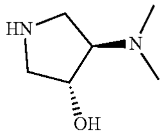 | 131 |
| 57C | (3R,4S)-4-(Dimethylamino) pyrrolidin-3-ol | 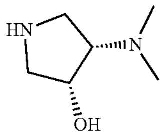 | 131 |
| 58C | (3S,4S)-N-Isopropyl-4-methylpyrrolidin-3-amine | 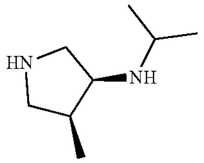 | 143 |
| 59C | (3S,4S)-4-(Isopropyl(methyl) amino)pyrrolidin-3-ol dihydrochloride | 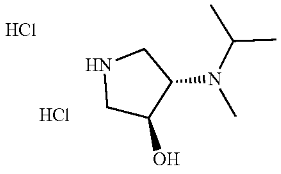 | 159 |
| 60C | (S)-1-(((2S,3S)-2-Methylpyrrolidin-3-yl)amino)propan-2-ol dihydrochloride | 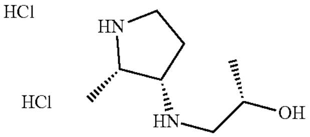 | 159 |
| 61C | (2S,3S)-N,N,2-Trimethylpyrrolidine-3-carboxamide hydrochloride | 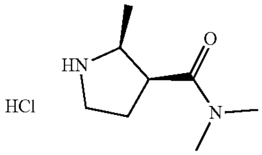 | 157 |

TABLE 16-continued

| Preparation | Chemical Name | Structure | MS (ES) m/z (M + 1) |
|---|---|---|---|
| 62C | (S)-1-(Methyl((2S,3S)-2-methylpyrrolidin-3-yl)amino)propan-2-ol dihydrochloride | 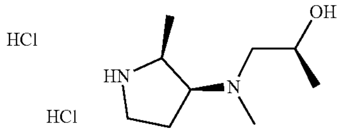 | 173 |
| 63C | (R)-1-(Methyl((2S,3S)-2-methylpyrrolidin-3-yl)amino)propan-2-ol dihydrochloride | 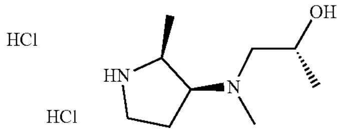 | 173 |
| 64C | (2S,3S)-N-Isopropyl-2-methylpyrrolidin-3-amine dihydrochloride | 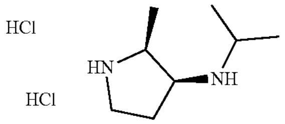 | 143 |
| 65C | (2R,3S)-N-Isopropyl-2-methylpyrrolidin-3-amine | 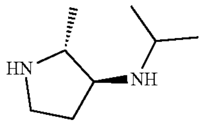 | |
| 66C | (3R,4R)-N-Isopropyl-4-methoxypyrrolidin-3-amine | 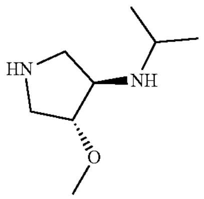 | |
| 67C | (3R,4S)-N-Isopropyl-4-methoxypyrrolidin-3-amine | 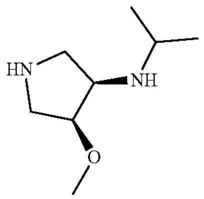 | |
| 68C | N,N-Dimethyl-2-azabicyclo[3.2.0]heptan-6-amine dihydrochloride | 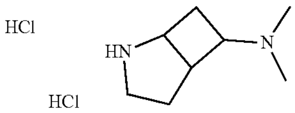 | 141 |
| 69C | N,N-Dimethyl-1-(2-methylpyrrolidin-3-yl)methanamine dihydrochloride, Mix of Cis Isomers | 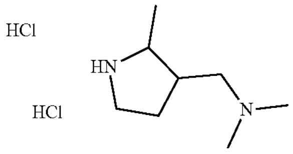 | 143 |
| 70C | (2S)-N-(Bicyclo[1.1.1]pentan-1-yl)-2-methylpyrrolidin-3-amine hydrochloride | 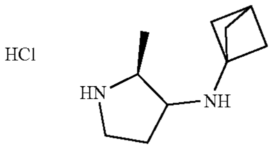 | 167 |

TABLE 16-continued

| Preparation | Chemical Name | Structure | MS (ES) m/z (M + 1) |
|---|---|---|---|
| 71C | (2S,3S)-N-(2-Fluoroethyl)-2-methylpyrrolidin-3-amine dihydrochloride | 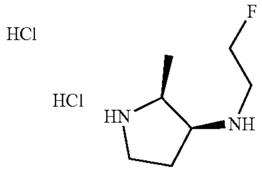 | 147 |
| 190D | N,N-Dimethyl-1-oxa-7-azaspiro[4.4]nonan-3-amine | 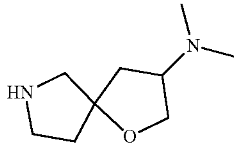 | 171 |
| 191D | 6-(Methyl-d3)-2,6-diazaspiro[3.4]octane | 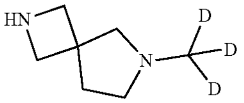 [SMILES: [2H]C([2H])([2H])N1CCC2(CNC2)C1] | 130 |
| 192D | (R)-N,N-Dimethyl-1-(pyrrolidin-3-yl)azetidin-3-amine | 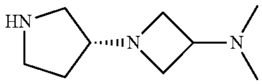 | 170 |
| 193D | (S)-N,N-Dimethyl-1-(pyrrolidin-3-yl)azetidin-3-amine | 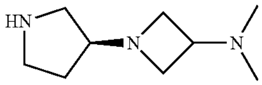 | 170 |
| 194D | (R)-3-(Azetidin-1-yl)pyrrolidine | 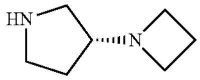 | 127 |
| 195D [1] | 4-(Azetidin-1-yl)pyrrolidin-3-ol | 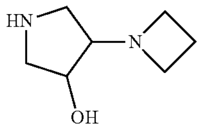 | 143 |
| 196D | (R)-2-(1-(Pyrrolidin-3-yl)azetidin-3-yl)propan-2-ol | 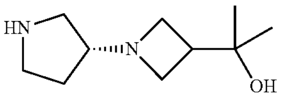 | 185 |
| 197D | (3S,3'R)-N,N-Dimethyl-[1,3'-bipyrrolidin]-3-amine | 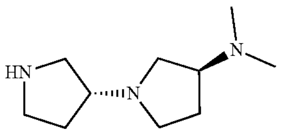 | 184 |
| 198D | (3S,3'S)-N,N-Dimethyl-[1,3'-bipyrrolidin]-3-amine | 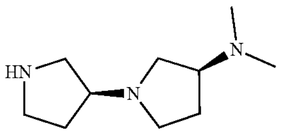 | 184 |
| 199D | (S)-1,3'-Bipyrrolidine | 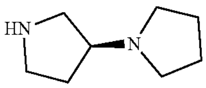 | 141 |
| 200D | (R)-1,3'-Bipyrrolidine | 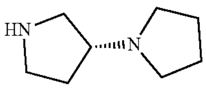 | 141 |

TABLE 16-continued

| Preparation | Chemical Name | Structure | MS (ES) m/z (M + 1) |
|---|---|---|---|
| 201D | (2S,3'R)-2-(Methoxymethyl)-1,3'-bipyrrolidine | 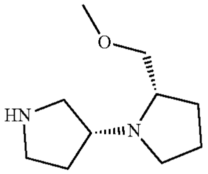 | 185 |
| 202D | (2S,3'S)-2-(Methoxymethyl)-1,3'-bipyrrolidine | 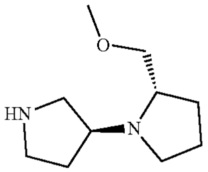 | 185 |
| 203D | (2R,3'R)-2-(Methoxymethyl)-1,3'-bipyrrolidine | 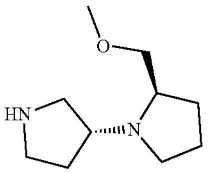 | 185 |
| 204D | (2R,3'S)-2-(Methoxymethyl)-1,3'-bipyrrolidine | 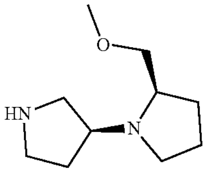 | 185 |
| 205D | (3S,3'R)-[1,3'-Bipyrrolidin]-3-ol | 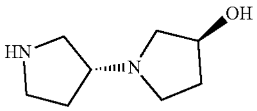 [SMILES: O[C@H]1CCN([C@@H]2CCNC2)C1] | 157 |
| 206D | (3S,3'R)-3-Methoxy-1,3'-bipyrrolidine | 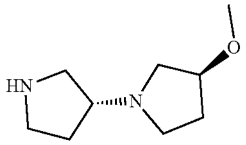 | 171 |
| 207D | (R)-1-(4-(Pyrrolidin-3-yl)piperazin-1-yl)ethan-1-one bistrifluoroacetic acid | 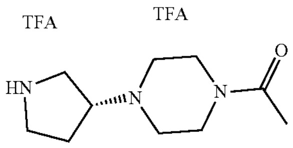 | 198 |
| 208D | (S)-1-(4-(Pyrrolidin-3-yl)piperazin-1-yl)ethan-1-one | 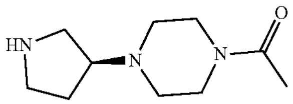 | 198 |
| 209D | (R)-1-Isopropyl-4-(pyrrolidin-3-yl)piperazine | 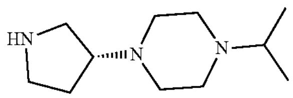 | 198 |
| 210D | (S)-1-Isopropyl-4-(pyrrolidin-3-yl)piperazine | 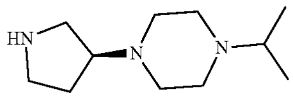 | 198 |

TABLE 16-continued

| Preparation | Chemical Name | Structure | MS (ES) m/z (M + 1) |
|---|---|---|---|
| 211D | (S)-1-ethyl-4-(Pyrrolidin-3-yl)piperazine | 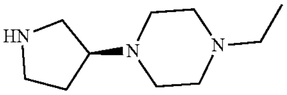 | 184 |
| 212D | (R)-1-ethyl-4-(Pyrrolidin-3-yl)piperazine | 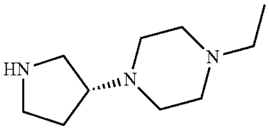 | 184 |
| 213D | (R)-2-(4-(Pyrrolidin-3-yl)piperazin-1-yl)ethan-1-ol | 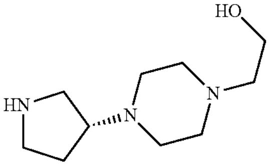 [SMILES: OCCN1CCN([C@@H]2CCNC2)CC1] | 200 |
| 214D | (R)-1-(Oxetan-3-yl)-4-(pyrrolidin-3-yl)piperazine | 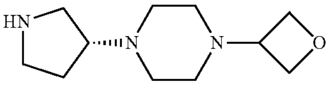 [SMILES: C1C[C@@H](N2CCN(C3COC3)CC2)CN1] | 212 |
| 215D | (R)-1-(Pyrrolidin-3-yl)-4-(2,2,2-trifluoroethyl)piperazine | 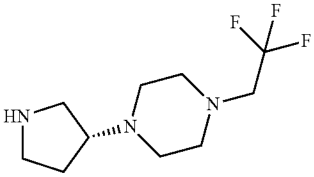 [SMILES: FC(F)(F)CN1CCN([C@@H]2CCNC2)CC1] | 238 |
| 216D | (R)-1-Cyclopropyl-4-(pyrrolidin-3-yl)piperazine | 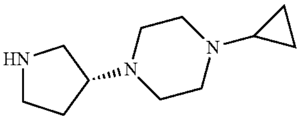 [SMILES: C1C[C@@H](N2CCN(C3CC3)CC2)CN1] | 196 |
| 217D | (R)-2-Methyl-1-(4-(pyrrolidin-3-yl)piperazin-1-yl)propan-2-ol | 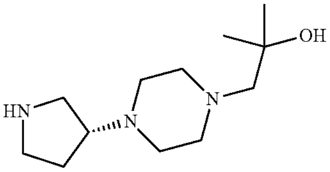 [SMILES: CC(C)(O)CN1CCN([C@@H]2CCNC2)CC1] | 228 |
| 218D | (R)-1-(2-Methoxyethyl)-4-(pyrrolidin-3-yl)piperazine | 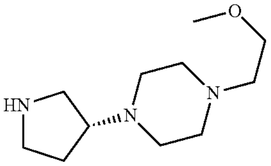 | 214 |
| 219D | (R)-2,4-Dimethyl-1-((R)-pyrrolidin-3-yl)piperazine trifluoroacetic acid | TFA 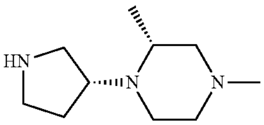 | 184 |
| 220D | (S)-2,4-Dimethyl-1-((R)-pyrrolidin-3-yl)piperazine trifluoroacetic acid | TFA 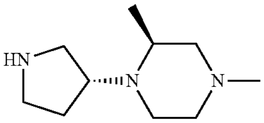 | 184 |

TABLE 16-continued

| Preparation | Chemical Name | Structure | MS (ES) m/z (M + 1) |
|---|---|---|---|
| 221D | (R)-2,4-Dimethyl-1-((S)-pyrrolidin-3-yl)piperazine trifluoroacetic acid | 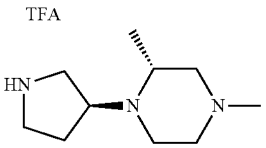 | 184 |
| 222D | (S)-2,4-Dimethyl-1-((S)-pyrrolidin-3-yl)piperazine | 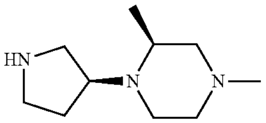 | 184 |
| 223D | (S)-1,2-Dimethyl-4-((R)-pyrrolidin-3-yl)piperazine | 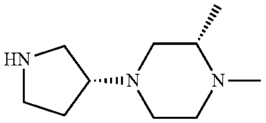 | 184 |
| 224D | (R)-1,2-Dimethyl-4-((R)-pyrrolidin-3-yl)piperazine | 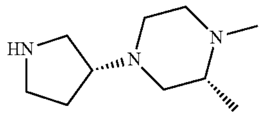 | 184 |
| 225D | (2R,6S)-1,2,6-Trimethyl-4-((R)-pyrrolidin-3-yl)piperazine | 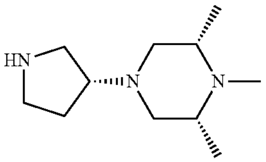 | 198 |
| 226D | (2R,6R)-1,2,6-Trimethyl-4-((R)-pyrrolidin-3-yl)piperazine | 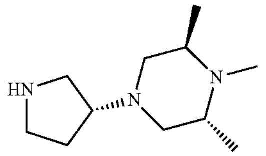 | 198 |
| 227D | (2S,6S)-1,2,6-Trimethyl-4-((R)-pyrrolidin-3-yl)piperazine | 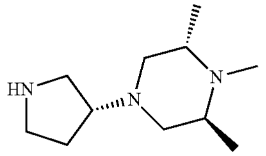 | 198 |
| 228D | ((S)-1-Methyl-4-((R)-pyrrolidin-3-yl)piperazin-2-yl)methanol | 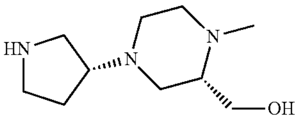 | 200 |
| 229D | ((R)-1-Methyl-4-((R)-pyrrolidin-3-yl)piperazin-2-yl)methanol | 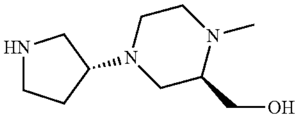 | 200 |
| 230D | (R)-2,2,4-Trimethyl-1-(pyrrolidin-3-yl)piperazine | 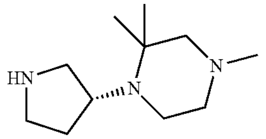 | 198 |

TABLE 16-continued

| Preparation | Chemical Name | Structure | MS (ES) m/z (M + 1) |
|---|---|---|---|
| 231D | (R)-1,2,2-Trimethyl-4-(pyrrolidin-3-yl)piperazine | 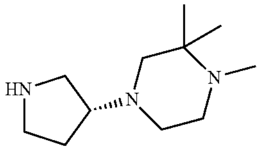 | 198 |
| 232D | (S)-2-(Methoxymethyl)-1-methyl-4-((R)-pyrrolidin-3-yl)piperazine | 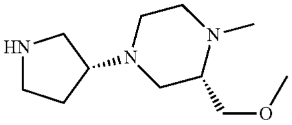 | 214 |
| 233D | (R)-2-(Methoxymethyl)-1-methyl-4-((R)-pyrrolidin-3-yl)piperazine | 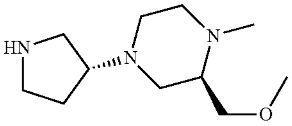 | 214 |
| 234D | ((S)-4-Methyl-1-((R)-pyrrolidin-3-yl)piperazin-2-yl)methanol | 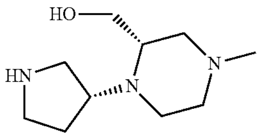 | 200 |
| 235D | ((R)-4-Methyl-1-((R)-pyrrolidin-3-yl)piperazin-2-yl)methanol | 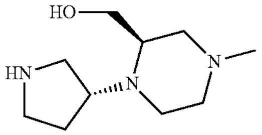 | 200 |
| 236D | 4-Methyl-7-(pyrrolidin-3-yl)-4,7-diazaspiro[2.5]octane dihydrochloride | 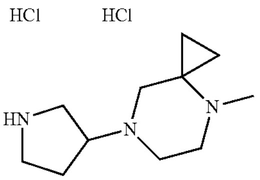 | 196 |
| 237D | 7-(Pyrrolidin-3-yl)-4,7-diazaspiro[2.5]octane dihydrochloride | 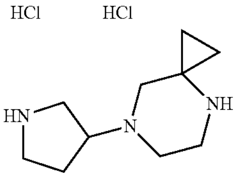 | 182 |
| 238D | 3,3-Dimethyl-1-(pyrrolidin-3-yl)piperazine dihydrochloride | 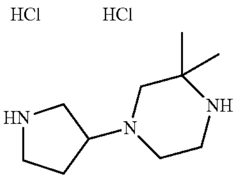 | 184 |
| 239D | (3S,5S)-3,5-Dimethyl-1-((R)-pyrrolidin-3-yl)piperazine | 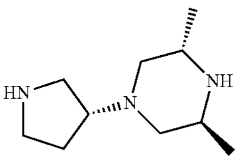 | 184 |

TABLE 16-continued

| Preparation | Chemical Name | Structure | MS (ES) m/z (M + 1) |
|---|---|---|---|
| 240D | (2R,5S)-1,2,5-Trimethyl-4-((S)-pyrrolidin-3-yl)piperazine | 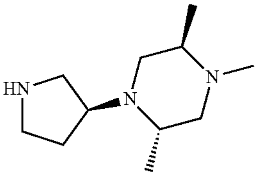 | 198 |
| 241D | (1S,4S)-2-Methyl-5-((R)-pyrrolidin-3-yl)-2,5-diazabicyclo[2.2.1] heptane | 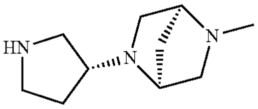 | 182 |
| 242D | (1R,4R)-2-Methyl-5-((R)-pyrrolidin-3-yl)-2,5-diazabicyclo[2.2.1] heptane | 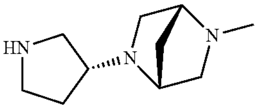 | 182 |
| 243D | 3-Methyl-8-((R)-pyrrolidin-3-yl)-3,8-diazabicyclo[3.2.1]octane | 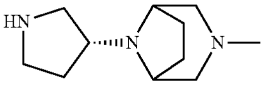 | 196 |
| 244D | 3-Methyl-6-((R)-pyrrolidin-3-yl)-3,6-diazabicyclo[3.1.1] heptane | 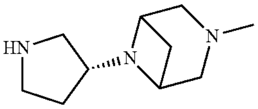 | 182 |
| 245D | 1-Methyl-4-((2S,3S)-2-methylpyrrolidin-3-yl)piperazine dihydrochloride | HCl HCl 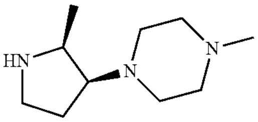 | 184 |
| 246D | 1-Methyl-4-((2R,3R)-2-methylpyrrolidin-3-yl)piperazine dihydrochloride | HCl HCl 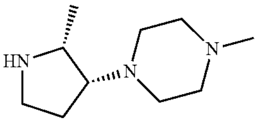 | 184 |
| 247D | 1-Methyl-4-((2S,3R)-2-methylpyrrolidin-3-yl)piperazine dihydrochloride | HCl HCl 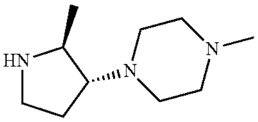 | 184 |
| 248D | 1-Methyl-4-((2R,3S)-2-methylpyrrolidin-3-yl)piperazine dihydrochloride | HCl HCl 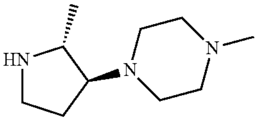 | 184 |

TABLE 16-continued

| Preparation | Chemical Name | Structure | MS (ES) m/z (M + 1) |
|---|---|---|---|
| 249D | 1-Ethyl-4-((2S,3S)-2-methylpyrrolidin-3-yl)piperazine dihydrochloride | 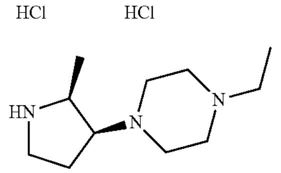 | 198 |
| 250D | 1-Isopropyl-4-((2S,3S)-2-methylpyrrolidin-3-yl)piperazine dihydrochloride | 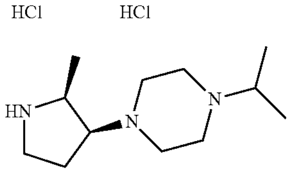 | 212 |
| 251D | 1-(2-Methoxyethyl)-4-((2S,3S)-2-methylpyrrolidin-3-yl)piperazine dihydrochloride | 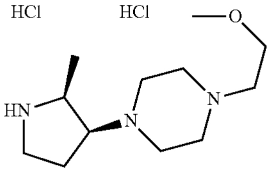 [SMILES: Cl ; Cl ; COCCN1CCN([C@H]2CCN[C@H]2C)CC1] | 228 |
| 252D | (S)-1-(4-((2S,3S)-2-Methylpyrrolidin-3-yl)piperazin-1-yl)propan-2-ol dihydrochloride | 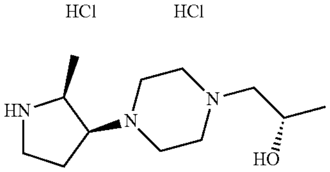 [SMILES: Cl ; Cl ; C[C@H](O)CN1CCN([C@H]2CCN[C@H]2C)CC1] | 228 |
| 253D | (R)-1-(4-((2S,3S)-2-Methylpyrrolidin-3-yl)piperazin-1-yl)propan-2-ol dihydrochloride | 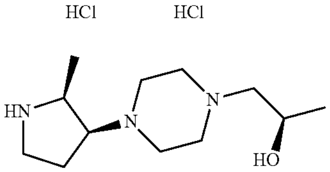 [SMILES: Cl ; Cl ; C[C@@H]1NCC[C@@H]1N1CCN(C[C@@H](C)O)CC1] | 228 |
| 254D | 1-(2-Fluoroethyl)-4-((2S,3S)-2-methylpyrrolidin-3-yl)piperazine dihydrochloride | 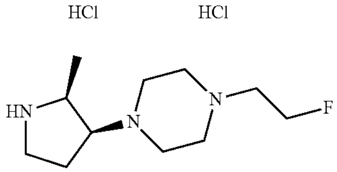 | 216 |
| 255D | (S)-1,2-Dimethyl-4-((2S,3S)-2-methylpyrrolidin-3-yl)piperazine dihydrochloride | 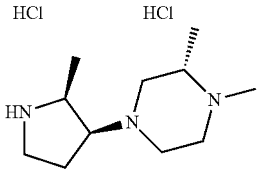 | 198 |
| 256D | (S)-2,4-Dimethyl-1-((2S,3S)-2-methylpyrrolidin-3-yl)piperazine dihydrochloride | 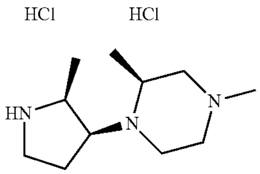 | 198 |

TABLE 16-continued

| Preparation | Chemical Name | Structure | MS (ES) m/z (M + 1) |
|---|---|---|---|
| 257D | ((S)-4-Methyl-1-((2S,3S)-2-methylpyrrolidin-3-yl)piperazin-2-yl)methanol dihydrochloride | 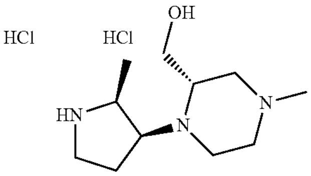 | 214 |
| 258D | (S)-2-(Fluoromethyl)-4-methyl-1-((2S,3S)-2-methylpyrrolidin-3-yl)piperazine dihydrochloride | 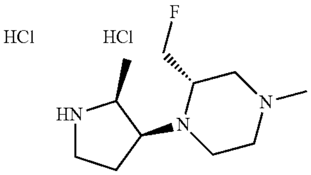 | 216 |
| 259D | 8-methyl-3-((2S,3S)-2-Methylpyrrolidin-3-yl)-3,8-diazabicyclo[3.2.1]octane dihydrochloride | 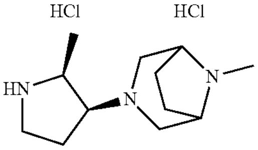 | 210 |
| 260D | 1-methyl-4-((3S,5S)-5-Methylpyrrolidin-3-yl)piperazine dihydrochloride | 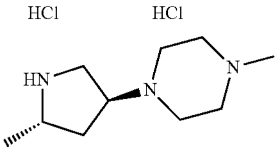 | 184 |
| 261D | 1-methyl-4-((3R,5S)-5-Methylpyrrolidin-3-yl)piperazine dihydrochloride | 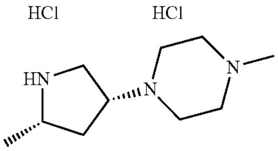 | 184 |
| 262D [2] | 4-((S)-2,4-Dimethylpiperazin-1-yl)pyrrolidin-3-ol, Isomer 2 | 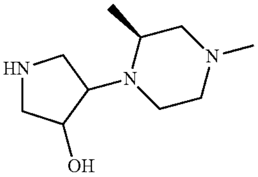 | 200 |
| 263D [2] | 4-((S)-2,4-Dimethylpiperazin-1-yl)pyrrolidin-3-ol, Isomer 1 | 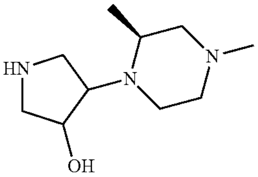 | 200 |
| 264D [3] | 4-((S)-3,4-Dimethylpiperazin-1-yl)pyrrolidin-3-ol | 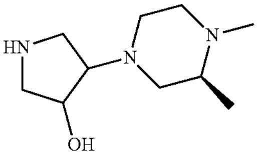 | 200 |
| 265D [4] | 4-(3-methyl-3,8-diazabicyclo[3.2.1]octan-8-yl)pyrrolidin-3-ol | 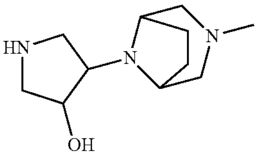 | 212 |

TABLE 16-continued

| Preparation | Chemical Name | Structure | MS (ES) m/z (M + 1) |
|---|---|---|---|
| 266D [5] | (2S)-4-(4-Methoxypyrrolidin-3-yl)-1,2-dimethylpiperazine | 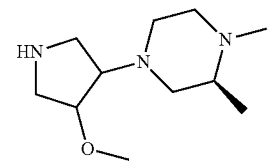 | 214 |
| 267D [6] | 8-(4-Methoxypyrrolidin-3-yl)-3-methyl-3,8-diazabicyclo[3.2.1]octane | 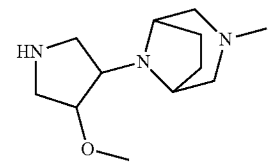 [SMILES: COC1CNCC1N1C2CCC1CN(C)C2] | 226 |
| 268D | (S)-1-(Pyrrolidin-3-yl)piperidine trifluoroacetic acid | TFA 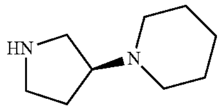 | 155 |
| 269D | (R)-1-(Pyrrolidin-3-yl)piperidine trifluoroacetic acid | TFA 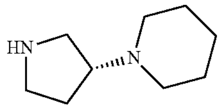 | 155 |
| 270D | (R)-N,N-Dimethyl-1-(pyrrolidin-3-yl)piperidin-4-amine trifluoroacetic acid | TFA 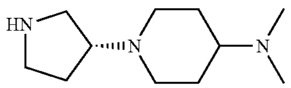 | 198 |
| 271D | (S)-1-((R)-Pyrrolidin-3-yl)piperidin-3-ol | TFA 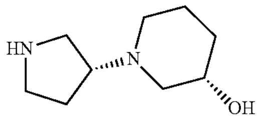 | 171 |
| 272D | (R)-1-((R)-Pyrrolidin-3-yl)piperidin-3-ol | 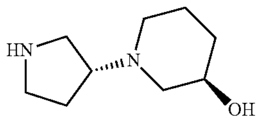 [SMILES: O[C@@H]1CCCN([C@@H]2CCNC2)C1] | 171 |
| 273D | (R)-4-Methoxy-1-(pyrrolidin-3-yl)piperidine | 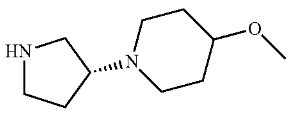 | 185 |
| 274D | (R)-1-(Pyrrolidin-3-yl)piperidine-4-carbonitrile | 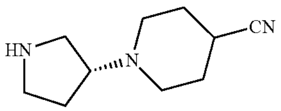 [SMILES: N#CC1CCN([C@@H]2CCNC2)CC1] | 180 |
| 275D | (R)-1-(Pyrrolidin-3-yl)piperidin-4-ol | 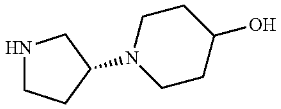 | 171 |

TABLE 16-continued

| Preparation | Chemical Name | Structure | MS (ES) m/z (M + 1) |
| --- | --- | --- | --- |
| 276D [7] | 3-Methyl-1-((S)-pyrrolidin-3-yl)piperidin-3-ol, Isomer 1 | 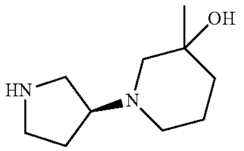 | 185 |
| 277D [7] | 3-Methyl-1-((S)-pyrrolidin-3-yl)piperidin-3-ol, Isomer 2 | 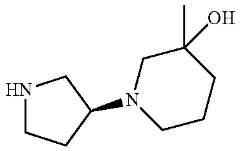 | 185 |
| 278D | (R)-4-Methyl-1-(pyrrolidin-3-yl)piperidin-4-ol | 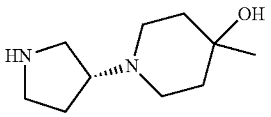 | 185 |
| 279D | (R)-4-Fluoro-1-(pyrrolidin-3-yl)piperidine | 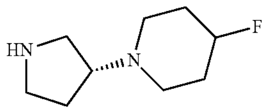 [SMILES: FC1CCN([C@@H]2CCNC2)CC1] | 173 |
| 280D | 1-((2S,3S)-2-Methylpyrrolidin-3-yl)piperidine | 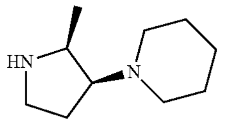 | 169 |
| 281D [8] | 4-(Piperidin-1-yl)pyrrolidin-3-ol dihydrochloride | HCl HCl 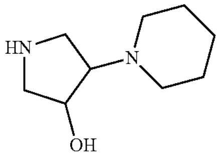 | 171 |
| 282D [9] | 1-(4-Methoxypyrrolidin-3-yl)piperidine, Isomer 1 | 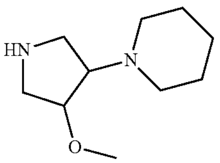 | 185 |
| 283D [9] | 1-(4-Methoxypyrrolidin-3-yl)piperidine, Isomer 2 | 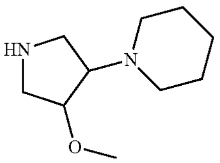 | 185 |
| 284D | (R)-4-(Pyrrolidin-3-yl)thiomorpholine | 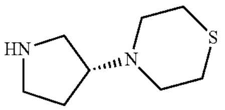 [SMILES: C1C[C@@H](N2CCSCC2)CN1] | 173 |

TABLE 16-continued

| Preparation | Chemical Name | Structure | MS (ES) m/z (M + 1) |
|---|---|---|---|
| 285D | N,N-Dimethyl-1-(4-((R)-pyrrolidin-3-yl)morpholin-2-yl)methanamine | 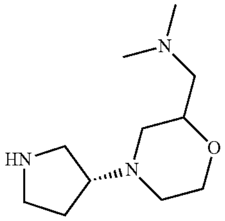 | 214 |
| 286D | N,N-Dimethyl-1-(4-((S)-pyrrolidin-3-yl)morpholin-2-yl)methanamine | 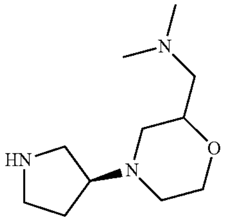 | 214 |
| 287D | 4-((2S,3S)-2-Methylpyrrolidin-3-yl)morpholine dihydrochloride | HCl HCl 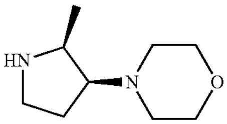 | 171 |
| 288D | 6-((2S,3S)-2-Methylpyrrolidin-3-yl)-3-oxa-6-azabicyclo[3.1.1]heptane dihydrochloride | HCl HCl 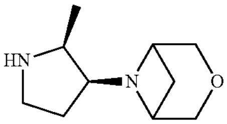 | 183 |
| 289D | (R)-4-(Pyrrolidin-3-yl)-1,4-oxazepane | 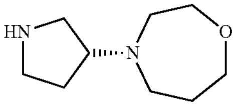 | 171 |
| 290D | (R)-1-Methyl-4-(pyrrolidin-3-yl)-1,4-diazepane | 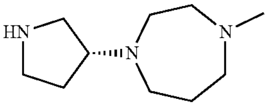 | 184 |
| 291D | (R)-1-(4-(Pyrrolidin-3-yl)-1,4-diazepan-1-yl)ethan-1-one | 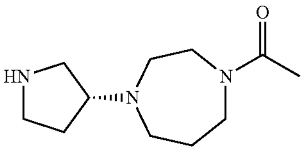 | 212 |
| 292D | (S)-1-Methyl-4-(pyrrolidin-3-yl)-1,4-diazepane | 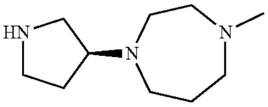 | 184 |
| 293D [10] | 4-(1,4-Oxazepan-4-yl)pyrrolidin-3-ol | 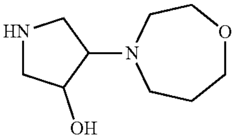 [SMILES: OC1CNCC1N1CCCOCC1] | 187 |

TABLE 16-continued

| Preparation | Chemical Name | Structure | MS (ES) m/z (M + 1) |
|---|---|---|---|
| 294D [11] | 4-(4-Methoxypyrrolidin-3-yl)-1,4-oxazepane | 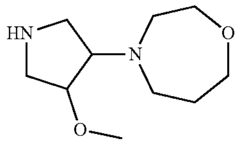 | 201 |
| 295D | (3aR,6aS)-2-Methyl-5-((R)-pyrrolidin-3-yl)octahydropyrrolo[3,4-c]pyrrole | 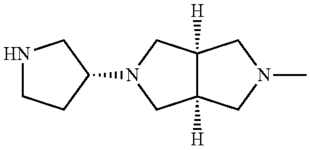 | 196 |
| 296D | (3aR,6aS)-2-Methyl-5-((S)-pyrrolidin-3-yl)octahydropyrrolo[3,4-c]pyrrole | 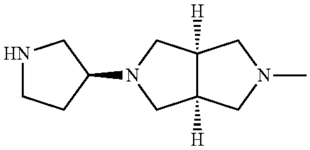 | 196 |
| 297D | (R)-2-((R)-Pyrrolidin-3-yl)octahydropyrrolo[1,2-a]pyrazine | 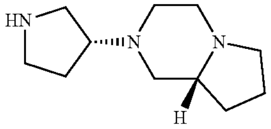 [SMILES: C1C[C@@H]2CN([C@@H]3CCNC3)CCN2C1] | 196 |
| 298D | (7S,8aS)-7-Fluoro-2-((S)-pyrrolidin-3-yl)octahydropyrrolo[1,2-a]pyrazine | 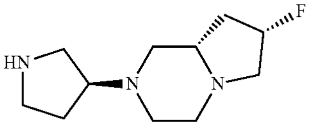 [SMILES: F[C@H]1C[C@H]2CN([C@H]3CCNC3)CCN2C1] | 214 |
| 299D | (3aR,6aS)-5-((R)-Pyrrolidin-3-yl)hexahydro-1H-furo[3,4-c]pyrrole | 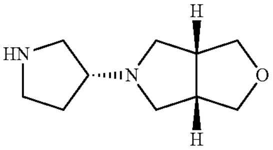 [SMILES: C1C[C@@H](N2C[C@H]3COC[C@H]3C2)CN1] | 183 |
| 300D | (R)-2-Methyl-6-(pyrrolidin-3-yl)-2,6-diazaspiro[3.4]octane | 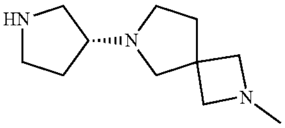 | 196 |
| 301D | (R)-2-(Pyrrolidin-3-yl)-2-azaspiro[3.3]heptane | 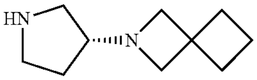 [SMILES: C1CC2(C1)CN([C@@H]1CCNC1)C2] | 167 |
| 302D | (S)-2-(Pyrrolidin-3-yl)-2-azaspiro[3.3]heptane | 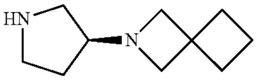 [SMILES: C1CC2(C1)CN([C@H]1CCNC1)C2] | 167 |
| 303D | (R)-N,1-Dimethyl-N-((R)-pyrrolidin-3-yl)pyrrolidin-3-amine | 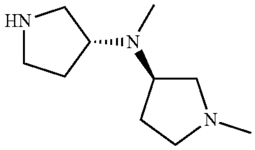 | 184 |

TABLE 16-continued

| Preparation | Chemical Name | Structure | MS (ES) m/z (M + 1) |
|---|---|---|---|
| 304D | (S)-N,1-Dimethyl-N-((R)-pyrrolidin-3-yl)pyrrolidin-3-amine | 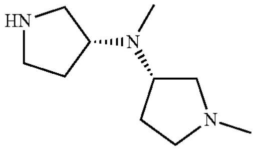 | 184 |
| 305D | (R)-N,1-Dimethyl-N-((S)-pyrrolidin-3-yl)pyrrolidin-3-amine | 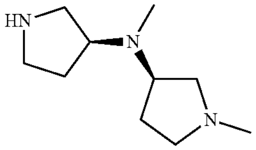 | 184 |
| 306D | (S)-N,1-Dimethyl-N-((S)-pyrrolidin-3-yl)pyrrolidin-3-amine | 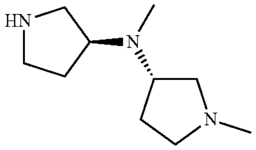 | 184 |
| 307D | (R)-N,N-Dimethyl-2-(pyrrolidin-3-yl)acetamide | 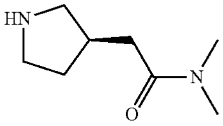 | 157 |
| 308D | (R)-N,N-Dimethyl-2-(pyrrolidin-3-yloxy)ethan-1-amine | 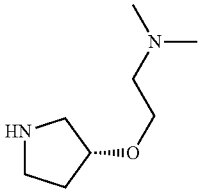 | 159 |
| 309D | (S)-N,N-Dimethyl-2-(pyrrolidin-3-yloxy)ethan-1-amine | 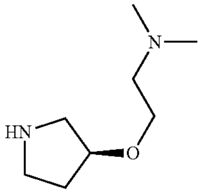 | 159 |
| 310D | (R)-N,N-Dimethyl-1-(1-(pyrrolidin-3-yl)azetidin-3-yl)methanamine | 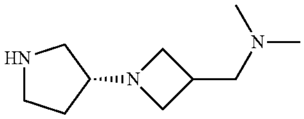 | 184 |
| 311D | (S)-N,N-Dimethyl-1-(1-(pyrrolidin-3-yl)azetidin-3-yl)methanamine | 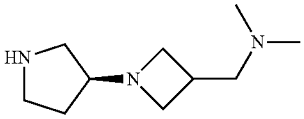 | 184 |
| 312D | (2S,3S)-2-Methyl-N-(1-methylcyclopropyl)pyrrolidin-3-amine dihydrochloride | 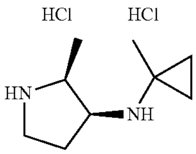 | 155 |

TABLE 16-continued

| Preparation | Chemical Name | Structure | MS (ES) m/z (M + 1) |
|---|---|---|---|
| 313D | 3-(((2S)-2-Methylpyrrolidin-3-yl)amino)bicyclo[1.1.1]pentan-1-ol dihydrochloride | 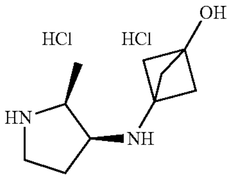 | 183 |
| 314D | (2S,3S)-N-(1-Fluoro-2-methylpropan-2-yl)-2-methylpyrrolidin-3-amine dihydrochloride | 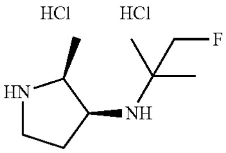 | 175 |
| 315D | (3S,4S)-4-Fluoro-N-isopropylpyrrolidin-3-amine | 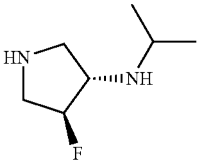 | 147 |
| 316D | (3R,4S)-4-Fluoro-N-isopropylpyrrolidin-3-amine | 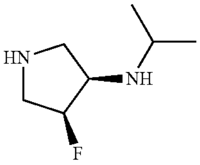 | 147 |
| 317D | (3R,4S)-4-(Isopropylamino)pyrrolidin-3-ol | 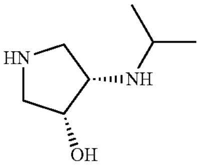 | 145 |
| 318D | (3S,4S)-4-(Isopropylamino) pyrrolidin-3-ol | 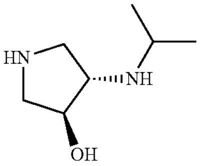 | 145 |
| 319D | (3S,4R)-4-(Isopropylamino) pyrrolidin-3-ol | 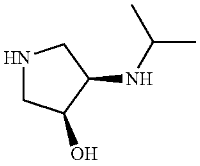 | 145 |
| 320D [12] | 4-((Dimethylamino) methyl)pyrrolidin-3-ol | 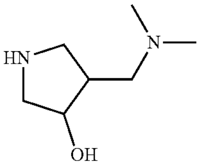 | 145 |

TABLE 16-continued

| Preparation | Chemical Name | Structure | MS (ES) m/z (M + 1) |
|---|---|---|---|
| 321D [13] | 4-((Dimethylamino) methyl)pyrrolidin-3-ol | 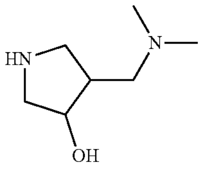 | 145 |
| 322D [14] | 4-(Isopropylamino)-3-methylpyrrolidin-3-ol | 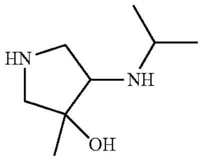 | 159 |
| 323D [15] | 4-(Isopropylamino)-3-methylpyrrolidin-3-ol, Isomer 1 | 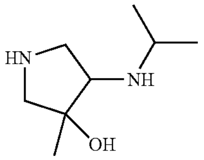 | 159 |
| 324D [15] | 4-(Isopropylamino)-3-methylpyrrolidin-3-ol, Isomer 2 | 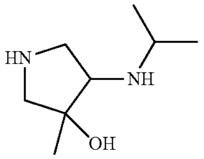 | 159 |
| 325D [16] | 4-(Isopropyl(methyl) amino)-3-methylpyrrolidin-3-ol, Isomer 1 | 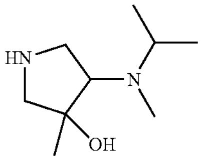 | 173 |
| 326D [16] | 4-(Isopropyl(methyl) amino)-3-methylpyrrolidin-3-ol, Isomer 2 | 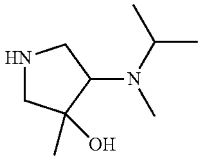 | 173 |
| 327D [17] | 4-(Isopropylamino)-3-methylpyrrolidin-3-ol | 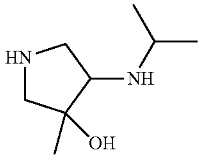 | 173 |
| 328D | (3R,4S)-N-Isopropyl-4-methylpyrrolidin-3-amine | 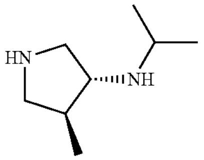 | 143 |
| 329D | (3R,4S)-N-Isopropyl-N,4-dimethylpyrrolidin-3-amine | 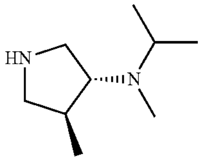 | 157 |

TABLE 16-continued

| Preparation | Chemical Name | Structure | MS (ES) m/z (M + 1) |
|---|---|---|---|
| 330D | 2-((3R,4S)-4-(Dimethylamino) pyrrolidin-3-yl)propan-2-ol | 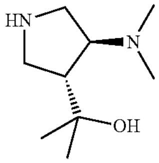 | 173 |
| 331D | (3S,4R)-N-Isopropyl-4-methoxypyrrolidin-3-amine | 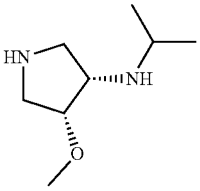 | 159 |
| 332D | (3R,4S)-N-Isopropyl-4-methoxypyrrolidin-3-amine dihydrochloride | 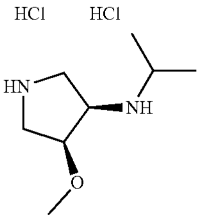 | 159 |
| 333D | (3S,4S)-N-Isopropyl-4-methoxypyrrolidin-3-amine | 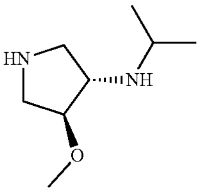 | 159 |
| 334D [18] | 4-(Diethylamino) pyrrolidin-3-ol, Isomer 1 | 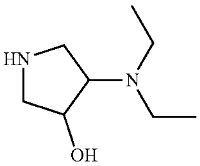 | 159 |
| 335D [18] | 4-(Diethylamino) pyrrolidin-3-ol, Isomer 2 | 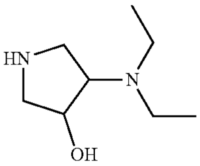 | 159 |
| 336D | (3-(Isopropylamino) pyrrolidin-3-yl)methanol | 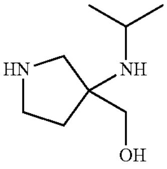 | 159 |
| 337D | (3-(4-Methylpiperazin-1-yl)pyrrolidin-3-yl)methanol, Isomer 1 | 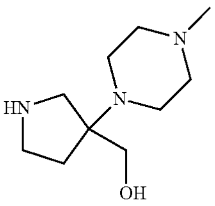 | 200 |

TABLE 16-continued

| Preparation | Chemical Name | Structure | MS (ES) m/z (M + 1) |
|---|---|---|---|
| 338D | (3-(4-Methylpiperazin-1-yl)pyrrolidin-3-yl)methanol, Isomer 2 | 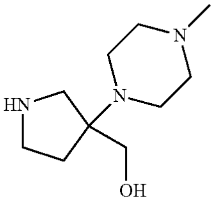 | 200 |
| 339D | (2S)-1-(Octahydro-4H-pyrrolo[3,2-b]pyridin-4-yl)propan-2-ol dihydrochloride | 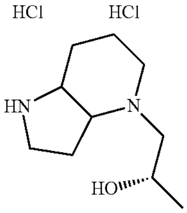 | 185 |
| 340D | (2R)-1-(Octahydro-4H-pyrrolo[3,2-b]pyridin-4-yl)propan-2-ol dihydrochloride | 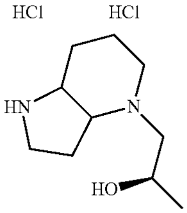 | 185 |
| 341D | 2-(Octahydro-4H-pyrrolo[3,2-b]pyridin-4-yl)ethan-1-ol dihydrochloride | 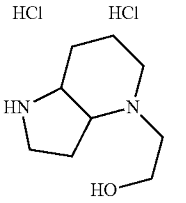 [SMILES: Cl ; Cl ; OCCN1CCCC2NCCC21] | 171 |
| 342D | N-Isopropyl-2-oxa-6-azaspiro[3.4]octan-8-amine | 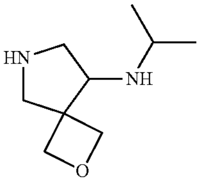 | 171 |
| 343D | 2-Methyl-2,7-diazaspiro[4.4]nonane | 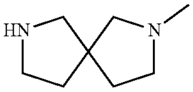 | 141 |
| 344D | (3S,4S)-4-Fluoro-N-(propan-2-yl-1,1,1,3,3,3-d6)pyrrolidin-3-amine | 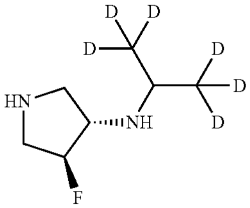 [SMILES: [2H]C([2H])([2H])C(N[C@H]1CNC[C@@H]1F)C([2H])([2H])[2H]] | 153 |

TABLE 16-continued

| Preparation | Chemical Name | Structure | MS (ES) m/z (M + 1) |
|---|---|---|---|
| 345D | (3R,4S)-4-((Propan-2-yl-1,1,1,3,3,3-d6)amino)pyrrolidin-3-ol | 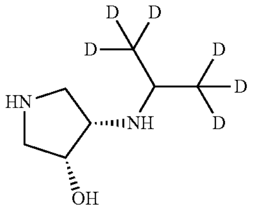 [SMILES: [2H]C([2H])([2H])C(N[C@H]1CNC[C@H]1O)C([2H])([2H])[2H]] | 151 |
| 346D | (3R,4R)-4-((Propan-2-yl-1,1,1,3,3,3-d6)amino)pyrrolidin-3-ol | 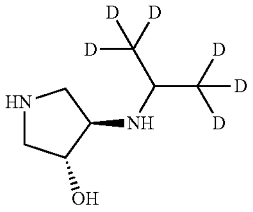 [SMILES: [2H]C([2H])([2H])C(N[C@@H]1CNC[C@H]1O)C([2H])([2H])[2H]] | 151 |
| 347D | (S)-N-(Propan-2-yl-1,1,1,3,3,3-d6)-5-azaspiro[2.4]heptan-7-amine | 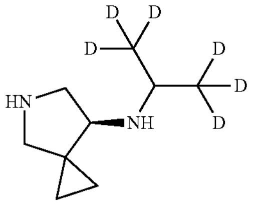 [SMILES: [2H]C([2H])([2H])C(N[C@@H]1CNCC12CC2)C([2H])([2H])[2H]] | 161 |
| 348D | (3S,4S)-4-Fluoro-N-(propan-2-yl-d7)pyrrolidin-3-amine | 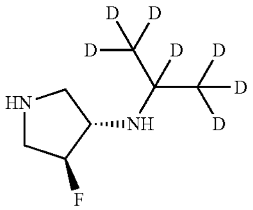 [SMILES: [2H]C([2H])([2H])C([2H])(N[C@H]1CNC[C@@H]1F)C([2H])([2H])[2H]] | 154 |
| 349D [19] | (3S,4S)-4-Fluoropyrrolidin-3-amine | 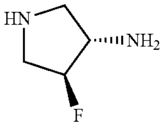 | |
| 350D | 1-((2S,3S)-2-Methylpyrrolidin-3-yl)-4-(propan-2-yl-1,1,1,3,3,3-d6)piperazine dihydrochloride | 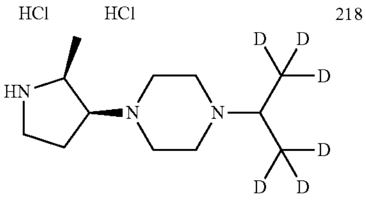 | 218 |
| 351D | 1-(Ethyl-d5)-4-((2S,3S)-2-methylpyrrolidin-3-yl)piperazine dihydrochloride | 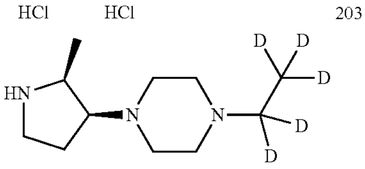 | 203 |
| 352D | (2S,3S)-N,2-Dimethylpyrrolidine-3-carboxamide | 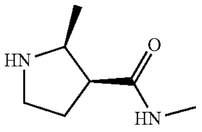 | 143 |

TABLE 16-continued

| Preparation | Chemical Name | Structure | MS (ES) m/z (M + 1) |
|---|---|---|---|
| 353D | (3S,4R)-N-Isopropyl-4-methylpyrrolidin-3-amine | 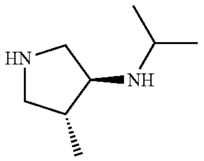 | 143 |
| 354D | (3S,4R)-4-(Isopropyl(methyl) amino)pyrrolidin-3-ol | 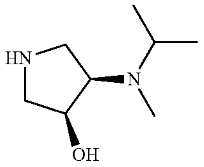 | 159 |
| 355D | (3S,4S)-4-(Isopropyl(methyl) amino)pyrrolidin-3-ol | 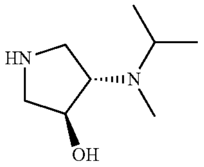 | 159 |
| 356D | (3R,4R)-4-(Isopropyl(methyl) amino)pyrrolidin-3-ol | 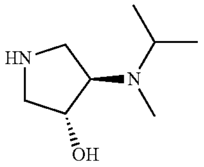 | 159 |
| 357D | (3R,4S)-4-(Isopropyl(methyl) amino)pyrrolidin-3-ol | 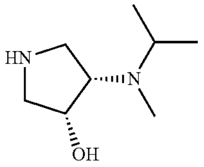 | 159 |
| 358D | (2R,3R)-2-Methylpyrrolidin-3-amine | 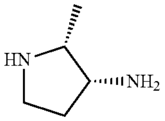 | 101 |
| 359D | 2-(((2S,3S)-2-Methylpyrrolidin-3-yl)amino)ethan-1-ol | 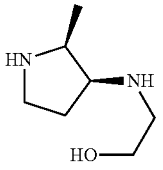 | 145 |
| 360D | Hexahydro-1H-furo[3,4-b]pyrrol-3-amine | 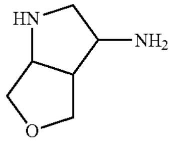 | 129 |

TABLE 16-continued

| Preparation | Chemical Name | Structure | MS (ES) m/z (M + 1) |
|---|---|---|---|
| 361D | (3R,5S)-5-Methylpyrrolidin-3-amine | 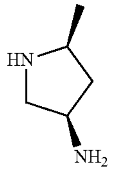 | 101 |

[1] Mix of Trans Isomers
[2] Clean Trans Isomers, Separated in Preparations 5D and 6D
[3] Clean Trans Isomer, Separated in Preparation 7D
[4] Mix of Trans Isomers
[5] Clean Trans Isomer, Separated in Preparation 7D
[6] Mix of Trans Isomers
[7] Clean Isomers, Separated in Preparations 89D and 90D
[8] Mix of Trans Isomers
[9] Clean Trans Isomers, Separated in Preparations 9D and 10D
[10] Mix of Trans Isomers
[11] Mix of Trans Isomers
[12] Mix of Cis Isomers
[13] Mix of Trans Isomers
14 Mix of Trans Isomers (nitrogen and oxygen substituents)
[15] Clean Trans Isomers (nitrogen and oxygen substituents)
[16] Clean Trans Isomers (nitrogen and oxygen substituents)
[17] Clean Cis Isomer (nitrogen and oxygen substituents)
[18] Clean Trans Isomers, Separated in Preparations 12D and 13D
[19] Byproduct from impurity in Preparation 348D

Preparation 81B

(1S,5R)—N,N-Dimethyl-3-azabicyclo[3.1.0]hexan-1-amine

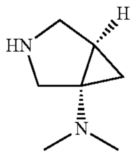

Benzyl (1S,5R)-1-((tert-butoxycarbonyl)amino)-3-azabicyclo[3.1.0]hexane-3-carboxylate. A mixture of tert-butyl ((1S,5R)-3-azabicyclo[3.1.0]hexan-1-yl)carbamate (0.250 g, 1.26 mmol) and triethylamine (0.47 mL, 3.28 mmol) in DCM (2.5 mL) was cooled to −78° C. A solution of benzyl chloroformate (0.195 mL, 1.32 mmol) in DCM (1.1 mL) was added slowly over 5 min. The reaction mixture was allowed to warm to RT and stirred for 16 h. The mixture was quenched with slow addition of 1M aqueous HCl (2.5 mL), stirred for a few minutes, and passed through a hydrophobic filter. The aqueous material trapped by the filter was extracted with DCM (2×10 mL). The organic layers, including the original filtrate, were combined and concentrated under reduced pressure. The crude material was purified on silica eluting 0-50% acetone in cyclohexane to obtain benzyl (1S,5R)-1-((tert-butoxycarbonyl)amino)-3-azabicyclo[3.1.0]hexane-3-carboxylate (0.395 g, 88%) as a white solid. MS (ES) m/z=277 (M+1-tButyl).

Benzyl (1S,5R)-1-amino-3-azabicyclo[3.1.0]hexane-3-carboxylate. Trifluoroacetic acid (1.69 mL) was added to a solution of benzyl (1S,5R)-1-((tert-butoxycarbonyl)amino)-3-azabicyclo[3.1.0]hexane-3-carboxylate (0.392 g, 1.10 mmol) in DCM (6 mL). The reaction mixture was stirred for 3 h at RT, then concentrated under reduced pressure. The residue was purified on strong cation exchange media (10 g), eluting first with MeOH, then with 2M ammoniated MeOH. The basic fraction was concentrated under reduced pressure to obtain benzyl (1S,5R)-1-amino-3-azabicyclo[3.1.0]hexane-3-carboxylate (0.246 g, 95%) as a colorless oil. MS (ES) m/z=233 (M+1).

Benzyl (1S,5R)-1-(dimethylamino)-3-azabicyclo[3.1.0]hexane-3-carboxylate. Paraformaldehyde (1.62 g, 51.3 mmol) was added portionwise to a solution of benzyl (1S,5R)-1-amino-3-azabicyclo[3.1.0]hexane-3-carboxylate (0.243 g, 1.03 mmol) in formic acid (2.0 mL). The reaction mixture was stirred for 2 h at 100° C., then cooled to RT. The mixture was diluted with water, pH adjusted to ~14 with 4N aqueous NaOH, and diluted with MTBE (50 mL). The layers were separated and the aqueous layer was extracted with MTBE (2×50 mL). The combined organic layers were washed with brine, dried over sodium sulfate, filtered, and concentrated under reduced pressure to obtain benzyl (1S,5R)-1-(dimethylamino)-3-azabicyclo[3.1.0]hexane-3-carboxylate (0.279 g, quant) as a yellow oil. MS (ES) m/z=261 (M+1).

(1S,5R)—N,N-Dimethyl-3-azabicyclo[3.1.0]hexan-1-amine. Benzyl (1S,5R)-1-(dimethylamino)-3-azabicyclo[3.1.0]hexane-3-carboxylate (0.279 g, 1.05 mmol) and palladium(II) hydroxide (20 wt % on carbon; 0.111 g) were combined in MeOH (3 mL). The mixture was cycled between vacuum and nitrogen three times, then exposed to hydrogen (1 atm) and stirred overnight. The mixture was filtered through diatomaceous earth and the solids were washed with MeOH. The combined filtrates were concentrated under reduced pressure to obtain the title compound (0.120 g, 72%) as an orange oil. MS (ES) m/z=127 (M+1).

The following compounds in Table 17 were prepared in similar manner as described in Preparation 81B. Various methods were used to purify the compounds, which would be apparent to one skilled in the art.

TABLE 17

| Prep-aration | Chemical Name | Structure | MS (ES) m/z (M + 1) |
|---|---|---|---|
| 82B | (1R,5S)-N,N-Dimethyl-3-azabicyclo[3.1.0]hexan-1-amine | 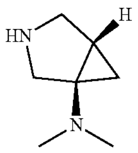 | 127 |
| 83B | 1-((1R,5R)-3-Azabicyclo[3.1.0]hexan-1-yl)-N,N-dimethylmethanamine | 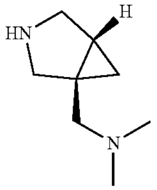 | 141 |
| 84B | 1-((1S,5S)-3-Azabicyclo[3.1.0]hexan-1-yl)-N,N-dimethylmethanamine | 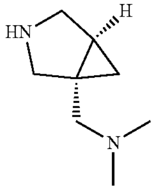 | 141 |

Preparations 362D and 363D

Benzyl 8-(dimethylamino)-2-oxa-6-azaspiro[3.4]octane-6-carboxylate, Isomers 1 and 2

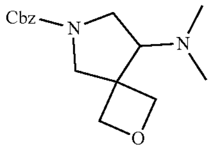 [SMILES: CN(C)C1CN(C(=O)OCc2ccccc2)CC12COC2]

N,N-dimethyl-2-oxa-6-azaspiro[3.4]octan-8-amine was used in a manner analogous to the method of Preparation 81B (substep benzyl (1S,5R)-1-((tert-butoxycarbonyl)amino)-3-azabicyclo[3.1.0]hexane-3-carboxylate) to afford the racemic compound (0.50 g, 53%). MS (ES) m/z=291 (M+1). Title compound Isomers 1 and 2 were separated with Prep-Chiral-SFC; Chiralpak-IG, 20×250 mm, 30% (MeOH w/ 0.5% dimethylethylamine) in $CO_2$, 80 mL/min.

Preparation 85B (S)—N,N-Bis(methyl-d3)pyrrolidin-3-amine

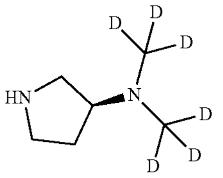 [SMILES: [2H]C([2H])([2H])N([C@H]1CCNC1)C([2H])([2H])[2H]]

Benzyl (S)-3-((tert-butoxycarbonyl)(methyl-d3)amino)pyrrolidine-1-carboxylate. To a 0° C. suspension of sodium hydride (60 wt %; 0.15 g, 3.7 mmol) in DMF (2 mL) was slowly added a solution of benzyl (S)-3-((tert-butoxycarbonyl)amino)pyrrolidine-1-carboxylate (1.0 g, 3.1 mmol) in DMF (5 mL). The reaction mixture was stirred for 30 min at 0° C., then warmed to RT. The reaction mixture was stirred for 30 min at RT, then cooled to 0° C. Iodomethane-d3 (0.22 mL, 3.4 mmol) was added. The reaction mixture was stirred for 30 min at 0° C., then warmed to RT and stirred for 2 h. The mixture was diluted with water (20 mL) and extracted with EtOAc (3×100 mL). The combined organic layers were washed with brine, dried over sodium sulfate, filtered, and concentrated under reduced pressure. The crude material was purified on silica eluting 0-100% EtOAc in heptane to obtain benzyl (S)-3-((tert-butoxycarbonyl)(methyl-d3)amino)pyrrolidine-1-carboxylate (0.98 g, 93%) as a colorless oil.

tert-Butyl (S)-(methyl-d3)(pyrrolidin-3-yl)carbamate. Pd/C (10 wt %; 0.28 g) was added to a solution of benzyl (S)-3-((tert-butoxycarbonyl)(methyl-d3)amino)pyrrolidine-1-carboxylate (0.900 g, 2.67 mmol) in MeOH (10 mL). The reaction mixture was exposed to hydrogen (1 atm) and stirred. After reaction completion (monitored by LC-MS), the mixture was filtered through diatomaceous earth and the solids were washed with MeOH. The combined filtrates were concentrated under reduced pressure to obtain tert-butyl (S)-(methyl-d3)(pyrrolidin-3-yl)carbamate (0.516 g, 95%) as a waxy solid.

(S)—N,N-Bis(methyl-d3)pyrrolidin-3-amine. Lithium aluminum deuteride (0.160 g, 3.81 mmol) was added to a solution of tert-butyl (S)-(methyl-d3)(pyrrolidin-3-yl)carbamate (0.516 g, 2.54 mmol). The reaction mixture was stirred for 30 min at RT, then 6 h at 70° C. The Fieser workup for aluminum hydride reactions was carried out. The filtrate was concentrated under reduced pressure to give the crude title compound which was used without further purification.

Preparation 72C

N,N-Dimethyl-1-((2S,3R)-2-methylpyrrolidin-3-yl)methanamine

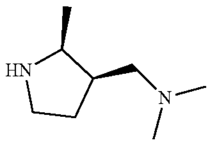

Lithium aluminum hydride (1M in ether, 13.7 mL, 13.7 mmol) was added to a solution of (2S,3S)—N,N,2-trimethylpyrrolidine-3-carboxamide hydrochloride (0.660 g, 3.43 mmol) at 0° C. The reaction mixture was stirred for 30 min at 0° C., then 18 h at RT. The Fieser workup for aluminum hydride reactions was carried out. The filtrate was concentrated under reduced pressure to give the crude title compound (0.405 g, 83%) which was used without further purification. MS (ES) m/z=143 (M+1).

The following compounds in Table 18 were prepared in similar manner as described in Preparation 72C. Various methods were used to purify the compounds, which would be apparent to one skilled in the art.

TABLE 18

| Prep-ara-tion | Chemical Name | Structure | MS (ES) m/z (M + 1) |
|---|---|---|---|
| 364D | N-Methyl-1-((2S,3R)-2-methylpyrrolidin-3-yl)methanamine | 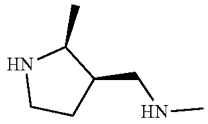 | 129 |
| 365D | (R)-N,N-Dimethyl-2-(pyrrolidin-3-yl)ethan-1-amine | 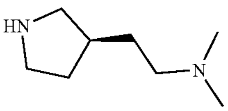 | 143 |

Preparation 73C

2-Methyl-2,6-diazabicyclo[3.2.1]octane, Mix of Cis Isomers

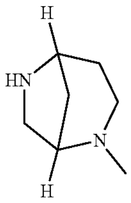

Lithium aluminum hydride (2M in THF; 1.7 mL, 3.4 mmol) was added to THE (3.4 mL) under nitrogen at 0° C. A solution of tert-butyl 2,6-diazabicyclo[3.2.1]octane-2-carboxylate (Mix of Cis Isomers; 0.330 g, 1.49 mmol) in THE (1.7 mL) was added dropwise over 1-2 min. The reaction mixture was warmed to RT and stirred for 18 h. Additional lithium aluminum hydride (2M in THF; 1.7 mL, 3.4 mmol) was added at RT and the reaction mixture was stirred for a total of 6 days. The mixture was diluted with THE (10 mL) and cooled to 0° C. Distilled water (0.32 mL), 1M aqueous NaOH (0.32 mL), and distilled water (1.0 mL) were added dropwise. The mixture was warmed to RT and stirred for 15 min. Magnesium sulfate was added, the mixture was filtered, and the solids were washed with DCM. The combined filtrates were concentrated under reduced pressure to obtain the crude title compound (0.143 g) as a yellow oil. MS (ES) m/z=127 (M+1).

The following compounds in Table 19 were prepared in similar manner as described in Preparation 73C. Lithium aluminum deuteride may have been used in place of lithium aluminum hydride. Various methods were used to purify the compounds, which would be apparent to one skilled in the art.

TABLE 19

| Preparation | Chemical Name | Structure | MS (ES) m/z (M + 1) |
|---|---|---|---|
| 366D | 4-(Methyl-d3)octahydro-1H-pyrrolo[3,2-b]pyridine | 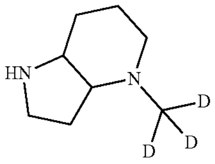 [SMILES: [2H]C([2H])([2H])N1CCCC2NCCC21] | 6 |
| 367D | (S)-1-(Methyl-d3)-4-(pyrrolidin-3-yl)piperazine | 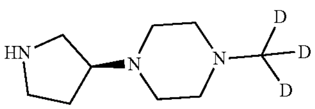 [SMILES: [2H]C([2H])([2H])N1CCN([C@H]2CCNC2)CC1] | 6 |
| 368D | (R)-1-(Methyl-d3)-4-(pyrrolidin-3-yl)piperazine | 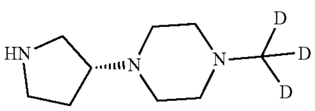 [SMILES: [2H]C([2H])([2H])N1CCN([C@@H]2CCNC2)CC1] | 6 |

Preparation 369D tert-Butyl (R)-4-(pyrrolidin-3-yl)piperazine-1-carboxylate

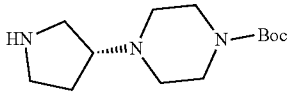 [SMILES: CC(C)(C)OC(=O)N1CCN([C@@H]2CCNC2)CC1]

tert-Butyl (R)-4-(1-((benzyloxy)carbonyl)pyrrolidin-3-yl)piperazine-1-carboxylate (1.44 g, 3.70 mmol) and palladium hydroxide on carbon (0.104 g) were placed in a flask. The flask was cycled through vacuum and nitrogen three times. EtOH (10 mL) was added. The flask was placed under hydrogen (balloon) and the reaction mixture was stirred at RT for 16 h. The mixture was filtered through diatomaceous earth and the filter cake was washed with EtOH. The combined filtrates were concentrated under reduced pressure to give the title compound (0.89 g, 94%). MS (ES) m/z=256 (M+1).

The following compounds in Table 20 were prepared in similar manner as described in Preparation NEW. In some cases, a benzyl protecting groups was removed. Various methods were used to purify the compounds, which would be apparent to one skilled in the art.

TABLE 20

| Preparation | Chemical Name | Structure | MS (ES) m/z (M + 1) |
|---|---|---|---|
| 370D | tert-Butyl (S)-4-(pyrrolidin-3-yl)piperazine-1-carboxylate | 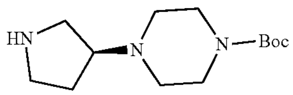 [SMILES: CC(C)(C)OC(=O)N1CCN([C@H]2CCNC2)CC1] | 256 |
| 371D | 8-Methyl-3-((R)-pyrrolidin-3-yl)-3,8-diazabicyclo[3.2.1]octane | 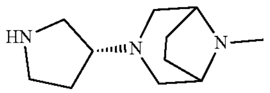 | 196 |
| 372D | 6-Methyl-3-((R)-pyrrolidin-3-yl)-3,6-diazabicyclo[3.1.1]heptane | 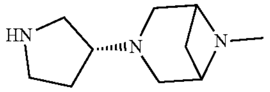 | 182 |
| 373D | 3-Fluoro-1-((R)-pyrrolidin-3-yl)pyiperidine | 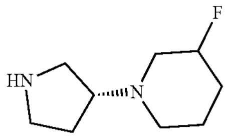 [SMILES: FC1CCCN([C@@H]2CCNC2)C1] | 173 |
| 374D | (3R,4R)-4-(Isopropylamino)pyrrolidin-3-ol | 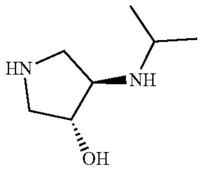 | 145 |
| 375D [1] | 4-(Isopropylamino)pyrrolidin-3-ol | 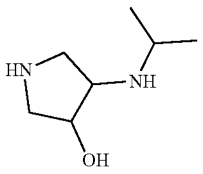 | 145 |
| 376D [2] | 4-(Methoxymethyl)-N,N-dimethylpyrrolidin-3-amine | 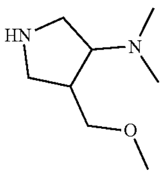 | 159 |
| 377D [3] | (3-(Diethylamino)pyrrolidin-3-yl)methanol, Isomer 1 | 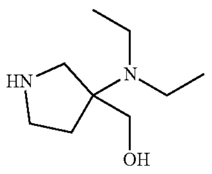 | 173 |

TABLE 20-continued

| Preparation | Chemical Name | Structure | MS (ES) m/z (M + 1) |
| --- | --- | --- | --- |
| 378D [3] | (3-(Diethylamino)pyrrolidin-3-yl)methanol, Isomer 2 | 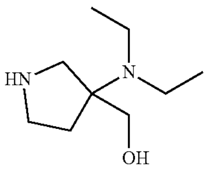 | 173 |
| 379D [4] | N,N-Dimethyl-2-oxa-6-azaspiro[3.4]octan-8-amine, Idomer 1 | 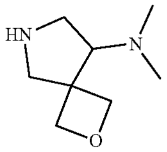 | 157 |
| 380D [4] | N,N-Dimethyl-2-oxa-6-azaspiro[3.4]octan-8-amine, Isomer 2 | 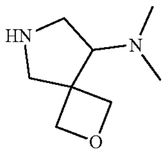 | 157 |
| 381D | (S)-1-(Propan-2-yl-1,1,1,3,3,3-d6)-4-(pyrrolidin-3-yl)piperazine | 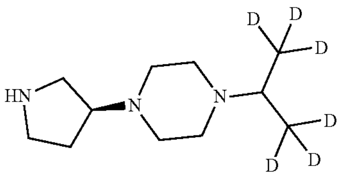 [SMILES: [2H]C([2H])([2H])C(N1CCN([C@H]2CCNC2)CC1)C([2H])([2H])[2H]] | 204 |

[1] Mix of Trans Isomers

[2] Mix of Cis Isomers

[3] Clean Isomers, Separated in Preparations 142D and 143D

[4] Clean Isomers, Separated in Preparations 362D and 363D

Preparation 57 tert-Butyl 8-(6-(2-((tert-butoxycarbonyl)amino)-3-cyano-7-fluorothieno[3,2-c]pyridin-4-yl)-5-fluoro-3-((1-(morpholinomethyl)cyclopropyl)methoxy)-7,9-dihydrofuro[3,4-f]quinazolin-1-yl)-3,8-diazabicyclo[3.2.1]octane-3-carboxylate

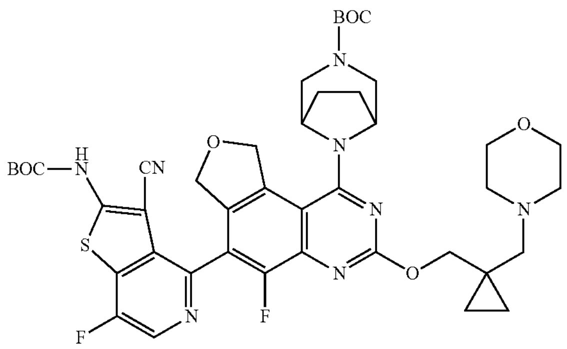 [SMILES: CC(C)(C)OC(=O)Nc1sc2c(F)cnc(-c3c4c(c5c(N6C7CCC6CN(C(=O)OC(C)(C)C)C7)nc(OCC6(CN7CCOCC7)CC6)nc5c3F)COC4)c2c1C#N]

To a solution of (1-(morpholinomethyl)cyclopropyl) methanol (0.980 g, 5.74 mmol) in THE (10 mL) was added lithium bis(trimethylsilyl)amide (1 M in THF, 3.44 mL, 3.44 mmol) at RT. After 10 min, a solution of tert-butyl 8-(6-(2-((tert-butoxycarbonyl)amino)-3-cyano-7-fluorothieno[3,2-c]pyridin-4-yl)-3-(ethylsulfonyl)-5-fluoro-7,9-dihydrofuro[3,4-f]quinazolin-1-yl)-3,8-diazabicyclo[3.2.1]octane-3-carboxylate (0.900 g, 1.15 mmol) in THE (10 mL) was added dropwise. After 2 h, the reaction mixture was diluted with EtOAc (200 mL) and washed with water (2×200 mL) and brine (100 mL). The organics were dried over anhydrous $Na_2SO_4$, filtered and concentrated under reduced pressure. The residue was purified on silica eluting with PE/EtOAc (1:1) to obtain the title compound (0.720 g, 73%) as an off-white solid. MS (ES) m/z=861 (M+1).

The following compounds in Table 21 were prepared in similar manner as described in Preparation 57. Various methods were used to purify the compounds, which would be apparent to one skilled in the art.

TABLE 21

| Preparation | Chemical Name | Structure | MS (ES) m/z (M + 1) |
|---|---|---|---|
| 58 | tert-Butyl 8-(6-(2-((tert-butoxycarbonyl)amino)-3-cyano-5-fluorobenzo[b]thiophen-4-yl)-5-fluoro-3-((1-(morpholinomethyl)cyclo-propyl)methoxy)-7,9-dihydrofuro[3,4-f]quinazolin-1-yl)-3,8-diazabicyclo[3.2.1]octane-3-carboxylate | 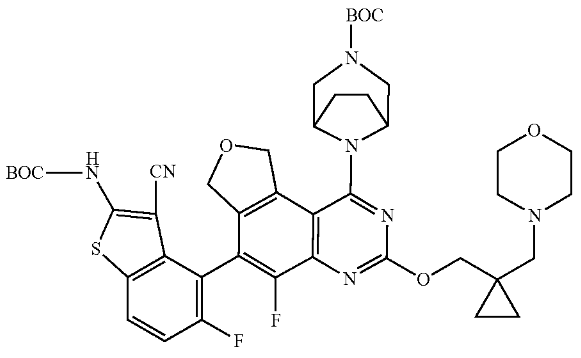 [SMILES: CC(C)(C)OC(=O)Nc1sc2ccc(F)c(-c3c4c(c5c(N6C7CCC6CN(C(=O)OC(C)(C)C)C7)nc(OCC6(CN7CCOCC7)CC6)nc5c3F)COC4)c2c1C#N] | 860 |
| 59 | tert-Butyl 8-(6-(2-((tert-butoxycarbonyl)amino)-3-cyano-7-fluorothieno[3,2-c]pyridin-4-yl)-5-fluoro-3-((1-((4-methylpiperazin-1-yl)methyl)cyclopropyl)meth-oxy)-7,9-dihydrofuro[3,4-f]quinazolin-1-yl)-3,8-diazabicyclo[3.2.1]octan-3-carboxylate | 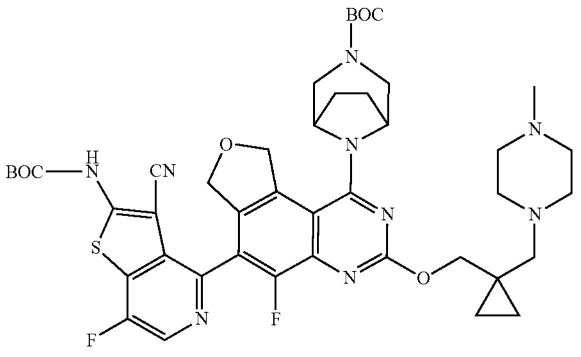 [SMILES: CN1CCN(CC2(COc3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)CC2)CC1] | 874 |
| 60 | tert-Butyl 8-(6-(2-((tert-butoxycarbonyl)amino)-3-cyano-7-fluorothieno[3,2-c]pyridin-4-yl)-5-fluoro-3-((1-(((S)-3-fluoropyrrolidin-1-yl)methyl)cyclopropyl)meth-oxy)-7,9-dihydrofuro[3,4-f]quinazolin-1-yl)-3,8-diazabicyclo[3.2.1]octan-3-carboxylate | 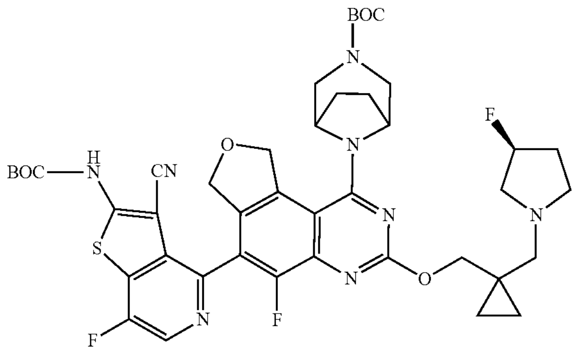 [SMILES: CC(C)(C)OC(=O)Nc1sc2c(F)cnc(-c3c4c(c5c(N6C7CCC6CN(C(=O)OC(C)(C)C)C7)nc(OCC6(CN7CC[C@H](F)C7)CC6)nc5c3F)COC4)c2c1C#N] | 863 |
| 61 | tert-Butyl 8-(6-(2-((tert-butoxycarbonyl)amino)-3-cyano-7-fluorothieno[3,2-c]pyridin-4-yl)-5-fluoro-3-((1-(((R)-3-fluoropyrrolidin-1-yl)methyl)cyclopropyl)meth-oxy)-7,9-dihydrofuro[3,4-f]quinazolin-1-yl)-3,8-diazabicyclo[3.2.1]octane-3-carboxylate | 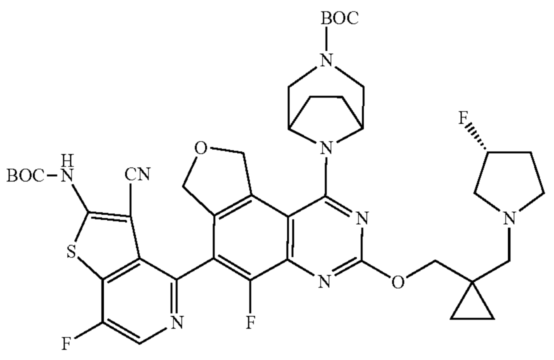 [SMILES: CC(C)(C)OC(=O)Nc1sc2c(F)cnc(-c3c4c(c5c(N6C7CCC6CN(C(=O)OC(C)(C)C)C7)nc(OCC6(CN7CC[C@@H](F)C7)CC6)nc5c3F)COC4)c2c1C#N] | 863 |

TABLE 21-continued

| Preparation | Chemical Name | Structure | MS (ES) m/z (M + 1) |
|---|---|---|---|
| 62 | tert-Butyl 8-(6-(2-((tert-butoxycarbonyl)amino)-3-cyano-7-fluorothieno[3,2-c]pyridin-4-yl)-5-fluoro-3-((1-(((S)-3-fluoropyrrolidin-1-yl)methyl)cyclopropyl)methoxy)-7,9-dihydrofuro[3,4-f]quinazolin-1-yl)-3,8-diazabicyclo[3.2.1]octane-3-carboxylate | 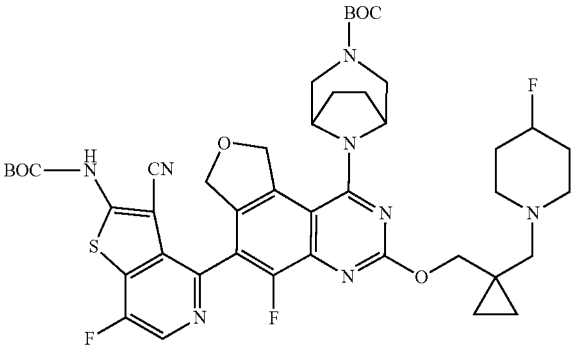 [SMILES: CC(C)(C)OC(=O)Nc1sc2c(F)cnc(-c3c4c(c5c(N6C7CCC6CN(C(=O)OC(C)(C)C)C7)nc(OCC6(CN7CCC(F)CC7)CC6)nc5c3F)COC4)c2c1C#N] | 878 |
| 63 | tert-Butyl 8-(6-(2-((tert-butoxycarbonyl)amino)-3-cyano-7-fluorothieno[3,2-c]pyridin-4-yl)-5-fluoro-3-((1-((6-methyl-2,6-diazaspiro[3.3]heptan-2-yl)methyl)cyclopropyl)methoxy)-7,9-dihydrofuro[3,4-f]quinazolin-1-yl)-3,8-diazabicyclo[3.2.1]octane-3-carboxylate | 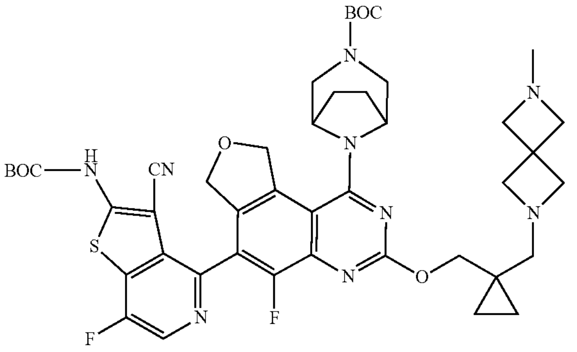 [SMILES: CN1CC2(C1)CN(CC1(COc3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)CC1)C2] | 886 |
| 64 | tert-Butyl 8-(6-(2-((tert-butoxycarbonyl)amino)-3-cyano-7-fluorothieno[3,2-c]pyridin-4-yl)-3-((1-((4,4-difluoropiperidin-1-yl)methyl)cyclopropyl)methoxy)-5-fluoro-7,9-dihydrofuro[3,4-f]quinazolin-1-yl)-3,8-diazabicyclo[3.2.1]octane-3-carboxylate | 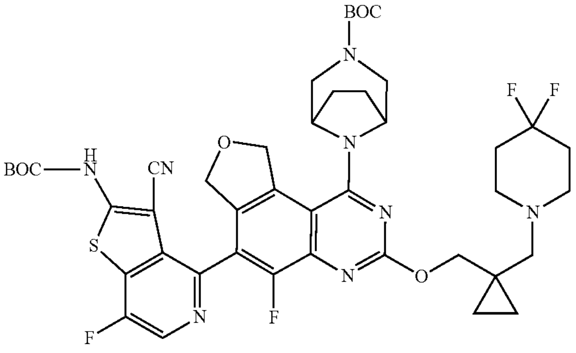 [SMILES: CC(C)(C)OC(=O)Nc1sc2c(F)cnc(-c3c4c(c5c(N6C7CCC6CN(C(=O)OC(C)(C)C)C7)nc(OCC6(CN7CCC(F)(F)CC7)CC6)nc5c3F)COC4)c2c1C#N] | 895 |
| 65 | tert-Butyl 8-(6-(2-((tert-butoxycarobnyl)amino)-3-cyano-7-fluorothieno[3,2-c]pyridin-4-yl)-3-((1-((6,6-difluoro-3-azabicyclo[3.1.0]hexan-3-yl)methyl)cyclopropyl)methoxy)-5-fluoro-7,9-dihydrofuro[3,4-f]quinazolin-1-yl)-3,8-diazabicyclo[3.2.1]octane-3-carboxylate | 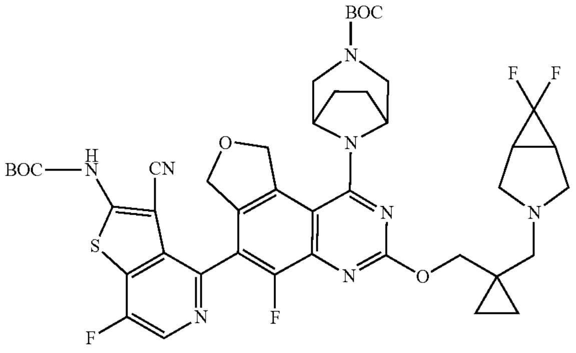 [SMILES: CC(C)(C)OC(=O)Nc1sc2c(F)cnc(-c3c4c(c5c(N6C7CCC6CN(C(=O)OC(C)(C)C)C7)nc(OCC6(CN7CC8C(C7)C8(F)F)CC6)nc5c3F)COC4)c2c1C#N] | 893 |

TABLE 21-continued

| Preparation | Chemical Name | Structure | MS (ES) m/z (M + 1) |
| --- | --- | --- | --- |
| 66 | tert-Butyl 8-(6-(2-((tert-butoxycarbonyl)amino)-3-cyano-7-fluorothieno[3,2-c]pyridin-4-yl)-5-fluoro-3-((1-((3-methoxyazetidin-1-yl)methyl)cyclopropyl)methoxy)-7,9-dihydrofuro[3,4-f]quinazolin-1-yl)-3,8-diazabicyclo[3.2.1]octane-3-carboxylate | 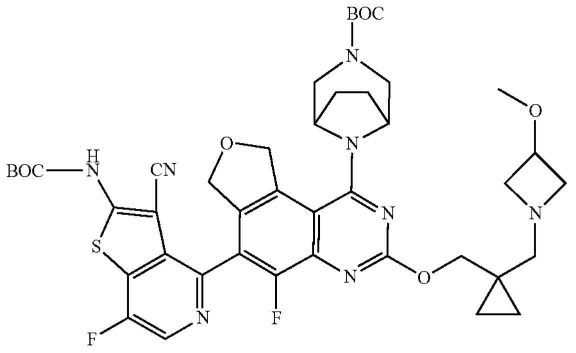 [SMILES: COC1CN(CC2(COc3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)CC2)C1] | 861 |
| 67 | tert-Butyl 8-(6-(2-((tert-butoxycarbonyl)amino)-3-cyano-7-fluorothieno[3,2-c]pyridin-4-yl)-5-fluoro-3-((1-((3-(fluoromethyl)azetidin-1-yl)methyl)cyclopropyl)methoxy)-7,9-dihydrofuro[3,4-f]quinazolin-1-yl)-3,8-diazabicyclo[3.2.1]octane-3-carboxylate | 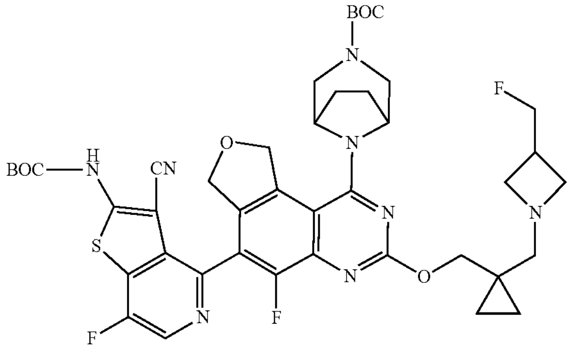 [SMILES: CC(C)(C)OC(=O)Nc1sc2c(F)cnc(-c3c4c(c5c(N6C7CCC6CN(C(=O)OC(C)(C)C)C7)nc(OCC6(CN7CC(CF)C7)CC6)nc5c3F)COC4)c2c1C#N] | 863 |
| 68 | tert-Butyl 8-(6-(2-((tert-butoxycarbonyl)amino)-3-cyano-7-fluorothieno[3,2-c]pyridin-4-yl)-5-fluoro-3-((1-(((R)-3-methylmorpholino)methyl) cyclopropyl)methoxy)-7,9-dihydrofuro[3,4-f]quinazolin-1-yl)-3,8-diazabicyclo[3.2.1]octane-3-carboxylate | 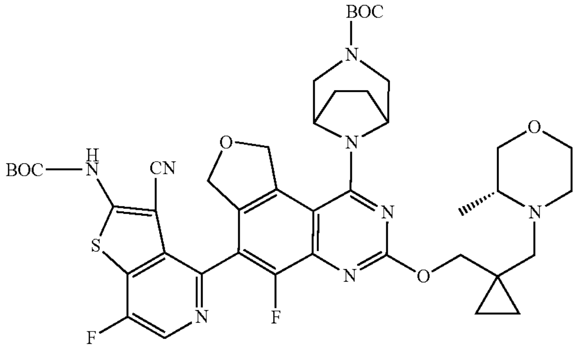 [SMILES: C[C@@H]1COCCN1CC1(COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)CC1] | 876 |
| 69 | tert-Butyl 8-(3-((1-(((1S,4S)-2-oxa-5-azabicyclo[2.2.1]heptan-5-yl)methyl)cyclopropyl)methoxy)-6-(2-((tert-butoxycarbonyl)amino)-3-cyano-7-fluorothieno[3,2-c]pyridin-4-yl)-5-fluoro-7,9-dihydrofuro[3,4-f]quinazolin-1-yl)-3,8-diazabicyclo[3.2.1]octane-3-carboxylate | 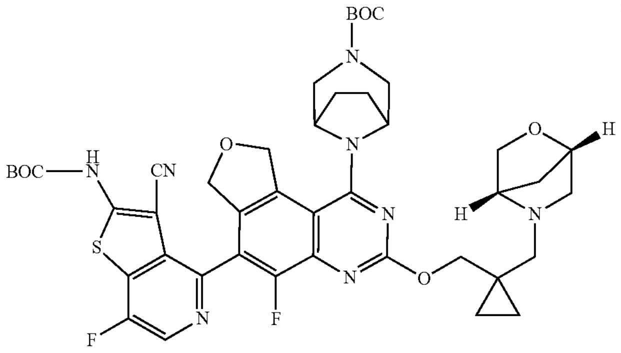 [SMILES: CC(C)(C)OC(=O)Nc1sc2c(F)cnc(-c3c4c(c5c(N6C7CCC6CN(C(=O)OC(C)(C)C)C7)nc(OCC6(CN7C[C@@H]8C[C@H]7CO8)CC6)nc5c3F)COC4)c2c1C#N] | 873 |

TABLE 21-continued

| Preparation | Chemical Name | Structure | MS (ES) m/z (M + 1) |
| --- | --- | --- | --- |
| 70 | tert-Butyl 8-(6-(2-((tert-butoxycarbonyl)amino)-3-cyano-7-fluorothieno[3,2-c]pyridin-4-yl)-5-fluoro-3-((1-(hydroxymethyl)cyclopropyl)methoxy)-7,9-dihydrofuro[3,4-f]quinazolin-1-yl)-3,8-diazabicyclo[3.2.1]octane-3-carboxylate | 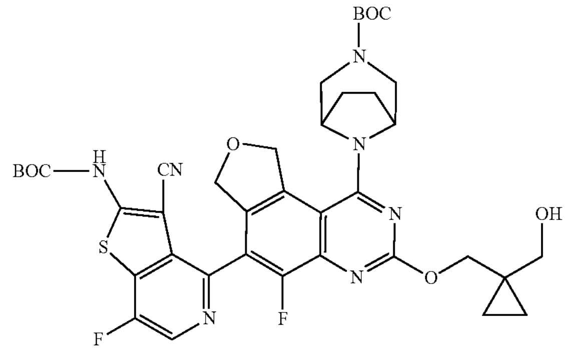 [SMILES: CC(C)(C)OC(=O)Nc1sc2c(F)cnc(-c3c4c(c5c(N6C7CCC6CN(C(=O)OC(C)(C)C)C7)nc(OCC6(CO)CC6)nc5c3F)COC4)c2c1C#N] | 792 |
| 71 | tert-Butyl (3-cyano-7-fluoro-4-(5-fluoro-3-((1-(morpholinomethyl)cyclopropyl)methoxy)-7,9-dihydrofuro[3,4-f]quinazolin-6-yl)thieno[3,2-c]pyridin-2-yl)carbamate | 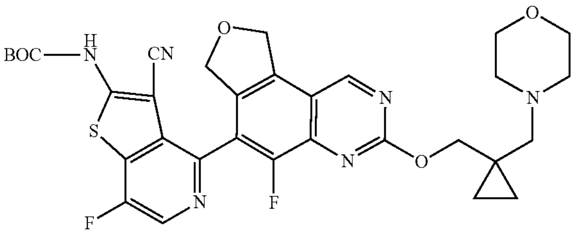 [SMILES: CC(C)(C)OC(=O)Nc1sc2c(F)cnc(-c3c4c(c5cnc(OCC6(CN7CCOCC7)CC6)nc5c3F)COC4)c2c1C#N] | 651 |
| 72 | tert-Butyl (3-cyano-7-fluoro-4-(5-fluoro-3-((1-(((S)-3-fluoropyrrolidin-1-yl)methyl)cyclopropyl)methoxy)-7,9-dihydrofuro[3,4-f]quinazolin-6-yl)thieno[3,2-c]pyridin-2-yl)carbamate | 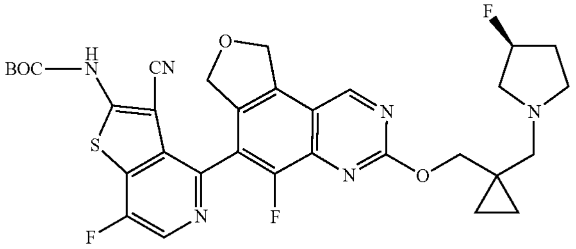 [SMILES: CC(C)(C)OC(=O)Nc1sc2c(F)cnc(-c3c4c(c5cnc(OCC6(CN7CC[C@H](F)C7)CC6)nc5c3F)COC4)c2c1C#N] | 653 |
| 73 | tert-Butyl (3-cyano-7-fluoro-4-(5-fluoro-3-((1-(((R)-3-fluoropyrrolidin-1-yl)methyl)cyclopropyl)methoxy)-7,9-dihydrofuro[3,4-f]quinazolin-6-yl)thieno[3,2-c]pyridin-2-yl)carbamate | 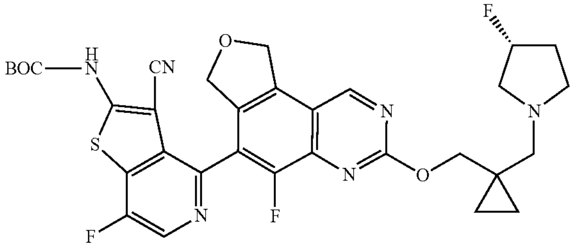 [SMILES: CC(C)(C)OC(=O)Nc1sc2c(F)cnc(-c3c4c(c5cnc(OCC6(CN7CC[C@@H](F)C7)CC6)nc5c3F)COC4)c2c1C#N] | 653 |
| 74 | tert-Butyl (3-cyano-7-fluoro-4-(5-fluoro-3-((1-((4-methylpiperazin-1-yl)methyl)cyclopropyl)methoxy)-7,9-dihydrofuro[3,4-f]quinazolin-6-yl)thieno[3,2-c]pyridin-2-yl)carbamate | 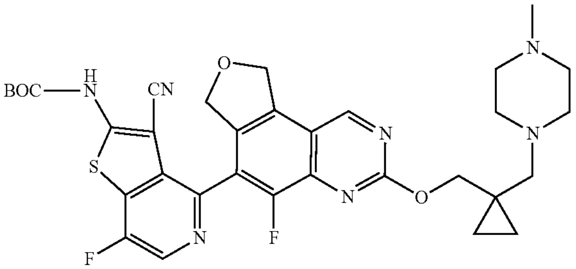 [SMILES: CN1CCN(CC2(COc3ncc4c5c(c(-c6ncc(F)c7sc(NC(=O)OC(C)(C)C)c(C#N)c67)c(F)c4n3)COC5)CC2)CC1] | 664 |

TABLE 21-continued

| Preparation | Chemical Name | Structure | MS (ES) m/z (M + 1) |
|---|---|---|---|
| 75 | tet-Butyl (3-cyano-7-fluoro-4-(5-fluoro-3-((1-(morpholinomethyl)cyclo-butyl)methoxy)-7,9-dihydrofuro[3,4-f]quinazolin-6-yl)thieno[3,2-c]pyridin2-yl)carbamate | 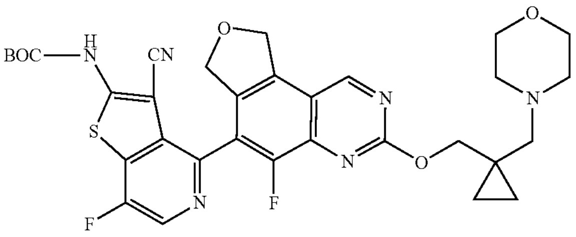 [SMILES: CC(C)(C)OC(=O)Nc1sc2c(F)cnc(-c3c4c(c5cnc(OCC6(CN7CCOCC7)CC6)nc5c3F)COC4)c2c1C#N] | 665 |
| 76 | tert-Butyl (4-(3-((1-(azetidin-1-ylmethyl)cyclopropyl)meth-oxy)-5-fluoro-7,9-dihydrofuro[3,4-f]quinazolin-6-yl)-3-cyano-7-fluorothieno[3,2-c]pyridin-2-yl)carbamate | 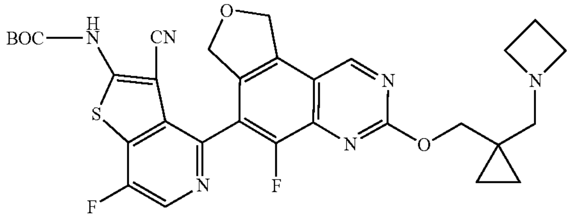 [SMILES: CC(C)(C)OC(=O)Nc1sc2c(F)cnc(-c3c4c(c5cnc(OCC6(CN7CCC7)CC6)nc5c3F)COC4)c2c1C#N] | 621 |
| 77 | tert-Butyl (4-(3-((1-((6-oxa-2-azaspiro[3.4]octan-2-yl)methyl)cyclopropyl)meth-oxy)-5-fluoro-7,9-dihydrofuro[3,4-f]quinazolin-6-yl)-3-cyano-7-fluorothieno[3,2-c]pyridin-2-yl)carbamate | 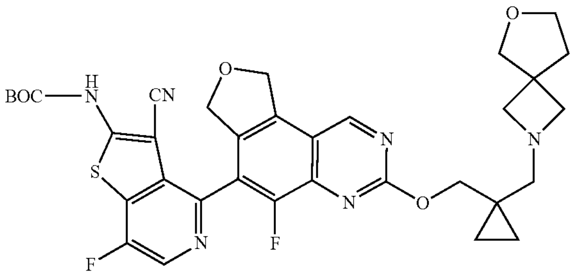 [SMILES: CC(C)(C)OC(=O)Nc1sc2c(F)cnc(-c3c4c(c5cnc(OCC6(CN7CC8(CCOC8)C7)CC6)nc5c3F)COC4)c2c1C#N] | 677 |
| 78 | tert-Butyl (3-cyano-4-(3-((1-((6,6-difluoro-3-azabicyclo[3.1.0]hexan-3-yl)methyl)cyclopropyl)meth-oxy)-5-fluoro-7,9-dihydrofuro[3,4-f]quinazolin-6-yl)-7-fluorothieno[3,2-c]pyridin-2-yl)carbamate | 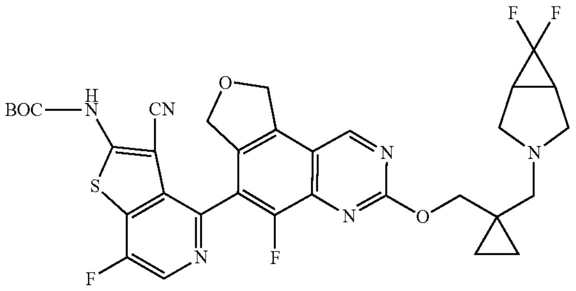 [SMILES: CC(C)(C)OC(=O)Nc1sc2c(F)cnc(-c3c4c(c5cnc(OCC6(CN7CC8C(C7)C8(F)F)CC6)nc5c3F)COC4)c2c1C#N] | 683 |
| 79 | tert-Butyl (3-cyano-7-fluoro-4-(5-fluoro-3-((1-((3-fluoroazetidin-1-yl)methyl)cyclopropyl)meth-oxy)-7,9-dihydrofuro[3,4-f]quinazolin-6-yl)thieno[3,2-c]pyridin-2-yl)carbamate | 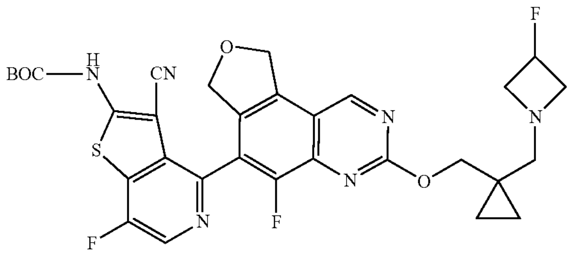 [SMILES: CC(C)(C)OC(=O)Nc1sc2c(F)cnc(-c3c4c(c5cnc(OCC6(CN7CC(F)C7)CC6)nc5c3F)COC4)c2c1C#N] | 639 |

TABLE 21-continued

| Preparation | Chemical Name | Structure | MS (ES) m/z (M + 1) |
|---|---|---|---|
| 80 | tert-Butyl (3-cyano-4-(3-((1-((4,4-difluoropiperidin-1-yl)methyl)cyclopropyl)meth-oxy)-5-fluoro-7,9-dihydrofuro[3,4-f]quinazolin-6-yl)-7-fluorothieno[3,2-c]pyridin-2-yl)carbamate | 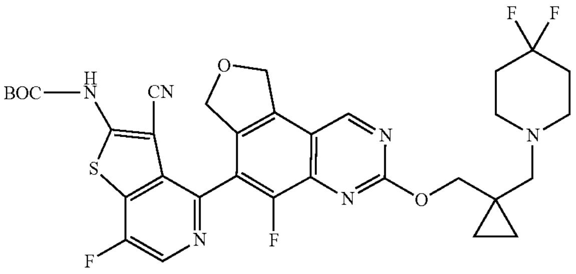 [SMILES: CC(C)(C)OC(=O)Nc1sc2c(F)cnc(-c3c4c(c5cnc(OCC6(CN7CCC(F)(F)CC7)CC6)nc5c3F)COC4)c2c1C#N] | 685 |
| 81 | tert-Butyl (4-(3-((1-(((1S,4S)-2-oxa-5-azabicyclo[2.2.1]heptan-5-yl)methyl)cyclopropyl)meth-oxy)-5-fluoro-7,9-dihydrofuro[3,4-f]quinazolin-6-yl)-3-cyano-7-fluorothieno[3,2-c]pyridin-2-yl)carbamate | 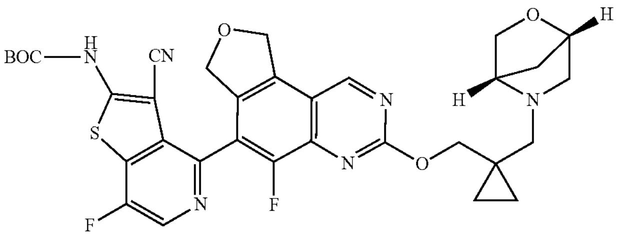 [SMILES: CC(C)(C)OC(=O)Nc1sc2c(F)cnc(-c3c4c(c5cnc(OCC6(CN7C[C@@H]8C[C@H]7CO8)CC6)nc5c3F)COC4)c2c1C#N] | 663 |
| 82 | tert-Butyl (3-cyano-4-(3-(2,2-dimethyl-3-morpholinopropoxy)-5-fluoro-7,9-dihydrofuro[3,4-f]quinazolin-6-yl)-7-fluorothieno[3,2-c]pyridin-2-yl)carbamate | 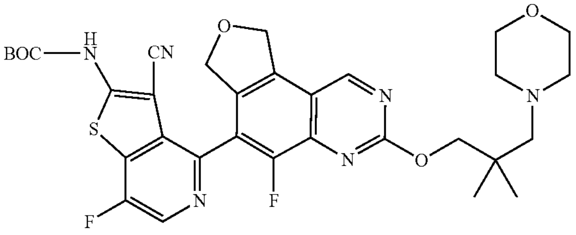 [SMILES: CC(C)(COc1ncc2c3c(c(-c4ncc(F)c5sc(NC(=O)OC(C)(C)C)c(C#N)c45)c(F)c2n1)COC3)CN1CCOCC1] | 653 |
| 83 | tert-Butyl (3-cyano-7-fluoro-4-(5-fluoro-3-((1-((3-(2-hydroxypropan-2-yl)azetidin-1-yl)methyl)cyclopropyl)meth-oxy)-7,9-dihydrofuro[3,4-f]quinazolin-6-yl)thieno[3,2-c]pyridin-2-yl)carbamate | 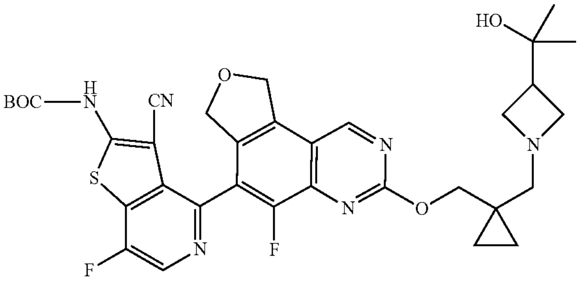 [SMILES: CC(C)(C)OC(=O)Nc1sc2c(F)cnc(-c3c4c(c5cnc(OCC6(CN7CC(C(C)(C)O)C7)CC6)nc5c3F)COC4)c2c1C#N] | 679 |
| 84 | tert-Butyl (3-cyano-4-(3-((1-((4-ethyl-3-oxopiperazin-1-yl)methyl)cyclopropyl)meth-oxy)-5-fluoro-7,9-dihydrofuro[3,4-f]quinazolin-6-yl)-7-fluorothieno[3,2-c]pyridin-2-yl)carbamate | 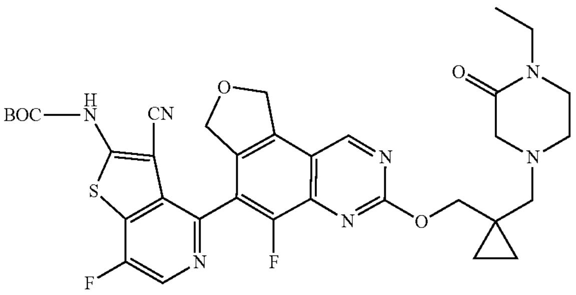 [SMILES: CCN1CCN(CC2(COc3ncc4c5c(c(-c6ncc(F)c7sc(NC(=O)OC(C)(C)C)c(C#N)c67)c(F)c4n3)COC5)CC2)CC1=O] | 692 |

TABLE 21-continued

| Preparation | Chemical Name | Structure | MS (ES) m/z (M + 1) |
|---|---|---|---|
| 85 | tert-Butyl (4-(3-((1-((7-oxa-2-azaspiro[3.5]nonan-2-yl)methyl)cyclopropyl)meth-oxy)-5-fluoro-7,9-dihydrofuro[3,4-f]quinazolin-6-yl)-3-cyano-7-fluorothieno[3,2-c]pyridin-2-yl)carbamate | 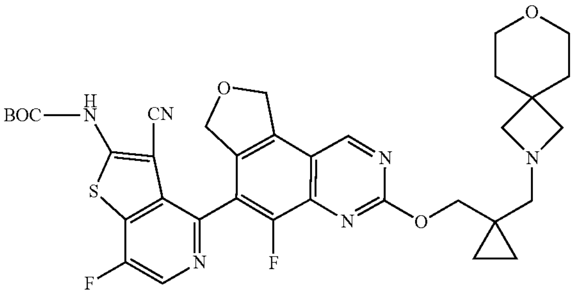 [SMILES: CC(C)(C)OC(=O)Nc1sc2c(F)cnc(-c3c4c(c5cnc(OCC6(CN7CC8(CCOCC8)C7)CC6)nc5c3F)COC4)c2c1C#N] | 691 |
| 86 | (1-(((6-Bromo-5-fluoro-7,9-dihydrofuro[3,4-f]quinazolin-3-yl)oxy)methyl)-2,2-difluorocyclopropyl)meth-anol | 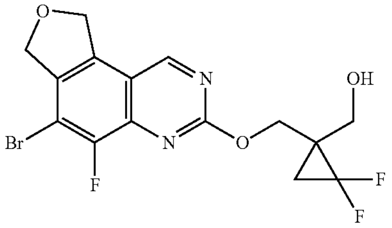 [SMILES: OCC1(COc2ncc3c4c(c(Br)c(F)c3n2)COC4)CC1(F)F] | 404 |
| 87 | tert-Butyl (4-(1-(3-((R)-2-((tert-butyldimethylsilyl)oxy)pro-pyl)-3,8-diazabicyclo[3.2.1]octan-8-yl)-5-fluoro-3-((1-(morpholinomethyl-d2)cyclopropyl)methoxy-d2)-7,9-dihydrofuro[3,4-f]quinazolin-6-yl)-3-cyano-7-fluorothieno[3,2-c]pyridin-2-yl)carbamate | 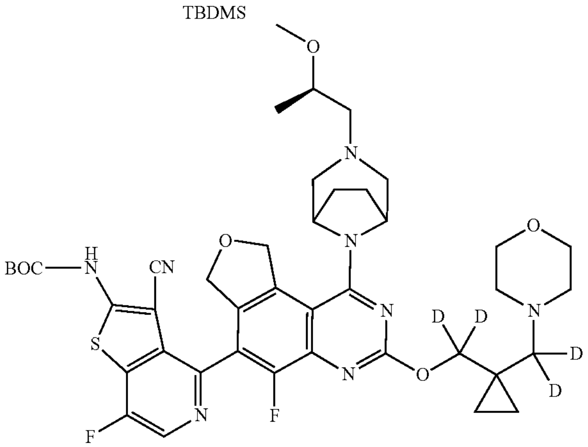 [SMILES: [2H]C([2H])(Oc1nc(N2C3CCC2CN(C[C@@H](C)OC)C3)c2c3c(c(-c4ncc(F)c5sc(NC(=O)OC(C)(C)C)c(C#N)c45)c(F)c2n1)COC3)C1(C([2H])([2H])N2CCOCC2)CC1] | 937 |
| 21A | tert-Butyl (4-(3-((2-((1,4-oxazepan-4-yl)methyl)cyclopropyl)meth-oxy)5-fluoro-7,9-dihydrofuro[3,4-f]quinazolin-6-yl)-3-cyano-7-fluorothieno[3,2-c]pyridin-2-yl)carbamate | 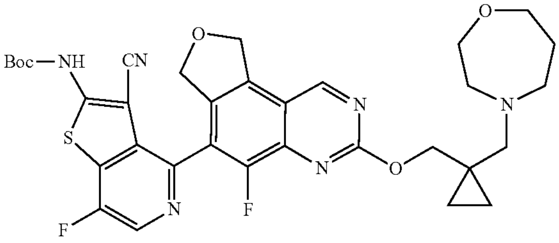 [SMILES: CC(C)(C)OC(=O)Nc1sc2c(F)cnc(-c3c4c(c5cnc(OCC6(CN7CCCOCC7)CC6)nc5c3F)COC4)c2c1C#N] | 665 |
| 22A | tert-Butyl (3-cyano-7-fluoro-4-(5-fluoro-3-((1-((4-fluoropiperidin-1-yl)methyl)cyclopropyl)meth-oxy)-7,9-dihydrofuro[3,4-f]quinazolin-6-yl)thieno[3,2-c]pyridin-2-yl)carbamate | 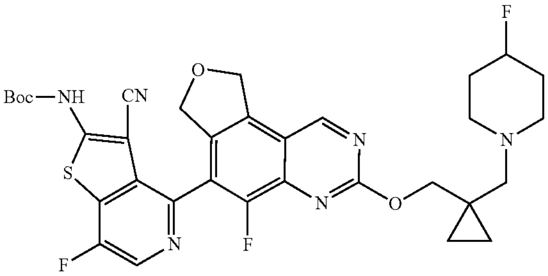 [SMILES: CC(C)(C)OC(=O)Nc1sc2c(F)cnc(-c3c4c(c5cnc(OCC6(CN7CCC(F)CC7)CC6)nc5c3F)COC4)c2c1C#N] | 667 |

TABLE 21-continued

| Preparation | Chemical Name | Structure | MS (ES) m/z (M + 1) |
|---|---|---|---|
| 23A | tert-Butyl (4-(3-((1-((-3-oxa-8-azabicyclo[3.2.1]octan-8-yl)methyl)cyclopropyl)methoxy)-5-fluoro-7,9-dihydrofuro[3,4-f]quinazolin-6-yl)-3-cyano-7-fluorothieno[3,2-c]pyridin-2-yl)carbamate | 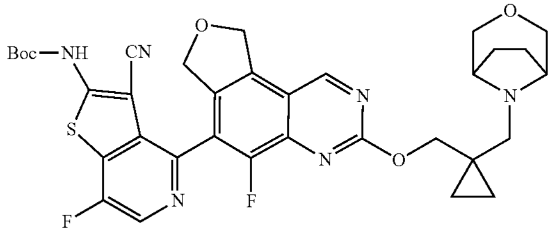 [SMILES: CC(C)(C)OC(=O)Nc1sc2c(F)cnc(-c3c4c(c5cnc(OCC6(CN7C8CCC7COC8)CC6)nc5c3F)COC4)c2c1C#N] | 677 |
| 24A | tert-Butyl (4-(3-((1-(((1R,4R)-2-oxa-5-azabicyclo[2.2.1]heptan-5-yl)methyl)cyclopropyl)methoxy)-5-fluoro-7,9-dihydrofuro[3,4-f]quinazolin-6-yl)-3-cyano-7-fluorothieno[3,2-c]pyridin-2-yl)carbamate | 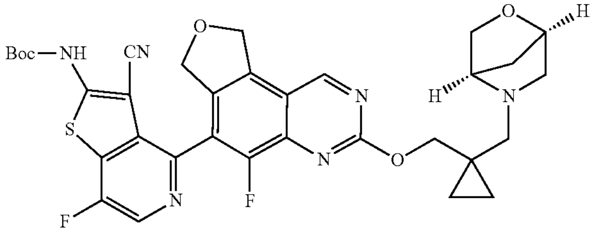 [SMILES: CC(C)(C)OC(=O)Nc1sc2c(F)cnc(-c3c4c(c5cnc(OCC6(CN7C[C@H]8C[C@@H]7CO8)CC6)nc5c3F)COC4)c2c1C#N] | 663 |
| 25A | tert-Butyl 8-(3-((1-((7-oxa-2-azaspiro[3.5]nonan-2-yl)methyl)cyclopropyl)methoxy)-6-(2-((tert-butoxycarbonyl)amino)-3-cyano-7-fluorothieno[3,2-c]pyridin-2-yl)-5-fluoro-7,9-dihydrofuro[3,4-f]quinazolin-1-yl)-3,8-diazabicyclo[3.2.1]octane-3-carboxylate | 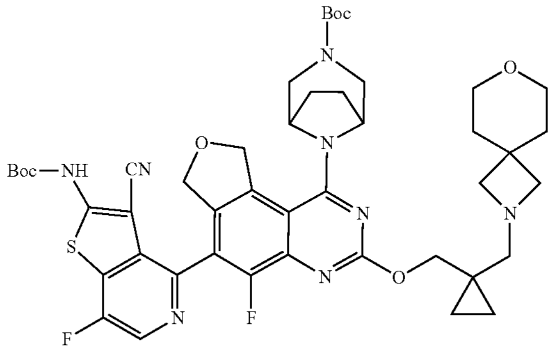 [SMILES: CC(C)(C)OC(=O)Nc1sc2c(F)cnc(-c3c4c(c5c(N6C7CCC6CN(C(=O)OC(C)(C)C)C7)nc(OCC6(CN7CC8(CCOCC8)C7)CC6)nc5c3F)COC4)c2c1C#N] | 902 |
| 26A | tert-Butyl 8-(6-(2-((tert-butoxycarbonyl)amino)-3-cyano-7-fluorothieno[3,2-c]pyridin-4-yl)-5-fluoro-3-((1-(((R)-3-methoxypyrrolidin-1-yl)methyl)cyclopropyl)methoxy)-7,9-dihydrofuro[3,4-f]quinazolin-1-yl)-3,8-diazabicyclo[3.2.1]octane-3-carboxylate | 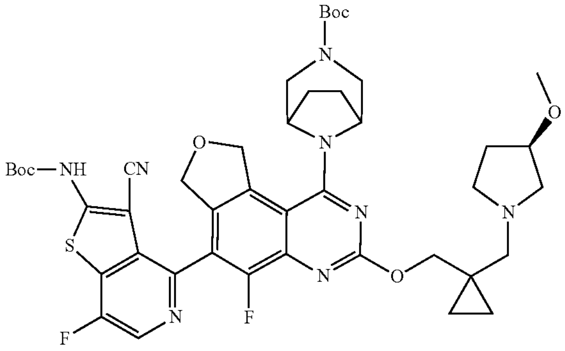 [SMILES: CO[C@@H]1CCN(CC2(COc3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)CC2)C1] | 875 |
| 27A | tert-Butyl 8-(6-(2-((tert-butoxycarbonyl)amino)-3-cyano-7-fluorothieno[3,2-c]pyridin-4-yl)-5-fluoro-3-((1-(pyrrolidin-1-ylmethyl)cyclopropyl)methoxy)-7,9-dihydrofuro[3,4-f]quinazolin-1-yl)-3,8-diazabicyclo[3.2.1]octane-3-carboxylate | 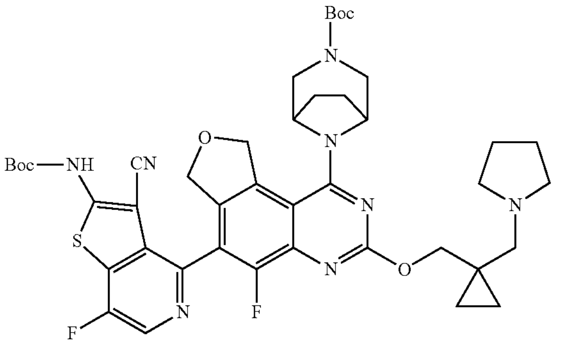 [SMILES: CC(C)(C)OC(=O)Nc1sc2c(F)cnc(-c3c4c(c5c(N6C7CCC6CN(C(=O)OC(C)(C)C)C7)nc(OCC6(CN7CCCC7)CC6)nc5c3F)COC4)c2c1C#N] | 845 |

TABLE 21-continued

| Preparation | Chemical Name | Structure | MS (ES) m/z (M + 1) |
|---|---|---|---|
| 28A | tert-Butyl 8-(6-(2-((tert-butoxycarbonyl)amino)-3-cyano-7-fluorothieno[3,2-c]pyridin-4-yl)-5-fluoro-3-((1-((3-hydroxyazetidin-1-yl)methyl)cyclopropyl)methoxy)-7,9-dihydrofuro[3,4-f]quinazolin-1-yl)-3,8-diazabicyclo[3.2.1]octane-3-carboxylatec | 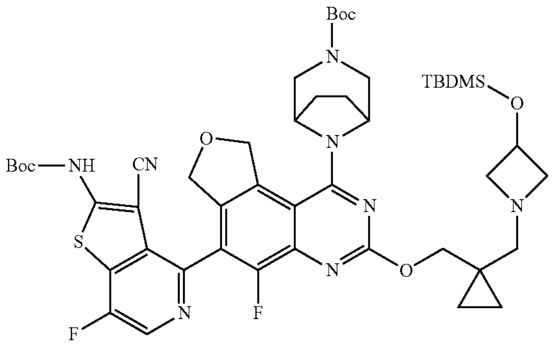 | 961 |
| 29A | tert-Butyl 8-(3-((1-((3-oxa-8-azabicyclo[3.2.1]octan-8-yl)methyl)cyclopropyl)methoxy)-6-(2-((tert-butoxycarbonyl)amino)-3-cyano-7-fluorothieno[3,2-c]pyridin-4-yl)-5-fluoro-7,9-dihydrofuro[3,4-f]quinazolin-1-yl)-3,8-diazabicyclo[3.2.1]octane-3-carboxylate | 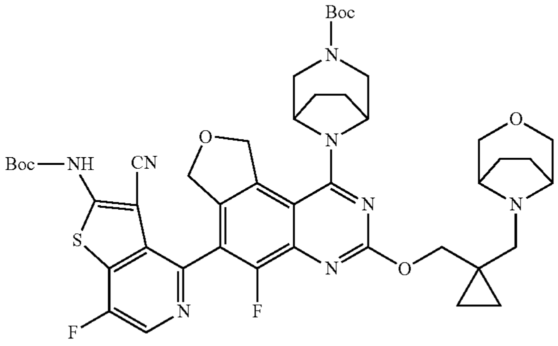 [SMILES: CC(C)(C)OC(=O)Nc1sc2c(F)cnc(-c3c4c(c5c(N6C7CCC6CN(C(=O)OC(C)(C)C)C7)nc(OCC6(CN7C8CCC7COC8)CC6)nc5c3F)COC4)c2c1C#N] | 887 |
| 30A | tert-Butyl 8-(6-(2-((tert-butoxycarbonyl)amino)-3-cyano-7-fluorothieno[3,2-c]pyridin-4-yl)-5-fluoro-3-((1-((3-fluoropiperidin-1-yl)methyl)cyclopropyl)methoxy)-7,9-dihydrofuro[3,4-f]quinazolin-1-yl)-3,8-diazabicyclo[3.2.1]octane-3-carboxylate | 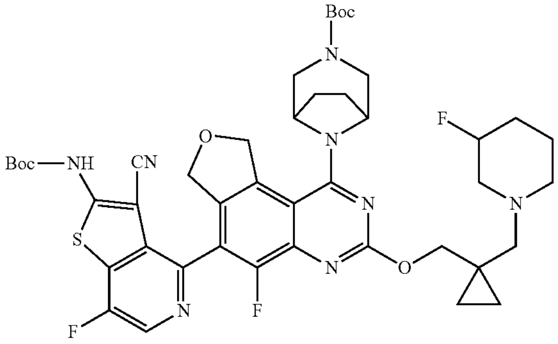 [SMILES: CC(C)(C)OC(=O)Nc1sc2c(F)cnc(-c3c4c(c5c(N6C7CCC6CN(C(=O)OC(C)(C)C)C7)nc(OCC6(CN7CCCC(F)C7)CC6)nc5c3F)COC4)c2c1C#N] | 877 |
| 31A | tert-Butyl 8-(6-(2-((tert-butoxycarbonyl)amino)-3-cyano-7-fluorothieno[3,2-c]pyridin-4-yl)-3-((1-((3,3-dimethylazetidin-1-yl)methyl)cyclopropyl)methoxy)-5-fluoro-7,9-dihydrofuro[3,4-f]quinazolin-1-yl)-3,8-diazabicyclo[3.2.1]octane-3-carboxylate | 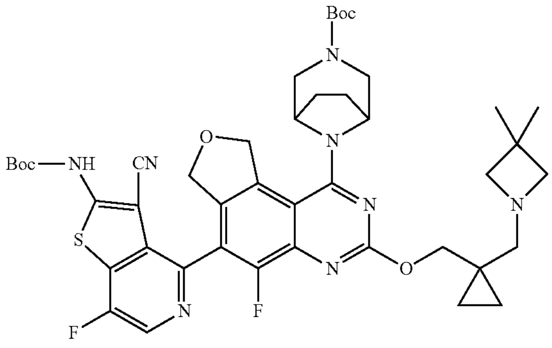 [SMILES: CC1(C)CN(CC2(COc3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)CC2)C1] | 859 |

TABLE 21-continued

| Preparation | Chemical Name | Structure | MS (ES) m/z (M + 1) |
|---|---|---|---|
| 32A | tert-Butyl 8-(6-(2-((tert-butoxycarbonyl)amino)-3-cyano-7-fluorothieno[3,2-c]pyridin-4-yl)-3-((1-(((3R,4S)-3,4-difluoropyrrolidin-1-yl)methyl)cyclopropyl)methoxy)-5-fluoro-7,9-dihydrofuro[3,4-f]quinazolin-1-yl)-3,8-diazabicyclo[3.2.1]octane-3-carboxylate | 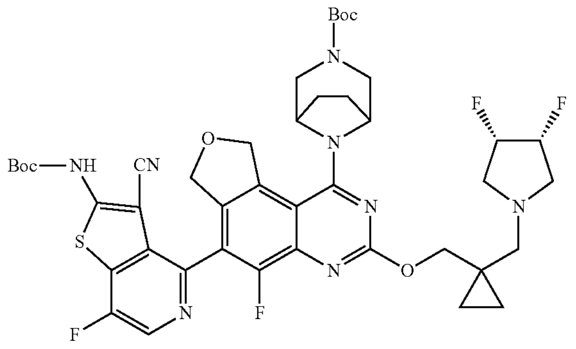 [SMILES: CC(C)(C)OC(=O)Nc1sc2c(F)cnc(-c3c4c(c5c(N6C7CCC6CN(C(=O)OC(C)(C)C)C7)nc(OCC6(CN7C[C@@H](F)[C@@H](F)C7)CC6)nc5c3F)COC4)c2c1C#N] | 881 |
| 33A | tert-Butyl 8-(6-(2-((tert-butoxycarbonyl)amino)-3-cyano-7-fluorothieno[3,2-c]pyridin-4-yl)-5-fluoro-3-((1-((3-fluoroazetidin-1-yl)methyl)cyclopropyl)methoxy)-7,9-dihydrofuro[3,4-f]quinazolin-1-yl)-3,8-diazabicyclo[3.2.1]octane-3-carboxylate | 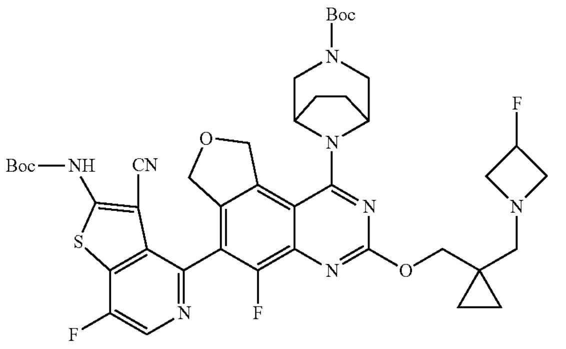 [SMILES: CC(C)(C)OC(=O)Nc1sc2c(F)cnc(-c3c4c(c5c(N6C7CCC6CN(C(=O)OC(C)(C)C)C7)nc(OCC6(CN7CC(F)C7)CC6)nc5c3F)COC4)c2c1C#N] | 849 |
| 34A | tert-Butyl 8-(3-((1-((8-oxa-8-oxa-3-azabicyclo[3.2.1]octan-3-yl)methyl)cyclopropyl)methoxy)-6-(2-((tert-butoxycarbonyl)amino)-3-cyano-7-fluorothieno[3,2-c]pyridin-4-yl)-5-fluoro-7,9-dihydrofuro[3,4-f]quinazolin-1-yl)-3,8-diazabicyclo[3.2.1]octane-3-carboxylate | 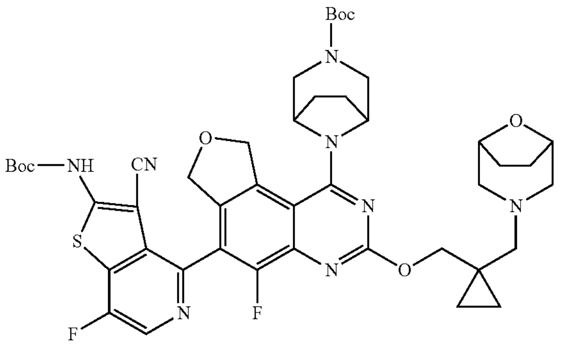 [SMILES: CC(C)(C)OC(=O)Nc1sc2c(F)cnc(-c3c4c(c5c(N6C7CCC6CN(C(=O)OC(C)(C)C)C7)nc(OCC6(CN7CC8CCC(C7)O8)CC6)nc5c3F)COC4)c2c1C#N] | 887 |
| 35A | tert-Butyl 8-(6-(2-((tert-butoxycarbonyl)amino)-3-cyano-7-fluorothieno[3,2-c]pyridin-4-yl)-5-fluoro-3-(2-methyl-3-morpholinopropoxy)-7,9-dihydrofuro[3,4-f]quinazolin-1-yl)-3,8-diazabicyclo[3.2.1]octane-3-carboxylate | 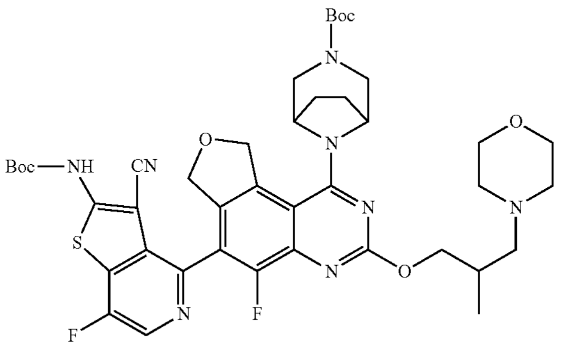 [SMILES: CC(COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3)CN1CCOCC1] | 849 |

TABLE 21-continued

| Preparation | Chemical Name | Structure | MS (ES) m/z (M + 1) |
|---|---|---|---|
| 36A | tert-Butyl 8-(6-(2-((tert-butoxycarbonyl)amino)-3-cyano-7-fluorothieno[3,2-c]pyridin-4-yl)-5-fluoro-3-((3-(morpholinomethyl)oxetan-3-yl)methoxy)-7,9-dihydrofuro[3,4-f]quinazolin-1-yl)-3,8-diazabicyclo[3.2.1]octane-3-carboxylate | 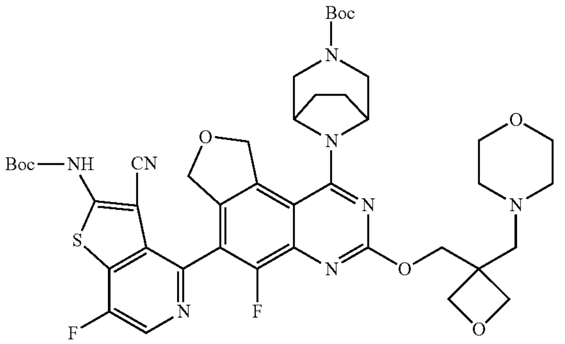 [SMILES: CC(C)(C)OC(=O)Nc1sc2c(F)cnc(-c3c4c(c5c(N6C7CCC6CN(C(=O)OC(C)(C)C)C7)nc(OCC6(CN7CCOCC7)COC6)nc5c3F)COC4)c2c1C#N] | 877 |
| 37A | tert-Butyl 8-(6-(2-((tert-butoxycarbonyl)amino)-3-cyano-7-fluorothieno[3,2-c]pyridin-4-yl)-3-(2,2-dimethyl-3-morpholinopropoxy)-5-fluoro-7,9-dihydrofuro[3,4-f]quinazolin-1-yl)-3,8-diazabicyclo[3.2.1]octane-3-carboxylate | 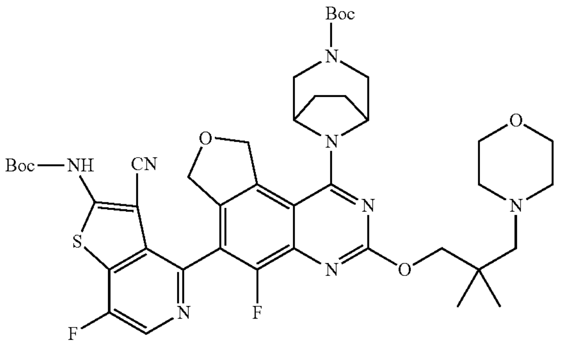 [SMILES: CC(C)(COc1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3)CN1CCOCC1] | 863 |
| 86B | tert-Butyl (4-(3-((1-(((1S,4S)-2-oxa-5-azabicyclo[2.2.1]heptan-5-yl)methyl)cyclopropyl)methoxy)-5-chloro-7,9-dihydrofuro[3,4-f]quinazolin-6-yl)-3-cyano-7-fluorobenzo[b]thiophen-2-yl)carbamate | 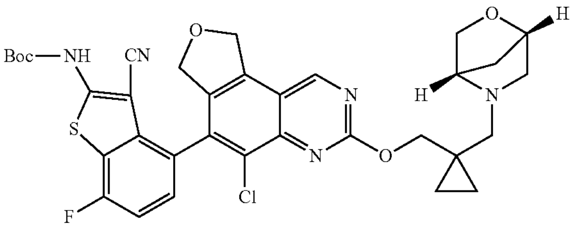 [SMILES: CC(C)(C)OC(=O)Nc1sc2c(F)ccc(-c3c4c(c5cnc(OCC6(CN7C[C@@H]8C[C@H]7CO8)CC6)nc5c3Cl)COC4)c2c1C#N] | 678 |
| 87B | tert-Butyl 8-(3-((1-((1,4-oxazepan-4-yl)methyl)cyclopropyl)methoxy)-6-(2-((tert-butoxycarbonyl)amino)-3-cyano-7-fluorothieno[3,2-c]pyridin-4-yl)-5-fluoro-7,9-dihydrofuro[3,4-f]quinazolin-1-yl)-3,8-diazabicyclo[3.2.1]octane-3-carboxylate | 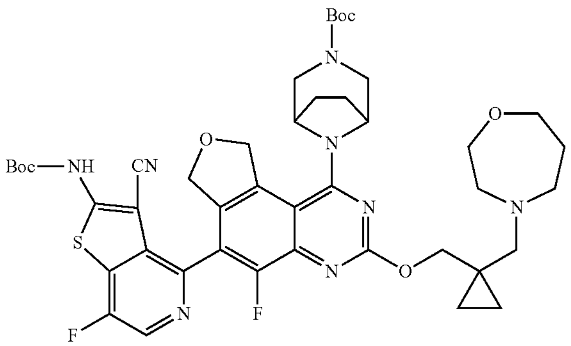 [SMILES: CC(C)(C)OC(=O)Nc1sc2c(F)cnc(-c3c4c(c5c(N6C7CCC6CN(C(=O)OC(C)(C)C)C7)nc(OCC6(CN7CCCOCC7)CC6)nc5c3F)COC4)c2c1C#N] | 875 |

TABLE 21-continued

| Preparation | Chemical Name | Structure | MS (ES) m/z (M + 1) |
|---|---|---|---|
| 88B | tert-Butyl 8-(6-(2-((tert-butoxycarbonyl)amino)-3-cyano-7-fluorothieno[3,2-c]pyridin-4-yl)-5-fluoro-3-((1-(((3aR,6aS)-tetrahydro-1H-furo[3,4-c]pyrrol-5(3H)-yl)methyl)cyclopropyl)methoxy)-7,9-dihydrofuro[3,4-f]quinazolin-1-yl)-3,8-diazabicyclo[3.2.1]octane-3-carboxylate | 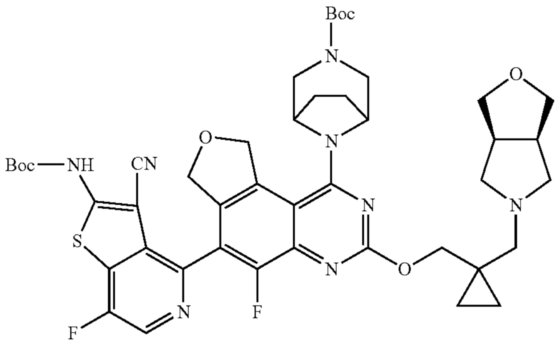 [SMILES: CC(C)(C)OC(=O)Nc1sc2c(F)cnc(-c3c4c(c5c(N6C7CCC6CN(C(=O)OC(C)(C)C)C7)nc(OCC6(CN7C[C@H]8COC[C@H]8C7)CC6)nc5c3F)COC4)c2c1C#N] | 887 |

Preparation 38A tert-Butyl (3-cyano-7-fluoro-4-(5-fluoro-3-(3-morpholinoazetidin-1-yl)-7,9-dihydrofuro[3,4-f]quinazolin-6-yl)thieno[3,2-c]pyridin-2-yl)carbamate

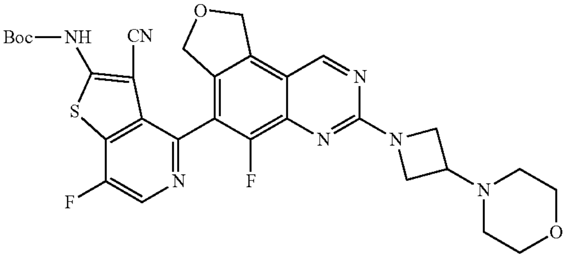

To tert-butyl (3-cyano-4-(3-(ethylsulfonyl)-5-fluoro-7,9-dihydrofuro[3,4-f]quinazolin-6-yl)-7-fluorothieno[3,2-c] pyridin-2-yl)carbamate (0.200 g, 0.349 mmol) was added diisopropylethylamine (0.180 g, 1.39 mmol), 4-(azetidin-3-yl)morpholine (0.099 g, 0.70 mmol), and THE (3 mL). The reaction mixture was heated at 70° C. After 1 h, the mixture was concentrated under reduced pressure. The residue was purified on strong cation exchange media (10 g), eluting first with MeOH, then with 2M ammoniated MeOH. The basic fraction was concentrated under reduced pressure to obtain the title compound (0.170 g, 780%) as a brown solid. MS (ES) m/z=622 (M+1).

The following compounds in Table 22 were prepared in similar manner as described in Preparation 38A. Various bases, such as sodium hydride or lithium bis(trimethylsilyl) amide, were used in place of diisopropyl ethyl amine. Various methods were used to purify the compounds, which would be apparent to one skilled in the art.

TABLE 22

| Preparation | Chemical Name | Structure | MS (ES) m/z (M + 1) |
|---|---|---|---|
| 39A | tert-Butyl (3-cyano-7-fluoro-4-(5-fluoro-3-(3-(methyl(oxetan-3-yl)amino)azetidin-1-yl)-7,9-dihydrofuro[3,4-f]quinazolin-6-yl)thieno[3,2-c]pyridin-2-yl)carbamate | 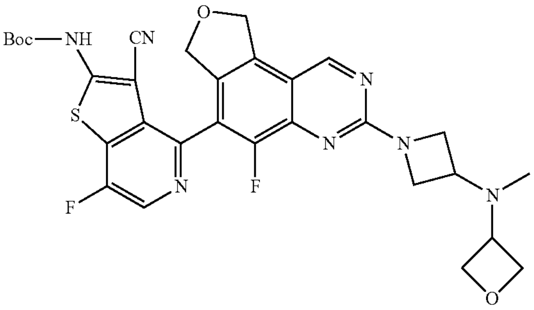 [SMILES: CN(C1COC1)C1CN(c2ncc3c4c(c(-c5ncc(F)c6sc(NC(=O)OC(C)(C)C)c(C#N)c56)c(F)c3n2)COC4)C1] | 622 |

TABLE 22-continued

| Preparation | Chemical Name | Structure | MS (ES) m/z (M + 1) |
|---|---|---|---|
| 40A | tert-Butyl (3-cyano-7-fluoro-4-(5-fluoro-3-(3-((S)-3-fluropyrrolidin-1-yl)azetidin-1-yl)-7,9-dihydrofuro[3,4-f]quinazolin-6-yl)thieno[3,2-c]pyridin-2-yl)carbamate | 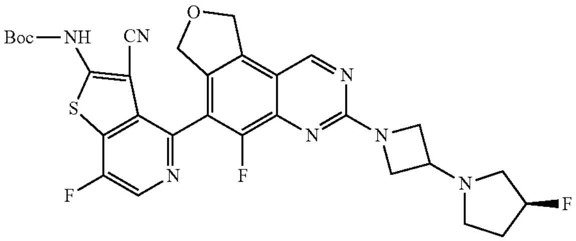 [SMILES: CC(C)(C)OC(=O)Nc1sc2c(F)cnc(-c3c4c(c5cnc(N6CC(N7CC[C@H](F)C7)C6)nc5c3F)COC4)c2c1C#N] | 624 |
| 41A | tert-Butyl (3-cyano-7-fluoro-4-(5-fluoro-3-(3-((R)-3-fluoropyrrolidin-1-yl)azetidin-1-yl)-7,9-dihydrofuro[3,4-f]quinazolin-6-yl)thieno[3,2-c]pyridin-2-yl)carbamate | 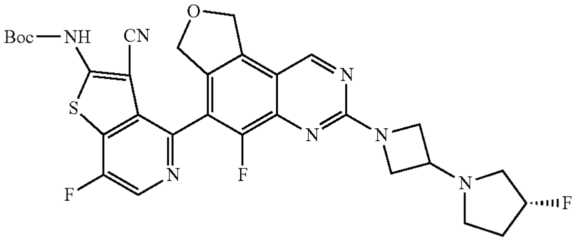 [SMILES: CC(C)(C)OC(=O)Nc1sc2c(F)cnc(-c3c4c(c5cnc(N6CC(N7CC[C@@H](F)C7)C6)nc5c3F)COC4)c2c1C#N] | 624 |
| 42A | tert-Butyl (3-cyano-4-(3-(3-(cyclopropyl(methyl)amino)azetidin-1-yl)-5-fluoro-7,9-dihydrofuro[3,4-f]quinazolin-6-yl)-7-fluorothieno[3,2-c]pyridin-2-yl)carbamate | 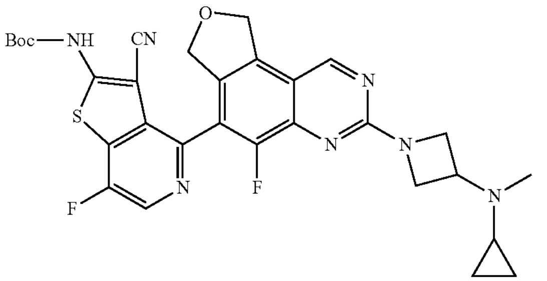 [SMILES: CN(C1CC1)C1CN(c2ncc3c4c(c(-c5ncc(F)c6sc(NC(=O)OC(C)(C)C)c(C#N)c56)c(F)c3n2)COC4)C1] | 606 |
| 43A | tert-Butyl (3-cyano-4-(3-(3-(1-(dimethylamino)cyclopropyl)azetidin-1-yl)-5-fluoro-7,9-dihydrofuro[3,4-f]quinazolin-6-yl)-7-fluorothieno[3,2-c]pyridin-2-yl)carbamate | 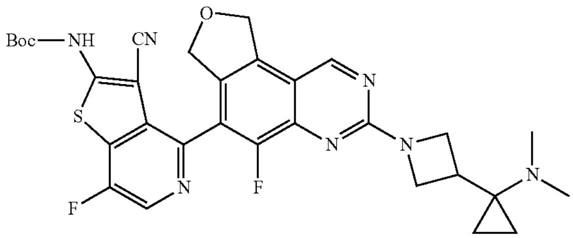 [SMILES: CN(C)C1(C2CN(c3ncc4c5c(c(-c6ncc(F)c7sc(NC(=O)OC(C)(C)C)c(C#N)c67)c(F)c4n3)COC5)C2)CC1] | 620 |
| 44A | tert-Butyl (3-cyano-7-fluoro-4-(5-fluoro-3-(1-methyl-1,6-diazaspiro[3.3]heptan-6-yl)-7,9-dihydrofuro[3,4-f]quinazolin-6-yl)thieno[3,2-c]pyridin-2-yl)carbamate | 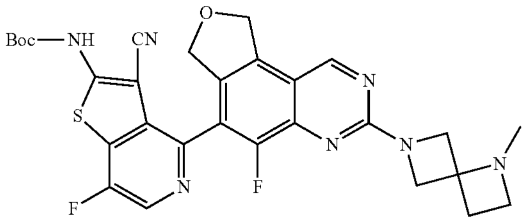 [SMILES: CN1CCC12CN(c1ncc3c4c(c(-c5ncc(F)c6sc(NC(=O)OC(C)(C)C)c(C#N)c56)c(F)c3n1)COC4)C2] | 592 |
| 45A | tert-Butyl (3aR,6aS)-5-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)hexahydropyrrolo[3,4-c]pyrrole-2(1H)-carboxylate | 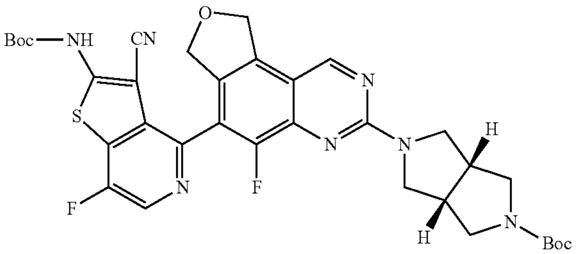 [SMILES: CC(C)(C)OC(=O)Nc1sc2c(F)cnc(-c3c4c(c5cnc(N6C[C@H]7CN(C(=O)OC(C)(C)C)C[C@H]7C6)nc5c3F)COC4)c2c1C#N] | 692 |

TABLE 22-continued

| Preparation | Chemical Name | Structure | MS (ES) m/z (M + 1) |
|---|---|---|---|
| 46A | tert-Butyl (3-cyano-4-(3-((S)-3-(dimethylamino)pyrrolidin-1-yl)-5-fluoro-7,9-dihydrofuro[3,4-f]quinazolin-6-yl)-7-fluorothieno[3,2-c]pyridin-2-yl)carbamate | 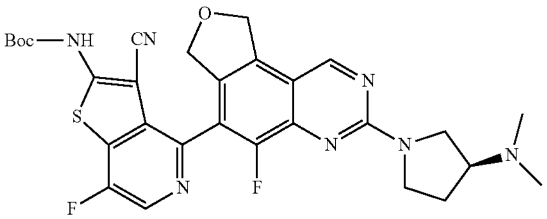 [SMILES: CN(C)[C@H]1CCN(c2ncc3c4c(c(-c5ncc(F)c6sc(NC(=O)OC(C)(C)C)c(C#N)c56)c(F)c3n2)COC4)C1] | 594 |
| 47A[1] | rel-tert-Butyl (3-cyano-4-(3-((3R,4R)-3-(dimethylamino)-4-hydroxypyrrolidin-1-yl)-5-fluoro-7,9-dihydrofuro[3,4-f]quinazolin-6-yl)-7-fluorothieno[3,2-c]pyridin-2-yl)carbamate, Trans Isomer 1 | 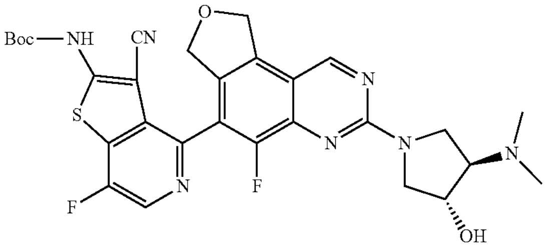 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@H]1O] | 610 |
| 48A [1] | rel-tert-Butyl (3-cyano-4-(3-((3R,4R)-3-(dimethylamino)-4-hydroxypyrrolidin-1-yl)-5-fluoro-7,9-dihydrofuro[3,4-f]quinazolin-6-yl)-7-fluorothieno[3,2-c]pyridin-2-yl)carbamate, Trans Isomer 2 | 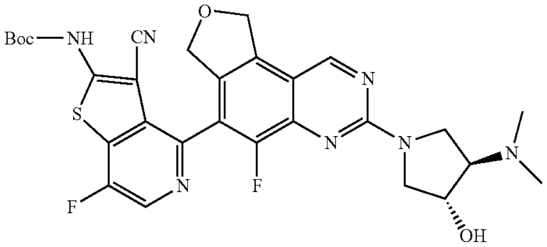 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@H]1O] | 610 |
| 49A | tert-Butyl (3-cyano-4-(3-((R)-2-((dimethylamino)methyl)pyrrolidin-1-yl)-5-fluoro-7,9-dihydrofuro[3,4-f]quinazolin-6-yl)-7-fluorothieno[3,2-c]pyridin-2-yl)carbamate | 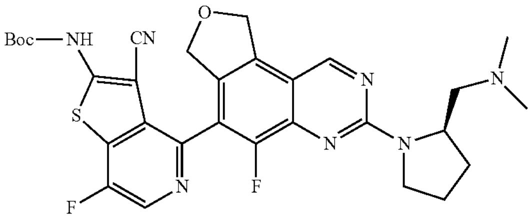 [SMILES: CN(C)C[C@H]1CCCN1c1ncc2c3c(c(-c4ncc(F)c5sc(NC(=O)OC(C)(C)C)c(C#N)c45)c(F)c2n1)COC3] | 608 |
| 50A | tert-Butyl (3-cyano-4-(3-((S)-2-((dimethylamino)methyl)pyrrolidin-2-yl)-5-fluoro-7,9-dihydrofuro[3,4-f]quinazolin-6-yl)-7-fluorothieno[3,2-c]pyridin-2-yl)carbamate | 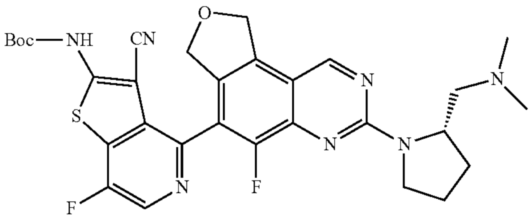 [SMILES: CN(C)C[C@@H]1CCCN1c1ncc2c3c(c(-c4ncc(F)c5sc(NC(=O)OC(C)(C)C)c(C#N)c45)c(F)c2n1)COC3] | 608 |
| 51A | tert-Butyl (3-cyano-7-fluoro-4-(5-fluoro-3-(6-methyl-3,6-diazabicyclo[3.1.1]heptan-3-yl)-7,9-dihydrofuro[3,4-f]quinazolin-6-yl)thieno[3,2-c]pyridin-2-yl)carbamate | 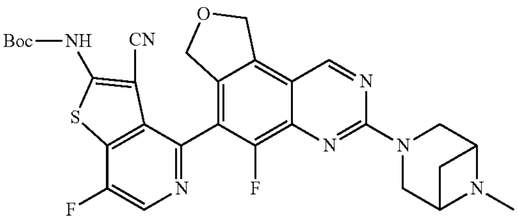 [SMILES: CN1C2CC1CN(c1ncc3c4c(c(-c5ncc(F)c6sc(NC(=O)OC(C)(C)C)c(C#N)c56)c(F)c3n1)COC4)C2] | 592 |

TABLE 22-continued

| Preparation | Chemical Name | Structure | MS (ES) m/z (M + 1) |
|---|---|---|---|
| 52A | tert-Butyl (3-cyano-7-fluoro-4-(5-fluoro-3-((7S,8aS)-7-fluorohexahydropyrrolo[1,2-a]pyrazin-2(1H)-yl)-7,9-dihydrofuro[3,4-f]quinazolin-6-yl)thieno[3,2-c]pyridin-2-yl)carbamate | 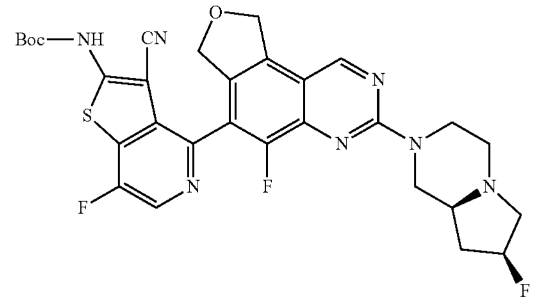 [SMILES: CC(C)(C)OC(=O)Nc1sc2c(F)cnc(-c3c4c(c5cnc(N6CCN7C[C@@H](F)C[C@H]7C6)nc5c3F)COC4)c2c1C#N] | 624 |
| 53A | tert-Butyl (3-cyano-4-(3-(3-(dimethylamino)-3-methylpyrrolidin-1-yl)-5-fluoro-7,9-dihydrofuro[3,4-f]quinazolin-6-yl)-7-fluorothieno[3,2-c]pyridin-2-yl)carbamate | 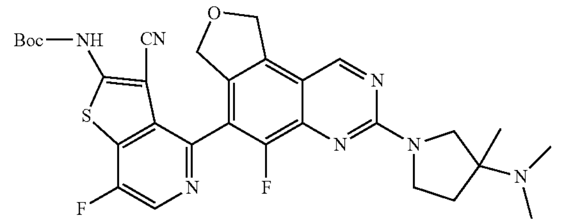 [SMILES: CN(C)C1(C)CCN(c2ncc3c4c(c(-c5ncc(F)c6sc(NC(=O)OC(C)(C)C)c(C#N)c56)c(F)c3n2)COC4)C1] | 608 |
| 54A | tert-Butyl (3-cyano-7-fluoro-4-(5-fluoro-3-(4-methylpiperazin-1-yl)-7,9-dihydrofuro[3,4-f]quinazolin-6-yl)thieno[3,2-c]pyridin-2-yl)carbamate | 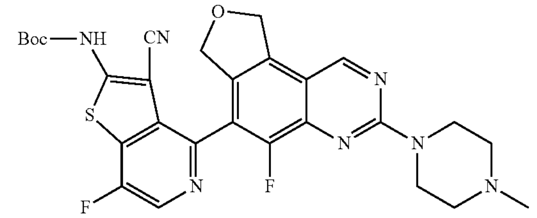 [SMILES: CN1CCN(c2ncc3c4c(c(-c5ncc(F)c6sc(NC(=O)OC(C)(C)C)c(C#N)c56)c(F)c3n2)COC4)CC1] | 580 |
| 55A | tert-Butyl (3-cyano-7-fluoro-4-(5-fluoro-3-((1S,4S)-5-methyl-2,5-diazabicyclo[2.2.1]heptan-2-yl)-7,9-dihydrofuro[3,4-f]quinazolin-6-yl)thieno[3,2-c]pyridin-2-yl)carbamate | 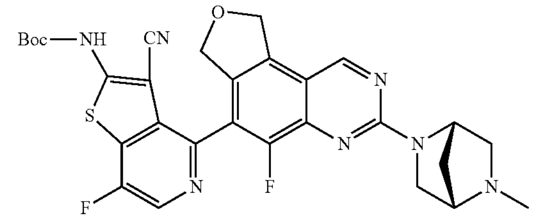 [SMILES: CN1C[C@@H]2C[C@H]1CN2c1ncc2c3c(c(-c4ncc(F)c5sc(NC(=O)OC(C)(C)C)c(C#N)c45)c(F)c2n1)COC3] | 592 |
| 56A | tert-Butyl (3-cyano-7-fluoro-4-(5-fluoro-3-(hexahydropyrrolo[1,2-a]pyrazin-2(1H)-yl)-7,9-dihydrofuro[3,4-f]quinazolin-6-yl)thieno[3,2-c]pyridin-2-yl)carbamate | 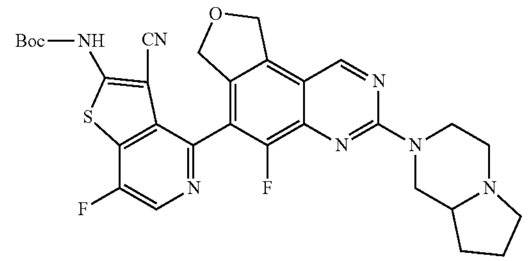 [SMILES: CC(C)(C)OC(=O)Nc1sc2c(F)cnc(-c3c4c(c5cnc(N6CCN7CCCC7C6)nc5c3F)COC4)c2c1C#N] | 606 |
| 57A | tert-Butyl (3-cyano-7-fluoro-4-(5-fluoro-3-((1R,4R)-5-methyl-2,5-diazabicyclo[2.2.1]heptan-2-yl)-7,9-dihydrofuro[3,4-f]quinazolin-6-yl)thieno[3,2-c]pyridin-2-yl)carbamate | 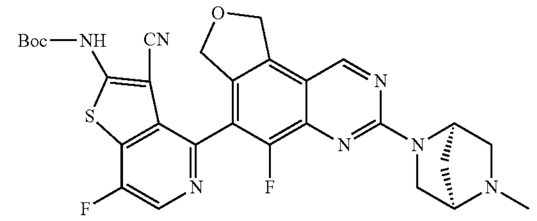 [SMILES: CN1C[C@H]2C[C@@H]1CN2c1ncc2c3c(c(-c4ncc(F)c5sc(NC(=O)OC(C)(C)C)c(C#N)c45)c(F)c2n1)COC3] | 592 |

TABLE 22-continued

| Preparation | Chemical Name | Structure | MS (ES) m/z (M + 1) |
|---|---|---|---|
| 58A | tert-Butyl (3-cyano-4-(3-((3R,4S)-3-(dimethylamino)-4-fluoropyrrolidin-1-yl)-5-fluoro-7,9-dihydrofuro[3,4-f]quinazolin-6-yl)-7-fluorothieno[3,2-c]pyridin-2-yl)carbamate | 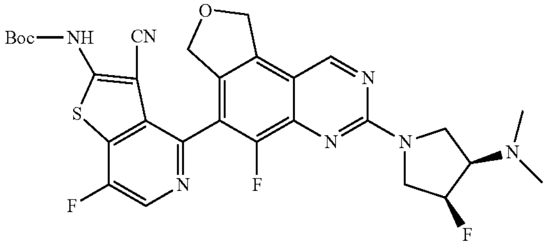 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@@H]1F] | 612 |
| 59A | tert-Butyl (3-cyano-4-(3-((3R,4R)-3-(dimethylamino)-4-fluoropyrrolidin-1-yl)-5-fluoro-7,9-dihydrofuro[3,4-f]quinazolin-6-yl)-7-fluorothieno[3,2-c]pyridin-2-yl)carbamate | 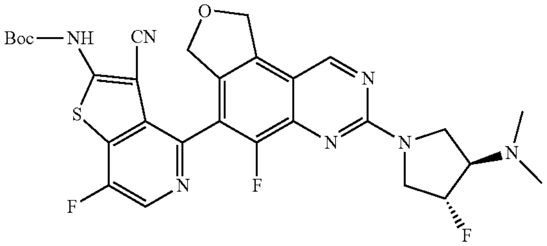 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@H]1F] | 612 |
| 60A | tert-Butyl (3-cyano-4-(3-((3S,4S)-3-(dimethylamino)-4-fluoropyrrolidin-1-yl)-5-fluoro-7,9-dihydrofuro[3,4-f]quinazolin-6-yl)-7-fluorothieno[3,2-c]pyridin-2-yl)carbamate | 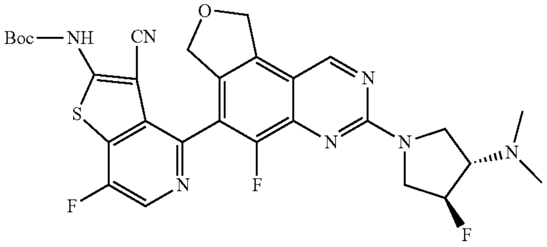 [SMILES: CN(C)[C@H]1CN(c2ncc3c4c(c(-c5ncc(F)c6sc(NC(=O)OC(C)(C)C)c(C#N)c56)c(F)c3n2)COC4)C[C@@H]1F] | 612 |
| 61A | tert-Butyl (3-cyano-4-(3-((3S,4R)-3-(dimethylamino)-4-fluoropyrrolidin-1-yl)-5-fluoro-7,9-dihydrofuro[3,4-f]quinazolin-6-yl)-7-fluorothieno[3,2-c]pyridin-2-yl)carbamate | 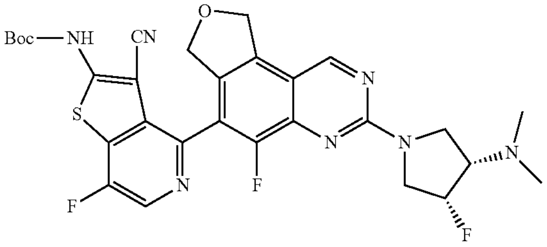 [SMILES: CN(C)[C@H]1CN(c2ncc3c4c(c(-c5ncc(F)c6sc(NC(=O)OC(C)(C)C)c(C#N)c56)c(F)c3n2)COC4)C[C@H]1F] | 612 |
| 62A | tert-Butyl (3-cyano-4-(3-((3S,4S)-3-(dimethylamino)-4-methylpyrrolidin-1-yl)-5-fluoro-7,9-dihydrofuro[3,4-f]quinazolin-6-yl)-7-fluorothieno[3,2-c]pyridin-2-yl)carbamate | 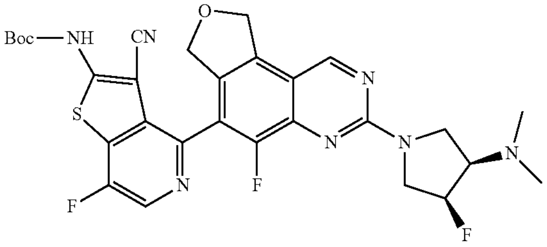 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@@H]1F] | 608 |
| 63A | tert-Butyl (3-cyano-7-fluoro-4-(5-fluoro-3-((S)-3-(methylamino)pyrrolidin-1-yl)-7,9-dihydrofuro[3,4-f]quinazolin-6-yl)thieno[3,2-c]pyridin-2-yl)carbamate | 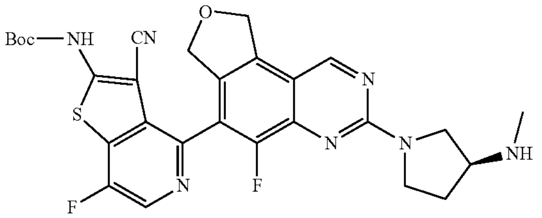 [SMILES: CN[C@H]1CCN(c2ncc3c4c(c(-c5ncc(F)c6sc(NC(=O)OC(C)(C)C)c(C#N)c56)c(F)c3n2)COC4)C1] | 580 |

TABLE 22-continued

| Preparation | Chemical Name | Structure | MS (ES) m/z (M + 1) |
|---|---|---|---|
| 64A | tert-Butyl (3-cyano-4-(3-(3-(dimethylamino)-3-(hydroxymethyl)pyrrolidin-1-yl)-5-fluoro-7,9-dihydrofuro[3,4-f]quinazolin-6-yl)-7-fluorothieno[3,2-c]pyridin-2-yl)carbamate | 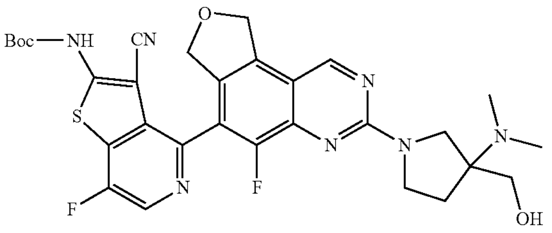 [SMILES: CN(C)C1(CO)CCN(c2ncc3c4c(c(-c5ncc(F)c6sc(NC(=O)OC(C)(C)C)c(C#N)c56)c(F)c3n2)COC4)C1] | 624 |
| 65A | tert-Butyl (4R)-6-(6-(2-((tert-butoxycarobnyl)amino)-3-cyano-7-fluorothieno[3,2-c]pyridin-4-yl)-5-fluoro-7,9-dihydrofuro[3,4-f]quinazolin-3-yl)-1,6-diazaspiro[3.4]octane-1-carboxylate | 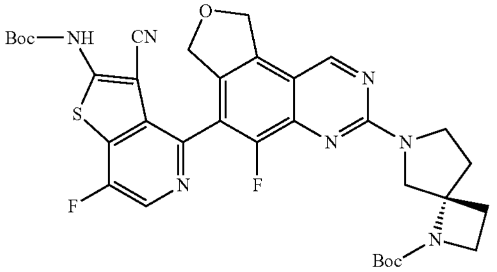 [SMILES: CC(C)(C)OC(=O)Nc1sc2c(F)cnc(-c3c4c(c5cnc(N6CC[C@@]7(CCN7C(=O)OC(C)(C)C)C6)nc5c3F)COC4)c2c1C#N] | 692 |
| 66A | tert-Butyl (3-cyano-4-(3-((R)-2-((dimethylamino)methyl) morpholino)-5-fluoro-7,9-dihydrofuro[3,4-f]quinazolin-6-yl)-7-fluorothieno[3,2-c]pyridin-2-yl)carbamate | 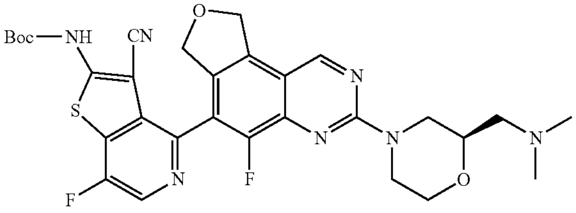 [SMILES: CN(C)C[C@@H]1CN(c2ncc3c4c(c(-c5ncc(F)c6sc(NC(=O)OC(C)(C)C)c(C#N)c56)c(F)c3n2)COC4)CCO1] | 624 |
| 67A | tert-Butyl (4S)-6-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)-1,6-diazaspiro[3.4]octane-1-carboxylate | 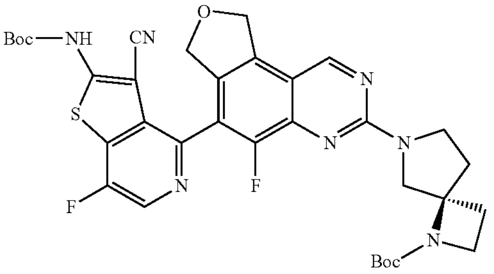 [SMILES: CC(C)(C)OC(=O)Nc1sc2c(F)cnc(-c3c4c(c5cnc(N6CC[C@]7(CCN7C(=O)OC(C)(C)C)C6)nc5c3F)COC4)c2c1C#N] | 692 |
| 68A | tert-Butyl (4-(3-((S)-3-amino-3-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 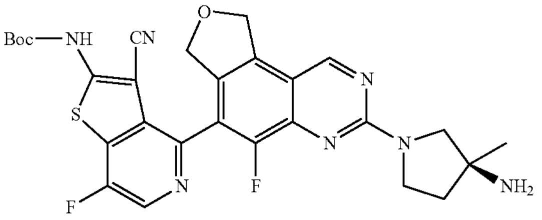 [SMILES: CC(C)(C)OC(=O)Nc1sc2c(F)cnc(-c3c4c(c5cnc(N6CC[C@](C)(N)C6)nc5c3F)COC4)c2c1C#N] | 580 |
| 69A | tert-Butyl (3-cyano-4-(3-((S)-3-(dimethylamino)-3-methylpyrrolidin-1-yl)-5-fluoro-7,9-dihydrofuro[3,4-f]quinazolin-6-yl)-7-fluorothieno[3,2-c]pyridin-2-yl)carbamate | 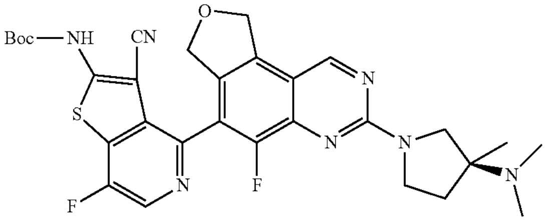 [SMILES: CN(C)[C@@]1(C)CCN(c2ncc3c4c(c(-c5ncc(F)c6sc(NC(=O)OC(C)(C)C)c(C#N)c56)c(F)c3n2)COC4)C1] | 608 |

TABLE 22-continued

| Preparation | Chemical Name | Structure | MS (ES) m/z (M + 1) |
|---|---|---|---|
| 70A | tert-Butyl (3-cyano-4-(3-((3S,4R)-3-(dimethylamino)-4-hydroxypyrrolidin-1-yl)-5-fluoro-7,9-dihydrofuro[3,4-f]quinazolin-6-yl)-7-fluorothieno[3,2-c]pyridin-2-yl)carbamate | 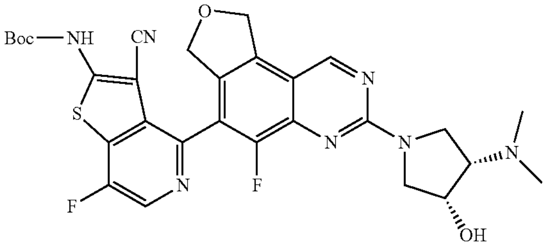 [SMILES: CN(C)[C@H]1CN(c2ncc3c4c(c(-c5ncc(F)c6sc(NC(=O)OC(C)(C)C)c(C#N)c56)c(F)c3n2)COC4)C[C@H]1O] | 610 |
| 71A | tert-Butyl (3-cyano-4-(3-((3R,4S)-3-(dimethylamino)-4-hydroxypyrrolidin-1-yl)-5-fluoro-7,9-dihydrofuro[3,4-f]quinazolin-6-yl)-7-fluorothieno[3,2-c]pyridin-2-yl)carbamate | 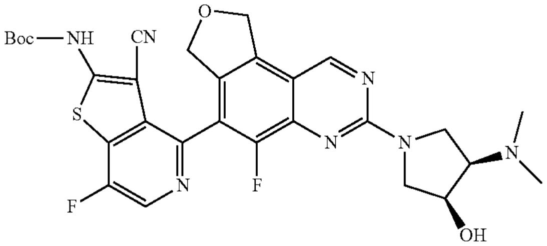 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@@H]1O] | 610 |
| 72A | tert-Butyl (3-cyano-4-(3-((1R,4R,5S)-5-(dimethylamino)-2-azabicyclo[2.1.1]hexan-2-yl)-5-fluoro-7,9-dihydrofuro[3,4-f]quinazolin-6-yl)-7-fluorothieno[3,2-c]pyridin-2-yl)carbamate | 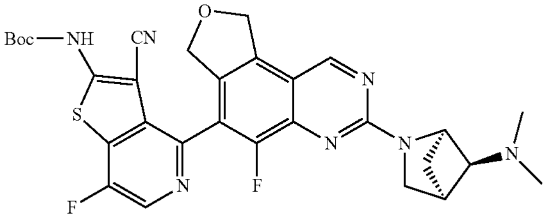 [SMILES: CN(C)[C@H]1[C@@H]2C[C@H]1N(c1ncc3c4c(c(-c5ncc(F)c6sc(NC(=O)OC(C)(C)C)c(C#N)c56)c(F)c3n1)COC4)C2] | 606 |
| 73A | tert-Butyl (3-cyano-4-(3-((1S,4S,5R)-5-(dimethylamino)-2-azabicyclo[2.1.1]hexan-2-yl)-5-fluoro-7,9-dihydrofuro[3,4-f]quinazolin-6-yl)-7-fluorothieno[3,2-c]pyridin-2-yl)carbamate | 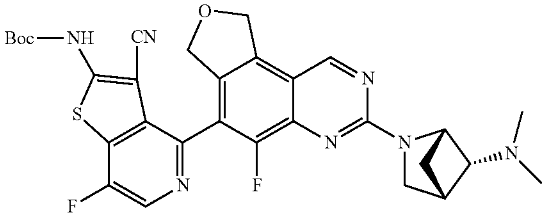 [SMILES: CN(C)[C@@H]1[C@H]2C[C@@H]1N(c1ncc3c4c(c(-c5ncc(F)c6sc(NC(=O)OC(C)(C)C)c(C#N)c56)c(F)c3n1)COC4)C2] | 606 |
| 74A | tert-Butyl (4-(5-chloro-3-(3-morpholinoazetidin-1-yl)-7,9-dihydrofuro[3,4-f]quinazolin-6-yl)-3-cyano-7-fluorobenzo[b]thiophen-2-yl)carbamate | 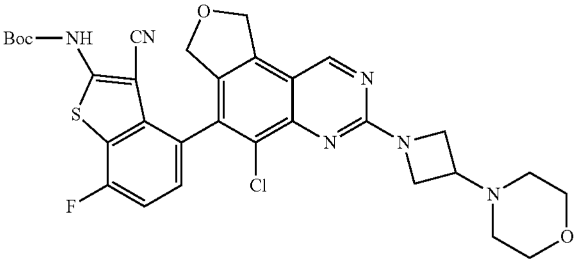 [SMILES: CC(C)(C)OC(=O)Nc1sc2c(F)ccc(-c3c4c(c5cnc(N6CC(N7CCOCC7)C6)nc5c3Cl)COC4)c2c1C#N] | 637 |
| 75A | tert-Butyl (4-(5-chloro-3-((R)-3-(dimethylamino)pyrrolidin-1-yl)-7,9-dihydrofuro[3,4-f]quinazolin-6-yl)-3-cyano-7-fluorobenzo[b]thiophen-2-yl)carbamate | 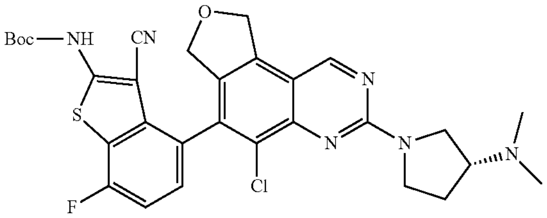 [SMILES: CN(C)[C@@H]1CCN(c2ncc3c4c(c(-c5ccc(F)c6sc(NC(=O)OC(C)(C)C)c(C#N)c56)c(Cl)c3n2)COC4)C1] | 609 |

TABLE 22-continued

| Preparation | Chemical Name | Structure | MS (ES) m/z (M + 1) |
|---|---|---|---|
| 76A | tert-Butyl (4-(5-chloro-3-((S)-3-(dimethylamino)pyrrolidin-1-yl)-7,9-dihydrofuro[3,4-f]quinazolin-6-yl)-3-cyano-7-fluorobenzo[b]thiophen-2-yl)carbamate | 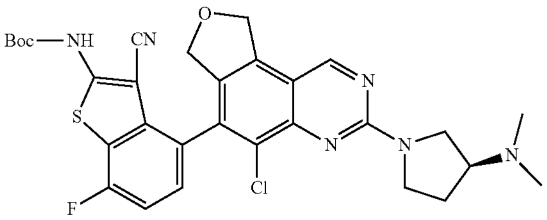 [SMILES: CN(C)[C@H]1CCN(c2ncc3c4c(c(-c5ccc(F)c6sc(NC(=O)OC(C)(C)C)c(C#N)c56)c(Cl)c3n2)COC4)C1] | 609 |
| 77A | tert-Butyl (3-cyano-4-(3-((S)-3-(dimethylamino)pyrrolidin-1-yl)-5-fluoro-7,9-dihydrofuro[3,4-f]quinazolin-6-yl)-5-fluorobenzo[b]thiophen-2-yl)carbamate | 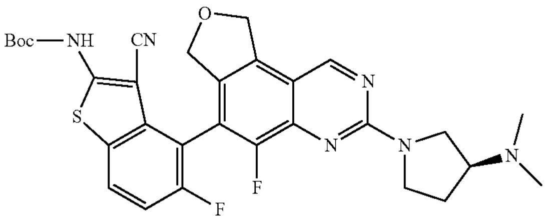 [SMILES: CN(C)[C@H]1CCN(c2ncc3c4c(c(-c5c(F)ccc6sc(NC(=O)OC(C)(C)C)c(C#N)c56)c(F)c3n2)COC4)C1] | 593 |
| 78A [2] | rel-tert-Butyl (3-cyano-4-(3-((3R,4R)-3-(dimethylamino)-4-hydroxypyrrolidin-1-yl)-5-fluoro-7,9-dihydrofuro[3,4-f]quinazolin-6-yl)-5-fluorobenzo[b]thiophen-2-yl)carbamate | 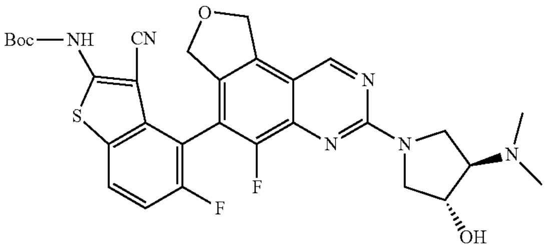 [SMILES: CN(C)[C@@H]1CN(c2ncc3c4c(c(-c5c(F)ccc6sc(NC(=O)OC(C)(C)C)c(C#N)c56)c(F)c3n2)COC4)C[C@H]1O] | 609 |
| 79A | tert-Butyl (3-cyano-5-fluoro-4-(5-fluoro-3-(3-(1-methyl-1H-imidazol-2-yl)pyrrolidin-1-yl)-7,9-dihydrofuro[3,4-f]quinazolin-6-yl)benzo[b]thiophen-2-yl)carbamate | 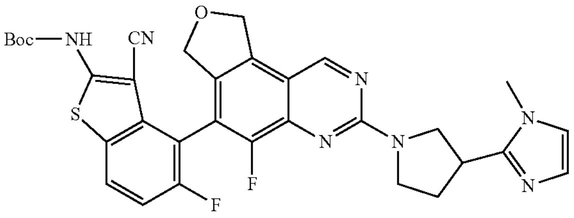 [SMILES: Cn1ccnc1C1CCN(c2ncc3c4c(c(-c5c(F)ccc6sc(NC(=O)OC(C)(C)C)c(C#N)c56)c(F)c3n2)COC4)C1] | 630 |
| 80A [3] | (S)-1-(4-Bromo-5-fluoro-1,3-dihydrofuro[3,4-f]quinolin-7-yl)-N,N-dimethylpyrrolidin-3-amine | 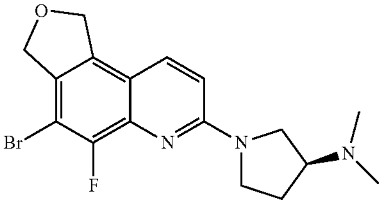 [SMILES: CN(C)[C@H]1CCN(c2ccc3c4c(c(Br)c(F)c3n2)COC4)C1] | 380, 382 |
| 81A | tert-Butyl 8-(6-(2-((tert-butoxycarbonyl)amino)-3-cyano-7-fluorothieno[3,2-c]pyridin-4-yl)-3-((S)-3-(dimethylamino)pyrrolidin-1-yl)-5-fluoro-7,9-dihydrofuro[3,4-f]quinazolin-1-yl)-3,8-diazabicyclo[3.2.1]octane-3-carboxylate | 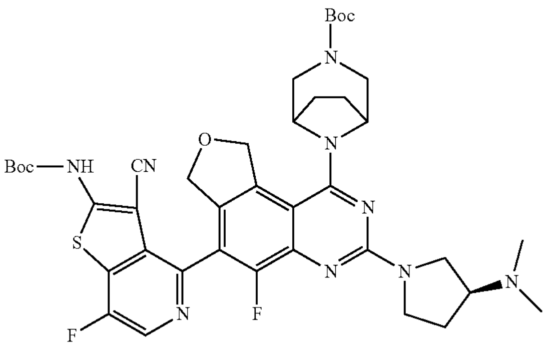 [SMILES: CN(C)[C@H]1CCN(c2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1] | 804 |

TABLE 22-continued

| Preparation | Chemical Name | Structure | MS (ES) m/z (M + 1) |
|---|---|---|---|
| 82A | tert-Butyl 8-(6-(2-((tert-butoxycarbonyl)amino)-3-cyano-7-fluorothieno[3,2-c]pyridin-4-yl)-3-((R)-3-(dimethylamino)pyrrolidin-1-yl)-5-fluoro-7,9-dihydrofuro[3,4-f]quinazolin-1-yl)-3,8-diazabicyclo[3.2.1]octane-3-carboxylate | 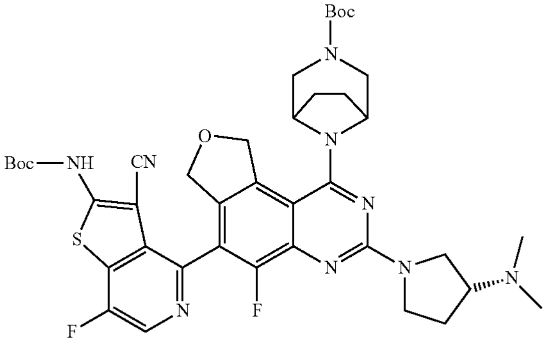 | 804 |
| 83A | tert-Butyl 8-(6-(2-((tert-butoxycarbonyl)amino)-3-cyano-7-fluorothieno[3,2-c]pyridin-4-yl)-5-fluoro-3-(4-(2-hydroxyethyl)piperazin-1-yl)-7,9-dihydrofuro[3.4-f]quinazolin-1-yl)-3,8-diazabicyclo[3.2.1]octane-3-carboxylate | 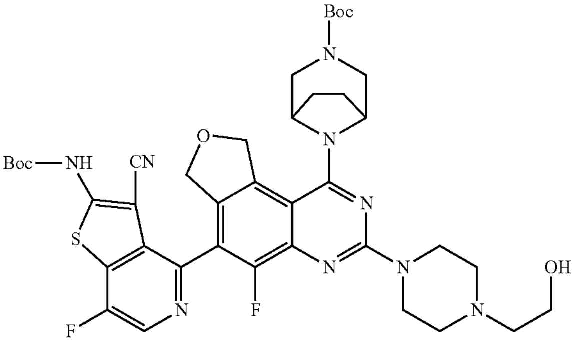 [SMILES: CC(C)(C)OC(=O)Nc1sc2c(F)cnc(-c3c4c(c5c(N6C7CCC6CN(C(=O)OC(C)(C)C)C7)nc(N6CCN(CCO)CC6)nc5c3F)COC4)c2c1C#N] | 820 |
| 84A | tert-Butyl 8-(6-(2-((tert-butoxycarbonyl)amino)-3-cyano-7-fluorothieno[3,2-c]pyridin-4-yl)-5-fluoro-3-(4-(3-hydroxypropyl)piperazin-1-yl)-7,9-dihydrofuro[3,4-f]quinazolin-1-yl)-3,8-diazabicyclo[3.2.1]octane-3-carboxylate | 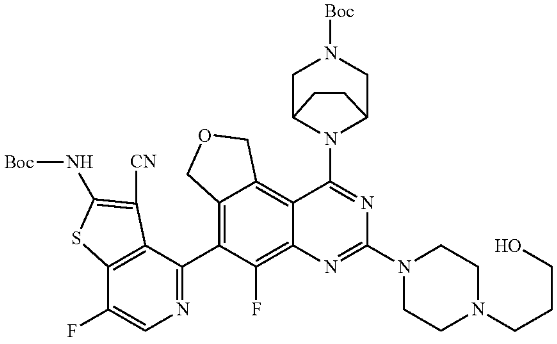 [SMILES: CC(C)(C)OC(=O)Nc1sc2c(F)cnc(-c3c4c(c5c(N6C7CCC6CN(C(=O)OC(C)(C)C)C7)nc(N6CCN(CCCO)CC6)nc5c3F)COC4)c2c1C#N] | 834 |
| 89B | tert-Butyl (3-cyano-4-(3-(1-(dimethylamino)-3-azabicyclo[3.2.10]heptan-3-yl)-5-fluoro-7,9-dihydrofuro[3,4-f]quinazolin-6-yl)-7-fluorothieno[3,2-c]pyridin-2-yl)carbamate | 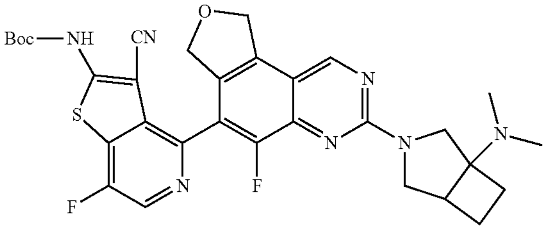 [SMILES: CN(C)C12CCC1CN(c1ncc3c4c(c(-c5ncc(F)c6sc(NC(=O)OC(C)(C)C)c(C#N)c56)c(F)c3n1)COC4)C2] | 620 |
| 90B | tert-Butyl (3-cyano-4-(3-(7-(dimethylamino)-4-azaspiro[2.4]heptan-4-yl)-5-fluoro-7,9-dihydrofuro[3,4-f]quinazolin-6-yl)-7-fluorothieno[3,2-c]pyridin-2-yl)carbamate | 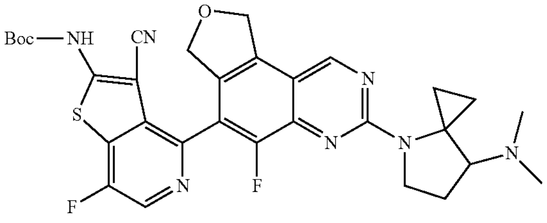 [SMILES: CN(C)C1CCN(c2ncc3c4c(c(-c5ncc(F)c6sc(NC(=O)OC(C)(C)C)c(C#N)c56)c(F)c3n2)COC4)C12CC2] | 620 |

TABLE 22-continued

| Preparation | Chemical Name | Structure | MS (ES) m/z (M + 1) |
|---|---|---|---|
| 91B | tert-Butyl (3-cyano-7-fluoro-4-(5-fluoro-3-(4-methylhexahydropyrrolo[3,2-b]pyrrol-1(2H)-yl)-7,9-dihydrofuro[3,4-f]quinazolin-6-yl)thieno[3,2-c]pyridin-2-yl)carbamate | 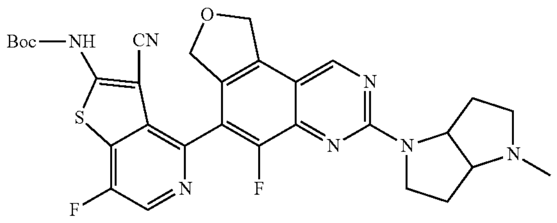 [SMILES: CN1CCC2C1CCN2c1ncc2c3c(c(-c4ncc(F)c5sc(NC(=O)OC(C)(C)C)c(C#N)c45)c(F)c2n1)COC3] | 606 |
| 92B | tert-Butyl (3-cyano-7-fluoro-4-(5-fluoro-3-((3S,4R)-3-hydroxy-4-(isopropyl(methyl)amino)pyrrolidin-1-yl)-7,9-dihydrofuro[3,4-f]quinazolin-6-yl)thieno[3,2-c]pyridin-2-yl)carbamate | 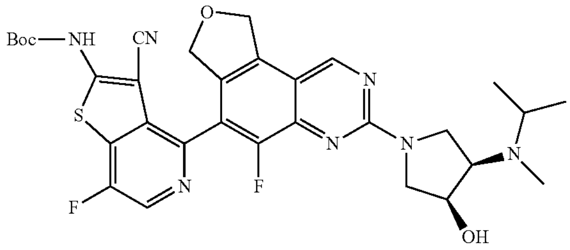 [SMILES: CC(C)N(C)[C@@H]1CN(c2ncc3c4c(c(-c5ncc(F)c6sc(NC(=O)OC(C)(C)C)c(C#N)c56)c(F)c3n2)COC4)C[C@@H]1O] | 638 |
| 93B | tert-Butyl (3-cyano-4-(3-((3R,4S)-3-(diethylamino)-4-hydroxypyrrolidin-1-yl)-5-fluoro-7,9-dihydrofuro[3,4-f]quinazolin-6-yl)-7-fluorothieno[3,2-c]pyridin-2-yl)carbamate | 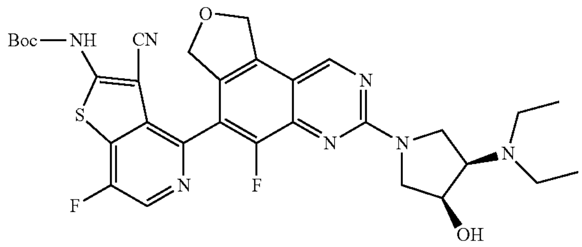 [SMILES: CCN(CC)[C@@H]1CN(c2ncc3c4c(c(-c5ncc(F)c6sc(NC(=O)OC(C)(C)C)c(C#N)c56)c(F)c3n2)COC4)C[C@@H]1O] | 638 |
| 94B | tert-Butyl (3-cyano-4-(3-((3R,4S)-3-(ethyl(methyl)amino)-4-hydroxypyrrolidin-1-yl)-5-fluoro-7,9-dihydrofuro[3,4-f]quinazolin-6-yl)-7-fluorothieno[3,2-c]pyridin-2-yl)carbamate | 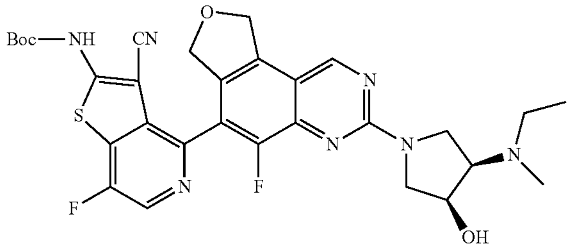 [SMILES: CCN(C)[C@@H]1CN(c2ncc3c4c(c(-c5ncc(F)c6sc(NC(=O)OC(C)(C)C)c(C#N)c56)c(F)c3n2)COC4)C[C@@H]1O] | 624 |
| 95B | tert-Butyl (3-cyano-4-(3-(4-((dimethylamino)methyl)-1H-imidazol-1-yl)-5-fluoro-7,9-dihydrofuro[3,4-f]quinazolin-6-yl)-7-fluorothieno[3,2-c]pyridin-2-yl)carbamate | 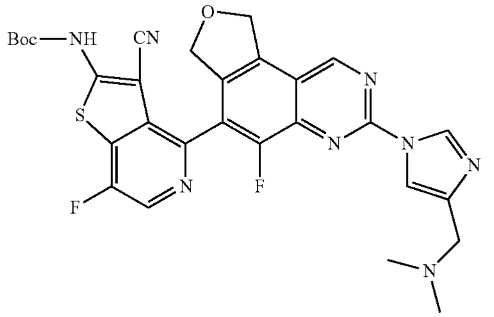 [SMILES: CN(C)Cc1cn(-c2ncc3c4c(c(-c5ncc(F)c6sc(NC(=O)OC(C)(C)C)c(C#N)c56)c(F)c3n2)COC4)cn1] | 605 |
| 96B | tert-Butyl 6-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)octahydro-1H-pyrrolo[3,4-b]pyridine-1-carboxylate | 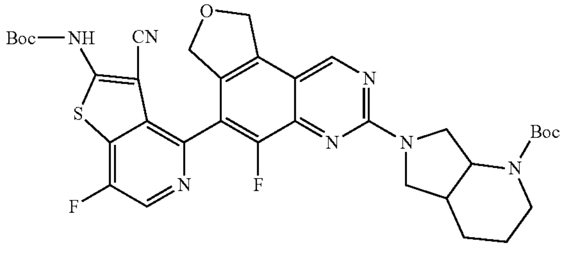 [SMILES: CC(C)(C)OC(=O)Nc1sc2c(F)cnc(-c3c4c(c5cnc(N6CC7CCCN(C(=O)OC(C)(C)C)C7C6)nc5c3F)COC4)c2c1C#N] | 706 |

TABLE 22-continued

| Preparation | Chemical Name | Structure | MS (ES) m/z (M + 1) |
|---|---|---|---|
| 97B [4] | (S)-1-(4-Bromo-5-chloro-1,3-dihydrofuro[3,4-f]quinolin-7-yl)-N,N-dimethylpyrrolidin-3-amine | 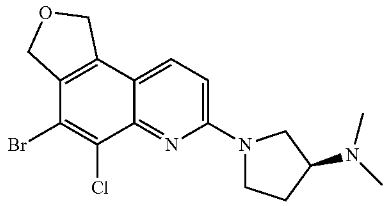 [SMILES: CN(C)[C@H]1CCN(c2ccc3c4c(c(Br)c(Cl)c3n2)COC4)C1] | 396, 398 |
| 98B | tert-Butyl (4-(5-chloro-3-((3R,4S)-3-(dimethylamino)-4-hydroxypyrrolidin-1-yl)-7,9-dihydrofuro[3,4-f]quinazolin-6-yl)-3-cyano-5-fluorobenzo[b]thiophen-2-yl)carbamate | 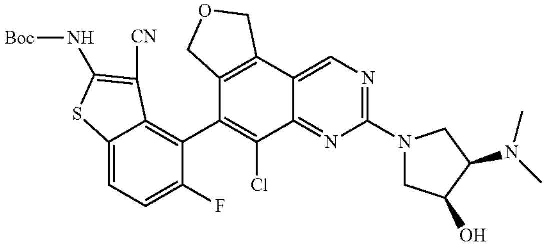 [SMILES: CN(C)[C@@H]1CN(c2ncc3c4c(c(-c5c(F)ccc6sc(NC(=O)OC(C)(C)C)c(C#N)c56)c(Cl)c3n2)COC4)C[C@@H]1O] | 625 |
| 99B | tert-Butyl (3-cyano-7-fluoro-4-(5-fluoro-3-(3-(isopropyl(methyl)amino)pyrrolidin-1-yl)-7,9-dihydrofuro[3,4-f]quinazolin-6-yl)thieno[3,2-c]pyridin-2-yl)carbamate | 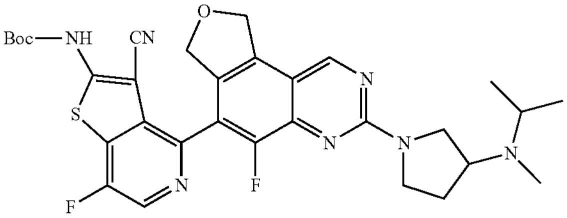 [SMILES: CC(C)N(C)C1CCN(c2ncc3c4c(c(-c5ncc(F)c6sc(NC(=O)OC(C)(C)C)c(C#N)c56)c(F)c3n2)COC4)C1] | 622 |
| 100B | tert-Butyl (3-cyano-4-(3-((3R,4S)-3-(dimethylamino)-4-methylpyrrolidin-1-yl)-5-fluoro-7,9-dihydrofuro[3,4-f]quinazolin-6-yl)-7-fluorothieno[3,2-c]pyridin-2-yl)carbamate | 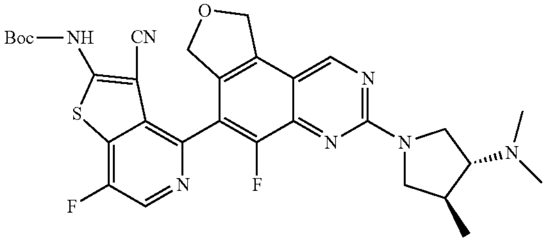 [SMILES: C[C@H]1CN(c2ncc3c4c(c(-c5ncc(F)c6sc(NC(=O)OC(C)(C)C)c(C#N)c56)c(F)c3n2)COC4)C[C@@H]1N(C)C] | 608 |
| 101B | tert-Butyl (3-cyano-7-fluoro-4-(5-fluoro-3-(2-oxotetrahydrofuro[3,4-d]oxazol-3(2H)-yl)-7,9-dihydrofuro[3,4-f]quinazolin-6-yl)thieno[3,2-c]pyridin-2-yl)carbamate | 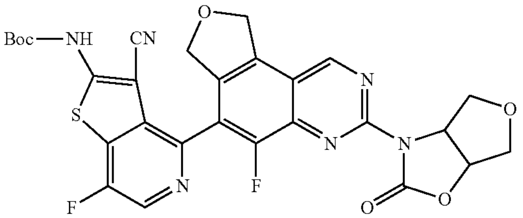 [SMILES: CC(C)(C)OC(=O)Nc1sc2c(F)cnc(-c3c4c(c5cnc(N6C(=O)OC7COCC76)nc5c3F)COC4)c2c1C#N] | |
| 102B | tert-Butyl (3-cyano-4-(3-(3-((dimethylamino)methyl)-1H-pyrazol-1-yl)-5-fluoro-7,9-dihydrofuro[3,4-f]quinazolin-6-yl)-7-fluorothieno[3,2-c]pyridin-2-yl)carbamate | 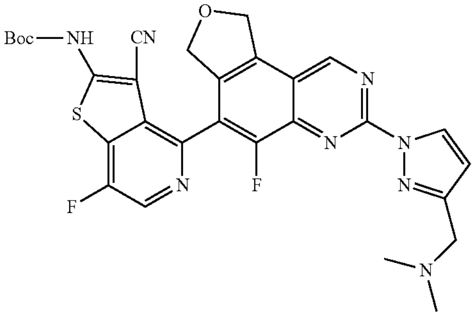 [SMILES: CN(C)Cc1ccn(-c2ncc3c4c(c(-c5ncc(F)c6sc(NC(=O)OC(C)(C)C)c(C#N)c56)c(F)c3n2)COC4)n1] | 605 |

TABLE 22-continued

| Preparation | Chemical Name | Structure | MS (ES) m/z (M + 1) |
|---|---|---|---|
| 103B | tert-Butyl (3-cyano-7-fluoro-4-(5-fluoro-3-(3-(4-hydroxypiperidin-1-yl)azetidin-1-yl)-7,9-dihydrofuro[3,4-f]quinazolin-6-yl)thieno[3,2-c]pyridin-2-yl)carbamate | 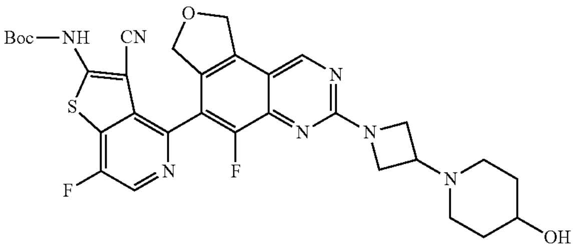 [SMILES: CC(C)(C)OC(=O)Nc1sc2c(F)cnc(-c3c4c(c5cnc(N6CC(N7CCC(O)CC7)C6)nc5c3F)COC4)c2c1C#N] | 636 |
| 104B | tert-Butyl (4-(3-((1S,5S)-2,6-diazabicyclo[3.2.0]heptan-2-yl)-5-fluoro-7,9-dihydrofuro[3,4-f]quinazolin-6-yl)-3-cyano-7-fluorothieno[3,2-c]pyridin-2-yl)carbamate | 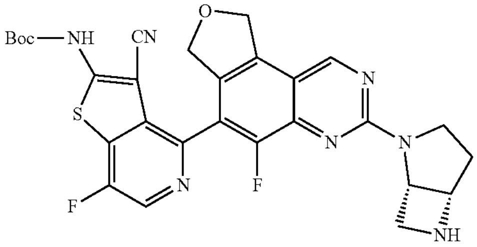 [SMILES: CC(C)(C)OC(=O)Nc1sc2c(F)cnc(-c3c4c(c5cnc(N6CC[C@@H]7NC[C@@H]76)nc5c3F)COC4)c2c1C#N] | 578 |
| 105B | tert-Butyl (3-cyano-7-fluoro-4-(5-fluoro-3-((2S,5S)-6-methyl-2,6-diazabicyclo[3.2.10]heptan-2-yl)-7,9-dihydrofuro[3,4-f]quinazolin-6-yl)thieno[3,2-c]pyridin-2-yl)carbamate | 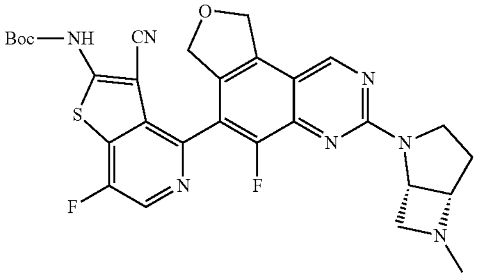 [SMILES: CN1C[C@H]2[C@@H]1CCN2c1ncc2c3c(c(-c4ncc(F)c5sc(NC(=O)OC(C)(C)C)c(C#N)c45)c(F)c2n1)COC3] | 592 |
| 106B | tert-Butyl (3-cyano-7-fluoro-4-(5-fluoro-3-((2S,3S)-2-methyl-3-(methylamino)pyrrolidin-1-yl)-7,9-dihydrofuro[3,4-f]quinazolin-6-yl)thieno[3,2-c]pyridin-2-yl)carbamate | 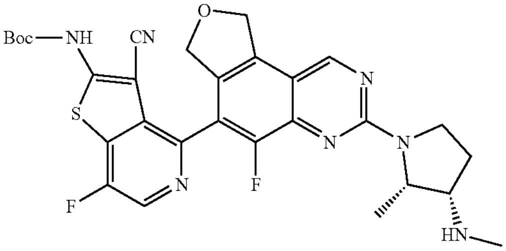 [SMILES: CN[C@H]1CCN(c2ncc3c4c(c(-c5ncc(F)c6sc(NC(=O)OC(C)(C)C)c(C#N)c56)c(F)c3n2)COC4)[C@H]1C] | 594 |
| 107B | tert-Butyl (3R)-4-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)-3-methylpiperazine-1-carboxylate | 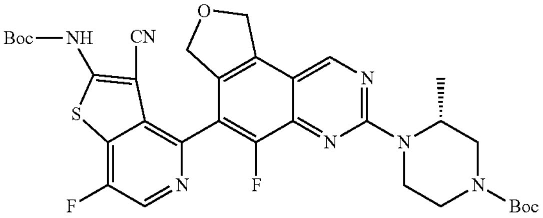 [SMILES: C[C@@H]1CN(C(=O)OC(C)(C)C)CCN1c1ncc2c3c(c(-c4ncc(F)c5sc(NC(=O)OC(C)(C)C)c(C#N)c45)c(F)c2n1)COC3] | 680 |
| 108B | tert-butyl (3-cyano-4-(3-(3-(difluoromethyl)-4-(dimethylamino)pyrrolidin-1-yl)-5-fluoro-7,9-dihydrofuro[3,4-f]quinazolin-6-yl)-7-fluorothieno[3,2-c]pyridin-2-yl)carbamate, Mix of Trans Isomers | 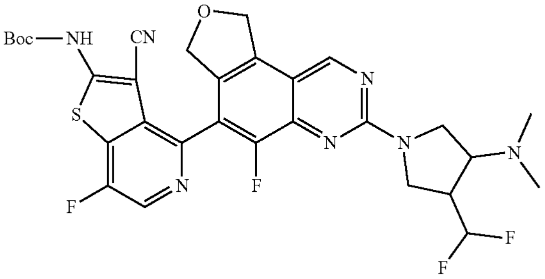 [SMILES: CN(C)C1CN(c2ncc3c4c(c(-c5ncc(F)c6sc(NC(=O)OC(C)(C)C)c(C#N)c56)c(F)c3n2)COC4)CC1C(F)F] | 644 |

TABLE 22-continued

| Preparation | Chemical Name | Structure | MS (ES) m/z (M + 1) |
|---|---|---|---|
| 109B | tert-Butyl (5S)-7-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)-1,7-diazaspiro[4.4]nonane-1-carboxylate | 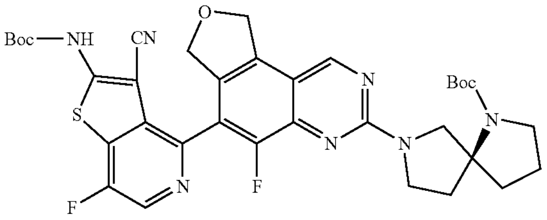 [SMILES: CC(C)(C)OC(=O)Nc1sc2c(F)cnc(-c3c4c(c5cnc(N6CC[C@@]7(CCCN7C(=O)OC(C)(C)C)C6)nc5c3F)COC4)c2c1C#N] | 706 |
| 110B | tert-Butyl (3-cyano-4-(3-(4-(dimethylamino)-2-methylpyrrolidin-1-yl)-5-fluoro-7,9-dihydrofuro[3,4-f]quinazolin-6-yl)-7-fluorothieno[3,2-c]pyridin-2-yl)carbamate | 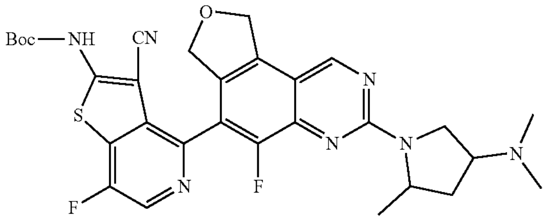 [SMILES: CC1CC(N(C)C)CN1c1ncc2c3c(c(-c4ncc(F)c5sc(NC(=O)OC(C)(C)C)c(C#N)c45)c(F)c2n1)COC3] | 608 |
| 111B | tert-Butyl (3-cyano-4-(3-((S)-3-(dimethylamino)pyrrolidin-1-yl)-5-fluoro-7,9-dihydrofuro[3,4-f]quinazolin-6-yl)-7-methylthieno[3,2-c]pyridin-2-yl)carbamate | 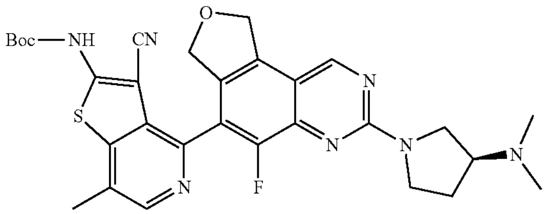 [SMILES: Cc1cnc(-c2c3c(c4cnc(N5CC[C@H](N(C)C)C5)nc4c2F)COC3)c2c(C#N)c(NC(=O)OC(C)(C)C)sc12] | 590 |
| 112B | tet-Butyl (3-cyano-4-(3-((S)-3-(cyclobutylamino)pyrrolidin-1-yl)-5-fluoro-7,9-dihydrofuro[3,4-f]quinazolin-6-yl)-7-fluorothieno[3,2-c]pyridin-2-yl)carbamate | 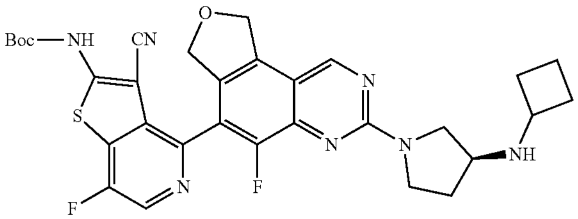 [SMILES: CC(C)(C)OC(=O)Nc1sc2c(F)cnc(-c3c4c(c5cnc(N6CC[C@H](NC7CCC7)C6)nc5c3F)COC4)c2c1C#N] | 620 |
| 113B | tert-Butyl (3-cyano-7-fluoro-4-(5-fluoro-3-((S)-3-((2-hydroxyethyl)(methyl)amino)pyrrolidin-1-yl)-7,9-dihydrofuro[3,4-f]quinazolin-6-yl)thieno[3,2-c]pyridin-2-yl)carbamate | 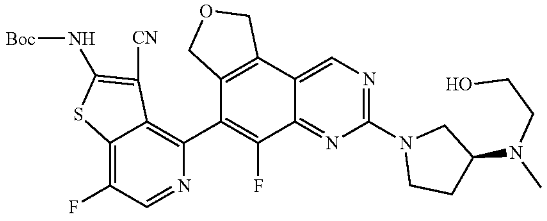 [SMILES: CN(CCO)[C@H]1CCN(c2ncc3c4c(c(-c5ncc(F)c6sc(NC(=O)OC(C)(C)C)c(C#N)c56)c(F)c3n2)COC4)C1] | 624 |
| 114B | tert-Butyl (4-(5-chloro-3-((S)-3-(dimethylamino)pyrrolidin-1-yl)-7,9-dihydrofuro[3,4-f]quinazolin-6-yl)-3-cyano-7-fluorothieno[3,2-c]pyridin-2-yl)carbamate | 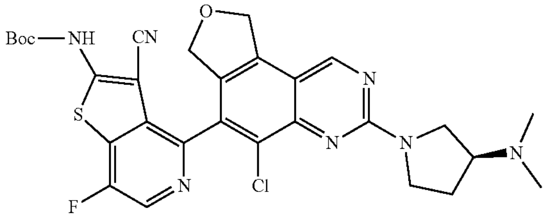 | 610 |

TABLE 22-continued

| Preparation | Chemical Name | Structure | MS (ES) m/z (M + 1) |
|---|---|---|---|
| 115B | tert-Butyl 7-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)-1,7-diazaspiro[4.4]nonane-1-carboxylate | 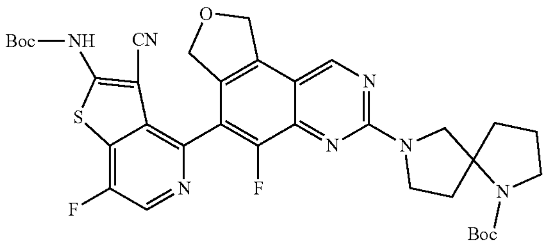 [SMILES: CC(C)(C)OC(=O)Nc1sc2c(F)cnc(-c3c4c(c5cnc(N6CCC7(CCCN7C(=O)OC(C)(C)C)C6)nc5c3F)COC4)c2c1C#N] | 706 |
| 116B | tert-Butyl (3-cyano-4-(3-((S)-3-(diethylamino)pyrrolidin-1-yl)-5-fluoro-7,9-dihydrofuro[3,4-f]quinazolin-6-yl)-7-fluorothieno[3,2-c]pyridin-2-yl)carbamate | 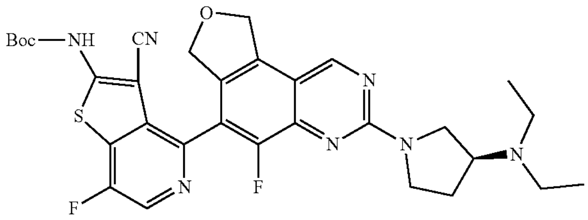 [SMILES: CCN(CC)[C@H]1CCN(c2ncc3c4c(c(-c5ncc(F)c6sc(NC(=O)OC(C)(C)C)c(C#N)c56)c(F)c3n2)COC4)C1] | 622 |
| 117B | tert-Butyl (4-(3-(3-(1H-imidazol-1-yl)azetidin-1-yl)-5-fluoro-7,9-dihydrofuro[3,4-f]quinazolin-6-yl)-3-cyano-7-fluorothieno[3,2-c]pyridin-2-yl)carbamate | 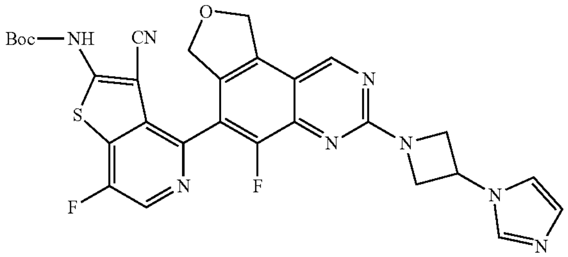 [SMILES: CC(C)(C)OC(=O)Nc1sc2c(F)cnc(-c3c4c(c5cnc(N6CC(n7ccnc7)C6)nc5c3F)COC4)c2c1C#N] | 603 |
| 118B | tert-Butyl (4-(3-((S)-3-(bis(methyl-d3)amino)pyrrolidin-1-yl)-5-fluoro-7,9-dihydrofuro[3,4-f]quinazolin-6-yl)-3-cyano-7-fluorothieno[3,2-c]pyridin-2-yl)carbamate | 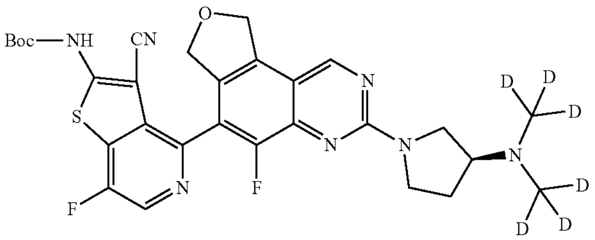 [SMILES: [2H]C([2H])([2H])N([C@H]1CCN(c2ncc3c4c(c(-c5ncc(F)c6sc(NC(=O)OC(C)(C)C)c(C#N)c56)c(F)c3n2)COC4)C1)C([2H])([2H])[2H]] | 600 |
| 119B | tert-Butyl (3-cyano-4-(3-(3-(cyclopropylamino)pyrrolidin-1-yl)-5-fluoro-7,9-dihydrofuro[3,4-f]quinazolin-6-yl)-7-fluorothieno[3,2-c]pyridin-2-yl)carbamate | 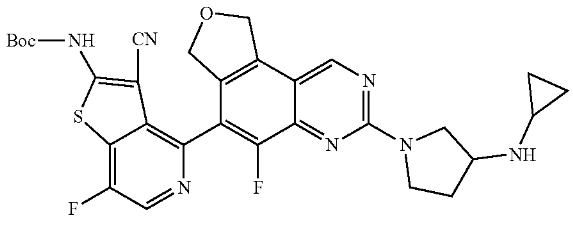 [SMILES: CC(C)(C)OC(=O)Nc1sc2c(F)cnc(-c3c4c(c5cnc(N6CCC(NC7CC7)C6)nc5c3F)COC4)c2c1C#N] | 606 |
| 120B | tert-Butyl (3-cyano-7-fluoro-4-(5-fluoro-3-(3-(isopropylamino)pyrrolidin-1-yl)-7,9-dihydrofuro[3,4-f]quinazolin-6-yl)thieno[3,2-c]pyridin-2-yl)carbamate | 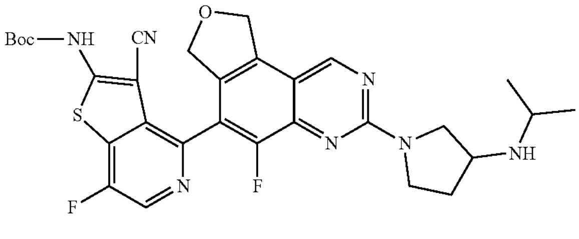 [SMILES: CC(C)NC1CCN(c2ncc3c4c(c(-c5ncc(F)c6sc(NC(=O)OC(C)(C)C)c(C#N)c56)c(F)c3n2)COC4)C1] | 608 |

TABLE 22-continued

| Preparation | Chemical Name | Structure | MS (ES) m/z (M + 1) |
|---|---|---|---|
| 121B | tert-Butyl (1-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)pyrrolidin-3-yl)(ethyl)carbamate | 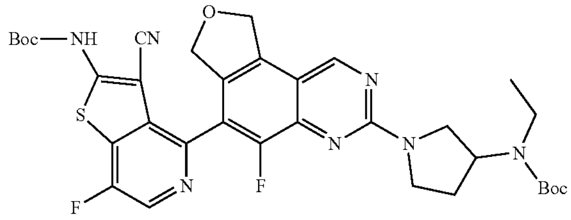 [SMILES: CCN(C(=O)OC(C)(C)C)C1CCN(c2ncc3c4c(c(-c5ncc(F)c6sc(NC(=O)OC(C)(C)C)c(C#N)c56)c(F)c3n2)COC4)C1] | 694 |
| 122B | tert-Butyl (3-cyano-4-(3-((4aR,7aS)-1,4-dimethyloctahydro-6H-pyrrolo[3,4-b]pyrazin-6-yl)-5-fluoro-7,9-dihydrofuro[3,4-f]quinazolin-6-yl)-7-fluorothieno[3,2-c]pyridin-2-yl)carbamate | 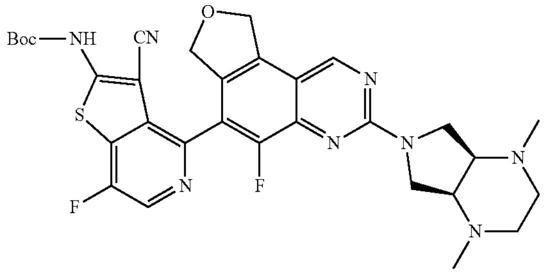 [SMILES: CN1CCN(C)[C@H]2CN(c3ncc4c5c(c(-c6ncc(F)c7sc(NC(=O)OC(C)(C)C)c(C#N)c67)c(F)c4n3)COC5)C[C@H]21] | 635 |
| 123B | tert-Butyl (3-cyano-7-fluoro-4-(5-fluoro-3-((1S,5S)-6-methyl-3,6-diazabicyclo[3.2.0]heptan-3-yl)-7,9-dihydrofuro[3,4-f]quinazolin-6-yl)thieno[3,2-c]pyridin-2-yl)carbamate | 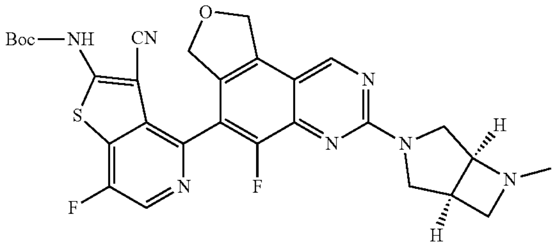 [SMILES: CN1C[C@H]2CN(c3ncc4c5c(c(-c6ncc(F)c7sc(NC(=O)OC(C)(C)C)c(C#N)c67)c(F)c4n3)COC5)C[C@H]21] | 592 |
| 124B | tert-Butyl (3-cyano-7-fluoro-4-(5-fluoro-3-((1R,5R)-6-methyl-3,6-diazabicyclo[3.2.0]heptan-3-yl)-7,9-dihydrofuro[3,4-f]quinazolin-6-yl)thieno[3,2-c]pyridin-2-yl)carbamate | 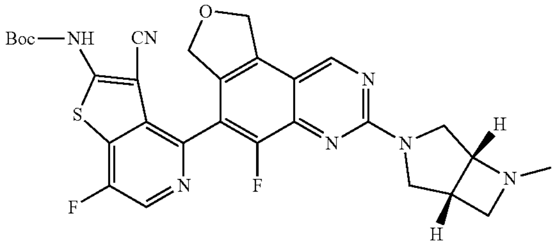 [SMILES: CN1C[C@@H]2CN(c3ncc4c5c(c(-c6ncc(F)c7sc(NC(=O)OC(C)(C)C)c(C#N)c67)c(F)c4n3)COC5)C[C@@H]21] | 592 |
| 125B | tert-Butyl (3-cyano-4-(3-((S)-3-((dimethylamino)methyl) pyrrolidin-1-yl)-5-fluoro-7,9-dihydrofuro[3,4-f]quinazolin-6-yl)-7-fluorothieno[3,2-c]pyridin-2-yl)carbamate | 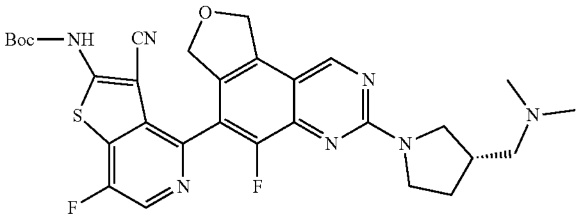 [SMILES: CN(C)C[C@@H]1CCN(c2ncc3c4c(c(-c5ncc(F)c6sc(NC(=O)OC(C)(C)C)c(C#N)c56)c(F)c3n2)COC4)C1] | 608 |
| 126B | tert-Butyl (3-cyano-4-(3-((R)-3-((dimethylamino)methyl) pyrrolidin-1-yl)-5-fluoro-7,9-dihydrofuro[3,4-f]quinazolin-6-yl)-7-fluorotheno[3,2-c]pyridin-2-yl)carbamate | 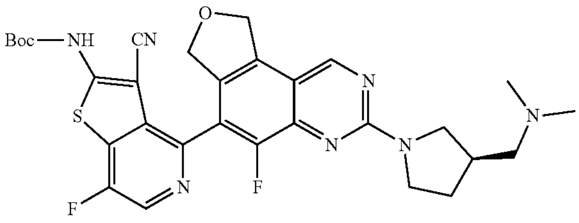 [SMILES: CN(C)C[C@H]1CCN(c2ncc3c4c(c(-c5ncc(F)c6sc(NC(=O)OC(C)(C)C)c(C#N)c56)c(F)c3n2)COC4)C1] | 608 |

TABLE 22-continued

| Preparation | Chemical Name | Structure | MS (ES) m/z (M + 1) |
|---|---|---|---|
| 127B | tert-Butyl (4-(5-chloro-3-((1R,5R)-6-methyl-3,6-diazabicyclo[3.2.0]heptan-3-yl)-7,9-dihydrofuro[3,4-f]quinazolin-6-yl)-3-cyano-7-fluorobenzo[b]thiophen-2-yl)carbamate | 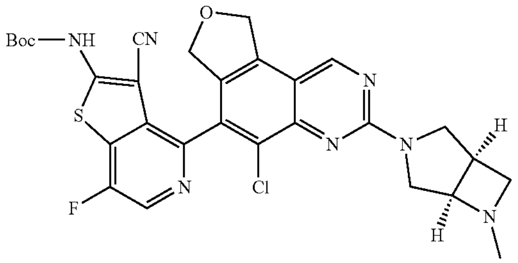 [SMILES: CN1C[C@@H]2CN(c3ncc4c5c(c(-c6ncc(F)c7sc(NC(=O)OC(C)(C)C)c(C#N)c67)c(Cl)c4n3)COC5)C[C@@H]21] | 607 |
| 128B | tert-Butyl (4-(5-chloro-3-((1S,5S)-6-methyl-3,6-diazabicyclo[3.2.0]heptan-3-yl)-7,9-dihydrofuro[3,4-f]quinazolin-6-yl)-3-cyano-7-fluorobenzo[b]thiophen-2-yl)carbamate | 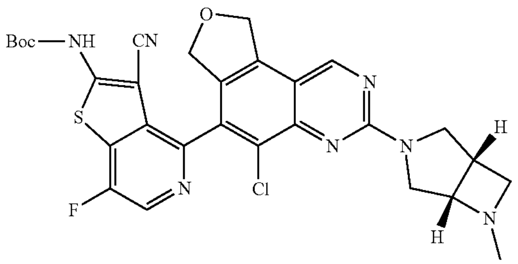 [SMILES: CN1C[C@H]2CN(c3ncc4c5c(c(-c6ncc(F)c7sc(NC(=O)OC(C)(C)C)c(C#N)c67)c(Cl)c4n3)COC5)C[C@H]21] | 607 |
| 129B | tert-Butyl (3-cyano-4-(3-(3-(dimethylamino)-2-methylpyrrolidin-1-yl)-5-fluoro-7,9-dihydrofuro[3,4-f]quinazolin-6-yl)-7-fluorothieno[3,2-c]pyridin-2-yl)carbamate | 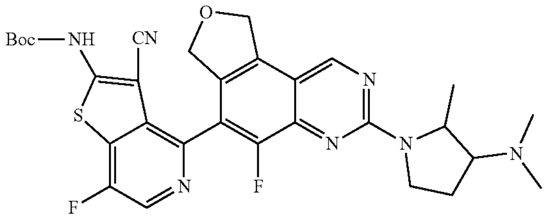 [SMILES: CC1C(N(C)C)CCN1c1ncc2c3c(c(-c4ncc(F)c5sc(NC(=O)OC(C)(C)C)c(C#N)c45)c(F)c2n1)COC3] | 608 |
| 130B | tert-Butyl (3-cyano-7-fluoro-4-(5-fluoro-3-(5-methyl-2,5-diazaspiro[3.5]nonan-2-yl)-7,9-dihydrofuro[3,4-f]quinazolin-6-yl)thieno[3,2-c]pyridin-2-yl)carbamate | 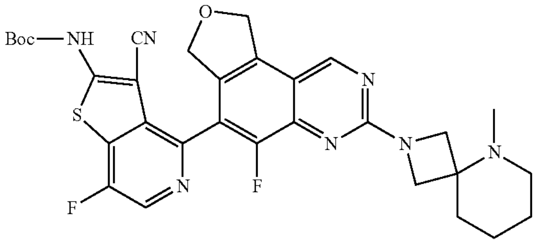 [SMILES: CN1CCCCC12CN(c1ncc3c4c(c(-c5ncc(F)c6sc(NC(=O)OC(C)(C)C)c(C#N)c56)c(F)c3n1)COC4)C2] | 619 |
| 131B | tert-Butyl (3-cyano-4-(3-((2S,4S)-4-(dimethylamino)-2-(hydroxymethyl)pyrrolidin-1-yl)-5-fluoro-7,9-dihydrofuro[3,4-f]quinazolin-6-yl)-7-fluorothieno[3,2-c]pyridin-2-yl)carbamate | 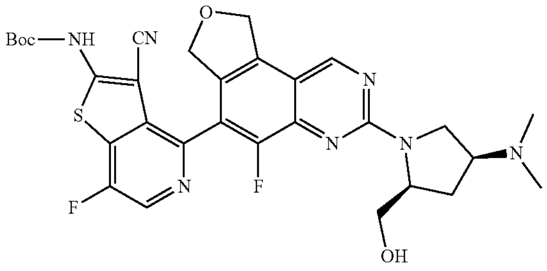 [SMILES: CN(C)[C@H]1C[C@@H](CO)N(c2ncc3c4c(c(-c5ncc(F)c6sc(NC(=O)OC(C)(C)C)c(C#N)c56)c(F)c3n2)COC4)C1] | 624 |
| 132B | tert-Butyl (3-cyano-7-fluoro-4-(5-fluoro-3-(4-methylhexahydropyrrolo[3,4-b][1,4]oxazin-6(2H)-yl)-7,9-dihydrofuro[3,4-f]quinazolin-6-yl)thieno[3,2-c]pyridin-2-yl)carbamate, Mix of Cis Isomers | 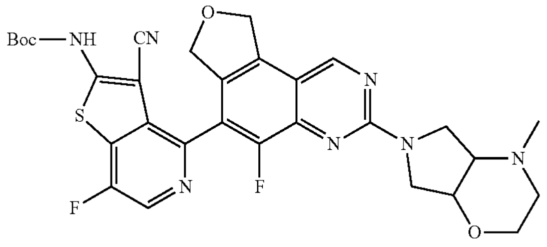 [SMILES: CN1CCOC2CN(c3ncc4c5c(c(-c6ncc(F)c7sc(NC(=O)OC(C)(C)C)c(C#N)c67)c(F)c4n3)COC5)CC21] | 622 |

TABLE 22-continued

| Preparation | Chemical Name | Structure | MS (ES) m/z (M + 1) |
|---|---|---|---|
| 133B | tert-Butyl (3-cyano-7-fluoro-4-(5-fluoro-3-(5-methyl-2,5-diazaspiro[3.4]octan-2-yl)-7,9-dihydrofuro[3,4-f]quinazolin-6-yl)thieno[3,2-c]pyridin-2-yl)carbamate | 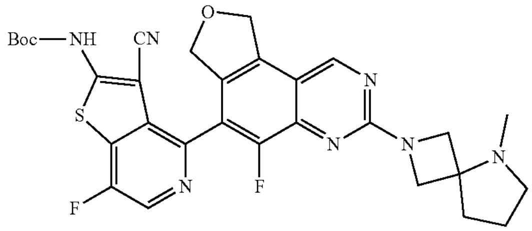 [SMILES: CN1CCCC12CN(c1ncc3c4c(c(-c5ncc(F)c6sc(NC(=O)OC(C)(C)C)c(C#N)c56)c(F)c3n1)COC4)C2] | 606 |
| 134B | tert-Butyl (3-cyano-7-fluoro-4-(5-fluoro-3-(3-methyl-3,6-diazabicyclo[3.1.1]heptan-6-yl)-7,9-dihydrofuro[3,4-f]quinazolin-6-yl)thieno[3,2-c]pyridin-2-yl)carbamate | 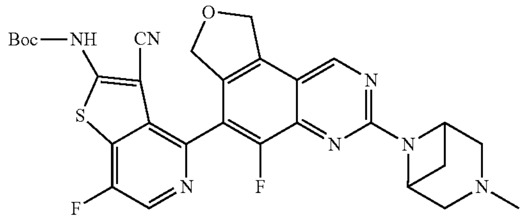 [SMILES: CN1CC2CC(C1)N2c1ncc2c3c(c(-c4ncc(F)c5sc(NC(=O)OC(C)(C)C)c(C#N)c45)c(F)c2n1)COC3] | 592 |
| 135B | tert-Butyl (4-(5-chloro-3-((S)-3-(dimethylamino)pyrrolidin-1-yl)-7,9-dihydrofuro[3,4-f]quinazolin-6-yl)-3-cyano-5-fluorobenzo[b]thiophen-2-yl)carbamate | 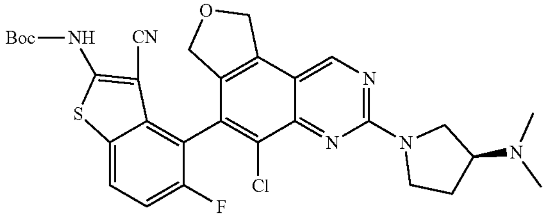 [SMILES: CN(C)[C@H]1CCN(c2ncc3c4c(c(-c5c(F)ccc6sc(NC(=O)OC(C)(C)C)c(C#N)c56)c(Cl)c3n2)COC4)C1] | 609 |
| 136B | tert-Butyl (3-cyano-7-fluoro-4-(5-fluoro-3-((3aR,6aR)-1-methylhexahydropyrrolo[3,4-b]pyrrol-5(1H)-yl)-7,9-dihydrofuro[3,4-f]quinazolin-6-yl)thieno[3,2-c]pyridin-2-yl)carbamate | 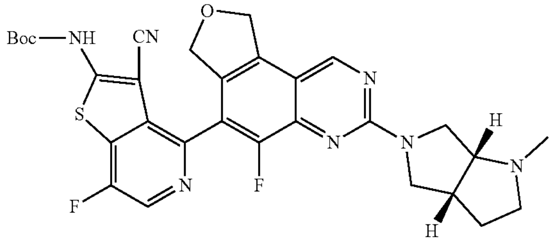 [SMILES: CN1CC[C@@H]2CN(c3ncc4c5c(c(-c6ncc(F)c7sc(NC(=O)OC(C)(C)C)c(C#N)c67)c(F)c4n3)COC5)C[C@@H]21] | 606 |
| 137B | tert-Butyl (3-cyano-7-fluoro-4-(5-fluoro-3-((3aS,6aS)-1-methylhexahydropyrrolo[3,4-b]pyrrol-5(1H)-yl)-7,9-dihydrofuro[3,4-f]quinazolin-6-yl)thieno[3,2-c]pyridin-2-yl)carbamate | 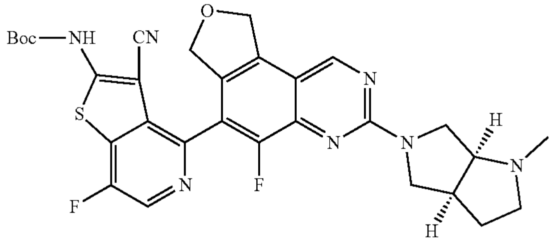 [SMILES: CN1CC[C@H]2CN(c3ncc4c5c(c(-c6ncc(F)c7sc(NC(=O)OC(C)(C)C)c(C#N)c67)c(F)c4n3)COC5)C[C@H]21] | 606 |
| 138B | tert-Butyl (3-cyano-4-(3-((R)-2-((dimethylamino)methyl) morpholino)-5-fluoro-7,9-dihydrofuro[3,4-f]quinazolin-6-yl)-7-fluorothieno[3,2-c]pyridin-2-yl)carbamate | 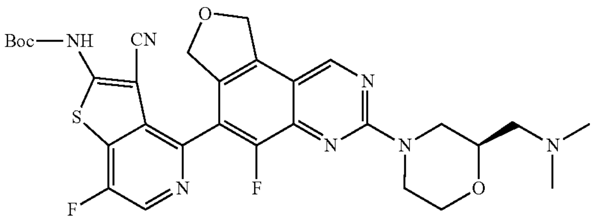 [SMILES: CN(C)C[C@@H]1CN(c2ncc3c4c(c(-c5ncc(F)c6sc(NC(=O)OC(C)(C)C)c(C#N)c56)c(F)c3n2)COC4)CCO1] | 624 |

TABLE 22-continued

| Preparation | Chemical Name | Structure | MS (ES) m/z (M + 1) |
| --- | --- | --- | --- |
| 139B | tert-Butyl (3-cyano-4-(3-(5-(dimethylamino)-2-azaspiro[3.3]heptan-2-yl)-5-fluoro-7,9-dihydrofuro[3,4-f]quinazolin-6-yl)-7-fluorothieno[3,2-c]pyridin-2-yl)carbamate | 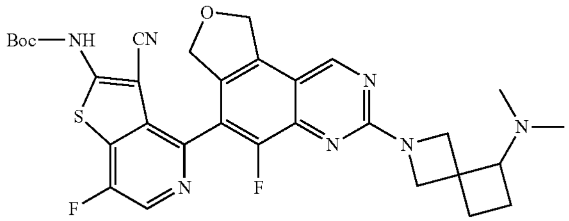 [SMILES: CN(C)C1CCC12CN(c1ncc3c4c(c(-c5ncc(F)c6sc(NC(=O)OC(C)(C)C)c(C#N)c56)c(F)c3n1)COC4)C2] | 620 |
| 140B | tert-Butyl (3-cyano-4-(3-(3-((dimethylamino)methyl) pyrrolidin-1-yl)-5-fluoro-7,9-dihydrofuro[3,4-f]quinazolin-6-yl)-7-fluorothieno[3,2-c]pyridin-2-yl)carbamate | 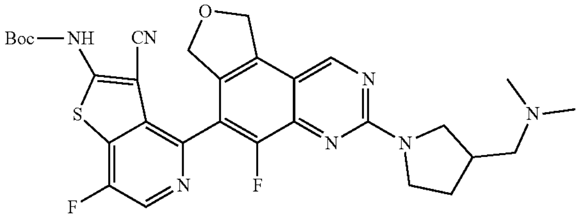 [SMILES: CN(C)CC1CCN(c2ncc3c4c(c(-c5ncc(F)c6sc(NC(=O)OC(C)(C)C)c(C#N)c56)c(F)c3n2)COC4)C1] | 608 |
| 141B | tert-Butyl (4-(3-((R)-7-((tert-butoxycarbonyl)amino)-5-azaspiro[2.4]heptan-5-yl)-5-fluoro-7,9-dihydrofuro[3,4-f]quinazolin-6-yl)-3-cyano-7-fluorothieno[3,2-c]pyridin-2-yl)carbamate | 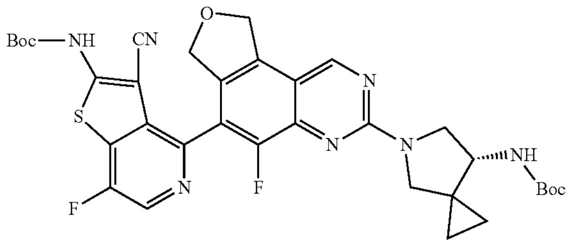 [SMILES: CC(C)(C)OC(=O)Nc1sc2c(F)cnc(-c3c4c(c5cnc(N6C[C@H](NC(=O)OC(C)(C)C)C7(CC7)C6)nc5c3F)COC4)c2c1C#N] | 692 |
| 142B | tert-Butyl (4-(3-((S)-7-((tert-butoxycarbonyl)amino)-5-azaspiro[2.4]heptan-5-yl)-5-fluoro-7,9-dihydrofuro[3,4-f]quinazolin-6-yl)-3-cyano-7-fluorothieno[3,2-c]pyridin-2-yl)carbamate | 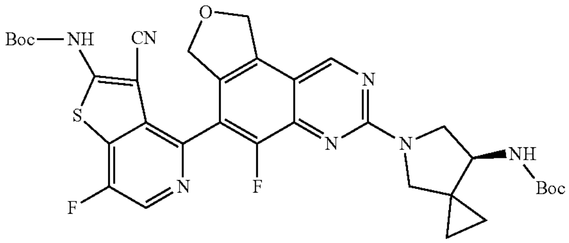 [SMILES: CC(C)(C)OC(=O)Nc1sc2c(F)cnc(-c3c4c(c5cnc(N6C[C@@H](NC(=O)OC(C)(C)C)C7(CC7)C6)nc5c3F)COC4)c2c1C#N] | 692 |
| 143B | tert-Butyl (3-cyano-7-fluoro-4-(5-fluoro-3-(6-methyl-2,6-diazaspiro[3.3]heptan-2-yl)-7,9-dihydrofuro[3,4-f]quinazolin-6-yl)thieno[3,2-c]pyridin-2-yl)carbamate | 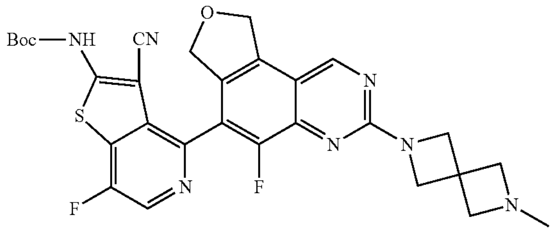 [SMILES: CN1CC2(C1)CN(c1ncc3c4c(c(-c5ncc(F)c6sc(NC(=O)OC(C)(C)C)c(C#N)c56)c(F)c3n1)COC4)C2] | 592 |
| 144B | tert-Butyl (4-(3-(4-(azetidin-1-yl)piperidin-1-yl)-5-fluoro-7,9-dihydrofuro[3,4-f]quinazolin-6-yl)-3-cyano-7-fluorothieno[3,2-c]pyridin-2-yl)carbamate | 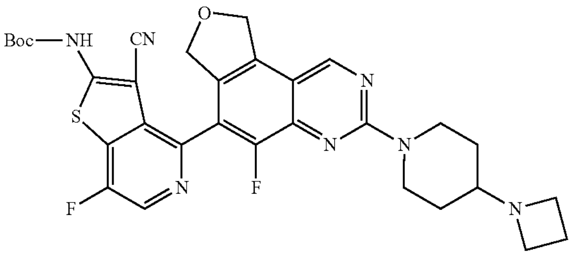 [SMILES: CC(C)(C)OC(=O)Nc1sc2c(F)cnc(-c3c4c(c5cnc(N6CCC(N7CCC7)CC6)nc5c3F)COC4)c2c1C#N] | 620 |

TABLE 22-continued

| Preparation | Chemical Name | Structure | MS (ES) m/z (M + 1) |
|---|---|---|---|
| 145B | tert-Butyl (4-(3-((S)-3-(azetidin-1-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 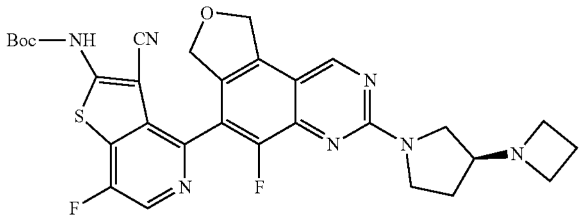 [SMILES: CC(C)(C)OC(=O)Nc1sc2c(F)cnc(-c3c4c(c5cnc(N6CC[C@H](N7CCC7)C6)nc5c3F)COC4)c2c1C#N] | 606 |
| 146B | tert-butyl (3-cyano-7-fluoro-4-(5-fluoro-3-(4-(3-methoxyazetidin-1-yl)piperidin-1-yl)-7,9-dihydrofuro[3,4-f]quinazolin-6-yl)thieno[3,2-c]pyridin-2-yl)carbamate | 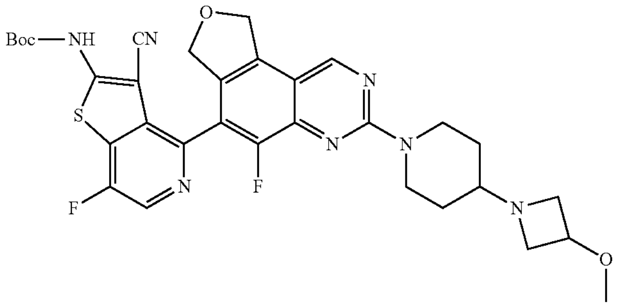 [SMILES: COC1CN(C2CCN(c3ncc4c5c(c(-c6ncc(F)c7sc(NC(=O)OC(C)(C)C)c(C#N)c67)c(F)c4n3)COC5)CC2)C1] | 650 |
| 147B | tert-Butyl (3-cyano-4-(3-((R)-3-(dimethylamino)pyrrolidin-1-yl)-5-fluoro-7,9-dihydrofuro[3,4-f]quinazolin-6-yl)-7-fluorothieno[3,2-c]pyridin-2-yl)carbamate | 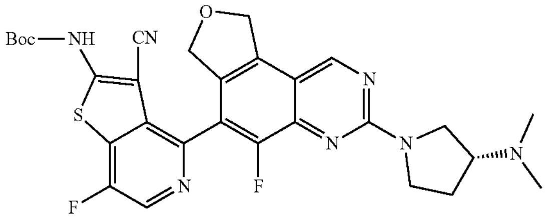 [SMILES: CN(C)[C@@H]1CCN(c2ncc3c4c(c(-c5ncc(F)c6sc(NC(=O)OC(C)(C)C)c(C#N)c56)c(F)c3n2)COC4)C1] | 594 |
| 148B | tert-Butyl (3-cyano-4-(3-(3-(dimethylamino)piperidin-1-yl)-5-fluoro-7,9-dihydrofuro[3,4-f]qunazolin-6-yl)-7-fluorothieno[3,2-c]pyridin-2-yl)carbamate | 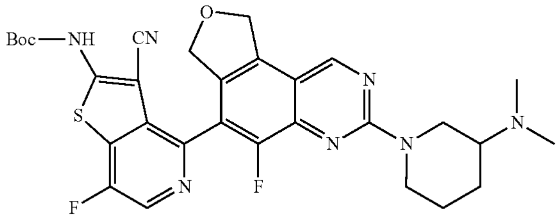 [SMILES: CN(C)C1CCCN(c2ncc3c4c(c(-c5ncc(F)c6sc(NC(=O)OC(C)(C)C)c(C#N)c56)c(F)c3n2)COC4)C1] | 608 |
| 149B | tert-Butyl (4-(3-(6-((tert-butoxycarbonyl)amino)-2-azaspiro[3.3]heptan-2-yl)-5-fluoro-7,9-dihydrofuro[3,4-f]quinazolin-6-yl)-3-cyano-7-fluorothieno[3,2-c]pyridin-2-yl)carbamate | 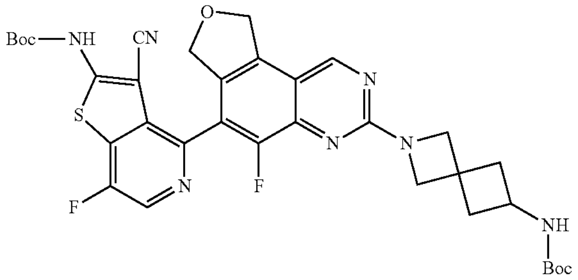 [SMILES: CC(C)(C)OC(=O)Nc1sc2c(F)cnc(-c3c4c(c5cnc(N6CC7(CC(NC(=O)OC(C)(C)C)C7)C6)nc5c3F)COC4)c2c1C#N] | 692 |
| 150B | tert-Butyl (3-cyano-7-fluoro-4-(5-fluoro-3-(3-hydroxy-[1,3'-biazetidin]-1'-yl)-7,9-dihydrofuro[3,4-f]quinazolin-6-yl)thieno[3,2-c]pyridin-2-yl)carbamate | 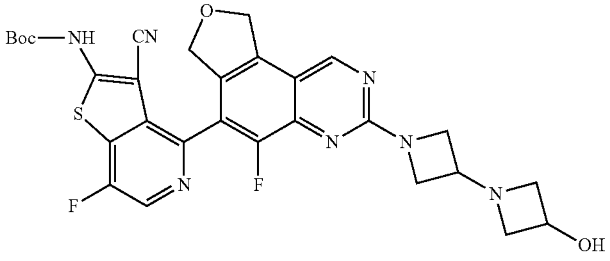 [SMILES: CC(C)(C)OC(=O)Nc1sc2c(F)cnc(-c3c4c(c5cnc(N6CC(N7CC(O)C7)C6)nc5c3F)COC4)c2c1C#N] | 608 |

TABLE 22-continued

| Preparation | Chemical Name | Structure | MS (ES) m/z (M + 1) |
|---|---|---|---|
| 151B | tert-Butyl (3-cyano-7-fluoro-4-(5-fluoro-3-(3-methyl-3-(pyrrolidin-1-yl)azetidin-1-yl)-7,9-dihydrofuro[3,4-f]quinazolin-6-yl)thieno[3,2-c]pyridin-2-yl)carbamate | 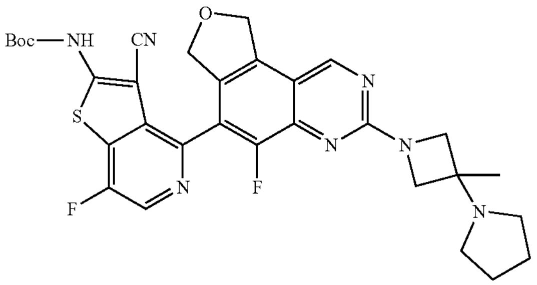 [SMILES: CC(C)(C)OC(=O)Nc1sc2c(F)cnc(-c3c4c(c5cnc(N6CC(C)(N7CCCC7)C6)nc5c3F)COC4)c2c1C#N] | 620 |
| 152B | tert-Butyl (3-cyano-4-(3-(3-cyclopropyl-3-hydroxyazetidin-1-yl)-5-fluoro-7,9-dihydrofuro[3,4-f]quinazolin-6-yl)-7-fluorothieno[3,2-c]pyridin-2-yl)carbamate | 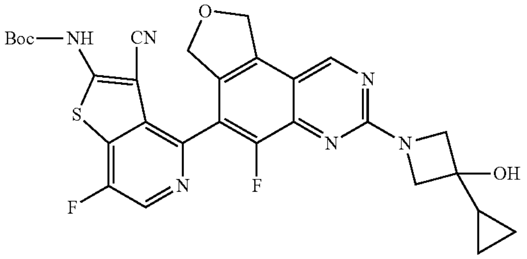 [SMILES: CC(C)(C)OC(=O)Nc1sc2c(F)cnc(-c3c4c(c5cnc(N6CC(O)(C7CC7)C6)nc5c3F)COC4)c2c1C#N] | 593 |
| 153B | tert-Butyl (3-cyano-7-fluoro-4-(5-fluoro-3-(6-methyl-2,6-diazaspiro[3.4]octan-2-yl)-7,9-dihydrofuro[3,4-f]quinazolin-6-yl)thieno[3,2-c]pyridin-2-yl)carbamate | 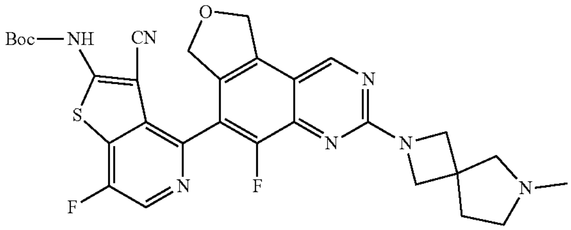 [SMILES: CN1CCC2(C1)CN(c1ncc3c4c(c(-c5ncc(F)c6sc(NC(=O)OC(C)(C)C)c(C#N)c56)c(F)c3n1)COC4)C2] | 606 |
| 154B | tert-Butyl (3-cyano-4-(3-(4-(dimethylamino)piperidin-1-yl)-5-fluoro-7,9-dihydrofuro[3,4-f]quinazolin-6-yl)-7-fluorothieno[3,2-c]pyridin-2-yl)carbamate | 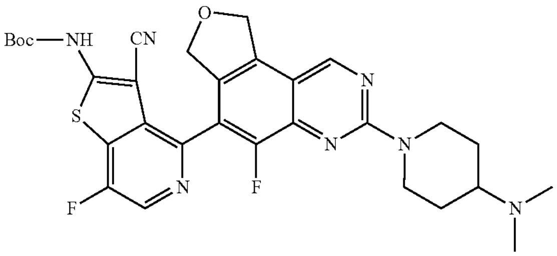 [SMILES: CN(C)C1CCN(c2ncc3c4c(c(-c5ncc(F)c6sc(NC(=O)OC(C)(C)C)c(C#N)c56)c(F)c3n2)COC4)CC1] | 608 |
| 155B | tert-Butyl (3-cyano-4-(3-((3S,4S)-3-(dimethylamino)-4-(hydroxymethyl)pyrrolidin-1-yl)-5-fluoro-7,9-dihydrofuro[3,4-f]quinazolin-6-yl)-7-fluorothieno[3,2-c]pyridin-2-yl)carbamate | 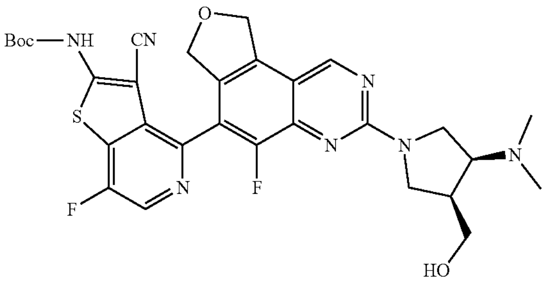 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@@H]1CO] | |

TABLE 22-continued

| Preparation | Chemical Name | Structure | MS (ES) m/z (M + 1) |
| --- | --- | --- | --- |
| 156B | tert-Butyl (3-cyano-4-(3-((3R,4R)-3-(dimethylamino)-4-(hydroxymethyl)pyrrolidin-1-yl)-5-fluoro-7,9-dihydrofuro[3,4-f]quinazolin-6-yl)-7-fluorothieno[3,2-c]pyridin-2-yl)carbamate | 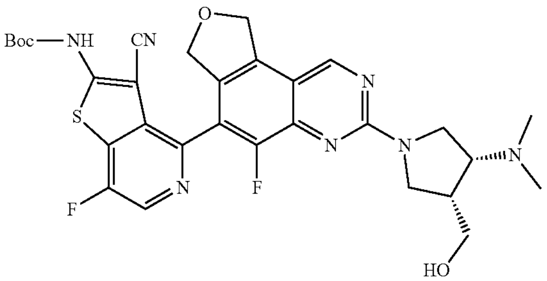 [SMILES: CN(C)[C@H]1CN(c2ncc3c4c(c(-c5ncc(F)c6sc(NC(=O)OC(C)(C)C)c(C#N)c56)c(F)c3n2)COC4)C[C@H]1CO] | |
| 157B | tert-Butyl (3-cyano-4-(3-((3S,4R)-3-(dimethylamino)-4-(hydroxymethyl)pyrrolidin-1-yl)-5-fluoro-7,9-dihydrofuro[3,4-f]quinazolin-6-yl)-7-fluorothieno[3,2-c]pyridin-2-yl)carbamate | 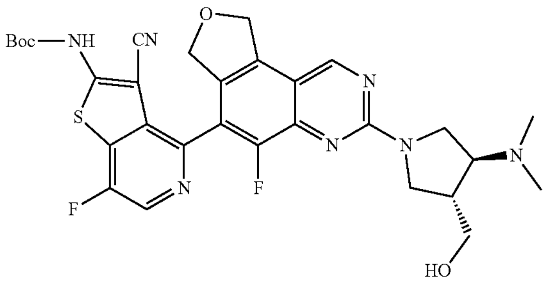 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@H]1CO] | |
| 158B | tert-Butyl (3-cyano-4-(3-((3R,4S)-3-(dimethylamino)-4-(hydroxymethyl)pyrrolidin-1-yl)-5-fluoro-7,9-dihydrofuro[3,4-f]quinazolin-6-yl)-7-fluorothieno[3,2-c]pyridin-2-yl)carbamate | 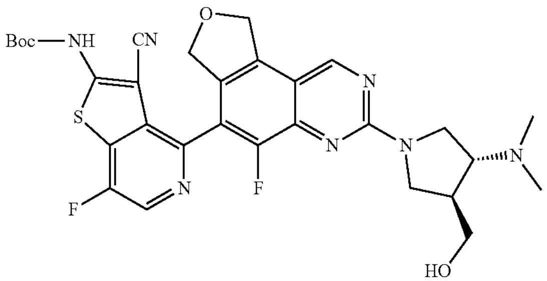 [SMILES: CN(C)[C@H]1CN(c2ncc3c4c(c(-c5ncc(F)c6sc(NC(=O)OC(C)(C)C)c(C#N)c56)c(F)c3n2)COC4)C[C@@H]1CO] | |
| 159B | tert-Butyl (4-(3-((2S,3S)-3-amino-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 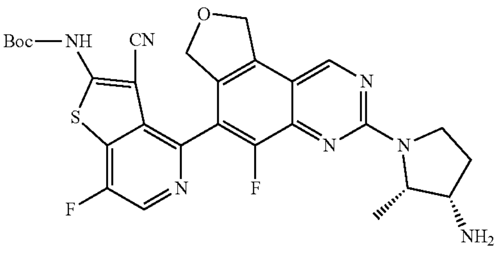 [SMILES: C[C@H]1[C@@H](N)CCN1c1ncc2c3c(c(-c4ncc(F)c5sc(NC(=O)OC(C)(C)C)c(C#N)c45)c(F)c2n1)COC3] | 580 |
| 160B | tert-Butyl (4-(5-chloro-3-(3-(dimethylamino)-3-(hydroxymethyl)pyrrolidin-1-yl)-7,9-dihydrofuro[3,4-f]quinazolin-6-yl)-3-cyano-5-fluorobenzo[b]thiophen-2-yl)carbamate | 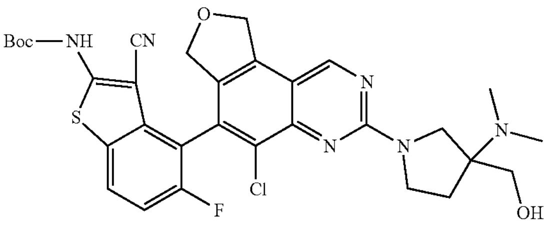 | 639 |

TABLE 22-continued

| Preparation | Chemical Name | Structure | MS (ES) m/z (M + 1) |
|---|---|---|---|
| 161B | tert-Butyl (3-cyano-4-(3-((3S,4S)-3-(dimethylamino)-4-methoxypyrrolidin-1-yl)-5-fluoro-7,9-dihydrofuro[3,4-f]quinazolin-6-yl)-7-fluorothieno[3,2-c]pyridin-2-yl)carbamate | 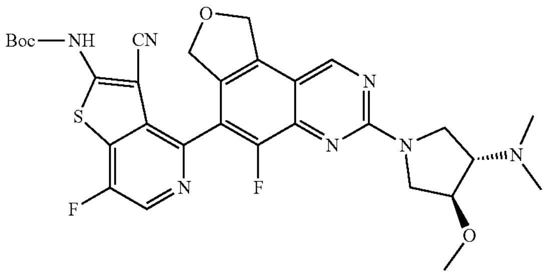 [SMILES: CO[C@H]1CN(c2ncc3c4c(c(-c5ncc(F)c6sc(NC(=O)OC(C)(C)C)c(C#N)c56)c(F)c3n2)COC4)C[C@@H]1N(C)C] | 624 |
| 162B | tert-Butyl (3-cyano-4-(3-((3R,4S)-3-(dimethylamino)-4-methoxypyrrolidin-1-yl)-5-fluoro-7,9-dihydrofuro[3,4-f]quinazolin-6-yl)-7-fluorothieno[3,2-c]pyridin-2-yl)carbamate | 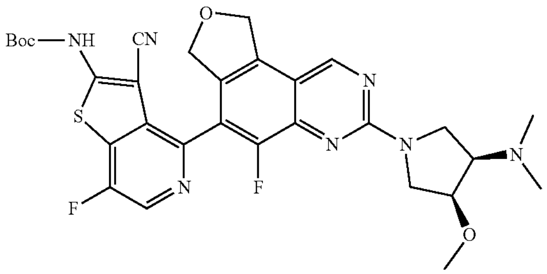 [SMILES: CO[C@H]1CN(c2ncc3c4c(c(-c5ncc(F)c6sc(NC(=O)OC(C)(C)C)c(C#N)c56)c(F)c3n2)COC4)C[C@H]1N(C)C] | 624 |
| 163B | tert-Butyl (4-(3-((1S,5S)-2,6-diazabicyclo[3.2.0]heptan-2-yl)-5-fluoro-7,9-dihydrofuro[3,4-f]quinazolin-6-yl)-3-cyano-7-fluorothieno[3,2-c]pyridin-2-yl)carbamate | 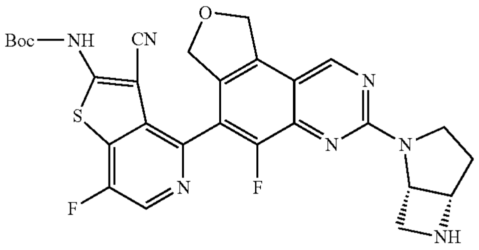 [SMILES: CC(C)(C)OC(=O)Nc1sc2c(F)cnc(-c3c4c(c5cnc(N6CC[C@@H]7NC[C@@H]76)nc5c3F)COC4)c2c1C#N] | 578 |
| 164B[5] | tert-Butyl (4-(5-chloro-3-((3S,4S)-3-(dimethylamino)-4-(hydroxymethyl)pyrrolidin-1-yl)-7,9-dihydrofuro[3,4-f]quinazolin-6-yl)-3-cyano-7-fluorothieno[3,2-c]pyridin-2-yl)carbamate, Atropisomer 1 | 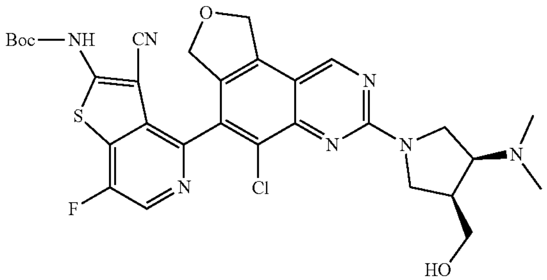 | 640 |
| 165B[6] | tert-Butyl (4-(5-chloro-3-((3S,4S)-3-(dimethylamino)-4-(hydroxymethyl)pyrrolidin-1-yl)-7,9-dihydrofuro[3,4-f]quinazolin-6-yl)-3-cyano-7-fluorothieno[3,2-c]pyridin-2-yl)carbamate, Atropisomer 2 | 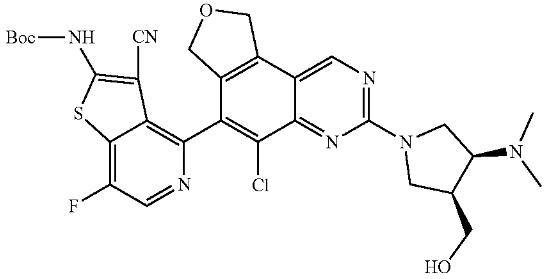 | 640 |

TABLE 22-continued

| Preparation | Chemical Name | Structure | MS (ES) m/z (M + 1) |
| --- | --- | --- | --- |
| 166B | tert-Butyl (3-cyano-4-(3-((1R,5S)-1-((dimethylamino)methyl)-3-azabicyclo[3.1.0]hexan-3-yl)-5-fluoro-7,9-dihydrofuro[3,4-f]quinazolin-6-yl)-7-fluorothieno[3,2-c]pyridin-2-yl)carbamate | 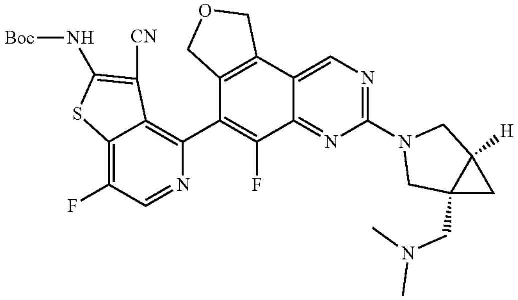 [SMILES: CN(C)C[C@@]12C[C@@H]1CN(c1ncc3c4c(c(-c5ncc(F)c6sc(NC(=O)OC(C)(C)C)c(C#N)c56)c(F)c3n1)COC4)C2] | 620 |
| 167B | tert-Butyl (3-cyano-4-(3-((1S,5R)-1-((dimethylamino)methyl)-3-azabicyclo[3.1.0]hexan-3-yl)-5-fluoro-7,9-dihydrofuro[3,4-f]quinazolin-6-yl)-7-fluorothieno[3,2-c]pyridin-2-yl)carbamate | 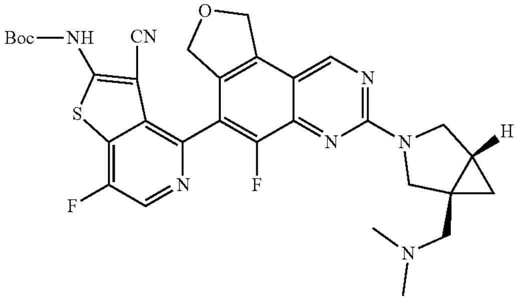 [SMILES: CN(C)C[C@]12C[C@H]1CN(c1ncc3c4c(c(-c5ncc(F)c6sc(NC(=O)OC(C)(C)C)c(C#N)c56)c(F)c3n1)COC4)C2] | 620 |
| 168B | tert-Butyl (3-cyano-4-(3-((1R,5S)-1-(dimethylamino)-3-azabicyclo[3.1.0]hexan-3-yl)-5-fluoro-7,9-dihydrofuro[3,4-f]quinazolin-6-yl)-7-fluorothieno[3,2-c]pyridin-2-yl)carbamate | 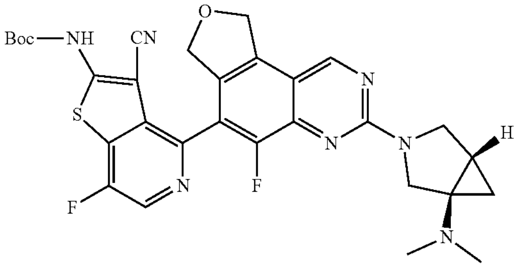 [SMILES: CN(C)[C@]12C[C@H]1CN(c1ncc3c4c(c(-c5ncc(F)c6sc(NC(=O)OC(C)(C)C)c(C#N)c56)c(F)c3n1)COC4)C2] | 606 |
| 169B | tert-Butyl (3-cyano-4-(3-((1S,5R)-1-(dimethylamino)-3-azabicyclo[3.1.0]hexan-3-yl)-5-fluoro-7,9-dihydrofuro[3,4-f]quinazolin-6-yl)-7-fluorothieno[3,2-c]pyridin-2-yl)carbamate | 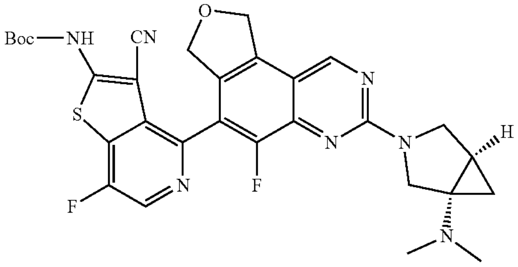 [SMILES: CN(C)[C@@]12C[C@@H]1CN(c1ncc3c4c(c(-c5ncc(F)c6sc(NC(=O)OC(C)(C)C)c(C#N)c56)c(F)c3n1)COC4)C2] | 606 |
| 170B | tert-Butyl 8-(6-(2-((tert-butoxycarbonyl)amino)-3-cyano-7-fluorothieno[3,2-c]pyridin-4-yl)-5-fluoro-3-(5-methylhexahydropyrrolo[3,4-c]pyrrol-2(1H)-yl)-7,9-dihydrofuro[3,4-f]quinazolin-1-yl)-3,8-diazabicyclo[3.2.1]octane-3-carboxylate | 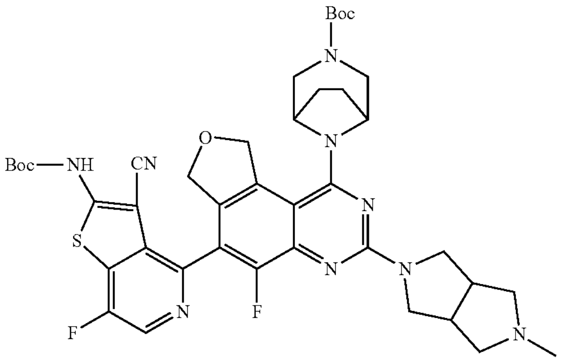 [SMILES: CN1CC2CN(c3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)CC2C1] | 816 |

TABLE 22-continued

| Preparation | Chemical Name | Structure | MS (ES) m/z (M + 1) |
|---|---|---|---|
| 171B | tert-Butyl 8-(6-(2-((tert-butoxycarbonyl)amino)-3-cyano-7-fluorothieno[3,2-c]pyridin-4-yl)-5-fluoro-3-(1-methyl-1,6-diazaspiro[3.3]heptan-6-yl)-7,9-dihydrofuro[3,4-f]quinazolin-1-yl)-3,8-diazabicyclo[3.2.1]octane-3-carboxylate | 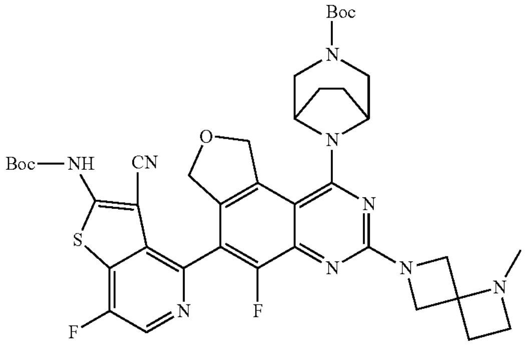 [SMILES: CN1CCC12CN(c1nc(N3C4CCC3CN(C(=O)OC(C)(C)C)C4)c3c4c(c(-c5ncc(F)c6sc(NC(=O)OC(C)(C)C)c(C#N)c56)c(F)c3n1)COC4)C2] | 802 |
| 172B | tert-Butyl 8-(6-(2-((tert-butoxycarbonyl)amino)-3-cyano-7-fluorothieno[3,2-c]pyridin-4-yl)-3-((R)-3-((dimethylamino)methyl) pyrrolidin-1-yl)-5-fluoro-7,9-dihydrofuro[3,4-f]quinazolin-1-yl)-3,8-diazabicyclo[3.2.1]octane-3-carboxylate | 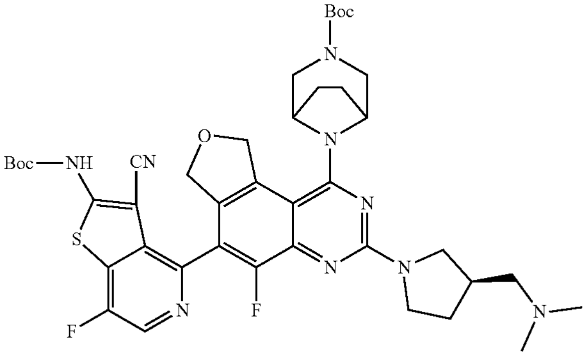 [SMILES: CN(C)C[C@H]1CCN(c2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1] | 818 |
| 173B | tert-Butyl 8-(6-(2-((tert-butoxycarbonyl)amino)-3-cyano-7-fluorothieno[3,2-c]pyridin-4-yl)-3-((S)-3-(diethylamino)pyrrolidin-1-yl)-5-fluoro-7,9-dihydrofuro[3,4-f]quinazolin-1-yl)-3,8-diazabicyclo[3.2.1]octane-3-carboxylate | 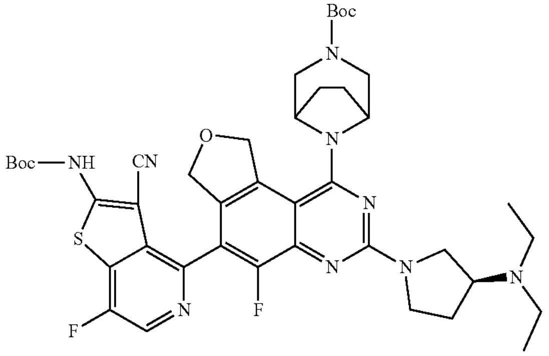 [SMILES: CCN(CC)[C@H]1CCN(c2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1] | 832 |
| 174B | tert-Butyl 8-(6-(2-((tert-butoxycarbonyl)amino)-3-cyano-7-fluorothieno[3,2-c]pyridin-4-yl)-5-fluoro-3-((3aR,6aR)-1-methylhexahydropyrrolo[3,4-b]pyrrol-5(1H)-yl)-7,9-dihydrofuro[3,4-f]quinazolin-1-yl)-3,8-diazabicyclo[3.2.1]octane-3-carboxylate | 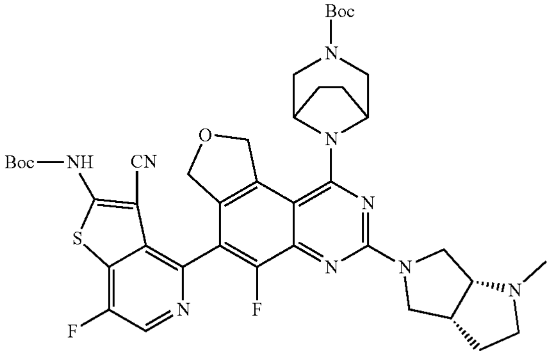 [SMILES: CN1CC[C@@H]2CN(c3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)C[C@@H]21] | 816 |

TABLE 22-continued

| Preparation | Chemical Name | Structure | MS (ES) m/z (M + 1) |
|---|---|---|---|
| 175B | tert-Butyl 8-(6-(2-((tert-butoxycarbonyl)amino)-3-cyano-7-fluorothieno[3,2-c]pyridin-4-yl)-5-fluoro-3-((3aS,6aS)-1-methylhexahydropyrrolo[3,4-b]pyrrol-5(1H)-yl)-7,9-dihydrofuro[3,4-f]quinazolin-1-yl)-3,8-diazabicyclo[3.2.1]octane-3-carboxylate | 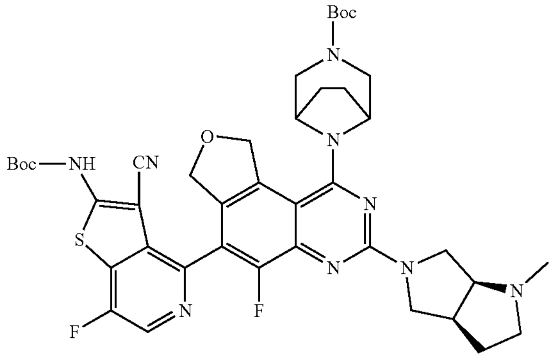 [SMILES: CN1CC[C@H]2CN(c3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)C[C@H]21] | 816 |
| 176B | tert-Butyl 8-(6-(2-((tert-butoxycarbonyl)amino)-3-cyano-7-fluorothieno[3,2-c]pyridin-4-yl)-5-fluoro-3-(5-methyl-2,5-diazaspiro[3.4]octan-2-yl)-7,9-dihydrofuro[3,4-f]quinazolin-1-yl)-3,8-diazabicyclo[3.2.1]octane-3-carboxylate | 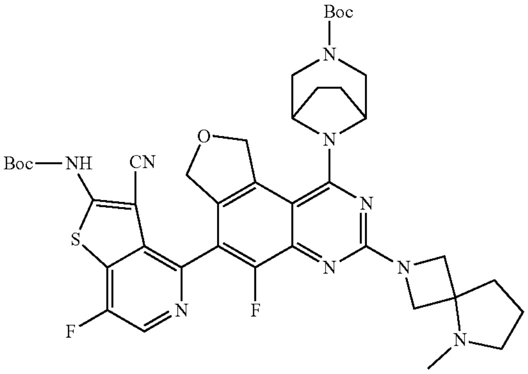 [SMILES: CN1CCCC12CN(c1nc(N3C4CCC3CN(C(=O)OC(C)(C)C)C4)c3c4c(c(-c5ncc(F)c6sc(NC(=O)OC(C)(C)C)c(C#N)c56)c(F)c3n1)COC4)C2] | 816 |
| 177B | tert-Butyl 8-(6-(2-((tert-butoxycarbonyl)amino)-3-cyano-7-fluorothieno[3,2-c]pyridin-4-yl)-5-fluoro-3-((S)-hexahydropyrrolo[1,2-a]pyrazin-2(1H)-yl)-7,9-dihydrofuro[3,4-f]quinazolin-1-yl)-3,8-diazabicyclo[3.2.1]octane-3-carboxylate | 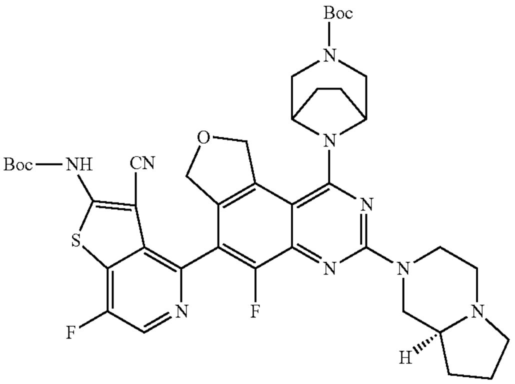 [SMILES: CC(C)(C)OC(=O)Nc1sc2c(F)cnc(-c3c4c(c5c(N6C7CCC6CN(C(=O)OC(C)(C)C)C7)nc(N6CCN7CCC[C@H]7C6)nc5c3F)COC4)c2c1C#N] | 816 |
| 178B | tert-Butyl 8-(6-(2-((tert-butoxycarbonyl)amino)-3-cyano-7-fluorothieno[3,2-c]pyridin-4-yl)-3-((S)-3-(dimethylamino)-3-methylpyrrolidin-1-yl)-5-fluoro-7,9-dihydrofuro[3,4-f]quinazolin-1-yl)-3,8-diazabicyclo[3.2.1]octane-3-carboxylate | 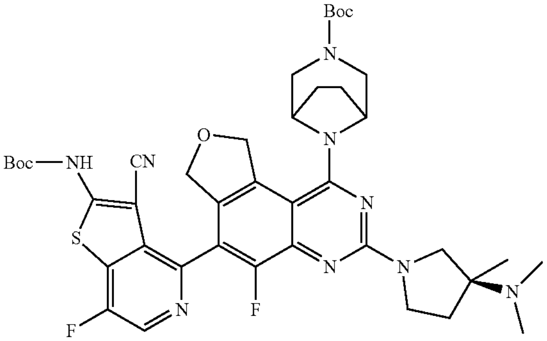 [SMILES: CN(C)[C@@]1(C)CCN(c2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)C1] | 818 |

TABLE 22-continued

| Preparation | Chemical Name | Structure | MS (ES) m/z (M + 1) |
|---|---|---|---|
| 179B | tert-Butyl 8-(6-(2-((tert-butoxycarbonyl)amino)-3-cyano-7-fluorothieno[3,2-c]pyridin-4-yl)-5-fluoro-3-(3-(pyrrolidin-1-yl)azetidin-1-yl)-7,9-dihydrofuro[3,4-f]quinazolin-1-yl)-3,8-diazabicyclo[3.2.1]octane-3-carboxylate | 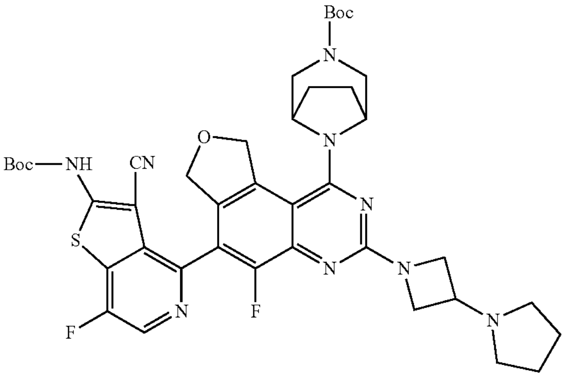 [SMILES: CC(C)(C)OC(=O)Nc1sc2c(F)cnc(-c3c4c(c5c(N6C7CCC6CN(C(=O)OC(C)(C)C)C7)nc(N6CC(N7CCCC7)C6)nc5c3F)COC4)c2c1C#N] | 816 |
| 180B | tert-Butyl 8-(6-(2-((tert-butoxycarbonyl)amino)-3-cyano-7-fluorothieno[3,2-c]pyridin-4-yl)-5-fluoro-3-(3-methyl-3,6-diazabicyclo[3.1.1]heptan-6-yl)-7,9-dihydrofuro[3,4-f]quinazolin-1-yl)-3,8-diazabicyclo[3.2.1]octane-3-carboxylate | 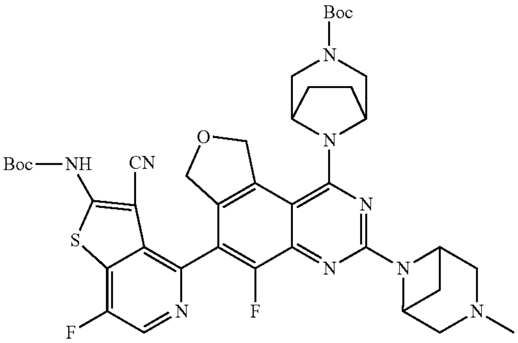 [SMILES: CN1CC2CC(C1)N2c1nc(N2C3CCC2CN(C(=O)OC(C)(C)C)C3)c2c3c(c(-c4ncc(F)c5sc(NC(=O)OC(C)(C)C)c(C#N)c45)c(F)c2n1)COC3] | 802 |
| 181B | tert-Butyl 8-(6-(2-((tert-butoxycarbonyl)amino)-3-cyano-7-fluorothieno[3,2-c]pyridin-4-yl)-3-((1R,5S,8R)-8-(dimethylamino)-3-azabicyclo[3.2.1]octan-3-yl)-5-fluoro-7,9-dihydrofuro[3,4-f]quinazolin-1-yl)-3,8-diazabicyclo[3.2.1]octane-3-carboxylate | 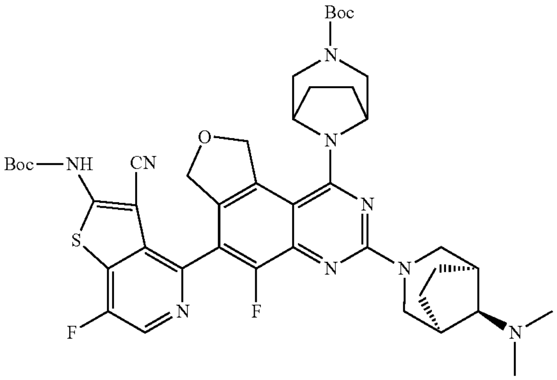 [SMILES: CN(C)[C@H]1[C@@H]2CC[C@H]1CN(c1nc(N3C4CCC3CN(C(=O)OC(C)(C)C)C4)c3c4c(c(-c5ncc(F)c6sc(NC(=O)OC(C)(C)C)c(C#N)c56)c(F)c3n1)COC4)C2] | 844 |
| 182B [7] | tert-Butyl 8-(6-(2-((tert-butoxycarbonyl)amino)-3-cyano-5-fluorobenzo[b]thiophen-4-yl)-3-((S)-3-(dimethylamino)pyrrolidin-1-yl)-5-fluoro-7,9-dihydrofuro[3,4-f]quinazolin-1-yl)-3,8-diazabicyclo[3.2.1]octane-3-carboxylate | 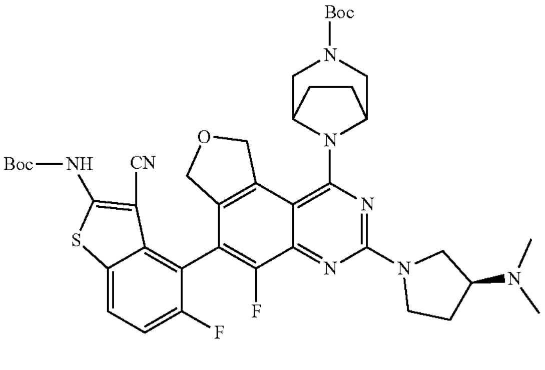 [SMILES: CN(C)[C@H]1CCN(c2nc(N3C4CCC3CN(C(=O)OC(C)(C)C)C4)c3c4c(c(-c5c(F)ccc6sc(NC(=O)OC(C)(C)C)c(C#N)c56)c(F)c3n2)COC4)C1] | 803 |

TABLE 22-continued

| Preparation | Chemical Name | Structure | MS (ES) m/z (M + 1) |
|---|---|---|---|
| 183B | tert-Butyl 8-(6-(2-((tert-butoxycarbonyl)amino)-3-cyano-7-fluorobenzo[b]thiophen-4-yl)-5-chloro-3-((S)-3-(dimethylamino)pyrrolidin-1-yl)-7,9-dihydrofuro[3,4-f]quinazolin-1-yl)-3,8-diazabicyclo[3.2.1]octane-3-carboxylate | 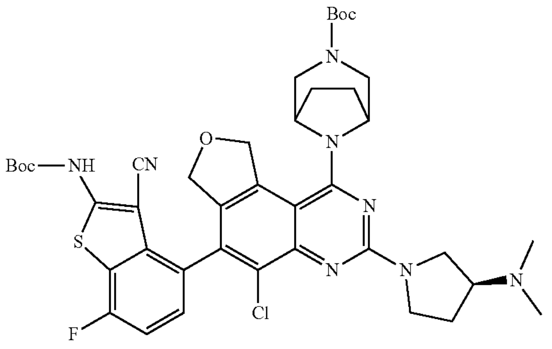 [SMILES: CN(C)[C@H]1CCN(c2nc(N3C4CCC3CN(C(=O)OC(C)(C)C)C4)c3c4c(c(-c5ccc(F)c6sc(NC(=O)OC(C)(C)C)c(C#N)c56)c(Cl)c3n2)COC4)C1] | 819 |
| 184B | tert-Butyl 8-(6-(2-((tert-butoxycarbonyl)amino)-3-cyano-5-fluorobenzo[b]thiophen-4-yl)-5-chloro-3-((S)-3-(dimethylamino)pyrrolidin-1-yl)-7,9-dihydrofuro[3,4-f]quinazolin-1-yl)-3,8-diazabicyclo[3.2.1]octane-3-carboxylate | 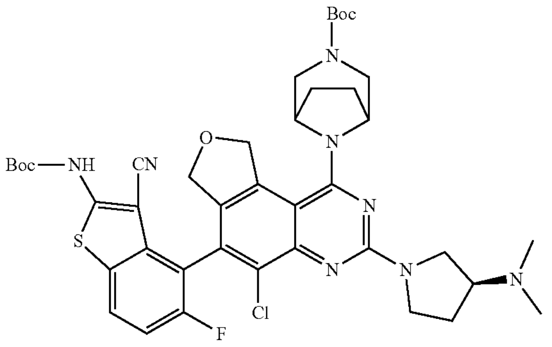 [SMILES: CN(C)[C@H]1CCN(c2nc(N3C4CCC3CN(C(=O)OC(C)(C)C)C4)c3c4c(c(-c5c(F)ccc6sc(NC(=O)OC(C)(C)C)c(C#N)c56)c(Cl)c3n2)COC4)C1] | 819 |
| 185B [8] | tert-Butyl (3aR,6aS)-5-(6-(2-((tert-butoxycarbonyl)amino)-3-cyano-5-fluorobenzo[b]thiophen-4-yl)-5-fluoro-7,9-dihydrofuro[3,4-f]quinazolin-3-yl)hexahydropyrrolo[3,4-c]pyrrole-2(1H)-carboxylate | 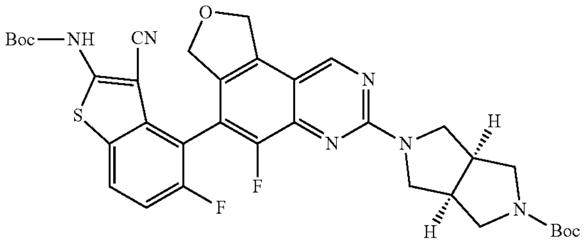 [SMILES: CC(C)(C)OC(=O)Nc1sc2ccc(F)c(-c3c4c(c5cnc(N6C[C@H]7CN(C(=O)OC(C)(C)C)C[C@H]7C6)nc5c3F)COC4)c2c1C#N] | 691 |
| 186B [8] | tert-Butyl (3-cyano-5-fluoro-4-(5-fluoro-3-(1-methyl-1,6-diazaspiro[3.3]heptan-6-yl)-7,9-dihydrofuro[3,4-f]quinazolin-6-yl)benzo[b]thiophen-2-yl)carbamate | 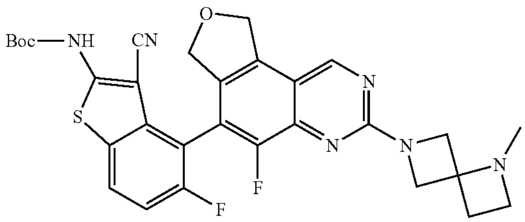 [SMILES: CN1CCC12CN(c1ncc3c4c(c(-c5c(F)ccc6sc(NC(=O)OC(C)(C)C)c(C#N)c56)c(F)c3n1)COC4)C2] | 591 |
| 187B [8] | tert-Butyl (3-cyano-4-(3-((3R,4S)-3-(dimethylamino)-4-hydroxypyrrolidin-1-yl)-5-fluoro-7,9-dihydrofuro[3,4-f]quinazolin-6-yl)-5-fluorobenzo[b]thiophen-2-yl)carbamate | 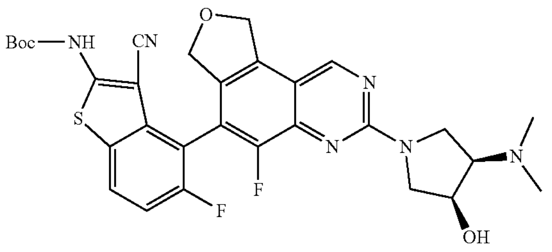 [SMILES: CN(C)[C@@H]1CN(c2ncc3c4c(c(-c5c(F)ccc6sc(NC(=O)OC(C)(C)C)c(C#N)c56)c(F)c3n2)COC4)C[C@@H]1O] | 609 |

TABLE 22-continued

| Preparation | Chemical Name | Structure | MS (ES) m/z (M + 1) |
|---|---|---|---|
| 188B [8] | tert-Butyl (3-cyano-5-fluoro-4-(5-fluoro-3-((1S,4S)-5-methyl-2,5-diazabicyclo[2.2.1]heptan-2-yl)-7,9-dihydrofuro[3,4-f]quinazolin-6-yl)benzo[b]thiophen-2-yl)carbamate | 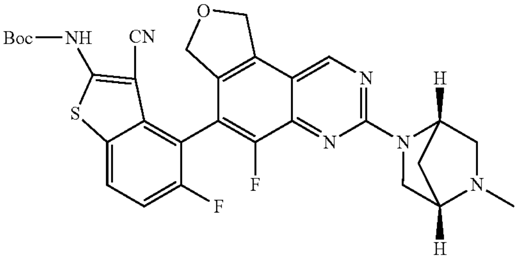 [SMILES: CN1C[C@@H]2C[C@H]1CN2c1ncc2c3c(c(-c4c(F)ccc5sc(NC(=O)OC(C)(C)C)c(C#N)c45)c(F)c2n1)COC3] | 591 |
| 189B [8] | tert-Butyl (3-cyano-4-(3-((R)-3-((dimethylamino)methyl) pyrrolidin-1-yl)-5-fluoro-7,9-dihydrofuro[3,4-f]quinazolin-6-yl)-5-fluorobenzo[b]thiophen-2-yl)carbamate | 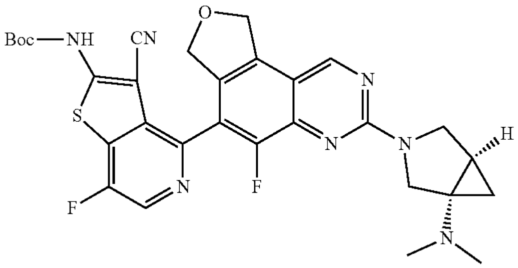 [SMILES: CN(C)[C@@]12C[C@@H]1CN(c1ncc3c4c(c(-c5ncc(F)c6sc(NC(=O)OC(C)(C)C)c(C#N)c56)c(F)c3n1)COC4)C2] | 607 |
| 190B [8] | tert-Butyl (3-cyano-4-(3-((S)-3-((dimethylamino)methyl) pyrrolidin-1-yl)-5-fluoro-7,9-dihydrofuro[3,4-f]quinazolin-6-yl)-5-fluorobenzo[b]thiophen-2-yl)carbamate | 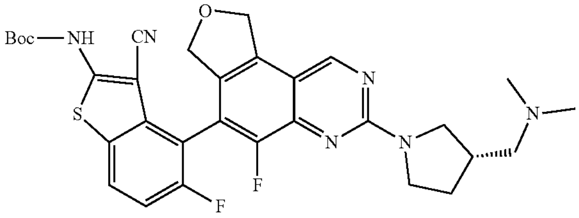 [SMILES: CN(C)C[C@@H]1CCN(c2ncc3c4c(c(-c5c(F)ccc6sc(NC(=O)OC(C)(C)C)c(C#N)c56)c(F)c3n2)COC4)C1] | 607 |
| 191B [8] | tert-Butyl (3-cyano-4-(3-((S)-7-(dimethylamino)-5-azaspiro[2.4]heptan-5-yl)-5-fluoro-7,9-dihydrofuro[3,4-f]quinazolin-6-yl)-5-fluorobenzo[b]thiophen-2-yl)carbamate | 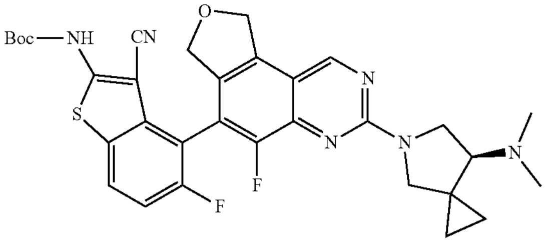 [SMILES: CN(C)[C@@H]1CN(c2ncc3c4c(c(-c5c(F)ccc6sc(NC(=O)OC(C)(C)C)c(C#N)c56)c(F)c3n2)COC4)CC12CC2] | 619 |
| 192B | tert-Butyl (3-cyano-7-fluoro-4-(5-fluoro-3-(5-methylhexahydropyrrolo[3,4-b]pyrrol-1(2H)-yl)-7,9-dihydrofuro[3,4-f]quinazolin-6-yl)thieno[3,2-c]pyridin-2-yl)carbamate, Mix of Cis Isomers | 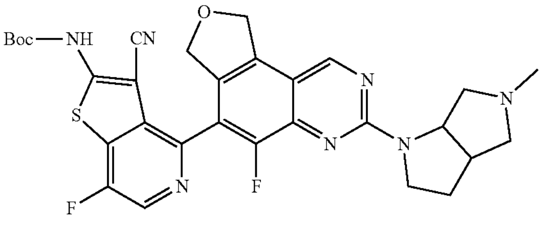 [SMILES: CN1CC2CCN(c3ncc4c5c(c(-c6ncc(F)c7sc(NC(=O)OC(C)(C)C)c(C#N)c67)c(F)c4n3)COC5)C2C1] | |
| 74C | tert-Butyl (3-cyano-7-fluoro-4-(5-fluoro-3-(4-methyloctahydro-1H-pyrrolo[3,2-b]pyridin-1-yl)-7,9-dihydrofuro[3,4-f]quinazolin-6-yl)thieno[3,2-c]pyridin-2-yl)carbamate, Mix of Cis Isomers | 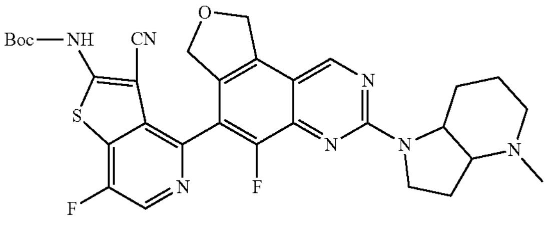 [SMILES: CN1CCCC2C1CCN2c1ncc2c3c(c(-c4ncc(F)c5sc(NC(=O)OC(C)(C)C)c(C#N)c45)c(F)c2n1)COC3] | 620 |

TABLE 22-continued

| Preparation | Chemical Name | Structure | MS (ES) m/z (M + 1) |
|---|---|---|---|
| 75C | tert-Butyl (3-cyano-4-(3-(3-(cyclopropyl(methyl)amino)pyrrolidin-1-yl)-5-fluoro-7,9-dihydrofuro[3,4-f]quinazolin-6-yl)-7-fluorothieno[3,2-c]pyridin-2-yl)carbamate | 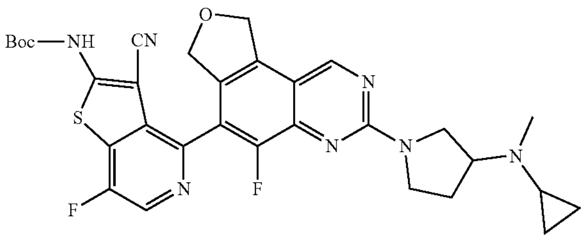 [SMILES: CN(C1CC1)C1CCN(c2ncc3c4c(c(-c5ncc(F)c6sc(NC(=O)OC(C)(C)C)c(C#N)c56)c(F)c3n2)COC4)C1] | 620 |
| 76C | tert-Butyl (1R,5R)-6-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)-2,6-diazabicyclo[3.2.0]heptane-2-carboxylate | 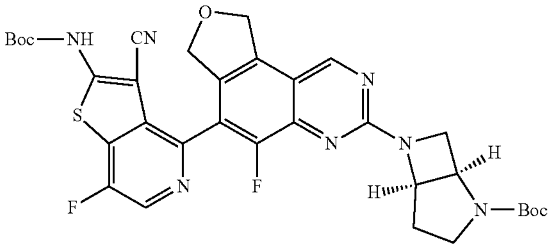 [SMILES: CC(C)(C)OC(=O)Nc1sc2c(F)cnc(-c3c4c(c5cnc(N6C[C@@H]7[C@H]6CCN7C(=O)OC(C)(C)C)nc5c3F)COC4)c2c1C#N] | 678 |
| 77C | tert-Butyl 6-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)-2,6-diazabicyclo[3.2.0]heptane-2-carboxylate, Mix of Cis Isomers | 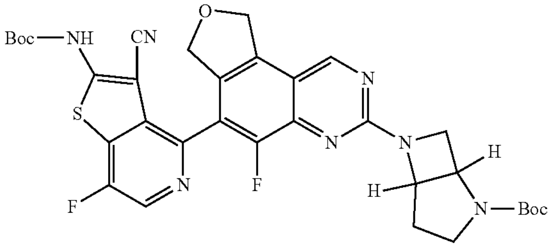 | 678 |
| 78C | tert-Butyl (3-cyano-7-fluoro-4-(5-fluoro-3-(3-morpholinopyrrolidin-1-yl)-7,9-dihydrofuro[3,4-f]quinazolin-6-yl)thieno[3,2-c]pyridin-2-yl)carbamate | 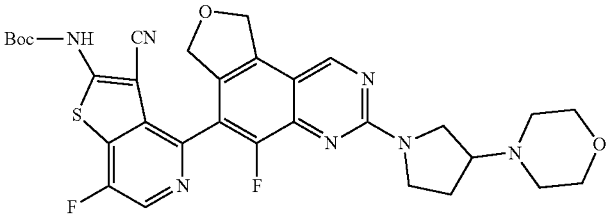 [SMILES: CC(C)(C)OC(=O)Nc1sc2c(F)cnc(-c3c4c(c5cnc(N6CCC(N7CCOCC7)C6)nc5c3F)COC4)c2c1C#N] | 636 |
| 79C | tert-Butyl (3-cyano-7-fluoro-4-(5-fluoro-3-((S)-3-(isobutyl(methyl)amino)pyrrolidin-1-yl)-7,9-dihydrofuro[3,4-f]quinazolin-6-yl)thieno[3,2-c]pyridin-2-yl)carbamate | 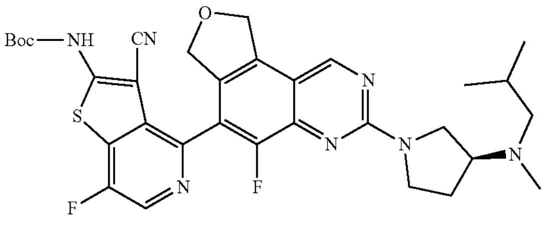 [SMILES: CC(C)CN(C)[C@H]1CCN(c2ncc3c4c(c(-c5ncc(F)c6sc(NC(=O)OC(C)(C)C)c(C#N)c56)c(F)c3n2)COC4)C1] | 636 |
| 80C | tert-Butyl (3-cyano-4-(3-((S)-3-((cyclopropylmethyl)(methyl)amino)pyrrolidin-1-yl)-5-fluoro-7,9-dihydrofuro[3,4-f]quinazolin-6-yl)-7-fluorothieno[3,2-c]pyridin-2-yl)carbamate | 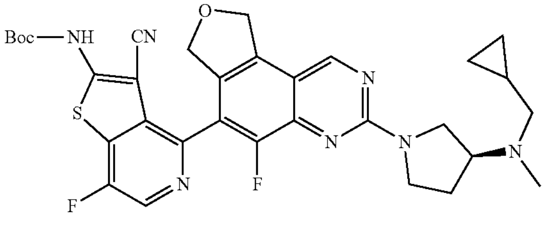 [SMILES: CN(CC1CC1)[C@H]1CCN(c2ncc3c4c(c(-c5ncc(F)c6sc(NC(=O)OC(C)(C)C)c(C#N)c56)c(F)c3n2)COC4)C1] | 634 |

TABLE 22-continued

| Preparation | Chemical Name | Structure | MS (ES) m/z (M + 1) |
|---|---|---|---|
| 81C | tert-Butyl (3-cyano-7-fluoro-4-(5-fluoro-3-((S)-3-(3-methoxyazetidin-1-yl)pyrrolidin-1-yl)-7,9-dihydrofuro[3,4-f]quinazolin-6-yl)thieno[3,2-c]pyridin-2-yl)carbamate | 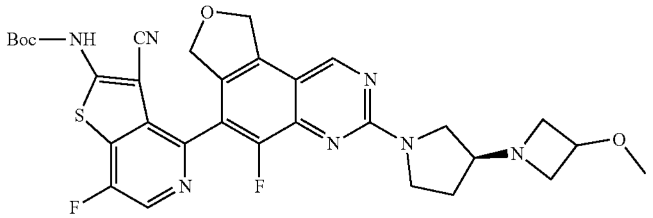 [SMILES: COC1CN([C@H]2CCN(c3ncc4c5c(c(-c6ncc(F)c7sc(NC(=O)OC(C)(C)C)c(C#N)c67)c(F)c4n3)COC5)C2)C1] | 636 |
| 82C | tert-Butyl (3-cyano-7-fluoro-4-(5-fluoro-3-((S)-3-((2-hydroxy-2-methylpropyl)(methyl)amino)pyrrolidin-1-yl)-7,9-dihydrofuro[3,4-f]quinazolin-6-yl)thieno[3,2-c]pyridin-2-yl)carbamate | 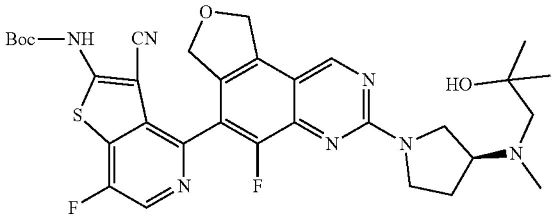 [SMILES: CN(CC(C)(C)O)[C@H]1CCN(c2ncc3c4c(c(-c5ncc(F)c6sc(NC(=O)OC(C)(C)C)c(C#N)c56)c(F)c3n2)COC4)C1] | 652 |
| 83C | tert-Butyl (4-(3-((S)-3-(tert-butylamino)pyrrolidin-1-yl)-5-fluoro-7,9-dihydrofuro[3,4-f]quinazolin-6-yl)-3-cyano-7-fluorothieno[3,2-c]pyridin-2-yl)carbamate | 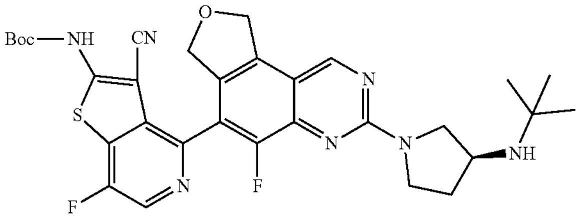 [SMILES: CC(C)(C)N[C@H]1CCN(c2ncc3c4c(c(-c5ncc(F)c6sc(NC(=O)OC(C)(C)C)c(C#N)c56)c(F)c3n2)COC4)C1] | 622 |
| 84C | tert-Butyl (3-cyano-7-fluoro-4-(5-fluoro-3-((1R,5S)-3-methyl-3,6-diazabicyclo[3.2.1]octan-6-yl)-7,9-dihydrofuro[3,4-f]quinazolin-6-yl)thieno[3,2-c]pyridin-2-yl)carbamate | 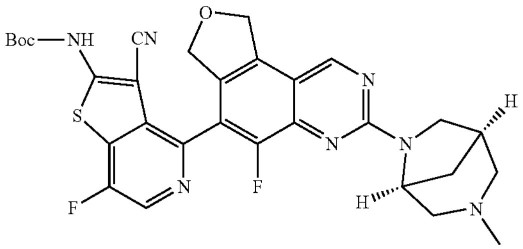 [SMILES: CN1C[C@H]2C[C@@H](C1)N(c1ncc3c4c(c(-c5ncc(F)c6sc(NC(=O)OC(C)(C)C)c(C#N)c56)c(F)c3n1)COC4)C2] | 606 |
| 85C | tert-Butyl (3-cyano-7-fluoro-4-(5-fluoro-3-(2-methyl-2,6-diazabicyclo[3.2.1]ocatn-6-yl)-7,9-dihydrofuro[3,4-f]quinazolin-6-yl)thieno[3,2-c]pyridin-2-yl)carbamate, Mix of Cis Isomers | 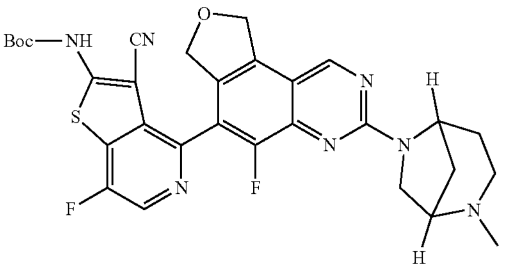 [SMILES: CN1CCC2CC1CN2c1ncc2c3c(c(-c4ncc(F)c5sc(NC(=O)OC(C)(C)C)c(C#N)c45)c(F)c2n1)COC3] | 606 |
| 86C | tert-Butyl (3-cyano-4-(3-(8-(dimethylamino)-2-oxa-6-azaspiro[3.4]octan-6-yl)-5-fluoro-7,9-dihydrofuro[3,4-f]quinazolin-6-yl)-7-fluorothieno[3,2-c]pyridin-2-yl)carbamate | 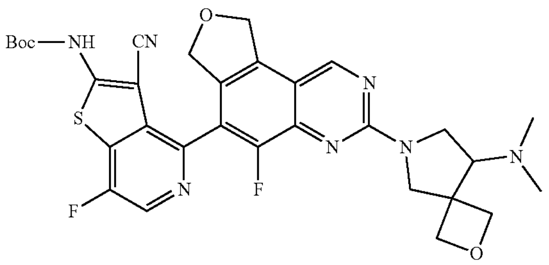 [SMILES: CN(C)C1CN(c2ncc3c4c(c(-c5ncc(F)c6sc(NC(=O)OC(C)(C)C)c(C#N)c56)c(F)c3n2)COC4)CC12COC2] | 636 |

TABLE 22-continued

| Preparation | Chemical Name | Structure | MS (ES) m/z (M + 1) |
|---|---|---|---|
| 87C | tert-Butyl (3-cyano-7-fluoro-4-(5-fluoro-3-(3-methyl-3,6-diazabicyclo[3.2.0]heptan-6-yl)-7,9-dihydrofuro[3,4-f]quinazolin-6-yl)thieno[3,2-c]pyridin-2-yl)carbamate, Mix of Cis Isomers | 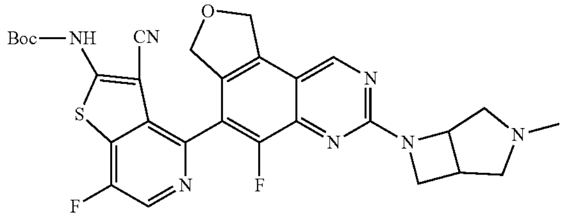 [SMILES: CN1CC2CN(c3ncc4c5c(c(-c6ncc(F)c7sc(NC(=O)OC(C)(C)C)c(C#N)c67)c(F)c4n3)COC5)C2C1] | 592 |
| 88C | tert-Butyl (3-cyano-7-fluoro-4-(5-fluoro-3-(8-(isopropylamino)-2-oxa-6-azaspiro[3.4]octan-6-yl)-7,9-dihydrofuro[3,4-f]quinazolin-6-yl)thieno[3,2-c]pyridin-2-yl)carbamate | 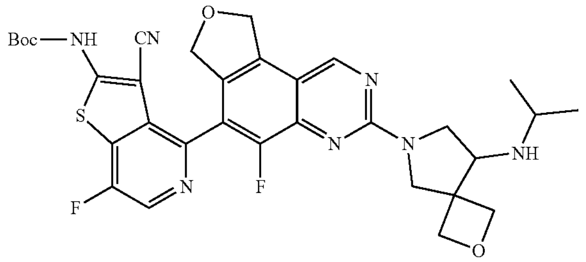 [SMILES: CC(C)NC1CN(c2ncc3c4c(c(-c5ncc(F)c6sc(NC(=O)OC(C)(C)C)c(C#N)c56)c(F)c3n2)COC4)CC12COC2] | 650 |
| 89C | tert-Butyl (3-cyano-4-(3-(3,3-dimethyl-4-(methylamino)pyrrolidin-1-yl)-5-fluoro-7,9-dihydrofuro[3,4-f]quinazolin-6-yl)-7-fluorothieno[3,2-c]pyridin-2-yl)carbamate | 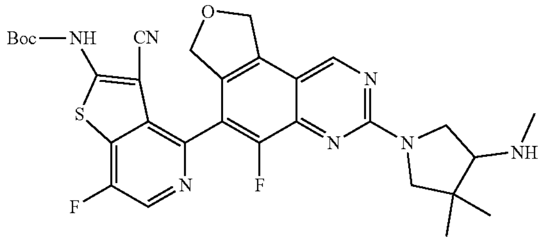 [SMILES: CNC1CN(c2ncc3c4c(c(-c5ncc(F)c6sc(NC(=O)OC(C)(C)C)c(C#N)c56)c(F)c3n2)COC4)CC1(C)C] | 608 |
| 90C | tert-Butyl (3-cyano-7-fluoro-4-(5-fluoro-3-((R)-7-(isopropylamino)-5-azaspiro[2.4]heptan-5-yl)-7,9-dihydrofuro[3,4-f]quinazolin-6-yl)thieno[3,2-c]pyridin-2-yl)carbamate | 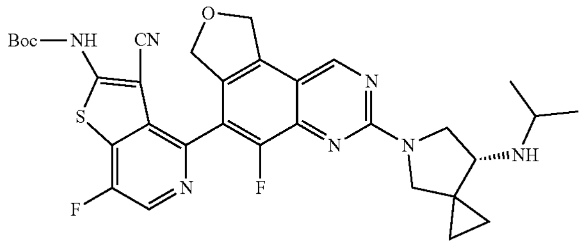 | 634 |
| 91C | tert-Butyl 1-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)octahydro-4H-pyrrolo[3,2-b]pyridine-4-carboxylate, Mix of Cis Isomers | 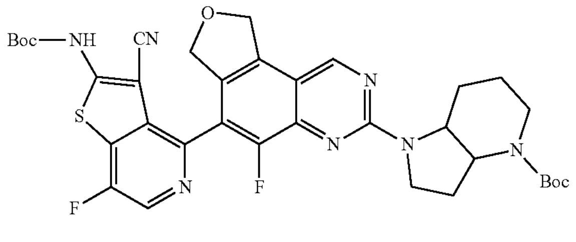 [SMILES: CC(C)(C)OC(=O)Nc1sc2c(F)cnc(-c3c4c(c5cnc(N6CCC7C6CCCN7C(=O)OC(C)(C)C)nc5c3F)COC4)c2c1C#N] | 706 |
| 92C | tert-Butyl (3-cyano-4-(3-((S)-3-(dimethylamino)pyrrolidin-1-yl)-5-fluoro-7,9-dihydrofuro[3,4-f]quinazolin-6-yl)benzo[b]thiophen-2-yl)carbamate | 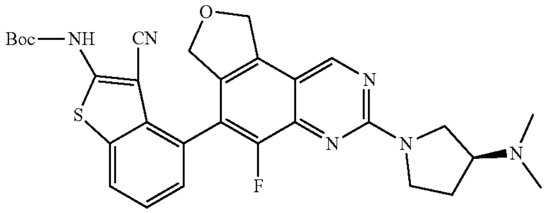 [SMILES: CN(C)[C@H]1CCN(c2ncc3c4c(c(-c5cccc6sc(NC(=O)OC(C)(C)C)c(C#N)c56)c(F)c3n2)COC4)C1] | 575 |

TABLE 22-continued

| Preparation | Chemical Name | Structure | MS (ES) m/z (M + 1) |
|---|---|---|---|
| 93C | tert-Butyl (3-cyano-7-fluoro-4-(5-fluoro-3-((3S,4S)-3-(isopropylamino)-4-methylpyrrolidin-1-yl)-7,9-dihydrofuro[3,4-f]quinazolin-6-yl)thieno[3,2-c]pyridin-2-yl)carbamate | 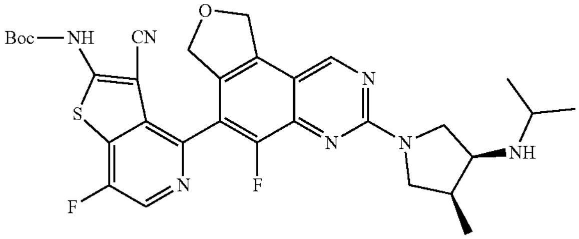 [SMILES: CC(C)N[C@@H]1CN(c2ncc3c4c(c(-c5ncc(F)c6sc(NC(=O)OC(C)(C)C)c(C#N)c56)c(F)c3n2)COC4)C[C@@H]1C] | 622 |
| 94C | tert-Butyl ((7S)-5-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)-5-azaspiro[2.4]heptan-7-yl)(methyl)carbamate | 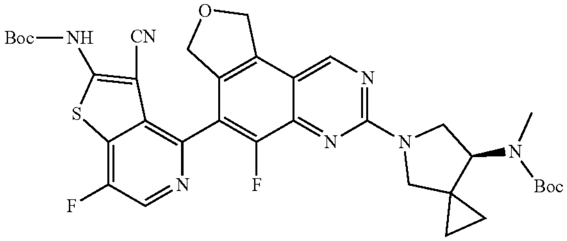 [SMILES: CN(C(=O)OC(C)(C)C)[C@@H]1CN(c2ncc3c4c(c(-c5ncc(F)c6sc(NC(=O)OC(C)(C)C)c(C#N)c56)c(F)c3n2)COC4)CC12CC2] | 706 |
| 95C | tert-Butyl (3-cyano-7-fluoro-4-(5-fluoro-3-(7-(isopropylamino)-5-azaspiro[2.4]heptan-5-yl)-7,9-dihydrofuro[3,4-f]quinazolin-6-yl)thieno[3,2-c]pyridin-2-yl)carbamate | 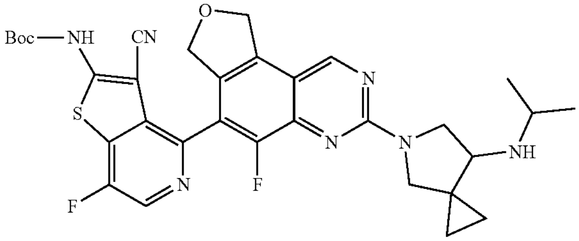 [SMILES: CC(C)NC1CN(c2ncc3c4c(c(-c5ncc(F)c6sc(NC(=O)OC(C)(C)C)c(C#N)c56)c(F)c3n2)COC4)CC12CC2] | 634 |
| 96C | tert-Butyl (3-cyano-7-fluoro-4-(5-fluoro-3-((S)-3-(4-methylpiperazin-1-yl)pyrrolidin-1-yl)-7,9-dihydrofuro[3,4-f]quinazolin-6-yl)thieno[3,2-c]pyridin-2-yl)carbamate | 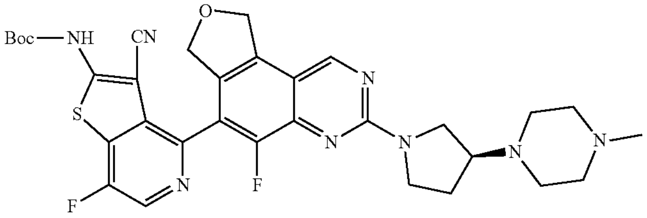 [SMILES: CN1CCN([C@H]2CCN(c3ncc4c5c(c(-c6ncc(F)c7sc(NC(=O)OC(C)(C)C)c(C#N)c67)c(F)c4n3)COC5)C2)CC1] | 649 |
| 97C | tert-Butyl (3-cyano-7-fluoro-4-(5-fluoro-3-((R)-3-(4-methylpiperazin-1-yl)pyrrolidin-1-yl)-7,9-dihydrofuro[3,4-f]quinazolin-6-yl)thieno[3,2-c]pyridin-2-yl)carbamate | 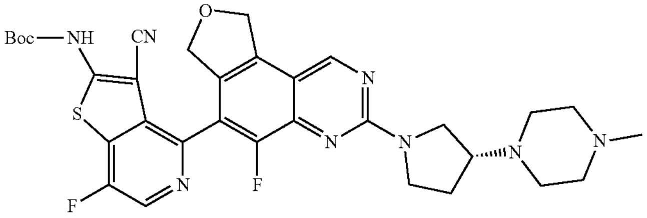 [SMILES: CN1CCN([C@@H]2CCN(c3ncc4c5c(c(-c6ncc(F)c7sc(NC(=O)OC(C)(C)C)c(C#N)c67)c(F)c4n3)COC5)C2)CC1] | 649 |
| 98C | tert-Butyl (3-cyano-7-fluoro-4-(5-fluoro-3-((3R,4S)-3-(isopropylamino)-4-methoxypyrrolidin-1-yl)-7,9-dihydrofuro[3,4-f]quinazolin-6-yl)thieno[3,2-c]pyridin-2-yl)carbamate | 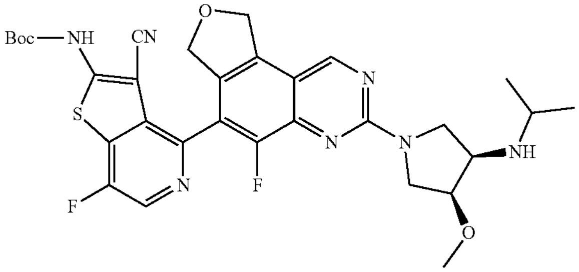 [SMILES: CO[C@H]1CN(c2ncc3c4c(c(-c5ncc(F)c6sc(NC(=O)OC(C)(C)C)c(C#N)c56)c(F)c3n2)COC4)C[C@H]1NC(C)C] | 638 |

TABLE 22-continued

| Preparation | Chemical Name | Structure | MS (ES) m/z (M + 1) |
|---|---|---|---|
| 99C | tert-Butyl (3-cyano-7-fluoro-4-(5-fluoro-3-((3R,4R)-3-(isopropylamino)-4-methoxypyrrolidin-1-yl)-7,9-dihydrofuro[3,4-f]quinazolin-6-yl)thieno[3,2-c]pyridin-2-yl)carbamate | 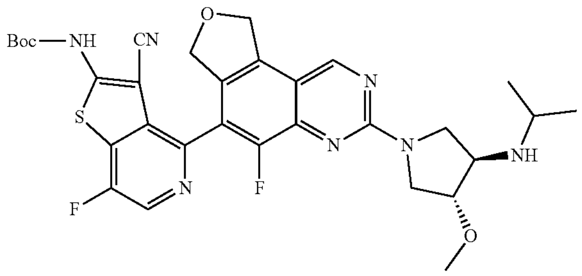 [SMILES: CO[C@@H]1CN(c2ncc3c4c(c(-c5ncc(F)c6sc(NC(=O)OC(C)(C)C)c(C#N)c56)c(F)c3n2)COC4)C[C@H]1NC(C)C] | 638 |
| 100C | tert-Butyl (3-cyano-7-fluoro-4-(5-fluoro-3-((3S)-3-(methyl(tetrahydrofuran-3-yl)amino)pyrrolidin-1-yl)-7,9-dihydrofuro[3,4-f]quinazolin-6-yl)thieno[3,2-c]pyridin-2-yl)carbamate | 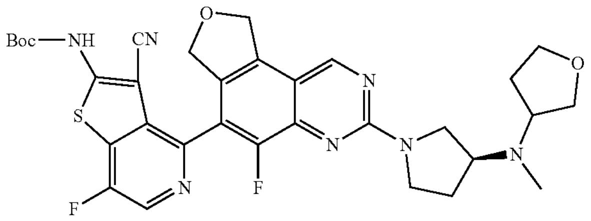 [SMILES: CN(C1CCOC1)[C@H]1CCN(c2ncc3c4c(c(-c5ncc(F)c6sc(NC(=O)OC(C)(C)C)c(C#N)c56)c(F)c3n2)COC4)C1] | 650 |
| 101C | tert-Butyl (3-cyano-7-fluoro-4-(5-fluoro-3-((S)-3-((2-methoxyethyl)(methyl)amino)pyrrolidin-1-yl)-7,9-dihydrofuro[3,4-f]quinazolin-6-yl)thieno[3,2-c]pyridin-2-yl)carbamate | 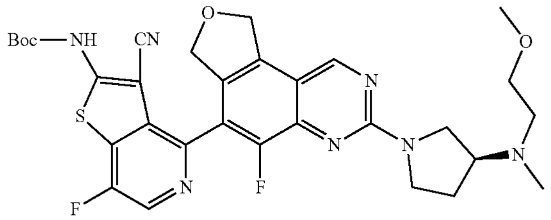 [SMILES: COCCN(C)[C@H]1CCN(c2ncc3c4c(c(-c5ncc(F)c6sc(NC(=O)OC(C)(C)C)c(C#N)c56)c(F)c3n2)COC4)C1] | 638 |
| 102C | tert-Butyl (3-cyano-7-fluoro-4-(5-fluoro-3-((3S)-3-((1-methoxypropan-2-yl)(methyl)amino)pyrrolidin-1-yl)-7,9-dihydrofuro[3,4-f]quinazolin-6-yl)thieno[3,2-c]pyridin-2-yl)carbamate | 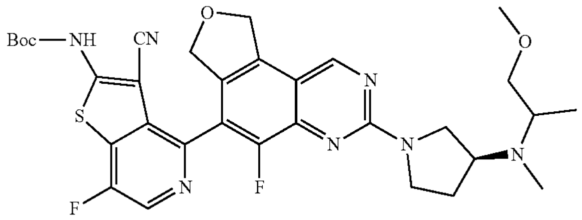 [SMILES: COCC(C)N(C)[C@H]1CCN(c2ncc3c4c(c(-c5ncc(F)c6sc(NC(=O)OC(C)(C)C)c(C#N)c56)c(F)c3n2)COC4)C1] | 652 |
| 103C | tert-Butyl (3-cyano-7-fluoro-4-(5-fluoro-3-((3S)-3-(methyl((tetrahydrofuran-2-yl)methyl)amino)pyrrolidin-1-yl)-7,9-dihydrofuro[3,4-f]quinazolin-6-yl)thieno[3,2-c]pyridin-2-yl)carbamate | 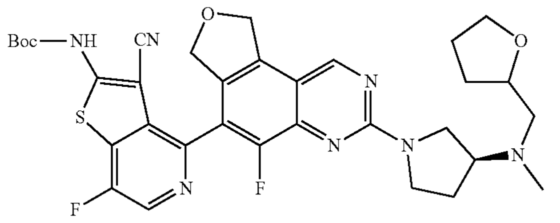 [SMILES: CN(CC1CCCO1)[C@H]1CCN(c2ncc3c4c(c(-c5ncc(F)c6sc(NC(=O)OC(C)(C)C)c(C#N)c56)c(F)c3n2)COC4)C1] | 664 |
| 104C | tert-Butyl (3-cyano-7-fluoro-4-(5-fluoro-3-((3S)-3-(methyl((tetrahydro-2H-pyran-2-yl)methyl)amino)pyrrolidin-1-yl)-7,9-dihydrofuro[3,4-f]quinazolin-6-yl)thieno[3,2-c]pyridin-2-yl)carbamate | 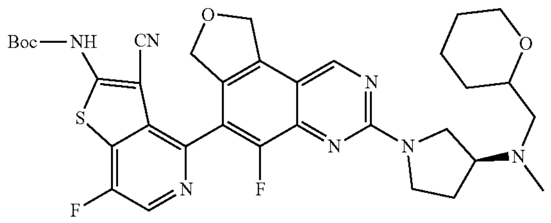 [SMILES: CN(CC1CCCCO1)[C@H]1CCN(c2ncc3c4c(c(-c5ncc(F)c6sc(NC(=O)OC(C)(C)C)c(C#N)c56)c(F)c3n2)COC4)C1] | 678 |

TABLE 22-continued

| Preparation | Chemical Name | Structure | MS (ES) m/z (M + 1) |
|---|---|---|---|
| 105C | tert-Butyl (3-cyano-7-fluoro-4-(5-fluoro-3-((S)-3-(methyl(2-(methylamino)-2-oxoethyl)amino)pyrrolidin-1-yl)-7,9-dihydrofuro[3,4-f]quinazolin-6-yl)thieno[3,2-c]pyridin-2-yl)carbamate | 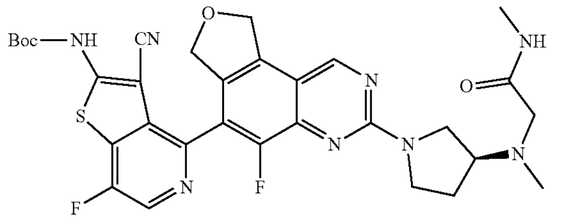 [SMILES: CNC(=O)CN(C)[C@H]1CCN(c2ncc3c4c(c(-c5ncc(F)c6sc(NC(=O)OC(C)(C)C)c(C#N)c56)c(F)c3n2)COC4)C1] | 651 |
| 106C | tert-Butyl (4-(3-((3S)-3-((1-amino-1-oxopropan-2-yl)(methyl)amino)pyrrolidin-1-yl)-5-fluoro-7,9-dihydrofuro[3,4-f]quinazolin-6-yl)-3-cyano-7-fluorothieno[3,2-c]pyridin-2-yl)carbamate | 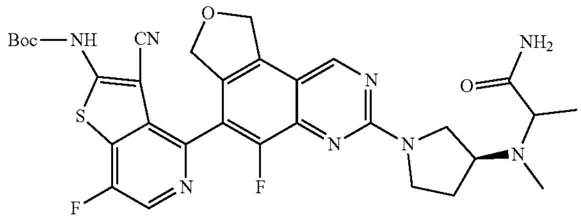 [SMILES: CC(C(N)=O)N(C)[C@H]1CCN(c2ncc3c4c(c(-c5ncc(F)c6sc(NC(=O)OC(C)(C)C)c(C#N)c56)c(F)c3n2)COC4)C1] | 651 |
| 107C [4] | (3S,4S)-1-(4-Bromo-5-chloro-1,3-dihydrofuro[3,4-f]quinazolin-7-yl)-4-(dimethylamino)pyrrolidin-3-ol | 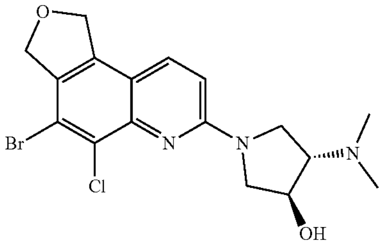 [SMILES: CN(C)[C@H]1CN(c2ccc3c4c(c(Br)c(Cl)c3n2)COC4)C[C@@H]1O] | 412 |
| 108C [4] | (3R,4R)-1-(4-Bromo-5-chloro-1,3-dihydrofuro[3,4-f]quinazolin-7-yl)-4-(dimethylamino)pyrrolidin-3-ol | 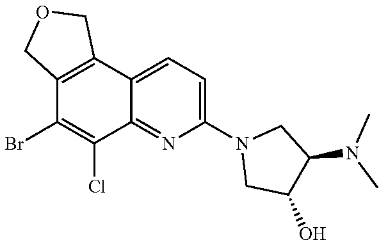 [SMILES: CN(C)[C@@H]1CN(c2ccc3c4c(c(Br)c(Cl)c3n2)COC4)C[C@H]1O] | 412 |
| 109C [4] | (3S,4R)-1-(4-Bromo-5-chloro-1,3-dihydrofuro[3,4-f]quinazolin-7-yl)-4-(dimethylamino)pyrrolidin-3-ol | 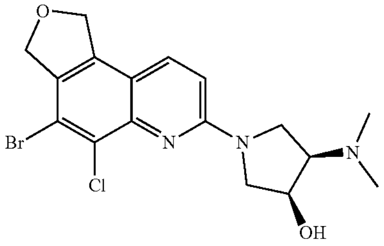 [SMILES: CN(C)[C@@H]1CN(c2ccc3c4c(c(Br)c(Cl)c3n2)COC4)C[C@@H]1O] | 412 |
| 110C [4] | (3R,4S)-1-(4-Bromo-5-chloro-1,3-dihydrofuro[3,4-f]quinolin-7-yl)-4-(dimethylamino)pyrrolidin-3-ol | 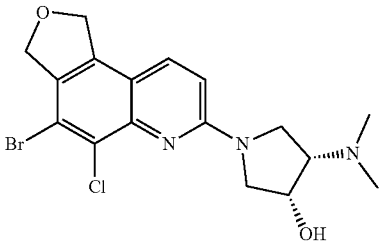 [SMILES: CN(C)[C@H]1CN(c2ccc3c4c(c(Br)c(Cl)c3n2)COC4)C[C@H]1O] | 412 |

TABLE 22-continued

| Preparation | Chemical Name | Structure | MS (ES) m/z (M + 1) |
|---|---|---|---|
| 111C | tert-Butyl (3-cyano-5-fluoro-4-(5-fluoro-3-((3S,4S)-4-(isopropylamino)-4-methylpyrrolidin-1-yl)-7,9-dihydrofuro[3,4-f]quinazolin-6-yl)benzo[b]thiophen-2-yl)carbamate | 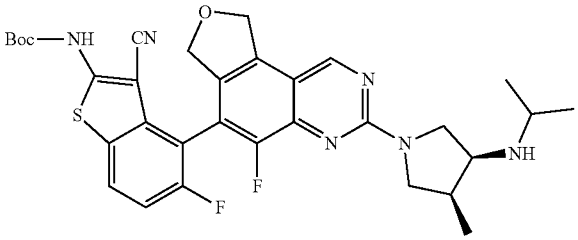 [SMILES: CC(C)N[C@@H]1CN(c2ncc3c4c(c(-c5c(F)ccc6sc(NC(=O)OC(C)(C)C)c(C#N)c56)c(F)c3n2)COC4)C[C@@H]1C] | 621 |
| 112C | tert-Butyl (3-cyano-4-(3-(3-(dimethylamino)-3-(hydroxymethyl)pyrrolidin-1-yl)-5-fluoro-7,9-dihydrofuro[3,4-f]quinazolin-6-yl)-5-fluorobenzo[b]thiophen-2-yl)carbamate | 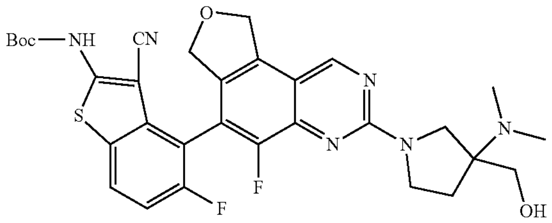 [SMILES: CN(C)C1(CO)CCN(c2ncc3c4c(c(-c5c(F)ccc6sc(NC(=O)OC(C)(C)C)c(C#N)c56)c(F)c3n2)COC4)C1] | 623 |
| 113C | tert-Butyl (4-(5-chloro-3-((3R,4R)-3-(dimethylamino)-4-hydroxypyrrolidin-1-yl)-7,9-dihydrofuro[3,4-f]quinazolin-6-yl)-3-cyano-7-fluorothieno[3,2-c]pyridin-2-yl)carbamate formic acid | 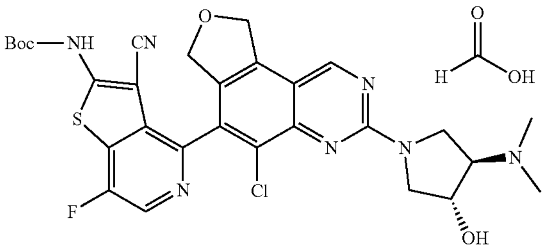 | 626 |
| 114C | tert-Butyl (4-(5-chloro-3-((3R,4S)-3-(dimethylamino)-4-hydroxypyrrolidin-1-yl)-7,9-dihydrofuro[3,4-f]quinazolin-6-yl)-3-cyano-7-fluorothieno[3,2-c]pyridin-2-yl)carbamate formic acid | 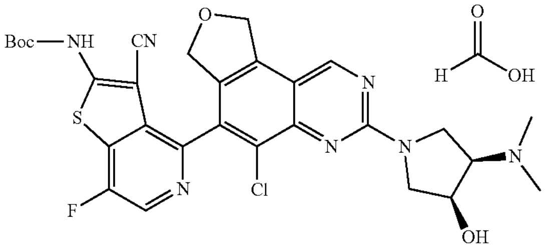 | 626 |
| 115C | tert-Butyl (4-(5-chloro-3-((3S,4R)-3-(dimethylamino)-4-hydroxypyrrolidin-1-yl)-7,9-dihydrofuro[3,4-f]quinazolin-6-yl)-3-cyano-7-fluorothieno[3,2-c]pyridin-2-yl)carbamate formic acid | 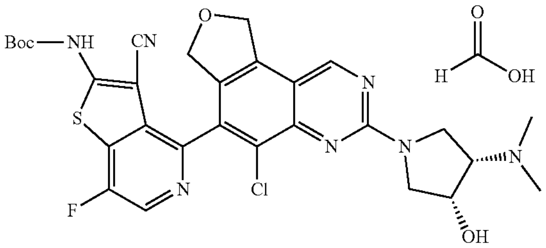 | 626 |
| 116C | tert-Butyl (4-(5-chloro-3-((3S,4R)-3-hydroxy-4-(isopropyl(methyl)amino) pyrrolidin-1-yl)-7,9-dihydrofuro[3,4-f]quinazolin-6-yl)-3-cyano-7-fluorothieno[3,2-c]pyridin-2-yl)carbamate formic acid | 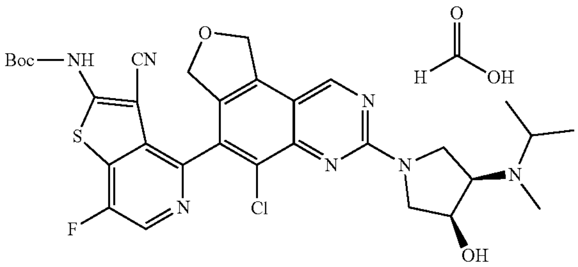 | 654 |

TABLE 22-continued

| Preparation | Chemical Name | Structure | MS (ES) m/z (M + 1) |
|---|---|---|---|
| 117C | tert-Butyl (4-(5-chloro-3-((3S,4S)-3-hydroxy-4-(isopropyl(methyl)amino)pyrrolidin-1-yl)-7,9-dihydrofuro[3,4-f]quinazolin-6-yl)-3-cyano-7-fluorothieno[3,2-c]pyridin-2-yl)carbamate formic acid | 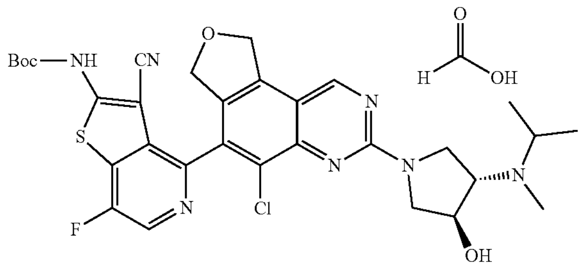 | 654 |
| 118C | tert-Butyl (4-(5-chloro-3-((2S,3S)-3-(((S)-2-hydroxypropyl)amino)-2-methylpyrrolidin-1-yl)-7,9-dihydrofuro[3,4-f]quinazolin-6-yl)-3-cyano-7-fluorothieno[3,2-c]pyridin-2-yl)carbamate | 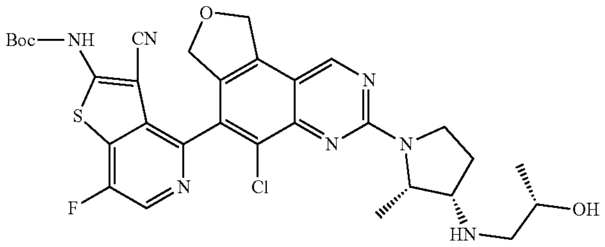 [SMILES: C[C@H](O)CN[C@H]1CCN(c2ncc3c4c(c(-c5ncc(F)c6sc(NC(=O)OC(C)(C)C)c(C#N)c56)c(Cl)c3n2)COC4)[C@H]1C] | 654 |
| 119C | tert-Butyl (4-(3-((2S,3S)-3-amino-2-methylpyrrolidin-1-yl)-5-chloro-7,9-dihydrofuro[3,4-f]quinazolin-6-yl)-3-cyano-7-fluorothieno[3,2-c]pyridin-2-yl)carbamate | 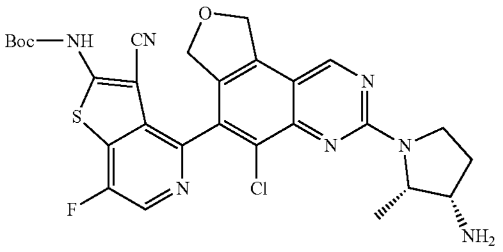 | 596 |
| 120C | tert-Butyl (4-(5-chloro-3-((S)-3-(isopropylamino)pyrrolidin-1-yl)-7,9-dihydrofuro[3,4-f]quinazolin-6-yl)-3-cyano-7-fluorothieno[3,2-c]pyridin-2-yl)carbamate formic acid | 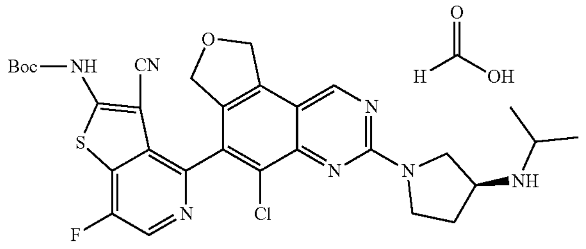 | 624 |
| 121C | tert-Butyl (4-(5-chloro-3-((2S,3R)-3-((dimethylamino)methyl)-2-methylpyrrolidin-1-yl)-7,9-dihydrofuro[3,4-f]quinazolin-6-yl)-3-cyano-7-fluorothieno[3,2-c]pyridin-2-yl)carbamate | 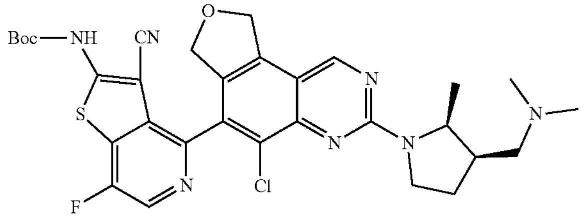 [SMILES: C[C@H]1[C@@H](CN(C)C)CCN1c1ncc2c3c(c(-c4ncc(F)c5sc(NC(=O)OC(C)(C)C)c(C#N)c45)c(Cl)c2n1)COC3] | 638 |
| 122C | tert-Butyl (4-(5-chloro-3-((2S,3S)-3-(((S)-2-hydroxypropyl)(methyl)amino)-2-methylpyrrolidin-1-yl)-7,9-dihydrofuro[3,4-f]quinazolin-6-yl)-3-cyano-7-fluorothieno[3,2-c]pyridin-2-yl)carbamate | 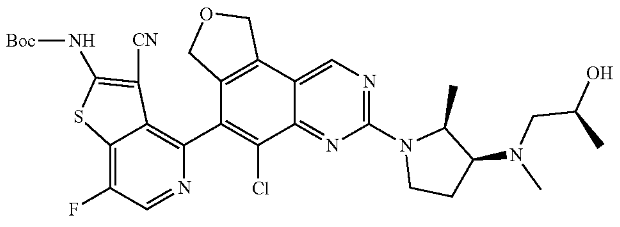 [SMILES: C[C@H](O)CN(C)[C@H]1CCN(c2ncc3c4c(c(-c5ncc(F)c6sc(NC(=O)OC(C)(C)C)c(C#N)c56)c(Cl)c3n2)COC4)[C@H]1C] | 668 |

TABLE 22-continued

| Preparation | Chemical Name | Structure | MS (ES) m/z (M + 1) |
|---|---|---|---|
| 123C | tert-Butyl (4-(5-chloro-3-((2S,3S)-3-(((R)-2-hydroxypropyl)(methyl)amino)-2-methylpyrrolidin-1-yl)-7,9-dihydrofuro[3,4-f]quinazolin-6-yl)-3-cyano-7-fluorothieno[3,2-c]pyridin-2-yl)carbamate | 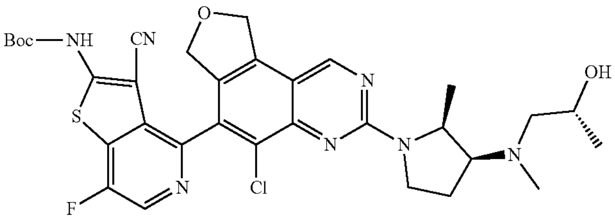 [SMILES: C[C@@H](O)CN(C)[C@H]1CCN(c2ncc3c4c(c(-c5ncc(F)c6sc(NC(=O)OC(C)(C)C)c(C#N)c56)c(Cl)c3n2)COC4)[C@H]1C] | 668 |
| 124C | tert-Butyl (4-(5-chloro-3-((2S,3S)-3-(isopropylamino)-2-methylpyrrolidin-1-yl)-7,9-dihydrofuro[3,4-f]quinazolin-6-yl)-3-cyano-7-fluorothieno[3,2-c]pyridin-2-yl)carbamate | 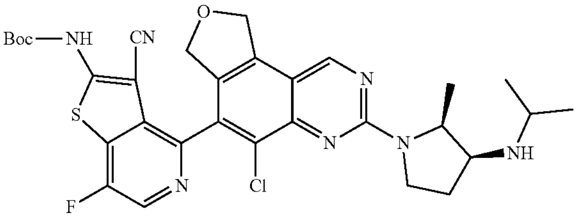 | 638 |
| 125C | tert-Butyl (3-cyano-5-fluoro-4-(5-fluoro-3-((2R,3S)-3-(isopropylamino)-2-methylpyrrolidin-1-yl)-7,9-dihydrofuro[3,4-f]quinazolin-6-yl)benzo[b]thiophen-2-yl)carbamate | 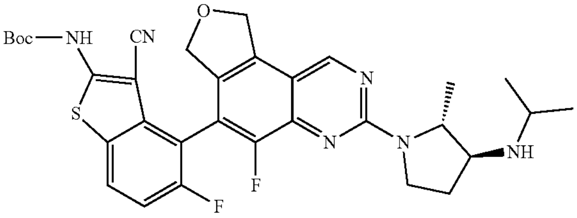 [SMILES: CC(C)N[C@H]1CCN(c2ncc3c4c(c(-c5c(F)ccc6sc(NC(=O)OC(C)(C)C)c(C#N)c56)c(F)c3n2)COC4)[C@@H]1C] | 621 |
| 126C | tert-Butyl (3-cyano-5-fluoro-4-(5-fluoro-3-((3R,4R)-3-(isopropylamino)-4-methoxypyrrolidin-1-yl)-7,9-dihydrofuro[3,4-f]quinazolin-6-yl)benzo[b]thiophen-2-yl)carbamate | 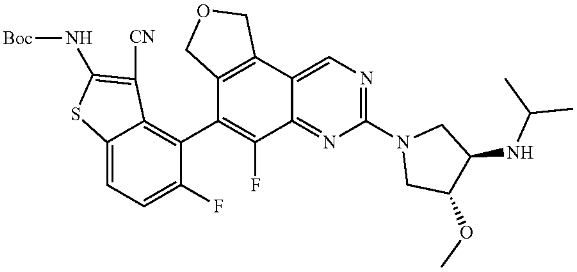 [SMILES: CO[C@@H]1CN(c2ncc3c4c(c(-c5c(F)ccc6sc(NC(=O)OC(C)(C)C)c(C#N)c56)c(F)c3n2)COC4)C[C@H]1NC(C)C] | 637 |
| 127C | tert-Butyl (3-cyano-5-fluoro-4-(5-fluoro-3-((3R,4S)-3-(isopropylamino)-4-methoxypyrrolidin-1-yl)-7,9-dihydrofuro[3,4-f]quinazolin-6-yl)benzo[b]thiophen-2-yl)carbamate | 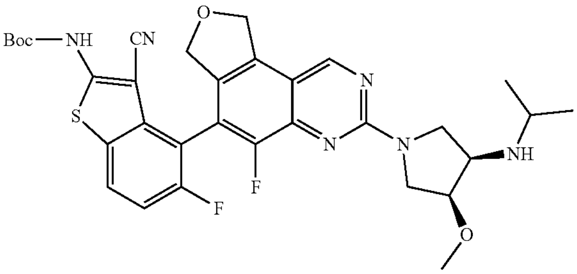 [SMILES: CO[C@H]1CN(c2ncc3c4c(c(-c5c(F)ccc6sc(NC(=O)OC(C)(C)C)c(C#N)c56)c(F)c3n2)COC4)C[C@H]1NC(C)C] | 637 |
| 128C | tert-Butyl (3-cyano-4-(3-(6-(dimethylamino)-4-azaspiro[2.4]heptan-4-yl)-5-fluoro-7,9-dihydrofuro[3,4-f]quinazolin-6-yl)-7-fluorothieno[3,2-c]pyridin-2-yl)carbamate | 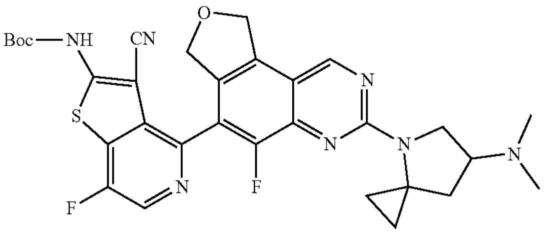 [SMILES: CN(C)C1CN(c2ncc3c4c(c(-c5ncc(F)c6sc(NC(=O)OC(C)(C)C)c(C#N)c56)c(F)c3n2)COC4)C2(CC2)C1] | 620 |

TABLE 22-continued

| Preparation | Chemical Name | Structure | MS (ES) m/z (M + 1) |
|---|---|---|---|
| 129C | tert-Butyl (3-cyano-4-(3-(6-(dimethylamino)-2-azabicyclo[3.2.0]heptan-2-yl)-5-fluoro-7,9-dihydrofuro[3,4-f]quinazolin-6-yl)-7-fluorothieno[3,2-c]pyridin-2-yl)carbamate | 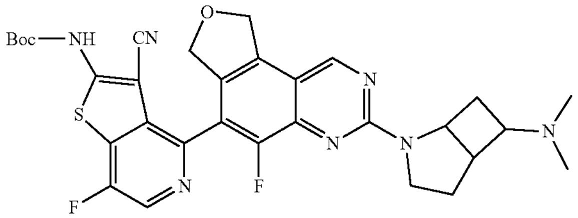 [SMILES: CN(C)C1CC2C1CCN2c1ncc2c3c(c(-c4ncc(F)c5sc(NC(=O)OC(C)(C)C)c(C#N)c45)c(F)c2n1)COC3] | 620 |
| 130C | tert-Butyl (3-cyano-4-(3-(3-((dimethylamino)methyl)-2-methylpyrrolidin-1-yl)-5-fluoro-7,9-dihydrofuro[3,4-f]quinazolin-6-yl)-7-fluorothieno[3,2-c]pyridin-2-yl)carbamate, Mix of Cis Isomers | 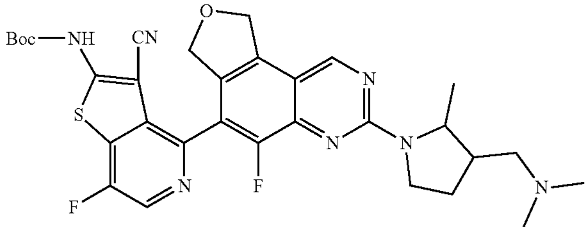 [SMILES: CC1C(CN(C)C)CCN1c1ncc2c3c(c(-c4ncc(F)c5sc(NC(=O)OC(C)(C)C)c(C#N)c45)c(F)c2n1)COC3] | 622 |
| 131C | tert-Butyl (3-cyano-7-fluoro-4-(5-fluoro-3-((3S,4S)-3-hydroxy-4-(isopropyl(methyl)amino) pyrrolidin-1-yl)-7,9-dihydrofuro[3,4-f]quinazolin-6-yl)thieno[3,2-c]pyridin-2-yl)carbamate | 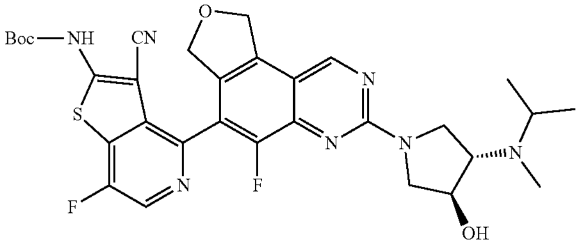 [SMILES: CC(C)N(C)[C@H]1CN(c2ncc3c4c(c(-c5ncc(F)c6sc(NC(=O)OC(C)(C)C)c(C#N)c56)c(F)c3n2)COC4)C[C@@H]1O] | 638 |
| 132C | tert-Butyl (4-(3-((2S)-3-(bicyclo[1.1.1]pentan-1-ylamino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 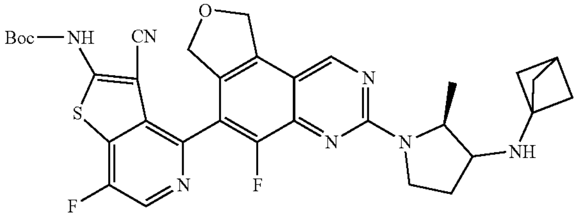 [SMILES: C[C@H]1C(NC23CC(C2)C3)CCN1c1ncc2c3c(c(-c4ncc(F)c5sc(NC(=O)OC(C)(C)C)c(C#N)c45)c(F)c2n1)COC3] | 646 |
| 133C | tert-Butyl (3-cyano-7-fluoro-4-(5-fluoro-3-((2S,3S)-3-((2-fluoroethyl)amino)-2-methylpyrrolidin-1-yl)-7,9-dihydrofuro[3,4-f]quinazolin-6-yl)thieno[3,2-c]pyridin-2-yl)carbamate | 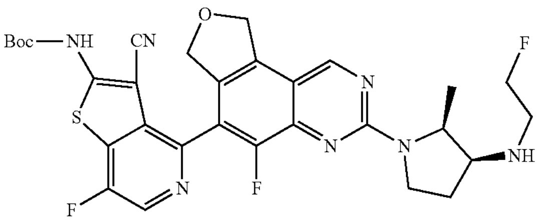 [SMILES: C[C@H]1[C@@H](NCCF)CCN1c1ncc2c3c(c(-c4ncc(F)c5sc(NC(=O)OC(C)(C)C)c(C#N)c45)c(F)c2n1)COC3] | 626 |
| 134C | tert-Butyl (7-chloro-3-cyano-4-(3-((S)-3-(dimethylamino)pyrrolidin-1-yl)-5-fluoro-7,9-dihydrofuro[3,4-f]quinazolin-6-yl)thieno[3,2-c]pyridin-2-yl)carbamate | 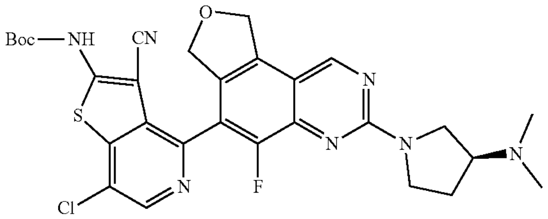 [SMILES: CN(C)[C@H]1CCN(c2ncc3c4c(c(-c5ncc(Cl)c6sc(NC(=O)OC(C)(C)C)c(C#N)c56)c(F)c3n2)COC4)C1] | 610 |

TABLE 22-continued

| Preparation | Chemical Name | Structure | MS (ES) m/z (M + 1) |
|---|---|---|---|
| 135C | tert-Butyl (7-chloro-3-cyano-4-(3-((3R,4S)-3-(dimethylamino)-4-hydroxypyrrolidin-1-yl)-5-fluoro-7,9-dihydrofuro[3,4-f]quinazolin-6-yl)thieno[3,2-c]pyridin-2-yl)carbamate | 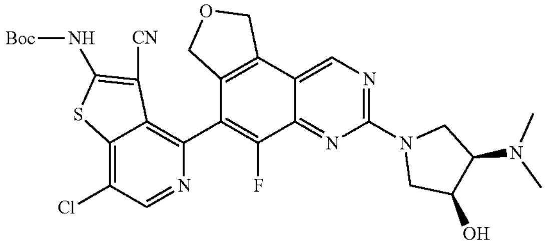 [SMILES: CN(C)[C@@H]1CN(c2ncc3c4c(c(-c5ncc(Cl)c6sc(NC(=O)OC(C)(C)C)c(C#N)c56)c(F)c3n2)COC4)C[C@@H]1O] | 626 |
| 136C | tert-Butyl (7-chloro-3 cyano-4-(5-fluoro-3-((3S,4S)-3-hydroxy-4-(isopropyl(methyl)amino) pyrrolidin-1-yl)-7,9-dihydrofuro[3,4-f]quinazolin-6-yl)thieno[3,2-c]pyridin-2-yl)carbamate | 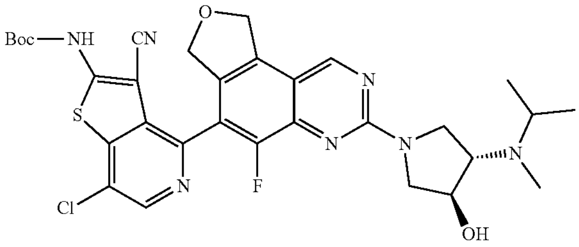 [SMILES: CC(C)N(C)[C@H]1CN(c2ncc3c4c(c(-c5ncc(Cl)c6sc(NC(=O)OC(C)(C)C)c(C#N)c56)c(F)c3n2)COC4)C[C@@H]1O] | 654 |
| 137C | tert-Butyl (4-(3-((2S,3S)-3-amino-2-methylpyrrolidin-1-yl)-5-fluoro-7,9-dihydrofuro[3,4-f]quinazolin-6-yl)-7-chloro-3-cyanothieno[3,2-c]pyridin-2-yl)carbamate | 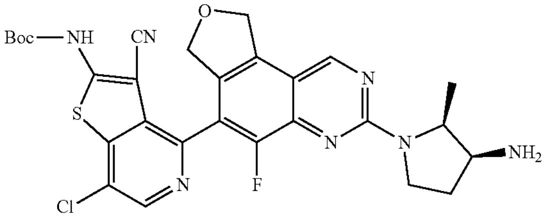 [SMILES: C[C@H]1[C@@H](N)CCN1c1ncc2c3c(c(-c4ncc(Cl)c5sc(NC(=O)OC(C)(C)C)c(C#N)c45)c(F)c2n1)COC3] | 596 |
| 382D | tert-Butyl (4-(5-chloro-3-((3R,4S)-3-hydroxy-4-(isopropyl(methyl)amino) pyrrolidin-1-yl)-7,9-dihydrofuro[3,4-f]quinzolin-6-yl)-3-cyano-7-fluorothieno[3,2-c]pyridin-2-yl)carbamate formic acid | 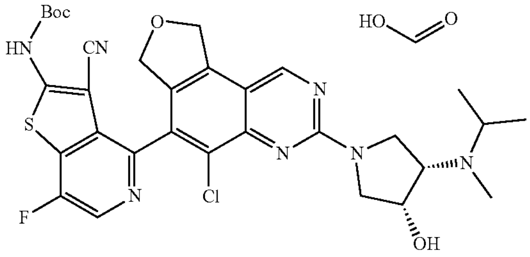 [SMILES: CC(C)N(C)[C@H]1CN(c2ncc3c4c(c(-c5ncc(F)c6sc(NC(=O)OC(C)(C)C)c(C#N)c56)c(Cl)c3n2)COC4)C[C@H]1O ; O=CO] | 654 |
| 383D | tert-Butyl (4-(5-chloro-3-((3R,4R)-3-hydroxy-4-(isopropyl(methyl)amino) pyrrolidin-1-yl)-7,9-dihydrofuro[3,4-f]quinazolin-6-yl)-3-cyano-7-fluorothieno[3,2-c]pyridin-2-yl)carbamate | 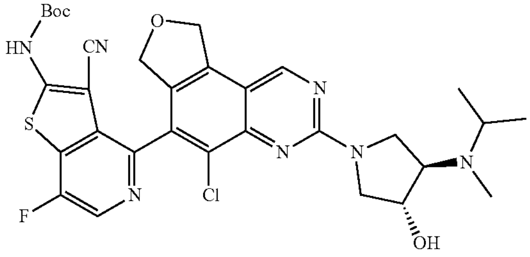 [SMILES: CC(C)N(C)[C@@H]1CN(c2ncc3c4c(c(-c5ncc(F)c6sc(NC(=O)OC(C)(C)C)c(C#N)c56)c(Cl)c3n2)COC4)C[C@H]1O] | 654 |
| 384D | tert-Butyl (4-(5-chloro-3-((2S,3R)-2-methyl-3-((methylamino)methyl)py-rrolidin-1-yl)-7,9-dihydrofuro[3,4-f]quinazolin-6-yl)-3-cyano-7-flurothieno[3,2-c]pyridin-2-yl)carbamate | 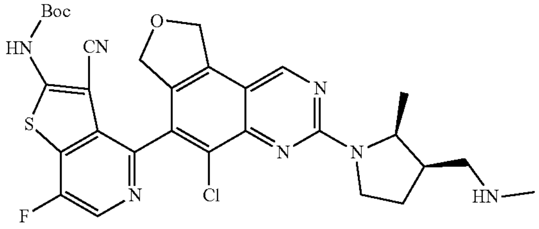 [SMILES: CNC[C@H]1CCN(c2ncc3c4c(c(-c5ncc(F)c6sc(NC(=O)OC(C)(C)C)c(C#N)c56)c(Cl)c3n2)COC4)[C@H]1C] | 624 |

TABLE 22-continued

| Preparation | Chemical Name | Structure | MS (ES) m/z (M + 1) |
|---|---|---|---|
| 385D | tert-Butyl (4-(5-chloro-3-((2R,3R)-2-methyl-3-(4-methylpiperazin-1-yl)pyrrolidin-1-yl)-7,9-dihydrofuro[3,4-f]quinazolin-6-yl)-3-cyano-7-fluorothieno[3,2-c]pyridin-2-yl)carbamate | 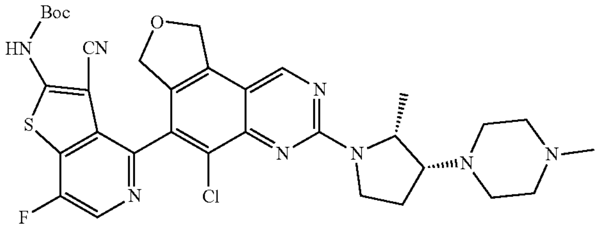 [SMILES: C[C@@H]1[C@H](N2CCN(C)CC2)CCN1c1ncc2c3c(c(-c4ncc(F)c5sc(NC(=O)OC(C)(C)C)c(C#N)c45)c(Cl)c2n1)COC3] | 679 |
| 386D | tert-Butyl (4-(5-chloro-3-((2S,3S)-2-methyl-3-(4-methylpiperazin-1-yl)pyrrolidin-1-yl)-7,9-dihydrofuro[3,4-f]quinazolin-6-yl)-3-cyano-7-fluorothieno[3,2-c]pyridin-2-yl)carbamate | 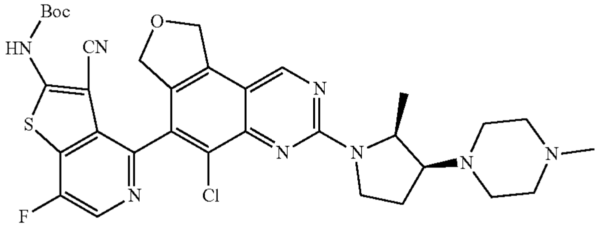 [SMILES: C[C@H]1[C@@H](N2CCN(C)CC2)CCN1c1ncc2c3c(c(-c4ncc(F)c5sc(NC(=O)OC(C)(C)C)c(C#N)c45)c(Cl)c2n1)COC3] | 679 |
| 387D | tert-Butyl (4-(5-chloro-3-((2S,3R)-2-methyl-3-(4-methylpiperazin-1-yl)pyrrolidin-1-yl)-7,9-dihydrofuro[3,4-f]quinazolin-6-yl)-3-cyano-7-fluorothieno[3,2-c]pyridin-2-yl)carbamate | 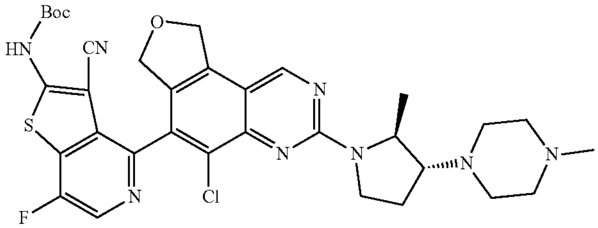 [SMILES: C[C@H]1[C@H](N2CCN(C)CC2)CCN1c1ncc2c3c(c(-c4ncc(F)c5sc(NC(=O)OC(C)(C)C)c(C#N)c45)c(Cl)c2n1)COC3] | 679 |
| 388D | tert-Butyl (4-(5-chloro-3-((R)-3-(4-methylpiperazin-1-yl)pyrrolidin-1-yl)-7,9-dihydrofuro[3,4-f]quinazolin-6-yl)-3-cyano-7-fluorothieno[3,2-c]pyridin-2-yl)carbamate | 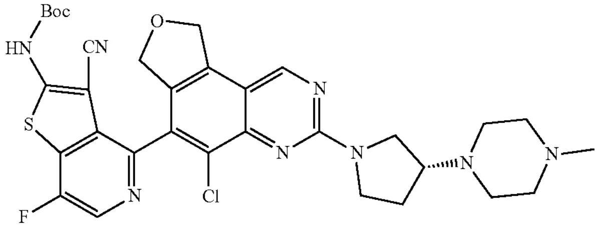 [SMILES: CN1CCN([C@@H]2CCN(c3ncc4c5c(c(-c6ncc(F)c7sc(NC(=O)OC(C)(C)C)c(C#N)c67)c(Cl)c4n3)COC5)C2)CC1] | 665 |
| 389D | tert-Butyl (4-(5-chloro-3-((S)-3-(4-methylpiperazin-1-yl)pyrrolidin-1-yl)-7,9-dihydrofuro[3,4-f]quinazolin-6-yl)-3-cyano-7-fluorothieno[3,2-c]pyridin-2-yl)carbamate | 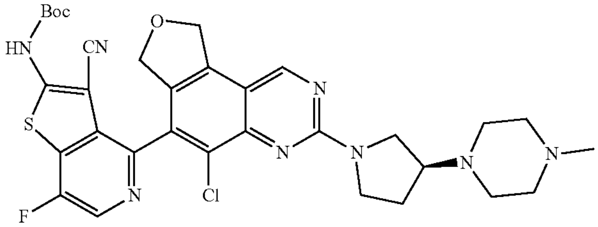 [SMILES: CN1CCN([C@H]2CCN(c3ncc4c5c(c(-c6ncc(F)c7sc(NC(=O)OC(C)(C)C)c(C#N)c67)c(Cl)c4n3)COC5)C2)CC1] | 665 |
| 390D | tert-Butyl (3-cyano-4-(3-(3-(dimethylamino)-1-oxa-7-azaspiro[4.4]nonan-7-yl)-5-fluoro-7,9-dihydrofuro[3,4-f]quinazolin-6-yl)-7-fluorothieno[3,2-c]pyridin-2-yl)carbamate | 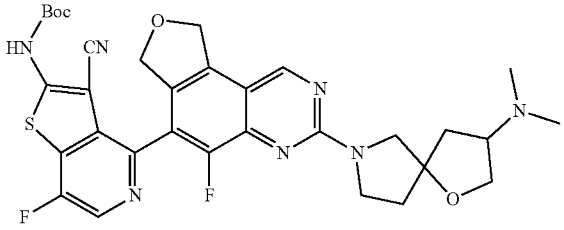 [SMILES: CN(C)C1COC2(CCN(c3ncc4c5c(c(-c6ncc(F)c7sc(NC(=O)OC(C)(C)C)c(C#N)c67)c(F)c4n3)COC5)C2)C1] | 650 |

TABLE 22-continued

| Preparation | Chemical Name | Structure | MS (ES) m/z (M + 1) |
|---|---|---|---|
| 391D | tert-Butyl (3-cyano-7-fluoro-4-(5-fluoro-3-(6-(methyl-d3)-2,6-diazaspiro[3.4]octan-2-yl)-7,9-dihydrofuro[3,4-f]quinazolin-6-yl)thieno[3,2-c]pyridin-2-yl)carbamate | 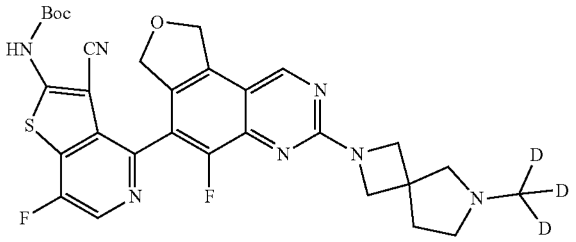 [SMILES: [2H]C([2H])([2H])N1CCC2(CN(c3ncc4c5c(c(-c6ncc(F)c7sc(NC(=O)OC(C)(C)C)c(C#N)c67)c(F)c4n3)COC5)C2)C1] | 609 |
| 392D | tert-Butyl (3-cyano-7-fluoro-4-(5-fluoro-3-(3-(4-methylpiperazin-1-yl)azetidin-1-yl)-7,9-dihydrofuro[3,4-f]quinazolin-6-yl)thieno[3,2-c]pyridin-2-yl)carbamate | 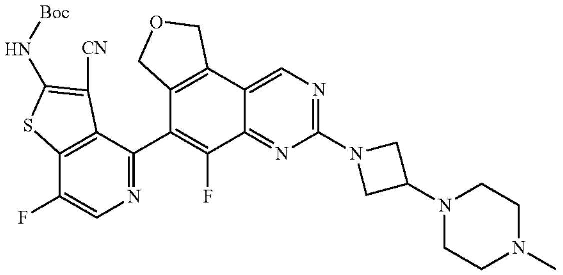 [SMILES: CN1CCN(C2CN(c3ncc4c5c(c(-c6ncc(F)c7sc(NC(=O)OC(C)(C)C)c(C#N)c67)c(F)c4n3)COC5)C2)CC1] | 635 |
| 393D | tert-Butyl (3-cyano-7-fluoro-4-(5-fluoro-3-(3-(4-methylpiperazin-1-yl)azetidin-1-yl)-7,9-dihydrofuro[3,4-f]quinazolin-6-yl)thieno[3,2-c]pyridin-2-yl)carbamate | 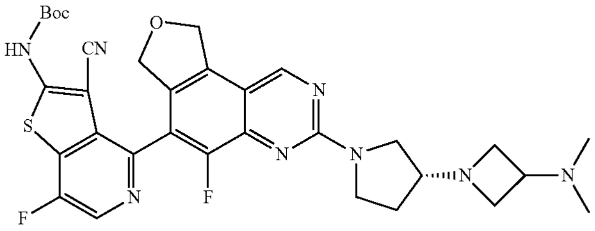 [SMILES: CN(C)C1CN([C@@H]2CCN(c3ncc4c5c(c(-c6ncc(F)c7sc(NC(=O)OC(C)(C)C)c(C#N)c67)c(F)c4n3)COC5)C2)C1] | 649 |
| 394D | tert-Butyl (3-cyano-7-fluoro-4-(5-fluoro-3-(3-(4-methylpiperazin-1-yl)azetidin-1-yl)-7,9-dihydrofuro[3,4-f]quinazolin-6-yl)thieno[3,2-c]pyridin-2-yl)carbamate | 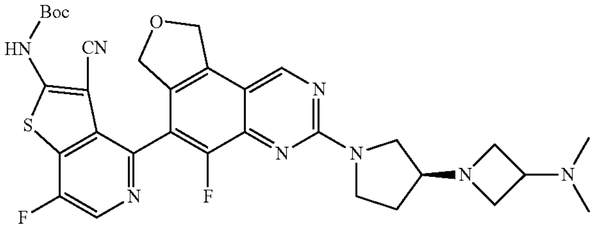 [SMILES: CN(C)C1CN([C@H]2CCN(c3ncc4c5c(c(-c6ncc(F)c7sc(NC(=O)OC(C)(C)C)c(C#N)c67)c(F)c4n3)COC5)C2)C1] | 649 |
| 395D | tert-Butyl (3-cyano-7-fluoro-4-(5-fluoro-3-(3-(4-methylpiperazin-1-yl)azetidin-1-yl)-7,9-dihydrofuro[3,4-f]quinazolin-6-yl)thieno[3,2-c]pyridin-2-yl)carbamate | 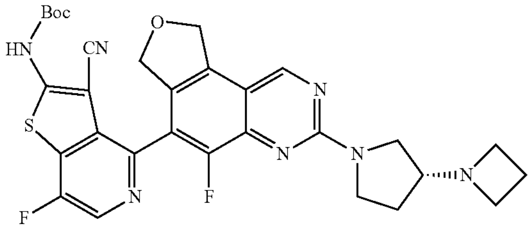 [SMILES: CC(C)(C)OC(=O)Nc1sc2c(F)cnc(-c3c4c(c5cnc(N6CC[C@@H](N7CCC7)C6)nc5c3F)COC4)c2c1C#N] | 606 |
| 396D[9] | tert-Butyl (3-cyano-7-fluoro-4-(5-fluoro-3-(3-(4-methylpiperazin-1-yl)azetidin-1-yl)-7,9-dihydrofuro[3,4-f]quinazolin-6-yl)thieno[3,2-c]pyridin-2-yl)carbamate | 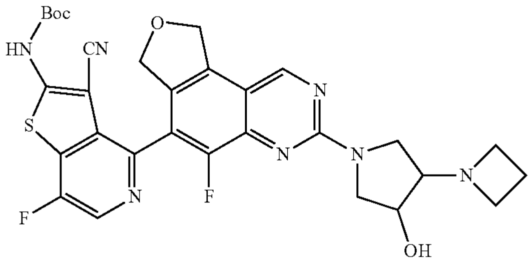 [SMILES: CC(C)(C)OC(=O)Nc1sc2c(F)cnc(-c3c4c(c5cnc(N6CC(O)C(N7CCC7)C6)nc5c3F)COC4)c2c1C#N] | 622 |

TABLE 22-continued

| Preparation | Chemical Name | Structure | MS (ES) m/z (M + 1) |
|---|---|---|---|
| 397D | tert-Butyl (3-cyano-7-fluoro-4-(5-fluoro-3-((R)-3-(3-(2-hydroxypropan-2-yl)azetidin-1-yl)pyrrolidin-1-yl)-7,9-dihydrofuro[3,4-f]quinazolin-6-yl)thieno[3,2-c]pyridin-2-yl)carbamate | 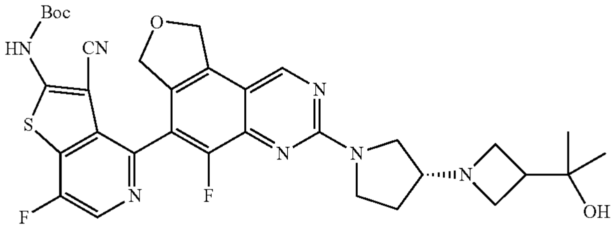 [SMILES: CC(C)(C)OC(=O)Nc1sc2c(F)cnc(-c3c4c(c5cnc(N6CC[C@@H](N7CC(C(C)(C)O)C7)C6)nc5c3F)COC4)c2c1C#N] | 664 |
| 398D | tert-Butyl (3-cyano-4-(3-((3S,3'R)-3-(dimethylamino)-[1,3'-bipyrrolidin]-1'-yl)-5-fluoro-7,9-dihydrofuro[3,4-f]quinazolin-6-yl)-7-fluorothieno[3,2-c]pyridin-2-yl)carbamate | 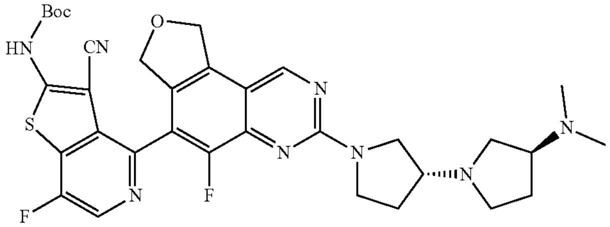 [SMILES: CN(C)[C@H]1CCN([C@@H]2CCN(c3ncc4c5c(c(-c6ncc(F)c7sc(NC(=O)OC(C)(C)C)c(C#N)c67)c(F)c4n3)COC5)C2)C1] | 663 |
| 399D | tert-Butyl (3-cyano-4-(3-((3S,3'S)-3-(dimethylamino)-[1,3'-bipyrrolidin]-1'-yl)-5-fluoro-7,9-dihydrofuro[3,4-f]quinazolin-6-yl)-7-fluorothieno[3,2-c]pyridin-2-yl)carbamate | 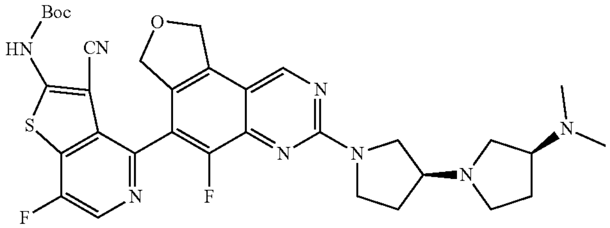 [SMILES: CN(C)[C@H]1CCN([C@H]2CCN(c3ncc4c5c(c(-c6ncc(F)c7sc(NC(=O)OC(C)(C)C)c(C#N)c67)c(F)c4n3)COC5)C2)C1] | 663 |
| 400D | tert-Butyl (4-(3-((S)-[1,3'-bipyrrolidin]-1'-yl)-5-fluoro-7,9-dihydrofuro[3,4-f]quinazolin-6-yl)-3-cyano-7-fluorothieno[3,2-c]pyridin-2-yl)carbamate | 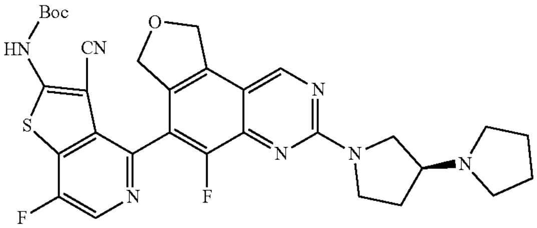 [SMILES: CC(C)(C)OC(=O)Nc1sc2c(F)cnc(-c3c4c(c5cnc(N6CC[C@H](N7CCCC7)C6)nc5c3F)COC4)c2c1C#N] | 620 |
| 401D | tert-Butyl (4-(3-((R)-[1,3'-bipyrrolidin]-1'-yl)-5-fluoro-7,9-dihydrofuro[3,4-f]quinazolin-6-yl)-3-cyano-7-fluorothieno[3,2-c]pyridin-2-yl)carbamate | 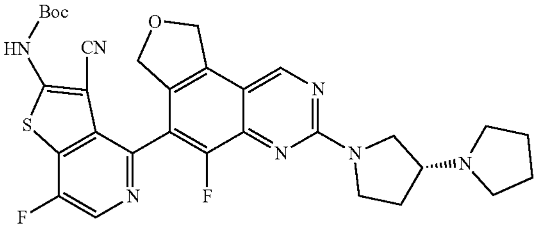 [SMILES: CC(C)(C)OC(=O)Nc1sc2c(F)cnc(-c3c4c(c5cnc(N6CC[C@@H](N7CCCC7)C6)nc5c3F)COC4)c2c1C#N] | 620 |
| 402D | tert-Butyl (3-cyano-7-fluoro-4-(5-fluoro-3-((2S,3'R)-2-(methoxymethyl)-[1,3'-bipyrrolidin]-1'-yl)-7,9-dihydrofuro[3,4-f]quinazolin-6-yl)thieno[3,2-c]pyridin-2-yl)carbamate | 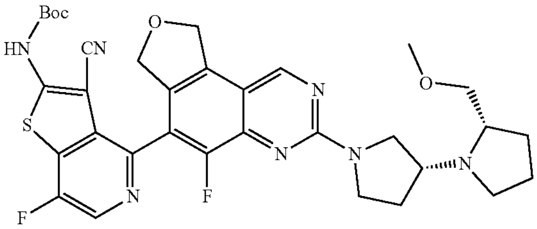 [SMILES: COC[C@@H]1CCCN1[C@@H]1CCN(c2ncc3c4c(c(-c5ncc(F)c6sc(NC(=O)OC(C)(C)C)c(C#N)c56)c(F)c3n2)COC4)C1] | 664 |

TABLE 22-continued

| Preparation | Chemical Name | Structure | MS (ES) m/z (M + 1) |
|---|---|---|---|
| 403D | tert-Butyl (3-cyano-7-fluoro-4-(5-fluoro-3-((2S,3'S)-2-(methoxymethyl)-[1,3'-bipyrrolidin]-1'-yl)-7,9-dihydrofuro[3,4-f]quinazolin-6-yl)thieno[3,2-c]pyridin-2-yl)carbamate | 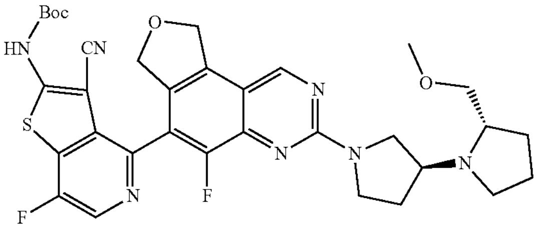 [SMILES: COC[C@@H]1CCCN1[C@H]1CCN(c2ncc3c4c(c(-c5ncc(F)c6sc(NC(=O)OC(C)(C)C)c(C#N)c56)c(F)c3n2)COC4)C1] | 664 |
| 404D | tert-Butyl (3-cyano-7-fluoro-4-(5-fluoro-3-((2R,3'R)-2-(methoxymethyl)-[1,3'-bipyrrolidin]-1'-yl)-7,9-dihydrofuro[3,4-f]quinazolin-6-yl)thieno[3,2-c]pyridin-2-yl)carbamate | 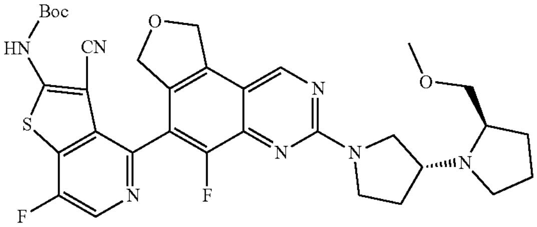 [SMILES: COC[C@H]1CCCN1[C@@H]1CCN(c2ncc3c4c(c(-c5ncc(F)c6sc(NC(=O)OC(C)(C)C)c(C#N)c56)c(F)c3n2)COC4)C1] | 664 |
| 405D | tert-Butyl (3-cyano-7-fluoro-4-(5-fluoro-3-((2R,3'S)-2-(methoxymethyl)-[1,3'-bipyrrolidin]-1'-yl)-7,9-dihydrofuro[3,4-f]quinazolin-6-yl)thieno[3,2-c]pyridin-2-yl)carbamate | 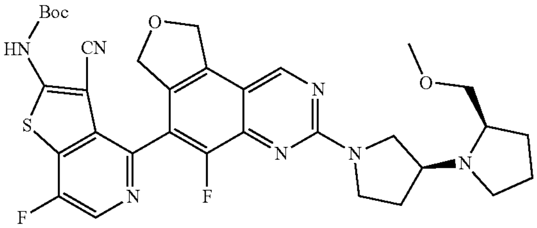 [SMILES: COC[C@H]1CCCN1[C@H]1CCN(c2ncc3c4c(c(-c5ncc(F)c6sc(NC(=O)OC(C)(C)C)c(C#N)c56)c(F)c3n2)COC4)C1] | 664 |
| 406D | tert-Butyl (3-cyano-7-fluoro-4-(5-fluoro-3-((3S,3'R)-3-hydroxy-[1,3'-bipyrrolidin]-1'-yl)-7,9-dihydrofuro[3,4-f]quinazolin-6-yl)thieno[3,2-c]pyridin-2-yl)carbamate | 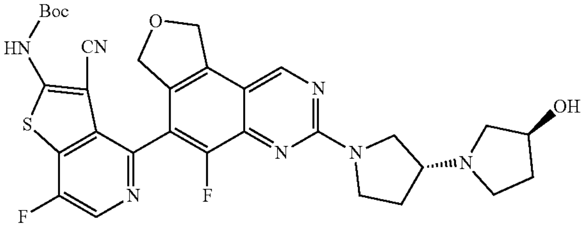 [SMILES: CC(C)(C)OC(=O)Nc1sc2c(F)cnc(-c3c4c(c5cnc(N6CC[C@@H](N7CC[C@H](O)C7)C6)nc5c3F)COC4)c2c1C#N] | 636 |
| 407D | tert-Butyl (3-cyano-7-fluoro-4-(5-fluoro-3-((3S,3'R)-3-methoxy-[1,3'-bipyrrolidin]-1'-yl)-7,9-dihydrofuro[3,4-f]quinazolin-6-yl)thieno[3,2-c]pyridin-2-yl)carbamate | 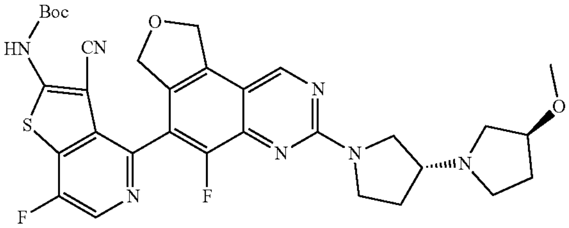 [SMILES: CO[C@H]1CCN([C@@H]2CCN(c3ncc4c5c(c(-c6ncc(F)c7sc(NC(=O)OC(C)(C)C)c(C#N)c67)c(F)c4n3)COC5)C2)C1] | 650 |
| 408D | tert-Butyl (4-(3-((R)-3-(4-acetylpiperazin-1-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 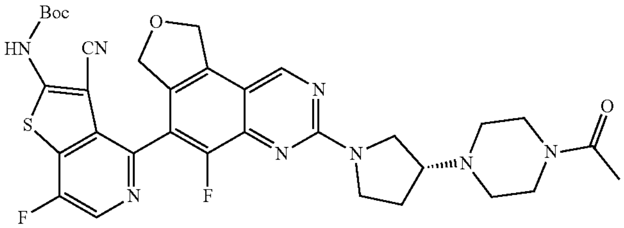 [SMILES: CC(=O)N1CCN([C@@H]2CCN(c3ncc4c5c(c(-c6ncc(F)c7sc(NC(=O)OC(C)(C)C)c(C#N)c67)c(F)c4n3)COC5)C2)CC1] | 677 |

TABLE 22-continued

| Preparation | Chemical Name | Structure | MS (ES) m/z (M + 1) |
|---|---|---|---|
| 409D | tert-Butyl (4-(3-((S)-3-(4-acetylpiperazin-1-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 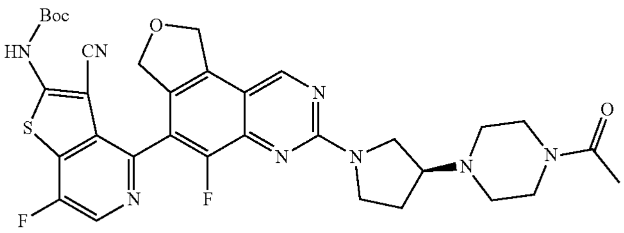 [SMILES: CC(=O)N1CCN([C@H]2CCN(c3ncc4c5c(c(-c6ncc(F)c7sc(NC(=O)OC(C)(C)C)c(C#N)c67)c(F)c4n3)COC5)C2)CC1] | 677 |
| 410D | tert-Butyl (3-cyano-7-fluoro-4-(5-fluoro-3-((R)-3-(4-isopropylpiperazin-1-yl)pyrrolidin-1-yl)-7,9-dihydrofuro[3,4-f]quinazolin-6-yl)thieno[3,2-c]pyridin-2-yl)carbamate | 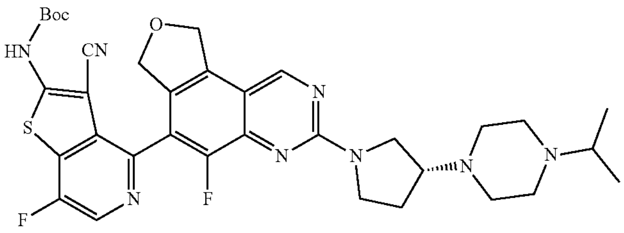 [SMILES: CC(C)N1CCN([C@@H]2CCN(c3ncc4c5c(c(-c6ncc(F)c7sc(NC(=O)OC(C)(C)C)c(C#N)c67)c(F)c4n3)COC5)C2)CC1] | 677 |
| 411D | tert-Butyl (3-cyano-7-fluoro-4-(5-fluoro-3-((S)-3-(4-isopropylpiperazin-1-yl)pyrrolidin-1-yl)-7,9-dihydrofuro[3,4-f]quinazolin-6-yl)thieno[3,2-c]pyridin-2-yl)carbamate | 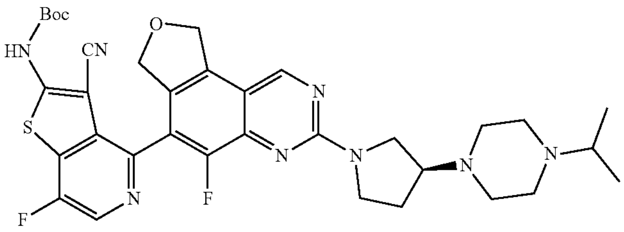 [SMILES: CC(C)N1CCN([C@H]2CCN(c3ncc4c5c(c(-c6ncc(F)c7sc(NC(=O)OC(C)(C)C)c(C#N)c67)c(F)c4n3)COC5)C2)CC1] | 677 |
| 412D | tert-Butyl (3-cyano-4-(3-((S)-3-(4-ethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 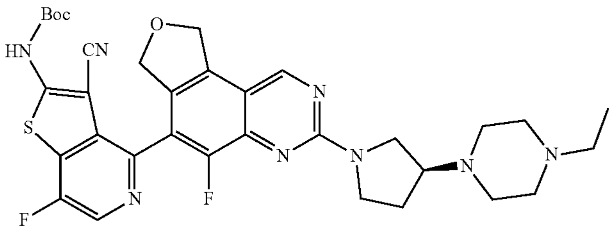 [SMILES: CCN1CCN([C@H]2CCN(c3ncc4c5c(c(-c6ncc(F)c7sc(NC(=O)OC(C)(C)C)c(C#N)c67)c(F)c4n3)COC5)C2)CC1] | 663 |
| 413D | tert-Butyl (3-cyano-4-(3-((R)-3-(4-ethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 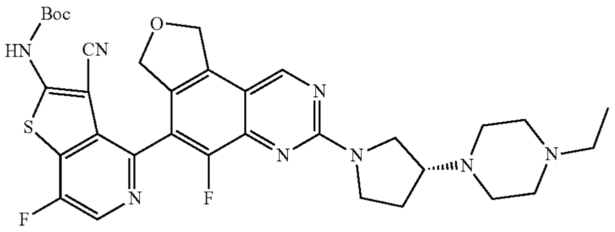 [SMILES: CCN1CCN([C@@H]2CCN(c3ncc4c5c(c(-c6ncc(F)c7sc(NC(=O)OC(C)(C)C)c(C#N)c67)c(F)c4n3)COC5)C2)CC1] | 663 |
| 414D | tert-Butyl (3-cyano-7-fluoro-4-(5-fluoro-3-((R)-3-(4-(2-hydroxyethyl)piperazin-1-yl)pyrrolidin-1-yl)-7,9-dihydrofuro[3,4-f]quinazolin-6-yl)thieno[3,2-c]pyridin-2-yl)carbamate | 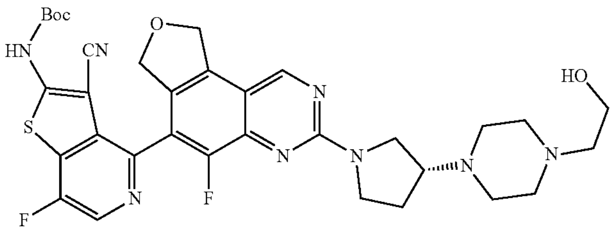 [SMILES: CC(C)(C)OC(=O)Nc1sc2c(F)cnc(-c3c4c(c5cnc(N6CC[C@@H](N7CCN(CCO)CC7)C6)nc5c3F)COC4)c2c1C#N] | 679 |

TABLE 22-continued

| Preparation | Chemical Name | Structure | MS (ES) m/z (M + 1) |
|---|---|---|---|
| 415D | tert-Butyl (3-cyano-7-fluoro-4-(5-fluoro-3-((R)-3-(4-(oxetan-3-yl)piperazin-1-yl)pyrrolidin-1-yl)-7,9-dihydrofuro[3,4-f]quinazolin-6-yl)thieno[3,2-c]pyridin-2-yl)carbamate | 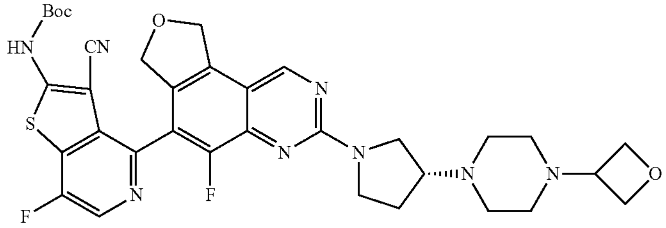 [SMILES: CC(C)(C)OC(=O)Nc1sc2c(F)cnc(-c3c4c(c5cnc(N6CC[C@@H](N7CCN(C8COC8)CC7)C6)nc5c3F)COC4)c2c1C#N] | 691 |
| 416D | tert-Butyl (3-cyano-7-fluoro-4-(5-fluoro-3-((R)-3-(4-(2,2,2-trifluoroethyl)piperazin-1-yl)pyrrolidin-1-yl)-7,9-dihydrofuro[3,4-f]quinazolin-6-yl)thieno[3,2-c]pyridin-2-yl)carbamate | 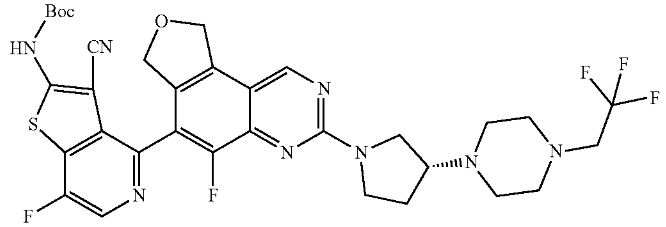 [SMILES: CC(C)(C)OC(=O)Nc1sc2c(F)cnc(-c3c4c(c5cnc(N6CC[C@@H](N7CCN(CC(F)(F)F)CC7)C6)nc5c3F)COC4)c2c1C#N] | 717 |
| 417D | tert-Butyl 4-((3R)-1-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)pyrrolidin-3-yl)piperazine-1-carboxylate | 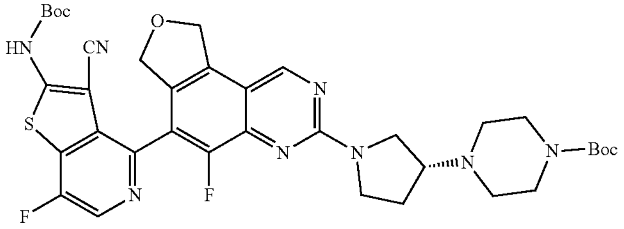 [SMILES: CC(C)(C)OC(=O)Nc1sc2c(F)cnc(-c3c4c(c5cnc(N6CC[C@@H](N7CCN(C(=O)OC(C)(C)C)CC7)C6)nc5c3F)COC4)c2c1C#N] | 735 |
| 418D | tert-Butyl 4-((3S)-1-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)pyrrolidin-3-yl)piperazine-1-carboxylate | 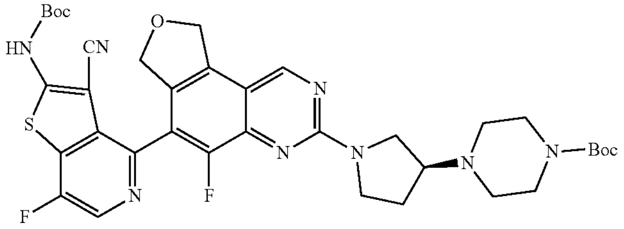 [SMILES: CC(C)(C)OC(=O)Nc1sc2c(F)cnc(-c3c4c(c5cnc(N6CC[C@H](N7CCN(C(=O)OC(C)(C)C)CC7)C6)nc5c3F)COC4)c2c1C#N] | 735 |
| 419D | tert-Butyl (3-cyano-4-(3-((R)-3-(4-cyclopropylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 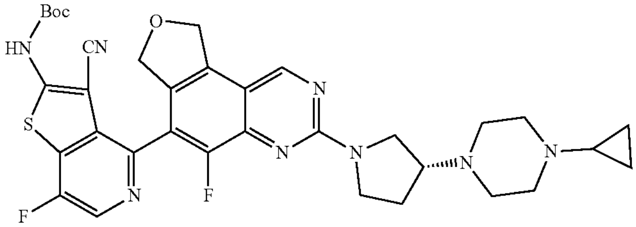 [SMILES: CC(C)(C)OC(=O)Nc1sc2c(F)cnc(-c3c4c(c5cnc(N6CC[C@@H](N7CCN(C8CC8)CC7)C6)nc5c3F)COC4)c2c1C#N] | 675 |
| 420D | tert-Butyl (3-cyano-7-fluoro-4-(5-fluoro-3-((R)-3-(4-(2-hydroxy-2-methylpropyl)piperazin-1-yl)pyrrolidin-1-yl)-7,9-dihydrofuro[3,4-f]quinazolin-6-yl)thieno[3,2-c]pyridin-2-yl)carbamate | 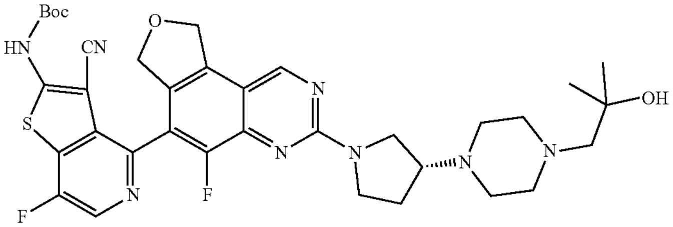 [SMILES: CC(C)(O)CN1CCN([C@@H]2CCN(c3ncc4c5c(c(-c6ncc(F)c7sc(NC(=O)OC(C)(C)C)c(C#N)c67)c(F)c4n3)COC5)C2)CC1] | 707 |

TABLE 22-continued

| Preparation | Chemical Name | Structure | MS (ES) m/z (M + 1) |
|---|---|---|---|
| 421D | tert-Butyl (3-cyano-7-fluoro-4-(5-fluoro-3-((R)-3-(4-(2-methoxyethyl)piperazin-1-yl)pyrrolidin-1-yl)-7,9-dihydrofuro[3,4-f]quinazolin-6-yl)thieno[3,2-c]pyridin-2-yl)carbamate | 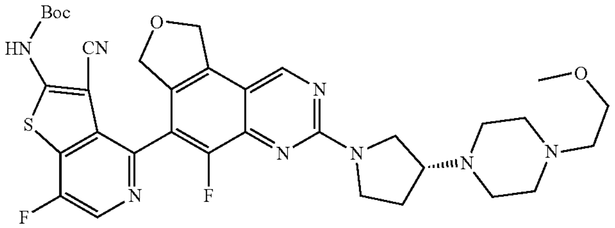 [SMILES: COCCN1CCN([C@@H]2CCN(c3ncc4c5c(c(-c6ncc(F)c7sc(NC(=O)OC(C)(C)C)c(C#N)c67)c(F)c4n3)COC5)C2)CC1] | 693 |
| 422D | tert-Butyl (3-cyano-4-(3-((R)-3-((R)-2,4-dimethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 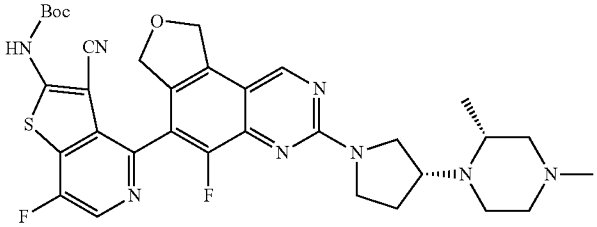 [SMILES: C[C@@H]1CN(C)CCN1[C@@H]1CCN(c2ncc3c4c(c(-c5ncc(F)c6sc(NC(=O)OC(C)(C)C)c(C#N)c56)c(F)c3n2)COC4)C1] | 663 |
| 423D | tert-Butyl (3-cyano-4-(3-((R)-3-((S)-2,4-dimethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 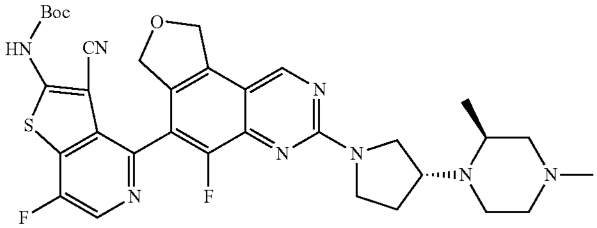 [SMILES: C[C@H]1CN(C)CCN1[C@@H]1CCN(c2ncc3c4c(c(-c5ncc(F)c6sc(NC(=O)OC(C)(C)C)c(C#N)c56)c(F)c3n2)COC4)C1] | 663 |
| 424D | tert-Butyl (3-cyano-4-(3-((S)-3-((R)-2,4-dimethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 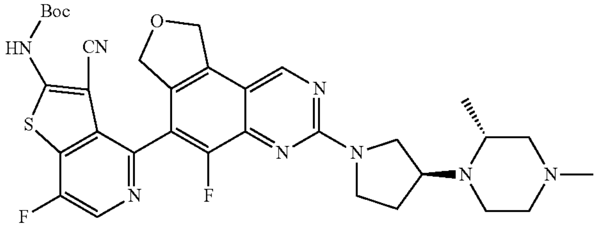 [SMILES: C[C@@H]1CN(C)CCN1[C@H]1CCN(c2ncc3c4c(c(-c5ncc(F)c6sc(NC(=O)OC(C)(C)C)c(C#N)c56)c(F)c3n2)COC4)C1] | 663 |
| 425D | tert-Butyl (3-cyano-4-(3-((S)-3-((S)-2,4-dimethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 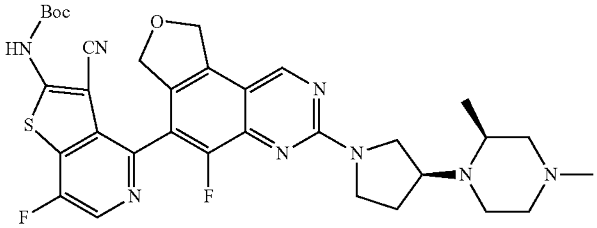 [SMILES: C[C@H]1CN(C)CCN1[C@H]1CCN(c2ncc3c4c(c(-c5ncc(F)c6sc(NC(=O)OC(C)(C)C)c(C#N)c56)c(F)c3n2)COC4)C1] | 663 |
| 426D | tert-Butyl (3-cyano-4-(3-((R)-3-((S)-3,4-dimethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 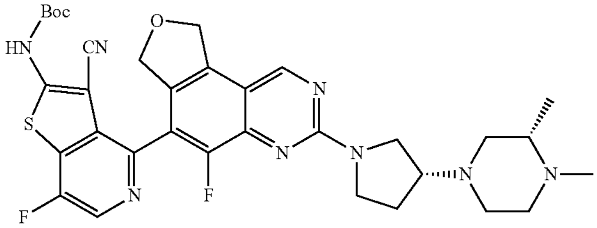 [SMILES: C[C@H]1CN([C@@H]2CCN(c3ncc4c5c(c(-c6ncc(F)c7sc(NC(=O)OC(C)(C)C)c(C#N)c67)c(F)c4n3)COC5)C2)CCN1C] | 663 |

TABLE 22-continued

| Preparation | Chemical Name | Structure | MS (ES) m/z (M + 1) |
|---|---|---|---|
| 427D | tert-Butyl (3-cyano-4-(3-((R)-3-((R)-3,4-dimethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 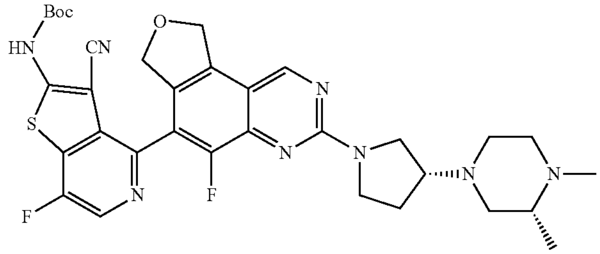 [SMILES: C[C@@H]1CN([C@@H]2CCN(c3ncc4c5c(c(-c6ncc(F)c7sc(NC(=O)OC(C)(C)C)c(C#N)c67)c(F)c4n3)COC5)C2)CCN1C] | 663 |
| 428D | tert-Butyl (3-cyano-7-fluoro-4-(5-fluoro-3-((R)-3-((3R,5S)-3,4,5-trimethylpiperazin-1-yl)pyrrolidin-1-yl)-7,9-dihydrofuro[3,4-f]quinazolin-6-yl)thieno[3,2-c]pyridin-2-yl)carbamate | 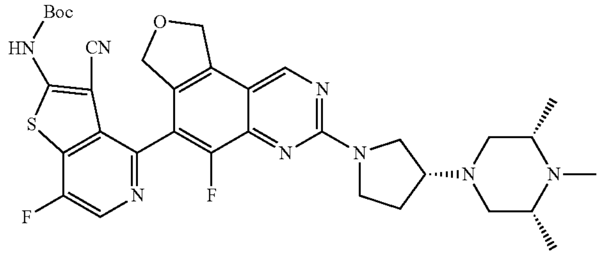 [SMILES: C[C@@H]1CN([C@@H]2CCN(c3ncc4c5c(c(-c6ncc(F)c7sc(NC(=O)OC(C)(C)C)c(C#N)c67)c(F)c4n3)COC5)C2)C[C@H](C)N1C] | 677 |
| 429D | tert-Butyl (3-cyano-7-fluoro-4-(5-fluoro-3-((R)-3-((3R,5R)-3,4,5-trimethylpiperazin-1-yl)pyrrolidin-1-yl)-7,9-dihydrofuro[3,4-f]quinazolin-6-yl)thieno[3,2-c]pyridin-2-yl)carbamate | 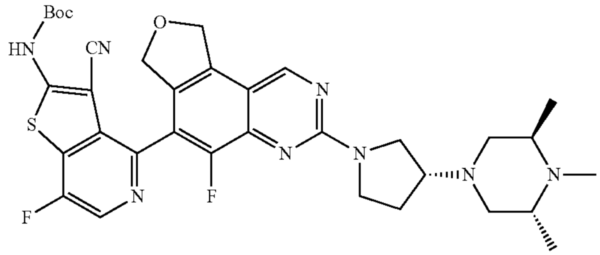 [SMILES: C[C@@H]1CN([C@@H]2CCN(c3ncc4c5c(c(-c6ncc(F)c7sc(NC(=O)OC(C)(C)C)c(C#N)c67)c(F)c4n3)COC5)C2)C[C@@H](C)N1C] | 677 |
| 430D | tert-Butyl (3-cyano-7-fluoro-4-(5-fluoro-3-((R)-3-((3S,5S)-3,4,5-trimethylpiperazin-1-yl)pyrrolidin-1-yl)-7,9-dihydrofuro[3,4-f]quinazolin-6-yl)thieno[3,2-c]pyridin-2-yl)carbamate | 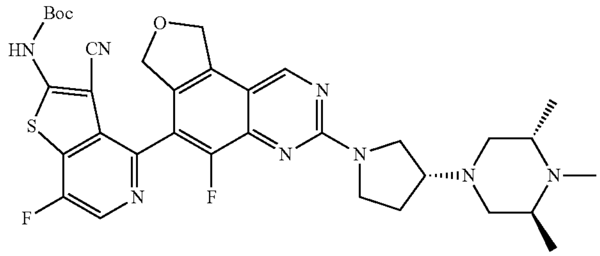 [SMILES: C[C@H]1CN([C@@H]2CCN(c3ncc4c5c(c(-c6ncc(F)c7sc(NC(=O)OC(C)(C)C)c(C#N)c67)c(F)c4n3)COC5)C2)C[C@H](C)N1C] | 677 |
| 431D | tert-Butyl (3-cyano-7-fluoro-4-(5-fluoro-3-((R)-3-((S)-3-(hydroxymethyl)-4-methylpiperazin-1-yl)pyrrolidin-1-yl)-7,9-dihydrofuro[3,4-f]quinazolin-6-yl)thieno[3,2-c]pyridin-2-yl)carbamate | 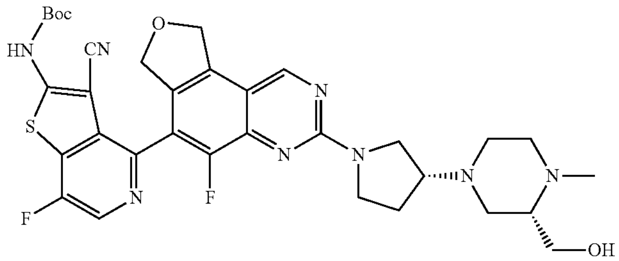 [SMILES: CN1CCN([C@@H]2CCN(c3ncc4c5c(c(-c6ncc(F)c7sc(NC(=O)OC(C)(C)C)c(C#N)c67)c(F)c4n3)COC5)C2)C[C@H]1CO] | 679 |
| 432D | tert-Butyl (3-cyano-7-fluoro-4-(5-fluoro-3-((R)-3-((R)-3-(hydroxymethyl)-4-methylpiperazin-1-yl)pyrrolidin-1-yl)-7,9-dihydrofuro[3,4-f]quinazolin-6-yl)thieno[3,2-c]pyridin-2-yl)carbamate | 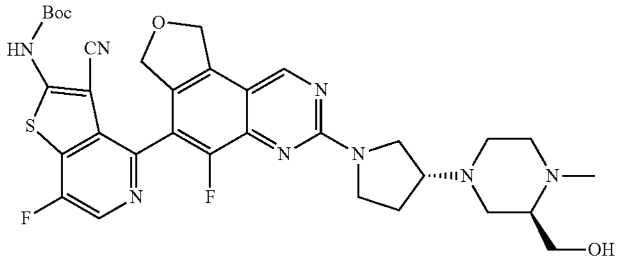 [SMILES: CN1CCN([C@@H]2CCN(c3ncc4c5c(c(-c6ncc(F)c7sc(NC(=O)OC(C)(C)C)c(C#N)c67)c(F)c4n3)COC5)C2)C[C@@H]1CO] | 679 |

TABLE 22-continued

| Preparation | Chemical Name | Structure | MS (ES) m/z (M + 1) |
|---|---|---|---|
| 433D | tert-Butyl (3-cyano-7-fluoro-4-(5-fluoro-3-((R)-3-(2,2,4-trimethylpiperazin-1-yl)pyrrolidin-1-yl)-7,9-dihydrofuro[3,4-f]quinazolin-6-yl)thieno[3,2-c]pyridin-2-yl)carbamate | 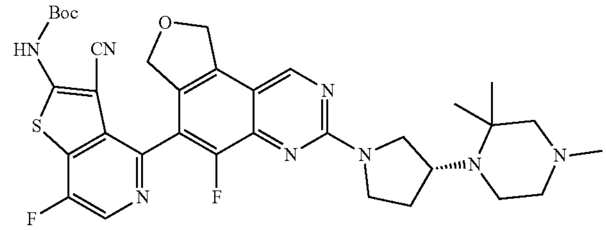 [SMILES: CN1CCN([C@@H]2CCN(c3ncc4c5c(c(-c6ncc(F)c7sc(NC(=O)OC(C)(C)C)c(C#N)c67)c(F)c4n3)COC5)C2)C(C)(C)C1] | 677 |
| 434D | tert-Butyl (3-cyano-7-fluoro-4-(5-fluoro-3-((R)-3-(3,3,4-trimethylpiperazin-1-yl)pyrrolidin-1-yl)-7,9-dihydrofuro[3,4-f]quinazolin-6-yl)thieno[3,2-c]pyridin-2-yl)carbamate | 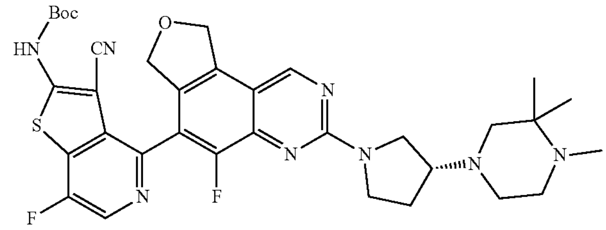 [SMILES: CN1CCN([C@@H]2CCN(c3ncc4c5c(c(-c6ncc(F)c7sc(NC(=O)OC(C)(C)C)c(C#N)c67)c(F)c4n3)COC5)C2)CC1(C)C] | 677 |
| 435D | tert-Butyl (3-cyano-7-fluoro-4-(5-fluoro-3-((R)-3-((S)-3-(methoxymethyl)-4-methylpiperazin-1-yl)pyrrolidin-1-yl)-7,9-dihydrofuro[3,4-f]quinazolin-6-yl)thieno[3,2-c]pyridinin-2-yl)carbamate | 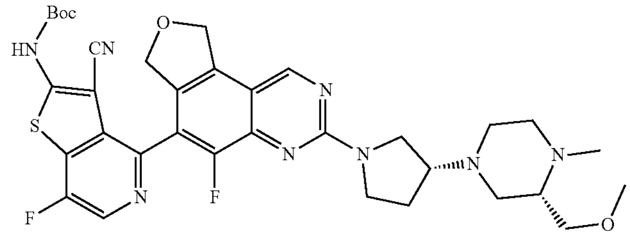 [SMILES: COC[C@@H]1CN([C@@H]2CCN(c3ncc4c5c(c(-c6ncc(F)c7sc(NC(=O)OC(C)(C)C)c(C#N)c67)c(F)c4n3)COC5)C2)CCN1C] | 693 |
| 436D | tert-Butyl (3-cyano-7-fluoro-4-(5-fluoro-3-((R)-3-((R)-3-(methoxymethyl)-4-methylpiperazin-1-yl)pyrrolidin-1-yl)-7,9-dihydrofuro[3,4-f]quinazolin-6-yl)thieno[3,2-c]pyridin-2-yl)carbamate | 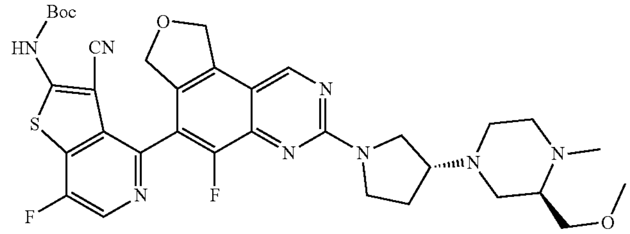 [SMILES: COC[C@H]1CN([C@@H]2CCN(c3ncc4c5c(c(-c6ncc(F)c7sc(NC(=O)OC(C)(C)C)c(C#N)c67)c(F)c4n3)COC5)C2)CCN1C] | 693 |
| 437D | tert-Butyl (3-cyano-7-fluoro-4-(5-fluoro-3-((R)-3-((S)-2-(hydroxymethyl)-4-methylpiperazin-1-yl)pyrrolidin-1-yl)-7,9-dihydrofuro[3,4-f]quinazolin-6-yl)thieno[3,2-c]pyridin-2-yl)carbamate | 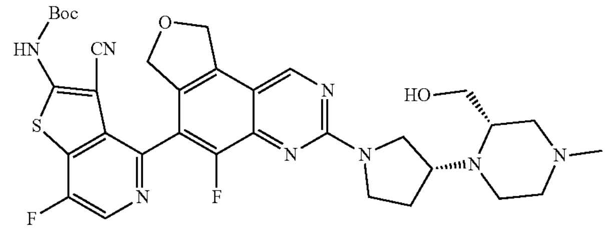 [SMILES: CN1CCN([C@@H]2CCN(c3ncc4c5c(c(-c6ncc(F)c7sc(NC(=O)OC(C)(C)C)c(C#N)c67)c(F)c4n3)COC5)C2)[C@H](CO)C1] | 679 |
| 438D | tert-Butyl (3-cyano-7-fluoro-4-(5-fluoro-3-((R)-3-((R)-2-(hydroxymethyl)-4-methylpiperazin-1-yl)pyrrolidin-1-yl)-7,9-dihydrofuro[3,4-f]quinazolin-6-yl)thieno[3,2-c]pyridin-2-yl)carbamate | 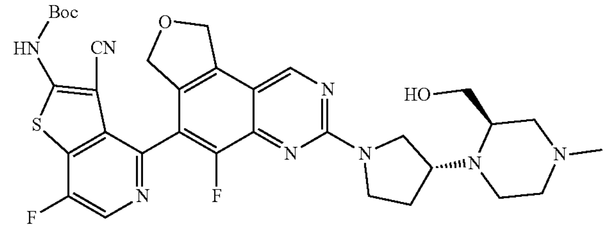 [SMILES: CN1CCN([C@@H]2CCN(c3ncc4c5c(c(-c6ncc(F)c7sc(NC(=O)OC(C)(C)C)c(C#N)c67)c(F)c4n3)COC5)C2)[C@@H](CO)C1] | 679 |

TABLE 22-continued

| Preparation | Chemical Name | Structure | MS (ES) m/z (M + 1) |
|---|---|---|---|
| 439D | tert-Butyl (3-cyano-7-fluoro-4-(5-fluoro-3-(3-(4-methyl-4,7-diazaspiro[2.5]octan-7-yl)pyrrolidin-1-yl)-7,9-dihydrofuro[3,4-f]quinazolin-6-yl)thieno[3,2-c]pyridin-2-yl)carbamate | 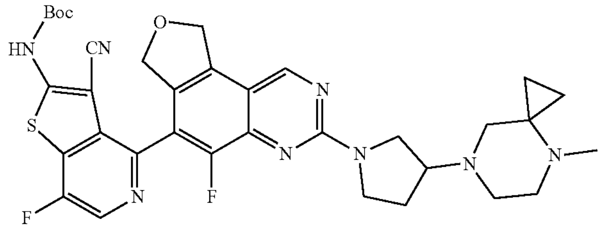 [SMILES: CN1CCN(C2CCN(c3ncc4c5c(c(-c6ncc(F)c7sc(NC(=O)OC(C)(C)C)c(C#N)c67)c(F)c4n3)COC5)C2)CC12CC2] | 675 |
| 440D | tert-Butyl (4-(3-(3-(4,7-diazaspiro[2.5]octan-7-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 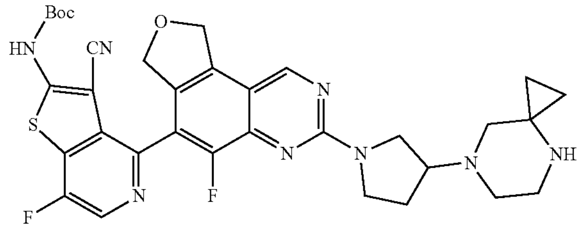 [SMILES: CC(C)(C)OC(=O)Nc1sc2c(F)cnc(-c3c4c(c5cnc(N6CCC(N7CCNC8(CC8)C7)C6)nc5c3F)COC4)c2c1C#N] | 661 |
| 441D | tert-Butyl (3-cyano-4-(3-(3-(3,3-dimethylpiperazin-1-yl)pyrrolidin-1-yl)-5-fluoro-7,9-dihydrofuo[3,4-f]quinazolin-6-yl)-7-fluorothieno[3,2-c]pyridin-2-yl)carbamate | 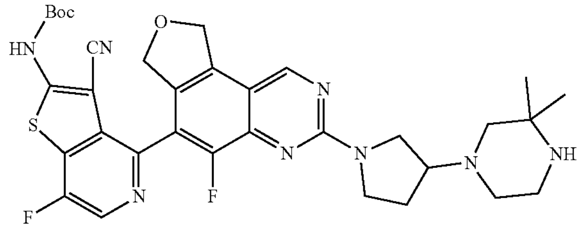 [SMILES: CC1(C)CN(C2CCN(c3ncc4c5c(c(-c6ncc(F)c7sc(NC(=O)OC(C)(C)C)c(C#N)c67)c(F)c4n3)COC5)C2)CCN1] | 663 |
| 442D | tert-Butyl (3-cyano-4-(3-((R)-3-((3S,5S)-3,5-dimethylpiperazin-1-yl)pyrrolidin-1-yl)-5-fluoro-7,9-dihydrofuro[3,4-f]quinazolin-6-yl)-7-fluorothieno[3,2-c]pyridin-2-yl)carbamate | 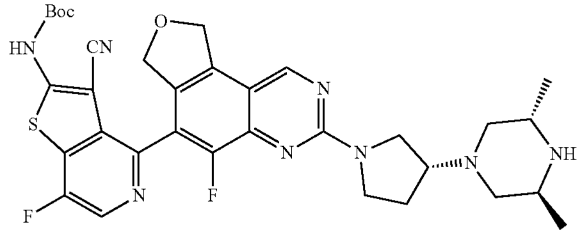 [SMILES: C[C@H]1CN([C@@H]2CCN(c3ncc4c5c(c(-c6ncc(F)c7sc(NC(=O)OC(C)(C)C)c(C#N)c67)c(F)c4n3)COC5)C2)C[C@H](C)N1] | 663 |
| 443D | tert-Butyl (3-cyano-7-fluoro-4-(5-fluoro-3-((S)-3-((2S,R)-2,4,5-trimethylpiperazin-1-yl)pyrrolidin-1-yl)-7,9-dihydrofuro[3,4-f]quinazolin-6-yl)thieno[3,2-c]pyridin-2-y)carbamate/ | 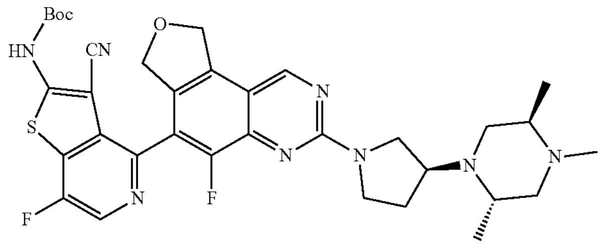 [SMILES: C[C@@H]1CN([C@H]2CCN(c3ncc4c5c(c(-c6ncc(F)c7sc(NC(=O)OC(C)(C)C)c(C#N)c67)c(F)c4n3)COC5)C2)[C@@H](C)CN1C] | 677 |
| 444D | tert-Butyl (3-cyano-7-fluoro-4-(5-fluoro-3-((R)-3-((1S,4S)-5-methyl-2,5-diazabicyclo[2.2.1]heptan-2-yl)pyrrolidin-1-yl)-7,9-dihydrofuro[3,4-f]quinazolin-6-yl)thieno[3,2-c]pyridin-2-yl)carbamate | 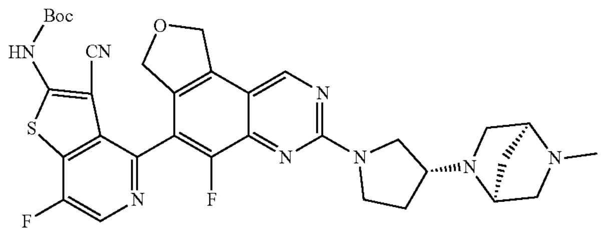 [SMILES: CN1C[C@@H]2C[C@H]1CN2[C@@H]1CCN(c2ncc3c4c(c(-c5ncc(F)c6sc(NC(=O)OC(C)(C)C)c(C#N)c56)c(F)c3n2)COC4)C1] | 661 |

TABLE 22-continued

| Preparation | Chemical Name | Structure | MS (ES) m/z (M + 1) |
| --- | --- | --- | --- |
| 445D | tert-Butyl (3-cyano-7-fluoro-4-(5-fluoro-3-((R)-3-((1R,4R)-5-methyl-2,5-diazabicyclo[2.2.1]heptan-2-yl)pyrrolidin-1-yl)-7,9-dihydrofuro[3,4-f]quinazolin-6-yl)thieno[3,2-c]pyridin-2-yl)carbamate | 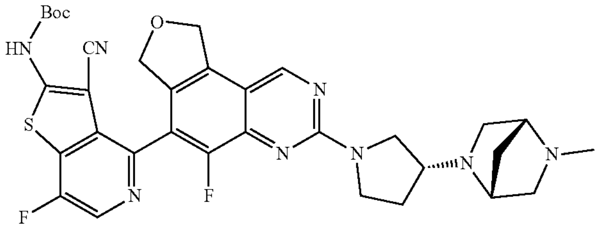 [SMILES: CN1C[C@H]2C[C@@H]1CN2[C@@H]1CCN(c2ncc3c4c(c(-c5ncc(F)c6sc(NC(=O)OC(C)(C)C)c(C#N)c56)c(F)c3n2)COC4)C1] | 661 |
| 446D | tert-Butyl (3-cyano-7-fluoro-4-(5-fluoro-3-((3R)-3-(3-methyl-3,8-diazabicyclo[3.2.1]octan-8-yl)pyrrolidin-1-yl)-7,9-dihydrofuro[3,4-f]quinazolin-6-yl)thieno[3,2-c]pyridin-2-yl)carbamate | 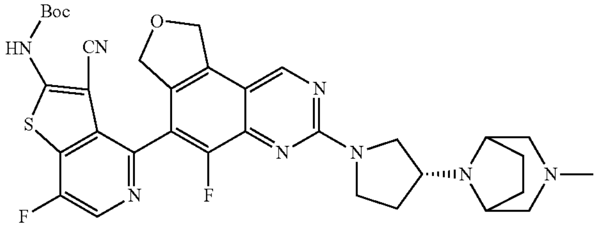 [SMILES: CN1CC2CCC(C1)N2[C@@H]1CCN(c2ncc3c4c(c(-c5ncc(F)c6sc(NC(=O)OC(C)(C)C)c(C#N)c56)c(F)c3n2)COC4)C1] | 675 |
| 447D | tert-Butyl (3-cyano-7-fluoro-4-(5-fluoro-3-((3R)-3-(8-methyl-3,8-diazabicyclo[3.2.1]octan-3-yl)pyrrolidin-1-yl)-7,9-dihydrofuro[3,4-f]quinazolin-6-yl)thieno[3,2-c]pyridin-2-yl)carbamate | 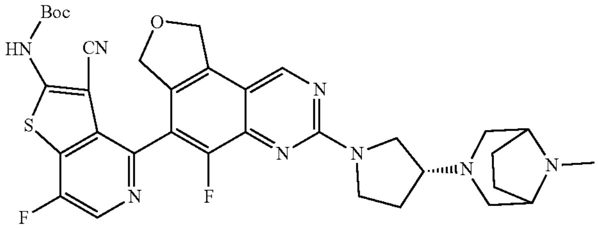 [SMILES: CN1C2CCC1CN([C@@H]1CCN(c3ncc4c5c(c(-c6ncc(F)c7sc(NC(=O)OC(C)(C)C)c(C#N)c67)c(F)c4n3)COC5)C1)C2] | 675 |
| 448D | tert-Butyl (3-cyano-7-fluoro-4-(5-fluoro-3-((3R)-3-(6-methyl-3,6-diazabicyclo[3.1.1]heptan-3-yl)pyrrolidin-1-yl)-7,9-dihydrofuro[3,4-f]quinazolin-6-yl)thieno[3,2-c]pyridin-2-yl)carbamate | 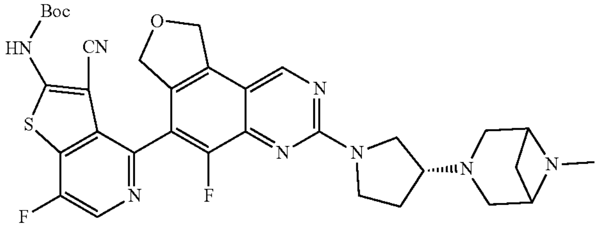 [SMILES: CN1C2CC1CN([C@@H]1CCN(c3ncc4c5c(c(-c6ncc(F)c7sc(NC(=O)OC(C)(C)C)c(C#N)c67)c(F)c4n3)COC5)C1)C2] | 661 |
| 449D | tert-Butyl (3-cyano-7-fluoro-4-(5-fluoro-3-((3R)-3-(3-methyl-3,6-diazabicyclo[3.1.1]heptan-6-yl)pyrrolidin-1-yl)-7,9-dihydrofuro[3,4-f]quinazolin-6-yl)thieno[3,2-c]pyridin-2-yl)carbamate | 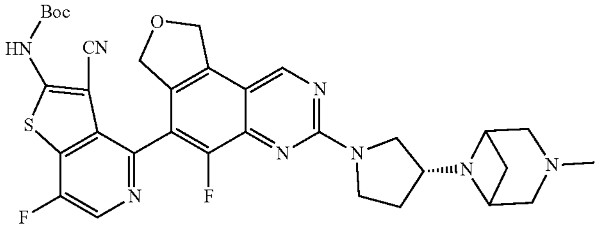 [SMILES: CN1CC2CC(C1)N2[C@@H]1CCN(c2ncc3c4c(c(-c5ncc(F)c6sc(NC(=O)OC(C)(C)C)c(C#N)c56)c(F)c3n2)COC4)C1] | 661 |
| 450D | tert-Butyl (3-cyano-7-fluoro-4-(5-fluoro-3-((2S,3S)-2-methyl-3-(4-methylpiperazin-1-yl)pyrrolidin-1-yl)-7,9-dihydrofuro[3,4-f]quinazolin-6-yl)thieno[3,2-c]pyridin-2-yl)carbamate | 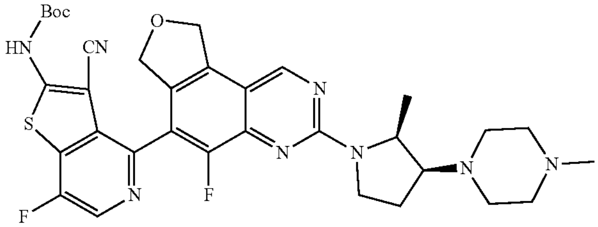 [SMILES: C[C@H]1[C@@H](N2CCN(C)CC2)CCN1c1ncc2c3c(c(-c4ncc(F)c5sc(NC(=O)OC(C)(C)C)c(C#N)c45)c(F)c2n1)COC3] | 663 |

TABLE 22-continued

| Preparation | Chemical Name | Structure | MS (ES) m/z (M + 1) |
|---|---|---|---|
| 451D | tert-Butyl (3-cyano-7-fluoro-4-(5-fluoro-3-((2R,3R)-2-methyl-3-(4-methylpiperazin-1-y)pyrrolidin-1-yl)-7,9-dihydrofuro[3,4-f]quinazolin-6-yl)thieno[3,2-c]pyridin-2-yl)carbamate | 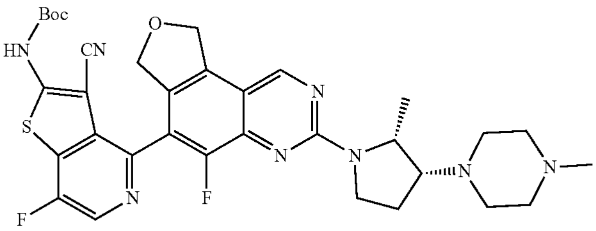 [SMILES: C[C@@H]1[C@H](N2CCN(C)CC2)CCN1c1ncc2c3c(c(-c4ncc(F)c5sc(NC(=O)OC(C)(C)C)c(C#N)c45)c(F)c2n1)COC3] | 663 |
| 452D | tert-Butyl (3-cyano-7-fluoro-4-(5-fluoro-3-((2S,3R)-2-methyl-3-(4-methylpiperazin-1-yl)pyrrolidin-1-yl)-7,9-dihydrofuro[3,4-f]quinazolin-6-yl)thieno[3,2-c]pyridin-2-yl)carbamate | 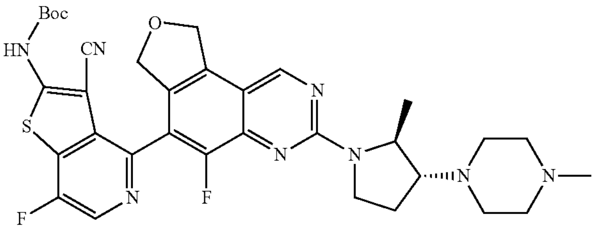 [SMILES: C[C@H]1[C@H](N2CCN(C)CC2)CCN1c1ncc2c3c(c(-c4ncc(F)c5sc(NC(=O)OC(C)(C)C)c(C#N)c45)c(F)c2n1)COC3] | 663 |
| 453D | tert-Butyl (3-cyano-7-fluoro-4-(5-fluoro-3-((2R,3S)-2-methyl-3-(4-methylpiperazin-1-yl)pyrrolidin-1-yl)-7,9-dihydrofuro[3,4-f]quinazolin-6-yl)thieno[3,2-c]pyridin-2-yl)carbamate | 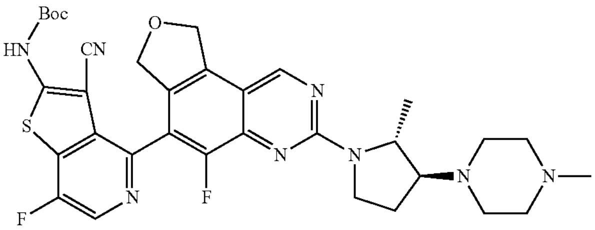 [SMILES: C[C@@H]1[C@@H](N2CCN(C)CC2)CCN1c1ncc2c3c(c(-c4ncc(F)c5sc(NC(=O)OC(C)(C)C)c(C#N)c45)c(F)c2n1)COC3] | 663 |
| 454D | tert-Butyl (3-cyano-4-(3-((2S,3S)-3-(4-ethylpiperazin-1-yl)-2-methylpyrrolidin-1-yl)-5-fluoro-7,9-dihydrofuro[3,4-f]quinazolin-6-yl)-7-fluorothieno[3,2-c]pyridin-2-yl)carbamate | 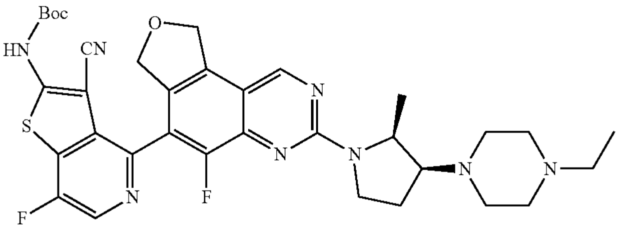 [SMILES: CCN1CCN([C@H]2CCN(c3ncc4c5c(c(-c6ncc(F)c7sc(NC(=O)OC(C)(C)C)c(C#N)c67)c(F)c4n3)COC5)[C@H]2C)CC1] | 677 |
| 455D | tert-Butyl (3-cyano-7-fluoro-4-(5-fluoro-3-((2S,3S)-3-(4-isopropylpiperazin-1-yl)-2-methylpyrrolidin-1-yl)-7,9-dihydrofuro[3,4-f]quinazolin-6-yl)thieno[3,2-c]pyridin-2-yl)carbamate | 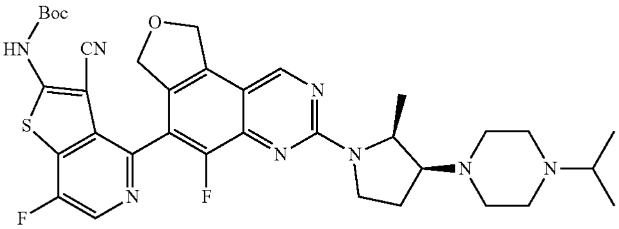 | 691 |
| 456D | tert-Butyl (3-cyano-7-fluoro-4-(5-fluoro-3-((2S,3S)-3-(4-(2-methoxyethyl)piperazin-1-yl)-2-methylpyrrolidin-1-yl)-7,9-dihydrofuro[3,4-f]quinazolin-6-yl)thieno[3,2-c]pyridin-2-yl)carbamate | 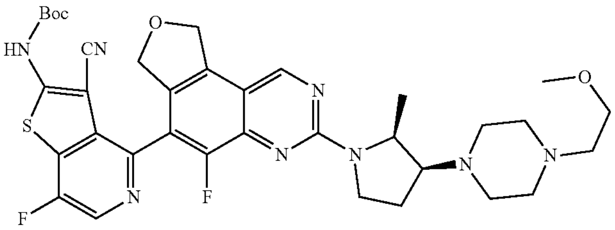 [SMILES: COCCN1CCN([C@H]2CCN(c3ncc4c5c(c(-c6ncc(F)c7sc(NC(=O)OC(C)(C)C)c(C#N)c67)c(F)c4n3)COC5)[C@H]2C)CC1] | 707 |

TABLE 22-continued

| Preparation | Chemical Name | Structure | MS (ES) m/z (M + 1) |
|---|---|---|---|
| 457D | tert-Butyl (3-cyano-7-fluoro-4-(5-fluoro-3-((2S,3S)-3-(4-((S)-2-hydroxypropyl)piperazin-1-yl)-2-methylpyrrolidin-1-yl)-7,9-dihydrofuro[3,4-f]quinazolin-6-yl)thieno[3,2-c]pyridin-2-yl)carbamate | 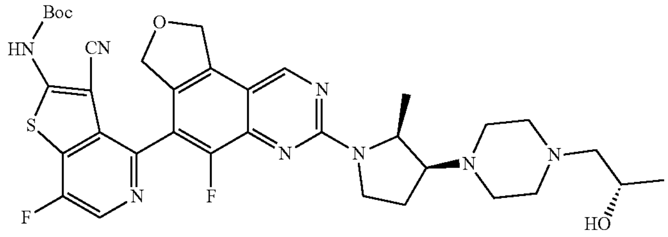 [SMILES: C[C@H](O)CN1CCN([C@H]2CCN(c3ncc4c5c(c(-c6ncc(F)c7sc(NC(=O)OC(C)(C)C)c(C#N)c67)c(F)c4n3)COC5)[C@H]2C)CC1] | 707 |
| 458D | tert-Butyl (3-cyano-7-fluoro-4-(5-fluoro-3-((2S,3S)-3-(4-((R)-2-hydroxypropyl)piperazin-1-yl)-2-methylpyrrolidin-1-yl)-7,9-dihydrofuro[3,4-f]quinazolin-6-yl)thieno[3,2-c]pyridin-2-yl)carbamate | 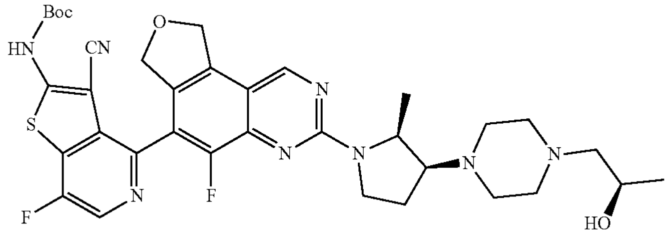 [SMILES: C[C@@H](O)CN1CCN([C@H]2CCN(c3ncc4c5c(c(-c6ncc(F)c7sc(NC(=O)OC(C)(C)C)c(C#N)c67)c(F)c4n3)COC5)[C@H]2C)CC1] | 707 |
| 459D | tert-Butyl (3-cyano-7-fluoro-4-(5-fluoro-3-((2S,3S)-3-(4-(2-fluoroethyl)piperazin-1-yl)-2-methylpyrrolidin-1-yl)-7,9-dihydrofuro[3,4-f]quinazolin-6-yl)thieno[3,2-c]pyridin-2-yl)carbamate | 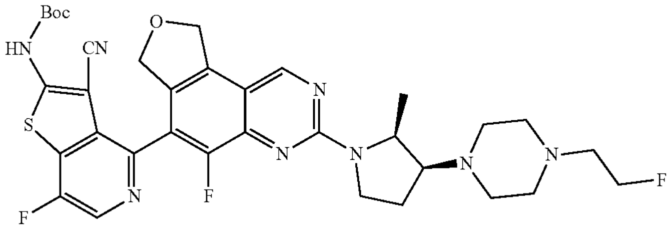 [SMILES: C[C@H]1[C@@H](N2CCN(CCF)CC2)CCN1c1ncc2c3c(c(-c4ncc(F)c5sc(NC(=O)OC(C)(C)C)c(C#N)c45)c(F)c2n1)COC3] | 695 |
| 460D | tert-Butyl (3-cyano-4-(3-((2S,3S)-3-((S)-3,4-dimethylpiperazin-1-yl)-2-methylpyrrolidin-1-yl)-5-fluoro-7,9-dihydrofuro[3,4-f]quinazolin-6-yl)-7-fluorothieno[3,2-c]pyridin-2-yl)carbamate | 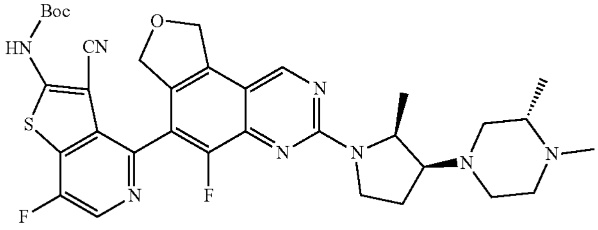 [SMILES: C[C@H]1CN([C@H]2CCN(c3ncc4c5c(c(-c6ncc(F)c7sc(NC(=O)OC(C)(C)C)c(C#N)c67)c(F)c4n3)COC5)[C@H]2C)CCN1C] | 677 |
| 461D | tert-Butyl (3-cyano-4-(3-((2S,3S)-3-((S)-2,4-dimethylpiperazin-1-yl)-2-methylpyrrolidin-1-yl)-5-fluoro-7,9-dihydrofuro[3,4-f]quinazolin-6-yl)-7-fluorothieno[3,2-c]pyridin-2-yl)carbamate | 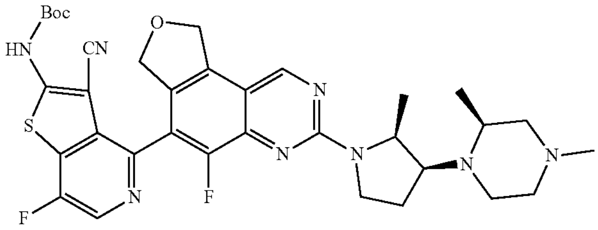 [SMILES: C[C@H]1[C@@H](N2CCN(C)C[C@@H]2C)CCN1c1ncc2c3c(c(-c4ncc(F)c5sc(NC(=O)OC(C)(C)C)c(C#N)c45)c(F)c2n1)COC3] | 677 |
| 462D | tert-Butyl (3-cyano-7-fluoro-4-(5-fluoro-3-((2S,3S)-3-((S)-2-(hydroxymethyl)-4-methylpiperazin-1-yl)-2-methylpyrrolidin-1-yl)-7,9-dihydrofuro[3,4-f]quinazolin-6-yl)thieno[3,2-c]pyridin-2-yl)carbamate | 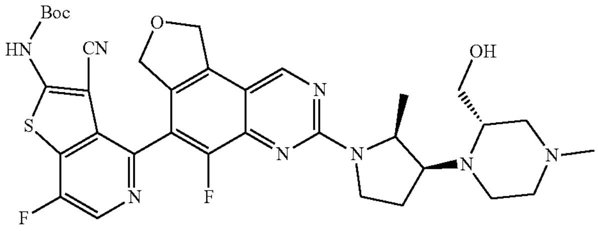 [SMILES: C[C@H]1[C@@H](N2CCN(C)C[C@H]2CO)CCN1c1ncc2c3c(c(-c4ncc(F)c5sc(NC(=O)OC(C)(C)C)c(C#N)c45)c(F)c2n1)COC3] | 693 |

TABLE 22-continued

| Preparation | Chemical Name | Structure | MS (ES) m/z (M + 1) |
|---|---|---|---|
| 463D | tert-Butyl (3-cyano-7-fluoro-4-(5-fluoro-3-((2S,3S)-3-((S)-2-(fluoromethyl)-4-methylpiperazin-1-yl)-2-methylpyrrolidin-1-yl)-7,9-dihydrofuro[3,4-f]quinazolin-6-yl)thieno[3,2-c]pyridin-2-yl)carbamate | 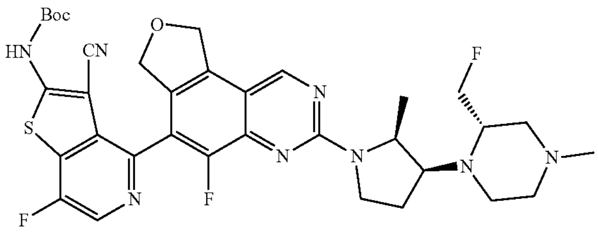 [SMILES: C[C@H]1[C@@H](N2CCN(C)C[C@H]2CF)CCN1c1ncc2c3c(c(-c4ncc(F)c5sc(NC(=O)OC(C)(C)C)c(C#N)c45)c(F)c2n1)COC3] | 695 |
| 464D | tert-Butyl (3-cyano-7-fluoro-4-(5-fluoro-3-((2S,3S)-2-methyl-3-(8-methyl-3,8-diazabicyclo[3.2.1]octan-3-yl)pyrrolidin-1-yl)-7,9-dihydrofuro[3,4-f]quinazolin-6-yl)thieno[3,2-c]pyridin-2-yl)carbamate | 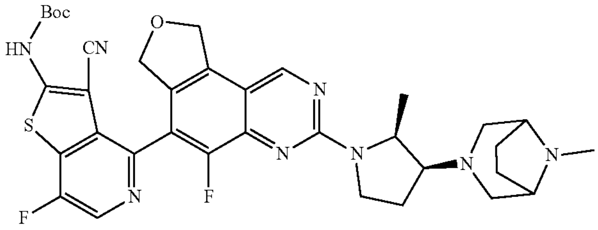 [SMILES: C[C@H]1[C@@H](N2CC3CCC(C2)N3C)CCN1c1ncc2c3c(c(-c4ncc(F)c5sc(NC(=O)OC(C)(C)C)c(C#N)c45)c(F)c2n1)COC3] | 689 |
| 465D | tert-Butyl (3-cyano-7-fluoro-4-(5-fluoro-3-((2S,4S)-2-methyl-4-(4-methylpiperazin-1-yl)pyrrolidin-1-yl)-7,9-dihydrofuro[3,4-f]quinazolin-6-yl)thieno[3,2-c]pyridin-2-yl)carbamate | 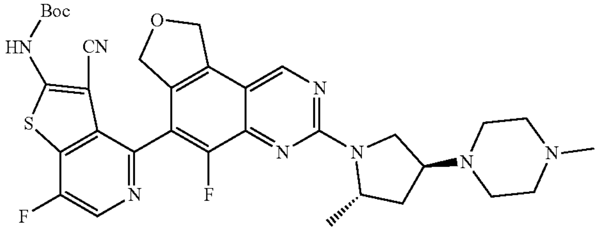 [SMILES: C[C@H]1C[C@H](N2CCN(C)CC2)CN1c1ncc2c3c(c(-c4ncc(F)c5sc(NC(=O)OC(C)(C)C)c(C#N)c45)c(F)c2n1)COC3] | 663 |
| 466D | tert-Butyl (3-cyano-7-fluoro-4-(5-fluoro-3-((2S,4R)-2-methyl-4-(4-methylpiperazin-1-yl)pyrrolidin-1-yl)-7,9-dihydrofuro[3,4-f]quinazolin-6-yl)thieno[3,2-c]pyridin-2-yl)carbamate | 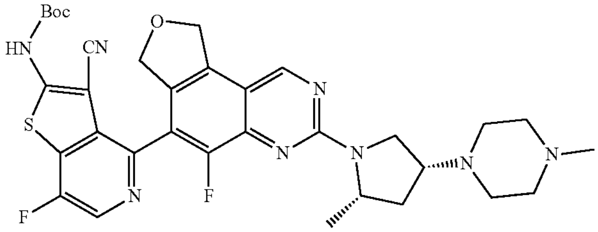 [SMILES: C[C@H]1C[C@@H](N2CCN(C)CC2)CN1c1ncc2c3c(c(-c4ncc(F)c5sc(NC(=O)OC(C)(C)C)c(C#N)c45)c(F)c2n1)COC3] | 663 |
| 467D[10] | tert-Butyl (3-cyano-7-fluoro-4-(5-fluoro-3-(3-hydroxy-4-(4-methylpiperazin-1-yl)pyrrolidin-1-yl)-7,9-dihydrofuro[3,4-f]quinazolin-6-yl)thieno[3,2-c]pyridin-2-yl)carbamate | 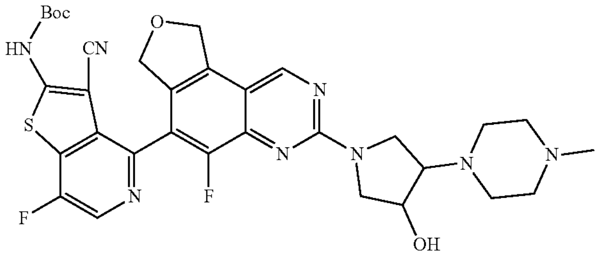 [SMILES: CN1CCN(C2CN(c3ncc4c5c(c(-c6ncc(F)c7sc(NC(=O)OC(C)(C)C)c(C#N)c67)c(F)c4n3)COC5)CC2O)CC1] | 665 |
| 468D | tert-Butyl (3-cyano-7-fluoro-4-(5-fluoro-3-((3R,4R)-3-hydroxy-4-(4-methylpiperazin-1-yl)pyrrolidin-1-yl)-7,9-dihydrofuro[3,4-f]quinazolin-6-yl)thieno[3,2-c]pyridin-2-yl)carbamate | 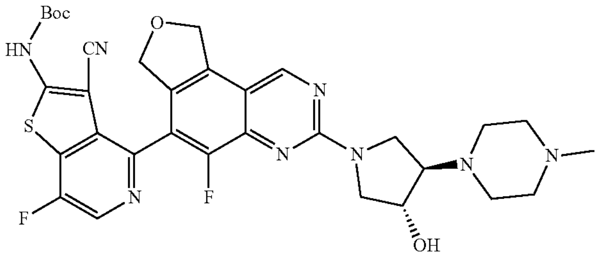 [SMILES: CN1CCN([C@@H]2CN(c3ncc4c5c(c(-c6ncc(F)c7sc(NC(=O)OC(C)(C)C)c(C#N)c67)c(F)c4n3)COC5)C[C@H]2O)CC1] | 665 |

TABLE 22-continued

| Preparation | Chemical Name | Structure | MS (ES) m/z (M + 1) |
|---|---|---|---|
| 469D | tert-Butyl (3-cyano-7-fluoro-4-(5-fluoro-3-((3S,4S)-3-hydroxy-4-(4-methylpiperazin-1-yl)pyrrolidin-1-yl)-7,9-dihydrofuro[3,4-f]quinazolin-6-yl)thieno[3,2-c]pyridin-2-yl)carbamate | 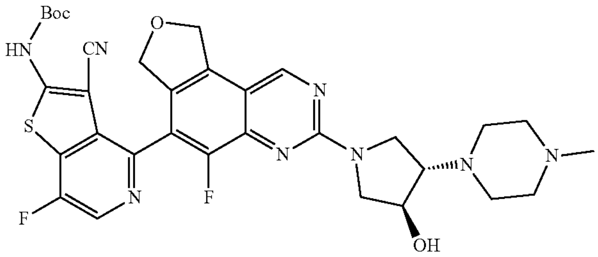 [SMILES: CN1CCN([C@H]2CN(c3ncc4c5c(c(-c6ncc(F)c7sc(NC(=O)OC(C)(C)C)c(C#N)c67)c(F)c4n3)COC5)C[C@@H]2O)CC1] | 665 |
| 470D [11] | tert-Butyl (3-cyano-4-(3-(3-((S)-2,4-dimethylpiperazin-1-yl)-4-hydroxypyrrolidin-1-yl)-5-fluoro-7,9-dihydrofuro[3,4-f]quinazolin-6-yl)-7-fluorothieno[3,2-c]pyridin-2-yl)carbamate, Isomer 2 | 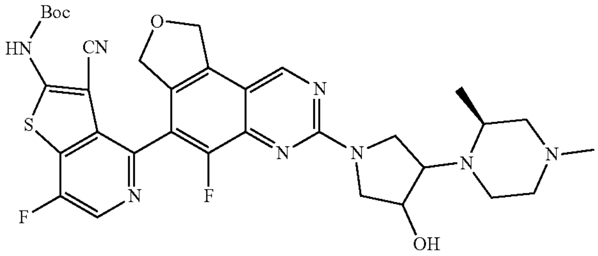 [SMILES: C[C@H]1CN(C)CCN1C1CN(c2ncc3c4c(c(-c5ncc(F)c6sc(NC(=O)OC(C)(C)C)c(C#N)c56)c(F)c3n2)COC4)CC1O] | 679 |
| 471D [11] | tert-Butyl (3-cyano-4-(3-(3-((S)-2,4-dimethylpiperazin-1-yl)-4-hydroxypyrrolidin-1-yl)-5-fluoro-7,9-dihydrofuro[3,4-f]quinazolin-6-yl)-7-fluorothieno[3,2-c]pyridin-2-yl)carbamate. Isomer 1 | 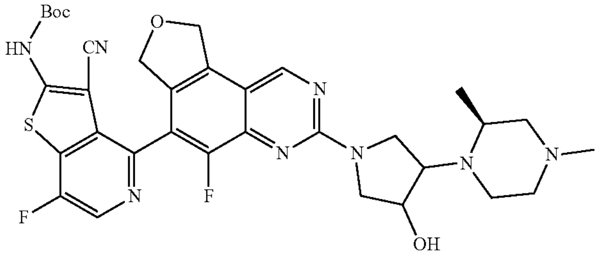 [SMILES: C[C@H]1CN(C)CCN1C1CN(c2ncc3c4c(c(-c5ncc(F)c6sc(NC(=O)OC(C)(C)C)c(C#N)c56)c(F)c3n2)COC4)CC1O] | 679 |
| 472D [12] | tert-Butyl (3-cyano-4-(3-(3-((S)-3,4-dimethylpiperazin-1-yl)-4-hydroxypyrrolidin-1-yl)-5-fluoro-7,9-dihydrofuro[3,4-f]quinazolin-6-yl)-7-fluorothieno[3,2-c]pyridin-2-yl)carbamate | 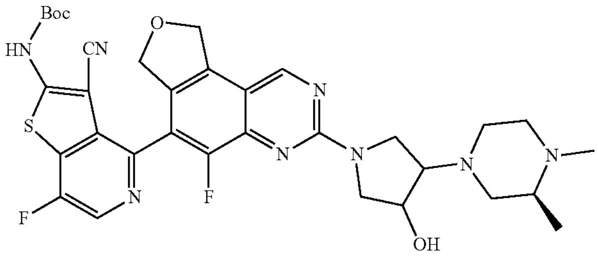 [SMILES: C[C@H]1CN(C2CN(c3ncc4c5c(c(-c6ncc(F)c7sc(NC(=O)OC(C)(C)C)c(C#N)c67)c(F)c4n3)COC5)CC2O)CCN1C] | 679 |
| 473D [13] | tert-Butyl (3-cyano-7-fluoro-4-(5-fluoro-3-(3-hydroxy-4-(3-methyl-3,8-diazabicyclo[3.2.1]octan-8-yl)pyrrolidin-1-yl)-7,9-dihydrofuro[3,4-f]quinazolin-6-yl)thieno[3,2-c]pyridin-2-yl)carbamate | 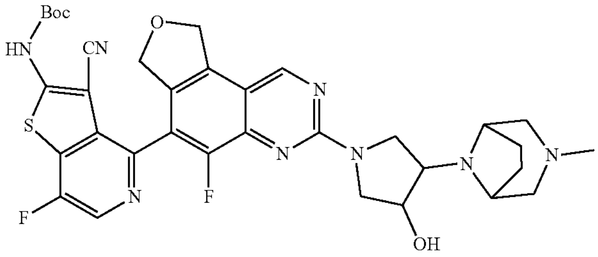 [SMILES: CN1CC2CCC(C1)N2C1CN(c2ncc3c4c(c(-c5ncc(F)c6sc(NC(=O)OC(C)(C)C)c(C#N)c56)c(F)c3n2)COC4)CC1O] | 691 |
| 474D [14] | tert-Butyl (3-cyano-4-(3-(3-((S)-3,4-dimethylpiperazin-1-yl)-4-methoxypyrrolidin-1-yl)-5-fluoro-7,9-dihydrofuro[3,4-f]quinazolin-6-yl)-7-fluorothieno[3,2-c]pyridin-2-yl)carbamate | 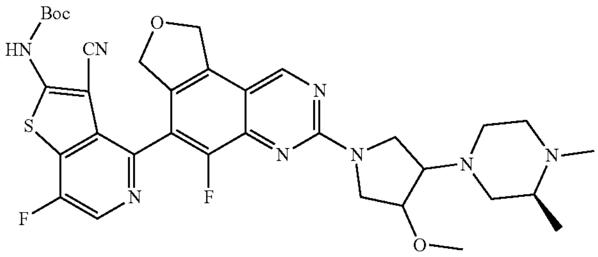 [SMILES: COC1CN(c2ncc3c4c(c(-c5ncc(F)c6sc(NC(=O)OC(C)(C)C)c(C#N)c56)c(F)c3n2)COC4)CC1N1CCN(C)[C@@H](C)C1] | 693 |

TABLE 22-continued

| Preparation | Chemical Name | Structure | MS (ES) m/z (M + 1) |
|---|---|---|---|
| 475D [15] | tert-Butyl (3-cyano-7-fluoro-4-(5-fluoro-3-(3-methoxy-4-(3-methyl-3,8-diazabicyclo[3.2.1]octan-8-yl)pyrrolidin-1-yl)-7.9-dihydrofuro[3,4-f]quinazolin-6-yl)thieno[3,2-c]pyridin-2-yl)carbamate | 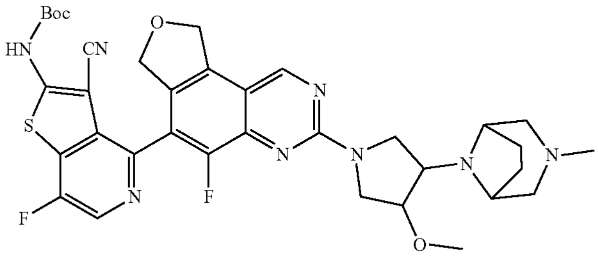 [SMILES: COC1CN(c2ncc3c4c(c(-c5ncc(F)c6sc(NC(=O)OC(C)(C)C)c(C#N)c56)c(F)c3n2)COC4)CC1N1C2CCC1CN(C)C2] | 705 |
| 476D | tert-Butyl (3-cyano-7-fluoro-4-(5-fluoro-3-((S)-3-(piperidin-1-yl)pyrrolidin-1-yl)-7,9-dihydrofuro[3,4-f]qunazolin-6-yl)thieno[3,2-c]pyridin-2-yl)carbamate | 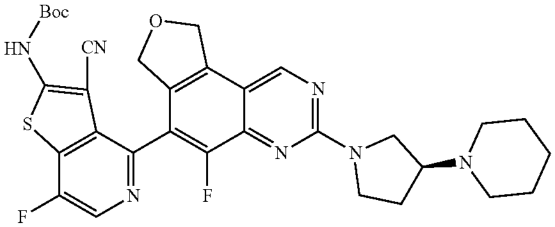 [SMILES: CC(C)(C)OC(=O)Nc1sc2c(F)cnc(-c3c4c(c5cnc(N6CC[C@H](N7CCCCC7)C6)nc5c3F)COC4)c2c1C#N] | 634 |
| 477D | tert-Butyl (3-cyano-7-fluoro-4-(5-fluoro-3-((R)-3-(piperidin-1-yl)pyrrolidin-1-yl)-7,9-dihydrofuro[3,4-f]quinazolin-6-yl)thieno[3,2-c]pyridin-2-yl)carbamate | 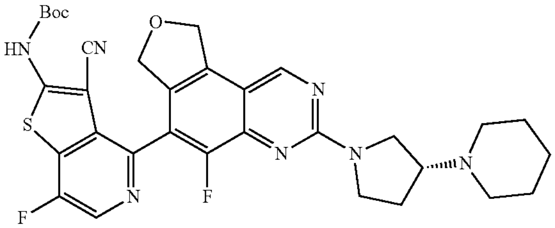 | 634 |
| 478D | tert-Butyl (3-cyano-4-(3-((R)-3-(4-(dimethylamino)piperidin-1-yl)pyrrolidin-1-yl)-5-fluoro-7,9-dihydrofuro[3,4-f]quinazolin-6-yl)-7-fluorothieno[3,2-c]pyridin-2-yl)carbamate | 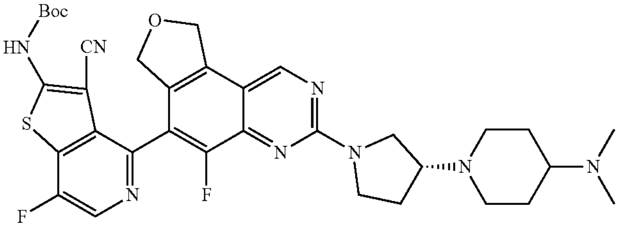 [SMILES: CN(C)C1CCN([C@@H]2CCN(c3ncc4c5c(c(-c6ncc(F)c7sc(NC(=O)OC(C)(C)C)c(C#N)c67)c(F)c4n3)COC5)C2)CC1] | 677 |
| 479D | tert-Butyl (3-cyano-7-fluoro-4-(5-fluoro-3-((R)-3-((S)-3-hydroxypiperidin-1-yl)pyrrolidin-1-yl)-7,9-dihydrofuro[3,4-f]quinazolin-6-yl)thieno[3,2-c]pyridin-2-yl)carbamate | 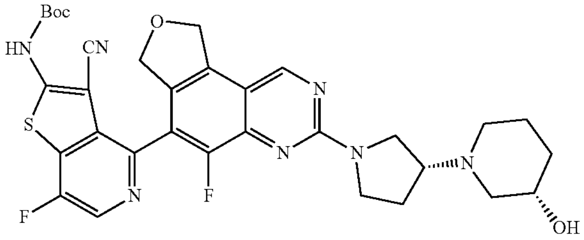 [SMILES: CC(C)(C)OC(=O)Nc1sc2c(F)cnc(-c3c4c(c5cnc(N6CC[C@@H](N7CCC[C@H](O)C7)C6)nc5c3F)COC4)c2c1C#N] | 650 |
| 480D | tert-Butyl (3-cyano-7-fluoro-4-(5-fluoro-3-((R)-3-((R)-3-hydroxypiperidin-1-yl)pyrrolidin-1-yl)-7,9-dihydrofuro[3,4-f]quinazolin-6-yl)thieno[3,2-c]pyridin-2-yl)carbamate | 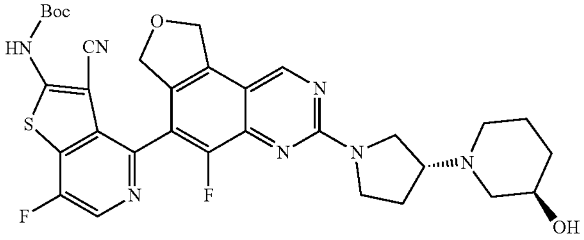 [SMILES: CC(C)(C)OC(=O)Nc1sc2c(F)cnc(-c3c4c(c5cnc(N6CC[C@@H](N7CCC[C@@H](O)C7)C6)nc5c3F)COC4)c2c1C#N] | 650 |

TABLE 22-continued

| Preparation | Chemical Name | Structure | MS (ES) m/z (M + 1) |
|---|---|---|---|
| 481D | tert-Butyl (3-cyano-7-fluoro-4-(5-fluoro-3-((R)-3-(4-methoxypiperidin-1-yl)pyrrolidin-1-yl)-7,9-dihydrofuro[3,4-f]quinazolin-6-yl)thieno[3,2-c]pyridin-2-yl)carbamate | 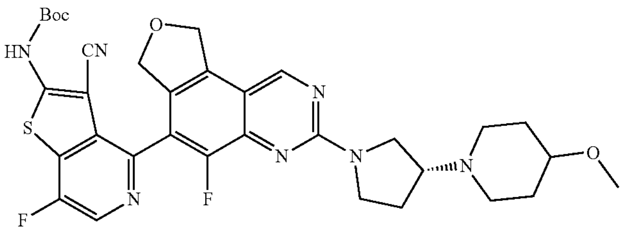 [SMILES: COC1CCN([C@@H]2CCN(c3ncc4c5c(c(-c6ncc(F)c7sc(NC(=O)OC(C)(C)C)c(C#N)c67)c(F)c4n3)COC5)C2)CC1] | 664 |
| 482D | tert-Butyl (3-cyano-4-(3-((R)-3-(4-cyanopiperidin-1-yl)pyrrolidin-1-yl)-5-fluoro-7,9-dihydrofuro[3,4-f]quinazolin-6-yl)-7-fluorothieno[3,2-c]pyridin-2-yl)carbamate | 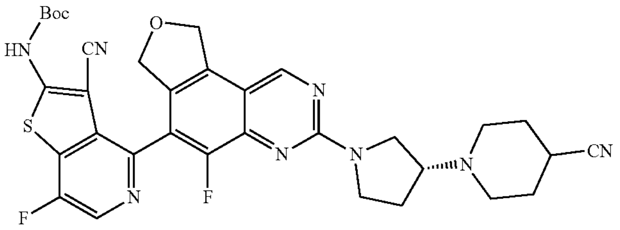 [SMILES: CC(C)(C)OC(=O)Nc1sc2c(F)cnc(-c3c4c(c5cnc(N6CC[C@@H](N7CCC(C#N)CC7)C6)nc5c3F)COC4)c2c1C#N] | 659 |
| 483D | tert-Butyl (3-cyano-7-fluoro-4-(5-fluoro-3-((R)-3-(4-hydroxypiperidin-1-yl)pyrrolidin-1-yl)-7,9-dihydrofuro[3,4-f]quinazolin-6-yl)thieno[3,2-c]pyridin-2-yl)carbamate | 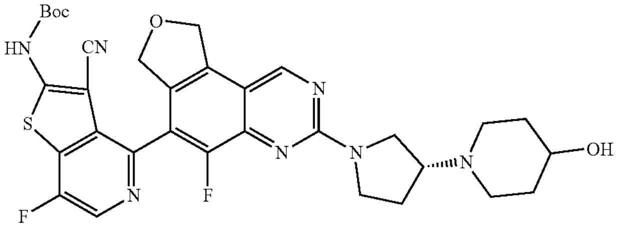 [SMILES: CC(C)(C)OC(=O)Nc1sc2c(F)cnc(-c3c4c(c5cnc(N6CC[C@@H](N7CCC(O)CC7)C6)nc5c3F)COC4)c2c1C#N] | 650 |
| 484D [16] | tert-Butyl (3-cyano-7-fluoro-4-(5-fluoro-3-((3S)-3-(3-hydroxy-3-methylpiperidin-1-yl)pyrrolidin-1-yl)-7,9-dihydrofuro[3,4-f]quinazolin-6-yl)thieno[3,2-c]pyridin-2-yl)carbamate, Isomer 1 | 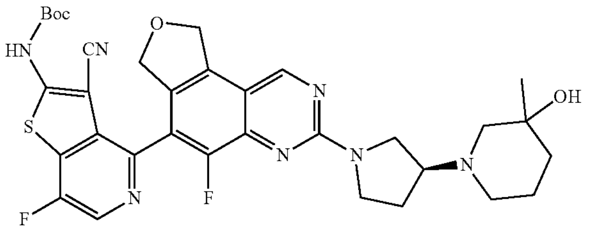 [SMILES: CC1(O)CCCN([C@H]2CCN(c3ncc4c5c(c(-c6ncc(F)c7sc(NC(=O)OC(C)(C)C)c(C#N)c67)c(F)c4n3)COC5)C2)C1] | 664 |
| 485D [16] | tert-Butyl (3-cyano-7-fluoro-4-(5-fluoro-3-((3S)-3-(3-hydroxy-3-methylpiperidin-1-yl)pyrrolidin-1-yl)-7,9-dihydrofuro[3,4-f]quinazolin-6-yl)thieno[3,2-c]pyridin-2-yl)carbamate, Isomer 2 | 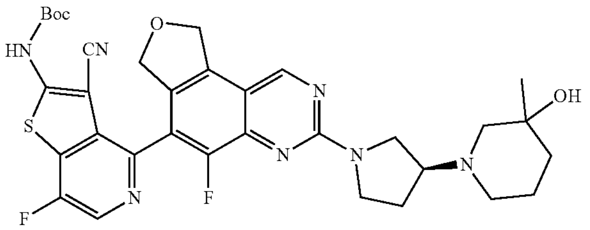 [SMILES: CC1(O)CCCN([C@H]2CCN(c3ncc4c5c(c(-c6ncc(F)c7sc(NC(=O)OC(C)(C)C)c(C#N)c67)c(F)c4n3)COC5)C2)C1] | 664 |
| 486D | tert-Butyl (3-cyano-7-fluoro-4-(5-fluoro-3-((R)-3-(4-hydroxy-4-methylpiperidin-1-yl)pyrrolidin-1-yl)-7,9-dihydrofuro[3,4-f]quinazolin-6-yl)thieno[3,2-c]pyridin-2-yl)carbamate | 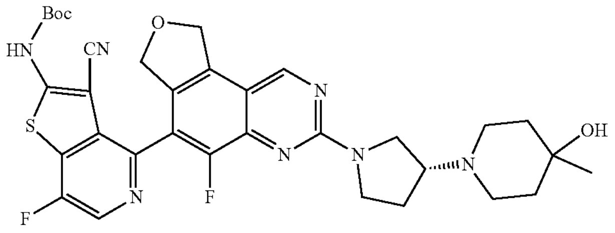 [SMILES: CC1(O)CCN([C@@H]2CCN(c3ncc4c5c(c(-c6ncc(F)c7sc(NC(=O)OC(C)(C)C)c(C#N)c67)c(F)c4n3)COC5)C2)CC1] | 664 |

TABLE 22-continued

| Preparation | Chemical Name | Structure | MS (ES) m/z (M + 1) |
| --- | --- | --- | --- |
| 487D | tert-Butyl (3-cyano-7-fluoro-4-(5-fluoro-3-((R)-3-(4-fluoropiperidin-1-yl)pyrrolidin-1-yl)-7,9-dihydrofuro[3,4-f]quinazolin-6-yl)thieno[3,2-c]pyridin-2-yl)carbamate | 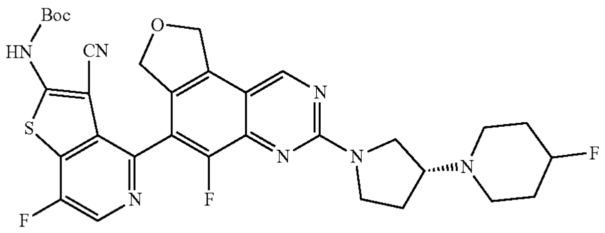 [SMILES: CC(C)(C)OC(=O)Nc1sc2c(F)cnc(-c3c4c(c5cnc(N6CC[C@@H](N7CCC(F)CC7)C6)nc5c3F)COC4)c2c1C#N] | 652 |
| 488D | tert-Butyl (3-cyano-7-fluoro-4-(5-fluoro-3-((3R)-3-(3-fluoropiperidin-1-yl)pyrrolidin-1-yl)-7,9-dihydrofuro[3,4-f]quinazolin-6-yl)thieno[3,2-c]pyridin-2-yl)carbamate | 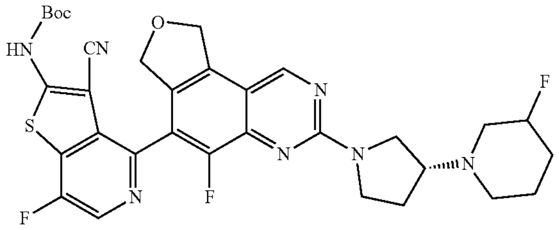 [SMILES: CC(C)(C)OC(=O)Nc1sc2c(F)cnc(-c3c4c(c5cnc(N6CC[C@@H](N7CCCC(F)C7)C6)nc5c3F)COC4)c2c1C#N] | 652 |
| 489D | tert-Butyl (3-cyano-7-fluoro-4-(5-fluoro-3-((2S,3S)-2-methyl-3-(piperidin-1-yl)pyrrolidin-1-yl)-7,9-dihydrofuro[3,4-f]quinazolin-6-yl)thieno[3,2-c]pyridin-2-yl)carbamate | 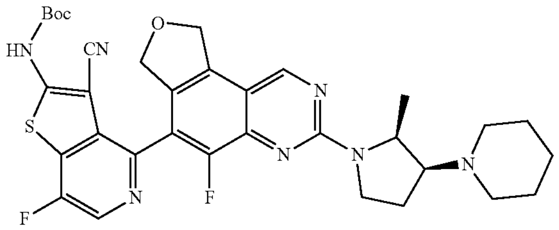 [SMILES: C[C@H]1[C@@H](N2CCCCC2)CCN1c1ncc2c3c(c(-c4ncc(F)c5sc(NC(=O)OC(C)(C)C)c(C#N)c45)c(F)c2n1)COC3] | 648 |
| 490D [17] | tert-Butyl (3-cyano-7-fluoro-4-(5-fluoro-3-(3-hydroxy-4-(piperidin-1-yl)pyrrolidin-1-yl)-7,9-dihydrofuro[3,4-f]quinazolin-6-yl)thieno[3,2-c]pyridin-2-yl)carbamate | 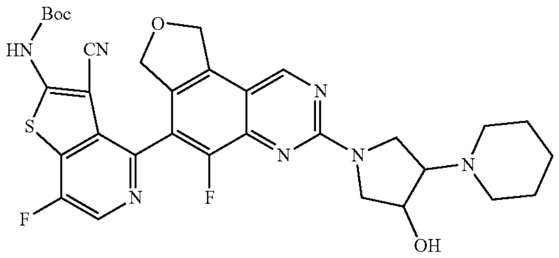 [SMILES: CC(C)(C)OC(=O)Nc1sc2c(F)cnc(-c3c4c(c5cnc(N6CC(O)C(N7CCCCC7)C6)nc5c3F)COC4)c2c1C#N] | 650 |
| 491D [18] | tert-Butyl (3-cyano-7-fluoro-4-(5-fluoro-3-(3-methoxy-4-(piperidin-1-yl)pyrrolidin-1-yl)-7,9-dihydrofuro[3,4-f]quinazolin-6-yl)thieno[3,2-c]pyridin-2-yl)carbamate, Isomer 1 | 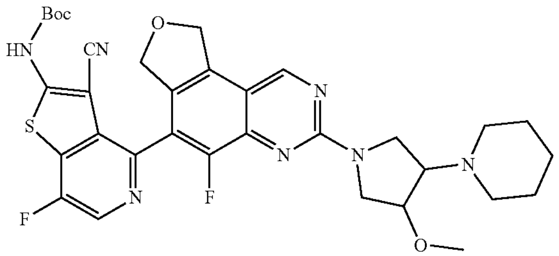 [SMILES: COC1CN(c2ncc3c4c(c(-c5ncc(F)c6sc(NC(=O)OC(C)(C)C)c(C#N)c56)c(F)c3n2)COC4)CC1N1CCCCC1] | 664 |
| 492D [18] | tert-Butyl (3-cyano-7-fluoro-4-(5-fluoro-3-(3-methoxy-4-(piperidin-1-yl)pyrrolidin-1-yl)-7,9-dihydrofuro[3,4-f]quinazolin-6-yl)thieno[3,2-c]pyridin-2-yl)carbamate, Isomer 2 | 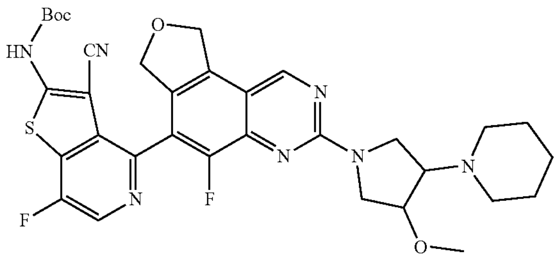 [SMILES: COC1CN(c2ncc3c4c(c(-c5ncc(F)c6sc(NC(=O)OC(C)(C)C)c(C#N)c56)c(F)c3n2)COC4)CC1N1CCCCC1] | 664 |

TABLE 22-continued

| Preparation | Chemical Name | Structure | MS (ES) m/z (M + 1) |
|---|---|---|---|
| 493D | tert-Butyl (3-cyano-7-fluoro-4-(5-fluoro-3-((R)-3-thiomorpholinopyrrolidin-1-yl)-7,9-dihydrofuro[3,4-f]quinazolin-6-y)thieno[3,2-c]pyridin-2-yl)carbamate | 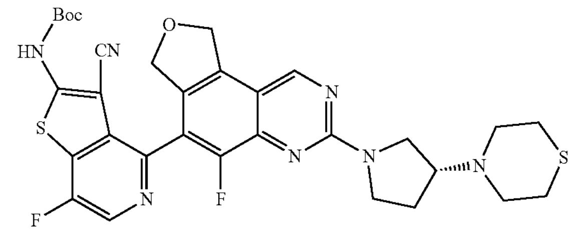 [SMILES: CC(C)(C)OC(=O)Nc1sc2c(F)cnc(-c3c4c(c5cnc(N6CC[C@@H](N7CCSCC7)C6)nc5c3F)COC4)c2c1C#N] | 652 |
| 494D | tert-Butyl (3-cyano-4-(3-((3R)-3-(2-((dimethylamino)methyl) morpholino)pyrrolidin-1-yl)-5-fluoro-7,9-dihydrofuro[3,4-f]quinazolin-6-yl)-7-fluorothieno[3,2-c]pyridin-2-yl)carbamate | 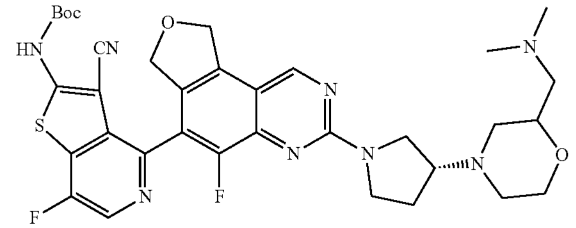 [SMILES: CN(C)CC1CN([C@@H]2CCN(c3ncc4c5c(c(-c6ncc(F)c7sc(NC(=O)OC(C)(C)C)c(C#N)c67)c(F)c4n3)COC5)C2)CCO1] | 693 |
| 495D | tert-Butyl (3-cyano-4-(3-((3S)-3-(2-((dimethylamino)methyl) morpholino)pyrrolidin-1-yl)-5-fluoro-7,9-dihydrofuro[3,4-f]quinazolin-6-yl)-7-fluorothieno[3,2-c]pyridin-2-yl)carbamate | 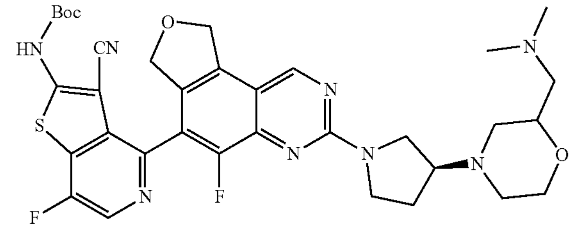 [SMILES: CN(C)CC1CN([C@H]2CCN(c3ncc4c5c(c(-c6ncc(F)c7sc(NC(=O)OC(C)(C)C)c(C#N)c67)c(F)c4n3)COC5)C2)CCO1] | 693 |
| 496D | tert-Butyl (3-cyano-7-fluoro-4-(5-fluoro-3-((2S,3S)-2-methyl-3-morpholinopyrrolidin-1-yl)-7,9-dihydrofuro[3,4-f]quinazolin-6-yl)thieno[3,2-c]pyridin-2-yl)carbamate | 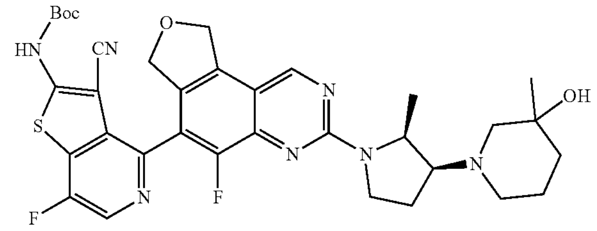 [SMILES: C[C@H]1[C@@H](N2CCCC(C)(O)C2)CCN1c1ncc2c3c(c(-c4ncc(F)c5sc(NC(=O)OC(C)(C)C)c(C#N)c45)c(F)c2n1)COC3] | 650 |
| 497D | tert-Butyl (4-(3-((2S,3S)-3-(3-oxa-6-azabicyclo[3.1.1]heptan-6-yl)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 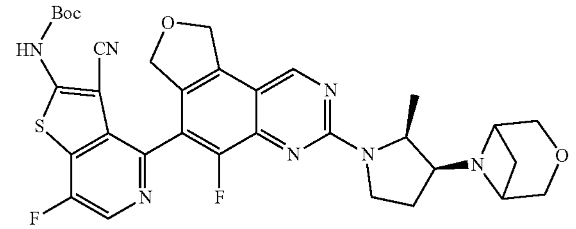 [SMILES: C[C@H]1[C@@H](N2C3COCC2C3)CCN1c1ncc2c3c(c(-c4ncc(F)c5sc(NC(=O)OC(C)(C)C)c(C#N)c45)c(F)c2n1)COC3] | 662 |
| 498D | tert-Butyl (4-(3-((R)-3-(1,4-oxazepan-4-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 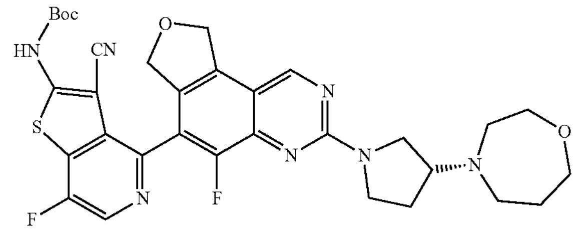 | 650 |

TABLE 22-continued

| Preparation | Chemical Name | Structure | MS (ES) m/z (M + 1) |
|---|---|---|---|
| 499D | tert-Butyl (3-cyano-7-fluoro-4-(5-fluoro-3-((R)-3-(4-methyl-1,4-diazepan-1-yl)pyrrolidin-1-yl)-7,9-dihydrofuro[3,4-f]quinazolin-6-yl)thieno[3,2-c]pyridin-2-yl)carbamate | 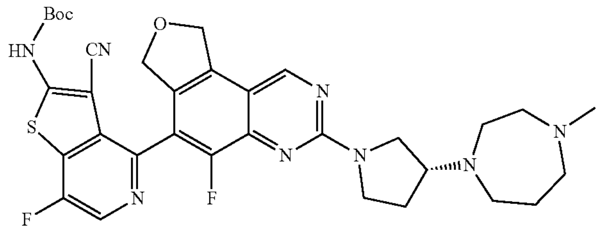 [SMILES: CN1CCCN([C@@H]2CCN(c3ncc4c5c(c(-c6ncc(F)c7sc(NC(=O)OC(C)(C)C)c(C#N)c67)c(F)c4n3)COC5)C2)CC1] | 663 |
| 500D | tert-Butyl (4-(3-((R)-3-(4-acetyl-1,4-diazepan-1-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 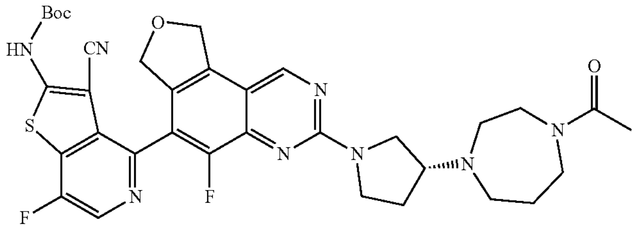 [SMILES: CC(=O)N1CCCN([C@@H]2CCN(c3ncc4c5c(c(-c6ncc(F)c7sc(NC(=O)OC(C)(C)C)c(C#N)c67)c(F)c4n3)COC5)C2)CC1] | 691 |
| 501D | tert-Butyl (3-cyano-7-fluoro-4-(5-fluoro-3-((S)-3-(4-methyl-1,4-diazepan-1-yl)pyrrolidin-1-yl)-7,9-dihydrofuro[3,4-f]quinazolin-6-yl)thieno[3,2-c]pyridin-2-yl)carbamate | 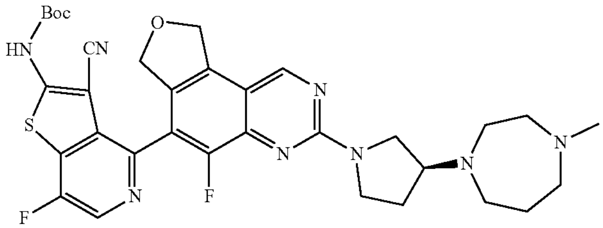 [SMILES: CN1CCCN([C@H]2CCN(c3ncc4c5c(c(-c6ncc(F)c7sc(NC(=O)OC(C)(C)C)c(C#N)c67)c(F)c4n3)COC5)C2)CC1] | 663 |
| 502D [19] | tert-Butyl (3-cyano-7-fluoro-4-(5-fluoro-3-(3-hydroxy-4-(1,4-oxazepan-4-yl)pyrrolidin-1-yl)-7,9-dihydrofuro[3,4-f]quinazolin-6-yl)thieno[3,2-c]pyridin-2-yl)carbamate | 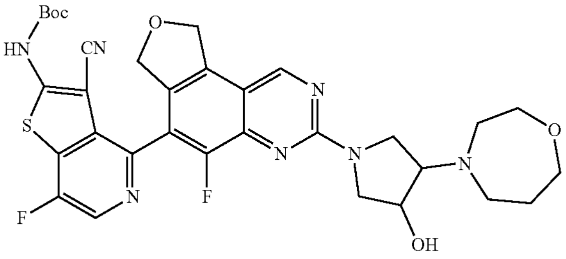 [SMILES: CC(C)(C)OC(=O)Nc1sc2c(F)cnc(-c3c4c(c5cnc(N6CC(O)C(N7CCCOCC7)C6)nc5c3F)COC4)c2c1C#N] | 666 |
| 503D [20] | tert-Butyl (3-cyano-7-fluroo-4-(5-fluoro-3-(3-methoxy-4-(1,4-oxazepan-4-yl)pyrrolidin-1-yl)-7,9-dihydrofuro[3,4-f]quinazolin-6-yl)thieno[3,2-c]pyridin-2-yl)carbamate | 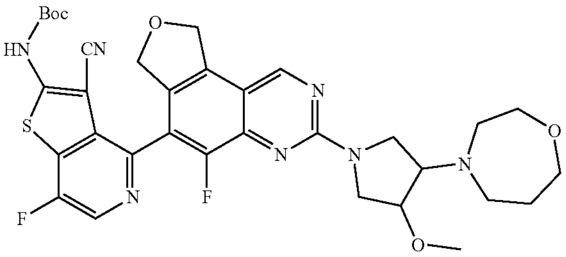 [SMILES: COC1CN(c2ncc3c4c(c(-c5ncc(F)c6sc(NC(=O)OC(C)(C)C)c(C#N)c56)c(F)c3n2)COC4)CC1N1CCCOCC1] | 680 |
| 504D | tert-Butyl (3-cyano-7-fluoro-4-(5-fluoro-3-((R)-3-((3aR,6aS)-5-methylhexahydropyrrolo[3,4-c]pyrrol-2(1H)-yl)pyrrolidin-1-yl)-7,9-dihydrofuro[3,4-f]quinazolin-6-yl)thieno[3,2-c]pyridin-2-yl)carbamate | 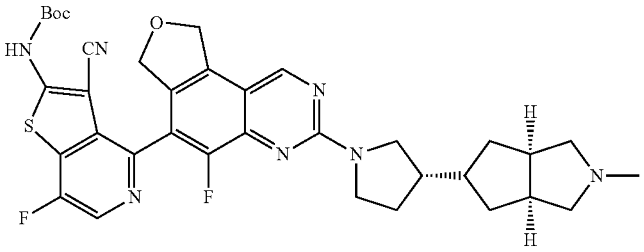 [SMILES: CN1C[C@H]2CC([C@@H]3CCN(c4ncc5c6c(c(-c7ncc(F)c8sc(NC(=O)OC(C)(C)C)c(C#N)c78)c(F)c5n4)COC6)C3)C[C@H]2C1] | 675 |

TABLE 22-continued

| Preparation | Chemical Name | Structure | MS (ES) m/z (M + 1) |
|---|---|---|---|
| 505D | tert-Butyl (3-cyano-7-fluoro-4-(5-fluoro-3-((S)-3-((3aR,6aS)-5-methylhexahydropyrrolo[3,4-c]pyrrol-2(1H)-yl)pyrrolidin-1-yl)-7,9-dihydrofuro[3,4-f]quinazolin-6-yl)thieno[3,2-c]pyridin-2-yl)carbamate | 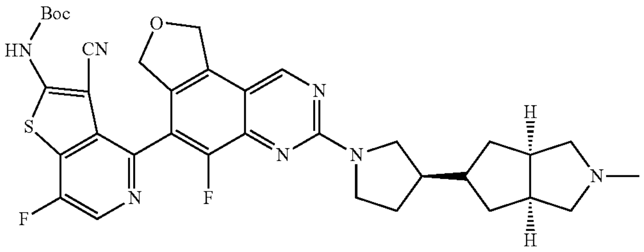 [SMILES: CN1C[C@H]2CC([C@H]3CCN(c4ncc5c6c(c(-c7ncc(F)c8sc(NC(=O)OC(C)(C)C)c(C#N)c78)c(F)c5n4)COC6)C3)C[C@H]2C1] | 675 |
| 506D | tert-Butyl (3-cyano-7-fluoro-4-(5-fluoro-3-((R)-3-((R)-hexahydropyrrolo[1,2-a]pyrazin-2(1H)-yl)pyrrolidin-1-yl)-7,9-dihydrofuro[3,4-f]quinazolin-6-yl)thieno[3,2-c]pyridin-2-yl)carbamate | 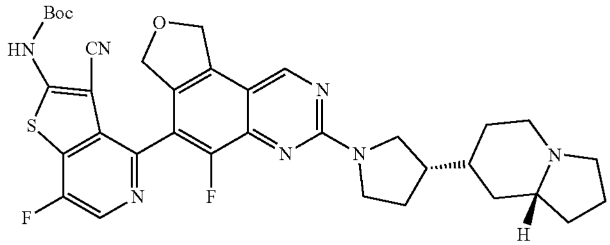 [SMILES: CC(C)(C)OC(=O)Nc1sc2c(F)cnc(-c3c4c(c5cnc(N6CC[C@@H](C7CCN8CCC[C@@H]8C7)C6)nc5c3F)COC4)c2c1C#N] | 675 |
| 507D | tert-Butyl (3-cyano-7-fluoro-4-(5-fluoro-3-((S)-3-((7S,8aS)-7-fluorohexahydropyrrolo[1,2-a]pyrazin-2(1H)-yl)pyrrolidin-1-yl)-7,9-dihydrofuro[3,4-f]quinazolin-6-yl)thieno[3,2-c]pyridin-2-y)carbamate | 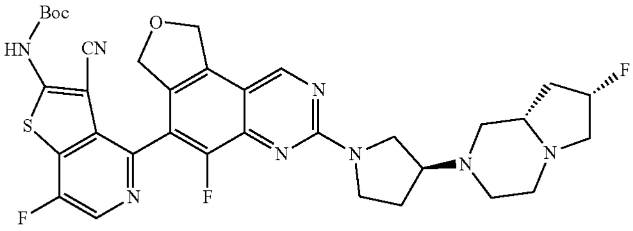 [SMILES: CC(C)(C)OC(=O)Nc1sc2c(F)cnc(-c3c4c(c5cnc(N6CC[C@H](N7CCN8C[C@@H](F)C[C@H]8C7)C6)nc5c3F)COC4)c2c1C#N] | 693 |
| 508D | tert-Butyl (3-cyano-7-fluoro-4-(5-fluoro-3-((R)-3-((3aR,6aS)-tetrahydro-1H-furo[3,4-c]pyrrol-5(3H)-yl)pyrrolidin-1-yl)-7,9-dihydrofuro[3,4-f]quinazolin-6-yl)thieno[3,2-c]pyridin-2-yl)carbamate | 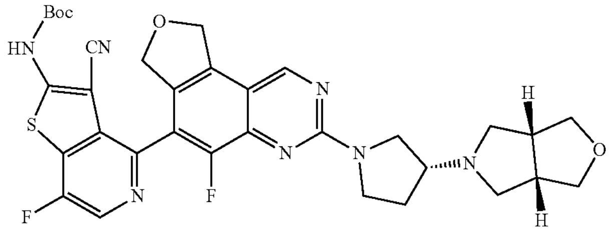 [SMILES: CC(C)(C)OC(=O)Nc1sc2c(F)cnc(-c3c4c(c5cnc(N6CC[C@@H](N7C[C@H]8COC[C@H]8C7)C6)nc5c3F)COC4)c2c1C#N] | 662 |
| 509D | tert-Butyl (3-cyano-7-fluoro-4-(5-fluoro-3-((R)-3-(2-methyl-2,6-diazaspiro[3.4]octan-6-yl)pyrrolidin-1-yl)-7,9-dihydrofuro[3,4-f]quinazolin-6-yl)thieno[3,2-c]pyridin-2-yl)carbamate | 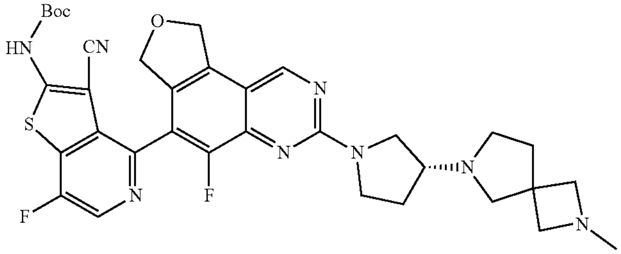 [SMILES: CN1CC2(CCN([C@@H]3CCN(c4ncc5c6c(c(-c7ncc(F)c8sc(NC(=O)OC(C)(C)C)c(C#N)c78)c(F)c5n4)COC6)C3)C2)C1] | 675 |
| 510D | tert-Butyl (4-(3-((R)-3-(2-azaspiro[3.3]heptan-2-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 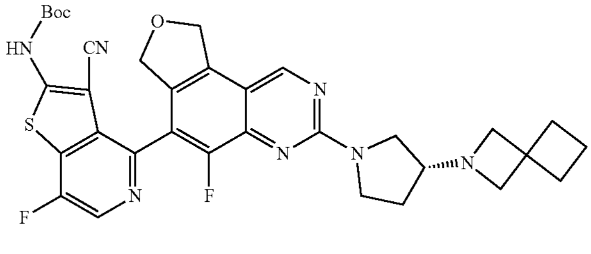 [SMILES: CC(C)(C)OC(=O)Nc1sc2c(F)cnc(-c3c4c(c5cnc(N6CC[C@@H](N7CC8(CCC8)C7)C6)nc5c3F)COC4)c2c1C#N] | 646 |

TABLE 22-continued

| Preparation | Chemical Name | Structure | MS (ES) m/z (M + 1) |
|---|---|---|---|
| 511D | tert-Butyl (4-(3-((S)-3-(2-azaspiro[3.3]heptan-2-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 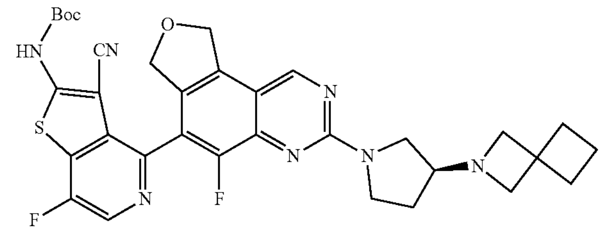 [SMILES: CC(C)(C)OC(=O)Nc1sc2c(F)cnc(-c3c4c(c5cnc(N6CC[C@H](N7CC8(CCC8)C7)C6)nc5c3F)COC4)c2c1C#N] | 646 |
| 512D | tert-Butyl (4-(3-((R)-3-(2-oxa-7-azaspiro[3.5]nonan-7-yl)pyrrolidin-1-yl)-5-fluoro-7,9-dihydrofuro[3,4-f]quinazolin-6-yl)-3-cyano-7-fluorothieno[3,2-c]pyridin-2-yl)carbamate | 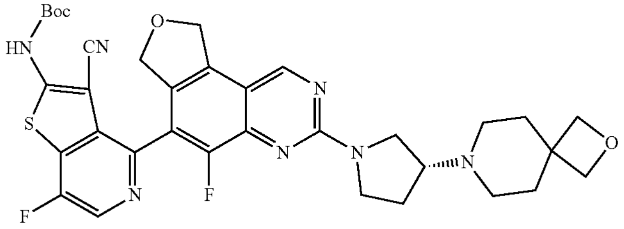 [SMILES: CC(C)(C)OC(=O)Nc1sc2c(F)cnc(-c3c4c(c5cnc(N6CC[C@@H](N7CCC8(CC7)COC8)C6)nc5c3F)COC4)c2c1C#N] | 676 |
| 513D | tert-Butyl (3-cyano-7-fluoro-4-(5-fluoro-3-((3S)-3-(methyl(tetrahydrofuran-3-yl)amino)pyrrolidin-1-yl)-7,9-dihydrofuro[3,4-f]quinazolin-6-yl)thieno[3,2-c]pyridin-2-yl)carbamate | 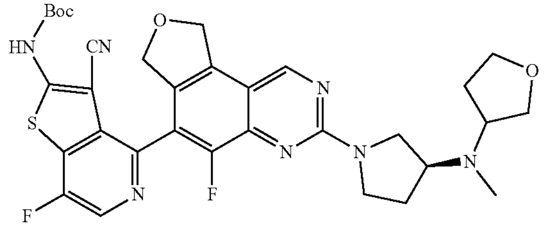 [SMILES: CN(C1CCOC1)[C@H]1CCN(c2ncc3c4c(c(-c5ncc(F)c6sc(NC(=O)OC(C)(C)C)c(C#N)c56)c(F)c3n2)COC4)C1] | 650 |
| 514D | tert-Butyl (3-cyano-7-fluoro-4-(5-fluoro-3-((3S)-3-(methyl((tetrahydrofuran-2-yl)methyl)amino)pyrrolidin-1-yl)-7,9-dihydrofuro[3,4-f]quinazolin-6-y)thieno[3,2-c]pyridin-2-yl)carbamate | 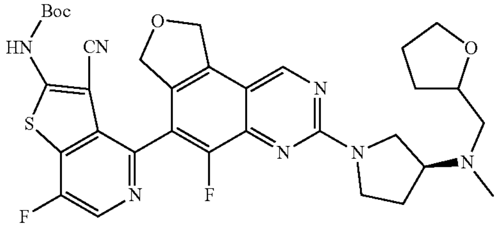 [SMILES: CN(CC1CCCO1)[C@H]1CCN(c2ncc3c4c(c(-c5ncc(F)c6sc(NC(=O)OC(C)(C)C)c(C#N)c56)c(F)c3n2)COC4)C1] | 664 |
| 515D | tert-Butyl (3-cyano-7-fluoro-4-(5-fluoro-3-((R)-3-(methyl((R)-1-methylpyrrolidin-3-yl)amino)pyrrolidin-1-yl)-7,9-dihydrofuro[3,4-f]quinazolin-6-yl)thieno[3,2-c]pyridin-2-yl)carbamate | 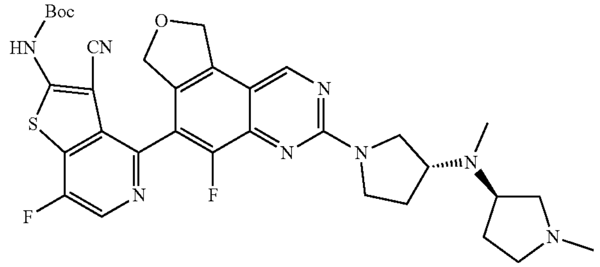 [SMILES: CN1CC[C@@H](N(C)[C@@H]2CCN(c3ncc4c5c(c(-c6ncc(F)c7sc(NC(=O)OC(C)(C)C)c(C#N)c67)c(F)c4n3)COC5)C2)C1] | 663 |
| 516D | tert-Butyl (3-cyano-7-fluoro-4-(5-fluoro-3-((R)-3-(methyl((S)-1-methylpyrrolidin-3-yl)amino)pyrrolidin-1-yl)-7,9-dihydrofuro[3,4-f]quinazolin-6-yl)thieno[3,2-c]pyridin-2-yl)carbamate | 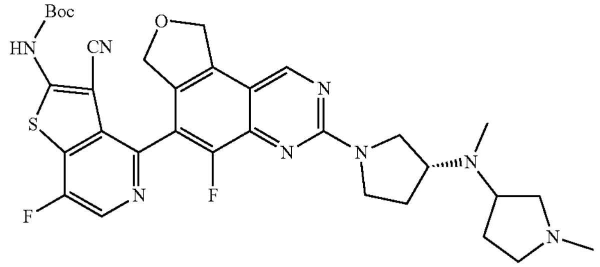 [SMILES: CN1CCC(N(C)[C@@H]2CCN(c3ncc4c5c(c(-c6ncc(F)c7sc(NC(=O)OC(C)(C)C)c(C#N)c67)c(F)c4n3)COC5)C2)C1] | 663 |

TABLE 22-continued

| Preparation | Chemical Name | Structure | MS (ES) m/z (M + 1) |
|---|---|---|---|
| 517D | tert-Butyl (3-cyano-7-fluoro-4-(5-fluoro-3-((S)-3-(methyl((R)-1-methylpyrrolidin-3-yl)amino)pyrrolidin-1-yl)-7,9-dihydrofuro[3,4-f]quinazolin-6-yl)thieno[3,2-c]pyridin-2-y)carbamate | 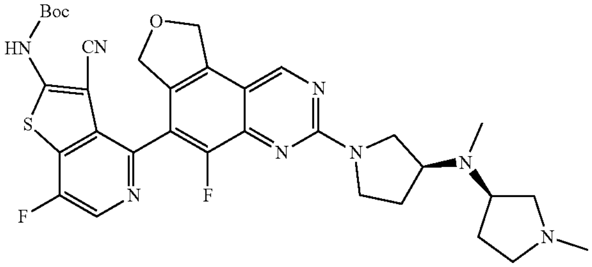 [SMILES: CN1CC[C@@H](N(C)[C@H]2CCN(c3ncc4c5c(c(-c6ncc(F)c7sc(NC(=O)OC(C)(C)C)c(C#N)c67)c(F)c4n3)COC5)C2)C1] | 663 |
| 518D | tert-Butyl (3-cyano-7-fluoro-4-(5-fluoro-3-((S)-3-(methyl((S)-1-methylpyrrolidin-3-yl)amino)pyrrolidin-1-yl)-7,9-dihydrofuro[3,4-f]quinazolin-6-yl)thieno[3,2-c]pyridin-2-yl)carbamate | 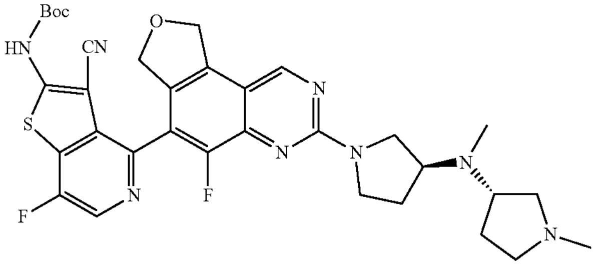 [SMILES: CN1CC[C@H](N(C)[C@H]2CCN(c3ncc4c5c(c(-c6ncc(F)c7sc(NC(=O)OC(C)(C)C)c(C#N)c67)c(F)c4n3)COC5)C2)C1] | 663 |
| 519D | tert-Butyl (3-cyano-4-(3-((S)-3-(2-(dimethylamino)ethyl)pyrrolidin-1-yl)-5-fluoro-7,9-dihydrofuro[3,4-f]quinazolin-6-yl)-7-fluorothieno[3,2-c]pyridin-2-yl)carbamate | 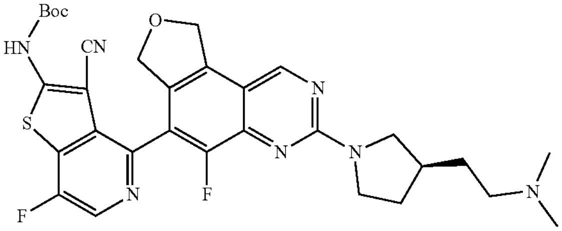 [SMILES: CN(C)CC[C@H]1CCN(c2ncc3c4c(c(-c5ncc(F)c6sc(NC(=O)OC(C)(C)C)c(C#N)c56)c(F)c3n2)COC4)C1] | 622 |
| 520D | tert-Butyl (4-(3-(3-(tert-Butyl(methyl)amino)pyrrolidin-1-yl)-5-fluoro-7,9-dihydrofuro[3,4-f]quinazolin-6-yl)-3-cyano-7-fluorothieno[3,2-c]pyridin-2-yl)carbamate | 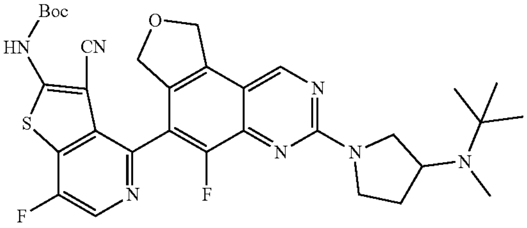 [SMILES: CN(C1CCN(c2ncc3c4c(c(-c5ncc(F)c6sc(NC(=O)OC(C)(C)C)c(C#N)c56)c(F)c3n2)COC4)C1)C(C)(C)C] | 636 |
| 521D | tert-Butyl (3-cyano-4-(3-((R)-3-(2-(dimethylamino)ethoxy)pyrrolidin-1-yl)-5-fluoro-7,9-dihydrofuro[3,4-f]quinazolin-6-yl)-7-fluorothieno[3,2-c]pyridin-2-yl)carbamate | 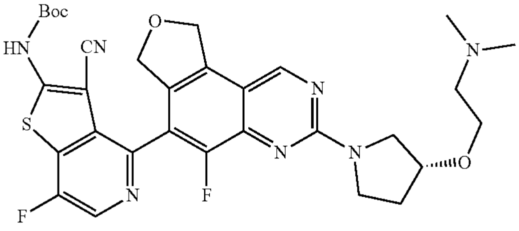 [SMILES: CN(C)CCO[C@@H]1CCN(c2ncc3c4c(c(-c5ncc(F)c6sc(NC(=O)OC(C)(C)C)c(C#N)c56)c(F)c3n2)COC4)C1] | 638 |
| 522D | tert-Butyl (3-cyano-4-(3-((S)-3-(2-(dimethylamino)ethoxy)pyrrolidin-1-yl)-5-fluoro-7,9-dihydrofuro[3,4-f]quinazolin-6-yl)-7-fluorothieino[3,2-c]pyridin-2-yl)carbamate | 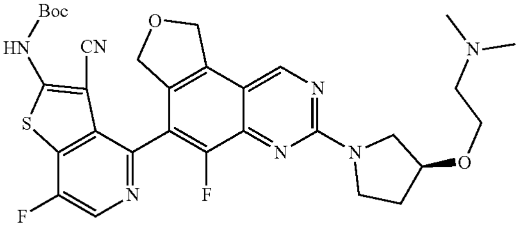 [SMILES: CN(C)CCO[C@H]1CCN(c2ncc3c4c(c(-c5ncc(F)c6sc(NC(=O)OC(C)(C)C)c(C#N)c56)c(F)c3n2)COC4)C1] | 638 |

TABLE 22-continued

| Preparation | Chemical Name | Structure | MS (ES) m/z (M + 1) |
|---|---|---|---|
| 523D | tert-Butyl (3-cyano-4-(3-((R)-3-(3-((dimethylamino)methyl)azetidin-1-yl)pyrrolidin-1-yl)-5-fluoro-7,9-dihydrofuro[3,4-f]quinazolin-6-yl)-7-fluorothieno[3,2-c]pyridin-2-yl)carbamate | 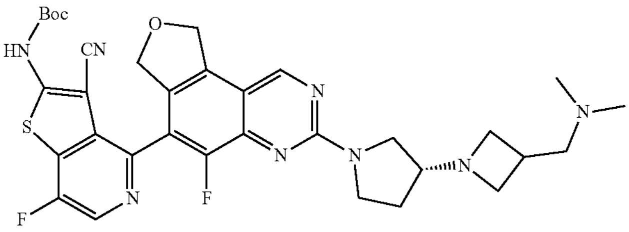 [SMILES: CN(C)CC1CN([C@@H]2CCN(c3ncc4c5c(c(-c6ncc(F)c7sc(NC(=O)OC(C)(C)C)c(C#N)c67)c(F)c4n3)COC5)C2)C1] | 663 |
| 524D | tert-Butyl (3-cyano-4-(3-((S)-3-(3-((dimethylamino)methyl)azetidin-1-yl)pyrrolidin-1-yl)-5-fluoro-7,9-dihydrofuro[3,4-f]quinazolin-6-yl)-7-fluorothieno[3,2-c]pyridin-2-yl)carbamate | 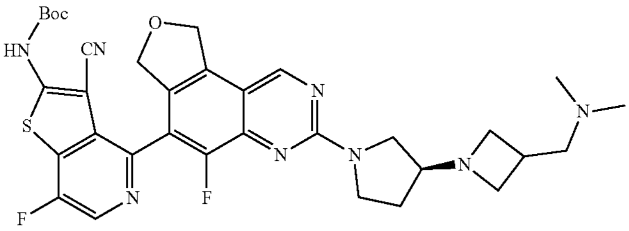 [SMILES: CN(C)CC1CN([C@H]2CCN(c3ncc4c5c(c(-c6ncc(F)c7sc(NC(=O)OC(C)(C)C)c(C#N)c67)c(F)c4n3)COC5)C2)C1] | 663 |
| 525D | tert-Butyl (3-cyano-7-fluoro-4-(5-fluoro-3-((S)-3-hydroxypyrrolidin-1-yl)-7,9-dihydrofuro[3,4-f]quinazolin-6-yl)thieno[3,2-c]pyridin-2-yl)carbamate | 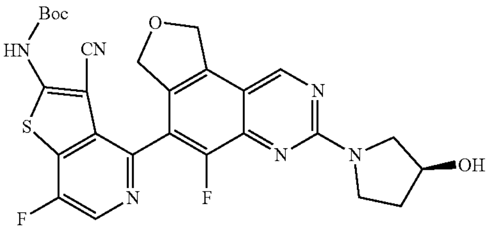 [SMILES: CC(C)(C)OC(=O)Nc1sc2c(F)cnc(-c3c4c(c5cnc(N6CC[C@H](O)C6)nc5c3F)COC4)c2c1C#N] | 567 |
| 526D | tert-Butyl (3-cyano-7-fluoro-4-(5-fluoro-3-(3-((1-methylpiperidin-4-yl)oxy)pyrrolidin-1-yl)-7,9-dihydrofuro[3,4-f]quinazolin-6-yl)thieno[3,2-c]pyridin-2-yl)carbamate | 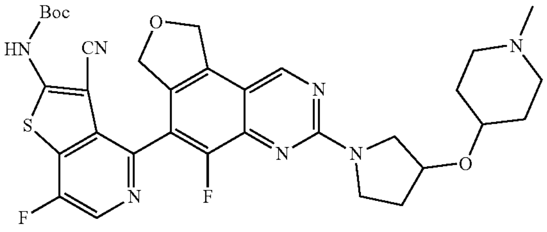 [SMILES: CN1CCC(OC2CCN(c3ncc4c5c(c(-c6ncc(F)c7sc(NC(=O)OC(C)(C)C)c(C#N)c67)c(F)c4n3)COC5)C2)CC1] | 664 |
| 527D | tert-Butyl (3-cyano-7-fluoro-4-(5-fluoro-3-((2S,3S)-2-methyl-3-((1-methylcyclopropyl)amino)pyrrolidin-1-yl)-7,9-dihydrofuro[3,4-f]quinazolin-6-yl)thieno[3,2-c]pyridin-2-yl)carbamate | 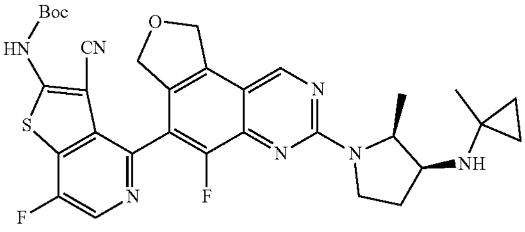 [SMILES: C[C@H]1[C@@H](NC2(C)CC2)CCN1c1ncc2c3c(c(-c4ncc(F)c5sc(NC(=O)OC(C)(C)C)c(C#N)c45)c(F)c2n1)COC3] | 634 |
| 528D | tert-Butyl (3-cyano-7-fluoro-4-(5-fluoro-3-((2S,3S)-3-((3-hydroxybicyclo[1.1.1]pentan-1-yl)amino)-2-methylpyrrolidin-1-yl)-7,9-dihydrofuro[3,4-f]quinazolin-6-yl)thieno[3,2-c]pyridin-2-yl)carbamate | 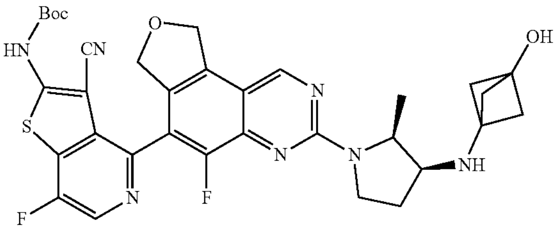 [SMILES: C[C@H]1[C@@H](NC23CC(O)(C2)C3)CCN1c1ncc2c3c(c(-c4ncc(F)c5sc(NC(=O)OC(C)(C)C)c(C#N)c45)c(F)c2n1)COC3] | |

TABLE 22-continued

| Preparation | Chemical Name | Structure | MS (ES) m/z (M + 1) |
|---|---|---|---|
| 529D | tert-Butyl (3-cyano-7-fluoro-4-(5-fluoro-3-((2S,3S)-3-((1-fluoro-2-methylpropan-2-yl)amino)-2-methylpyrrolidin-1-yl)-7,9-dihydrofuro[3,4-f]quinazolin-6-yl)thieno[3,2-c]pyridin-2-yl)carbamate | 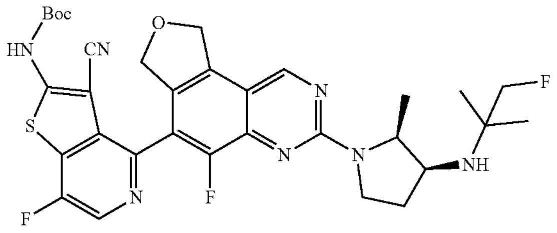 [SMILES: C[C@H]1[C@@H](NC(C)(C)CF)CCN1c1ncc2c3c(c(-c4ncc(F)c5sc(NC(=O)OC(C)(C)C)c(C#N)c45)c(F)c2n1)COC3] | 654 |
| 530D | tert-Butyl (4-(3-((3S,4R)-3-((tert-butoxycarbonyl)amino)-4-fluoropyrrolidin-1-yl)-5-fluoro-7,9-dihydrofuro[3,4-f]quinazolin-6-yl)-3-cyano-7-fluorothieno[3,2-c]pyridin-2-yl)carbamate | 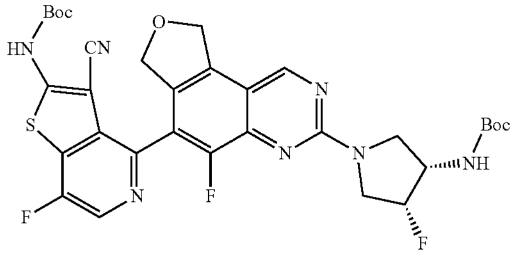 [SMILES: CC(C)(C)OC(=O)Nc1sc2c(F)cnc(-c3c4c(c5cnc(N6C[C@@H](F)[C@@H](NC(=O)OC(C)(C)C)C6)nc5c3F)COC4)c2c1C#N] | 684 |
| 531D | tert-Butyl (3-cyano-7-fluoro-4-(5-fluoro-3-((3S,4S)-3-fluoro-4-(isopropylamino)pyrrolidin-1-yl)-7,9-dihydrofuro[3,4-f]quinazolin-6-yl)thieno[3,2-c]pyridin-2-yl)carbamate | 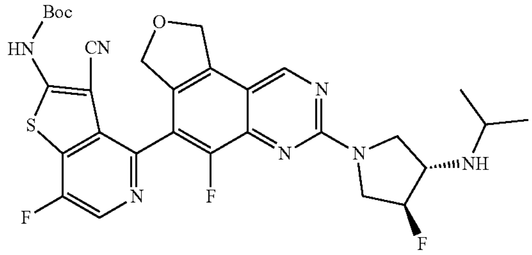 [SMILES: CC(C)N[C@H]1CN(c2ncc3c4c(c(-c5ncc(F)c6sc(NC(=O)OC(C)(C)C)c(C#N)c56)c(F)c3n2)COC4)C[C@@H]1F] | 626 |
| 532D | tert-Butyl (3-cyano-7-fluoro-4-(5-fluoro-3-((3S,4R)-3-fluoro-4-(isopropylamino)pyrrolidin-1-yl)-7,9-dihydrofuro[3,4-f]quinazolin-6-yl)thieno[3,2-c]pyridin-2-yl)carbamate | 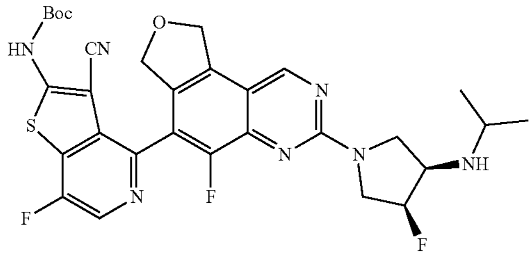 [SMILES: CC(C)N[C@@H]1CN(c2ncc3c4c(c(-c5ncc(F)c6sc(NC(=O)OC(C)(C)C)c(C#N)c56)c(F)c3n2)COC4)C[C@@H]1F] | 626 |
| 533D [21] | tert-Butyl (3-cyano-7-fluoro-4-(5-fluoro-3-(3-hydroxy-4-(isopropyl(methyl)amino) pyrrolidin-1-yl)-7,9-dihydrofuro[3,4-f]quinazolin-6-yl)thieno[3,2-c]pyridin-2-yl)carbamate | 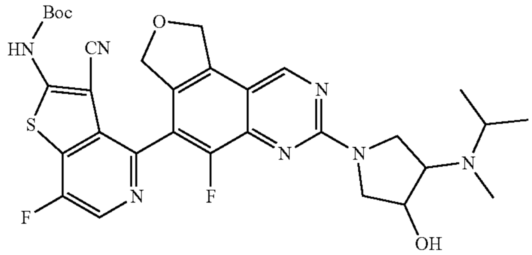 [SMILES: CC(C)N(C)C1CN(c2ncc3c4c(c(-c5ncc(F)c6sc(NC(=O)OC(C)(C)C)c(C#N)c56)c(F)c3n2)COC4)CC1O] | 638 |
| 534D | tert-Butyl (3-cyano-7-fluoro-4-(5-fluoro-3-((3R,4S)-3-hydroxy-4-(isopropylamino)pyrrolidin-1-yl)-7,9-dihydrofuro[3,4-f]quinazolin-6-yl)thieno[3,2-c]pyridin-2-yl)carbamate | 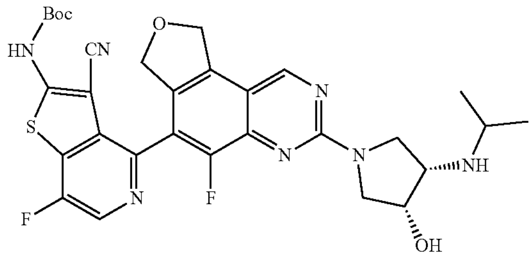 [SMILES: CC(C)N[C@H]1CN(c2ncc3c4c(c(-c5ncc(F)c6sc(NC(=O)OC(C)(C)C)c(C#N)c56)c(F)c3n2)COC4)C[C@H]1O] | 624 |

TABLE 22-continued

| Preparation | Chemical Name | Structure | MS (ES) m/z (M + 1) |
|---|---|---|---|
| 535D | tert-Butyl (3-cyano-7-fluoro-4-(5-fluoro-3-((3S,4S)-3-hydroxy-4-(isopropylamino)pyrrolidin-1-yl)-7,9-dihydrofuro[3,4-f]quinazolin-6-yl)thieno[3,2-c]pyridin-2-yl)carbamate | 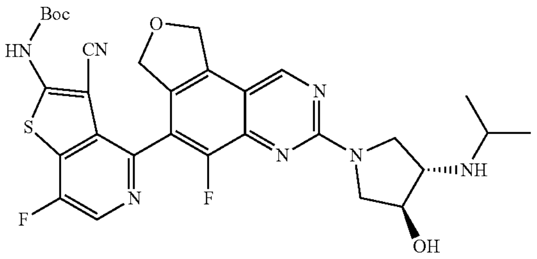 [SMILES: CC(C)N[C@H]1CN(c2ncc3c4c(c(-c5ncc(F)c6sc(NC(=O)OC(C)(C)C)c(C#N)c56)c(F)c3n2)COC4)C[C@@H]1O] | 624 |
| 536D | tert-Butyl (3-cyano-7-fluoro-4-(5-fluoro-3-((3S,4R)-3-hydroxy-4-(isopropylamino)pyrrolidin-1-yl)-7,9-dihydrofuro[3,4-f]quinazolin-6-yl)thieno[3,2-c]pyridin-2-yl)carbamate | 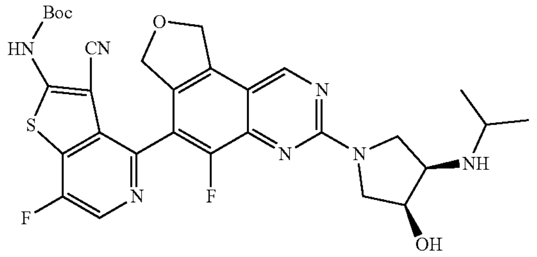 [SMILES: CC(C)N[C@@H]1CN(c2ncc3c4c(c(-c5ncc(F)c6sc(NC(=O)OC(C)(C)C)c(C#N)c56)c(F)c3n2)COC4)C[C@@H]1O] | 624 |
| 537D | tert-Butyl (3-cyano-7-fluoro-4-(5-fluoro-3-((3R,4R)-3-hydroxy-4-(isopropylamino)pyrrolidin-1-yl)-7,9-dihydrofuro[3,4-f]quinazolin-6-yl)thieno[3,2-c]pyridin-2-yl)carbamate | 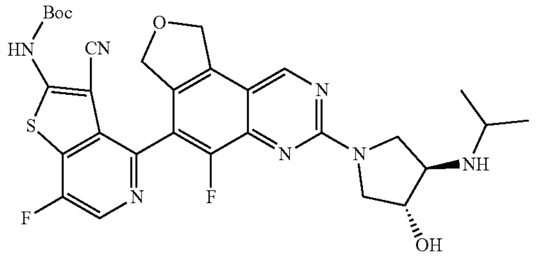 [SMILES: CC(C)N[C@@H]1CN(c2ncc3c4c(c(-c5ncc(F)c6sc(NC(=O)OC(C)(C)C)c(C#N)c56)c(F)c3n2)COC4)C[C@H]1O] | 624 |
| 538D [22] | tert-Butyl (3-cyano-7-fluoro-4-(5-fluoro-3-(3-hydroxy-4-(isopropylamino)pyrrolidin-1-yl)-7,9-dihydrofuro[3,4-f]quinazolin-6-yl)thieno[3,2-c]pyridin-2-yl)carbamate | 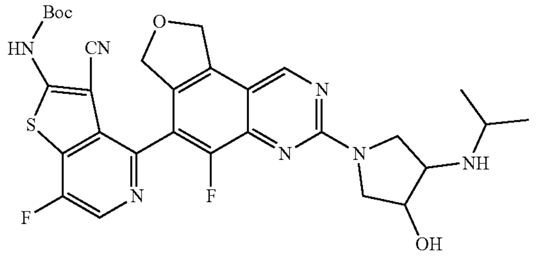 [SMILES: CC(C)NC1CN(c2ncc3c4c(c(-c5ncc(F)c6sc(NC(=O)OC(C)(C)C)c(C#N)c56)c(F)c3n2)COC4)CC1O] | 624 |
| 539D [23] | tert-Butyl (3-cyano-4-(3-(3-((dimethylamino)methyl)-4-hydroxypyrrolidin-1-yl)-5-fluoro-7,9-dihydrofuro[3,4-f]quinazolin-6-yl)-7-fluorothieino[3,2-c]pyridin-2-yl)carbamate | 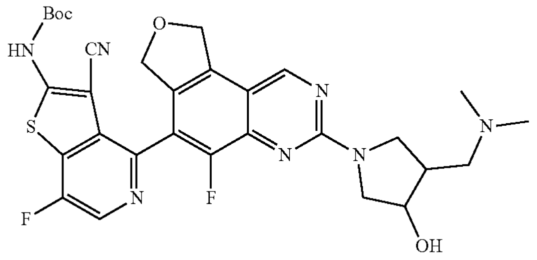 [SMILES: CN(C)CC1CN(c2ncc3c4c(c(-c5ncc(F)c6sc(NC(=O)OC(C)(C)C)c(C#N)c56)c(F)c3n2)COC4)CC1O] | 624 |

TABLE 22-continued

| Preparation | Chemical Name | Structure | MS (ES) m/z (M + 1) |
|---|---|---|---|
| 540D [24] | tert-Butyl (3-cyano-4-(3-(3-((dimethylamino)methyl)-4-hydroxypyrrolidin-1-yl)-5-fluoro-7,9-dihydrofuro[3,4-f]quinazolin-6-yl)-7-fluorothieno[3,2-c]pyridin-2-yl)carbamate | 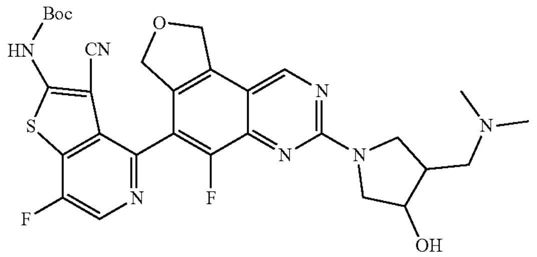 [SMILES: CN(C)CC1CN(c2ncc3c4c(c(-c5ncc(F)c6sc(NC(=O)OC(C)(C)C)c(C#N)c56)c(F)c3n2)COC4)CC1O] | 624 |
| 541D [25] | tert-Butyl (3-cyano-7-fluoro-4-(5-fluoro-3-(3-hydroxy-4-(isopropylamino)-3-methylpyrrolidin-1-yl)-7,9-dihydrofuro[3,4-f]quinazolin-6-yl)thieno[3,2-c]pyridin-2-yl)carbamate | 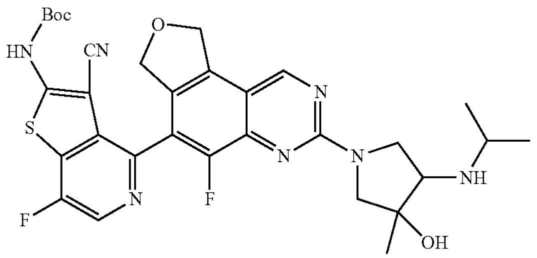 [SMILES: CC(C)NC1CN(c2ncc3c4c(c(-c5ncc(F)c6sc(NC(=O)OC(C)(C)C)c(C#N)c56)c(F)c3n2)COC4)CC1(C)O] | 638 |
| 542D [26] | tert-Butyl (3-cyano-7-fluoro-4-(5-fluoro-3-(3-hydroxy-4-(isopropylamino)-3-methylpyrrolidin-1-yl)-7,9-dihydrofuro[3,4-f]quinazolin-6-yl)thieno[3,2-c]pyridin-2-yl)carbamate, Isomer 1 | 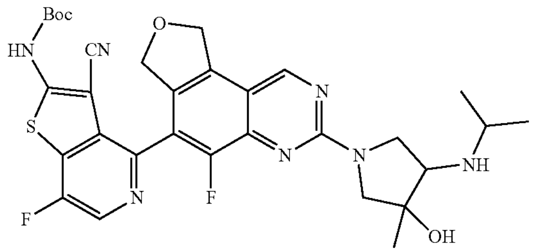 [SMILES: CC(C)NC1CN(c2ncc3c4c(c(-c5ncc(F)c6sc(NC(=O)OC(C)(C)C)c(C#N)c56)c(F)c3n2)COC4)CC1(C)O] | 638 |
| 543D [26] | tert-Butyl (3-cyano-7-fluoro-4-(5-fluoro-3-(3-hydroxy-4-(isopropylamino)-3-methylpyrrolidin-1-yl)-7,9-dihydrofuro[3,4-f]quinazolin-6-yl)thieno[3,2-c]pyridin-2-yl)carbamate, Isomer 2 | 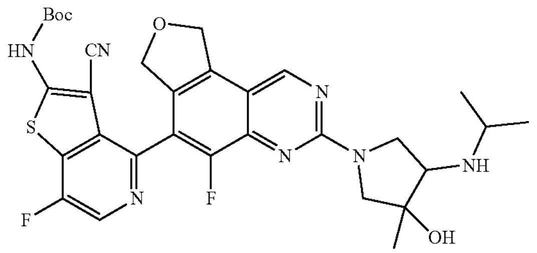 [SMILES: CC(C)NC1CN(c2ncc3c4c(c(-c5ncc(F)c6sc(NC(=O)OC(C)(C)C)c(C#N)c56)c(F)c3n2)COC4)CC1(C)O] | 638 |
| 544D [27] | tert-Butyl (3-cyano-7-fluoro-4-(5-fluoro-3-(3-hydroxy-4-(isopropyl(methyl)amino)-3-methylpyrrolidin-1-yl)-7,9-dihydrofuro[3,4-f]quinazolin-6-yl)thieno[3,2-c]pyridin-2-yl)carbamate, Isomer 1 | 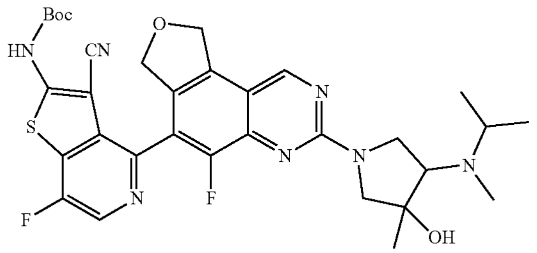 [SMILES: CC(C)N(C)C1CN(c2ncc3c4c(c(-c5ncc(F)c6sc(NC(=O)OC(C)(C)C)c(C#N)c56)c(F)c3n2)COC4)CC1(C)O] | 652 |
| 545D [27] | tert-Butyl (3-cyano-7-fluoro-4-(5-fluoro-3-(3-hydroxy-4-(isopropyl(methyl)amino)-3-methylpyrrolidin-1-yl)-7,9-dihydrofuro[3,4-f]quinazolin-6-yl)thieno[3,2-c]pyridin-2-yl)carbamate, Isomer 2 | 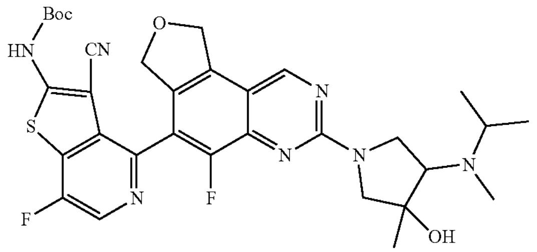 [SMILES: CC(C)N(C)C1CN(c2ncc3c4c(c(-c5ncc(F)c6sc(NC(=O)OC(C)(C)C)c(C#N)c56)c(F)c3n2)COC4)CC1(C)O] | 652 |

TABLE 22-continued

| Preparation | Chemical Name | Structure | MS (ES) m/z (M + 1) |
|---|---|---|---|
| 546D [28] | tert-Butyl (3-cyano-7-fluoro-4-(5-fluoro-3-(3-hydroxy-4-(isopropylamino)-3-methylpyrrolidin-1-yl)-7,9-dihydrofuro[3,4-f]quinazolin-6-yl)thieno[3,2-c]pyridin-2-yl)carbamate | 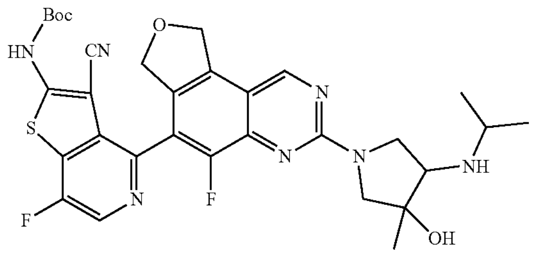 [SMILES: CC(C)NC1CN(c2ncc3c4c(c(-c5ncc(F)c6sc(NC(=O)OC(C)(C)C)c(C#N)c56)c(F)c3n2)COC4)CC1(C)O] | 638 |
| 549D | tert-Butyl (3-cyano-7-fluoro-4-(5-fluoro-3-((2S,3R)-3-hydroxy-2-methylpyrrolidin-1-yl)-7,9-dihydrofuro[3,4-f]quinazolin-6-yl)thieno[3,2-c]pyridin-2-yl)carbamate | 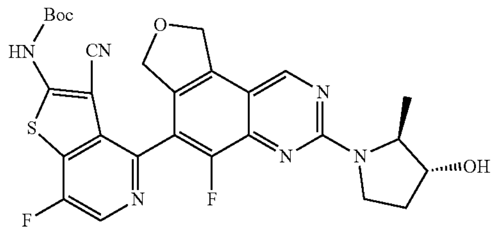 [SMILES: C[C@H]1[C@H](O)CCN1c1ncc2c3c(c(-c4ncc(F)c5sc(NC(=O)OC(C)(C)C)c(C#N)c45)c(F)c2n1)COC3] | 581 |
| 550D [29] | tert-Butyl (3-cyano-4-(3-(3-(dimethylamino)-4-(methoxymethyl)pyrrolidin-1-yl)-5-fluoro-7,9-dihydrofuro[3,4-f]quinazolin-6-yl)-7-fluorothieno[3,2-c]pyridin-2-yl)carbamate | 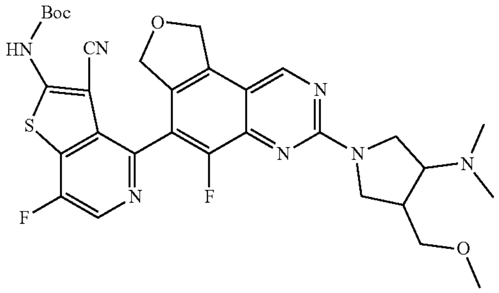 [SMILES: COCC1CN(c2ncc3c4c(c(-c5ncc(F)c6sc(NC(=O)OC(C)(C)C)c(C#N)c56)c(F)c3n2)COC4)CC1N(C)C] | 638 |
| 551D | tert-Butyl (3-cyano-7-fluoro-4-(5-fluoro-3-((3R,4S)-3-(isopropylamino)-4-methylpyrrolidin-1-yl)-7,9-dihydrofuro[3,4-f]quinazolin-6-yl)thieno[3,2-c]pyridin-2-yl)carbamate | 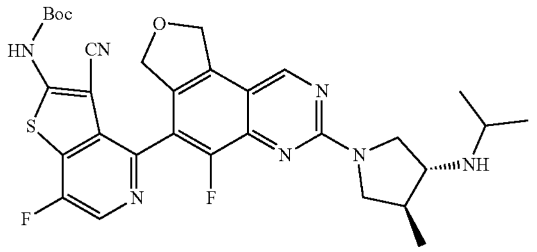 [SMILES: CC(C)N[C@H]1CN(c2ncc3c4c(c(-c5ncc(F)c6sc(NC(=O)OC(C)(C)C)c(C#N)c56)c(F)c3n2)COC4)C[C@@H]1C] | 622 |
| 552D | tert-Butyl (3-cyano-7-fluoro-4-(5-fluoro-3-((3R,4S)-3-(isopropyl(methyl)amino)-4-methylpyrroldiin-1-y)-7,9-dihydrofuro[3,4-f]quinazolin-6-yl)thieno[3,2-c]pyridin-2-yl)carbamate | 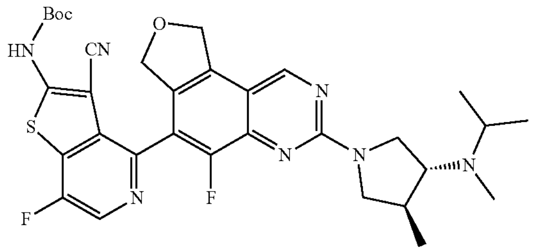 [SMILES: CC(C)N(C)[C@H]1CN(c2ncc3c4c(c(-c5ncc(F)c6sc(NC(=O)OC(C)(C)C)c(C#N)c56)c(F)c3n2)COC4)C[C@@H]1C] | 636 |

TABLE 22-continued

| Preparation | Chemical Name | Structure | MS (ES) m/z (M + 1) |
|---|---|---|---|
| 553D | tert-Buyl (3-cyano-4-(3-((3S,4R)-3-(dimethylamino)-4-(2-hydroxypropan-2-yl)pyrrolidin-1-yl)-5-fluoro-7,9-dihydrofuro[3,4-f]quinazolin-6-yl)-7-fluorothieno[3,2-c]pyridin-2-yl)carbamate | 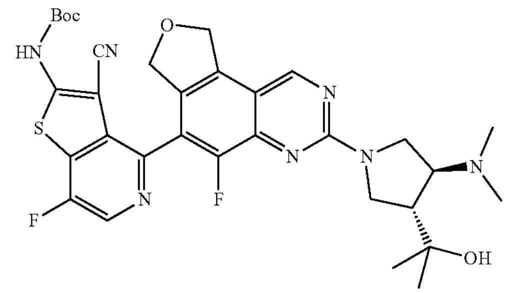 [SMILES: CN(C)[C@@H]1CN(c2ncc3c4c(c(-c5ncc(F)c6sc(NC(=O)OC(C)(C)C)c(C#N)c56)c(F)c3n2)COC4)C[C@H]1C(C)(C)O] | 652 |
| 554D | tert-Butyl (3-cyano-7-fluoro-4-(5-fluoro-3-((3S,4R)-3-(isopropylamino)-4-methoxypyrroliidn-1-yl)-7,9-dihydrofuro[3,4-f]quinazolin-6-yl)thieno[3,2-c]pyridin-2-yl)carbamate | 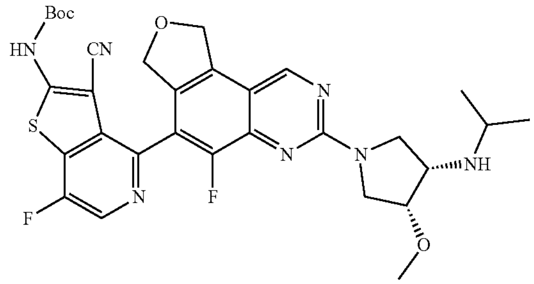 [SMILES: CO[C@@H]1CN(c2ncc3c4c(c(-c5ncc(F)c6sc(NC(=O)OC(C)(C)C)c(C#N)c56)c(F)c3n2)COC4)C[C@@H]1NC(C)C] | 638 |
| 555D | tert-Butyl (3-cyano-7-fluoro-4-(5-fluoro-3-((3R,4S)-3-(isopropylamino)-4-methoxypyrrolidin-1-yl)-7,9-dihydrofuro[3,4-f]quinazolin-6-yl)thieno[3,2-c]pyridin-2-yl)carbamate | 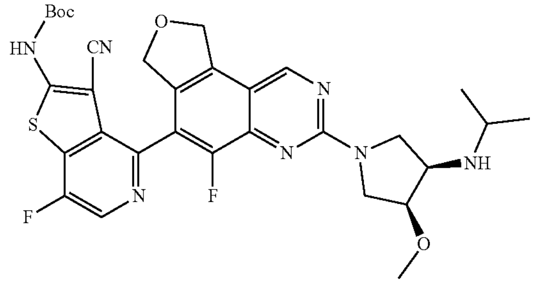 [SMILES: CO[C@H]1CN(c2ncc3c4c(c(-c5ncc(F)c6sc(NC(=O)OC(C)(C)C)c(C#N)c56)c(F)c3n2)COC4)C[C@H]1NC(C)C] | 638 |
| 556D | tert-Butyl (3-cyano-7-fluoro-4-(5-fluoro-3-((3S,4S)-3-(isopropylamino)-4-methoxypyrrolidin-1-yl)-7,9-dihydrofuro[3,4-f]quinazolin-6-yl)thieno[3,2-c]pyridin-2-yl)carbamate | 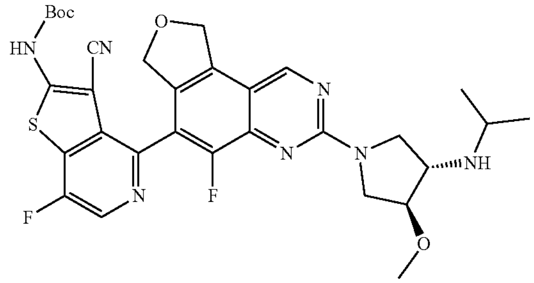 [SMILES: CO[C@H]1CN(c2ncc3c4c(c(-c5ncc(F)c6sc(NC(=O)OC(C)(C)C)c(C#N)c56)c(F)c3n2)COC4)C[C@@H]1NC(C)C] | 638 |
| 557D | tert-Butyl (3-cyano-7-fluoro-4-(5-fluoro-3-((3R,4S)-3-hydroxy-4-(isopropyl(methyl)amino)-pyrrolidin-1-yl)-7,9-dihydrofuro[3,4-f]quinazolin-6-yl)thieno[3,2-c]pyridin-2-yl)carbamate | 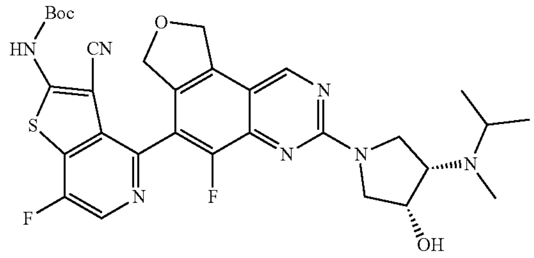 | 638 |

TABLE 22-continued

| Preparation | Chemical Name | Structure | MS (ES) m/z (M + 1) |
|---|---|---|---|
| 558D | tert-Butyl (3-cyano-7-fluoro-4-(5-fluoro-3-((3R,4R)-3-hydroxy-4-(isopropyl(methyl)amino)pyrrolidin-1-yl)-7,9-dihydrofuro[3,4-f]quinazolin-6-yl)thieno[3,2-c]pyridin-2-yl)carbamate | 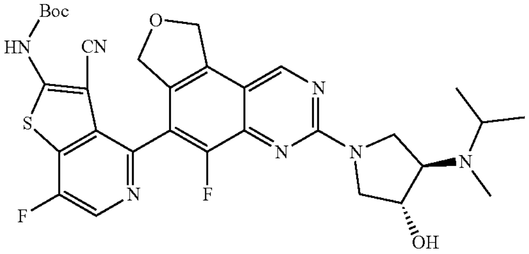 | 638 |
| 559D [30] | tert-Butyl (3-cyano-4-(3-(3-(diethylamino)-4-hydroxypyrrolidin-1-yl)-5-fluoro-7,9-dihydrofuro[3,4-f]quinazolin-6-yl)-7-fluorothieno[3,2-c]pyridin-2-yl)carbamate, Isomer 1 | 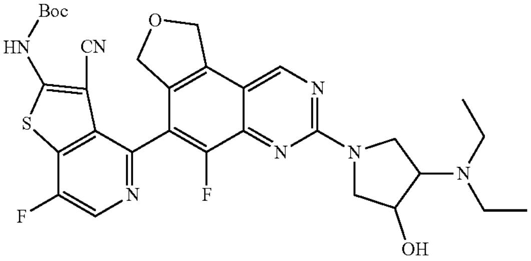 [SMILES: CCN(CC)C1CN(c2ncc3c4c(c(-c5ncc(F)c6sc(NC(=O)OC(C)(C)C)c(C#N)c56)c(F)c3n2)COC4)CC1O] | 638 |
| 560D [30] | tert-Butyl (3-cyano-4-(3-(3-(diethylamino)-4-hydroxypyrrolidin-1-yl)-5-fluoro-7,9-dihydrofuro[3,4-f]quinazolin-6-yl)-7-fluorothieno[3,2-c]pyridin-2-yl)carbamate, Isomer 2 | 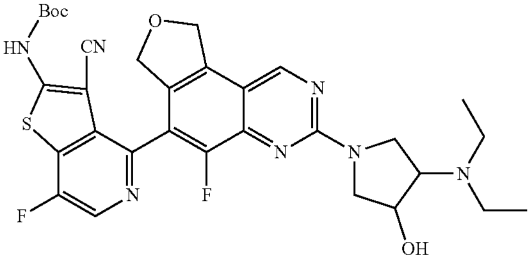 [SMILES: CCN(CC)C1CN(c2ncc3c4c(c(-c5ncc(F)c6sc(NC(=O)OC(C)(C)C)c(C#N)c56)c(F)c3n2)COC4)CC1O] | 638 |
| 561D | tert-Butyl (3-cyano-4-(3-((3S,4R)-3,4-dihydroxypyrrolidin-1-yl)-5-fluoro-7,9-dihydrofuro[3,4-f]quinazolin-6-yl)-7-fluorothieno[3,2-c]pyridin-2-yl)carbamate | 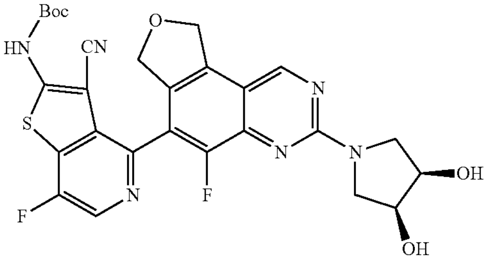 [SMILES: CC(C)(C)OC(=O)Nc1sc2c(F)cnc(-c3c4c(c5cnc(N6C[C@@H](O)[C@@H](O)C6)nc5c3F)COC4)c2c1C#N] | |
| 562D | tert-Butyl (3-cyano-7-fluoro-4-(5-fluoro-3-(3-(hydroxymethyl)-3-(isopropylamino)pyrrolidin-1-yl)-7,9-dihydrofuro[3,4-f]quinazolin-6-yl)thieno[3,2-c]pyridin-2-yl)carbamate | 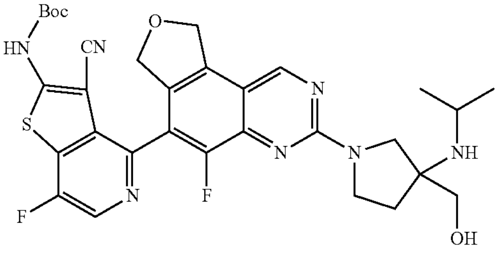 [SMILES: CC(C)NC1(CO)CCN(c2ncc3c4c(c(-c5ncc(F)c6sc(NC(=O)OC(C)(C)C)c(C#N)c56)c(F)c3n2)COC4)C1] | 638 |
| 563D [31] | tert-Butyl (3-cyano-4-(3-(3-(diethylamino)-3-(hydroxymethyl)pyrrolidin-1-yl)-5-fluoro-7,9-dihydrofuro[3,4-f]quinazolin-6-yl)-7-fluorothieno[3,2-c]pyridin-2-yl)carbamate, Isomer 1 | 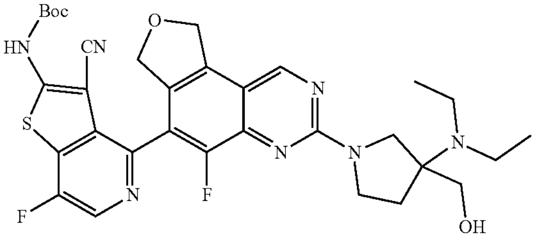 [SMILES: CCN(CC)C1(CO)CCN(c2ncc3c4c(c(-c5ncc(F)c6sc(NC(=O)OC(C)(C)C)c(C#N)c56)c(F)c3n2)COC4)C1] | 652 |

TABLE 22-continued

| Preparation | Chemical Name | Structure | MS (ES) m/z (M + 1) |
|---|---|---|---|
| 564D [31] | tert-Butyl (3-cyano-4-(3-(3-(diethylamino)-3-(hydroxymethyl)pyrrolidin-1-yl)-5-fluoro-7,9-dihydrofuro[3,4-f]quinazolin-6-yl)-7-fluorothieno[3,2-c]pyridin-2-yl)carbamate, Isomer 2 | 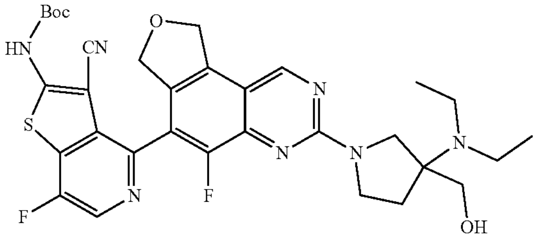 [SMILES: CCN(CC)C1(CO)CCN(c2ncc3c4c(c(-c5ncc(F)c6sc(NC(=O)OC(C)(C)C)c(C#N)c56)c(F)c3n2)COC4)C1] | 652 |
| 565D | tert-Butyl (3-cyano-7-fluoro-4-(5-fluoro-3-(3-(hydroxymethyl)-3-(4-methylpiperazin-1-yl)pyrrolidin-1-yl)-7,9-dihydrofuro[3,4-f]quinazolin-6-yl)thieno[3,2-c]pyridin-2-yl)carbamate, Isomer 1 | 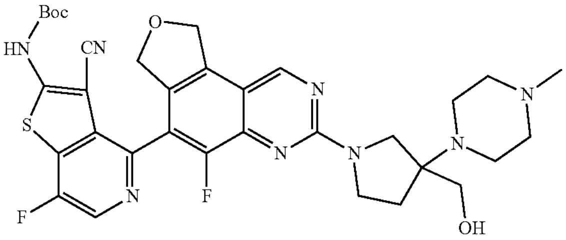 [SMILES: CN1CCN(C2(CO)CCN(c3ncc4c5c(c(-c6ncc(F)c7sc(NC(=O)OC(C)(C)C)c(C#N)c67)c(F)c4n3)COC5)C2)CC1] | 679 |
| 566D | tert-Butyl (3-cyano-7-fluoro-4-(5-fluoro-3-(3-(hydroxymethyl)-3-(4-methylpiperazin-1-yl)pyrrolidin-1-yl)-7,9-dihydrofuro[3,4-f]quinazolin-6-yl)thieno[3,2-c]pyridin-2-yl)carbamate, Isomer 2 | 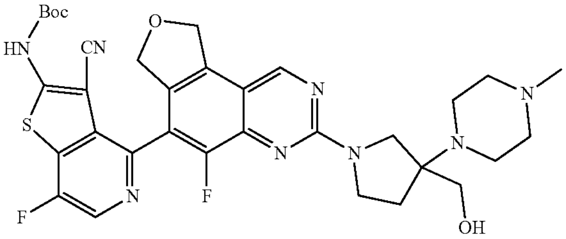 [SMILES: CN1CCN(C2(CO)CCN(c3ncc4c5c(c(-c6ncc(F)c7sc(NC(=O)OC(C)(C)C)c(C#N)c67)c(F)c4n3)COC5)C2)CC1] | 679 |
| 567D | tert-Butyl (3S)-4-(6-(2-((tert-butoxycarbonyl)amino)-3-cyano-7-fluorothieno[3,2-c]pyridin-4-yl)-5-fluoro-7,9-dihydrofuro[3,4-f]quinazolin-3-yl)-3-methyl-1,4-diazepane-1-carboxylate | 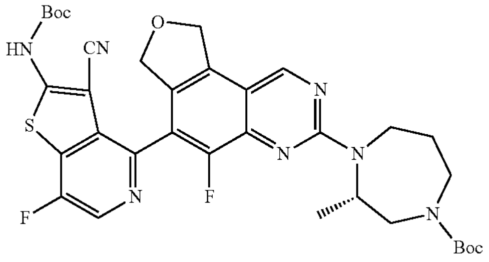 [SMILES: C[C@H]1CN(C(=O)OC(C)(C)C)CCCN1c1ncc2c3c(c(-c4ncc(F)c5sc(NC(=O)OC(C)(C)C)c(C#N)c45)c(F)c2n1)COC3] | 694 |
| 568D | tert-Butyl (3-cyano-4-(3-((1R,5S,6r)-6-(dimethylamino)-3-azabicyclo[3.1.0]hexan-3-yl)-5-fluoro-7,9-dihydrofuro[3,4-f]quinazolin-6-yl)-7-fluorothieno[3,2-c]pyridin-2-yl)carbamate | 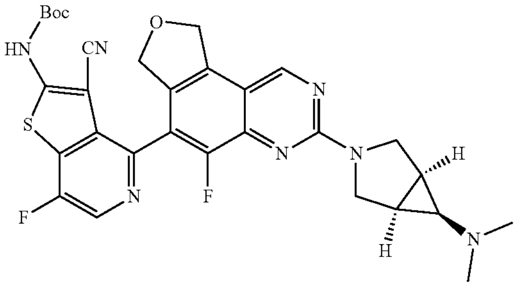 [SMILES: CN(C)[C@@H]1[C@@H]2CN(c3ncc4c5c(c(-c6ncc(F)c7sc(NC(=O)OC(C)(C)C)c(C#N)c67)c(F)c4n3)COC5)C[C@@H]21] | 606 |

TABLE 22-continued

| Preparation | Chemical Name | Structure | MS (ES) m/z (M + 1) |
|---|---|---|---|
| 569D | tert-Butyl (3-cyano-7-fluoro-4-(5-fluoro-3-(4-((S)-2-hydroxypropyl)octahydro-1H-pyrrolo[3,2-b]pyridin-1-yl)-7,9-dihydrofuro[3,4-f]quinazolin-6-yl)thieno[3,2-c]pyridin-2-yl)carbamate | 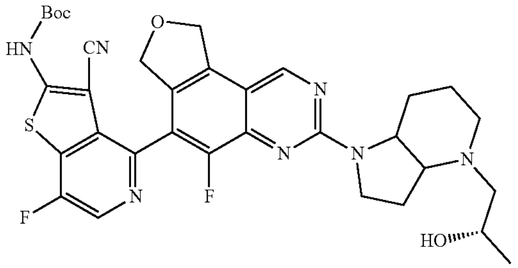 [SMILES: C[C@H](O)CN1CCCC2C1CCN2c1ncc2c3c(c(-c4ncc(F)c5sc(NC(=O)OC(C)(C)C)c(C#N)c45)c(F)c2n1)COC3] | 664 |
| 570D | tert-Butyl (3-cyano-7-fluoro-4-(5-fluoro-3-(4-((R)-2-hydroxypropyl)octahydro-1H-pyrrolo[3,2-b]pyridin-1-yl)-7,9-dihydrofuro[3,4-f]quinazolin-6-yl)thieno[3,2-c]pyridin-2-yl)carbamate | 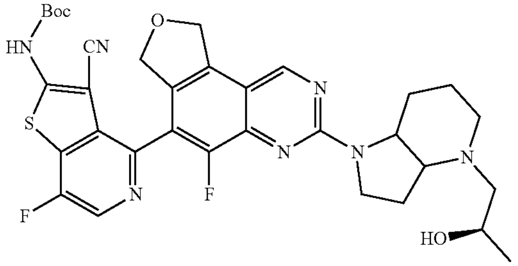 [SMILES: C[C@@H](O)CN1CCCC2C1CCN2c1ncc2c3c(c(-c4ncc(F)c5sc(NC(=O)OC(C)(C)C)c(C#N)c45)c(F)c2n1)COC3] | 664 |
| 571D | tert-Butyl (3-cyano-7-fluoro-4-(5-fluoro-3-(4-(2-hydroxyethyl)octahydro-1H-pyrrolo[3,2-b]pyridin-1-yl)-7,9-dihydrofuro[3,4-f]quinazolin-6-yl)thieno[3,2-c]pyridin-2-yl)carbamate | 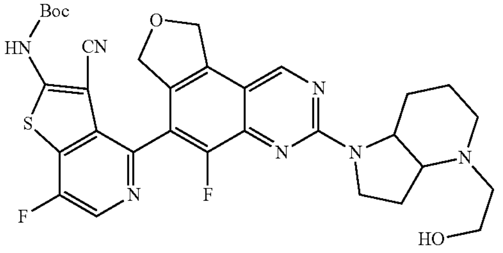 [SMILES: CC(C)(C)OC(=O)Nc1sc2c(F)cnc(-c3c4c(c5cnc(N6CCC7C6CCCN7CCO)nc5c3F)COC4)c2c1C#N] | 650 |
| 572D | tert-Butyl (3-cyano-7-fluroo-4-(5-fluoro-3-(8-(isopropylamino)-2-oxa-6-azaspiro[3.4]octan-6-yl)-7,9-dihydrofuro[3,4-f]quinazolin-6-yl)thieno[3,2-c]pyridin-2-yl)carbamate | 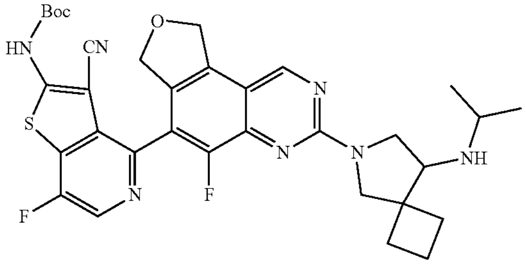 [SMILES: CC(C)NC1CN(c2ncc3c4c(c(-c5ncc(F)c6sc(NC(=O)OC(C)(C)C)c(C#N)c56)c(F)c3n2)COC4)CC12CCC2] | 650 |
| 573D | tert-Butyl (3-cyano-4-(3-(8-(dimethylamino)-2-oxa-6-azaspiro[3.4]octan-6-yl)-5-fluoro-7,9-dihydrofuro[3,4-f]quinazolin-6-yl)-7-fluorothieno[3,2-c]pyridin-2-yl)carbamate, Isomer 1 | 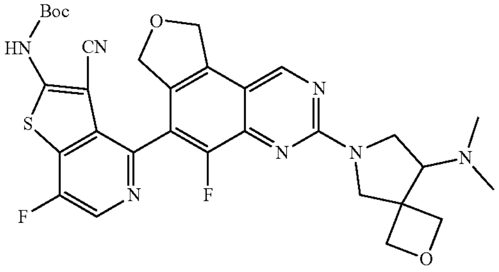 [SMILES: CN(C)C1CN(c2ncc3c4c(c(-c5ncc(F)c6sc(NC(=O)OC(C)(C)C)c(C#N)c56)c(F)c3n2)COC4)CC12COC2] | 636 |

TABLE 22-continued

| Preparation | Chemical Name | Structure | MS (ES) m/z (M + 1) |
|---|---|---|---|
| 574D | tert-Butyl (3-cyano-4-(3-(8-(dimethylamino)-2-oxa-6-azaspiro[3.4]octan-6-yl)-5-fluoro-7,9-dihydrofuro[3,4-f]quinazolin-6-yl)-7-fluorothieno[3,2-c]pyridin-2-yl)carbamate, Isomer 2 | 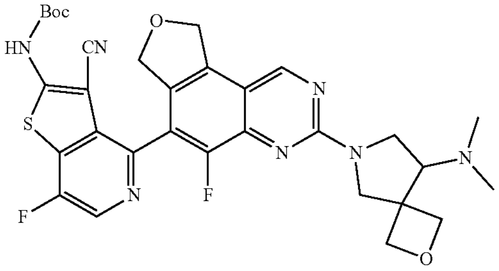 [SMILES: CN(C)C1CN(c2ncc3c4c(c(-c5ncc(F)c6sc(NC(=O)OC(C)(C)C)c(C#N)c56)c(F)c3n2)COC4)CC12COC2] | 636 |
| 575D | tert-Butyl (3-cyano-7-fluoro-4-(5-fluoro-3-(7-methyl-2,7-diazaspiro[4.4]nonan-2-yl)-7,9-dihydrofuro[3,4-f]quinazolin-6-yl)thieno[3,2-c]pyridin-2-yl)carbamate | 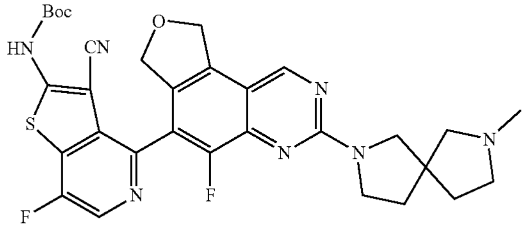 [SMILES: CN1CCC2(CCN(c3ncc4c5c(c(-c6ncc(F)c7sc(NC(=O)OC(C)(C)C)c(C#N)c67)c(F)c4n3)COC5)C2)C1] | 620 |
| 576D | tert-Butyl (3-cyano-7-fluoro-4-(5-fluoro-3-((3S,4S)-3-fluoro-4-((propan-2-yl-1,1,1,3,3,3-d6)amino)pyrrolidin-1-yl)-7,9-dihydrofuro[3,4-f]quinazolin-6-yl)thieno[3,2-c]pyridin-2-yl)carbamate | 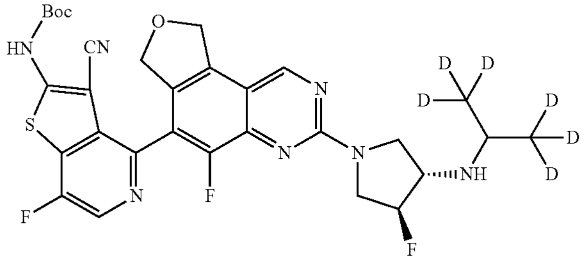 [SMILES: [2H]C([2H])([2H])C(N[C@H]1CN(c2ncc3c4c(c(-c5ncc(F)c6sc(NC(=O)OC(C)(C)C)c(C#N)c56)c(F)c3n2)COC4)C[C@@H]1F)C([2H])([2H])[2H]] | 632 |
| 577D | tert-Butyl (3-cyano-7-fluoro-4-(5-fluoro-3-((3R,4S)-3-hydroxy-4-((propan-2-yl-1,1,1,3,3,3-d6)amino)pyrrolidin-1-yl)-7,9-dihydrofuro[3,4-f]quinazolin-6-yl)thieno[3,2-c]pyridin-2-yl)carbamate | 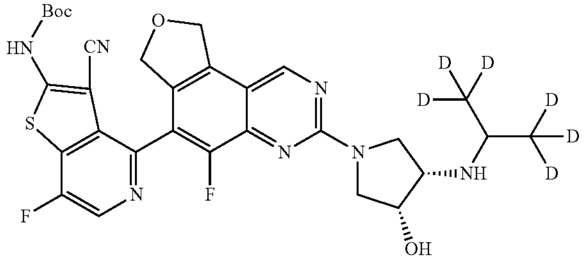 [SMILES: [2H]C([2H])([2H])C(N[C@H]1CN(c2ncc3c4c(c(-c5ncc(F)c6sc(NC(=O)OC(C)(C)C)c(C#N)c56)c(F)c3n2)COC4)C[C@H]1O)C([2H])([2H])[2H]] | 630 |
| 578D | tert-Butyl (3-cyano-7-fluoro-4-(5-fluoro-3-((3R,4R)-3-hydroxy-4-((propan-2-yl-1,1,1,3,3,3-d6)amino)pyrrolidin-1-yl)-7,9-dihydrofuro[3,4-f]quinazolin-6-yl)thieno[3,2-c]pyridin-2-yl)carbamate | 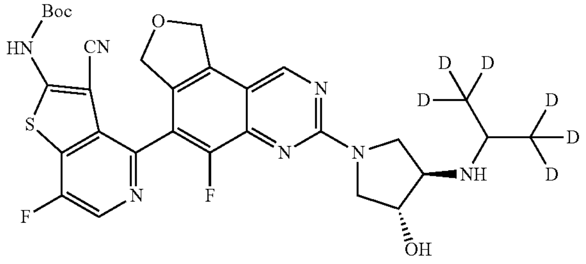 [SMILES: [2H]C([2H])([2H])C(N[C@@H]1CN(c2ncc3c4c(c(-c5ncc(F)c6sc(NC(=O)OC(C)(C)C)c(C#N)c56)c(F)c3n2)COC4)C[C@H]1O)C([2H])([2H])[2H]] | 630 |
| 579D | tert-Butyl (3-cyano-7-fluoro-4-(5-fluoro-3-(4-(methyl-d3)octahydro-1H-pyrrolo[3,2-b]pyridin-1-yl)-7,9-dihydrofuro[3,4-f]quinazolin-6-yl)thieno[3,2-c]pyridin-2-yl)carbamate | 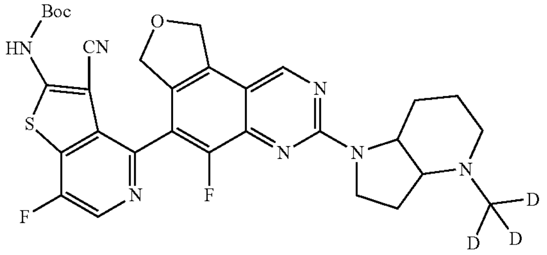 [SMILES: [2H]C([2H])([2H])N1CCCC2C1CCN2c1ncc2c3c(c(-c4ncc(F)c5sc(NC(=O)OC(C)(C)C)c(C#N)c45)c(F)c2n1)COC3] | 623 |

TABLE 22-continued

| Preparation | Chemical Name | Structure | MS (ES) m/z (M + 1) |
|---|---|---|---|
| 580D | tert-Butyl (3-cyano-7-fluoro-4-(5-fluoro-3-((S)-3-(4-(methyl-d3)piperazin-1-yl)pyrrolidin-1-yl)-7,9-dihydrofuro[3,4-f]quianzolin-6-yl)thieno[3,2-c]pyridin-2-yl)carbamate | 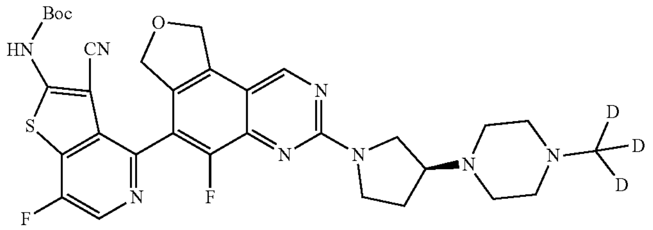 [SMILES: [2H]C([2H])([2H])N1CCN([C@H]2CCN(c3ncc4c5c(c(-c6ncc(F)c7sc(NC(=O)OC(C)(C)C)c(C#N)c67)c(F)c4n3)COC5)C2)CC1] | 652 |
| 581D | tert-Butyl (3-cyano-7-fluoro-4-(5-fluoro-3-((R)-3-(4-(methyl-d3)piperazin-1-yl)pyrrolidin-1-yl)-7,9-dihydrofuro[3,4-f]quinazolin-6-yl)thieno[3,2-c]pyridin-2-yl)carbamate | 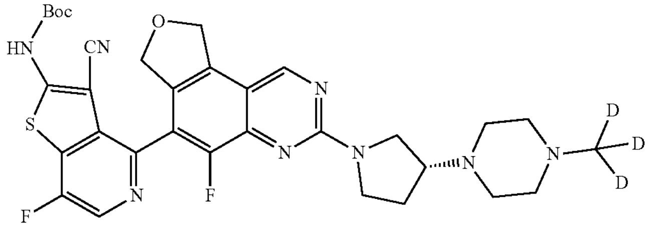 [SMILES: [2H]C([2H])([2H])N1CCN([C@@H]2CCN(c3ncc4c5c(c(-c6ncc(F)c7sc(NC(=O)OC(C)(C)C)c(C#N)c67)c(F)c4n3)COC5)C2)CC1] | 652 |
| 582D | tert-Butyl (3-cyano-7-fluoro-4-(5-fluoro-3-((S)-7-((propan-2-yl-1,1,1,3,3,3-d6)amino)-5-azaspiro[2.4]heptan-5-yl)-7,9-dihydrofuro[3,4-f]quinazolin-6-yl)thieno[3,2-c]pyridin-2-yl)carbamate | 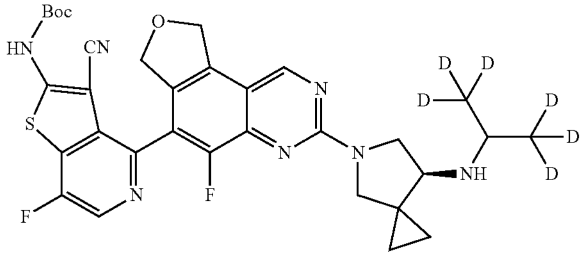 [SMILES: [2H]C([2H])([2H])C(N[C@@H]1CN(c2ncc3c4c(c(-c5ncc(F)c6sc(NC(=O)OC(C)(C)C)c(C#N)c56)c(F)c3n2)COC4)CC12CC2)C([2H])([2H])[2H]] | 640 |
| 583D | tert-Butyl (3-cyano-7-fluoro-4-(5-fluoro-3-((3S,4S)-3-fluoro-4-((propan-2-yl-d7)amino)pyrrolidin-1-yl)-7,9-dihydrofuro[3,4-f]quinazolin-6-yl)thieno[3,2-c]pyridin-2-yl)carbamate | 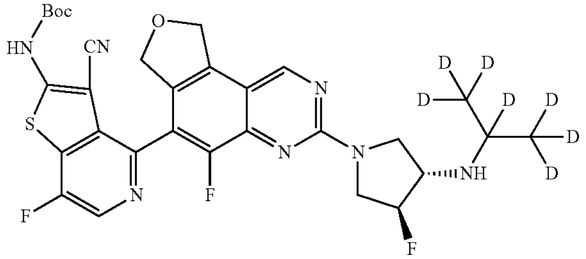 [SMILES: [2H]C([2H])([2H])C([2H])(N[C@H]1CN(c2ncc3c4c(c(-c5ncc(F)c6sc(NC(=O)OC(C)(C)C)c(C#N)c56)c(F)c3n2)COC4)C[C@@H]1F)C([2H])([2H])[2H]] | 633 |
| 584D [32] | tert-Butyl (4-(3-((3S,4S)-3-amino-4-fluoropyrrolidin-1-yl)-5-fluoro-7,9-dihydrofuro[3,4-f]quinazolin-6-yl)-3-cyano-7-fluorothieno[3,2-c]pyridin-2-yl)carbamate | 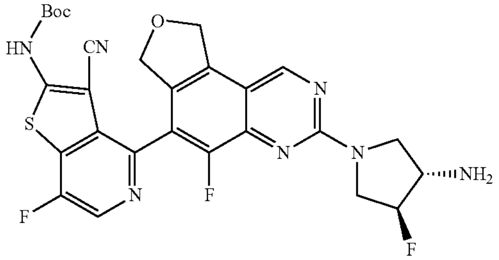 [SMILES: CC(C)(C)OC(=O)Nc1sc2c(F)cnc(-c3c4c(c5cnc(N6C[C@H](N)[C@@H](F)C6)nc5c3F)COC4)c2c1C#N] | 584 |
| 585D | tert-Butyl (3-cyano-7-fluoro-4-(5-fluoro-3-((S)-3-(4-(propan-2-yl-1,1,1,3,3,3-d6)piperazin-1-yl)pyrrolidin-1-yl)-7,9-dihydrofuro[3,4-f]quinazolin-6-yl)thieno[3,2-c]pyridin-2-yl)carbamate | 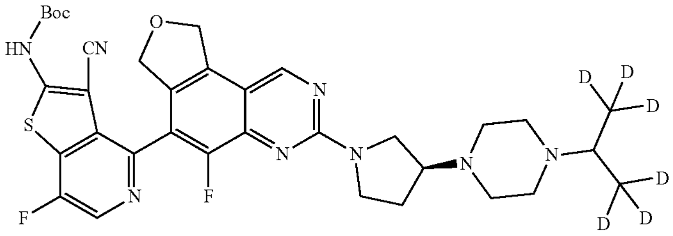 [SMILES: [2H]C([2H])([2H])C(N1CCN([C@H]2CCN(c3ncc4c5c(c(-c6ncc(F)c7sc(NC(=O)OC(C)(C)C)c(C#N)c67)c(F)c4n3)COC5)C2)CC1)C([2H])([2H])[2H]] | 683 |

TABLE 22-continued

| Preparation | Chemical Name | Structure | MS (ES) m/z (M + 1) |
|---|---|---|---|
| 586D | tert-Butyl (3-cyano-7-fluoro-4-(5-fluoro-3-((2S,3S)-2-methyl-3-(4-(propan-2-yl-1,1,1,3,3,3-d6)piperazin-1-yl)pyrrolidin-1-yl)-7,9-dihydrofuro[3,4-f]quinazolin-6-yl)thieno[3,2-c]pyridin-2-yl)carbamate | 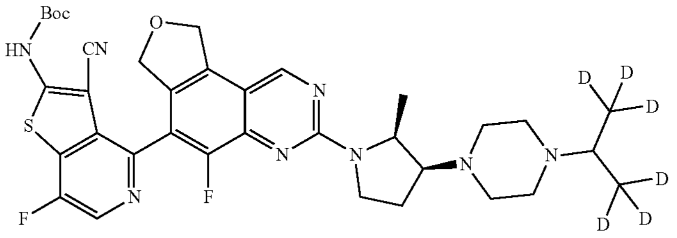 [SMILES: [2H]C([2H])([2H])C(N1CCN([C@H]2CCN(c3ncc4c5c(c(-c6ncc(F)c7sc(NC(=O)OC(C)(C)C)c(C#N)c67)c(F)c4n3)COC5)[C@H]2C)CC1)C([2H])([2H])[2H]] | 697 |
| 587D | tert-Butyl (3-cyano-4-(3-((2S,3S)-3-(4-(ethyl-d5)piperazin-1-yl)-2-methylpyrrolidin-1-yl)-5-fluoro-7,9-dihydrofuro[3,4-f]quinazolin-6-yl)-7-fluorothieno[3,2-c]pyridin-2-yl)carbamate | 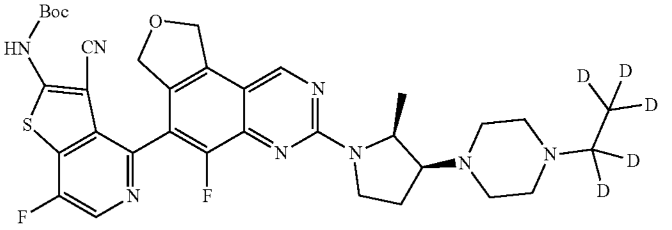 [SMILES: [2H]C([2H])([2H])C([2H])([2H])N1CCN([C@H]2CCN(c3ncc4c5c(c(-c6ncc(F)c7sc(NC(=O)OC(C)(C)C)c(C#N)c67)c(F)c4n3)COC5)[C@H]2C)CC1] | 682 |
| 588D | tert-Butyl (3-cyano-4-(3-((S)-3-(dimethylamino)pyrrolidin-1-yl)-5-fluoro-7,9-dihydrofuro[3,4-f]quinazolin-6-yl)-5-fluorothieno[2,3-b]pyridin-2-yl)carbamate | 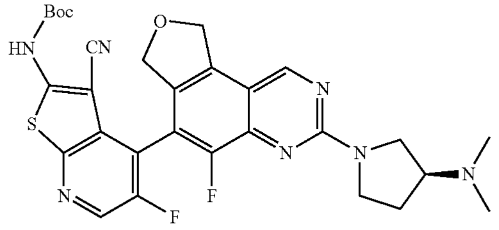 [SMILES: CN(C)[C@H]1CCN(c2ncc3c4c(c(-c5c(F)cnc6sc(NC(=O)OC(C)(C)C)c(C#N)c56)c(F)c3n2)COC4)C1] | 594 |
| 589D | tert-Butyl (3-cyano-5-fluoro-4-(5-fluoro-3-((3R,4S)-3-(isopropylamino)-4-methoxypyrrolidin-1-yl)-7,9-dihydrofuro[3,4-f]quinazolin-6-yl)thieno[2,3-b]pyridin-2-yl)carbamate | 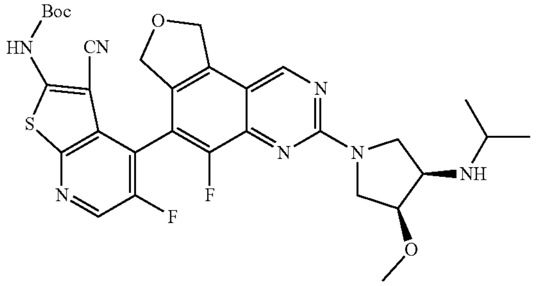 [SMILES: CO[C@H]1CN(c2ncc3c4c(c(-c5c(F)cnc6sc(NC(=O)OC(C)(C)C)c(C#N)c56)c(F)c3n2)COC4)C[C@H]1NC(C)C] | 638 |
| 590D | tert-Butyl (3-cyano-5-fluoro-4-(5-fluoro-3-((R)-3-(4-methylpiperazin-1-yl)pyrrolidin-1-yl)-7,9-dihdyrofuro[3,4-f]quinazolin-6-yl)thieno[2,3-b]pyridin-2-yl)carbamate | 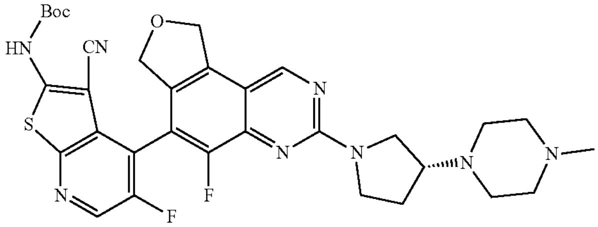 [SMILES: CN1CCN([C@@H]2CCN(c3ncc4c5c(c(-c6c(F)cnc7sc(NC(=O)OC(C)(C)C)c(C#N)c67)c(F)c4n3)COC5)C2)CC1] | 649 |
| 591D | tert-Butyl (3-cyano-5-fluoro-4-(5-fluoro-3-((3S,4R)-3-(isopropylamino)-4-methylpyrrolidin-1-yl)-7,9-dihydrofuro[3,4-f]quinazolin-6-yl)benzo[b]thiophen-2-y)carbamate | 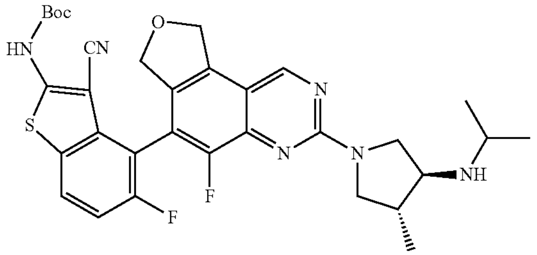 [SMILES: CC(C)N[C@@H]1CN(c2ncc3c4c(c(-c5c(F)ccc6sc(NC(=O)OC(C)(C)C)c(C#N)c56)c(F)c3n2)COC4)C[C@H]1C] | 621 |

TABLE 22-continued

| Preparation | Chemical Name | Structure | MS (ES) m/z (M + 1) |
|---|---|---|---|
| 592D | tert-Butyl (3-cyano-4-(3-((3S,4R)-3-(dimethylamino)-4-hydroxypyrrolidin-1-yl)-5-fluoro-7,9-dihydrofuro[3,4-f]quinazolin-6-yl)-5-fluorobenzo[b]thiophen-2-yl)carbamate | 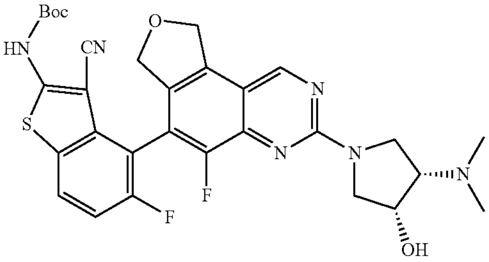 [SMILES: CN(C)[C@H]1CN(c2ncc3c4c(c(-c5c(F)ccc6sc(NC(=O)OC(C)(C)C)c(C#N)c56)c(F)c3n2)COC4)C[C@H]1O] | 609 |
| 593D [8] | tert-Butyl (3-cyano-5-fluoro-4-(5-fluoro-3-((R)-3-(4-methylpiperazin-1-yl)pyrrolidin-1-yl)-7,9-dihydrofuro[3,4-f]quinazolin-6-yl)benzo[b]thiophen-2-yl)carbamate | 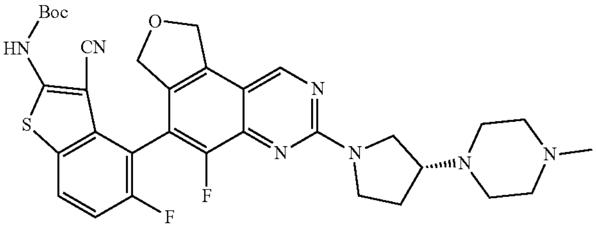 [SMILES: CN1CCN([C@@H]2CCN(c3ncc4c5c(c(-c6c(F)ccc7sc(NC(=O)OC(C)(C)C)c(C#N)c67)c(F)c4n3)COC5)C2)CC1] | 648 |
| 594D [8] | tert-Butyl (3-cyano-5-fluoro-4-(5-fluoro-3-((S)-3-(4-methylpiperazin-1-yl)pyrrolidin-1-yl)-7,9-dihydrofuro[3,4-f]quinazolin-6-yl)benzo[b]thiophen-2-yl)carbamate | 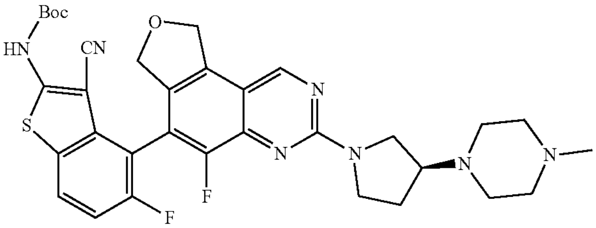 [SMILES: CN1CCN([C@H]2CCN(c3ncc4c5c(c(-c6c(F)ccc7sc(NC(=O)OC(C)(C)C)c(C#N)c67)c(F)c4n3)COC5)C2)CC1] | 648 |
| 595D | tert-Butyl (3-cyano-5-fluoro-4-(5-fluoro-3-((3S,4R)-3-hydroxy-4-(isopropyl(methyl)amino) pyrrolidin-1-yl)-7,9-dihydrofuro[3,4-f]quinazolin-6-yl)benzo[b]thiophen-2-yl)carbamate | 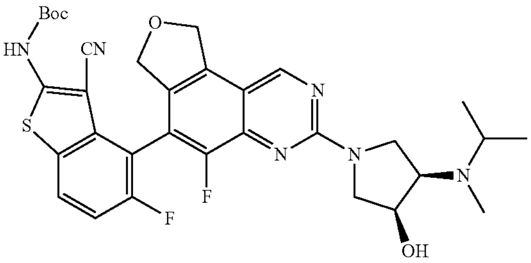 [SMILES: CC(C)N(C)[C@@H]1CN(c2ncc3c4c(c(-c5c(F)ccc6sc(NC(=O)OC(C)(C)C)c(C#N)c56)c(F)c3n2)COC4)C[C@@H]1O] | 637 |
| 596D | tert-Butyl (3-cyano-5-fluoro-4-(5-fluoro-3-((3S,4S)-3-hydroxy-4-(isopropyl(methyl)amino) pyrrolidin-1-yl)-7,9-dihydrofuro[3,4-f]quinazolin-6-yl)benzo[b]thiophen-2-yl)carbamate | 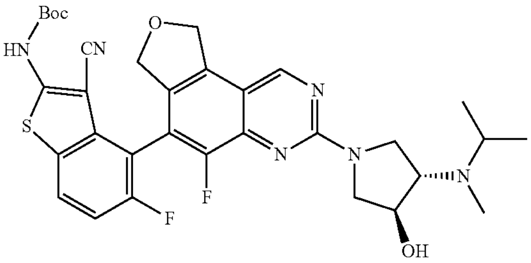 [SMILES: CC(C)N(C)[C@H]1CN(c2ncc3c4c(c(-c5c(F)ccc6sc(NC(=O)OC(C)(C)C)c(C#N)c56)c(F)c3n2)COC4)C[C@@H]1O] | 637 |
| 597D | tert-Butyl (3-cyano-5-fluoro-4-(5-fluoro-3-((3R,4R)-3-hydroxy-4-(isopropyl(methyl)amino) pyrrolidin-1-yl)-7,9-dihydrofuro[3,4-f]quinazolin-6-yl)benzo[b]thiophen-2-yl)carbamate | 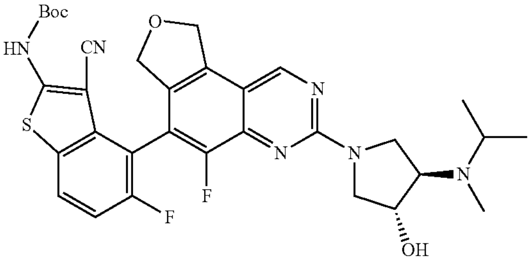 [SMILES: CC(C)N(C)[C@@H]1CN(c2ncc3c4c(c(-c5c(F)ccc6sc(NC(=O)OC(C)(C)C)c(C#N)c56)c(F)c3n2)COC4)C[C@H]1O] | 637 |

TABLE 22-continued

| Preparation | Chemical Name | Structure | MS (ES) m/z (M + 1) |
|---|---|---|---|
| 598D | tert-Butyl (3-cyano-5-fluoro-4-(5-fluoro-3-((3R,4S)-3-hydroxy-4-(isopropyl(methyl)amino)pyrrolidin-1-yl)-7,9-dihydrofuro[3,4-f]quinazolin-6-yl)benzo[b]thiophen-2-yl)carbamate | 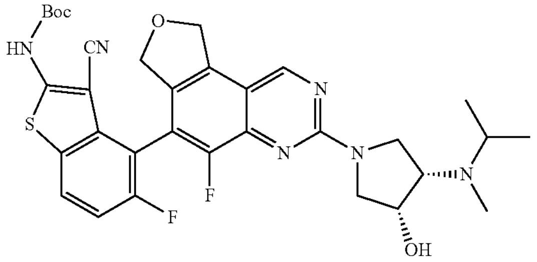 [SMILES: CC(C)N(C)[C@H]1CN(c2ncc3c4c(c(-c5c(F)ccc6sc(NC(=O)OC(C)(C)C)c(C#N)c56)c(F)c3n2)COC4)C[C@H]1O] | 637 |
| 599D | tert-Butyl (4-(3-((2R,3R)-3-amino-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 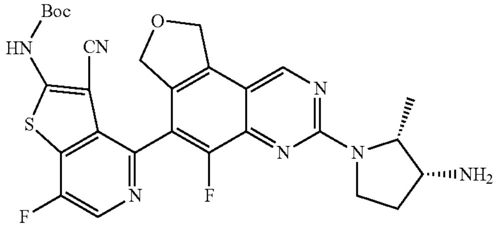 [SMILES: C[C@@H]1[C@H](N)CCN1c1ncc2c3c(c(-c4ncc(F)c5sc(NC(=O)OC(C)(C)C)c(C#N)c45)c(F)c2n1)COC3] | 580 |
| 600D | tert-Butyl (3-cyano-7-fluoro-4-(5-fluoro-3-((2S,3S)-3-((2-hydroxyethyl)amino)-2-methylpyrrolidin-1-yl)-7,9-dihydrofuro[3,4-f]quinazolin-6-yl)thieno[3,2-c]pyridin-2-yl)carbamate | 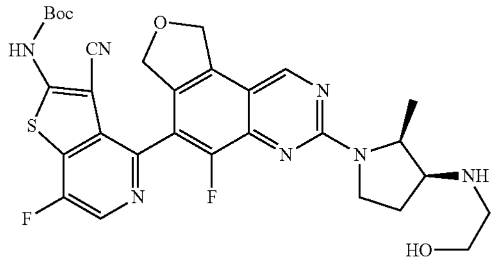 [SMILES: C[C@H]1[C@@H](NCCO)CCN1c1ncc2c3c(c(-c4ncc(F)c5sc(NC(=O)OC(C)(C)C)c(C#N)c45)c(F)c2n1)COC3] | 624 |
| 601D | tert-Butyl (4-(3-(3-aminohexahydro-1H-furo[3,4-b]pyrrol-1-yl)-5-fluoro-7,9-dihydrofuro[3,4-f]quinazolin-6-yl)-3-cyano-7-fluorothieno[3,2-c]pyridin-2-yl)carbamate | 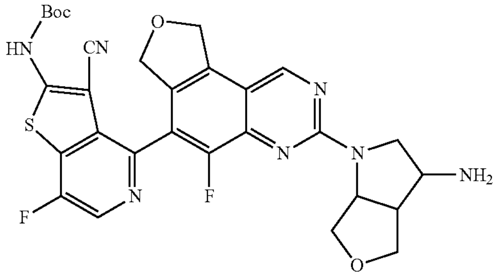 [SMILES: CC(C)(C)OC(=O)Nc1sc2c(F)cnc(-c3c4c(c5cnc(N6CC(N)C7COCC76)nc5c3F)COC4)c2c1C#N] | 608 |
| 602D | tert-Butyl (4-(3-((2S,4R)-4-amino-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 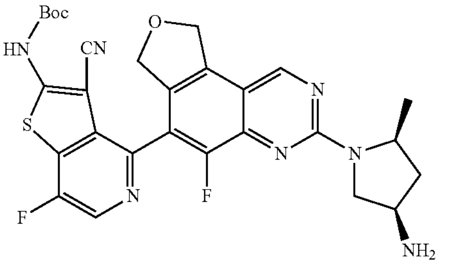 [SMILES: C[C@H]1C[C@@H](N)CN1c1ncc2c3c(c(-c4ncc(F)c5sc(NC(=O)OC(C)(C)C)c(C#N)c45)c(F)c2n1)COC3] | 580 |
| 603D [33] | 2-Amino-4-(3-(dihydro-1H,4H-3a,6a-(methanooxymethano)pyrrolo[3,4-c]pyrrol-2(3H)-yl)-5-fluoro-7,9-dihydrofuro[3,4-f]quinazolin-6-yl)-7-fluorothieno[3,2-c]pyridine-3-carbonitrile | 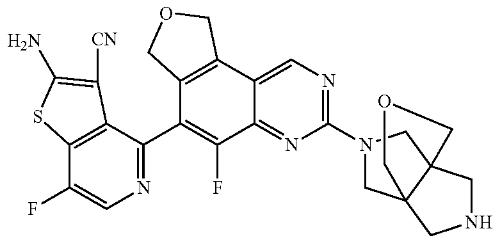 [SMILES: N#Cc1c(N)sc2c(F)cnc(-c3c4c(c5cnc(N6CC78CNCC7(COC8)C6)nc5c3F)COC4)c12] | 534 |

TABLE 22-continued

| Preparation | Chemical Name | Structure | MS (ES) m/z (M + 1) |
|---|---|---|---|
| 604D | tert-Butyl (4-(3-((2S,3S)-3-((tert-butoxycarbonyl)amino)-2-methylpyrrolidin-1-yl)-5-fluoro-7,9-dihydrofuro[3,4-f]quinazolin-6-yl)-3-cyano-5-fluorobenzo[b]thiophen-2-yl)carbamate | 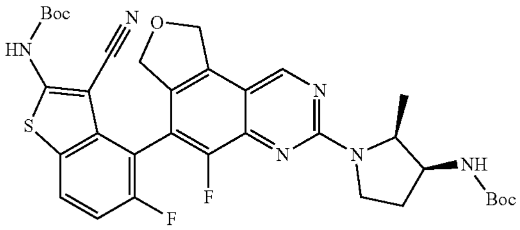 [SMILES: C[C@H]1[C@@H](NC(=O)OC(C)(C)C)CCN1c1ncc2c3c(c(-c4c(F)ccc5sc(NC(=O)OC(C)(C)C)c(C#N)c45)c(F)c2n1)COC3] | 679 |
| 605D | tert-Butyl 6-(6-(2-((tert-butoxycarbonyl)amino)-3-cyano-7-fluorothieno[3,2-c]pyridin-4-yl)-5-chloro-7,9-dihydrofuro[3,4-f]quinazolin-3-yl)-1,6-diazaspiro[3.4]octane-1-carboxylate | 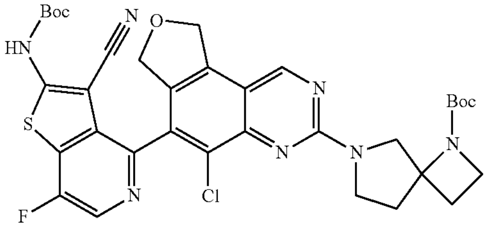 [SMILES: CC(C)(C)OC(=O)Nc1sc2c(F)cnc(-c3c4c(c5cnc(N6CCC7(CCN7C(=O)OC(C)(C)C)C6)nc5c3Cl)COC4)c2c1C#N] | 708 |

[1] Preparations 47A and 48A represent separated trans isomers pairs
[2] Preparation 78A - both trans isomers present
[3] Starting material - 4-bromo-7-chloro-5-fluoro-1,3-dihydrofuro[3,4-f]quinazoline
[4] Starting material - 4-bromo-5,7-dichloro-1,3-dihydrofuro[3,4-f]quinazoline
[5] Single atropisomer (from precursor in Preparation 17B)
[6] Single atropisomer (from precurosr in Preparation 18B)
[7] Single atropisomer (from precursor in Preparation 9B)
[8] Single atropisomer (from precursor in Preparation 14B)
[9] Mix of Trans Isomers
[10] Mix of Trans Isomers
[11] Clean Trans Isomers, Separated in Preparations 5D and 6D
[12] Clean Trans Isomer, Separated in Preparation 7D
[13] Mix of Trans Isomers
[14] Clean Trans Isomer, Separated in Preparation 7D
[15] Mix of Trans Isomers
[16] Clean Isomers, Separated in Preparations 89D and 90D
[17] Mix of Trans Isomers
[18] Clean Trans Isomers, Separated in Preparations 9D and 10D
[19] Mix of Trans Isomers
[20] Mix of Tarns Isomers
[21] Mix of Trans Isomers
[22] Mix of Trans Isomers
[23] Mix of Cis Isomers
[24] Mix of Trans Isomers
[25] Mix of Trans Isomers (nitrogen and oxygen substituents)
[26] Clean Trans Isomers (nitrogen and oxygen substituents)
[27] Clean Trans Isomers (nitrogen and oxygen substituents)
[28] Clean Cis Isomer (nitrogen and oxygen substituents)
[29] Mix of Cis Isomers
[30] Clean Trans Isomers, Separated in Preparations 12D and 13D
[31] Clean Isomers, Separated in Preparations 142D and 143D
[32] Byproduct from impurity in Preparatino 583D
[33] After completion, reaction was concentrated and material was deprotected with TFA in DCM Preparation 88 tert-Butyl 8-(3-((1-((4-acetylpiperazin-1-yl)methyl)cyclopropyl)methoxy)-6-(2-((tert-butoxycarbonyl)amino)-3-cyano-7-fluorothieno[3,2-c]pyridin-4-yl)-5-fluoro-7,9-dihydrofuro[3,4-f]quinazolin-1-yl)-3,8-diazabicyclo[3.2.1]octane-3-carboxylate

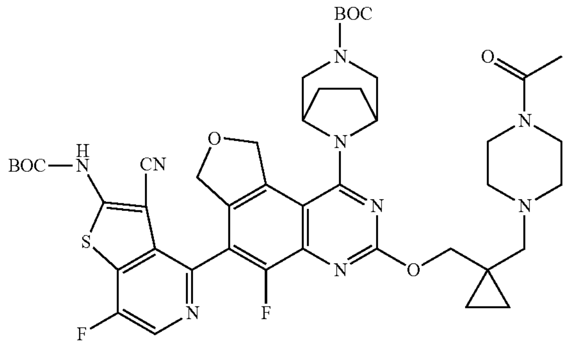 [SMILES: CC(=O)N1CCN(CC2(COc3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)CC2)CC1]

tert-Butyl 8-(6-(2-((tert-butoxycarbonyl)amino)-3-cyano-7-fluorothieno[3,2-c]pyridin-4-yl)-5-fluoro-3-((1-(hydroxymethyl)cyclopropyl)methoxy)-7,9-dihydrofuro[3,4-f]quinazolin-1-yl)-3,8-diazabicyclo[3.2.1]octane-3-carboxylate, ethanesulfonyl chloride, and 1-(piperazin-1-yl)ethan-1-one were used in a manner analogous to the methods of Preparations 17 and 18 to afford the title compound (0.064 g, 62%) as a yellow solid. MS (ES) m/z=902 (M+1).

Preparation 89

6-Bromo-3-((2,2-difluoro-1-(morpholinomethyl)cyclopropyl)methoxy)-5-fluoro-7,9-dihydrofuro[3,4-f]quinazoline

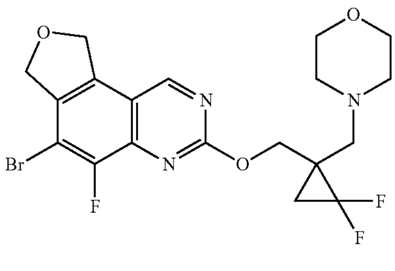 [SMILES: Fc1c(Br)c2c(c3cnc(OCC4(CN5CCOCC5)CC4(F)F)nc13)COC2]

(1-(((6-Bromo-5-fluoro-7,9-dihydrofuro[3,4-f]quinazolin-3-yl)oxy)methyl)-2,2-difluorocyclopropyl)methanol, methanesulfonic anhydride, and morpholine were used in a manner analogous to the methods of Preparations 17 and 18 to afford the title compound (1.5 g, 61%) as a yellow solid. MS (ES) m/z=474 (M+1).

Preparations 90 and 91

6-Bromo-3-((2,2-difluoro-1-(morpholinomethyl)cyclopropyl)methoxy)-5-fluoro-7,9-dihydrofuro[3,4-f]quinazoline, Isomer 1 and Isomer 2

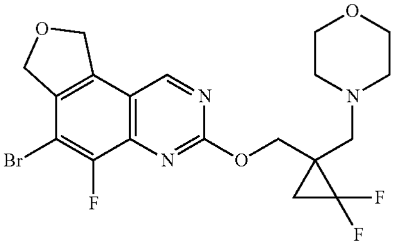 [SMILES: Fc1c(Br)c2c(c3cnc(OCC4(CN5CCOCC5)CC4(F)F)nc13)COC2]

Chiral separation of 6-bromo-3-((2,2-difluoro-1-(morpholinomethyl)cyclopropyl)methoxy)-5-fluoro-7,9-dihydrofuro[3,4-f]quinazoline (supercritical fluid chromatography; CHIRALPAK IG, 30×250 mm, 45% 1:1 DCM:MeOH (with 0.1% 2M ammoniated methanol):55% $CO_2$, 100 mL/min) was performed, to afford the title compounds (Isomer 1 0.63 g; Isomer 2 0.52 g) as yellow solids. MS (ES) m/z=474 (M+1), for both.

Preparation 193B tert-Butyl 8-(6-(2-((tert-butoxycarbonyl)amino)-3-cyano-7-fluorothieno[3,2-c]pyridin-4-yl)-5-fluoro-3-((1-formylcyclopropyl)methoxy)-7,9-dihydrofuro[3,4-f]quinazolin-1-yl)-3,8-diazabicyclo[3.2.1]octane-3-carboxylate

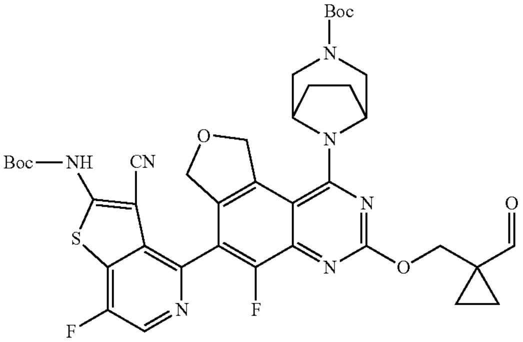 [SMILES: CC(C)(C)OC(=O)Nc1sc2c(F)cnc(-c3c4c(c5c(N6C7CCC6CN(C(=O)OC(C)(C)C)C7)nc(OCC6(C=O)CC6)nc5c3F)COC4)c2c1C#N]

Combined tert-butyl 8-(6-(2-((tert-butoxycarbonyl)amino)-3-cyano-7-fluorothieno[3,2-c]pyridin-4-yl)-5-fluoro-3-((1-(hydroxymethyl)cyclopropyl)methoxy)-7,9-dihydrofuro[3,4 -f]quinazolin-1-yl)-3,8-diazabicyclo[3.2.1]octane-3-carboxylate (0.37 g, 0.47 mmol), DCM (4.7 mL), and Dess-Martin periodinane (0.24 g, 0.56 mmol). The reaction mixture was stirred for 3 h. A small amount of Dess-Martin periodinane was added. After an additional 1 h, the mixture was diluted with DCM and aqueous sodium bicarbonate, then stirred vigorously for 10 min. The layers were separated. The organic layer was washed with water and brine, dried over magnesium sulfate, filtered, and concentrated under reduced pressure to give the title compound (0.34 g, 91%). MS (ES) m/z=790 (M+1).

Preparation 194B tert-Butyl 8-(6-(2-((tert-butoxycarbonyl)amino)-3-cyano-7-fluorothieno[3,2-c]pyridin-4-yl)-5-fluoro-3-((1-(((S)-2-

(fluoromethyl)azetidin-1-yl)methyl)cyclopropyl)methoxy)-7,9-dihydrofuro[3,4-f]quinazolin-1-yl)-3,8-diazabicyclo[3.2.1]octane-3-carboxylate

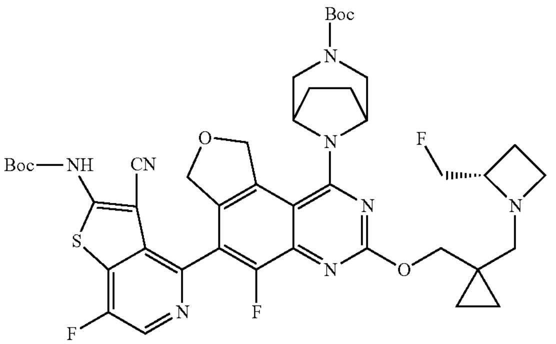 [SMILES: CC(C)(C)OC(=O)Nc1sc2c(F)cnc(-c3c4c(c5c(N6C7CCC6CN(C(=O)OC(C)(C)C)C7)nc(OCC6(CN7CC[C@H]7CF)CC6)nc5c3F)COC4)c2c1C#N]

Combined tert-butyl 8-(6-(2-((tert-butoxycarbonyl)amino)-3-cyano-7-fluorothieno[3,2-c]pyridin-4-yl)-5-fluoro-3-((1-formylcyclopropyl)methoxy)-7,9-dihydrofuro[3,4-f]quinazolin-1-yl)-3,8-diazabicyclo[3.2.1]octane-3-carboxylate (0.165 g, 0.209 mmol), DCM (0.81 mL), and MeOH (0.25 mL). Added (S)-2-(fluoromethyl)azetidine 2,2,2-trifluoroacetate (79 wt %, 0.107 g, 0.418 mmol) as a solution in DCM (0.5 mL). The reaction mixture was stirred for 5 min, then sodium triacetoxyborohydride (0.155 g, 0.731 mmol) was added. The reaction mixture was stirred overnight, then loaded onto a strong cation exchange cartridge. The cartridge was eluted with MeOH (75 mL), then ammoniated methanol. The latter fraction was concentrated under reduced pressure. The residue was purified by silica gel chromatography, eluting with a gradient of 0-20% ammoniated MeOH in DCM, to give the title compound (0.15 g, 84%). MS (ES) m/z=863 (M+1).

Preparation 195B tert-Butyl 8-(6-(2-((tert-butoxycarbonyl)amino)-3-cyano-7-fluorothieno[3,2-c]pyridin-4-yl)-5 -fluoro-3-((1-(((S)-2-(methoxymethyl)azetidin-1-yl)methyl)cyclopropyl)methoxy)-7,9-dihydrofuro[3,4-f]quinazolin-1-yl)-3,8-diazabicyclo[3.2.1]octane-3-carboxylate

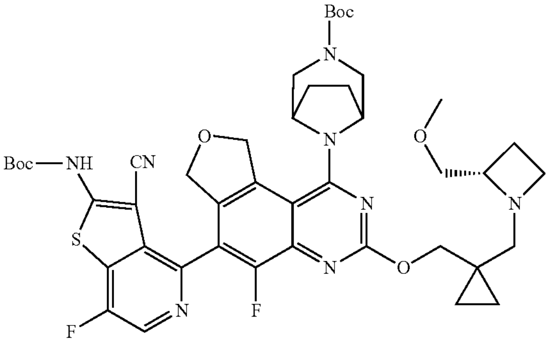 [SMILES: COC[C@@H]1CCN1CC1(COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)CC1]

(S)-2-(Methoxymethyl)azetidine 2,2,2-trifluoroacetate was used in a manner analogous to the method of Preparation 194B to afford the title compound (0.080 g, 48%). MS (ES) m/z=875 (M+1).

The following compounds in Table 23 were prepared in similar manner as described in Preparations 17 and 18, using tert-butyl 8-(6-(2-((tert-butoxycarbonyl)amino)-3-cyano-7-fluorothieno[3,2-c]pyridin-4-yl)-5-fluoro-3-((1-(hydroxymethyl)cyclopropyl)methoxy)-7,9-dihydrofuro[3,4-f]quinazolin-1-yl)-3,8-diazabicyclo[3.2.1]octane-3-carboxylate. Various methods were used to purify the compounds, which would be apparent to one skilled in the art.

TABLE 23

| Preparation | Chemical Name | Structure | MS (ES) m/z (M + 1) |
|---|---|---|---|
| 85A | tert-Butyl 8-(6-(2-((tert-butoxycarbonyl)amino)-3-cyano-7-fluorothieno[3,2-c]pyridin-4-yl)-3-((1-((4-cyanopiperidin-1-yl)methyl)cyclopropyl)methoxy)-5-fluoro-7,9-dihydrofuro[3,4-f]quinazolin-1-yl)-3,8-diazabicyclo[3.2.1 ]octane-3-carboxylate | 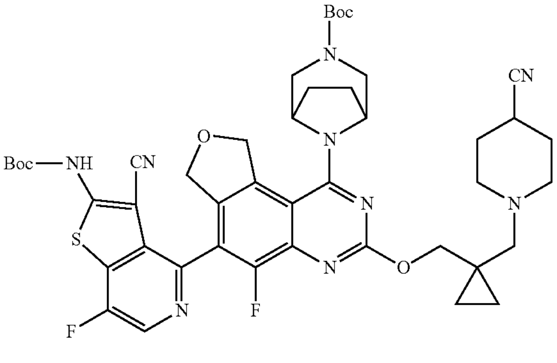 [SMILES: CC(C)(C)OC(=O)Nc1sc2c(F)cnc(-c3c4c(c5c(N6C7CCC6CN(C(=O)OC(C)(C)C)C7)nc(OCC6(CN7CCC(C#N)CC7)CC6)nc5c3F)COC4)c2c1C#N] | 885 |

TABLE 23-continued

| Preparation | Chemical Name | Structure | MS (ES) m/z (M + 1) |
|---|---|---|---|
| 86A | tert-Butyl 8-(3-((1-((2-oxa-6-azaspiro[3.3]heptan-6-yl)methyl)cyclopropyl) methoxy)-6-(2-((tert-butoxycarbonyl)amino)-3-cyano-7-fluorothieno[3,2-c]pyridin-4-yl)-5-fluoro-7,9-dihydrofuro[3,4-f]quinazolin-1-yl)-3,8-diazabicyclo[3.2.1]octane-3-carboxylate | 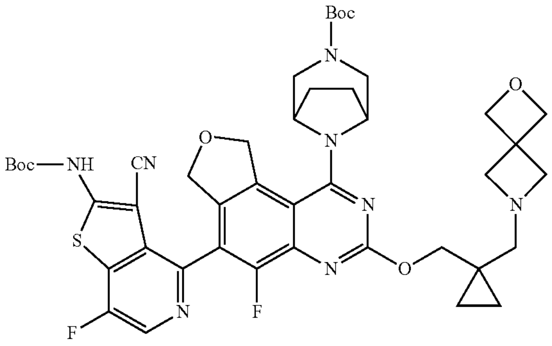 [SMILES: CC(C)(C)OC(=O)Nc1sc2c(F)cnc(-c3c4c(c5c(N6C7CCC6CN(C(=O)OC(C)(C)C)C7)nc(OCC6(CN7CC8(COC8)C7)CC6)nc5c3F)COC4)c2c1C#N] | 873 |
| 87A | tert-Butyl 8-(6-(2-((tert-butoxycarbonyl)amino)-3-cyano-7-fluorothieno[3,2-c]pyridin-4-yl)-5-fluoro-3-((1-((4-(2,2,2-trifluoroethyl)piperazin-1-yl)methyl)cyclopropyl) methoxy)-7,9-dihydrofuro[3,4-f]quinazolin-1-yl)-3,8-diazabicyclo[3.2.1]octane-3-carboxylate | 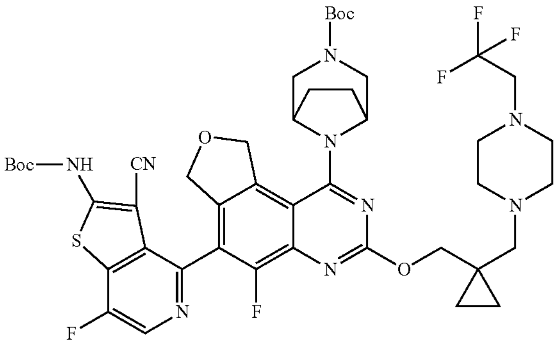 [SMILES: CC(C)(C)OC(=O)Nc1sc2c(F)cnc(-c3c4c(c5c(N6C7CCC6CN(C(=O)OC(C)(C)C)C7)nc(OCC6(CN7CCN(CC(F)(F)F)CC7)CC6)nc5c3F)COC4)c2c1C#N] | 942 |
| 88A | tert-Butyl 8-(6-(2-((tert-butoxycarbonyl)amino)-3-cyano-7-fluorothieno[3,2-c]pyridin-4-yl)-5-fluoro-3-((1-(((S)-3-methylmorpholino)methyl) cyclopropyl)methoxy)-7,9-dihydrofuro[3,4-f]quinazolin-1-yl)-3,8-diazabicyclo[3.2.1]octane-3-carboxylate | 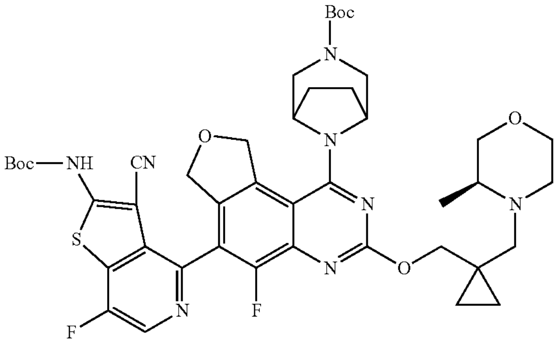 [SMILES: C[C@H]1COCCN1CC1(COc2nc(N3C4CCC3CN(C(=O)OC(C)(C)C)C4)c3c4c(c(-c5ncc(F)c6sc(NC(=O)OC(C)(C)C)c(C#N)c56)c(F)c3n2)COC4)CC1] | 875 |
| 89A | tert-Butyl 8-(6-(2-((tert-butoxycarbonyl)amino)-3-cyano-7-fluorothieno[3,2-c]pyridin-4-yl)-3-((1-(((2R,6S)-2,6-dimethylmorpholino)methyl)cyclopropyl)methoxy)-5-fluoro-7,9-dihydrofuro[3,4-f]quinazolin-1-yl)-3,8-diazabicyclo[3.2.1]octane-3-carboxylate | 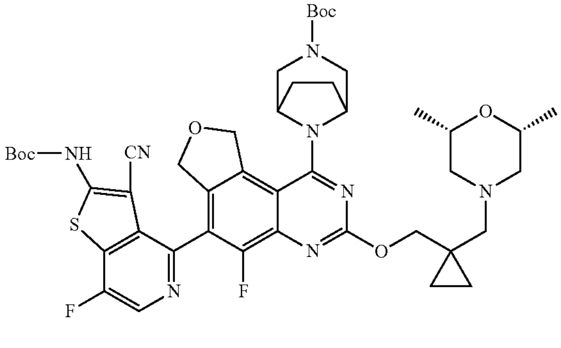 [SMILES: C[C@@H]1CN(CC2(COc3nc(N4C5CCC4CN(C(=O)OC(C)(C)C)C5)c4c5c(c(-c6ncc(F)c7sc(NC(=O)OC(C)(C)C)c(C#N)c67)c(F)c4n3)COC5)CC2)C[C@H](C)O1] | 889 |

TABLE 23-continued

| Preparation | Chemical Name | Structure | MS (ES) m/z (M + 1) |
|---|---|---|---|
| 90A | tert-Butyl 8-(6-(2-((tert-butoxycarbonyl)amino)-3-cyano-7-fluorothieno[3,2-c]pyridin-4-yl)-5-fluoro-3-((1-(((S)-2-(hydroxymethyl)azetidin-1-yl)methyl)cyclopropyl)methoxy)-7,9-dihydrofuro[3,4-f]quinazolin-1-yl)-3,8-diazabicyclo[3.2.1]octane-3-carboxylate | 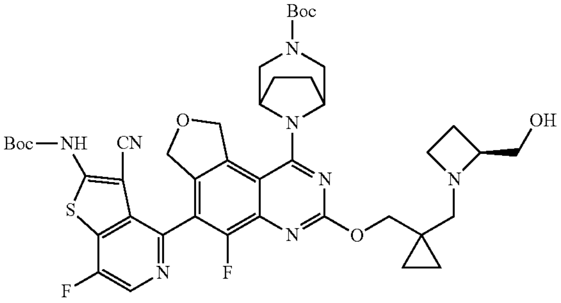 [SMILES: CC(C)(C)OC(=O)Nc1sc2c(F)cnc(-c3c4c(c5c(N6C7CCC6CN(C(=O)OC(C)(C)C)C7)nc(OCC6(CN7CC[C@H]7CO)CC6)nc5c3F)COC4)c2c1C#N] | 861 |
| 91A | tert-Butyl 8-(6-(2-((tert-butoxycarbonyl)amino)-3-cyano-7-fluorothieno[3,2-c]pyridin-4-yl)-3-((1-(((R)-3-cyanopyrrolidin-1-yl)methyl)cyclopropyl)methoxy)-5-fluoro-7,9-dihydrofuro[3,4-f]quinazolin-1-yl)-3,8-diazabicyclo[3.2.1]octane-3-carboxylate | 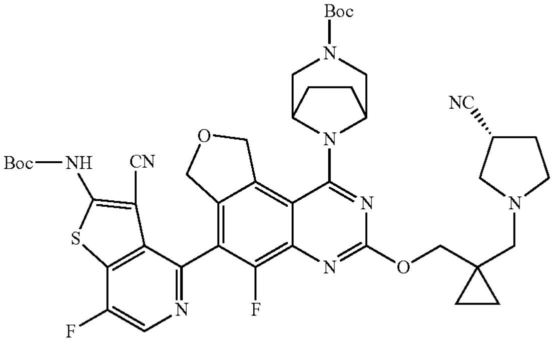 [SMILES: CC(C)(C)OC(=O)Nc1sc2c(F)cnc(-c3c4c(c5c(N6C7CCC6CN(C(=O)OC(C)(C)C)C7)nc(OCC6(CN7CC[C@@H](C#N)C7)CC6)nc5c3F)COC4)c2c1C#N] | 870 |
| 92A | tert-Butyl 8-(3-((1-((6-oxa-2-azaspiro[3.4]octan-2-yl)methyl)cyclopropyl)methoxy)-6-(2-((tert-butoxycarbonyl)amino)-3-cyano-7-fluorothieno[3,2-c]pyridin-4-yl)-5-fluoro-7,9-dihydrofuro[3,4-f]quinazolin-1-yl)-3,8-diazabicyclo[3.2.1]octane-3-carboxylate | 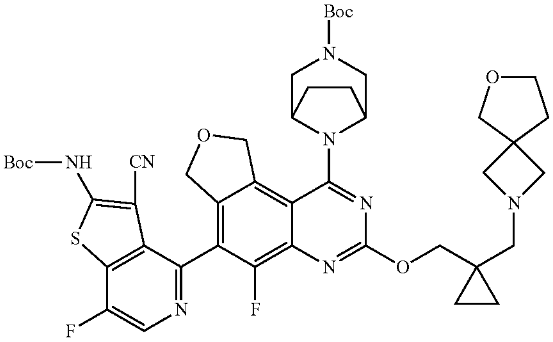 [SMILES: CC(C)(C)OC(=O)Nc1sc2c(F)cnc(-c3c4c(c5c(N6C7CCC6CN(C(=O)OC(C)(C)C)C7)nc(OCC6(CN7CC8(CCOC8)C7)CC6)nc5c3F)COC4)c2c1C#N] | 887 |
| 93A | tert-Butyl 8-(6-(2-((tert-butoxycarbonyl)amino)-3-cyano-7-fluorothieno[3,2-c]pyridin-4-yl)-3-((1-(((S)-3-cyanopyrrolidin-1-yl)methyl)cyclopropyl)methoxy)-5-fluoro-7,9-dihydrofuro[3,4-f]quinazolin-1-yl)-3,8-diazabicyclo[3.2.1]octane-3-carboxylate | 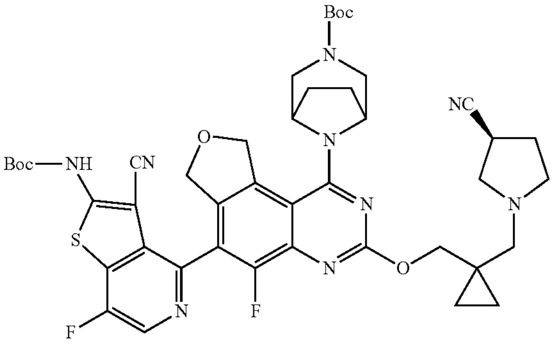 [SMILES: CC(C)(C)OC(=O)Nc1sc2c(F)cnc(-c3c4c(c5c(N6C7CCC6CN(C(=O)OC(C)(C)C)C7)nc(OCC6(CN7CC[C@H](C#N)C7)CC6)nc5c3F)COC4)c2c1C#N] | 870 |

TABLE 23-continued

| Preparation | Chemical Name | Structure | MS (ES) m/z (M + 1) |
|---|---|---|---|
| 94A | tert-Butyl 8-(3-((1-(((1R,4R)-2-oxa-5-azabicyclo[2.2.1]heptan-5-yl)methyl)cyclopropyl) methoxy)-6-(2-((tert-butoxycarbonyl)amino)-3-cyano-7-fluorothieno[3,2-c]pyridin-4-yl)-5-fluoro-7,9-dihydrofuro[3,4-f]quinazolin-1-yl)-3,8-diazabicyclo[3.2.1]octane-3-carboxylate | 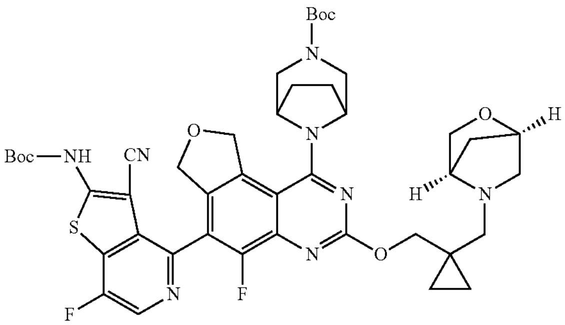 [SMILES: CC(C)(C)OC(=O)Nc1sc2c(F)cnc(-c3c4c(c5c(N6C7CCC6CN(C(=O)OC(C)(C)C)C7)nc(OCC6(CN7C[C@H]8C[C@@H]7CO8)CC6)nc5c3F)COC4)c2c1C#N] | 873 |

Preparation 92 tert-Butyl (3-cyano-4-(3-((2,2-difluoro-1-(morpholinomethyl)cyclopropyl)methoxy)-5-fluoro-7,9-dihydrofuro[3,4-f]quinazolin-6-yl)-7-fluorothieno[3,2-c]pyridin-2-yl)carbamate, Isomer 1

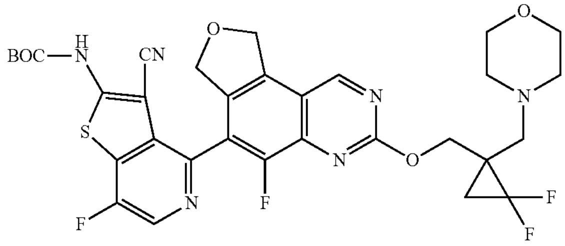 [SMILES: CC(C)(C)OC(=O)Nc1sc2c(F)cnc(-c3c4c(c5cnc(OCC6(CN7CCOCC7)CC6(F)F)nc5c3F)COC4)c2c1C#N]

6-Bromo-3-((2,2-difluoro-1-(morpholinomethyl)cyclopropyl)methoxy)-5-fluoro-7,9-dihydrofuro[3,4-f]quinazoline, Isomer 1 was used in a manner analogous to the method of Preparation 33 to afford the title compound (0.36 g, 59%) as a yellow solid. MS (ES) m/z=687 (M+1).

Preparation 93 tert-Butyl (3-cyano-4-(3-((2,2-difluoro-1-(morpholinomethyl)cyclopropyl)methoxy)-5-fluoro-7,9-dihydrofuro[3,4-f]quinazolin-6-yl)-7-fluorothieno[3,2-c]pyridin-2-yl)carbamate, Isomer 2

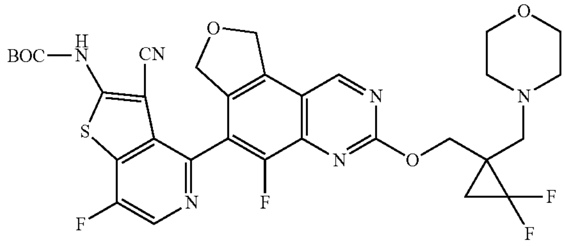 [SMILES: CC(C)(C)OC(=O)Nc1sc2c(F)cnc(-c3c4c(c5cnc(OCC6(CN7CCOCC7)CC6(F)F)nc5c3F)COC4)c2c1C#N]

6-Bromo-3-((2,2-difluoro-1-(morpholinomethyl)cyclopropyl)methoxy)-5-fluoro-7,9-dihydrofuro[3,4-f]quinazoline, Isomer 2 was used in a manner analogous to the method of Preparation 33 to afford the title compound (0.50 g, 63%) as a yellow solid. MS (ES) m/z=687 (M+1).

Preparation 95A tert-Butyl (3-cyano-4-(7-((S)-3-(dimethylamino)pyrrolidin-1-yl)-5-fluoro-1,3-dihydrofuro[3,4-f]quinolin-4-yl)-7-fluorothieno[3,2-c]pyridin-2-yl)carbamate

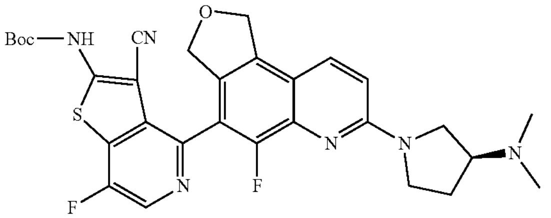 [SMILES: CN(C)[C@H]1CCN(c2ccc3c4c(c(-c5ncc(F)c6sc(NC(=O)OC(C)(C)C)c(C#N)c56)c(F)c3n2)COC4)C1]

(S)-1-(4-Bromo-5-fluoro-1,3-dihydrofuro[3,4-f]quinolin-7-yl)—N,N-dimethylpyrrolidin-3-amine was used in a manner analogous to the method of Preparation 33 to afford the title compound (0.32 g, 21%). MS (ES) m/z=593 (M+1).

Preparation 196B tert-Butyl (3-cyano-4-(7-((S)-3-(dimethylamino)pyrrolidin-1-yl)-5-fluoro-1,3-dihydrofuro[3,4-f]quinolin-4-yl)-7-fluorothieno[3,2-c]pyridin-2-yl)carbamate

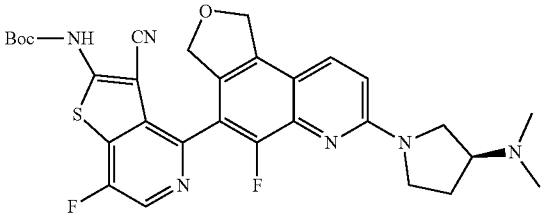 [SMILES: CN(C)[C@H]1CCN(c2ccc3c4c(c(-c5ncc(F)c6sc(NC(=O)OC(C)(C)C)c(C#N)c56)c(F)c3n2)COC4)C1]

(S)-1-(4-Bromo-5-chloro-1,3-dihydrofuro[3,4-f]quinolin-7-yl)—N,N-dimethylpyrrolidin-3-amine was used in a manner analogous to the method of Preparation 33 to afford the title compound (0.060 g, 8%). MS (ES) m/z=609 (M+1).

The following compounds in Table 24 were prepared in similar manner as described in Preparation 33. Various methods were used to purify the compounds, which would be apparent to one skilled in the art.

TABLE 24

| Preparation | Chemical Name | Structure | MS (ES) m/z (M + 1) |
|---|---|---|---|
| 138C | tert-Butyl (4-(5-chloro-7-((3S,4S)-3-(dimethylamino)-4-hydroxypyrrolidin-1-yl)-1,3-dihydrofuro[3,4-f]quinolin-4-yl)-3-cyano-7-fluorothieno[3,2-c]pyridin-2-yl)carbamate | 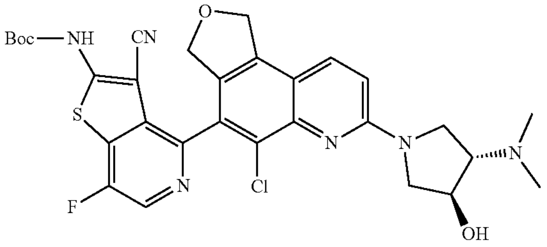 [SMILES: CN(C)[C@H]1CN(c2ccc3c4c(c(-c5ncc(F)c6sc(NC(=O)OC(C)(C)C)c(C#N)c56)c(Cl)c3n2)COC4)C[C@@H]1O] | 625 |
| 139C | tert-Butyl (4-(5-chloro-7-((3R,4R)-3-(dimethylamino)-4-hydroxypyrrolidin-1-yl)-1,3-dihydrofuro[3,4-f]quinolin-4-yl)-3-cyano-7-fluorothieno[3,2-c]pyridin-2-yl)carbamate | 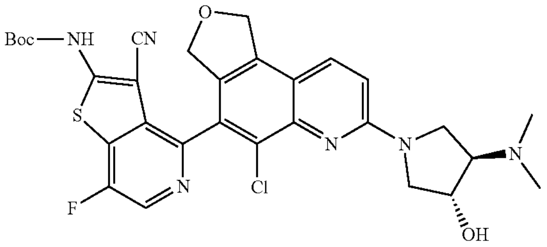 [SMILES: CN(C)[C@@H]1CN(c2ccc3c4c(c(-c5ncc(F)c6sc(NC(=O)OC(C)(C)C)c(C#N)c56)c(Cl)c3n2)COC4)C[C@H]1O] | 625 |
| 140C | tert-Butyl (4-(5-chloro-7-((3R,4S)-3-(dimethylamino)-4-hydroxypyrrolidin-1-yl)-1,3-dihydrofuro[3,4-f]quinolin-4-yl)-3-cyano-7-fluorothieno[3,2-c]pyridin-2-yl)carbamate | 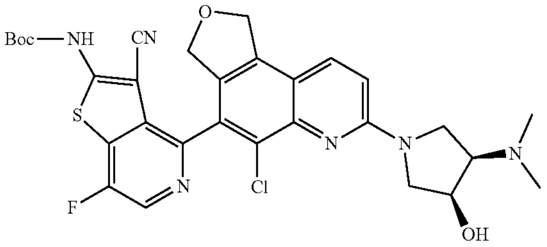 [SMILES: CN(C)[C@@H]1CN(c2ccc3c4c(c(-c5ncc(F)c6sc(NC(=O)OC(C)(C)C)c(C#N)c56)c(Cl)c3n2)COC4)C[C@@H]1O] | 625 |
| 141C | tert-Butyl (4-(5-chloro-7-((3S,4R)-3-(dimethylamino)-4-hydroxypyrrolidin-1-yl)-1,3-dihydrofuro[3,4-f]quinolin-4-yl)-3-cyano-7-fluorothieno[3,2-c]pyridin-2-yl)carbamate | 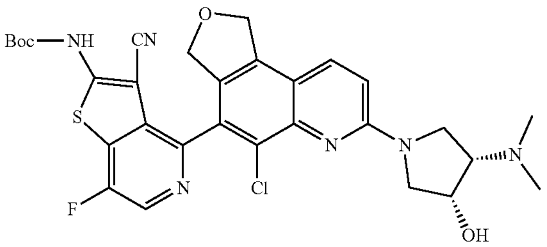 [SMILES: CN(C)[C@H]1CN(c2ccc3c4c(c(-c5ncc(F)c6sc(NC(=O)OC(C)(C)C)c(C#N)c56)c(Cl)c3n2)COC4)C[C@H]1O] | 625 |

The following compounds in Table 25 were prepared in similar manner as described in Preparation 33B. Various methods were used to purify the compounds, which would be apparent to one skilled in the art.

TABLE 25

| Preparation | Chemical Name | Structure | MS (ES) m/z (M + 1) |
|---|---|---|---|
| 197B | tert-Butyl (3-cyano-7-fluoro-4-(5-fluoro-3-((2S,3S)-3-(isopropylamino)-2-methylpyrrolidin-1-yl)-7,9-dihydrofuro[3,4-f]quinazolin-6-yl)thieno[3,2-c]pyridin-2-yl)carbamate | 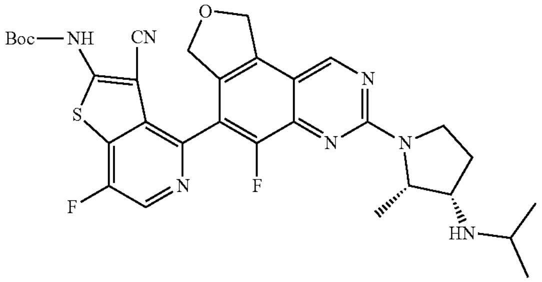 [SMILES: CC(C)N[C@H]1CCN(c2ncc3c4c(c(-c5ncc(F)c6sc(NC(=O)OC(C)(C)C)c(C#N)c56)c(F)c3n2)COC4)[C@H]1C] | 622 |
| 142C | tert-Butyl (4-(5-chloro-3-((2S,3S)-3-(dimethylamino)-2-methylpyrrolidin-1-yl)-7,9-dihydrofuro[3,4-f]quinazolin-6-yl)-3-cyano-7-fluorothieno[3,2-c]pyridin-2-yl)carbamate | 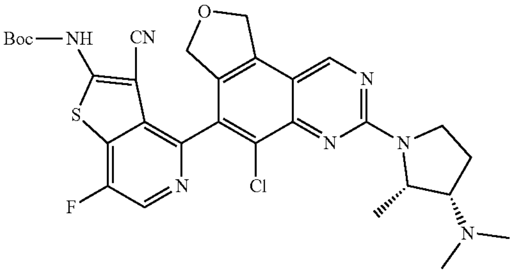 [SMILES: C[C@H]1[C@@H](N(C)C)CCN1c1ncc2c3c(c(-c4ncc(F)c5sc(NC(=O)OC(C)(C)C)c(C#N)c45)c(Cl)c2n1)COC3] | 624 |
| 143C | tert-Butyl (4-(5-chloro-3-((2S,3S)-3-(ethylamino)-2-methylpyrrolidin-1-yl)-7,9-dihydrofuro[3,4-f]quinazolin-6-yl)-3-cyano-7-fluorothieno[3,2-c]pyridin-2-yl)carbamate | 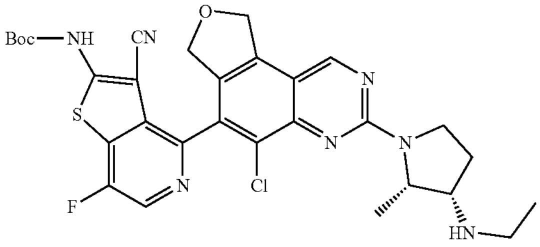 [SMILES: CCN[C@H]1CCN(c2ncc3c4c(c(-c5ncc(F)c6sc(NC(=O)OC(C)(C)C)c(C#N)c56)c(Cl)c3n2)COC4)[C@H]1C] | 624 |
| 144C | tert-Butyl (4-(3-((2S,3S)-3-(((R)-2-((tert-butyldimethylsilyl)oxy)propyl)(methyl)amino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 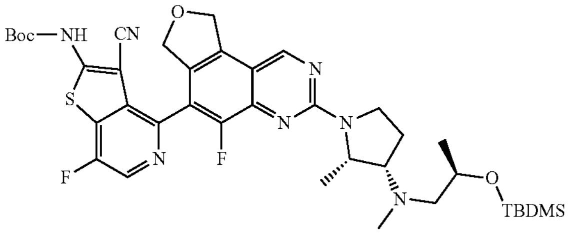 | 766 |
| 145C | tert-Butyl (4-(3-((2S,3S)-3-(((S)-2-((tert-butyldimethylsilyl)oxy)propyl)amino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 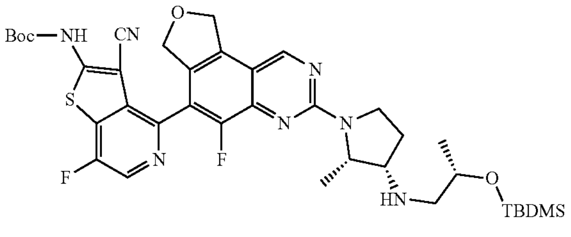 | 752 |
| 146C | tert-Butyl (4-(3-((2S,3S)-3-(((S)-2-((tert-butyldimethylsilyl)oxy)propyl)(methyl)amino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 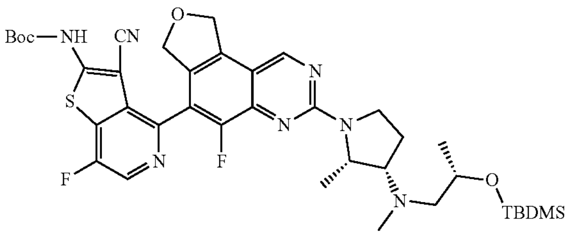 | 766 |

TABLE 25-continued

| Preparation | Chemical Name | Structure | MS (ES) m/z (M + 1) |
| --- | --- | --- | --- |
| 147C | tert-Butyl (3-cyano-7-fluoro-4-(5-fluoro-3-((2S,3S)-3-(isobutylamino)-2-methylpyrrolidin-1-yl)-7,9-dihydrofuro[3,4-f]quinazolin-6-yl)thieno[3,2-c]pyridin-2-yl)carbamate | 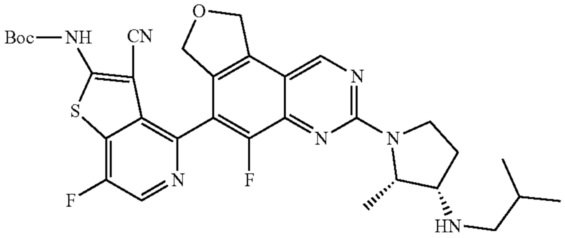 [SMILES: CC(C)CN[C@H]1CCN(c2ncc3c4c(c(-c5ncc(F)c6sc(NC(=O)OC(C)(C)C)c(C#N)c56)c(F)c3n2)COC4)[C@H]1C] | 636 |
| 148C | tert-Butyl (3-cyano-4-(3-((2S,3S)-3-(ethylamino)-2-methylpyrrolidin-1-yl)-5-fluoro-7,9-dihydrofuro[3,4-f]quinazolin-6-yl)-7-fluorothieno[3,2-c]pyridin-2-yl)carbamate | 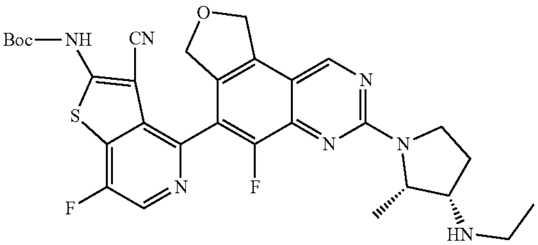 [SMILES: CCN[C@H]1CCN(c2ncc3c4c(c(-c5ncc(F)c6sc(NC(=O)OC(C)(C)C)c(C#N)c56)c(F)c3n2)COC4)[C@H]1C] | 608 |
| 149C | tert-Butyl (4-(3-((2S,3S)-3-((2-((tert-butyldimethylsilyl)oxy)-2-methylpropyl)amino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 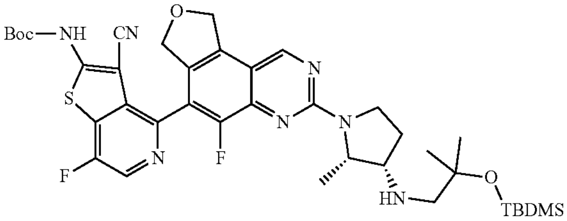 | 766 |
| 150C | tert-Butyl (4-(3-((2S,3S)-3-((2-((tert-butyldimethylsilyl)oxy)-2-methylpropyl)(methyl)amino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 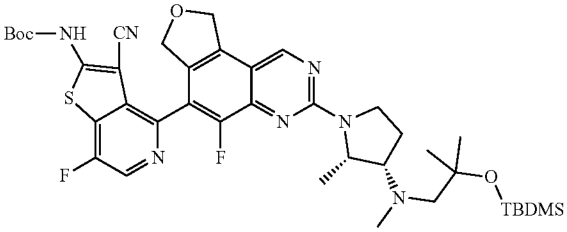 | 780 |
| 151C | tert-Butyl (4-(3-((2S,3S)-3-((3-((tert-butyldimethylsilyl)oxy)-3-methylcyclobutyl)amino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 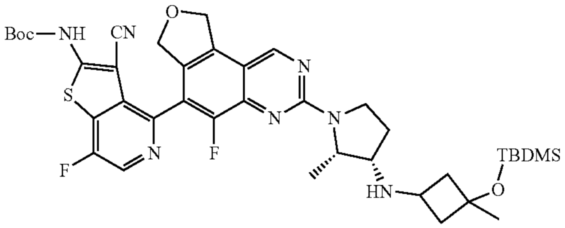 | 778 |
| 152C | tert-Butyl (4-(3-((2S,3S)-3-((3-((tert-butyldimethylsilyl)oxy)-3-methylcyclobutyl)(methyl)amino)-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate | 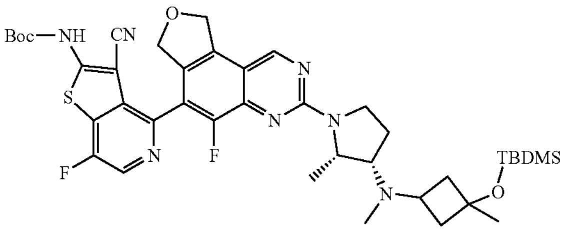 | 792 |

TABLE 25-continued

| Preparation | Chemical Name | Structure | MS (ES) m/z (M + 1) |
|---|---|---|---|
| 153C | tert-Butyl (7-chloro-3-cyano-4-(5-fluoro-3-((2S,3S)-3-(isopropylamino)-2-methylpyrrolidin-1-yl)-7,9-dihydrofuro[3,4-f]quinazolin-6-yl)thieno[3,2-c]pyridin-2-yl)carbamate | 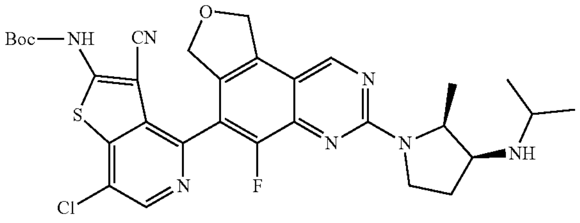 [SMILES: CC(C)N[C@H]1CCN(c2ncc3c4c(c(-c5ncc(Cl)c6sc(NC(=O)OC(C)(C)C)c(C#N)c56)c(F)c3n2)COC4)[C@H]1C] | 638 |

Preparation 94

4-(1-(3,8-Diazabicyclo[3.2.1]octan-8-yl)-5-fluoro-3-((1-(morpholinomethyl)cyclopropyl)methoxy)-7,9-dihydrofuro[3,4-f]quinazolin-6-yl)-2-amino-7-fluorothieno[3,2-c]pyridine-3-carbonitrile

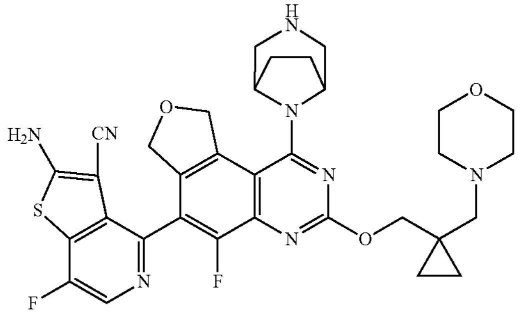 [SMILES: N#Cc1c(N)sc2c(F)cnc(-c3c4c(c5c(N6C7CCC6CNC7)nc(OCC6(CN7CCOCC7)CC6)nc5c3F)COC4)c12]

To a stirred mixture of tert-butyl 8-(6-(2-((tert-butoxycarbonyl)amino)-3-cyano-7-fluorothieno[3,2-c]pyridin-4-yl)-5-fluoro-3-((1-(morpholinomethyl)cyclopropyl)methoxy)-7,9-dihydrofuro[3,4-f]quinazolin-1-yl)-3,8-diazabicyclo[3.2.1]octane-3-carboxylate (0.720 g, 0.836 mmol) in DCM (10 mL) was added TFA (10 mL) at RT. After 2 h, the reaction mixture was concentrated under reduced pressure. The residue was dissolved in DCM (200 mL) and washed with saturated aq. $NaHCO_3$ (200 mL), water (200 mL), and brine (100 mL). The organics were dried over anhydrous $Na_2SO_4$, filtered and concentrated under reduced pressure to give the crude title compound as a light brown solid. MS (ES) m/z=661 (M+1).

The following compounds in Table 26 were prepared in similar manner as described in Preparation 94. Various methods were used to purify the compounds, which would be apparent to one skilled in the art.

TABLE 26

| Preparation | Chemical Name | Structure | MS (ES) m/z (M + 1) |
|---|---|---|---|
| 95 | 4-(1-(3,8-Diazabicyclo[3.2.1]octan-8-yl)-5-fluoro-3-((1-(morpholinomethyl)cyclopropyl)methoxy)-7,9-dihydrofuro[3,4-f]quinazolin-6-yl)-2-amino-5-fluorobenzo[b]thiophene-3-carbonitrile | 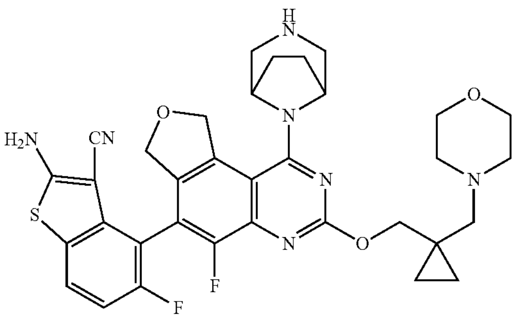 [SMILES: N#Cc1c(N)sc2ccc(F)c(-c3c4c(c5c(N6C7CCC6CNC7)nc(OCC6(CN7CCOCC7)CC6)nc5c3F)COC4)c12] | 660 |

TABLE 26-continued

| Preparation | Chemical Name | Structure | MS (ES) m/z (M + 1) |
|---|---|---|---|
| 96 | 4-(1-(3,8-Diazabicyclo[3.2.1]octan-8-yl)-5-fluoro-3-((1-((4-methylpiperazin-1-yl)methyl)cyclopropyl)meth-oxy)-7,9-dihydrofuro[3,4-f]quinazolin-6-yl)-2-amino-7-fluorothieno[3,2-c]pyridine-3-carbonitrile | 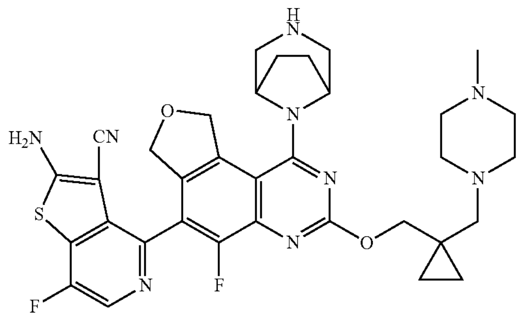 [SMILES: CN1CCN(CC2(COc3nc(N4C5CCC4CNC5)c4c5c(c(-c6ncc(F)c7sc(N)c(C#N)c67)c(F)c4n3)COC5)CC2)CC1] | 674 |
| 97 | 4-(1-(3,8-Diazabicyclo[3.2.1]octan-8-yl)-5-fluoro-3-((1-(((S)-3-fluoropyrrolidin-1-yl)methyl)cyclopropyl)meth-oxy)-7,9-dihydrofuro[3,4-f]quinazolin-6-yl)-2-amino-7-fluorothieno[3,2-c]pyridine-3-carbonitrile | 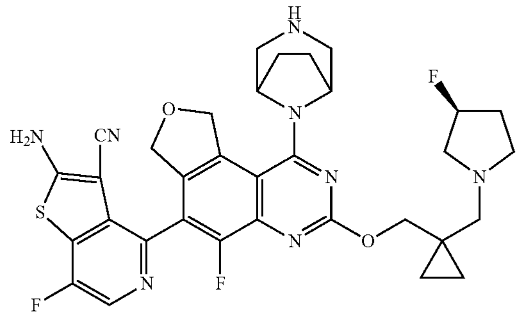 [SMILES: N#Cc1c(N)sc2c(F)cnc(-c3c4c(c5c(N6C7CCC6CNC7)nc(OCC6(CN7CC[C@H](F)C7)CC6)nc5c3F)COC4)c12] | 663 |
| 98 | 4-(1-(3,8-Diazabicyclo[3.2.1]octan-8-yl)-5-fluoro-3-((1-(((R)-3-fluoropyrrolidin-1-yl)methyl)cyclopropyl)meth-oxy)-7,8-dihydrofuro[3,4-f]quinazolin-6-yl)-2-amino-7-fluorothieno[3,2-c]pyridine-3-carbonitrile | 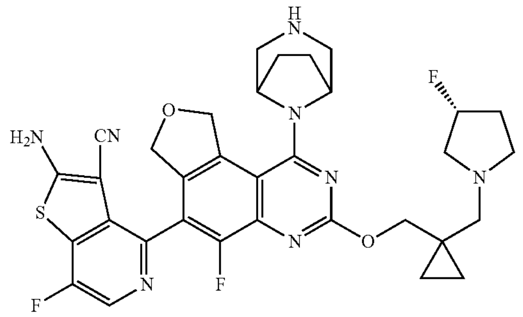 [SMILES: N#Cc1c(N)sc2c(F)cnc(-c3c4c(c5c(N6C7CCC6CNC7)nc(OCC6(CN7CC[C@@H](F)C7)CC6)nc5c3F)COC4)c12] | 663 |
| 99 | 4-(1-(3,8-Diazabicyclo[3.2.1]octan-8-yl)-5-fluoro-3-((1-((4-fluoropiperidin-1-yl)methyl)cyclopropyl)meth-oxy)-7,9-dihydrofuro[3,4-f]quinazolin-6-yl)-2-amino-7-fluorothieno[3,2-c]pyridine-3-carbonitrile | 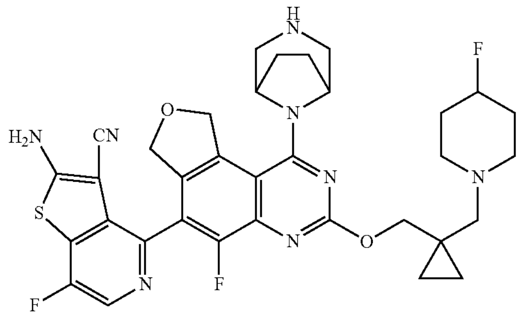 | 677 |

TABLE 26-continued

| Preparation | Chemical Name | Structure | MS (ES) m/z (M + 1) |
| --- | --- | --- | --- |
| 100 | 4-(1-(3,8-Diazabicyclo[3.2.1]octan-8-yl)-5-fluoro-3-((1-((6-methyl-2,6-diazaspiro[3.3]heptan-2-yl)methyl)cyclopropyl)methoxy)-7,9-dihydrofuro[3,4-f]quinazolin-6-yl)-2-amino-7-fluorothieno[3,2-c]pyridine-3-carbonitrile | 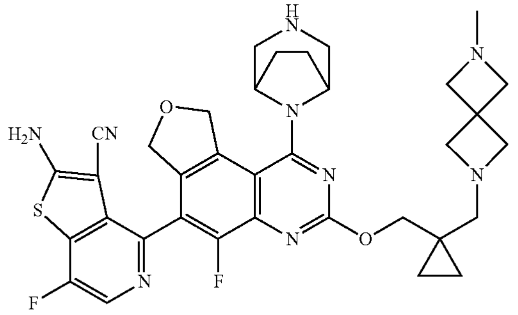 [SMILES: CN1CC2(C1)CN(CC1(COc3nc(N4C5CCC4CNC5)c4c5c(c(-c6ncc(F)c7sc(N)c(C#N)c67)c(F)c4n3)COC5)CC1)C2] | 686 |
| 101 | 4-(1-(3,8-Diazabicyclo[3.2.1]octan-8-yl)-3-((1-((4,4-difluoropiperidin-1-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 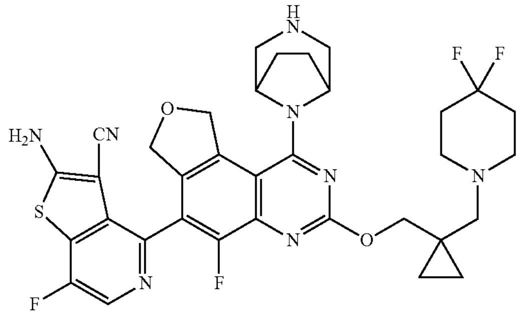 [SMILES: N#Cc1c(N)sc2c(F)cnc(-c3c4c(c5c(N6C7CCC6CNC7)nc(OCC6(CN7CCC(F)(F)CC7)CC6)nc5c3F)COC4)c12] | 695 |
| 102 | 4-(1-(3,8-Diazabicyclo[3.2.1]octan-8-yl)-3-((1-((6,6-difluoro-3-azabicyclo[3.1.0]hexan-3-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 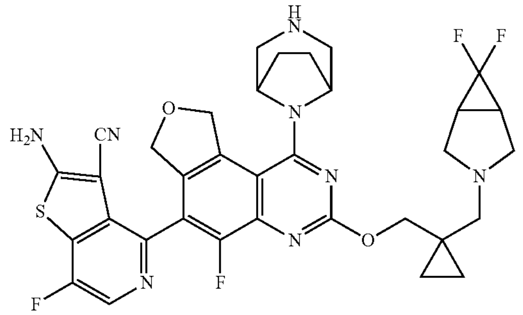 [SMILES: N#Cc1c(N)sc2c(F)cnc(-c3c4c(c5c(N6C7CCC6CNC7)nc(OCC6(CN7CC8C(C7)C8(F)F)CC6)nc5c3F)COC4)c12] | 693 |
| 103 | 4-(1-(3,8-Diazabicyclo[3.2.1]octan-8-yl)-5-fluoro-3-((1-((3-methoxyazetidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 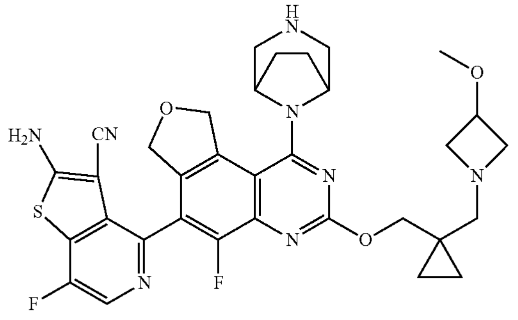 [SMILES: COC1CN(CC2(COc3nc(N4C5CCC4CNC5)c4c5c(c(-c6ncc(F)c7sc(N)c(C#N)c67)c(F)c4n3)COC5)CC2)C1] | 661 |

TABLE 26-continued

| Preparation | Chemical Name | Structure | MS (ES) m/z (M + 1) |
|---|---|---|---|
| 104 | 4-(1-(3,8-Diazabicyclo[3.2.1]octan-8-yl)-5-fluoro-3-((1-((3-(fluoromethyl)azetidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 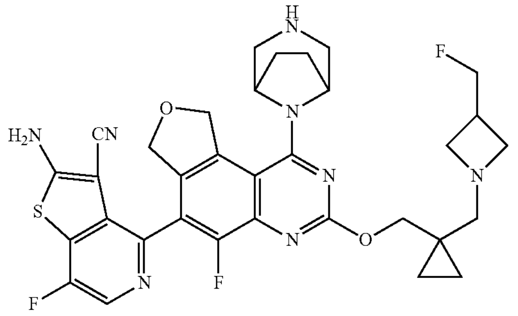 [SMILES: N#Cc1c(N)sc2c(F)cnc(-c3c4c(c5c(N6C7CCC6CNC7)nc(OCC6(CN7CC(CF)C7)CC6)nc5c3F)COC4)c12] | 663 |
| 105 | 4-(1-(3,8-Diazabicyclo[3.2.1]octan-8-yl)-5-fluoro-3-((1-(((R)-3-methylmorpholino)methyl)cyclopropyl)methoxy)-7,9-dihydrofuro[3,4-f]quinazolin-6-yl)-2-amino-7-fluorothieno[3,2-c]pyridine-3-carbonitrile | 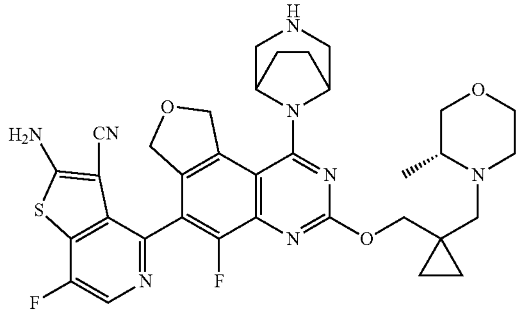 [SMILES: C[C@@H]1COCCN1CC1(COc2nc(N3C4CCC3CNC4)c3c4c(c(-c5ncc(F)c6sc(N)c(C#N)c56)c(F)c3n2)COC4)CC1] | 675 |
| 106 | 4-(3-((1-(((1S,4S)-2-oxa-5-Azabicyclo[2.2.1]heptan-5-yl)methyl)cyclopropyl)methoxy)-1-(3,8-diazabicyclo[3.2.1]octan-8-yl)-5-fluoro-7,9-dihydrofuro[3,4-f]quinazolin-6-yl)-2-amino-7-fluorothieno[3,2-c]pyridine-3-carbonitrile | 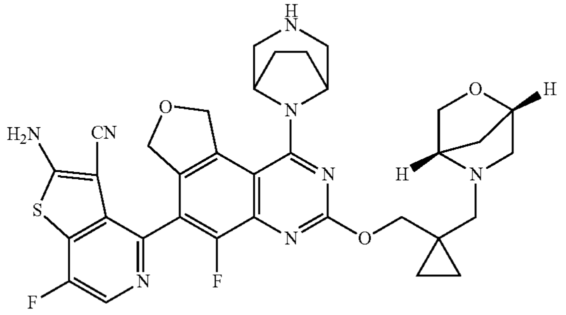 [SMILES: N#Cc1c(N)sc2c(F)cnc(-c3c4c(c5c(N6C7CCC6CNC7)nc(OCC6(CN7C[C@@H]8C[C@H]7CO8)CC6)nc5c3F)COC4)c12] | 673 |
| 107 | 4-(3-((1-((4-Acetylpiperazin-1-yl)methyl)cyclopropyl)methoxy)-1-(3,8-diazabicyclo[3.2.1]octan-8-yl)-5-fluoro-7,9-dihydrofuro[3,4-f]quinazolin-6-yl)-2-amino-7-fluorothieno[3,2-c]pyridine-3-carbonitrile | 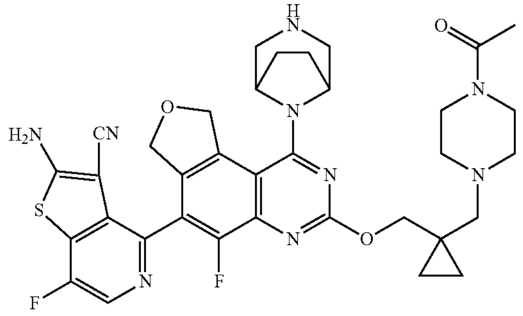 [SMILES: CC(=O)N1CCN(CC2(COc3nc(N4C5CCC4CNC5)c4c5c(c(-c6ncc(F)c7sc(N)c(C#N)c67)c(F)c4n3)COC5)CC2)CC1] | 702 |

TABLE 26-continued

| Preparation | Chemical Name | Structure | MS (ES) m/z (M + 1) |
|---|---|---|---|
| 96A | 4-(1-(3,8-Diazabicyclo[3.2.1]octan-8-yl)-3-((1-((4-cyanopiperidin-1-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 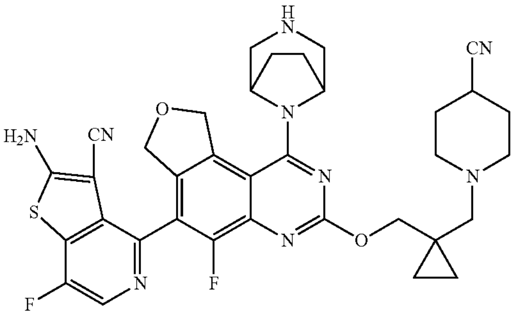 [SMILES: N#Cc1c(N)sc2c(F)cnc(-c3c4c(c5c(N6C7CCC6CNC7)nc(OCC6(CN7CCC(C#N)CC7)CC6)nc5c3F)COC4)c12] | 684 |
| 97A | 4-(3-((1-((7-Oxa-2-azaspiro[3.5]nonan-2-yl)methyl)cyclopropyl)methoxy)-1-(3,8-diazabicyclo[3.2.1]octan-8-yl)-5-fluoro-7,9-dihyrofuro[3,4-f]quinazolin-6-yl)-2-amino-7-fluorothieno[3,2-c]pyridine-3-carbonitrile | 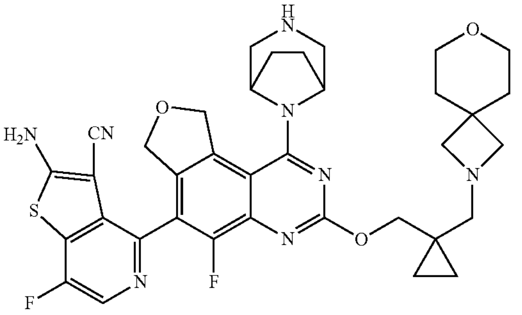 [SMILES: N#Cc1c(N)sc2c(F)cnc(-c3c4c(c5c(N6C7CCC6CNC7)nc(OCC6(CN7CC8(CCOCC8)C7)CC6)nc5c3F)COC4)c12] | 701 |
| 98A | 4-(1-(3,8-Diazabicyclo[3.2.1]octan-8-yl)-5-fluoro-3-((1-(((R)-3-methoxypyrrolidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 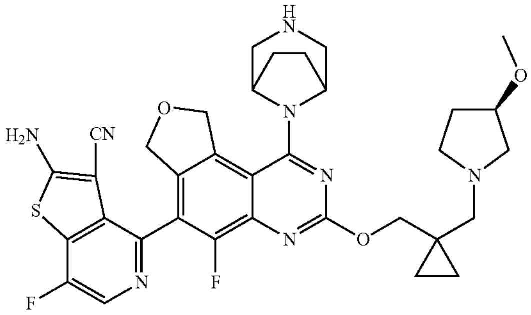 [SMILES: CO[C@@H]1CCN(CC2(COc3nc(N4C5CCC4CNC5)c4c5c(c(-c6ncc(F)c7sc(N)c(C#N)c67)c(F)c4n3)COC5)CC2)C1] | 675 |
| 99A | 4-(3-((1-((2-Oxa-6-azaspiro[3.3]heptan-6-yl)methyl)cyclopropyl)methoxy)-1-(3,8-diazabicyclo[3.2.1]octan-8-yl)-5-fluoro-7,9-dihydrofuro[3,4-f]quinazolin-6-yl)-2-amino-7-fluorothieno[3,2-c]pyridine-3-carbonitrile | 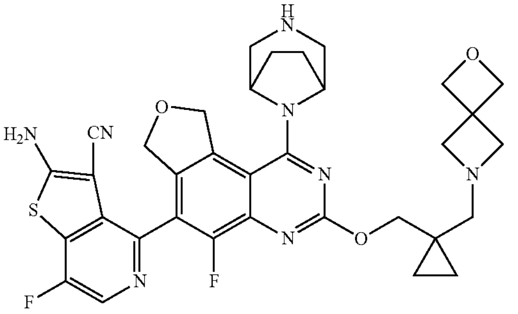 [SMILES: N#Cc1c(N)sc2c(F)cnc(-c3c4c(c5c(N6C7CCC6CNC7)nc(OCC6(CN7CC8(COC8)C7)CC6)nc5c3F)COC4)c12] | 673 |

TABLE 26-continued

| Preparation | Chemical Name | Structure | MS (ES) m/z (M + 1) |
| --- | --- | --- | --- |
| 100A | 4-(1-(3,8-Diazabicyclo[3.2.1]octan-8-yl)-5-fluoro-3-((1-(pyrrolidin-1-ylmethyl)cyclopropyl)methoxy)-7,9-dihydrofuro[3,4-f]quinazolin-6-yl)-2-amino-7-fluorothieno[3,2-c]pyridine-3-carbonitrile | 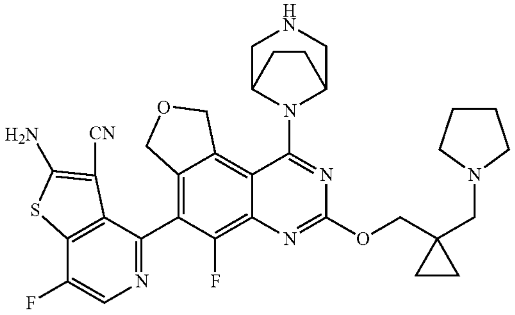 [SMILES: N#Cc1c(N)sc2c(F)cnc(-c3c4c(c5c(N6C7CCC6CNC7)nc(OCC6(CN7CCCC7)CC6)nc5c3F)COC4)c12] | 645 |
| 101A | 4-(1-(3,8-Diazabicyclo[3.2.1]octan--8-yl)-5-fluoro-3-((1-((3-hydroxyaetidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 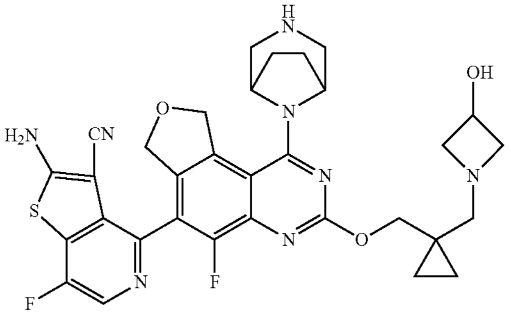 [SMILES: N#Cc1c(N)sc2c(F)cnc(-c3c4c(c5c(N6C7CCC6CNC7)nc(OCC6(CN7CC(O)C7)CC6)nc5c3F)COC4)c12] | 647 |
| 102A | 4-(1-(3,8-Diazabicyclo[3.2.1]octan-8-yl)-5-fluoro-3-((1-((4-(2,2,2-trifluoroethyl)piperazin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 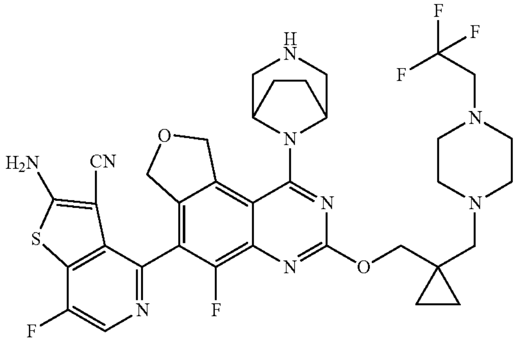 [SMILES: N#Cc1c(N)sc2c(F)cnc(-c3c4c(c5c(N6C7CCC6CNC7)nc(OCC6(CN7CCN(CC(F)(F)F)CC7)CC6)nc5c3F)COC4)c12] | 742 |
| 103A | 4-(3-((1-((3-Oxa-8-azabicyclo[3.2.1]octan-8-yl)methyl)cyclopropyl)methoxy)-1-(3,8-diazabicyclo[3.2.1]octan-8-yl)-5-fluoro-7,9-dihydrofuro[3,4-f]quinazolin-6-yl)-2-amino-7-fluorothieno[3,2-c]pyridine-3-carbonitrile | 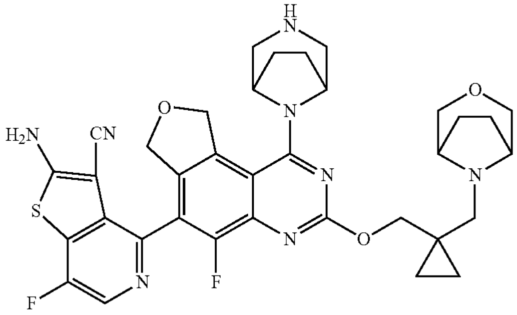 [SMILES: N#Cc1c(N)sc2c(F)cnc(-c3c4c(c5c(N6C7CCC6CNC7)nc(OCC6(CN7C8CCC7COC8)CC6)nc5c3F)COC4)c12] | 687 |

TABLE 26-continued

| Preparation | Chemical Name | Structure | MS (ES) m/z (M + 1) |
|---|---|---|---|
| 104A | 4-(1-(3,8-Diazabicyclo[3.2.1]octan-8-yl)-5-fluoro-3-((1-((3-fluoropiperidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 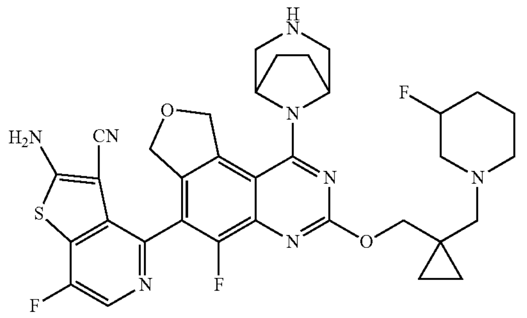 [SMILES: N#Cc1c(N)sc2c(F)cnc(-c3c4c(c5c(N6C7CCC6CNC7)nc(OCC6(CN7CCCC(F)C7)CC6)nc5c3F)COC4)c12] | 677 |
| 105A | 4-(1-(3,8-Diazabicyclo[3.2.1]octan-8-yl)-5-fluoro-3-((1-(((S)-3-methylmorpholino)methyl)cyclopropyl)methoxy)-7,9-dihydrofuro[3,4-f]quinazolin-6-yl)-2-amino-7-fluorothieno[3,2-c]pyridine-3-carbonitrile | 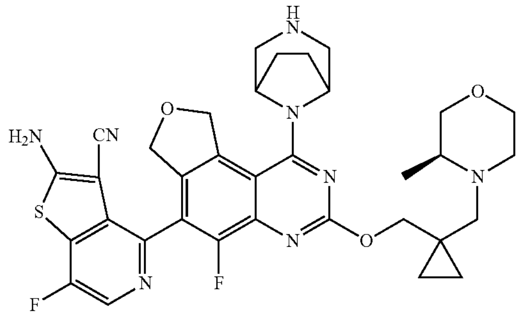 [SMILES: C[C@H]1COCCN1CC1(COc2nc(N3C4CCC3CNC4)c3c4c(c(-c5ncc(F)c6sc(N)c(C#N)c56)c(F)c3n2)COC4)CC1] | 675 |
| 106A | 4-(1-(3,8-Diazabicyclo[3.2.1]octan-8-yl)-3-((1-(((2R,6S)-2,6-dimethylmorpholino)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 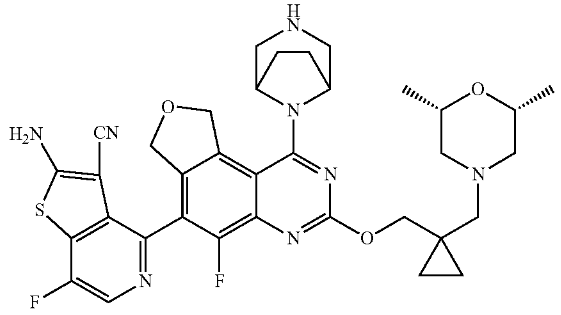 [SMILES: C[C@@H]1CN(CC2(COc3nc(N4C5CCC4CNC5)c4c5c(c(-c6ncc(F)c7sc(N)c(C#N)c67)c(F)c4n3)COC5)CC2)C[C@H](C)O1] | 689 |
| 107A | 4-(1-(3,8-Diazabicyclo[3.2.1]octan-8-yl)-5-fluoro-3-((1-(((S)-2-(hydroxymethyl)azetidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 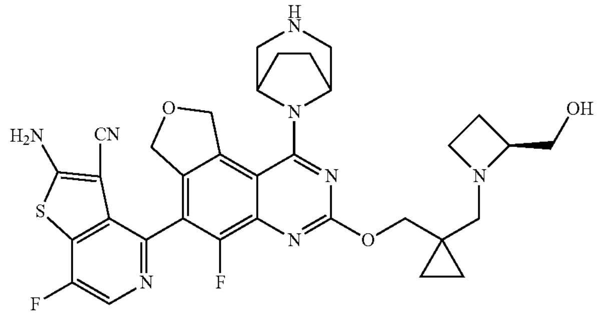 [SMILES: N#Cc1c(N)sc2c(F)cnc(-c3c4c(c5c(N6C7CCC6CNC7)nc(OCC6(CN7CC[C@H]7CO)CC6)nc5c3F)COC4)c12] | 661 |

TABLE 26-continued

| Preparation | Chemical Name | Structure | MS (ES) m/z (M + 1) |
|---|---|---|---|
| 108A | 4-(1-(3,8-Diazabicyclo[3.2.1]octan-8-yl)-3-((1-((3,3-dimethylazetidin-1-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 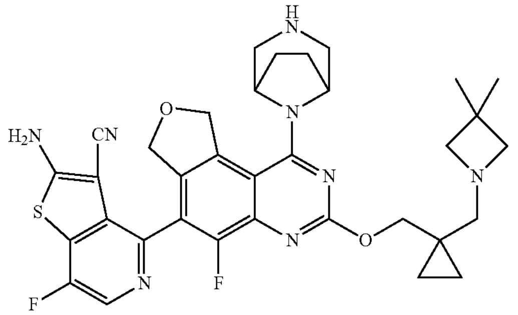 [SMILES: CC1(C)CN(CC2(COc3nc(N4C5CCC4CNC5)c4c5c(c(-c6ncc(F)c7sc(N)c(C#N)c67)c(F)c4n3)COC5)CC2)C1] | 659 |
| 109A | 4-(1-(3,8-Diazabicyclo[3.2.1]octan-8-yl)-3-((1-(((R)-3-cyanopyrrolidin-1-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 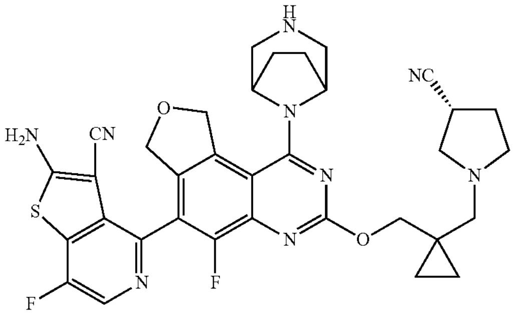 [SMILES: N#Cc1c(N)sc2c(F)cnc(-c3c4c(c5c(N6C7CCC6CNC7)nc(OCC6(CN7CC[C@@H](C#N)C7)CC6)nc5c3F)COC4)c12] | 670 |
| 110A | 4-(3-((1-((6-Oxa-2-azaspiro[3.4]octan-2-yl)methyl)cyclopropyl)methoxy)-1-(3,8-azabicyclo[3.2.1]octan-8-yl)-5-fluoro-7,9-dihydrofuro[3,4-f]quinazolin-6-yl)-2-amino-7-fluorothieno[3,2-c]pyridine-3-carbonitrile | 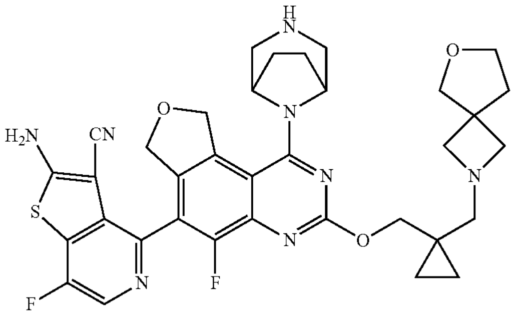 [SMILES: N#Cc1c(N)sc2c(F)cnc(-c3c4c(c5c(N6C7CCC6CNC7)nc(OCC6(CN7CC8(CCOC8)C7)CC6)nc5c3F)COC4)c12] | 687 |
| 111A | 4-(1-(3,8-Diazabicyclo[3.2.1]octan-8-yl)-3-((1-(((S)-3-cyanopyrrolidin-1-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 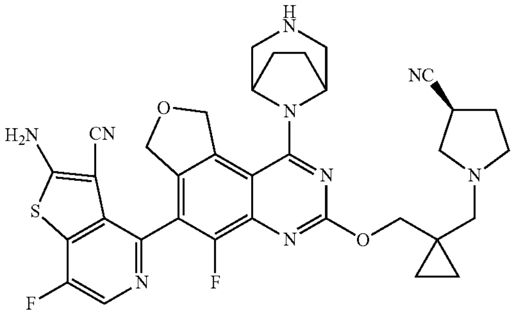 [SMILES: N#Cc1c(N)sc2c(F)cnc(-c3c4c(c5c(N6C7CCC6CNC7)nc(OCC6(CN7CC[C@H](C#N)C7)CC6)nc5c3F)COC4)c12] | 670 |

TABLE 26-continued

| Preparation | Chemical Name | Structure | MS (ES) m/z (M + 1) |
|---|---|---|---|
| 112A | 4-(3-((1-(((1R,4R)-2-Oxa-5-azabicyclo[2.2.1]heptan-5-yl)methyl)cyclopropyl)methoxy)-1-(3,8-diazabicyclo[3.2.1]octan-8-yl)-5-fluoro-7,9-dihydrofuro[3,4-f]quinazolin-6-yl)-2-amino-7-fluorothieno[3,2-c]pyridine-3-carbonitrile | 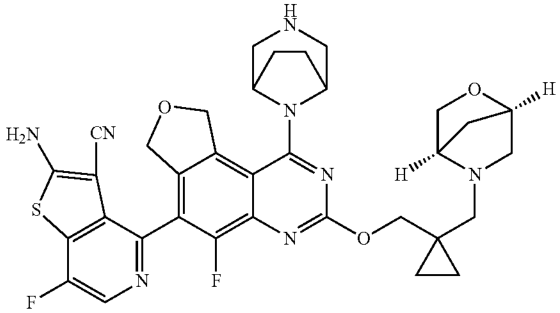 [SMILES: N#Cc1c(N)sc2c(F)cnc(-c3c4c(c5c(N6C7CCC6CNC7)nc(OCC6(CN7C[C@H]8C[C@@H]7CO8)CC6)nc5c3F)COC4)c12] | 673 |
| 113A | 4-(1-(3,8-Diazabicyclo[3.2.1]octan-8-yl)-3-((1-(((3R,4S)-3,4-difluoropyrrolidin-1-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrie | 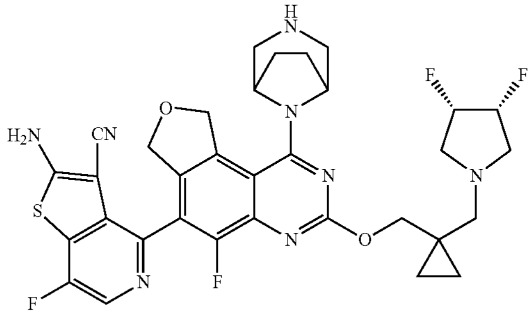 [SMILES: N#Cc1c(N)sc2c(F)cnc(-c3c4c(c5c(N6C7CCC6CNC7)nc(OCC6(CN7C[C@@H](F)[C@@H](F)C7)CC6)nc5c3F)COC4)c12] | 681 |
| 114A | 4-(1-(3,8-Diazabicyclo[3.2.1]octa-n 8-yl)-5-fluro-3-((1-((3-fluoroazetidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 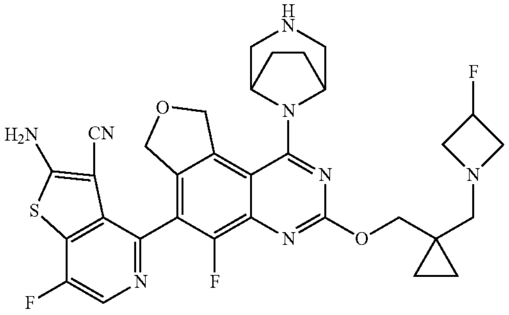 [SMILES: N#Cc1c(N)sc2c(F)cnc(-c3c4c(c5c(N6C7CCC6CNC7)nc(OCC6(CN7CC(F)C7)CC6)nc5c3F)COC4)c12] | 649 |
| 115A | 4-(3-((1-((8-Oxa-3-azabicyclo[3.2.1]octan-3-yl)methyl)cyclopropyl)methoxy)-1-(3,8-diazabicyclo[3.2.1]octan-8-yl)-5-fluoro-7,9-dihydrofuro[3,4-f]quinazolin-6-yl)-2-amino-7-fluorothieno[3,2-c]pyridine-3-carbonitrile | 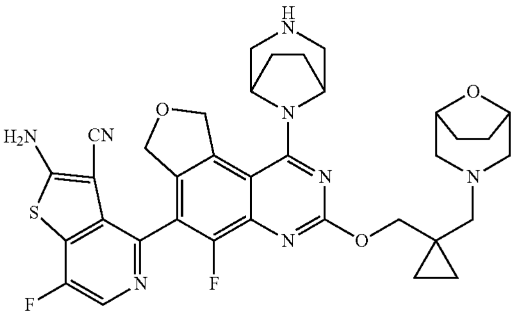 [SMILES: N#Cc1c(N)sc2c(F)cnc(-c3c4c(c5c(N6C7CCC6CNC7)nc(OCC6(CN7CC8CCC(C7)O8)CC6)nc5c3F)COC4)c12] | 687 |

TABLE 26-continued

| Preparation | Chemical Name | Structure | MS (ES) m/z (M + 1) |
|---|---|---|---|
| 116A | 4-(1-(3,8-Diazabicyclo[3.2.1]octan-8-yl)-5-fluoro-3-(2-methyl-3-morpholinopropoxy)-7,9-dihydrofuro[3,4-f]quinazolin-6-yl)-2-amino-7-fluorothieno[3,2-c]pyridine-3-carbonitrile | 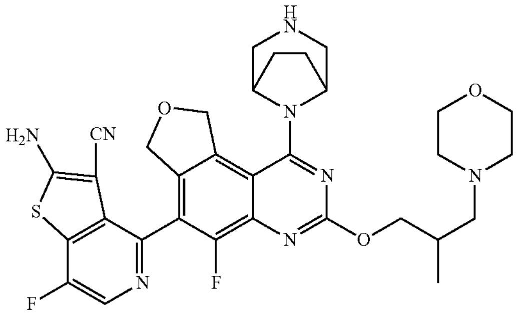 [SMILES: CC(COc1nc(N2C3CCC2CNC3)c2c3c(c(-c4ncc(F)c5sc(N)c(C#N)c45)c(F)c2n1)COC3)CN1CCOCC1] | 649 |
| 117A | 4-(1-(3,8-Diazabicyclo[3.2.1]octan-8-yl)-5-fluoro-3-((3-(morpholinomethyl)oxetan-3-yl)methoxy)-7,9-dihydrofuro[3,4-f]quinazolin-6-yl)-2-amino-7-fluorothieno[3,2-c]pyridine-3-carbonitrile | 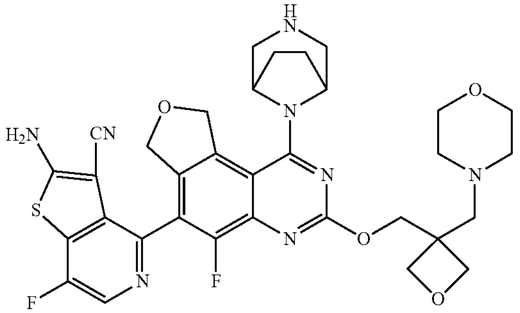 [SMILES: N#Cc1c(N)sc2c(F)cnc(-c3c4c(c5c(N6C7CCC6CNC7)nc(OCC6(CN7CCOCC7)COC6)nc5c3F)COC4)c12] | 677 |
| 118A | 4-(1-(3,8-Diazabicyclo[3.2.1]octan-8-yl)-3-(2,2-dimethyl-3-morpholinopropoxy)-5-fluoro-7,9-dihydrofuro[3,4-f]quinazolin-6-yl)-2-amino-7-fluorothieno[3,2-c]pyridine-3-carbonitrile | 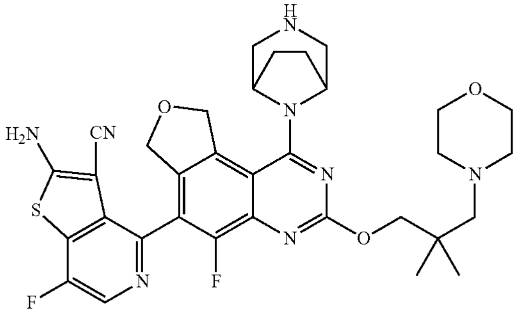 [SMILES: CC(C)(COc1nc(N2C3CCC2CNC3)c2c3c(c(-c4ncc(F)c5sc(N)c(C#N)c45)c(F)c2n1)COC3)CN1CCOCC1] | 663 |
| 119A | 4-(1-(3,8-Diazabicyclo[3.2.1]octan-8-yl)-3-((S)-3-(dimethylamino)pyrrolidin-1-yl)-5-fluoro-7,9-dihydrofuro[3,4-f]quinazolin-6-yl)-2-amino-7-fluorothieno[3,2-c]pyridine-3-carbonitrile | 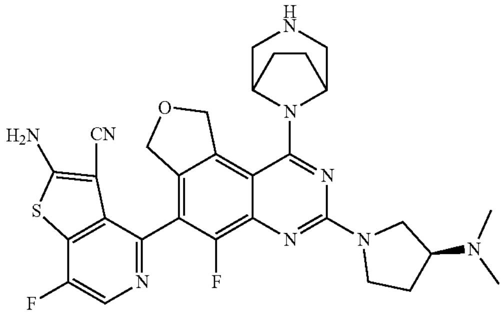 [SMILES: CN(C)[C@H]1CCN(c2nc(N3C4CCC3CNC4)c3c4c(c(-c5ncc(F)c6sc(N)c(C#N)c56)c(F)c3n2)COC4)C1] | 604 |

TABLE 26-continued

| Preparation | Chemical Name | Structure | MS (ES) m/z (M + 1) |
|---|---|---|---|
| 120A | 4-(1-(3,8-Diazabicyclo[3.2.1]octan-8-yl)-3-((R)-3-(dimethylamino)pyrrolidin-1-yl)-5-fluoro-7,9-dihydrofuro[3,4-f]quinazolin-6-yl)-2-amino-7-fluorothieno[3,2-c]pyridine-3-carbonitrile | 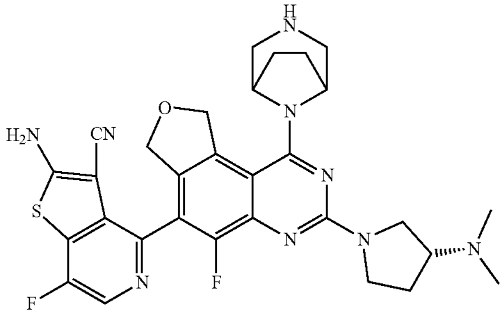 | 604 |
| 121A | 4-(1-(3,8-Diazabicyclo[3.2.1]octan-8-yl)-5-fluoro-3-(4-(2-hydroxyethyl)piperazin-1-yl)-7,9-dihydrofuro[3,4-f]quinazolin-6-yl)-2-amino-7-fluorothieno[3,2-c]pyridine-3-carbonitrile | 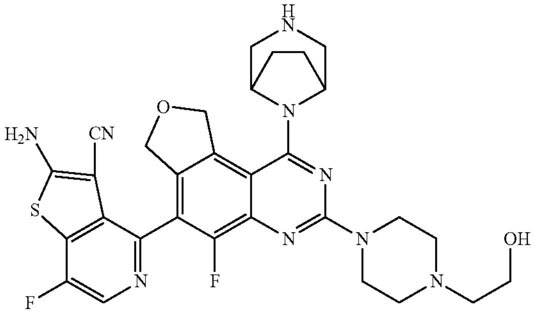 [SMILES: N#Cc1c(N)sc2c(F)cnc(-c3c4c(c5c(N6C7CCC6CNC7)nc(N6CCN(CCO)CC6)nc5c3F)COC4)c12] | |
| 122A | 4-(1-(3,8-Diazabicyclo[3.2.1]octan-8-yl)-5-fluoro-3-(4-(3-hydroxypropyl)piperazin-1-yl)-7,9-dihydrofuro[3,4-f]quinazolin-6-yl)-2-amino-7-fluorothieno[3,2-c]pyridine-3-carbonitrile | 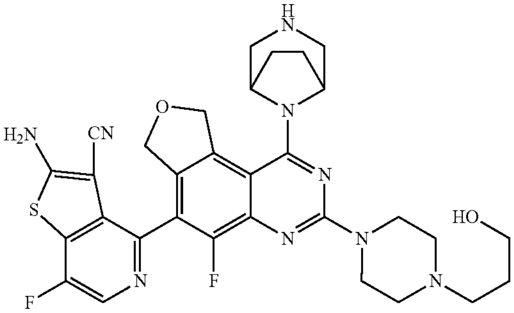 [SMILES: N#Cc1c(N)sc2c(F)cnc(-c3c4c(c5c(N6C7CCC6CNC7)nc(N6CCN(CCCO)CC6)nc5c3F)COC4)c12] | |
| 123A | 2-Amino-7-fluoro-4-(5-fluoro-3-((3aR,6aS)-hexahydropyrrolo[3,4-c]pyrrol-2(1H)-yl)-7,9-dihydrofuro[3,4-f]quinazolin-6-yl)thieno[3,2-c]pyridine-3-carbonitrile | 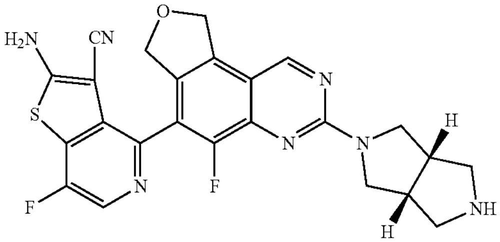 [SMILES: N#Cc1c(N)sc2c(F)cnc(-c3c4c(c5cnc(N6C[C@H]7CNC[C@H]7C6)nc5c3F)COC4)c12] | 492 |
| 124A | 2-Amino-7-fluoro-4-(5-fluoro-3-((S)-1,6-diazaspiro[3,4]octan-6-yl)-7,9-dihydrofuro[3,4-f]quinazolin-6-yl)thieno[3,2-c]pyridine-3-carbonitrile | 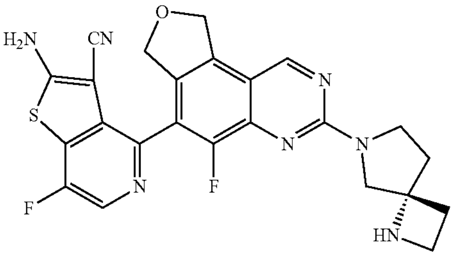 [SMILES: N#Cc1c(N)sc2c(F)cnc(-c3c4c(c5cnc(N6CC[C@@]7(CCN7)C6)nc5c3F)COC4)c12] | 492 |

TABLE 26-continued

| Preparation | Chemical Name | Structure | MS (ES) m/z (M + 1) |
|---|---|---|---|
| 198B | 2-Amino-7-fluoro-4-(5-fluoro-3-(octanhydro-6H-pyrrolo[3,4-b]pyridin-6-yl)-7,9-dihydrofuro[3,4-f]quinazolin-6-yl)thieno[3,2-c]pyridine-3-carbonitrile | 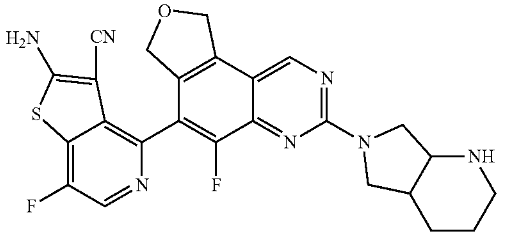 [SMILES: N#Cc1c(N)sc2c(F)cnc(-c3c4c(c5cnc(N6CC7CCCNC7C6)nc5c3F)COC4)c12] | 506 |
| 199B | 2-Amino-4-(3-(6-amino-2-azaspiro[3.3]heptan-2-yl)-5-fluoro-7,9-dihydrofuro[3,4-f]quinazolin-6-yl)-7-fluorothieno[3,2-c]pyridine-3-carbonitrile | 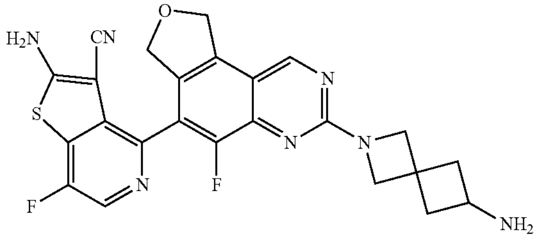 [SMILES: N#Cc1c(N)sc2c(F)cnc(-c3c4c(c5cnc(N6CC7(CC(N)C7)C6)nc5c3F)COC4)c12] | 492 |
| 200B | 4-(3-((1-((1,4-Oxazepan-4-yl)methyl)cyclopropyl)meth-oxy)-1-(3,8-diazabicyclo[3.2.1]octan-8-yl)-5-fluoro-7,9-dihydrofuro[3,4-f]quinazolin-6-yl)-2-amino-7-fluorothieno[3,2-c]pyridine-3-carbonitrile | 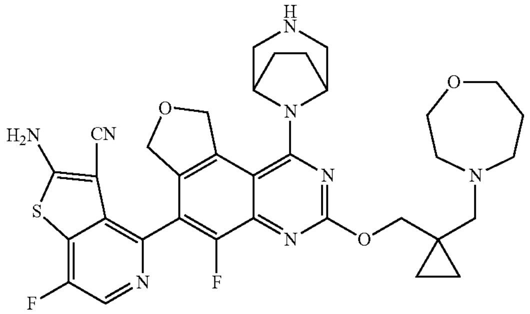 [SMILES: N#Cc1c(N)sc2c(F)cnc(-c3c4c(c5c(N6C7CCC6CNC7)nc(OCC6(CN7CCCOCC7)CC6)nc5c3F)COC4)c12] | 675 |
| 201B | 4-(1-(3,8-Diazabicyclo[3.22.1]ocstan-8-yl)-5-fluoro-3-(5-methylhexahydropyrrolo[3,4-c]pyrrol-2(1H)-yl)-7,9-dihydrofuro[3,4-f]quinazolin-6-yl)-2-amino-7-fluorothieno[3,2-c]pyriidine-3-carbonitrile | 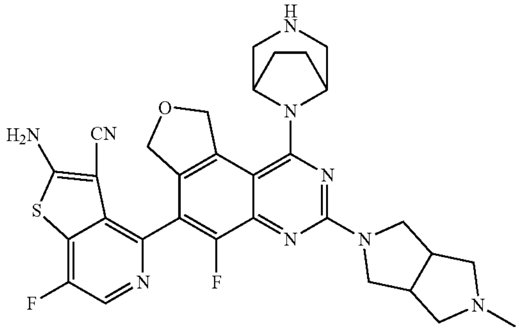 [SMILES: CN1CC2CN(c3nc(N4C5CCC4CNC5)c4c5c(c(-c6ncc(F)c7sc(N)c(C#N)c67)c(F)c4n3)COC5)CC2C1] | 616 |
| 202B | 4-(1-(3,8-Diazabicyclo[3.2.1]octan-8-yl)-5-fluoro-3-(1-methyl-1,6-diazaspiro[3.3]heptan-6-yl)-7,9-dihydrofuro[3,4-f]quinazolin-6-yl)-2-amino-7-fluorothieno[3,2-c]pyridine-3-carbonitrile | 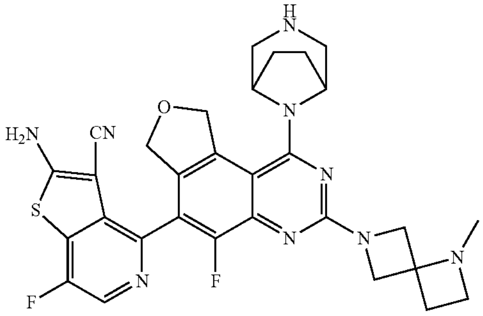 [SMILES: CN1CCC12CN(c1nc(N3C4CCC3CNC4)c3c4c(c(-c5ncc(F)c6sc(N)c(C#N)c56)c(F)c3n1)COC4)C2] | 602 |

TABLE 26-continued

| Preparation | Chemical Name | Structure | MS (ES) m/z (M + 1) |
|---|---|---|---|
| 203B | 4-(1-(3,8-Diazabicyclo[3.2.1]octan-8-yl)-3-((R)-3-((dimethylamino)methyl) pyrrolidin-1-yl)-5-fluoro-7,9-dihydrofuro[3,4-f]quinazolin-6-yl)-2-amino-7-fluorothieno[3,2-c]pyridine-3-carbonitrile | 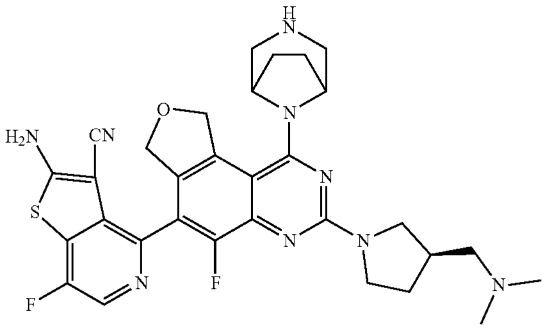 [SMILES: CN(C)C[C@H]1CCN(c2nc(N3C4CCC3CNC4)c3c4c(c(-c5ncc(F)c6sc(N)c(C#N)c56)c(F)c3n2)COC4)C1] | 618 |
| 204B | 4-(1-(3,8-Diazabicyclo[3.2.1]octan-8-yl)-3-((S)-3-(diethylamino)pyrrolidin-1-yl)-5-fluoro-7,9-dihydrofuro[3,4-f]quinazolin-6-yl)-2-amino-7-fluorothieno[3,2-c]pyridine-3-carbonitrile | 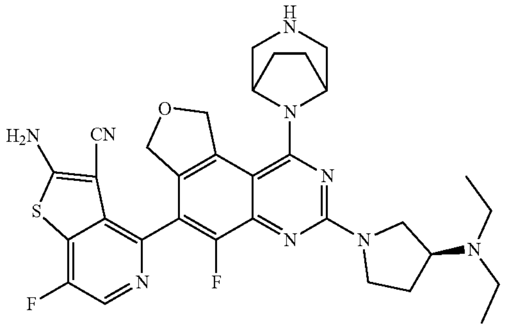 [SMILES: CCN(CC)[C@H]1CCN(c2nc(N3C4CCC3CNC4)c3c4c(c(-c5ncc(F)c6sc(N)c(C#N)c56)c(F)c3n2)COC4)C1] | 632 |
| 205B | 4-(1-(3,8-Diazabicyclo[3.2.1]octan-8-yl)-5-fluoro-3-((3aR,6aR)-1-methylhexahydropyrrolo[3,4-b]pyrrol-5(1H)-yl)-7,9-dihydrofuro[3,4-f]quinazolin-6-yl)-2-amino-7-fluorothieno[3,2-c]pyridine-3-carbonitrile | 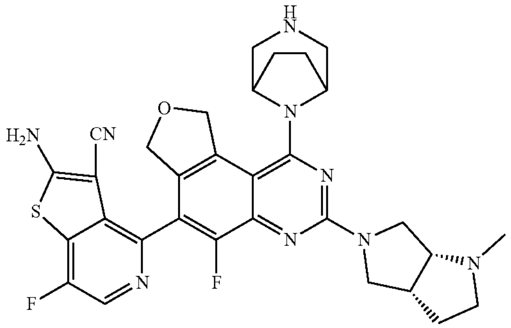 [SMILES: CN1CC[C@@H]2CN(c3nc(N4C5CCC4CNC5)c4c5c(c(-c6ncc(F)c7sc(N)c(C#N)c67)c(F)c4n3)COC5)C[C@@H]21] | 616 |
| 206B | 4-(1-(3,8-Diazabicyclo[3.2.1]octan-8-yl)-5-fluoro-3-((3aS,6aS)-1-methylhexahydropyrrolo[3,4-b]pyrrol-5(1H)-yl)-7,9-dihydrofuro[3,4-f]quinazolin-6-yl)-2-amino-7-fluorothieno[3,2-c]pyridine-3-carbonitrile | 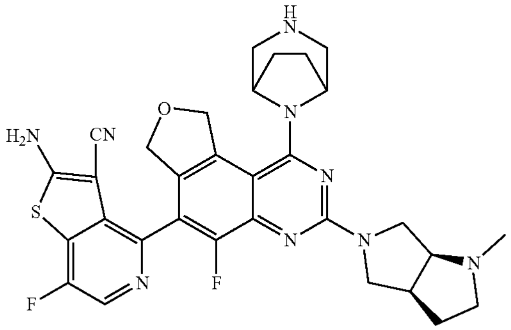 [SMILES: CN1CC[C@H]2CN(c3nc(N4C5CCC4CNC5)c4c5c(c(-c6ncc(F)c7sc(N)c(C#N)c67)c(F)c4n3)COC5)C[C@H]21] | 616 |

TABLE 26-continued

| Preparation | Chemical Name | Structure | MS (ES) m/z (M + 1) |
|---|---|---|---|
| 207B | 4-(1-(3,8-Diazabicyclo[3.2.1]octan-8-yl)-5-fluoro-3-(5-methyl-2,5-diazaspiro[3.4]octan-2-yl)-7,9-dihydrofuro[3,4-f]quinazolin-6-yl)-2-amino-7-fluorothieno[3,2-c]pyridine-3-carbonitirle | 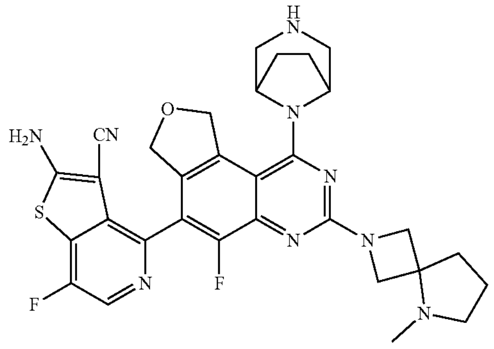 [SMILES: CN1CCCC12CN(c1nc(N3C4CCC3CNC4)c3c4c(c(-c5ncc(F)c6sc(N)c(C#N)c56)c(F)c3n1)COC4)C2] | 616 |
| 208B | 4-(1-(3,8-Diazabicyclo[3.2.1]octan-8-yl)-5-fluoro-3-((S)-hexahydropyrrolo[1,2-a]pyrazin-2(1H)-yl)-7,9-dihydrofuro[3,4-f]quinazolin-6-yl)-2-amino-7-fluorothieno[3,2-c]pyridine-3-carbonitrile | 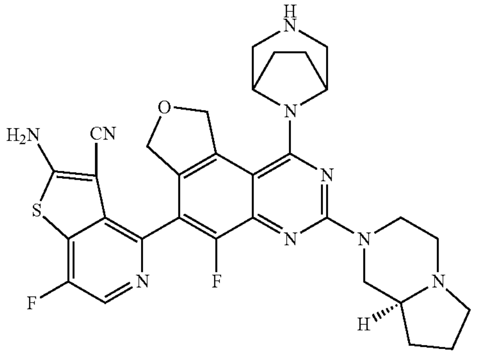 [SMILES: N#Cc1c(N)sc2c(F)cnc(-c3c4c(c5c(N6C7CCC6CNC7)nc(N6CCN7CCC[C@H]7C6)nc5c3F)COC4)c12] | 616 |
| 209B | 4-(1-(3,8-Diazabicyclo[3.2.1]octan-8-yl)-3-((S)-3-(dimethylamino)-3-methylpyrrolidin-1-yl)-5-fluoro-7,9-dihydrofuro[3,4-f]quinazolin-6-yl)-2-amino-7-fluorothieno[3,2-c]pyridine-3-carbonitrile | 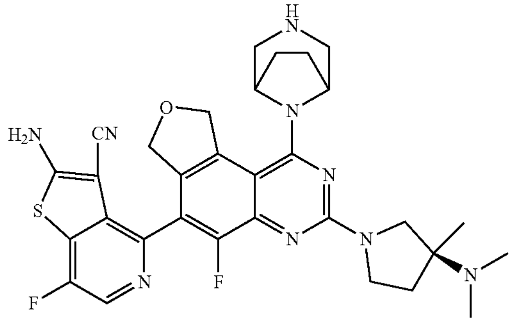 [SMILES: CN(C)[C@@]1(C)CCN(c2nc(N3C4CCC3CNC4)c3c4c(c(-c5ncc(F)c6sc(N)c(C#N)c56)c(F)c3n2)COC4)C1] | 618 |
| 210B | 4-(1-(3,8-Diazabicyclo[3.2.1]octan-8-yl)-5-fluoro-3-(3-(pyrrolidin-1-yl)azetidin-1-yl)-7,9-dihydrofuro[3,4-f]quinazolin-6-yl)-2-amino-7-fluorothieno[3,2-c]pyridine-3-carbonitrile | 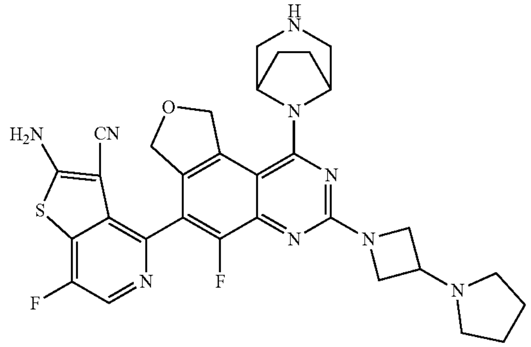 [SMILES: N#Cc1c(N)sc2c(F)cnc(-c3c4c(c5c(N6C7CCC6CNC7)nc(N6CC(N7CCCC7)C6)nc5c3F)COC4)c12] | 616 |

TABLE 26-continued

| Preparation | Chemical Name | Structure | MS (ES) m/z (M + 1) |
|---|---|---|---|
| 211B | 4-(1-(3,8-Diazabicyclo[3.2.1]octan-8-yl)-5-fluoro-3-(3-methyl-3,6-diazabicyclo[3.1.1]heptan-6-yl)-7,9-dihydrofuro[3,4-f]quinazolin-6-yl)-2-amino-7-fluorothieno[3,2-c]pyridine-3-carbonitrile | 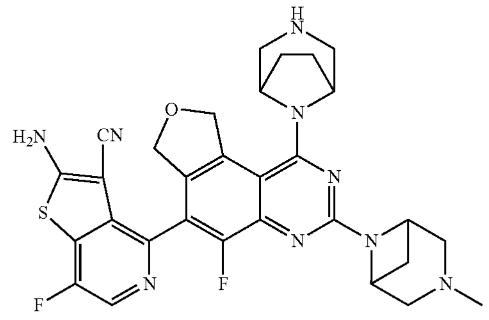 [SMILES: CN1CC2CC(C1)N2c1nc(N2C3CCC2CNC3)c2c3c(c(-c4ncc(F)c5sc(N)c(C#N)c45)c(F)c2n1)COC3] | 602 |
| 212B | 4-(1-(3,8-Diazabicyclo[3.2.1]octan-8-yl)-3-((1R,5S,8R)-8-(dimethylamino)-3-azabicyclo[3.2.1]octan-3-yl)-5-fluoro-7,9-dihydrofuro[3,4-f]quinazolin-6-yl)-2-amino-7-fluorothieno[3,2-c]pyridine-3-carbonitrile | 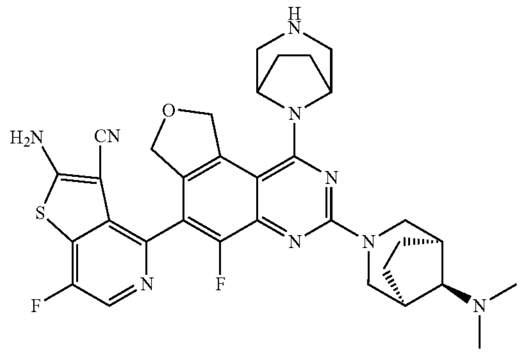 [SMILES: CN(C)[C@H]1[C@@H]2CC[C@H]1CN(c1nc(N3C4CCC3CNC4)c3c4c(c(-c5ncc(F)c6sc(N)c(C#N)c56)c(F)c3n1)COC4)C2] | 644 |
| 213B | 4-(1-(3,8-Diazabicyclo[3.2.1]octan-8-yl)-5-fluoro-3-((1-(((3aR,6aS)-tetrahydro-1H-furo[3,4-c]pyrrol-5(3H)-yl)methyl)cyclopropyl)methoxy)-7,9-dihydrofuro[3,4-f]quinazolin-6-yl)-2-amino-7-fluorothieno[3,2-c]pyridine-3-carbonitrile | 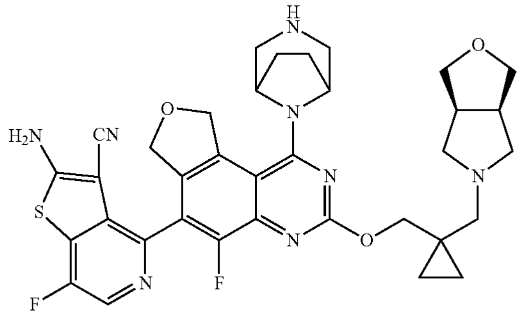 [SMILES: N#Cc1c(N)sc2c(F)cnc(-c3c4c(c5c(N6C7CCC6CNC7)nc(OCC6(CN7C[C@H]8COC[C@H]8C7)CC6)nc5c3F)COC4)c12] | 687 |
| 214B | 4-(1-(3,8-Diazabicyclo[3.2.1]octan-8-yl)-5-fluoro-3-((1-(((S)-2-(fluoromethyl)azetidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 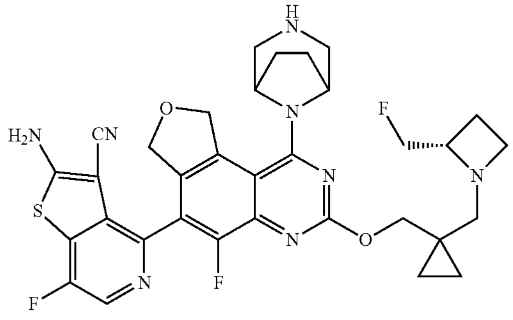 [SMILES: N#Cc1c(N)sc2c(F)cnc(-c3c4c(c5c(N6C7CCC6CNC7)nc(OCC6(CN7CC[C@H]7CF)CC6)nc5c3F)COC4)c12] | 663 |

TABLE 26-continued

| Preparation | Chemical Name | Structure | MS (ES) m/z (M + 1) |
|---|---|---|---|
| 215B | 4-(1-(3,8-Diazabicyclo[3.2.1]octan-8-yl)-5-fluoro-3-((1-(((S)-2-(methoxymethyl)azetidin-1-yl)methyl)cyclopropyl)methoxy)-7,9-dihydrofuro[3,4-f]quinazolin-6-yl)-2-amino-7-fluorothieno[3,2-c]pyridine-3-carbonitrile | 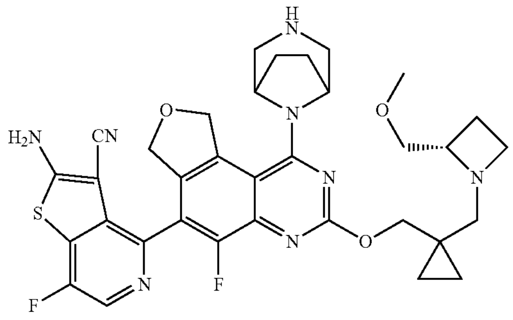 [SMILES: COC[C@@H]1CCN1CC1(COc2nc(N3C4CCC3CNC4)c3c4c(c(-c5ncc(F)c6sc(N)c(C#N)c56)c(F)c3n2)COC4)CC1] | 675 |
| 216B [1] | 4-(1-(3,8-Diazabicyclo[3.2.1]octan-8-yl)-3-((S)-3-(dimethylamino)pyrrolidin-1-yl)-5-fluoro-7,9-dihydrofuro[3,4-f]quinazolin-6-yl)-2-amino-5-fluorobenzo[b]thiophene-3-carbonitrile | 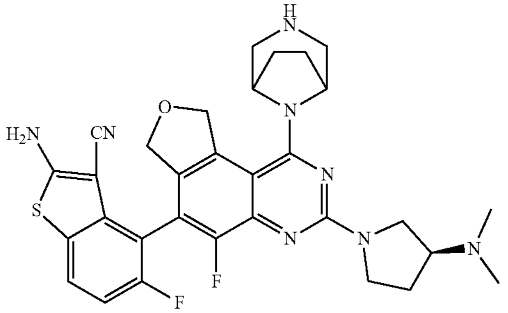 [SMILES: CN(C)[C@H]1CCN(c2nc(N3C4CCC3CNC4)c3c4c(c(-c5c(F)ccc6sc(N)c(C#N)c56)c(F)c3n2)COC4)C1] | 603 |
| 217B | 4-(1-(3,8-Diazabicyclo[3.2.1]octan-8-yl)-5-chloro-3-((S)-3-(dimethylamino)pyrrolidin-1-yl)-7,9-dihydrofuro[3,4-f]quinazolin-6-yl)-2-amino-7-fluorobenzo[b]thiophene-3-carbonitrile | 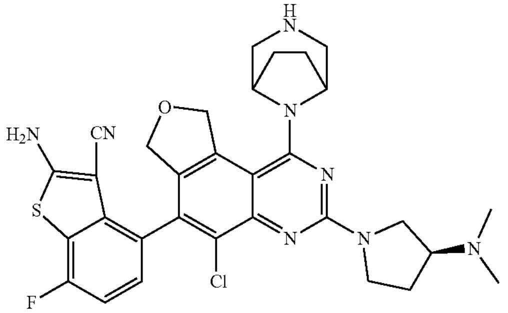 [SMILES: CN(C)[C@H]1CCN(c2nc(N3C4CCC3CNC4)c3c4c(c(-c5ccc(F)c6sc(N)c(C#N)c56)c(Cl)c3n2)COC4)C1] | 619 |
| 218B | 4-(1-(3,8-Diazabicyclo[3.2.1]octan-8-yl)-5-chloro-3-((S)-3-(dimethylamino)pyrrolidin-1-yl)-7,9-dihydrofuro[3,4-f]quinazolin-6-yl)-2-amino-5-fluorobenzo[b]thiophene-3-carbonitrile | 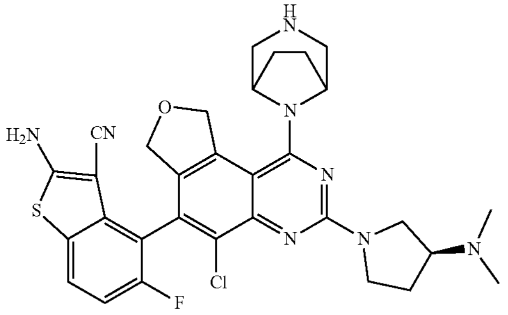 [SMILES: CN(C)[C@H]1CCN(c2nc(N3C4CCC3CNC4)c3c4c(c(-c5c(F)ccc6sc(N)c(C#N)c56)c(Cl)c3n2)COC4)C1] | 619 |
| 606D | 2-Amino-4-(3-((2S,3S)-3-amino-2-methylpyrrolidin-1-yl)-5-fluoro-7,9-dihydrofuro[3,4-f]quinazolin-6-yl)-5-fluorobenzo[b]thiophene-3-carbonitrile | 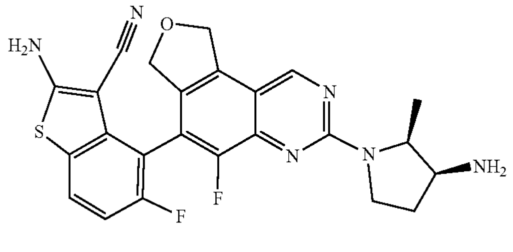 [SMILES: C[C@H]1[C@@H](N)CCN1c1ncc2c3c(c(-c4c(F)ccc5sc(N)c(C#N)c45)c(F)c2n1)COC3] | 479 |

TABLE 26-continued

| Preparation | Chemical Name | Structure | MS (ES) m/z (M + 1) |
|---|---|---|---|
| 607D | 2-Amino-4-(5-chloro-3-(1,6-diazaspiro[3.4]octan-6-yl)-7,9-dihydrofuro[3,4-f]quinazolin-6-yl)-7-fluorothieno[3,2-c]pyridine-3-carbonitrile formic acid | 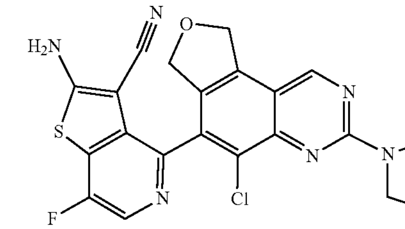 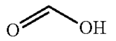 | 508 |

[1] Single atropisomer (from precursor in Preparation 9B)

Example 1

2-Amino-7-fluoro-4-(5-fluoro-1-(3-((R)-2-hydroxypropyl)-3,8-diazabicyclo[3.2.1]octan-8-yl)-3-((1-(morpholinomethyl)cyclopropyl)methoxy)-7,9-dihydrofuro[3,4-f]quinazolin-6-yl)thieno[3,2-c]pyridine-3-carbonitrile

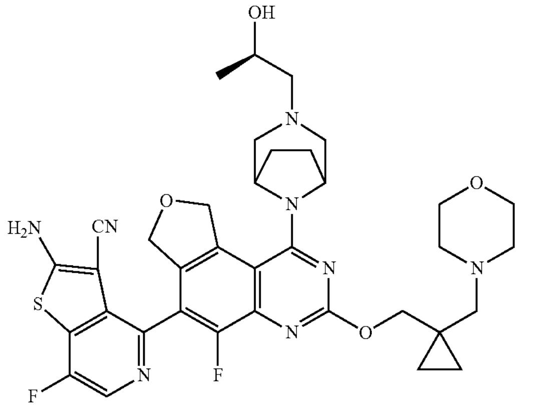 [SMILES: C[C@@H](O)CN1CC2CCC(C1)N2c1nc(OCC2(CN3CCOCC3)CC2)nc2c(F)c(-c3ncc(F)c4sc(N)c(C#N)c34)c3c(c12)COC3]

To a solution of 4-(1-(3,8-diazabicyclo[3.2.1]octan-8-yl)-5-fluoro-3-((1-(morpholinomethyl)cyclopropyl)methoxy)-7,9-dihydrofuro[3,4-f]quinazolin-6-yl)-2-amino-7-fluorothieno[3,2-c]pyridine-3-carbonitrile (0.150 g, 0.227 mmol) in DCM (2 mL) and MeOH (2 mL) was added (R)-2-hydroxypropanal (0.042 g, 0.568 mmol). After 5 min, sodium cyanoborohydride (0.043 g, 0.681 mmol) was added in portions. The reaction mixture was stirred for 1 h at RT, then diluted with water. The mixture was extracted with 10:1 DCM:MeOH (2×150 mL). The combined organic layers were washed with brine (2×100 mL), dried over anhydrous $Na_2SO_4$, filtered and concentrated. The residue was purified by reversed phase purification, eluting with 45% to 55% ACN in 10 mM aq. $NH_4HCO_3$ with 0.05% $NH_4OH$, to give the title compound (0.079 g, 48%) as a white solid. MS (ES) m/z=719 (M+1).

The following compounds in Table 27 were prepared in similar manner as described in Example 1. (2R)-2-((Tetrahydro-2H-pyran-2-yl)oxy)propanal was substituted for (R)-2-hydroxypropanal in some cases. Various methods (including, but not limited to, strong cation exchange chromatography with ammoniated methanol) were used to purify the compounds, which would be apparent to one skilled in the art.

TABLE 27

| Example | Chemical Name | Structure | MS (ES) m/z (M + 1) |
|---|---|---|---|
| 2 | 2-Amino-7-fluoro-4-(5-fluoro-1-(3-(3-hydroxypropyl)-3,8-diazabicyclo[3.2.1]octan-8-yl)-3-((1-(morpholinomethyl)cyclopropyl)methoxy)-7,9-dihydrofuro[3,4-f]quinazolin-6-yl)thieno[3,2-c]pyridine-3-carbonitrile | 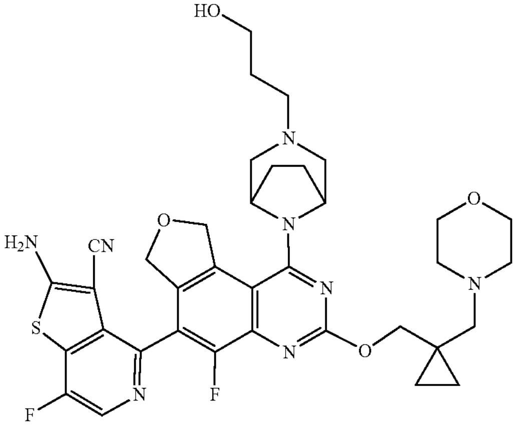 [SMILES: N#Cc1c(N)sc2c(F)cnc(-c3c4c(c5c(N6C7CCC6CN(CCCO)C7)nc(OCC6(CN7CCOCC7)CC6)nc5c3F)COC4)c12] | 719 |

TABLE 27-continued

| Example | Chemical Name | Structure | MS (ES) m/z (M + 1) |
|---|---|---|---|
| 3 [1] | 2-Ammino-5-fluoro-4-(5-fluoro-1-(3-(3-hydroxypropyl)-3,8-diazabicyclo[3.2.1]octan-8-yl)-3-((1-(morpholinomethyl)cyclo-propyl)methoxy)-7,9-dihydrofuro[3,4-f]quinazolin-6-yl)benzo[b]thiophene-3-carbonitrile, Isomer 1 | 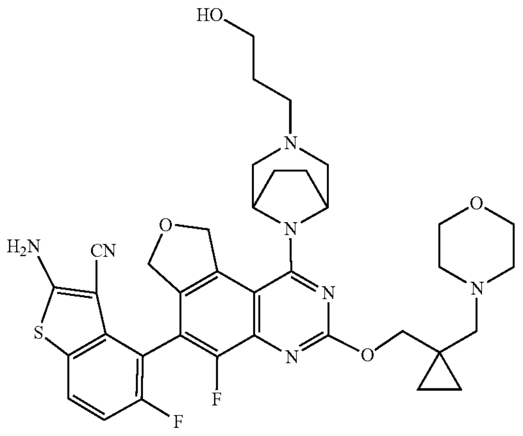 [SMILES: N#Cc1c(N)sc2ccc(F)c(-c3c4c(c5c(N6C7CCC6CN(CCCO)C7)nc(OCC6(CN7CCOCC7)CC6)nc5c3F)COC4)c12] | 718 |
| 4 [1] | 2-Amino-5-fluoro-4-(5-fluoro-1-(3-(3-hydroxypropyl)-3,8-diazabicyclo[3.2.1]octan-8-yl)-3-((1-(morpholinomethyl)cyclo-propyl)methoxy)-7,9-dihydrofuro[3,4-f]quinazolin-6-yl)benzo[b]thiophene-3-carbonitrile, Isomer 2 | 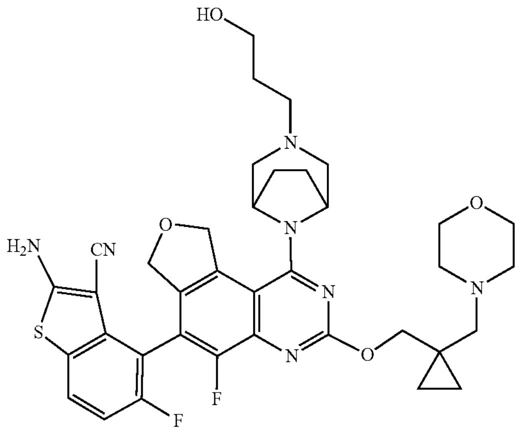 [SMILES: N#Cc1c(N)sc2ccc(F)c(-c3c4c(c5c(N6C7CCC6CN(CCCO)C7)nc(OCC6(CN7CCOCC7)CC6)nc5c3F)COC4)c12] | 718 |
| 5 | 2-Amino-5-fluoro-4-(5-fluoro-1-(3-((R)-2-hydroxypropyl)-3,8-diazabicyclo[3.2.1]octan-8-yl)-3-((1-(morpholinomethyl)cyclo-propyl)methoxy)-7,9-dihydrofuro[3,4-f]quinazolin-6-yl)benzo[b]thiophene-3-carbonitrile | 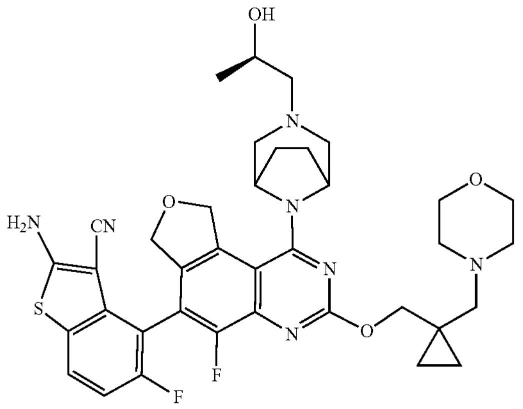 [SMILES: C[C@@H](O)CN1CC2CCC(C1)N2c1nc(OCC2(CN3CCOCC3)CC2)nc2c(F)c(-c3c(F)ccc4sc(N)c(C#N)c34)c3c(c12)COC3] | 718 |

TABLE 27-continued

| Example | Chemical Name | Structure | MS (ES) m/z (M + 1) |
|---|---|---|---|
| 6 | 2-Amino-7-fluoro-4-(5-fluoro-1-(3-((R)-2-hydroxypropyl)-3,8-diazabicyclo[3.2.1]octan-8-yl)-3-((1-((4-methylpiperazin-1-yl)methyl)cyclopropyl)methoxy)-7,9-dihydrofuro[3,4-f]quinazolin-6-yl)thieno[3,2-c]pyridine-3-carbonitrile | 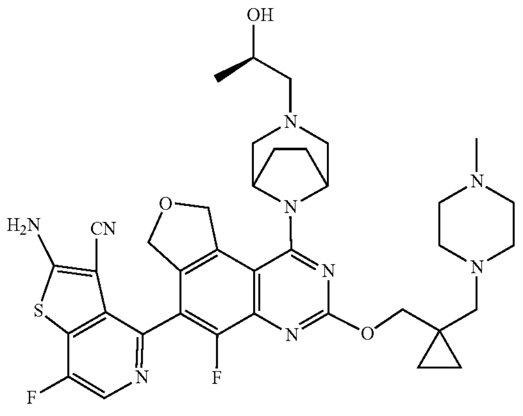 [SMILES: C[C@@H](O)CN1CC2CCC(C1)N2c1nc(OCC2(CN3CCN(C)CC3)CC2)nc2c(F)c(-c3ncc(F)c4sc(N)c(C#N)c34)c3c(c12)COC3] | 732 |
| 7 | 2-Amino-7-fluoro-4-(5-fluoro-3-((1-(((S)-3-fluoropyrrolidin-1-yl)methyl)cyclopropyl)methoxy)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 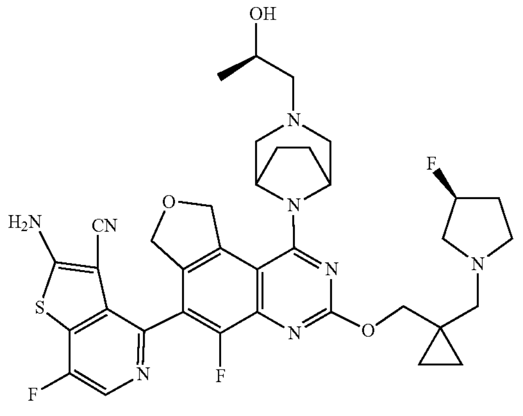 [SMILES: C[C@@H](O)CN1CC2CCC(C1)N2c1nc(OCC2(CN3CC[C@H](F)C3)CC2)nc2c(F)c(-c3ncc(F)c4sc(N)c(C#N)c34)c3c(c12)COC3] | 721 |
| 8 | 2-Amino-7-fluoro-4-(5-fluoro-3-((1-(((R)-3-fluoropyrrolidin-1-yl)methyl)cyclopropyl)methoxy)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 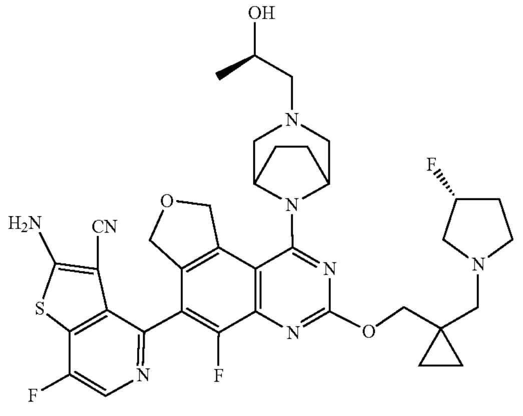 [SMILES: C[C@@H](O)CN1CC2CCC(C1)N2c1nc(OCC2(CN3CC[C@@H](F)C3)CC2)nc2c(F)c(-c3ncc(F)c4sc(N)c(C#N)c34)c3c(c12)COC3] | 721 |

TABLE 27-continued

| Example | Chemical Name | Structure | MS (ES) m/z (M + 1) |
|---|---|---|---|
| 9 | 2-Amino-7-fluoro-4-(5-fluoro-3-((1-((4-fluoropiperidin-1-yl)methyl)cyclopropyl)methoxy)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 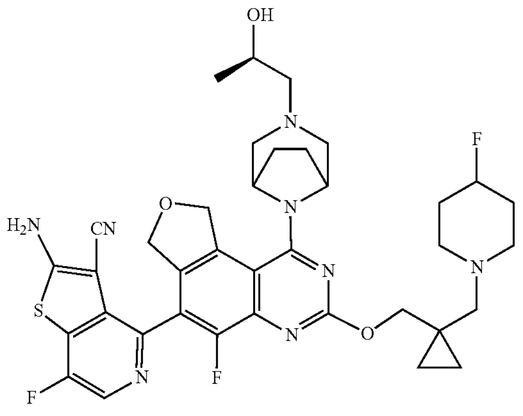 [SMILES: C[C@@H](O)CN1CC2CCC(C1)N2c1nc(OCC2(CN3CCC(F)CC3)CC2)nc2c(F)c(-c3ncc(F)c4sc(N)c(C#N)c34)c3c(c12)COC3] | 735 |
| 10 | 2-Amino-7-fluoro-4-(5-fluoro-1-(3-((R)-2-hydroxypropyl)-3,8-diazabicyclo[3.2.1]octan-8-yl)-3-((1-((6-methyl-2,6-diazaspiro[3.3]heptan-2-yl)methyl)cyclopropyl)methoxy)-7,9-dihydrofuro[3,4-f]quinazolin-6-yl)thieno[3,2-c]pyridine-3-carbonitrile | 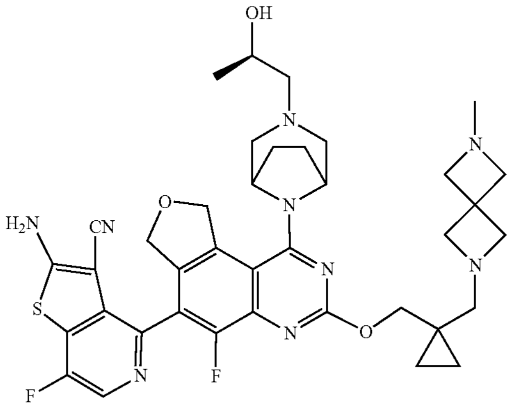 [SMILES: C[C@@H](O)CN1CC2CCC(C1)N2c1nc(OCC2(CN3CC4(CN(C)C4)C3)CC2)nc2c(F)c(-c3ncc(F)c4sc(N)c(C#N)c34)c3c(c12)COC3] | 744 |
| 11 | 2-Amino-4-(3-((1-((4,4-difluoropiperidin-1-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 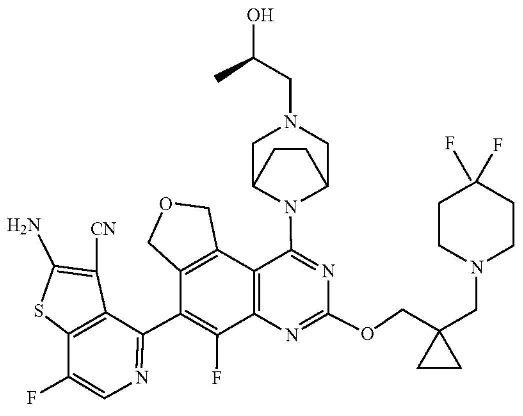 | 753 |

TABLE 27-continued

| Example | Chemical Name | Structure | MS (ES) m/z (M + 1) |
|---|---|---|---|
| 12 | 2-Amino-4-(3-((1-((6,6-difluoro-3-azabicyclo[3.1.0]hexan-3-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 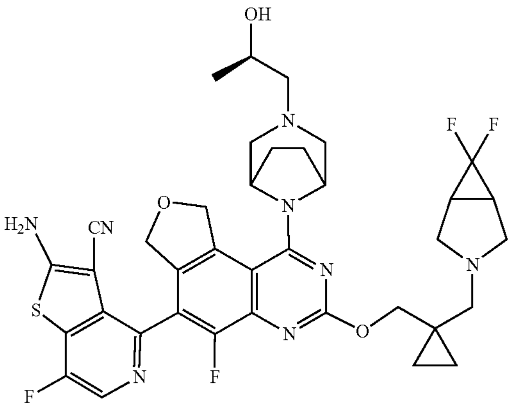 [SMILES: C[C@@H](O)CN1CC2CCC(C1)N2c1nc(OCC2(CN3CC4C(C3)C4(F)F)CC2)nc2c(F)c(-c3ncc(F)c4sc(N)c(C#N)c34)c3c(c12)COC3] | 751 |
| 13 | 2-Amino-7-fluoro-4-(5-fluoro-3-((1-((3-methoxyazetidin-1-yl)methyl)cyclopropyl)methoxy)-1-(3-(2-methoxyethyl)-3,8-diazabicyclo[3.2.1]octan-8-yl)-7,9-dihydrofuro[3,4-f]quinazolin-6-yl)thieno[3,2-c]pyridine-3-carbonitrile | 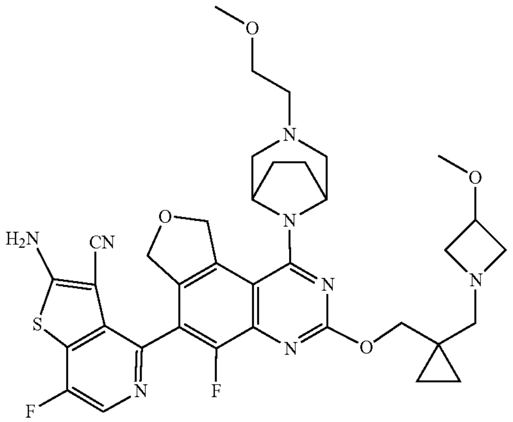 [SMILES: COCCN1CC2CCC(C1)N2c1nc(OCC2(CN3CC(OC)C3)CC2)nc2c(F)c(-c3ncc(F)c4sc(N)c(C#N)c34)c3c(c12)COC3] | 719 |
| 14 | 2-Amino-7-fluoro-4-(5-fluoro-1-(3-((R)-2-hydroxypropyl)-3,8-diazabicyclo[3.2.1]octan-8-yl)-3-((1-((3-methoxyazetidin-1-yl)methyl)cyclopropyl)methoxy)-7,9-dihydrofuro[3,4-f]quinazolin-6-yl)thieno[3,2-c]pyridine-3-carbonitrile | 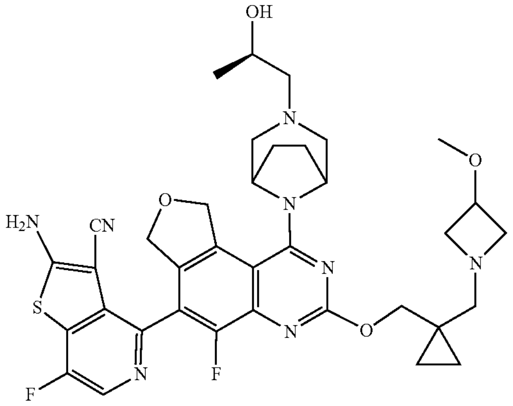 [SMILES: COC1CN(CC2(COc3nc(N4C5CCC4CN(C[C@@H](C)O)C5)c4c5c(c(-c6ncc(F)c7sc(N)c(C#N)c67)c(F)c4n3)COC5)CC2)C1] | 719 |

TABLE 27-continued

| Example | Chemical Name | Structure | MS (ES) m/z (M + 1) |
| --- | --- | --- | --- |
| 15 | 2-Amino-7-fluoro-4-(5-fluoro-3-((1-((3-(fluoromethyl)azetidin-1-yl)methyl)cyclopropyl)methoxy)-1-(3-((R)-2-hdyroxypropyl)-3,8-diazabicyclo[3.2.1]octan-8-yl)-7,9-dihydrofuro[3,4-f]quinazolin-6-yl)thieno[3,2-c]pyridine-3-carbonitrile | 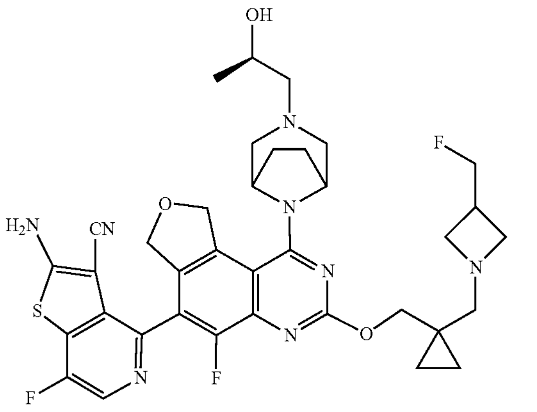 [SMILES: C[C@@H](O)CN1CC2CCC(C1)N2c1nc(OCC2(CN3CC(CF)C3)CC2)nc2c(F)c(-c3ncc(F)c4sc(N)c(C#N)c34)c3c(c12)COC3] | 721 |
| 16 | 2-Amino-7-fluoro-4-(5-fluoro-1-(3-((R)-2-hydroxypropyl)-3,8-diazabicyclo[3.2.1]octan-8-yl)-3-((1-(((R)-3-methylmorpholino)methyl)cyclopropyl)methoxy)-7,9-dihydrofuro[3,4-f]quinazolin-6-yl)thieno[3,2-c]pyridine-3-carbonitrile | 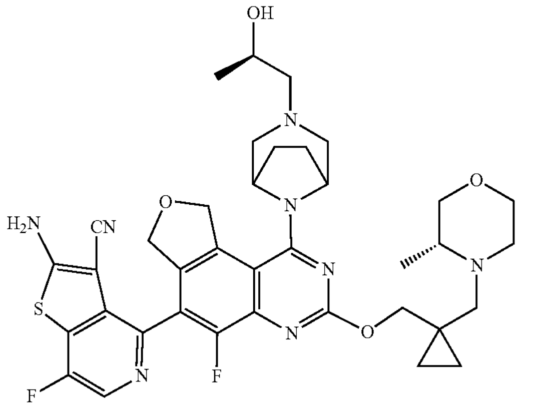 [SMILES: C[C@@H]1COCCN1CC1(COc2nc(N3C4CCC3CN(C[C@@H](C)O)C4)c3c4c(c(-c5ncc(F)c6sc(N)c(C#N)c56)c(F)c3n2)COC4)CC1] | 733 |
| 17 | 4-(3-((1-(((1S,4S)-2-Oxa-5-azabicyclo[2.2.1]heptan-5-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-2-amino-7-fluorothieno[3,2-c]pyridine-3-carbonitrile | 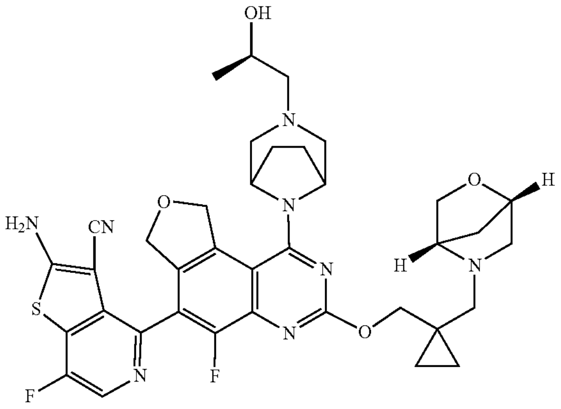 [SMILES: C[C@@H](O)CN1CC2CCC(C1)N2c1nc(OCC2(CN3C[C@@H]4C[C@H]3CO4)CC2)nc2c(F)c(-c3ncc(F)c4sc(N)c(C#N)c34)c3c(c12)COC3] | 731 |

TABLE 27-continued

| Example | Chemical Name | Structure | MS (ES) m/z (M + 1) |
|---|---|---|---|
| 18 | 4-(3-((1-((4-Acetylpiperazin-1-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-2-amino-7-fluorothieno[3,2-c]pyridine-3-carbonitrile | 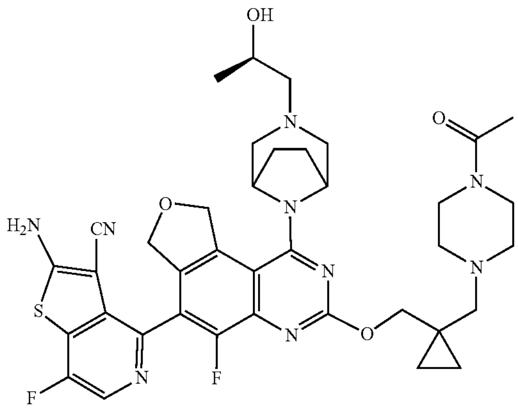 [SMILES: CC(=O)N1CCN(CC2(COc3nc(N4C5CCC4CN(C[C@@H](C)O)C5)c4c5c(c(-c6ncc(F)c7sc(N)c(C#N)c67)c(F)c4n3)COC5)CC2)CC1] | 760 |
| 1A | 2-Amino-4-(3-((1-((4-cyanopiperidin-1-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 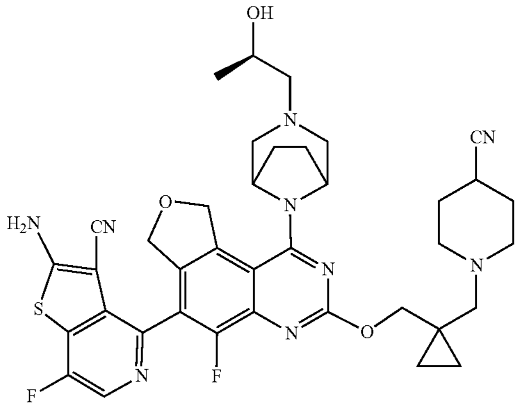 [SMILES: C[C@@H](O)CN1CC2CCC(C1)N2c1nc(OCC2(CN3CCC(C#N)CC3)CC2)nc2c(F)c(-c3ncc(F)c4sc(N)c(C#N)c34)c3c(c12)COC3] | 742 |
| 2A | 4-(3-((1-((7-Oxa-2-azaspiro[3.5]nonan-2-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-2-amino-7-fluorothieno[3,2-c]pyridine-3-carbonitrile | 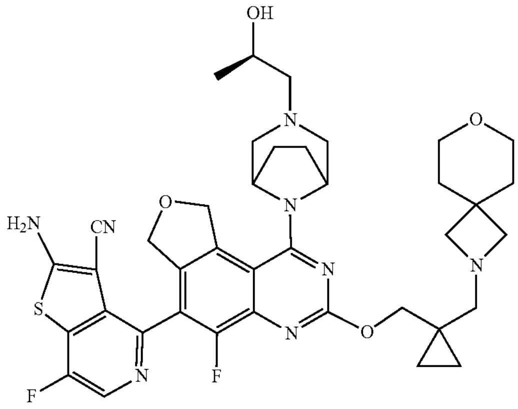 [SMILES: C[C@@H](O)CN1CC2CCC(C1)N2c1nc(OCC2(CN3CC4(CCOCC4)C3)CC2)nc2c(F)c(-c3ncc(F)c4sc(N)c(C#N)c34)c3c(c12)COC3] | 759 |

TABLE 27-continued

| Example | Chemical Name | Structure | MS (ES) m/z (M + 1) |
| --- | --- | --- | --- |
| 3A | 2-Amino-7-fluoro-4-(5-fluoro-1-(3-((R)-2-hydroxypropyl)-3,8-diazabicyclo[3.2.1]octan-8-yl)-3-((1-(((R)-3-methoxypyrrolidin-1-yl)methyl)cyclopropyl)methoxy)-7,9-dihydrofuro[3,4-f]quinazolin-6-yl)thieno[3,2-c]pyridine-3-carbonitrile | 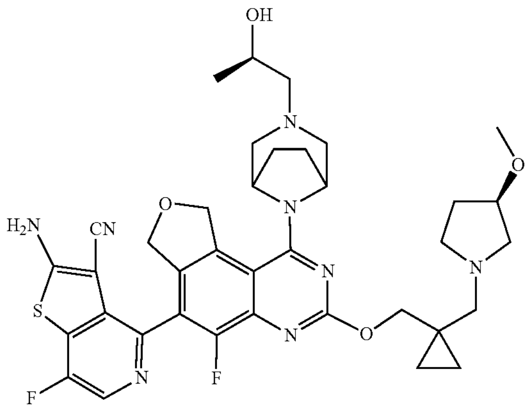 [SMILES: CO[C@@H]1CCN(CC2(COc3nc(N4C5CCC4CN(C[C@@H](C)O)C5)c4c5c(c(-c6ncc(F)c7sc(N)c(C#N)c67)c(F)c4n3)COC5)CC2)C1] | 733 |
| 4A | 4-(3-((1-((2-Oxa-6-azaspiro[3.3]heptan-6-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-2-amino-7-fluorothieno[3,2-c]pyridine-3-carbonitrile | 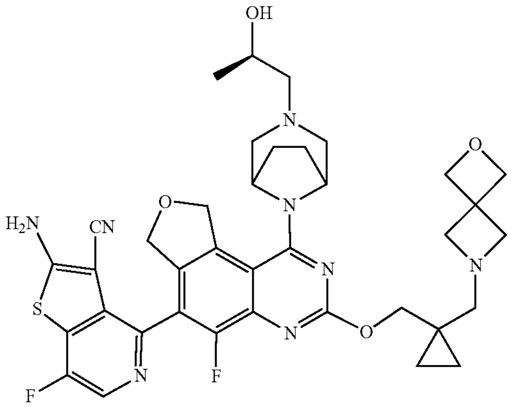 [SMILES: C[C@@H](O)CN1CC2CCC(C1)N2c1nc(OCC2(CN3CC4(COC4)C3)CC2)nc2c(F)c(-c3ncc(F)c4sc(N)c(C#N)c34)c3c(c12)COC3] | 731 |
| 5A | 2-Amino-7-fluoro-4-(5-fluoro-1-(3-((R)-2-hydroxypropyl)-3,8-diazabicyclo[3.2.1]octan-8-yl)-3-((1-(pyrrolidin-1-ylmethyl)cyclopropyl)methoxy)-7,9-dihydrofuro[3,4-f]quinazolin-6-yl)thieno[3,2-c]pyridine-3-carbonitrile | 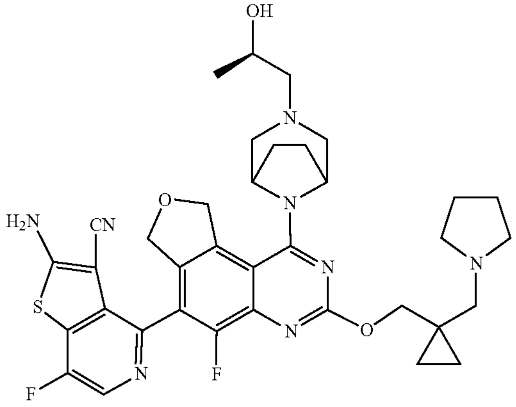 [SMILES: C[C@@H](O)CN1CC2CCC(C1)N2c1nc(OCC2(CN3CCCC3)CC2)nc2c(F)c(-c3ncc(F)c4sc(N)c(C#N)c34)c3c(c12)COC3] | 703 |

TABLE 27-continued

| Example | Chemical Name | Structure | MS (ES) m/z (M + 1) |
|---|---|---|---|
| 6A | 2-Amino-7-fluoro-4-(5-fluoro-3-((1-((3-hydroxyazetidin-1-yl)methyl)cyclopropyl)methoxy)-1-(3-(2-methoxyethyl)-3,8-diazabicyclo[3.2.1]octan-8-yl)-7,9-dihydrofuro[3,4-f]quinazolin-6-yl)thieno[3,2-c]pyridine-3-carbonitrile | 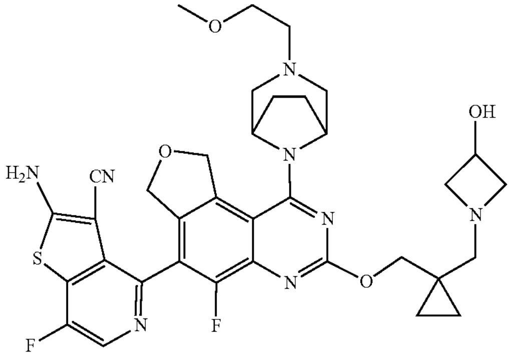 [SMILES: COCCN1CC2CCC(C1)N2c1nc(OCC2(CN3CC(O)C3)CC2)nc2c(F)c(-c3ncc(F)c4sc(N)c(C#N)c34)c3c(c12)COC3] | 705 |
| 7A | 2-Amino-7-fluoro-4-(5-fluoro-1-(3-((R)-2-hydroxypropyl)-3,8-diazabicyclo[3.2.1]octan-8-yl)-3-((1-((4-(2,2,2-trifluoroethyl)piperazin-1-yl)methyl)cyclopropyl)methoxy)-7,9-dihydrofuro[3,4-f]quinazolin-6-yl)thieno[3,2-c]pyridine-3-carbonitrile | 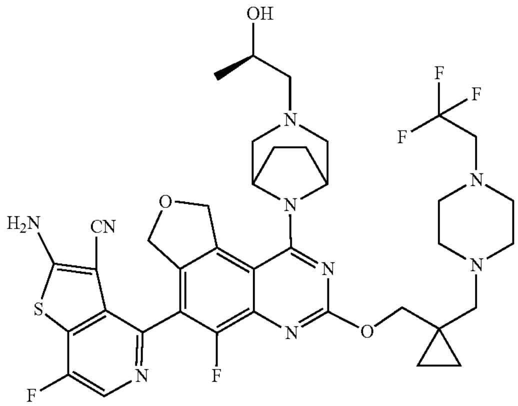 [SMILES: C[C@@H](O)CN1CC2CCC(C1)N2c1nc(OCC2(CN3CCN(CC(F)(F)F)CC3)CC2)nc2c(F)c(-c3ncc(F)c4sc(N)c(C#N)c34)c3c(c12)COC3] | 801 |
| 8A | 4-(3-((1-((3-Oxa-8-azabicyclo[3.2.1]octan-8-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-2-amino-7-fluorothieno[3,2-c]pyridine-3-carbonitrile | 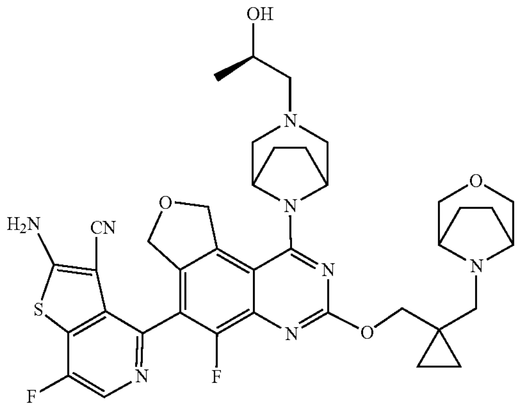 [SMILES: C[C@@H](O)CN1CC2CCC(C1)N2c1nc(OCC2(CN3C4CCC3COC4)CC2)nc2c(F)c(-c3ncc(F)c4sc(N)c(C#N)c34)c3c(c12)COC3] | 745 |

TABLE 27-continued

| Example | Chemical Name | Structure | MS (ES) m/z (M + 1) |
| --- | --- | --- | --- |
| 9A | 2-Amino-7-fluoro-4-(5-fluoro-3-((1-((3-fluoropiperidin-1-yl)methyl)cyclopropyl)methoxy)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 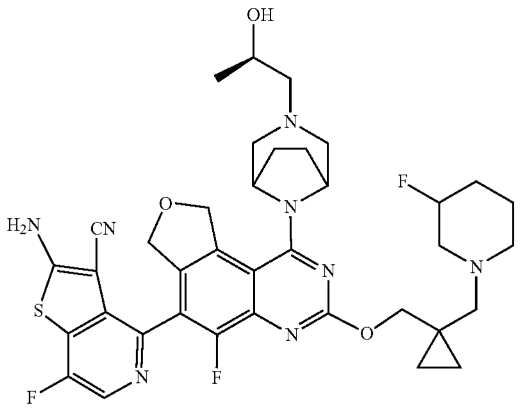 [SMILES: C[C@@H](O)CN1CC2CCC(C1)N2c1nc(OCC2(CN3CCCC(F)C3)CC2)nc2c(F)c(-c3ncc(F)c4sc(N)c(C#N)c34)c3c(c12)COC3] | 735 |
| 10A | 2-Amino-7-fluoro-4-(5-fluoro-1-(3-((R)-2-hydroxypropyl)-3,8-diazabicyclo[3.2.1]octan-8-yl)-3-((1-(((S)-3-methylmorpholino)methyl)cyclopropyl)methoxy)-7,9-dihydrofuro[3,4-f]quinazolin-6-yl)thieno[3,2-c]pyridine-3-carbonitrile | 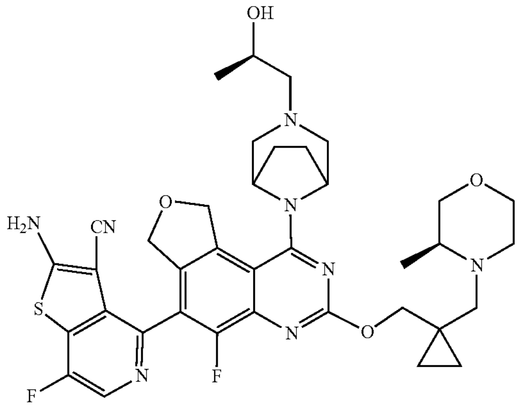 [SMILES: C[C@@H](O)CN1CC2CCC(C1)N2c1nc(OCC2(CN3CCOC[C@@H]3C)CC2)nc2c(F)c(-c3ncc(F)c4sc(N)c(C#N)c34)c3c(c12)COC3] | 733 |
| 11A | 2-Amino-4-(3-((1-(((2R,6S)-2,6-dimethylmorpholino)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 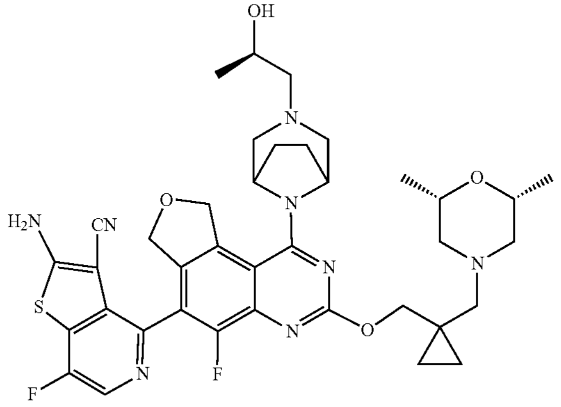 [SMILES: C[C@@H]1CN(CC2(COc3nc(N4C5CCC4CN(C[C@@H](C)O)C5)c4c5c(c(-c6ncc(F)c7sc(N)c(C#N)c67)c(F)c4n3)COC5)CC2)C[C@H](C)O1] | 747 |

TABLE 27-continued

| Example | Chemical Name | Structure | MS (ES) m/z (M + 1) |
|---|---|---|---|
| 12A | 2-Amino-7-fluoro-4-(5-fluoro-3-((1-(((S)-2-(hydroxymethyl)azetidin-1-yl)methyl)cyclopropyl)methoxy)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 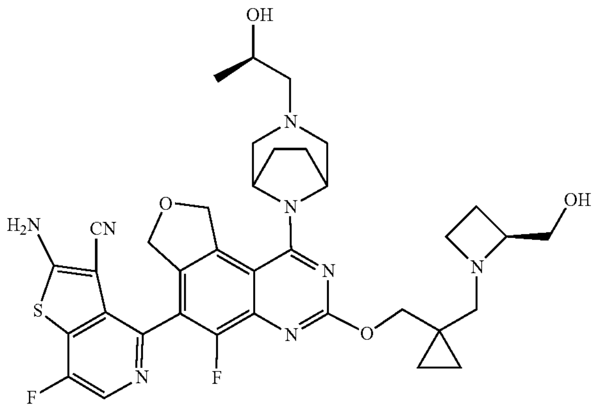 [SMILES: C[C@@H](O)CN1CC2CCC(C1)N2c1nc(OCC2(CN3CC[C@H]3CO)CC2)nc2c(F)c(-c3ncc(F)c4sc(N)c(C#N)c34)c3c(c12)COC3] | 719 |
| 13A | 2-Amino-4-(3-((1-((3,3-dimethylazetidin-1-yl)methyl)cyclopropyl)methoxy)-5-fluoro-1-(3-(2-methoxyethyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 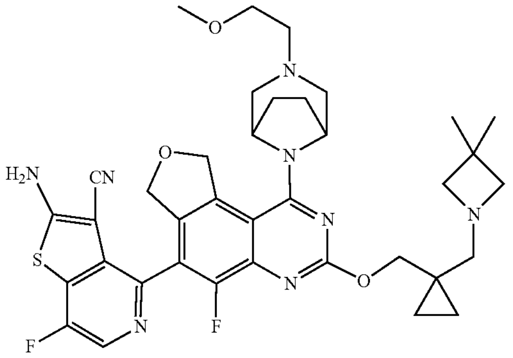 [SMILES: COCCN1CC2CCC(C1)N2c1nc(OCC2(CN3CC(C)(C)C3)CC2)nc2c(F)c(-c3ncc(F)c4sc(N)c(C#N)c34)c3c(c12)COC3] | 717 |
| 14A | 2-Amino-4-(3-((1-(((R)-3-cyanopyrrolidin-1-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 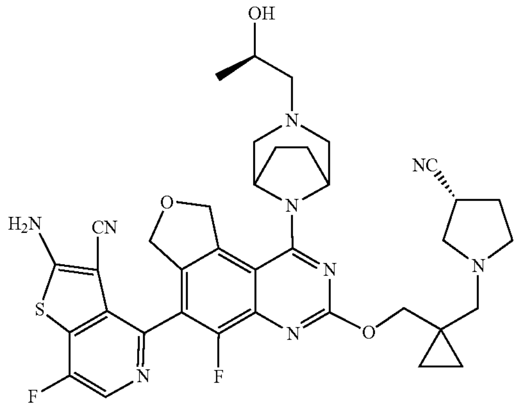 [SMILES: C[C@@H](O)CN1CC2CCC(C1)N2c1nc(OCC2(CN3CC[C@@H](C#N)C3)CC2)nc2c(F)c(-c3ncc(F)c4sc(N)c(C#N)c34)c3c(c12)COC3] | 728 |

TABLE 27-continued

| Example | Chemical Name | Structure | MS (ES) m/z (M + 1) |
|---|---|---|---|
| 15A | 4-(3-((1-((6-Oxa-2-azaspiro[3.4]octan-2-yl)methyl)cyclopropyl)methoxy)-5-fluoro-1-(3-((R)-2-hydroxypropyl)-3,8-diazabicyclo[3.2.1]octan-8-yl)-7,9-dihdyrofuro[3,4-f]quinazolin-6-yl)-2-amino-7-fluorothieno[3,2-c]pyridine-3-carbonitrile | 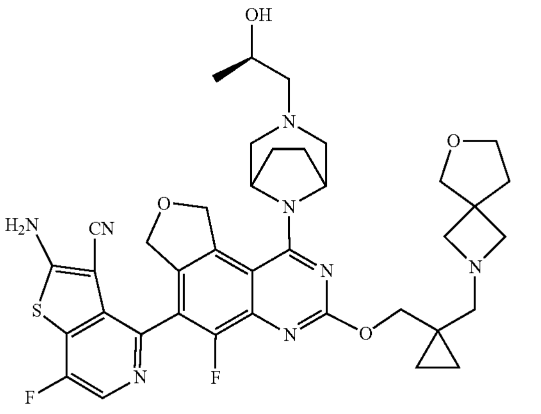 [SMILES: C[C@@H](O)CN1CC2CCC(C1)N2c1nc(OCC2(CN3CC4(CCOC4)C3)CC2)nc2c(F)c(-c3ncc(F)c4sc(N)c(C#N)c34)c3c(c12)COC3] | 745 |
| 16A | 2-Amino-4-(3-((1-(((S)-3-cyanopyrrolidin-1-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 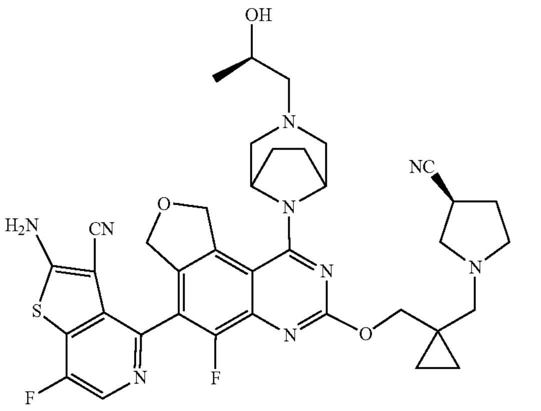 [SMILES: C[C@@H](O)CN1CC2CCC(C1)N2c1nc(OCC2(CN3CC[C@H](C#N)C3)CC2)nc2c(F)c(-c3ncc(F)c4sc(N)c(C#N)c34)c3c(c12)COC3] | 728 |
| 17A | 4-(3-((1-(((1R,4R)-2-Oxa-5-azabicyclo[2.2.1]heptan-5-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-2-amino-7-fluorothieno[3,2-c]pyridine-3-carbonitrile | 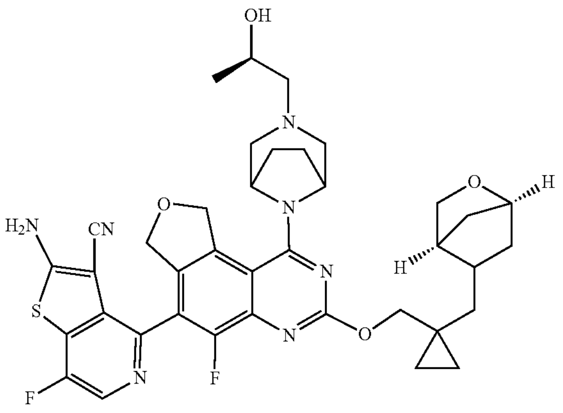 [SMILES: C[C@@H](O)CN1CC2CCC(C1)N2c1nc(OCC2(CC3C[C@H]4C[C@@H]3CO4)CC2)nc2c(F)c(-c3ncc(F)c4sc(N)c(C#N)c34)c3c(c12)COC3] | 731 |

TABLE 27-continued

| Example | Chemical Name | Structure | MS (ES) m/z (M + 1) |
|---|---|---|---|
| 18A | 2-Amino-4-(3-((1-(((3R,4S)-3,4-difluoropyrrolidin-1-yl)methyl)cyclopropyl)meth-oxy)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 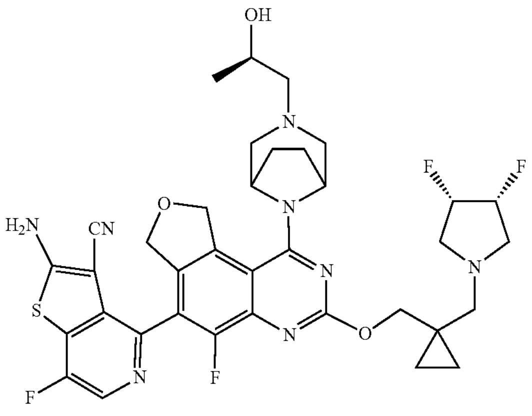 [SMILES: C[C@@H](O)CN1CC2CCC(C1)N2c1nc(OCC2(CN3C[C@@H](F)[C@@H](F)C3)CC2)nc2c(F)c(-c3ncc(F)c4sc(N)c(C#N)c34)c3c(c12)COC3] | 739 |
| 19A | 2-Amino-7-fluoro-4-(5-fluoro-3-((1-((3-fluoroazetidin-1-yl)methyl)cyclopropyl)meth-oxy)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 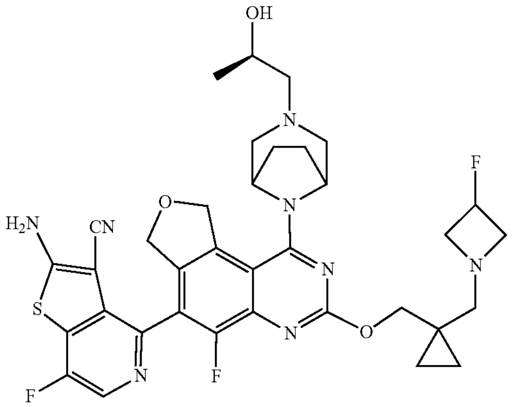 [SMILES: C[C@@H](O)CN1CC2CCC(C1)N2c1nc(OCC2(CN3CC(F)C3)CC2)nc2c(F)c(-c3ncc(F)c4sc(N)c(C#N)c34)c3c(c12)COC3] | 707 |
| 20A | 2-Amino-7-fluoro-4-(5-fluoro-3-((1-((3-fluoroazetidin-1-yl)methyl)cyclopropyl)meth-oxy)-1-(3-(3-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 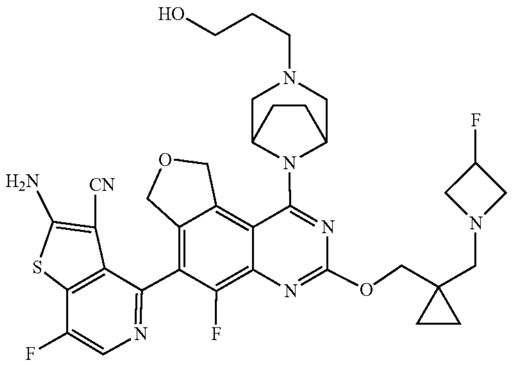 [SMILES: N#Cc1c(N)sc2c(F)cnc(-c3c4c(c5c(N6C7CCC6CN(CCCO)C7)nc(OCC6(CN7CC(F)C7)CC6)nc5c3F)COC4)c12] | 707 |

TABLE 27-continued

| Example | Chemical Name | Structure | MS (ES) m/z (M + 1) |
|---|---|---|---|
| 21A | 4-(3-((1-((8-Oxa-3-azabicyclo[3.2.1]octan-3-yl)methyl)cyclopropyl)methoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-2-amino-7-fluorothieno[3,2-c]pyridine-3-carbonitrile | 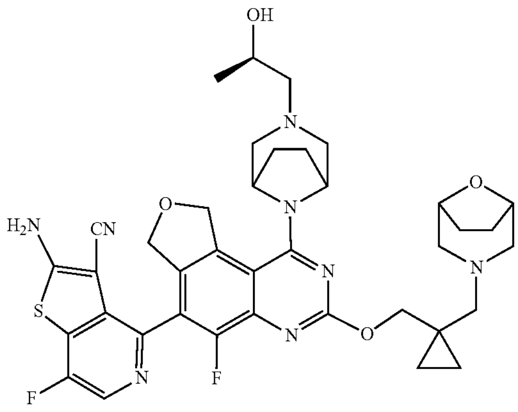 [SMILES: C[C@@H](O)CN1CC2CCC(C1)N2c1nc(OCC2(CN3CC4CCC(C3)O4)CC2)nc2c(F)c(-c3ncc(F)c4sc(N)c(C#N)c34)c3c(c12)COC3] | 745 |
| 22A | 2-Amino-7-fluoro-4-(5-fluoro-1-(3-((R)-2-hydroxypropyl)-3,8-diazabicyclo[3.2.1]octan-8-yl)-3-(2-methyl-3-morpholinopropoxy)-7,9-dihydrofuro[3,4-f]quinazolin-6-yl)thieno[3,2-c]pyridine-3-carbonitrile | 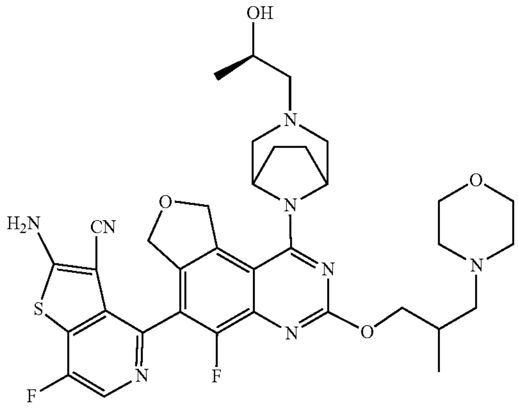 [SMILES: CC(COc1nc(N2C3CCC2CN(C[C@@H](C)O)C3)c2c3c(c(-c4ncc(F)c5sc(N)c(C#N)c45)c(F)c2n1)COC3)CN1CCOCC1] | 707 |
| 23A | 2-Amino-7-fluoro-4-(5-fluoro-1-(3-((R)-2-hydroxypropyl)-3,8-diazabicyclo[3.2.1]octan-8-yl)-3-((3-(morpholinomethyl)oxetan-3-yl)methoxy)-7,9-dihydrofuro[3,4-f]quinazolin-6-yl)thieno[3,2-c]pyridine-3-carbonitrile | 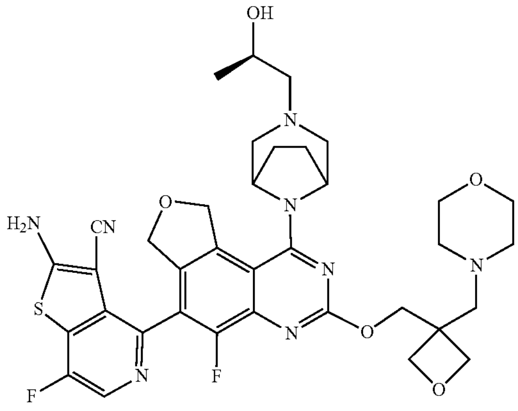 [SMILES: C[C@@H](O)CN1CC2CCC(C1)N2c1nc(OCC2(CN3CCOCC3)COC2)nc2c(F)c(-c3ncc(F)c4sc(N)c(C#N)c34)c3c(c12)COC3] | 735 |

TABLE 27-continued

| Example | Chemical Name | Structure | MS (ES) m/z (M + 1) |
| --- | --- | --- | --- |
| 24A | 2-Amino-4-(3-(2,2-dimethyl-3-morpholinopropoxy)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 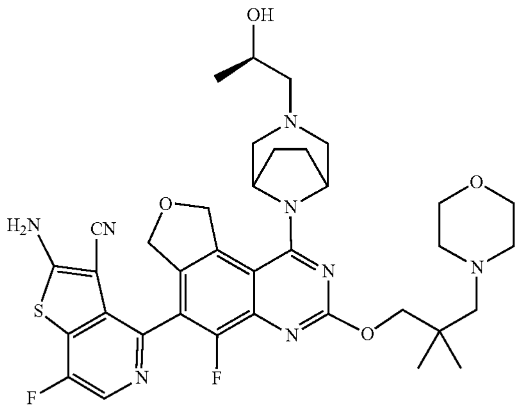 [SMILES: C[C@@H](O)CN1CC2CCC(C1)N2c1nc(OCC(C)(C)CN2CCOCC2)nc2c(F)c(-c3ncc(F)c4sc(N)c(C#N)c34)c3c(c12)COC3] | 721 |
| 25A | 2-Amino-4-(3-((S)-3-(dimethylamino)pyrrolidin-1-yl)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 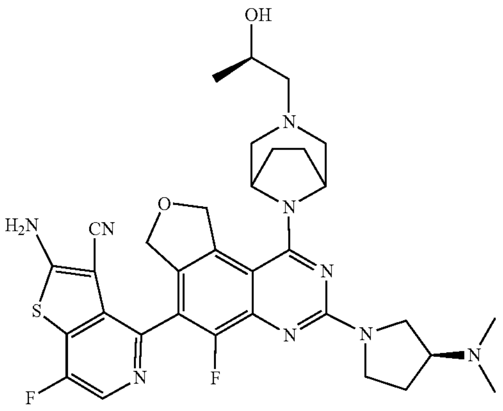 [SMILES: C[C@@H](O)CN1CC2CCC(C1)N2c1nc(N2CC[C@H](N(C)C)C2)nc2c(F)c(-c3ncc(F)c4sc(N)c(C#N)c34)c3c(c12)COC3] | 662 |
| 26A | 2-Amino-4-(3-((R)-3-(dimethylamino)pyrrolidin-1-yl)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 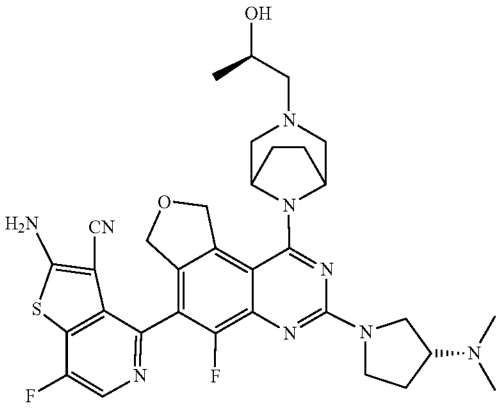 | 662 |

TABLE 27-continued

| Example | Chemical Name | Structure | MS (ES) m/z (M + 1) |
| --- | --- | --- | --- |
| 27A | 2-Amino-7-fluoro-4-(5-fluoro-3-(4-(2-hydroxyethyl)piperazin-1-yl)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 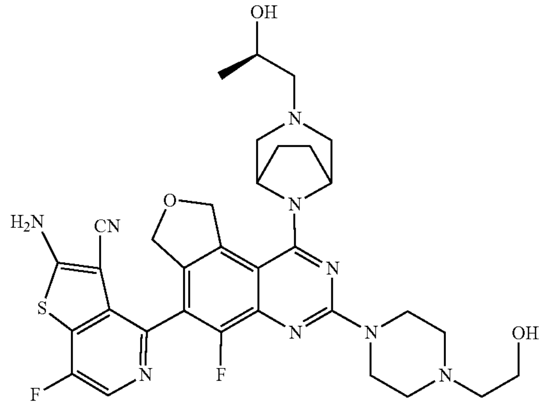 [SMILES: C[C@@H](O)CN1CC2CCC(C1)N2c1nc(N2CCN(CCO)CC2)nc2c(F)c(-c3ncc(F)c4sc(N)c(C#N)c34)c3c(c12)COC3] | 678 |
| 28A | 2-Amino-7-fluoro-4-(5-fluoro-1-(3-((R)-2-hydroxypropyl)-3,8-diazabicyclo[3.2.1]octan-8-yl)-3-(4-(3-hydroxypropyl)piperazin-1-yl)-7,9-dihydrofuro[3,4-f]quinazolin-6-yl)thieno[3,2-c]pyridine-3-carbonitrile | 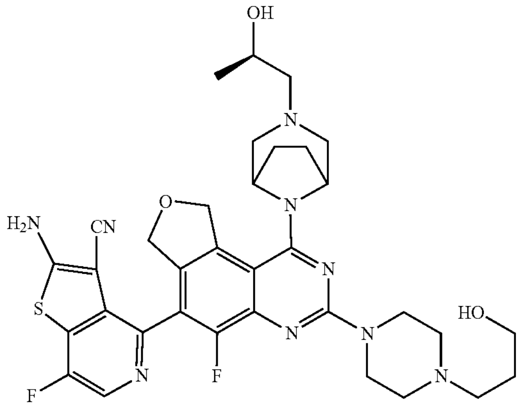 [SMILES: C[C@@H](O)CN1CC2CCC(C1)N2c1nc(N2CCN(CCCO)CC2)nc2c(F)c(-c3ncc(F)c4sc(N)c(C#N)c34)c3c(c12)COC3] | 692 |
| 1B | 4-(3-((1-((1,4-Oxazepan-4-yl)methyl)cyclopropyl)meth-oxy)-5-fluoro-1-(3-((R)-2-hydroxypropyl)-3,8-diazabicyclo[3.2.1]octan-8-yl)-7,9-dihydrofuro[3,4-f]quinazolin-6-yl)-2-amino-7-fluorothieno[3,2-c]pyridine-3-carbonitrile | 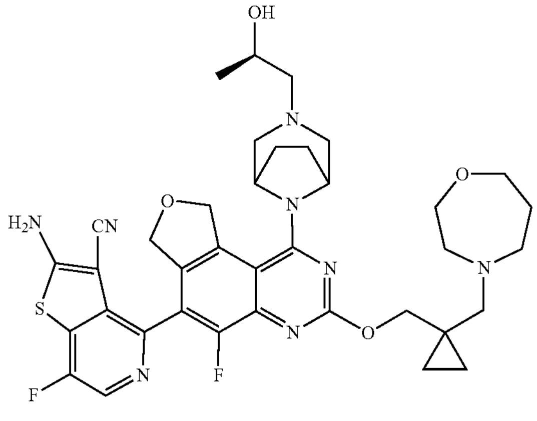 [SMILES: C[C@@H](O)CN1CC2CCC(C1)N2c1nc(OCC2(CN3CCCOCC3)CC2)nc2c(F)c(-c3ncc(F)c4sc(N)c(C#N)c34)c3c(c12)COC3] | 733 |
| 2B | 2-Amino-4-(3-((S)-3-(dimethylamino)pyrrolidin-1-yl)-5-fluoro-1-(3-methyl-3,8-diazabicyclo[3.2.1]octan-8-yl)-7,9-dihydrofuro[3,4-f]quinazolin-6-yl)-7-fluorothieno[3,2-c]pyridine-3-carbonitrile | 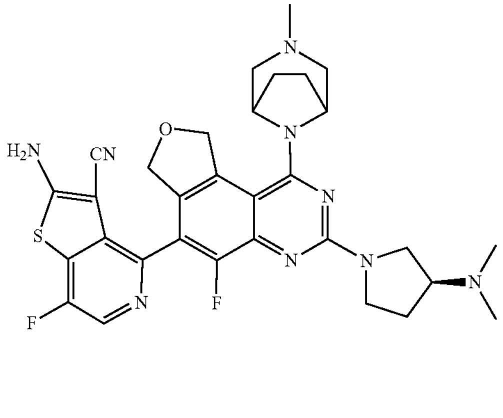 [SMILES: CN1CC2CCC(C1)N2c1nc(N2CC[C@H](N(C)C)C2)nc2c(F)c(-c3ncc(F)c4sc(N)c(C#N)c34)c3c(c12)COC3] | 618 |

TABLE 27-continued

| Example | Chemical Name | Structure | MS (ES) m/z (M + 1) |
|---|---|---|---|
| 3B | 2-Amino-4-(3-((S)-3-(dimethylamino)pyrrolidin-1-yl)-1-(3-ethyl-3,8-diazabicyclo[3.2.1]otan-8-yl)-5-fluoro-7,9-dihydrofuro[3,4-f]quinazolin-6-yl)-7-fluorothieno[3,2-c]pyridine-3-carbonitrile | 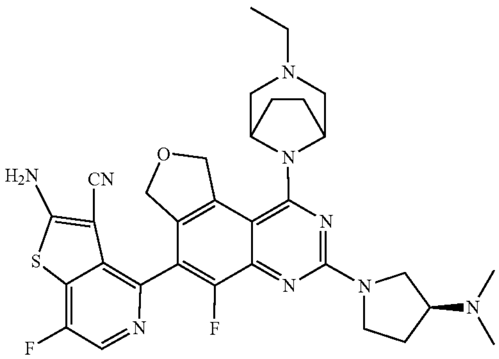 [SMILES: CCN1CC2CCC(C1)N2c1nc(N2CC[C@H](N(C)C)C2)nc2c(F)c(-c3ncc(F)c4sc(N)c(C#N)c34)c3c(c12)COC3] | 632 |
| 4B | 2-Amino-7-fluoro-4-(5-fluoro-1-(3-((R)-2-hydroxypropyl)-3,8-diazabicyclo[3.2.1]octan-8-yl)-3-(5-methylhexahydropyrrolo[3,4-c]pyrrol-2(1H)-yl)-7,9-dihydrofuro[3,4-f]quinazolin-6-yl)thieno[3,2-c]pyridine-3-carbonitrile | 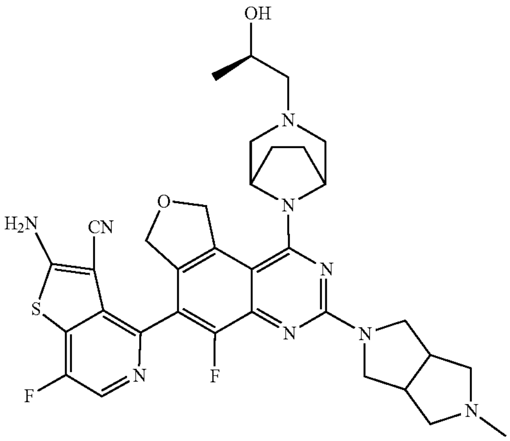 [SMILES: C[C@@H](O)CN1CC2CCC(C1)N2c1nc(N2CC3CN(C)CC3C2)nc2c(F)c(-c3ncc(F)c4sc(N)c(C#N)c34)c3c(c12)COC3] | 674 |
| 5B | 2-Amino-7-fluroo-4-(5-fluoro-1-(3-((R)-2-hydroxypropyl)-3,8-diazabicyclo[3.2.1]octan-8-yl)-3-(1-methyl-1,6-diazaspiro[3.3]heptan-6-yl)-7,9-dihydrofuro[3,4-f]quinazolin-6-yl)thieno[3,2-c]pyridine-3-carbonitrile | 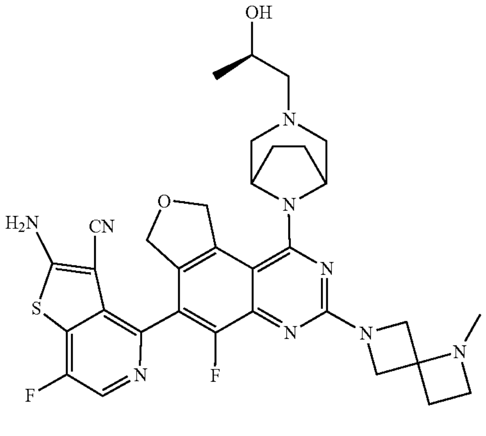 [SMILES: C[C@@H](O)CN1CC2CCC(C1)N2c1nc(N2CC3(CCN3C)C2)nc2c(F)c(-c3ncc(F)c4sc(N)c(C#N)c34)c3c(c12)COC3] | 660 |

TABLE 27-continued

| Example | Chemical Name | Structure | MS (ES) m/z (M + 1) |
| --- | --- | --- | --- |
| 6B | 2-Amino-4-(3-((R)-3-((dimethylamino)methyl) pyrrolidin-1-yl)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 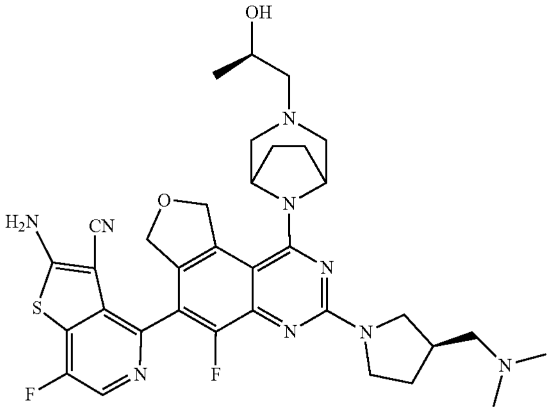 [SMILES: C[C@@H](O)CN1CC2CCC(C1)N2c1nc(N2CC[C@H](CN(C)C)C2)nc2c(F)c(-c3ncc(F)c4sc(N)c(C#N)c34)c3c(c12)COC3] | 676 |
| 7B | 2-Amino-4-(3-((S)-3-(dimethylamino)pyrrolidin-1-yl)-5-fluoro-1-(3-(3-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 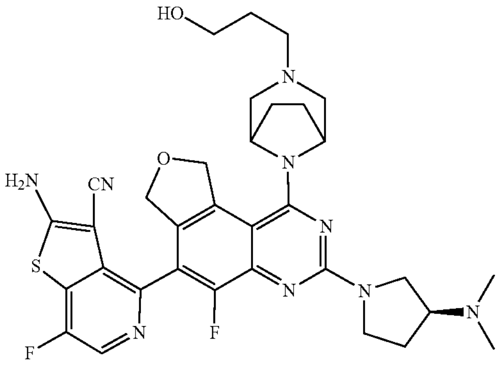 [SMILES: CN(C)[C@H]1CCN(c2nc(N3C4CCC3CN(CCCO)C4)c3c4c(c(-c5ncc(F)c6sc(N)c(C#N)c56)c(F)c3n2)COC4)C1] | 662 |
| 8B | 2-Amino-4-(3-((S)-3-(dimethylamino)pyrrolidin-1-yl)-5-fluoro-1-(3-(3-methoxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 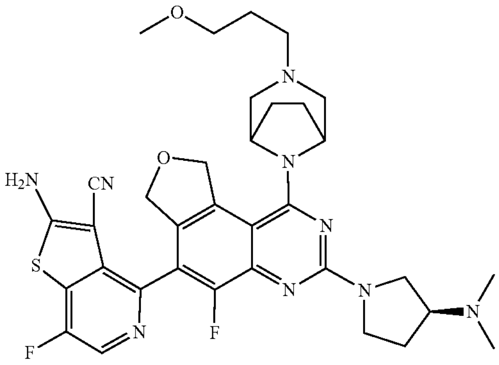 [SMILES: COCCCN1CC2CCC(C1)N2c1nc(N2CC[C@H](N(C)C)C2)nc2c(F)c(-c3ncc(F)c4sc(N)c(C#N)c34)c3c(c12)COC3] | 676 |
| 9B | 2-Amino-4-(3-((S)-3-(dimethylamino)pyrrolidin-1-yl)-5-fluoro-1-(3-(2-methoxyethyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 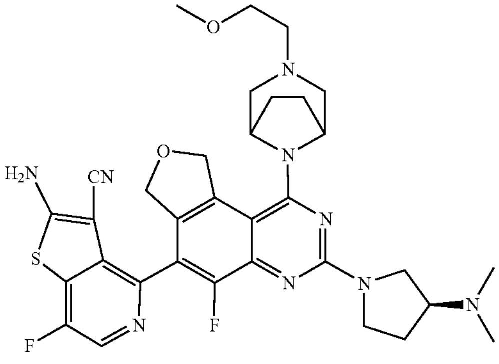 [SMILES: COCCN1CC2CCC(C1)N2c1nc(N2CC[C@H](N(C)C)C2)nc2c(F)c(-c3ncc(F)c4sc(N)c(C#N)c34)c3c(c12)COC3] | 662 |

TABLE 27-continued

| Example | Chemical Name | Structure | MS (ES) m/z (M + 1) |
|---|---|---|---|
| 10B | 2-Amino-4-(3-((S)-3-(dimethylamino)pyrrolidin-1-yl)-5-fluoro-1-(3-(((R)-oxetan-2-yl)methyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 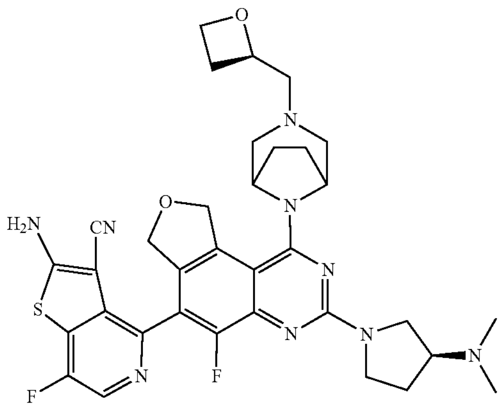 [SMILES: CN(C)[C@H]1CCN(c2nc(N3C4CCC3CN(C[C@H]3CCO3)C4)c3c4c(c(-c5ncc(F)c6sc(N)c(C#N)c56)c(F)c3n2)COC4)C1] | 674 |
| 11B | 2-Amino-4-(3-((S)-3-(diethylamino)pyrrolidin-1-yl)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 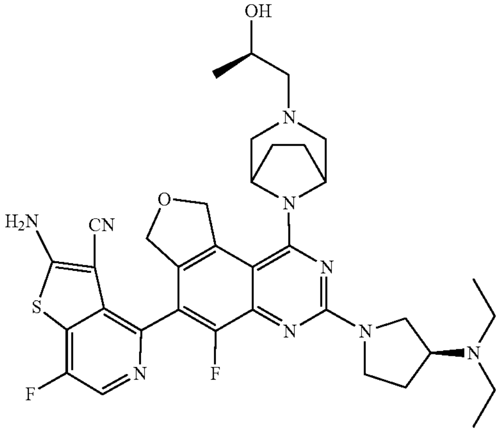 [SMILES: CCN(CC)[C@H]1CCN(c2nc(N3C4CCC3CN(C[C@@H](C)O)C4)c3c4c(c(-c5ncc(F)c6sc(N)c(C#N)c56)c(F)c3n2)COC4)C1] | 690 |
| 12B | 2-Amino-7-fluoro-4-(5-fluoro-1-(3-((R)-2-hydroxypropyl)-3,8-diazabicyclo[3.2.1]octan-8-yl)-3-((3aR,6aR)-1-methylhexahydropyrrolo[3,4-b]pyrrol-5(1H)-yl)-7,9-dihydrofuro[3,4-f]quinazolin-6-yl)thieno[3,2-c]pyridine-3-carbonitrile | 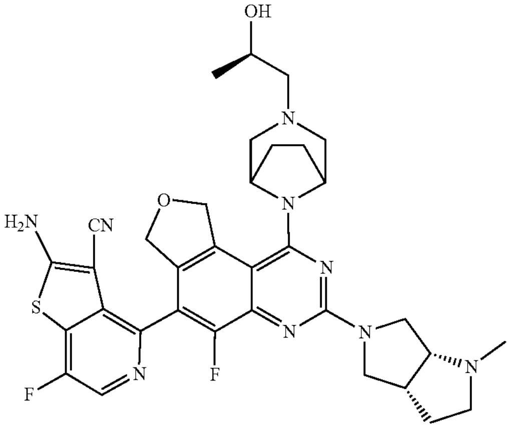 [SMILES: C[C@@H](O)CN1CC2CCC(C1)N2c1nc(N2C[C@H]3CCN(C)[C@H]3C2)nc2c(F)c(-c3ncc(F)c4sc(N)c(C#N)c34)c3c(c12)COC3] | 674 |

TABLE 27-continued

| Example | Chemical Name | Structure | MS (ES) m/z (M + 1) |
|---|---|---|---|
| 13B | 2-Amino-7-fluoro-4-(5-fluoro-1-(3-((R)-2-hydroxypropyl)-3,8-diazabicyclo[3.2.1]octan-8-yl)-3-((3aS,6aS)-1-methylhexahydropyrrolo[3,4-b]pyrrol-5(1H)-yl)-7,9-dihydrofuro[3,4-f]quinazolin-6-yl)thieno[3,2-c]pyridine-3-carbonitrile | 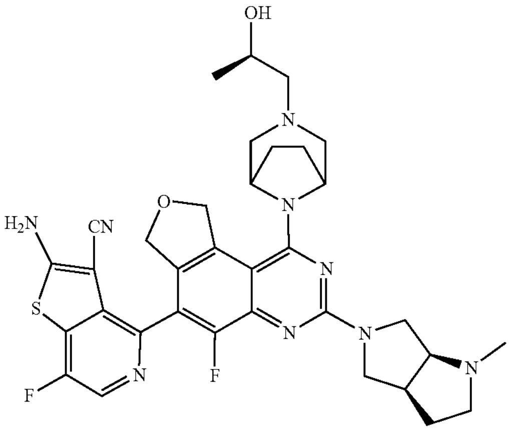 [SMILES: C[C@@H](O)CN1CC2CCC(C1)N2c1nc(N2C[C@@H]3CCN(C)[C@@H]3C2)nc2c(F)c(-c3ncc(F)c4sc(N)c(C#N)c34)c3c(c12)COC3] | 674 |
| 14B | 2-Amino-7-fluoro-4-(5-fluoro-1-(3-((R)-2-hydroxypropyl)-3,8-diazabicyclo[3.2.1]octan-8-yl)-3-(5-methyl-2,5-diazaspiro[3.4]octan-2-yl)-7,9-dihydrofuro[3,4-f]quinazolin-6-yl)thieno[3,2-c]pyridine-3-carbonitrile | 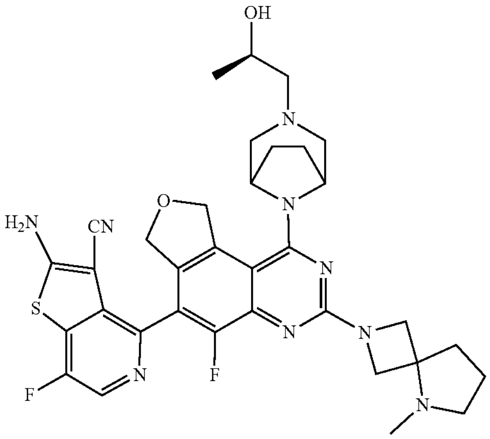 [SMILES: C[C@@H](O)CN1CC2CCC(C1)N2c1nc(N2CC3(CCCN3C)C2)nc2c(F)c(-c3ncc(F)c4sc(N)c(C#N)c34)c3c(c12)COC3] | 674 |
| 15B | 2-Amino-7-fluoro-4-(5-fluoro-3-((S)-hexahydropyrrolo[1,2-a]pyrazin-2(1H)-yl)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 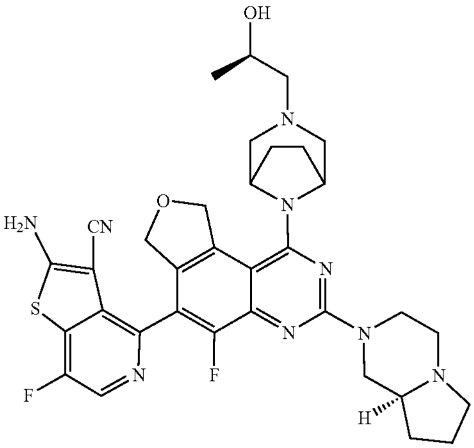 [SMILES: C[C@@H](O)CN1CC2CCC(C1)N2c1nc(N2CCN3CCC[C@H]3C2)nc2c(F)c(-c3ncc(F)c4sc(N)c(C#N)c34)c3c(c12)COC3] | 674 |

TABLE 27-continued

| Example | Chemical Name | Structure | MS (ES) m/z (M + 1) |
| --- | --- | --- | --- |
| 16B | 2-Amino-4-(3-((S)-3-(dimethylamino)-3-methylpyrrolidin-1-yl)-5-fluoro-1-(3-(2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 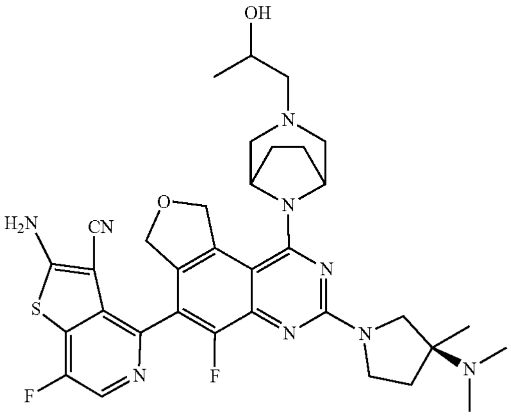 [SMILES: CC(O)CN1CC2CCC(C1)N2c1nc(N2CC[C@](C)(N(C)C)C2)nc2c(F)c(-c3ncc(F)c4sc(N)c(C#N)c34)c3c(c12)COC3] | 676 |
| 17B | 2-Amino-7-fluoro-4-(5-fluoro-1-(3-((R)-2-hydroxypropyl)-3,8-diazabicyclo[3.2.1]octan-8-yl)-3-(3-(pyrrolidin-1-yl)azetidin-1-yl)-7,9-dihydrofuro[3,4-f]quinazolin-6-yl)thieno[3,2-c]pyridine-3-carbonitrile | 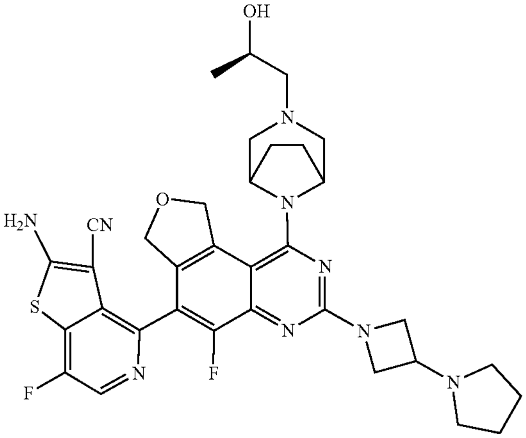 [SMILES: C[C@@H](O)CN1CC2CCC(C1)N2c1nc(N2CC(N3CCCC3)C2)nc2c(F)c(-c3ncc(F)c4sc(N)c(C#N)c34)c3c(c12)COC3] | 674 |
| 18B | 2-Amino-7-fluoro-4-(5-fluoro-1-(3-((R)-2-hydroxypropyl)-3,8-diazabicyclo[3.2.1]octan-8-yl)-3-(3-methyl-3,6-diazabicyclo[3.1.1]heptan-6-yl)-7,9-dihydrofuro[3,4-f]quinazolin-6-yl)thieno[3,2-c]pyridine-3-carbonitrile | 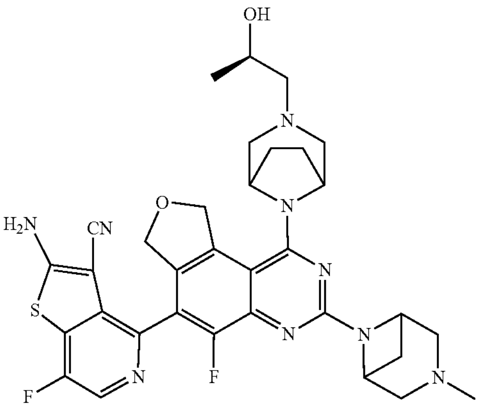 [SMILES: C[C@@H](O)CN1CC2CCC(C1)N2c1nc(N2C3CC2CN(C)C3)nc2c(F)c(-c3ncc(F)c4sc(N)c(C#N)c34)c3c(c12)COC3] | 660 |

TABLE 27-continued

| Example | Chemical Name | Structure | MS (ES) m/z (M + 1) |
|---|---|---|---|
| 19B | 2-Amino-4-(3-((1R,5S,8R)-8-(dimethylamino)-3-azabicyclo[3.2.1]octan-3-yl)-5-fluoro-1-(3-((R)-2-hydroxypropyl)-3,8-diazabicyclo[3.2.1]octan-8-yl)-7,9-dihydrofuro[3,4-f]quinazolin-6-yl)-7-fluorothieno[3,2-c]pyridine-3-carbonitrile | 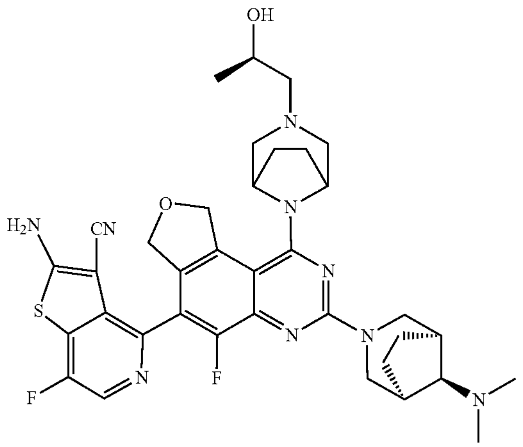 [SMILES: C[C@@H](O)CN1CC2CCC(C1)N2c1nc(N2C[C@H]3CC[C@@H](C2)[C@H]3N(C)C)nc2c(F)c(-c3ncc(F)c4sc(N)c(C#N)c34)c3c(c12)COC3] | 702 |
| 20B | 2-Amino-7-fluoro-4-(5-fluoro-1-(3-((R)-2-hydroxypropyl)-3,8-diazabicyclo[3.2.1]octan-8-yl)-3-((1-(((3aR,6aS)-tetrahydro-1H-furo[3,4-c]pyrrol-5(3H)-yl)methyl)cyclopropyl)methoxy)-7,9-dihydrofuro[3,4-f]quinazolin-6-yl)thieno[3,2-c]pyridine-3-carbonitrile | 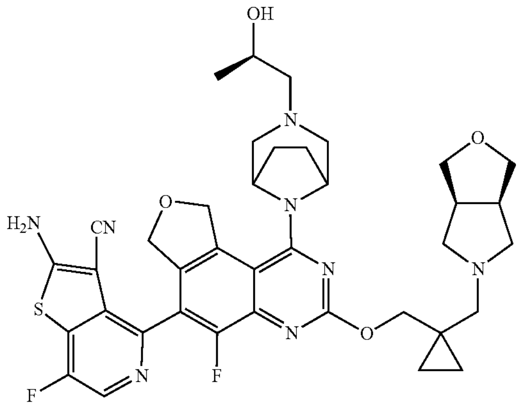 [SMILES: C[C@@H](O)CN1CC2CCC(C1)N2c1nc(OCC2(CN3C[C@H]4COC[C@H]4C3)CC2)nc2c(F)c(-c3ncc(F)c4sc(N)c(C#N)c34)c3c(c12)COC3] | 745 |
| 21B | 2-Amino-7-fluoro-4-(5-fluoro-3-((1-(((S)-2-(fluoromethyl)azetidin-1-yl)methyl)cyclopropyl)methoxy)-1-(3-((R)-2-hydroxypropyl)-3,8-diazabicyclo[3.2.1]octan-8-yl)-7,9-dihydrofuro[3,4-f]quinazolin-6-yl)thieno[3,2-c]pyridine-3-carbonitrile | 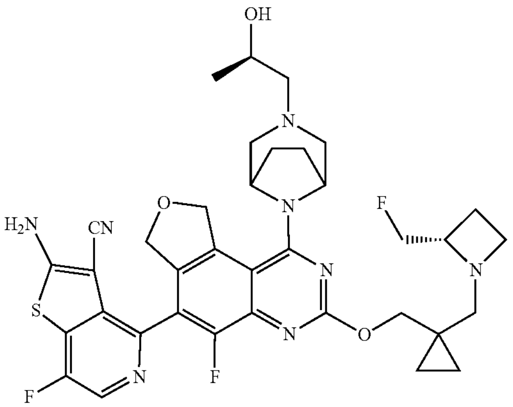 [SMILES: C[C@@H](O)CN1CC2CCC(C1)N2c1nc(OCC2(CN3CC[C@H]3CF)CC2)nc2c(F)c(-c3ncc(F)c4sc(N)c(C#N)c34)c3c(c12)COC3] | 721 |

TABLE 27-continued

| Example | Chemical Name | Structure | MS (ES) m/z (M + 1) |
|---|---|---|---|
| 22B | 2-Amino-7-fluoro-4-(5-fluoro-1-(3-((R)-2-hydroxypropyl)-3,8-diazabicyclo[3.2.1]octan-8-yl)-3-((1-(((S)-2-(methoxymethyl)azetidin-1-yl)methyl)cyclopropyl)methoxy)-7,9-dihydrofuro[3,4-f]quinazolin-6-yl)thieno[3,2-c]pyridine-3-carbonitrile | 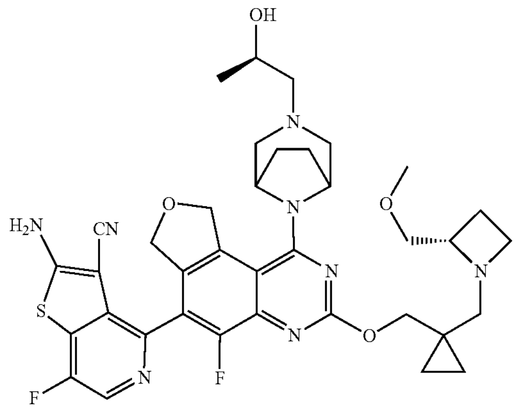 [SMILES: COC[C@@H]1CCN1CC1(COc2nc(N3C4CCC3CN(C[C@@H](C)O)C4)c3c4c(c(-c5ncc(F)c6sc(N)c(C#N)c56)c(F)c3n2)COC4)CC1] | 733 |
| 23B [2] | 2-Amino-4-(3-((S)-3-(dimethylamino)pyrrolidin-1-yl)-5-fluoro-1-(3-((R)-2-hydroxypropyl)-3,8-diazabicyclo[3.2.1]octan-8-yl)-7,9-dihydrofuro[3,4-f]quinazolin-6-yl)-5-fluorobenzo[b]thiophene-3-carbonitrile | 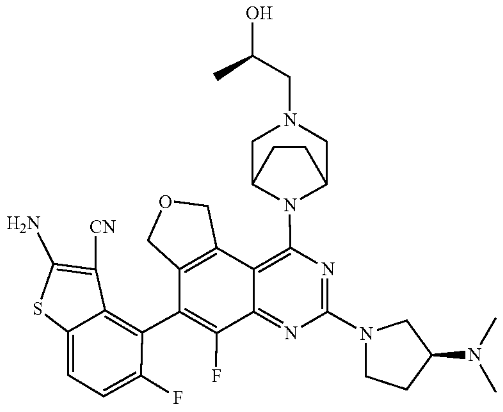 [SMILES: C[C@@H](O)CN1CC2CCC(C1)N2c1nc(N2CC[C@H](N(C)C)C2)nc2c(F)c(-c3c(F)ccc4sc(N)c(C#N)c34)c3c(c12)COC3] | 661 |
| 24B [3] | 2-Amino-4-(5-chloro-3-((S)-3-(dimethylamino)pyrrolidin-1-yl)-1-(3-((R)-2-hydroxypropyl)-3,8-diazabicyclo[3.2.1]octan-8-yl)-7,9-dihydrofuro[3,4-f]quinazolin-6-yl)-7-fluorobenzo[b]thiophene-3-carbonitrile. Atropisomer 1 | 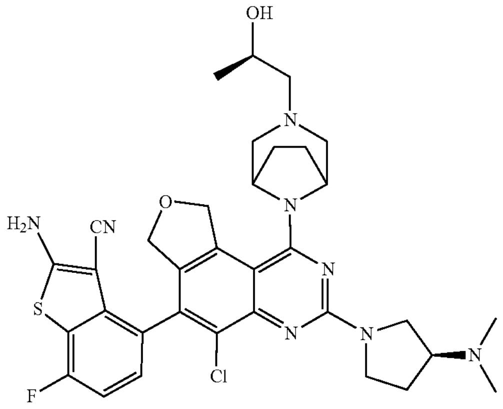 [SMILES: C[C@@H](O)CN1CC2CCC(C1)N2c1nc(N2CC[C@H](N(C)C)C2)nc2c(Cl)c(-c3ccc(F)c4sc(N)c(C#N)c34)c3c(c12)COC3] | 677 |

TABLE 27-continued

| Example | Chemical Name | Structure | MS (ES) m/z (M + 1) |
| --- | --- | --- | --- |
| 25B [3] | 2-Amino-4-(5-chlroo-3-((S)-3-(dimethylamino)pyrrolidin-1-yl)-1-(3-((R)-2-hydroxypropyl)-3,8-diazabicyclo[3.2.1]octan-8-yl)-7,9-dihydrofuro[3,4-f]quinazolin-6-yl)-7-fluorobenzo[b]thiophene-3-carbonitrile. Atropisomer 2 | 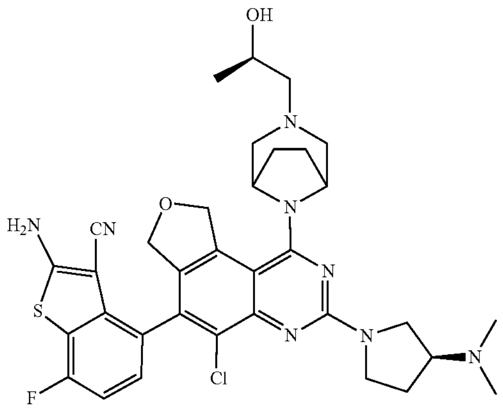 [SMILES: C[C@@H](O)CN1CC2CCC(C1)N2c1nc(N2CC[C@H](N(C)C)C2)nc2c(Cl)c(-c3ccc(F)c4sc(N)c(C#N)c34)c3c(c12)COC3] | 677 |
| 26B [4] | 2-Amino-4-(5-chloro-3-((S)-3-(dimethylamino)pyrrolidin-1-yl)-1-(3-((R)-2-hydroxypropyl)-3,8-diazabicyclo[3.2.1]octan-8-yl)-7,9-dihydrofuro[3,4-f]quinazolin-6-yl)-5-fluorobenzo[b]thiophene-3-carbonitrile, Atropisomer 1 | 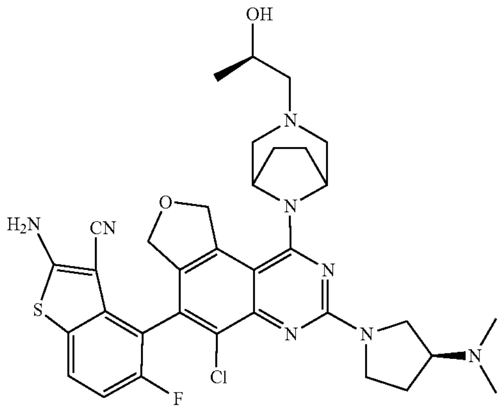 [SMILES: C[C@@H](O)CN1CC2CCC(C1)N2c1nc(N2CC[C@H](N(C)C)C2)nc2c(Cl)c(-c3c(F)ccc4sc(N)c(C#N)c34)c3c(c12)COC3] | 677 |
| 27B [4] | 2-Amino-4-(5-chloro-3-((S)-3-(dimethylamino)pyrrolidin-1-yl)-1-(3-((R)-2-hydroxypropyl)-3,8-diazabicyclo[3.2.1]octan-8-yl)-7,9-dihydrofuro[3,4-f]quinazolin-6-yl)-5-fluorobenzo[b]thiophene-3-carbonitrile, Atropisomer 2 | 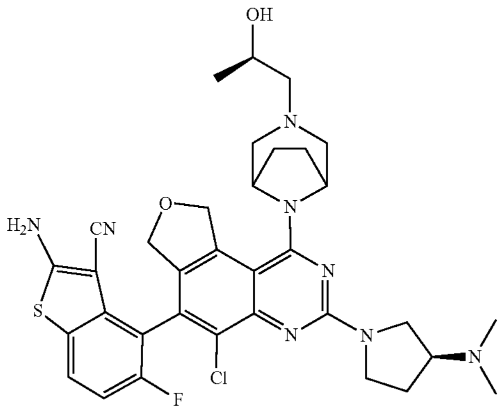 [SMILES: C[C@@H](O)CN1CC2CCC(C1)N2c1nc(N2CC[C@H](N(C)C)C2)nc2c(Cl)c(-c3c(F)ccc4sc(N)c(C#N)c34)c3c(c12)COC3] | 677 |

[1] Prep-Chiral-HPLC; CHIRAL ART Cellulose-SZ, 20 x 250 mm, 50% Hexanes (with 10 mM ammoniated methanol: 50% EtOH, 20 mL/min

[2] Single atropisomer (from precursor in Preparation 9B)

[3] Prep-Chiral-HPLC; CHIRAL ART Cellulose-SZ, 30 x 250 mm, 50% Hexanes (with 10 mM ammoniated methanol): 50% EtOH, 40 mL/min

[4] Prep-Chiral-HPLC; Chiralpak-IG, 30 x 250 mm, 10% MeOH in (1:1 Hexanes:MTBE w/0.5% 2M ammoniated methanol), 40 mL/min Example 29A 2-Amino-7-fluoro-4-(5-fluoro-3-((3 a R,6aS)-5-methylhexahydropyrrolo[3,4-c]pyrrol-2(1H)-yl)-7,9-dihydrofuro[3,4-f]quinazolin-6-yl)thieno[3,2-c]pyridine-3-carbonitrile

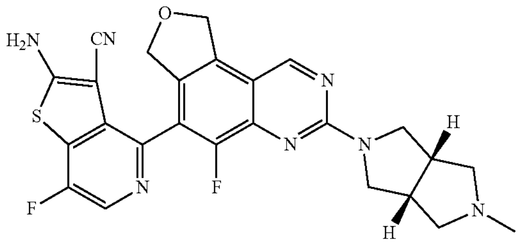 [SMILES: CN1C[C@@H]2CN(c3ncc4c5c(c(-c6ncc(F)c7sc(N)c(C#N)c67)c(F)c4n3)COC5)C[C@@H]2C1]

2-Amino-7-fluoro-4-(5-fluoro-3-((3aR,6aS)-hexahydropyrrolo[3,4-c]pyrrol-2(1H)-yl)-7,9-dihydrofuro[3,4-f]quinazolin-6-yl)thieno[3,2-c]pyridine-3-carbonitrile and formaldehyde (with acetic acid as the solvent) were used in a manner analogous to the method of Example 1 to afford the title compound (0.014 g, 48%). MS (ES) m/z=506 (M+1).

Example 30A

2-Amino-7-fluoro-4-(5-fluoro-3-((S)-1-methyl-1,6-diazaspiro[3.4]octan-6-yl)-7,9-dihydrofuro[3,4-f]quinazolin-6-yl)thieno[3,2-c]pyridine-3-carbonitrile

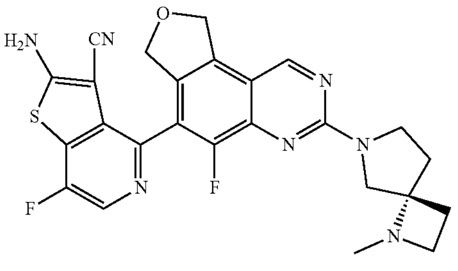 [SMILES: CN1CC[C@@]12CCN(c1ncc3c4c(c(-c5ncc(F)c6sc(N)c(C#N)c56)c(F)c3n1)COC4)C2]

2-Amino-7-fluoro-4-(5-fluoro-3-((S)-1,6-diazaspiro[3.4]octan-6-yl)-7,9-dihydrofuro[3,4-f]quinazolin-6-yl)thieno[3,2-c]pyridine-3-carbonitrile and formaldehyde (with acetic acid as the solvent) were used in a manner analogous to the method of Example 1 to afford the title compound (0.028 g, 51%). MS (ES) m/z=506 (M+1).

Example 19

2-Amino-7-fluoro-4-(5-fluoro-3-((1-(morpholinomethyl)cyclopropyl)methoxy)-7,9-dihydrofuro[3,4-f]quinazolin-6-yl)thieno[3,2-c]pyridine-3-carbonitrile

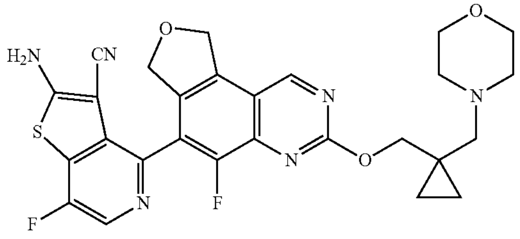

tert-Butyl(3-cyano-7-fluoro-4-(5-fluoro-3-((1-(morpholinomethyl)cyclopropyl)methoxy)-7,9-dihydrofuro[3,4-f]quinazolin-6-yl)thieno[3,2-c]pyridin-2-yl)carbamate (0.33 g, 0.51 mmol) and 1,1,1,3,3,3-hexafluoropropan-2-ol (4 mL) were combined. The mixture was stirred for 1 h at 100° C., then concentrated under reduced pressure. The residue was purified by reversed phase purification, eluting with 31% to 48% ACN in 10 mM aq. $NH_4HCO_3$, followed by lyophilization, to give the title compound (0.070 g, 29%) as a white solid. MS (ES) m/z=551 (M+1).

The following compounds in Table 28 were prepared in similar manner as described in Preparation 94 or Example 19. Various deprotecting reagents, such as HCl, TFA, or TBAF, were used. Various methods were used to purify the compounds, which would be apparent to one skilled in the art.

TABLE 28

| Example | Chemical Name | Structure | MS (ES) m/z (M + 1) |
|---|---|---|---|
| 20 | 2-Amino-7-fluoro-4-(5-fluoro-3-((1-(((S)-3-fluoropyrrolidin-1-yl)methyl)cyclopropyl) methoxy)-7,9-dihydrofuro[3,4-f]quinazolin-6-yl)thieno[3,2-c]pyridine-3-carbonitrile | 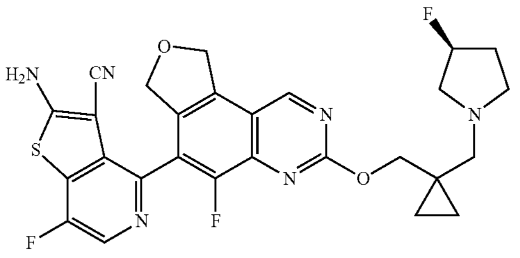 [SMILES: N#Cc1c(N)sc2c(F)cnc(-c3c4c(c5cnc(OCC6(CN7CC[C@H](F)C7)CC6)nc5c3F)COC4)c12] | 553 |

TABLE 28-continued

| Example | Chemical Name | Structure | MS (ES) m/z (M + 1) |
|---|---|---|---|
| 21 | 2-Amino-7-fluoro-4-(5-fluoro-3-((1-(((R)-3-fluoropyrrolidin-1-yl)methyl)cyclopropyl)methoxy)-7,9-dihydrofuro[3,4-f]quinazolin-6-yl)thieno[3,2-c]pyridine-3-carbonitrile | 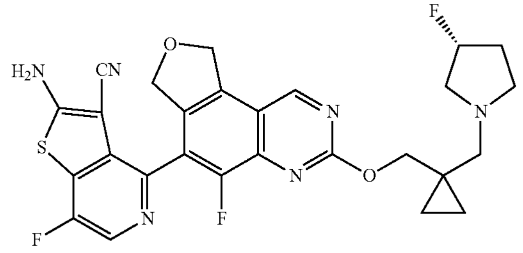 [SMILES: N#Cc1c(N)sc2c(F)cnc(-c3c4c(c5cnc(OCC6(CN7CC[C@@H](F)C7)CC6)nc5c3F)COC4)c12] | 553 |
| 22 | 2-Amino-7-fluoro-4-(5-fluoro-3-((1-((4-methylpiperazin-1-yl)methyl)cyclopropyl)methoxy)-7,9-dihydrofuro[3,4-f]quinazolin-6-yl)thieno[3,2-c]pyridine-3-carbonitrile | 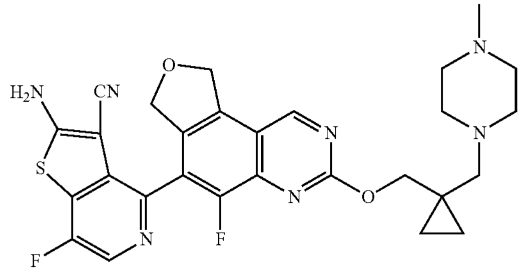 [SMILES: CN1CCN(CC2(COc3ncc4c5c(c(-c6ncc(F)c7sc(N)c(C#N)c67)c(F)c4n3)COC5)CC2)CC1] | 564 |
| 23 | 2-Amino-7-fluoro-4-(5-fluoro-3-((1-(morpholinomethyl)cyclobutyl)methoxy)-7,9-dihydrofuro[3,4-f]quinazolin-6-yl)thieno[3,2-c]pyridine-3-carbonitrile | 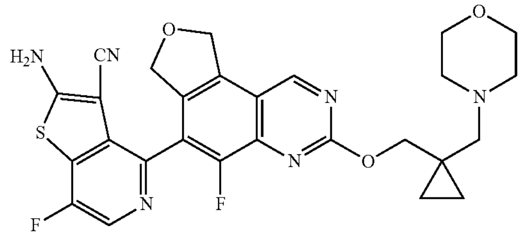 [SMILES: N#Cc1c(N)sc2c(F)cnc(-c3c4c(c5cnc(OCC6(CN7CCOCC7)CC6)nc5c3F)COC4)c12] | 565 |
| 24 | 2-Amino-4-(3-((1-(azetidin-1-ylmethyl)cyclopropyl)methoxy)-5-fluoro-7,9-dihydrofuro[3,4-f]quinazolin-6-yl)-7-fluorothieno[3,2-c]pyridine-3-carbonitrile | 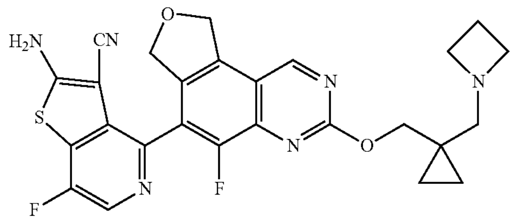 [SMILES: N#Cc1c(N)sc2c(F)cnc(-c3c4c(c5cnc(OCC6(CN7CCC7)CC6)nc5c3F)COC4)c12] | 521 |
| 25 | 4-(3-((1-((6-Oxa-2-azaspiro[3.4]octan-2-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 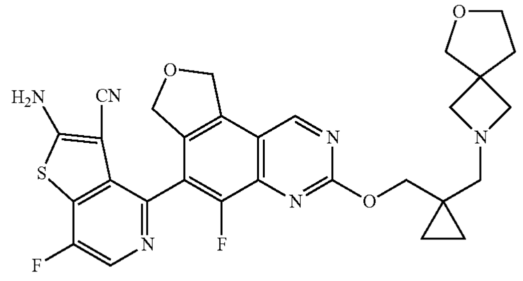 [SMILES: N#Cc1c(N)sc2c(F)cnc(-c3c4c(c5cnc(OCC6(CN7CC8(CCOC8)C7)CC6)nc5c3F)COC4)c12] | 577 |

TABLE 28-continued

| Example | Chemical Name | Structure | MS (ES) m/z (M + 1) |
| --- | --- | --- | --- |
| 26 | 2-Amino-4-(3-((1-((6,6-difluoro-3-azabicyclo[3.1.0]hexan-3-yl)methyl)cyclopropyl) methoxy)-5-fluoro-7,9-dihydrofuro[3,4-f]quinazolin-6-yl)-7-fluorothieno[3,2-c]pyridine-3-carbonitrile | 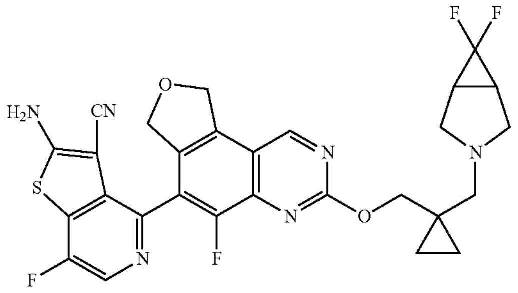 | 583 |
| 27 | 2-Amino-7-fluoro-4-(5-fluoro-3-((1-((3-fluoroazetidin-1-yl)methyl)cyclopropyl) methoxy)-7,9-dihydrofuro[3,4-f]quinazolin-6-yl)thieno[3,2-c]pyridine-3-carbonitrile | 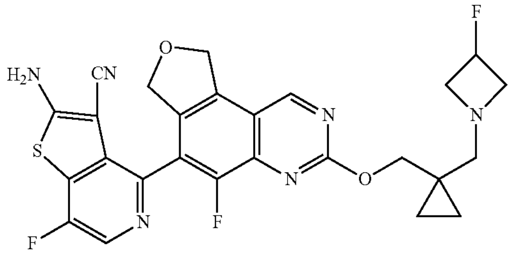 [SMILES: N#Cc1c(N)sc2c(F)cnc(-c3c4c(c5cnc(OCC6(CN7CC(F)C7)CC6)nc5c3F)COC4)c12] | 539 |
| 28 | 2-Amino-4-(3-((1-((4,4-difluoropiperidin-1-yl)methyl)cyclopropyl) methoxy)-5-fluoro-7,9-dihydrofuro[3,4-f]quinazolin-6-yl)-7-fluorothieno[3,2-c]pyridine-3-carbonitrile | 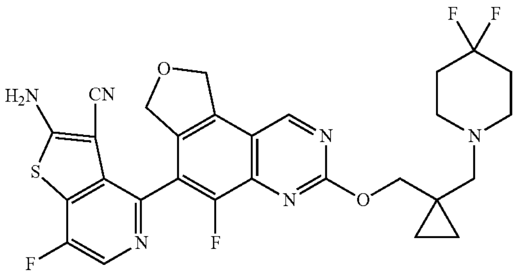 [SMILES: N#Cc1c(N)sc2c(F)cnc(-c3c4c(c5cnc(OCC6(CN7CCC(F)(F)CC7)CC6)nc5c3F)COC4)c12] | 585 |
| 29 | 4-(3-((1-(((1S,4S)-2-Oxa-5-azabicyclo[2.2.1]heptan-5-yl)methyl)cyclopropyl) methoxy)-5-fluoro-7,9-dihydrofuro[3,4-f]quinazolin-6-yl)-2-amino-7-fluorothieno[3,2-c]pyridine-3-carbonitrile | 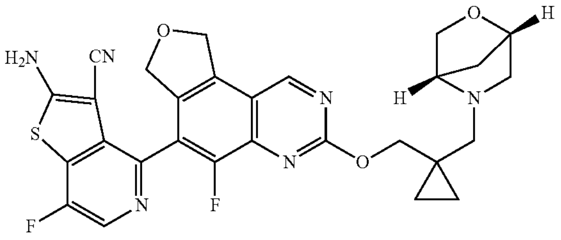 [SMILES: N#Cc1c(N)sc2c(F)cnc(-c3c4c(c5cnc(OCC6(CN7C[C@@H]8C[C@H]7CO8)CC6)nc5c3F)COC4)c12] | 563 |
| 30 | 2-Amino-4-(3-(2,2-dimethyl-3-morpholinopropoxy)-5-fluoro-7,9-dihydrofuro[3,4-f]quinazolin-6-yl)-7-fluorothieno[3,2-c]pyridine-3-carbonitrile | 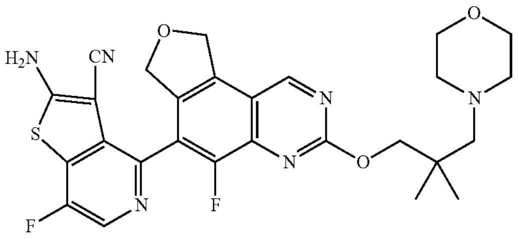 [SMILES: CC(C)(COc1ncc2c3c(c(-c4ncc(F)c5sc(N)c(C#N)c45)c(F)c2n1)COC3)CN1CCOCC1] | 553 |

TABLE 28-continued

| Example | Chemical Name | Structure | MS (ES) m/z (M + 1) |
| --- | --- | --- | --- |
| 31 | 2-Amino-7-fluoro-4-(5-fluoro-3-((1-((3-(2-hydroxypropan-2-yl)azetidin-1-yl)methyl)cyclopropyl)methoxy)-7,9-dihydrofuro[3,4-f]quinazolin-6-yl)thieno[3,2-c]pyridine-3-carbonitrile | 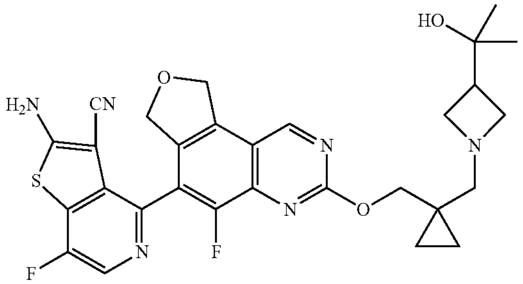 [SMILES: CC(C)(O)C1CN(CC2(COc3ncc4c5c(c(-c6ncc(F)c7sc(N)c(C#N)c67)c(F)c4n3)COC5)CC2)C1] | 579 |
| 32 | 2-Amino-4-(3-((1-((4-ethyl-3-oxopiperazin-1-yl)methyl)cyclopropyl)methoxy)-5-fluoro-7,9-dihydrofuro[3,4-f]quinazolin-6-yl)-7-fluorothieno[3,2-c]pyridine-3-carbonitrile | 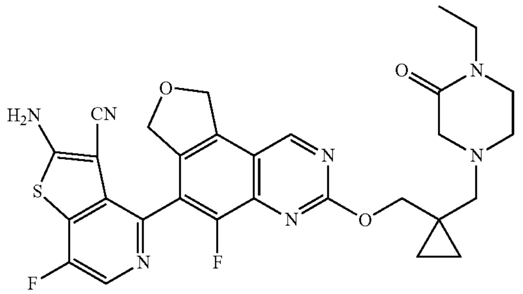 [SMILES: CCN1CCN(CC2(COc3ncc4c5c(c(-c6ncc(F)c7sc(N)c(C#N)c67)c(F)c4n3)COC5)CC2)CC1=O] | 592 |
| 33 | 4-(3-((1-((7-Oxa-2-azaspiro[3.5]nonan-2-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 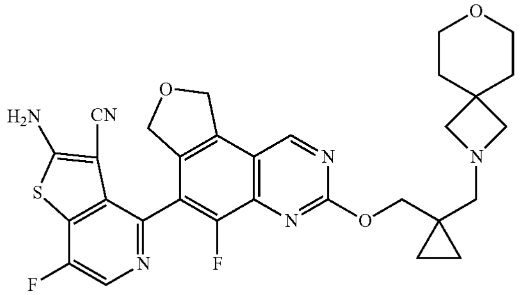 [SMILES: N#Cc1c(N)sc2c(F)cnc(-c3c4c(c5cnc(OCC6(CN7CC8(CCOCC8)C7)CC6)nc5c3F)COC4)c12] | 591 |
| 34 | 2-Amino-4-(3-((2,2-difluoro-1-(morpholinomethyl)cyclopropyl)methoxy)-5-fluoro-7,9-dihydrofuro[3,4-f]quinazolin-6-yl)-7-fluorothieno[3,2-c]pyridine-3-carbonitrile, Isomer 1 | 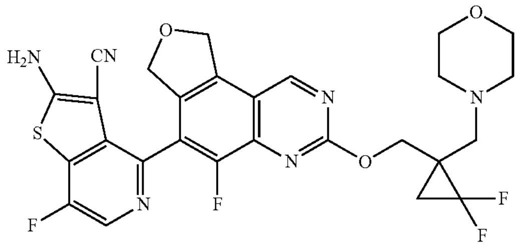 [SMILES: N#Cc1c(N)sc2c(F)cnc(-c3c4c(c5cnc(OCC6(CN7CCOCC7)CC6(F)F)nc5c3F)COC4)c12] | 587 |
| 35 | 2-Amino-4-(3-((2,2-difluoro-1-(morpholinomethyl)cyclopropyl)methoxy)-5-fluoro-7,9-dihydrofuro[3,4-f]quinazolin-6-yl)-7-fluorothieno[3,2-c]pyridine-3-carbonitrile, Isomer 2 | 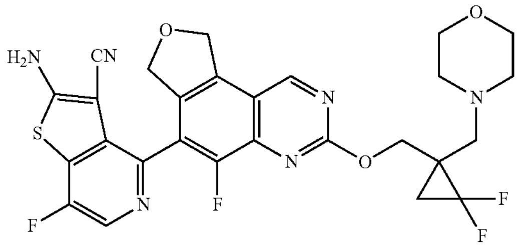 [SMILES: N#Cc1c(N)sc2c(F)cnc(-c3c4c(c5cnc(OCC6(CN7CCOCC7)CC6(F)F)nc5c3F)COC4)c12] | 587 |

TABLE 28-continued

| Example | Chemical Name | Structure | MS (ES) m/z (M + 1) |
|---|---|---|---|
| 36 | 2-Amino-7-fluoro-4-(5-fluoro-7-((1-(morpholinomethyl) cyclopropyl)methoxy)-1,3-dihydrofuro[3,4-f]quinolin-4-yl)thieno[3,2-c]pyridine-3-carbonitrile | 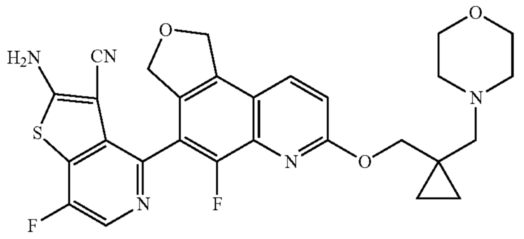 [SMILES: N#Cc1c(N)sc2c(F)cnc(-c3c4c(c5ccc(OCC6(CN7CCOCC7)CC6)nc5c3F)COC4)c12] | 550 |
| 37 | 2-Amino-7-fluoro-4-(5-fluoro-1-(3-((R)-2-hydroxypropyl)-3,8-diazabicyclo[3.2.1]octan-8-yl)-3-((1-(morpholinomethyl-d2)cyclopropyl)methoxy-d2)-7,9-dihydrofuro[3,4-f]quinazolin-6-yl)thieno[3,2-c]pyridine-3-carbonitrile | 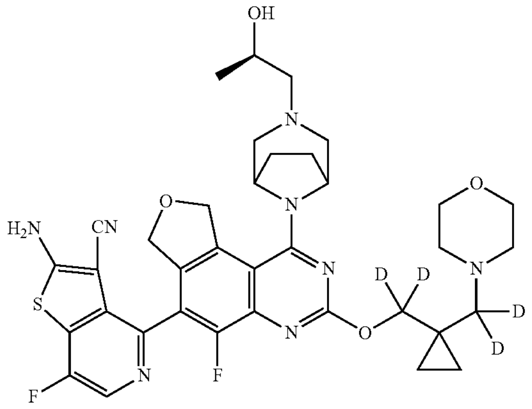 [SMILES: [2H]C([2H])(Oc1nc(N2C3CCC2CN(C[C@@H](C)O)C3)c2c3c(c(-c4ncc(F)c5sc(N)c(C#N)c45)c(F)c2n1)COC3)C1(C([2H])([2H])N2CCOCC2)CC1] | 723 |
| 31A | 4-(3-((1-((1,4-Oxazepan-4-yl)methyl)cyclopropyl) methoxy)-5-fluoro-7,9-dihydrofuro[3,4-f]quinazolin-6-yl)-2-amino-7-fluorothieno[3,2-c]pyridine-3-carbonitrile | 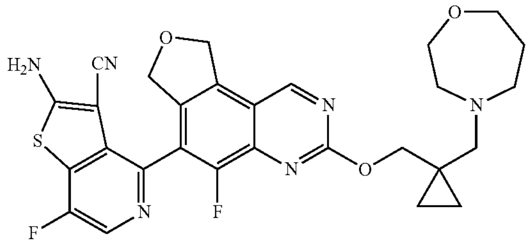 [SMILES: N#Cc1c(N)sc2c(F)cnc(-c3c4c(c5cnc(OCC6(CN7CCCOCC7)CC6)nc5c3F)COC4)c12] | 565 |
| 32A | 2-Amino-7-fluoro-4-(5-fluoro-3-((1-((4-fluoropiperidin-1-yl)methyl)cyclopropyl) methoxy)-7,9-dihydrofuro[3,4-f]quinazolin-6-yl)thieno[3,2-c]pyridine-3-carbonitrile | 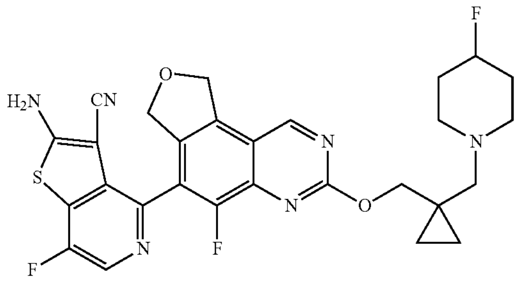 [SMILES: N#Cc1c(N)sc2c(F)cnc(-c3c4c(c5cnc(OCC6(CN7CCC(F)CC7)CC6)nc5c3F)COC4)c12] | 567 |
| 33A | 4-(3-((1-((3-Oxa-8-azabicyclo[3.2.1]octan-8-yl)methyl)cyclopropyl) methoxy)-5-fluoro-7,9-dihydrofuro[3,4-f]quinazolin-6-yl)-2-amino-7-fluorothieno[3,2-c]pyridine-3-carbonitrile | 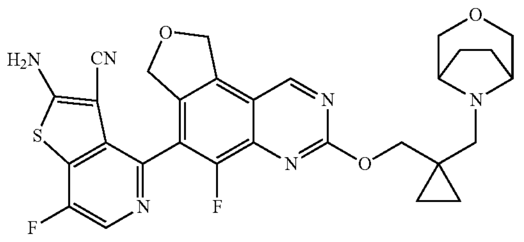 [SMILES: N#Cc1c(N)sc2c(F)cnc(-c3c4c(c5cnc(OCC6(CN7C8CCC7COC8)CC6)nc5c3F)COC4)c12] | 577 |

TABLE 28-continued

| Example | Chemical Name | Structure | MS (ES) m/z (M + 1) |
|---|---|---|---|
| 34A | 4-(3-((1-(((1R,4R)-2-Oxa-5-azabicyclo[2.2.1 ]heptan-5-yl)methyl)cyclopropyl)methoxy)-5-fluoro-7,9-dihydrofuro[3,4-f]quinazolin-6-yl)-2-amino-7-fluorothieno[3,2-c]pyridine-3-carbonitrile | 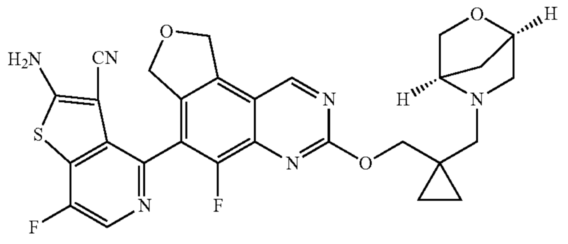 [SMILES: N#Cc1c(N)sc2c(F)cnc(-c3c4c(c5cnc(OCC6(CN7C[C@H]8C[C@@H]7CO8)CC6)nc5c3F)COC4)c12] | 563 |
| 35A | 2-Amino-7-fluoro-4-(5-fluoro-3-(3-morpholinoazetidin-1-yl)-7,9-dihydrofuro[3,4-f]quinazolin-6-yl)thieno[3,2-c]pyridine-3-carbonitrile | 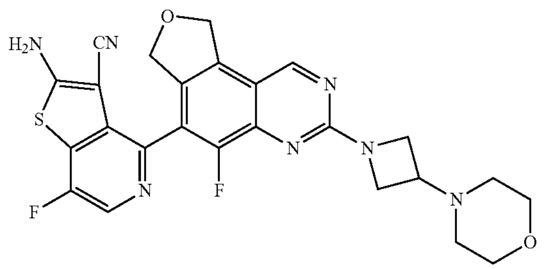 | 522 |
| 36A | 2-Amino-7-fluoro-4-(5-fluoro-3-(3-(methyl(oxetan-3-yl)amino)azetidin-1-yl)-7,9-dihydrofuro[3,4-f]quinazolin-6-yl)thieno[3,2-c]pyridine-3-carbonitrile | 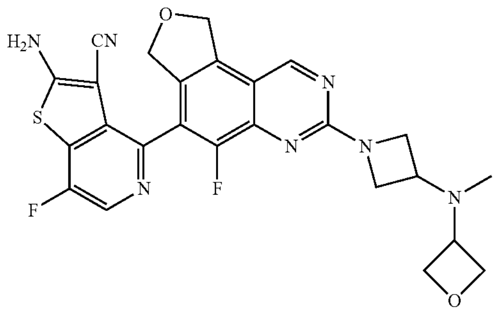 [SMILES: CN(C1COC1)C1CN(c2ncc3c4c(c(-c5ncc(F)c6sc(N)c(C#N)c56)c(F)c3n2)COC4)C1] | 522 |
| 37A | 2-Amino-7-fluoro-4-(5-fluoro-3-(3-((S)-3-fluoropyrrolidin-1-yl)azetidin-1-yl)-7,9-dihydrofuro[3,4-f]quinazolin-6-yl)thieno[3,2-c]pyridine-3-carbonitrile | 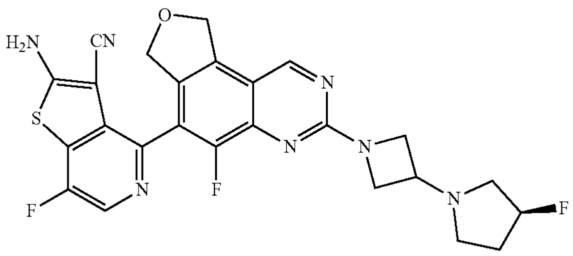 [SMILES: N#Cc1c(N)sc2c(F)cnc(-c3c4c(c5cnc(N6CC(N7CC[C@H](F)C7)C6)nc5c3F)COC4)c12] | 524 |
| 38A | 2-Amino-7-fluoro-4-(5-fluoro-3-(3-((R)-3-fluoropyrrolidin-1-yl)azetidin-1-yl)-7,9-dihydrofuro[3,4-f]quinazolin-6-yl)thieno[3,2-c]pyridine-3-carbonitrile | 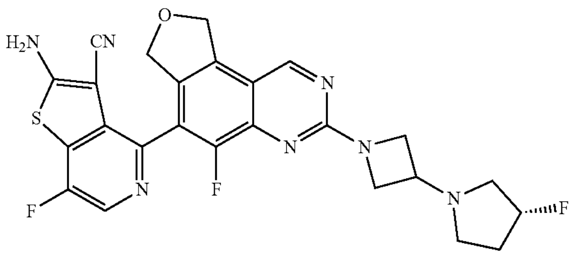 [SMILES: N#Cc1c(N)sc2c(F)cnc(-c3c4c(c5cnc(N6CC(N7CC[C@@H](F)C7)C6)nc5c3F)COC4)c12] | 524 |

TABLE 28-continued

| Example | Chemical Name | Structure | MS (ES) m/z (M + 1) |
|---|---|---|---|
| 39A | 2-Amino-4-(3-(3-(cyclopropyl(methyl)amino)azetidin-1-yl)-5-fluoro-7,9-dihydrofuro[3,4-f]quinazolin-6-yl)-7-fluorothieno[3,2-c]pyridine-3-carbonitrile | 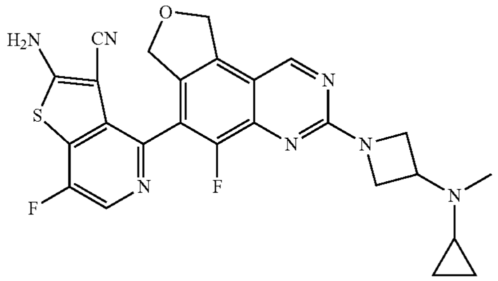 [SMILES: CN(C1CC1)C1CN(c2ncc3c4c(c(-c5ncc(F)c6sc(N)c(C#N)c56)c(F)c3n2)COC4)C1] | 506 |
| 40A | 2-Amino-4-(3-(3-(1-(dimethylamino)cyclopropyl)azetidin-1-yl)-5-fluoro-7,9-dihydrofuro[3,4-f]quinazolin-6-yl)-7-fluorothieno[3,2-c]pyridine-3-carbonitrile | 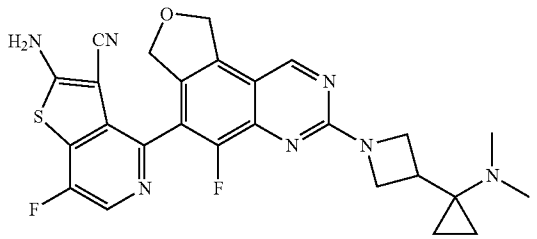 [SMILES: CN(C)C1(C2CN(c3ncc4c5c(c(-c6ncc(F)c7sc(N)c(C#N)c67)c(F)c4n3)COC5)C2)CC1] | 520 |
| 41A | 2-Amino-7-fluoro-4-(5-fluoro-3-(1-methyl-1,6-diazaspiro[3.3]heptan-6-yl)-7,9-dihydrofuro[3,4-f]quinazolin-6-yl)thieno[3,2-c]pyridine-3-carbonitrile | 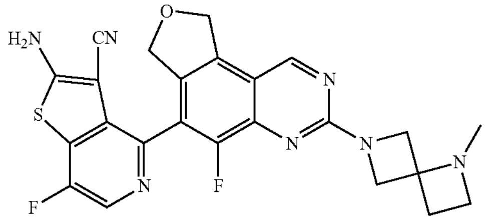 [SMILES: CN1CCC12CN(c1ncc3c4c(c(-c5ncc(F)c6sc(N)c(C#N)c56)c(F)c3n1)COC4)C2] | 492 |
| 42A | 2-Amino-4-(3-((S)-3-(dimethylamino)pyrrolidin-1-yl)-5-fluoro-7,9-dihydrofuro[3,4-f]quinazolin-6-yl)-7-fluorothieno[3,2-c]pyridine-3-carbonitrile | 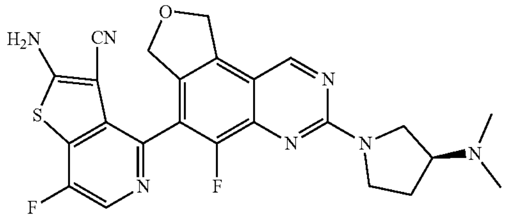 [SMILES: CN(C)[C@H]1CCN(c2ncc3c4c(c(-c5ncc(F)c6sc(N)c(C#N)c56)c(F)c3n2)COC4)C1] | 494 |
| 43A [1] | rel-2-Amino-4-(3-((3R,4R)-3-(dimethylamino)-4-hydroxypyrrolidin-1-yl)-5-fluoro-7,9-dihydrofuro[3,4-f]quinazolin-6-yl)-7-fluorothieno[3,2-c]pyridine-3-carbonitrile, Trans Isomer 1 | 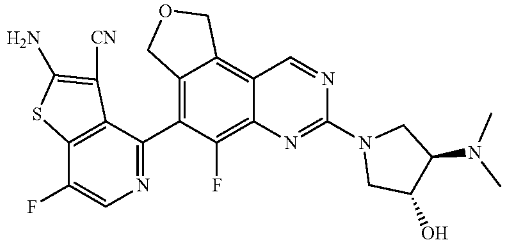 [SMILES: CN(C)[C@@H]1CN(c2ncc3c4c(c(-c5ncc(F)c6sc(N)c(C#N)c56)c(F)c3n2)COC4)C[C@H]1O] | 510 |
| 44A [1] | rel-2-Amino-4-(3-((3R,4R)-3-(dimethylamino)-4-hydroxypyrrolidin-1-yl)-5-fluoro-7,9-dihydrofuro[3,4-f]quinazolin-6-yl)-7-fluorothieno[3,2-c]pyridine-3-carbonitrile, Trans Isomer 2 | 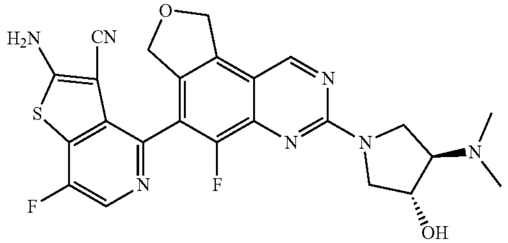 [SMILES: CN(C)[C@@H]1CN(c2ncc3c4c(c(-c5ncc(F)c6sc(N)c(C#N)c56)c(F)c3n2)COC4)C[C@H]1O] | 510 |

TABLE 28-continued

| Example | Chemical Name | Structure | MS (ES) m/z (M + 1) |
|---|---|---|---|
| 45A | 2-Amino-4-(3-((R)-2-((dimethylamino)methyl) pyrrolidin-1-yl)-5-fluoro-7,9-dihydrofuro[3,4-f]quinazolin-6-yl)-7-fluorothieno[3,2-c]pyridine-3-carbonitrile | 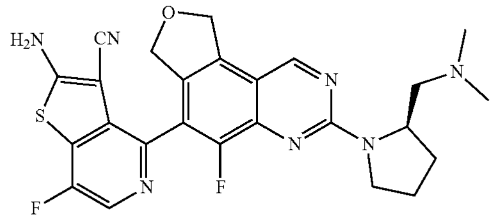 [SMILES: CN(C)C[C@H]1CCCN1c1ncc2c3c(c(-c4ncc(F)c5sc(N)c(C#N)c45)c(F)c2n1)COC3] | 508 |
| 46A | 2-Amino-4-(3-((S)-2-((dimethylamino)methyl) pyrrolidin-1-yl)-5-fluoro-7,9-dihydrofuro[3,4-f]quinazolin-6-yl)-7-fluorothieno[3,2-c]pyridine-3-carbonitrile | 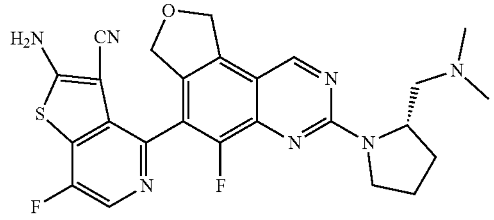 [SMILES: CN(C)C[C@@H]1CCCN1c1ncc2c3c(c(-c4ncc(F)c5sc(N)c(C#N)c45)c(F)c2n1)COC3] | 508 |
| 47A | 2-Amino-7-fluoro-4-(5-fluoro-3-(6-methyl-3,6-diazabicyclo[3.1.1]heptan-3-yl)-7,9-dihydrofuro[3,4-f]quinazolin-6-yl)thieno[3,2-c]pyridine-3-carbonitrile | 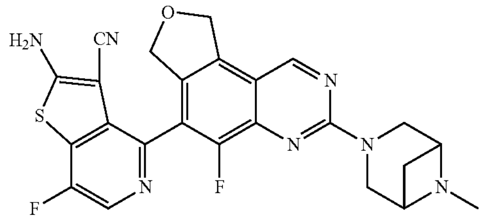 [SMILES: CN1C2CC1CN(c1ncc3c4c(c(-c5ncc(F)c6sc(N)c(C#N)c56)c(F)c3n1)COC4)C2] | 492 |
| 48A | 2-Amino-7-fluoro-4-(5-fluoro-3-((7S,8aS)-7-fluorohexahydropyrrolo [1,2-a]pyrazin-2(1H)-yl)-7,9-dihydrofuro[3,4-f]quinazolin-6-yl)thieno[3,2-c]pyridine-3-carbonitrile | 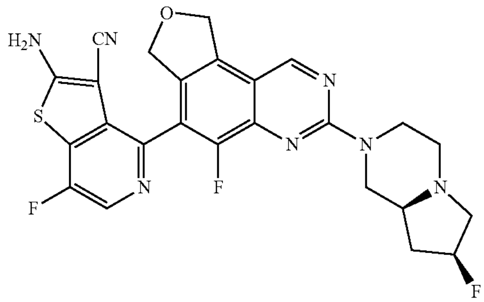 [SMILES: N#Cc1c(N)sc2c(F)cnc(-c3c4c(c5cnc(N6CCN7C[C@@H](F)C[C@H]7C6)nc5c3F)COC4)c12] | 524 |
| 49A | 2-Amino-4-(3-(3-(dimethylamino)-3-methylpyrrolidin-1-yl)-5-fluoro-7,9-dihydrofuro[3,4-f]quinazolin-6-yl)-7-fluorothieno[3,2-c]pyridine-3-carbonitrile | 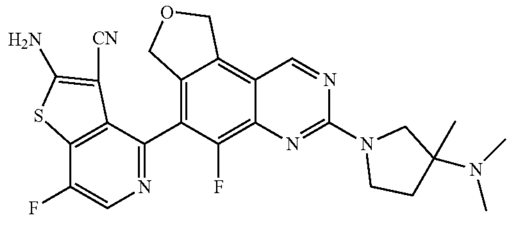 [SMILES: CN(C)C1(C)CCN(c2ncc3c4c(c(-c5ncc(F)c6sc(N)c(C#N)c56)c(F)c3n2)COC4)C1] | 508 |
| 50A | 2-Amino-7-fluoro-4-(5-fluoro-3-(4-methylpiperazin-1-yl)-7,9-dihydrofuro[3,4-f]quinazolin-6-yl)thieno[3,2-c]pyridine-3-carbonitrile | 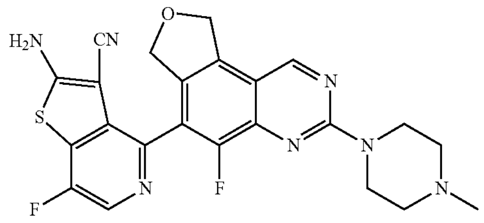 [SMILES: CN1CCN(c2ncc3c4c(c(-c5ncc(F)c6sc(N)c(C#N)c56)c(F)c3n2)COC4)CC1] | 480 |

TABLE 28-continued

| Example | Chemical Name | Structure | MS (ES) m/z (M + 1) |
|---|---|---|---|
| 51A | 2-Amino-7-fluoro-4-(5-fluoro-3-((1S,4S)-5-methyl-2,5-diazabicyclo[2.2.1]heptan-2-yl)-7,9-dihydrofuro[3,4-f]quinazolin-6-yl)thieno[3,2-c]pyridine-3-carbonitrile | 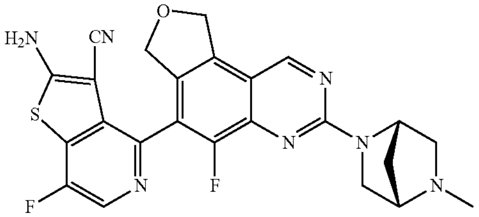 [SMILES: CN1C[C@@H]2C[C@H]1CN2c1ncc2c3c(c(-c4ncc(F)c5sc(N)c(C#N)c45)c(F)c2n1)COC3] | 492 |
| 52A | 2-Amino-7-fluoro-4-(5-fluoro-3-(hexahydropyrrolo[1,2-a]pyrazin-2(1H)-yl)-7,9-dihydrofuro[3,4-f]quinazolin-6-yl)thieno[3,2-c]pyridine-3-carbonitrile | 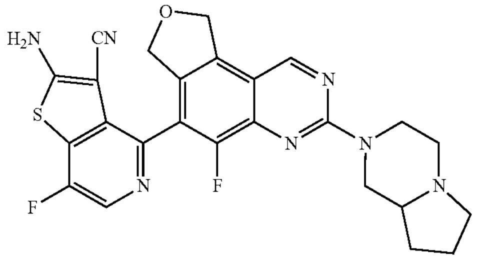 [SMILES: N#Cc1c(N)sc2c(F)cnc(-c3c4c(c5cnc(N6CCN7CCCC7C6)nc5c3F)COC4)c12] | 506 |
| 53A | 2-Amino-7-fluoro-4-(5-fluoro-3-((1R,4R)-5-methyl-2,5-diazabicyclo[2.2.1]heptan-2-yl)-7,9-dihydrofuro[3,4-f]quinazolin-6-yl)thieno[3,2-c]pyridine-3-carbonitrile | 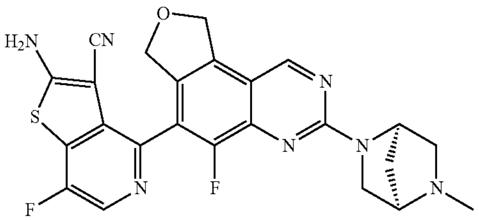 [SMILES: CN1C[C@H]2C[C@@H]1CN2c1ncc2c3c(c(-c4ncc(F)c5sc(N)c(C#N)c45)c(F)c2n1)COC3] | 492 |
| 54A | 2-Amino-4-(3-((3R,4S)-3-(dimethylamino)-4-fluoropyrrolidin-1-yl)-5-fluoro-7,9-dihydrofuro[3,4-f]quinazolin-6-yl)-7-fluorothieno[3,2-c]pyridine-3-carbonitrile | 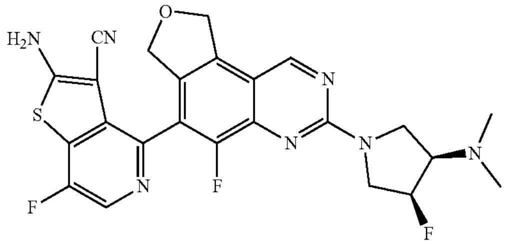 [SMILES: CN(C)[C@@H]1CN(c2ncc3c4c(c(-c5ncc(F)c6sc(N)c(C#N)c56)c(F)c3n2)COC4)C[C@@H]1F] | 512 |
| 55A | 2-Amino-4-(3-((3R,4R)-3-(dimethylamino)-4-fluoropyrrolidin-1-yl)-5-fluoro-7,9-dihydrofuro[3,4-f]quinazolin-6-yl)-7-fluorothieno[3,2-c]pyridine-3-carbonitrile | 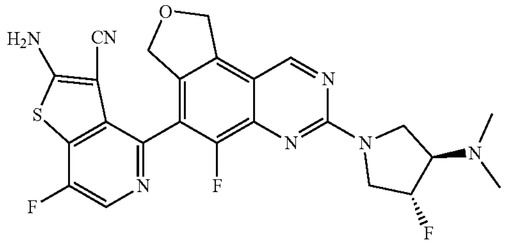 [SMILES: CN(C)[C@@H]1CN(c2ncc3c4c(c(-c5ncc(F)c6sc(N)c(C#N)c56)c(F)c3n2)COC4)C[C@H]1F] | 512 |
| 56A | 2-Amino-4-(3-((3S,4S)-3-(dimethylamino)-4-fluoropyrrolidin-1-yl)-5-fluoro-7,9-dihydrofuro[3,4-f]quinazolin-6-yl)-7-fluorothieno[3,2-c]pyridine-3-carbonitrile | 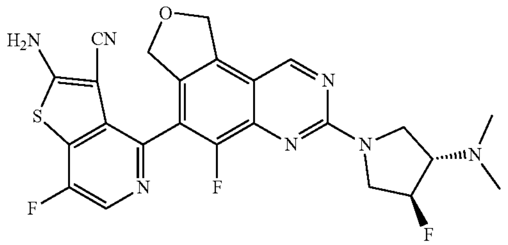 [SMILES: CN(C)[C@H]1CN(c2ncc3c4c(c(-c5ncc(F)c6sc(N)c(C#N)c56)c(F)c3n2)COC4)C[C@@H]1F] | 512 |

TABLE 28-continued

| Example | Chemical Name | Structure | MS (ES) m/z (M + 1) |
|---|---|---|---|
| 57A | 2-Amino-4-(3-((3S,4R)-3-(dimethylamino)-4-fluoropyrrolidin-1-yl)-5-fluoro-7,9-dihydrofuro[3,4-f]quinazolin-6-yl)-7-fluorothieno[3,2-c]pyridine-3-carbonitrile | 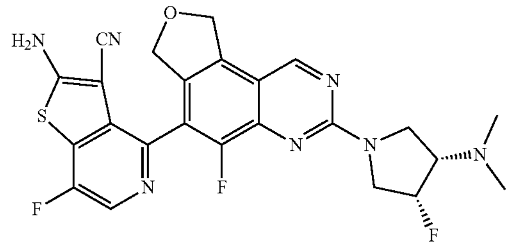 [SMILES: CN(C)[C@H]1CN(c2ncc3c4c(c(-c5ncc(F)c6sc(N)c(C#N)c56)c(F)c3n2)COC4)C[C@H]1F] | 512 |
| 58A | 2-Amino-4-(3-((3S,4S)-3-(dimethylamino)-4-methylpyrrolidin-1-yl)-5-fluoro-7,9-dihydrofuro[3,4-f]quinazolin-6-yl)-7-fluorothieno[3,2-c]pyridine-3-carbonitrile | 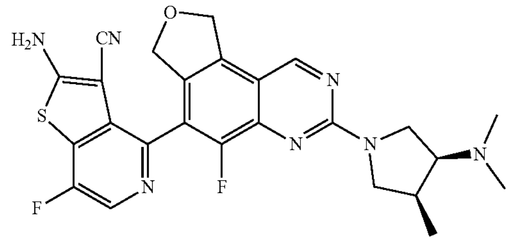 [SMILES: C[C@H]1CN(c2ncc3c4c(c(-c5ncc(F)c6sc(N)c(C#N)c56)c(F)c3n2)COC4)C[C@H]1N(C)C] | 508 |
| 59A | 2-Amino-7-fluoro-4-(5-fluoro-3-((S)-3-(methylamino)pyrrolidin-1-yl)-7,9-dihydrofuro[3,4-f]quinazolin-6-yl)thieno[3,2-c]pyridine-3-carbonitrile | 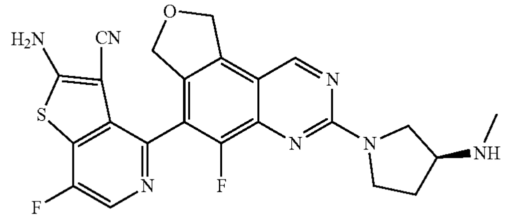 [SMILES: CN[C@H]1CCN(c2ncc3c4c(c(-c5ncc(F)c6sc(N)c(C#N)c56)c(F)c3n2)COC4)C1] | 480 |
| 60A [2] | 2-Amino-4-(3-(3-(dimethylamino)-3-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile, Enantiomer 1 | 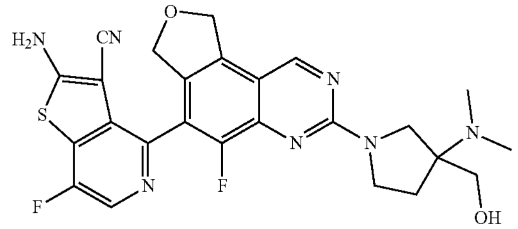 [SMILES: CN(C)C1(CO)CCN(c2ncc3c4c(c(-c5ncc(F)c6sc(N)c(C#N)c56)c(F)c3n2)COC4)C1] | 524 |
| 61A [2] | 2-Amino-4-(3-(3-(dimethylamino)-3-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile, Enantiomer 2 | 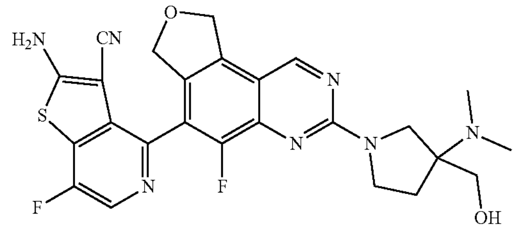 [SMILES: CN(C)C1(CO)CCN(c2ncc3c4c(c(-c5ncc(F)c6sc(N)c(C#N)c56)c(F)c3n2)COC4)C1] | 524 |
| 62A | 2-Amino-4-(3-((R)-2-((dimethylamino)methyl)morpholino)-5-fluoro-7,9-dihydrofuro[3,4-f]quinazolin-6-yl)-7-fluorothieno[3,2-c]pyridine-3-carbonitrile | 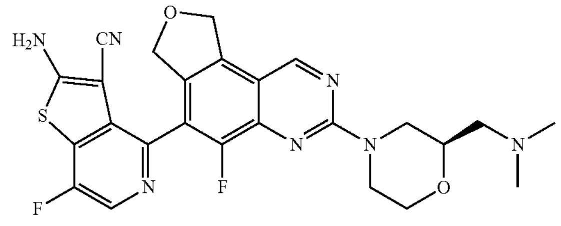 [SMILES: CN(C)C[C@@H]1CN(c2ncc3c4c(c(-c5ncc(F)c6sc(N)c(C#N)c56)c(F)c3n2)COC4)CCO1] | 524 |

TABLE 28-continued

| Example | Chemical Name | Structure | MS (ES) m/z (M + 1) |
|---|---|---|---|
| 63A | 2-Amino-7-fluoro-4-(5-fluoro-3-((R)-1,6-diazaspiro[3.4]octan-6-yl)-7,9-dihydrofuro[3,4-f]quinazolin-6-yl)thieno[3,2-c]pyridine-3-carbonitrile | 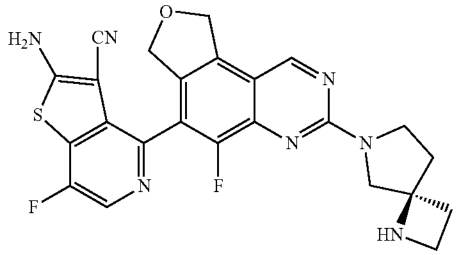 [SMILES: N#Cc1c(N)sc2c(F)cnc(-c3c4c(c5cnc(N6CC[C@]7(CCN7)C6)nc5c3F)COC4)c12] | 492 |
| 64A | 2-Amino-4-(3-((S)-3-amino-3-methylpyrrolidin-1-yl)-5-fluoro-7,9-dihydrofuro[3,4-f]quinazolin-6-yl)-7-fluorothieno[3,2-c]pyridine-3-carbonitrile | 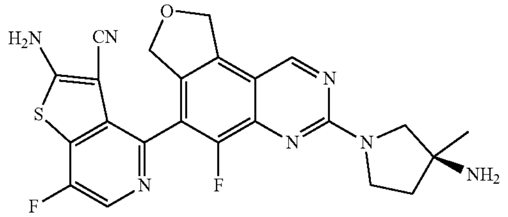 [SMILES: C[C@]1(N)CCN(c2ncc3c4c(c(-c5ncc(F)c6sc(N)c(C#N)c56)c(F)c3n2)COC4)C1] | 480 |
| 65A | 2-Amino-4-(3-((S)-3-(dimethylamino)-3-methylpyrrolidin-1-yl)-5-fluoro-7,9-dihydrofuro[3,4-f]quinazolin-6-yl)-7-fluorothieno[3,2-c]pyridine-3-carbonitrile | 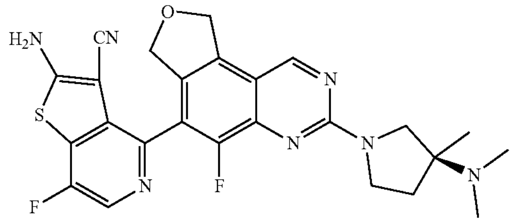 [SMILES: CN(C)[C@@]1(C)CCN(c2ncc3c4c(c(-c5ncc(F)c6sc(N)c(C#N)c56)c(F)c3n2)COC4)C1] | 508 |
| 66A | 2-Amino-4-(3-((3S,4R)-3-(dimethylamino)-4-hydroxypyrrolidin-1-yl)-5-fluoro-7,9-dihydrofuro[3,4-f]quinazolin-6-yl)-7-fluorothieno[3,2-c]pyridine-3-carbonitrile | 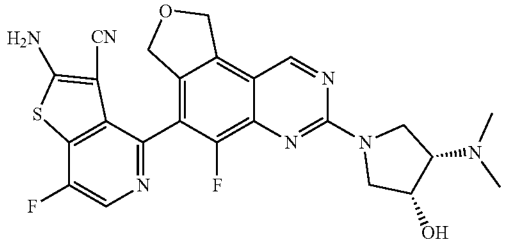 [SMILES: CN(C)[C@H]1CN(c2ncc3c4c(c(-c5ncc(F)c6sc(N)c(C#N)c56)c(F)c3n2)COC4)C[C@H]1O] | 510 |
| 67A | 2-Amino-4-(3-((3R,4S)-3-(dimethylamino)-4-hydroxypyrrolidin-1-yl)-5-fluoro-7,9-dihydrofuro[3,4-f]quinazolin-6-yl)-7-fluorothieno[3,2-c]pyridine-3-carbonitrile | 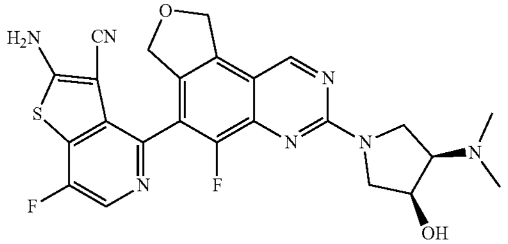 | 510 |
| 68A | 2-Amino-4-(3-((1R,4R,5S)-5-(dimethylamino)-2-azabicyclo[2.1.1]hexan-2-yl)-5-fluoro-7,9-dihydrofuro[3,4-f]quinazolin-6-yl)-7-fluorothieno[3,2-c]pyridine-3-carbonitrile | 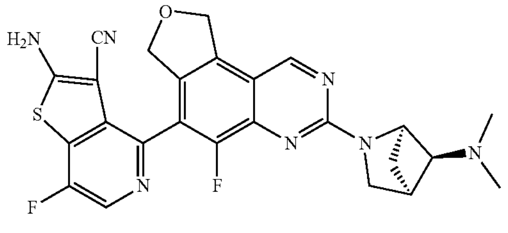 [SMILES: CN(C)[C@H]1[C@@H]2C[C@H]1N(c1ncc3c4c(c(-c5ncc(F)c6sc(N)c(C#N)c56)c(F)c3n1)COC4)C2] | 506 |

TABLE 28-continued

| Example | Chemical Name | Structure | MS (ES) m/z (M + 1) |
|---|---|---|---|
| 69A | 2-Amino-4-(3-((1S,4S,5R)-5-(dimethylamino)-2-azabicyclo[2.1.1 ]hexan-2-yl)-5-fluoro-7,9-dihydrofuro[3,4-f]quinazolin-6-yl)-7-fluorothieno[3,2-c]pyridine-3-carbonitrile | 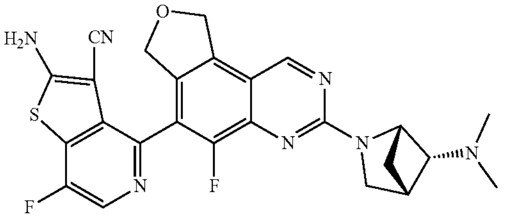 [SMILES: CN(C)[C@@H]1[C@H]2C[C@@H]1N(c1ncc3c4c(c(-c5ncc(F)c6sc(N)c(C#N)c56)c(F)c3n1)COC4)C2] | 506 |
| 70A [3] | 2-Amino-4-(5-chloro-3-(3-morpholinoazetidin-1-yl)-7,9-dihydrofuro[3,4-f]quinazolin-6-yl)-7-fluorobenzo[b]thiophene-3-carbonitrile, Atropisomer 1 | 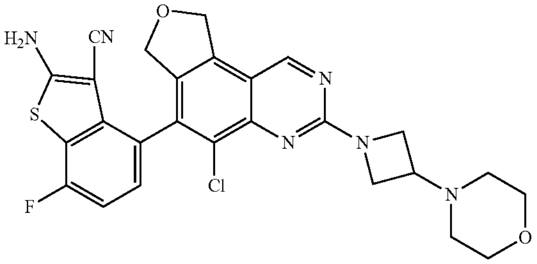 [SMILES: N#Cc1c(N)sc2c(F)ccc(-c3c4c(c5cnc(N6CC(N7CCOCC7)C6)nc5c3Cl)COC4)c12] | 537 |
| 71A [3] | 2-Amino-4-(5-chloro-3-(3-morpholinoazetidin-1-yl)-7,9-dihydrofuro[3,4-f]quinazolin-6-yl)-7-fluorobenzo[b]thiophene-3-carbonitrile, Atropisomer 2 | 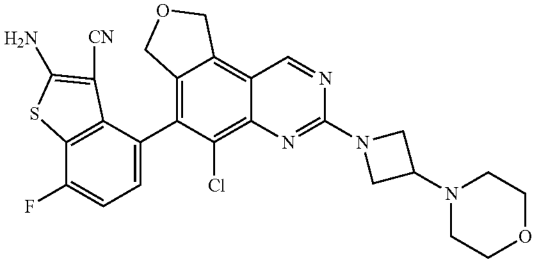 [SMILES: N#Cc1c(N)sc2c(F)ccc(-c3c4c(c5cnc(N6CC(N7CCOCC7)C6)nc5c3Cl)COC4)c12] | 537 |
| 72A [4] | 2-Amino-4-(5-chloro-3-((R)-3-(dimethylamino)pyrrolidin-1-yl)-7,9-dihydrofuro[3,4-f]quinazolin-6-yl)-7-fluorobenzo[b]thiophene-3-carbonitrile, Atropisomer 1 | 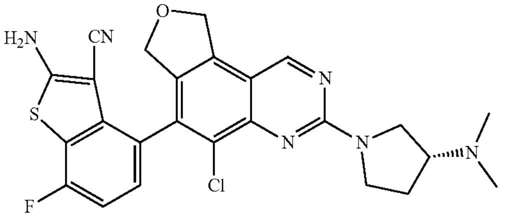 [SMILES: CN(C)[C@@H]1CCN(c2ncc3c4c(c(-c5ccc(F)c6sc(N)c(C#N)c56)c(Cl)c3n2)COC4)C1] | 509 |
| 73A [4] | 2-Amino-4-(5-chloro-3-((R)-3-(dimethylamino)pyrrolidin-1-yl)-7,9-dihydrofuro[3,4-f]quinazolin-6-yl)-7-fluorobenzo[b]thiophene-3-carbonitrile, Atropisomer 2 | 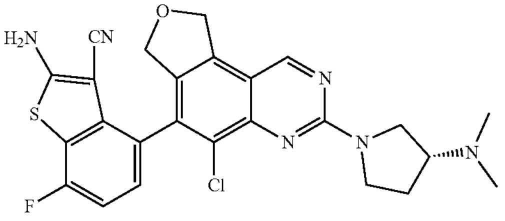 [SMILES: CN(C)[C@@H]1CCN(c2ncc3c4c(c(-c5ccc(F)c6sc(N)c(C#N)c56)c(Cl)c3n2)COC4)C1] | 509 |
| 74A [5] | 2-Amino-4-(5-chloro-3-((S)-3-(dimethylamino)pyrrolidin-1-yl)-7,9-dihydrofuro[3,4-f]quinazolin-6-yl)-7-fluorobenzo[b]thiophene-3-carbonitrile, Atropsiomer 1 | 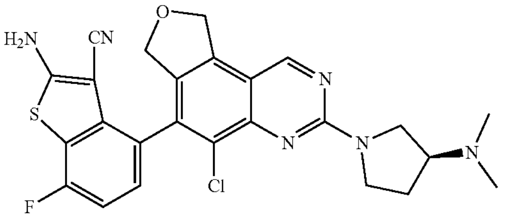 | 509 |

TABLE 28-continued

| Example | Chemical Name | Structure | MS (ES) m/z (M + 1) |
|---|---|---|---|
| 75A [5] | 2-Amino-4-(5-chloro-3-((S)-3-(dimethylamino)pyrrolidin-1-yl)-7,9-dihydrofuro[3,4-f]quinazolin-6-yl)-7-fluorobenzo[b]thiophene-3-carbonitrile, Atropsiomer 2 | 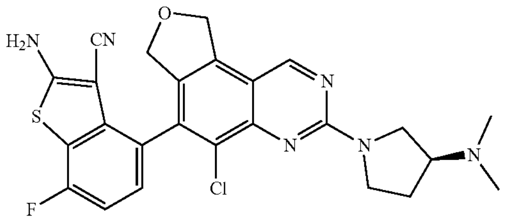 | 509 |
| 76A [6] | 2-Amino-4-(3-((S)-3-(dimethylamino)pyrrolidin-1-yl)-5-fluoro-7,9-dihydrofuro[3,4-f]quinazolin-6-yl)-5-fluorobenzo[b]thiophene-3-carbonitrile, Atropisomer 1 | 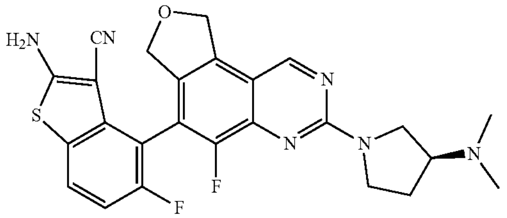 [SMILES: CN(C)[C@H]1CCN(c2ncc3c4c(c(-c5c(F)ccc6sc(N)c(C#N)c56)c(F)c3n2)COC4)C1] | 493 |
| 77A [6] | 2-Amino-4-(3-((S)-3-(dimethylamino)pyrrolidin-1-yl)-5-fluoro-7,9-dihydrofuro[3,4-f]quinazolin-6-yl)-5-fluorobenzo[b]thiophene-3-carbonitrile, Atropsiomer 2 | 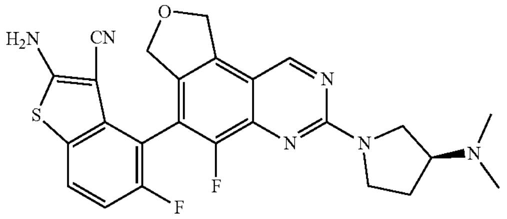 [SMILES: CN(C)[C@H]1CCN(c2ncc3c4c(c(-c5c(F)ccc6sc(N)c(C#N)c56)c(F)c3n2)COC4)C1] | 493 |
| 78A [7] | rel-2-Amino-4-(3-((3R,4R)-3-(dimethylamino)-4-hydroxypyrrolidin-1-yl)-5-fluoro-7,9-dihydrofuro[3,4-f]quinazolin-6-yl)-5-fluorobenzo[b]thiophene-3-carbonitrile, Diastereomer 1 | 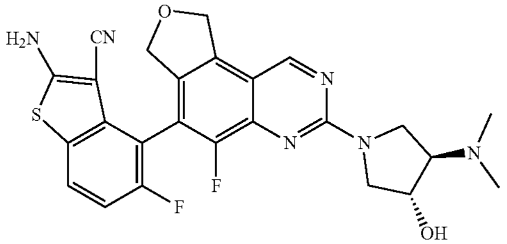 [SMILES: CN(C)[C@@H]1CN(c2ncc3c4c(c(-c5c(F)ccc6sc(N)c(C#N)c56)c(F)c3n2)COC4)C[C@H]1O] | 509 |
| 79A [7] | rel-2-Amino-4-(3-((3R,4R)-3-(dimethylamino)-4-hydroxypyrrolidin-1-yl)-5-fluoro-7,9-dihydrofuro[3,4-f]quinazolin-6-yl)-5-fluorobenzo[b]thiophene-3-carbonitrile, Diastereomer 2 | 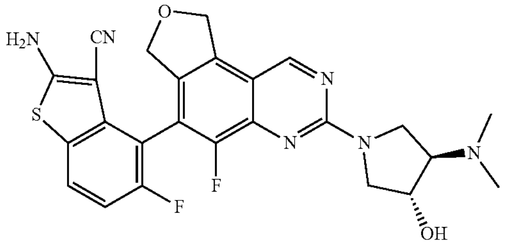 [SMILES: CN(C)[C@@H]1CN(c2ncc3c4c(c(-c5c(F)ccc6sc(N)c(C#N)c56)c(F)c3n2)COC4)C[C@H]1O] | 509 |
| 80A [7] | rel-2-Amino-4-(3-((3R,4R)-3-(dimethylamino)-4-hydroxypyrrolidin-1-yl)-5-fluoro-7,9-dihydrofuro[3,4-f]quinazolin-6-yl)-5-fluorobenzo[b]thiophene-3-carbonitrile, Diastereomer 3 | 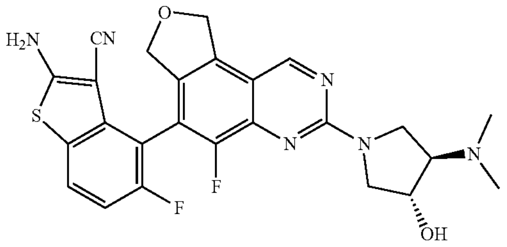 [SMILES: CN(C)[C@@H]1CN(c2ncc3c4c(c(-c5c(F)ccc6sc(N)c(C#N)c56)c(F)c3n2)COC4)C[C@H]1O] | 509 |

TABLE 28-continued

| Example | Chemical Name | Structure | MS (ES) m/z (M + 1) |
|---|---|---|---|
| 81A [7] | rel-2-Amino-4-(3-((3R,4R)-3-(dimethylamino)-4-hydroxypyrrolidin-1-yl)-5-fluoro-7,9-dihydrofuro[3,4-f]quinazolin-6-yl)-5-fluorobenzo[b]thiophene-3-carbonitrile, Diastereomer 4 | 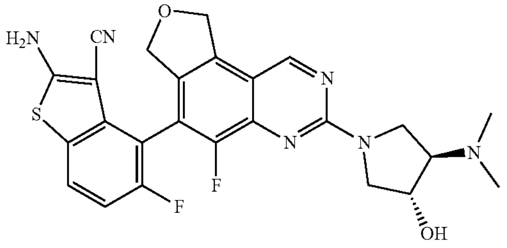 [SMILES: CN(C)[C@@H]1CN(c2ncc3c4c(c(-c5c(F)ccc6sc(N)c(C#N)c56)c(F)c3n2)COC4)C[C@H]1O] | 509 |
| 82A [8] | 2-Amino-5-fluoro-4-(5-fluoro-3-(3-(1-methyl-1H-imidazol-2-yl)pyrrolidin-1-yl)-7,9-dihydrofuro[3,4-f]quinazolin-6-yl)benzo[b]thiophene-3-carbonitrile, Diastereomer Mix 1 | 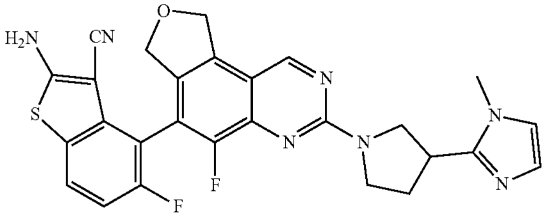 [SMILES: Cn1ccnc1C1CCN(c2ncc3c4c(c(-c5c(F)ccc6sc(N)c(C#N)c56)c(F)c3n2)COC4)C1] | 530 |
| 83A [8] | 2-Amino-5-fluoro-4-(5-fluoro-3-(3-(1-methyl-1H-imidazol-2-yl)pyrrolidin-1-yl)-7,9-dihydrofuro[3,4-f]quinazolin-6-yl)benzo[b]thiophene-3-carbonitrile, Diastereomer Mix 2 | 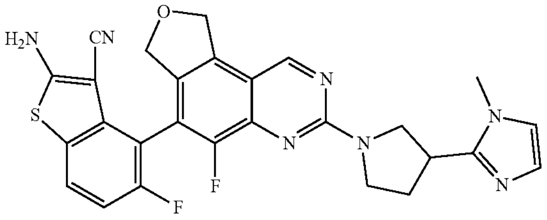 [SMILES: Cn1ccnc1C1CCN(c2ncc3c4c(c(-c5c(F)ccc6sc(N)c(C#N)c56)c(F)c3n2)COC4)C1] | 530 |
| 84A | 2-Amino-4-(7-((S)-3-(dimethylamino)pyrrolidin-1-yl)-5-fluoro-1,3-dihydrofuro[3,4-f]quinolin-4-yl)-7-fluorothieno[3,2-c]pyridine-3-carbonitrile | 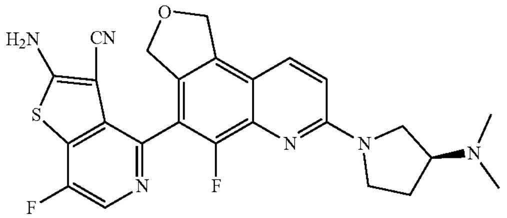 | 493 |
| 28B | 2-Amino-7-fluoro-4-(5-fluoro-3-((2S,3S)-3-(isopropylamino)-2-methylpyrrolidin-1-yl)-7,9-dihydrofuro[3,4-f]quinazolin-6-yl)thieno[3,2-c]pyridine-3-carbonitrile | 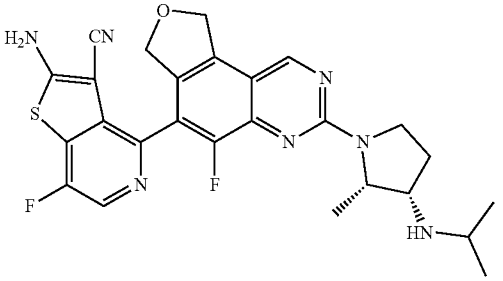 [SMILES: CC(C)N[C@H]1CCN(c2ncc3c4c(c(-c5ncc(F)c6sc(N)c(C#N)c56)c(F)c3n2)COC4)[C@H]1C] | 522 |
| 29B [9] | 2-Amino-4-(5-chloro-3-(3-(dimethylamino)-3-(hydroxymethyl)pyrrolidin-1-yl)-7,9-dihydrofuro[3,4-f]quinazolin-6-yl)-5-fluorobenzo[b]thiophene-3-carbonitrile, Diastereomer 1 | 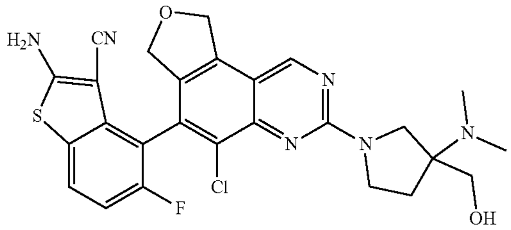 [SMILES: CN(C)C1(CO)CCN(c2ncc3c4c(c(-c5c(F)ccc6sc(N)c(C#N)c56)c(Cl)c3n2)COC4)C1] | 539 |

TABLE 28-continued

| Example | Chemical Name | Structure | MS (ES) m/z (M + 1) |
|---|---|---|---|
| 30B [9] | 2-Amino-4-(5-chloro-3-(3-(dimethylamino)-3-(hydroxymethyl)pyrrolidin-1-yl)-7,9-dihydrofuro[3,4-f]quinazolin-6-yl)-5-fluorobenzo[b]thiophene-3-carbonitrile, Diastereomer 2 | 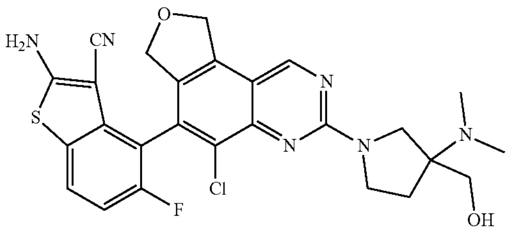 [SMILES: CN(C)C1(CO)CCN(c2ncc3c4c(c(-c5c(F)ccc6sc(N)c(C#N)c56)c(Cl)c3n2)COC4)C1] | 539 |
| 31B [9] | 2-Amino-4-(5-chloro-3-(3-(dimethylamino)-3-(hydroxymethyl)pyrrolidin-1-yl)-7,9-dihydrofuro[3,4-f]quinazolin-6-yl)-5-fluorobenzo[b]thiophene-3-carbonitrile, Diastereomer 3 | 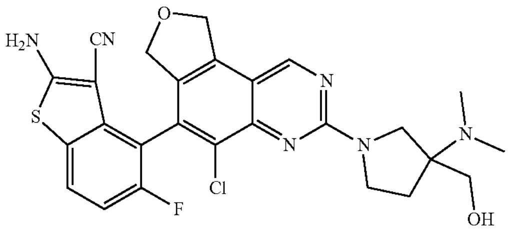 [SMILES: CN(C)C1(CO)CCN(c2ncc3c4c(c(-c5c(F)ccc6sc(N)c(C#N)c56)c(Cl)c3n2)COC4)C1] | 539 |
| 32B [9] | 2-Amino-4-(5-chloro-3-(3-(dimethylamino)-3-(hydroxymethyl)pyrrolidin-1-yl)-7,9-dihydrofuro[3,4-f]quinazolin-6-yl)-5-fluorobenzo[b]thiophene-3-carbonitrile, Diastereomer 4 | 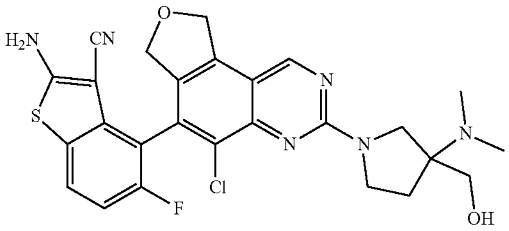 [SMILES: CN(C)C1(CO)CCN(c2ncc3c4c(c(-c5c(F)ccc6sc(N)c(C#N)c56)c(Cl)c3n2)COC4)C1] | 539 |
| 33B | 2-Amino-4-(3-((3S,4S)-3-(dimethylamino)-4-methoxypyrrolidin-1-yl)-5-fluoro-7,9-dihydrofuro[3,4-f]quinazolin-6-yl)-7-fluorothieno[3,2-c]pyridine-3-carbonitrile | 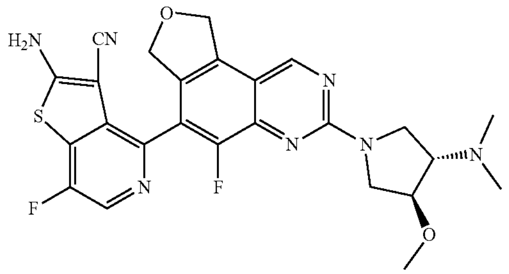 [SMILES: CO[C@H]1CN(c2ncc3c4c(c(-c5ncc(F)c6sc(N)c(C#N)c56)c(F)c3n2)COC4)C[C@@H]1N(C)C] | 524 |
| 34B | 2-Amino-4-(3-((3R,4S)-3-(dimethylamino)-4-methoxypyrrolidin-1-yl)-5-fluoro-7,9-dihydrofuro[3,4-f]quinazolin-6-yl)-7-fluorothieno[3,2-c]pyridine-3-carbonitrile | 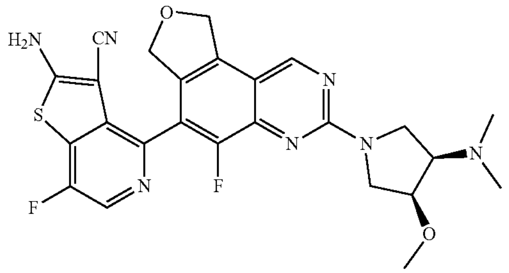 [SMILES: CO[C@H]1CN(c2ncc3c4c(c(-c5ncc(F)c6sc(N)c(C#N)c56)c(F)c3n2)COC4)C[C@H]1N(C)C] | 524 |
| 35B [10] | 2-Amino-4-(3-(1-(dimethylamino)-3-azabicyclo[3.2.0]heptan-3-yl)-5-fluoro-7,9-dihydrofuro[3,4-f]quinazolin-6-yl)-7-fluorothieno[3,2-c]pyridine-3-carbonitrile, Isomer 1 | 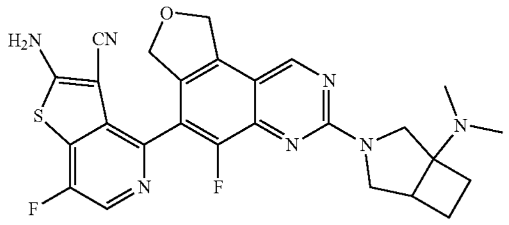 [SMILES: CN(C)C12CCC1CN(c1ncc3c4c(c(-c5ncc(F)c6sc(N)c(C#N)c56)c(F)c3n1)COC4)C2] | 520 |

TABLE 28-continued

| Example | Chemical Name | Structure | MS (ES) m/z (M + 1) |
|---|---|---|---|
| 36B [10] | 2-Amino-4-(3-(1-(dimethylamino)-3-azabicyclo[3.2.0]heptan-3-yl)-5-fluoro-7,9-dihydrofuro[3,4-f]quinazolin-6-yl)-7-fluorothieno[3,2-c]pyridine-3-carbonitrile, Isomer 2 | 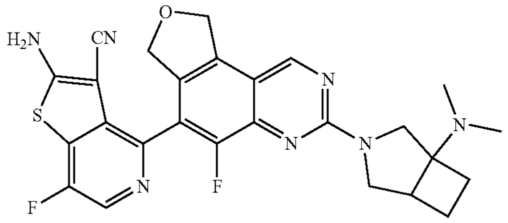 [SMILES: CN(C)C12CCC1CN(c1ncc3c4c(c(-c5ncc(F)c6sc(N)c(C#N)c56)c(F)c3n1)COC4)C2] | 520 |
| 37B | 2-Amino-4-(3-(7-(dimethylamino)-4-azaspiro[2.4]heptan-4-yl)-5-fluoro-7,9-dihydrofuro[3,4-f]quinazolin-6-yl)-7-fluorothieno[3,2-c]pyridine-3-carbonitrile | 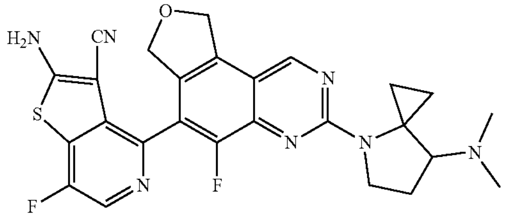 [SMILES: CN(C)C1CCN(c2ncc3c4c(c(-c5ncc(F)c6sc(N)c(C#N)c56)c(F)c3n2)COC4)C12CC2] | 520 |
| 38B [11] | 2-Amino-7-fluoro-4-(5-fluoro-3-(4-methylhexahydropyrrolo[3,2-b]pyrrol-1(2H)-yl)-7,9-dihydrofuro[3,4-f]quinazolin-6-yl)thieno[3,2-c]pyridine-3-carbonitrile, Isomer 1 | 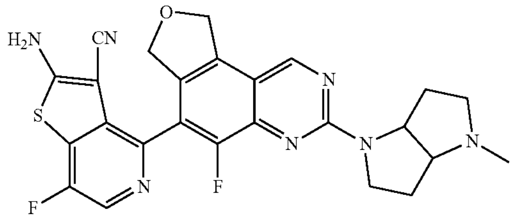 [SMILES: CN1CCC2C1CCN2c1ncc2c3c(c(-c4ncc(F)c5sc(N)c(C#N)c45)c(F)c2n1)COC3] | 506 |
| 39B [11] | 2-Amino-7-fluoro-4-(5-fluoro-3-(4-methylhexahydropyrrolo[3,2-b]pyrrol-1(2H)-yl)-7,9-dihydrofuro[3,4-f]quinazolin-6-yl)thieno[3,2-c]pyridine-3-carbonitrile, Isomer 2 | 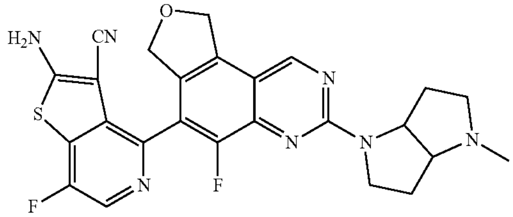 [SMILES: CN1CCC2C1CCN2c1ncc2c3c(c(-c4ncc(F)c5sc(N)c(C#N)c45)c(F)c2n1)COC3] | 506 |
| 40B | 2-Amino-7-fluoro-4-(5-fluoro-3-((3S,4R)-3-hydroxy-4-(isopropyl(methyl)amino)pyrrolidin-1-yl)-7,9-dihydrofuro[3,4-f]quinazolin-6-yl)thieno[3,2-c]pyridine-3-carbonitrile | 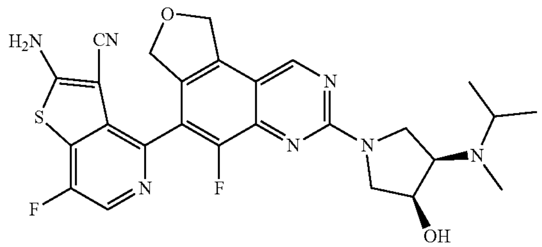 [SMILES: CC(C)N(C)[C@@H]1CN(c2ncc3c4c(c(-c5ncc(F)c6sc(N)c(C#N)c56)c(F)c3n2)COC4)C[C@@H]1O] | 538 |
| 41B | 2-Amino-4-(3-((3R,4S)-3-(diethylamino)-4-hydroxypyrrolidin-1-yl)-5-fluoro-7,9-dihydrofuro[3,4-f]quinazolin-6-yl)-7-fluorothieno[3,2-c]pyridine-3-carbonitrile | 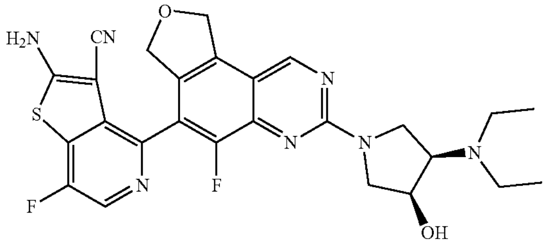 [SMILES: CCN(CC)[C@@H]1CN(c2ncc3c4c(c(-c5ncc(F)c6sc(N)c(C#N)c56)c(F)c3n2)COC4)C[C@@H]1O] | 538 |

TABLE 28-continued

| Example | Chemical Name | Structure | MS (ES) m/z (M + 1) |
|---|---|---|---|
| 42B | 2-Amino-4-(3-((3R,4S)-3-(ethyl(methyl)amino)-4-hydroxypyrrolidin-1-yl)-5-fluoro-7,9-dihydrofuro[3,4-f]quinazolin-6-yl)-7-fluorothieno[3,2-c]pyridine-3-carbonitrile | 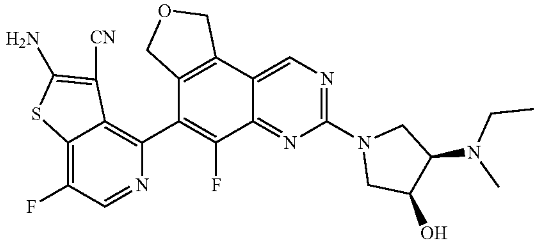 [SMILES: CCN(C)[C@@H]1CN(c2ncc3c4c(c(-c5ncc(F)c6sc(N)c(C#N)c56)c(F)c3n2)COC4)C[C@@H]1O] | 524 |
| 43B | 2-Amino-4-(3-(4-((dimethylamino)methyl)-1H-imidazol-1-yl)-5-fluoro-7,9-dihydrofuro[3,4-f]quinazolin-6-yl)-7-fluorothieno[3,2-c]pyridine-3-carbonitrile | 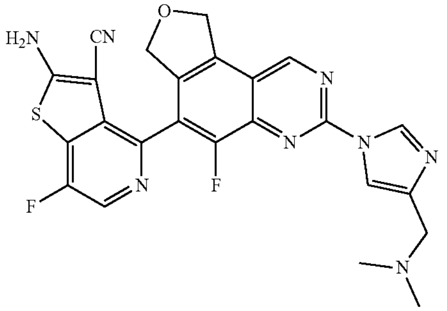 [SMILES: CN(C)Cc1cn(-c2ncc3c4c(c(-c5ncc(F)c6sc(N)c(C#N)c56)c(F)c3n2)COC4)cn1] | 505 |
| 44B | 2-Amino-4-(5-chloro-7-((S)-3-(dimethylamino)pyrrolidin-1-yl)-1,3-dihydrofuro[3,4-f]quinolin-4-yl)-7-fluorothieno[3,2-c]pyridine-3-carbonitrile | 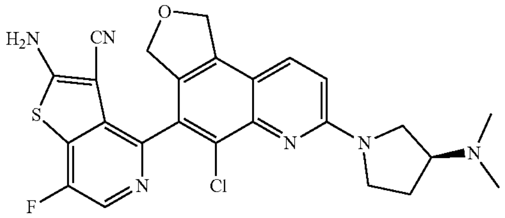 [SMILES: CN(C)[C@H]1CCN(c2ccc3c4c(c(-c5ncc(F)c6sc(N)c(C#N)c56)c(Cl)c3n2)COC4)C1] | 509 |
| 45B [12] | 2-Amino-4-(5-chloro-3-((3R,4S)-3-(dimethylamino)-4-hydroxypyrrolidin-1-yl)-7,9-dihydrofuro[3,4-f]quinazolin-6-yl)-5-fluorobenzo[b]thiophene-3-carbonitrile, Atropisomer 1 | 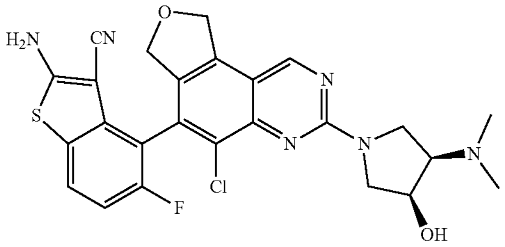 | 525 |
| 46B [12] | 2-Amino-4-(5-chloro-3-((3R,4S)-3-(dimethylamino)-4-hydroxypyrrolidin-1-yl)-7,9-dihydrofuro[3,4-f]quinazolin-6-yl)-5-fluorobenzo[b]thiophene-3-carbonitrile, Atropisomer 2 | 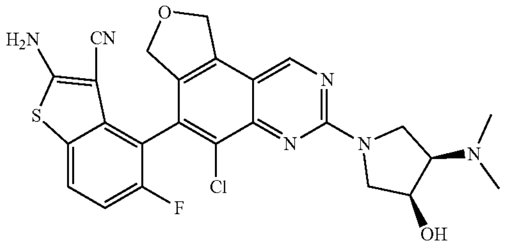 | 525 |
| 47B | 2-Amino-7-fluoro-4-(5-fluoro-3-(3-(isopropyl(methyl)amino) pyrrolidin-1-yl)-7,9-dihydrofuro[3,4-f]quinazolin-6-yl)thieno[3,2-c]pyridine-3-carbonitrile | 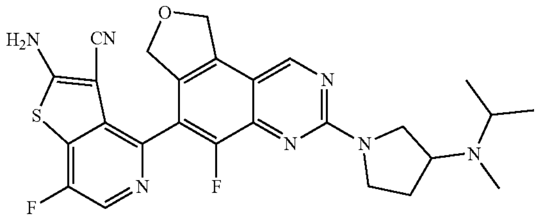 [SMILES: CC(C)N(C)C1CCN(c2ncc3c4c(c(-c5ncc(F)c6sc(N)c(C#N)c56)c(F)c3n2)COC4)C1] | 522 |

TABLE 28-continued

| Example | Chemical Name | Structure | MS (ES) m/z (M + 1) |
|---|---|---|---|
| 48B [13] | 2-Amino-7-fluoro-4-(5-fluoro-3-(3-(isopropyl(methyl)amino) pyrrolidin-1-yl)-7,9-dihydrofuro[3,4-f]quinazolin-6-yl)thieno[3,2-c]pyridine-3-carbonitrile, Isomer 1 | 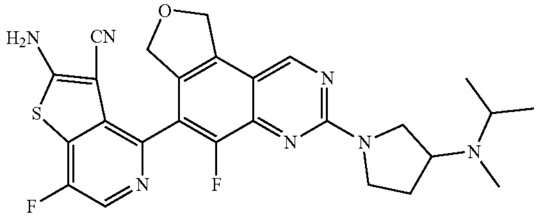 [SMILES: CC(C)N(C)C1CCN(c2ncc3c4c(c(-c5ncc(F)c6sc(N)c(C#N)c56)c(F)c3n2)COC4)C1] | 522 |
| 49B [13] | 2-Amino-7-fluoro-4-(5-fluoro-3-(3-(isopropyl(methyl)amino) pyrrolidin-1-yl)-7,9-dihydrofuro[3,4-f]quinazolin-6-yl)thieno[3,2-c]pyridine-3-carbonitrile, Isomer 1 | 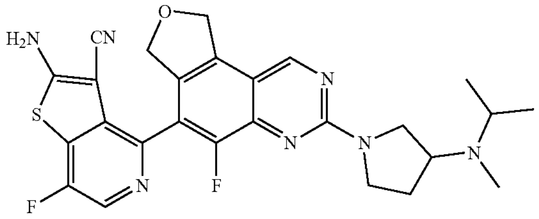 [SMILES: CC(C)N(C)C1CCN(c2ncc3c4c(c(-c5ncc(F)c6sc(N)c(C#N)c56)c(F)c3n2)COC4)C1] | 522 |
| 50B | 2-Amino-4-(3-((3R,4S)-3-(dimethylamino)-4-methylpyrrolidin-1-yl)-5-fluoro-7,9-dihydrofuro[3,4-f]quinazolin-6-yl)-7-fluorothieno[3,2-c]pyridine-3-carbonitrile | 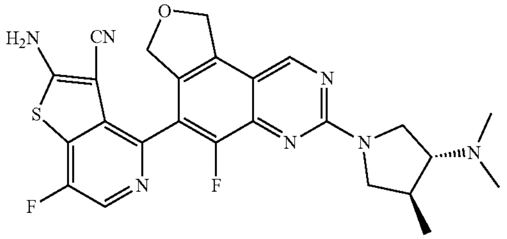 [SMILES: C[C@H]1CN(c2ncc3c4c(c(-c5ncc(F)c6sc(N)c(C#N)c56)c(F)c3n2)COC4)C[C@@H]1N(C)C] | 508 |
| 51B | 2-Amino-7-fluoro-4-(5-fluoro-3-(2-oxotetrahydrofuro[3,4-d]oxazol-3(2H)-yl)-7,9-dihydrofuro[3,4-f]quinazolin-6-yl)thieno[3,2-c]pyridine-3-carbonitrile | 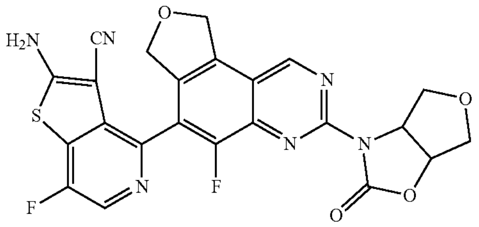 [SMILES: N#Cc1c(N)sc2c(F)cnc(-c3c4c(c5cnc(N6C(=O)OC7COCC76)nc5c3F)COC4)c12] | 509 |
| 52B | 2-Amino-4-(3-(3-((dimethylamino)methyl)-1H-pyrazol-1-yl)-5-fluoro-7,9-dihydrofuro[3,4-f]quinazolin-6-yl)-7-fluorothieno[3,2-c]pyridine-3-carbonitrile | 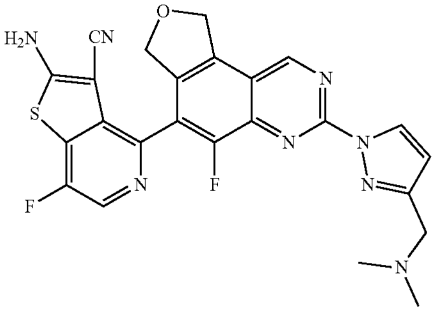 [SMILES: CN(C)Cc1ccn(-c2ncc3c4c(c(-c5ncc(F)c6sc(N)c(C#N)c56)c(F)c3n2)COC4)n1] | 505 |
| 53B | 2-Amino-7-fluoro-4-(5-fluoro-3-(3-(4-hydroxypiperidin-1-yl)azetidin-1-yl)-7,9-dihydrofuro[3,4-f]quinazolin-6-yl)thieno[3,2-c]pyridine-3-carbonitrile | 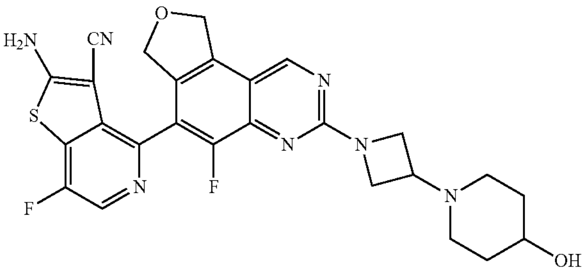 [SMILES: N#Cc1c(N)sc2c(F)cnc(-c3c4c(c5cnc(N6CC(N7CCC(O)CC7)C6)nc5c3F)COC4)c12] | 536 |

TABLE 28-continued

| Example | Chemical Name | Structure | MS (ES) m/z (M + 1) |
|---|---|---|---|
| 54B | 4-(3-((1S,5S)-2,6-Diazabicyclo[3.2.0]heptan-2-yl)-5-fluoro-7,9-dihydrofuro[3,4-f]quinazolin-6-yl)-2-amino-7-fluorothieno[3,2-c]pyridine-3-carbonitrile | 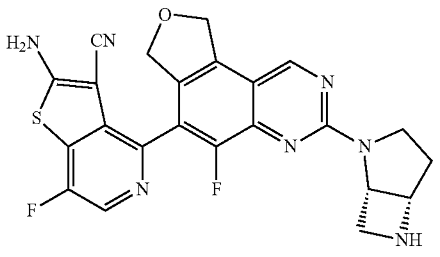 [SMILES: N#Cc1c(N)sc2c(F)cnc(-c3c4c(c5cnc(N6CC[C@@H]7NC[C@@H]76)nc5c3F)COC4)c12] | 478 |
| 55B | 2-Amino-7-fluoro-4-(5-fluoro-3-((1S,5S)-6-methyl-2,6-diazabicyclo[3.2.0]heptan-2-yl)-7,9-dihydrofuro[3,4-f]quinazolin-6-yl)thieno[3,2-c]pyridine-3-carbonitrile | 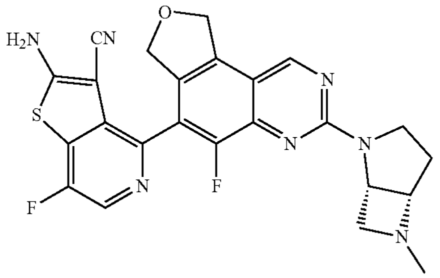 [SMILES: CN1C[C@H]2[C@@H]1CCN2c1ncc2c3c(c(-c4ncc(F)c5sc(N)c(C#N)c45)c(F)c2n1)COC3] | 492 |
| 56B | 2-Amino-7-fluoro-4-(5-fluoro-3-((2S,3S)-2-methyl-3-(methylamino)pyrrolidin-1-yl)-7,9-dihydrofuro[3,4-f]quinazolin-6-yl)thieno[3,2-c]pyridine-3-carbonitrile | 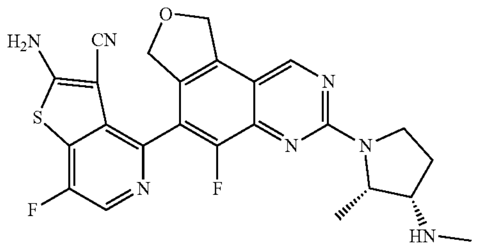 [SMILES: CN[C@H]1CCN(c2ncc3c4c(c(-c5ncc(F)c6sc(N)c(C#N)c56)c(F)c3n2)COC4)[C@H]1C] | 494 |
| 57B | 2-Amino-7-fluoro-4-(5-fluoro-3-((R)-2-methylpiperazin-1-yl)-7,9-dihydrofuro[3,4-f]quinazolin-6-yl)thieno[3,2-c]pyridine-3-carbonitrile | 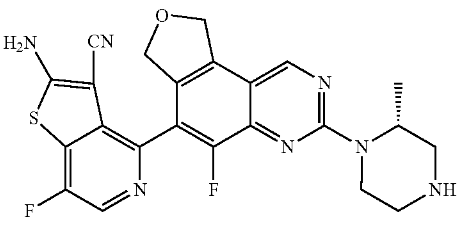 [SMILES: C[C@@H]1CNCCN1c1ncc2c3c(c(-c4ncc(F)c5sc(N)c(C#N)c45)c(F)c2n1)COC3] | 480 |
| 58B [14] | 2-Amino-4-(3-(3-(difluoromethyl)-4-(dimethylamino)pyrrolidin-1-yl)-5-fluoro-7,9-dihydrofuro[3,4-f]quinazolin-6-yl)-7-fluorothieno[3,2-c]pyridine-3-carbonitrile | 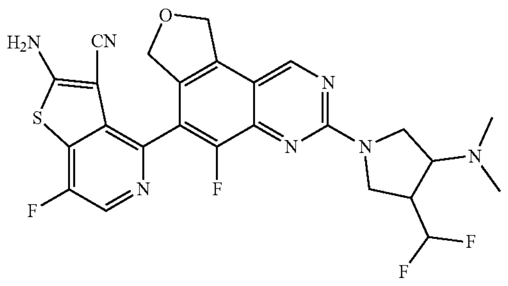 [SMILES: CN(C)C1CN(c2ncc3c4c(c(-c5ncc(F)c6sc(N)c(C#N)c56)c(F)c3n2)COC4)CC1C(F)F] | 544 |

TABLE 28-continued

| Example | Chemical Name | Structure | MS (ES) m/z (M + 1) |
|---|---|---|---|
| 59B [14] | 2-Amino-4-(3-(3-(difluoromethyl)-4-(dimethylamino)pyrrolidin-1-yl)-5-fluoro-7,9-dihydrofuro[3,4-f]quinazolin-6-yl)-7-fluorothieno[3,2-c]pyridine-3-carbonitrile | 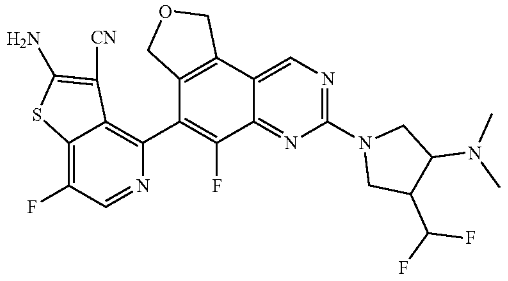 [SMILES: CN(C)C1CN(c2ncc3c4c(c(-c5ncc(F)c6sc(N)c(C#N)c56)c(F)c3n2)COC4)CC1C(F)F] | 544 |
| 60B | 2-Amino-7-fluoro-4-(5-fluoro-3-((S)-1,7-diazaspiro[4.4]nonan-7-yl)-7,9-dihydrofuro[3,4-f]quinazolin-6-yl)thieno[3,2-c]pyridine-3-carbonitrile | 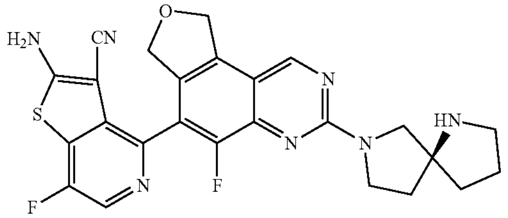 [SMILES: N#Cc1c(N)sc2c(F)cnc(-c3c4c(c5cnc(N6CC[C@@]7(CCCN7)C6)nc5c3F)COC4)c12] | 506 |
| 61B [15] | 2-Amino-4-(3-(4-(dimethylamino)-2-methylpyrrolidin-1-yl)-5-fluoro-7,9-dihydrofuro[3,4-f]quinazolin-6-yl)-7-fluorothieno[3,2-c]pyridine-3-carbonitrile | 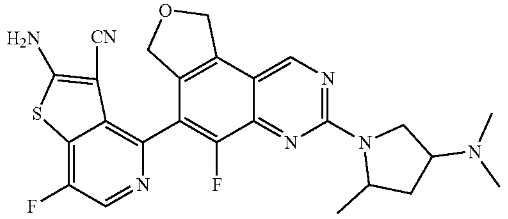 [SMILES: CC1CC(N(C)C)CN1c1ncc2c3c(c(-c4ncc(F)c5sc(N)c(C#N)c45)c(F)c2n1)COC3] | 508 |
| 62B [15] | 2-Amino-4-(3-(4-(dimethylamino)-2-methylpyrrolidin-1-yl)-5-fluoro-7,9-dihydrofuro[3,4-f]quinazolin-6-yl)-7-fluorothieno[3,2-c]pyridine-3-carbonitrile | 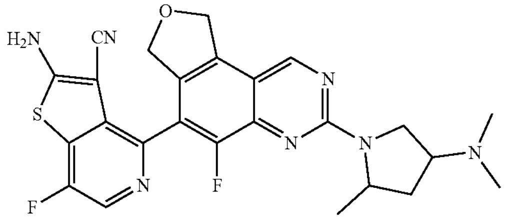 [SMILES: CC1CC(N(C)C)CN1c1ncc2c3c(c(-c4ncc(F)c5sc(N)c(C#N)c45)c(F)c2n1)COC3] | 508 |
| 63B | 2-Amino-4-(3-((S)-3-(dimethylamino)pyrrolidin-1-yl)-5-fluoro-7,9-dihydrofuro[3,4-f]quinazolin-6-yl)-7-methylthieno[3,2-c]pyridine-3-carbonitrile | 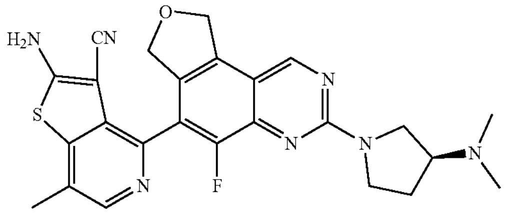 | 490 |
| 64B | 2-Amino-4-(3-((S)-3-(cyclobutylamino)pyrrolidin-1-yl)-5-fluoro-7,9-dihydrofuro[3,4-f]quinazolin-6-yl)-7-fluorothieno[3,2-c]pyridine-3-carbonitrile | 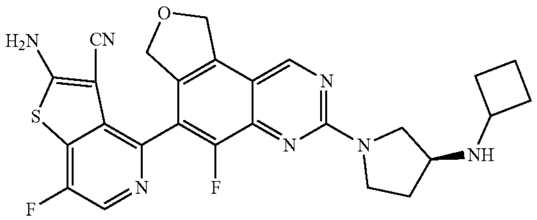 [SMILES: N#Cc1c(N)sc2c(F)cnc(-c3c4c(c5cnc(N6CC[C@H](NC7CCC7)C6)nc5c3F)COC4)c12] | 520 |

TABLE 28-continued

| Example | Chemical Name | Structure | MS (ES) m/z (M + 1) |
| --- | --- | --- | --- |
| 65B | 2-Amino-7-fluoro-4-(5-fluoro-3-((S)-3-((2-hydroxyethyl)(methyl)amino)pyrrolidin-1-yl)-7,9-dihydrofuro[3,4-f]quinazolin-6-yl)thieno[3,2-c]pyridine-3-carbonitrile | 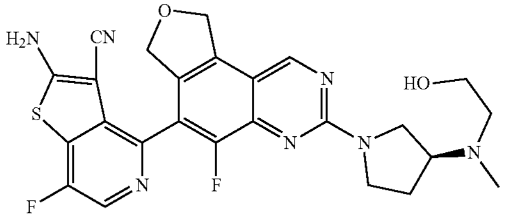 [SMILES: CN(CCO)[C@H]1CCN(c2ncc3c4c(c(-c5ncc(F)c6sc(N)c(C#N)c56)c(F)c3n2)COC4)C1] | 524 |
| 66B [16] | 2-Amino-4-(5-chloro-3-((S)-3-(dimethylamino)pyrrolidin-1-yl)-7,9-dihydrofuro[3,4-f]quinazolin-6-yl)-7-fluorothieno[3,2-c]pyridine-3-carbonitrile, Atropisomer 1 | 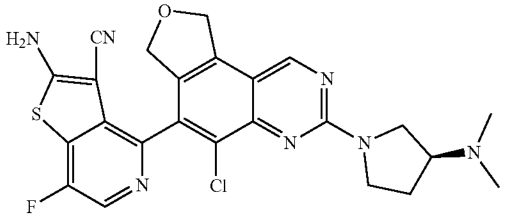 [SMILES: CN(C)[C@H]1CCN(c2ncc3c4c(c(-c5ncc(F)c6sc(N)c(C#N)c56)c(Cl)c3n2)COC4)C1] | 511 |
| 67B [16] | 2-Amino-4-(5-chloro-3-((S)-3-(dimethylamino)pyrrolidin-1-yl)-7,9-dihydrofuro[3,4-f]quinazolin-6-yl)-7-fluorothieno[3,2-c]pyridine-3-carbonitrile, Atropisomer 2 | 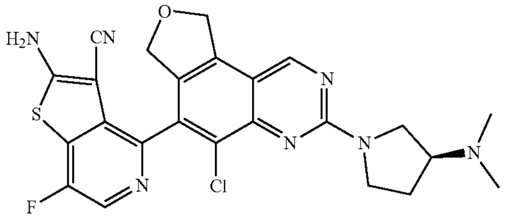 | 511 |
| 68B | 2-Amino-7-fluoro-4-(5-fluoro-3-(1,7-diazaspiro[4.4]nonan-7-yl)-7,9-dihydrofuro[3,4-f]quinazolin-6-yl)thieno[3,2-c]pyridine-3-carbonitrile | 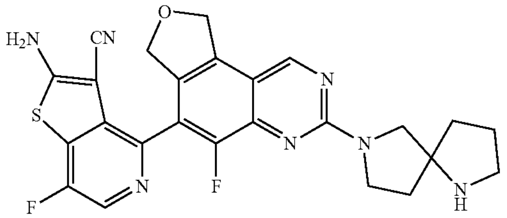 [SMILES: N#Cc1c(N)sc2c(F)cnc(-c3c4c(c5cnc(N6CCC7(CCCN7)C6)nc5c3F)COC4)c12] | 506 |
| 69B | 2-Amino-4-(3-((S)-3-(diethylamino)pyrrolidin-1-yl)-5-fluoro-7,9-dihydrofuro[3,4-f]quinazolin-6-yl)-7-fluorothieno[3,2-c]pyridine-3-carbonitrile | 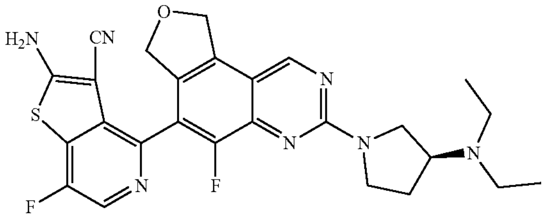 [SMILES: CCN(CC)[C@H]1CCN(c2ncc3c4c(c(-c5ncc(F)c6sc(N)c(C#N)c56)c(F)c3n2)COC4)C1] | 522 |
| 70B | 4-(3-(3-(1H-Imidazol-1-yl)azetidin-1-yl)-5-fluoro-7,9-dihydrofuro[3,4-f]quinazolin-6-yl)-2-amino-7-fluorothieno[3,2-c]pyridine-3-carbonitrile | 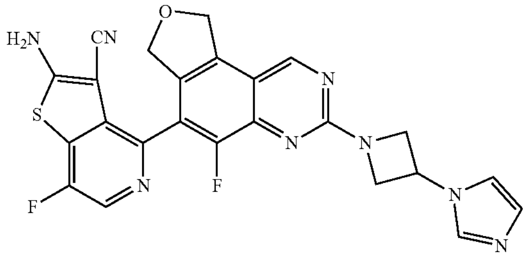 [SMILES: N#Cc1c(N)sc2c(F)cnc(-c3c4c(c5cnc(N6CC(n7ccnc7)C6)nc5c3F)COC4)c12] | 503 |

TABLE 28-continued

| Example | Chemical Name | Structure | MS (ES) m/z (M + 1) |
| --- | --- | --- | --- |
| 71B | 2-Amino-4-(3-((S)-3-(bis(methyl-d3)amino)pyrrolidin-1-yl)-5-fluoro-7,9-dihydrofuro[3,4-f]quinazolin-6-yl)-7-fluorothieno[3,2-c]pyridine-3-carbonitrile | 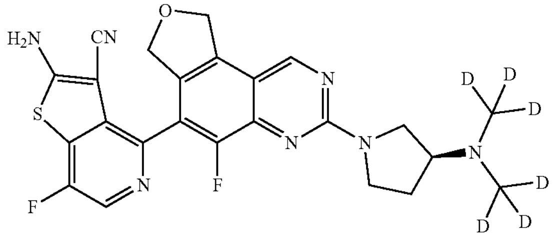 [SMILES: [2H]C([2H])([2H])N([C@H]1CCN(c2ncc3c4c(c(-c5ncc(F)c6sc(N)c(C#N)c56)c(F)c3n2)COC4)C1)C([2H])([2H])[2H]] | 500 |
| 72B | 2-Amino-4-(3-(3-(cyclopropylamino) pyrrolidin-1-yl)-5-fluoro-7,9-dihydrofuro[3,4-f]quinazolin-6-yl)-7-fluorothieno[3,2-c]pyridine-3-carbonitrile | 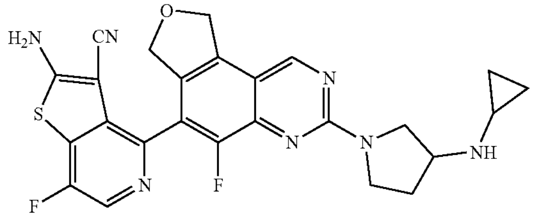 [SMILES: N#Cc1c(N)sc2c(F)cnc(-c3c4c(c5cnc(N6CCC(NC7CC7)C6)nc5c3F)COC4)c12] | 506 |
| 73B | 2-Amino-7-fluoro-4-(5-fluoro-3-(3-(isopropylamino)pyrrolidin-1-yl)-7,9-dihydrofuro[3,4-f]quinazolin-6-yl)thieno[3,2-c]pyridine-3-carbonitrile | 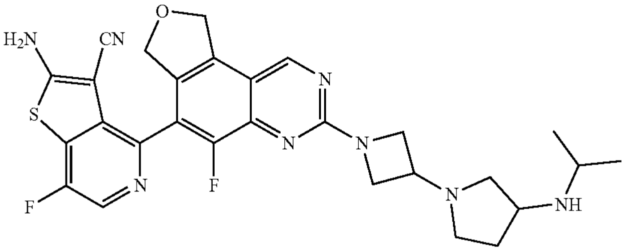 [SMILES: CC(C)NC1CCN(C2CN(c3ncc4c5c(c(-c6ncc(F)c7sc(N)c(C#N)c67)c(F)c4n3)COC5)C2)C1] | 508 |
| 74B | 2-Amino-4-(3-(3-(ethylamino)pyrrolidin-1-yl)-5-fluoro-7,9-dihydrofuro[3,4-f]quinazolin-6-yl)-7-fluorothieno[3,2-c]pyridine-3-carbonitrile | 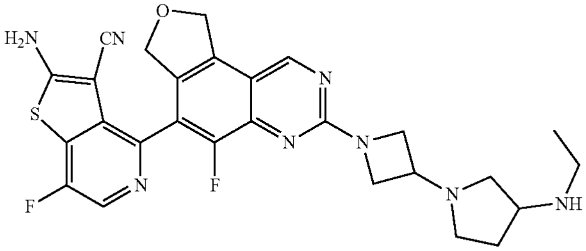 [SMILES: CCNC1CCN(C2CN(c3ncc4c5c(c(-c6ncc(F)c7sc(N)c(C#N)c67)c(F)c4n3)COC5)C2)C1] | 494 |
| 75B | 2-Amino-4-(3-((4aR,7aS)-1,4-dimethyloctahydro-6H-pyrrolo[3,4-b]pyrazin-6-yl)-5-fluoro-7,9-dihydrofuro[3,4-f]quinazolin-6-yl)-7-fluorothieno[3,2-c]pyridine-3-carbonitrile | 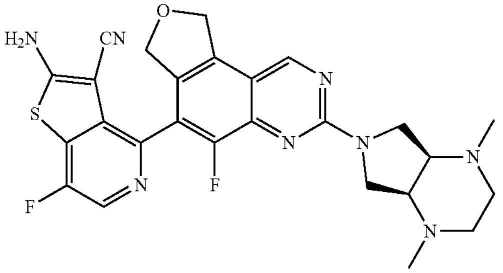 [SMILES: CN1CCN(C)[C@H]2CN(c3ncc4c5c(c(-c6ncc(F)c7sc(N)c(C#N)c67)c(F)c4n3)COC5)C[C@H]21] | 535 |
| 76B | 2-Amino-7-fluoro-4-(5-fluoro-3-((1S,5S)-6-methyl-3,6-diazabicyclo[3.2.0]heptan-3-yl)-7,9-dihydrofuro[3,4-f]quinazolin-6-yl)thieno[3,2-c]pyridine-3-carbonitrile | 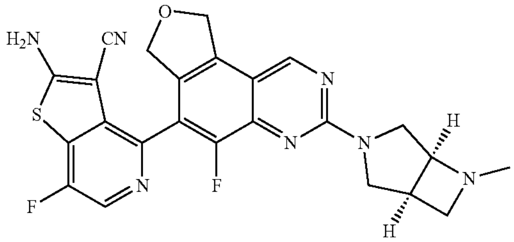 [SMILES: CN1C[C@H]2CN(c3ncc4c5c(c(-c6ncc(F)c7sc(N)c(C#N)c67)c(F)c4n3)COC5)C[C@H]21] | 492 |

TABLE 28-continued

| Example | Chemical Name | Structure | MS (ES) m/z (M + 1) |
|---|---|---|---|
| 77B | 2-Amino-7-fluoro-4-(5-fluoro-3-((1R,5R)-6-methyl-3,6-diazabicyclo[3.2.0]heptan-3-yl)-7,9-dihydrofuro[3,4-f]quinazolin-6-yl)thieno[3,2-c]pyridine-3-carbonitrile | 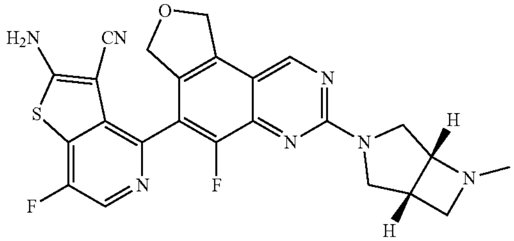 [SMILES: CN1C[C@@H]2CN(c3ncc4c5c(c(-c6ncc(F)c7sc(N)c(C#N)c67)c(F)c4n3)COC5)C[C@@H]21] | 492 |
| 78B | 2-Amino-4-(3-((S)-3-((dimethylamino)methyl) pyrrolidin-1-yl)-5-fluoro-7,9-dihydrofuro[3,4-f]quinazolin-6-yl)-7-fluorothieno[3,2-c]pyridine-3-carbonitrile | 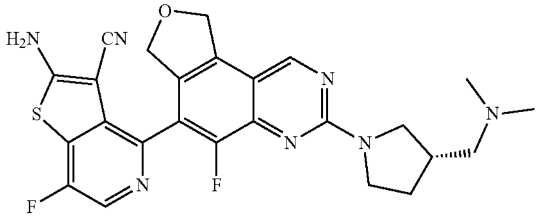 [SMILES: CN(C)C[C@@H]1CCN(c2ncc3c4c(c(-c5ncc(F)c6sc(N)c(C#N)c56)c(F)c3n2)COC4)C1] | 508 |
| 79B | 2-Amino-4-(3-((R)-3-((dimethylamino)methyl) pyrrolidin-1-yl)-5-fluoro-7,9-dihydrofuro[3,4-f]quinazolin-6-yl)-7-fluorothieno[3,2-c]pyridine-3-carbonitrile | 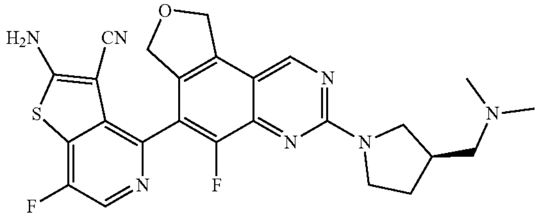 [SMILES: CN(C)C[C@H]1CCN(c2ncc3c4c(c(-c5ncc(F)c6sc(N)c(C#N)c56)c(F)c3n2)COC4)C1] | 508 |
| 80B | 2-Amino-4-(5-chloro-3-((1R,5R)-6-methyl-3,6-diazabicyclo[3.2.0]heptan-3-yl)-7,9-dihydrofuro[3,4-f]quinazolin-6-yl)-7-fluorobenzo[b]thiophene-3-carbonitrile | 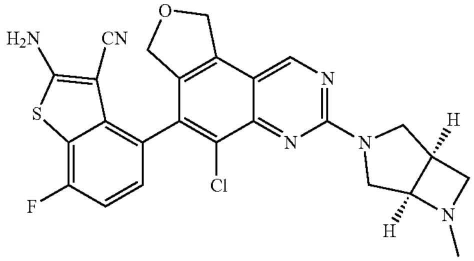 [SMILES: CN1C[C@@H]2CN(c3ncc4c5c(c(-c6ccc(F)c7sc(N)c(C#N)c67)c(Cl)c4n3)COC5)C[C@@H]21] | 507 |
| 81B | 2-Amino-4-(5-chloro-3-((1S,5S)-6-methyl-3,6-diazabicyclo[3.2.0]heptan-3-yl)-7,9-dihydrofuro[3,4-f]quinazolin-6-yl)-7-fluorobenzo[b]thiophene-3-carbonitrile | 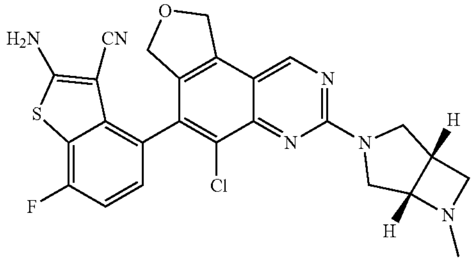 [SMILES: CN1C[C@H]2CN(c3ncc4c5c(c(-c6ccc(F)c7sc(N)c(C#N)c67)c(Cl)c4n3)COC5)C[C@H]21] | 507 |
| 82B [17] | 2-Amino-4-(3-(3-(dimethylamino)-2-methylpyrrolidin-1-yl)-5-fluoro-7,9-dihydrofuro[3,4-f]quinazolin-6-yl)-7-fluorothieno[3,2-c]pyridine-3-carbonitrile, Diastereomer 1 | 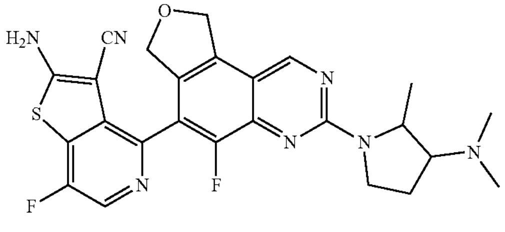 [SMILES: CC1C(N(C)C)CCN1c1ncc2c3c(c(-c4ncc(F)c5sc(N)c(C#N)c45)c(F)c2n1)COC3] | 508 |

TABLE 28-continued

| Example | Chemical Name | Structure | MS (ES) m/z (M + 1) |
|---|---|---|---|
| 83B [17] | 2-Amino-4-(3-(3-(dimethylamino)-2-methylpyrrolidin-1-yl)-5-fluoro-7,9-dihydrofuro[3,4-f]quinazolin-6-yl)-7-fluorothieno[3,2-c]pyridine-3-carbonitrile, Diastereomer 2 | 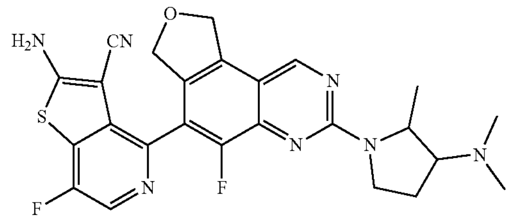 [SMILES: CC1C(N(C)C)CCN1c1ncc2c3c(c(-c4ncc(F)c5sc(N)c(C#N)c45)c(F)c2n1)COC3] | 508 |
| 84B [17] | 2-Amino-4-(3-(3-(dimethylamino)-2-methylpyrrolidin-1-yl)-5-fluoro-7,9-dihydrofuro[3,4-f]quinazolin-6-yl)-7-fluorothieno[3,2-c]pyridine-3-carbonitrile, Diastereomer 3 | 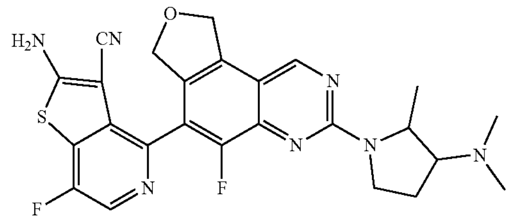 [SMILES: CC1C(N(C)C)CCN1c1ncc2c3c(c(-c4ncc(F)c5sc(N)c(C#N)c45)c(F)c2n1)COC3] | 508 |
| 85B [17] | 2-Amino-4-(3-(3-(dimethylamino)-2-methylpyrrolidin-1-yl)-5-fluoro-7,9-dihydrofuro[3,4-f]quinazolin-6-yl)-7-fluorothieno[3,2-c]pyridine-3-carbonitrile, Diastereomer 4 | 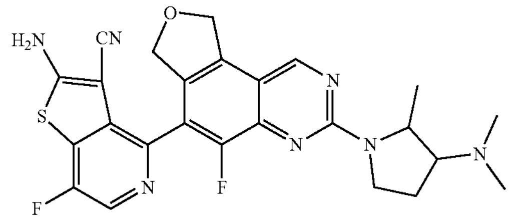 [SMILES: CC1C(N(C)C)CCN1c1ncc2c3c(c(-c4ncc(F)c5sc(N)c(C#N)c45)c(F)c2n1)COC3] | 508 |
| 86B | 2-Amino-7-fluoro-4-(5-fluoro-3-(5-methyl-2,5-diazaspiro[3.5]nonan-2-yl)-7,9-dihydrofuro[3,4-f]quinazolin-6-yl)thieno[3,2-c]pyridine-3-carbonitrile | 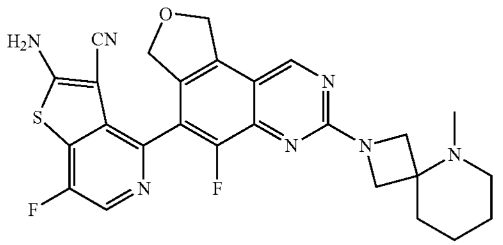 [SMILES: CN1CCCCC12CN(c1ncc3c4c(c(-c5ncc(F)c6sc(N)c(C#N)c56)c(F)c3n1)COC4)C2] | 520 |
| 87B | 2-Amino-4-(3-((2S,4S)-4-(dimethylamino)-2-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile | 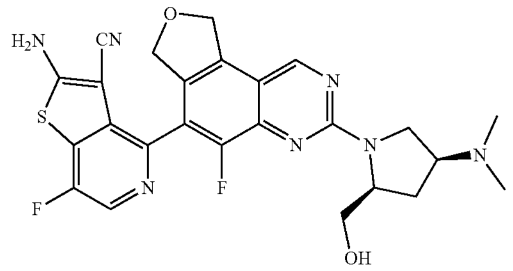 [SMILES: CN(C)[C@H]1C[C@@H](CO)N(c2ncc3c4c(c(-c5ncc(F)c6sc(N)c(C#N)c56)c(F)c3n2)COC4)C1] | 524 |
| 88B [18] | 4-(3-((1-(((1S,4S)-2-Oxa-5-azabicyclo[2.2.1]heptan-5-yl)methyl)cyclopropyl) methoxy)-5-chloro-7,9-dihydrofuro[3,4-f]quinazolin-6-yl)-2-amino-7-fluorobenzo[b]thiophene-3-carbonitrile, Atropisomer 1 | 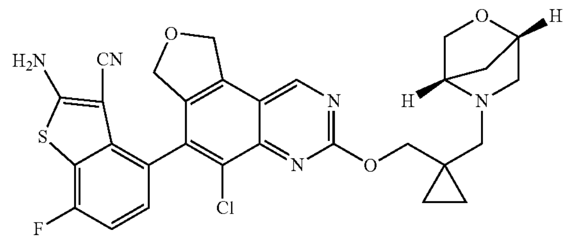 [SMILES: N#Cc1c(N)sc2c(F)ccc(-c3c4c(c5cnc(OCC6(CN7C[C@@H]8C[C@H]7CO8)CC6)nc5c3Cl)COC4)c12] | 578 |

TABLE 28-continued

| Example | Chemical Name | Structure | MS (ES) m/z (M + 1) |
| --- | --- | --- | --- |
| 89B [18] | 4-(3-((1-(((1S,4S)-2-Oxa-5-azabicyclo[2.2.1]heptan-5-yl)methyl)cyclopropyl) methoxy)-5-chloro-7,9-dihydrofuro[3,4-f]quinazolin-6-yl)-2-amino-7-fluorobenzo[b]thiophene-3-carbonitrile, Atropisomer 2 | 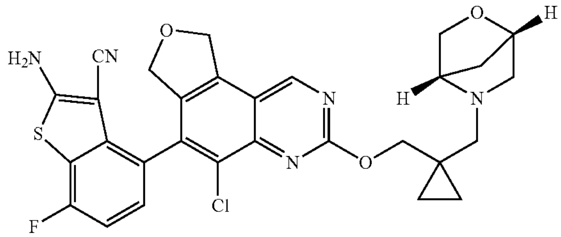 [SMILES: N#Cc1c(N)sc2c(F)ccc(-c3c4c(c5cnc(OCC6(CN7C[C@@H]8C[C@H]7CO8)CC6)nc5c3Cl)COC4)c12] | 578 |
| 90B [19] | 2-Amino-7-fluoro-4-(5-fluoro-3-(4-methylhexahydropyrrolo [3,4-b][1,4]oxazin-6(2H)-yl)-7,9-dihydrofuro[3,4-f]quinazolin-6-yl)thieno[3,2-c]pyridine-3-carbonitrile | 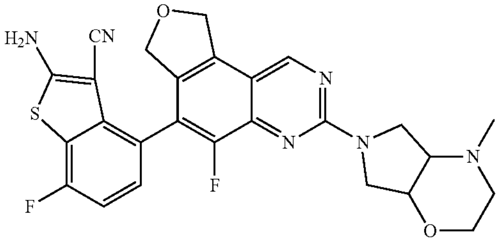 | 522 |
| 91B [19] | 2-Amino-7-fluoro-4-(5-fluoro-3-(4-methylhexahydropyrrolo [3,4-b][1,4]oxazin-6(2H)-yl)-7,9-dihydrofuro[3,4-f]quinazolin-6-yl)thieno[3,2-c]pyridine-3-carbonitrile | 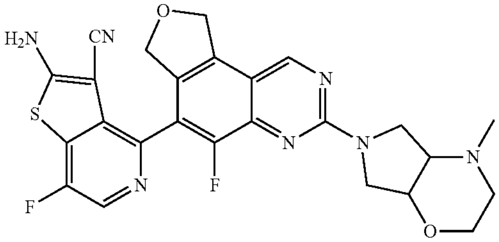 [SMILES: CN1CCOC2CN(c3ncc4c5c(c(-c6ncc(F)c7sc(N)c(C#N)c67)c(F)c4n3)COC5)CC21] | 522 |
| 92B | 2-Amino-7-fluoro-4-(5-fluoro-3-(5-methyl-2,5-diazaspiro[3.4]octan-2-yl)-7,9-dihydrofuro[3,4-f]quinazolin-6-yl)thieno[3,2-c]pyridine-3-carbonitrile | 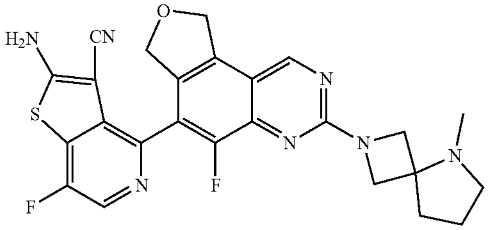 [SMILES: CN1CCCC12CN(c1ncc3c4c(c(-c5ncc(F)c6sc(N)c(C#N)c56)c(F)c3n1)COC4)C2] | 506 |
| 93B | 2-Amino-7-fluoro-4-(5-fluoro-3-(3-methyl-3,6-diazabicyclo[3.1.1]heptan-6-yl)-7,9-dihydrofuro[3,4-f]quinazolin-6-yl)thieno[3,2-c]pyridine-3-carbonitrile | 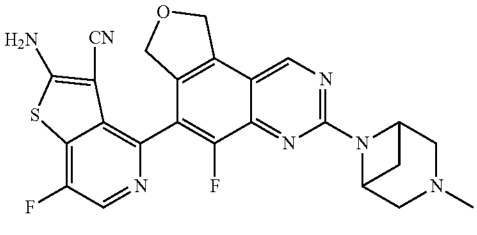 [SMILES: CN1CC2CC(C1)N2c1ncc2c3c(c(-c4ncc(F)c5sc(N)c(C#N)c45)c(F)c2n1)COC3] | 492 |
| 94B [20] | 2-Amino-4-(5-chloro-3-((S)-3-(dimethylamino)pyrrolidin-1-yl)-7,9-dihydrofuro[3,4-f]quinazolin-6-yl)-5-fluorobenzo[b]thiophene-3-carbonitrile, Atropisomer 1 | 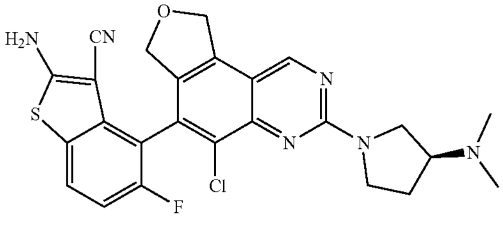 [SMILES: CN(C)[C@H]1CCN(c2ncc3c4c(c(-c5c(F)ccc6sc(N)c(C#N)c56)c(Cl)c3n2)COC4)C1] | 509 |

TABLE 28-continued

| Example | Chemical Name | Structure | MS (ES) m/z (M + 1) |
|---|---|---|---|
| 95B [20] | 2-Amino-4-(5-chloro-3-((S)-3-(dimethylamino)pyrrolidin-1-yl)-7,9-dihydrofuro[3,4-f]quinazolin-6-yl)-5-fluorobenzo[b]thiophene-3-carbonitrile, Atropisomer 2 | 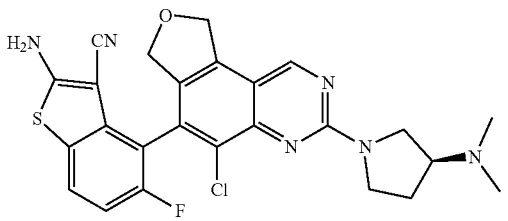 [SMILES: CN(C)[C@H]1CCN(c2ncc3c4c(c(-c5c(F)ccc6sc(N)c(C#N)c56)c(Cl)c3n2)COC4)C1] | 509 |
| 96B | 2-Amino-7-fluoro-4-(5-fluoro-3-((3aR,6aR)-1-methylhexahydropyrrolo[3,4-b]pyrrol-5(1H)-yl)-7,9-dihydrofuro[3,4-f]quinazolin-6-yl)thieno[3,2-c]pyridine-3-carbonitrile formic acid | 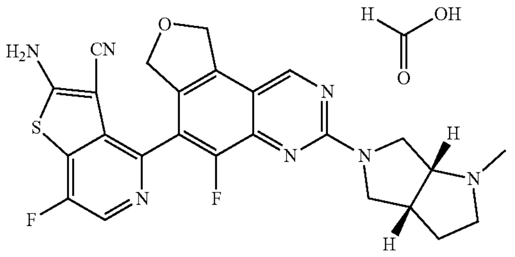 [SMILES: CN1CC[C@@H]2CN(c3ncc4c5c(c(-c6ncc(F)c7sc(N)c(C#N)c67)c(F)c4n3)COC5)C[C@@H]21 ; O=CO] | 506 |
| 97B | 2-Amino-7-fluoro-4-(5-fluoro-3-((3aS,6aS)-1-methylhexahydropyrrolo[3,4-b]pyrrol-5(1H)-yl)-7,9-dihydrofuro[3,4-f]quinazolin-6-yl)thieno[3,2-c]pyridine-3-carbonitrile | 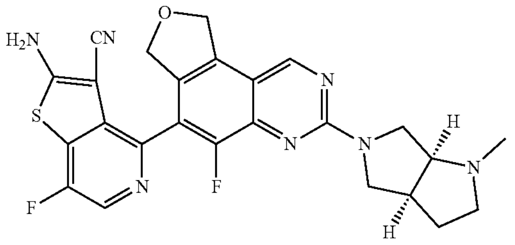 [SMILES: CN1CC[C@H]2CN(c3ncc4c5c(c(-c6ncc(F)c7sc(N)c(C#N)c67)c(F)c4n3)COC5)C[C@H]21] | 506 |
| 98B | 2-Amino-4-(3-((R)-2-((dimethylamino)methyl)morpholino)-5-fluoro-7,9-dihydrofuro[3,4-f]quinazolin-6-yl)-7-fluorothieno[3,2-c]pyridine-3-carbonitrile | 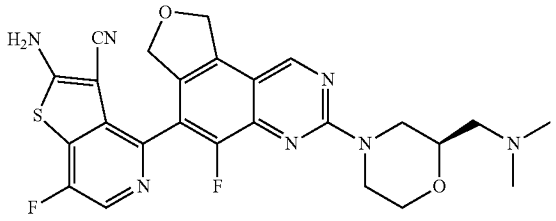 [SMILES: CN(C)C[C@@H]1CN(c2ncc3c4c(c(-c5ncc(F)c6sc(N)c(C#N)c56)c(F)c3n2)COC4)CCO1] | 524 |
| 99B | 2-Amino-4-(3-(5-(dimethylamino)-2-azaspiro[3.3 ]heptan-2-yl)-5-fluoro-7,9-dihydrofuro[3,4-f]quinazolin-6-yl)-7-fluorothieno[3,2-c]pyridine-3-carbonitrile | 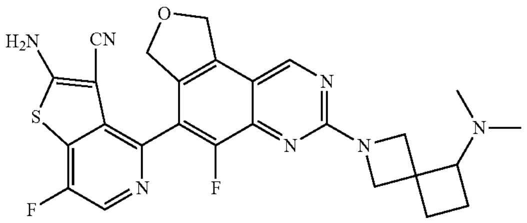 [SMILES: CN(C)C1CCC12CN(c1ncc3c4c(c(-c5ncc(F)c6sc(N)c(C#N)c56)c(F)c3n1)COC4)C2] | 520 |
| 100B | 2-Amino-4-(3-(3-((dimethylamino)methyl)pyrrolidin-1-yl)-5-fluoro-7,9-dihydrofuro[3,4-f]quinazolin-6-yl)-7-fluorothieno[3,2-c]pyridine-3-carbonitrile | 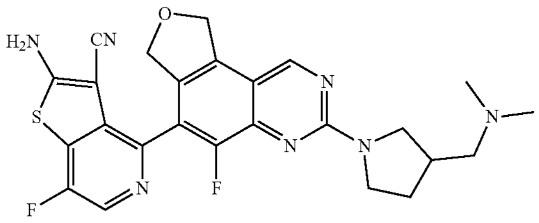 [SMILES: CN(C)CC1CCN(c2ncc3c4c(c(-c5ncc(F)c6sc(N)c(C#N)c56)c(F)c3n2)COC4)C1] | 508 |

TABLE 28-continued

| Example | Chemical Name | Structure | MS (ES) m/z (M + 1) |
|---|---|---|---|
| 101B | 2-Amino-4-(3-((R)-7-amino-5-azaspiro[2.4]heptan-5-yl)-5-fluoro-7,9-dihydrofuro[3,4-f]quinazolin-6-yl)-7-fluorothieno[3,2-c]pyridine-3-carbonitrile | 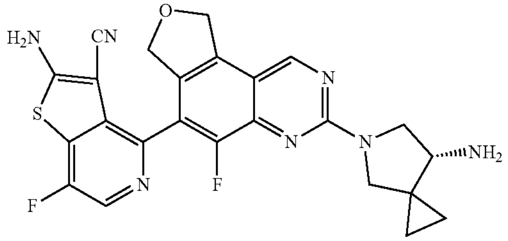 [SMILES: N#Cc1c(N)sc2c(F)cnc(-c3c4c(c5cnc(N6C[C@H](N)C7(CC7)C6)nc5c3F)COC4)c12] | 492 |
| 102B | 2-Amino-4-(3-((S)-7-amino-5-azaspiro[2.4]heptan-5-yl)-5-fluoro-7,9-dihydrofuro[3,4-f]quinazolin-6-yl)-7-fluorothieno[3,2-c]pyridine-3-carbonitrile | 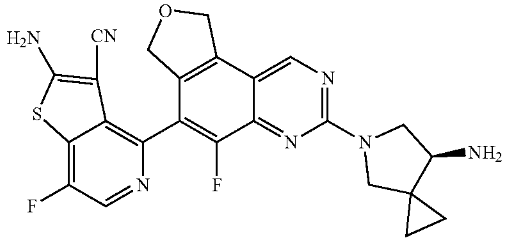 [SMILES: N#Cc1c(N)sc2c(F)cnc(-c3c4c(c5cnc(N6C[C@@H](N)C7(CC7)C6)nc5c3F)COC4)c12] | 492 |
| 103B | 2-Amino-7-fluoro-4-(5-fluoro-3-(6-methyl-2,6-diazaspiro[3.3]heptan-2-yl)-7,9-dihydrofuro[3,4-f]quinazolin-6-yl)thieno[3,2-c]pyridine-3-carbonitrile | 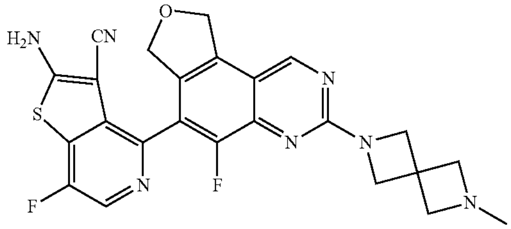 [SMILES: CN1CC2(C1)CN(c1ncc3c4c(c(-c5ncc(F)c6sc(N)c(C#N)c56)c(F)c3n1)COC4)C2] | 492 |
| 104B | 2-Amino-4-(3-(4-(azetidin-1-yl)piperidin-1-yl)-5-fluoro-7,9-dihydrofuro[3,4-f]quinazolin-6-yl)-7-fluorothieno[3,2-c]pyridine-3-carbonitrile | 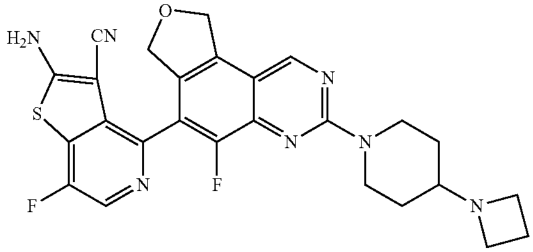 [SMILES: N#Cc1c(N)sc2c(F)cnc(-c3c4c(c5cnc(N6CCC(N7CCC7)CC6)nc5c3F)COC4)c12] | 520 |
| 105B | 2-Amino-4-(3-((S)-3-(azetidin-1-yl)pyrrolidin-1-yl)-5-fluoro-7,9-dihydrofuro[3,4-f]quinazolin-6-yl)-7-fluorothieno[3,2-c]pyridine-3-carbonitrile | 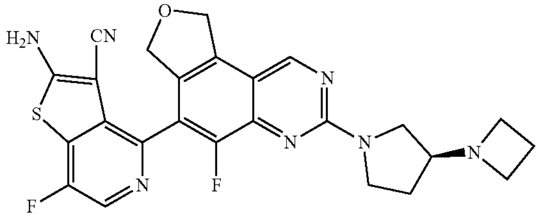 [SMILES: N#Cc1c(N)sc2c(F)cnc(-c3c4c(c5cnc(N6CC[C@H](N7CCC7)C6)nc5c3F)COC4)c12] | 506 |
| 106B | 2-Amino-7-fluoro-4-(5-fluoro-3-(4-(3-methoxyazetidin-1-yl)piperidin-1-yl)-7,9-dihydrofuro[3,4-f]quinazolin-6-yl)thieno[3,2-c]pyridine-3-carbonitrile | 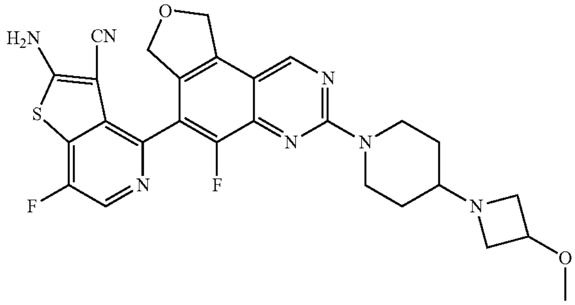 [SMILES: COC1CN(C2CCN(c3ncc4c5c(c(-c6ncc(F)c7sc(N)c(C#N)c67)c(F)c4n3)COC5)CC2)C1] | 550 |

TABLE 28-continued

| Example | Chemical Name | Structure | MS (ES) m/z (M + 1) |
|---|---|---|---|
| 107B | 2-Amino-4-(3-((R)-3-(dimethylamino)pyrrolidin-1-yl)-5-fluoro-7,9-dihydrofuro[3,4-f]quinazolin-6-yl)-7-fluorothieno[3,2-c]pyridine-3-carbonitrile | 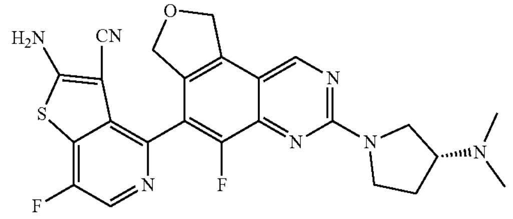 [SMILES: CN(C)[C@@H]1CCN(c2ncc3c4c(c(-c5ncc(F)c6sc(N)c(C#N)c56)c(F)c3n2)COC4)C1] | 494 |
| 108B [21] | 2-Amino-4-(3-(3-(dimethylamino)piperidin-1-yl)-5-fluoro-7,9-dihydrofuro[3,4-f]quinazolin-6-yl)-7-fluorothieno[3,2-c]pyridine-3-carbonitrile, Isomer 1 | 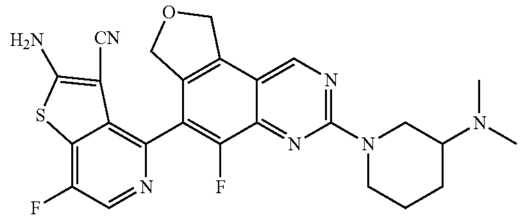 [SMILES: CN(C)C1CCCN(c2ncc3c4c(c(-c5ncc(F)c6sc(N)c(C#N)c56)c(F)c3n2)COC4)C1] | 508 |
| 109B [21] | 2-Amino-4-(3-(3-(dimethylamino)piperidin-1-yl)-5-fluoro-7,9-dihydrofuro[3,4-f]quinazolin-6-yl)-7-fluorothieno[3,2-c]pyridine-3-carbonitrile, Isomer 2 | 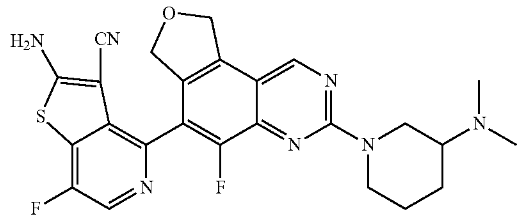 [SMILES: CN(C)C1CCCN(c2ncc3c4c(c(-c5ncc(F)c6sc(N)c(C#N)c56)c(F)c3n2)COC4)C1] | 508 |
| 110B [22] | 2-Amino-7-fluoro-4-(5-fluoro-3-(hexahydropyrrolo[1,2-alpyrazin-2(1H)-yl)-7,9-dihydrofuro[3,4-f]quinazolin-6-yl)thieno[3,2-c]pyridine-3-carbonitrile, Isomer 1 | 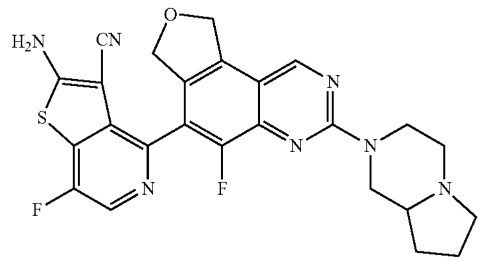 [SMILES: N#Cc1c(N)sc2c(F)cnc(-c3c4c(c5cnc(N6CCN7CCCC7C6)nc5c3F)COC4)c12] | 506 |
| 111B [22] | 2-Amino-7-fluoro-4-(5-fluoro-3-(hexahydropyrrolo[1,2-a]pyrazin-2(1H)-yl)-7,9-dihydrofuro[3,4-f]quinazolin-6-yl)thieno[3,2-c]pyridine-3-carbonitrile, Isomer 2 | 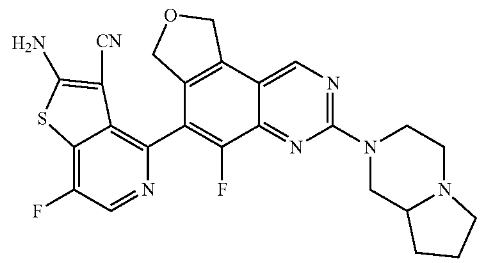 [SMILES: N#Cc1c(N)sc2c(F)cnc(-c3c4c(c5cnc(N6CCN7CCCC7C6)nc5c3F)COC4)c12] | 506 |
| 112B | 2-Amino-7-fluoro-4-(5-fluoro-3-(3-hydroxy-[1,3'-biazetidin]-1'-yl)-7,9-dihydrofuro[3,4-f]quinazolin-6-yl)thieno[3,2-c]pyridine-3-carbonitrile | 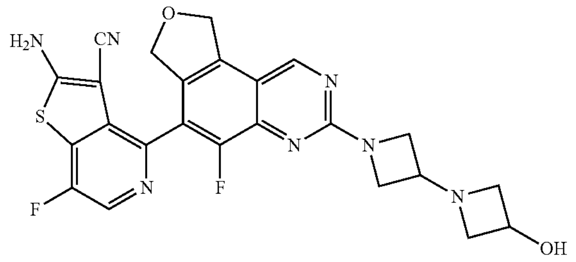 [SMILES: N#Cc1c(N)sc2c(F)cnc(-c3c4c(c5cnc(N6CC(N7CC(O)C7)C6)nc5c3F)COC4)c12] | 508 |

TABLE 28-continued

| Example | Chemical Name | Structure | MS (ES) m/z (M + 1) |
|---|---|---|---|
| 113B | 2-Amino-7-fluoro-4-(5-fluoro-3-(3-methyl-3-(pyrrolidin-1-yl)azetidin-1-yl)-7,9-dihydrofuro[3,4-f]quinazolin-6-yl)thieno[3,2-c]pyridine-3-carbonitrile formic acid | 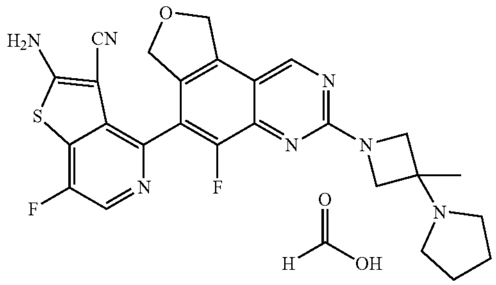 | 520 |
| 114B | 2-Amino-4-(3-(3-cyclopropyl-3-hydroxyazetidin-1-yl)-5-fluoro-7,9-dihydrofuro[3,4-f]quinazolin-6-yl)-7-fluorothieno[3,2-c]pyridine-3-carbonitrile | 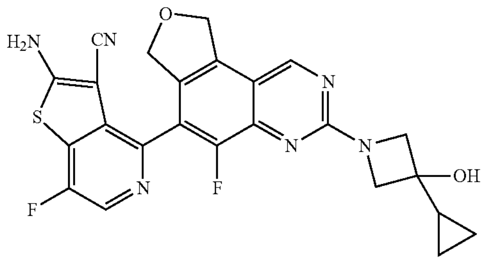 [SMILES: N#Cc1c(N)sc2c(F)cnc(-c3c4c(c5cnc(N6CC(O)(C7CC7)C6)nc5c3F)COC4)c12] | 493 |
| 115B | 2-Amino-7-fluoro-4-(5-fluoro-3-(6-methyl-2,6-diazaspiro[3.4]octan-2-yl)-7,9-dihydrofuro[3,4-f]quinazolin-6-yl)thieno[3,2-c]pyridine-3-carbonitrile | 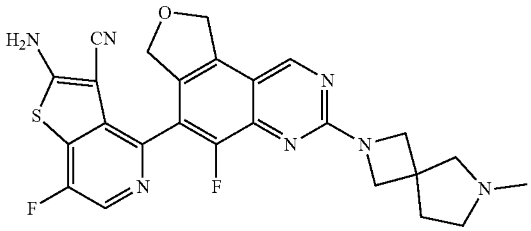 [SMILES: CN1CCC2(C1)CN(c1ncc3c4c(c(-c5ncc(F)c6sc(N)c(C#N)c56)c(F)c3n1)COC4)C2] | 506 |
| 116B | 2-Amino-4-(3-(4-(dimethylamino)piperidin-1-yl)-5-fluoro-7,9-dihydrofuro[3,4-f]quinazolin-6-yl)-7-fluorothieno[3,2-c]pyridine-3-carbonitrile | 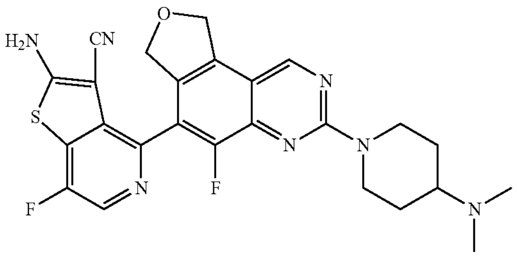 [SMILES: CN(C)C1CCN(c2ncc3c4c(c(-c5ncc(F)c6sc(N)c(C#N)c56)c(F)c3n2)COC4)CC1] | 508 |
| 117B | 2-Amino-4-(3-((3S,4S)-3-(dimethylamino)-4-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile | 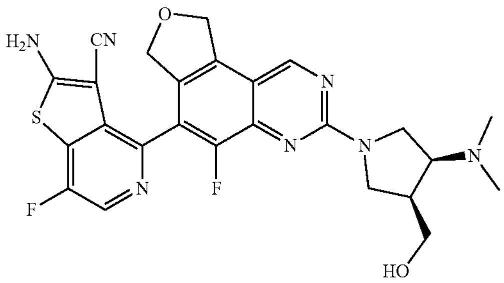 | 524 |

TABLE 28-continued

| Example | Chemical Name | Structure | MS (ES) m/z (M + 1) |
|---|---|---|---|
| 118B | 2-Amino-4-(3-((3R,4R)-3-(dimethylamino)-4-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile | 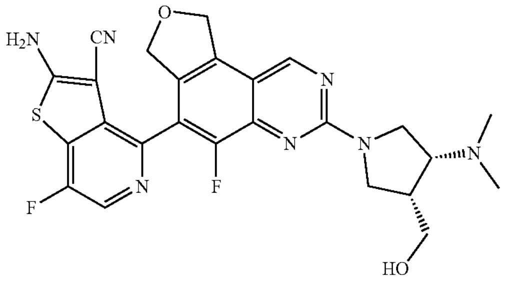 [SMILES: CN(C)[C@H]1CN(c2ncc3c4c(c(-c5ncc(F)c6sc(N)c(C#N)c56)c(F)c3n2)COC4)C[C@H]1CO] | 524 |
| 119B | 2-Amino-4-(3-((3S,4R)-3-(dimethylamino)-4-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile | 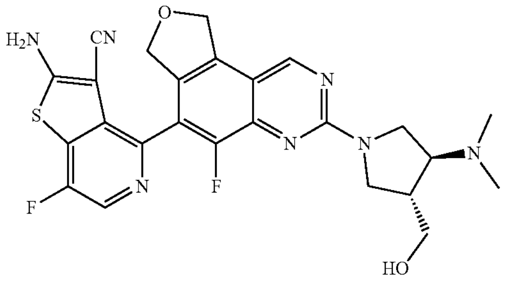 [SMILES: CN(C)[C@@H]1CN(c2ncc3c4c(c(-c5ncc(F)c6sc(N)c(C#N)c56)c(F)c3n2)COC4)C[C@H]1CO] | 524 |
| 120B | 2-Amino-4-(3-((3R,4S)-3-(dimethylamino)-4-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile | 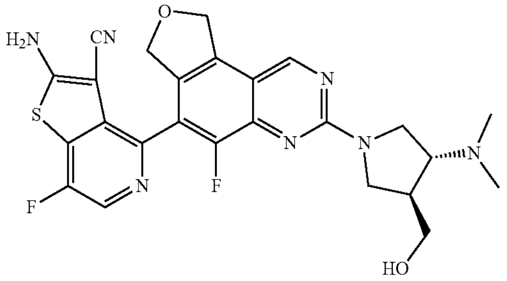 [SMILES: CN(C)[C@H]1CN(c2ncc3c4c(c(-c5ncc(F)c6sc(N)c(C#N)c56)c(F)c3n2)COC4)C[C@@H]1CO] | 524 |
| 121B [23] | 2-Amino-4-(5-chloro-3-((3S,4S)-3-(dimethylamino)-4-(hydroxymethyl)pyrrolidin-1-yl)-7,9-dihydrofuro[3,4-f]quinazolin-6-yl)-7-fluorothieno[3,2-c]pyridine-3-carbonitrile, Atropisomer 1 | 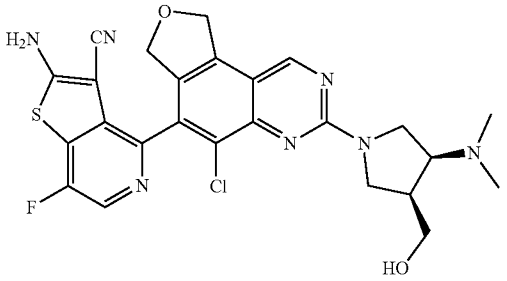 | 540 |
| 122B [24] | 2-Amino-4-(5-chloro-3-((3S,4S)-3-(dimethylamino)-4-(hydroxymethyl)pyrrolidin-1-yl)-7,9-dihydrofuro[3,4-f]quinazolin-6-yl)-7-fluorothieno[3,2-c]pyridine-3-carbonitrile, Atropisomer 2 | 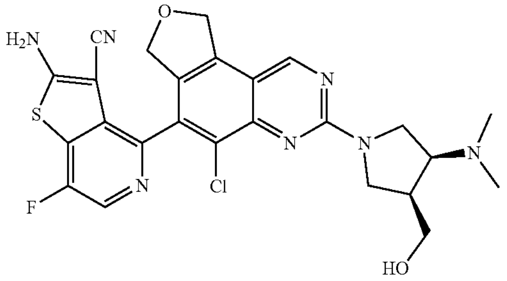 [SMILES: CN(C)[C@@H]1CN(c2ncc3c4c(c(-c5ncc(F)c6sc(N)c(C#N)c56)c(Cl)c3n2)COC4)C[C@@H]1CO] | 540 |

TABLE 28-continued

| Example | Chemical Name | Structure | MS (ES) m/z (M + 1) |
|---|---|---|---|
| 123B | 2-Amino-4-(3-((1R,5S)-1-((dimethylamino)methyl)-3-azabicyclo[3.1.0]hexan-3-yl)-5-fluoro-7,9-dihydrofuro[3,4-f]quinazolin-6-yl)-7-fluorothieno[3,2-c]pyridine-3-carbonitrile | 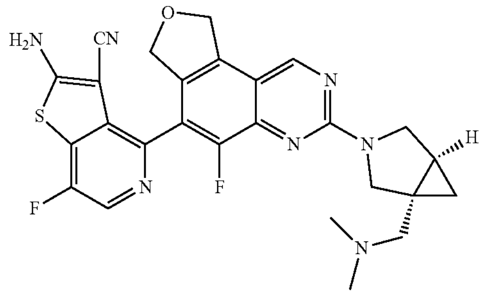 [SMILES: CN(C)C[C@@]12C[C@@H]1CN(c1ncc3c4c(c(-c5ncc(F)c6sc(N)c(C#N)c56)c(F)c3n1)COC4)C2] | 520 |
| 124B | 2-Amino-4-(3-((1S,5R)-1-((dimethylamino)methyl)-3-azabicyclo[3.1.0]hexan-3-yl)-5-fluoro-7,9-dihydrofuro[3,4-f]quinazolin-6-yl)-7-fluorothieno[3,2-c]pyridine-3-carbonitrile | 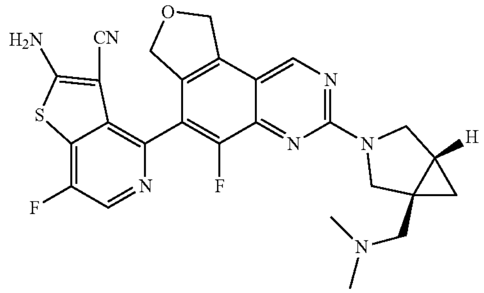 [SMILES: CN(C)C[C@]12C[C@H]1CN(c1ncc3c4c(c(-c5ncc(F)c6sc(N)c(C#N)c56)c(F)c3n1)COC4)C2] | 520 |
| 125B | 2-Amino-4-(3-((1R,5S)-1-(dimethylamino)-3-azabicyclo[3.1.0]hexan-3-yl)-5-fluoro-7,9-dihydrofuro[3,4-f]quinazolin-6-yl)-7-fluorothieno[3,2-c]pyridine-3-carbonitrile | 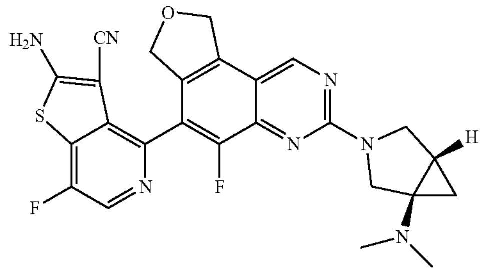 [SMILES: CN(C)[C@]12C[C@H]1CN(c1ncc3c4c(c(-c5ncc(F)c6sc(N)c(C#N)c56)c(F)c3n1)COC4)C2] | 506 |
| 126B [25] | 2-Amino-4-(3-((R)-3-(dimethylamino)-3-methylpyrrolidin-1-yl)-5-fluoro-7,9-dihydrofuro[3,4-f]quinazolin-6-yl)-7-fluorothieno[3,2-c]pyridine-3-carbonitrile | 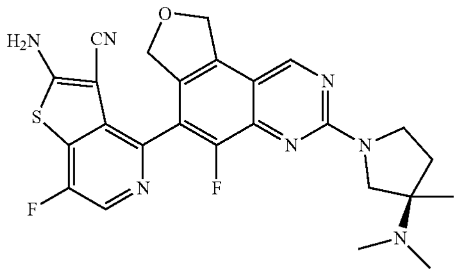 [SMILES: CN(C)[C@]1(C)CCN(c2ncc3c4c(c(-c5ncc(F)c6sc(N)c(C#N)c56)c(F)c3n2)COC4)C1] | 508 |
| 127B [25] | 2-Amino-4-(3-((3R,4S)-3-(dimethylamino)-4-methylpyrrolidin-1-yl)-5-fluoro-7,9-dihydrofuro[3,4-f]quinazolin-6-yl)-7-fluorothieno[3,2-c]pyridine-3-carbonitrile | 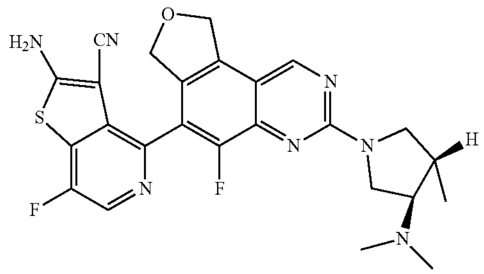 [SMILES: C[C@H]1CN(c2ncc3c4c(c(-c5ncc(F)c6sc(N)c(C#N)c56)c(F)c3n2)COC4)C[C@@H]1N(C)C] | 508 |

TABLE 28-continued

| Example | Chemical Name | Structure | MS (ES) m/z (M + 1) |
|---|---|---|---|
| 128B | 2-Amino-4-(3-((1S,5R)-1-(dimethylamino)-3-azabicyclo[3.1.0]hexan-3-yl)-5-fluoro-7,9-dihydrofuro[3,4-f]quinazolin-6-yl)-7-fluorothieno[3,2-c]pyridine-3-carbonitrile | 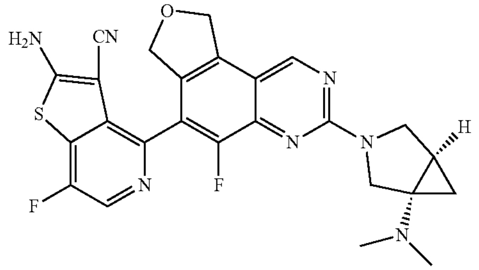 [SMILES: CN(C)[C@@]12C[C@@H]1CN(c1ncc3c4c(c(-c5ncc(F)c6sc(N)c(C#N)c56)c(F)c3n1)COC4)C2] | 506 |
| 129B [26] | 2-Amino-5-fluoro-4-(5-fluoro-3-((3aR,6aS)-hexahydropyrrolo[3,4-c]pyrrol-2(1H)-yl)-7,9-dihydrofuro[3,4-f]quinazolin-6-yl)benzo[b]thiophene-3-carbonitrile | 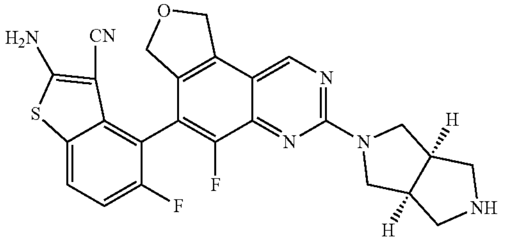 [SMILES: N#Cc1c(N)sc2ccc(F)c(-c3c4c(c5cnc(N6C[C@H]7CNC[C@H]7C6)nc5c3F)COC4)c12] | 491 |
| 130B [26] | 2-Amino-5-fluoro-4-(5-fluoro-3-(1-methyl-1,6-diazaspiro[3.3]heptan-6-yl)-7,9-dihydrofuro[3,4-f]quinazolin-6-yl)benzo[b]thiophene-3-carbonitrile | 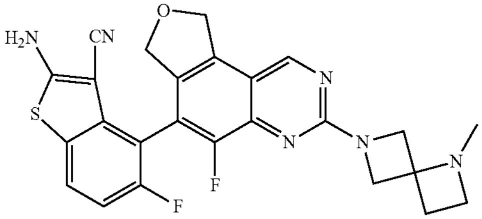 [SMILES: CN1CCC12CN(c1ncc3c4c(c(-c5c(F)ccc6sc(N)c(C#N)c56)c(F)c3n1)COC4)C2] | 491 |
| 131B [26] | 2-Amino-4-(3-((3R,4S)-3-(dimethylamino)-4-hydroxypyrrolidin-1-yl)-5-fluoro-7,9-dihydrofuro[3,4-f]quinazolin-6-yl)-5-fluorobenzo[b]thiophene-3-carbonitrile | 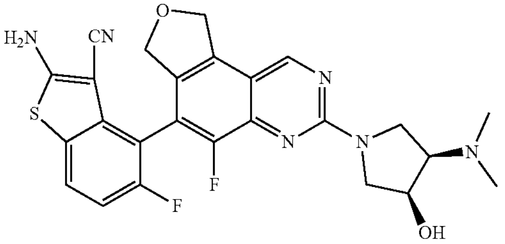 [SMILES: CN(C)[C@@H]1CN(c2ncc3c4c(c(-c5c(F)ccc6sc(N)c(C#N)c56)c(F)c3n2)COC4)C[C@@H]1O] | 509 |
| 132B [26] | 2-Amino-5-fluoro-4-(5-fluoro-3-((1S,4S)-5-methyl-2,5-diazabicyclo[2.2.1]heptan-2-yl)-7,9-dihydrofuro[3,4-f]quinazolin-6-yl)benzo[b]thiophene-3-carbonitrile | 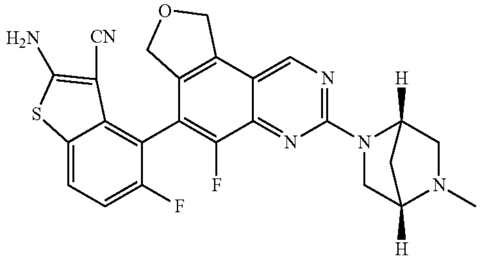 [SMILES: CN1C[C@@H]2C[C@H]1CN2c1ncc2c3c(c(-c4c(F)ccc5sc(N)c(C#N)c45)c(F)c2n1)COC3] | 491 |
| 133B [26] | 2-Amino-4-(3-((R)-3-((dimethylamino)methyl)pyrrolidin-1-yl)-5-fluoro-7,9-dihydrofuro[3,4-f]quinazolin-6-yl)-5-fluorobenzo[b]thiophene-3-carbonitrile | 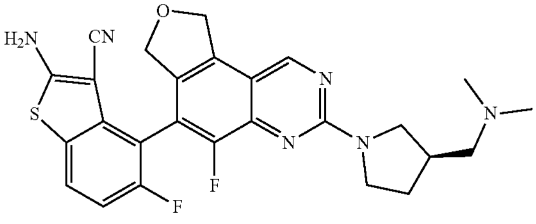 [SMILES: CN(C)C[C@H]1CCN(c2ncc3c4c(c(-c5c(F)ccc6sc(N)c(C#N)c56)c(F)c3n2)COC4)C1] | 507 |

TABLE 28-continued

| Example | Chemical Name | Structure | MS (ES) m/z (M + 1) |
|---|---|---|---|
| 134B [26] | 2-Amino-4-(3-((S)-3-((dimethylamino)methyl) pyrrolidin-1-yl)-5-fluoro-7,9-dihydrofuro[3,4-f]quinazolin-6-yl)-5-fluorobenzo[b]thiophene-3-carbonitrile | 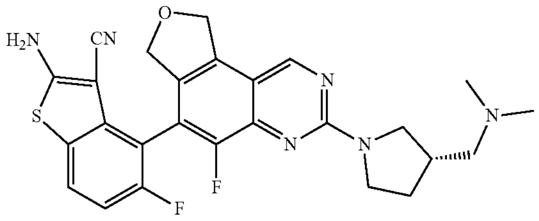 [SMILES: CN(C)C[C@@H]1CCN(c2ncc3c4c(c(-c5c(F)ccc6sc(N)c(C#N)c56)c(F)c3n2)COC4)C1] | 507 |
| 135B [26] | 2-Amino-4-(3-((S)-7-(dimethylamino)-5-azaspiro[2.4]heptan-5-yl)-5-fluoro-7,9-dihydrofuro[3,4-f]quinazolin-6-yl)-5-fluorobenzo[b]thiophene-3-carbonitrile | 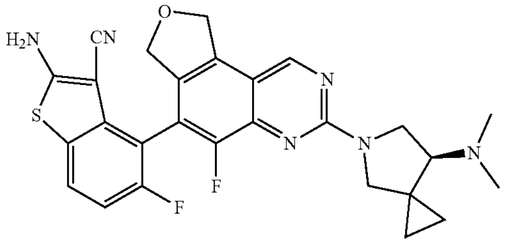 [SMILES: CN(C)[C@@H]1CN(c2ncc3c4c(c(-c5c(F)ccc6sc(N)c(C#N)c56)c(F)c3n2)COC4)CC12CC2] | 519 |
| 136B | 2-Amino-7-fluoro-4-(5-fluoro-3-(5-methylhexahydropyrrolo [3,4-b]pyrrol-1(2H)-yl)-7,9-dihydrofuro[3,4-f]quinazolin-6-yl)thieno[3,2-c]pyridine-3-carbonitrile | 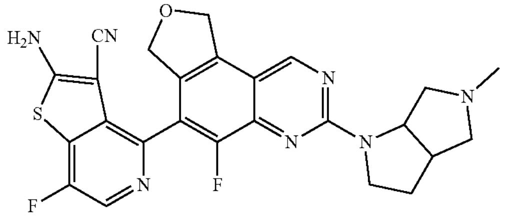 [SMILES: CN1CC2CCN(c3ncc4c5c(c(-c6ncc(F)c7sc(N)c(C#N)c67)c(F)c4n3)COC5)C2C1] | 506 |
| 1C [27] | 2-Amino-7-fluoro-4-(5-fluoro-3-(4-methyloctahydro-1H-pyrrolo[3,2-b]pyridin-1-yl)-7,9-dihydrofuro[3,4-f]quinazolin-6-yl)thieno[3,2-c]pyridine-3-carbonitrile | 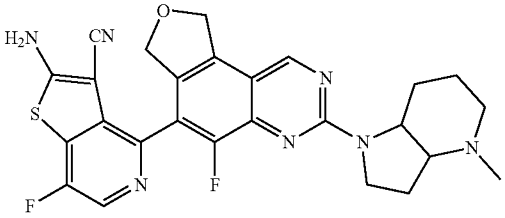 [SMILES: CN1CCCC2C1CCN2c1ncc2c3c(c(-c4ncc(F)c5sc(N)c(C#N)c45)c(F)c2n1)COC3] | 520 |
| 2C [28] | 2-Amino-7-fluoro-4-(5-fluoro-3-(4-methyloctahydro-1H-pyrrolo[3,2-b]pyridin-1-yl)-7,9-dihydrofuro[3,4-f]quinazolin-6-yl)thieno[3,2-c]pyridine-3-carbonitrile | 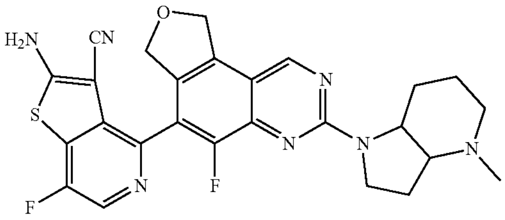 [SMILES: CN1CCCC2C1CCN2c1ncc2c3c(c(-c4ncc(F)c5sc(N)c(C#N)c45)c(F)c2n1)COC3] | 520 |
| 3C [28] | 2-Amino-7-fluoro-4-(5-fluoro-3-(4-methyloctahydro-1H-pyrrolo[3,2-b]pyridin-1-yl)-7,9-dihydrofuro[3,4-f]quinazolin-6-yl)thieno[3,2-c]pyridine-3-carbonitrile | 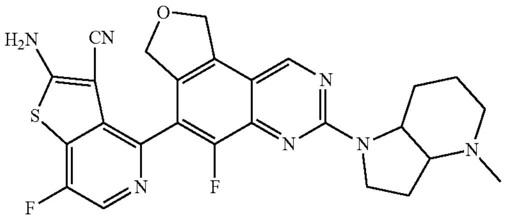 [SMILES: CN1CCCC2C1CCN2c1ncc2c3c(c(-c4ncc(F)c5sc(N)c(C#N)c45)c(F)c2n1)COC3] | 520 |

TABLE 28-continued

| Example | Chemical Name | Structure | MS (ES) m/z (M + 1) |
|---|---|---|---|
| 4C | 2-Amino-4-(3-(3-(cyclopropyl(methyl)amino)pyrrolidin-1-yl)-5-fluoro-7,9-dihydrofuro[3,4-f]quinazolin-6-yl)-7-fluorothieno[3,2-c]pyridine-3-carbonitrile | 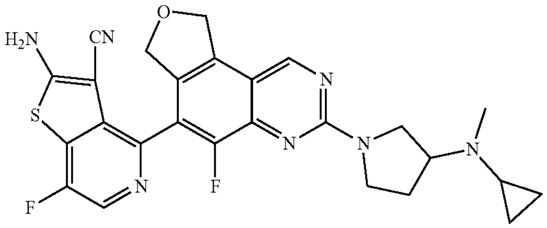 [SMILES: CN(C1CC1)C1CCN(c2ncc3c4c(c(-c5ncc(F)c6sc(N)c(C#N)c56)c(F)c3n2)COC4)C1] | 520 |
| 5C [29] | 2-Amino-4-(3-(3-(cyclopropyl(methyl)amino)pyrrolidin-1-yl)-5-fluoro-7,9-dihydrofuro[3,4-f]quinazolin-6-yl)-7-fluorothieno[3,2-c]pyridine-3-carbonitrile, Isomer 1 | 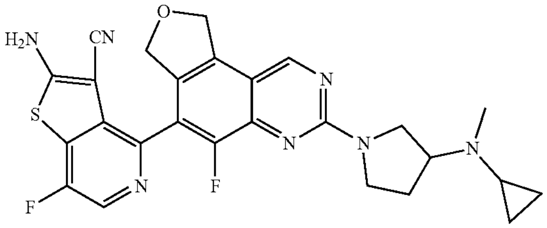 [SMILES: CN(C1CC1)C1CCN(c2ncc3c4c(c(-c5ncc(F)c6sc(N)c(C#N)c56)c(F)c3n2)COC4)C1] | 520 |
| 6C [29] | 2-Amino-4-(3-(3-(cyclopropyl(methyl)amino)pyrrolidin-1-yl)-5-fluoro-7,9-dihydrofuro[3,4-f]quinazolin-6-yl)-7-fluorothieno[3,2-c]pyridine-3-carbonitrile, Isomer 2 | 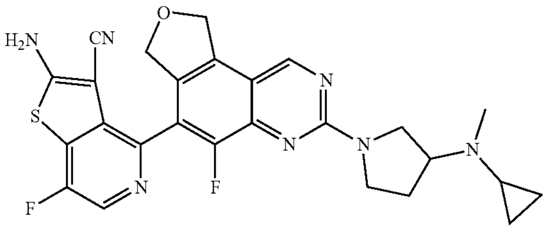 [SMILES: CN(C1CC1)C1CCN(c2ncc3c4c(c(-c5ncc(F)c6sc(N)c(C#N)c56)c(F)c3n2)COC4)C1] | 520 |
| 7C | 4-(3-((1R,5R)-2,6-Diazabicyclo[3.2.0]heptan-6-yl)-5-fluoro-7,9-dihydrofuro[3,4-f]quinazolin-6-yl)-2-amino-7-fluorothieno[3,2-c]pyridine-3-carbonitrile | 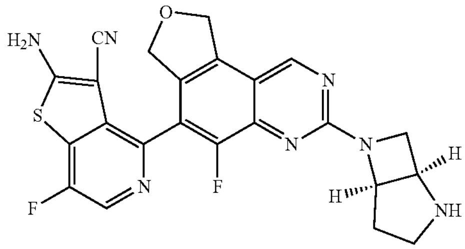 [SMILES: N#Cc1c(N)sc2c(F)cnc(-c3c4c(c5cnc(N6C[C@H]7NCC[C@H]76)nc5c3F)COC4)c12] | 478 |
| 8C [30] | 4-(3-((1S,5S)-2,6-Diazabicyclo[3.2.0]heptan-6-yl)-5-fluoro-7,9-dihydrofuro[3,4-f]quinazolin-6-yl)-2-amino-7-fluorothieno[3,2-c]pyridine-3-carbonitrile | 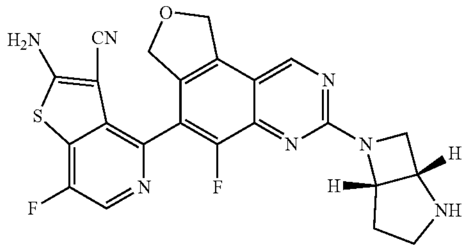 [SMILES: N#Cc1c(N)sc2c(F)cnc(-c3c4c(c5cnc(N6C[C@@H]7NCC[C@@H]76)nc5c3F)COC4)c12] | 478 |
| 9C | 2-Amino-7-fluoro-4-(5-fluoro-3-(3-morpholinopyrrolidin-1-yl)-7,9-dihydrofuro[3,4-f]quinazolin-6-yl)thieno[3,2-c]pyridine-3-carbonitrile | 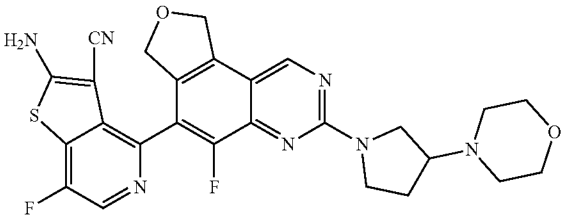 [SMILES: N#Cc1c(N)sc2c(F)cnc(-c3c4c(c5cnc(N6CCC(N7CCOCC7)C6)nc5c3F)COC4)c12] | 536 |

TABLE 28-continued

| Example | Chemical Name | Structure | MS (ES) m/z (M + 1) |
|---|---|---|---|
| 10C [31] | 2-Amino-7-fluoro-4-(5-fluoro-3-(3-morpholinopyrrolidin-1-yl)-7,9-dihydrofuro[3,4-f]quinazolin-6-yl)thieno[3,2-c]pyridine-3-carbonitrile, Isomer 1 | 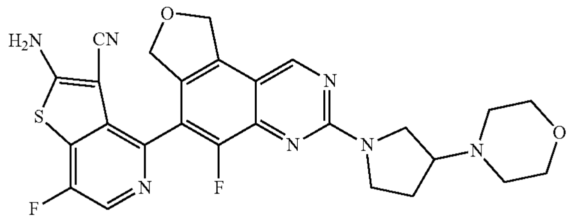 [SMILES: N#Cc1c(N)sc2c(F)cnc(-c3c4c(c5cnc(N6CCC(N7CCOCC7)C6)nc5c3F)COC4)c12] | 536 |
| 11C [31] | 2-Amino-7-fluoro-4-(5-fluoro-3-(3-morpholinopyrrolidin-1-yl)-7,9-dihydrofuro[3,4-f]quinazolin-6-yl)thieno[3,2-c]pyridine-3-carbonitrile, Isomer 2 | 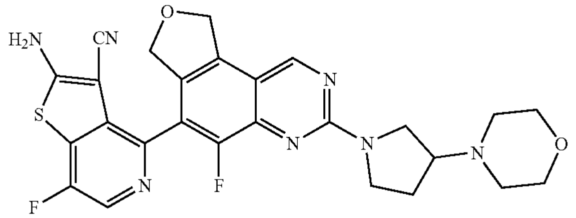 [SMILES: N#Cc1c(N)sc2c(F)cnc(-c3c4c(c5cnc(N6CCC(N7CCOCC7)C6)nc5c3F)COC4)c12] | 536 |
| 12C | 2-Amino-7-fluoro-4-(5-fluoro-3-((S)-3-(isobutyl(methyl)amino) pyrrolidin-1-yl)-7,9-dihydrofuro[3,4-f]quinazolin-6-yl)thieno[3,2-c]pyridine-3-carbonitrile | 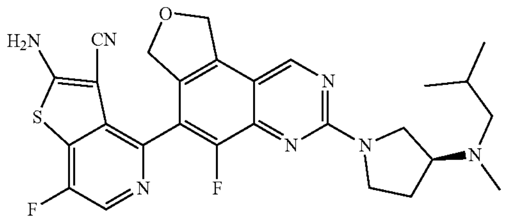 [SMILES: CC(C)CN(C)[C@H]1CCN(c2ncc3c4c(c(-c5ncc(F)c6sc(N)c(C#N)c56)c(F)c3n2)COC4)C1] | 536 |
| 13C | 2-Amino-4-(3-((S)-3-((cyclopropylmethyl) (methyl) amino)pyrrolidin-1-yl)-5-fluoro-7,9-dihydrofuro[3,4-f]quinazolin-6-yl)-7-fluorothieno[3,2-c]pyridine-3-carbonitrile | 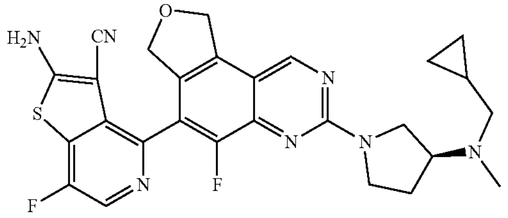 [SMILES: CN(CC1CC1)[C@H]1CCN(c2ncc3c4c(c(-c5ncc(F)c6sc(N)c(C#N)c56)c(F)c3n2)COC4)C1] | 534 |
| 14C | 2-Amino-7-fluoro-4-(5-fluoro-3-((S)-3-(3-methoxyazetidin-1-yl)pyrrolidin-1-yl)-7,9-dihydrofuro[3,4-f]quinazolin-6-yl)thieno[3,2-c]pyridine-3-carbonitrile | 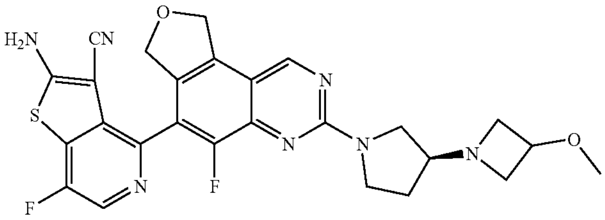 [SMILES: COC1CN([C@H]2CCN(c3ncc4c5c(c(-c6ncc(F)c7sc(N)c(C#N)c67)c(F)c4n3)COC5)C2)C1] | 536 |
| 15C | 2-Amino-7-fluoro-4-(5-fluoro-3-((S)-3-((2-hydroxy-2-methylpropyl)(methyl) amino)pyrrolidin-1-yl)-7,9-dihydrofuro[3,4-f]quinazolin-6-yl)thieno[3,2-c]pyridine-3-carbonitrile | 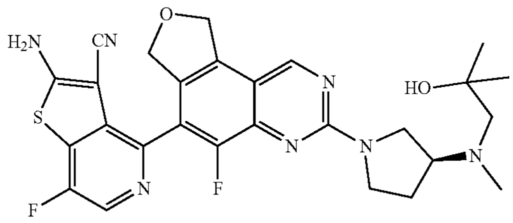 [SMILES: CN(CC(C)(C)O)[C@H]1CCN(c2ncc3c4c(c(-c5ncc(F)c6sc(N)c(C#N)c56)c(F)c3n2)COC4)C1] | 552 |

TABLE 28-continued

| Example | Chemical Name | Structure | MS (ES) m/z (M + 1) |
|---|---|---|---|
| 16C | 2-Amino-4-(3-((S)-3-(tert-butylamino)pyrrolidin-1-yl)-5-fluoro-7,9-dihydrofuro[3,4-f]quinazolin-6-yl)-7-fluorothieno[3,2-c]pyridine-3-carbonitrile | 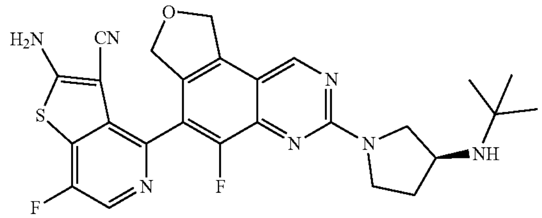 [SMILES: CC(C)(C)N[C@H]1CCN(c2ncc3c4c(c(-c5ncc(F)c6sc(N)c(C#N)c56)c(F)c3n2)COC4)C1] | 522 |
| 17C | 2-Amino-7-fluoro-4-(5-fluoro-3-((1R,5S)-3-methyl-3,6-diazabicyclo[3.2.1]octan-6-yl)-7,9-dihydrofuro[3,4-f]quinazolin-6-yl)thieno[3,2-c]pyridine-3-carbonitrile | 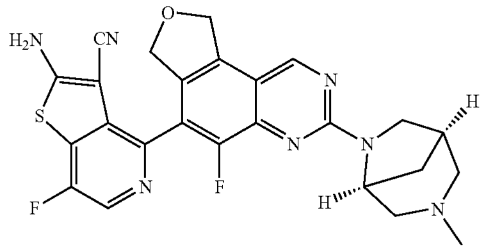 [SMILES: CN1C[C@H]2C[C@@H](C1)N(c1ncc3c4c(c(-c5ncc(F)c6sc(N)c(C#N)c56)c(F)c3n1)COC4)C2] | 506 |
| 18C [32] | 2-Amino-7-fluoro-4-(5-fluoro-3-(2-methyl-2,6-diazabicyclo[3.2.1]octan-6-yl)-7,9-dihydrofuro[3,4-f]quinazolin-6-yl)thieno[3,2-c]pyridine-3-carbonitrile | 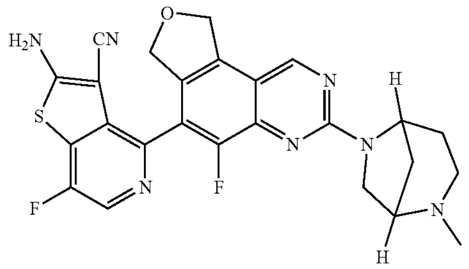 [SMILES: CN1CCC2CC1CN2c1ncc2c3c(c(-c4ncc(F)c5sc(N)c(C#N)c45)c(F)c2n1)COC3] | 506 |
| 19C [32] | 2-Amino-7-fluoro-4-(5-fluoro-3-(2-methyl-2,6-diazabicyclo[3.2.1]octan-6-yl)-7,9-dihydrofuro[3,4-f]quinazolin-6-yl)thieno[3,2-c]pyridine-3-carbonitrile | 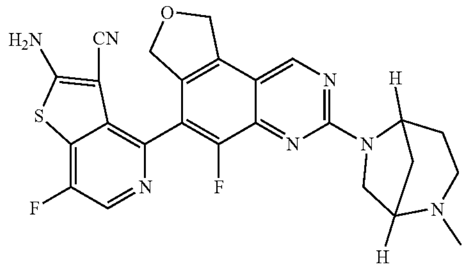 [SMILES: CN1CCC2CC1CN2c1ncc2c3c(c(-c4ncc(F)c5sc(N)c(C#N)c45)c(F)c2n1)COC3] | 506 |
| 20C | 2-Amino-4-(3-(8-(dimethylamino)-2-oxa-6-azaspiro[3.4]octan-6-yl)-5-fluoro-7,9-dihydrofuro[3,4-f]quinazolin-6-yl)-7-fluorothieno[3,2-c]pyridine-3-carbonitrile | 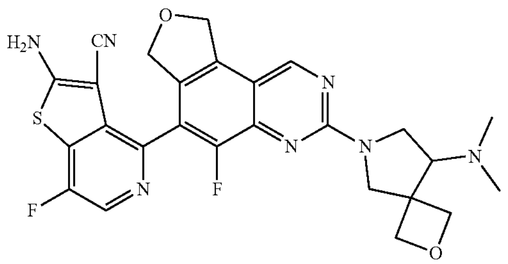 [SMILES: CN(C)C1CN(c2ncc3c4c(c(-c5ncc(F)c6sc(N)c(C#N)c56)c(F)c3n2)COC4)CC12COC2] | 536 |
| 21C [33] | 2-Amino-7-fluoro-4-(5-fluoro-3-(3-methyl-3,6-diazabicyclo[3.2.0]heptan-6-yl)-7,9-dihydrofuro[3,4-f]quinazolin-6-yl)thieno[3,2-c]pyridine-3-carbonitrile | 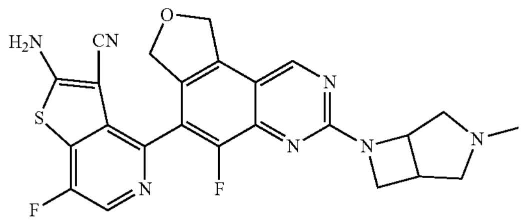 [SMILES: CN1CC2CN(c3ncc4c5c(c(-c6ncc(F)c7sc(N)c(C#N)c67)c(F)c4n3)COC5)C2C1] | 492 |

TABLE 28-continued

| Example | Chemical Name | Structure | MS (ES) m/z (M + 1) |
| --- | --- | --- | --- |
| 22C | 2-Amino-7-fluoro-4-(5-fluoro-3-(8-(isopropylamino)-2-oxa-6-azaspiro[3.4]octan-6-yl)-7,9-dihydrofuro[3,4-f]quinazolin-6-yl)thieno[3,2-c]pyridine-3-carbonitrile | 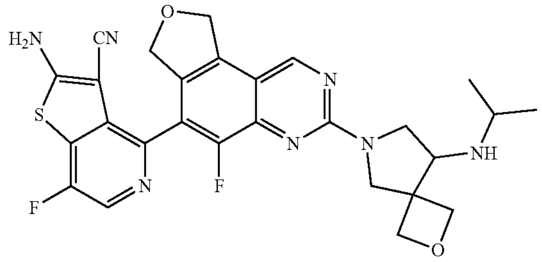 [SMILES: CC(C)NC1CN(c2ncc3c4c(c(-c5ncc(F)c6sc(N)c(C#N)c56)c(F)c3n2)COC4)CC12COC2] | 550 |
| 23C | 2-Amino-4-(3-(3,3-dimethyl-4-(methylamino)pyrrolidin-1-yl)-5-fluoro-7,9-dihydrofuro[3,4-f]quinazolin-6-yl)-7-fluorothieno[3,2-c]pyridine-3-carbonitrile | 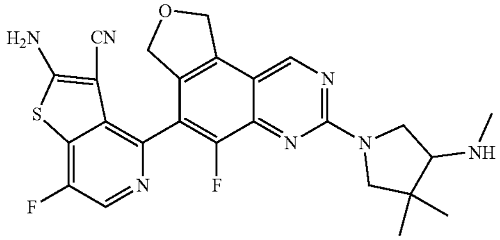 [SMILES: CNC1CN(c2ncc3c4c(c(-c5ncc(F)c6sc(N)c(C#N)c56)c(F)c3n2)COC4)CC1(C)C] | 508 |
| 24C [34] | 2-Amino-4-(3-(3,3-dimethyl-4-(methylamino)pyrrolidin-1-yl)-5-fluoro-7,9-dihydrofuro[3,4-f]quinazolin-6-yl)-7-fluorothieno[3,2-c]pyridine-3-carbonitrile, Isomer 1 | 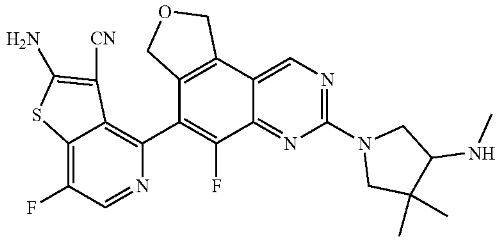 [SMILES: CNC1CN(c2ncc3c4c(c(-c5ncc(F)c6sc(N)c(C#N)c56)c(F)c3n2)COC4)CC1(C)C] | 508 |
| 25C [34] | 2-Amino-4-(3-(3,3-dimethyl-4-(methylamino)pyrrolidin-1-yl)-5-fluoro-7,9-dihydrofuro[3,4-f]quinazolin-6-yl)-7-fluorothieno[3,2-c]pyridine-3-carbonitrile, Isomer 2 | 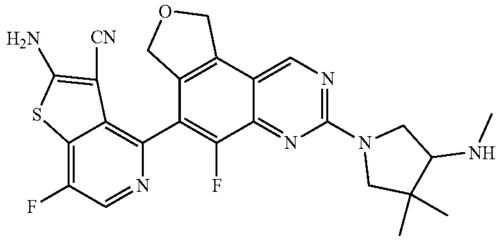 [SMILES: CNC1CN(c2ncc3c4c(c(-c5ncc(F)c6sc(N)c(C#N)c56)c(F)c3n2)COC4)CC1(C)C] | 508 |
| 26C | 2-Amino-7-fluoro-4-(5-fluoro-3-((R)-7-(isopropylamino)-5-azaspiro[2.4]heptan-5-yl)-7,9-dihydrofuro[3,4-f]quinazolin-6-yl)thieno[3,2-c]pyridine-3-carbonitrile | 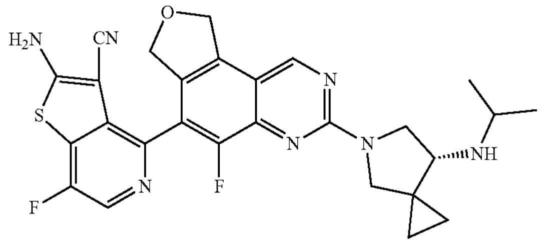 [SMILES: CC(C)N[C@H]1CN(c2ncc3c4c(c(-c5ncc(F)c6sc(N)c(C#N)c56)c(F)c3n2)COC4)CC12CC2] | 534 |
| 27C [35] | 2-Amino-7-fluoro-4-(5-fluoro-3-(octahydro-1H-pyrrolo[3,2-b]pyridin-1-yl)-7,9-dihydrofuro[3,4-f]quinazolin-6-yl)thieno[3,2-c]pyridine-3-carbonitrile | 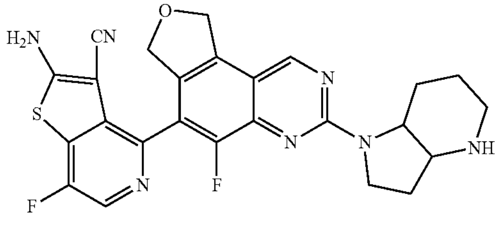 [SMILES: N#Cc1c(N)sc2c(F)cnc(-c3c4c(c5cnc(N6CCC7NCCCC76)nc5c3F)COC4)c12] | 506 |

TABLE 28-continued

| Example | Chemical Name | Structure | MS (ES) m/z (M + 1) |
|---|---|---|---|
| 28C [36] | 2-Amino-7-fluoro-4-(5-fluoro-3-(octahydro-1H-pyrrolo[3,2-b]pyridin-1-yl)-7,9-dihydrofuro[3,4-f]quinazolin-6-yl)thieno[3,2-c]pyridine-3-carbonitrile | 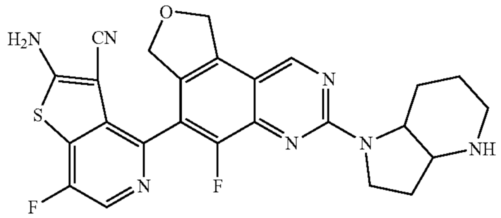 [SMILES: N#Cc1c(N)sc2c(F)cnc(-c3c4c(c5cnc(N6CCC7NCCCC76)nc5c3F)COC4)c12] | 506 |
| 29C [36] | 2-Amino-7-fluoro-4-(5-fluoro-3-(octahydro-1H-pyrrolo[3,2-b]pyridin-1-yl)-7,9-dihydrofuro[3,4-f]quinazolin-6-yl)thieno[3,2-c]pyridine-3-carbonitrile | 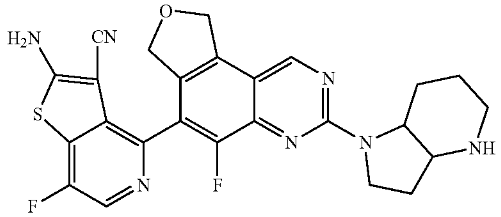 [SMILES: N#Cc1c(N)sc2c(F)cnc(-c3c4c(c5cnc(N6CCC7NCCCC76)nc5c3F)COC4)c12] | 506 |
| 30C [37] | 2-Amino-4-(3-((S)-3-(dimethylamino)pyrrolidin-1-yl)-5-fluoro-7,9-dihydrofuro[3,4-f]quinazolin-6-yl)benzo[b]thiophene-3-carbonitrile, Isomer 1 | 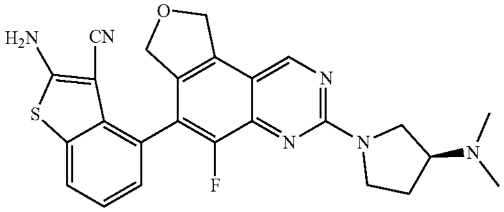 [SMILES: CN(C)[C@H]1CCN(c2ncc3c4c(c(-c5cccc6sc(N)c(C#N)c56)c(F)c3n2)COC4)C1] | 475 |
| 31C [37] | 2-Amino-4-(3-((S)-3-(dimethylamino)pyrrolidin-1-yl)-5-fluoro-7,9-dihydrofuro[3,4-f]quinazolin-6-yl)benzo[b]thiophene-3-carbonitrile, Isomer 2 | 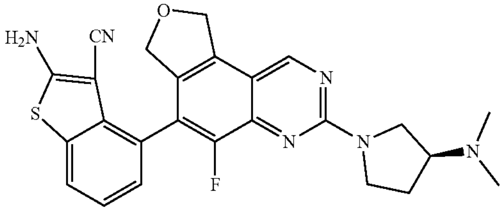 [SMILES: CN(C)[C@H]1CCN(c2ncc3c4c(c(-c5cccc6sc(N)c(C#N)c56)c(F)c3n2)COC4)C1] | 475 |
| 32C | 2-Amino-7-fluoro-4-(5-fluoro-3-((3S,4S)-3-(isopropylamino)-4-methylpyrrolidin-1-yl)-7,9-dihydrofuro[3,4-f]quinazolin-6-yl)thieno[3,2-c]pyridine-3-carbonitrile | 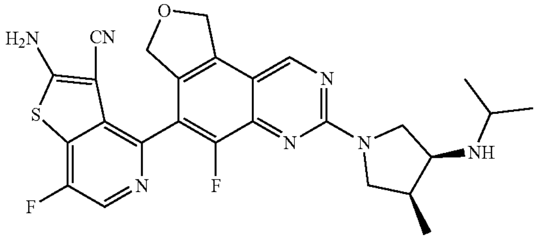 [SMILES: CC(C)N[C@@H]1CN(c2ncc3c4c(c(-c5ncc(F)c6sc(N)c(C#N)c56)c(F)c3n2)COC4)C[C@@H]1C] | 522 |
| 33C | 2-Amino-7-fluoro-4-(5-fluoro-3-((S)-7-(methylamino)-5-azaspiro[2.4]heptan-5-yl)-7,9-dihydrofuro[3,4-f]quinazolin-6-yl)thieno[3,2-c]pyridine-3-carbonitrile | 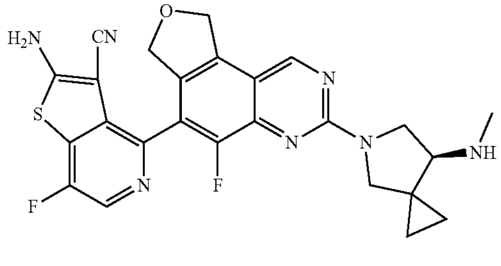 [SMILES: CN[C@@H]1CN(c2ncc3c4c(c(-c5ncc(F)c6sc(N)c(C#N)c56)c(F)c3n2)COC4)CC12CC2] | 506 |

TABLE 28-continued

| Example | Chemical Name | Structure | MS (ES) m/z (M + 1) |
|---|---|---|---|
| 34C | 2-Amino-7-fluoro-4-(5-fluoro-3-(7-(isopropylamino)-5-azaspiro[2.4]heptan-5-yl)-7,9-dihydrofuro[3,4-f]quinazolin-6-yl)thieno[3,2-c]pyridine-3-carbonitrile | 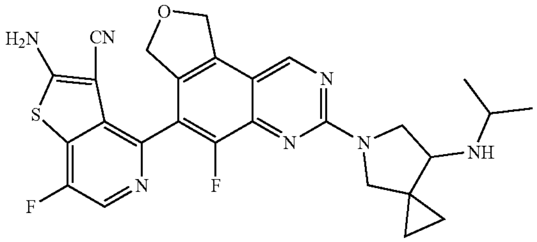 [SMILES: CC(C)NC1CN(c2ncc3c4c(c(-c5ncc(F)c6sc(N)c(C#N)c56)c(F)c3n2)COC4)CC12CC2] | 534 |
| 35C [38] | 2-Amino-7-fluoro-4-(5-fluoro-3-(7-(isopropylamino)-5-azaspiro[2.4]heptan-5-yl)-7,9-dihydrofuro[3,4-f]quinazolin-6-yl)thieno[3,2-c]pyridine-3-carbonitrile, Isomer 1 | 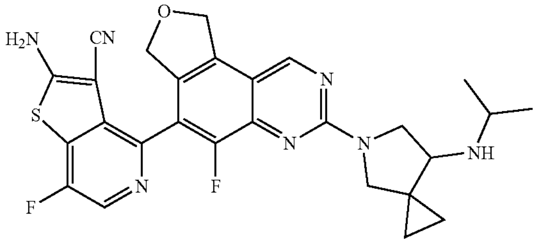 [SMILES: CC(C)NC1CN(c2ncc3c4c(c(-c5ncc(F)c6sc(N)c(C#N)c56)c(F)c3n2)COC4)CC12CC2] | 534 |
| 36C [38] | 2-Amino-7-fluoro-4-(5-fluoro-3-(7-(isopropylamino)-5-azaspiro[2.4]heptan-5-yl)-7,9-dihydrofuro[3,4-f]quinazolin-6-yl)thieno[3,2-c]pyridine-3-carbonitrile, Isomer 2 | 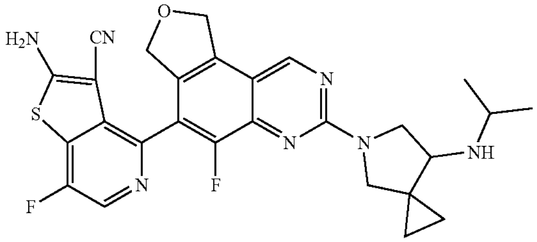 [SMILES: CC(C)NC1CN(c2ncc3c4c(c(-c5ncc(F)c6sc(N)c(C#N)c56)c(F)c3n2)COC4)CC12CC2] | 534 |
| 37C | 2-Amino-7-fluoro-4-(5-fluoro-3-((S)-3-(4-methylpiperazin-1-yl)pyrrolidin-1-yl)-7,9-dihydrofuro[3,4-f]quinazolin-6-yl)thieno[3,2-c]pyridine-3-carbonitrile | 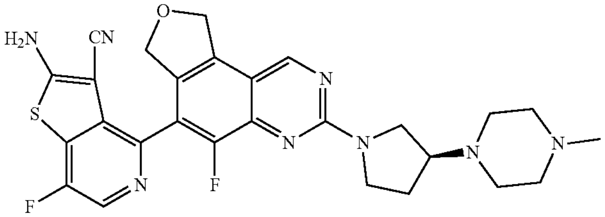 [SMILES: CN1CCN([C@H]2CCN(c3ncc4c5c(c(-c6ncc(F)c7sc(N)c(C#N)c67)c(F)c4n3)COC5)C2)CC1] | 549 |
| 38C | 2-Amino-7-fluoro-4-(5-fluoro-3-((R)-3-(4-methylpiperazin-1-yl)pyrrolidin-1-yl)-7,9-dihydrofuro[3,4-f]quinazolin-6-yl)thieno[3,2-c]pyridine-3-carbonitrile | 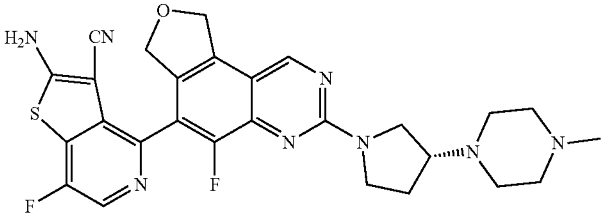 [SMILES: CN1CCN([C@@H]2CCN(c3ncc4c5c(c(-c6ncc(F)c7sc(N)c(C#N)c67)c(F)c4n3)COC5)C2)CC1] | 549 |
| 39C | 2-Amino-7-fluoro-4-(5-fluoro-3-((3R,4S)-3-(isopropylamino)-4-methoxypyrrolidin-1-yl)-7,9-dihydrofuro[3,4-f]quinazolin-6-yl)thieno[3,2-c]pyridine-3-carbonitrile | 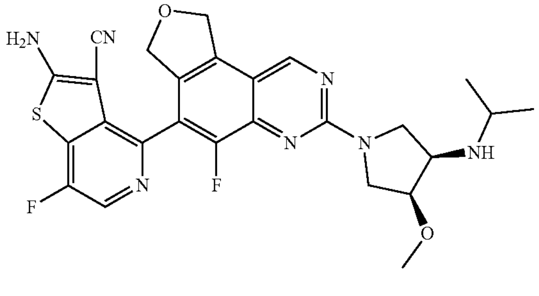 [SMILES: CO[C@H]1CN(c2ncc3c4c(c(-c5ncc(F)c6sc(N)c(C#N)c56)c(F)c3n2)COC4)C[C@H]1NC(C)C] | 538 |

TABLE 28-continued

| Example | Chemical Name | Structure | MS (ES) m/z (M + 1) |
|---|---|---|---|
| 40C | 2-Amino-7-fluoro-4-(5-fluoro-3-((3R,4R)-3-(isopropylamino)-4-methoxypyrrolidin-1-yl)-7,9-dihydrofuro[3,4-f]quinazolin-6-yl)thieno[3,2-c]pyridine-3-carbonitrile | 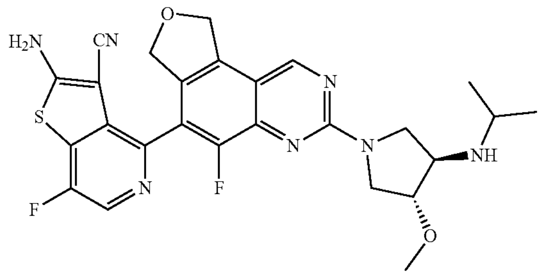 [SMILES: CO[C@@H]1CN(c2ncc3c4c(c(-c5ncc(F)c6sc(N)c(C#N)c56)c(F)c3n2)COC4)C[C@H]1NC(C)C] | 538 |
| 41C | 2-Amino-7-fluoro-4-(5-fluoro-3-((3S)-3-(methyl(tetrahydrofuran-3-yl)amino)pyrrolidin-1-yl)-7,9-dihydrofuro[3,4-f]quinazolin-6-yl)thieno[3,2-c]pyridine-3-carbonitrile | 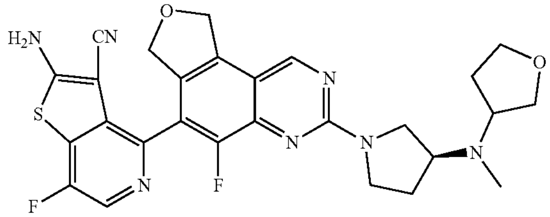 [SMILES: CN(C1CCOC1)[C@H]1CCN(c2ncc3c4c(c(-c5ncc(F)c6sc(N)c(C#N)c56)c(F)c3n2)COC4)C1] | 550 |
| 42C | 2-Amino-7-fluoro-4-(5-fluoro-3-((S)-3-((2-methoxyethyl)(methyl) amino)pyrrolidin-1-yl)-7,9-dihydrofuro[3,4-f]quinazolin-6-yl)thieno[3,2-c]pyridine-3-carbonitrile | 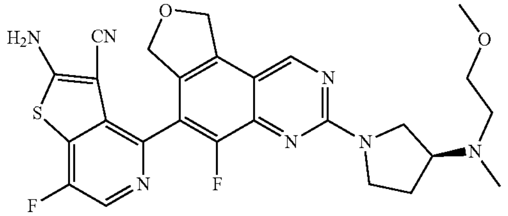 [SMILES: COCCN(C)[C@H]1CCN(c2ncc3c4c(c(-c5ncc(F)c6sc(N)c(C#N)c56)c(F)c3n2)COC4)C1] | 538 |
| 43C | 2-Amino-7-fluoro-4-(5-fluoro-3-((3S)-3-((1-methoxypropan-2-yl)(methyl)amino) pyrrolidin-1-yl)-7,9-dihydrofuro[3,4-f]quinazolin-6-yl)thieno[3,2-c]pyridine-3-carbonitrile | 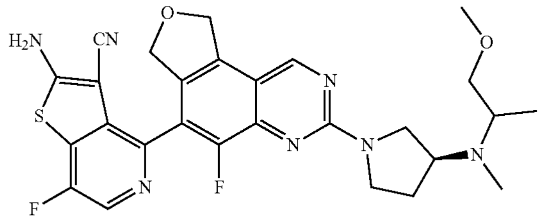 [SMILES: COCC(C)N(C)[C@H]1CCN(c2ncc3c4c(c(-c5ncc(F)c6sc(N)c(C#N)c56)c(F)c3n2)COC4)C1] | 552 |
| 44C | 2-Amino-7-fluoro-4-(5-fluoro-3-((3S)-3-(methyl((tetrahydrofuran-2-yl)methyl)amino) pyrrolidin-1-yl)-7,9-dihydrofuro[3,4-f]quinazolin-6-yl)thieno[3,2-c]pyridine-3-carbonitrile | 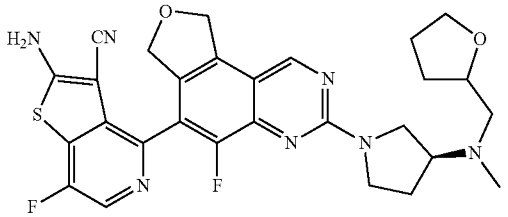 [SMILES: CN(CC1CCCO1)[C@H]1CCN(c2ncc3c4c(c(-c5ncc(F)c6sc(N)c(C#N)c56)c(F)c3n2)COC4)C1] | 564 |
| 45C | 2-Amino-7-fluoro-4-(5-fluoro-3-((3S)-3-(methyl((tetrahydro-2H-pyran-2-yl)methyl)amino) pyrrolidin-1-yl)-7,9-dihydrofuro[3,4-f]quinazolin-6-yl)thieno[3,2-c]pyridine-3-carbonitrile | 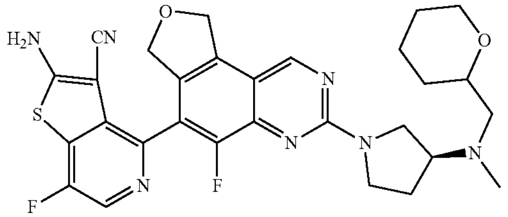 [SMILES: CN(CC1CCCCO1)[C@H]1CCN(c2ncc3c4c(c(-c5ncc(F)c6sc(N)c(C#N)c56)c(F)c3n2)COC4)C1] | 578 |

TABLE 28-continued

| Example | Chemical Name | Structure | MS (ES) m/z (M + 1) |
|---|---|---|---|
| 46C | 2-(((3S)-1-(6-(2-Amino-3-cyano-7-fluorothieno[3,2-c]pyridin-4-yl)-5-fluoro-7,9-dihydrofuro[3,4-f]quinazolin-3-yl)pyrrolidin-3-yl)(methyl)amino)-N-methylacetamide | 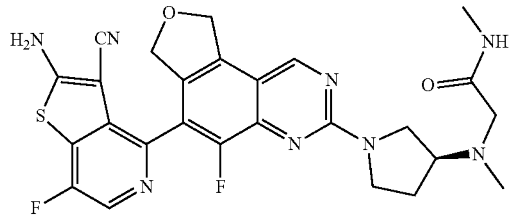 [SMILES: CNC(=O)CN(C)[C@H]1CCN(c2ncc3c4c(c(-c5ncc(F)c6sc(N)c(C#N)c56)c(F)c3n2)COC4)C1] | 551 |
| 47C | 2-(((3S)-1-(6-(2-Amino-3-cyano-7-fluorothieno[3,2-c]pyridin-4-yl)-5-fluoro-7,9-dihydrofuro[3,4-f]quinazolin-3-yl)pyrrolidin-3-yl)(methyl)amino) propanamide | 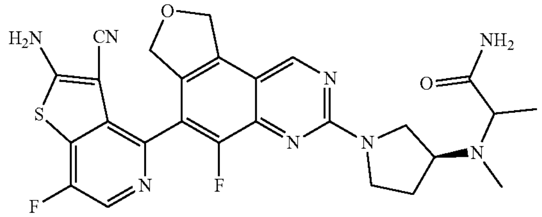 [SMILES: CC(C(N)=O)N(C)[C@H]1CCN(c2ncc3c4c(c(-c5ncc(F)c6sc(N)c(C#N)c56)c(F)c3n2)COC4)C1] | 551 |
| 48C [39] | 2-(((3S)-1-(6-(2-Amino-3-cyano-7-fluorothieno[3,2-c]pyridin-4-yl)-5-fluoro-7,9-dihydrofuro[3,4-f]quinazolin-3-yl)pyrrolidin-3-yl)(methyl)amino) propanamide, Isomer 1 | 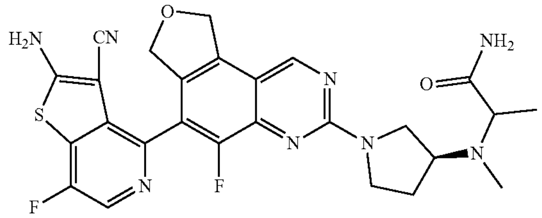 [SMILES: CC(C(N)=O)N(C)[C@H]1CCN(c2ncc3c4c(c(-c5ncc(F)c6sc(N)c(C#N)c56)c(F)c3n2)COC4)C1] | 551 |
| 49C [39] | 2-(((3S)-1-(6-(2-Amino-3-cyano-7-fluorothieno[3,2-c]pyridin-4-yl)-5-fluoro-7,9-dihydrofuro[3,4-f]quinazolin-3-yl)pyrrolidin-3-yl)(methyl)amino) propanamide, Isomer 2 | 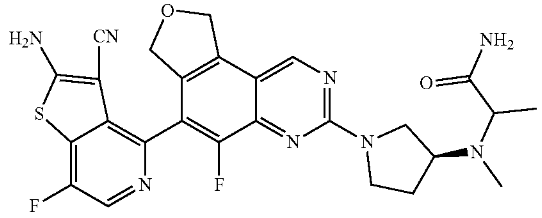 [SMILES: CC(C(N)=O)N(C)[C@H]1CCN(c2ncc3c4c(c(-c5ncc(F)c6sc(N)c(C#N)c56)c(F)c3n2)COC4)C1] | 551 |
| 50C [40] | 2-Amino-4-(5-chloro-7-((3S,4S)-3-(dimethylamino)-4-hydroxypyrrolidin-1-yl)-1,3-dihydrofuro[3,4-f]quinolin-4-yl)-7-fluorothieno[3,2-c]pyridine-3-carbonitrile, Atropisomer 1 | 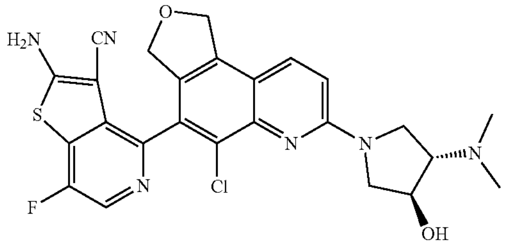 [SMILES: CN(C)[C@H]1CN(c2ccc3c4c(c(-c5ncc(F)c6sc(N)c(C#N)c56)c(Cl)c3n2)COC4)C[C@@H]1O] | 525 |
| 51C [40] | 2-Amino-4-(5-chloro-7-((3S,4S)-3-(dimethylamino)-4-hydroxypyrrolidin-1-yl)-1,3-dihydrofuro[3,4-f]quinolin-4-yl)-7-fluorothieno[3,2-c]pyridine-3-carbonitrile, Atropisomer 2 | 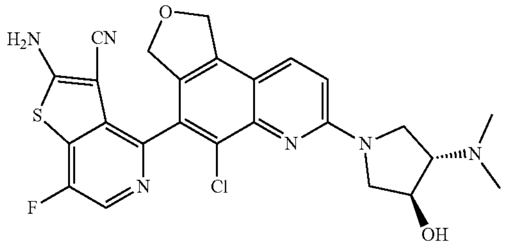 [SMILES: CN(C)[C@H]1CN(c2ccc3c4c(c(-c5ncc(F)c6sc(N)c(C#N)c56)c(Cl)c3n2)COC4)C[C@@H]1O] | 525 |

TABLE 28-continued

| Example | Chemical Name | Structure | MS (ES) m/z (M + 1) |
|---|---|---|---|
| 52C [41] | 2-Amino-4-(5-chloro-7-((3R,4R)-3-(dimethylamino)-4-hydroxypyrrolidin-1-yl)-1,3-dihydrofuro[3,4-f]quinolin-4-yl)-7-fluorothieno[3,2-c]pyridine-3-carbonitrile, Atropisomer 1 | 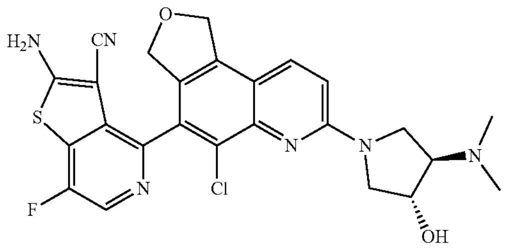 [SMILES: CN(C)[C@@H]1CN(c2ccc3c4c(c(-c5ncc(F)c6sc(N)c(C#N)c56)c(Cl)c3n2)COC4)C[C@H]1O] | 525 |
| 53C [41] | 2-Amino-4-(5-chloro-7-((3R,4R)-3-(dimethylamino)-4-hydroxypyrrolidin-1-yl)-1,3-dihydrofuro[3,4-f]quinolin-4-yl)-7-fluorothieno[3,2-c]pyridine-3-carbonitrile, Atropisomer 2 | 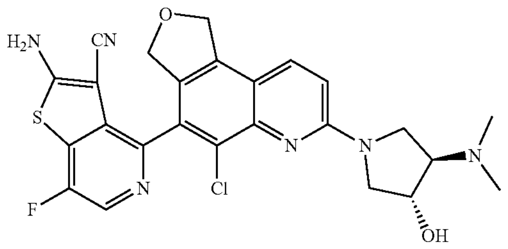 [SMILES: CN(C)[C@@H]1CN(c2ccc3c4c(c(-c5ncc(F)c6sc(N)c(C#N)c56)c(Cl)c3n2)COC4)C[C@H]1O] | 525 |
| 54C [42] | 2-Amino-4-(5-chloro-7-((3R,4S)-3-(dimethylamino)-4-hydroxypyrrolidin-1-yl)-1,3-dihydrofuro[3,4-f]quinolin-4-yl)-7-fluorothieno[3,2-c]pyridine-3-carbonitrile, Atropisomer 1 | 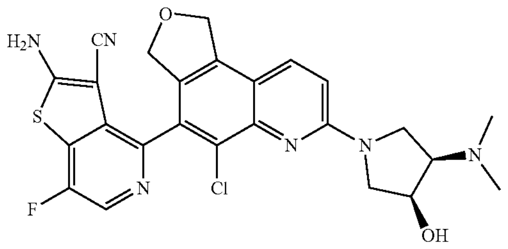 [SMILES: CN(C)[C@@H]1CN(c2ccc3c4c(c(-c5ncc(F)c6sc(N)c(C#N)c56)c(Cl)c3n2)COC4)C[C@@H]1O] | 525 |
| 55C [42] | 2-Amino-4-(5-chloro-7-((3R,4S)-3-(dimethylamino)-4-hydroxypyrrolidin-1-yl)-1,3-dihydrofuro[3,4-f]quinolin-4-yl)-7-fluorothieno[3,2-c]pyridine-3-carbonitrile, Atropisomer 2 | 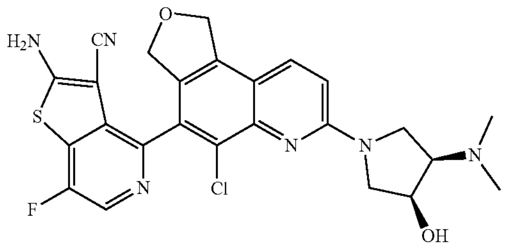 [SMILES: CN(C)[C@@H]1CN(c2ccc3c4c(c(-c5ncc(F)c6sc(N)c(C#N)c56)c(Cl)c3n2)COC4)C[C@@H]1O] | 525 |
| 56C [43] | 2-Amino-4-(5-chloro-7-((3S,4R)-3-(dimethylamino)-4-hydroxypyrrolidin-1-yl)-1,3-dihydrofuro[3,4-f]quinolin-4-yl)-7-fluorothieno[3,2-c]pyridine-3-carbonitrile, Atropisomer 1 | 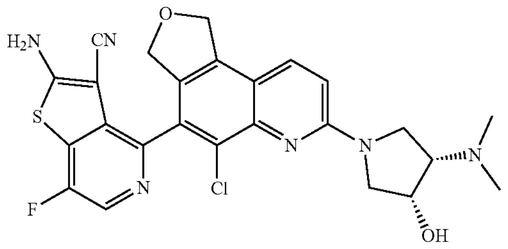 [SMILES: CN(C)[C@H]1CN(c2ccc3c4c(c(-c5ncc(F)c6sc(N)c(C#N)c56)c(Cl)c3n2)COC4)C[C@H]1O] | 525 |
| 57C [43] | 2-Amino-4-(5-chloro-7-((3S,4R)-3-(dimethylamino)-4-hydroxypyrrolidin-1-yl)-1,3-dihydrofuro[3,4-f]quinolin-4-yl)-7-fluorothieno[3,2-c]pyridine-3-carbonitrile, Atropisomer 2 | 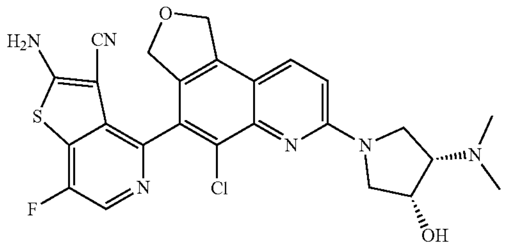 [SMILES: CN(C)[C@H]1CN(c2ccc3c4c(c(-c5ncc(F)c6sc(N)c(C#N)c56)c(Cl)c3n2)COC4)C[C@H]1O] | 525 |

TABLE 28-continued

| Example | Chemical Name | Structure | MS (ES) m/z (M + 1) |
|---|---|---|---|
| 58C [44] | 2-Amino-5-fluoro-4-(5-fluoro-3-((3S,4S)-3-(isopropylamino)-4-methylpyrrolidin-1-yl)-7,9-dihydrofuro[3,4-f]quinazolin-6-yl)benzo[b]thiophene-3-carbonitrile, Atropisomer 1 | 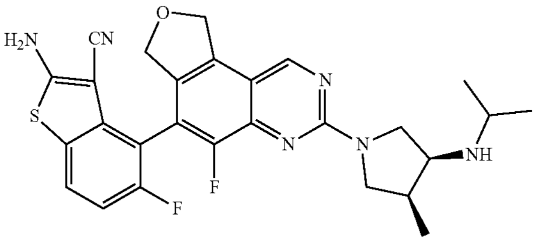 [SMILES: CC(C)N[C@@H]1CN(c2ncc3c4c(c(-c5c(F)ccc6sc(N)c(C#N)c56)c(F)c3n2)COC4)C[C@@H]1C] | 521 |
| 59C [44] | 2-Amino-5-fluoro-4-(5-fluoro-3-((3S,4S)-3-(isopropylamino)-4-methylpyrrolidin-1-yl)-7,9-dihydrofuro[3,4-f]quinazolin-6-yl)benzo[b]thiophene-3-carbonitrile, Atropisomer 2 | 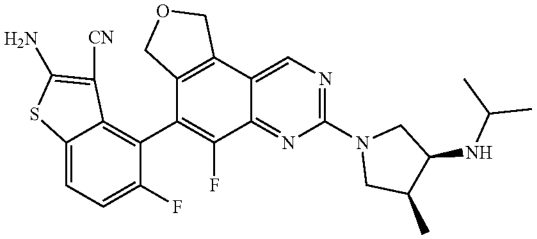 [SMILES: CC(C)N[C@@H]1CN(c2ncc3c4c(c(-c5c(F)ccc6sc(N)c(C#N)c56)c(F)c3n2)COC4)C[C@@H]1C] | 521 |
| 60C [45] | 2-Amino-4-(3-(3-(dimethylamino)-3-(hydroxymethyl) pyrrolidin-1-yl)-5-fluoro-7,9-dihydrofuro[3,4-f]quinazolin-6-yl)-5-fluorobenzo[b]thiophene-3-carbonitrile, Diastereomer 1 | 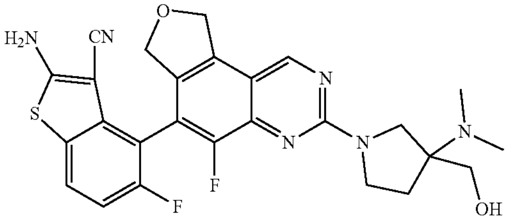 [SMILES: CN(C)C1(CO)CCN(c2ncc3c4c(c(-c5c(F)ccc6sc(N)c(C#N)c56)c(F)c3n2)COC4)C1] | 523 |
| 61C [45] | 2-Amino-4-(3-(3-(dimethylamino)-3-(hydroxymethyl) pyrrolidin-1-yl)-5-fluoro-7,9-dihydrofuro[3,4-f]quinazolin-6-yl)-5-fluorobenzo[b]thiophene-3-carbonitrile, Diastereomer 2 | 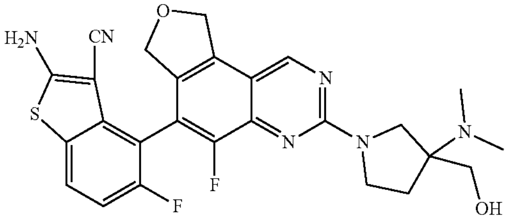 [SMILES: CN(C)C1(CO)CCN(c2ncc3c4c(c(-c5c(F)ccc6sc(N)c(C#N)c56)c(F)c3n2)COC4)C1] | 523 |
| 62C [45] | 2-Amino-4-(3-(3-(dimethylamino)-3-(hydroxymethyl) pyrrolidin-1-yl)-5-fluoro-7,9-dihydrofuro[3,4-f]quinazolin-6-yl)-5-fluorobenzo[b]thiophene-3-carbonitrile, Diastereomer 3 | 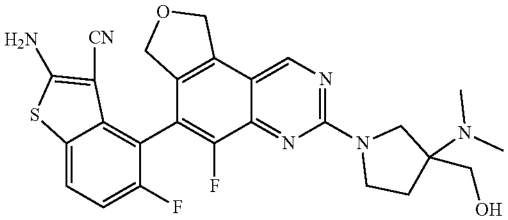 [SMILES: CN(C)C1(CO)CCN(c2ncc3c4c(c(-c5c(F)ccc6sc(N)c(C#N)c56)c(F)c3n2)COC4)C1] | 523 |
| 63C [45] | 2-Amino-4-(3-(3-(dimethylamino)-3-(hydroxymethyl) pyrrolidin-1-yl)-5-fluoro-7,9-dihydrofuro[3,4-f]quinazolin-6-yl)-5-fluorobenzo[b]thiophene-3-carbonitrile, Diastereomer 4 | 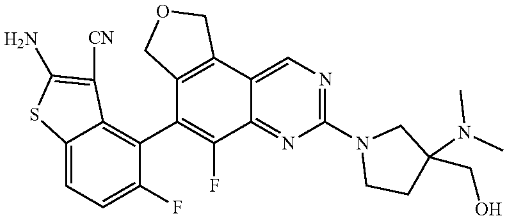 [SMILES: CN(C)C1(CO)CCN(c2ncc3c4c(c(-c5c(F)ccc6sc(N)c(C#N)c56)c(F)c3n2)COC4)C1] | 523 |

TABLE 28-continued

| Example | Chemical Name | Structure | MS (ES) m/z (M + 1) |
|---|---|---|---|
| 64C [46] | 2-Amino-4-(5-chloro-3-((3R,4R)-3-(dimethylamino)-4-hydroxypyrrolidin-1-yl)-7,9-dihydrofuro[3,4-f]quinazolin-6-yl)-7-fluorothieno[3,2-c]pyridine-3-carbonitrile, Atropisomer 1 | 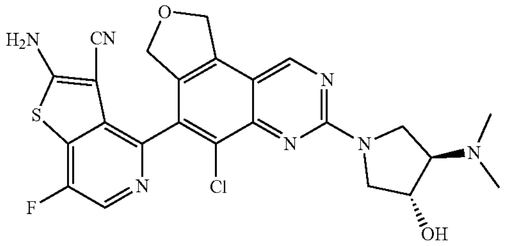 [SMILES: CN(C)[C@@H]1CN(c2ncc3c4c(c(-c5ncc(F)c6sc(N)c(C#N)c56)c(Cl)c3n2)COC4)C[C@H]1O] | 526 |
| 65C [46] | 2-Amino-4-(5-chloro-3-((3R,4R)-3-(dimethylamino)-4-hydroxypyrrolidin-1-yl)-7,9-dihydrofuro[3,4-f]quinazolin-6-yl)-7-fluorothieno[3,2-c]pyridine-3-carbonitrile, Atropisomer 2 | 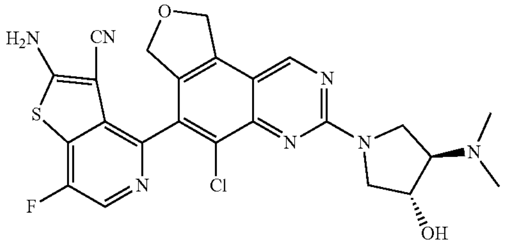 [SMILES: CN(C)[C@@H]1CN(c2ncc3c4c(c(-c5ncc(F)c6sc(N)c(C#N)c56)c(Cl)c3n2)COC4)C[C@H]1O] | 526 |
| 66C [47] | 2-Amino-4-(5-chloro-3-((3R,4S)-3-(dimethylamino)-4-hydroxypyrrolidin-1-yl)-7,9-dihydrofuro[3,4-f]quinazolin-6-yl)-7-fluorothieno[3,2-c]pyridine-3-carbonitrile, Atropisomer 1 formic acid | 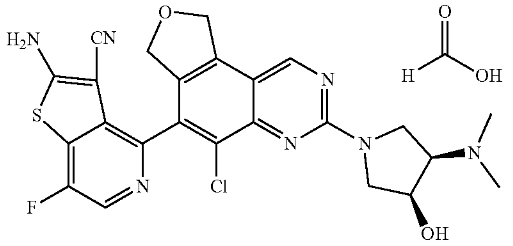 | 526 |
| 67C [47] | 2-Amino-4-(5-chloro-3-((3R,4S)-3-(dimethylamino)-4-hydroxypyrrolidin-1-yl)-7,9-dihydrofuro[3,4-f]quinazolin-6-yl)-7-fluorothieno[3,2-c]pyridine-3-carbonitrile, Atropisomer 2 formic acid | 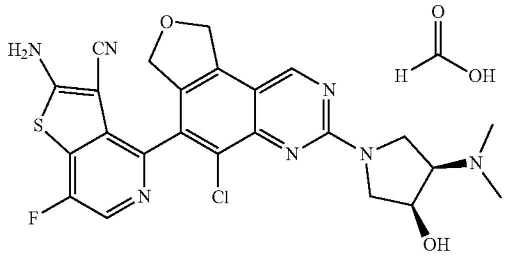 | 526 |
| 68C [48] | 2-Amino-4-(5-chloro-3-((3S,4R)-3-(dimethylamino)-4-hydroxypyrrolidin-1-yl)-7,9-dihydrofuro[3,4-f]quinazolin-6-yl)-7-fluorothieno[3,2-c]pyridine-3-carbonitrile, Atropsiomer 1 formic acid | 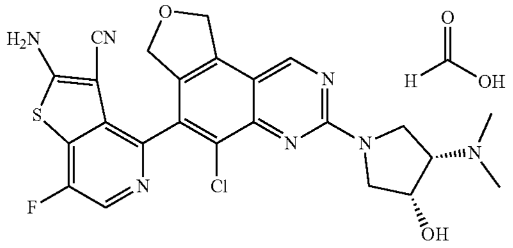 | 526 |
| 69C [48] | 2-Amino-4-(5-chloro-3-((3S,4R)-3-(dimethylamino)-4-hydroxypyrrolidin-1-yl)-7,9-dihydrofuro[3,4-f]quinazolin-6-yl)-7-fluorothieno[3,2-c]pyridine-3-carbonitrile, Atropsiomer 2 formic acid | 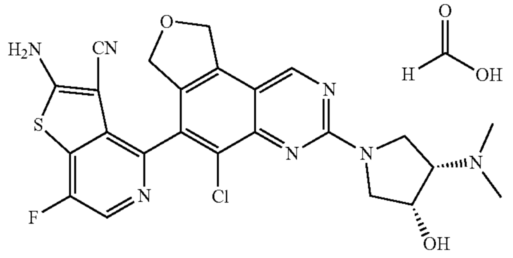 | 526 |

TABLE 28-continued

| Example | Chemical Name | Structure | MS (ES) m/z (M + 1) |
|---|---|---|---|
| 70C [49] | 2-Amino-4-(5-chloro-3-((3S,4R)-3-hydroxy-4-(isopropyl(methyl)amino) pyrrolidin-1-yl)-7,9-dihydrofuro[3,4-f]quinazolin-6-yl)-7-fluorothieno[3,2-c]pyridine-3-carbonitrile, Atropisomer 1 | 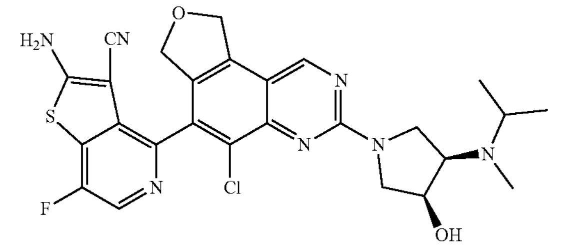 [SMILES: CC(C)N(C)[C@@H]1CN(c2ncc3c4c(c(-c5ncc(F)c6sc(N)c(C#N)c56)c(Cl)c3n2)COC4)C[C@@H]1O] | 554 |
| 710 [49] | 2-Amino-4-(5-chloro-3-((3S,4R)-3-hydroxy-4-(isopropyl(methyl)amino) pyrrolidin-1-yl)-7,9-dihydrofuro[3,4-f]quinazolin-6-yl)-7-fluorothieno[3,2-c]pyridine-3-carbonitrile, Atropisomer 2 | 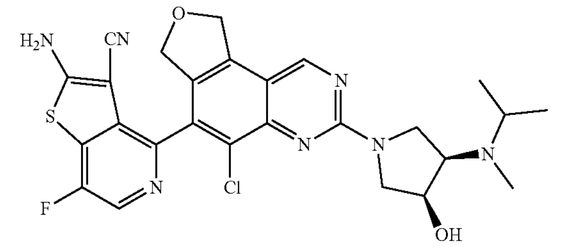 | 554 |
| 72C [50] | 2-Amino-4-(5-chloro-3-((3S,4S)-3-hydroxy-4-(isopropyl(methyl)amino) pyrrolidin-1-yl)-7,9-dihydrofuro[3,4-f]quinazolin-6-yl)-7-fluorothieno[3,2-c]pyridine-3-carbonitrile, Atropisomer 1 | 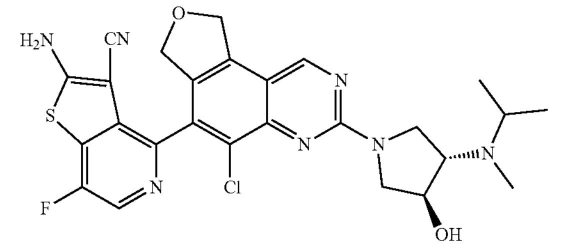 [SMILES: CC(C)N(C)[C@H]1CN(c2ncc3c4c(c(-c5ncc(F)c6sc(N)c(C#N)c56)c(Cl)c3n2)COC4)C[C@@H]1O] | 554 |
| 73C [50] | 2-Amino-4-(5-chloro-3-((3S,4S)-3-hydroxy-4-(isopropyl(methyl)amino) pyrrolidin-1-yl)-7,9-dihydrofuro[3,4-f]quinazolin-6-yl)-7-fluorothieno[3,2-c]pyridine-3-carbonitrile, Atropisomer 2 | 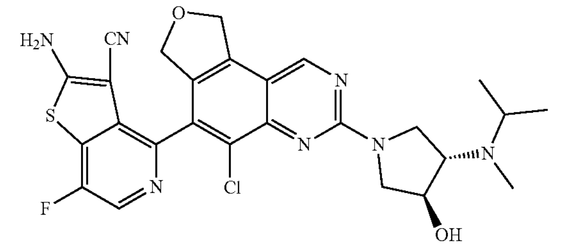 [SMILES: CC(C)N(C)[C@H]1CN(c2ncc3c4c(c(-c5ncc(F)c6sc(N)c(C#N)c56)c(Cl)c3n2)COC4)C[C@@H]1O] | 554 |
| 74C [51] | 2-Amino-4-(5-chloro-3-((2S,3S)-3-(((S)-2-hydroxypropyl)amino)-2-methylpyrrolidin-1-yl)-7,9-dihydrofuro[3,4-f]quinazolin-6-yl)-7-fluorothieno[3,2-c]pyridine-3-carbonitrile, Atropisomer 1 | 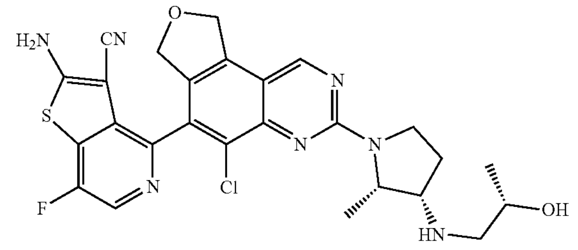 [SMILES: C[C@H](O)CN[C@H]1CCN(c2ncc3c4c(c(-c5ncc(F)c6sc(N)c(C#N)c56)c(Cl)c3n2)COC4)[C@H]1C] | 554 |
| 75C [51] | 2-Amino-4-(5-chloro-3-((2S,3S)-3-(((S)-2-hydroxypropyl)amino)-2-methylpyrrolidin-1-yl)-7,9-dihydrofuro[3,4-f]quinazolin-6-yl)-7-fluorothieno[3,2-c]pyridine-3-carbonitrile, Atropisomer 2 | 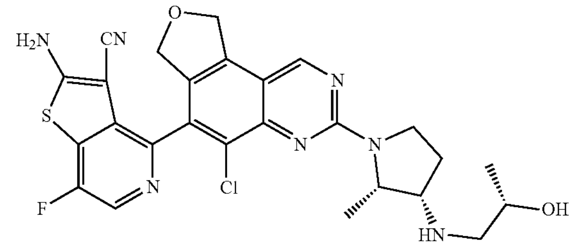 [SMILES: C[C@H](O)CN[C@H]1CCN(c2ncc3c4c(c(-c5ncc(F)c6sc(N)c(C#N)c56)c(Cl)c3n2)COC4)[C@H]1C] | 554 |

TABLE 28-continued

| Example | Chemical Name | Structure | MS (ES) m/z (M + 1) |
|---|---|---|---|
| 76C [52] | 2-Amino-4-(5-chloro-3-((2S,3S)-3-(dimethylamino)-2-methylpyrrolidin-1-yl)-7,9-dihydrofuro[3,4-f]quinazolin-6-yl)-7-fluorothieno[3,2-c]pyridine-3-carbonitrile, Atropisomer 1 | 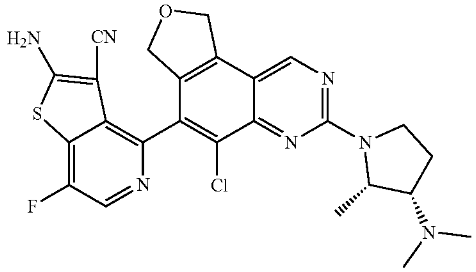 [SMILES: C[C@H]1[C@@H](N(C)C)CCN1c1ncc2c3c(c(-c4ncc(F)c5sc(N)c(C#N)c45)c(Cl)c2n1)COC3] | 524 |
| 77C [52] | 2-Amino-4-(5-chloro-3-((2S,3S)-3-(dimethylamino)-2-methylpyrrolidin-1-yl)-7,9-dihydrofuro[3,4-f]quinazolin-6-yl)-7-fluorothieno[3,2-c]pyridine-3-carbonitrile, Atropisomer 2 | 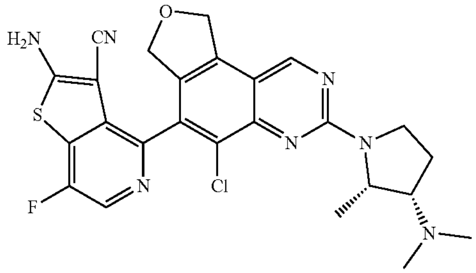 [SMILES: C[C@H]1[C@@H](N(C)C)CCN1c1ncc2c3c(c(-c4ncc(F)c5sc(N)c(C#N)c45)c(Cl)c2n1)COC3] | 524 |
| 78C [53] | 2-Amino-4-(5-chloro-3-((2S,3S)-3-(ethylamino)-2-methylpyrrolidin-1-yl)-7,9-dihydrofuro[3,4-f]quinazolin-6-yl)-7-fluorothieno[3,2-c]pyridine-3-carbonitrile, Atropisomer 1 | 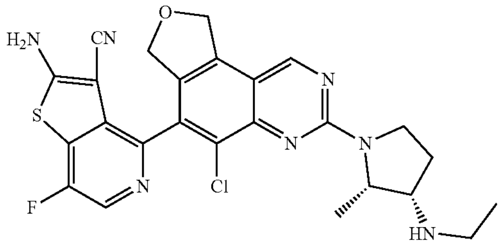 [SMILES: CCN[C@H]1CCN(c2ncc3c4c(c(-c5ncc(F)c6sc(N)c(C#N)c56)c(Cl)c3n2)COC4)[C@H]1C] | 524 |
| 79C [53] | 2-Amino-4-(5-chloro-3-((2S,3S)-3-(ethylamino)-2-methylpyrrolidin-1-yl)-7,9-dihydrofuro[3,4-f]quinazolin-6-yl)-7-fluorothieno[3,2-c]pyridine-3-carbonitrile, Atropisomer 2 | 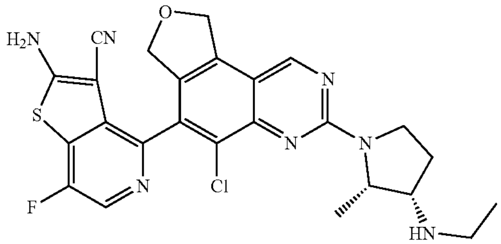 [SMILES: CCN[C@H]1CCN(c2ncc3c4c(c(-c5ncc(F)c6sc(N)c(C#N)c56)c(Cl)c3n2)COC4)[C@H]1C] | 524 |
| 80C [54] | 2-Amino-4-(5-chloro-3-((S)-3-(isopropylamino) pyrrolidin-1-yl)-7,9-dihydrofuro[3,4-f]quinazolin-6-yl)-7-fluorothieno[3,2-c]pyridine-3-carbonitrile, Atropisomer 1 | 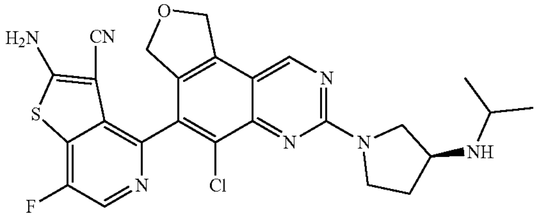 [SMILES: CC(C)N[C@H]1CCN(c2ncc3c4c(c(-c5ncc(F)c6sc(N)c(C#N)c56)c(Cl)c3n2)COC4)C1] | 524 |
| 81C [54] | 2-Amino-4-(5-chloro-3-((S)-3-(isopropylamino) pyrrolidin-1-yl)-7,9-dihydrofuro[3,4-f]quinazolin-6-yl)-7-fluorothieno[3,2-c]pyridine-3-carbonitrile, Atropisomer 2 | 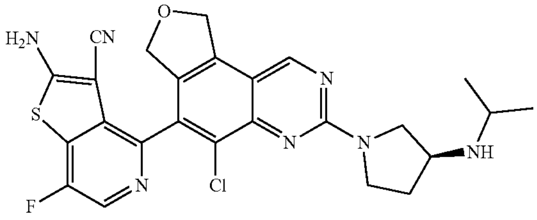 [SMILES: CC(C)N[C@H]1CCN(c2ncc3c4c(c(-c5ncc(F)c6sc(N)c(C#N)c56)c(Cl)c3n2)COC4)C1] | 524 |

TABLE 28-continued

| Example | Chemical Name | Structure | MS (ES) m/z (M + 1) |
|---|---|---|---|
| 82C [55] | 2-Amino-4-(5-chloro-3-((2S,3R)-3-((dimethylamino)methyl)-2-methylpyrrolidin-1-yl)-7,9-dihydrofuro[3,4-f]quinazolin-6-yl)-7-fluorothieno[3,2-c]pyridine-3-carbonitrile, Atropisomer 1 | 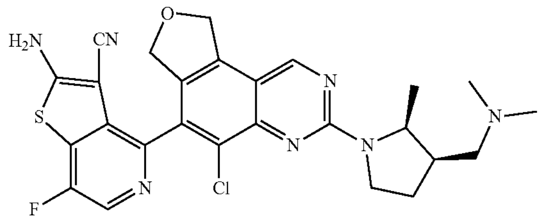 [SMILES: C[C@H]1[C@@H](CN(C)C)CCN1c1ncc2c3c(c(-c4ncc(F)c5sc(N)c(C#N)c45)c(Cl)c2n1)COC3] | 538 |
| 83C [55] | 2-Amino-4-(5-chloro-3-((2S,3R)-3-((dimethylamino)methyl)-2-methylpyrrolidin-1-yl)-7,9-dihydrofuro[3,4-f]quinazolin-6-yl)-7-fluorothieno[3,2-c]pyridine-3-carbonitrile, Atropisomer 2 | 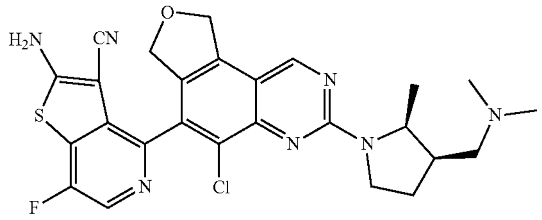 [SMILES: C[C@H]1[C@@H](CN(C)C)CCN1c1ncc2c3c(c(-c4ncc(F)c5sc(N)c(C#N)c45)c(Cl)c2n1)COC3] | 538 |
| 84C [56] | 2-Amino-4-(5-chloro-3-((2S,3S)-3-(((S)-2-hydroxypropyl)(methyl) amino)-2-methylpyrrolidin-1-yl)-7,9-dihydrofuro[3,4-f]quinazolin-6-yl)-7-fluorothieno[3,2-c]pyridine-3-carbonitrile, Atropisomer 1 | 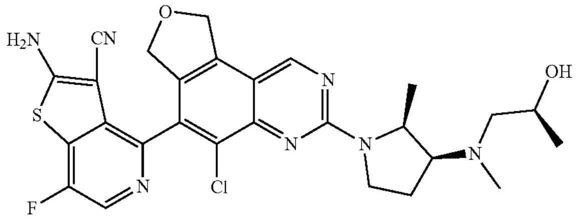 [SMILES: C[C@H](O)CN(C)[C@H]1CCN(c2ncc3c4c(c(-c5ncc(F)c6sc(N)c(C#N)c56)c(Cl)c3n2)COC4)[C@H]1C] | 568 |
| 85C [56] | 2-Amino-4-(5-chloro-3-((2S,3S)-3-(((S)-2-hydroxypropyl)(methyl) amino)-2-methylpyrrolidin-1-yl)-7,9-dihydrofuro[3,4-f]quinazolin-6-yl)-7-fluorothieno[3,2-c]pyridine-3-carbonitrile, Atropisomer 2 | 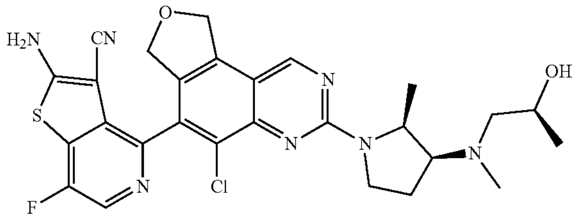 [SMILES: C[C@H](O)CN(C)[C@H]1CCN(c2ncc3c4c(c(-c5ncc(F)c6sc(N)c(C#N)c56)c(Cl)c3n2)COC4)[C@H]1C] | 568 |
| 86C [57] | 2-Amino-4-(5-chloro-3-((2S,3S)-3-(((R)-2-hydroxypropyl)(methyl) amino)-2-methylpyrrolidin-1-yl)-7,9-dihydrofuro[3,4-f]quinazolin-6-yl)-7-fluorothieno[3,2-c]pyridine-3-carbonitrile, Atropisomer 1 | 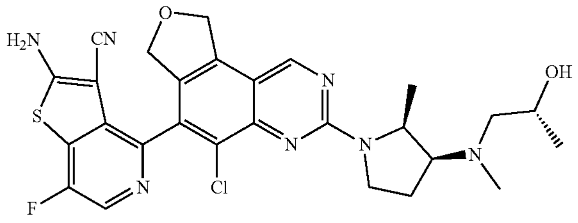 [SMILES: C[C@@H](O)CN(C)[C@H]1CCN(c2ncc3c4c(c(-c5ncc(F)c6sc(N)c(C#N)c56)c(Cl)c3n2)COC4)[C@H]1C] | 568 |
| 87C [57] | 2-Amino-4-(5-chloro-3-((2S,3S)-3-(((R)-2-hydroxypropyl)(methyl) amino)-2-methylpyrrolidin-1-yl)-7,9-dihydrofuro[3,4-f]quinazolin-6-yl)-7-fluorothieno[3,2-c]pyridine-3-carbonitrile, Atropisomer 2 | 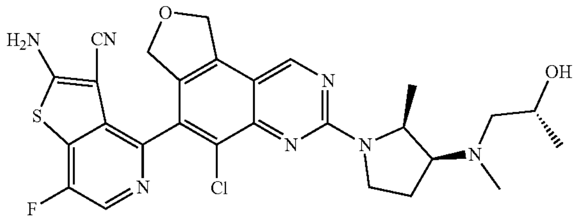 [SMILES: C[C@@H](O)CN(C)[C@H]1CCN(c2ncc3c4c(c(-c5ncc(F)c6sc(N)c(C#N)c56)c(Cl)c3n2)COC4)[C@H]1C] | 568 |

TABLE 28-continued

| Example | Chemical Name | Structure | MS (ES) m/z (M + 1) |
|---|---|---|---|
| 88C [58] | 2-Amino-4-(5-chloro-3-((2S,3S)-3-(isopropylamino)-2-methylpyrrolidin-1-yl)-7,9-dihydrofuro[3,4-f]quinazolin-6-yl)-7-fluorothieno[3,2-c]pyridine-3-carbonitrile, Atropisomer 2 | 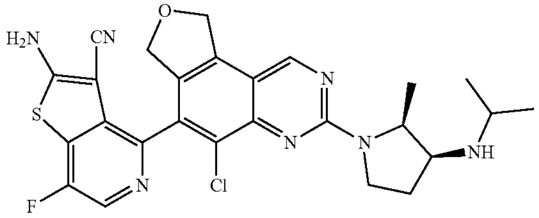 [SMILES: CC(C)N[C@H]1CCN(c2ncc3c4c(c(-c5ncc(F)c6sc(N)c(C#N)c56)c(Cl)c3n2)COC4)[C@H]1C] | 538 |
| 89C [59] | 2-Amino-5-fluoro-4-(5-fluoro-3-((2R,3S)-3-(isopropylamino)-2-methylpyrrolidin-1-yl)-7,9-dihydrofuro[3,4-f]quinazolin-6-yl)benzo[b]thiophene-3-carbonitrile, Atropisomer 1 | 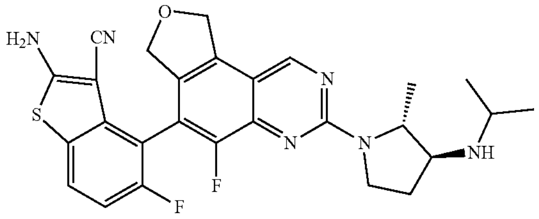 [SMILES: CC(C)N[C@H]1CCN(c2ncc3c4c(c(-c5c(F)ccc6sc(N)c(C#N)c56)c(F)c3n2)COC4)[C@@H]1C] | 521 |
| 90C [59] | 2-Amino-5-fluoro-4-(5-fluoro-3-((2R,3S)-3-(isopropylamino)-2-methylpyrrolidin-1-yl)-7,9-dihydrofuro[3,4-f]quinazolin-6-yl)benzo[b]thiophene-3-carbonitrile, Atropisomer 2 | 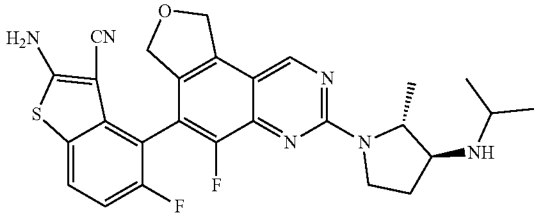 [SMILES: CC(C)N[C@H]1CCN(c2ncc3c4c(c(-c5c(F)ccc6sc(N)c(C#N)c56)c(F)c3n2)COC4)[C@@H]1C] | 521 |
| 91C [60] | 2-Amino-5-fluoro-4-(5-fluoro-3-((3R,4R)-3-(isopropylamino)-4-methoxypyrrolidin-1-yl)-7,9-dihydrofuro[3,4-f]quinazolin-6-yl)benzo[b]thiophene-3-carbonitrile, Atropisomer 1 | 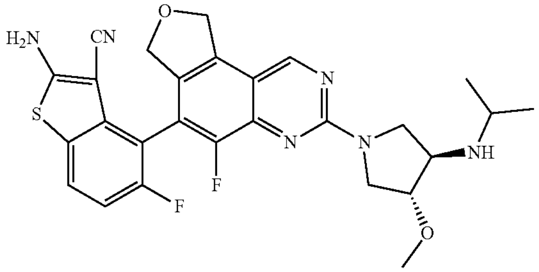 [SMILES: CO[C@@H]1CN(c2ncc3c4c(c(-c5c(F)ccc6sc(N)c(C#N)c56)c(F)c3n2)COC4)C[C@H]1NC(C)C] | 537 |
| 92C [60] | 2-Amino-5-fluoro-4-(5-fluoro-3-((3R,4R)-3-(isopropylamino)-4-methoxypyrrolidin-1-yl)-7,9-dihydrofuro[3,4-f]quinazolin-6-yl)benzo[b]thiophene-3-carbonitrile, Atropisomer 2 | 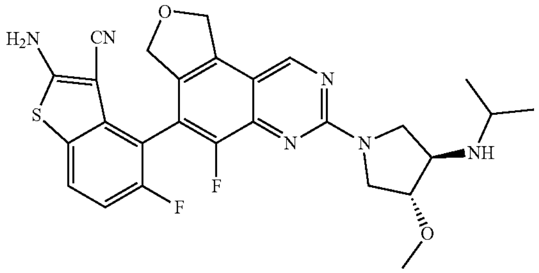 [SMILES: CO[C@@H]1CN(c2ncc3c4c(c(-c5c(F)ccc6sc(N)c(C#N)c56)c(F)c3n2)COC4)C[C@H]1NC(C)C] | 537 |
| 93C [61] | 2-Amino-5-fluoro-4-(5-fluoro-3-((3R,4S)-3-(isopropylamino)-4-methoxypyrrolidin-1-yl)-7,9-dihydrofuro[3,4-f]quinazolin-6-yl)benzo[b]thiophene-3-carbonitrile, Atropisomer 1 | 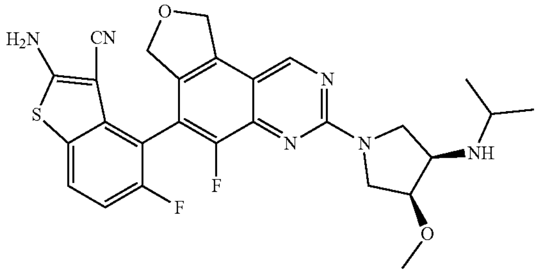 [SMILES: CO[C@H]1CN(c2ncc3c4c(c(-c5c(F)ccc6sc(N)c(C#N)c56)c(F)c3n2)COC4)C[C@H]1NC(C)C] | 537 |

TABLE 28-continued

| Example | Chemical Name | Structure | MS (ES) m/z (M + 1) |
|---|---|---|---|
| 94C [61] | 2-Amino-5-fluoro-4-(5-fluoro-3-((3R,4S)-3-(isopropylamino)-4-methoxypyrrolidin-1-yl)-7,9-dihydrofuro[3,4-f]quinazolin-6-yl)benzo[b]thiophene-3-carbonitrile, Atropisomer 2 | 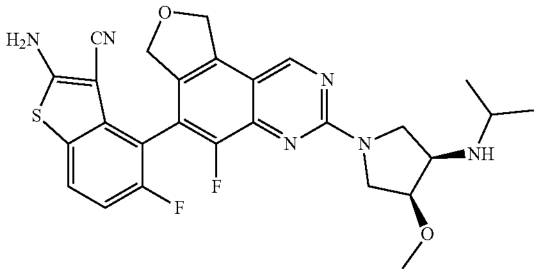 [SMILES: CO[C@H]1CN(c2ncc3c4c(c(-c5c(F)ccc6sc(N)c(C#N)c56)c(F)c3n2)COC4)C[C@H]1NC(C)C] | 537 |
| 95C [62] | 2-Amino-4-(3-(6-(dimethylamino)-4-azaspiro[2.4]heptan-4-yl)-5-fluoro-7,9-dihydrofuro[3,4-f]quinazolin-6-yl)-7-fluorothieno[3,2-c]pyridine-3-carbonitrile, Isomer 1 | 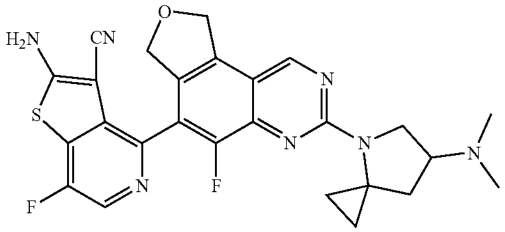 [SMILES: CN(C)C1CN(c2ncc3c4c(c(-c5ncc(F)c6sc(N)c(C#N)c56)c(F)c3n2)COC4)C2(CC2)C1] | 520 |
| 96C [62] | 2-Amino-4-(3-(6-(dimethylamino)-4-azaspiro[2.4]heptan-4-yl)-5-fluoro-7,9-dihydrofuro[3,4-f]quinazolin-6-yl)-7-fluorothieno[3,2-c]pyridine-3-carbonitrile, Isomer 2 | 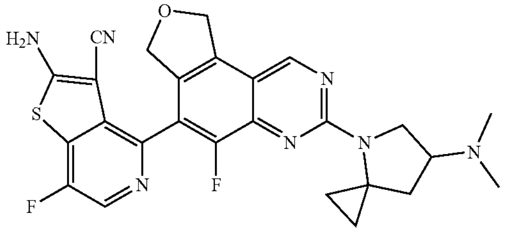 [SMILES: CN(C)C1CN(c2ncc3c4c(c(-c5ncc(F)c6sc(N)c(C#N)c56)c(F)c3n2)COC4)C2(CC2)C1] | 520 |
| 97C [63] | 2-Amino-4-(3-(6-(dimethylamino)-2-azabicyclo[3.2.0]heptan-2-yl)-5-fluoro-7,9-dihydrofuro[3,4-f]quinazolin-6-yl)-7-fluorothieno[3,2-c]pyridine-3-carbonitrile, Isomer 1 | 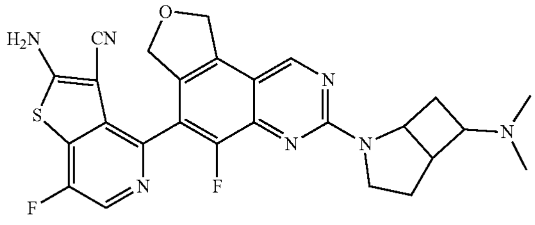 [SMILES: CN(C)C1CC2C1CCN2c1ncc2c3c(c(-c4ncc(F)c5sc(N)c(C#N)c45)c(F)c2n1)COC3] | 520 |
| 98C [63] | 2-Amino-4-(3-(6-(dimethylamino)-2-azabicyclo[3.2.0]heptan-2-yl)-5-fluoro-7,9-dihydrofuro[3,4-f]quinazolin-6-yl)-7-fluorothieno[3,2-c]pyridine-3-carbonitrile, Isomer 2 | 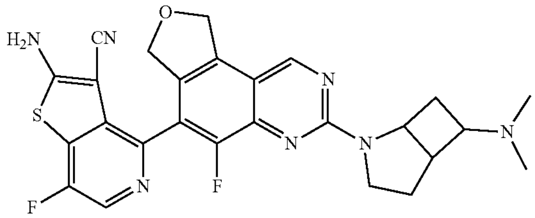 [SMILES: CN(C)C1CC2C1CCN2c1ncc2c3c(c(-c4ncc(F)c5sc(N)c(C#N)c45)c(F)c2n1)COC3] | 520 |
| 99C [64] | 2-Amino-4-(3-(3-((dimethylamino)methyl)-2-methylpyrrolidin-1-yl)-5-fluoro-7,9-dihydrofuro[3,4-f]quinazolin-6-yl)-7-fluorothieno[3,2-c]pyridine-3-carbonitrile | 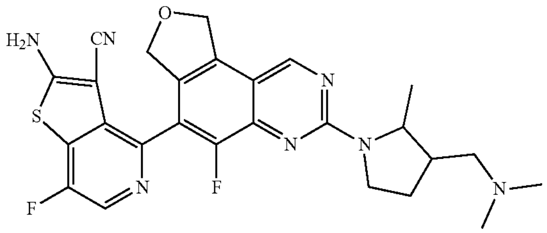 [SMILES: CC1C(CN(C)C)CCN1c1ncc2c3c(c(-c4ncc(F)c5sc(N)c(C#N)c45)c(F)c2n1)COC3] | 522 |

TABLE 28-continued

| Example | Chemical Name | Structure | MS (ES) m/z (M + 1) |
|---|---|---|---|
| 100C [64] | 2-Amino-4-(3-(3-((dimethylamino)methyl)-2-methylpyrrolidin-1-yl)-5-fluoro-7,9-dihydrofuro[3,4-f]quinazolin-6-yl)-7-fluorothieno[3,2-c]pyridine-3-carbonitrile | 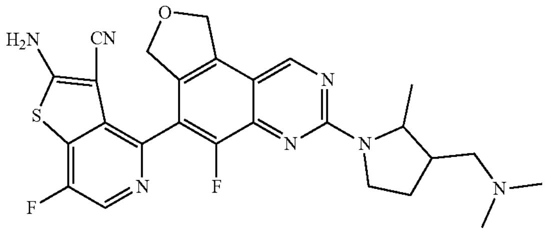 [SMILES: CC1C(CN(C)C)CCN1c1ncc2c3c(c(-c4ncc(F)c5sc(N)c(C#N)c45)c(F)c2n1)COC3] | 522 |
| 101C | 2-Amino-7-fluoro-4-(5-fluoro-3-((3S,4S)-3-hydroxy-4-(isopropyl(methyl)amino) pyrrolidin-1-yl)-7,9-dihydrofuro[3,4-f]quinazolin-6-yl)thieno[3,2-c]pyridine-3-carbonitrile | 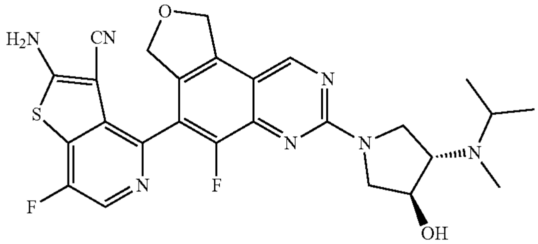 [SMILES: CC(C)N(C)[C@H]1CN(c2ncc3c4c(c(-c5ncc(F)c6sc(N)c(C#N)c56)c(F)c3n2)COC4)C[C@@H]1O] | 538 |
| 102C [65] | 2-Amino-4-(3-((2S)-3-(bicyclo[1.1.1]pentan-1-ylamino)-2-methylpyrrolidin-1-yl)-5-fluoro-7,9-dihydrofuro[3,4-f]quinazolin-6-yl)-7-fluorothieno[3,2-c]pyridine-3-carbonitrile, Isomer 1 | 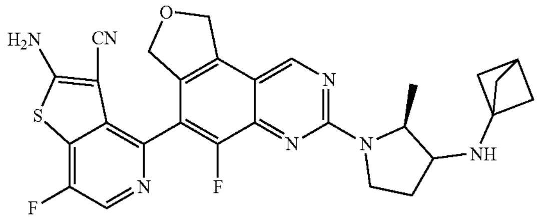 [SMILES: C[C@H]1C(NC23CC(C2)C3)CCN1c1ncc2c3c(c(-c4ncc(F)c5sc(N)c(C#N)c45)c(F)c2n1)COC3] | 546 |
| 103C [65] | 2-Amino-4-(3-((2S)-3-(bicyclo[1.1.1]pentan-1-ylamino)-2-methylpyrrolidin-1-yl)-5-fluoro-7,9-dihydrofuro[3,4-f]quinazolin-6-yl)-7-fluorothieno[3,2-c]pyridine-3-carbonitrile, Isomer 2 | 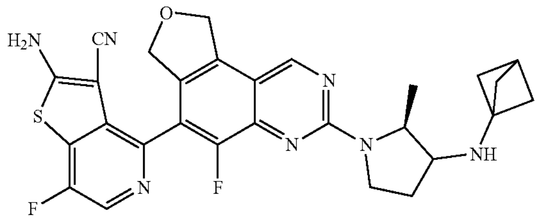 [SMILES: C[C@H]1C(NC23CC(C2)C3)CCN1c1ncc2c3c(c(-c4ncc(F)c5sc(N)c(C#N)c45)c(F)c2n1)COC3] | 546 |
| 104C | 2-Amino-7-fluoro-4-(5-fluoro-3-((2S,3S)-3-((2-fluoroethyl)amino)-2-methylpyrrolidin-1-yl)-7,9-dihydrofuro[3,4-f]quinazolin-6-yl)thieno[3,2-c]pyridine-3-carbonitrile | 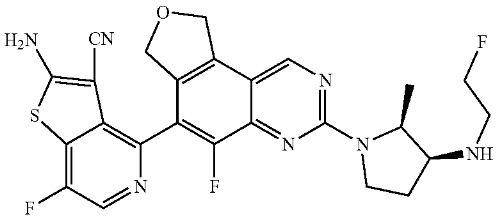 [SMILES: C[C@H]1[C@@H](NCCF)CCN1c1ncc2c3c(c(-c4ncc(F)c5sc(N)c(C#N)c45)c(F)c2n1)COC3] | 526 |
| 105C | 2-Amino-7-fluoro-4-(5-fluoro-3-((2S,3S)-3-(((R)-2-hydroxypropyl)(methyl) amino)-2-methylpyrrolidin-1-yl)-7,9-dihydrofuro[3,4-f]quinazolin-6-yl)thieno[3,2-c]pyridine-3-carbonitrile | 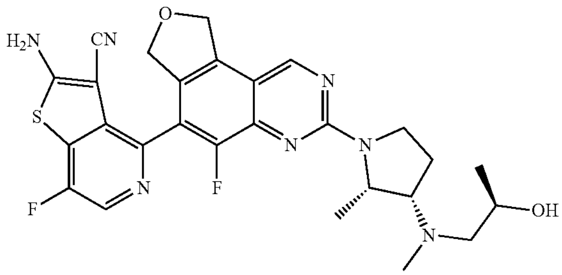 [SMILES: C[C@@H](O)CN(C)[C@H]1CCN(c2ncc3c4c(c(-c5ncc(F)c6sc(N)c(C#N)c56)c(F)c3n2)COC4)[C@H]1C] | 552 |

TABLE 28-continued

| Example | Chemical Name | Structure | MS (ES) m/z (M + 1) |
|---|---|---|---|
| 106C | 2-Amino-7-fluoro-4-(5-fluoro-3-((2S,3S)-3-(((S)-2-hydroxypropyl)(methyl)amino)-2-methylpyrrolidin-1-yl)-7,9-dihydrofuro[3,4-f]quinazolin-6-yl)thieno[3,2-c]pyridine-3-carbonitrile trifluoroacetic acid | 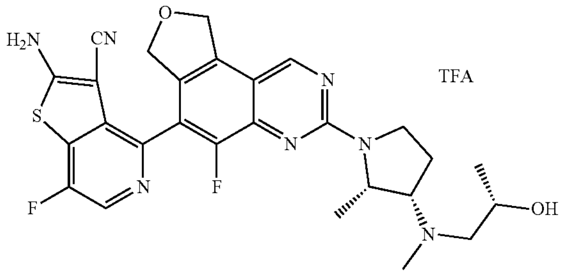 TFA | 552 |
| 107C | 2-Amino-7-fluoro-4-(5-fluoro-3-((2S,3S)-3-(isobutylamino)-2-methylpyrrolidin-1-yl)-7,9-dihydrofuro[3,4-f]quinazolin-6-yl)thieno[3,2-c]pyridine-3-carbonitrile | 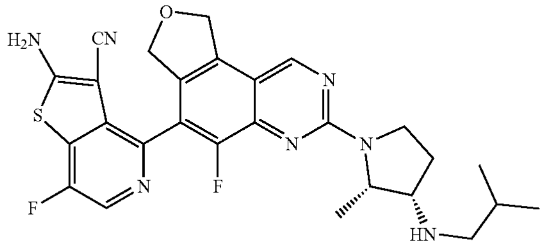 | 536 |
| 108C | 2-Amino-4-(3-((2S,3S)-3-(ethylamino)-2-methylpyrrolidin-1-yl)-5-fluoro-7,9-dihydrofuro[3,4-f]quinazolin-6-yl)-7-fluorothieno[3,2-c]pyridine-3-carbonitrile | 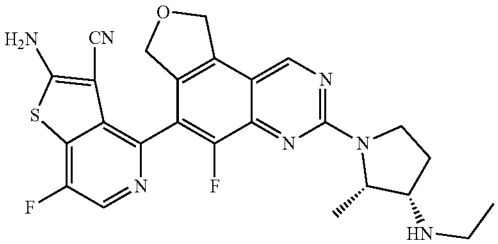 | 508 |
| 109C | 2-Amino-7-fluoro-4-(5-fluoro-3-((2S,3S)-3-(((S)-2-hydroxypropyl)amino)-2-methylpyrrolidin-1-yl)-7,9-dihydrofuro[3,4-f]quinazolin-6-yl)thieno[3,2-c]pyridine-3-carbonitrile trifluoroacetic acid | 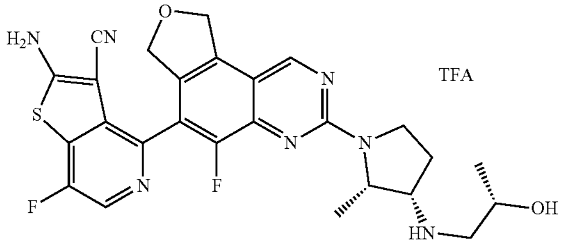 TFA | 538 |
| 110C | 2-Amino-7-fluoro-4-(5-fluoro-3-((2S,3S)-3-((2-hydroxy-2-methylpropyl)amino)-2-methylpyrrolidin-1-yl)-7,9-dihydrofuro[3,4-f]quinazolin-6-yl)thieno[3,2-c]pyridine-3-carbonitrile | 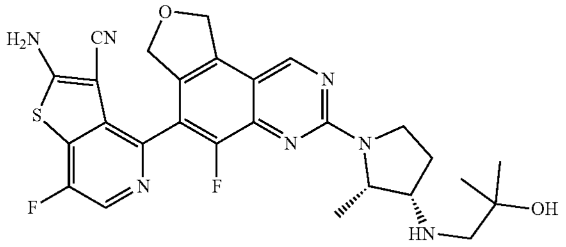 | 552 |
| 111C | 2-Amino-7-fluoro-4-(5-fluoro-3-((2S,3S)-3-((2-hydroxy-2-methylpropyl)(methyl)amino)-2-methylpyrrolidin-1-yl)-7,9-dihydrofuro[3,4-f]quinazolin-6-yl)thieno[3,2-c]pyridine-3-carbonitrile | 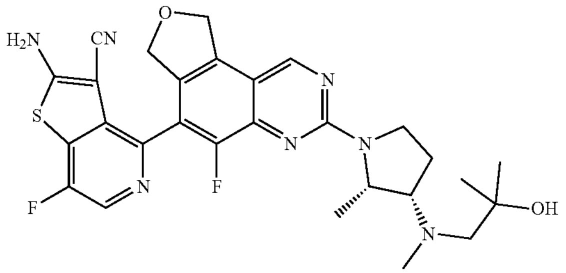 | 566 |

TABLE 28-continued

| Example | Chemical Name | Structure | MS (ES) m/z (M + 1) |
| --- | --- | --- | --- |
| 112C [66] | 2-Amino-7-fluoro-4-(5-fluoro-3-((2S,3S)-3-((3-hydroxy-3-methylcyclobutyl)amino)-2-methylpyrrolidin-1-yl)-7,9-dihydrofuro[3,4-f]quinazolin-6-yl)thieno[3,2-c]pyridine-3-carbonitrile, Isomer 1 | 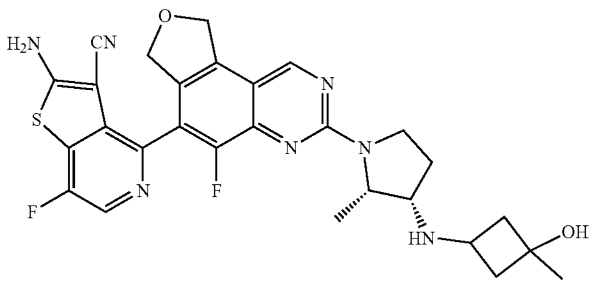 [SMILES: C[C@H]1[C@@H](NC2CC(C)(O)C2)CCN1c1ncc2c3c(c(-c4ncc(F)c5sc(N)c(C#N)c45)c(F)c2n1)COC3] | 564 |
| 113C [66] | 2-Amino-7-fluoro-4-(5-fluoro-3-((2S,3S)-3-((3-hydroxy-3-methylcyclobutyl)amino)-2-methylpyrrolidin-1-yl)-7,9-dihydrofuro[3,4-f]quinazolin-6-yl)thieno[3,2-c]pyridine-3-carbonitrile, Isomer 2 | 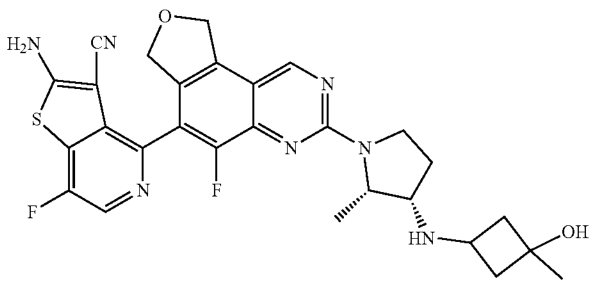 [SMILES: C[C@H]1[C@@H](NC2CC(C)(O)C2)CCN1c1ncc2c3c(c(-c4ncc(F)c5sc(N)c(C#N)c45)c(F)c2n1)COC3] | 564 |
| 114C [67] | 2-Amino-7-fluoro-4-(5-fluoro-3-((2S,3S)-3-((3-hydroxy-3-methylcyclobutyl)(methyl)amino)-2-methylpyrrolidin-1-yl)-7,9-dihydrofuro[3,4-f]quinazolin-6-yl)thieno[3,2-c]pyridine-3-carbonitrile, Isomer 1 | 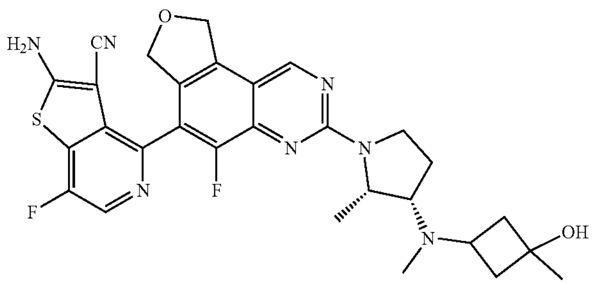 [SMILES: C[C@H]1[C@@H](N(C)C2CC(C)(O)C2)CCN1c1ncc2c3c(c(-c4ncc(F)c5sc(N)c(C#N)c45)c(F)c2n1)COC3] | 578 |
| 115C [67] | 2-Amino-7-fluoro-4-(5-fluoro-3-((2S,3S)-3-((3-hydroxy-3-methylcyclobutyl)(methyl)amino)-2-methylpyrrolidin-1-yl)-7,9-dihydrofuro[3,4-f]quinazolin-6-yl)thieno[3,2-c]pyridine-3-carbonitrile, Isomer 2 | 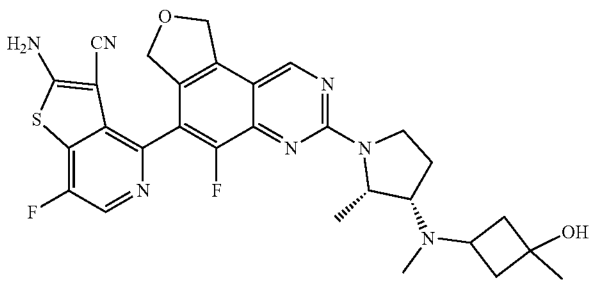 [SMILES: C[C@H]1[C@@H](N(C)C2CC(C)(O)C2)CCN1c1ncc2c3c(c(-c4ncc(F)c5sc(N)c(C#N)c45)c(F)c2n1)COC3] | 578 |
| 116C | 2-Amino-7-chloro-4-(3-((S)-3-(dimethylamino)pyrrolidin-1-yl)-5-fluoro-7,9-dihydrofuro[3,4-f]quinazolin-6-yl)thieno[3,2-c]pyridine-3-carbonitrile | 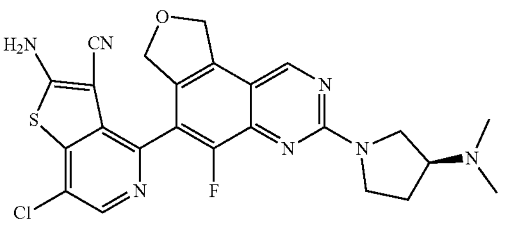 [SMILES: CN(C)[C@H]1CCN(c2ncc3c4c(c(-c5ncc(Cl)c6sc(N)c(C#N)c56)c(F)c3n2)COC4)C1] | 510 |

TABLE 28-continued

| Example | Chemical Name | Structure | MS (ES) m/z (M + 1) |
|---|---|---|---|
| 117C | 2-Amino-7-chloro-4-(3-((3R,4S)-3-(dimethylamino)-4-hydroxypyrrolidin-1-yl)-5-fluoro-7,9-dihydrofuro[3,4-f]quinazolin-6-yl)thieno[3,2-c]pyridine-3-carbonitrile | 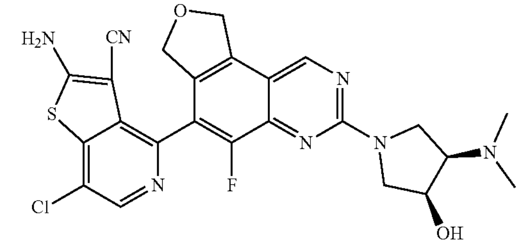 [SMILES: CN(C)[C@@H]1CN(c2ncc3c4c(c(-c5ncc(Cl)c6sc(N)c(C#N)c56)c(F)c3n2)COC4)C[C@@H]1O] | 526 |
| 118C | 2-Amino-7-chloro-4-(5-fluoro-3-((3S,4S)-3-hydroxy-4-(isopropyl(methyl)amino) pyrrolidin-1-yl)-7,9-dihydrofuro[3,4-f]quinazolin-6-yl)thieno[3,2-c]pyridine-3-carbonitrile | 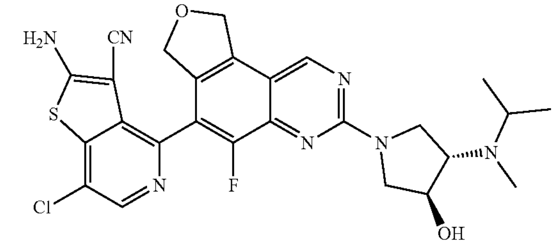 [SMILES: CC(C)N(C)[C@H]1CN(c2ncc3c4c(c(-c5ncc(Cl)c6sc(N)c(C#N)c56)c(F)c3n2)COC4)C[C@@H]1O] | 554 |
| 119C | 2-Amino-7-chloro-4-(5-fluoro-3-((2S,3S)-3-(isopropylamino)-2-methylpyrrolidin-1-yl)-7,9-dihydrofuro[3,4-f]quinazolin-6-yl)thieno[3,2-c]pyridine-3-carbonitrile | 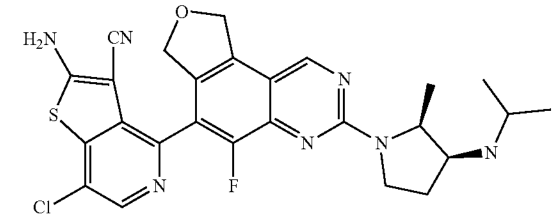 [SMILES: CC(C)N[C@H]1CCN(c2ncc3c4c(c(-c5ncc(Cl)c6sc(N)c(C#N)c56)c(F)c3n2)COC4)[C@H]1C] | 538 |
| 1D [68] | 2-Amino-4-(5-chloro-3-((3R,4S)-3-hydroxy-4-(isopropyl(methyl)amino) pyrrolidin-1-yl)-7,9-dihydrofuro[3,4-f]quinazolin-6-yl)-7-fluorothieno[3,2-c]pyridine-3-carbonitrile, Atropisomer 1 | 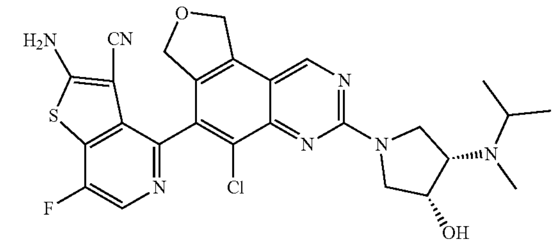 [SMILES: CC(C)N(C)[C@H]1CN(c2ncc3c4c(c(-c5ncc(F)c6sc(N)c(C#N)c56)c(Cl)c3n2)COC4)C[C@H]1O] | 554 |
| 2D [68] | 2-Amino-4-(5-chloro-3-((3R,4S)-3-hydroxy-4-(isopropyl(methyl)amino) pyrrolidin-1-yl)-7,9-dihydrofuro[3,4-f]quinazolin-6-yl)-7-fluorothieno[3,2-c]pyridine-3-carbonitrile, Atropisomer 2 | 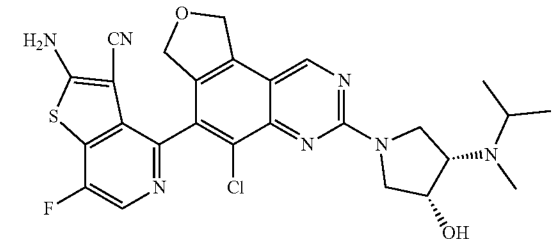 [SMILES: CC(C)N(C)[C@H]1CN(c2ncc3c4c(c(-c5ncc(F)c6sc(N)c(C#N)c56)c(Cl)c3n2)COC4)C[C@H]1O] | 554 |
| 3D [69] | 2-Amino-4-(5-chloro-3-((3R,4R)-3-hydroxy-4-(isopropyl(methyl)amino) pyrrolidin-1-yl)-7,9-dihydrofuro[3,4-f]quinazolin-6-yl)-7-fluorothieno[3,2-c]pyridine-3-carbonitrile, Atropisomer 1 | 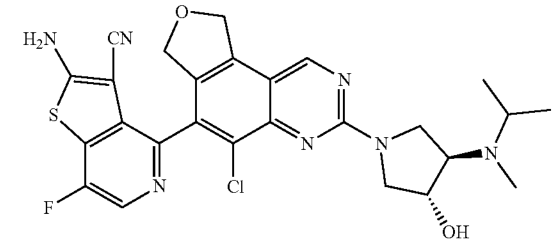 [SMILES: CC(C)N(C)[C@@H]1CN(c2ncc3c4c(c(-c5ncc(F)c6sc(N)c(C#N)c56)c(Cl)c3n2)COC4)C[C@H]1O] | 554 |

TABLE 28-continued

| Example | Chemical Name | Structure | MS (ES) m/z (M + 1) |
|---|---|---|---|
| 4D [69] | 2-Amino-4-(5-chloro-3-((3R,4R)-3-hydroxy-4-(isopropyl(methyl)amino) pyrrolidin-1-yl)-7,9-dihydrofuro[3,4-f]quinazolin-6-yl)-7-fluorothieno[3,2-c]pyridine-3-carbonitrile, Atropisomer 2 | 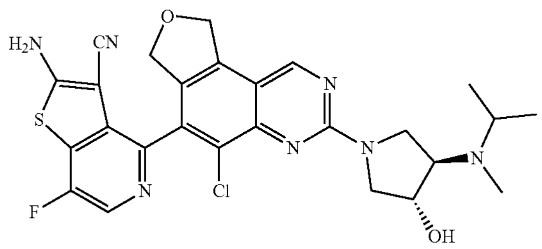 [SMILES: CC(C)N(C)[C@@H]1CN(c2ncc3c4c(c(-c5ncc(F)c6sc(N)c(C#N)c56)c(Cl)c3n2)COC4)C[C@H]1O] | 554 |
| 5D [70] | 2-Amino-4-(5-chloro-3-((2S,3R)-2-methyl-3-((methylamino)methyl) pyrrolidin-1-yl)-7,9-dihydrofuro[3,4-f]quinazolin-6-yl)-7-fluorothieno[3,2-c]pyridine-3-carbonitrile, Atropisomer 1 | 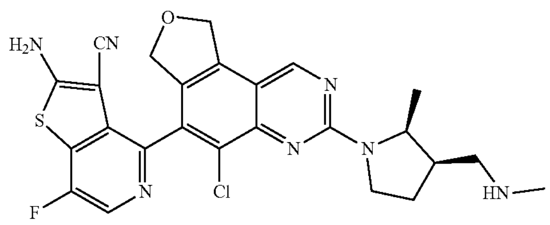 [SMILES: CNC[C@H]1CCN(c2ncc3c4c(c(-c5ncc(F)c6sc(N)c(C#N)c56)c(Cl)c3n2)COC4)[C@H]1C] | 524 |
| 6D [70] | 2-Amino-4-(5-chloro-3-((2S,3R)-2-methyl-3-((methylamino)methyl) pyrrolidin-1-yl)-7,9-dihydrofuro[3,4-f]quinazolin-6-yl)-7-fluorothieno[3,2-c]pyridine-3-carbonitrile, Atropisomer 2 | 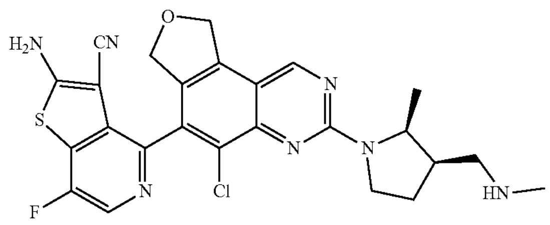 [SMILES: CNC[C@H]1CCN(c2ncc3c4c(c(-c5ncc(F)c6sc(N)c(C#N)c56)c(Cl)c3n2)COC4)[C@H]1C] | 524 |
| 7D [71] | 2-Amino-4-(5-chloro-3-((2R,3R)-2-methyl-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 1 | 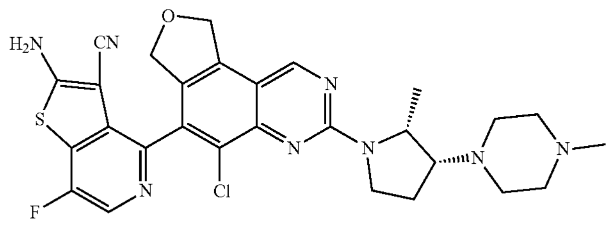 [SMILES: C[C@@H]1[C@H](N2CCN(C)CC2)CCN1c1ncc2c3c(c(-c4ncc(F)c5sc(N)c(C#N)c45)c(Cl)c2n1)COC3] | 579 |
| 8D [71] | 2-Amino-4-(5-chloro-3-((2R,3R)-2-methyl-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 2 | 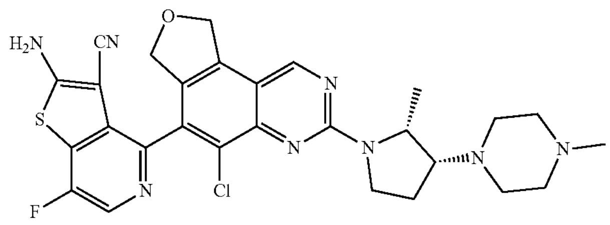 [SMILES: C[C@@H]1[C@H](N2CCN(C)CC2)CCN1c1ncc2c3c(c(-c4ncc(F)c5sc(N)c(C#N)c45)c(Cl)c2n1)COC3] | 579 |
| 9D [72] | 2-Amino-4-(5-chloro-3-((2S,3S)-2-methyl-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 1 | 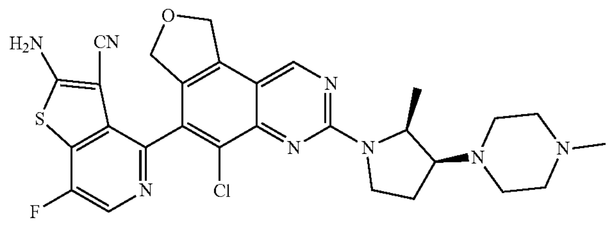 [SMILES: C[C@H]1[C@@H](N2CCN(C)CC2)CCN1c1ncc2c3c(c(-c4ncc(F)c5sc(N)c(C#N)c45)c(Cl)c2n1)COC3] | 579 |

TABLE 28-continued

| Example | Chemical Name | Structure | MS (ES) m/z (M + 1) |
|---|---|---|---|
| 10D [72] | 2-Amino-4-(5-chloro-3-((2S,3S)-2-methyl-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 2 | 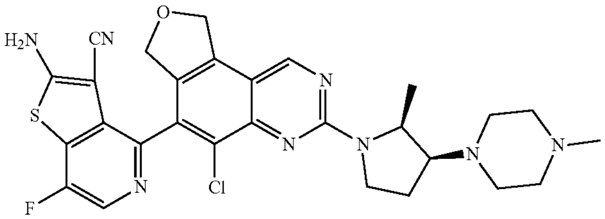 [SMILES: C[C@H]1[C@@H](N2CCN(C)CC2)CCN1c1ncc2c3c(c(-c4ncc(F)c5sc(N)c(C#N)c45)c(Cl)c2n1)COC3] | 579 |
| 11D [73] | 2-Amino-4-(5-chloro-3-((2S,3R)-2-methyl-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 1 | 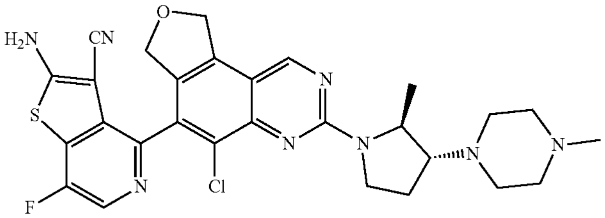 [SMILES: C[C@H]1[C@H](N2CCN(C)CC2)CCN1c1ncc2c3c(c(-c4ncc(F)c5sc(N)c(C#N)c45)c(Cl)c2n1)COC3] | 579 |
| 12D [73] | 2-Amino-4-(5-chloro-3-((2S,3R)-2-methyl-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 2 | 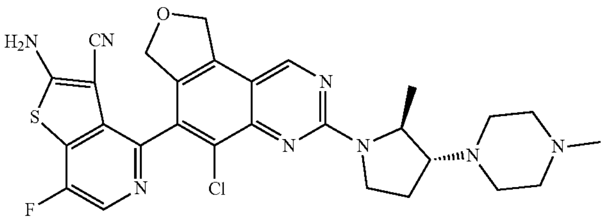 [SMILES: C[C@H]1[C@H](N2CCN(C)CC2)CCN1c1ncc2c3c(c(-c4ncc(F)c5sc(N)c(C#N)c45)c(Cl)c2n1)COC3] | 579 |
| 13D [74] | 2-Amino-4-(5-chloro-3-((R)-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 1 | 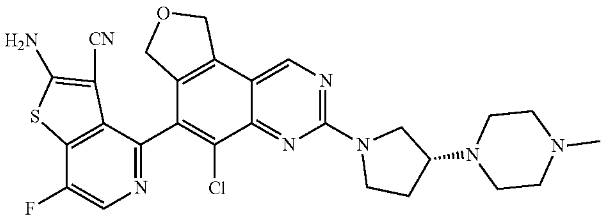 [SMILES: CN1CCN([C@@H]2CCN(c3ncc4c5c(c(-c6ncc(F)c7sc(N)c(C#N)c67)c(Cl)c4n3)COC5)C2)CC1] | 565 |
| 14D [74] | 2-Amino-4-(5-chloro-3-((R)-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 2 | 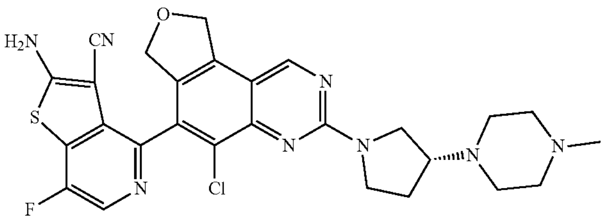 [SMILES: CN1CCN([C@@H]2CCN(c3ncc4c5c(c(-c6ncc(F)c7sc(N)c(C#N)c67)c(Cl)c4n3)COC5)C2)CC1] | 565 |
| 15D [75] | 2-Amino-4-(5-chloro-3-((S)-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 1 | 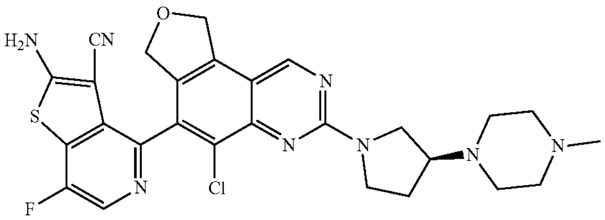 [SMILES: CN1CCN([C@H]2CCN(c3ncc4c5c(c(-c6ncc(F)c7sc(N)c(C#N)c67)c(Cl)c4n3)COC5)C2)CC1] | 565 |

TABLE 28-continued

| Example | Chemical Name | Structure | MS (ES) m/z (M + 1) |
|---|---|---|---|
| 16D [75] | 2-Amino-4-(5-chloro-3-((S)-3-(4-methylpiperazin-1-yl)pyrrolidin-1-yl)-7,9-dihydrofuro[3,4-f]quinazolin-6-yl)-7-fluorothieno[3,2-c]pyridine-3-carbonitrile, Atropisomer 2 | 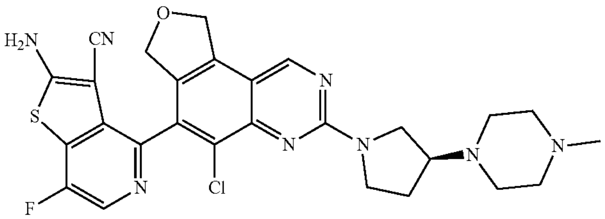 [SMILES: CN1CCN([C@H]2CCN(c3ncc4c5c(c(-c6ncc(F)c7sc(N)c(C#N)c67)c(Cl)c4n3)COC5)C2)CC1] | 565 |
| 17D | 2-Amino-4-(3-(3-(dimethylamino)-1-oxa-7-azaspiro[4.4]nonan-7-yl)-5-fluoro-7,9-dihydrofuro[3,4-f]quinazolin-6-yl)-7-fluorothieno[3,2-c]pyridine-3-carbonitrile | 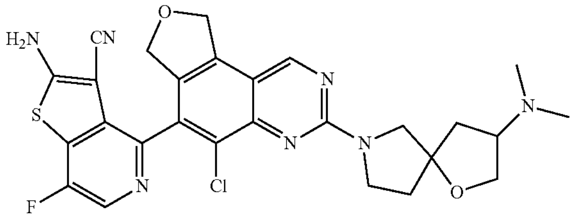 [SMILES: CN(C)C1COC2(CCN(c3ncc4c5c(c(-c6ncc(F)c7sc(N)c(C#N)c67)c(Cl)c4n3)COC5)C2)C1] | 550 |
| 18D [76] | 2-Amino-4-(3-(3-(dimethylamino)-1-oxa-7-azaspiro[4.4]nonan-7-yl)-5-fluoro-7,9-dihydrofuro[3,4-f]quinazolin-6-yl)-7-fluorothieno[3,2-c]pyridine-3-carbonitrile, Isomer 1 | 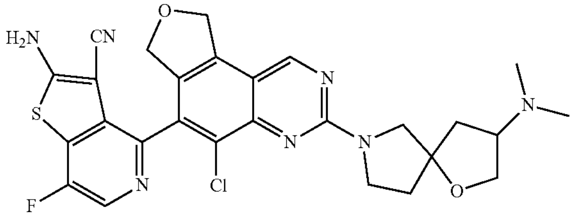 [SMILES: CN(C)C1COC2(CCN(c3ncc4c5c(c(-c6ncc(F)c7sc(N)c(C#N)c67)c(Cl)c4n3)COC5)C2)C1] | 550 |
| 19D [76] | 2-Amino-4-(3-(3-(dimethylamino)-1-oxa-7-azaspiro[4.4]nonan-7-yl)-5-fluoro-7,9-dihydrofuro[3,4-f]quinazolin-6-yl)-7-fluorothieno[3,2-c]pyridine-3-carbonitrile, Isomer 2 | 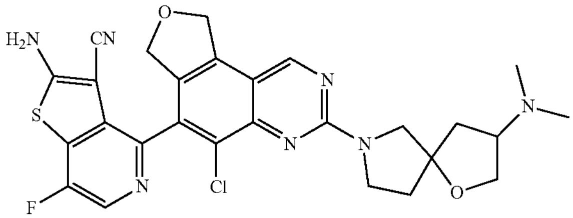 [SMILES: CN(C)C1COC2(CCN(c3ncc4c5c(c(-c6ncc(F)c7sc(N)c(C#N)c67)c(Cl)c4n3)COC5)C2)C1] | 550 |
| 20D | 2-Amino-7-fluoro-4-(5-fluoro-3-(6-(methyl-d3)-2,6-diazaspiro[3.4]octan-2-yl)-7,9-dihydrofuro[3,4-f]quinazolin-6-yl)thieno[3,2-c]pyridine-3-carbonitrile | 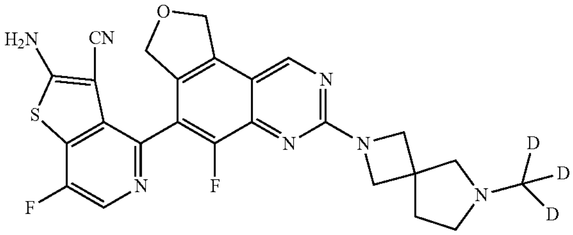 [SMILES: [2H]C([2H])([2H])N1CCC2(CN(c3ncc4c5c(c(-c6ncc(F)c7sc(N)c(C#N)c67)c(F)c4n3)COC5)C2)C1] | 509 |
| 21D | 2-Amino-7-fluoro-4-(5-fluoro-3-(3-(4-methylpiperazin-1-yl)azetidin-1-yl)-7,9-dihydrofuro[3,4-f]quinazolin-6-yl)thieno[3,2-c]pyridine-3-carbonitrile | 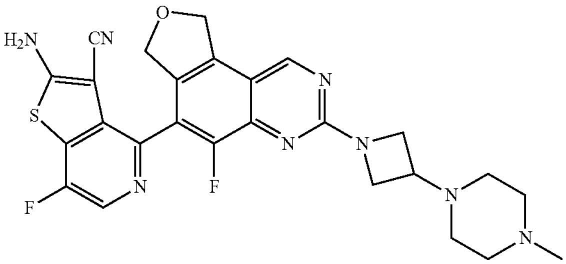 [SMILES: CN1CCN(C2CN(c3ncc4c5c(c(-c6ncc(F)c7sc(N)c(C#N)c67)c(F)c4n3)COC5)C2)CC1] | 535 |

TABLE 28-continued

| Example | Chemical Name | Structure | MS (ES) m/z (M + 1) |
|---|---|---|---|
| 22D | 2-Amino-4-(3-((R)-3-(3-(dimethylamino)azetidin-1-yl)pyrrolidin-1-yl)-5-fluoro-7,9-dihydrofuro[3,4-f]quinazolin-6-yl)-7-fluorothieno[3,2-c]pyridine-3-carbonitrile | 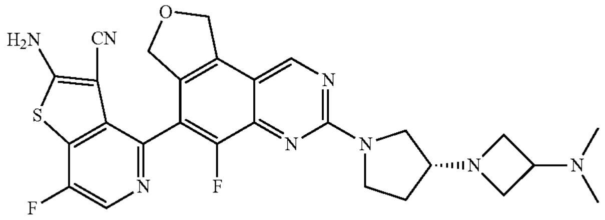 [SMILES: CN(C)C1CN([C@@H]2CCN(c3ncc4c5c(c(-c6ncc(F)c7sc(N)c(C#N)c67)c(F)c4n3)COC5)C2)C1] | 549 |
| 23D | 2-Amino-4-(3-((S)-3-(3-(dimethylamino)azetidin-1-yl)pyrrolidin-1-yl)-5-fluoro-7,9-dihydrofuro[3,4-f]quinazolin-6-yl)-7-fluorothieno[3,2-c]pyridine-3-carbonitrile | 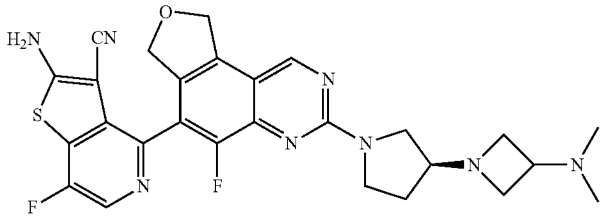 [SMILES: CN(C)C1CN([C@H]2CCN(c3ncc4c5c(c(-c6ncc(F)c7sc(N)c(C#N)c67)c(F)c4n3)COC5)C2)C1] | 549 |
| 24D | 2-Amino-4-(3-((R)-3-(azetidin-1-yl)pyrrolidin-1-yl)-5-fluoro-7,9-dihydrofuro[3,4-f]quinazolin-6-yl)-7-fluorothieno[3,2-c]pyridine-3-carbonitrile | 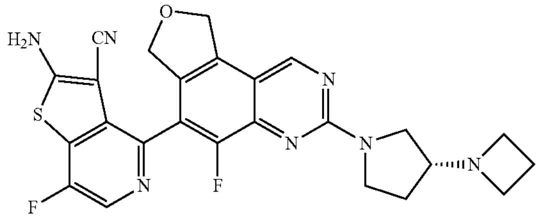 [SMILES: N#Cc1c(N)sc2c(F)cnc(-c3c4c(c5cnc(N6CC[C@@H](N7CCC7)C6)nc5c3F)COC4)c12] | 506 |
| 25D [77] | 2-Amino-4-(3-(3-(azetidin-1-yl)-4-hydroxypyrrolidin-1-yl)-5-fluoro-7,9-dihydrofuro[3,4-f]quinazolin-6-yl)-7-fluorothieno[3,2-c]pyridine-3-carbonitrile | 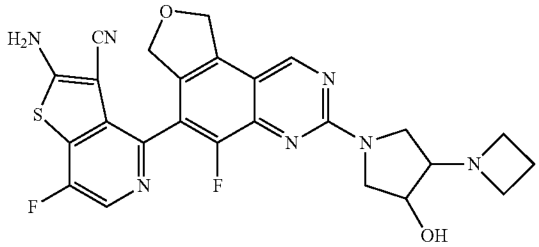 [SMILES: N#Cc1c(N)sc2c(F)cnc(-c3c4c(c5cnc(N6CC(O)C(N7CCC7)C6)nc5c3F)COC4)c12] | 522 |
| 26D | 2-Amino-7-fluoro-4-(5-fluoro-3-((R)-3-(3-(2-hydroxypropan-2-yl)azetidin-1-yl)pyrrolidin-1-yl)-7,9-dihydrofuro[3,4-f]quinazolin-6-yl)thieno[3,2-c]pyridine-3-carbonitrile | 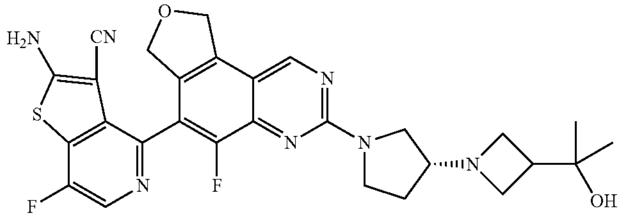 [SMILES: CC(C)(O)C1CN([C@@H]2CCN(c3ncc4c5c(c(-c6ncc(F)c7sc(N)c(C#N)c67)c(F)c4n3)COC5)C2)C1] | 564 |
| 27D | 2-Amino-4-(3-((3S,3'R)-3-(dimethylamino)-[1,3'-bipyrrolidin]-1'-yl)-5-fluoro-7,9-dihydrofuro[3,4-f]quinazolin-6-yl)-7-fluorothieno[3,2-c]pyridine-3-carbonitrile | 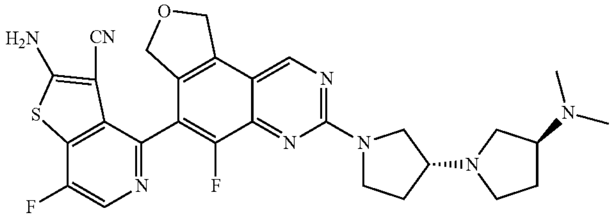 [SMILES: CN(C)[C@H]1CCN([C@@H]2CCN(c3ncc4c5c(c(-c6ncc(F)c7sc(N)c(C#N)c67)c(F)c4n3)COC5)C2)C1] | 563 |

TABLE 28-continued

| Example | Chemical Name | Structure | MS (ES) m/z (M + 1) |
|---|---|---|---|
| 28D | 2-Amino-4-(3-((3S,3'S)-3-(dimethylamino)-[1,3'-bipyrrolidin]-1'-yl)-5-fluoro-7,9-dihydrofuro[3,4-f]quinazolin-6-yl)-7-fluorothieno[3,2-c]pyridine-3-carbonitrile | 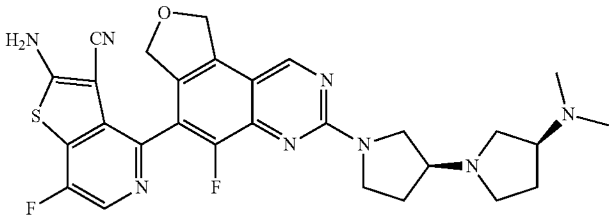 [SMILES: CN(C)[C@H]1CCN([C@H]2CCN(c3ncc4c5c(c(-c6ncc(F)c7sc(N)c(C#N)c67)c(F)c4n3)COC5)C2)C1] | 563 |
| 29D | 4-(3-((S)-[1,3'-Bipyrrolidin]-1'-yl)-5-fluoro-7,9-dihydrofuro[3,4-f]quinazolin-6-yl)-2-amino-7-fluorothieno[3,2-c]pyridine-3-carbonitrile | 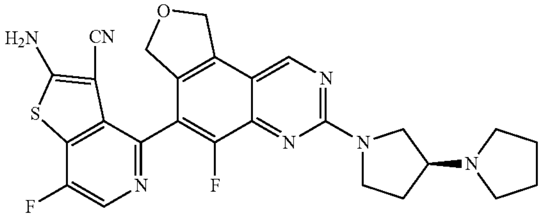 [SMILES: N#Cc1c(N)sc2c(F)cnc(-c3c4c(c5cnc(N6CC[C@H](N7CCCC7)C6)nc5c3F)COC4)c12] | 520 |
| 30D | 4-(3-((R)-[1,3'-Bipyrrolidin]-1'-yl)-5-fluoro-7,9-dihydrofuro[3,4-f]quinazolin-6-yl)-2-amino-7-fluorothieno[3,2-c]pyridine-3-carbonitrile | 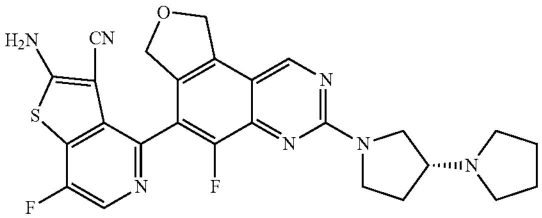 [SMILES: N#Cc1c(N)sc2c(F)cnc(-c3c4c(c5cnc(N6CC[C@@H](N7CCCC7)C6)nc5c3F)COC4)c12] | 520 |
| 31D | 2-Amino-7-fluoro-4-(5-fluoro-3-((2S,3'R)-2-(methoxymethyl)-[1,3'-bipyrrolidin]-1'-yl)-7,9-dihydrofuro[3,4-f]quinazolin-6-yl)thieno[3,2-c]pyridine-3-carbonitrile | 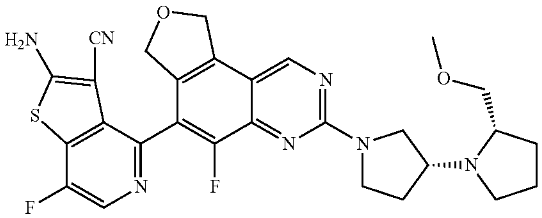 [SMILES: COC[C@@H]1CCCN1[C@@H]1CCN(c2ncc3c4c(c(-c5ncc(F)c6sc(N)c(C#N)c56)c(F)c3n2)COC4)C1] | 564 |
| 32D | 2-Amino-7-fluoro-4-(5-fluoro-3-((2S,3'S)-2-(methoxymethyl)-[1,3'-bipyrrolidin]-1'-yl)-7,9-dihydrofuro[3,4-f]quinazolin-6-yl)thieno[3,2-c]pyridine-3-carbonitrile | 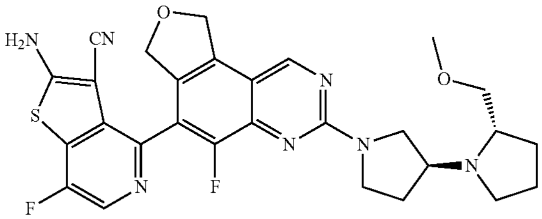 [SMILES: COC[C@@H]1CCCN1[C@H]1CCN(c2ncc3c4c(c(-c5ncc(F)c6sc(N)c(C#N)c56)c(F)c3n2)COC4)C1] | 564 |
| 33D | 2-Amino-7-fluoro-4-(5-fluoro-3-((2R,3'R)-2-(methoxymethyl)-[1,3'-bipyrrolidin]-1'-yl)-7,9-dihydrofuro[3,4-f]quinazolin-6-yl)thieno[3,2-c]pyridine-3-carbonitrile | 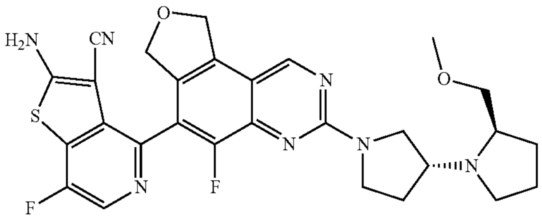 [SMILES: COC[C@H]1CCCN1[C@@H]1CCN(c2ncc3c4c(c(-c5ncc(F)c6sc(N)c(C#N)c56)c(F)c3n2)COC4)C1] | 564 |

TABLE 28-continued

| Example | Chemical Name | Structure | MS (ES) m/z (M + 1) |
| --- | --- | --- | --- |
| 34D | 2-Amino-7-fluoro-4-(5-fluoro-3-((2R,3'S)-2-(methoxymethyl)-[1,3'-bipyrrolidin]-1'-yl)-7,9-dihydrofuro[3,4-f]quinazolin-6-yl)thieno[3,2-c]pyridine-3-carbonitrile | 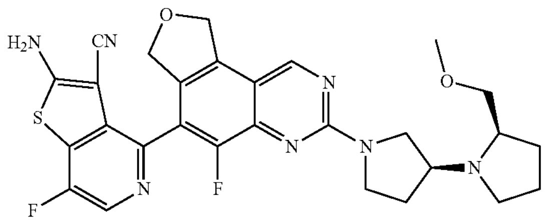 [SMILES: COC[C@H]1CCCN1[C@H]1CCN(c2ncc3c4c(c(-c5ncc(F)c6sc(N)c(C#N)c56)c(F)c3n2)COC4)C1] | 564 |
| 35D | 2-Amino-7-fluoro-4-(5-fluoro-3-((3S,3'R)-3-hydroxy-[1,3'-bipyrrolidin]-1'-yl)-7,9-dihydrofuro[3,4-f]quinazolin-6-yl)thieno[3,2-c]pyridine-3-carbonitrile | 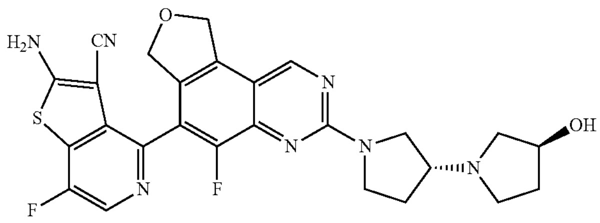 [SMILES: N#Cc1c(N)sc2c(F)cnc(-c3c4c(c5cnc(N6CC[C@@H](N7CC[C@H](O)C7)C6)nc5c3F)COC4)c12] | 536 |
| 36D | 2-Amino-7-fluoro-4-(5-fluoro-3-((3S,3'R)-3-methoxy-[1,3'-bipyrrolidin]-1'-yl)-7,9-dihydrofuro[3,4-f]quinazolin-6-yl)thieno[3,2-c]pyridine-3-carbonitrile | 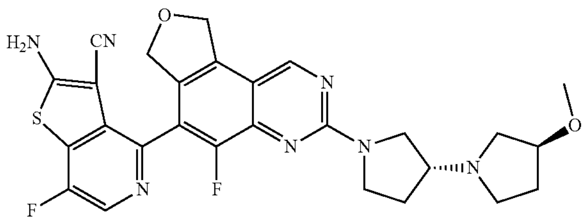 [SMILES: CO[C@H]1CCN([C@@H]2CCN(c3ncc4c5c(c(-c6ncc(F)c7sc(N)c(C#N)c67)c(F)c4n3)COC5)C2)C1] | 550 |
| 37D | 4-(3-((R)-3-(4-Acetylpiperazin-1-yl)pyrrolidin-1-yl)-5-fluoro-7,9-dihydrofuro[3,4-f]quinazolin-6-yl)-2-amino-7-fluorothieno[3,2-c]pyridine-3-carbonitrile | 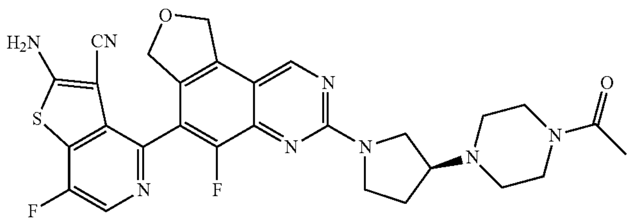 [SMILES: CC(=O)N1CCN([C@H]2CCN(c3ncc4c5c(c(-c6ncc(F)c7sc(N)c(C#N)c67)c(F)c4n3)COC5)C2)CC1] | 577 |
| 38D | 4-(3-((S)-3-(4-Acetylpiperazin-1-yl)pyrrolidin-1-yl)-5-fluoro-7,9-dihydrofuro[3,4-f]quinazolin-6-yl)-2-amino-7-fluorothieno[3,2-c]pyridine-3-carbonitrile | 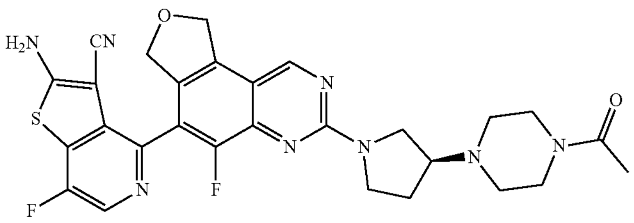 [SMILES: CC(=O)N1CCN([C@H]2CCN(c3ncc4c5c(c(-c6ncc(F)c7sc(N)c(C#N)c67)c(F)c4n3)COC5)C2)CC1] | 577 |
| 39D | 2-Amino-7-fluoro-4-(5-fluoro-3-((R)-3-(4-isopropylpiperazin-1-yl)pyrrolidin-1-yl)-7,9-dihydrofuro[3,4-f]quinazolin-6-yl)thieno[3,2-c]pyridine-3-carbonitrile | 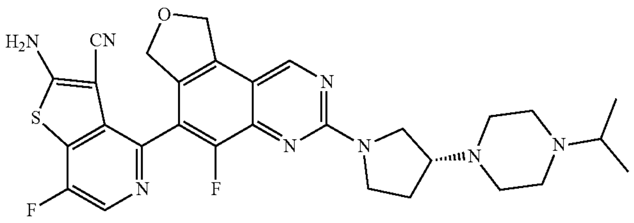 [SMILES: CC(C)N1CCN([C@@H]2CCN(c3ncc4c5c(c(-c6ncc(F)c7sc(N)c(C#N)c67)c(F)c4n3)COC5)C2)CC1] | 577 |

TABLE 28-continued

| Example | Chemical Name | Structure | MS (ES) m/z (M + 1) |
| --- | --- | --- | --- |
| 40D | 2-Amino-7-fluoro-4-(5-fluoro-3-((S)-3-(4-isopropylpiperazin-1-yl)pyrrolidin-1-yl)-7,9-dihydrofuro[3,4-f]quinazolin-6-yl)thieno[3,2-c]pyridine-3-carbonitrile | 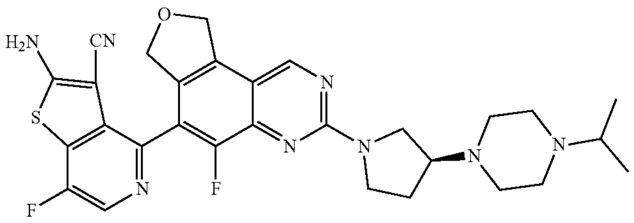 [SMILES: CC(C)N1CCN([C@H]2CCN(c3ncc4c5c(c(-c6ncc(F)c7sc(N)c(C#N)c67)c(F)c4n3)COC5)C2)CC1] | 577 |
| 41D | 2-Amino-4-(3-((S)-3-(4-ethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 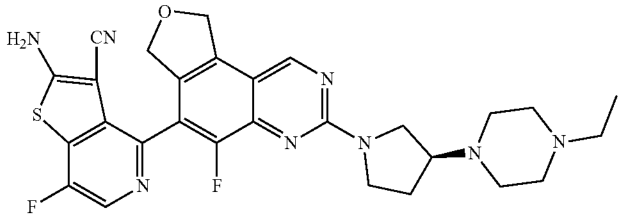 [SMILES: CCN1CCN([C@H]2CCN(c3ncc4c5c(c(-c6ncc(F)c7sc(N)c(C#N)c67)c(F)c4n3)COC5)C2)CC1] | 563 |
| 42D | 2-Amino-4-(3-((R)-3-(4-ethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 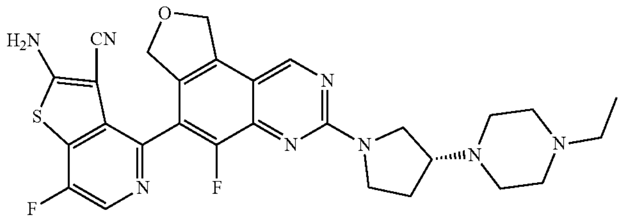 [SMILES: CCN1CCN([C@@H]2CCN(c3ncc4c5c(c(-c6ncc(F)c7sc(N)c(C#N)c67)c(F)c4n3)COC5)C2)CC1] | 563 |
| 43D | 2-Amino-7-fluoro-4-(5-fluoro-3-((R)-3-(4-(2-hydroxyethyl)piperazin-1-yl)pyrrolidin-1-yl)-7,9-dihydrofuro[3,4-f]quinazolin-6-yl)thieno[3,2-c]pyridine-3-carbonitrile | 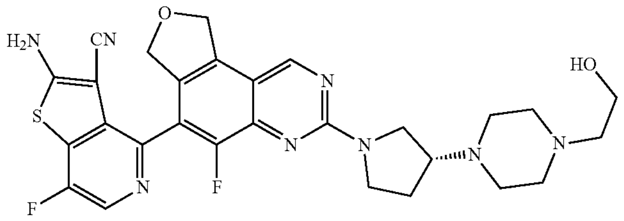 [SMILES: N#Cc1c(N)sc2c(F)cnc(-c3c4c(c5cnc(N6CC[C@@H](N7CCN(CCO)CC7)C6)nc5c3F)COC4)c12] | 579 |
| 44D | 2-Amino-7-fluoro-4-(5-fluoro-3-((R)-3-(4-(oxetan-3-yl)piperazin-1-yl)pyrrolidin-1-yl)-7,9-dihydrofuro[3,4-f]quinazolin-6-yl)thieno[3,2-c]pyridine-3-carbonitrile | 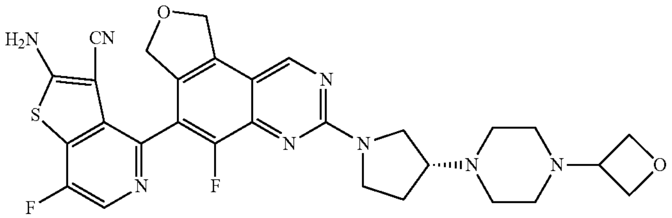 [SMILES: N#Cc1c(N)sc2c(F)cnc(-c3c4c(c5cnc(N6CC[C@@H](N7CCN(C8COC8)CC7)C6)nc5c3F)COC4)c12] | 591 |
| 45D | 2-Amino-7-fluoro-4-(5-fluoro-3-((R)-3-(4-(2,2,2-trifluoroethyl)piperazin-1-yl)pyrrolidin-1-yl)-7,9-dihydrofuro[3,4-f]quinazolin-6-yl)thieno[3,2-c]pyridine-3-carbonitrile | 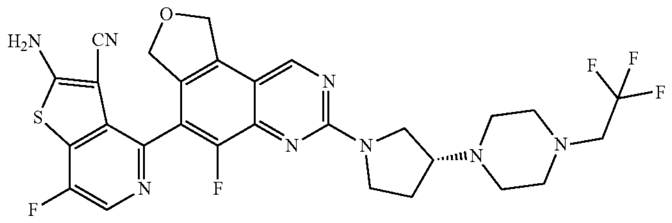 [SMILES: N#Cc1c(N)sc2c(F)cnc(-c3c4c(c5cnc(N6CC[C@@H](N7CCN(CC(F)(F)F)CC7)C6)nc5c3F)COC4)c12] | 617 |

TABLE 28-continued

| Example | Chemical Name | Structure | MS (ES) m/z (M + 1) |
|---|---|---|---|
| 46D | 2-Amino-7-fluoro-4-(5-fluoro-3-((R)-3-(piperazin-1-yl)pyrrolidin-1-yl)-7,9-dihydrofuro[3,4-f]quinazolin-6-yl)thieno[3,2-c]pyridine-3-carbonitrile | 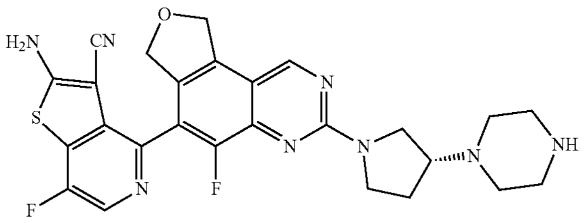 [SMILES: N#Cc1c(N)sc2c(F)cnc(-c3c4c(c5cnc(N6CC[C@@H](N7CCNCC7)C6)nc5c3F)COC4)c12] | 535 |
| 47D | 2-Amino-7-fluoro-4-(5-fluoro-3-((S)-3-(piperazin-1-yl)pyrrolidin-1-yl)-7,9-dihydrofuro[3,4-f]quinazolin-6-yl)thieno[3,2-c]pyridine-3-carbonitrile | 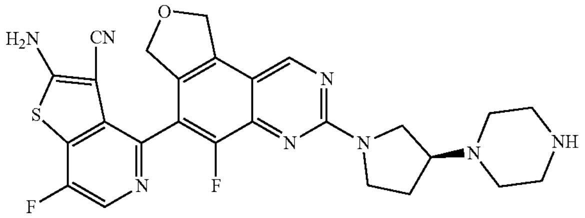 [SMILES: N#Cc1c(N)sc2c(F)cnc(-c3c4c(c5cnc(N6CC[C@H](N7CCNCC7)C6)nc5c3F)COC4)c12] | 535 |
| 48D | 2-Amino-4-(3-((R)-3-(4-cyclopropylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 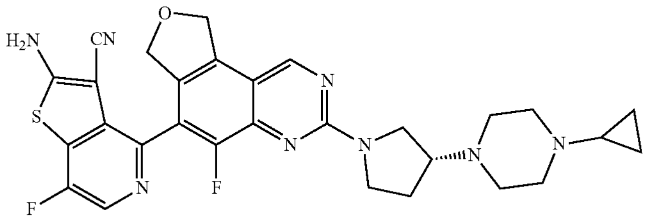 [SMILES: N#Cc1c(N)sc2c(F)cnc(-c3c4c(c5cnc(N6CC[C@@H](N7CCN(C8CC8)CC7)C6)nc5c3F)COC4)c12] | 575 |
| 49D | 2-Amino-7-fluoro-4-(5-fluoro-3-((R)-3-(4-(2-hydroxy-2-methylpropyl)piperazin-1-yl)pyrrolidin-1-yl)-7,9-dihydrofuro[3,4-f]quinazolin-6-yl)thieno[3,2-c]pyridine-3-carbonitrile formic acid | 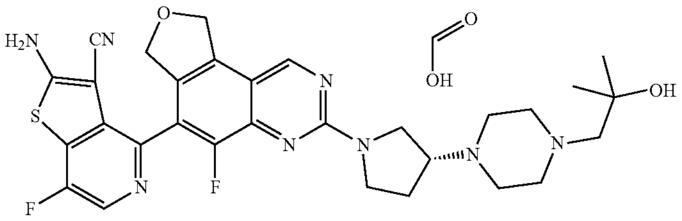 | 607 |
| 50D | 2-Amino-7-fluoro-4-(5-fluoro-3-((R)-3-(4-(2-methoxyethyl)piperazin-1-yl)pyrrolidin-1-yl)-7,9-dihydrofuro[3,4-f]quinazolin-6-yl)thieno[3,2-c]pyridine-3-carbonitrile formic acid | 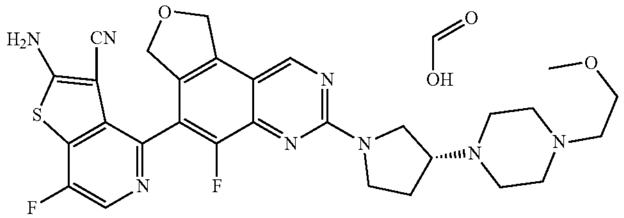 | 593 |
| 51D | 2-Amino-4-(3-((R)-3-((R)-2,4-dimethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 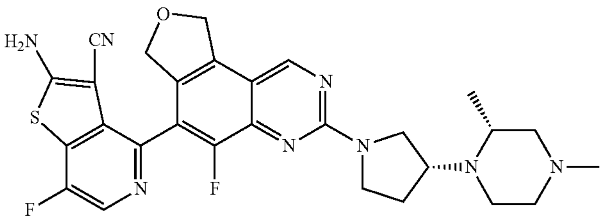 [SMILES: C[C@@H]1CN(C)CCN1[C@@H]1CCN(c2ncc3c4c(c(-c5ncc(F)c6sc(N)c(C#N)c56)c(F)c3n2)COC4)C1] | 563 |

TABLE 28-continued

| Example | Chemical Name | Structure | MS (ES) m/z (M + 1) |
|---|---|---|---|
| 52D | 2-Amino-4-(3-((R)-3-((S)-2,4-dimethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 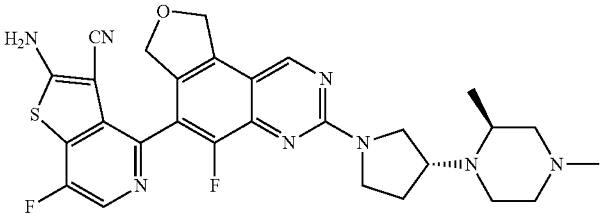 [SMILES: C[C@H]1CN(C)CCN1[C@@H]1CCN(c2ncc3c4c(c(-c5ncc(F)c6sc(N)c(C#N)c56)c(F)c3n2)COC4)C1] | 563 |
| 53D | 2-Amino-4-(3-((S)-3-((R)-2,4-dimethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 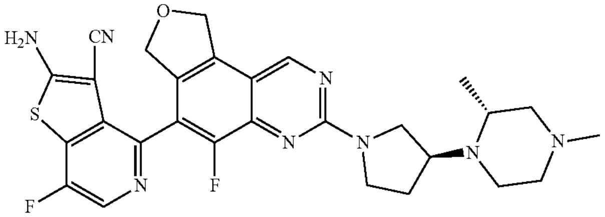 [SMILES: C[C@@H]1CN(C)CCN1[C@H]1CCN(c2ncc3c4c(c(-c5ncc(F)c6sc(N)c(C#N)c56)c(F)c3n2)COC4)C1] | 563 |
| 54D | 2-Amino-4-(3-((S)-3-((S)-2,4-dimethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile formic acid | 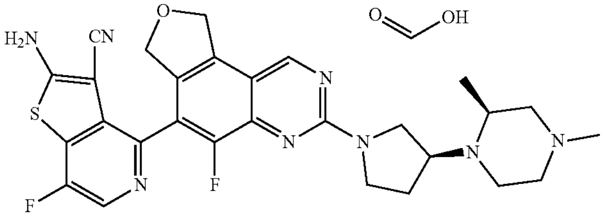 [SMILES: C[C@H]1CN(C)CCN1[C@H]1CCN(c2ncc3c4c(c(-c5ncc(F)c6sc(N)c(C#N)c56)c(F)c3n2)COC4)C1 ; O=CO] | 563 |
| 55D | 2-Amino-4-(3-((R)-3-((S)-3,4-dimethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 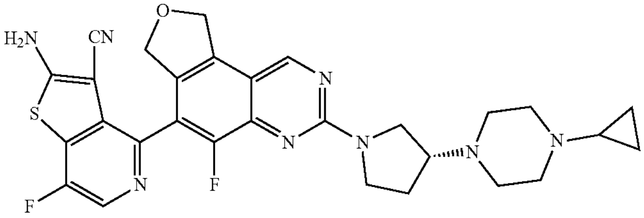 [SMILES: N#Cc1c(N)sc2c(F)cnc(-c3c4c(c5cnc(N6CC[C@@H](N7CCN(C8CC8)CC7)C6)nc5c3F)COC4)c12] | 563 |
| 56D | 2-Amino-4-(3-((R)-3-((R)-3,4-dimethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 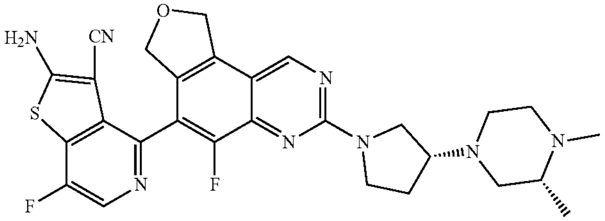 [SMILES: C[C@@H]1CN([C@@H]2CCN(c3ncc4c5c(c(-c6ncc(F)c7sc(N)c(C#N)c67)c(F)c4n3)COC5)C2)CCN1C] | 563 |
| 57D | 2-Amino-7-fluoro-4-(5-fluoro-3-((R)-3-((3R,5S)-3,4,5-trimethylpiperazin-1-yl)pyrrolidin-1-yl)-7,9-dihydrofuro[3,4-f]quinazolin-6-yl)thieno[3,2-c]pyridine-3-carbonitrile | 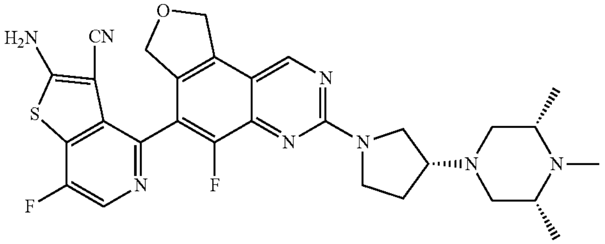 [SMILES: C[C@@H]1CN([C@@H]2CCN(c3ncc4c5c(c(-c6ncc(F)c7sc(N)c(C#N)c67)c(F)c4n3)COC5)C2)C[C@H](C)N1C] | 577 |

TABLE 28-continued

| Example | Chemical Name | Structure | MS (ES) m/z (M + 1) |
|---|---|---|---|
| 58D | 2-Amino-7-fluoro-4-(5-fluoro-3-((R)-3-((3R,5R)-3,4,5-trimethylpiperazin-1-yl)pyrrolidin-1-yl)-7,9-dihydrofuro[3,4-f]quinazolin-6-yl)thieno[3,2-c]pyridine-3-carbonitrile | 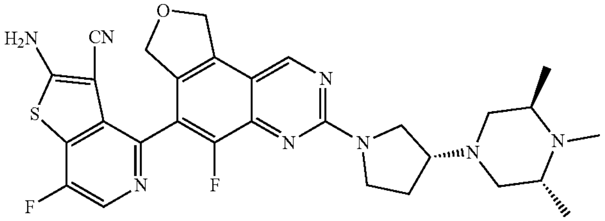 [SMILES: C[C@@H]1CN([C@@H]2CCN(c3ncc4c5c(c(-c6ncc(F)c7sc(N)c(C#N)c67)c(F)c4n3)COC5)C2)C[C@@H](C)N1C] | 577 |
| 59D | 2-Amino-7-fluoro-4-(5-fluoro-3-((R)-3-((3S,5S)-3,4,5-trimethylpiperazin-1-yl)pyrrolidin-1-yl)-7,9-dihydrofuro[3,4-f]quinazolin-6-yl)thieno[3,2-c]pyridine-3-carbonitrile | 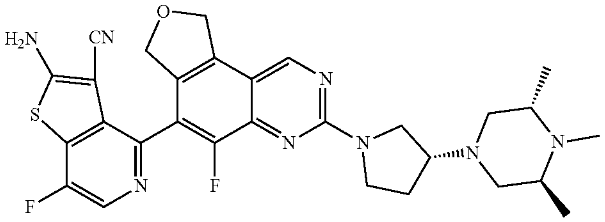 [SMILES: C[C@H]1CN([C@@H]2CCN(c3ncc4c5c(c(-c6ncc(F)c7sc(N)c(C#N)c67)c(F)c4n3)COC5)C2)C[C@H](C)N1C] | 577 |
| 60D | 2-Amino-7-fluoro-4-(5-fluoro-3-((R)-3-((S)-3-(hydroxymethyl)-4-methylpiperazin-1-yl)pyrrolidin-1-yl)-7,9-dihydrofuro[3,4-f]quinazolin-6-yl)thieno[3,2-c]pyridine-3-carbonitrile | 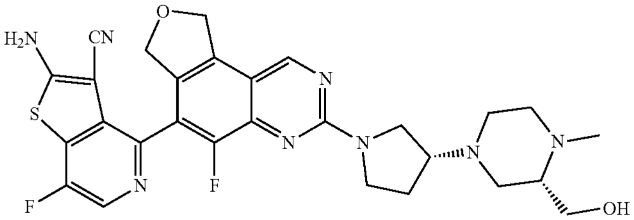 [SMILES: CN1CCN([C@@H]2CCN(c3ncc4c5c(c(-c6ncc(F)c7sc(N)c(C#N)c67)c(F)c4n3)COC5)C2)C[C@H]1CO] | 579 |
| 61D | 2-Amino-7-fluoro-4-(5-fluoro-3-((R)-3-((R)-3-(hydroxymethyl)-4-methylpiperazin-1-yl)pyrrolidin-1-yl)-7,9-dihydrofuro[3,4-f]quinazolin-6-yl)thieno[3,2-c]pyridine-3-carbonitrile | 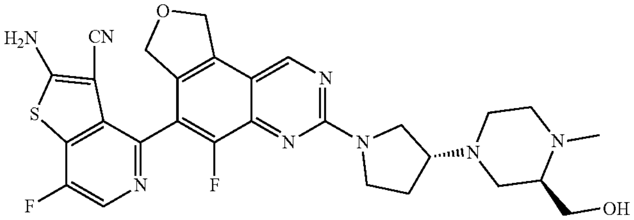 [SMILES: CN1CCN([C@@H]2CCN(c3ncc4c5c(c(-c6ncc(F)c7sc(N)c(C#N)c67)c(F)c4n3)COC5)C2)C[C@@H]1CO] | 579 |
| 62D | 2-Amino-7-fluoro-4-(5-fluoro-3-((R)-3-(2,2,4-trimethylpiperazin-1-yl)pyrrolidin-1-yl)-7,9-dihydrofuro[3,4-f]quinazolin-6-yl)thieno[3,2-c]pyridine-3-carbonitrile | 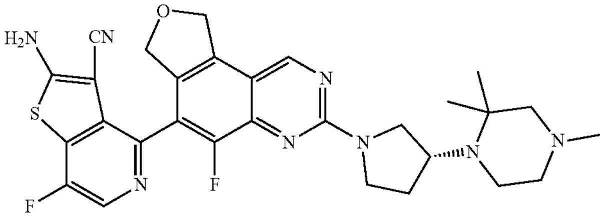 [SMILES: CN1CCN([C@@H]2CCN(c3ncc4c5c(c(-c6ncc(F)c7sc(N)c(C#N)c67)c(F)c4n3)COC5)C2)C(C)(C)C1] | 577 |
| 63D | 2-Amino-7-fluoro-4-(5-fluoro-3-((R)-3-(3,3,4-trimethylpiperazin-1-yl)pyrrolidin-1-yl)-7,9-dihydrofuro[3,4-f]quinazolin-6-yl)thieno[3,2-c]pyridine-3-carbonitrile | 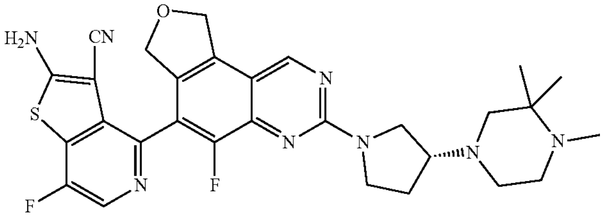 [SMILES: CN1CCN([C@@H]2CCN(c3ncc4c5c(c(-c6ncc(F)c7sc(N)c(C#N)c67)c(F)c4n3)COC5)C2)CC1(C)C] | 577 |

TABLE 28-continued

| Example | Chemical Name | Structure | MS (ES) m/z (M + 1) |
| --- | --- | --- | --- |
| 64D | 2-Amino-7-fluoro-4-(5-fluoro-3-((R)-3-((S)-3-(methoxymethyl)-4-methylpiperazin-1-yl)pyrrolidin-1-yl)-7,9-dihydrofuro[3,4-f]quinazolin-6-yl)thieno[3,2-c]pyridine-3-carbonitrile | 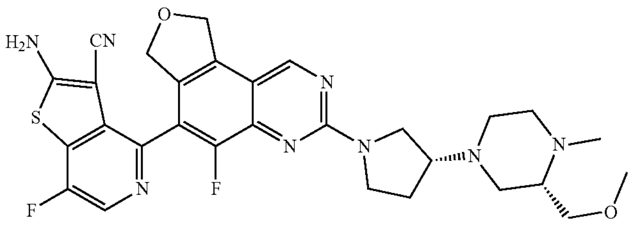 [SMILES: COC[C@@H]1CN([C@@H]2CCN(c3ncc4c5c(c(-c6ncc(F)c7sc(N)c(C#N)c67)c(F)c4n3)COC5)C2)CCN1C] | 593 |
| 65D | 2-Amino-7-fluoro-4-(5-fluoro-3-((R)-3-((R)-3-(methoxymethyl)-4-methylpiperazin-1-yl)pyrrolidin-1-yl)-7,9-dihydrofuro[3,4-f]quinazolin-6-yl)thieno[3,2-c]pyridine-3-carbonitrile | 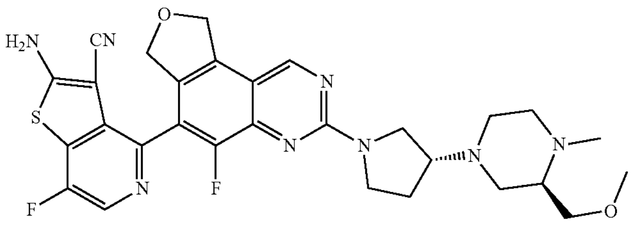 [SMILES: COC[C@H]1CN([C@@H]2CCN(c3ncc4c5c(c(-c6ncc(F)c7sc(N)c(C#N)c67)c(F)c4n3)COC5)C2)CCN1C] | 593 |
| 66D | 2-Amino-7-fluoro-4-(5-fluoro-3-((R)-3-((S)-2-(hydroxymethyl)-4-methylpiperazin-1-yl)pyrrolidin-1-yl)-7,9-dihydrofuro[3,4-f]quinazolin-6-yl)thieno[3,2-c]pyridine-3-carbonitrile | 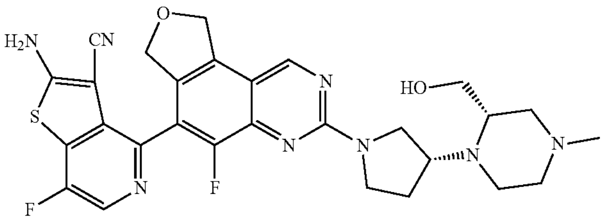 [SMILES: CN1CCN([C@@H]2CCN(c3ncc4c5c(c(-c6ncc(F)c7sc(N)c(C#N)c67)c(F)c4n3)COC5)C2)[C@H](CO)C1] | 579 |
| 67D | 2-Amino-7-fluoro-4-(5-fluoro-3-((R)-3-((R)-2-(hydroxymethyl)-4-methylpiperazin-1-yl)pyrrolidin-1-yl)-7,9-dihydrofuro[3,4-f]quinazolin-6-yl)thieno[3,2-c]pyridine-3-carbonitrile | 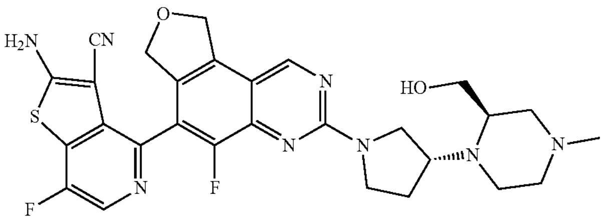 [SMILES: CN1CCN([C@@H]2CCN(c3ncc4c5c(c(-c6ncc(F)c7sc(N)c(C#N)c67)c(F)c4n3)COC5)C2)[C@@H](CO)C1] | 579 |
| 68D | 2-Amino-7-fluoro-4-(5-fluoro-3-(3-(4-methyl-4,7-diazaspiro[2.5]octan-7-yl)pyrrolidin-1-yl)-7,9-dihydrofuro[3,4-f]quinazolin-6-yl)thieno[3,2-c]pyridine-3-carbonitrile | 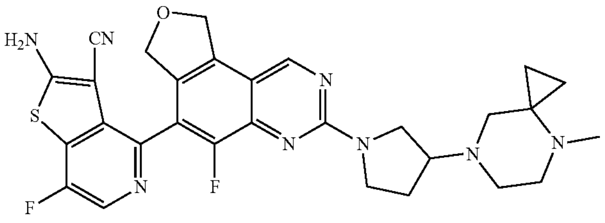 [SMILES: CN1CCN(C2CCN(c3ncc4c5c(c(-c6ncc(F)c7sc(N)c(C#N)c67)c(F)c4n3)COC5)C2)CC12CC2] | 575 |
| 69D | 4-(3-(3-(4,7-Diazaspiro[2.5]octan-7-yl)pyrrolidin-1-yl)-5-fluoro-7,9-dihydrofuro[3,4-f]quinazolin-6-yl)-2-amino-7-fluorothieno[3,2-c]pyridine-3-carbonitrile | 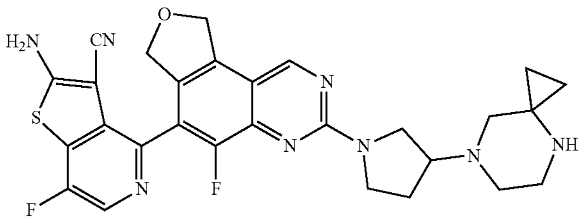 [SMILES: N#Cc1c(N)sc2c(F)cnc(-c3c4c(c5cnc(N6CCC(N7CCNC8(CC8)C7)C6)nc5c3F)COC4)c12] | 561 |

TABLE 28-continued

| Example | Chemical Name | Structure | MS (ES) m/z (M + 1) |
|---|---|---|---|
| 70D | 2-Amino-4-(3-(3-(3,3-dimethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 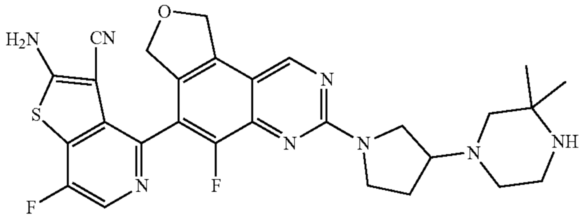 [SMILES: CC1(C)CN(C2CCN(c3ncc4c5c(c(-c6ncc(F)c7sc(N)c(C#N)c67)c(F)c4n3)COC5)C2)CCN1] | 563 |
| 71D | 2-Amino-4-(3-((R)-3-((3S,5S)-3,5-dimethylpiperazin-1-yl)pyrrolidin-1-yl)-5-fluoro-7,9-dihydrofuro[3,4-f]quinazolin-6-yl)-7-fluorothieno[3,2-c]pyridine-3-carbonitrile | 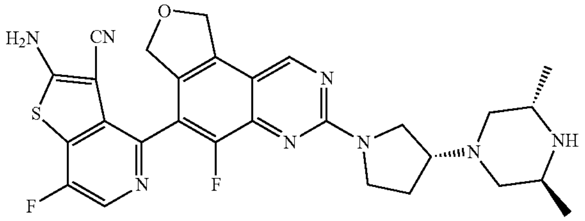 [SMILES: C[C@H]1CN([C@@H]2CCN(c3ncc4c5c(c(-c6ncc(F)c7sc(N)c(C#N)c67)c(F)c4n3)COC5)C2)C[C@H](C)N1] | 563 |
| 72D | 2-Amino-7-fluoro-4-(5-fluoro-3-((S)-3-((2S,5R)-2,4,5-trimethylpiperazin-1-yl)pyrrolidin-1-yl)-7,9-dihydrofuro[3,4-f]quinazolin-6-yl)thieno[3,2-c]pyridine-3-carbonitrile | 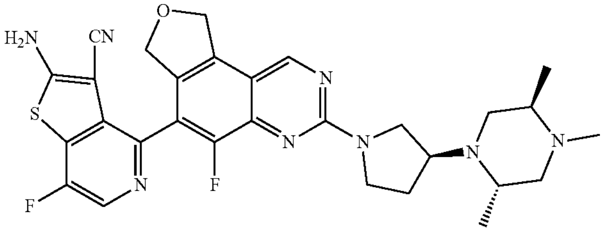 [SMILES: C[C@@H]1CN([C@H]2CCN(c3ncc4c5c(c(-c6ncc(F)c7sc(N)c(C#N)c67)c(F)c4n3)COC5)C2)[C@@H](C)CN1C] | 577 |
| 73D | 2-Amino-7-fluoro-4-(5-fluoro-3-((R)-3-((1S,4S)-5-methyl-2,5-diazabicyclo[2.2.1]heptan-2-yl)pyrrolidin-1-yl)-7,9-dihydrofuro[3,4-f]quinazolin-6-yl)thieno[3,2-c]pyridine-3-carbonitrile | 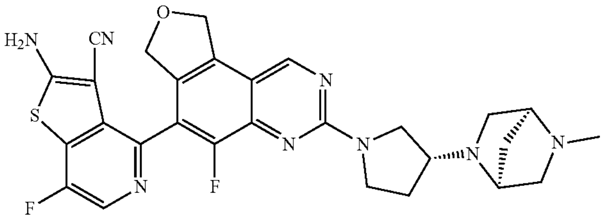 [SMILES: CN1C[C@@H]2C[C@H]1CN2[C@@H]1CCN(c2ncc3c4c(c(-c5ncc(F)c6sc(N)c(C#N)c56)c(F)c3n2)COC4)C1] | 561 |
| 74D | 2-Amino-7-fluoro-4-(5-fluoro-3-((R)-3-((1R,4R)-5-methyl-2,5-diazabicyclo[2.2.1]heptan-2-yl)pyrrolidin-1-yl)-7,9-dihydrofuro[3,4-f]quinazolin-6-yl)thieno[3,2-c]pyridine-3-carbonitrile formic acid | 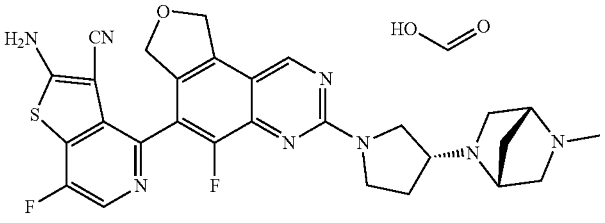 [SMILES: CN1C[C@H]2C[C@@H]1CN2[C@@H]1CCN(c2ncc3c4c(c(-c5ncc(F)c6sc(N)c(C#N)c56)c(F)c3n2)COC4)C1 ; O=CO] | 561 |
| 75D | 2-Amino-7-fluoro-4-(5-fluoro-3-((3R)-3-(3-methyl-3,8-diazabicyclo[3.2.1]octan-8-yl)pyrrolidin-1-yl)-7,9-dihydrofuro[3,4-f]quinazolin-6-yl)thieno[3,2-c]pyridine-3-carbonitrile | 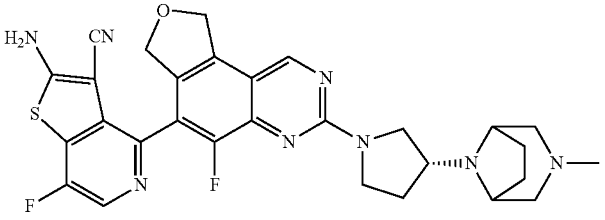 [SMILES: CN1CC2CCC(C1)N2[C@@H]1CCN(c2ncc3c4c(c(-c5ncc(F)c6sc(N)c(C#N)c56)c(F)c3n2)COC4)C1] | 575 |

TABLE 28-continued

| Example | Chemical Name | Structure | MS (ES) m/z (M + 1) |
|---|---|---|---|
| 76D | 2-Amino-7-fluoro-4-(5-fluoro-3-((3R)-3-(8-methyl-3,8-diazabicyclo[3.2.1]octan-3-yl)pyrrolidin-1-yl)-7,9-dihydrofuro[3,4-f]quinazolin-6-yl)thieno[3,2-c]pyridine-3-carbonitrile | 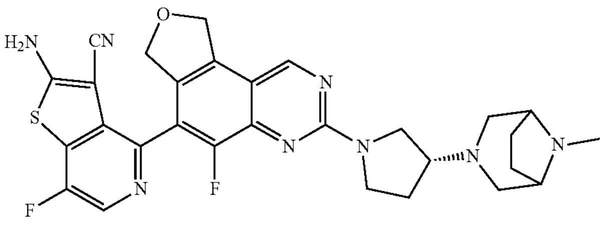 [SMILES: CN1C2CCC1CN([C@@H]1CCN(c3ncc4c5c(c(-c6ncc(F)c7sc(N)c(C#N)c67)c(F)c4n3)COC5)C1)C2] | 575 |
| 77D | 2-Amino-7-fluoro-4-(5-fluoro-3-((3R)-3-(6-methyl-3,6-diazabicyclo[3.1.1]heptan-3-yl)pyrrolidin-1-yl)-7,9-dihydrofuro[3,4-f]quinazolin-6-yl)thieno[3,2-c]pyridine-3-carbonitrile | 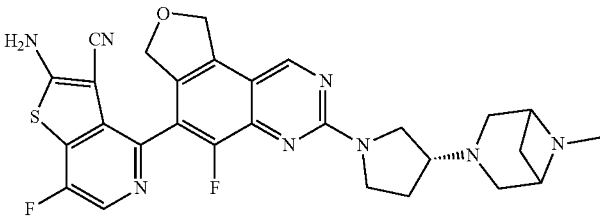 [SMILES: CN1C2CC1CN([C@@H]1CCN(c3ncc4c5c(c(-c6ncc(F)c7sc(N)c(C#N)c67)c(F)c4n3)COC5)C1)C2] | 561 |
| 78D | 2-Amino-7-fluoro-4-(5-fluoro-3-((3R)-3-(3-methyl-3,6-diazabicyclo[3.1.1]heptan-6-yl)pyrrolidin-1-yl)-7,9-dihydrofuro[3,4-f]quinazolin-6-yl)thieno[3,2-c]pyridine-3-carbonitrile | 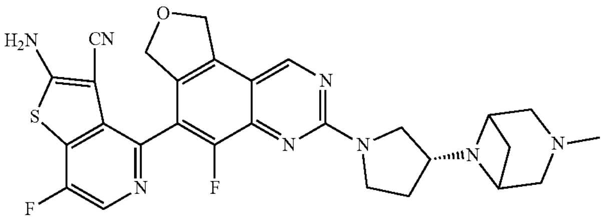 [SMILES: CN1CC2CC(C1)N2[C@@H]1CCN(c2ncc3c4c(c(-c5ncc(F)c6sc(N)c(C#N)c56)c(F)c3n2)COC4)C1] | 561 |
| 79D | 2-Amino-7-fluoro-4-(5-fluoro-3-((2S,3S)-2-methyl-3-(4-methylpiperazin-1-yl)pyrrolidin-1-yl)-7,9-dihydrofuro[3,4-f]quinazolin-6-yl)thieno[3,2-c]pyridine-3-carbonitrile | 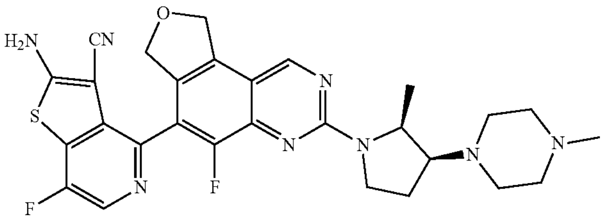 [SMILES: C[C@H]1[C@@H](N2CCN(C)CC2)CCN1c1ncc2c3c(c(-c4ncc(F)c5sc(N)c(C#N)c45)c(F)c2n1)COC3] | 563 |
| 80D | 2-Amino-7-fluoro-4-(5-fluoro-3-((2R,3R)-2-methyl-3-(4-methylpiperazin-1-yl)pyrrolidin-1-yl)-7,9-dihydrofuro[3,4-f]quinazolin-6-yl)thieno[3,2-c]pyridine-3-carbonitrile | 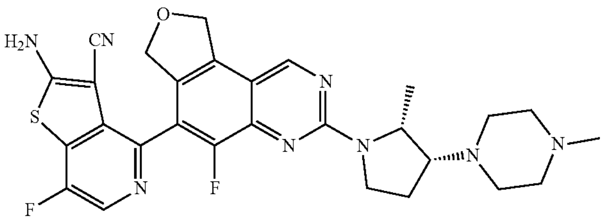 [SMILES: C[C@@H]1[C@H](N2CCN(C)CC2)CCN1c1ncc2c3c(c(-c4ncc(F)c5sc(N)c(C#N)c45)c(F)c2n1)COC3] | 563 |
| 81D | 2-Amino-7-fluoro-4-(5-fluoro-3-((2S,3R)-2-methyl-3-(4-methylpiperazin-1-yl)pyrrolidin-1-yl)-7,9-dihydrofuro[3,4-f]quinazolin-6-yl)thieno[3,2-c]pyridine-3-carbonitrile | 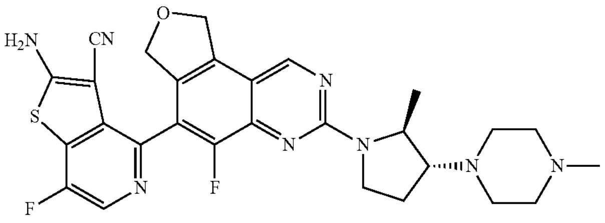 [SMILES: C[C@H]1[C@H](N2CCN(C)CC2)CCN1c1ncc2c3c(c(-c4ncc(F)c5sc(N)c(C#N)c45)c(F)c2n1)COC3] | 563 |

TABLE 28-continued

| Example | Chemical Name | Structure | MS (ES) m/z (M + 1) |
|---|---|---|---|
| 82D | 2-Amino-7-fluoro-4-(5-fluoro-3-((2R,3S)-2-methyl-3-(4-methylpiperazin-1-yl)pyrrolidin-1-yl)-7,9-dihydrofuro[3,4-f]quinazolin-6-yl)thieno[3,2-c]pyridine-3-carbonitrile | 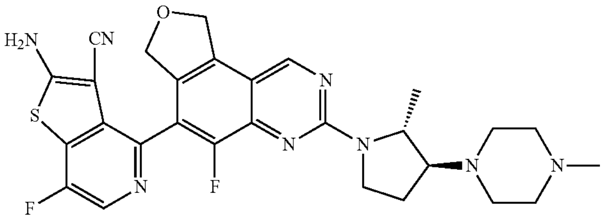 [SMILES: C[C@@H]1[C@@H](N2CCN(C)CC2)CCN1c1ncc2c3c(c(-c4ncc(F)c5sc(N)c(C#N)c45)c(F)c2n1)COC3] | 563 |
| 83D | 2-Amino-4-(3-((2S,3S)-3-(4-ethylpiperazin-1-yl)-2-methylpyrrolidin-1-yl)-5-fluoro-7,9-dihydrofuro[3,4-f]quinazolin-6-yl)-7-fluorothieno[3,2-c]pyridine-3-carbonitrile | 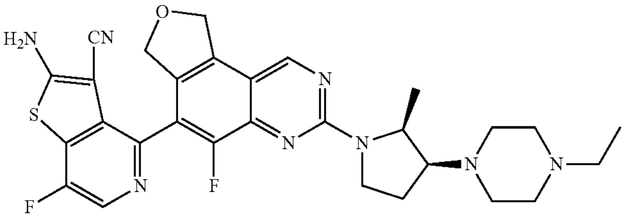 [SMILES: CCN1CCN([C@H]2CCN(c3ncc4c5c(c(-c6ncc(F)c7sc(N)c(C#N)c67)c(F)c4n3)COC5)[C@H]2C)CC1] | 577 |
| 84D | 2-Amino-7-fluoro-4-(5-fluoro-3-((2S,3S)-3-(4-isopropylpiperazin-1-yl)-2-methylpyrrolidin-1-yl)-7,9-dihydrofuro[3,4-f]quinazolin-6-yl)thieno[3,2-c]pyridine-3-carbonitrile | 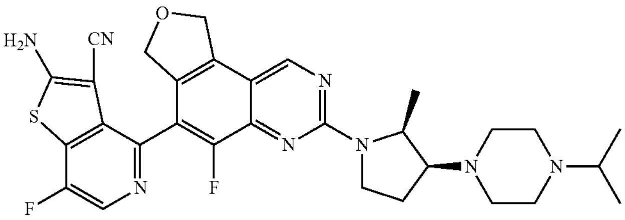 [SMILES: CC(C)N1CCN([C@H]2CCN(c3ncc4c5c(c(-c6ncc(F)c7sc(N)c(C#N)c67)c(F)c4n3)COC5)[C@H]2C)CC1] | 591 |
| 85D | 2-Amino-7-fluoro-4-(5-fluoro-3-((2S,3S)-3-(4-(2-methoxyethyl)piperazin-1-yl)-2-methylpyrrolidin-1-yl)-7,9-dihydrofuro[3,4-f]quinazolin-6-yl)thieno[3,2-c]pyridine-3-carbonitrile | 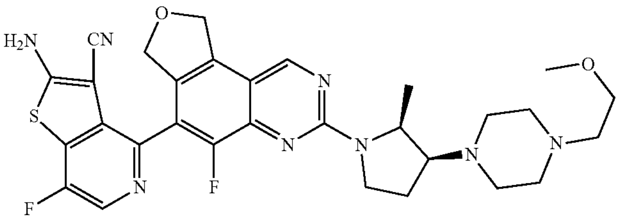 [SMILES: COCCN1CCN([C@H]2CCN(c3ncc4c5c(c(-c6ncc(F)c7sc(N)c(C#N)c67)c(F)c4n3)COC5)[C@H]2C)CC1] | 607 |
| 86D | 2-Amino-7-fluoro-4-(5-fluoro-3-((2S,3S)-3-(4-((S)-2-hydroxypropyl)piperazin-1-yl)-2-methylpyrrolidin-1-yl)-7,9-dihydrofuro[3,4-f]quinazolin-6-yl)thieno[3,2-c]pyridine-3-carbonitrile | 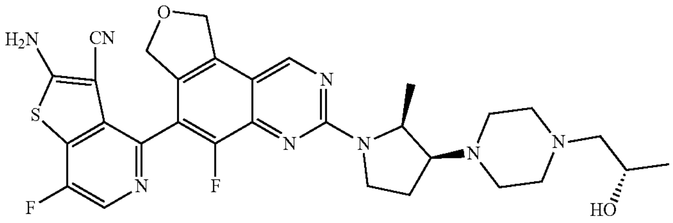 [SMILES: C[C@H](O)CN1CCN([C@H]2CCN(c3ncc4c5c(c(-c6ncc(F)c7sc(N)c(C#N)c67)c(F)c4n3)COC5)[C@H]2C)CC1] | 607 |
| 87D | 2-Amino-7-fluoro-4-(5-fluoro-3-((2S,3S)-3-(4-((R)-2-hydroxypropyl)piperazin-1-yl)-2-methylpyrrolidin-1-yl)-7,9-dihydrofuro[3,4-f]quinazolin-6-yl)thieno[3,2-c]pyridine-3-carbonitrile | 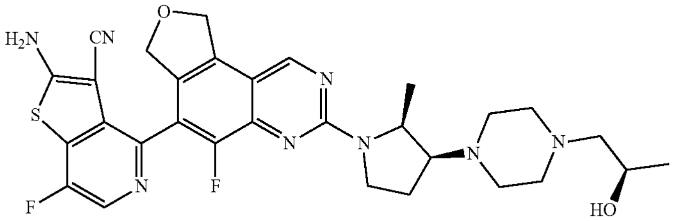 [SMILES: C[C@@H](O)CN1CCN([C@H]2CCN(c3ncc4c5c(c(-c6ncc(F)c7sc(N)c(C#N)c67)c(F)c4n3)COC5)[C@H]2C)CC1] | 607 |

TABLE 28-continued

| Example | Chemical Name | Structure | MS (ES) m/z (M + 1) |
|---|---|---|---|
| 88D | 2-Amino-7-fluoro-4-(5-fluoro-3-((2S,3S)-3-(4-(2-fluoroethyl)piperazin-1-yl)-2-methylpyrrolidin-1-yl)-7,9-dihydrofuro[3,4-f]quinazolin-6-yl)thieno[3,2-c]pyridine-3-carbonitrile | 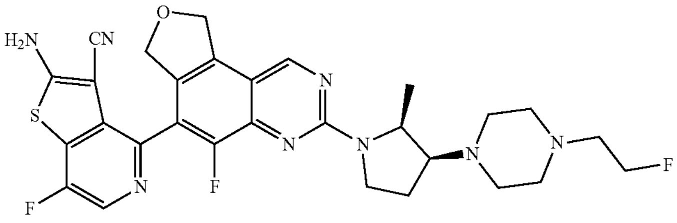 [SMILES: C[C@H]1[C@@H](N2CCN(CCF)CC2)CCN1c1ncc2c3c(c(-c4ncc(F)c5sc(N)c(C#N)c45)c(F)c2n1)COC3] | 595 |
| 89D | 2-Amino-4-(3-((2S,3S)-3-((S)-3,4-dimethylpiperazin-1-yl)-2-methylpyrrolidin-1-yl)-5-fluoro-7,9-dihydrofuro[3,4-f]quinazolin-6-yl)-7-fluorothieno[3,2-c]pyridine-3-carbonitrile | 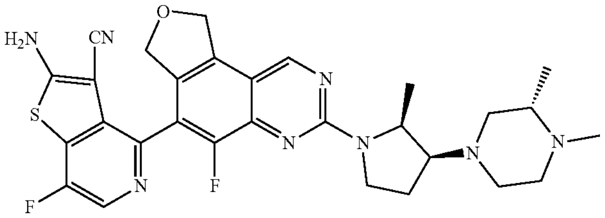 [SMILES: C[C@H]1CN([C@H]2CCN(c3ncc4c5c(c(-c6ncc(F)c7sc(N)c(C#N)c67)c(F)c4n3)COC5)[C@H]2C)CCN1C] | 577 |
| 90D | 2-Amino-4-(3-((2S,3S)-3-((S)-2,4-dimethylpiperazin-1-yl)-2-methylpyrrolidin-1-yl)-5-fluoro-7,9-dihydrofuro[3,4-f]quinazolin-6-yl)-7-fluorothieno[3,2-c]pyridine-3-carbonitrile | 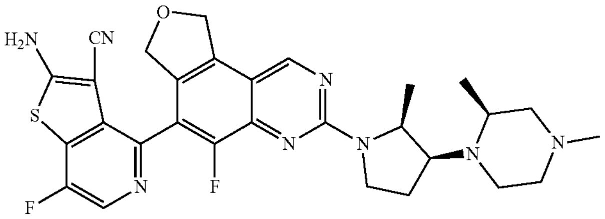 [SMILES: C[C@H]1[C@@H](N2CCN(C)C[C@@H]2C)CCN1c1ncc2c3c(c(-c4ncc(F)c5sc(N)c(C#N)c45)c(F)c2n1)COC3] | 577 |
| 91D | 2-Amino-7-fluoro-4-(5-fluoro-3-((2S,3S)-3-((S)-2-(hydroxymethyl)-4-methylpiperazin-1-yl)-2-methylpyrrolidin-1-yl)-7,9-dihydrofuro[3,4-f]quinazolin-6-yl)thieno[3,2-c]pyridine-3-carbonitrile | 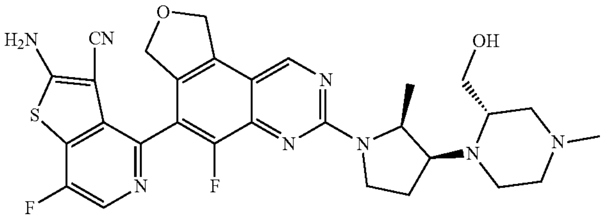 [SMILES: C[C@H]1[C@@H](N2CCN(C)C[C@H]2CO)CCN1c1ncc2c3c(c(-c4ncc(F)c5sc(N)c(C#N)c45)c(F)c2n1)COC3] | 593 |
| 92D | 2-Amino-7-fluoro-4-(5-fluoro-3-((2S,3S)-3-((S)-2-(fluoromethyl)-4-methylpiperazin-1-yl)-2-methylpyrrolidin-1-yl)-7,9-dihydrofuro[3,4-f]quinazolin-6-yl)thieno[3,2-c]pyridine-3-carbonitrile | 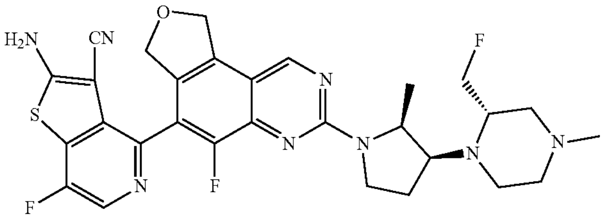 [SMILES: C[C@H]1[C@@H](N2CCN(C)C[C@H]2CF)CCN1c1ncc2c3c(c(-c4ncc(F)c5sc(N)c(C#N)c45)c(F)c2n1)COC3] | 595 |
| 93D | 2-Amino-7-fluoro-4-(5-fluoro-3-((2S,3S)-2-methyl-3-(8-methyl-3,8-diazabicyclo[3.2.1 ]octan-3-yl)pyrrolidin-1-yl)-7,9-dihydrofuro[3,4-f]quinazolin-6-yl)thieno[3,2-c]pyridine-3-carbonitrile | 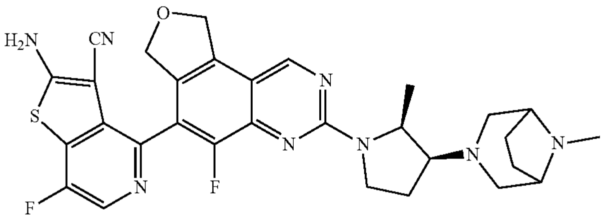 [SMILES: C[C@H]1[C@@H](N2CC3CCC(C2)N3C)CCN1c1ncc2c3c(c(-c4ncc(F)c5sc(N)c(C#N)c45)c(F)c2n1)COC3] | 589 |

TABLE 28-continued

| Example | Chemical Name | Structure | MS (ES) m/z (M + 1) |
|---|---|---|---|
| 94D | 2-Amino-7-fluoro-4-(5-fluoro-3-((2S,4S)-2-methyl-4-(4-methylpiperazin-1-yl)pyrrolidin-1-yl)-7,9-dihydrofuro[3,4-f]quinazolin-6-yl)thieno[3,2-c]pyridine-3-carbonitrile | 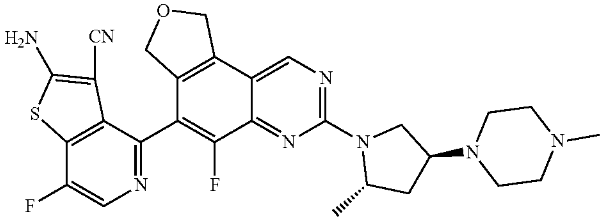 [SMILES: C[C@H]1C[C@H](N2CCN(C)CC2)CN1c1ncc2c3c(c(-c4ncc(F)c5sc(N)c(C#N)c45)c(F)c2n1)COC3] | 563 |
| 95D | 2-Amino-7-fluoro-4-(5-fluoro-3-((2S,4R)-2-methyl-4-(4-methylpiperazin-1-yl)pyrrolidin-1-yl)-7,9-dihydrofuro[3,4-f]quinazolin-6-yl)thieno[3,2-c]pyridine-3-carbonitrile | 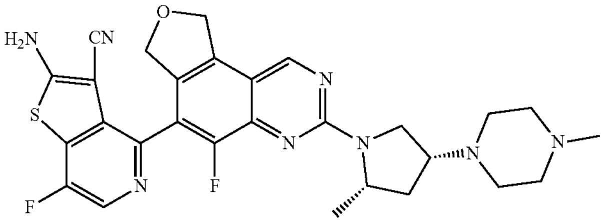 [SMILES: C[C@H]1C[C@@H](N2CCN(C)CC2)CN1c1ncc2c3c(c(-c4ncc(F)c5sc(N)c(C#N)c45)c(F)c2n1)COC3] | 563 |
| 96D [78] | 2-Amino-7-fluoro-4-(5-fluoro-3-(3-hydroxy-4-(4-methylpiperazin-1-yl)pyrrolidin-1-yl)-7,9-dihydrofuro[3,4-f]quinazolin-6-yl)thieno[3,2-c]pyridine-3-carbonitrile | 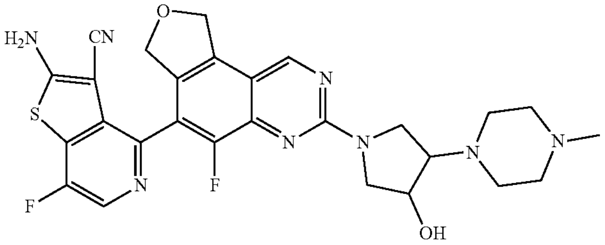 [SMILES: CN1CCN(C2CN(c3ncc4c5c(c(-c6ncc(F)c7sc(N)c(C#N)c67)c(F)c4n3)COC5)CC2O)CC1] | 565 |
| 97D | 2-Amino-7-fluoro-4-(5-fluoro-3-((3R,4R)-3-hydroxy-4-(4-methylpiperazin-1-yl)pyrrolidin-1-yl)-7,9-dihydrofuro[3,4-f]quinazolin-6-yl)thieno[3,2-c]pyridine-3-carbonitrile | 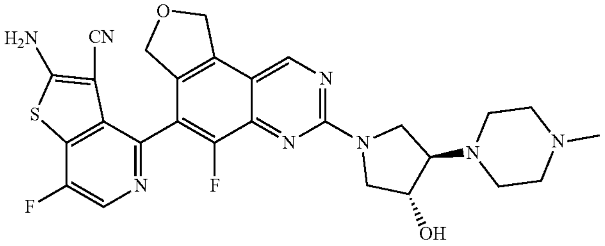 [SMILES: CN1CCN([C@@H]2CN(c3ncc4c5c(c(-c6ncc(F)c7sc(N)c(C#N)c67)c(F)c4n3)COC5)C[C@H]2O)CC1] | 565 |
| 98D | 2-Amino-7-fluoro-4-(5-fluoro-3-((3S,4S)-3-hydroxy-4-(4-methylpiperazin-1-yl)pyrrolidin-1-yl)-7,9-dihydrofuro[3,4-f]quinazolin-6-yl)thieno[3,2-c]pyridine-3-carbonitrile | 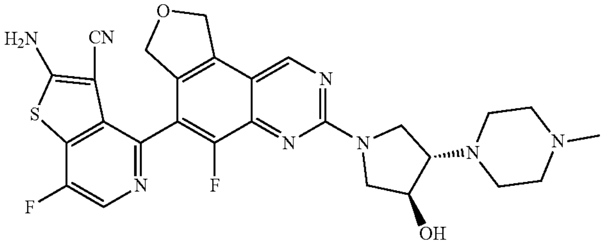 [SMILES: CN1CCN([C@H]2CN(c3ncc4c5c(c(-c6ncc(F)c7sc(N)c(C#N)c67)c(F)c4n3)COC5)C[C@@H]2O)CC1] | 565 |
| 99D [79] | 2-Amino-4-(3-(3-((S)-2,4-dimethylpiperazin-1-yl)-4-hydroxypyrrolidin-1-yl)-5-fluoro-7,9-dihydrofuro[3,4-f]quinazolin-6-yl)-7-fluorothieno[3,2-c]pyridine-3-carbonitrile. Isomer 2 | 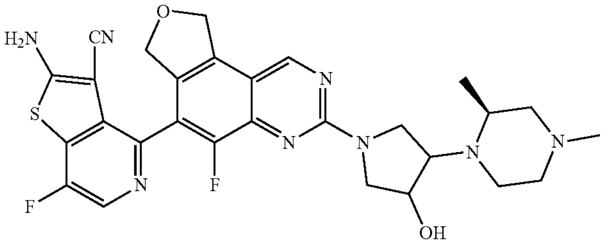 [SMILES: C[C@H]1CN(C)CCN1C1CN(c2ncc3c4c(c(-c5ncc(F)c6sc(N)c(C#N)c56)c(F)c3n2)COC4)CC1O] | 579 |

TABLE 28-continued

| Example | Chemical Name | Structure | MS (ES) m/z (M + 1) |
|---|---|---|---|
| 100D [79] | 2-Amino-4-(3-(3-((S)-2,4-dimethylpiperazin-1-yl)-4-hydroxypyrrolidin-1-yl)-5-fluoro-7,9-dihydrofuro[3,4-f]quinazolin-6-yl)-7-fluorothieno[3,2-c]pyridine-3-carbonitrile. Isomer 1 | 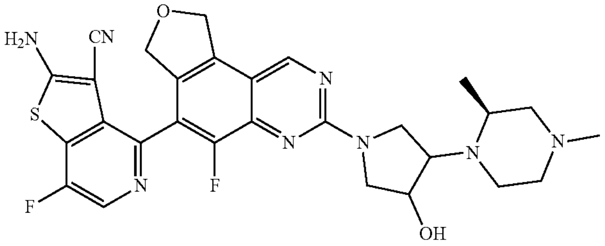 [SMILES: C[C@H]1CN(C)CCN1C1CN(c2ncc3c4c(c(-c5ncc(F)c6sc(N)c(C#N)c56)c(F)c3n2)COC4)CC1O] | 579 |
| 101D [80] | 2-Amino-4-(3-(3-((S)-3,4-dimethylpiperazin-1-yl)-4-hydroxypyrrolidin-1-yl)-5-fluoro-7,9-dihydrofuro[3,4-f]quinazolin-6-yl)-7-fluorothieno[3,2-c]pyridine-3-carbonitrile | 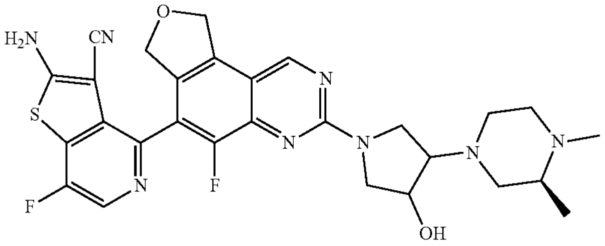 [SMILES: C[C@H]1CN(C2CN(c3ncc4c5c(c(-c6ncc(F)c7sc(N)c(C#N)c67)c(F)c4n3)COC5)CC2O)CCN1C] | 579 |
| 102D [81] | 2-Amino-7-fluoro-4-(5-fluoro-3-(3-hydroxy-4-(3-methyl-3,8-diazabicyclo[3.2.1]octan-8-yl)pyrrolidin-1-yl)-7,9-dihydrofuro[3,4-f]quinazolin-6-yl)thieno[3,2-c]pyridine-3-carbonitrile, Isomer 1 | 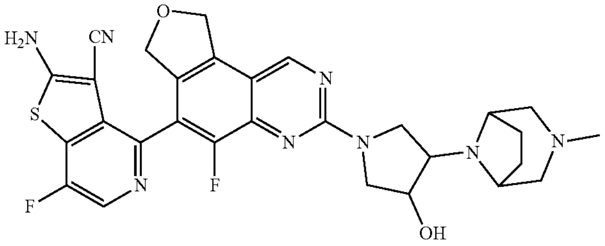 [SMILES: CN1CC2CCC(C1)N2C1CN(c2ncc3c4c(c(-c5ncc(F)c6sc(N)c(C#N)c56)c(F)c3n2)COC4)CC1O] | 591 |
| 103D [81] | 2-Amino-7-fluoro-4-(5-fluoro-3-(3-hydroxy-4-(3-methyl-3,8-diazabicyclo[3.2.1]octan-8-yl)pyrrolidin-1-yl)-7,9-dihydrofuro[3,4-f]quinazolin-6-yl)thieno[3,2-c]pyridine-3-carbonitrile, Isomer 2 | 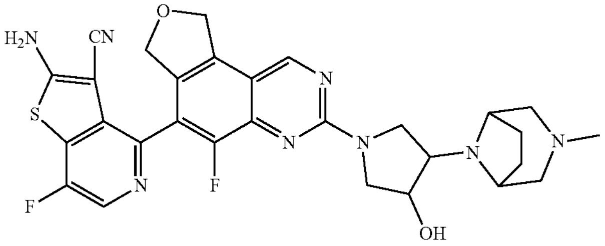 [SMILES: CN1CC2CCC(C1)N2C1CN(c2ncc3c4c(c(-c5ncc(F)c6sc(N)c(C#N)c56)c(F)c3n2)COC4)CC1O] | 591 |
| 104D [82] | 2-Amino-4-(3-(3-((S)-3,4-dimethylpiperazin-1-yl)-4-methoxypyrrolidin-1-yl)-5-fluoro-7,9-dihydrofuro[3,4-f]quinazolin-6-yl)-7-fluorothieno[3,2-c]pyridine-3-carbonitrile | 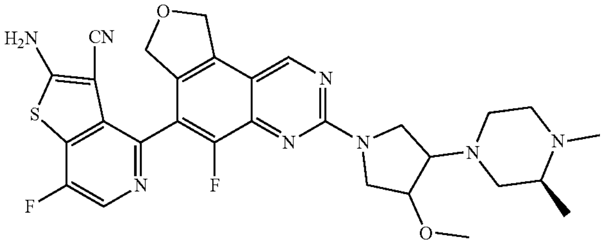 [SMILES: COC1CN(c2ncc3c4c(c(-c5ncc(F)c6sc(N)c(C#N)c56)c(F)c3n2)COC4)CC1N1CCN(C)[C@@H](C)C1] | 593 |
| 105D [83] | 2-Amino-7-fluoro-4-(5-fluoro-3-(3-methoxy-4-(3-methyl-3,8-diazabicyclo[3.2.1]octan-8-yl)pyrrolidin-1-yl)-7,9-dihydrofuro[3,4-f]quinazolin-6-yl)thieno[3,2-c]pyridine-3-carbonitrile, Isomer 1 | 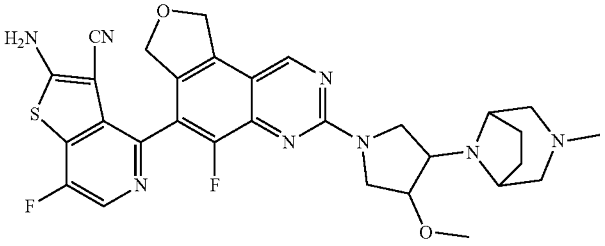 [SMILES: COC1CN(c2ncc3c4c(c(-c5ncc(F)c6sc(N)c(C#N)c56)c(F)c3n2)COC4)CC1N1C2CCC1CN(C)C2] | 605 |

TABLE 28-continued

| Example | Chemical Name | Structure | MS (ES) m/z (M + 1) |
|---|---|---|---|
| 106D [83] | 2-Amino-7-fluoro-4-(5-fluoro-3-(3-methoxy-4-(3-methyl-3,8-diazabicyclo[3.2.1 ]octan-8-yl)pyrrolidin-1-yl)-7,9-dihydrofuro[3,4-f]quinazolin-6-yl)thieno[3,2-c]pyridine-3-carbonitrile, Isomer 2 | 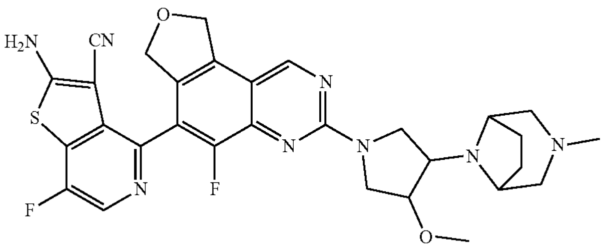 [SMILES: COC1CN(c2ncc3c4c(c(-c5ncc(F)c6sc(N)c(C#N)c56)c(F)c3n2)COC4)CC1N1C2CCC1CN(C)C2] | 605 |
| 107D | 2-Amino-7-fluoro-4-(5-fluoro-3-((S)-3-(piperidin-1-yl)pyrrolidin-1-yl)-7,9-dihydrofuro[3,4-f]quinazolin-6-yl)thieno[3,2-c]pyridine-3-carbonitrile | 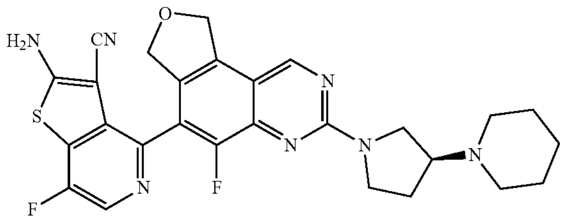 [SMILES: N#Cc1c(N)sc2c(F)cnc(-c3c4c(c5cnc(N6CC[C@H](N7CCCCC7)C6)nc5c3F)COC4)c12] | 534 |
| 108D | 2-Amino-7-fluoro-4-(5-fluoro-3-((R)-3-(piperidin-1-yl)pyrrolidin-1-yl)-7,9-dihydrofuro[3,4-f]quinazolin-6-yl)thieno[3,2-c]pyridine-3-carbonitrile | 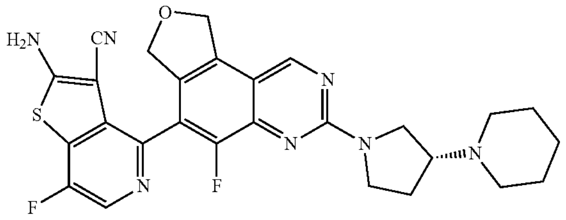 [SMILES: N#Cc1c(N)sc2c(F)cnc(-c3c4c(c5cnc(N6CC[C@@H](N7CCCCC7)C6)nc5c3F)COC4)c12] | 534 |
| 109D | 2-Amino-4-(3-((R)-3-(4-(dimethylamino)piperidin-1-yl)pyrrolidin-1-yl)-5-fluoro-7,9-dihydrofuro[3,4-f]quinazolin-6-yl)-7-fluorothieno[3,2-c]pyridine-3-carbonitrile | 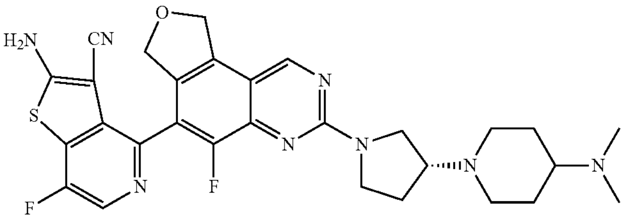 [SMILES: CN(C)C1CCN([C@@H]2CCN(c3ncc4c5c(c(-c6ncc(F)c7sc(N)c(C#N)c67)c(F)c4n3)COC5)C2)CC1] | 577 |
| 110D | 2-Amino-7-fluoro-4-(5-fluoro-3-((R)-3-((S)-3-hydroxypiperidin-1-yl)pyrrolidin-1-yl)-7,9-dihydrofuro[3,4-f]quinazolin-6-yl)thieno[3,2-c]pyridine-3-carbonitrile | 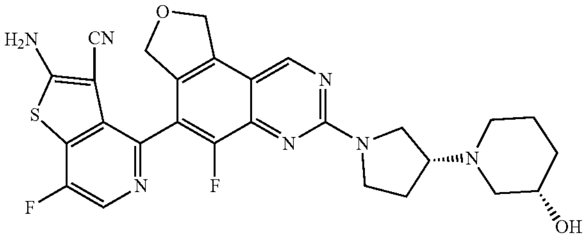 [SMILES: N#Cc1c(N)sc2c(F)cnc(-c3c4c(c5cnc(N6CC[C@@H](N7CCC[C@H](O)C7)C6)nc5c3F)COC4)c12] | 550 |
| 111D | 2-Amino-7-fluoro-4-(5-fluoro-3-((R)-3-((R)-3-hydroxypiperidin-1-yl)pyrrolidin-1-yl)-7,9-dihydrofuro[3,4-f]quinazolin-6-yl)thieno[3,2-c]pyridine-3-carbonitrile | 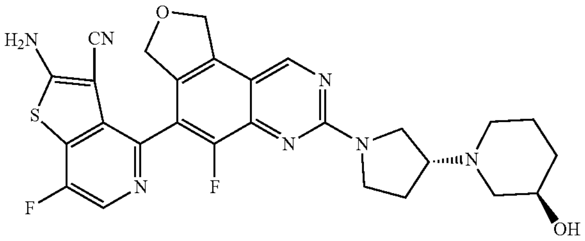 [SMILES: N#Cc1c(N)sc2c(F)cnc(-c3c4c(c5cnc(N6CC[C@@H](N7CCC[C@@H](O)C7)C6)nc5c3F)COC4)c12] | 550 |

TABLE 28-continued

| Example | Chemical Name | Structure | MS (ES) m/z (M + 1) |
|---|---|---|---|
| 112D | 2-Amino-7-fluoro-4-(5-fluoro-3-((R)-3-(4-methoxypiperidin-1-yl)pyrrolidin-1-yl)-7,9-dihydrofuro[3,4-f]quinazolin-6-yl)thieno[3,2-c]pyridine-3-carbonitrile | 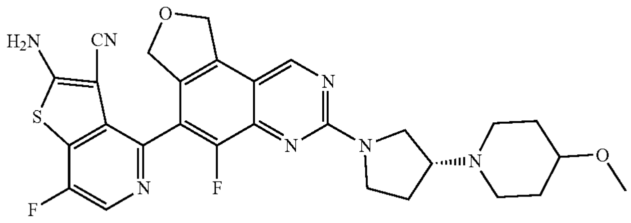 [SMILES: COC1CCN([C@@H]2CCN(c3ncc4c5c(c(-c6ncc(F)c7sc(N)c(C#N)c67)c(F)c4n3)COC5)C2)CC1] | 564 |
| 113D | 2-Amino-4-(3-((R)-3-(4-cyanopiperidin-1-yl)pyrrolidin-1-yl)-5-fluoro-7,9-dihydrofuro[3,4-f]quinazolin-6-yl)-7-fluorothieno[3,2-c]pyridine-3-carbonitrile | 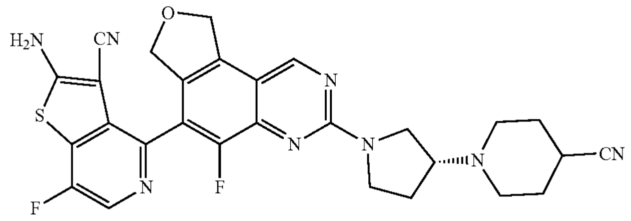 [SMILES: N#Cc1c(N)sc2c(F)cnc(-c3c4c(c5cnc(N6CC[C@@H](N7CCC(C#N)CC7)C6)nc5c3F)COC4)c12] | 559 |
| 114D | 2-Amino-7-fluoro-4-(5-fluoro-3-((R)-3-(4-hydroxypiperidin-1-yl)pyrrolidin-1-yl)-7,9-dihydrofuro[3,4-f]quinazolin-6-yl)thieno[3,2-c]pyridine-3-carbonitrile | 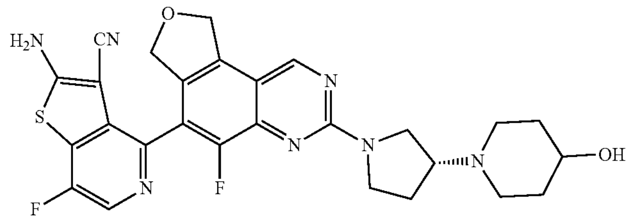 [SMILES: N#Cc1c(N)sc2c(F)cnc(-c3c4c(c5cnc(N6CC[C@@H](N7CCC(O)CC7)C6)nc5c3F)COC4)c12] | 550 |
| 115D | 2-Amino-7-fluoro-4-(5-fluoro-3-((3S)-3-(3-hydroxy-3-methylpiperidin-1-yl)pyrrolidin-1-yl)-7,9-dihydrofuro[3,4-f]quinazolin-6-yl)thieno[3,2-c]pyridine-3-carbonitrile, Isomer 1 | 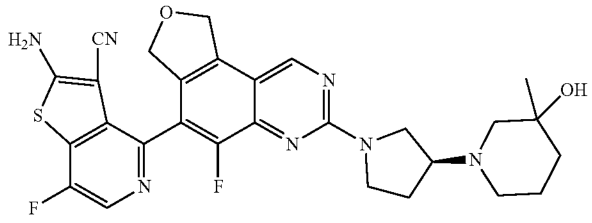 [SMILES: CC1(O)CCCN([C@H]2CCN(c3ncc4c5c(c(-c6ncc(F)c7sc(N)c(C#N)c67)c(F)c4n3)COC5)C2)C1] | 564 |
| 116D | 2-Amino-7-fluoro-4-(5-fluoro-3-((3S)-3-(3-hydroxy-3-methylpiperidin-1-yl)pyrrolidin-1-yl)-7,9-dihydrofuro[3,4-f]quinazolin-6-yl)thieno[3,2-c]pyridine-3-carbonitrile, Isomer 2 | 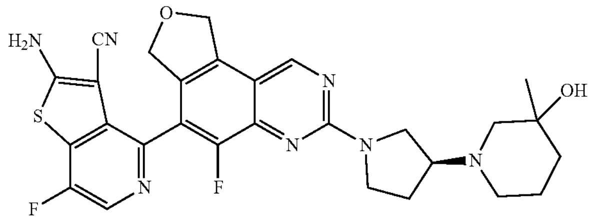 [SMILES: CC1(O)CCCN([C@H]2CCN(c3ncc4c5c(c(-c6ncc(F)c7sc(N)c(C#N)c67)c(F)c4n3)COC5)C2)C1] | 564 |
| 117D | 2-Amino-7-fluoro-4-(5-fluoro-3-((R)-3-(4-hydroxy-4-methylpiperidin-1-yl)pyrrolidin-1-yl)-7,9-dihydrofuro[3,4-f]quinazolin-6-yl)thieno[3,2-c]pyridine-3-carbonitrile | 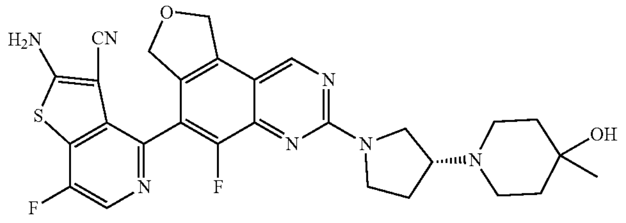 [SMILES: CC1(O)CCN([C@@H]2CCN(c3ncc4c5c(c(-c6ncc(F)c7sc(N)c(C#N)c67)c(F)c4n3)COC5)C2)CC1] | 564 |

TABLE 28-continued

| Example | Chemical Name | Structure | MS (ES) m/z (M + 1) |
|---|---|---|---|
| 118D | 2-Amino-7-fluoro-4-(5-fluoro-3-((R)-3-(4-fluoropiperidin-1-yl)pyrrolidin-1-yl)-7,9-dihydrofuro[3,4-f]quinazolin-6-yl)thieno[3,2-c]pyridine-3-carbonitrile | 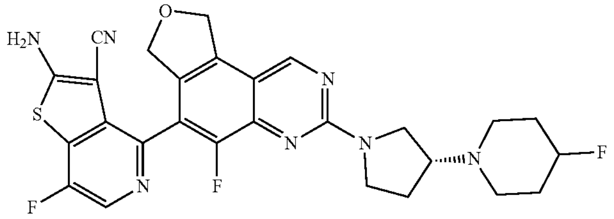 [SMILES: N#Cc1c(N)sc2c(F)cnc(-c3c4c(c5cnc(N6CC[C@@H](N7CCC(F)CC7)C6)nc5c3F)COC4)c12] | 552 |
| 119D | 2-Amino-7-fluoro-4-(5-fluoro-3-((3R)-3-(3-fluoropiperidin-1-yl)pyrrolidin-1-yl)-7,9-dihydrofuro[3,4-f]quinazolin-6-yl)thieno[3,2-c]pyridine-3-carbonitrile | 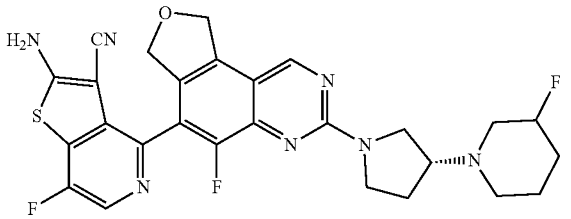 [SMILES: N#Cc1c(N)sc2c(F)cnc(-c3c4c(c5cnc(N6CC[C@@H](N7CCCC(F)C7)C6)nc5c3F)COC4)c12] | 552 |
| 120D | 2-Amino-7-fluoro-4-(5-fluoro-3-((2S,3S)-2-methyl-3-(piperidin-1-yl)pyrrolidin-1-yl)-7,9-dihydrofuro[3,4-f]quinazolin-6-yl)thieno[3,2-c]pyridine-3-carbonitrile | 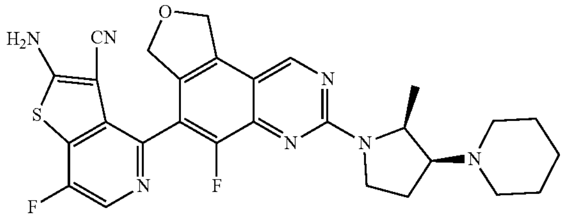 [SMILES: C[C@H]1[C@@H](N2CCCCC2)CCN1c1ncc2c3c(c(-c4ncc(F)c5sc(N)c(C#N)c45)c(F)c2n1)COC3] | 548 |
| 121D [84] | 2-Amino-7-fluoro-4-(5-fluoro-3-(3-hydroxy-4-(piperidin-1-yl)pyrrolidin-1-yl)-7,9-dihydrofuro[3,4-f]quinazolin-6-yl)thieno[3,2-c]pyridine-3-carbonitrile | 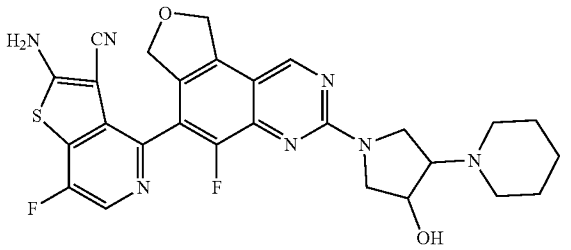 [SMILES: N#Cc1c(N)sc2c(F)cnc(-c3c4c(c5cnc(N6CC(O)C(N7CCCCC7)C6)nc5c3F)COC4)c12] | 550 |
| 122D [85] | 2-Amino-7-fluoro-4-(5-fluoro-3-(3-hydroxy-4-(piperidin-1-yl)pyrrolidin-1-yl)-7,9-dihydrofuro[3,4-f]quinazolin-6-yl)thieno[3,2-c]pyridine-3-carbonitrile, Isomer 1 | 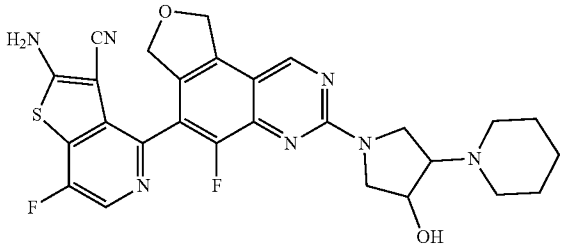 [SMILES: N#Cc1c(N)sc2c(F)cnc(-c3c4c(c5cnc(N6CC(O)C(N7CCCCC7)C6)nc5c3F)COC4)c12] | 550 |
| 123D [85] | 2-Amino-7-fluoro-4-(5-fluoro-3-(3-hydroxy-4-(piperidin-1-yl)pyrrolidin-1-yl)-7,9-dihydrofuro[3,4-f]quinazolin-6-yl)thieno[3,2-c]pyridine-3-carbonitrile, Isomer 2 | 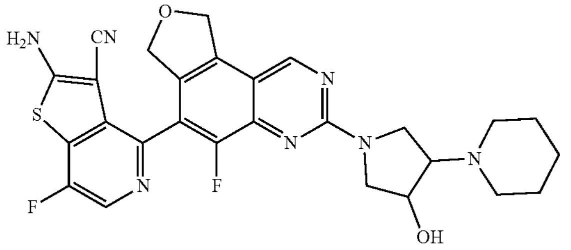 [SMILES: N#Cc1c(N)sc2c(F)cnc(-c3c4c(c5cnc(N6CC(O)C(N7CCCCC7)C6)nc5c3F)COC4)c12] | 550 |

TABLE 28-continued

| Example | Chemical Name | Structure | MS (ES) m/z (M + 1) |
|---|---|---|---|
| 124D [86] | 2-Amino-7-fluoro-4-(5-fluoro-3-(3-methoxy-4-(piperidin-1-yl)pyrrolidin-1-yl)-7,9-dihydrofuro[3,4-f]quinazolin-6-yl)thieno[3,2-c]pyridine-3-carbonitrile, Isomer 1 | 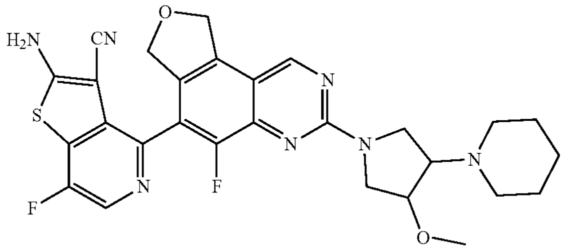 [SMILES: COC1CN(c2ncc3c4c(c(-c5ncc(F)c6sc(N)c(C#N)c56)c(F)c3n2)COC4)CC1N1CCCCC1] | 564 |
| 125D [86] | 2-Amino-7-fluoro-4-(5-fluoro-3-(3-methoxy-4-(piperidin-1-yl)pyrrolidin-1-yl)-7,9-dihydrofuro[3,4-f]quinazolin-6-yl)thieno[3,2-c]pyridine-3-carbonitrile, Isomer 2 | 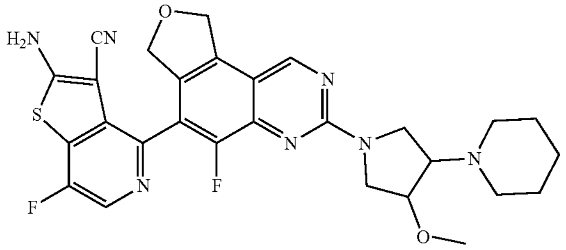 [SMILES: COC1CN(c2ncc3c4c(c(-c5ncc(F)c6sc(N)c(C#N)c56)c(F)c3n2)COC4)CC1N1CCCCC1] | 564 |
| 126D | 2-Amino-7-fluoro-4-(5-fluoro-3-((R)-3-thiomorpholinopyrrolidin-1-yl)-7,9- dihydrofuro[3,4-f]quinazolin-6-yl)thieno[3,2-c]pyridine-3-carbonitrile | 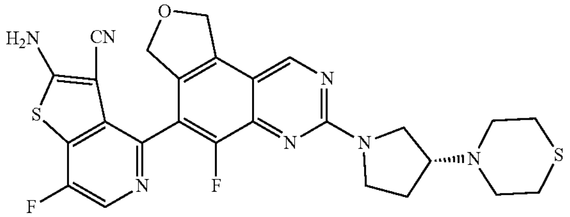 [SMILES: N#Cc1c(N)sc2c(F)cnc(-c3c4c(c5cnc(N6CC[C@@H](N7CCSCC7)C6)nc5c3F)COC4)c12] | 552 |
| 127D | 2-Amino-4-(3-((3R)-3-(2-((dimethylamino)methyl) morpholino)pyrrolidin-1-yl)-5-fluoro-7,9-dihydrofuro[3,4-f]quinazolin-6-yl)-7-fluorothieno[3,2-c]pyridine-3-carbonitrile | 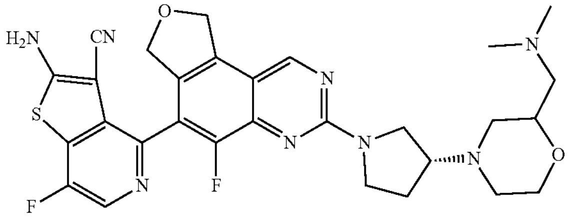 [SMILES: CN(C)CC1CN([C@@H]2CCN(c3ncc4c5c(c(-c6ncc(F)c7sc(N)c(C#N)c67)c(F)c4n3)COC5)C2)CCO1] | 593 |
| 128D | 2-Amino-4-(3-((3S)-3-(2-((dimethylamino)methyl) morpholino)pyrrolidin-1-yl)-5-fluoro-7,9-dihydrofuro[3,4-f]quinazolin-6-yl)-7-fluorothieno[3,2-c]pyridine-3-carbonitrile | 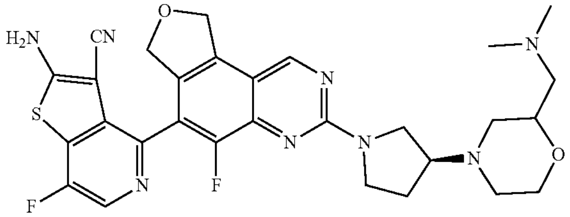 [SMILES: CN(C)CC1CN([C@H]2CCN(c3ncc4c5c(c(-c6ncc(F)c7sc(N)c(C#N)c67)c(F)c4n3)COC5)C2)CCO1] | 593 |
| 129D | 2-Amino-7-fluoro-4-(5-fluoro-3-((2S,3S)-2-methyl-3-morpholinopyrrolidin-1-yl)-7,9-dihydrofuro[3,4-f]quinazolin-6-yl)thieno[3,2-c]pyridine-3-carbonitrile | 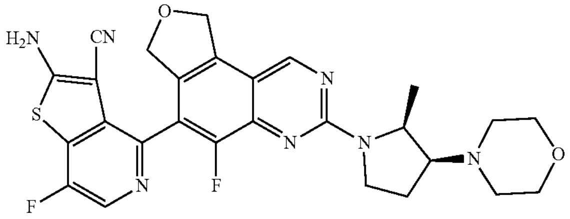 [SMILES: C[C@H]1[C@@H](N2CCOCC2)CCN1c1ncc2c3c(c(-c4ncc(F)c5sc(N)c(C#N)c45)c(F)c2n1)COC3] | 550 |

TABLE 28-continued

| Example | Chemical Name | Structure | MS (ES) m/z (M + 1) |
|---|---|---|---|
| 130D | 4-(3-((2S,3S)-3-(3-Oxa-6-azabicyclo[3.1.1]heptan-6-yl)-2-methylpyrrolidin-1-yl)-5-fluoro-7,9-dihydrofuro[3,4-f]quinazolin-6-yl)-2-amino-7-fluorothieno[3,2-c]pyridine-3-carbonitrile | 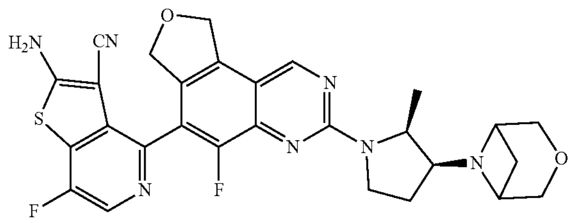 [SMILES: C[C@H]1[C@@H](N2C3COCC2C3)CCN1c1ncc2c3c(c(-c4ncc(F)c5sc(N)c(C#N)c45)c(F)c2n1)COC3] | 562 |
| 131D | 4-(3-((R)-3-(1,4-Oxazepan-4-yl)pyrrolidin-1-yl)-5-fluoro-7,9-dihydrofuro[3,4-f]quinazolin-6-yl)-2-amino-7-fluorothieno[3,2-c]pyridine-3-carbonitrile | 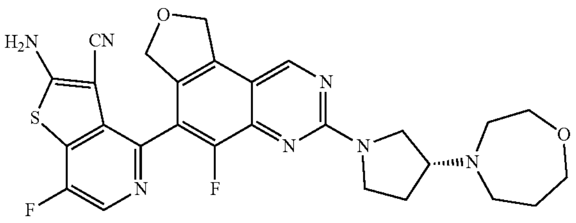 [SMILES: N#Cc1c(N)sc2c(F)cnc(-c3c4c(c5cnc(N6CC[C@@H](N7CCCOCC7)C6)nc5c3F)COC4)c12] | 550 |
| 132D | 2-Amino-7-fluoro-4-(5-fluoro-3-((R)-3-(4-methyl-1,4-diazepan-1-yl)pyrrolidin-1-yl)-7,9-dihydrofuro[3,4-f]quinazolin-6-yl)thieno[3,2-c]pyridine-3-carbonitrile | 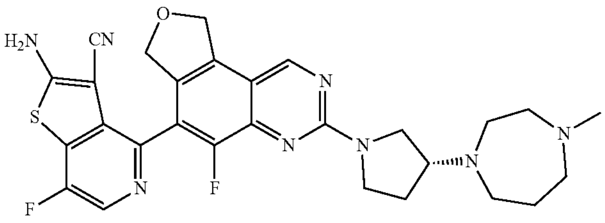 [SMILES: CN1CCCN([C@@H]2CCN(c3ncc4c5c(c(-c6ncc(F)c7sc(N)c(C#N)c67)c(F)c4n3)COC5)C2)CC1] | 563 |
| 133D | 4-(3-((R)-3-(4-Acetyl-1,4-diazepan-1-yl)pyrrolidin-1-yl)-5-fluoro-7,9-dihydrofuro[3,4-f]quinazolin-6-yl)-2-amino-7-fluorothieno[3,2-c]pyridine-3-carbonitrile | 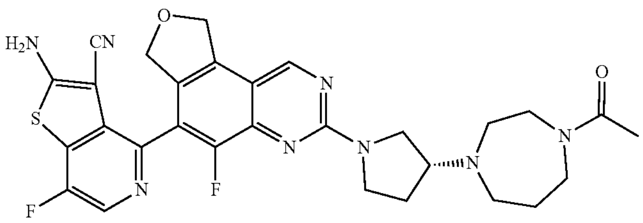 [SMILES: CC(=O)N1CCCN([C@@H]2CCN(c3ncc4c5c(c(-c6ncc(F)c7sc(N)c(C#N)c67)c(F)c4n3)COC5)C2)CC1] | 591 |
| 134D | 2-Amino-7-fluoro-4-(5-fluoro-3-((S)-3-(4-methyl-1,4-diazepan-1-yl)pyrrolidin-1-yl)-7,9-dihydrofuro[3,4-f]quinazolin-6-yl)thieno[3,2-c]pyridine-3-carbonitrile | 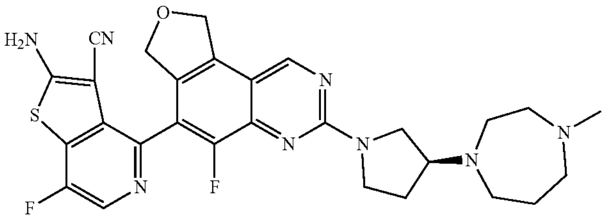 [SMILES: CN1CCCN([C@H]2CCN(c3ncc4c5c(c(-c6ncc(F)c7sc(N)c(C#N)c67)c(F)c4n3)COC5)C2)CC1] | 563 |
| 135D [87] | 2-Amino-7-fluoro-4-(5-fluoro-3-(3-hydroxy-4-(1,4-oxazepan-4-yl)pyrrolidin-1-yl)-7,9-dihydrofuro[3,4-f]quinazolin-6-yl)thieno[3,2-c]pyridine-3-carbonitrile, Isomer 1 | 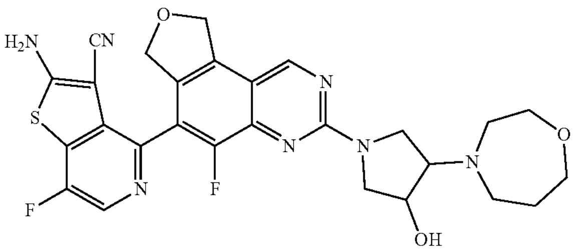 [SMILES: N#Cc1c(N)sc2c(F)cnc(-c3c4c(c5cnc(N6CC(O)C(N7CCCOCC7)C6)nc5c3F)COC4)c12] | 566 |

TABLE 28-continued

| Example | Chemical Name | Structure | MS (ES) m/z (M + 1) |
|---|---|---|---|
| 136D [87] | 2-Amino-7-fluoro-4-(5-fluoro-3-(3-hydroxy-4-(1,4-oxazepan-4-yl)pyrrolidin-1-yl)-7,9-dihydrofuro[3,4-f]quinazolin-6-yl)thieno[3,2-c]pyridine-3-carbonitrile, Isomer 2 | 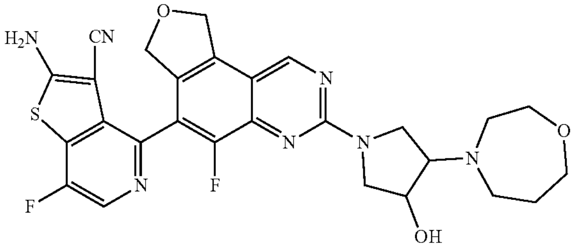 [SMILES: N#Cc1c(N)sc2c(F)cnc(-c3c4c(c5cnc(N6CC(O)C(N7CCCOCC7)C6)nc5c3F)COC4)c12] | 566 |
| 137D [88] | 2-Amino-7-fluoro-4-(5-fluoro-3-(3-methoxy-4-(1,4-oxazepan-4-yl)pyrrolidin-1-yl)-7,9-dihydrofuro[3,4-f]quinazolin-6-yl)thieno[3,2-c]pyridine-3-carbonitrile, Isomer 1 | 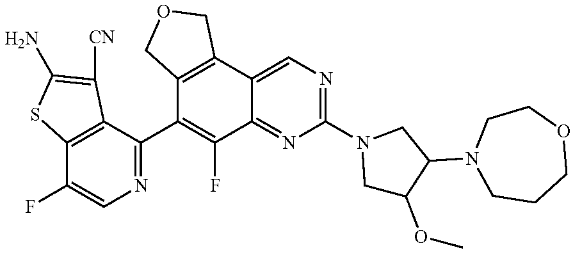 [SMILES: COC1CN(c2ncc3c4c(c(-c5ncc(F)c6sc(N)c(C#N)c56)c(F)c3n2)COC4)CC1N1CCCOCC1] | 580 |
| 138D [88] | 2-Amino-7-fluoro-4-(5-fluoro-3-(3-methoxy-4-(1,4-oxazepan-4-yl)pyrrolidin-1-yl)-7,9-dihydrofuro[3,4-f]quinazolin-6-yl)thieno[3,2-c]pyridine-3-carbonitrile, Isomer 2 | 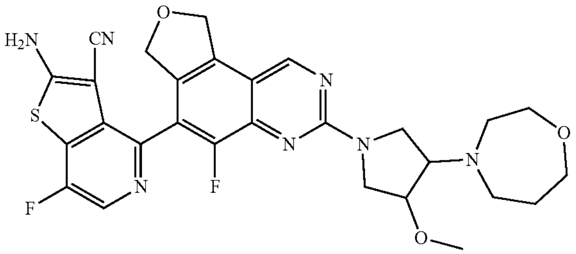 [SMILES: COC1CN(c2ncc3c4c(c(-c5ncc(F)c6sc(N)c(C#N)c56)c(F)c3n2)COC4)CC1N1CCCOCC1] | 580 |
| 139D | 2-Amino-7-fluoro-4-(5-fluoro-3-((R)-3-((3aR,6aS)-5-methylhexahydropyrrolo[3,4-c]pyrrol-2(1H)-yl)pyrrolidin-1-yl)-7,9-dihydrofuro[3,4-f]quinazolin-6-yl)thieno[3,2-c]pyridine-3-carbonitrile | 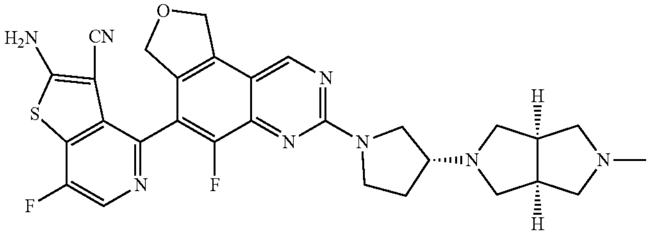 [SMILES: CN1C[C@@H]2CN([C@@H]3CCN(c4ncc5c6c(c(-c7ncc(F)c8sc(N)c(C#N)c78)c(F)c5n4)COC6)C3)C[C@@H]2C1] | 575 |
| 140D | 2-Amino-7-fluoro-4-(5-fluoro-3-((S)-3-((3aR,6aS)-5-methylhexahydropyrrolo[3,4-c]pyrrol-2(1H)-yl)pyrrolidin-1-yl)-7,9-dihydrofuro[3,4-f]quinazolin-6-yl)thieno[3,2-c]pyridine-3-carbonitrile | 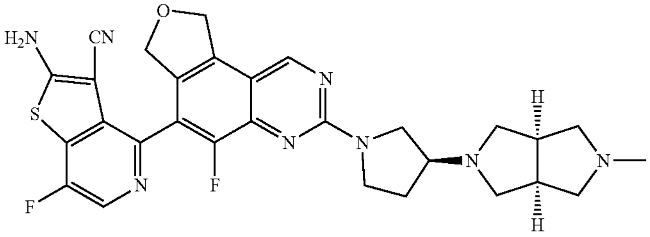 [SMILES: CN1C[C@@H]2CN([C@H]3CCN(c4ncc5c6c(c(-c7ncc(F)c8sc(N)c(C#N)c78)c(F)c5n4)COC6)C3)C[C@@H]2C1] | 575 |
| 141D | 2-Amino-7-fluoro-4-(5-fluoro-3-((R)-3-((R)-hexahydropyrrolo[1,2-a]pyrazin-2(1H)-yl)pyrrolidin-1-yl)-7,9-dihydrofuro[3,4-f]quinazolin-6-yl)thieno[3,2-c]pyridine-3-carbonitrile | 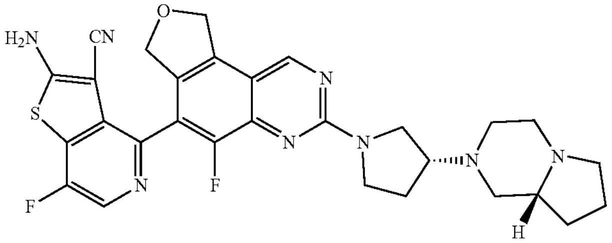 [SMILES: N#Cc1c(N)sc2c(F)cnc(-c3c4c(c5cnc(N6CC[C@@H](N7CCN8CCC[C@@H]8C7)C6)nc5c3F)COC4)c12] | 575 |

TABLE 28-continued

| Example | Chemical Name | Structure | MS (ES) m/z (M + 1) |
|---|---|---|---|
| 142D | 2-Amino-7-fluoro-4-(5-fluoro-3-((S)-3-((7S,8aS)-7-fluorohexahydropyrrolo[1,2-a]pyrazin-2(1H)-yl)pyrrolidin-1-yl)-7,9-dihydrofuro[3,4-f]quinazolin-6-yl)thieno[3,2-c]pyridine-3-carbonitrile | 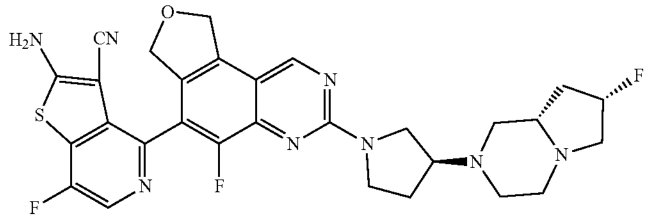 [SMILES: N#Cc1c(N)sc2c(F)cnc(-c3c4c(c5cnc(N6CC[C@H](N7CCN8C[C@@H](F)C[C@H]8C7)C6)nc5c3F)COC4)c12] | 593 |
| 143D | 2-Amino-7-fluoro-4-(5-fluoro-3-((R)-3-((3aR,6aS)-tetrahydro-1H-furo[3,4-c]pyrrol-5(3H)-yl)pyrrolidin-1-yl)-7,9-dihydrofuro[3,4-f]quinazolin-6-yl)thieno[3,2-c]pyridine-3-carbonitrile | 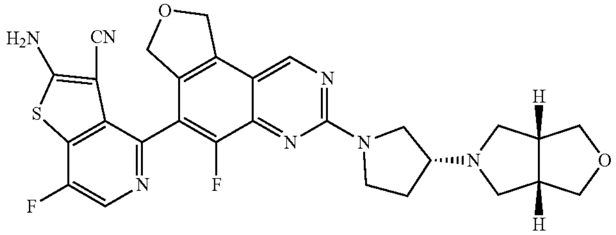 [SMILES: N#Cc1c(N)sc2c(F)cnc(-c3c4c(c5cnc(N6CC[C@@H](N7C[C@H]8COC[C@H]8C7)C6)nc5c3F)COC4)c12] | 562 |
| 144D | 2-Amino-7-fluoro-4-(5-fluoro-3-((R)-3-(2-methyl-2,6-diazaspiro[3.4]octan-6-yl)pyrrolidin-1-yl)-7,9-dihydrofuro[3,4-f]quinazolin-6-yl)thieno[3,2-c]pyridine-3-carbonitrile | 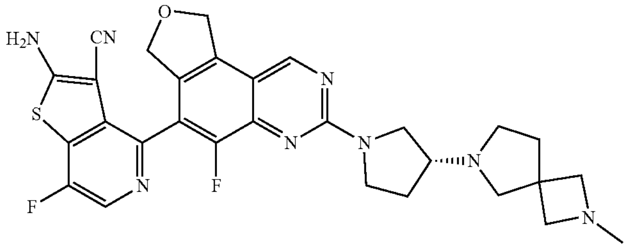 [SMILES: CN1CC2(CCN([C@@H]3CCN(c4ncc5c6c(c(-c7ncc(F)c8sc(N)c(C#N)c78)c(F)c5n4)COC6)C3)C2)C1] | 575 |
| 145D | 4-(3-((R)-3-(2-Azaspiro[3.3]heptan-2-yl)pyrrolidin-1-yl)-5-fluoro-7,9-dihydrofuro[3,4-f]quinazolin-6-yl)-2-amino-7-fluorothieno[3,2-c]pyridine-3-carbonitrile | 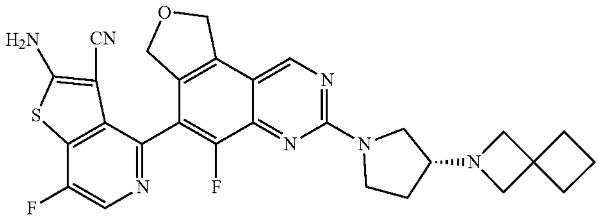 [SMILES: N#Cc1c(N)sc2c(F)cnc(-c3c4c(c5cnc(N6CC[C@@H](N7CC8(CCC8)C7)C6)nc5c3F)COC4)c12] | 546 |
| 146D | 4-(3-((S)-3-(2-Azaspiro[3.3]heptan-2-yl)pyrrolidin-1-yl)-5-fluoro-7,9-dihydrofuro[3,4-f]quinazolin-6-yl)-2-amino-7-fluorothieno[3,2-c]pyridine-3-carbonitrile | 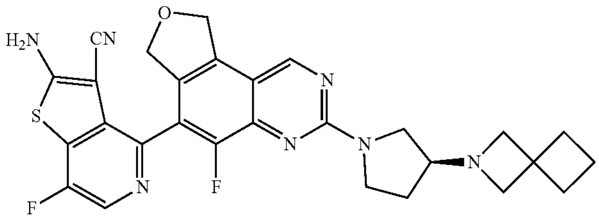 [SMILES: N#Cc1c(N)sc2c(F)cnc(-c3c4c(c5cnc(N6CC[C@H](N7CC8(CCC8)C7)C6)nc5c3F)COC4)c12] | 546 |
| 147D | 4-(3-((R)-3-(2-Oxa-7-azaspiro[3.5]nonan-7-yl)pyrrolidin-1-yl)-5-fluoro-7,9-dihydrofuro[3,4-f]quinazolin-6-yl)-2-amino-7-fluorothieno[3,2-c]pyridine-3-carbonitrile | 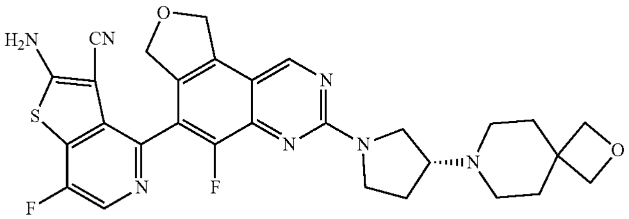 [SMILES: N#Cc1c(N)sc2c(F)cnc(-c3c4c(c5cnc(N6CC[C@@H](N7CCC8(CC7)COC8)C6)nc5c3F)COC4)c12] | 576 |

TABLE 28-continued

| Example | Chemical Name | Structure | MS (ES) m/z (M + 1) |
|---|---|---|---|
| 148D [89] | 2-Amino-7-fluoro-4-(5-fluoro-3-((3S)-3-(methyl(tetrahydrofuran-3-yl)amino)pyrrolidin-1-yl)-7,9-dihydrofuro[3,4-f]quinazolin-6-yl)thieno[3,2-c]pyridine-3-carbonitrile, Isomer 1 | 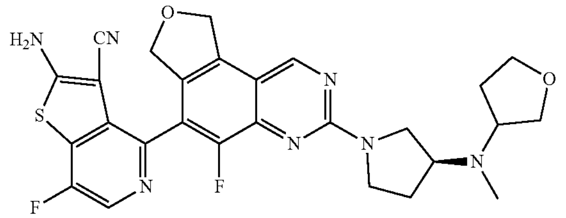 [SMILES: CN(C1CCOC1)[C@H]1CCN(c2ncc3c4c(c(-c5ncc(F)c6sc(N)c(C#N)c56)c(F)c3n2)COC4)C1] | 550 |
| 149D [89] | 2-Amino-7-fluoro-4-(5-fluoro-3-((3S)-3-(methyl(tetrahydrofuran-3-yl)amino)pyrrolidin-1-yl)-7,9-dihydrofuro[3,4-f]quinazolin-6-yl)thieno[3,2-c]pyridine-3-carbonitrile, Isomer 2 | 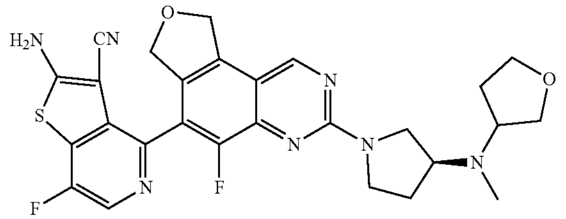 [SMILES: CN(C1CCOC1)[C@H]1CCN(c2ncc3c4c(c(-c5ncc(F)c6sc(N)c(C#N)c56)c(F)c3n2)COC4)C1] | 550 |
| 150D [90] | 2-Amino-7-fluoro-4-(5-fluoro-3-((3S)-3-(methyl((tetrahydrofuran-2-yl)methyl)amino) pyrrolidin-1-yl)-7,9-dihydrofuro[3,4-f]quinazolin-6-yl)thieno[3,2-c]pyridine-3-carbonitrile, Isomer 1 | 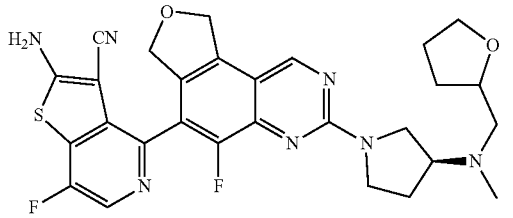 [SMILES: CN(CC1CCCO1)[C@H]1CCN(c2ncc3c4c(c(-c5ncc(F)c6sc(N)c(C#N)c56)c(F)c3n2)COC4)C1] | 564 |
| 151D [90] | 2-Amino-7-fluoro-4-(5-fluoro-3-((3S)-3-(methyl((tetrahydrofuran-2-yl)methyl)amino) pyrrolidin-1-yl)-7,9-dihydrofuro[3,4-f]quinazolin-6-yl)thieno[3,2-c]pyridine-3-carbonitrile, Isomer 2 | 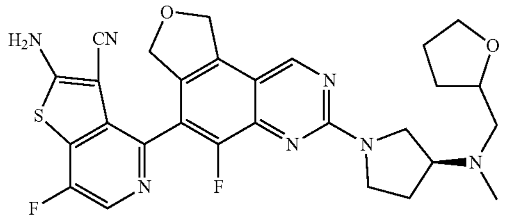 [SMILES: CN(CC1CCCO1)[C@H]1CCN(c2ncc3c4c(c(-c5ncc(F)c6sc(N)c(C#N)c56)c(F)c3n2)COC4)C1] | 564 |
| 152D | 2-Amino-7-fluoro-4-(5-fluoro-3-((R)-3-(methyl((R)-1-methylpyrrolidin-3-yl)amino)pyrrolidin-1-yl)-7,9-dihydrofuro[3,4-f]quinazolin-6-yl)thieno[3,2-c]pyridine-3-carbonitrile formic acid | 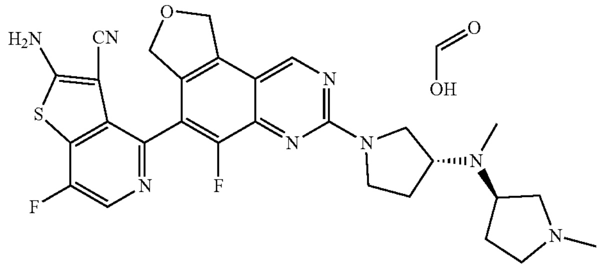 | 563 |
| 153D | 2-Amino-7-fluoro-4-(5-fluoro-3-((R)-3-(methyl((S)-1-methylpyrrolidin-3-yl)amino)pyrrolidin-1-yl)-7,9-dihydrofuro[3,4-f]quinazolin-6-yl)thieno[3,2-c]pyridine-3-carbonitrile formic acid | 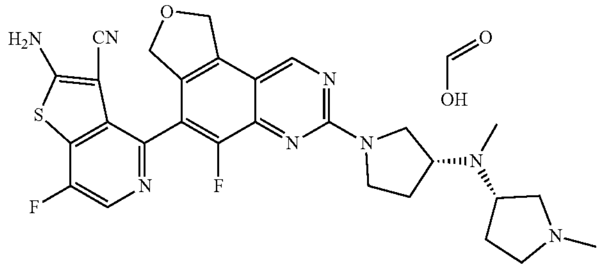 | 563 |

TABLE 28-continued

| Example | Chemical Name | Structure | MS (ES) m/z (M + 1) |
|---|---|---|---|
| 154D | 2-Amino-7-fluoro-4-(5-fluoro-3-((S)-3-(methyl((R)-1-methylpyrrolidin-3-yl)amino)pyrrolidin-1-yl)-7,9-dihydrofuro[3,4-f]quinazolin-6-yl)thieno[3,2-c]pyridine-3-carbonitrile formic acid | 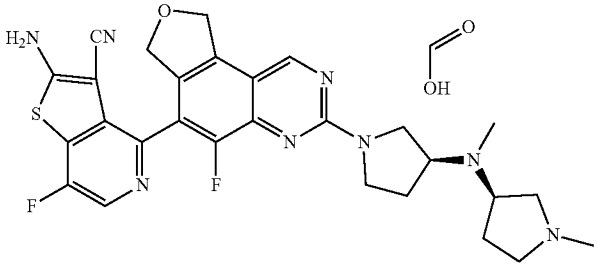 | 563 |
| 155D | 2-Amino-7-fluoro-4-(5-fluoro-3-((S)-3-(methyl((S)-1-methylpyrrolidin-3-yl)amino)pyrrolidin-1-yl)-7,9-dihydrofuro[3,4-f]quinazolin-6-yl)thieno[3,2-c]pyridine-3-carbonitrile formic acid | 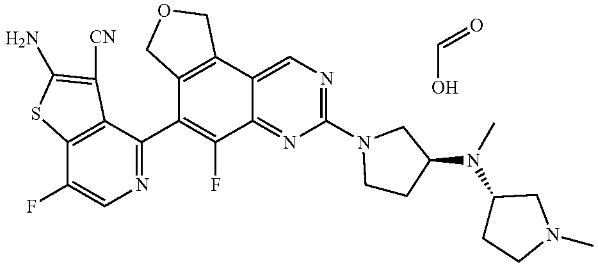 | 563 |
| 156D | 2-Amino-4-(3-((S)-3-(2-(dimethylamino)ethyl) pyrrolidin-1-yl)-5-fluoro-7,9-dihydrofuro[3,4-f]quinazolin-6-yl)-7-fluorothieno[3,2-c]pyridine-3-carbonitrile | 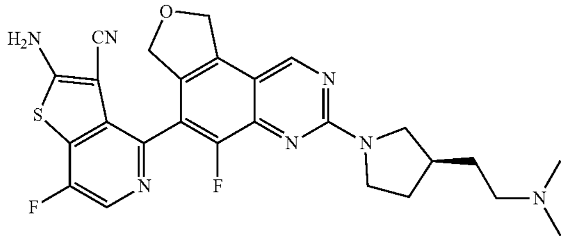 [SMILES: CN(C)CC[C@H]1CCN(c2ncc3c4c(c(-c5ncc(F)c6sc(N)c(C#N)c56)c(F)c3n2)COC4)C1] | 522 |
| 157D [91] | 2-Amino-4-(3-(3-(tert-butyl(methyl)amino) pyrrolidin-1-yl)-5-fluoro-7,9-dihydrofuro[3,4-f]quinazolin-6-yl)-7-fluorothieno[3,2-c]pyridine-3-carbonitrile, Isomer 1 | 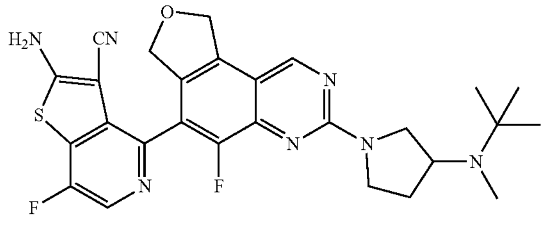 [SMILES: CN(C1CCN(c2ncc3c4c(c(-c5ncc(F)c6sc(N)c(C#N)c56)c(F)c3n2)COC4)C1)C(C)(C)C] | 536 |
| 158D [91] | 2-Amino-4-(3-(3-(tert-butyl(methyl)amino) pyrrolidin-1-yl)-5-fluoro-7,9-dihydrofuro[3,4-f]quinazolin-6-yl)-7-fluorothieno[3,2-c]pyridine-3-carbonitrile, Isomer 2 | 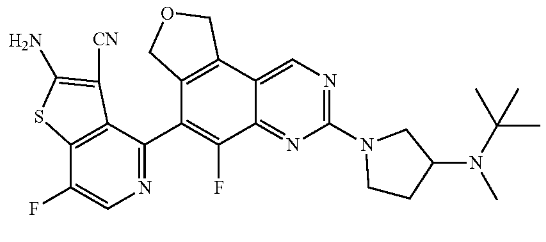 [SMILES: CN(C1CCN(c2ncc3c4c(c(-c5ncc(F)c6sc(N)c(C#N)c56)c(F)c3n2)COC4)C1)C(C)(C)C] | 536 |
| 159D | 2-Amino-4-(3-((R)-3-(2-(dimethylamino)ethoxy) pyrrolidin-1-yl)-5-fluoro-7,9-dihydrofuro[3,4-f]quinazolin-6-yl)-7-fluorothieno[3,2-c]pyridine-3-carbonitrile | 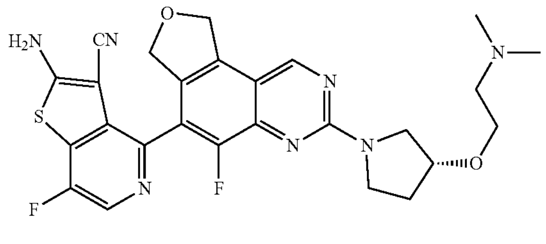 [SMILES: CN(C)CCO[C@@H]1CCN(c2ncc3c4c(c(-c5ncc(F)c6sc(N)c(C#N)c56)c(F)c3n2)COC4)C1] | 538 |

TABLE 28-continued

| Example | Chemical Name | Structure | MS (ES) m/z (M + 1) |
|---|---|---|---|
| 160D | 2-Amino-4-(3-((S)-3-(2-(dimethylamino)ethoxy) pyrrolidin-1-yl)-5-fluoro-7,9-dihydrofuro[3,4-f]quinazolin-6-yl)-7-fluorothieno[3,2-c]pyridine-3-carbonitrile | 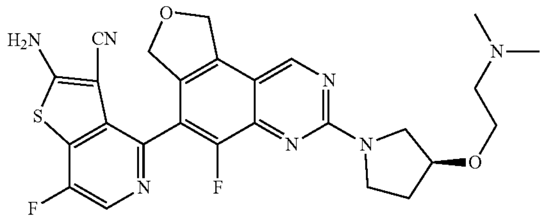 [SMILES: CN(C)CCO[C@H]1CCN(c2ncc3c4c(c(-c5ncc(F)c6sc(N)c(C#N)c56)c(F)c3n2)COC4)C1] | 538 |
| 161D | 2-Amino-4-(3-((R)-3-(3-((dimethylamino)methyl) azetidin-1-yl)pyrrolidin-1-yl)-5-fluoro-7,9-dihydrofuro[3,4-f]quinazolin-6-yl)-7-fluorothieno[3,2-c]pyridine-3-carbonitrile | 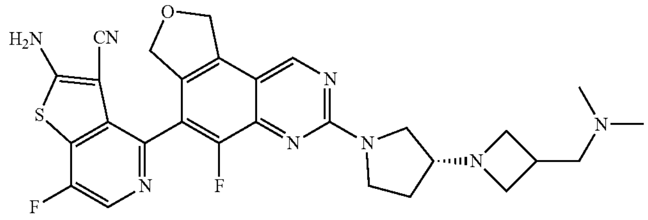 [SMILES: CN(C)CC1CN([C@@H]2CCN(c3ncc4c5c(c(-c6ncc(F)c7sc(N)c(C#N)c67)c(F)c4n3)COC5)C2)C1] | 563 |
| 162D | 2-Amino-4-(3-((S)-3-(3-((dimethylamino)methyl) azetidin-1-yl)pyrrolidin-1-yl)-5-fluoro-7,9-dihydrofuro[3,4-f]quinazolin-6-yl)-7-fluorothieno[3,2-c]pyridine-3-carbonitrile | 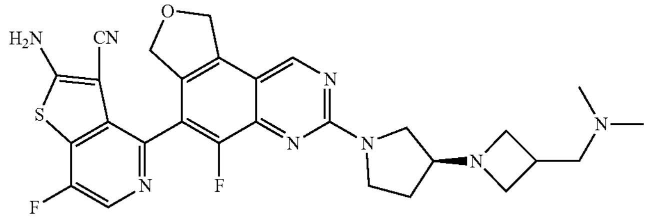 [SMILES: CN(C)CC1CN([C@H]2CCN(c3ncc4c5c(c(-c6ncc(F)c7sc(N)c(C#N)c67)c(F)c4n3)COC5)C2)C1] | 563 |
| 163D | 2-Amino-7-fluoro-4-(5-fluoro-3-((S)-3-hydroxypyrrolidin-1-yl)-7,9-dihydrofuro[3,4-f]quinazolin-6-yl)thieno[3,2-c]pyridine-3-carbonitrile | 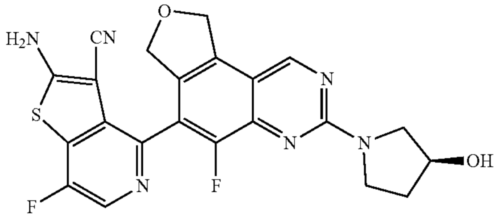 [SMILES: N#Cc1c(N)sc2c(F)cnc(-c3c4c(c5cnc(N6CC[C@H](O)C6)nc5c3F)COC4)c12] | 467 |
| 164D | 2-Amino-7-fluoro-4-(5-fluoro-3-(3-((1-methylpiperidin-4-yl)oxy)pyrrolidin-1-yl)-7,9-dihydrofuro[3,4-f]quinazolin-6-yl)thieno[3,2-c]pyridine-3-carbonitrile | 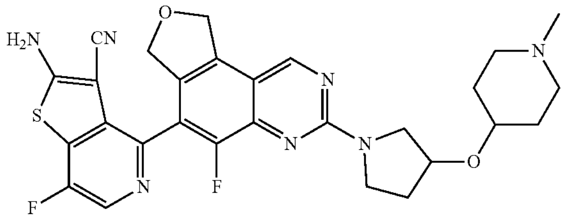 [SMILES: CN1CCC(OC2CCN(c3ncc4c5c(c(-c6ncc(F)c7sc(N)c(C#N)c67)c(F)c4n3)COC5)C2)CC1] | 564 |
| 165D | 2-Amino-4-(3-((2S,3S)-3-amino-2-methylpyrrolidin-1-yl)-5-fluoro-7,9-dihydrofuro[3,4-f]quinazolin-6-yl)-7-fluorothieno[3,2-c]pyridine-3-carbonitrile | 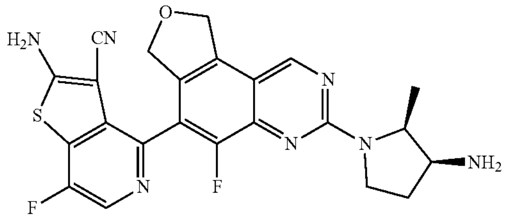 [SMILES: C[C@H]1[C@@H](N)CCN1c1ncc2c3c(c(-c4ncc(F)c5sc(N)c(C#N)c45)c(F)c2n1)COC3] | 480 |

TABLE 28-continued

| Example | Chemical Name | Structure | MS (ES) m/z (M + 1) |
|---|---|---|---|
| 166D | 2-Amino-7-fluoro-4-(5-fluoro-3-((2S,3S)-2-methyl-3-((1-methylcyclopropyl)amino) pyrrolidin-1-yl)-7,9-dihydrofuro[3,4-f]quinazolin-6-yl)thieno[3,2-c]pyridine-3-carbonitrile | 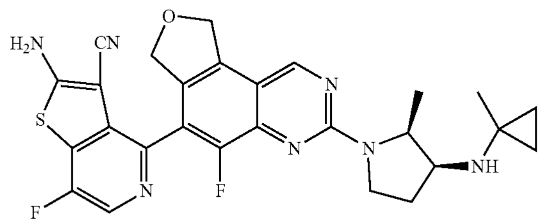 [SMILES: C[C@H]1[C@@H](NC2(C)CC2)CCN1c1ncc2c3c(c(-c4ncc(F)c5sc(N)c(C#N)c45)c(F)c2n1)COC3] | 534 |
| 167D | 2-Amino-7-fluoro-4-(5-fluoro-3-((2S,3S)-3-((3-hydroxybicyclo[1.1.1] pentan-1-yl)amino)-2-methylpyrrolidin-1-yl)-7,9-dihydrofuro[3,4-f]quinazolin-6-yl)thieno[3,2-c]pyridine-3-carbonitrile | 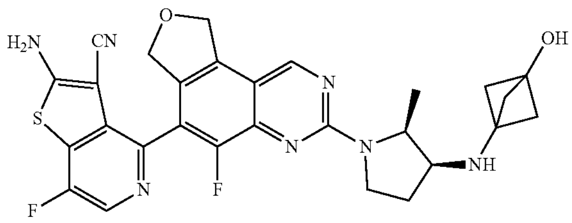 [SMILES: C[C@H]1[C@@H](NC23CC(O)(C2)C3)CCN1c1ncc2c3c(c(-c4ncc(F)c5sc(N)c(C#N)c45)c(F)c2n1)COC3] | 562 |
| 168D | 2-Amino-7-fluoro-4-(5-fluoro-3-((2S,3S)-3-(3-fluoro-2,2-dimethylpropyl)-2-methylpyrrolidin-1-yl)-7,9-dihydrofuro[3,4-f]quinazolin-6-yl)thieno[3,2-c]pyridine-3-carbonitrile | 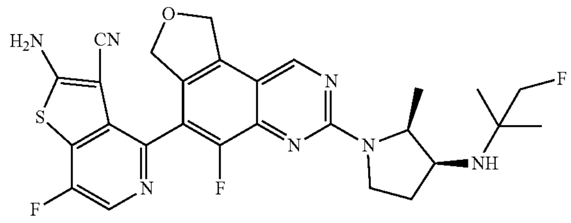 [SMILES: C[C@H]1[C@@H](NC(C)(C)CF)CCN1c1ncc2c3c(c(-c4ncc(F)c5sc(N)c(C#N)c45)c(F)c2n1)COC3] | 554 |
| 169D | 2-Amino-4-(3-((3S,4R)-3-amino-4-fluoropyrrolidin-1-yl)-5-fluoro-7,9-dihydrofuro[3,4-f]quinazolin-6-yl)-7-fluorothieno[3,2-c]pyridine-3-carbonitrile | 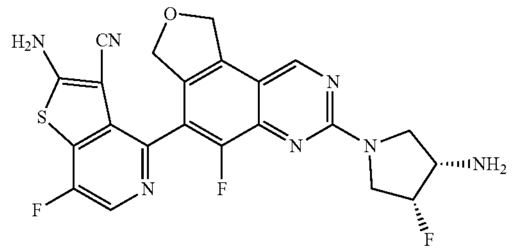 [SMILES: N#Cc1c(N)sc2c(F)cnc(-c3c4c(c5cnc(N6C[C@@H](F)[C@@H](N)C6)nc5c3F)COC4)c12] | 484 |
| 170D | 2-Amino-7-fluoro-4-(5-fluoro-3-((3S,4S)-3-fluoro-4-(isopropylamino)pyrrolidin-1-yl)-7,9-dihydrofuro[3,4-f]quinazolin-6-yl)thieno[3,2-c]pyridine-3-carbonitrile | 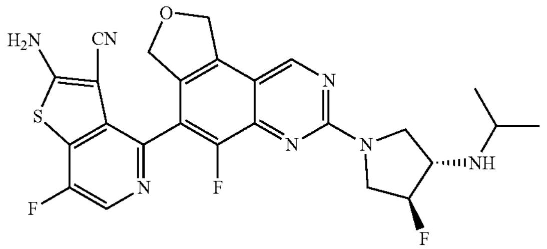 [SMILES: CC(C)N[C@H]1CN(c2ncc3c4c(c(-c5ncc(F)c6sc(N)c(C#N)c56)c(F)c3n2)COC4)C[C@@H]1F] | 526 |
| 171D | 2-Amino-7-fluoro-4-(5-fluoro-3-((3S,4R)-3-fluoro-4-(isopropylamino)pyrrolidin-1-yl)-7,9-dihydrofuro[3,4-f]quinazolin-6-yl)thieno[3,2-c]pyridine-3-carbonitrile | 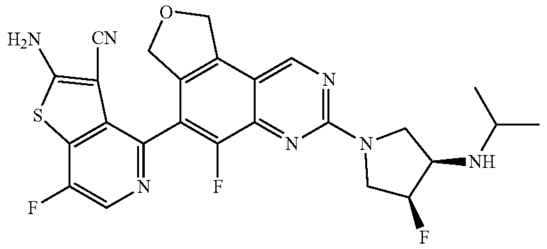 [SMILES: CC(C)N[C@@H]1CN(c2ncc3c4c(c(-c5ncc(F)c6sc(N)c(C#N)c56)c(F)c3n2)COC4)C[C@@H]1F] | 526 |

TABLE 28-continued

| Example | Chemical Name | Structure | MS (ES) m/z (M + 1) |
|---|---|---|---|
| 172D [92] | 2-Amino-7-fluoro-4-(5-fluoro-3-(3-hydroxy-4-(isopropyl(methyl)amino) pyrrolidin-1-yl)-7,9-dihydrofuro[3,4-f]quinazolin-6-yl)thieno[3,2-c]pyridine-3-carbonitrile, Isomer 1 | 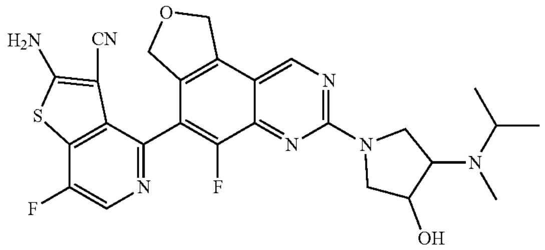 [SMILES: CC(C)N(C)C1CN(c2ncc3c4c(c(-c5ncc(F)c6sc(N)c(C#N)c56)c(F)c3n2)COC4)CC1O] | 538 |
| 173D [92] | 2-Amino-7-fluoro-4-(5-fluoro-3-(3-hydroxy-4-(isopropyl(methyl)amino) pyrrolidin-1-yl)-7,9-dihydrofuro[3,4-f]quinazolin-6-yl)thieno[3,2-c]pyridine-3-carbonitrile, Isomer 2 | 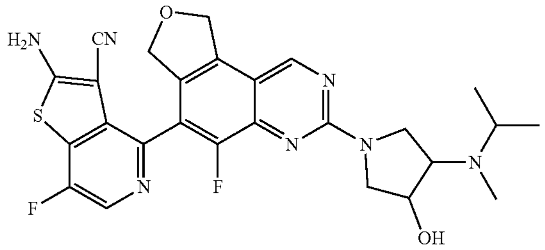 [SMILES: CC(C)N(C)C1CN(c2ncc3c4c(c(-c5ncc(F)c6sc(N)c(C#N)c56)c(F)c3n2)COC4)CC1O] | 538 |
| 174D | 2-Amino-7-fluoro-4-(5-fluoro-3-((3R,4S)-3-hydroxy-4-(isopropylamino)pyrrolidin-1-yl)-7,9-dihydrofuro[3,4-f]quinazolin-6-yl)thieno[3,2-c]pyridine-3-carbonitrile | 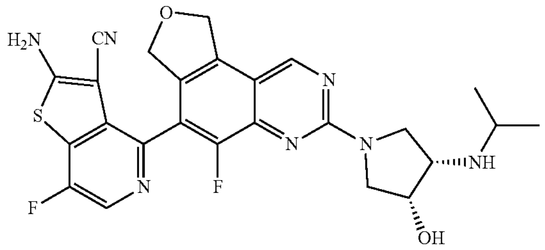 [SMILES: CC(C)N[C@H]1CN(c2ncc3c4c(c(-c5ncc(F)c6sc(N)c(C#N)c56)c(F)c3n2)COC4)C[C@H]1O] | 524 |
| 175D | 2-Amino-7-fluoro-4-(5-fluoro-3-((3S,4S)-3-hydroxy-4-(isopropylamino)pyrrolidin-1-yl)-7,9-dihydrofuro[3,4-f]quinazolin-6-yl)thieno[3,2-c]pyridine-3-carbonitrile | 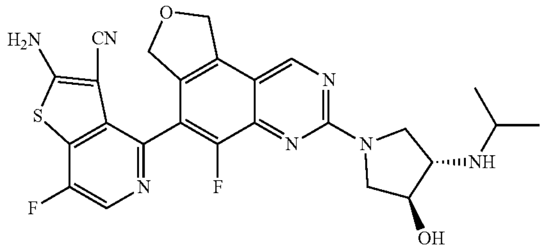 [SMILES: CC(C)N[C@H]1CN(c2ncc3c4c(c(-c5ncc(F)c6sc(N)c(C#N)c56)c(F)c3n2)COC4)C[C@@H]1O] | 524 |
| 176D | 2-Amino-7-fluoro-4-(5-fluoro-3-((3S,4R)-3-hydroxy-4-(isopropylamino) pyrrolidin-1-yl)-7,9-dihydrofuro[3,4-f]quinazolin-6-yl)thieno[3,2-c]pyridine-3-carbonitrile | 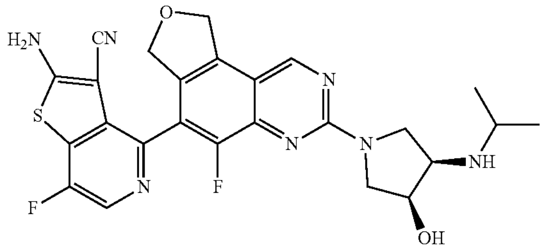 [SMILES: CC(C)N[C@@H]1CN(c2ncc3c4c(c(-c5ncc(F)c6sc(N)c(C#N)c56)c(F)c3n2)COC4)C[C@@H]1O] | 524 |
| 177D | 2-Amino-7-fluoro-4-(5-fluoro-3-((3R,4R)-3-hydroxy-4-(isopropylamino) pyrrolidin-1-yl)-7,9-dihydrofuro[3,4-f]quinazolin-6-yl)thieno[3,2-c]pyridine-3-carbonitrile | 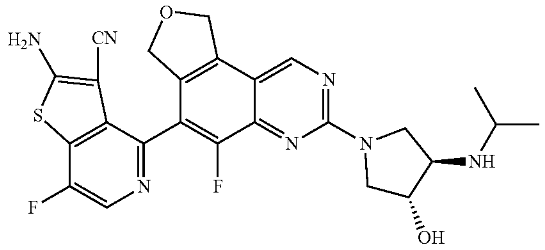 [SMILES: CC(C)N[C@@H]1CN(c2ncc3c4c(c(-c5ncc(F)c6sc(N)c(C#N)c56)c(F)c3n2)COC4)C[C@H]1O] | 524 |

TABLE 28-continued

| Example | Chemical Name | Structure | MS (ES) m/z (M + 1) |
|---|---|---|---|
| 178D [93] | 2-Amino-7-fluoro-4-(5-fluoro-3-(3-hydroxy-4-(isopropylamino) pyrrolidin-1-yl)-7,9-dihydrofuro[3,4-f]quinazolin-6-yl)thieno[3,2-c]pyridine-3-carbonitrile | 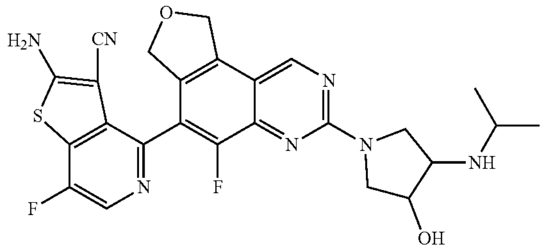 [SMILES: CC(C)NC1CN(c2ncc3c4c(c(-c5ncc(F)c6sc(N)c(C#N)c56)c(F)c3n2)COC4)CC1O] | 524 |
| 179D [94] | 2-Amino-4-(3-(3-((dimethylamino)methyl)-4-hydroxypyrrolidin-1-yl)-5-fluoro-7,9-dihydrofuro[3,4-f]quinazolin-6-yl)-7-fluorothieno[3,2-c]pyridine-3-carbonitrile | 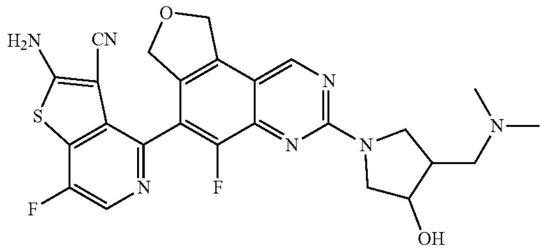 [SMILES: CN(C)CC1CN(c2ncc3c4c(c(-c5ncc(F)c6sc(N)c(C#N)c56)c(F)c3n2)COC4)CC1O] | 524 |
| 180D [95] | 2-Amino-4-(3-(3-((dimethylamino)methyl)-4-hydroxypyrrolidin-1-yl)-5-fluoro-7,9-dihydrofuro[3,4-f]quinazolin-6-yl)-7-fluorothieno[3,2-c]pyridine-3-carbonitrile | 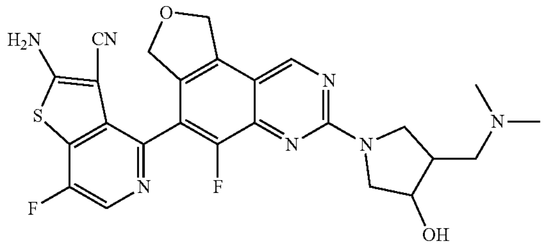 [SMILES: CN(C)CC1CN(c2ncc3c4c(c(-c5ncc(F)c6sc(N)c(C#N)c56)c(F)c3n2)COC4)CC1O] | 524 |
| 181D [96] | 2-Amino-4-(3-(3-((dimethylamino)methyl)-4-hydroxypyrrolidin-1-yl)-5-fluoro-7,9-dihydrofuro[3,4-f]quinazolin-6-yl)-7-fluorothieno[3,2-c]pyridine-3-carbonitrile, Isomer 1 | 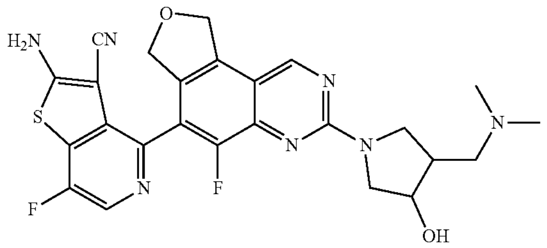 [SMILES: CN(C)CC1CN(c2ncc3c4c(c(-c5ncc(F)c6sc(N)c(C#N)c56)c(F)c3n2)COC4)CC1O] | 524 |
| 182D [96] | 2-Amino-4-(3-(3-((dimethylamino)methyl)-4-hydroxypyrrolidin-1-yl)-5-fluoro-7,9-dihydrofuro[3,4-f]quinazolin-6-yl)-7-fluorothieno[3,2-c]pyridine-3-carbonitrile, Isomer 2 | 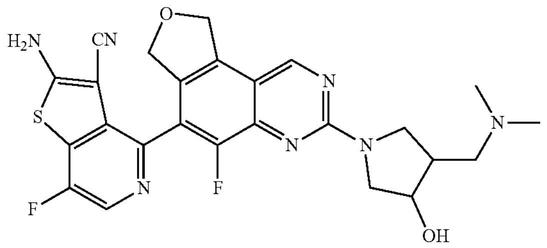 [SMILES: CN(C)CC1CN(c2ncc3c4c(c(-c5ncc(F)c6sc(N)c(C#N)c56)c(F)c3n2)COC4)CC1O] | 524 |
| 183D [97] | 2-Amino-7-fluoro-4-(5-fluoro-3-(3-hydroxy-4-(isopropylamino)-3-methylpyrrolidin-1-yl)-7,9-dihydrofuro[3,4-f]quinazolin-6-yl)thieno[3,2-c]pyridine-3-carbonitrile | 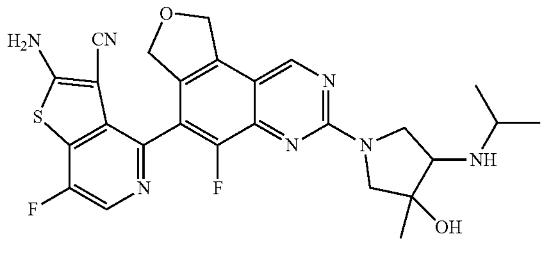 [SMILES: CC(C)NC1CN(c2ncc3c4c(c(-c5ncc(F)c6sc(N)c(C#N)c56)c(F)c3n2)COC4)CC1(C)O] | 538 |

TABLE 28-continued

| Example | Chemical Name | Structure | MS (ES) m/z (M + 1) |
| --- | --- | --- | --- |
| 184D [98] | 2-Amino-7-fluoro-4-(5-fluoro-3-(3-hydroxy-4-(isopropylamino)-3-methylpyrrolidin-1-yl)-7,9-dihydrofuro[3,4-f]quinazolin-6-yl)thieno[3,2-c]pyridine-3-carbonitrile, Isomer 1 | 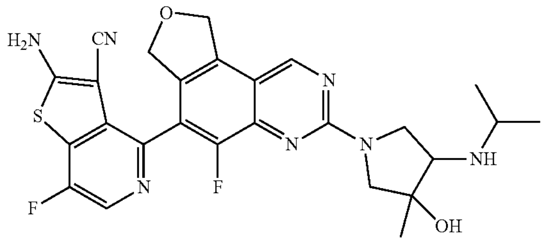 [SMILES: CC(C)NC1CN(c2ncc3c4c(c(-c5ncc(F)c6sc(N)c(C#N)c56)c(F)c3n2)COC4)CC1(C)O] | 538 |
| 185D [98] | 2-Amino-7-fluoro-4-(5-fluoro-3-(3-hydroxy-4-(isopropylamino)-3-methylpyrrolidin-1-yl)-7,9-dihydrofuro[3,4-f]quinazolin-6-yl)thieno[3,2-c]pyridine-3-carbonitrile, Isomer 2 | 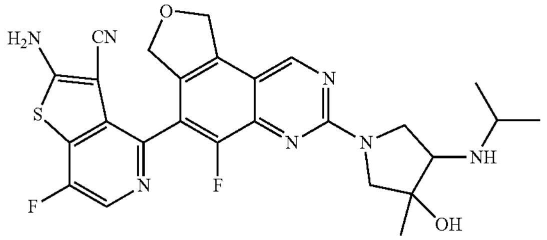 [SMILES: CC(C)NC1CN(c2ncc3c4c(c(-c5ncc(F)c6sc(N)c(C#N)c56)c(F)c3n2)COC4)CC1(C)O] | 538 |
| 186D [99] | 2-Amino-7-fluoro-4-(5-fluoro-3-(3-hydroxy-4-(isopropyl(methyl)amino)-3-methylpyrrolidin-1-yl)-7,9-dihydrofuro[3,4-f]quinazolin-6-yl)thieno[3,2-c]pyridine-3-carbonitrile, Isomer 1 | 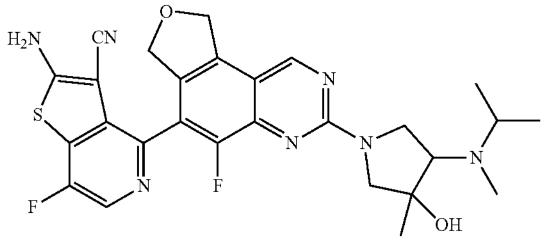 [SMILES: CC(C)N(C)C1CN(c2ncc3c4c(c(-c5ncc(F)c6sc(N)c(C#N)c56)c(F)c3n2)COC4)CC1(C)O] | 552 |
| 187D [99] | 2-Amino-7-fluoro-4-(5-fluoro-3-(3-hydroxy-4-(isopropyl(methyl)amino)-3-methylpyrrolidin-1-yl)-7,9-dihydrofuro[3,4-f]quinazolin-6-yl)thieno[3,2-c]pyridine-3-carbonitrile, Isomer 2 | 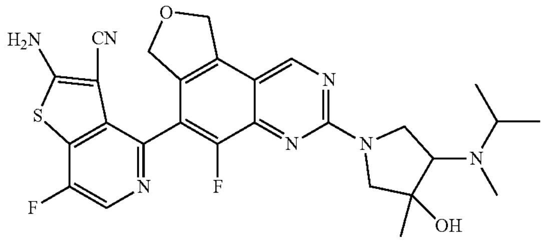 [SMILES: CC(C)N(C)C1CN(c2ncc3c4c(c(-c5ncc(F)c6sc(N)c(C#N)c56)c(F)c3n2)COC4)CC1(C)O] | 552 |
| 188D [100] | 2-Amino-7-fluoro-4-(5-fluoro-3-(3-hydroxy-4-(isopropylamino)-3-methylpyrrolidin-1-yl)-7,9-dihydrofuro[3,4-f]quinazolin-6-yl)thieno[3,2-c]pyridine-3-carbonitrile | 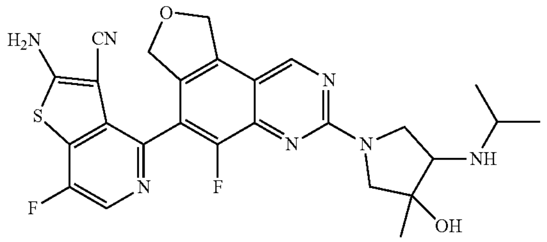 [SMILES: CC(C)NC1CN(c2ncc3c4c(c(-c5ncc(F)c6sc(N)c(C#N)c56)c(F)c3n2)COC4)CC1(C)O] | 538 |
| 189D | 2-Amino-7-fluoro-4-(5-fluoro-3-((2S,3R)-3-hydroxy-2-methylpyrrolidin-1-yl)-7,9-dihydrofuro[3,4-f]quinazolin-6-yl)thieno[3,2-c]pyridine-3-carbonitrile | 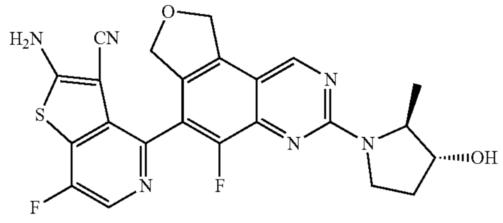 [SMILES: C[C@H]1[C@H](O)CCN1c1ncc2c3c(c(-c4ncc(F)c5sc(N)c(C#N)c45)c(F)c2n1)COC3] | 481 |

TABLE 28-continued

| Example | Chemical Name | Structure | MS (ES) m/z (M + 1) |
|---|---|---|---|
| 190D [101] | 2-Amino-4-(3-(3-(dimethylamino)-4-(methoxymethyl)pyrrolidin-1-yl)-5-fluoro-7,9-dihydrofuro[3,4-f]quinazolin-6-yl)-7-fluorothieno[3,2-c]pyridine-3-carbonitrile, Isomer 1 | 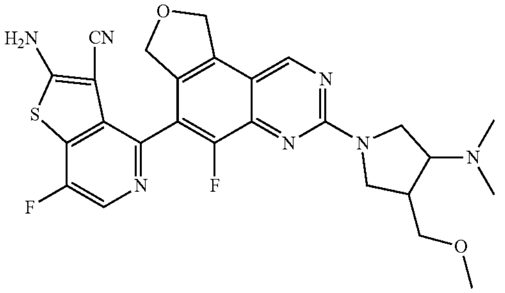 [SMILES: COCC1CN(c2ncc3c4c(c(-c5ncc(F)c6sc(N)c(C#N)c56)c(F)c3n2)COC4)CC1N(C)C] | 538 |
| 191D [101] | 2-Amino-4-(3-(3-(dimethylamino)-4-(methoxymethyl)pyrrolidin-1-yl)-5-fluoro-7,9-dihydrofuro[3,4-f]quinazolin-6-yl)-7-fluorothieno[3,2-c]pyridine-3-carbonitrile, Isomer 2 | 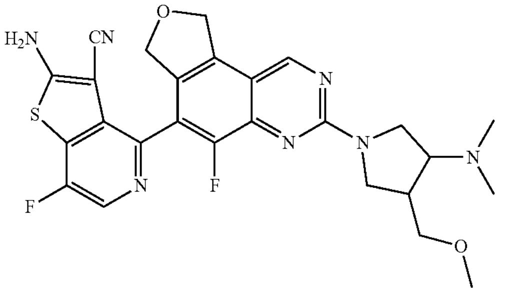 [SMILES: COCC1CN(c2ncc3c4c(c(-c5ncc(F)c6sc(N)c(C#N)c56)c(F)c3n2)COC4)CC1N(C)C] | 538 |
| 192D | 2-Amino-7-fluoro-4-(5-fluoro-3-((3R,4S)-3-(isopropylamino)-4-methylpyrrolidin-1-yl)-7,9-dihydrofuro[3,4-f]quinazolin-6-yl)thieno[3,2-c]pyridine-3-carbonitrile | 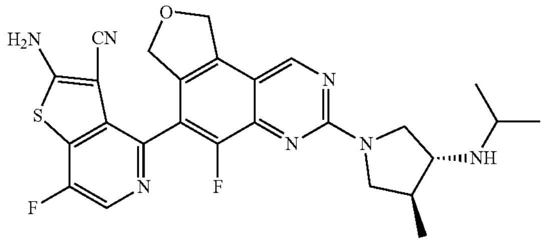 [SMILES: CC(C)N[C@H]1CN(c2ncc3c4c(c(-c5ncc(F)c6sc(N)c(C#N)c56)c(F)c3n2)COC4)C[C@@H]1C] | 522 |
| 193D | 2-Amino-7-fluoro-4-(5-fluoro-3-((3R,4S)-3-(isopropyl(methyl)amino)-4-methylpyrrolidin-1-yl)-7,9-dihydrofuro[3,4-f]quinazolin-6-yl)thieno[3,2-c]pyridine-3-carbonitrile | 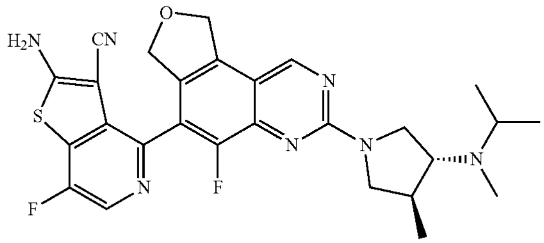 [SMILES: CC(C)N(C)[C@H]1CN(c2ncc3c4c(c(-c5ncc(F)c6sc(N)c(C#N)c56)c(F)c3n2)COC4)C[C@@H]1C] | 536 |
| 194D | 2-Amino-4-(3-((3S,4R)-3-(dimethylamino)-4-(2-hydroxypropan-2-yl)pyrrolidin-1-yl)-5-fluoro-7,9-dihydrofuro[3,4-f]quinazolin-6-yl)-7-fluorothieno[3,2-c]pyridine-3-carbonitrile | 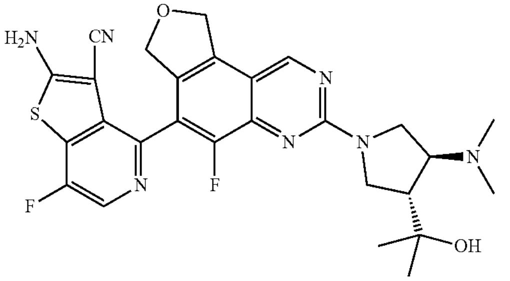 [SMILES: CN(C)[C@@H]1CN(c2ncc3c4c(c(-c5ncc(F)c6sc(N)c(C#N)c56)c(F)c3n2)COC4)C[C@H]1C(C)(C)O] | 552 |

TABLE 28-continued

| Example | Chemical Name | Structure | MS (ES) m/z (M + 1) |
| --- | --- | --- | --- |
| 195D | 2-Amino-7-fluoro-4-(5-fluoro-3-((3S,4R)-3-(isopropylamino)-4-methoxypyrrolidin-1-yl)-7,9-dihydrofuro[3,4-f]quinazolin-6-yl)thieno[3,2-c]pyridine-3-carbonitrile | 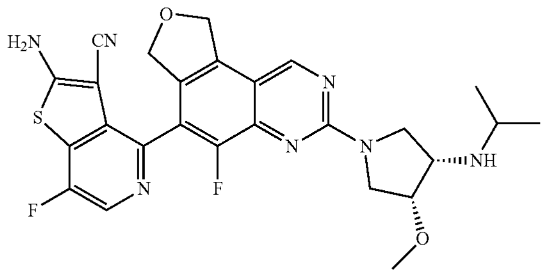 [SMILES: CO[C@@H]1CN(c2ncc3c4c(c(-c5ncc(F)c6sc(N)c(C#N)c56)c(F)c3n2)COC4)C[C@@H]1NC(C)C] | 538 |
| 197D | 2-Amino-7-fluoro-4-(5-fluoro-3-((3S,4S)-3-(isopropylamino)-4-methoxypyrrolidin-1-yl)-7,9-dihydrofuro[3,4-f]quinazolin-6-yl)thieno[3,2-c]pyridine-3-carbonitrile | 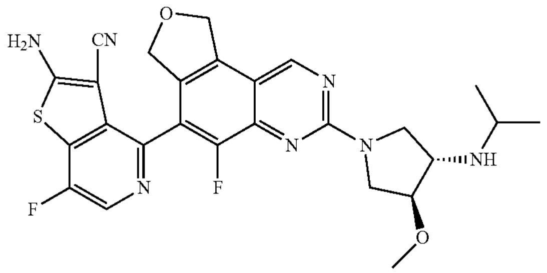 [SMILES: CO[C@H]1CN(c2ncc3c4c(c(-c5ncc(F)c6sc(N)c(C#N)c56)c(F)c3n2)COC4)C[C@@H]1NC(C)C] | 538 |
| 198D | 2-Amino-7-fluoro-4-(5-fluoro-3-((3R,4S)-3-hydroxy-4-(isopropyl(methyl)amino)pyrrolidin-1-yl)-7,9-dihydrofuro[3,4-f]quinazolin-6-yl)thieno[3,2-c]pyridine-3-carbonitrile | 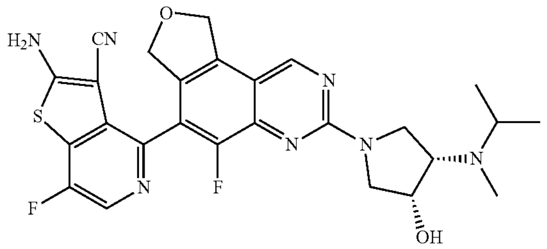 [SMILES: CC(C)N(C)[C@H]1CN(c2ncc3c4c(c(-c5ncc(F)c6sc(N)c(C#N)c56)c(F)c3n2)COC4)C[C@H]1O] | 538 |
| 199D | 2-Amino-7-fluoro-4-(5-fluoro-3-((3R,4R)-3-hydroxy-4-(isopropyl(methyl)amino)pyrrolidin-1-yl)-7,9-dihydrofuro[3,4-f]quinazolin-6-yl)thieno[3,2-c]pyridine-3-carbonitrile | 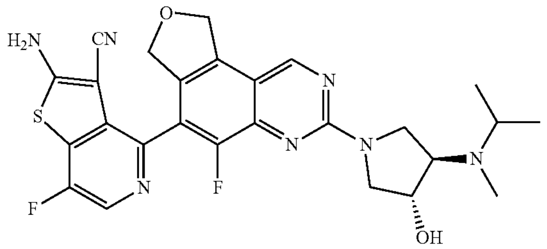 [SMILES: CC(C)N(C)[C@@H]1CN(c2ncc3c4c(c(-c5ncc(F)c6sc(N)c(C#N)c56)c(F)c3n2)COC4)C[C@H]1O] | 538 |
| 200D [102] | 2-Amino-4-(3-(3-(diethylamino)-4-hydroxypyrrolidin-1-yl)-5-fluoro-7,9-dihydrofuro[3,4-f]quinazolin-6-yl)-7-fluorothieno[3,2-c]pyridine-3-carbonitrile. Isomer 1 | 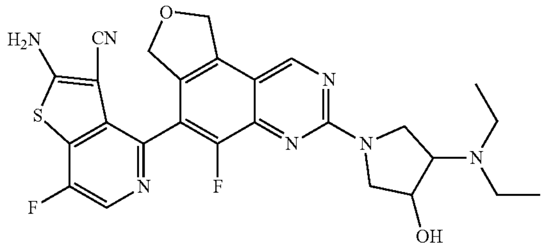 [SMILES: CCN(CC)C1CN(c2ncc3c4c(c(-c5ncc(F)c6sc(N)c(C#N)c56)c(F)c3n2)COC4)CC1O] | 538 |

TABLE 28-continued

| Example | Chemical Name | Structure | MS (ES) m/z (M + 1) |
|---|---|---|---|
| 201D [102] | 2-Amino-4-(3-(3-(diethylamino)-4-hydroxypyrrolidin-1-yl)-5-fluoro-7,9-dihydrofuro[3,4-f]quinazolin-6-yl)-7-fluorothieno[3,2-c]pyridine-3-carbonitrile. Isomer 2 | 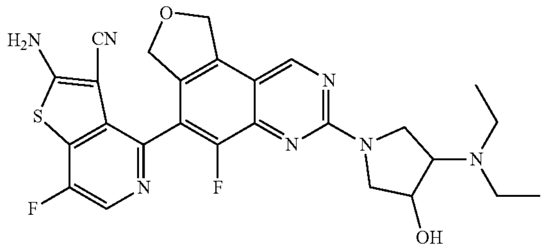 [SMILES: CCN(CC)C1CN(c2ncc3c4c(c(-c5ncc(F)c6sc(N)c(C#N)c56)c(F)c3n2)COC4)CC1O] | 538 |
| 202D | 2-Amino-4-(3-((3S,4R)-3,4-dihydroxypyrrolidin-1-yl)-5-fluoro-7,9-dihydrofuro[3,4-f]quinazolin-6-yl)-7-fluorothieno[3,2-c]pyridine-3-carbonitrile | 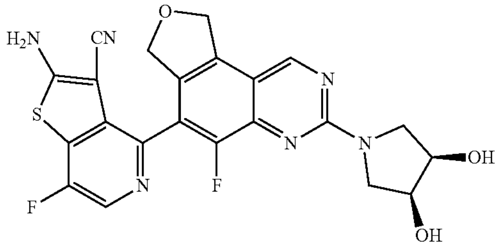 [SMILES: N#Cc1c(N)sc2c(F)cnc(-c3c4c(c5cnc(N6C[C@@H](O)[C@@H](O)C6)nc5c3F)COC4)c12] | 483 |
| 203D | 2-Amino-7-fluoro-4-(5-fluoro-3-(3-(hydroxymethyl)-3-(isopropylamino)pyrrolidin-1-yl)-7,9-dihydrofuro[3,4-f]quinazolin-6-yl)thieno[3,2-c]pyridine-3-carbonitrile | 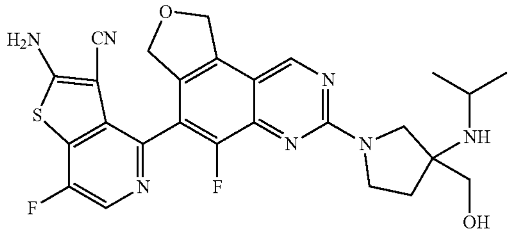 [SMILES: CC(C)NC1(CO)CCN(c2ncc3c4c(c(-c5ncc(F)c6sc(N)c(C#N)c56)c(F)c3n2)COC4)C1] | 538 |
| 204D [103] | 2-Amino-7-fluoro-4-(5-fluoro-3-(3-(hydroxymethyl)-3-(isopropylamino)pyrrolidin-1-yl)-7,9-dihydrofuro[3,4-f]quinazolin-6-yl)thieno[3,2-c]pyridine-3-carbonitrile, Isomer 1 | 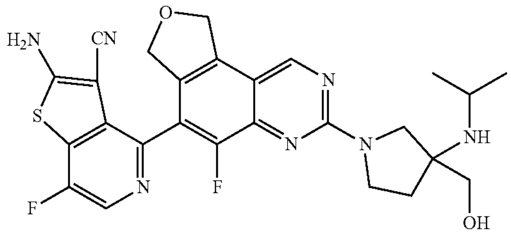 [SMILES: CC(C)NC1(CO)CCN(c2ncc3c4c(c(-c5ncc(F)c6sc(N)c(C#N)c56)c(F)c3n2)COC4)C1] | 538 |
| 205D [103] | 2-Amino-7-fluoro-4-(5-fluoro-3-(3-(hydroxymethyl)-3-(isopropylamino) pyrrolidin-1-yl)-7,9-dihydrofuro[3,4-f]quinazolin-6-yl)thieno[3,2-c]pyridine-3-carbonitrile, Isomer 2 | 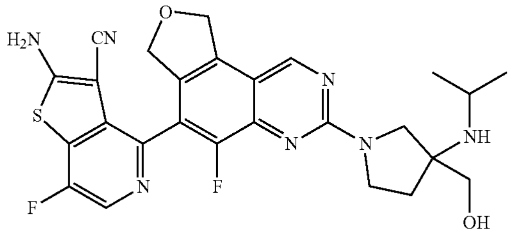 [SMILES: CC(C)NC1(CO)CCN(c2ncc3c4c(c(-c5ncc(F)c6sc(N)c(C#N)c56)c(F)c3n2)COC4)C1] | 538 |
| 206D | 2-Amino-4-(3-(3-(diethylamino)-3-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile, Isomer 1 | 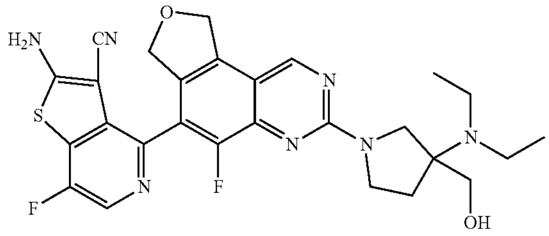 [SMILES: CCN(CC)C1(CO)CCN(c2ncc3c4c(c(-c5ncc(F)c6sc(N)c(C#N)c56)c(F)c3n2)COC4)C1] | 552 |

TABLE 28-continued

| Example | Chemical Name | Structure | MS (ES) m/z (M + 1) |
|---|---|---|---|
| 207D | 2-Amino-4-(3-(3-(diethylamino)-3-(hydroxymethyl)pyrrolidin-1-yl)-5-fluoro-7,9-dihydrofuro[3,4-f]quinazolin-6-yl)-7-fluorothieno[3,2-c]pyridine-3-carbonitrile, Isomer 2 | 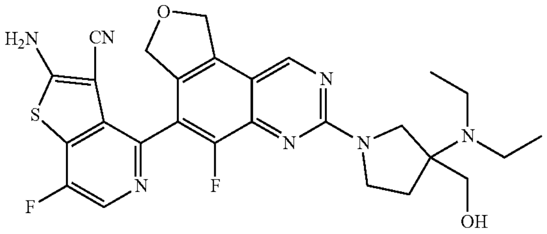 [SMILES: CCN(CC)C1(CO)CCN(c2ncc3c4c(c(-c5ncc(F)c6sc(N)c(C#N)c56)c(F)c3n2)COC4)C1] | 552 |
| 208D | 2-Amino-7-fluoro-4-(5-fluoro-3-(3-(hydroxymethyl)-3-(4-methylpiperazin-1-yl)pyrrolidin-1-yl)-7,9-dihydrofuro[3,4-f]quinazolin-6-yl)thieno[3,2-c]pyridine-3-carbonitrile, Isomer 1 | 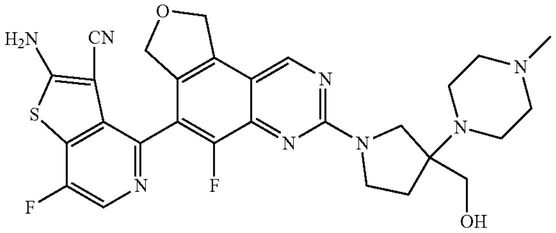 [SMILES: CN1CCN(C2(CO)CCN(c3ncc4c5c(c(-c6ncc(F)c7sc(N)c(C#N)c67)c(F)c4n3)COC5)C2)CC1] | 579 |
| 209D | 2-Amino-7-fluoro-4-(5-fluoro-3-(3-(hydroxymethyl)-3-(4-methylpiperazin-1-yl)pyrrolidin-1-yl)-7,9-dihydrofuro[3,4-f]quinazolin-6-yl)thieno[3,2-c]pyridine-3-carbonitrile, Isomer 2 | 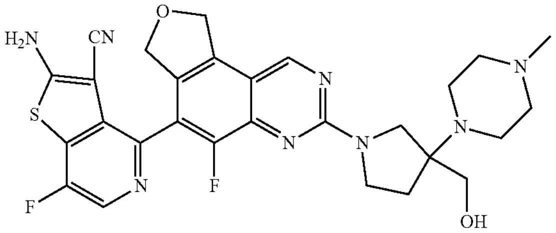 [SMILES: CN1CCN(C2(CO)CCN(c3ncc4c5c(c(-c6ncc(F)c7sc(N)c(C#N)c67)c(F)c4n3)COC5)C2)CC1] | 579 |
| 210D | 2-Amino-7-fluoro-4-(5-fluoro-3-((S)-2-methyl-1,4-diazepan-1-yl)-7,9-dihydrofuro[3,4-f]quinazolin-6-yl)thieno[3,2-c]pyridine-3-carbonitrile | 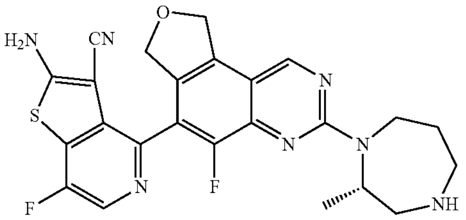 [SMILES: C[C@H]1CNCCCN1c1ncc2c3c(c(-c4ncc(F)c5sc(N)c(C#N)c45)c(F)c2n1)COC3] | 494 |
| 211D | 2-Amino-4-(3-((1R,5S,6r)-6-(dimethylamino)-3-azabicyclo[3.1.0]hexan-3-yl)-5-fluoro-7,9-dihydrofuro[3,4-f]quinazolin-6-yl)-7-fluorothieno[3,2-c]pyridine-3-carbonitrile | 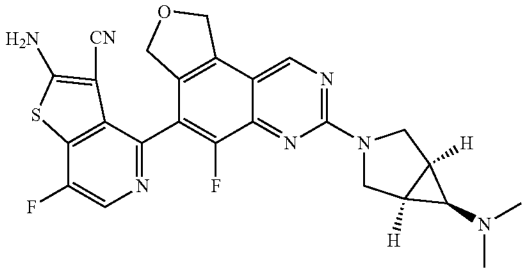 [SMILES: CN(C)[C@@H]1[C@@H]2CN(c3ncc4c5c(c(-c6ncc(F)c7sc(N)c(C#N)c67)c(F)c4n3)COC5)C[C@@H]21] | 506 |
| 212D [104] | 2-Amino-7-fluoro-4-(5-fluoro-3-(4-((S)-2-hydroxypropyl)octahydro-1H-pyrrolo[3,2-b]pyridin-1-yl)-7,9-dihydrofuro[3,4-f]quinazolin-6-yl)thieno[3,2-c]pyridine-3-carbonitrile, Isomer 1 | 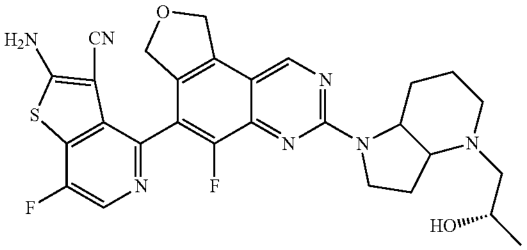 [SMILES: C[C@H](O)CN1CCCC2C1CCN2c1ncc2c3c(c(-c4ncc(F)c5sc(N)c(C#N)c45)c(F)c2n1)COC3] | 564 |

TABLE 28-continued

| Example | Chemical Name | Structure | MS (ES) m/z (M + 1) |
| --- | --- | --- | --- |
| 213D [104] | 2-Amino-7-fluoro-4-(5-fluoro-3-(4-((S)-2-hydroxypropyl)octahydro-1H-pyrrolo[3,2-b]pyridin-1-yl)-7,9-dihydrofuro[3,4-f]quinazolin-6-yl)thieno[3,2-c]pyridine-3-carbonitrile, Isomer 2 | 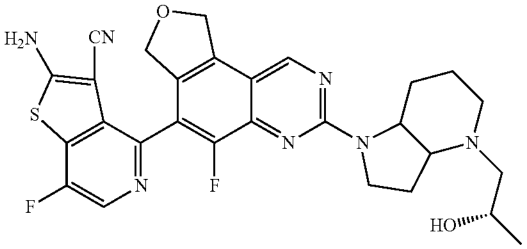 [SMILES: C[C@H](O)CN1CCCC2C1CCN2c1ncc2c3c(c(-c4ncc(F)c5sc(N)c(C#N)c45)c(F)c2n1)COC3] | 564 |
| 214D [105] | 2-Amino-7-fluoro-4-(5-fluoro-3-(4-((R)-2-hydroxypropyl)octahydro-1H-pyrrolo[3,2-b]pyridin-1-yl)-7,9-dihydrofuro[3,4-f]quinazolin-6-yl)thieno[3,2-c]pyridine-3-carbonitrile, Isomer 1 | 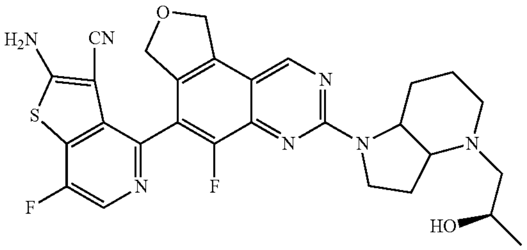 [SMILES: C[C@@H](O)CN1CCCC2C1CCN2c1ncc2c3c(c(-c4ncc(F)c5sc(N)c(C#N)c45)c(F)c2n1)COC3] | 564 |
| 215D [105] | 2-Amino-7-fluoro-4-(5-fluoro-3-(4-((R)-2-hydroxypropyl)octahydro-1H-pyrrolo[3,2-b]pyridin-1-yl)-7,9-dihydrofuro[3,4-f]quinazolin-6-yl)thieno[3,2-c]pyridine-3-carbonitrile, Isomer 2 | 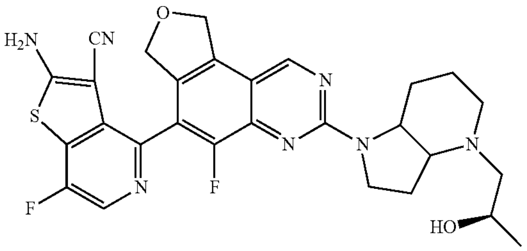 [SMILES: C[C@@H](O)CN1CCCC2C1CCN2c1ncc2c3c(c(-c4ncc(F)c5sc(N)c(C#N)c45)c(F)c2n1)COC3] | 564 |
| 216D [106] | 2-Amino-7-fluoro-4-(5-fluoro-3-(4-(2-hydroxyethyl)octahydro-1H-pyrrolo[3,2-b]pyridin-1-yl)-7,9-dihydrofuro[3,4-f]quinazolin-6-yl)thieno[3,2-c]pyridine-3-carbonitrile, Isomer 1 | 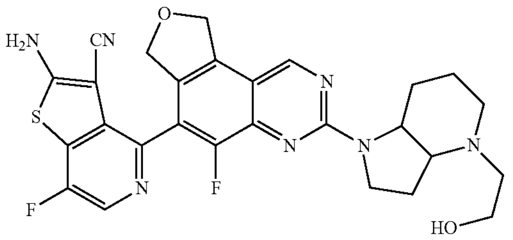 [SMILES: N#Cc1c(N)sc2c(F)cnc(-c3c4c(c5cnc(N6CCC7C6CCCN7CCO)nc5c3F)COC4)c12] | 550 |
| 217D [106] | 2-Amino-7-fluoro-4-(5-fluoro-3-(4-(2-hydroxyethyl)octahydro-1H-pyrrolo[3,2-b]pyridin-1-yl)-7,9-dihydrofuro[3,4-f]quinazolin-6-yl)thieno[3,2-c]pyridine-3-carbonitrile, Isomer 2 | 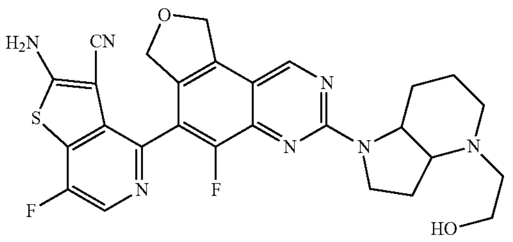 [SMILES: N#Cc1c(N)sc2c(F)cnc(-c3c4c(c5cnc(N6CCC7C6CCCN7CCO)nc5c3F)COC4)c12] | 550 |
| 218D [107] | 2-Amino-7-fluoro-4-(5-fluoro-3-(8-(isopropylamino)-2-oxa-6-azaspiro[3.4]octan-6-yl)-7,9-dihydrofuro[3,4-f]quinazolin-6-yl)thieno[3,2-c]pyridine-3-carbonitrile, Isomer 1 | 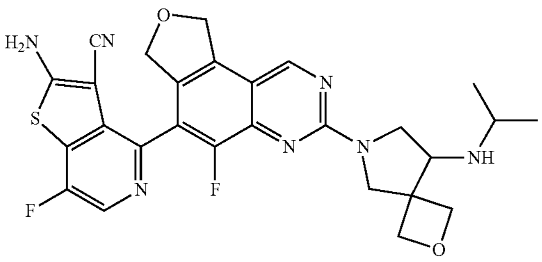 [SMILES: CC(C)NC1CN(c2ncc3c4c(c(-c5ncc(F)c6sc(N)c(C#N)c56)c(F)c3n2)COC4)CC12COC2] | 550 |

TABLE 28-continued

| Example | Chemical Name | Structure | MS (ES) m/z (M + 1) |
| --- | --- | --- | --- |
| 219D [107] | 2-Amino-7-fluoro-4-(5-fluoro-3-(8-(isopropylamino)-2-oxa-6-azaspiro[3.4]octan-6-yl)-7,9-dihydrofuro[3,4-f]quinazolin-6-yl)thieno[3,2-c]pyridine-3-carbonitrile, Isomer 2 | 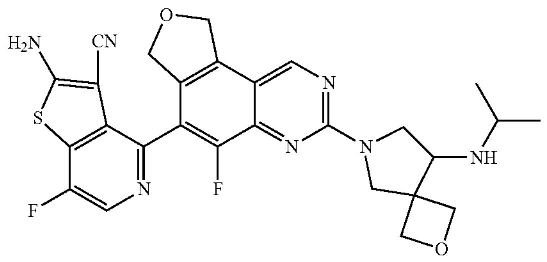 [SMILES: CC(C)NC1CN(c2ncc3c4c(c(-c5ncc(F)c6sc(N)c(C#N)c56)c(F)c3n2)COC4)CC12COC2] | 550 |
| 220D [108] | 2-Amino-4-(3-(8-(dimethylamino)-2-oxa-6-azaspiro[3.4]octan-6-yl)-5-fluoro-7,9-dihydrofuro[3,4-f]quinazolin-6-yl)-7-fluorothieno[3,2-c]pyridine-3-carbonitrile, Isomer 1 | 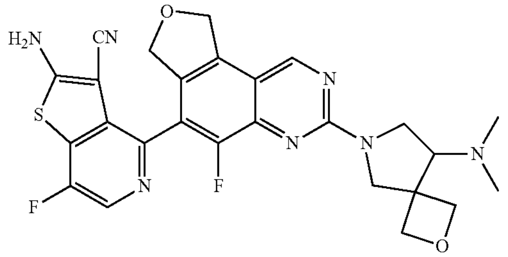 [SMILES: CN(C)C1CN(c2ncc3c4c(c(-c5ncc(F)c6sc(N)c(C#N)c56)c(F)c3n2)COC4)CC12COC2] | 536 |
| 221D [108] | 2-Amino-4-(3-(8-(dimethylamino)-2-oxa-6-azaspiro[3.4]octan-6-yl)-5-fluoro-7,9-dihydrofuro[3,4-f]quinazolin-6-yl)-7-fluorothieno[3,2-c]pyridine-3-carbonitrile, Isomer 2 | 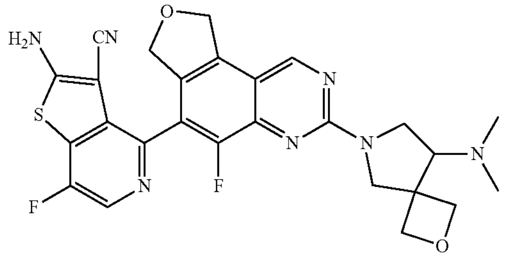 [SMILES: CN(C)C1CN(c2ncc3c4c(c(-c5ncc(F)c6sc(N)c(C#N)c56)c(F)c3n2)COC4)CC12COC2] | 536 |
| 222D [109] | 2-Amino-7-fluoro-4-(5-fluoro-3-(7-methyl-2,7-diazaspiro[4.4]nonan-2-yl)-7,9-dihydrofuro[3,4-f]quinazolin-6-yl)thieno[3,2-c]pyridine-3-carbonitrile, Isomer 1 | 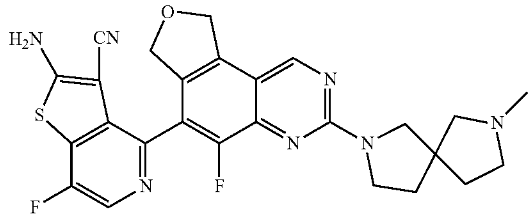 [SMILES: CN1CCC2(CCN(c3ncc4c5c(c(-c6ncc(F)c7sc(N)c(C#N)c67)c(F)c4n3)COC5)C2)C1] | 520 |
| 223D [109] | 2-Amino-7-fluoro-4-(5-fluoro-3-(7-methyl-2,7-diazaspiro[4.4]nonan-2-yl)-7,9-dihydrofuro[3,4-f]quinazolin-6-yl)thieno[3,2-c]pyridine-3-carbonitrile, Isomer 2 | 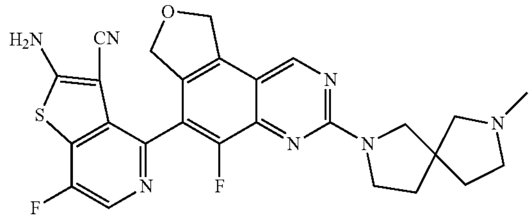 [SMILES: CN1CCC2(CCN(c3ncc4c5c(c(-c6ncc(F)c7sc(N)c(C#N)c67)c(F)c4n3)COC5)C2)C1] | 520 |
| 224D | 2-Amino-7-fluoro-4-(5-fluoro-3-((3S,4S)-3-fluoro-4-((propan-2-yl-1,1,1,3,3,3-d6)amino)pyrrolidin-1-yl)-7,9-dihydrofuro[3,4-f]quinazolin-6-yl)thieno[3,2-c]pyridine-3-carbonitrile | 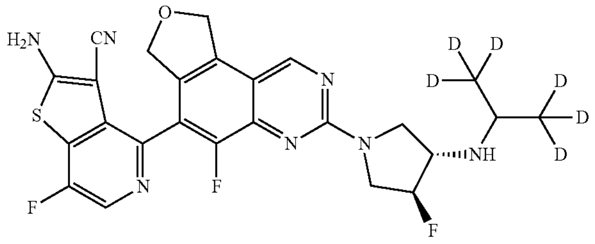 [SMILES: [2H]C([2H])([2H])C(N[C@H]1CN(c2ncc3c4c(c(-c5ncc(F)c6sc(N)c(C#N)c56)c(F)c3n2)COC4)C[C@@H]1F)C([2H])([2H])[2H]] | 532 |

TABLE 28-continued

| Example | Chemical Name | Structure | MS (ES) m/z (M + 1) |
|---|---|---|---|
| 225D | 2-Amino-7-fluoro-4-(5-fluoro-3-((3R,4S)-3-hydroxy-4-((propan-2-yl-1,1,1,3,3,3-d6)amino)pyrrolidin-1-yl)-7,9-dihydrofuro[3,4-f]quinazolin-6-yl)thieno[3,2-c]pyridine-3-carbonitrile | 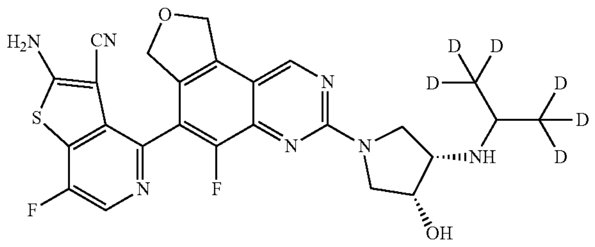 [SMILES: [2H]C([2H])([2H])C(N[C@H]1CN(c2ncc3c4c(c(-c5ncc(F)c6sc(N)c(C#N)c56)c(F)c3n2)COC4)C[C@H]1O)C([2H])([2H])[2H]] | 530 |
| 226D | 2-Amino-7-fluoro-4-(5-fluoro-3-((3R,4R)-3-hydroxy-4-((propan-2-yl-1,1,1,3,3,3-d6)amino)pyrrolidin-1-yl)-7,9-dihydrofuro[3,4-f]quinazolin-6-yl)thieno[3,2-c]pyridine-3-carbonitrile | 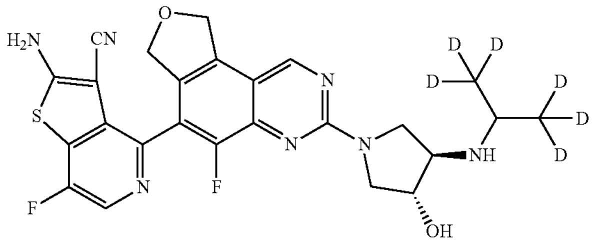 [SMILES: [2H]C([2H])([2H])C(N[C@@H]1CN(c2ncc3c4c(c(-c5ncc(F)c6sc(N)c(C#N)c56)c(F)c3n2)COC4)C[C@H]1O)C([2H])([2H])[2H]] | 530 |
| 227D | 2-Amino-7-fluoro-4-(5-fluoro-3-(4-(methyl-d3)octahydro-1H-pyrrolo[3,2-b]pyridin-1-yl)-7,9-dihydrofuro[3,4-f]quinazolin-6-yl)thieno[3,2-c]pyridine-3-carbonitrile | 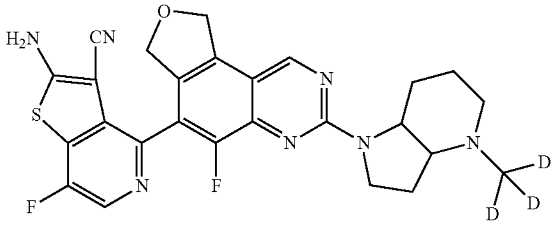 [SMILES: [2H]C([2H])([2H])N1CCCC2C1CCN2c1ncc2c3c(c(-c4ncc(F)c5sc(N)c(C#N)c45)c(F)c2n1)COC3] | 523 |
| 228D | 2-Amino-7-fluoro-4-(5-fluoro-3-((S)-3-(4-(methyl-d3)piperazin-1-yl)pyrrolidin-1-yl)-7,9-dihydrofuro[3,4-f]quinazolin-6-yl)thieno[3,2-c]pyridine-3-carbonitrile | 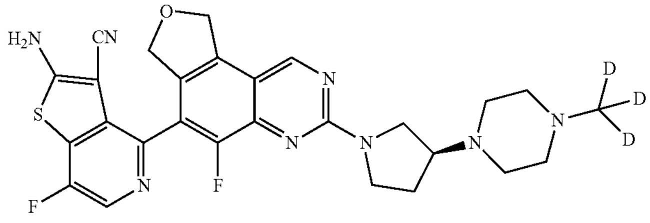 [SMILES: [2H]C([2H])([2H])N1CCN([C@H]2CCN(c3ncc4c5c(c(-c6ncc(F)c7sc(N)c(C#N)c67)c(F)c4n3)COC5)C2)CC1] | 552 |
| 229D | 2-Amino-7-fluoro-4-(5-fluoro-3-((R)-3-(4-(methyl-d3)piperazin-1-yl)pyrrolidin-1-yl)-7,9-dihydrofuro[3,4-f]quinazolin-6-yl)thieno[3,2-c]pyridine-3-carbonitrile | 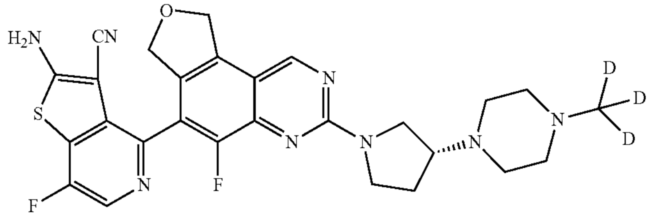 [SMILES: [2H]C([2H])([2H])N1CCN([C@@H]2CCN(c3ncc4c5c(c(-c6ncc(F)c7sc(N)c(C#N)c67)c(F)c4n3)COC5)C2)CC1] | 552 |
| 230D | 2-Amino-7-fluoro-4-(5-fluoro-3-((S)-7-((propan-2-yl-1,1,1,3,3,3-d6)amino)-5-azaspiro[2.4]heptan-5-yl)-7,9-dihydrofuro[3,4-f]quinazolin-6-yl)thieno[3,2-c]pyridine-3-carbonitrile | 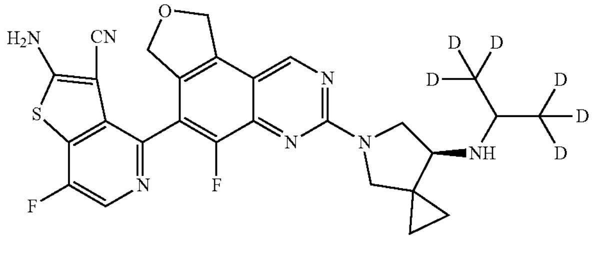 [SMILES: [2H]C([2H])([2H])C(N[C@@H]1CN(c2ncc3c4c(c(-c5ncc(F)c6sc(N)c(C#N)c56)c(F)c3n2)COC4)CC12CC2)C([2H])([2H])[2H]] | 540 |

TABLE 28-continued

| Example | Chemical Name | Structure | MS (ES) m/z (M + 1) |
|---|---|---|---|
| 231D | 2-Amino-7-fluoro-4-(5-fluoro-3-((3S,4S)-3-fluoro-4-((propan-2-yl-1,1,1,3,3,3-d6)amino)pyrrolidin-1-yl)-7,9-dihydrofuro[3,4-f]quinazolin-6-yl)thieno[3,2-c]pyridine-3-carbonitrile | 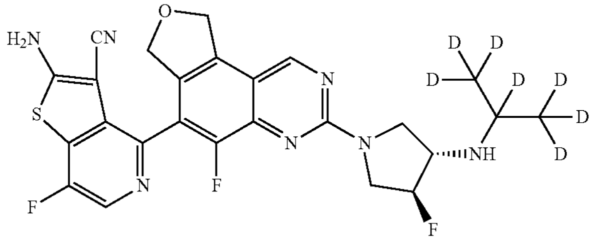 [SMILES: [2H]C([2H])([2H])C([2H])(N[C@H]1CN(c2ncc3c4c(c(-c5ncc(F)c6sc(N)c(C#N)c56)c(F)c3n2)COC4)C[C@@H]1F)C([2H])([2H])[2H]] | 533 |
| 232D [110] | 2-Amino-4-(3-((3S,4S)-3-amino-4-fluoropyrrolidin-1-yl)-5-fluoro-7,9-dihydrofuro[3,4-f]quinazolin-6-yl)-7-fluorothieno[3,2-c]pyridine-3-carbonitrile | 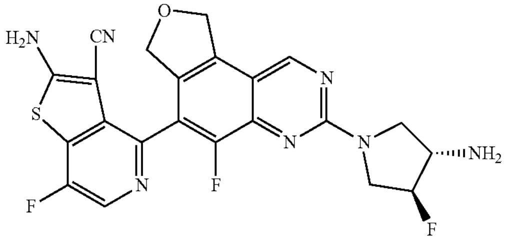 [SMILES: N#Cc1c(N)sc2c(F)cnc(-c3c4c(c5cnc(N6C[C@H](N)[C@@H](F)C6)nc5c3F)COC4)c12] | 484 |
| 233D | 2-Amino-7-fluoro-4-(5-fluoro-3-((S)-3-(4-(propan-2-yl-1,1,1,3,3,3-d6)piperazin-1-yl)pyrrolidin-1-yl)-7,9-dihydrofuro[3,4-f]quinazolin-6-yl)thieno[3,2-c]pyridine-3-carbonitrile | 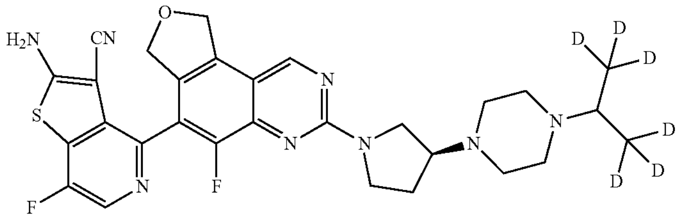 [SMILES: [2H]C([2H])([2H])C(N1CCN([C@H]2CCN(c3ncc4c5c(c(-c6ncc(F)c7sc(N)c(C#N)c67)c(F)c4n3)COC5)C2)CC1)C([2H])([2H])[2H]] | 583 |
| 234D | 2-Amino-7-fluoro-4-(5-fluoro-3-((2S,3S)-2-methyl-3-(4-(propan-2-yl-1,1,1,3,3,3-d6)piperazin-1-yl)pyrrolidin-1-yl)-7,9-dihydrofuro[3,4-f]quinazolin-6-yl)thieno[3,2-c]pyridine-3-carbonitrile | 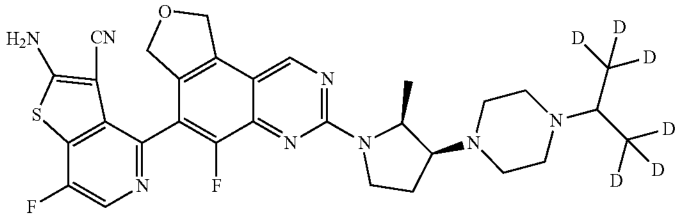 [SMILES: [2H]C([2H])([2H])C(N1CCN([C@H]2CCN(c3ncc4c5c(c(-c6ncc(F)c7sc(N)c(C#N)c67)c(F)c4n3)COC5)[C@H]2C)CC1)C([2H])([2H])[2H]] | 597 |
| 235D | 2-Amino-4-(3-((2S,3S)-3-(4-(ethyl-d5)piperazin-1-yl)-2-methylpyrrolidin-1-yl)-5-fluoro-7,9-dihydrofuro[3,4-f]quinazolin-6-yl)-7-fluorothieno[3,2-c]pyridine-3-carbonitrile | 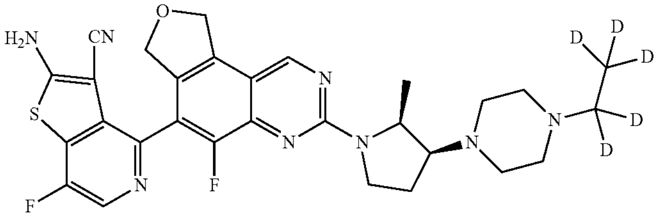 [SMILES: [2H]C([2H])([2H])C([2H])([2H])N1CCN([C@H]2CCN(c3ncc4c5c(c(-c6ncc(F)c7sc(N)c(C#N)c67)c(F)c4n3)COC5)[C@H]2C)CC1] | 582 |
| 236D [111] | 2-Amino-4-(3-((S)-3-(dimethylamino)pyrrolidin-1-yl)-5-fluoro-7,9-dihydrofuro[3,4-f]quinazolin-6-yl)-5-fluorothieno[2,3-b]pyridine-3-carbonitrile, Atropisomer 1 | 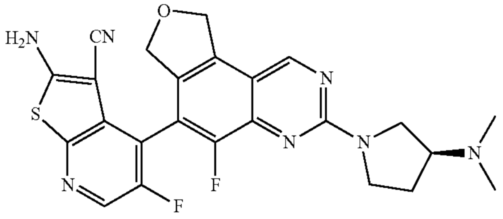 [SMILES: CN(C)[C@H]1CCN(c2ncc3c4c(c(-c5c(F)cnc6sc(N)c(C#N)c56)c(F)c3n2)COC4)C1] | 494 |

TABLE 28-continued

| Example | Chemical Name | Structure | MS (ES) m/z (M + 1) |
| --- | --- | --- | --- |
| 237D [111] | 2-Amino-4-(3-((S)-3-(dimethylamino)pyrrolidin-1-yl)-5-fluoro-7,9-dihydrofuro[3,4-f]quinazolin-6-yl)-5-fluorothieno[2,3-b]pyridine-3-carbonitrile, Atropisomer 2 | 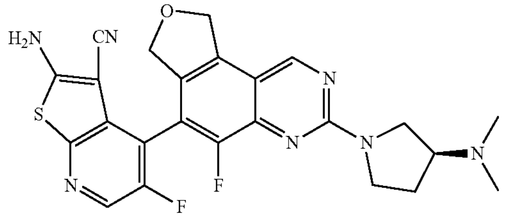 [SMILES: CN(C)[C@H]1CCN(c2ncc3c4c(c(-c5c(F)cnc6sc(N)c(C#N)c56)c(F)c3n2)COC4)C1] | 494 |
| 238D [112] | 2-Amino-5-fluoro-4-(5-fluoro-3-((3R,4S)-3-(isopropylamino)-4-methoxypyrrolidin-1-yl)-7,9-dihydrofuro[3,4-f]quinazolin-6-yl)thieno[2,3-b]pyridine-3-carbonitrile, Atropisomer 1 | 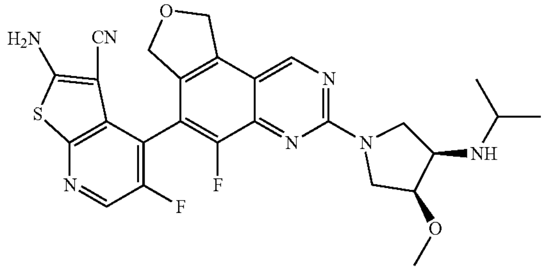 [SMILES: CO[C@H]1CN(c2ncc3c4c(c(-c5c(F)cnc6sc(N)c(C#N)c56)c(F)c3n2)COC4)C[C@H]1NC(C)C] | 538 |
| 239D [112] | 2-Amino-5-fluoro-4-(5-fluoro-3-((3R,4S)-3-(isopropylamino)-4-methoxypyrrolidin-1-yl)-7,9-dihydrofuro[3,4-f]quinazolin-6-yl)thieno[2,3-b]pyridine-3-carbonitrile, Atropisomer 2 | 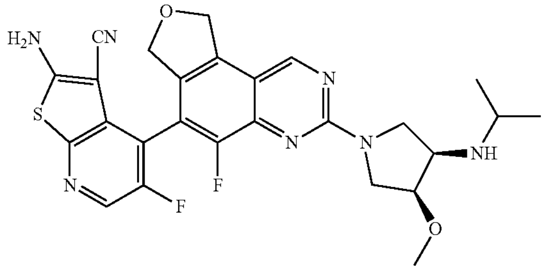 [SMILES: CO[C@H]1CN(c2ncc3c4c(c(-c5c(F)cnc6sc(N)c(C#N)c56)c(F)c3n2)COC4)C[C@H]1NC(C)C] | 538 |
| 240D [113] | 2-Amino-5-fluoro-4-(5-fluoro-3-((R)-3-(4-methylpiperazin-1-yl)pyrrolidin-1-yl)-7,9-dihydrofuro[3,4-f]quinazolin-6-yl)thieno[2,3-b]pyridine-3-carbonitrile, Atropisomer 1 | 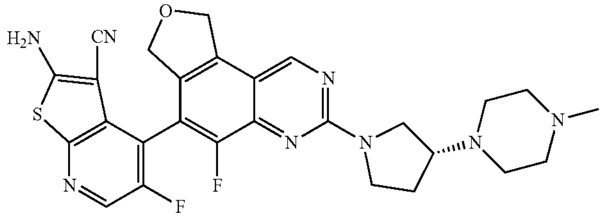 [SMILES: CN1CCN([C@@H]2CCN(c3ncc4c5c(c(-c6c(F)cnc7sc(N)c(C#N)c67)c(F)c4n3)COC5)C2)CC1] | 549 |
| 241D [113] | 2-Amino-5-fluoro-4-(5-fluoro-3-((R)-3-(4-methylpiperazin-1-yl)pyrrolidin-1-yl)-7,9-dihydrofuro[3,4-f]quinazolin-6-yl)thieno[2,3-b]pyridine-3-carbonitrile, Atropisomer 2 | 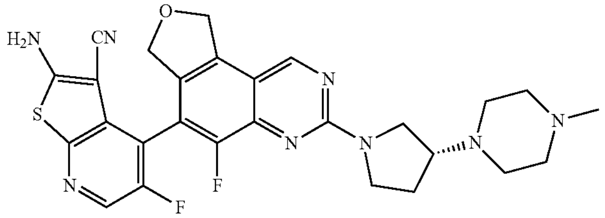 [SMILES: CN1CCN([C@@H]2CCN(c3ncc4c5c(c(-c6c(F)cnc7sc(N)c(C#N)c67)c(F)c4n3)COC5)C2)CC1] | 549 |
| 242D [114] | 2-Amino-5-fluoro-4-(5-fluoro-3-((3S,4R)-3-(isopropylamino)-4-methylpyrrolidin-1-yl)-7,9-dihydrofuro[3,4-f]quinazolin-6-yl)benzo[b]thiophene-3-carbonitrile, Atropisomer 1 | 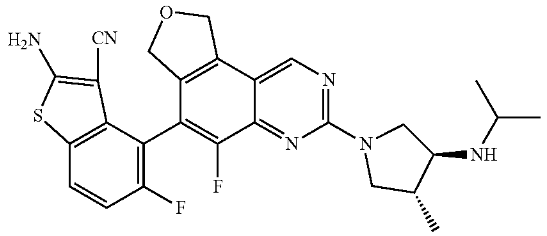 [SMILES: CC(C)N[C@@H]1CN(c2ncc3c4c(c(-c5c(F)ccc6sc(N)c(C#N)c56)c(F)c3n2)COC4)C[C@H]1C] | 521 |

TABLE 28-continued

| Example | Chemical Name | Structure | MS (ES) m/z (M + 1) |
|---|---|---|---|
| 243D [114] | 2-Amino-5-fluoro-4-(5-fluoro-3-((3S,4R)-3-(isopropylamino)-4-methylpyrrolidin-1-yl)-7,9-dihydrofuro[3,4-f]quinazolin-6-yl)benzo[b]thiophene-3-carbonitrile, Atropisomer 2 | 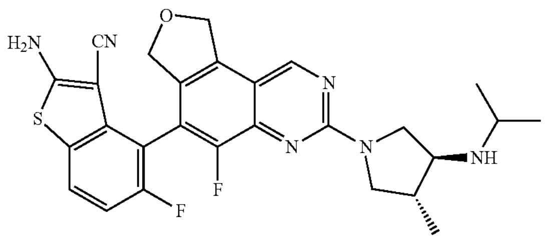 [SMILES: CC(C)N[C@@H]1CN(c2ncc3c4c(c(-c5c(F)ccc6sc(N)c(C#N)c56)c(F)c3n2)COC4)C[C@H]1C] | 521 |
| 244D [115] | 2-Amino-4-(3-((3S,4R)-3-(dimethylamino)-4-hydroxypyrrolidin-1-yl)-5-fluoro-7,9-dihydrofuro[3,4-f]quinazolin-6-yl)-5-fluorobenzo[b]thiophene-3-carbonitrile, Atropisomer 1 | 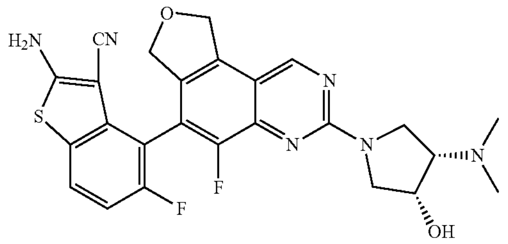 [SMILES: CN(C)[C@H]1CN(c2ncc3c4c(c(-c5c(F)ccc6sc(N)c(C#N)c56)c(F)c3n2)COC4)C[C@H]1O] | 509 |
| 245D [115] | 2-Amino-4-(3-((3S,4R)-3-(dimethylamino)-4-hydroxypyrrolidin-1-yl)-5-fluoro-7,9-dihydrofuro[3,4-f]quinazolin-6-yl)-5-fluorobenzo[b]thiophene-3-carbonitrile, Atropisomer 2 | 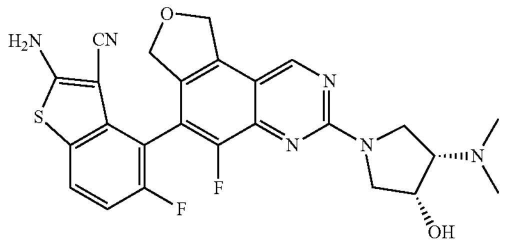 [SMILES: CN(C)[C@H]1CN(c2ncc3c4c(c(-c5c(F)ccc6sc(N)c(C#N)c56)c(F)c3n2)COC4)C[C@H]1O] | 509 |
| 246D [26] | 2-Amino-5-fluoro-4-(5-fluoro-3-((R)-3-(4-methylpiperazin-1-yl)pyrrolidin-1-yl)-7,9-dihydrofuro[3,4-f]quinazolin-6-yl)benzo[b]thiophene-3-carbonitrile, Atropisomer 1 | 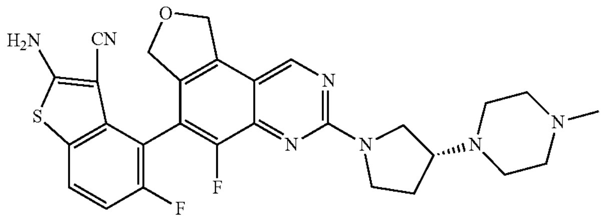 [SMILES: CN1CCN([C@@H]2CCN(c3ncc4c5c(c(-c6c(F)ccc7sc(N)c(C#N)c67)c(F)c4n3)COC5)C2)CC1] | 548 |
| 247D [26] | 2-Amino-5-fluoro-4-(5-fluoro-3-((S)-3-(4-methylpiperazin-1-yl)pyrrolidin-1-yl)-7,9-dihydrofuro[3,4-f]quinazolin-6-yl)benzo[b]thiophene-3-carbonitrile, Atropisomer 1 | 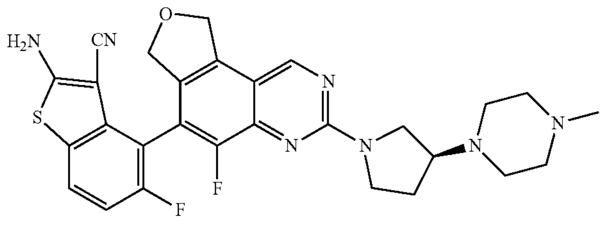 [SMILES: CN1CCN([C@H]2CCN(c3ncc4c5c(c(-c6c(F)ccc7sc(N)c(C#N)c67)c(F)c4n3)COC5)C2)CC1] | 548 |
| 248D [116] | 2-Amino-5-fluoro-4-(5-fluoro-3-((3S,4R)-3-hydroxy-4-(isopropyl(methyl)amino)pyrrolidin-1-yl)-7,9-dihydrofuro[3,4-f]quinazolin-6-yl)benzo[b]thiophene-3-carbonitrile, Atropisomer 1 | 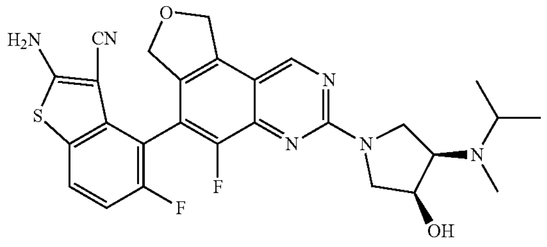 [SMILES: CC(C)N(C)[C@@H]1CN(c2ncc3c4c(c(-c5c(F)ccc6sc(N)c(C#N)c56)c(F)c3n2)COC4)C[C@@H]1O] | 537 |

TABLE 28-continued

| Example | Chemical Name | Structure | MS (ES) m/z (M + 1) |
|---|---|---|---|
| 249D [116] | 2-Amino-5-fluoro-4-(5-fluoro-3-((3S,4R)-3-hydroxy-4-(isopropyl(methyl)amino) pyrrolidin-1-yl)-7,9-dihydrofuro[3,4-f]quinazolin-6-yl)benzo[b]thiophene-3-carbonitrile, Atropisomer 2 | 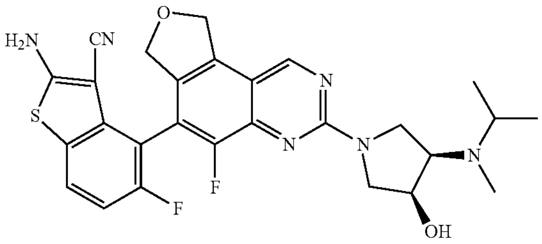 [SMILES: CC(C)N(C)[C@@H]1CN(c2ncc3c4c(c(-c5c(F)ccc6sc(N)c(C#N)c56)c(F)c3n2)COC4)C[C@@H]1O] | 537 |
| 250D [117] | 2-Amino-5-fluoro-4-(5-fluoro-3-((3S,4S)-3-hydroxy-4-(isopropyl(methyl)amino) pyrrolidin-1-yl)-7,9-dihydrofuro[3,4-f]quinazolin-6-yl)benzo[b]thiophene-3-carbonitrile, Atropisomer 1 | 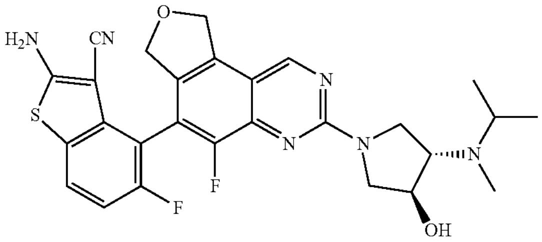 [SMILES: CC(C)N(C)[C@H]1CN(c2ncc3c4c(c(-c5c(F)ccc6sc(N)c(C#N)c56)c(F)c3n2)COC4)C[C@@H]1O] | 537 |
| 251D [117] | 2-Amino-5-fluoro-4-(5-fluoro-3-((3S,4S)-3-hydroxy-4-(isopropyl(methyl)amino) pyrrolidin-1-yl)-7,9-dihydrofuro[3,4-f]quinazolin-6-yl)benzo[b]thiophene-3-carbonitrile, Atropisomer 2 | 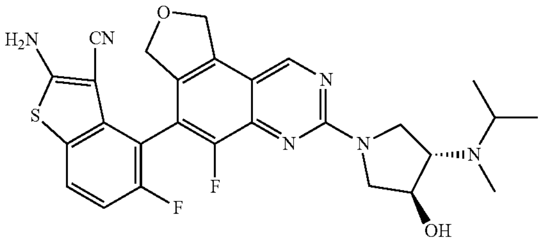 [SMILES: CC(C)N(C)[C@H]1CN(c2ncc3c4c(c(-c5c(F)ccc6sc(N)c(C#N)c56)c(F)c3n2)COC4)C[C@@H]1O] | 537 |
| 252D [118] | 2-Amino-5-fluoro-4-(5-fluoro-3-((3R,4R)-3-hydroxy-4-(isopropyl(methyl)amino) pyrrolidin-1-yl)-7,9-dihydrofuro[3,4-f]quinazolin-6-yl)benzo[b]thiophene-3-carbonitrile, Atropsiomer 1 | 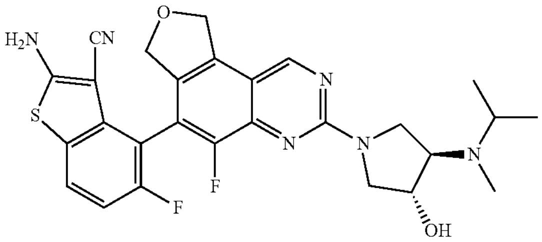 [SMILES: CC(C)N(C)[C@@H]1CN(c2ncc3c4c(c(-c5c(F)ccc6sc(N)c(C#N)c56)c(F)c3n2)COC4)C[C@H]1O] | 537 |
| 253D [118] | 2-Amino-5-fluoro-4-(5-fluoro-3-((3R,4R)-3-hydroxy-4-(isopropyl(methyl)amino) pyrrolidin-1-yl)-7,9-dihydrofuro[3,4-f]quinazolin-6-yl)benzo[b]thiophene-3-carbonitrile, Atropsiomer 2 | 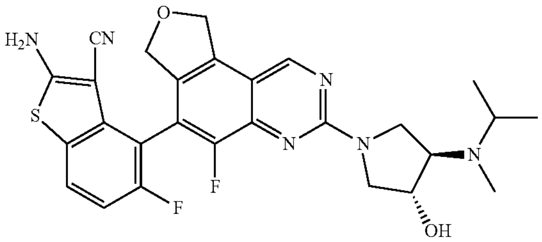 [SMILES: CC(C)N(C)[C@@H]1CN(c2ncc3c4c(c(-c5c(F)ccc6sc(N)c(C#N)c56)c(F)c3n2)COC4)C[C@H]1O] | 537 |
| 254D [119] | 2-Amino-5-fluoro-4-(5-fluoro-3-((3R,4S)-3-hydroxy-4-(isopropyl(methyl)amino) pyrrolidin-1-yl)-7,9-dihydrofuro[3,4-f]quinazolin-6-yl)benzo[b]thiophene-3-carbonitrile, Atropisomer 1 | 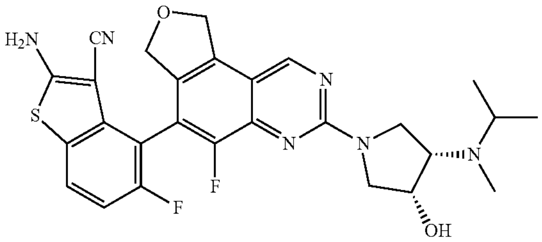 [SMILES: CC(C)N(C)[C@H]1CN(c2ncc3c4c(c(-c5c(F)ccc6sc(N)c(C#N)c56)c(F)c3n2)COC4)C[C@H]1O] | 537 |

TABLE 28-continued

| Example | Chemical Name | Structure | MS (ES) m/z (M + 1) |
|---|---|---|---|
| 255D [119] | 2-Amino-5-fluoro-4-(5-fluoro-3-((3R,4S)-3-hydroxy-4-(isopropyl(methyl)amino)pyrrolidin-1-yl)-7,9-dihydrofuro[3,4-f]quinazolin-6-yl)benzo[b]thiophene-3-carbonitrile, Atropisomer 2 | 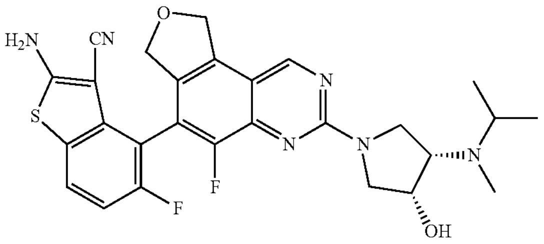 [SMILES: CC(C)N(C)[C@H]1CN(c2ncc3c4c(c(-c5c(F)ccc6sc(N)c(C#N)c56)c(F)c3n2)COC4)C[C@H]1O] | 537 |

[1] Clean Trans Isomers; separation of Trans Isomer Pairs occurred in Preparations 47A and 48A

[2] Prep-Chiral-HPLC; Phenomenex Lux i-Amylose-1, 30 × 150 mm, 10-53% (EtOH w/ 0.1% isopropylamine) in Heptane, 42.5 mL/min

[3] Prep-Chiral-HPLC; Phenomenex Lux Cellulose-4, 30 × 150 mm, 10-90% (1:1 MeOH:EtOH) in Heptane, 50 mL/min

[4] Prep-Chiral-HPLC; Phenomenex Lux Cellulose-2, 30 × 150 mm, 10-70% EtOH in Heptane, 42.5 mL/min

[5] Prep-Chiral-HPLC; Phenomenex Lux Cellulose-4, 30 × 150 mm, 10-55% (1:1 MeOH:EtOH) in Heptane, 50 mL/min

[6] Prep-Chiral-HPLC; Phenomenex Lux i-Amylose-3, 30 × 150 mm, 13-100% (EtOH w/ 0.1% isopropylamine) in Heptane, 42.5 mL/min

[7] Prep-Chiral-HPLC; Phenomenex Lux i-Amylose-3, 30 × 150 mm, 5-100% (1:1 MeOH:EtOH w/ 0.1% isopropylamine) in Heptane, 42.5 mL/min; diastereomers 78A-81A each consist of a single atropisomer and a single trans isomer.

[8] Prep-Chiral-HPLC; Phenomenex Lux Cellulose-1, 30 × 150 mm, 50-100% (Isopropanol w/ 0.1% isopropylamine) in Heptane, 40.0 mL/min

[9] Prep-Chiral-HPLC; Chiralpak-IK, 3 x 25 cm, 50% EtOH in (Hexanes w/ 10mM ammoniated methanol), the pure fraction afforded Diastereomer 4. Mixed fractions further separated with Prep-Chiral-HPLC; Chiralpak-IF, 3 x 25 cm, 30% EtOH in (Hexanes w/ 10mM ammoniated methanol), the pure fraction afforded Diastereomer 3. Mixed fractions further separated with Prep-Chiral-HPLC; Chiralpak-IH, 3 x 25 mm, 30% EtOH in (Hexanes w/ 10mM ammoniated methanol), the first pure fraction afforded Diastereomer 1 and the second pure fraction afforded Diastereomer 2.

[10] Prep-Chiral-HPLC; Phenomenex Lux i-Cellulose-5, 30 × 150 mm, 10-100% (Isopropanol w/ 0.1% isopropylamine) in Heptane, 36 mL/min

[11] Prep-Chiral-HPLC; Phenomenex Lux Cellulose-2, 30 × 150 mm, 5-45% (1:1 MeOH:EtOH w/ 0.1% isopropylamine) in Heptane, 42.5 mL/min

[12] Prep-Chiral-HPLC; Chiralpak-ID, 30 × 250 mm, 50% EtOH in (Hexanes w/ 10mM ammoniated methanol), 40 mL/min

[13] Prep-Chiral-SFC; S,S Whelk-O, 20 × 250 mm, 30% (EtOH w/ 0.5% dimethylethylamine) in $CO_2$, 80 mL/min

[14] Clean Trans Isomers; Prep-Chiral-SFC; Phenomenex Lux i-Cellulose-5, 30 x 150 mm, 15% (MeOH w/ 0.1% isopropylamine) in $CO_2$

[15] Example 61B is a mix of Cis Isomers, Example 62B is a mix of Trans Isomers; Prep-Chiral-HPLC; Phenomenex Lux i-Amylose-3, 30 × 150 mm, 5-70% EtOH in Heptane, 42.5 mL/min

[16] Prep-Chiral-HPLC; Phenomenex Lux Cellulose-2, 30 × 150 mm, 10-65% EtOH in Heptane, 42.5 mL/min

[17] Prep-HPLC; C18, 5-98% Acetonitrile in (10 mM ammonium acetate in 95:5 Water:MeOH), the first eluting peak contained Examples 82B and 83B, the second eluting peak contained Examples 84B and 85B. Examples 82B and 83B were further separated with Prep-Chiral-HPLC; Phenomenex Lux i-Cellulose-5, 30 × 150 mm, 6-80% (Isopropanol w/ 0.2% isopropylamine) in Heptane, 40 mL/min, Example 82B was the first eluting peak. Examples 84B and 85B were further separated with Prep-Chiral-HPLC; Phenomenex Lux i-Cellulose-5, 30 x 150 mm, 4-45% (1:1 MeOH:EtOH) in Heptane, 42.5 mL/min, Example 84B was the first eluting peak.

[18] Prep-Chiral-HPLC; Chiralpak-IK, 3 x 25 cm, 50% EtOH in (Hexanes w/ 10mM ammoniated methanol), 40 mL/min

[19] Clean Cis Isomers; Prep-Chiral-HPLC; Phenomenex Lux i-Amylose-1, 30 × 150 mm, 10-70% (EtOH w/ 0.1% isopropylamine) in Heptane, 42.5 mL/min

[20] Prep-Chiral-HPLC; Chiralpak-ID, 3 x 25 cm, 50% EtOH in (Hexanes w/ 10mM ammoniated methanol), 40 mL/min

[21] Prep-Chiral-SFC; Chiralpak-AD, 20 × 250 mm, 45% (MeOH w/ 0.5% dimethylethylamine) in $CO_2$, 80 mL/min

[22] Prep-Chiral-SFC; Chiralpak-IC, 20 × 250 mm, 45% (EtOH w/ 0.5% dimethylethylamine) in $CO_2$, 80 mL/min

[23] Single atropisomer (from precursor in Preparation 17B)

[24] Single atropisomer (from precursor in Preparation 18B)

[25] Ring-opened byproducts from Example 125B

[26] Single atropisomer (from precursor in Preparation 14B)

[27] Mix of Cis Isomers

[28] Clean Cis Isomers; Prep-Chiral-SFC; S,S Whelk-O, 20 × 250 mm, 40% (MeOH w/ 0.5% dimethylethylamine) in $CO_2$, 80 mL/min

[29] Prep-Chiral-HPLC; Chiralpak-IG, 19 × 150 mm, 70-100% Acetonitrile in 20 mM ammonium bicarbonate, 40 mL/min

[30] Prep-Chiral-SFC; Chiralpak-IC, 20 × 250 mm, 30% (EtOH w/ 0.5% dimethylethylamine) in $CO_2$, 80 mL/min. Example 8C was the second isomer to elute, and was assigned (S,S) stereochemistry after analysis of Example 7C (known (R,R) stereochemistry) matched the first isomer to elute.

[31] Prep-Chiral-HPLC; Chiralpak-IC, 20 × 150 mm, 70-100% Acetonitrile in 20 mM ammonium bicarbonate, 40 mL/min

[32] Clean Cis Isomers; Prep-Chiral-SFC; Chiralpak-IG, 20 × 250 mm, 45% (MeOH w/ 0.5% dimethylethylamine) in $CO_2$, 80 mL/min

[33] Mix of Cis Isomers

[34] Prep-Chiral-HPLC; Chiralpak-AD, 20 × 150 mm, 100% EtOH w/ 0.2% dimethylethylamine, 10 mL/min

[35] Mix of Cis Isomers

[36] Clean Cis Isomers; Prep-Chiral-SFC; Chiralpak-IH, 20 × 250 mm, 30% (MeOH w/ 0.5% dimethylethylamine) in $CO_2$, 80 mL/min

[37] Prep-Chiral-SFC; Chiralpak-IH, 20 × 250 mm, 30% (MeOH w/ 0.5% dimethylethylamine) in $CO_2$, 80 mL/min

[38] Prep-Chiral-SFC; Chiralpak-IC, 20 × 250 mm, 40% (MeOH w/ 0.5% dimethylethylamine) in $CO_2$, 80 mL/min

[39] Prep-Chiral-SFC; Chiralpak-IH, 20 × 250 mm, 30% (MeOH w/ 0.5% dimethylethylamine) in $CO_2$, 80 mL/min

[40] Prep-Chiral-HPLC; CHIRAL ART Cellulose-SB, 20 × 250 mm, 50% Hexanes (with 10 mM ammoniated methanol): 50% EtOH, 20 mL/min

[41] Prep-Chiral-HPLC; CHIRAL ART Cellulose-SB, 30 × 250 mm, 50% Hexanes (with 10 mM ammoniated methanol): 50% EtOH, 40 mL/min

[42] Prep-Chiral-SFC; Chiralpak-IG, 30 × 250 mm, 50% Hexanes (with 10 mM ammoniated methanol): 50% EtOH, 40 mL/min

[43] Prep-Chiral-HPLC; Chiralpak-IK, 30 × 250 mm, 50% Hexanes (with 10 mM ammoniated methanol): 50% EtOH, 40 mL/min

[44] Prep-Chiral-HPLC; Chiralpak-ID, 30 × 250 mm, 50% 1:1 Hexanes:MTBE (with 0.5% 2M ammoniated methanol): 50% MeOH, 40 mL/min

[45] Diastereomer refers to each compound being a single atropisomer and a single quaternary center. Prep-Chiral-HPLC; Chiralpak-IE, 30 × 250 mm, 80% 1:1 Hexanes:MTBE (with 0.5% 2M ammoniated methanol): 20% EtOH, 40 mL/min, the first eluting peak contained Examples 60C and 61C, the second eluting peak contained Example 62C, the third eluting peak contained Example 63C. Examples 60C and 61C were further separated with Prep-Chiral-SFC; Chiralpak-IH, 30 × 250 mm, 50% (MeOH with 20 mM ammoniated methanol) in $CO_2$, 90 mL/min, Example 60C was the first eluting peak.

[46] Prep-Chiral-HPLC; Phenomenex Lux Cellulose-4, 30 × 150 mm, 5-85% EtOH in Heptane, 42.5 mL/min TABLE 28-continued

| Example | Chemical Name | Structure | MS (ES) m/z (M + 1) |
|---|---|---|---|

[47] Prep-Chiral-HPLC; Phenomenex Lux Cellulose-4, 30 × 150 mm, 10-100% EtOH in Heptane, 42.5 mL/min
[48] Prep-Chiral-HPLC; Phenomenex Lux Cellulose-1, 30 × 150 mm, 10-75% EtOH in Heptane, 42.5 mL/min
[49] Prep-Chiral-HPLC; Phenomenex Lux i-Amylose-1, 30 × 150 mm, 10-55% (EtOH w/ 0.1% isopropylamine) in Heptane, 42.5 mL/min
[50] Prep-Chiral-HPLC; Phenomenex Lux Cellulose-2, 30 × 150 mm, 10-75% (EtOH w/ 0.1% isopropylamine) in Heptane, 42.5 mL/min
[51] Prep-Chiral-HPLC; Phenomenex Lux Cellulose-4, 30 × 150 mm, 10-63% EtOH in Heptane, 42.5 mL/min
[52] Prep-Chiral-HPLC; Phenomenex Lux i-Amylose-1, 30 × 150 mm, 10-40% EtOH in Heptane, 42.5 mL/min
[53] Prep-Chiral-HPLC; Phenomenex Lux i-Amylose-1, 30 × 150 mm, 10-40% (EtOH w/ 0.1% isopropylamine) in Heptane, 37.5 mL/min
[54] Prep-Chiral-HPLC; Phenomenex Lux Cellulose-2, 30 × 150 mm, 15-60% EtOH in Heptane, 40 mL/min
[55] Prep-Chiral-HPLC; Phenomenex Lux Cellulose-2, 30 × 150 mm, 15-45% 1:1 MeOH:EtOH in Heptane, 42.5 mL/min
[56] Prep-Chiral-HPLC; Phenomenex Lux Cellulose-4, 30 × 150 mm, 10-60% EtOH in Heptane, 37.5 mL/min
[57] Prep-Chiral-HPLC; Phenomenex Lux Cellulose-4, 30 × 150 mm, 10-55% EtOH in Heptane, 37.5 mL/min
[58] Prep-Chiral-HPLC; Phenomenex Lux Cellulose-4, 30 × 150 mm, 15-45% 1:1 MeOH:EtOH in Heptane, 37.5 mL/min
[59] Prep-Chiral-HPLC; Chiralpak-IG, 30 × 250 mm, 70% Hexanes (with 10 mM ammoniated methanol): 30% Isopropanol, 40 mL/min
[60] Prep-Chiral-HPLC; Chiral NQ(2)5u, 30 × 250 mm, 50% Hexanes (with 10 mM ammoniated methanol): 50% Isopropanol, 40 mL/min
[61] Prep-Chiral-HPLC; Chiral NQ(2)5u, 30 × 250 mm, 50% Hexanes (with 10 mM ammoniated methanol): 50% Isopropanol, 40 mL/min
[62] Prep-Chiral-HPLC; Phenomenex Lux Cellulose-2, 30 × 150 mm, 5-60% (EtOH w/ 0.1% isopropylamine) in Heptane, 42.5 mL/min
[63] Prep-Chiral-HPLC; Phenomenex Lux Cellulose-4, 30 × 150 mm, 10-90% Isopropanol in Heptane, 37.5 mL/min
[64] Clean Cis Isomers; Prep-Chiral-HPLC; Phenomenex Lux i-Cellulose-5, 30 x 150 mm, 5-45% (1:1 MeOH:EtOH w/ 0.1% isopropylamine) in Heptane, 42.5 mL/min
[65] Prep-HPLC; C18, Acetonitrile in Water
[66] Prep-Chiral-HPLC; Phenomenex Lux i-Amylose-1, 30 × 150 mm, 10-100% (EtOH w/0.1% isopropylamine) in Heptane, 40 mL/min
[67] Prep-Chiral-SFC; Phenomenex Lux Cellulose-4, 30 × 150 mm, 25% MeOH in $CO_2$, 37.5mL/min
[68] Prep-Chiral-HPLC; Phenomenex Lux Cellulose-4, 30 × 150 mm, 18-60% 1:1 MeOH:EtOH in Heptane, 50 mL/min
[69] Prep-Chiral-HPLC; Phenomenex Lux Cellulose-2, 30 × 150 mm, 15-100% 1:1 MeOH: EtOH in Heptane, 40 mL/min
[70] Prep-Chiral-HPLC; Phenomenex Lux Cellulose-2, 30 × 150 mm, 15-60% (1:1 MeOH:EtOH w/ 0.1% isopropylamine) in Heptane, 42.5 mL/min
[71] Prep-Chiral-HPLC; Phenomenex Lux Cellulose-2, 30 × 150 mm, 5-60% EtOH in Heptane, 42.5 mL/min
[72] Prep-Chiral-HPLC; Phenomenex Lux Cellulose-1, 30 × 150 mm, 10-100% Isopropanol in Heptane, 30 mL/min
[73] Prep-Chiral-HPLC; Phenomenex Lux Cellulose-2, 30 × 150 mm, 20-50% 1:1 MeOH: EtOH in Heptane, 42.5 mL/min
[74] Prep-Chiral-HPLC; Phenomenex Lux Cellulose-2, 30 × 150 mm, 10-100% 1:1 MeOH:EtOH in Heptane, 37.5 mL/min
[75] Prep-Chiral-HPLC; Phenomenex Lux Cellulose-2, 30 × 150 mm, 10-70% 1:1 MeOH:EtOH in Heptane, 37.5 mL/min
[76] Prep-Chiral-SFC; Chiralpak-AD, 20 × 250 mm, 45% (MeOH w/ 0.5% dimethylethylamine) in $CO_2$, 80 mL/min
[77] Mix of Trans Isomers
[78] Mix of Trans Isomers
[79] Clean Trans Isomers, Separated in Preparations 5D and 6D
[80] Clean Trans Isomer, Separated in Preparation 7D
[81] Clean Trans Isomers; Prep-Chiral-HPLC; Chiralpak-IG, 20 × 150 mm, 50-100% Acetonitrile in (20 mM ammonium bicarbonate in pH 9 buffer), 40 mL/min
[82] Clean Trans Isomer, Separated in Preparation 7D
[83] Clean Trans Isomers; Prep-Chiral-HPLC; Chiralpak-IG, 20 × 150 mm, 50-100% Acetonitrile in (20 mM ammonium bicarbonate in pH 9 buffer), 40 mL/min
[84] Mix of Trans Isomers
[85] Clean Trans Isomers; Prep-Chiral-SFC; Chiralpak-AD, 20 × 250 mm, 45% (MeOH w/ 0.5% dimethylethylamine) in $CO_2$, 80 mL/min
[86] Clean Trans Isomers, Separated in Preparations 9D and 10D
[87] Clean Trans Isomers; Prep-Chiral-HPLC; Chiralpak-IC, 20 × 150 mm, 70-100% Acetonitrile in (20 mM ammonium bicarbonate in pH 9 buffer), 40 mL/min
[88] Clean Trans Isomers; Prep-Chiral-HPLC; Chiralpak-IC, 20 × 150 mm, 70-100% Acetonitrile in (20 mM ammonium bicarbonate in pH 9 buffer), 40 mL/min
[89] Prep-Chiral-SFC; S,S Whelk-O, 20 × 150 mm, 30% (Isopropanol w/ 0.5% dimethylethylamine) in $CO_2$, 80 mL/min
[90] Prep-Chiral-SFC; Phenomenex Lux i-Amylose-1, 30 × 150 mm, 20% (EtOH w/ 0.1% isopropylamine) in $CO_2$
[91] Prep-Chiral-SFC; Phenomenex Lux i-Amylose-1, 30 × 150 mm, 18% (EtOH w/ 0.1% isopropylamine) in $CO_2$
[92] Clean Trans Isomers; Prep-Chiral-SFC; Chiralpak-IC, 20 × 250 mm, 40% (MeOH w/ 0.5% dimethylethylamine) in $CO_2$, 65 g/min
[93] Mix of Trans Isomers
[94] Mix of Cis Isomers
[95] Mix of Trans Isomers
[96] Clean Trans Isomers; Prep-Chiral-SFC; Chiralpak-AD, 20 × 250 mm, 45% (MeOH w/ 0.5% dimethylethylamine) in $CO_2$, 80 mL/min
[97] Mix of Trans Isomers (nitrogen and oxygen substituents)
[98] Clean Trans Isomers (nitrogen and oxygen substituents)
[99] Clean Trans Isomers (nitrogen and oxygen substituents)
[100] Clean Cis Isomer (nitrogen and oxygen substituents)
[101] Clean Cis Isomers; Prep-HPLC; C18, 35-70% Acetonitrile in (20 mM ammonium bicarbonate in pH 9 buffer), 40 mL/min
[102] Clean Trans Isomers, Separated in Preparations 12D and 13D
[103] Prep-Chiral-SFC; Chiralpak-AD, 20 × 250 mm, 40% (EtOH w/ 0.5% dimethylethylamine) in $CO_2$, 65 g/min
[104] Prep-Chiral-HPLC; Phenomenex Lux i-Amylose-1, 30 × 150 mm, 20-100% (EtOH w/ 0.1% isopropylamine) in Heptane, 45 mL/min
[105] Prep-Chiral-HPLC; Phenomenex Lux i-Amylose-3, 30 × 150 mm, 20-100% (1:1 MeOH:EtOH w/ 0.1% isopropylamine) in Heptane, 50 mL/min
[106] Prep-Chiral-HPLC; Phenomenex Lux i-Amylose-1, 30 × 150 mm, 10-60% (1:1 MeOH:EtOH w/ 0.1% isopropylamine) in Heptane, 34.5 mL/min
[107] Prep-Chiral-HPLC; Chiralpak-IG, 20 × 150 mm, 70-100% Acetonitrile in (20 mM ammonium bicarbonate in pH 9 buffer), 40 mL/min
[108] Clean Isomers, from ************
[109] Prep-Chiral-SFC; Chiralpak-IC, 20 × 250 mm, 45% (MeOH w/ 0.5% dimethylethylamine) in $CO_2$, 80 mL/min
[110] Separated byproduct from impurity in Example 231D
[111] Prep-Chiral-HPLC; Chiralpak-IG, 30 × 250 mm, 50% Hexanes (with 10 mM ammoniated methanol): 50% EtOH, 40 mL/min
[112] Prep-Chiral-HPLC; Chiral Art Cellulose-SC, 30 × 250 mm, 50% Hexanes (with 10 mM ammoniated methanol): 50% Isopropanol, 40 mL/min
[113] Prep-Chiral-HPLC; Chiralpak-IE, 30 × 250 mm, 70% 1:1 Hexanes:MTBE (with 0.5% 2M ammoniated methanol): 30% EtOH, 35 mL/min
[114] Prep-Chiral-HPLC; Chiralpak-IG, 30 × 250 mm, 50% Hexanes (with 10 mM ammoniated methanol): 50% EtOH, 40 mL/min
[115] Prep-Chiral-HPLC; Chiralpak-IK, 30 × 250 mm, 80% Hexanes (with 10 mM ammoniated methanol): 20% EtOH, 40 mL/min
[116] Prep-Chiral-HPLC; Chiralpak-ID, 30 × 250 mm, 50% Hexanes (with 10 mM ammoniated methanol): 50% EtOH, 40 mL/min
[117] Prep-Chiral-HPLC; Chiralpak-IG, 30 × 250 mm, 60% Hexanes (with 10 mM ammoniatedmethanol): 40% EtOH, 40 mL/min
[118] Prep-Chiral-HPLC; Chiral Art Cellulose-SZ, 30 × 250 mm, 70% Hexanes (with 10 mMammoniated methanol): 30% EtOH, 40 mL/min
[119] Prep-Chiral-HPLC; Chiralpak-IE, 30 × 250 mm, 75% 1:1 Hexanes:MTBE (with 0.5% 2M ammoniated methanol): 25% MeOH, 40 mL/min The following compounds in Table 29 were prepared in similar manner as described in Preparation 33B or Example 1. Various methods were used to purify the compounds, which would be apparent to one skilled in the art.

TABLE 29

| Example | Chemical Name | Structure | MS (ES) m/z (M + 1) |
| --- | --- | --- | --- |
| 137B | 2-Amino-7-fluoro-4-(5-fluoro-3-((1S,5S)-6-isopropyl-2,6-diazabicyclo[3.2.0]heptan-2-yl)-7,9-dihydrofuro-[3,4-f]quinazolin-6-yl)-thieno[3,2-c]pyridine-3-carbonitrile | 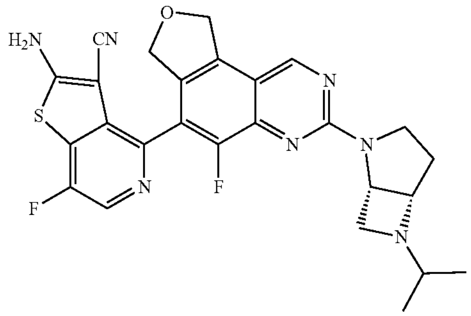 [SMILES: CC(C)N1C[C@H]2[C@@H]1CCN2c1ncc2c3c(c(-c4ncc(F)c5sc(N)c(C#N)c45)c(F)c2n1)COC3] | 520 |
| 138B [1] | 2-Amino-7-fluoro-4-(5-fluoro-3-(1-methyloctahydro-6H-pyrrolo[3,4-b]pyridin-6-yl)-7,9-dihydrofuro[3,4-f]quinazolin-6-yl)thieno[3,2-c]pyridine-3-carbonitrile, Isomer 1 | 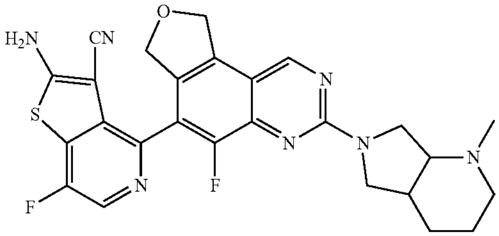 [SMILES: CN1CCCC2CN(c3ncc4c5c(c(-c6ncc(F)c7sc(N)c(C#N)c67)c(F)c4n3)COC5)CC21] | 520 |
| 139B [1] | 2-Amino-7-fluoro-4-(5-fluoro-3-(1-methyloctahydro-6H-pyrrolo[3,4-b]pyridin-6-yl)-7,9-dihydrofuro[3,4-f]quinazolin-6-yl)thieno[3,2-c]pyridine-3-carbonitrile, Isomer 2 | 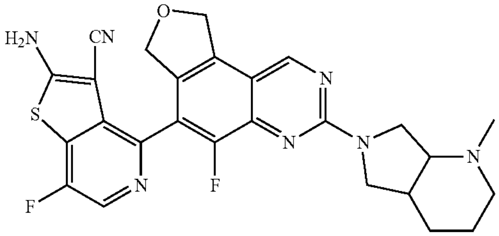 [SMILES: CN1CCCC2CN(c3ncc4c5c(c(-c6ncc(F)c7sc(N)c(C#N)c67)c(F)c4n3)COC5)CC21] | 520 |
| 140B | 2-Amino-7-fluoro-4-(5-fluoro-3-((S)-1-methyl-1,7-diazaspiro[4.4]-nonan-7-yl)-7,9-dihydro-furo[3,4-f]quinazolin-6-yl)thieno[3,2-c]pyridine-3-carbonitrile | 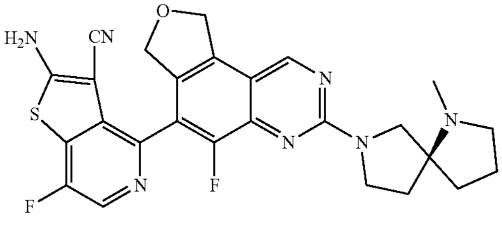 [SMILES: CN1CCC[C@@]12CCN(c1ncc3c4c(c(-c5ncc(F)c6sc(N)c(C#N)c56)c(F)c3n1)COC4)C2] | 520 |
| 141B | 2-Amino-7-fluoro-4-(5-fluoro-3-(1-methyl-1,7-diazaspiro[4.4]nonan-7-yl)-7,9-dihydrofuro[3,4-f]quinazolin-6-yl)thieno-[3,2-c]pyridine-3-carbonitrile | 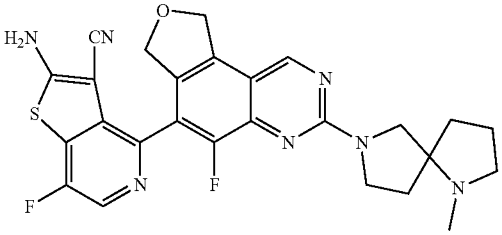 [SMILES: CN1CCCC12CCN(c1ncc3c4c(c(-c5ncc(F)c6sc(N)c(C#N)c56)c(F)c3n1)COC4)C2] | 520 |
| 142B [2] | 2-Amino-7-fluoro-4-(5-fluoro-3-((R)-1-methyl-1,7-diazaspiro[4.4]-nonan-7-yl)-7,9-dihydro-furo[3,4-f]quinazolin-6-yl)thieno[3,2-c]pyridine-3-carbonitrile | 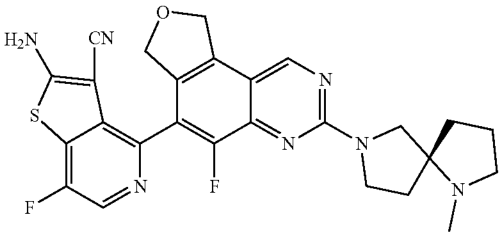 [SMILES: CN1CCC[C@]12CCN(c1ncc3c4c(c(-c5ncc(F)c6sc(N)c(C#N)c56)c(F)c3n1)COC4)C2] | 520 |

TABLE 29-continued

| Example | Chemical Name | Structure | MS (ES) m/z (M + 1) |
| --- | --- | --- | --- |
| 143B | 2-Amino-4-(3-((S)-3-(ethyl(methyl)amino)-pyrrolidin-1-yl)-5-fluoro-7,9-dihydrofuro[3,4-f]-quinazolin-6-yl)-7-fluorothieno[3,2-c]-pyridine-3-carbonitrile formic acid | 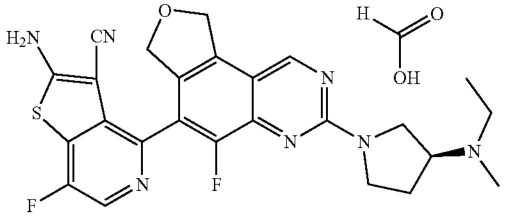 | 508 |
| 144B | 2-Amino-4-(3-((R)-7-(dimethylamino)-5-azaspiro[2.4]heptan-5-yl)-5-fluoro-7,9-dihydro-furo[3,4-f]quinazolin-6-yl)-7-fluorothieno[3,2-c]pyridine-3-carbonitrile | 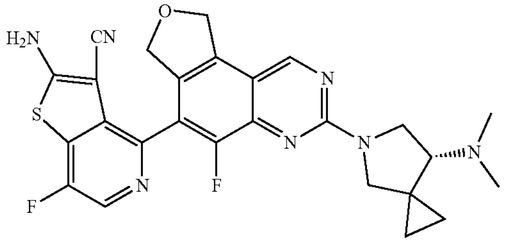 [SMILES: CN(C)[C@H]1CN(c2ncc3c4c(c(-c5ncc(F)c6sc(N)c(C#N)c56)c(F)c3n2)COC4)CC12CC2] | 520 |
| 145B | 2-Amino-4-(3-((S)-7-(dimethylamino)-5-azaspiro[2.4]heptan-5-yl)-5-fluoro-7,9-dihydro-furo[3,4-f]quinazolin-6-yl)-7-fluorothieno[3,2-c]pyridine-3-carbonitrile | 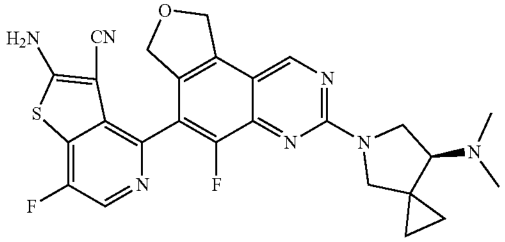 [SMILES: CN(C)[C@@H]1CN(c2ncc3c4c(c(-c5ncc(F)c6sc(N)c(C#N)c56)c(F)c3n2)COC4)CC12CC2] | 520 |
| 146B | 2-Amino-7-fluoro-4-(5-fluoro-3-((R)-1-methyl-1,6-diazaspiro[3.4]octan-6-yl)-7,9-dihydrofuro-[3,4-f]quinazolin-6-yl)-thieno[3,2-c]pyridine-3-carbonitrile | 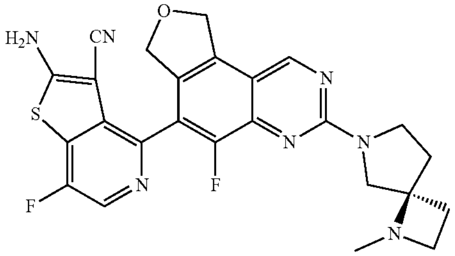 [SMILES: CN1CC[C@]12CCN(c1ncc3c4c(c(-c5ncc(F)c6sc(N)c(C#N)c56)c(F)c3n1)COC4)C2] | 506 |
| 147B | 2-Amino-4-(3-(6-(dimethylamino)-2-aza-spiro[3.3]heptan-2-yl)-5-fluoro-7,9-dihydro-furo[3,4-f]quinazolin-6-yl)-7-fluorothieno[3,2-c]pyridine-3-carbonitrile | 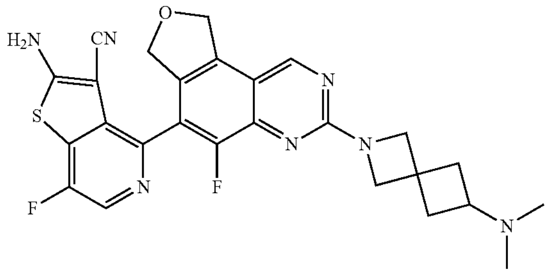 [SMILES: CN(C)C1CC2(C1)CN(c1ncc3c4c(c(-c5ncc(F)c6sc(N)c(C#N)c56)c(F)c3n1)COC4)C2] | 520 |
| 148B [3] | 2-Amino-5-fluoro-4-(5-fluoro-3-((3aR,6aS)-5-methylhexahydropyrrolo-[3,4-c]pyrrol-2(1H)-yl)-7,9-dihydrofuro[3,4-f]-quinazolin-6-yl)benzo-[b]thiophene-3-carbo-nitrile | 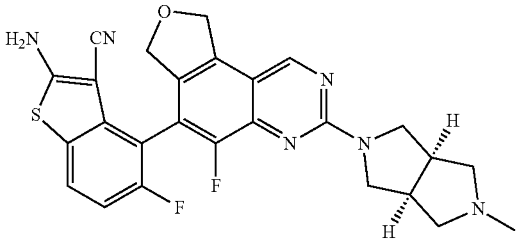 [SMILES: CN1C[C@@H]2CN(c3ncc4c5c(c(-c6c(F)ccc7sc(N)c(C#N)c67)c(F)c4n3)COC5)C[C@@H]2C1] | 505 |

TABLE 29-continued

| Example | Chemical Name | Structure | MS (ES) m/z (M + 1) |
|---|---|---|---|
| 120C | 2-Amino-7-fluoro-4-(5-fluoro-3-((S)-3-(methyl-(oxetan-3-ylmethyl)-amino)pyrrolidin-1-yl)-7,9-dihydrofuro[3,4-f]-quinazolin-6-yl)thieno-[3,2-c]pyridine-3-carbo-nitrile | 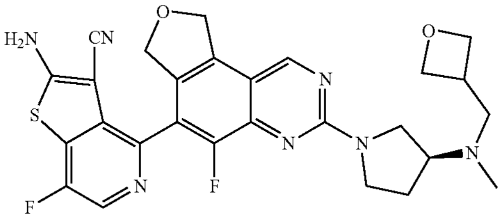 [SMILES: CN(CC1COC1)[C@H]1CCN(c2ncc3c4c(c(-c5ncc(F)c6sc(N)c(C#N)c56)c(F)c3n2)COC4)C1] | 550 |
| 121C | 2-Amino-7-fluoro-4-(5-fluoro-3-((1R,5R)-2-methyl-2,6-diazabicyclo-[3.2.0]heptan-6-yl)-7,9-dihydrofuro[3,4-f]quin-azolin-6-yl)thieno[3,2-c]pyridine-3-carbonitrile | 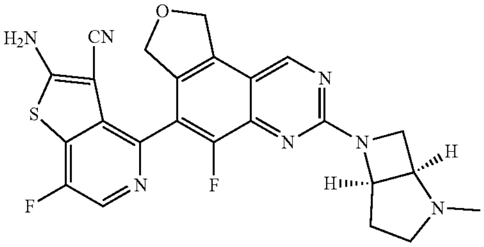 [SMILES: CN1CC[C@@H]2[C@H]1CN2c1ncc2c3c(c(-c4ncc(F)c5sc(N)c(C#N)c45)c(F)c2n1)COC3] | 492 |
| 256D | 2-Amino-7-fluoro-4-(5-fluoro-3-((S)-3-(((S)-2-hydroxypropyl)(methyl)-amino)pyrrolidin-1-yl)-7,9-dihydrofuro[3,4-f]-quinazolin-6-yl)thieno-[3,2-c]pyridine-3-carbo-nitrile | 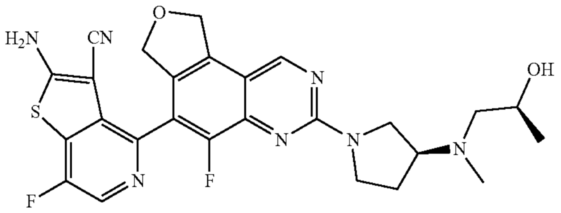 [SMILES: C[C@H](O)CN(C)[C@H]1CCN(c2ncc3c4c(c(-c5ncc(F)c6sc(N)c(C#N)c56)c(F)c3n2)COC4)C1] | 538 |
| 257D | 2-Amino-7-fluoro-4-(5-fluoro-3-(5-methyl-dihydro-1H,4H-3a,6a-(methanooxymethano)-pyrrolo[3,4-c]pyrrol-2(3H)-yl)-7,9-dihydro-furo[3,4-f]quinazolin-6-yl)thieno[3,2-c]pyridine-3-carbonitrile | 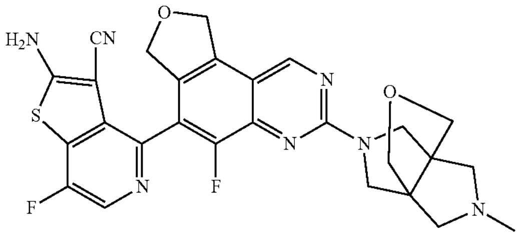 [SMILES: CN1CC23COCC2(C1)CN(c1ncc2c4c(c(-c5ncc(F)c6sc(N)c(C#N)c56)c(F)c2n1)COC4)C3] | 548 |
| 258D [4] | 2-Amino-5-fluoro-4-(5-fluoro-3-((2S,3S)-3-(iso-propylamino)-2-meth-ylpyrrolidin-1-yl)-7,9-dihydrofuro[3,4-f]quin-azolin-6-yl)benzo[b]-thiophene-3-carbonitrile, Atropisomer 1 | 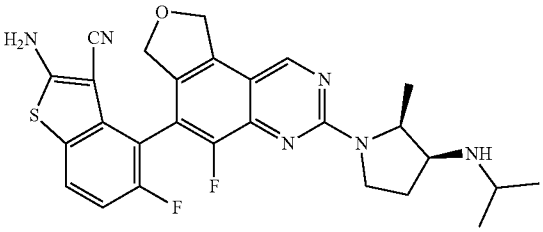 [SMILES: CC(C)N[C@H]1CCN(c2ncc3c4c(c(-c5c(F)ccc6sc(N)c(C#N)c56)c(F)c3n2)COC4)[C@H]1C] | 521 |
| 259D [4] | 2-Amino-5-fluoro-4-(5-fluoro-3-((2S,3S)-3-(isopropylamino)-2-methylpyrrolidin-1-yl)-7,9-dihydrofuro[3,4-f]-quinazolin-6-yl)benzo-[b]thiophene-3-carbo-nitrile, Atropisomer 2 | 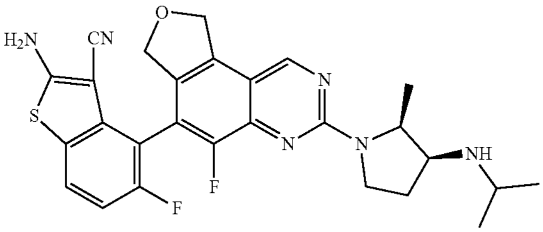 [SMILES: CC(C)N[C@H]1CCN(c2ncc3c4c(c(-c5c(F)ccc6sc(N)c(C#N)c56)c(F)c3n2)COC4)[C@H]1C] | 521 |

TABLE 29-continued

| Example | Chemical Name | Structure | MS (ES) m/z (M + 1) |
|---|---|---|---|
| 260D [5] | 2-Amino-4-(5-chloro-3-(1-methyl-1,6-diaza-spiro[3.4]octan-6-yl)-7,9-dihydrofuro[3,4-f]quin-azolin-6-yl)-7-fluoro-thieno[3,2-c]pyridine-3-carbonitrile, Diastereo-mer 1 | 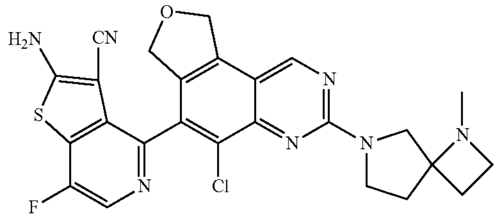 [SMILES: CN1CCC12CCN(c1ncc3c4c(c(-c5ncc(F)c6sc(N)c(C#N)c56)c(Cl)c3n1)COC4)C2] | 522 |
| 261D [5] | 2-Amino-4-(5-chloro-3-(1-methyl-1,6-diazaspiro-[3.4]octan-6-yl)-7,9-dihydrofuro[3,4-f]quin-azolin-6-yl)-7-fluoro-thieno[3,2-c]pyridine-3-carbonitrile, Diastereo-mer 2 | 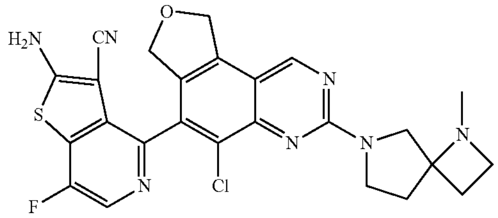 [SMILES: CN1CCC12CCN(c1ncc3c4c(c(-c5ncc(F)c6sc(N)c(C#N)c56)c(Cl)c3n1)COC4)C2] | 522 |
| 262D [5] | 2-Amino-4-(5-chloro-3-(1-methyl-1,6-diaza-spiro[3.4]octan-6-yl)-7,9-dihydrofuro[3,4-f]quin-azolin-6-yl)-7-fluoro-thieno[3,2-c]pyridine-3-carbonitrile, Diastereo-mer 3 | 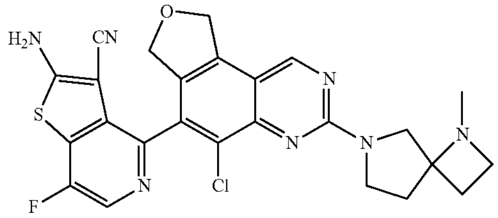 [SMILES: CN1CCC12CCN(c1ncc3c4c(c(-c5ncc(F)c6sc(N)c(C#N)c56)c(Cl)c3n1)COC4)C2] | 522 |

[1] Prep-HPLC; C18, 35-70% Acetonitrile in (20 mM ammonium bicarbonate in pH 9 buffer), 40 mL/min

[2] Prep-Chiral-SFC; Phenomenex Lux Cellulose-4, 30 x 100 mm, 40% MeOH in $CO_2$; the chiral purification was performed on Example 141B. Example 142B was the second isomer to elute, and was assigned (R) stereochemistry after analysis of Example 140B (known (S) stereochemistry) matched the first isomer to elute.

[3] Single atropisomer (from precursor in Preparation 14B)

[4] Prep-Chiral-HPLC; Chiralpak-ID, 30 x 250 mm, 70% Hexanes (with 10 mM ammoniated methanol): 30% EtOH, 40 mL/min

[5] Diastereomer refers to each compound being a single atropisomer and a single spiro center. Prep-Chiral-HPLC; Phenomenex Lux Cellulose-4, 30 x 150 mm, 10-60% 1:1 MeOH:EtOH in Heptane, 37.5 mL/min, the first eluting peak contained Examples 260D and 261D, the second eluting peak contained Example 262D and the fourth diastereomer. Examples 260D and 261D were further separated with Prep-Chiral-SFC; Phenomenex Lux Cellulose-3, 30 x 100 mm, 15% (MeOH w/0.1% isopropylamine) in $CO_2$, Example 260D was the first eluting peak. Example 262D and the fourth diastereomer were further separated with Prep-Chiral-HPLC; Phenomenex Lux i-Cellulose-5, 30 x 150 mm, 10-100% (Isopropanol w/0.1% isopropylamine) in Heptane, 34.5 mL/min, Example 262D was the first eluting peak.

Example 263D

2-Amino-7-fluoro-4-(5-fluoro-3-((2R,3R)-3-(isopropylamino)-2-methylpyrrolidin-1-yl)-7,9-dihydrofuro[3,4-f]quinazolin-6-yl)thieno[3,2-c]pyridine-3-carbonitrile

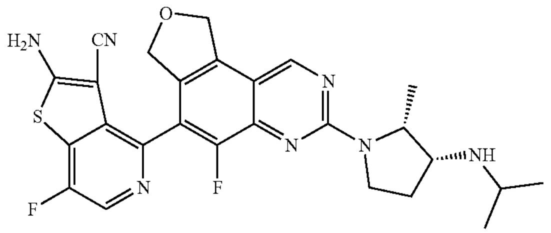 [SMILES: CC(C)N[C@@H]1CCN(c2ncc3c4c(c(-c5ncc(F)c6sc(N)c(C#N)c56)c(F)c3n2)COC4)[C@@H]1C]

tert-Butyl (4-(3-((2R,3R)-3-amino-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate (0.150 g, 0.259 mmol), acetone (0.038 mL, 0.518 mmol), and sodium triacetoxyborohydride (0.110 g, 0.518 mmol) were dissolved in MeOH (8 mL) and acetic acid (2 mL). The reaction mixture was heated at 50° C. for 18 h. Additional acetone (0.038 mL, 0.518 mmol), and sodium triacetoxyborohydride (0.110 g, 0.518 mmol) were added. The reaction mixture was heated at 50° C. for 18 h, then concentrated under reduced pressure and diluted with saturated aqueous sodium bicarbonate (20 mL). The mixture was extracted with EtOAc (3×40 mL). The combined organics were washed with brine, dried over anhydrous sodium sulfate, filtered, and concentrated under reduced pressure. The residue was purified on silica, eluting with 0-20% MeOH in DCM to obtain the BOC-protected intermediate, tert-butyl (3-cyano-7-fluoro-4-(5-fluoro-3-((2R,3R)-3-(isopropylamino)-2-methylpyrrolidin-1-yl)-7,9-dihydrofuro[3,4-f]quinazolin-6-yl)thieno[3,2-c]pyridin-2-yl)carbamate.

The intermediate was dissolved in DCM (5 mL) and treated with TFA (3 mL). The reaction mixture was heated at 38° C. for 1 h, then concentrated under reduced pressure. The residue was purified by reversed phase purification, eluting with 0-100% acetonitrile in 10 mM aqueous ammonium (with 5% MeOH), to give the title compound (0.022 g, 15%) as a yellow solid. MS (ES) m/z=522 (M+1).

The following compounds in Table 30 were prepared in similar manner as described in Example 263D. Various methods were used to purify the compounds, which would be apparent to one skilled in the art.

TABLE 30

| Example | Chemical Name | Structure | MS (ES) m/z (M + 1) |
|---|---|---|---|
| 264D | 2-Amino-4-(3-((2S,3S)-3-(ethyl(2-hydroxyethyl)amino)-2-methylpyrrolidin-1-yl)-5-fluoro-7,9-dihydrofuro-[3,4-f]quinazolin-6-yl)-7-fluorothieno[3,2-c]-pyridine-3-carbonitrile | 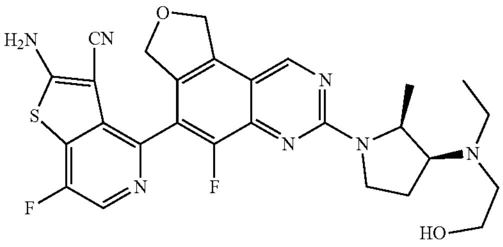 [SMILES: CCN(CCO)[C@H]1CCN(c2ncc3c4c(c(-c5ncc(F)c6sc(N)c(C#N)c56)c(F)c3n2)COC4)[C@H]1C] | 552 |
| 265D | 2-Amino-7-fluoro-4-(5-fluoro-3-((2S,3S)-3-((2-hydroxyethyl)(methyl)-amino)-2-methylpyrrolidin-1-yl)-7,9-dihydro-furo[3,4-f]quinazolin-6-yl)thieno[3,2-c]pyridine-3-carbonitrile | 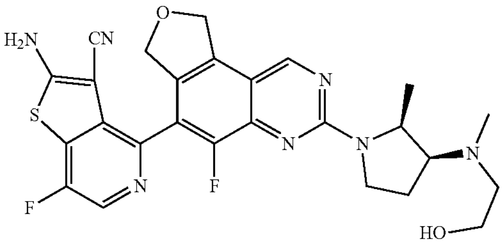 [SMILES: C[C@H]1[C@@H](N(C)CCO)CCN1c1ncc2c3c(c(-c4ncc(F)c5sc(N)c(C#N)c45)c(F)c2n1)COC3] | 538 |
| 266D | 2-Amino-4-(3-(3-(dimethylamino)hexahydro-1H-furo[3,4-b]-pyrrol-1-yl)-5-fluoro-7,9-dihydrofuro[3,4-f]-quinazolin-6-yl)-7-fluorothieno[3,2-c]-pyridine-3-carbonitrile | 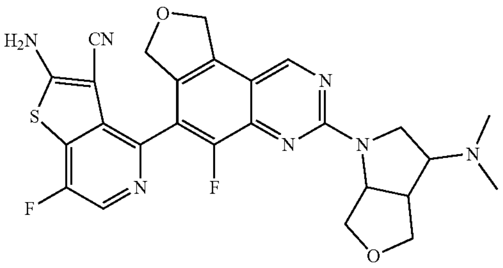 [SMILES: CN(C)C1CN(c2ncc3c4c(c(-c5ncc(F)c6sc(N)c(C#N)c56)c(F)c3n2)COC4)C2COCC12] | 536 |
| 267D [1] | 2-Amino-4-(3-(3-(dimethylamino)hexahydro-1H-furo[3,4-b]-pyrrol-1-yl)-5-fluoro-7,9-dihydrofuro[3,4-f]-quinazolin-6-yl)-7-fluorothieno[3,2-c]-pyridine-3-carbonitrile, Isomer 1 | 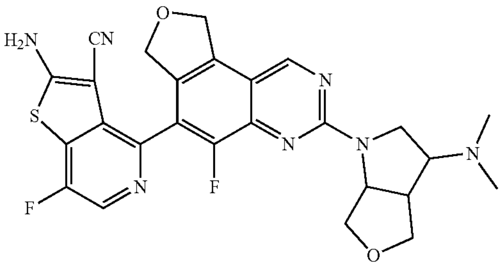 [SMILES: CN(C)C1CN(c2ncc3c4c(c(-c5ncc(F)c6sc(N)c(C#N)c56)c(F)c3n2)COC4)C2COCC12] | 536 |
| 268D [1] | 2-Amino-4-(3-(3-(dimethylamino)hexahydro-1H-furo[3,4-b]-pyrrol-1-yl)-5-fluoro-7,9-dihydrofuro[3,4-f]-quinazolin-6-yl)-7-fluorothieno[3,2-c]-pyridine-3-carbonitrile, Isomer 2 | 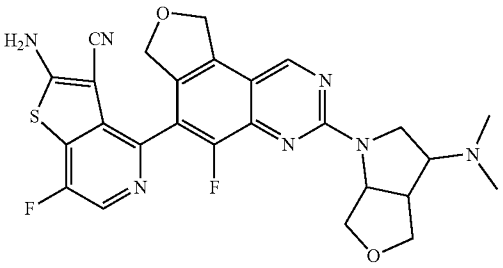 [SMILES: CN(C)C1CN(c2ncc3c4c(c(-c5ncc(F)c6sc(N)c(C#N)c56)c(F)c3n2)COC4)C2COCC12] | 536 |

TABLE 30-continued

| Example | Chemical Name | Structure | MS (ES) m/z (M + 1) |
|---|---|---|---|
| 269D | 2-Amino-7-fluoro-4-(5-fluoro-3-((2S,4R)-4-(isopropylamino)-2-methylpyrrolidin-1-yl)-7,9-dihydrofuro[3,4-f]-quinazolin-6-yl)thieno-[3,2-c]pyridine-3-carbonitrile | 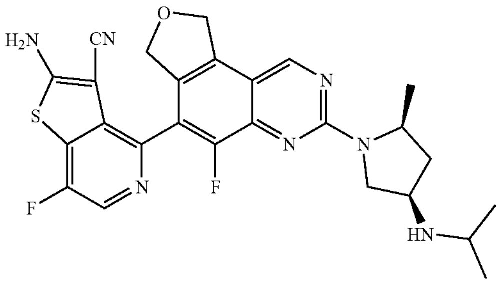 [SMILES: CC(C)N[C@@H]1C[C@H](C)N(c2ncc3c4c(c(-c5ncc(F)c6sc(N)c(C#N)c56)c(F)c3n2)COC4)C1] | 522 |
| 270D | 2-Amino-7-fluoro-4-(5-fluoro-3-((2S,3S)-2-methyl-3-((tetrahydro-furan-3-yl)amino)pyr-rolidin-1-yl)-7,9-dihydrofuro[3,4-f]-quinazolin-6-yl)thieno-[3,2-c]pyridine-3-carbonitrile | 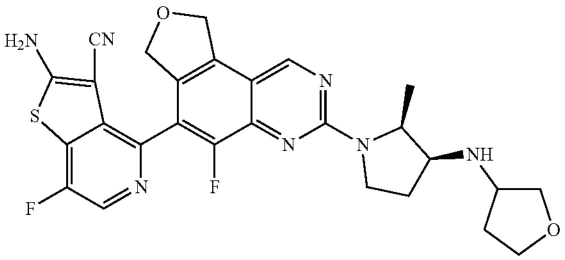 [SMILES: C[C@H]1[C@@H](NC2CCOC2)CCN1c1ncc2c3c(c(-c4ncc(F)c5sc(N)c(C#N)c45)c(F)c2n1)COC3] | 550 |
| 271D [2] | 2-Amino-7-fluoro-4-(5-fluoro-3-((2S,3S)-2-methyl-3-((tetrahydro-furan-3-yl)amino)pyr-rolidin-1-yl)-7,9-dihydrofuro[3,4-f]-quinazolin-6-yl)thieno-[3,2-c]pyridine-3-carbonitrile, Isomer 1 | 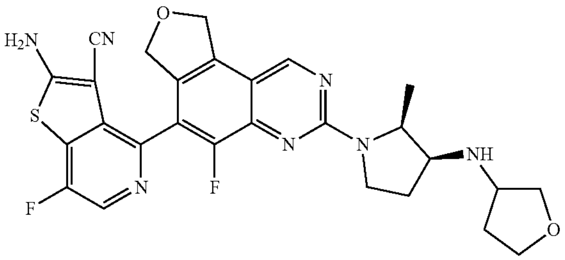 [SMILES: C[C@H]1[C@@H](NC2CCOC2)CCN1c1ncc2c3c(c(-c4ncc(F)c5sc(N)c(C#N)c45)c(F)c2n1)COC3] | 550 |
| 272D [2] | 2-Amino-7-fluoro-4-(5-fluoro-3-((2S,3S)-2-methyl-3-((tetrahydro-furan-3-yl)amino)pyr-rolidin-1-yl)-7,9-dihydrofuro[3,4-f]-quinazolin-6-yl)thieno-[3,2-c]pyridine-3-carbonitrile, Isomer 2 | 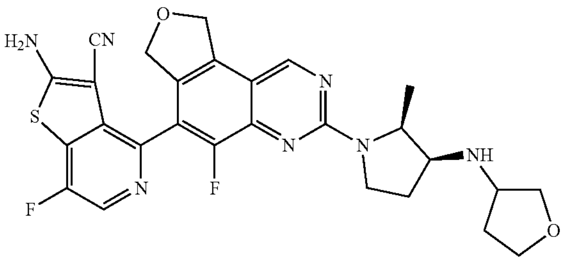 [SMILES: C[C@H]1[C@@H](NC2CCOC2)CCN1c1ncc2c3c(c(-c4ncc(F)c5sc(N)c(C#N)c45)c(F)c2n1)COC3] | 550 |

[1] Prep-Chiral-HPLC; Phenomenex Lux i-Amylose-3, 30 × 150 mm, 20-100% 1:1 MeOH:EtOH in Heptane, 40 mL/min

[2] Prep-Chiral-HPLC; Phenomenex Lux i-Amylose-1, 30 × 150 mm, 18-90% (1:1 MeOH:EtOH w/0.1% isopropylamine) in Heptane, 60 mL/min Example 273D 2-Amino-7-fluoro-4-(5-fluoro-3-(4-(propan-2-yl-d7)octahydro-1H-pyrrolo[3,2-b]pyridin-1-yl)-7,9-dihydrofuro[3,4-f]quinazolin-6-yl)thieno[3,2-c]pyridine-3-carbonitrile

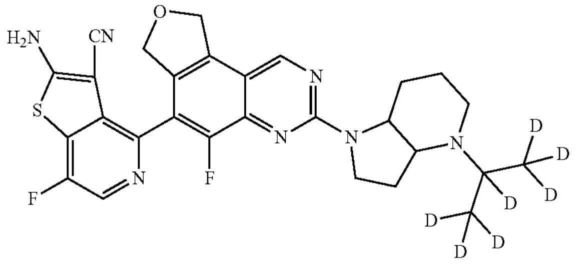 [SMILES: [2H]C([2H])([2H])C([2H])(N1CCCC2C1CCN2c1ncc2c3c(c(-c4ncc(F)c5sc(N)c(C#N)c45)c(F)c2n1)COC3)C([2H])([2H])[2H]]

A solution of 2-amino-7-fluoro-4-(5-fluoro-3-(octahydro-1H-pyrrolo[3,2-b]pyridin-1-yl)-7,9-dihydrofuro[3,4-f]quinazolin-6-yl)thieno[3,2-c]pyridine-3-carbonitrile (50 wt %, 0.045 g, 0.045 mmol) in acetonitrile was treated with diisopropylethylamine (0.039 mL, 0.22 mmol) and 2-iodopropane-1,1,1,2,3,3,3-d7 (0.0045 mL, 0.045 mmol). The reaction mixture was heated at 60° C. for 1 h, 70° C. for 3 days, then concentrated under reduced pressure. The residue was purified by reversed phase purification, eluting with acetonitrile in aqueous ammonium bicarbonate buffer, to give the title compound (0.018 g, 66%) as a yellow solid. MS (ES) m/z=555 (M+1).

Example 274D

2-Amino-4-(3-(4-(ethyl-d5)octahydro-1H-pyrrolo[3,2-b]pyridin-1-yl)-5-fluoro-7,9-dihydrofuro[3,4-f]quinazolin-6-yl)-7-fluorothieno[3,2-c]pyridine-3-carbonitrile

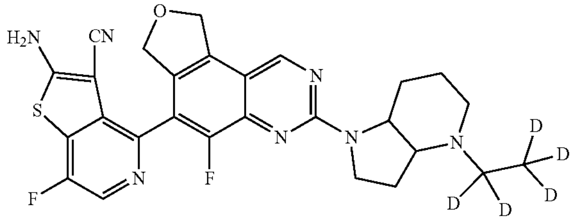 [SMILES: [2H]C([2H])([2H])C([2H])([2H])N1CCCC2C1CCN2c1ncc2c3c(c(-c4ncc(F)c5sc(N)c(C#N)c45)c(F)c2n1)COC3]

1-Iodoethane-1,1,2,2,2-d5 was used in a manner analogous to the method of Example 273D to afford the title compound (0.034 g, 77%) as a yellow solid. MS (ES) m/z=539 (M+1).

Example 122C

2-Amino-7-fluoro-4-(5-fluoro-3-((2S,3S)-2-methyl-3-(((R)-3,3,3-trifluoro-2-hydroxypropyl)amino)pyrrolidin-1-yl)-7,9-dihydrofuro[3,4-f]quinazolin-6-yl)thieno[3,2-c]pyridine-3-carbonitrile

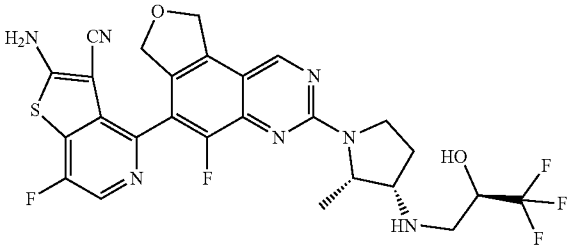 [SMILES: C[C@H]1[C@@H](NC[C@@H](O)C(F)(F)F)CCN1c1ncc2c3c(c(-c4ncc(F)c5sc(N)c(C#N)c45)c(F)c2n1)COC3]

A solution of tert-butyl (4-(3-((2S,3S)-3-amino-2-methylpyrrolidin-1-yl)-5-fluoro-7,9-dihydrofuro[3,4-f]quinazolin-6-yl)-3-cyano-7-fluorothieno[3,2-c]pyridin-2-yl)carbamate (0.150 g, 0.259 mmol) and (R)-2-(trifluoromethyl)oxirane (0.029 g, 0.259 mmol) in isopropanol (4 mL) was heated to 75° C. for 8 h, then cooled to RT. The material was purified by reversed phase purification, eluting with 10% to 100% ACN in water (both with 0.1% formic acid), to give the title compound (0.0054 g, 3.4%) as a yellow solid. MS (ES) m/z=592 (M+1).

Example 275D

2-Amino-7-fluoro-4-(5-fluoro-3-((2S,3S)-2-methyl-3-(((S)-3,3,3-trifluoro-2-hydroxypropyl)amino)pyrrolidin-1-yl)-7,9-dihydrofuro[3,4-f]quinazolin-6-yl)thieno[3,2-c]pyridine-3-carbonitrile formic acid

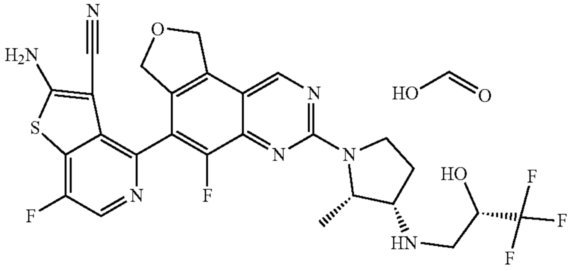

(S)-2-(Trifluoromethyl)oxirane was used in a manner analogous to the method of Example 122C to afford the title compound (0.0086 g, 5%). MS (ES) m/z=592 (M+1).

Biological Assays

The following assays demonstrate that the exemplified compounds are potent inhibitors of Kras G12C, G12D, and/or G12V and inhibit growth of certain tumors in vitro and/or in vivo.

PANC-1 Cellular Active RAS GTPase ELISA (KRas G12D Mutation)

The purpose of this assay is to measure the ability of test compounds to inhibit constitutive RAS GTPase activity in human PANC-1 (RRID:CVCL_0480) pancreatic ductal adenocarcinoma cells (Supplier: ATCC #CRL-1469). The RAS GTPase ELISA kit (Active Motif Cat #52097) contains a 96-well glutathione-coated capture plate and kit-supplied Glutathione-S-Transferase (GST)-fused to Raf-Ras Binding Domain (RBD) protein. Activated pan-RAS (GTP-bound) in cell extracts specifically bind to the Raf-RBD. Bound RAS is detected with a primary Ras antibody that recognizes human K-Ras (and H-Ras). An HRP-conjugated anti-rat IgG secondary antibody recognizes the primary antibody, and a development substrate solution facilitates a chemiluminescent readout.

PANC-1 cells are plated at a concentration of 75,000 cells/well in 80 μL complete media (DMEM, high-glucose, L-glutamine, GIBCO; 10% heat-inactivated fetal bovine serum, GIBCO) and incubated overnight at 37° C./5% $CO_2$. Approximately 24 hours later, 20 μL of (1:3) serially-diluted (in complete media) test compound (1-50 μM top concentration) and 20 μL of serially-diluted (in complete media) controls (Maximum signal wells: 0.5% DMSO and Minimum signal wells: 10 μM reference positive control compound) are added to the cell plate and incubated for 2 hours at 37° C./5% $CO_2$. Complete Lysis/Binding Buffer is prepared containing Protease Inhibitor cocktail (PIC) and stored on ice. One hour before cell plate incubation is completed, GST-Raf-RBD is diluted in lysis/binding buffer, and 50 μL of mixed buffer per well is added to the supplied opaque white ELISA assay plate and is incubated for a minimum of 1 hour at 4° C., with gently rocking. After 2 hours, the cells are washed with 100 μL ice-cold Ca2+/Mg2+-free PBS and lysed with 100 μL of kit supplied lysis/binding buffer (AM11). After 30-50 minutes of vigorous plate shaking at ambient temperature, cell plate is centrifuged at 410×g (approx. 1500 rpm) for 10 minutes. Wash buffer diluted to 1× with ultrapure $H_2O$ and 0.2 μm filtered is prepared at ambient temperature during the centrifugation step and then used to wash (3×100 μL) the GST-Raf-RBD coated assay plate. Next, 50 μL of cell lysate is added to the GST-Raf-RBD coated assay plate and incubated for 1 hour at ambient temperature with gentle shaking. During this incubation period, 1× Antibody Binding Buffer is prepared from thawed concentrate. The assay plate is washed 3×100 μL with 1× Wash Buffer, and then 50 μL of Primary RAS Antibody (kit supplied #101678), diluted 1:500 in 1× Antibody Binding buffer, is added. After a one hour of ambient incubation with gentle shaking, the assay plate is washed 3×100 μL with 1× Wash Buffer. Subsequently, 50 μL of Anti-rat HRP-conjugated IgG secondary antibody (0.25 μg/μL) (diluted 1:5000 in 1× Antibody Binding buffer) is added to each well of the assay plate and incubated an additional hour at ambient temperature with gentle shaking. Finally, the assay plate is washed 4×100 μL with 1× Wash buffer, followed by addition of 50 μL of mixed ambient temperature chemiluminescent working solution (combination of Reaction buffer with a chemiluminescence substrate). Data from each well's luminescent emission is recorded with a 2104 EnVision™ Plate Reader (Perkin Elmer) using a luminescence program optimized for the assay plate dimensions.

The signal is converted to percent inhibition using the following equation: % Inhibition=100−[(Test Compound Signal−Median Minimum Signal)/(Median Maximum Signal−Median Minimum Signal)×100]. The Maximum signal is a control well without inhibitor (DMSO). The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®, v17: $y=(A+((B-A)/(1+((x/C)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

In the above assay, compounds of Examples 1-3, 5-9, 11-18, 37, 1A-5A, 7A-11A, 13A-22A, 25A, 30A, 42A, 52A, 55A, 58A, 65A, 76A, 1B, 20B, 21B, and 105B were tested and all exhibited an ability to inhibit constitutive RAS GTPase activity indicating inhibition of KRas G12D mutant enzyme with a relative $IC_{50}$ of <100 nM. This data shows that compounds of Formula I as described herein are potent inhibitors of KRAS-GTP activity in this human pancreatic cancer cell culture demonstrating the ability to inhibit KRas G12D mutants.

MKN-45 Cellular Active RAS GTPase ELISA (KRas Wild-type)

The purpose of this assay is to measure the ability of test compounds to inhibit constitutive RAS GTPase activity in human MKN-45 gastric adenocarcinoma cell (Supplier: JCRB, SupplierID: JCRB 0254, Lot: 05222009). The RAS GTPase ELISA kit (Active Motif Cat #52097) contains a 96-well glutathione-coated capture plate and kit-supplied Glutathione-S-Transferase (GST)-fused to Raf-Ras Binding Domain (RBD) protein. Activated pan-RAS (GTP-bound) in cell extracts specifically bind to the Raf-RBD. Bound RAS is detected with a primary Ras antibody that recognizes human K-Ras (and H-Ras). An HRP-conjugated anti-rat IgG secondary antibody recognizes the primary antibody, and a development substrate solution facilitates a chemiluminescent readout.

MKN-45 cells are plated at a concentration of 75,000 cells/well in 80 μL complete media (DMEM, high-glucose, L-glutamine, GIBCO; 10% heat-inactivated fetal bovine serum, GIBCO) and incubated overnight at 37° C./5% $CO_2$. Approximately 24 hours later, 20 μL of (1:3) serially-diluted (in complete media) test compound (1-10 μM top concentration) and 20 μL of serially-diluted (in complete media) controls (Maximum signal wells: 0.1% DMSO and Minimum signal wells: 10 μM reference positive control compound) are added to the cell plate and incubated for 2 hours at 37° C./5% $CO_2$. Complete Lysis/Binding Buffer is prepared containing Protease Inhibitor cocktail (PIC) and stored on ice. One hour before cell plate incubation is completed, GST-Raf-RBD is diluted in lysis/binding buffer, and 50 μL of mixed buffer per well is added to the supplied opaque white ELISA assay plate and is incubated for a minimum of 1 hour at 4° C., with gently rocking. After 2 hours, the cells are washed with 100 μL ice-cold Ca2+/Mg2+-free PBS and lysed with 100 μL of kit supplied lysis/binding buffer (AM11). After 30-50 minutes of vigorous plate shaking at ambient temperature, cell plate is centrifuged at 410×g (approx. 1500 rpm) for 10 minutes. Wash buffer diluted to 1× with ultrapure $H_2O$ during the centrifugation step and then used to wash (3×100 μL) the GST-Raf-RBD coated assay plate. Next, 50 μL of cell lysate is added to the GST-Raf-RBD coated assay plate and incubated for 1 hour at ambient temperature with gentle shaking. During this incubation period, 1× Antibody Binding Buffer is prepared from thawed concentrate. The assay plate is washed 3×100 μL with 1× Wash Buffer, and then 50 μL of Primary RAS Antibody (kit supplied #101678), diluted 1:500 in 1× Antibody Binding buffer, is added. After a one hour of ambient incubation with gentle shaking, the assay plate is washed 3×100 μL with 1× Wash Buffer. Subsequently, 50 μL of Anti-rat HRP-conjugated IgG secondary antibody (0.25 μg/μL) (diluted 1:5000 in 1× Antibody Binding buffer) is added to each well of the assay plate and incubated an additional hour at ambient temperature with gentle shaking. Finally, the assay plate is washed 4×100 μL with 1× Wash buffer, followed by addition of 50 μL of mixed ambient temperature chemiluminescent working solution (combination of Reaction buffer with a chemiluminescence substrate). Data from each well's luminescent emission is recorded with a 2104 EnVision™ Plate Reader (Perkin Elmer) using a luminescence program optimized for the assay plate dimensions.

The signal is converted to percent inhibition using the following equation: % Inhibition=100−[(Test Compound Signal−Median Minimum Signal)/(Median Maximum Signal−Median Minimum Signal)×100]. The Maximum signal is a control well without inhibitor (DMSO). The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®, v17: y=(A+((B−A)/(1+((x/C)^D)))) where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds of Examples 1-3, 5-9, 11-18, 37, 1A, 3A, 4A, 6A, 7A, 9A, 10A, 13A-17A, 19A, 20A, 22A-25A, 1B-5B, 7B-11B, 13B, 14B, 17B, and 20B-23B were tested in both assays above (PANC-1 Cellular Active RAS GTPase ELISA and MKN-45 Cellular Active RAS GTPase ELISA) and all showed a significant (i.e., greater than 10-fold) selective inhibition preference for KRas G12D mutant over KRas wild-type.

Cellular Phospho-ERK AlphaLISA® Assay for KRAS Inhibition

The purpose of these assays is to quantify the ability of test compounds to selectively inhibit KRAS signaling in cells with amplified KRAS and expressing activating KRAS G12 mutations (Table 31). Cancer cell lines used in this study were selected based on the presence of homozygous activating KRAS G12 mutations, or amplification of the KRAS gene. In addition, these assays were performed in a set of RAS-less mouse embryonic fibroblast (MEF) cells which were engineered to only express KRAS wild type, HRAS, and NRAS, respectively (Table 31). MEF cells were used to confirm KRAS selectivity of the test compounds.

TABLE 31

| Cell Line Information | | |
|---|---|---|
| Cell Line Name | RAS Mutation/Features | Assay Seeding Density (Cells/Well) |
| MKN45 | WT KRAS Amplification/Human Gastric Cancer | 20,000 |
| SW620 | KRAS G12V/Human Colorectal Cancer | 20,000 |
| HPAC | KRAS G12D/Human Pancreatic Cancer | 2,500 |
| NCI-1373 | KRAS G12C/Human Lung Cancer | 5,000 |
| MEF-NRAS | RAS-less MEFs Expressing NRAS only | 20,000 |
| MEF-HRAS | RAS-less MEFs Expressing HRAS only | 10,000 |
| MEF-KRAS | RAS-less MEFs Expressing KRAS only | 2,500 |

The compounds' activity is determined by measuring changes in the phosphorylation levels of the downstream effector Extracellular Signal-regulated Kinase-1 and 2 (ERK1/2) in the compound treated cells. Phosphorylation levels of ERK-1/2 are measured using the AlphaLISA® SureFire® Ultra™ p-ERK 1/2 (Thr202/Tyr204) Assay Kit (#ALSU-PERK-A50K, PerkinElmer® Waltham, MA). The AlphaLISA® assay is a quantitative sandwich immunoassay that can be used to detect phosphorylation of target proteins from cellular lysates using bead-based Alpha technology. The assay kit contains two antibodies, one that binds the phospho-Thr202/Tyr204 epitope on ERK-1/2, and another one that recognizes a separate site on the protein. One of these antibodies is biotinylated and associated with streptavidin-coated Alpha Donor beads, the other antibody is conjugated to AlphaLISA® Acceptor beads. When ERK-1/2 is phosphorylated in cellular lysate, the Donor and Acceptor beads are brought into proximity with each other. When the Donor bead is excited by 600 nm wavelength light, a photosensitizer inside the bead converts ambient oxygen to an excited singlet state. When the Acceptor bead is within 200 nm of this reaction, the singlet oxygen reacts with the Acceptor leading to a chemiluminescent emission. The amount of light measured is proportional to the amount of phosphorylated ERK-1/2 in the lysate. The AlphaLISA® SureFire® Ultra™ p-ERK 1/2 (Thr202/Tyr204) Assay Kit contains AlphaLISA® antibody-conjugated Donor and Acceptor Beads, Lysis buffer concentrate, and a set of proprietary buffers (Activation Buffer, Reaction Buffer 1, Reaction Buffer 2, and Dilution Buffer).

To perform the assays, test compounds and controls are acoustically dispensed (Labcyte ECHO®, San Jose, CA) into a white 384-well assay plate (Proxiplate-384, PerkinElmer #6008280) in a 10-point 3-fold dilution series in 30 nL DMSO. Cells are then added to the assay plate in 8 μL per well assay medium (HBSS, Sigma #55021C, 10% FBS, GIBCO #10082-147) at a cell line specific density (Table 31). The final compound concentrations range from 0.5 to 10,000 nM and the final DMSO concentration is 0.375% in each well. Maximum signal control wells contain 0.375% DMSO only (negative control), and minimum signal control wells contain 10,000 nM control compound (positive control). Cells in suspension are incubated with the test and reference compounds for 2 h at 37° C./5% $CO_2$. Following the 2 h incubation, cells are lysed by adding 2 μL of the AlphaLISA® Lysis buffer concentrate (5×) supplemented with protease/phosphatase inhibitor cocktail (Thermo Scientific #78442). The assay plate is covered with an opaque lid and shaken at 750 rpm on a multi-plate shaker (Heidolph, Schwabach, Germany) for 30 min at room temperature to induce cell lysis. During the lysis, the AlphaLISA® Acceptor beads are diluted 1:50 in a prepared buffer mixture (1:1 AlphaLISA® Reaction Buffers 1 and 2 with a 1:25 dilution of AlphaLISA® Activation Buffer). Following cell lysis, plates are centrifuged briefly, and 5 μL per well prepared Acceptor beads are added. The plate is then covered and incubated in the dark for 2 h at room temperature. During the Acceptor bead incubation, Donor beads are prepared by diluting the Alpha streptavidin Donor beads 1:50 in AlphaLISA® Dilution buffer. Following the Acceptor bead incubation, 5 μL per well of Donor bead mixture is added to the plates. Plates are then covered and allowed to incubate in the dark at room temperature for 2 h. After this incubation period, the AlphaLISA signal is read using a PHERAstar® FSX multimode plate reader (BMG Labtech, Ortenberg, Germany) equipped with an AlphaLISA® compatible optics cube.

Raw signal obtained from the AlphaLISA® assay is analyzed using Genedata Screener® 17.0.3. Within the program, data is normalized to 32 wells treated with inhibition control (max inhibition/positive control) and 32 wells treated with 0.375% DMSO only (minimum inhibition/negative control) to calculate the % Activity of the compound:

$$\%\ \text{Activity} = 100 \times \left(1 - \frac{(\text{treated value} - \text{positive control})}{(\text{negative control} - \text{positive control})}\right) \quad \text{eq. 1}$$

% Activity values are fit to a four-parameter non-linear logistic equation using Genedata Screener® 17.0.3. to determine $IC_{50}$ values:

$$y = \text{Bottom} + \frac{\text{Top} - \text{Bottom}}{1 + \left(\frac{10^{Log(IC_{50})}}{10^{x}}\right)^{h}} \quad \text{eq. 2}$$

Where y=% Activity, Bottom=minimum asymptote, Top=maximum asymptote, x=compound concentration, $IC_{50}$=the compound concentration where half maximal activity is achieved, and h=the Hill Coefficient.

In the above assays, compounds of Examples indicated herein were tested and exhibited an ability to reduce levels of phosphorylated ERK-1/2 in cells expressing KRAS and KRAS variants indicating inhibition of constitutive RAS activity in cells expressing KRAS G12C (Examples 1, 3, 8, 9, 19-30, 32-36, 29A-44A, 47A-70A, 72A-79A, 82A-84A, 28B-30B, 33B-94B, 96B-120B, 122B-148B, 1C-49C, 51C, 53C, 54C, 57C, 58C, 60C, 61C, 65C, 67C, 69C-71C, 73C-79C, 81C, 83C-88C, 90C, 92C, 94C-122C, 2D, 3D, 5D, 6D, 8D-10D, 12D, 14D, 16D-99D, 101D-126D, 128D-195D, 197D-201D, 203D-207D, 209D-236D, 239D, 240D, 242D, 244D, 246D-248D, 250D-252D, 254D, 256D-259D, and 262D-275D), KRAS G12D (Examples 1-3, 5-9, 11-15, 19-30, 32-37, 25A, 29A-44A, 47A-67A, 70A, 73A, 74A, 76A, 78A, 79A, 82A-84A, 19B, 28B-30B, 33B-45B, 47B-51B, 53B-65B, 67B-94B, 96B-108B, 110B-148B, 1C-27C, 29C-49C, 51C, 53C, 54C, 57C, 58C, 60C, 61C, 65C, 67C, 69C, 70C, 73C, 75C-79C, 81C, 83C-88C, 90C, 92C, 94C-122C, 2D, 3D, 5D, 6D, 8D, 1OD, 12D, 14D, 16D, 18D-20D, 22D-46D, 48D-73D, 75D-81D, 83D-95D, 98D, 99D, 101D, 103D-139D, 141D-159D, 161D, 163D, 165D-178D, 180D, 181D, 183D-195D, 197D-201D, 203D-207D, 209D-236D, 239D, 240D, 242D, 244D, 246D-248D, 250D, 252D, 254D, 256D-259D, and 262D-275D), KRAS G12V (Examples 9, 19-30, 32-36, 29A-44A, 47A-62A, 64A-70A, 72A-74A, 76A, 78A, 79A, 82A-84A, 28B-30B, 33B-53B, 55B-88B, 90B-94B, 96B-107B, 110B-120B, 122B-136B, 138B-146B, 148B, 1C-27C, 29C-49C, 51C, 53C, 54C, 57C, 58C, 60C, 61C, 65C, 67C, 69C, 70C, 73C, 75C-78C, 81C, 83C-88C, 92C, 94C-120C, 122C, 2D, 3D, 6D, 8D, 1OD, 12D, 14D, 16D, 18D-46D, 48D-73D, 75D-81D, 83D-96D, 99D, 101D, 104D-133D, 135D-139D, 141D-143D, 145D-159D, 161D, 163D, 165D-173D, 175D, 177D, 178D, 180D, 183D-195D, 197D-203D, 206D, 207D, 209D, 211D-236D, 240D, 242D, 244D, 246D-248D, 250D, 252D, 254D, 256D-259D, and 262D-275D), or KRAS WT (Examples 2, 3, 9, 19-30, 32-36, 29A-44A, 47A-70A, 73A, 74A, 76A, 78A, 79A, 82A-84A, 28B-30B, 33B-88B, 90B-94B, 96B-108B, 110B-120B, 122B-148B, 1C-49C, 51C, 53C, 54C, 57C, 58C, 60C, 61C, 65C, 67C, 69C, 70C, 73C-79C, 81C, 83C-88C, 90C, 92C, 94C-122C, 2D, 3D, 5D, 6D, 8D-10D, 12D, 14D, 16D-46D, 48D-73D, 75D-81D, 83D-99D, 101D-143D, 145D-195D, 197D-207D, 209D-236D, 239D, 240D, 242D, 244D, 246D-248D, 250D, 252D, 254D, 256D-259D, and 262D-275D), with a relative IC50 of <500 nM. Compounds of Examples 1, 2, 4-15, 21, 22, 24-26, 29-34, 37, 29A, 34A-38A, 41A, 43A-47A, 53A, 59A, 60A, 62A-64A, 69A, 71A, 72A, 75A, 77A, 80A, 81A, 18B, 19B, 31B, 32B, 34B, 35B, 39B-43B, 46B, 48B, 51B-54B, 57B, 60B, 63B, 65B, 66B, 68B, 70B, 73B-77B, 83B, 86B, 87B, 89B, 93B, 95B, 98B, 99B, 101B-103B, 108B, 109B, 112B, 115B-121B, 123B, 124B, 136B, 140B-142B, 144B, 147B, 2C, 8C, 14C, 16C, 17C, 20C, 21C, 26C, 28C, 30C, 33C-36C, 38C, 40C, 46C-50C, 52C, 53C, 55C, 56C, 59C, 62C-64C, 66C, 68C, 71C, 72C, 74C, 80C, 82C, 89C, 91C, 93C, 101C, 112C, 113C, 118C, 121C, 1D, 4D, 5D, 7D, 9D, 11D, 13D, 15D, 17D, 18D, 20D-28D, 31D, 33D-35D, 37D, 38D, 40D, 43D, 44D, 46D, 47D, 51D-54D, 56D, 58D-62D, 64D-78D, 80D, 91D, 93D, 96D-106D, 109D-111D, 113D, 114D, 117D, 121D-123D, 126D-128D, 132D-136D, 139D, 140D, 144D, 147D, 148D, 150D, 152D-155D, 157D-162D, 164D, 172D-186D, 188D, 194D, 195D, 199D-210D, 212D, 216D, 218D, 222D, 223D, 225D, 226D, 228D, 229D, 232D, 233D, 237D, 238D, 241D, 243D, 245D, 249D, 251D, 253D, 255D, 259D-261D, 263D, and 268D, were tested in the Mouse Embryonic Fibroblasts cell line assays above (MEF-NRAS, MEF-HRAS) and all exhibited a relative IC50 of >2 μM. Compounds of Examples 8, 9, 19-30, 32-36, 29A-44A, 47A, 49A, 50A, 52A, 54A-69A, 72A, 74A-76A, 78A, 79A, 84A, 28B, 29B, 33B-36B, 39B-53B, 55B-60B, 62B-79B, 82B-87B, 90B, 91B, 96B-103B, 105B-107B, 109B-115B, 117B-120B, 122B-128B, 130B, 131B, 136B, 138B-144B, 147B, 1C-6C, 8C, 9C, 11C-22C, 24C-28C, 30C-38C, 40C-43C, 45C-49C, 51C, 53C, 54C, 57C, 60C, 65C, 67C, 69C, 70C, 73C, 74C, 76C, 77C, 84C, 87C, 88C, 98C, 99C, 101C, 104C-120C, 122C, 2D, 3D, 8D, 1OD, 14D, 18D-40D, 42D-46D, 48D-73D, 75D-80D, 83D-87D, 89D-93D, 95D-119D, 121D-145D, 147D-164D, 167D, 168D, 170D-173D, 175D-181D, 183D, 184D, 186D-188D, 190D, 192D-195D, 197D-204D, 206D, 207D, 209D, 212D, 213D, 215D-236D, 240D, 244D, 246D-251D, 254D, 256D, 257D, 259D, 262D-265D, 267D, 268D, 270D-272D, 274D, and 275D were tested in the three assays above (SW620, MEF-NRAS or MEF-HRAS Cellular Phospho-ERK AlphaLISA® Assays) and all showed a significant (i.e., greater than 10-fold) selective inhibition preference for KRas G12V mutant over HRAS and NRAS.

This data shows that compounds of Formula I as described herein are potent inhibitors of KRAS human cancer cells expressing KRAS demonstrating the ability to inhibit KRAS G12C, G12D or G12V mutants with a significant selective inhibition preference for KRAS mutants over HRAS or NRAS.

TABLE 32

| Abbreviations | |
|---|---|
| KRAS | Kirsten Rat Sarcoma Virus |
| NRAS | Neuroblastoma RAS Viral Oncogene Homolog |
| HRAS | Harvey Rat Sarcoma Virus |
| MEF | Mouse Embryonic Fibroblasts |

TABLE 32-continued

| Abbreviations | |
|---|---|
| ERK | Extracellular Signal-Regulated Kinase |
| AlphaLISA | Alpha-Linked Immunosorbent Assay |
| DMSO | Dimethyl Sulfoxide |
| HBSS | Hank's Balanced Salt Solution |
| FBS | Fetal Bovine Serum |
| $CO_2$ | Carbon Dioxide |

What is claimed is:

1. A compound of the formula:

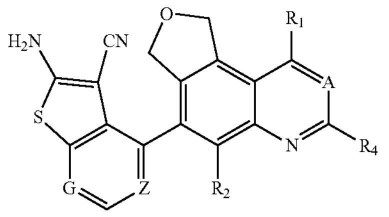

wherein:

A is —C(H)— or —N—;

Z is —C($R_{3c}$)- or —N—;

G is —C($R_{3b}$)- or —N—;

R is H;

$R_2$ is H, halogen, or methyl;

$R_{3b}$, and $R_{3c}$ are each independently H, halogen, or methyl;

$R_4$ is a N-linked cyclic amine, wherein the N-linked cyclic amine is a N-linked:

i. azetidine substituted with $R_{4a}$ and $R_{4b}$; or ii. pyrrolidine, piperidine, piperazine, or morpholine, each of which is optionally bridged by a $C_{1-3}$ alkylene, and each of which is optionally substituted with one or more halogen; hydroxyl; —$NR_{6a}R_{6a}$; (1-methylpiperidin-4-yl)oxy; $C_{1-3}$ alkoxy optionally substituted with-$NR_{6a}R_{6a}$; $C_{1-3}$ alkyl optionally substituted with one or more halogen, —$NR_{6a}R_{6a}$ or hydroxyl; an imidazole optionally substituted with a methyl; a monocyclic ring selected from azetidine, piperidine, piperazine, morpholine, oxazepane, or diazepane; a bicycle selected from hexahydro-1H-furo[3,4-c]pyrrole, octahydropyrrolo[3,4-c]pyrrole, or octahydropyrrolo[1,2-a]pyrazine; or a spirocycle selected from 4,7-diazaspiro[2.5]octane, 2-oxa-7-azaspiro[3.5] nonane, 2,6-diazaspiro[3.4]octane, or 2-azaspiro[3.3]heptane; wherein the monocyclic ring is optionally bridged by a $C_{1-3}$ alkylene, and can optionally be substituted with one or more halogen, hydroxyl, -CN, $C_{1-3}$ alkoxy, —$NR_{10}R_{10}$, cyclopropyl, oxetane, -CO-$C_{1-3}$ alkyl, or a $C_{1-3}$ alkyl optionally substituted with hydroxyl, $C_{1-3}$ alkoxy, —$NR_{10}R_{10}$, halogen, or -$CF_3$; and wherein the bicyclo or spirocyclo is each optionally substituted with a methyl or a halogen;

$R_{4a}$ is $NR_4R_{4d}$, cyclopropyl, azetidine, pyrrolidine, piperidine, piperazine, morpholine or imidazole, wherein the cyclopropyl, azetidine, pyrrolidine, piperidine, piperazine, or morpholine is optionally substituted with halogen, hydroxyl, $C_{1-3}$ alkoxy or —$NR_{6a}R_{6a}$;

$R_{4b}$ is H, hydroxyl, or $C_{1-3}$ alkyl;

$R_{4c}$ is independently cyclopropyl or oxetane;

$R_{4a}$ is independently $C_{1-3}$ alkyl;

each $R_{6a}$ is independently H, trideuteromethyl, a $C_{3-5}$ cycloalkyl, a N-methyl pyrrolidine, tetrahydrofuran, tetrahydropyran, bicyclo[1.1.1]pentan-1-yl, bicyclo [1.1.1]pentan-1-ol, or a $C_{1-3}$ alkyl optionally substituted with one or more deuterium, hydroxyl, methyl, methoxy, halogen, cyclopropyl, oxetane, tetrahydrofuran, tetrahydropyran, —CO-NHMe, or -CO-$NH_2$, wherein the $C_{3-5}$ cycloalkyl is optionally substituted with one or more hydroxyl or methyl;

$R_{10}$ is H or $C_{1-3}$ alkyl optionally substituted with one or more deuterium; or a pharmaceutically acceptable salt thereof.

2. The compound according to claim 1, wherein $R_4$is a N-linked cyclic amine, wherein the N-linked cyclic amine is a N-linked:

i. azetidine substituted with $R_{4a}$ and $R_{4b}$; or ii. pyrrolidine, piperidine, piperazine, or morpholine; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, piperazine, morpholine, a $C_{1-3}$ alkyl, or an imidazole optionally substituted with a methyl; wherein the azetidine is optionally substituted with hydroxyl or $C_{1-3}$ alkoxy; the piperazine is optionally substituted with a methyl, and the $C_{1-3}$ alkyl is optionally substituted with one or more halogen, —$NR_{6a}R_{6a}$ or hydroxyl;

$R_{4a}$ is $NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or —$NR_{6a}R_{6a}$; and each $R_{6a}$ is independently H, trideuteromethyl, a $C_{3-5}$ cycloalkyl, tetrahydrofuran, tetrahydropyran, bicyclo [1.1.1]pentan-1-yl, or a $C_{1-3}$ alkyl optionally substituted with one or more hydroxyl, methyl, methoxy, halogen, cyclopropyl, oxetane, tetrahydrofuran, tetrahydropyran, -CO-NHMe, or -CO-$NH_2$, wherein the $C_{3-5}$ cycloalkyl is optionally substituted with one or more hydroxyl or methyl; or a pharmaceutically acceptable salt thereof.

3. The compound according to claim 1, wherein $R_4$is a N-linked cyclic amine, wherein the N-linked cyclic amine is a N-linked:

i. azetidine substituted with $R_{4a}$ and $R_{4b}$; or ii. pyrrolidine, piperidine, piperazine, or morpholine; each of which is optionally bridged by a $C_{1-3}$ alkylene, and each of which is optionally substituted with one or more halogen, hydroxyl, $C_{1-3}$ alkoxy, —$NR_{6a}R_{6a}$, azetidine, a $C_{1-3}$ alkyl, or an imidazole optionally substituted with a methyl; wherein the azetidine is optionally substituted with hydroxyl or $C_{1-3}$ alkoxy; and the $C_{1-3}$ alkyl is optionally substituted with halogen-$NR_{6a}R_{6a}$ or hydroxyl; and $R_{4a}$ is $NR_{4c}R_{4d}$, cyclopropyl, azetidine, pyrrolidine, piperidine, morpholine or imidazole, wherein the cyclopropyl, azetidine, pyrrolidine, piperidine, or morpholine is optionally substituted with halogen, hydroxyl, $C_{1-3}$ alkoxy or —$NR_{6a}R_{6a}$; and each $R_{6a}$ is independently H, trideuteromethyl, a $C_{3-5}$ cycloalkyl or a $C_{1-3}$ alkyl optionally substituted with hydroxyl; or a pharmaceutically acceptable salt thereof.

4. The compound according to claim 1, wherein $R_{3b}$, and $R_{3c}$ are each independently H or halogen, and $R_4$is a N-linked cyclic amine, wherein the N-linked cyclic amine is a N-linked:

i. azetidine substituted with $R_{4a}$ and $R_{4b}$; or ii. pyrrolidine, piperidine, piperazine, or morpholine; each of which is optionally bridged by a $C_{1-3}$ alkylene, and each of which is optionally substituted with one or more halogen, hydroxyl, —$NR_{6a}R_{6a}$, imidazole or a $C_{1-3}$ alkyl; wherein the imidazole is optionally substituted with a methyl; and the $C_{1-3}$ alkyl is optionally substituted with-$NR_{6a}R_{6a}$ or hydroxyl;

$R_{4a}$ is $NR_{4c}R_{4d}$, cyclopropyl, azetidine, pyrrolidine, morpholine, wherein the cyclopropyl, azetidine, pyrrolidine or morpholine is optionally substituted with halogen, or —$NR_{6a}R_{6a}$;

$R_{4b}$ is H, or $C_{1-3}$ alkyl; and each $R_{6a}$ is independently H or $C_{1-3}$ alkyl; or a pharmaceutically acceptable salt thereof.

5. The compound according to claim 1, wherein G is —N-, or a pharmaceutically acceptable salt thereof.

6. The compound according to claim 1, wherein G is —C($R_{3b}$)-, or a pharmaceutically acceptable salt thereof.

7. The compound according to claim 6, wherein $R_{3b}$ is F, or a pharmaceutically acceptable salt thereof.

8. The compound according to claim 1, wherein Z is —N-, or a pharmaceutically acceptable salt thereof.

9. The compound according to claim 1, wherein Z is —C($R_{3c}$)-, or a pharmaceutically acceptable salt thereof.

10. The compound according to claim 9, wherein $R_{3c}$ is H or F, or a pharmaceutically acceptable salt thereof.

11. The compound according to claim 1, wherein $R_{3b}$, and $R_{3c}$ are each independently H or halogen, or a pharmaceutically acceptable salt thereof.

12. The compound according to claim 1, wherein A is —N-, or a pharmaceutically acceptable salt thereof.

13. The compound according to claim 1, wherein A is —C(H)-, or a pharmaceutically acceptable salt thereof.

14. The compound according to claim 1, wherein $R_2$ is For Cl, or a pharmaceutically acceptable salt thereof.

15. The compound according to claim 1, wherein $R_2$ is F, or a pharmaceutically acceptable salt thereof.

16. The compound according to claim 1, wherein $R_2$ is Cl, or a pharmaceutically acceptable salt thereof.

17. The compound according to claim 1, wherein $R_4$ is selected from:

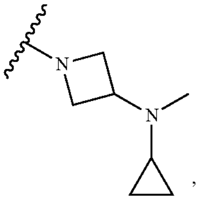 ,

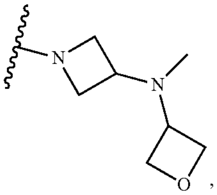 ,

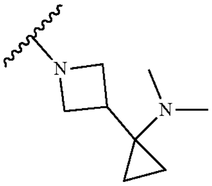 ,

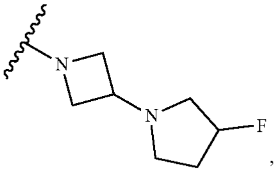 ,

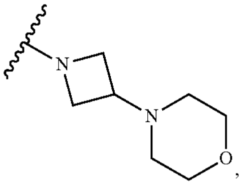 ,

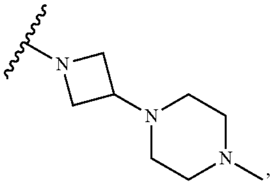 ,

-continued

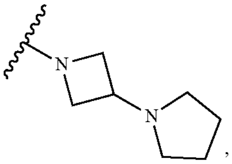 ,

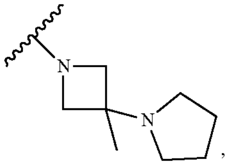 ,

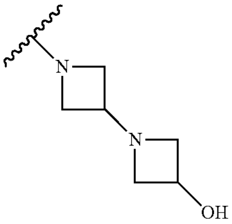 ,

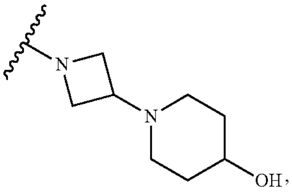 ,

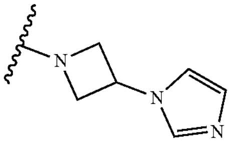 ,

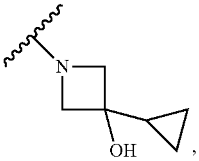 ,

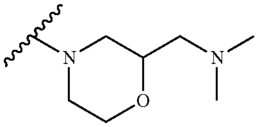

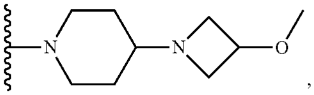 ,

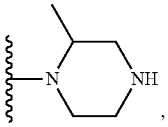 ,

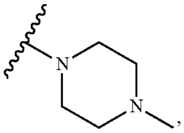 ,

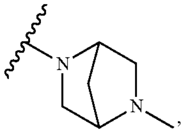 ,

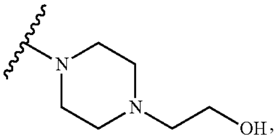 ,

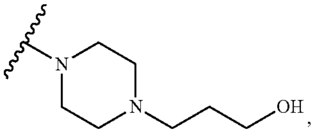 ,

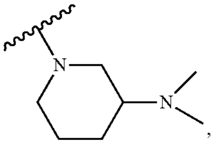 ,

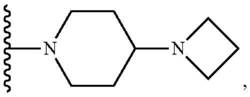 ,

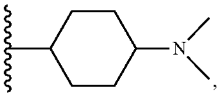 ,

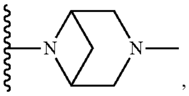 ,

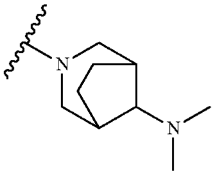

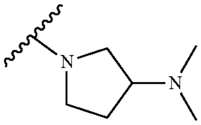

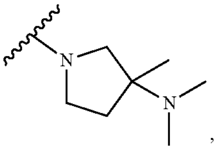 ,

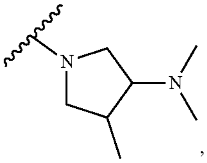 ,

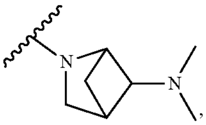 ,

-continued
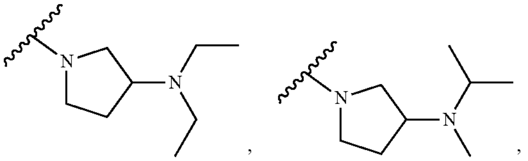
,
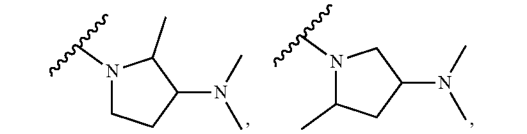
,
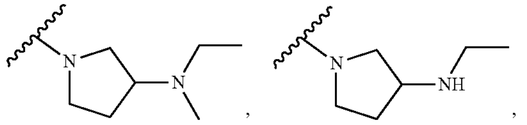
,
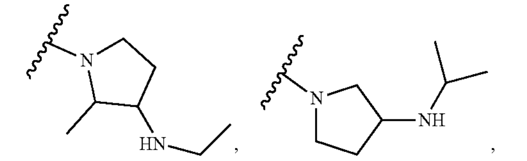
,
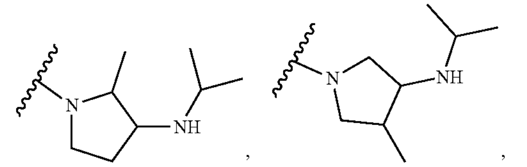
,
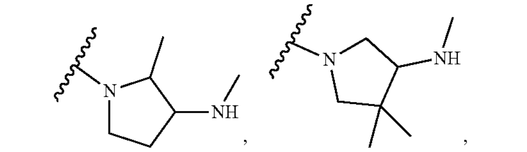
,
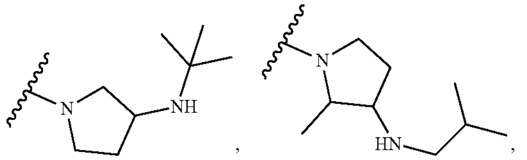
,
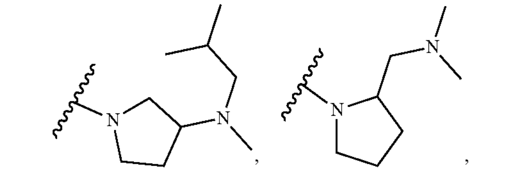
,
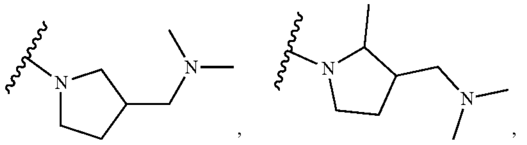
,
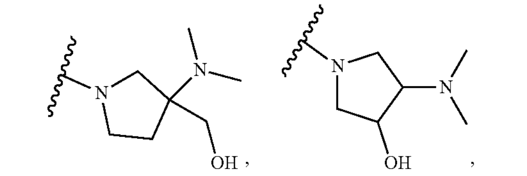
,
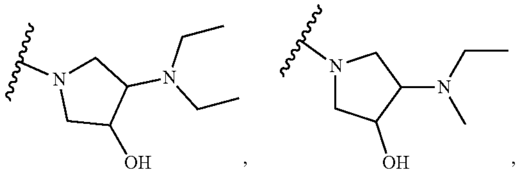
,
-continued
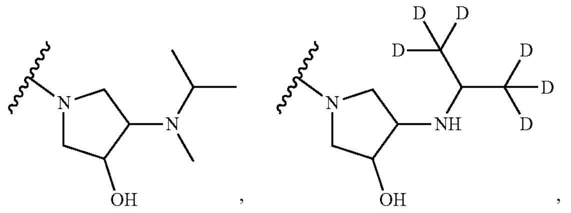
,
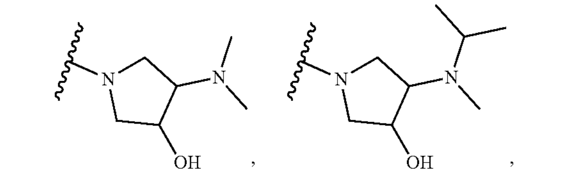
,
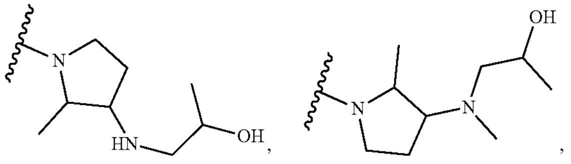
,
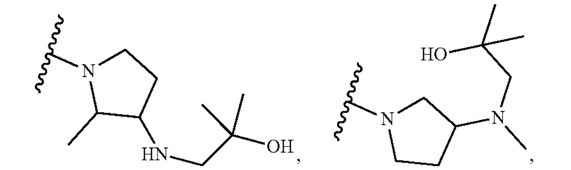
,
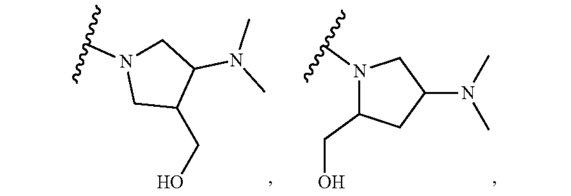
,
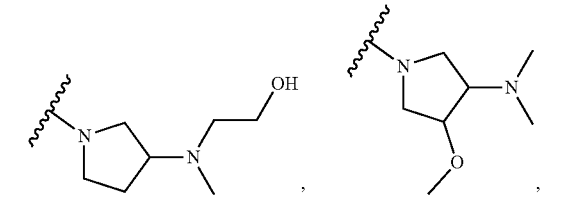
,
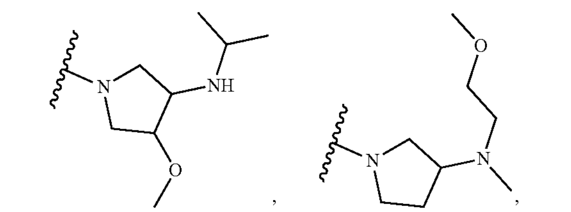
,
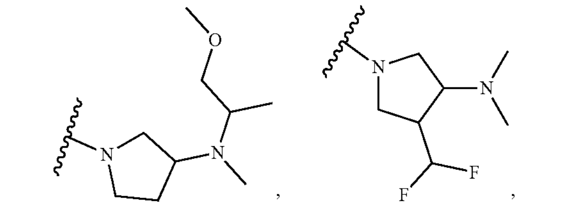
,
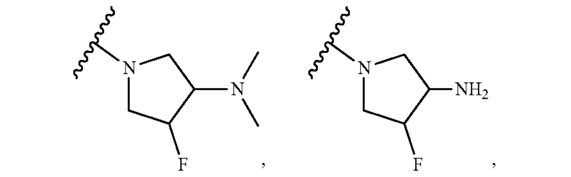
, -continued
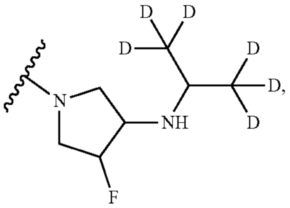
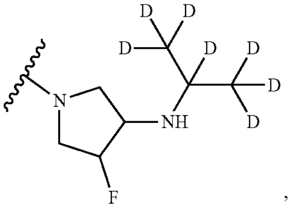
,
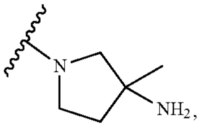
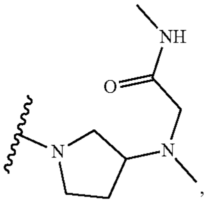
,
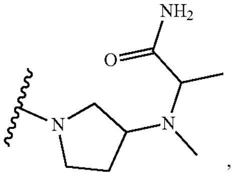
,
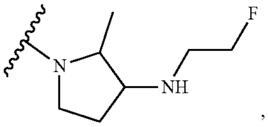
,
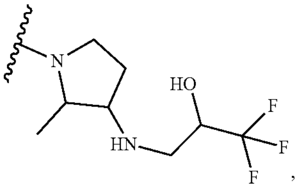
,
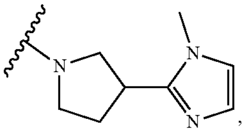
,
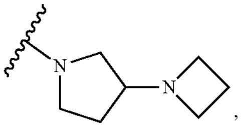
,
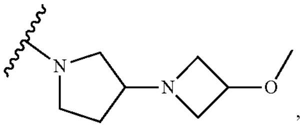
,
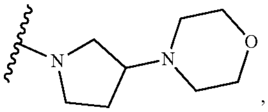
,
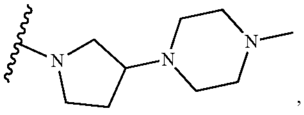
,
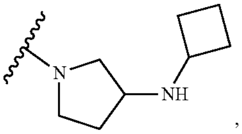
,
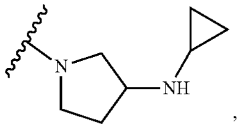
,
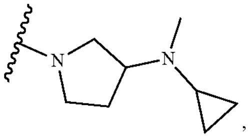
,
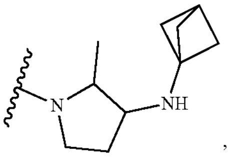
,
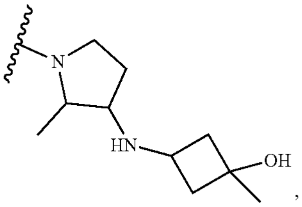
,
-continued
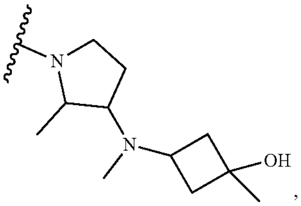
,
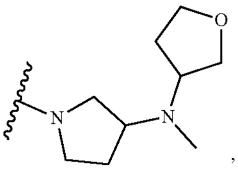
,
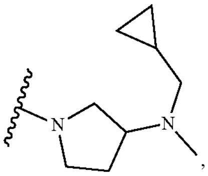
,
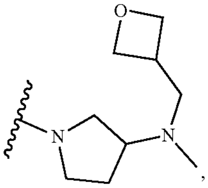
,
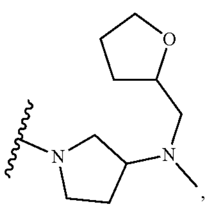
,
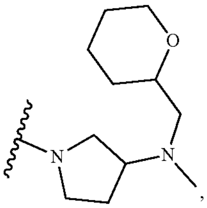
,
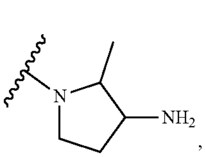
,
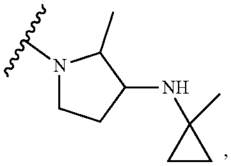
,
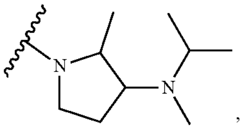
,
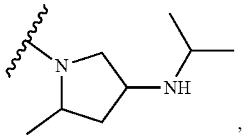
,
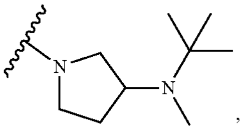
,
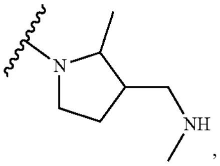
,
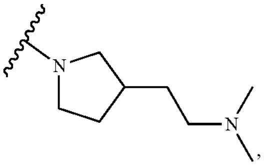
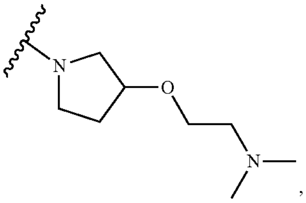
,
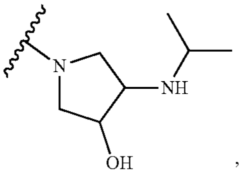
,
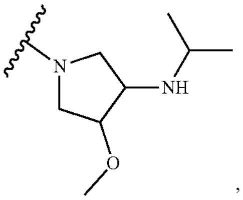
,
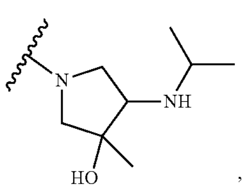
, -continued
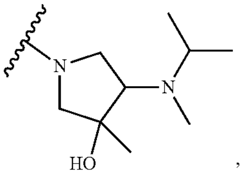,
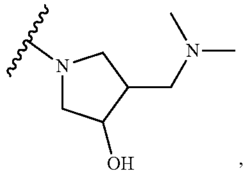,
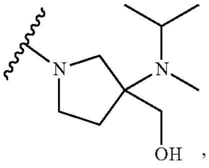,
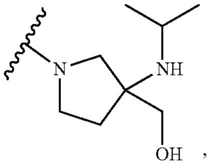,
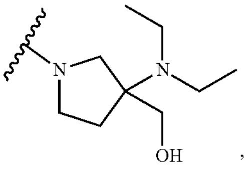,
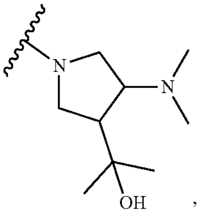,
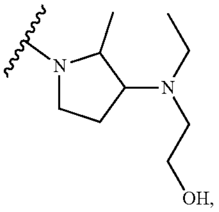
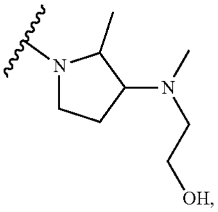
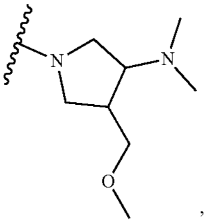,
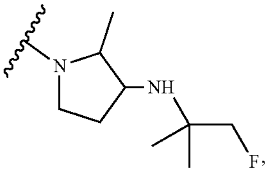
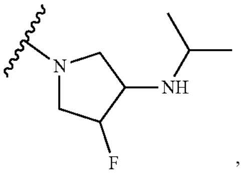,
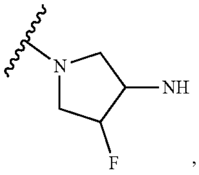,
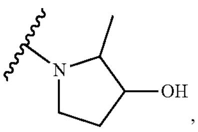,
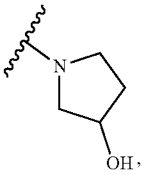
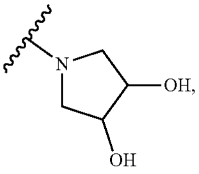
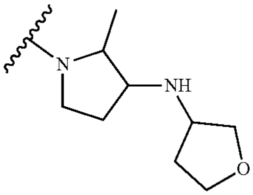,
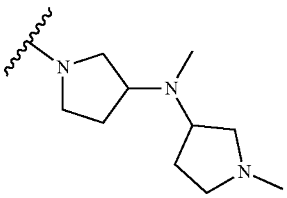,
-continued
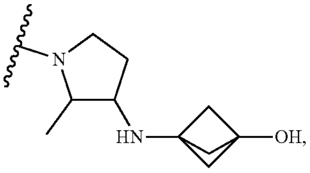
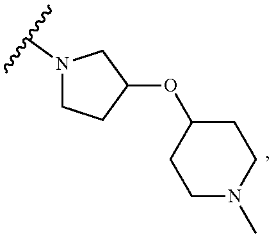
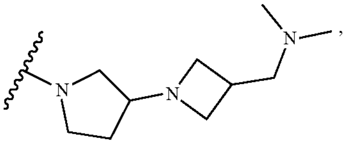
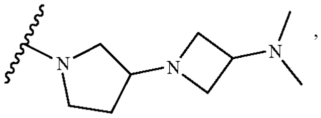
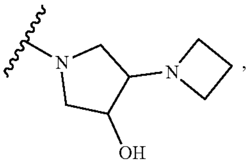
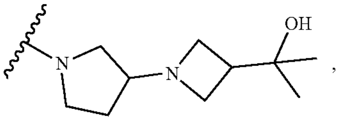
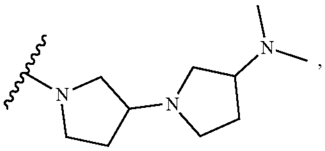
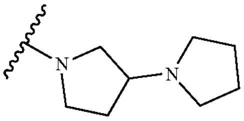,
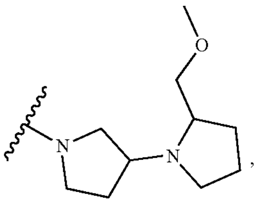
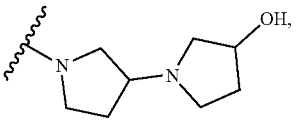
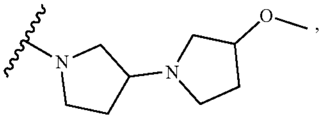
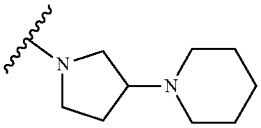,
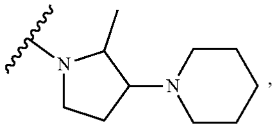

-continued
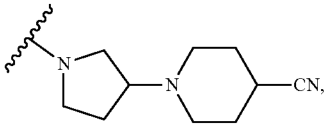
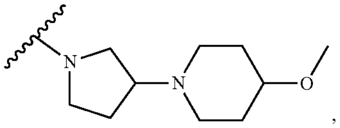
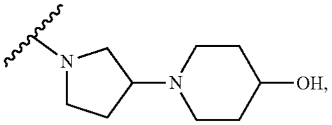
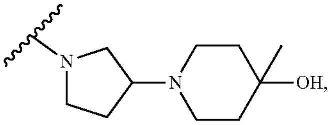
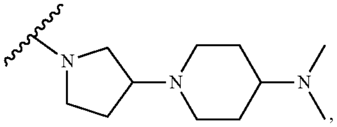
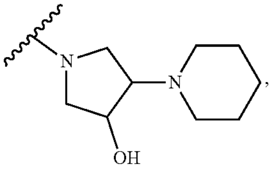
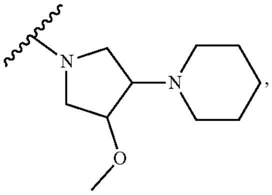
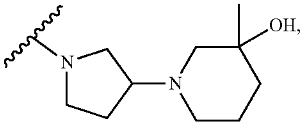
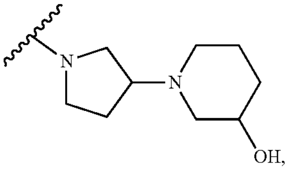
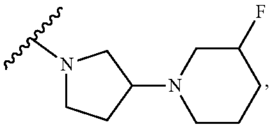
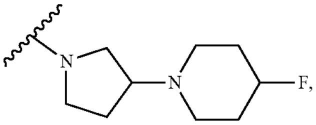
-continued
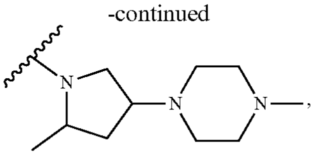
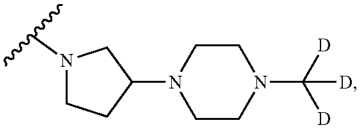
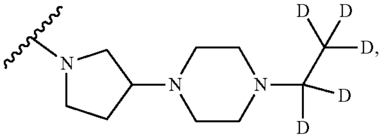
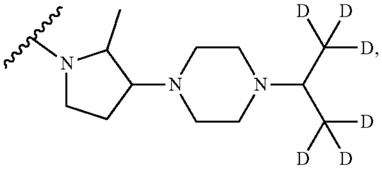
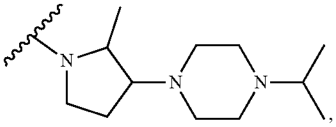
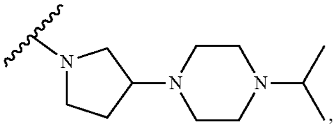
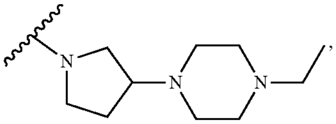
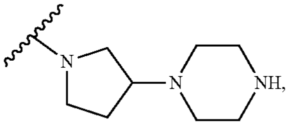
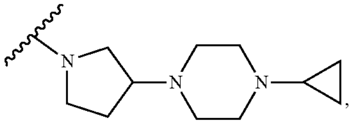
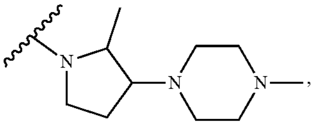
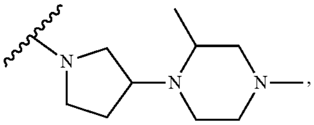
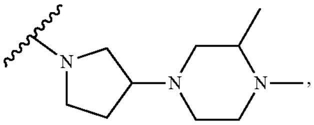
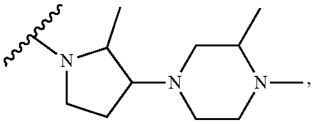

-continued
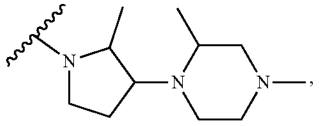
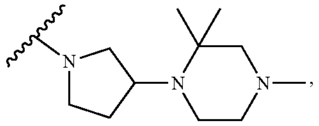
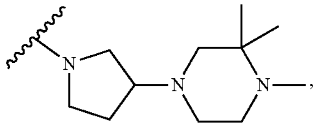
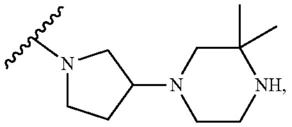
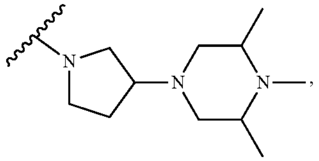
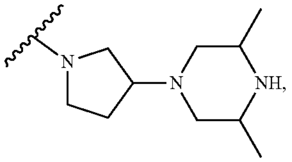
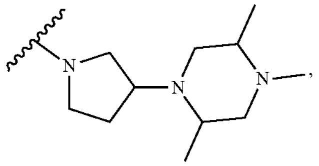
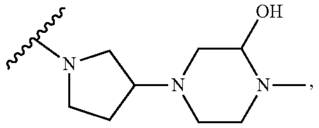
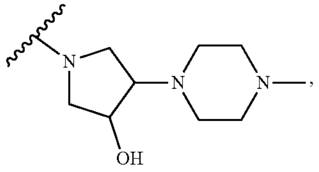
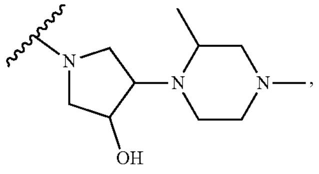
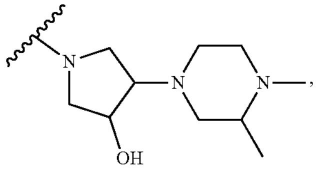
-continued
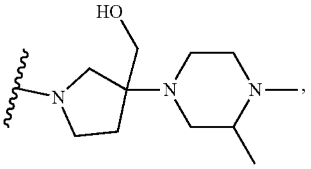
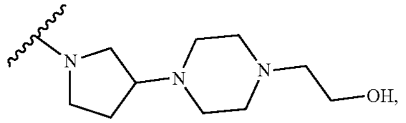
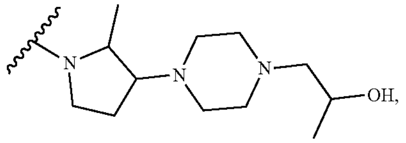
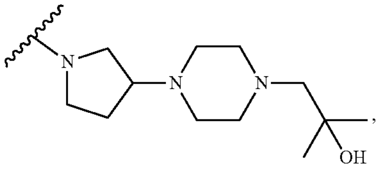
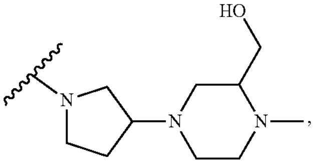
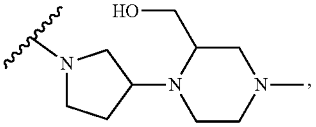
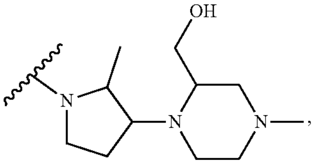
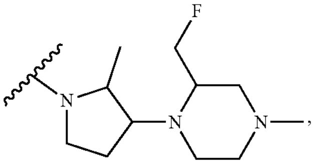
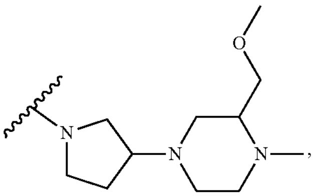
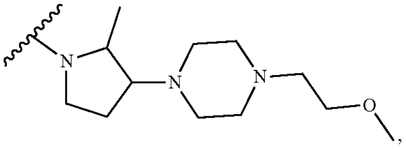
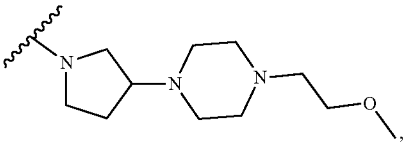

-continued
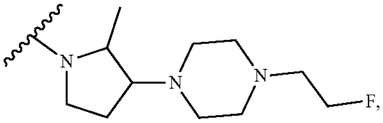,
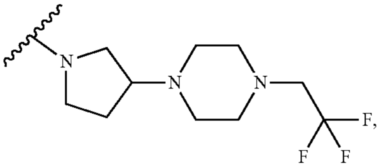,
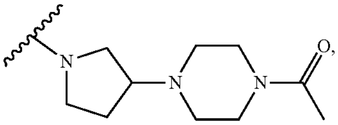,
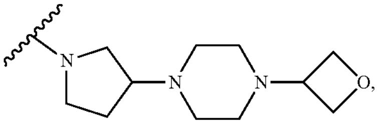,
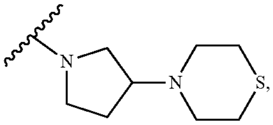,
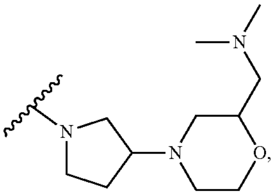,
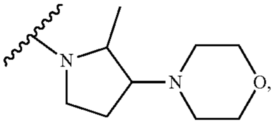,
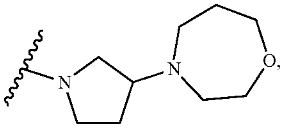,
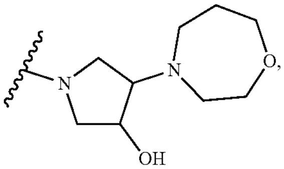,
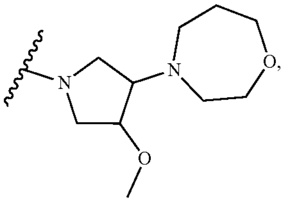,
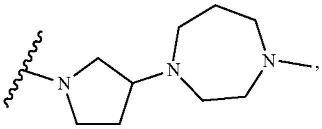,
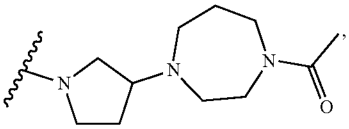,
-continued
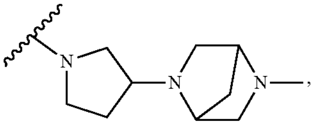,
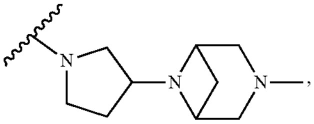,
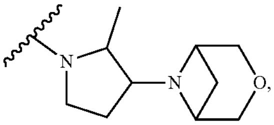,
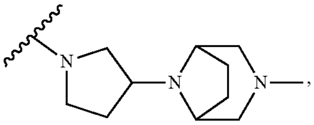,
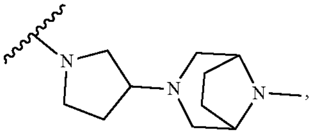,
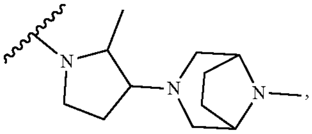,
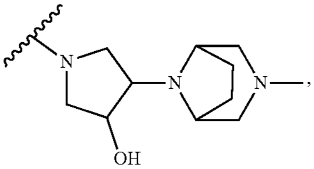,
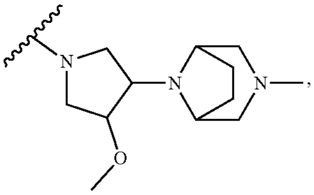,
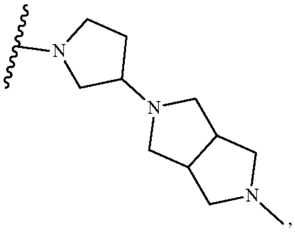,
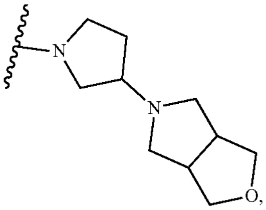,
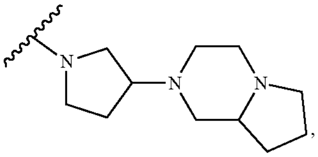, -continued
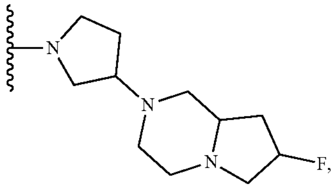
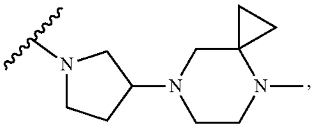
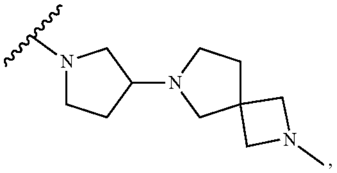
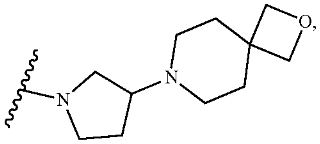
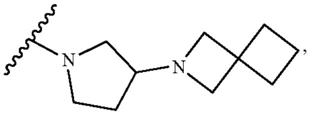
, and
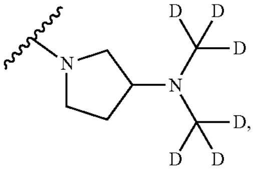
or a pharmaceutically acceptable salt thereof.
18. The compound according to claim 1, wherein $R_4$ is selected from:
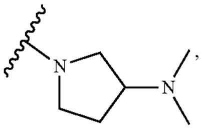
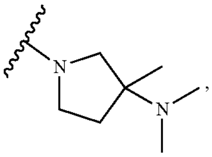
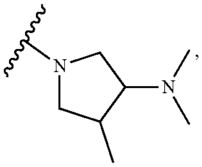
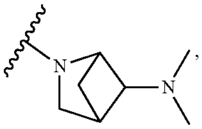
-continued
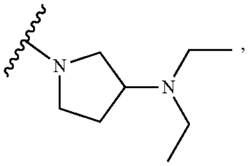
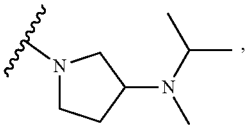
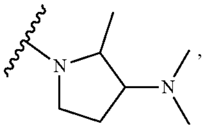
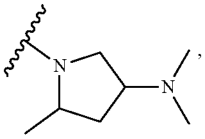
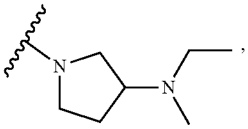
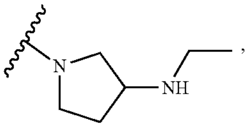
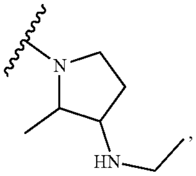
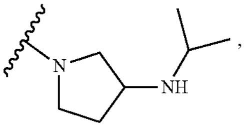
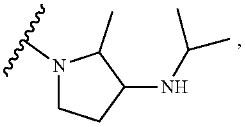
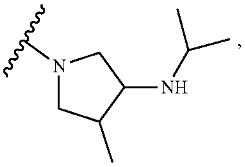
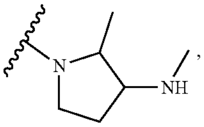
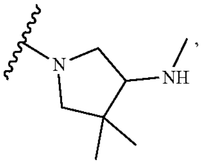

-continued
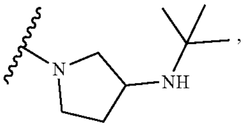
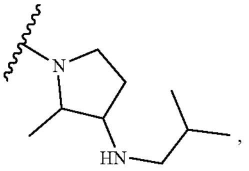
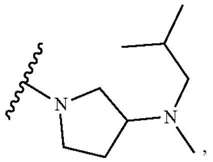
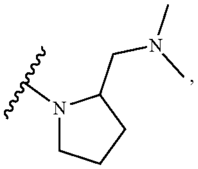
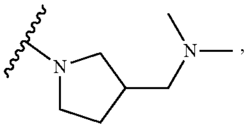
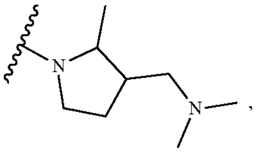
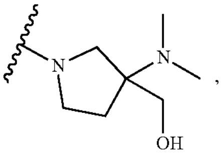
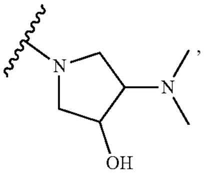
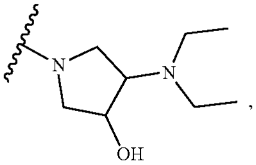
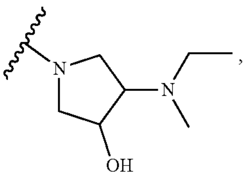
-continued
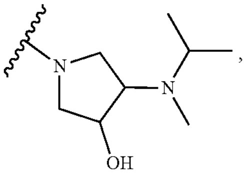
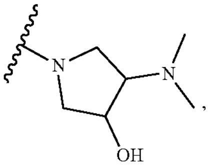
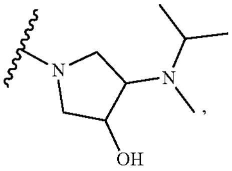
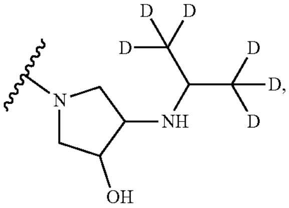
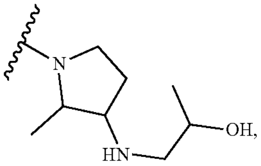
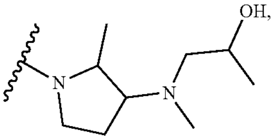
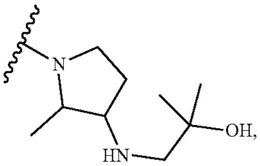
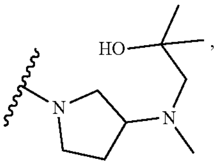
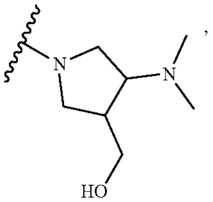

-continued
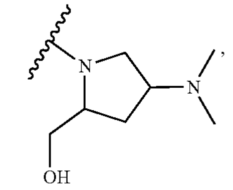
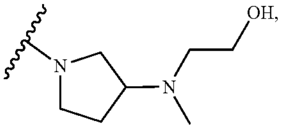
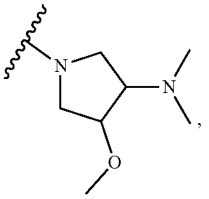
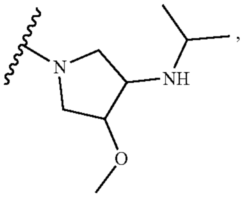
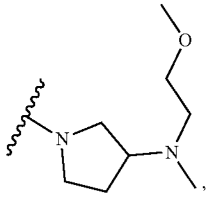
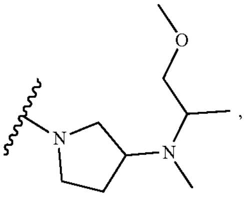
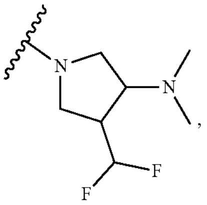
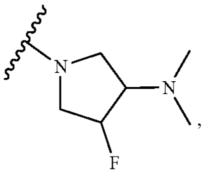
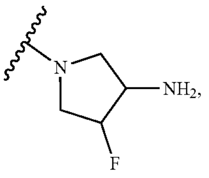
-continued
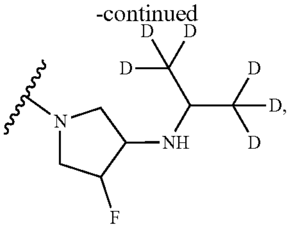
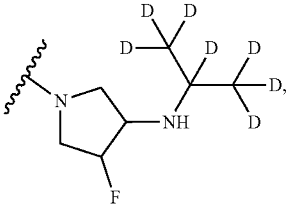
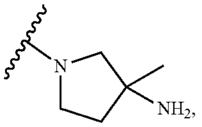
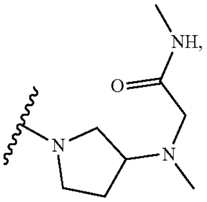
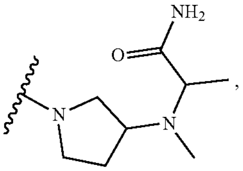
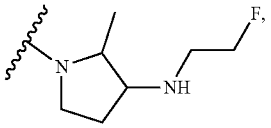
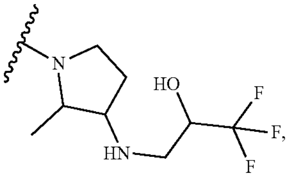
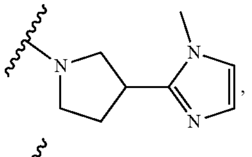
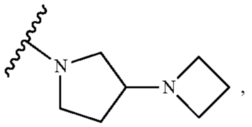
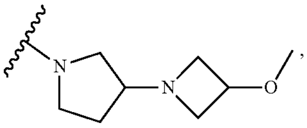
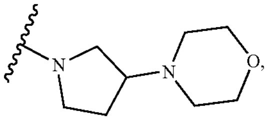

-continued
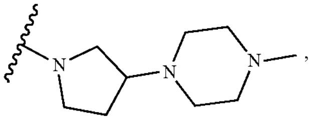
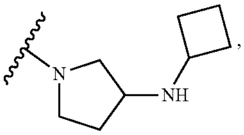
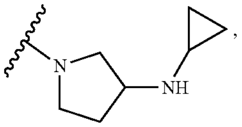
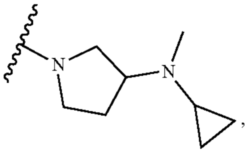
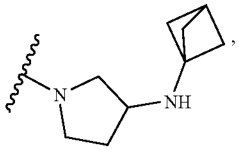
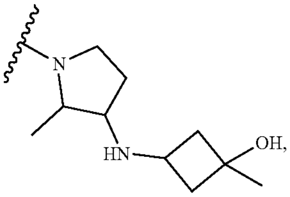
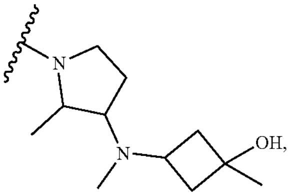
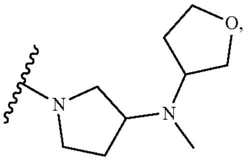
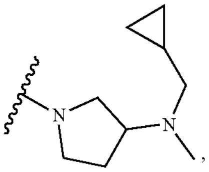
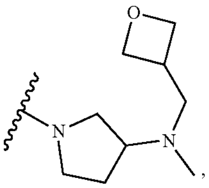
-continued
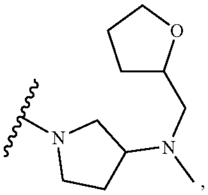
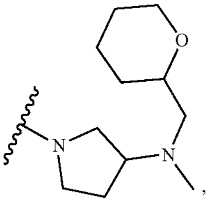
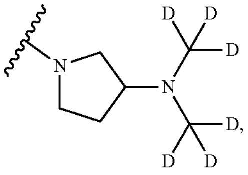
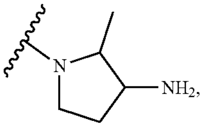
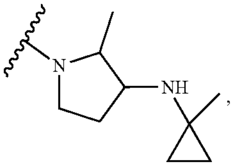
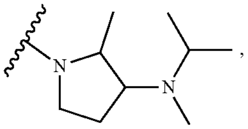
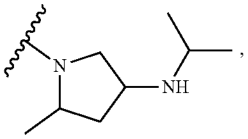
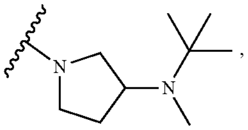
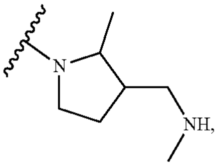
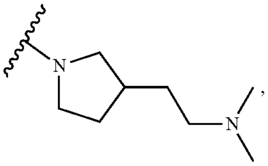

-continued
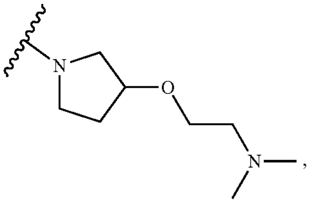,
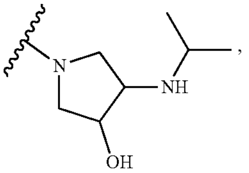,
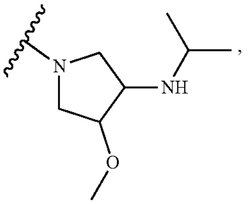,
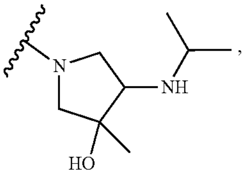,
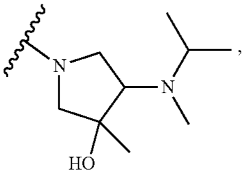,
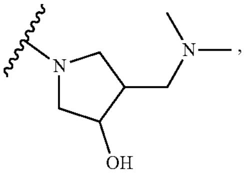,
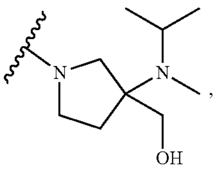,
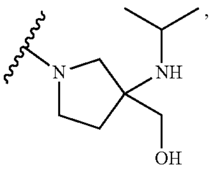,
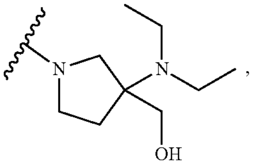,
-continued
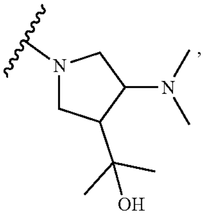,
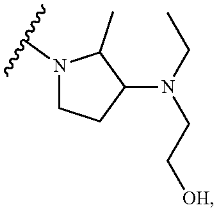,
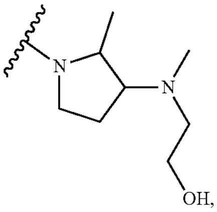,
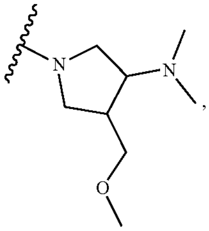,
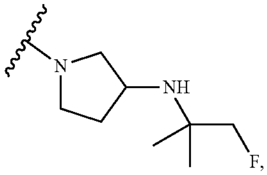,
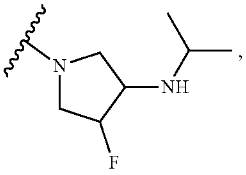,
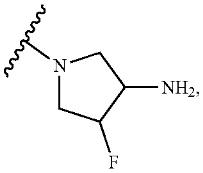,
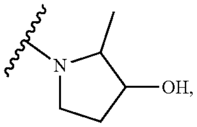,
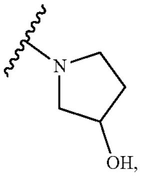, -continued
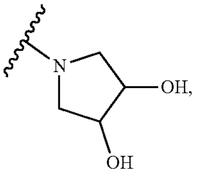
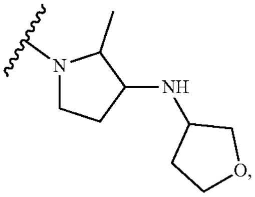
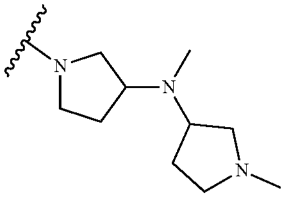
,
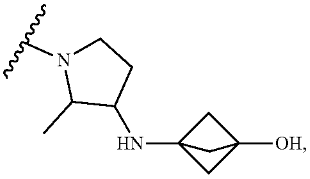
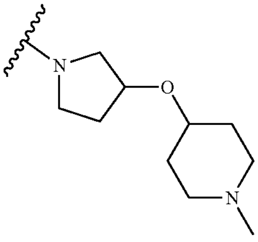
,
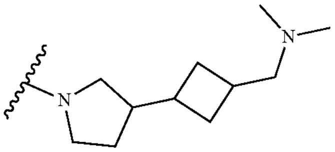
,
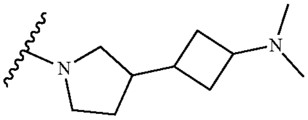
,
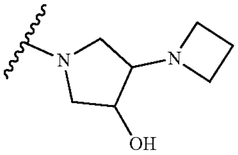
,
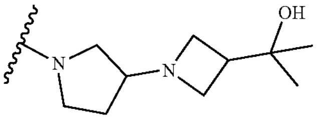
,
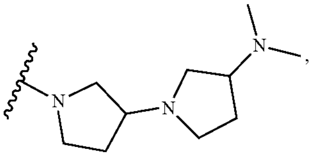
,
-continued
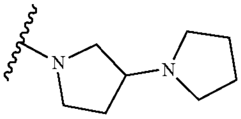
,
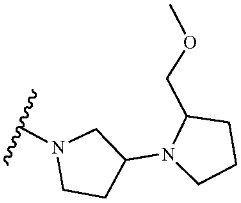
,
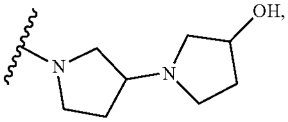
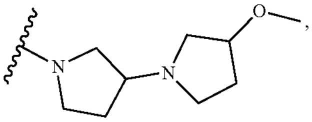
,
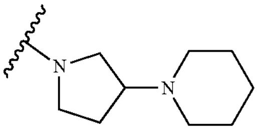
,
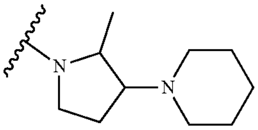
,
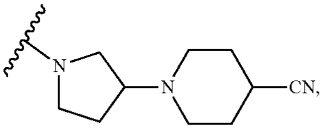
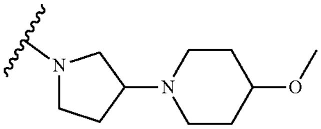
,
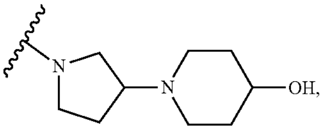
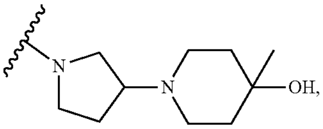
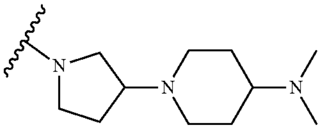
,
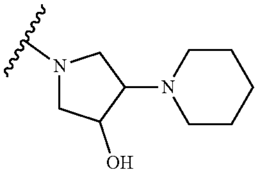
, -continued
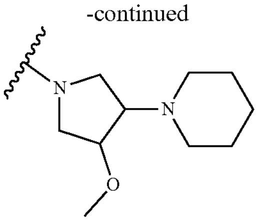,
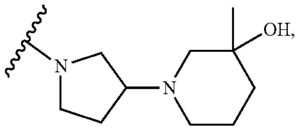
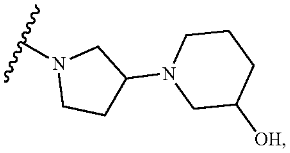
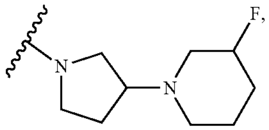
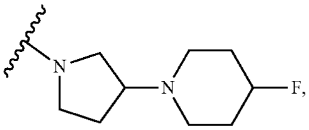
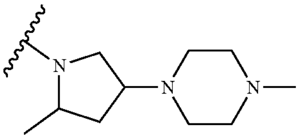,
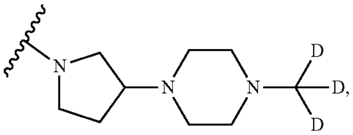
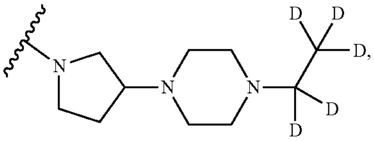
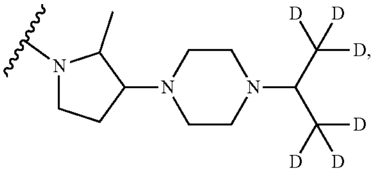
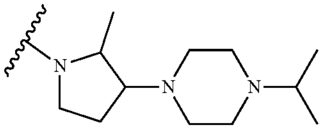,
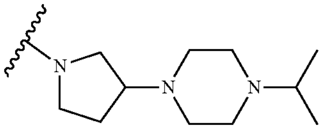,
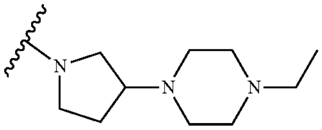,
-continued
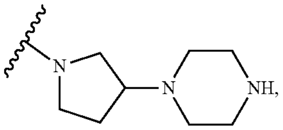
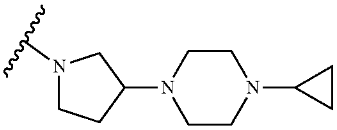,
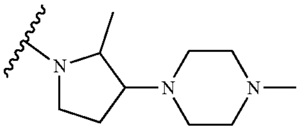,
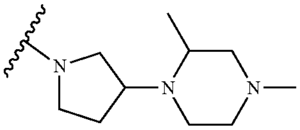,
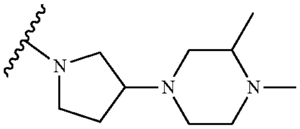,
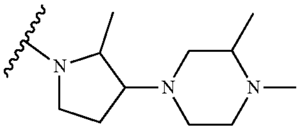,
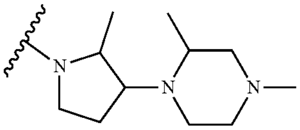,
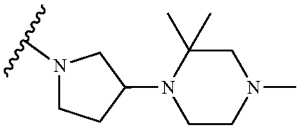,
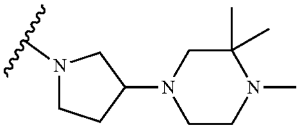,
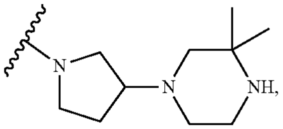
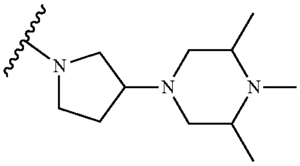,
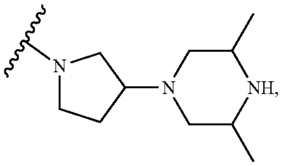

-continued
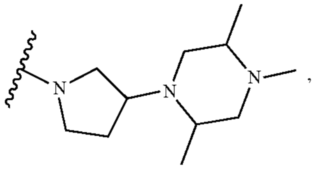
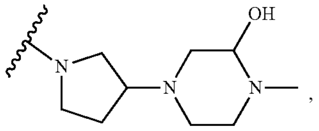
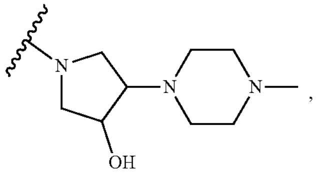
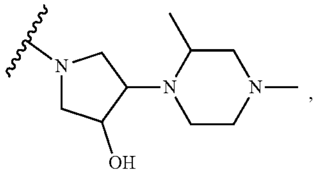
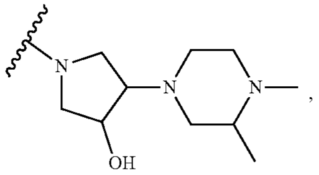
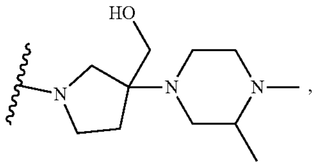
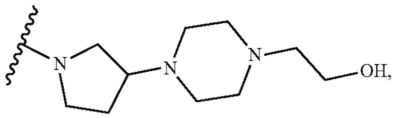
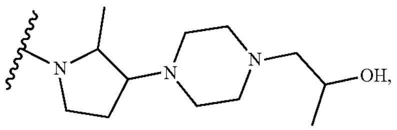
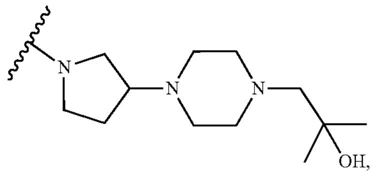
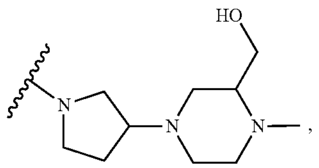
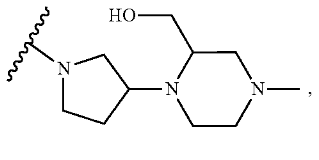
-continued
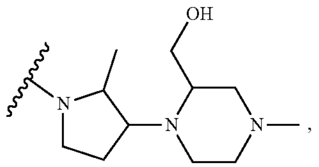
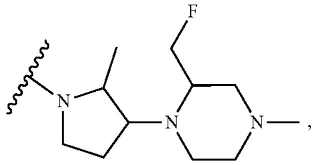
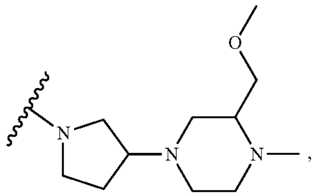
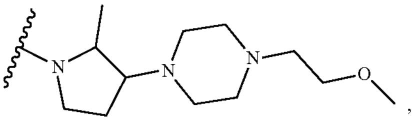
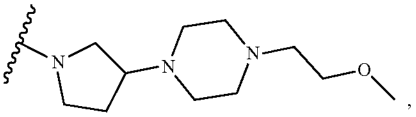
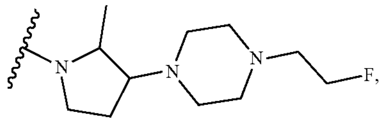
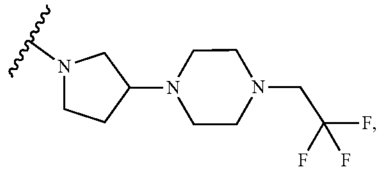
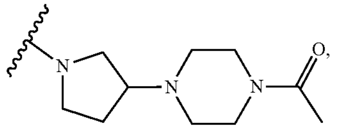
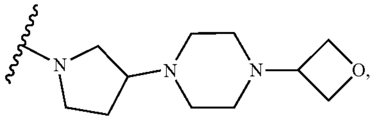
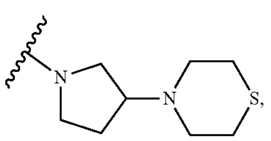
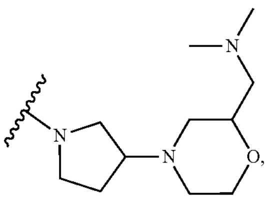

-continued
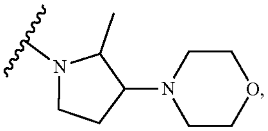
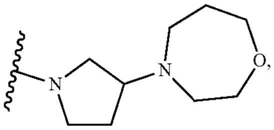
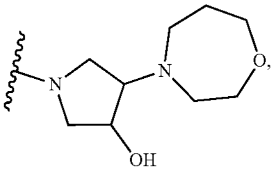
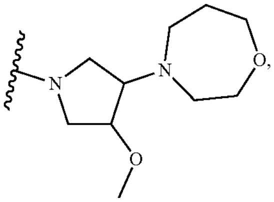
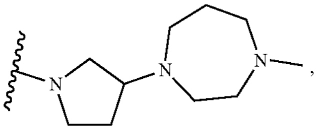
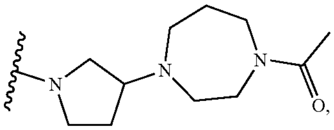
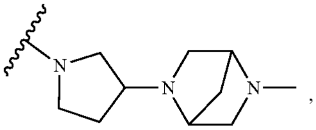
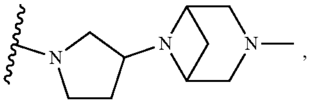
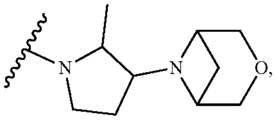
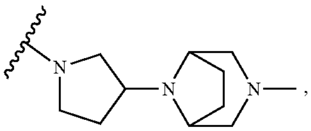
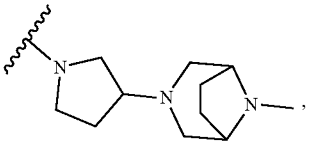
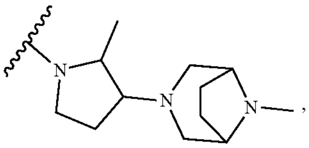
-continued
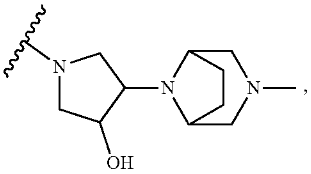
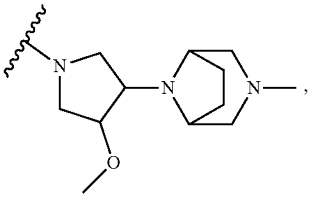
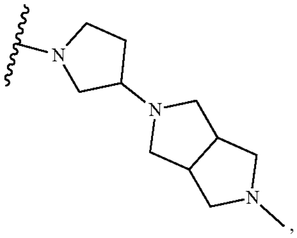
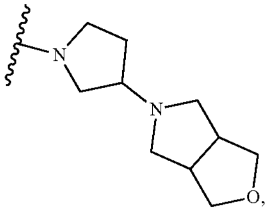
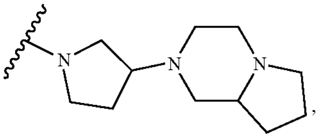
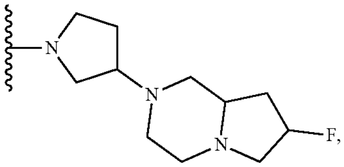
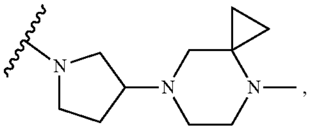
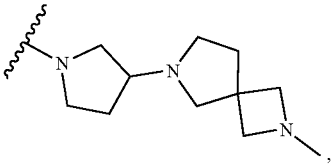
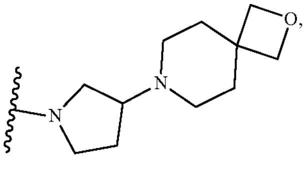
and -continued
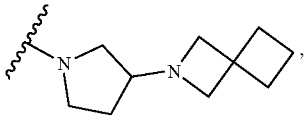
or a pharmaceutically acceptable salt thereof.
19. The compound according to claim 1, wherein the compound is selected from:
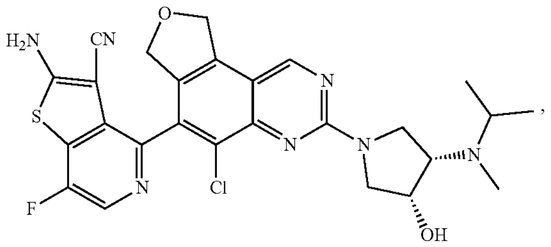
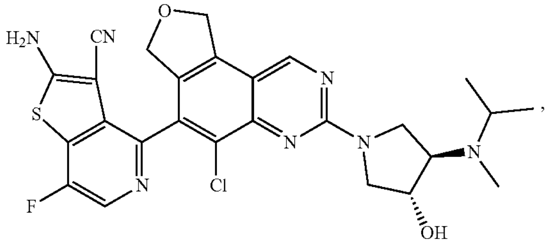
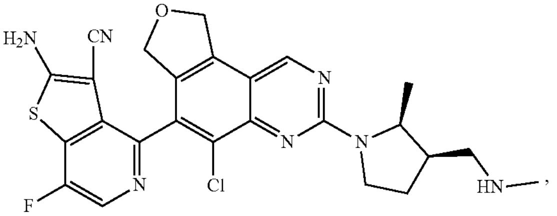
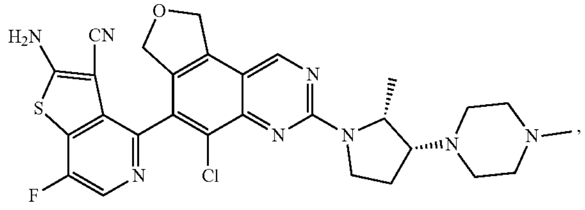
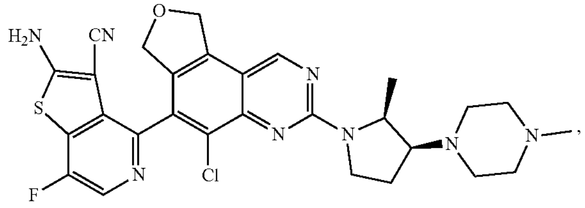
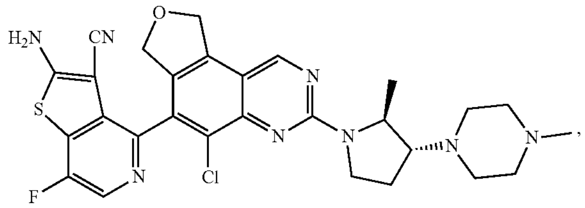
-continued
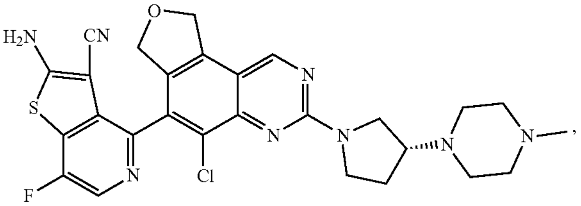
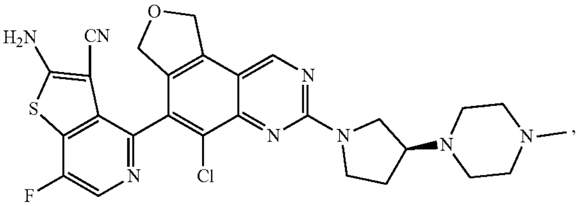
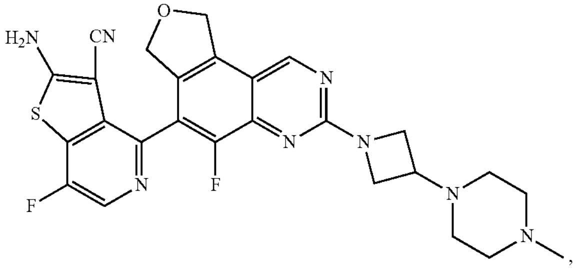
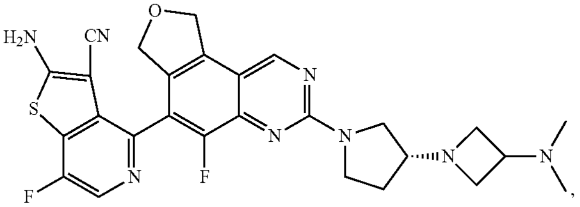
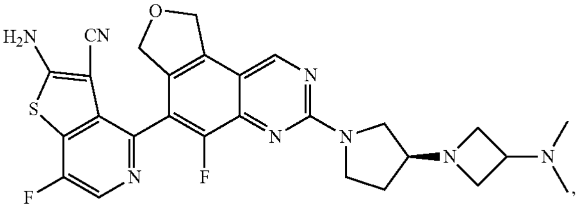
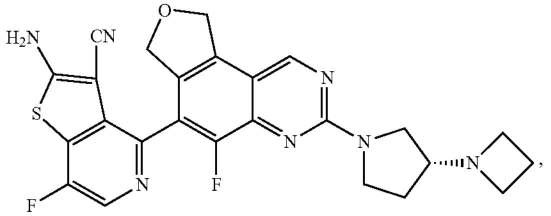
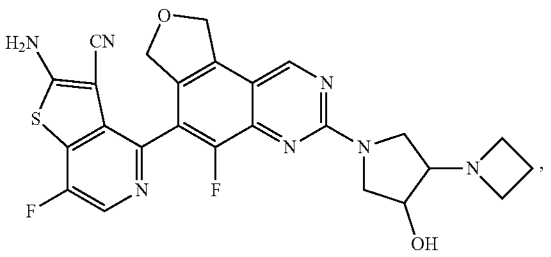

-continued
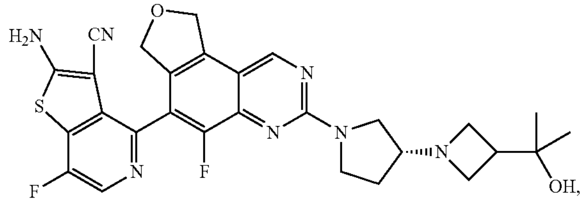
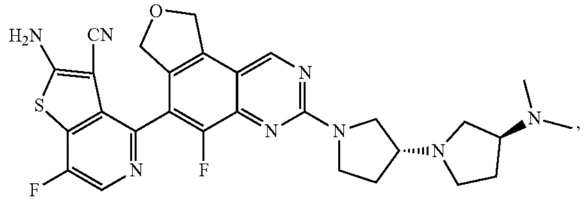
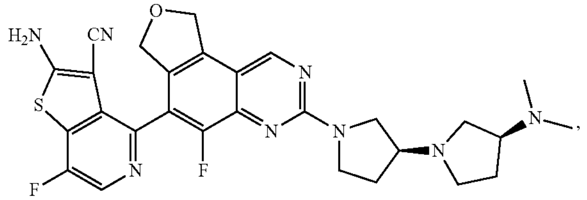
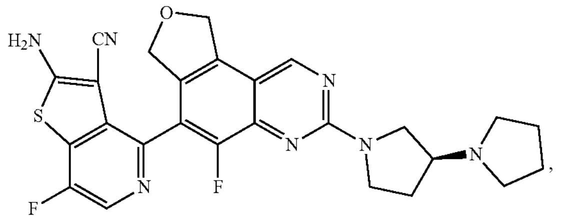
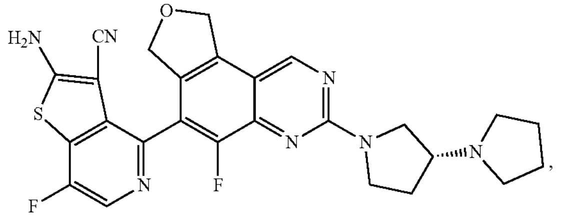
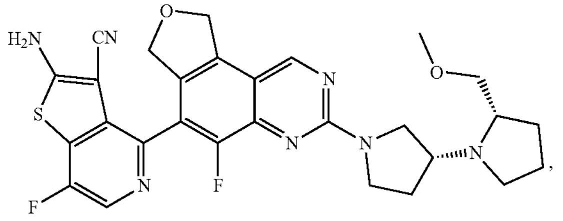
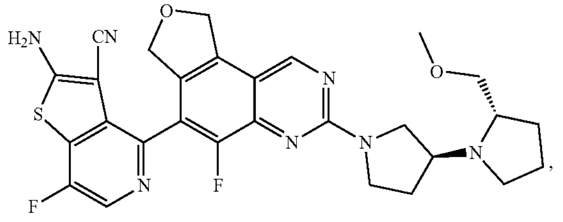
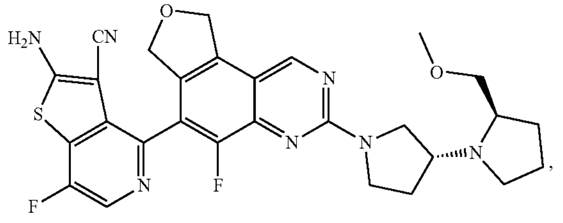
-continued
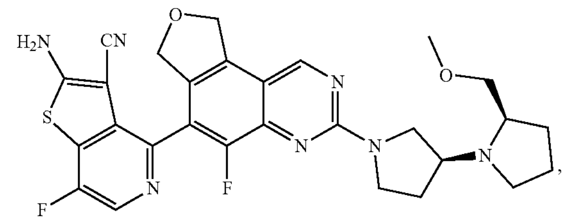
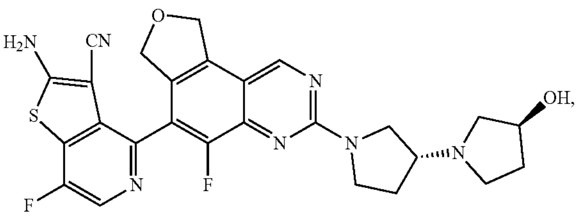
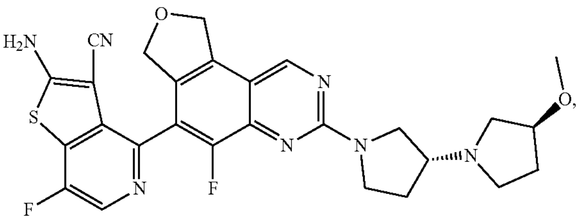
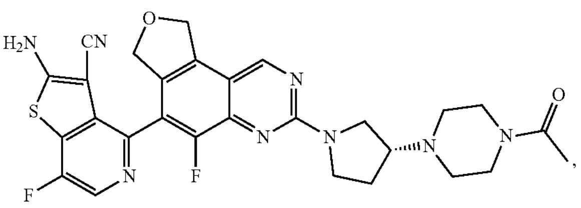
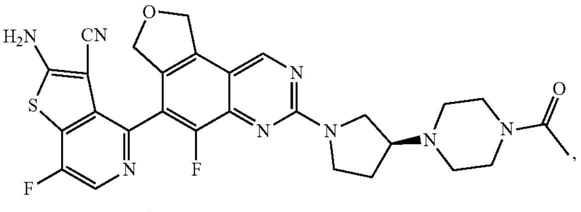
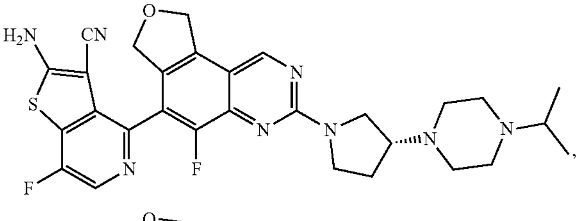
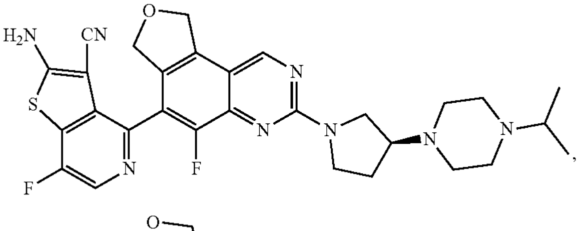
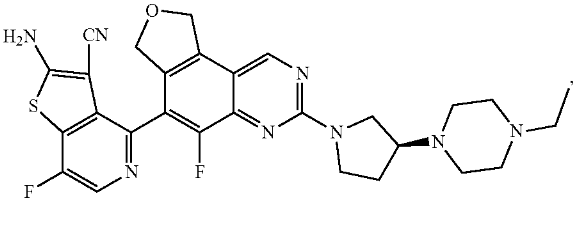

-continued
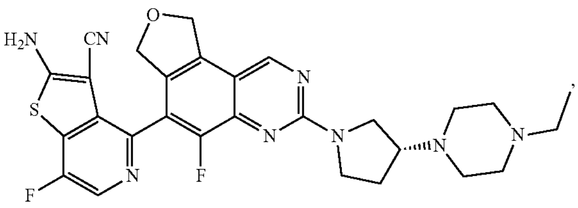
,
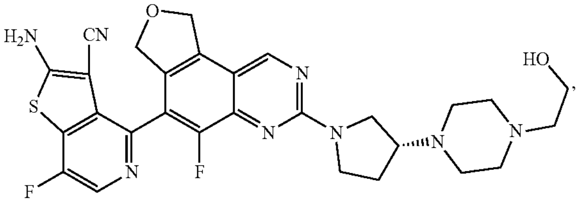
,
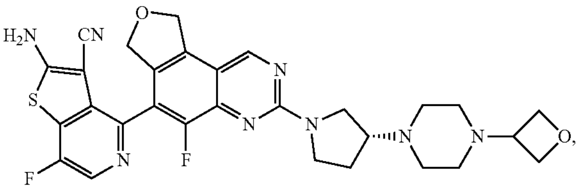
,
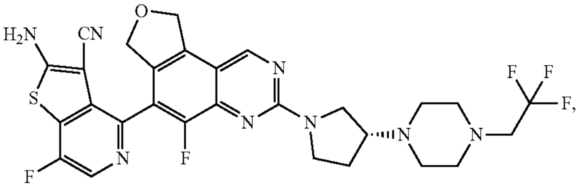
,
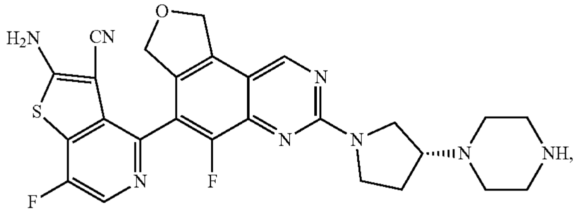
,
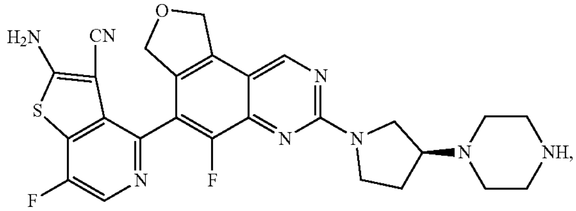
,
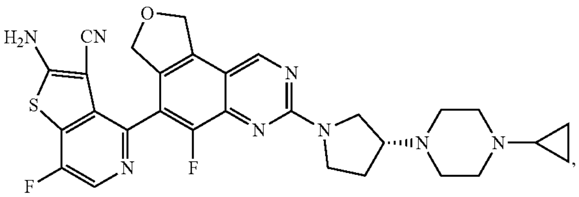
,
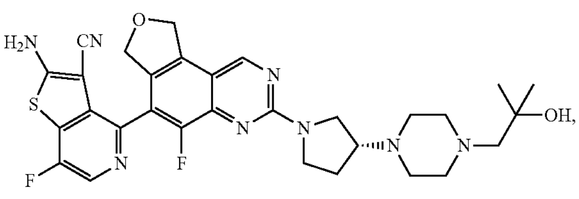
,
-continued
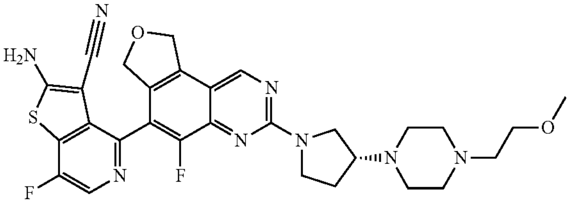
,
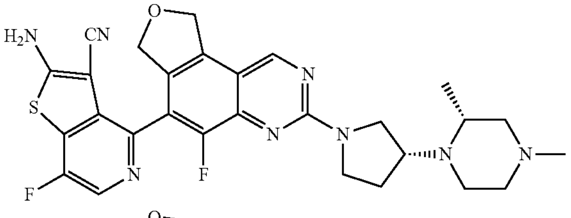
,
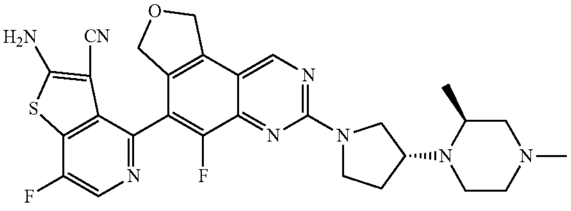
,
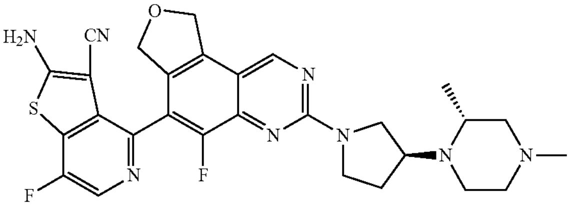
,
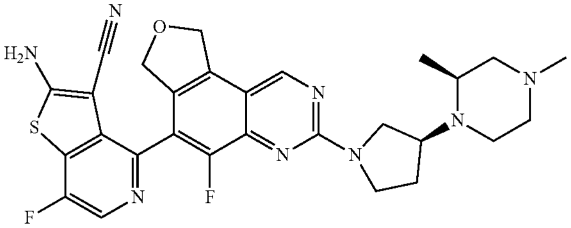
,
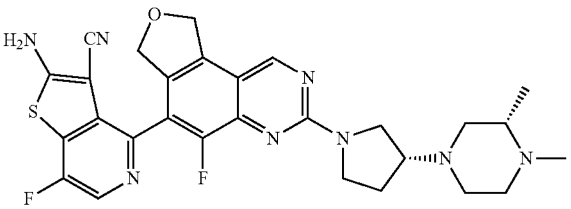
,
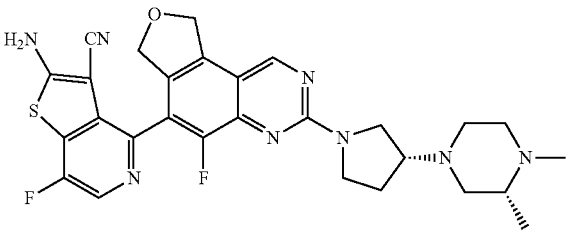
,
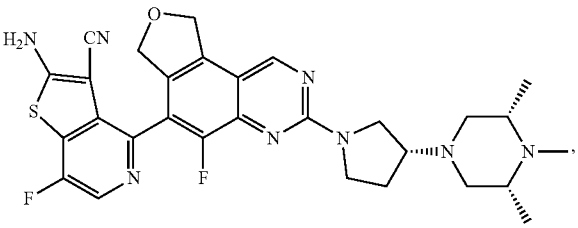
, -continued
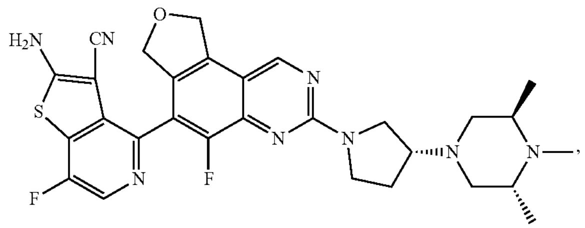
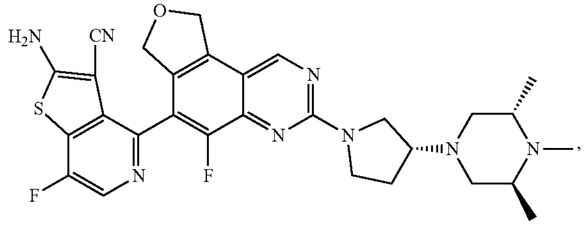
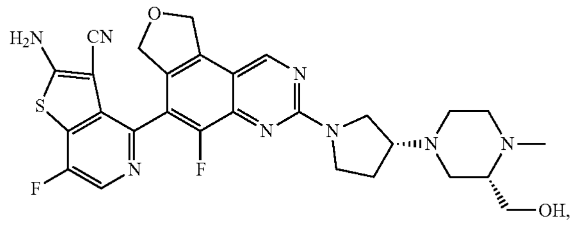
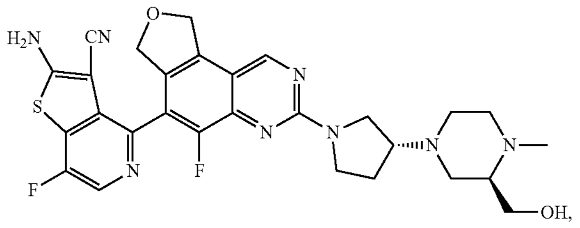
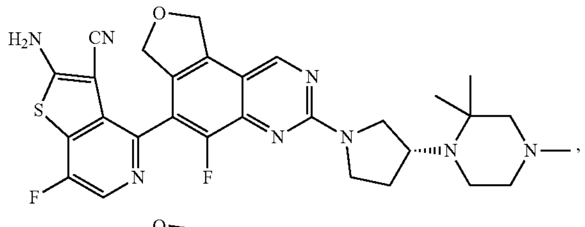
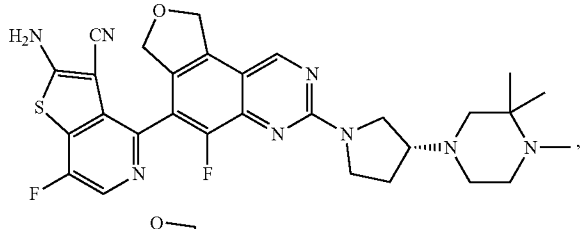
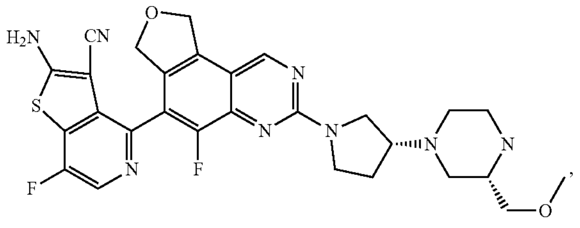
-continued
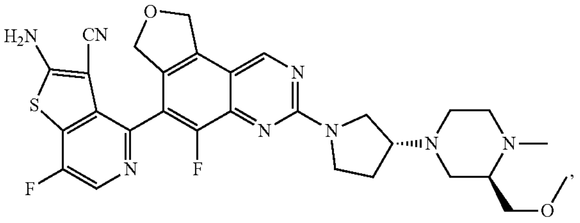
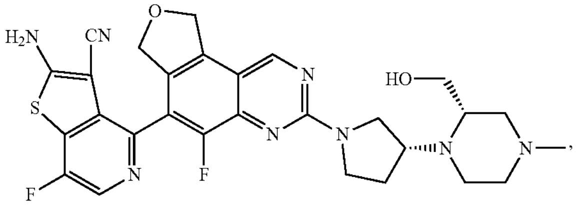
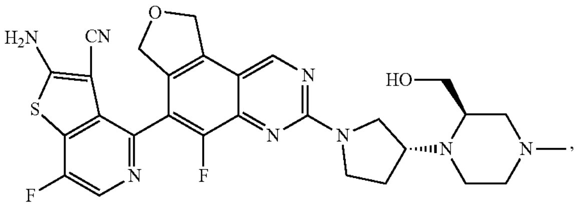
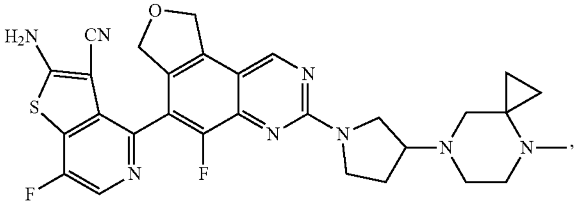
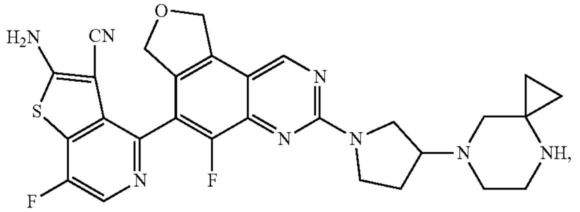
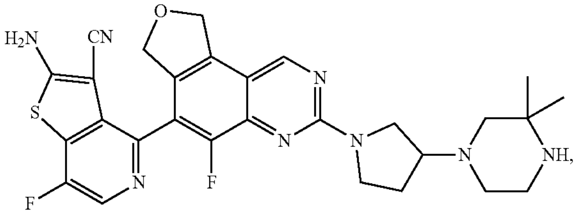
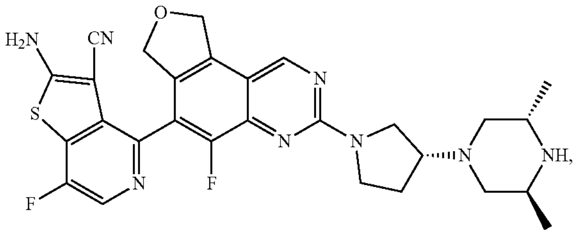
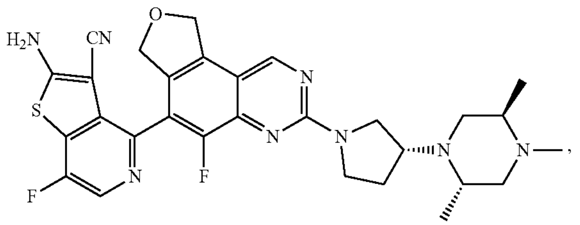

-continued
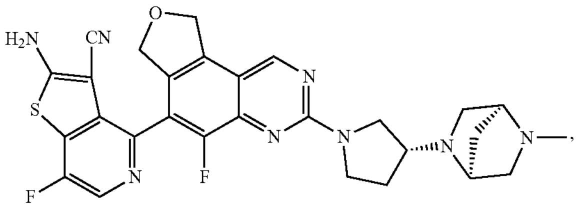
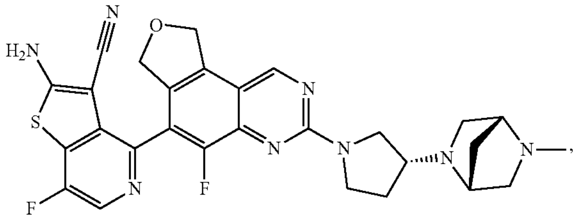
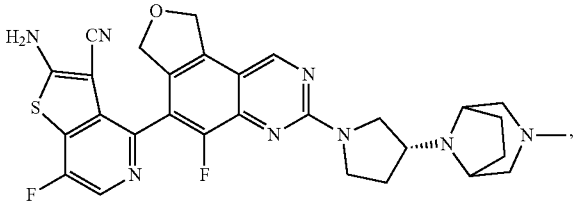
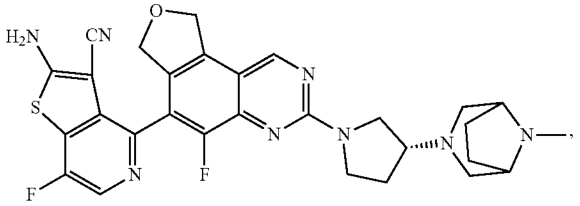
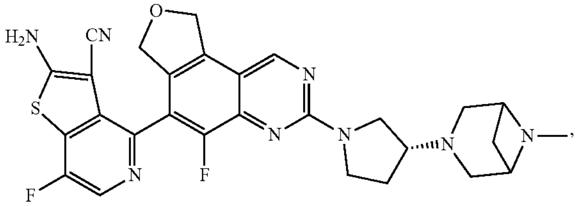
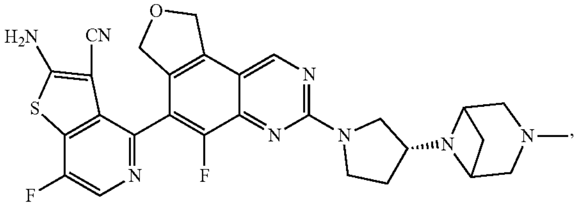
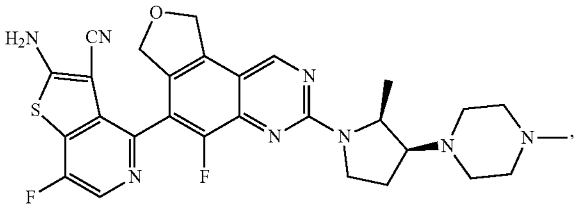
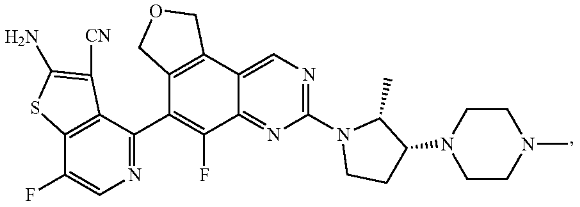
-continued
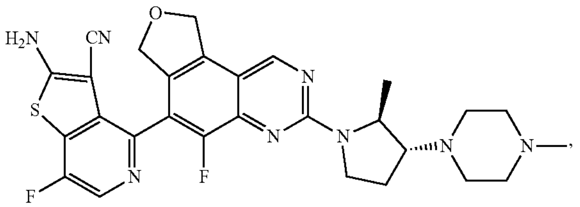
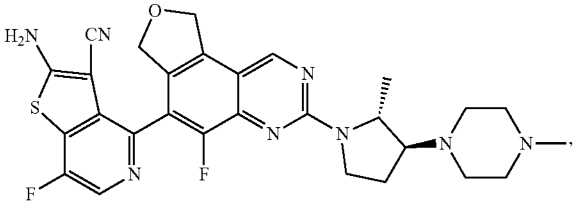
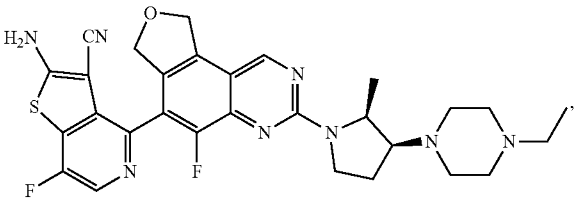
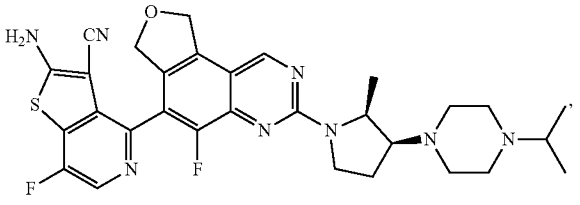
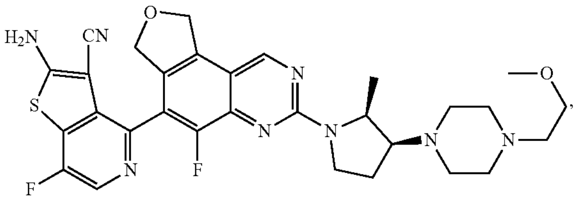
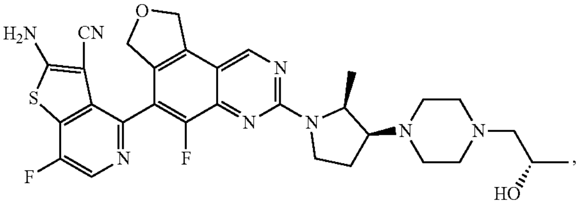
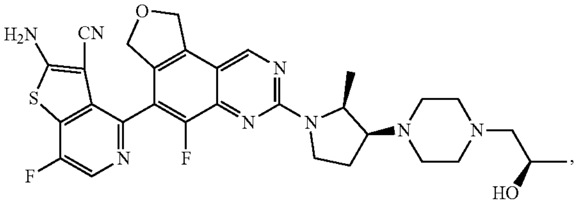
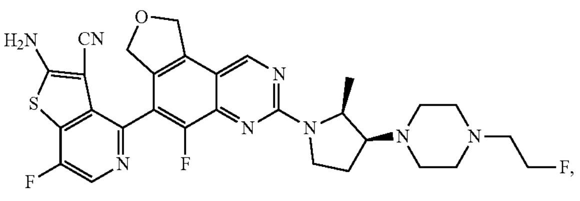

-continued
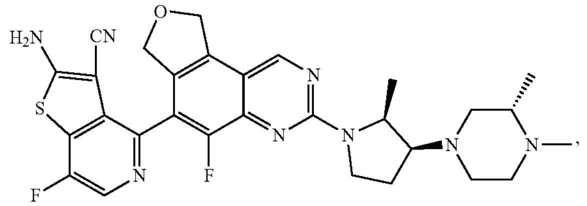
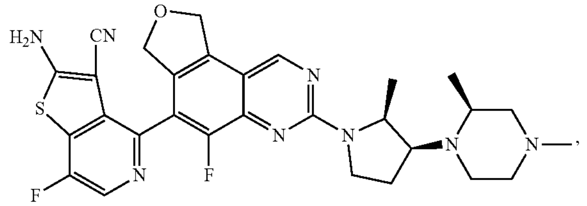
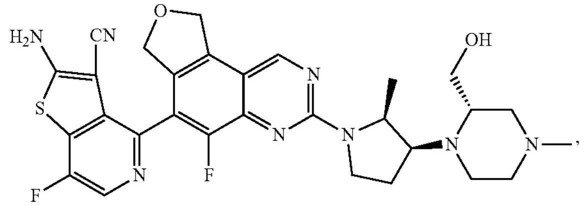
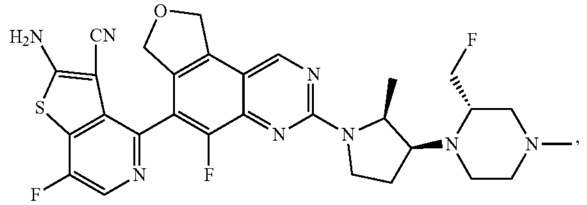
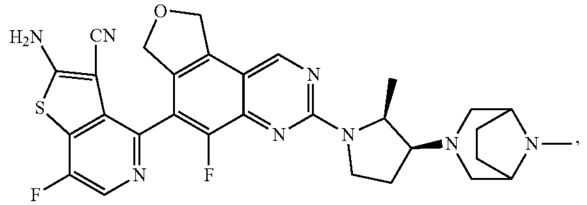
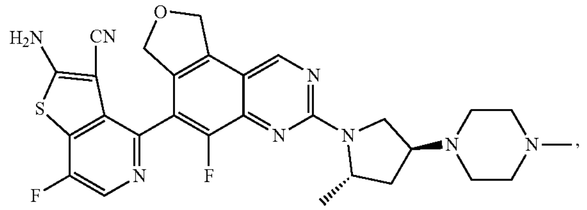
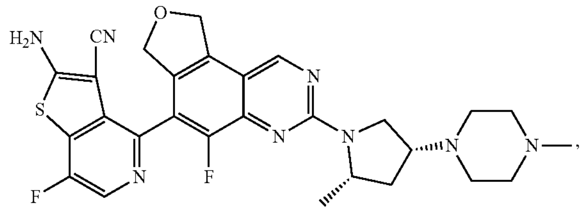
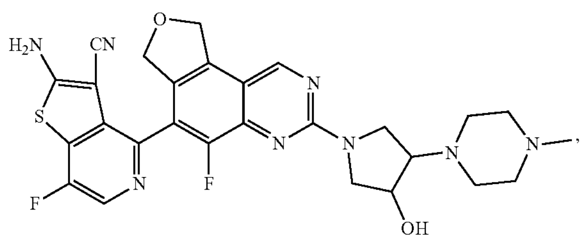
-continued
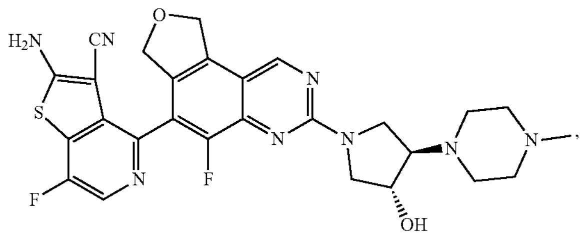
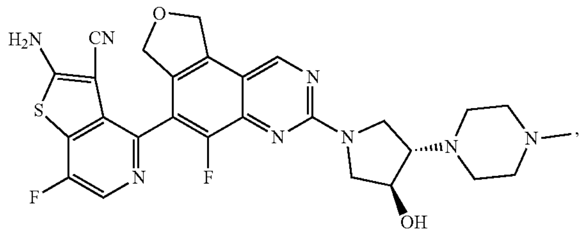
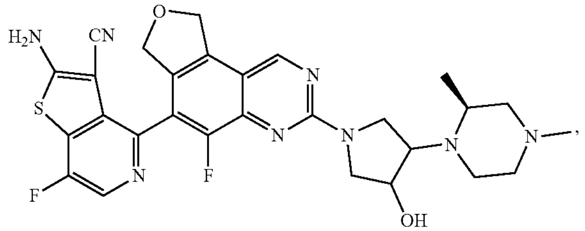
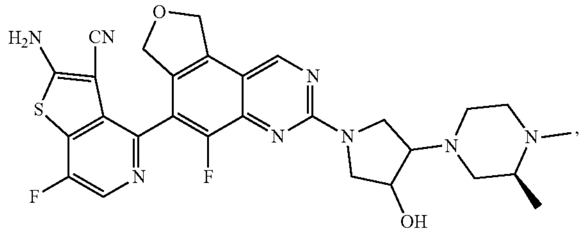
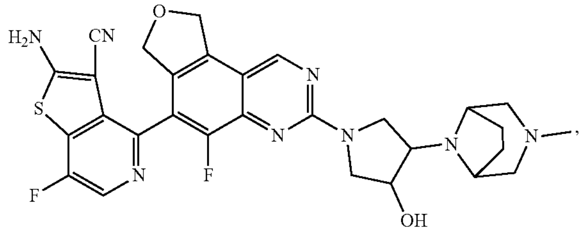
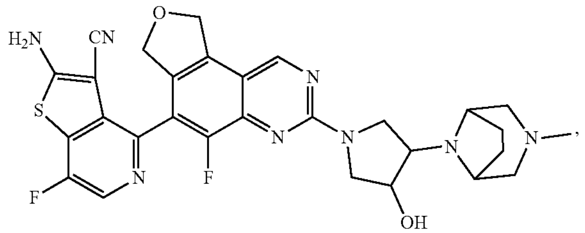
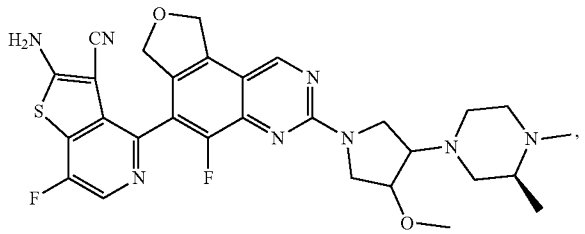

-continued
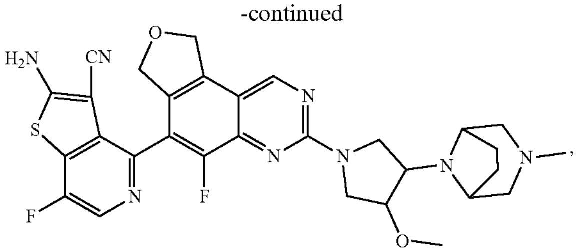,
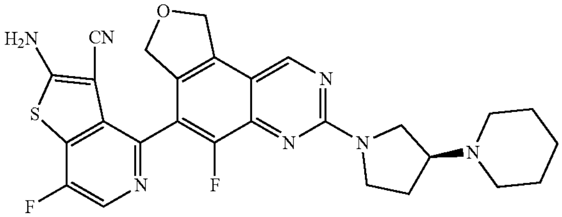,
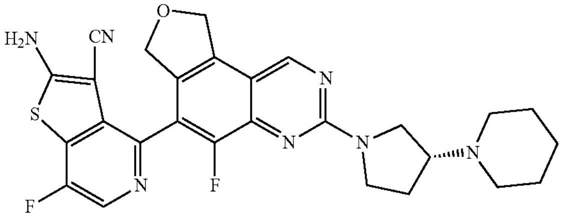,
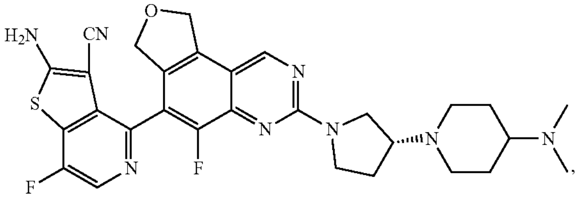,
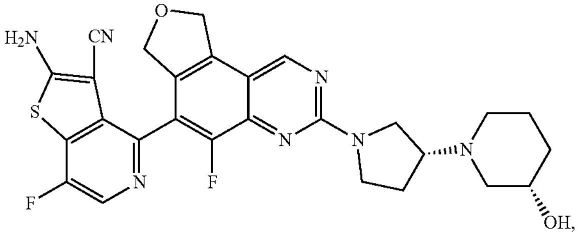,
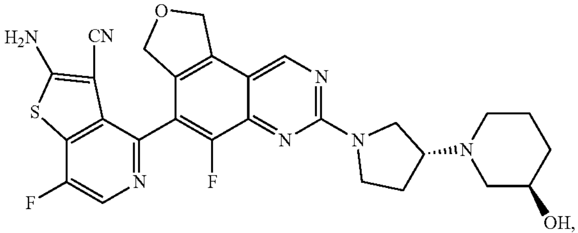,
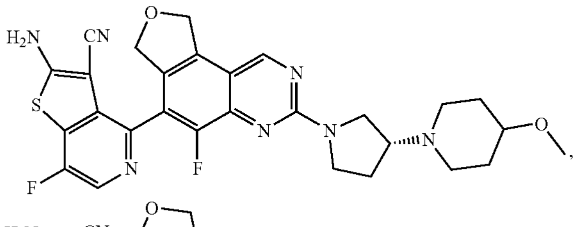,
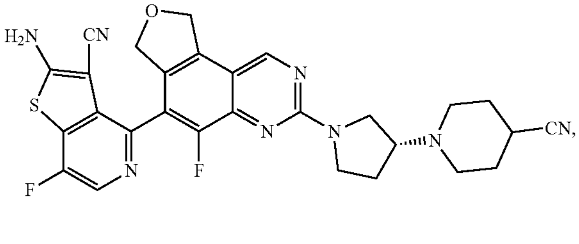,
-continued
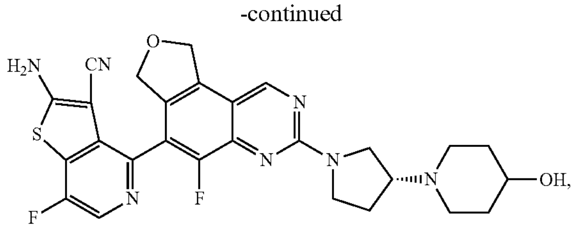,
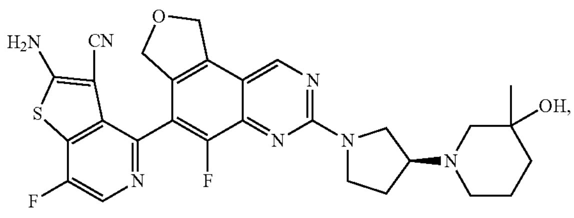,
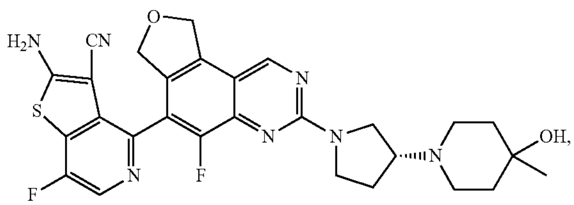,
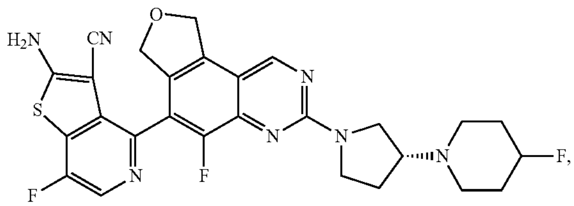,
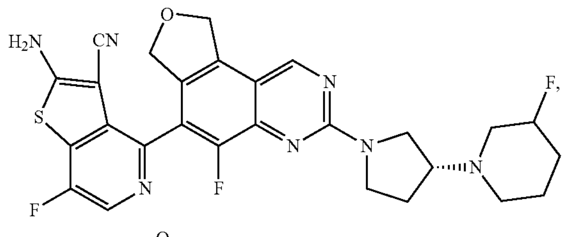,
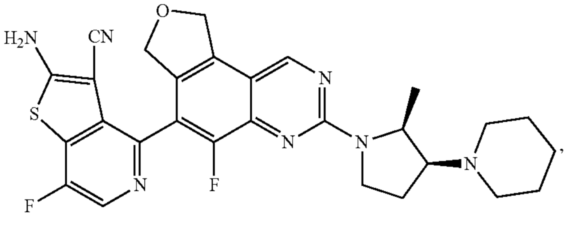,
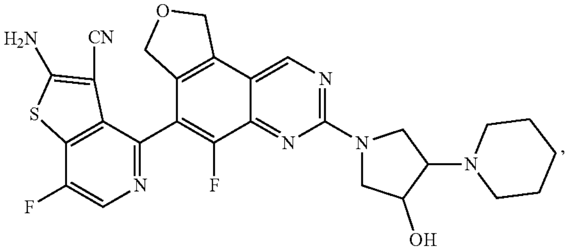,

1001
-continued
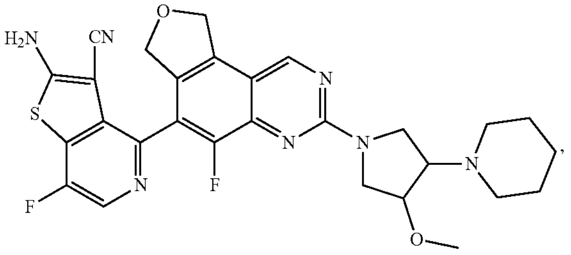
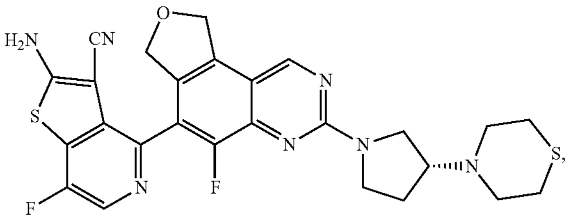
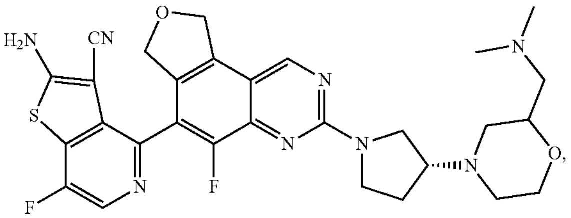
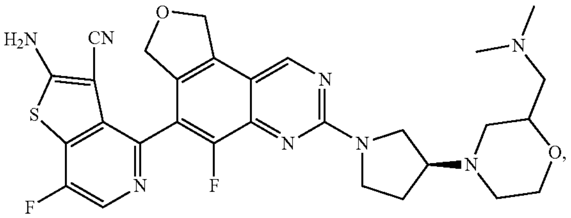
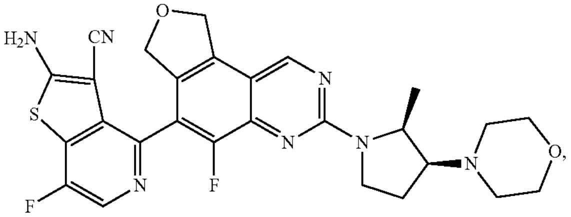
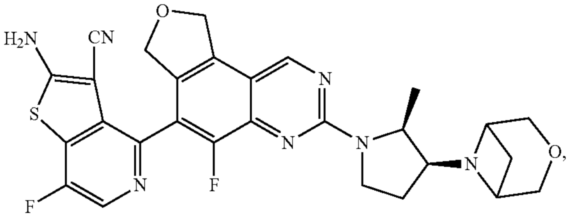
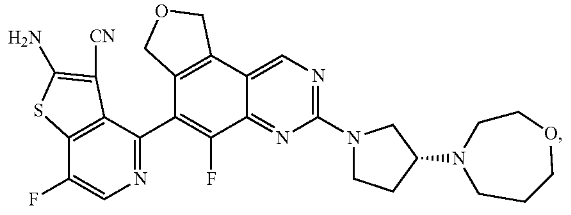
1002
-continued
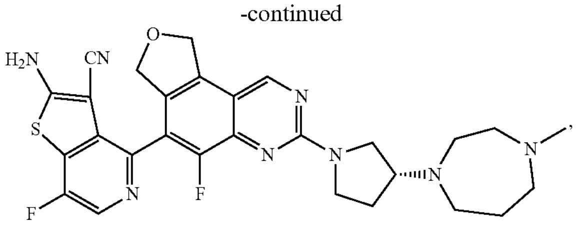
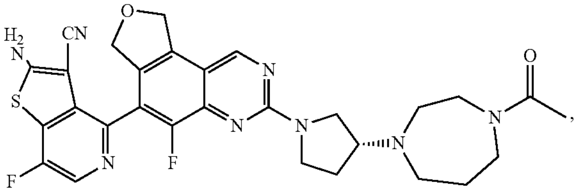
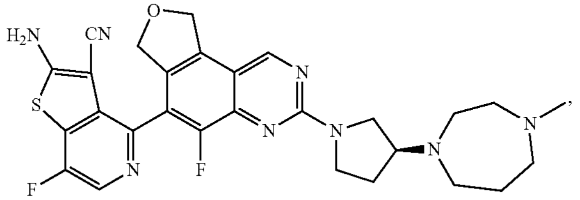
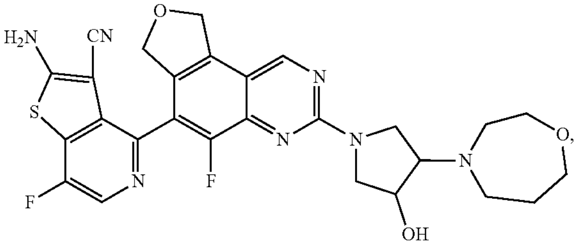
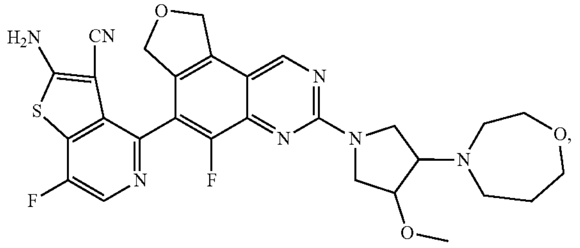
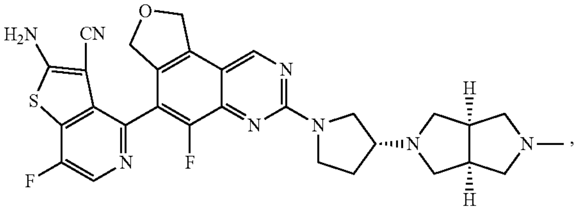
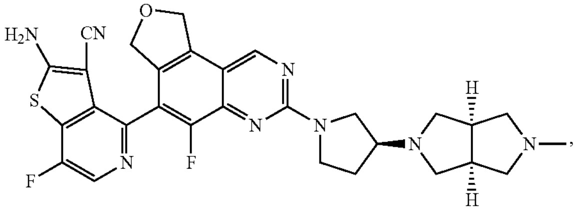
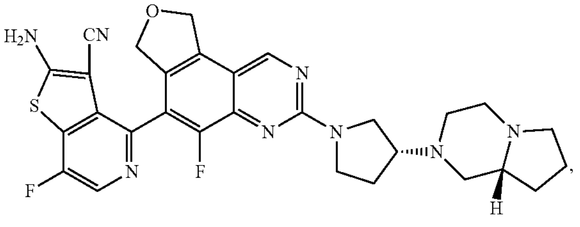

-continued
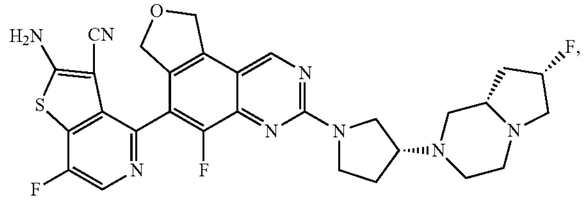
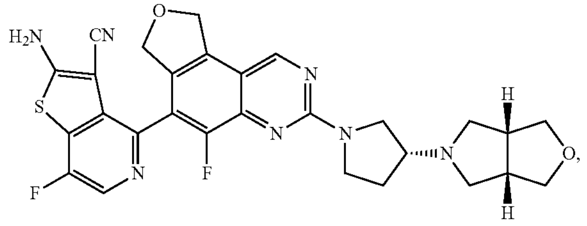
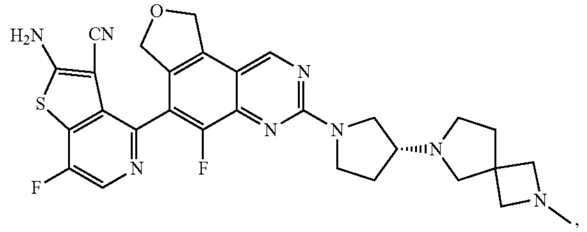
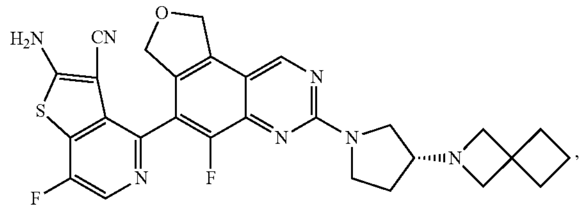
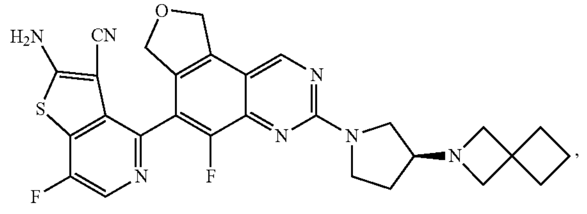
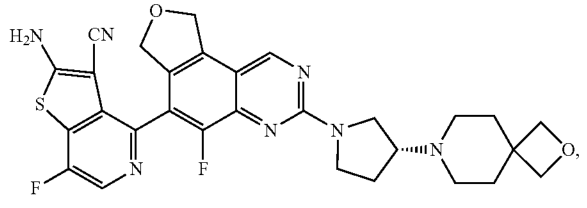
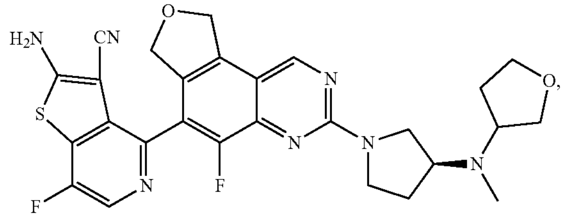
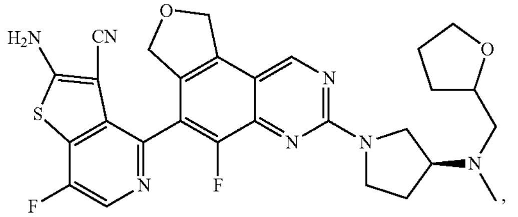
-continued
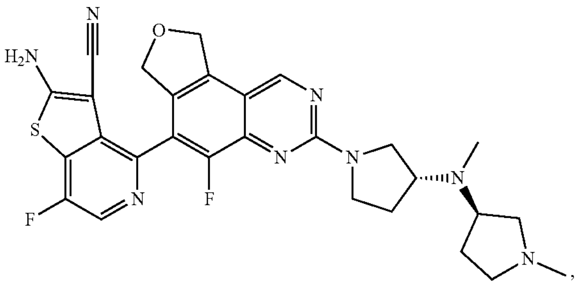
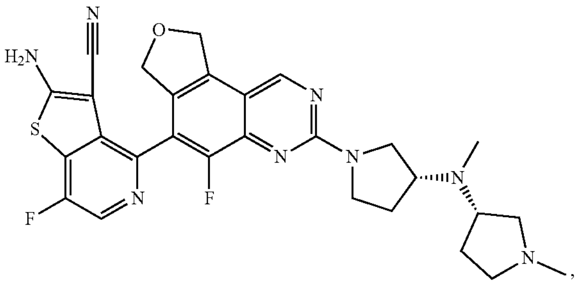
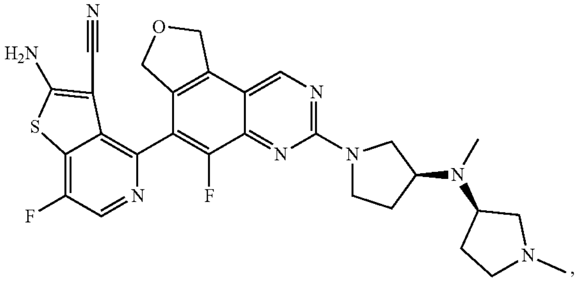
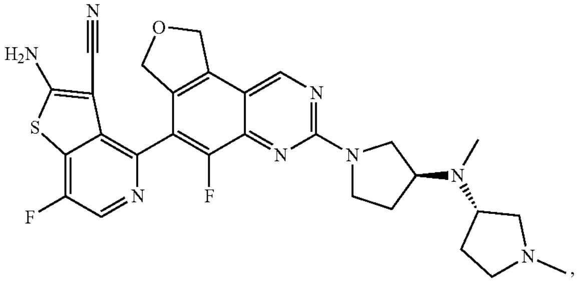
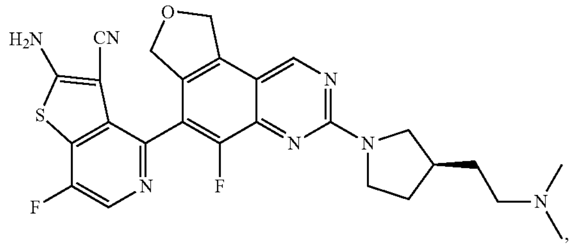
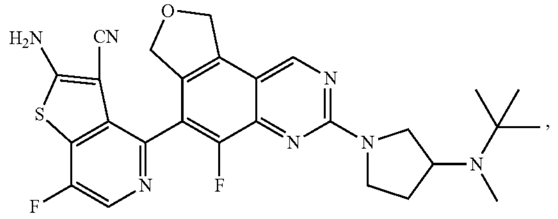

1005
-continued
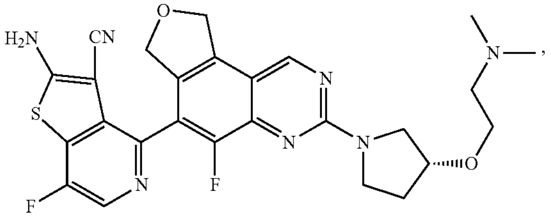
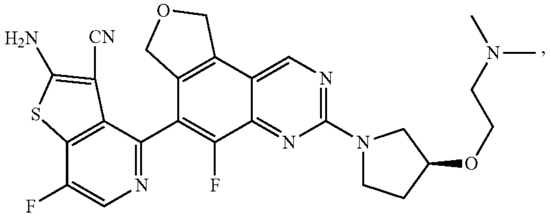
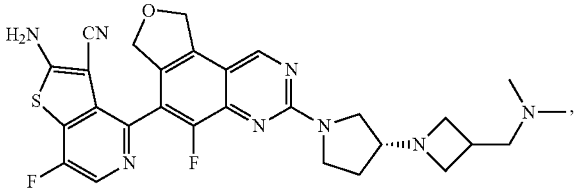
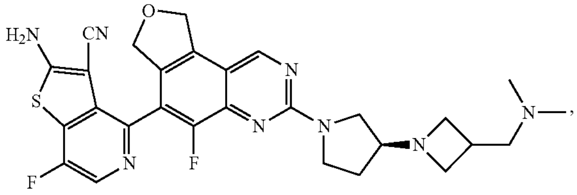
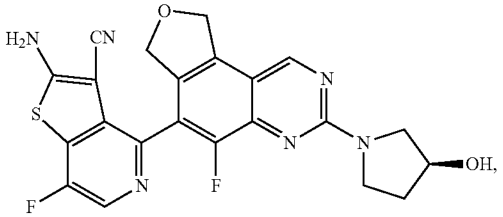
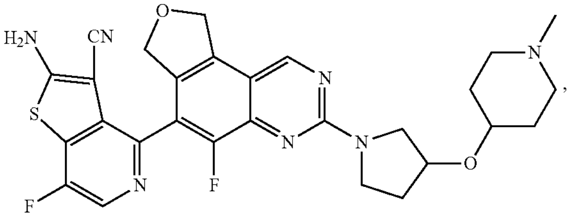
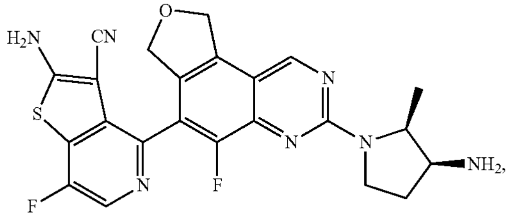
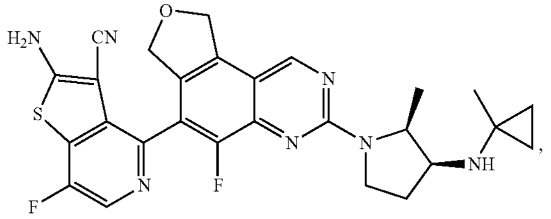
1006
-continued
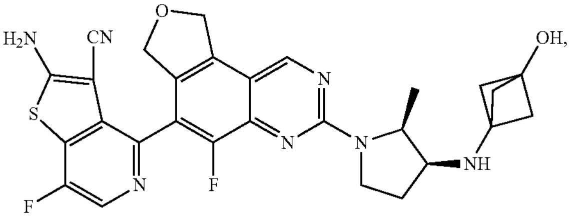
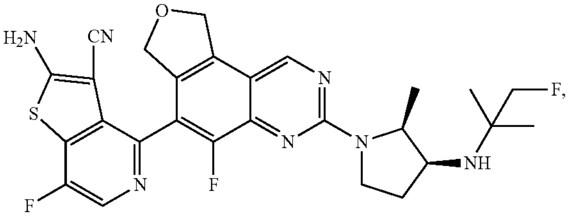
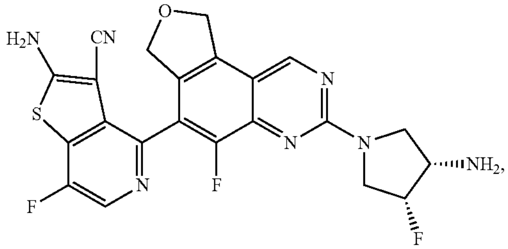
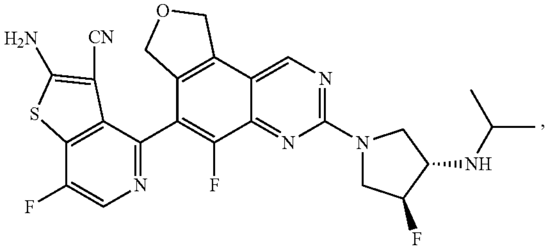
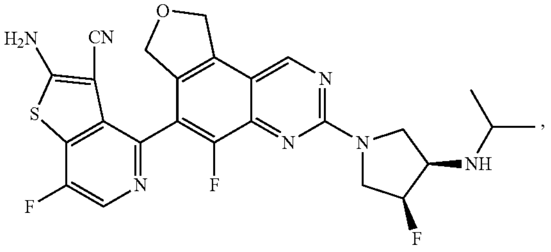
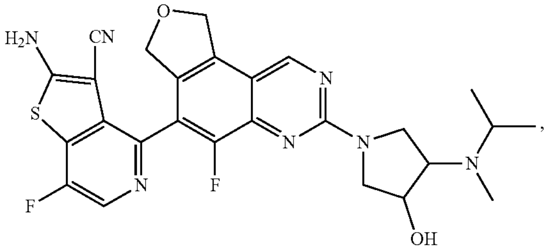
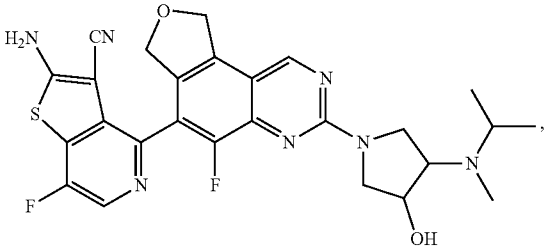

-continued
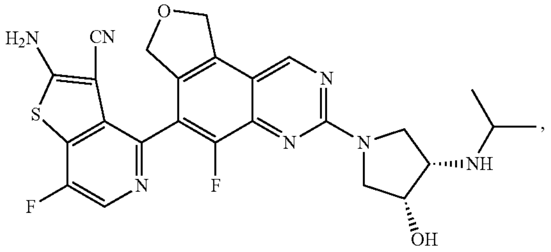
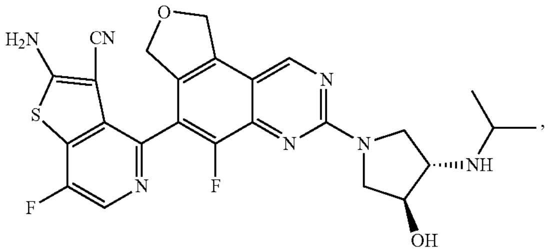
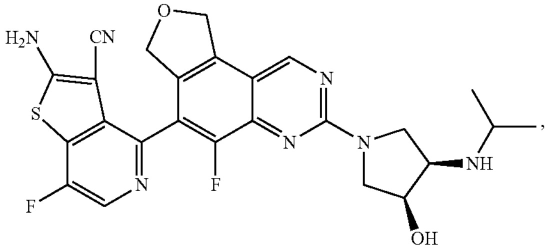
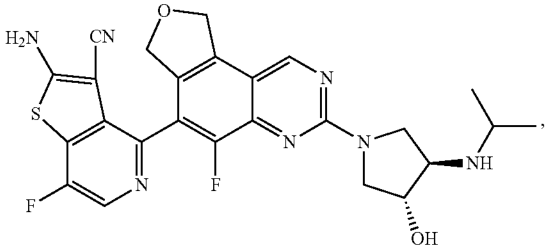
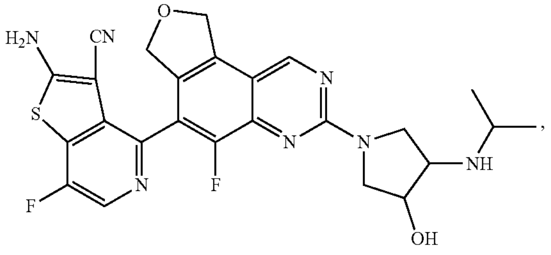
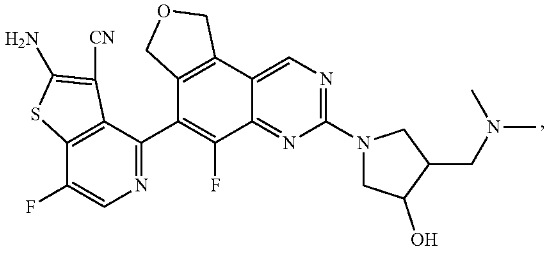
-continued
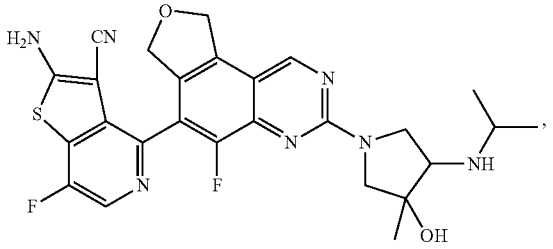
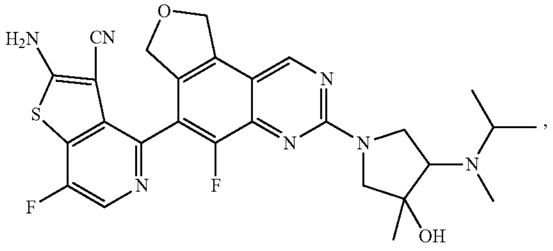
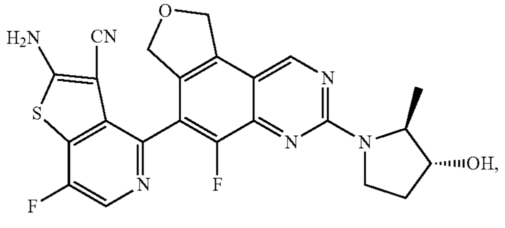
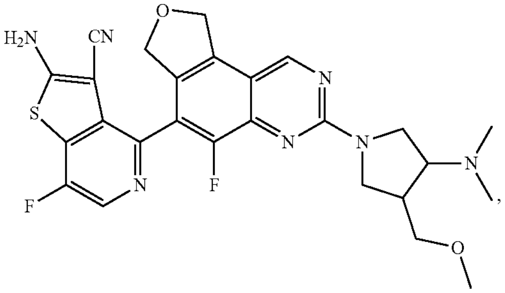
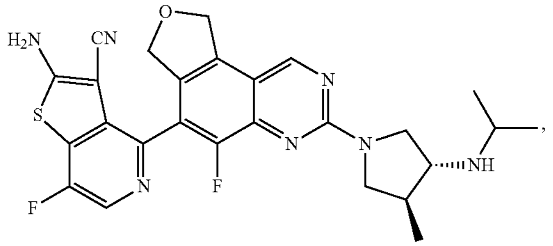
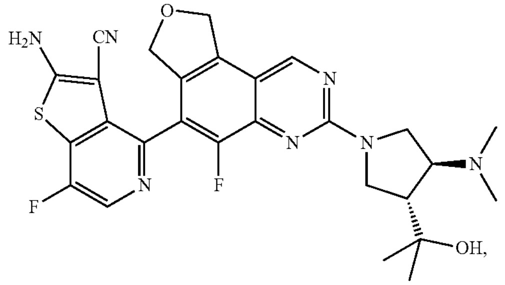

1009
-continued
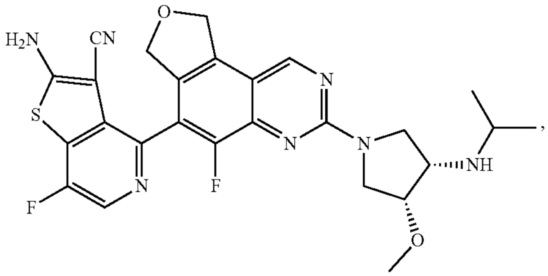
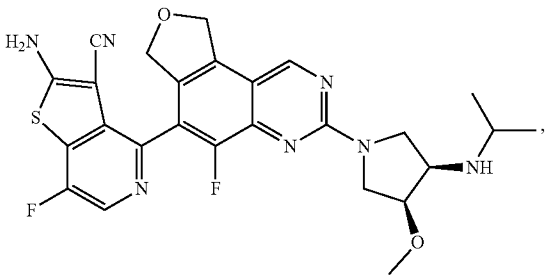
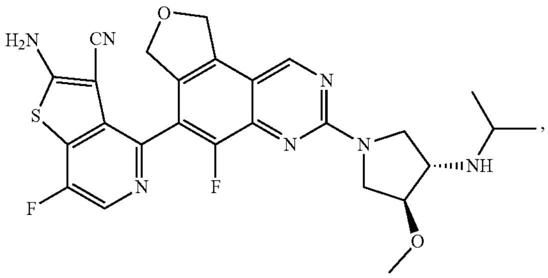
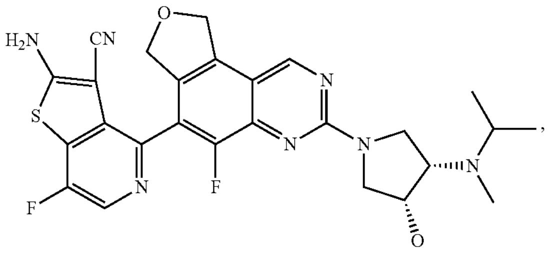
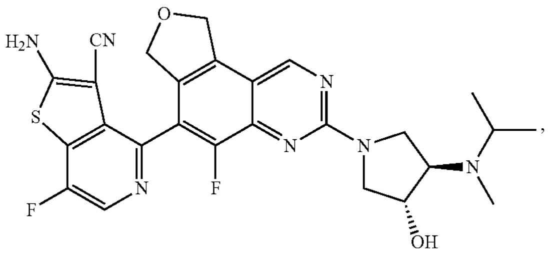
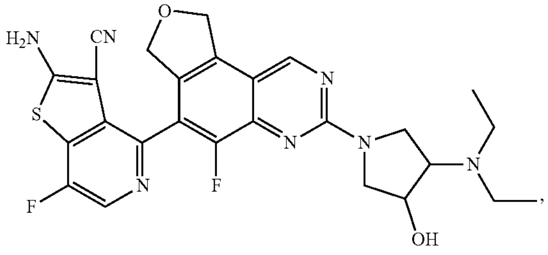
1010
-continued
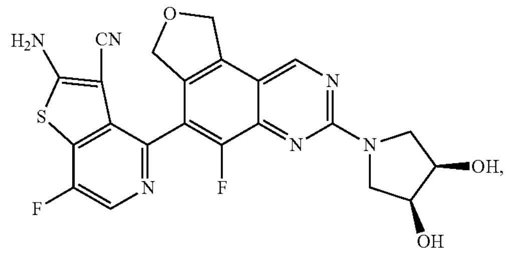
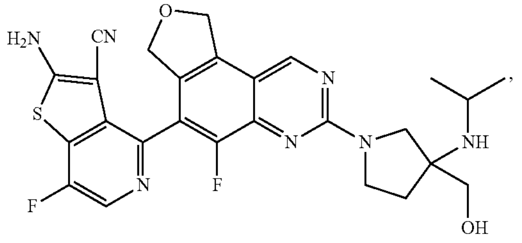
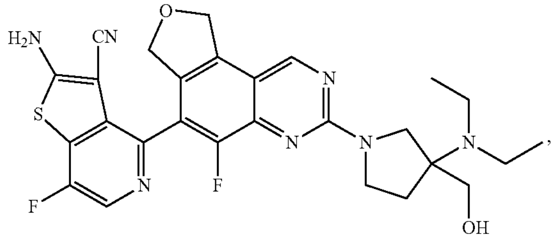
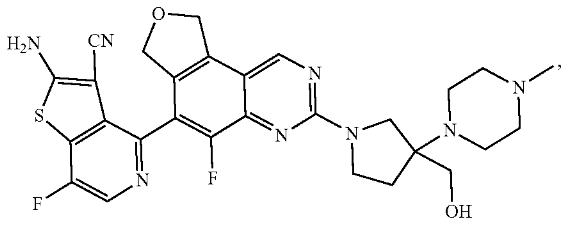
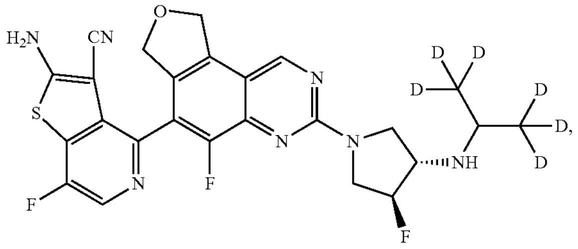
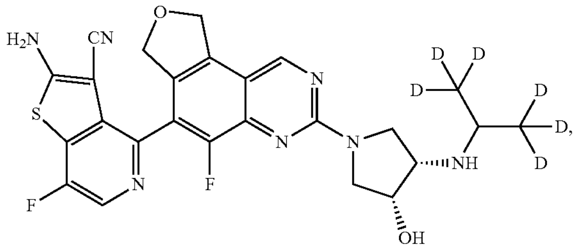
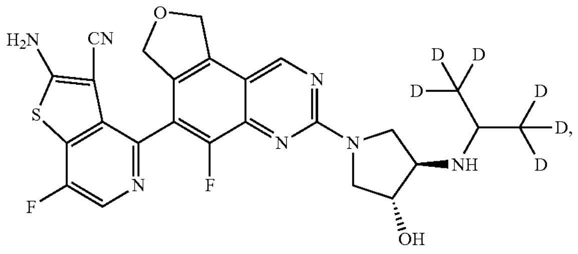

-continued
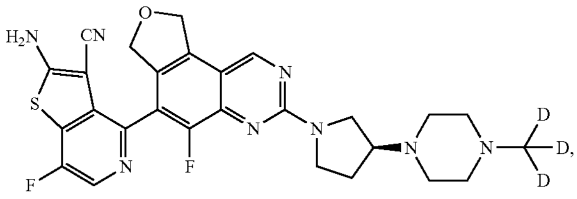
,
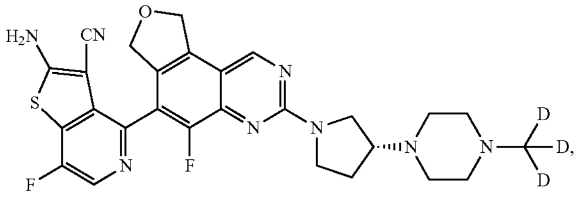
,
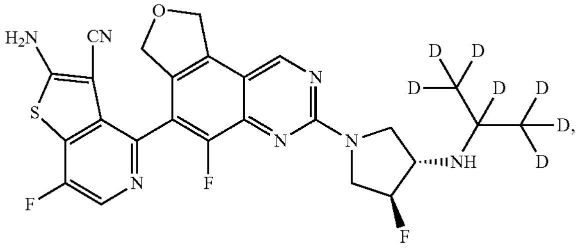
,
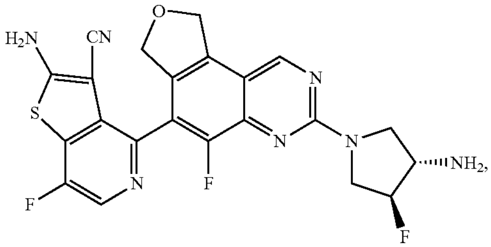
,
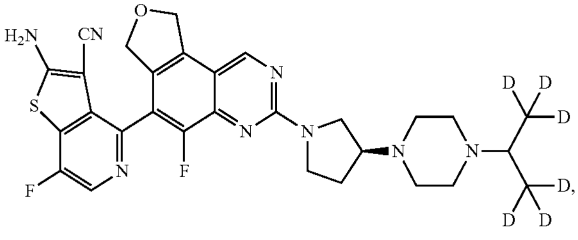
,
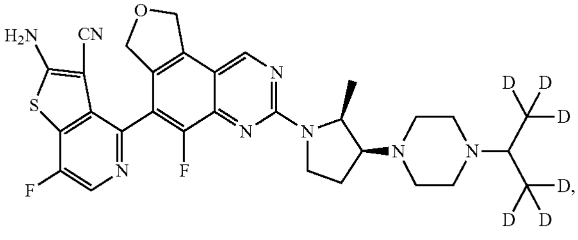
,
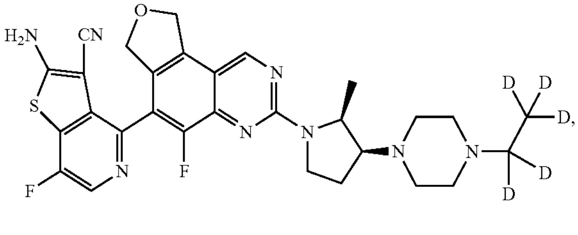
,
-continued
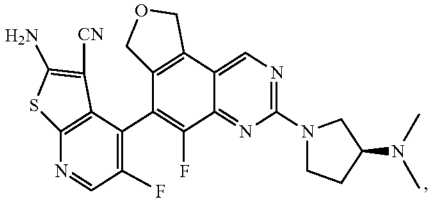
,
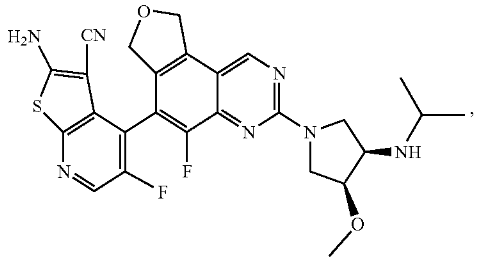
,
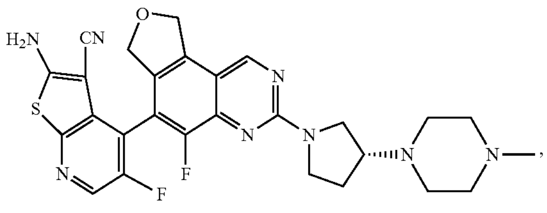
,
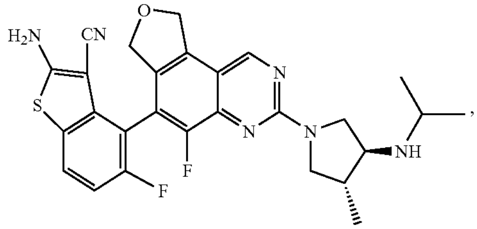
,
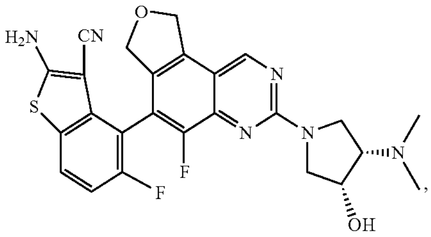
,
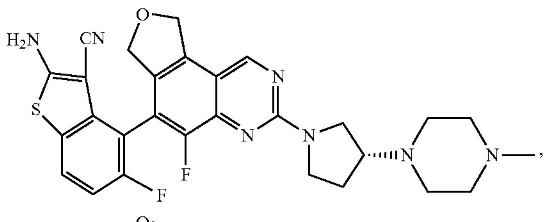
,
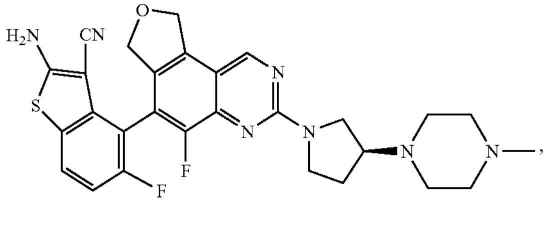
, -continued
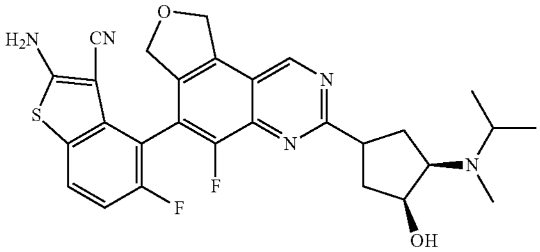
,
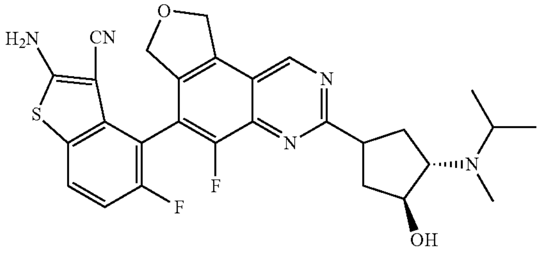
,
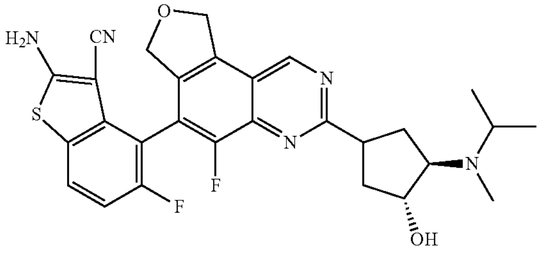
,
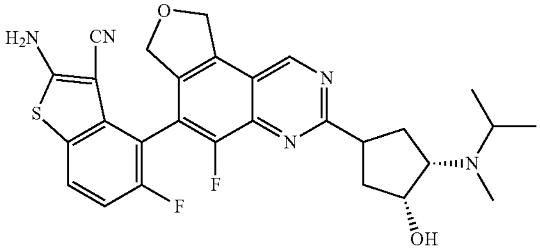
,
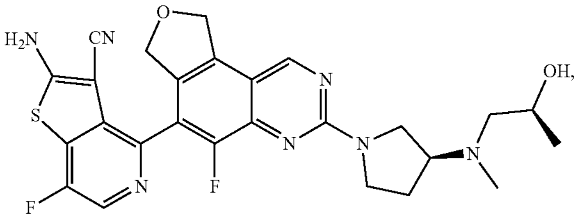
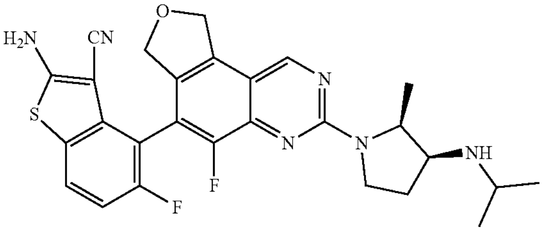
,
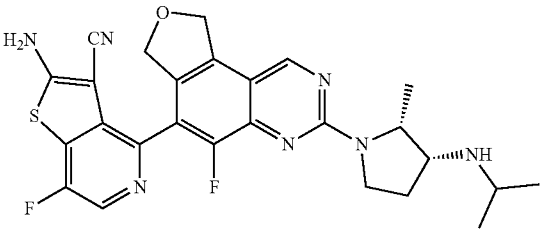
,
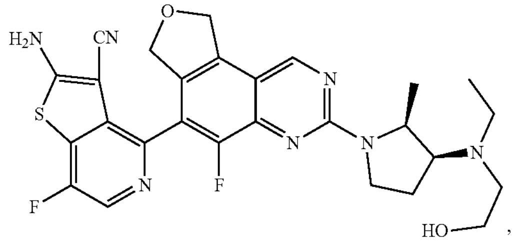
,
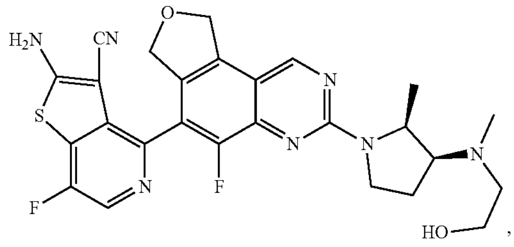
,
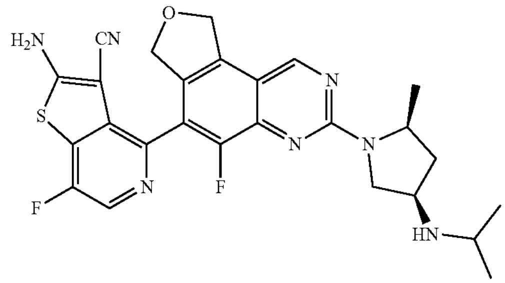
,
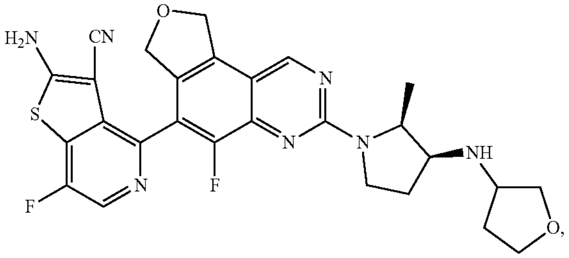
and
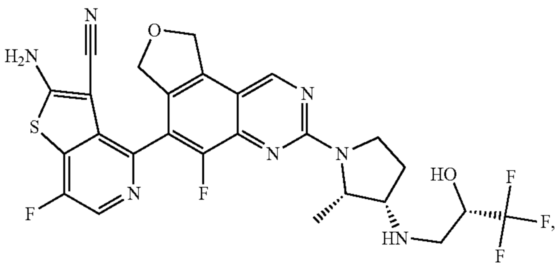
or a pharmaceutically acceptable salt thereof.
20. The compound of claim 1, wherein the compound is selected from:

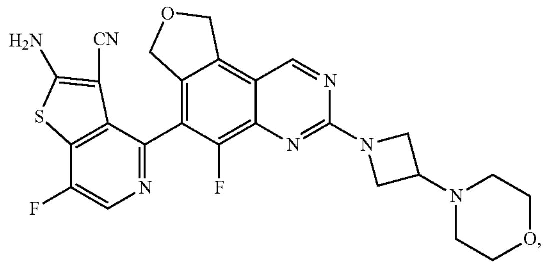
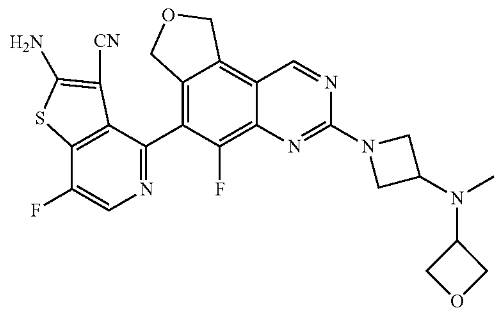
,
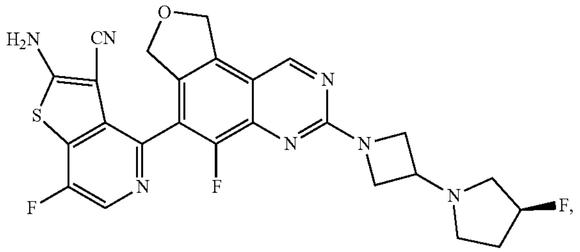
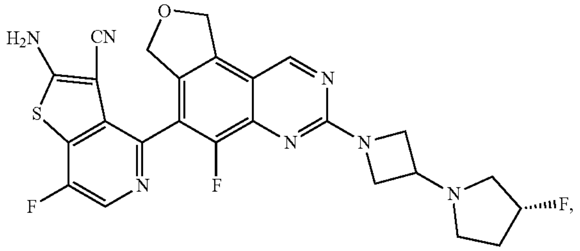
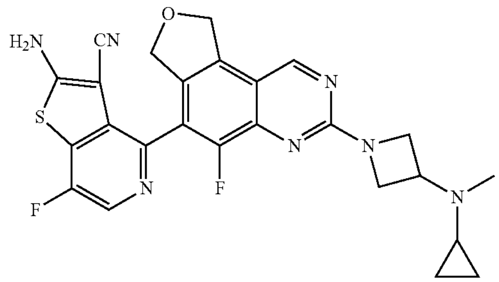
,
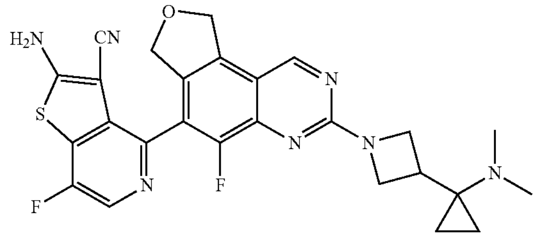
,
-continued
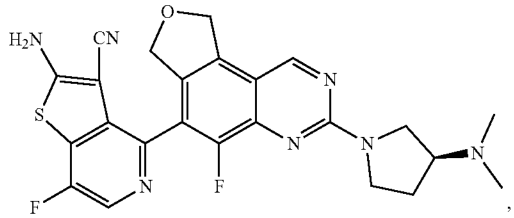
,
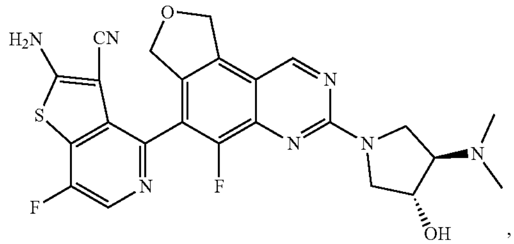
,
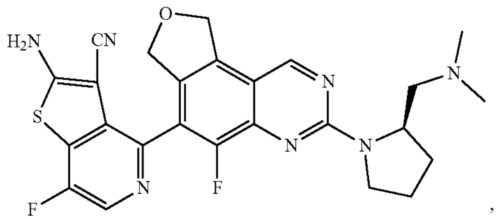
,
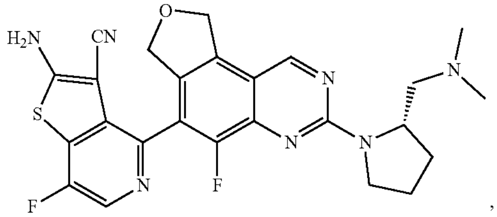
,
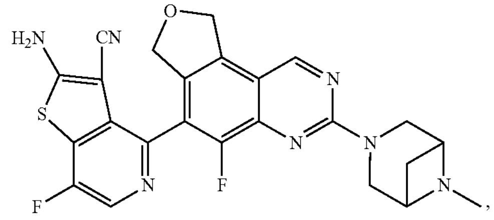
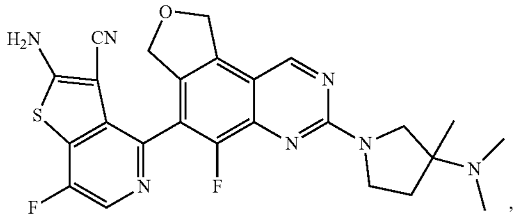
,
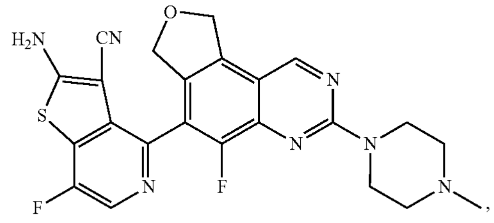

-continued
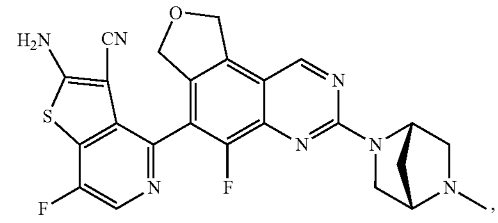
,
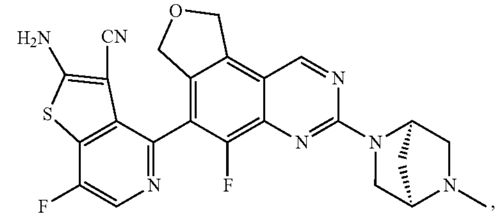
,
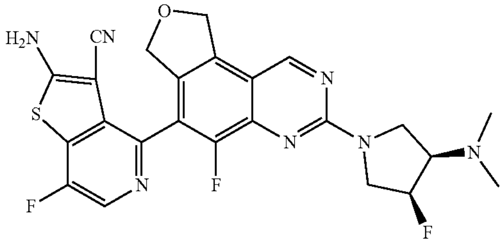
,
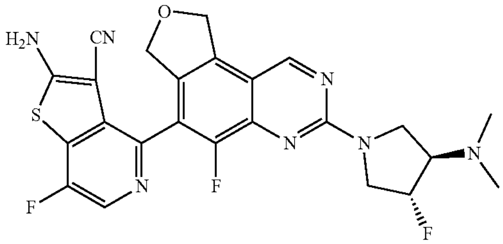
,
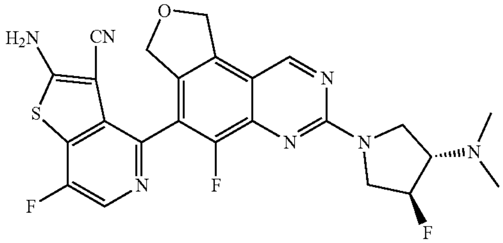
,
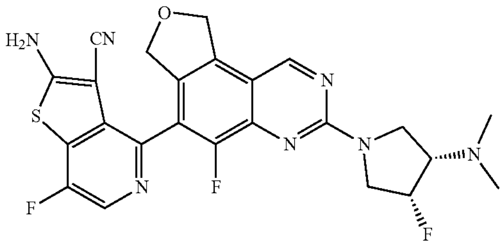
,
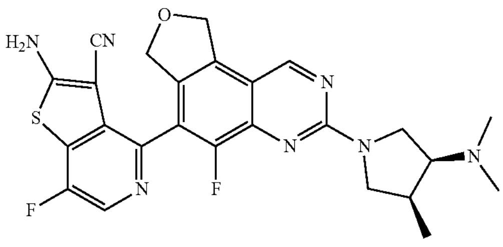
,
-continued
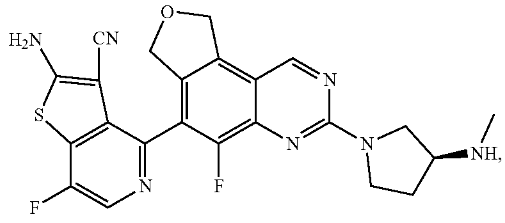
,
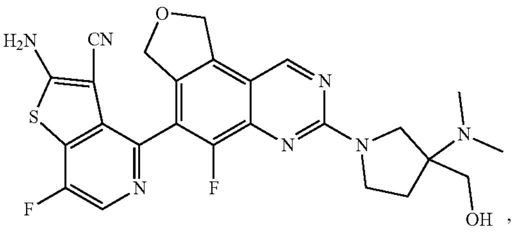
,
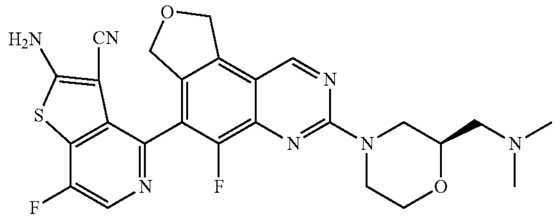
,
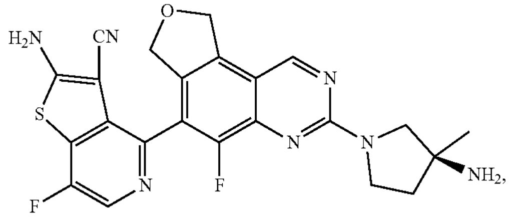
,
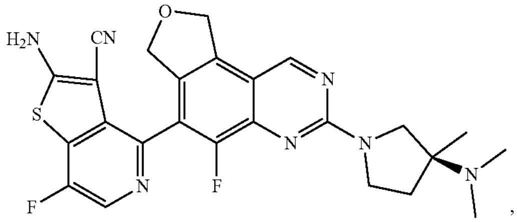
,
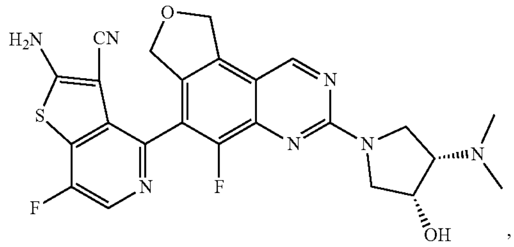
,
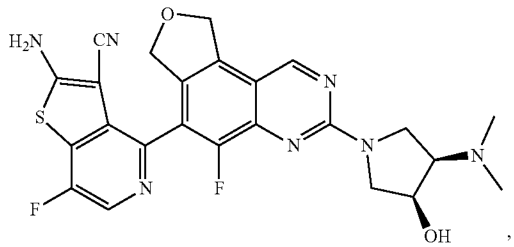
, -continued
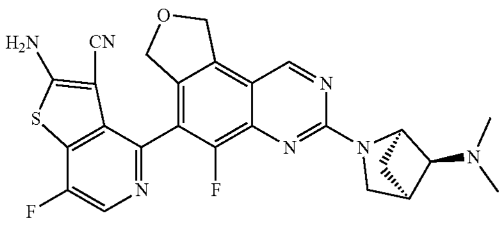,
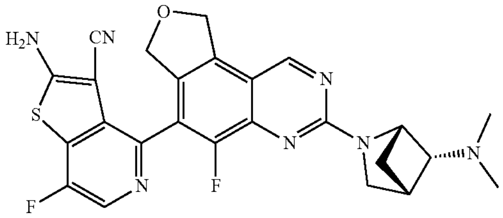,
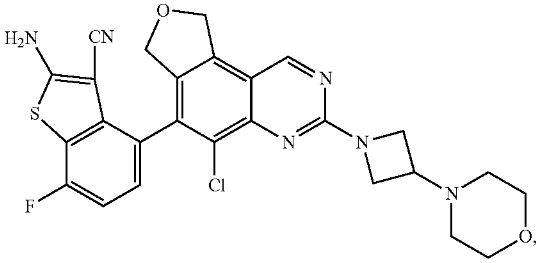,
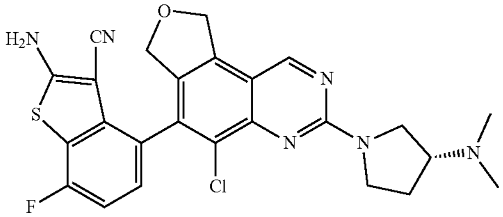,
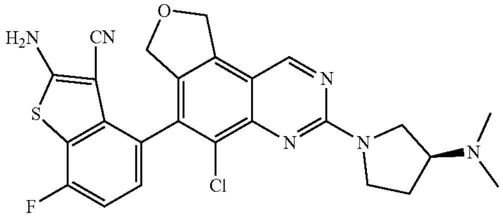,
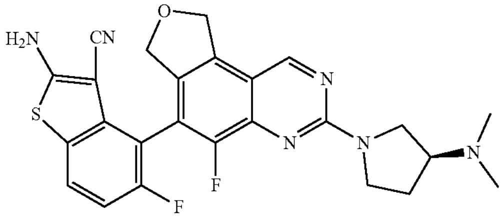,
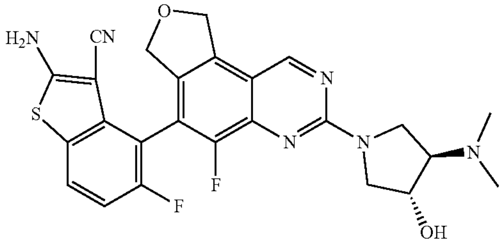,
-continued
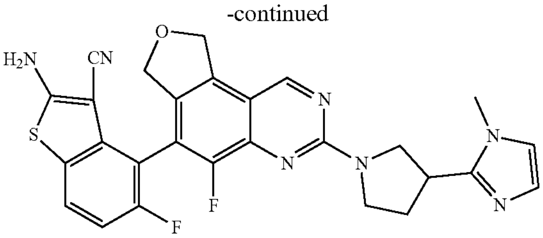,
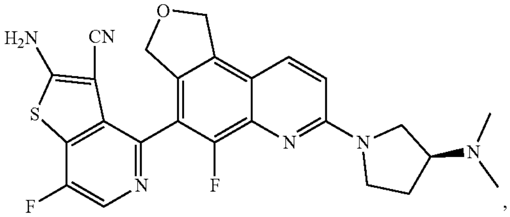,
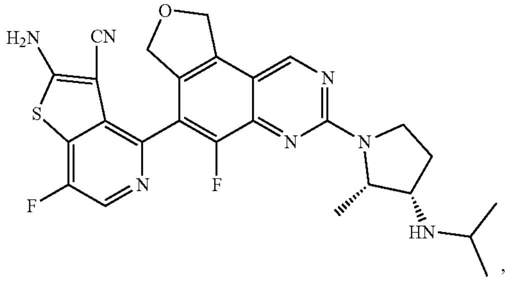,
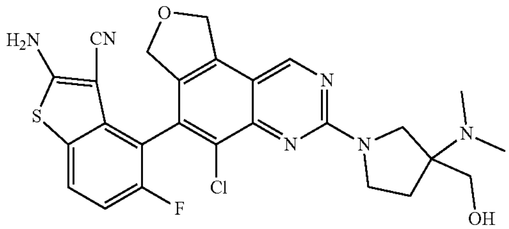,
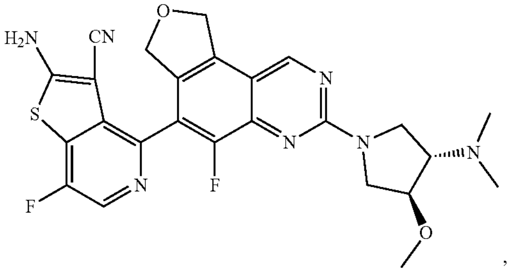,
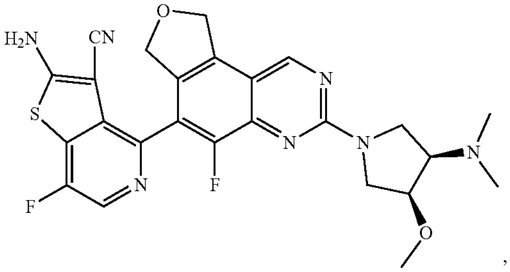,
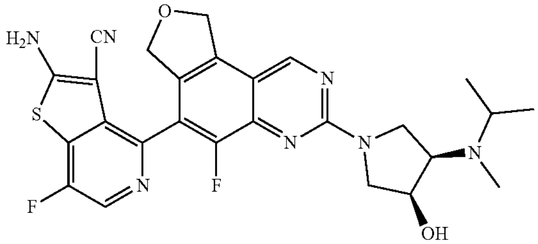, -continued
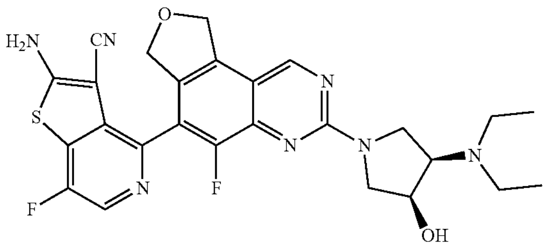
,
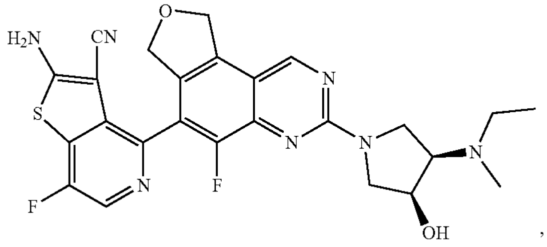
,
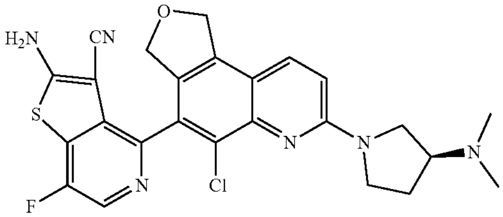
,
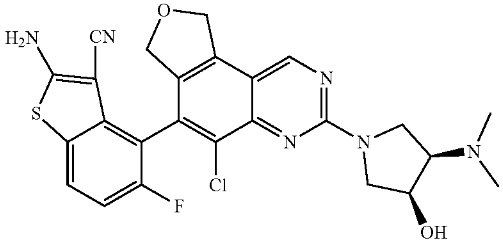
,
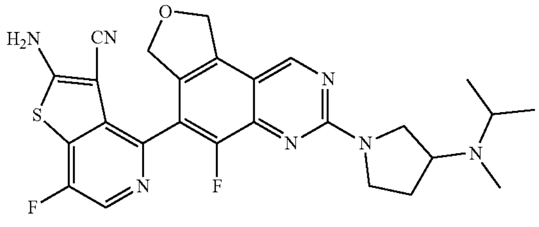
,
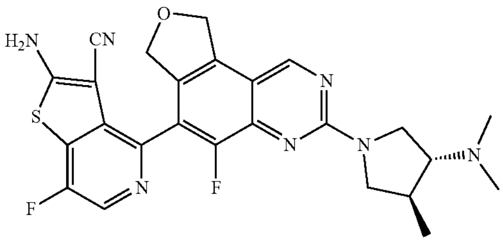
,
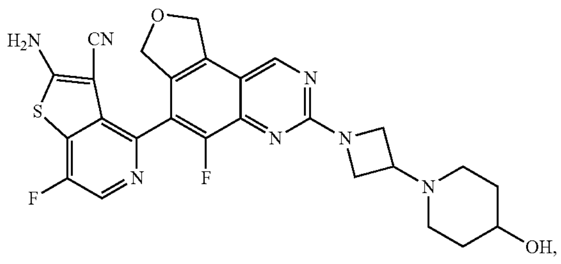
-continued
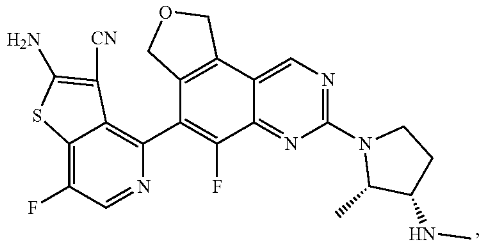
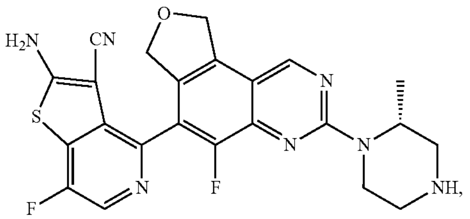
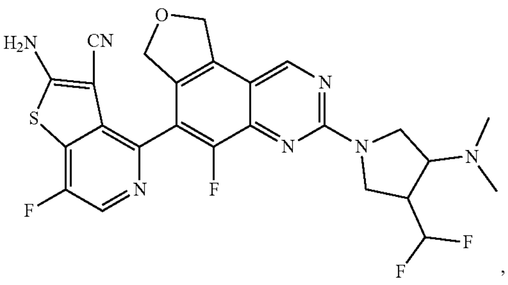
,
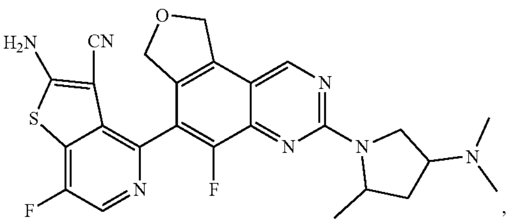
,
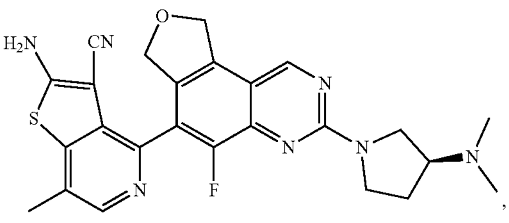
,
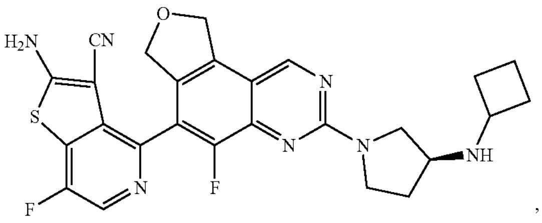
,
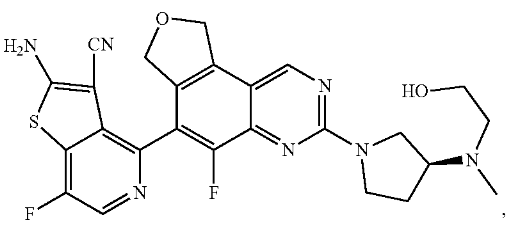
, -continued
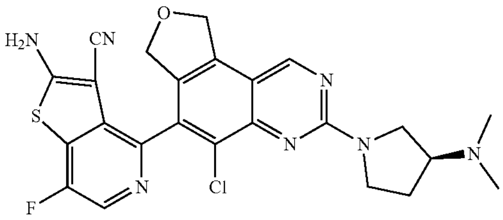
,
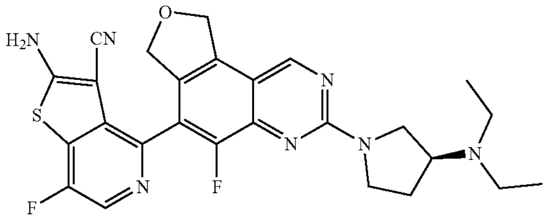
,
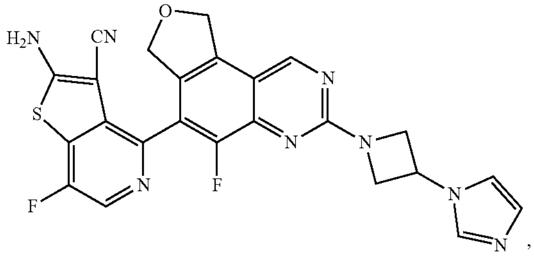
,
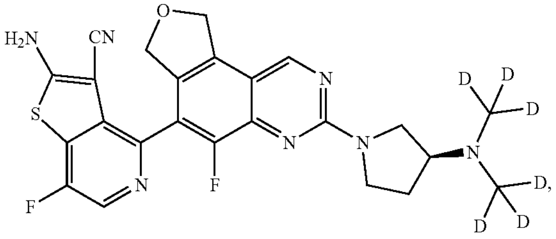
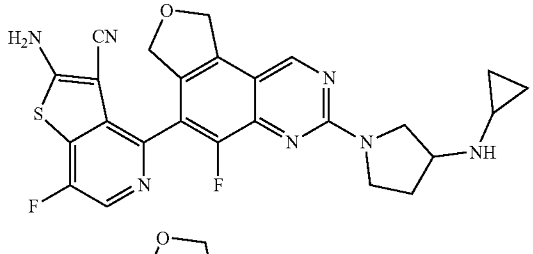
,
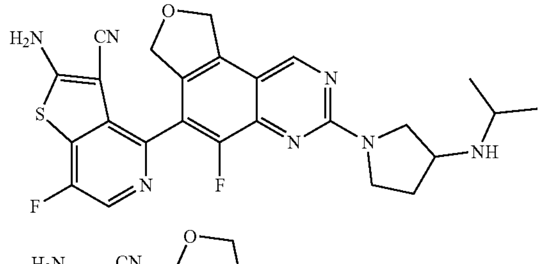
,
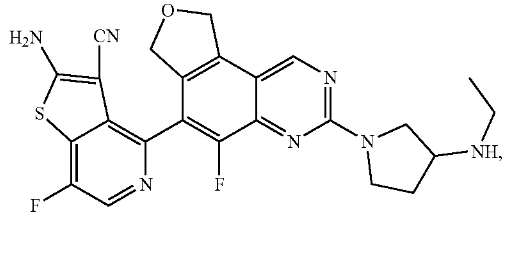
-continued
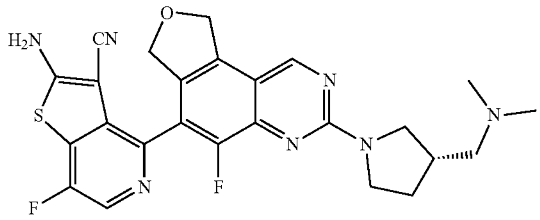
,
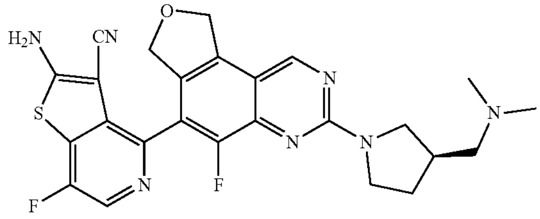
,
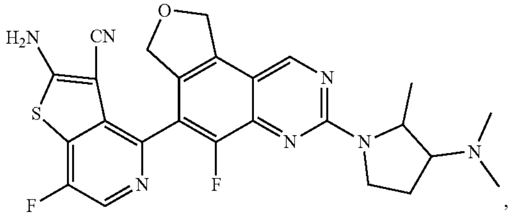
,
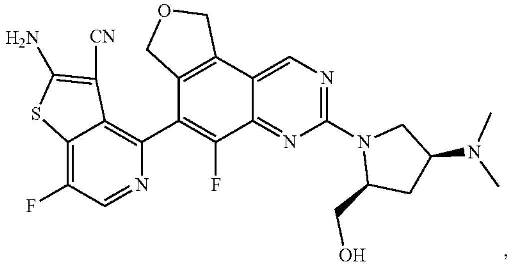
,
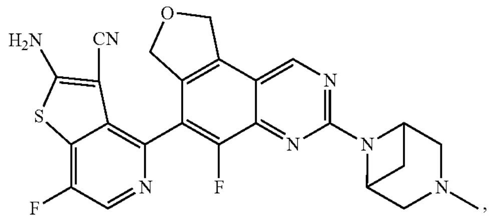
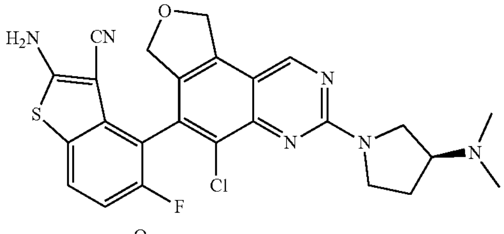
,
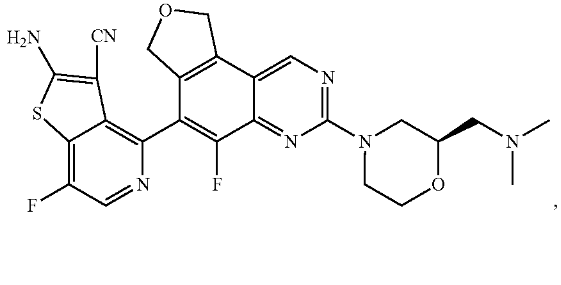
, -continued
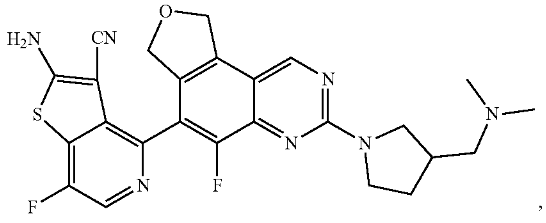
,
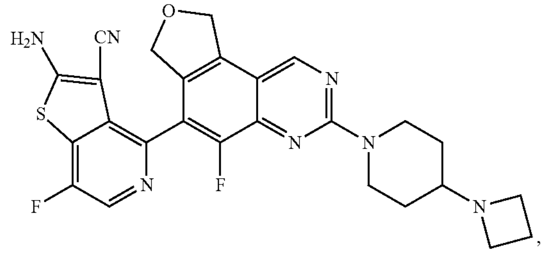
,
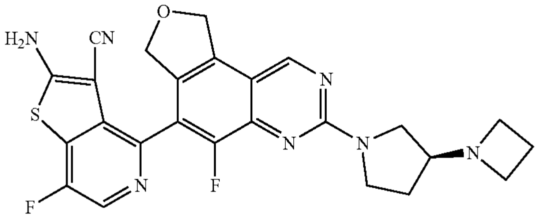
,
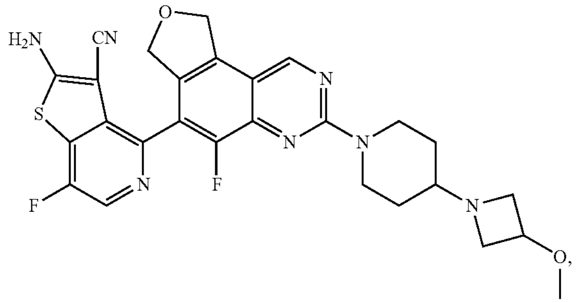
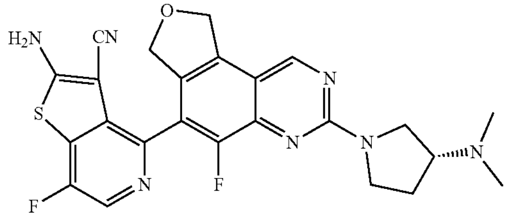
,
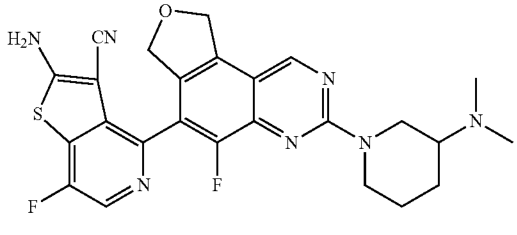
,
-continued
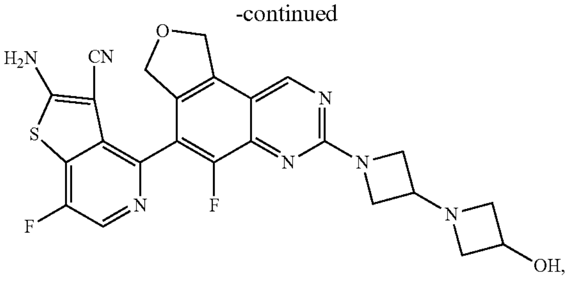
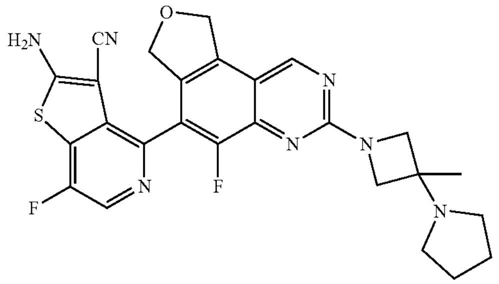
,
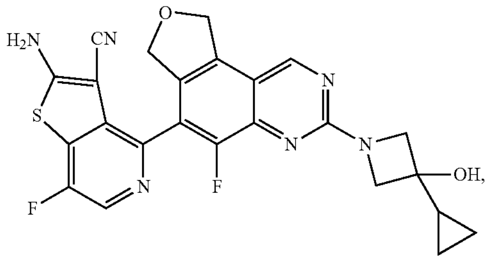
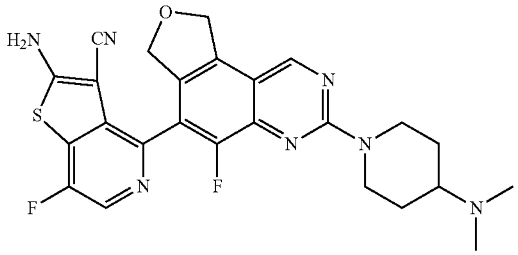
,
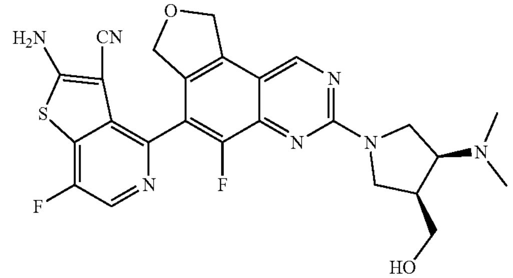
,
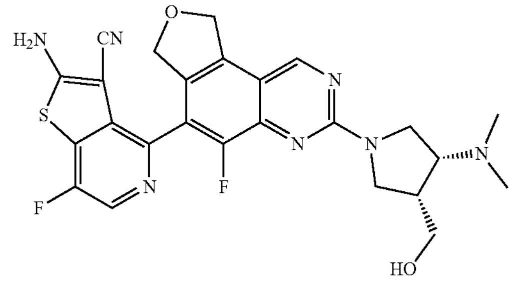
, -continued

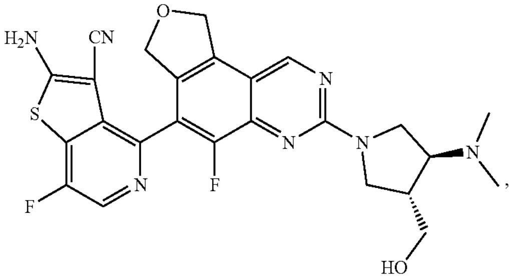

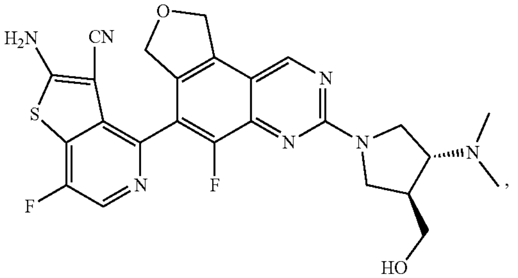

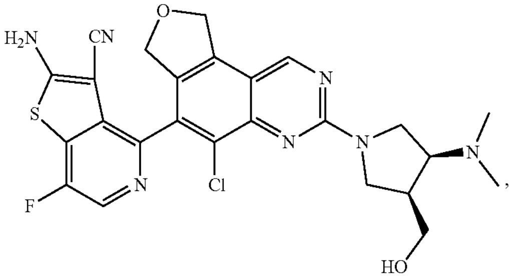

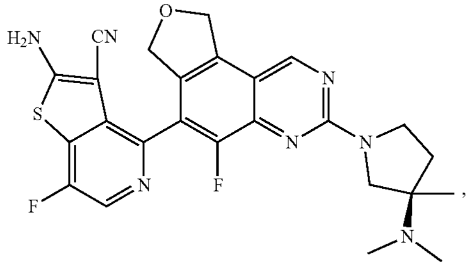

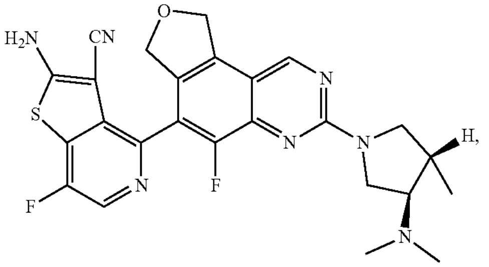

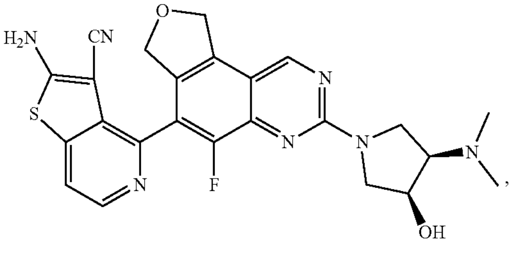

-continued

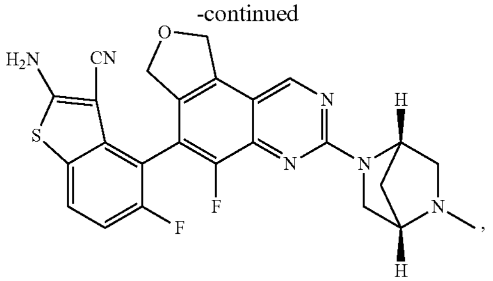

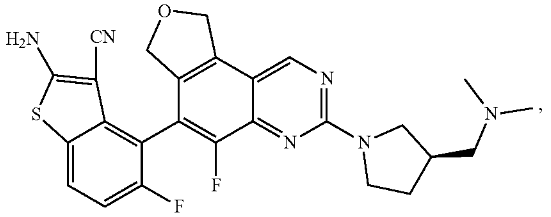

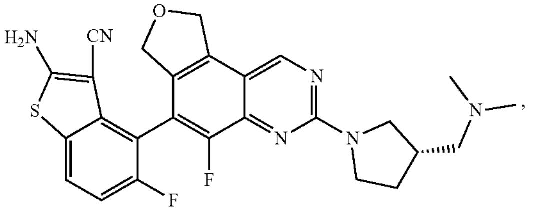

and

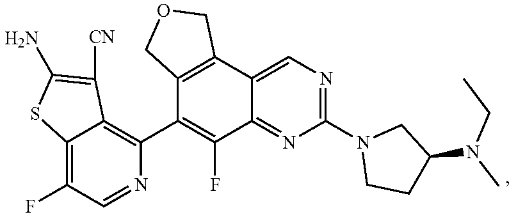

or a pharmaceutically acceptable salt thereof.

21. A pharmaceutical composition comprising a compound according to claim 1, or a pharmaceutically acceptable salt thereof, and a pharmaceutically acceptable carrier, diluent or excipient.

22. A pharmaceutical composition comprising a compound according to claim 19, or a pharmaceutically acceptable salt thereof, and a pharmaceutically acceptable carrier, diluent or excipient.

23. A pharmaceutical composition comprising a compound according to claim 20, or a pharmaceutically acceptable salt thereof, and a pharmaceutically acceptable carrier, diluent or excipient.

24. A method of treating a patient for cancer, comprising administering to a patient in need thereof, an effective amount of a pharmaceutical composition according to claim 21, wherein the cancer is selected from lung cancer, pancreatic cancer, cervical cancer, esophageal cancer, endometrial cancer, ovarian cancer, cholangiocarcinoma, and colorectal cancer.

25. A method of treating a patient for cancer, comprising administering to a patient in need thereof, an effective amount of a compound according to claim 1, or a pharmaceutically acceptable salt thereof, wherein the cancer is selected from lung cancer, pancreatic cancer, cervical cancer, esophageal cancer, endometrial cancer, ovarian cancer, cholangiocarcinoma, and colorectal cancer.

26. A method of treating a patient for cancer, comprising administering to a patient in need thereof, an effective amount of a compound according to claim 19, or a pharmaceutically acceptable salt thereof, wherein the cancer is selected from lung cancer, pancreatic cancer, cervical cancer, esophageal cancer, endometrial cancer, ovarian cancer, cholangiocarcinoma, and colorectal cancer.

27. A method of treating a patient for cancer, comprising administering to a patient in need thereof, an effective amount of a compound according to claim 20, or a pharmaceutically acceptable salt thereof, wherein the cancer is selected from lung cancer, pancreatic cancer, cervical cancer, esophageal cancer, endometrial cancer, ovarian cancer, cholangiocarcinoma, and colorectal cancer.

28. The method according to claim 25, wherein the patient is also administered an effective amount of one or more of a PD-1 inhibitor, a PD-L1 inhibitor, a CDK4/CDK6 inhibitor, an EGFR inhibitor, an ERK inhibitor, an Aurora A inhibitor, a SHP2 inhibitor, a platinum agent, and pemetrexed, or pharmaceutically acceptable salts thereof.

* * * * *